(12) United States Patent
Alonso et al.

(10) Patent No.: US 11,110,178 B2
(45) Date of Patent: *Sep. 7, 2021

(54) ANTIBODY ADJUVANT CONJUGATES

(71) Applicants: The Board of Trustees of the Leland Stanford Junior University, Stanford, CA (US); Bolt Biotherapeutics, Inc., Sunnyvale, CA (US)

(72) Inventors: Michael Nathaniel Alonso, Santa Clara, CA (US); Edgar George Engleman, Atherton, CA (US); Shelley Erin Ackerman, Mountain View, CA (US); Justin Kenkel, Mountain View, CA (US); Arthur Lee, San Jose, CA (US); David Y. Jackson, Belmont, CA (US)

(73) Assignees: The Board of Trustees of the Leland Standford Junior University, Stanford, CA (US); BOLT BIOTHERAPEUTICS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/817,864

(22) Filed: Mar. 13, 2020

(65) Prior Publication Data

US 2020/0206357 A1 Jul. 2, 2020

Related U.S. Application Data

(63) Continuation of application No. 16/140,309, filed on Sep. 24, 2018, now Pat. No. 10,675,358, which is a continuation of application No. PCT/US2017/041268, filed on Jul. 7, 2017.

(60) Provisional application No. 62/526,306, filed on Jun. 28, 2017, provisional application No. 62/522,623, filed on Jun. 20, 2017, provisional application No. 62/433,742, filed on Dec. 13, 2016, provisional application No. 62/432,530, filed on Dec. 9, 2016, provisional application No. 62/359,627, filed on Jul. 7, 2016, provisional application No. 62/359,626, filed on Jul. 7, 2016.

(51) Int. Cl.
*A61K 47/68* (2017.01)
*C07K 16/28* (2006.01)
*C07K 16/30* (2006.01)
*A61P 35/00* (2006.01)

(52) U.S. Cl.
CPC ...... *A61K 47/6801* (2017.08); *A61K 47/6849* (2017.08); *A61K 47/6851* (2017.08); *A61K 47/6855* (2017.08); *A61P 35/00* (2018.01); *C07K 16/2818* (2013.01); *C07K 16/28* (2013.01); *C07K 16/30* (2013.01)

(58) Field of Classification Search
None
See application file for complete search history.

(56) References Cited

U.S. PATENT DOCUMENTS

| | | |
|---|---|---|
| 4,459,296 A | 7/1984 | Ancher et al. |
| 4,689,338 A | 8/1987 | Gerster |
| 6,069,149 A | 5/2000 | Nanba et al. |
| 6,331,539 B1 | 12/2001 | Crooks et al. |
| 6,451,810 B1 | 9/2002 | Coleman et al. |
| 6,541,485 B1 | 4/2003 | Crooks et al. |
| 6,573,273 B1 | 6/2003 | Crooks et al. |
| 6,677,349 B1 | 1/2004 | Griesgraber |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,888,000 B2 | 5/2005 | Crooks et al. |
| 6,897,221 B2 | 5/2005 | Crooks et al. |
| 6,924,293 B2 | 8/2005 | Lindstrum |
| 7,030,131 B2 | 4/2006 | Crooks et al. |
| 7,112,677 B2 | 9/2006 | Griesgraber |
| 7,157,453 B2 | 1/2007 | Crooks et al. |
| 7,199,131 B2 | 4/2007 | Lindstrom |
| 7,375,180 B2 | 5/2008 | Gorden et al. |
| 7,393,859 B2 | 7/2008 | Coleman et al. |
| 7,427,629 B2 | 9/2008 | Kedl et al. |
| 7,700,321 B2 | 4/2010 | McPherson et al. |
| 7,799,800 B2 | 9/2010 | Wightman |

(Continued)

FOREIGN PATENT DOCUMENTS

| | | |
|---|---|---|
| CN | 103328005 A | 9/2013 |
| EA | 201891040 A1 | 10/2018 |

(Continued)

OTHER PUBLICATIONS

Adams, "Toll-like receptor agonists in cancer therapy," *Immunotherapy*, 1(6): 949-964 (2009).

(Continued)

*Primary Examiner* — Patricia Duffy
(74) *Attorney, Agent, or Firm* — Kyle A. Gurley; Bozicevic, Field & Francis LLP

(57) ABSTRACT

The invention provides an immunoconjugate comprising an antibody construct which includes an antigen binding domain and an Fc domain, an adjuvant moiety, and a linker, wherein each adjuvant moiety is covalently bonded to the antibody via the linker. Methods for treating cancer with the immunoconjugates of the invention are also described.

30 Claims, 588 Drawing Sheets
Specification includes a Sequence Listing.

(56) References Cited

U.S. PATENT DOCUMENTS

| | | |
|---|---|---|
| 7,923,560 B2 | 4/2011 | Wightman et al. |
| 7,943,609 B2 | 5/2011 | Griesgraber et al. |
| 8,017,779 B2 | 9/2011 | Merrill et al. |
| 8,071,336 B2 | 12/2011 | McPherson et al. |
| 8,124,085 B2 | 2/2012 | Nielsen et al. |
| 8,198,020 B2 | 6/2012 | Francois et al. |
| 8,207,162 B2 | 6/2012 | Griesgraber et al. |
| 8,277,810 B2 | 10/2012 | Long et al. |
| 8,435,800 B2 | 5/2013 | Gengrinovitch |
| 8,440,192 B2 | 5/2013 | Nielsen et al. |
| 8,470,980 B2 | 6/2013 | Hutchinson et al. |
| 8,481,029 B2 | 6/2013 | Glennie et al. |
| 8,518,405 B2 | 8/2013 | Mukherjee |
| 8,546,383 B2 | 10/2013 | Griesgraber et al. |
| 8,637,032 B2 | 1/2014 | Long et al. |
| 8,658,666 B2 | 2/2014 | Rice et al. |
| 8,709,418 B2 | 4/2014 | Okano et al. |
| 8,728,486 B2 | 5/2014 | David et al. |
| 8,741,291 B2 | 6/2014 | Bhat et al. |
| 8,828,398 B2 | 9/2014 | Kobayashi et al. |
| 8,841,417 B2 | 9/2014 | Wu et al. |
| 8,911,740 B2 | 12/2014 | Saito et al. |
| 8,937,160 B2 | 1/2015 | Kobayashi et al. |
| 8,951,528 B2 | 2/2015 | Stoermer et al. |
| 8,993,524 B2 | 3/2015 | Bedi et al. |
| 9,115,200 B2 | 8/2015 | Okano et al. |
| 9,169,325 B2 | 10/2015 | Keler et al. |
| 9,175,074 B2 | 11/2015 | Okano et al. |
| 9,180,188 B2 | 11/2015 | Kobayashi et al. |
| 9,181,334 B2 | 11/2015 | Kobayashi et al. |
| 9,181,348 B2 | 11/2015 | Kobayashi et al. |
| 9,192,667 B2 | 11/2015 | Hoves et al. |
| 9,205,148 B2 | 12/2015 | Langermann et al. |
| 9,243,069 B2 | 1/2016 | Johnson et al. |
| 9,248,127 B2 | 2/2016 | Perman et al. |
| 9,260,513 B2 | 2/2016 | Kobayashi et al. |
| 9,266,958 B2 | 2/2016 | Kobayashi et al. |
| 9,273,128 B2 | 3/2016 | Okano et al. |
| 9,273,130 B2 | 3/2016 | Kobayashi et al. |
| 9,308,253 B2 | 4/2016 | Kim et al. |
| 9,314,521 B2 | 4/2016 | Ossendorp et al. |
| 9,358,307 B2 | 6/2016 | Pitcovski et al. |
| 9,364,554 B2 | 6/2016 | Hutchinson et al. |
| 9,409,993 B2 | 8/2016 | Minamida et al. |
| 9,416,191 B2 | 8/2016 | Kobayashi et al. |
| 9,416,192 B2 | 8/2016 | Okano et al. |
| 9,416,193 B2 | 8/2016 | Saito et al. |
| 9,428,581 B2 | 8/2016 | Saito et al. |
| 9,441,005 B2 | 9/2016 | David et al. |
| 9,441,044 B2 | 9/2016 | Bedi et al. |
| 9,475,804 B2 | 10/2016 | Wightman |
| 9,498,541 B2 | 11/2016 | Chari et al. |
| 9,522,958 B2 | 12/2016 | Epstein et al. |
| 9,556,167 B2 | 1/2017 | Spiegel et al. |
| 9,573,993 B2 | 2/2017 | Okano et al. |
| 9,617,336 B2 | 4/2017 | Cojocaru et al. |
| 9,623,118 B2 | 4/2017 | Chang et al. |
| 9,676,849 B2 | 6/2017 | Farrington et al. |
| 9,676,854 B2 | 6/2017 | Liu et al. |
| 9,724,426 B2 | 8/2017 | Graversen et al. |
| 9,751,945 B2 | 9/2017 | Ploegh et al. |
| 9,770,506 B2 | 9/2017 | Ossendorp et al. |
| 9,827,329 B2 | 11/2017 | Li |
| 9,878,052 B2 | 1/2018 | Li |
| 9,902,724 B2 | 2/2018 | Wightman |
| 9,926,374 B2 | 3/2018 | Glennie et al. |
| 9,926,380 B2 | 3/2018 | Molldrem et al. |
| 10,000,539 B2 | 6/2018 | Mahr et al. |
| 10,005,772 B2 | 6/2018 | Stoermer et al. |
| 10,105,426 B2 | 10/2018 | Noelle et al. |
| 10,131,713 B2 | 11/2018 | Johnson et al. |
| 10,188,741 B2 | 1/2019 | Pitcovski et al. |
| 10,208,037 B2 | 2/2019 | David et al. |
| 10,328,158 B2 | 6/2019 | Li |
| 10,428,045 B2 | 10/2019 | Coburn et al. |
| 10,434,183 B2 | 10/2019 | Georges |
| 10,457,681 B2 | 10/2019 | Young et al. |
| 10,472,361 B2 | 11/2019 | Poudel et al. |
| 10,472,420 B2 | 11/2019 | Stoermer et al. |
| 10,487,084 B2 | 11/2019 | He et al. |
| 10,494,370 B2 | 12/2019 | Poudel et al. |
| 10,508,115 B2 | 12/2019 | He et al. |
| 10,519,131 B2 | 12/2019 | Coburn et al. |
| 10,533,007 B2 | 1/2020 | Glick et al. |
| 10,548,985 B2 | 2/2020 | Li |
| 10,548,988 B2 | 2/2020 | Li |
| 10,556,903 B2 | 2/2020 | Glick et al. |
| 10,640,499 B2 | 5/2020 | Chin et al. |
| 10,660,971 B2 | 5/2020 | Li |
| 10,675,358 B2 * | 6/2020 | Alonso ............... A61K 47/6851 |
| 10,682,365 B2 | 6/2020 | Krieg |
| 10,722,591 B2 | 7/2020 | Coffman et al. |
| 10,744,204 B2 | 8/2020 | Gao et al. |
| 10,744,206 B2 | 8/2020 | Li |
| 10,780,180 B2 | 9/2020 | Li |
| 10,849,984 B2 | 12/2020 | Georges |
| 2002/0146388 A1 | 10/2002 | Gillies |
| 2002/0155108 A1 | 10/2002 | Barbera-Guillem |
| 2003/0144283 A1 | 7/2003 | Coleman et al. |
| 2004/0038294 A1 | 2/2004 | Evangelista et al. |
| 2004/0091491 A1 | 5/2004 | Kedl et al. |
| 2004/0131587 A1 | 7/2004 | Thomas et al. |
| 2004/0171086 A1 | 9/2004 | Fink et al. |
| 2004/0191833 A1 | 9/2004 | Fink et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0113297 A1 | 5/2005 | Francois et al. |
| 2005/0158325 A1 | 7/2005 | Hammerbeck et al. |
| 2006/0018911 A1 | 1/2006 | Ault-Riche et al. |
| 2006/0142202 A1 | 6/2006 | Alkan et al. |
| 2007/0092521 A1 | 4/2007 | McPherson et al. |
| 2007/0166384 A1 | 7/2007 | Zarraga |
| 2008/0031887 A1 | 2/2008 | Lustgarten |
| 2008/0031900 A1 | 2/2008 | Lustgarten |
| 2008/0233140 A1 | 9/2008 | Banchereau et al. |
| 2008/0254047 A1 | 10/2008 | Banchereau et al. |
| 2009/0004192 A1 | 1/2009 | Pedersen et al. |
| 2009/0004194 A1 | 1/2009 | Kedl |
| 2009/0035323 A1 | 2/2009 | Stoermer et al. |
| 2009/0123467 A1 | 5/2009 | Bedi et al. |
| 2009/0155289 A1 | 6/2009 | Roberts et al. |
| 2009/0181022 A1 | 7/2009 | Nielsen et al. |
| 2009/0325315 A1 | 12/2009 | Hirai et al. |
| 2010/0004156 A1 | 1/2010 | Kaushal et al. |
| 2010/0158928 A1 | 6/2010 | Stoermer et al. |
| 2010/0291109 A1 | 11/2010 | Kedl |
| 2010/0317111 A1 | 12/2010 | Kedl et al. |
| 2011/0064752 A1 | 3/2011 | Hutchinson et al. |
| 2011/0182847 A1 | 7/2011 | Noelle et al. |
| 2011/0274653 A1 | 11/2011 | Banchereau et al. |
| 2011/0274685 A1 | 11/2011 | Keler et al. |
| 2011/0274692 A1 | 11/2011 | White et al. |
| 2012/0034213 A1 | 2/2012 | Hellmann |
| 2012/0039916 A1 | 2/2012 | Zurawski et al. |
| 2012/0045414 A1 | 2/2012 | Delucia |
| 2012/0064593 A1 | 3/2012 | Kohler et al. |
| 2012/0177652 A1 | 7/2012 | Nielsen et al. |
| 2012/0213771 A1 | 8/2012 | Keler et al. |
| 2012/0219615 A1 | 8/2012 | Hershberg et al. |
| 2012/0231023 A1 | 9/2012 | Zurawski et al. |
| 2012/0301465 A1 | 11/2012 | Dutartre et al. |
| 2012/0328605 A1 | 12/2012 | Larocque et al. |
| 2013/0039911 A1 | 2/2013 | Bedi et al. |
| 2013/0165455 A1 | 6/2013 | Carson et al. |
| 2013/0183311 A1 | 7/2013 | Nielsen et al. |
| 2013/0195794 A1 | 8/2013 | Heath et al. |
| 2013/0202596 A1 | 8/2013 | Salas et al. |
| 2013/0330350 A1 | 12/2013 | Dimasi |
| 2013/0336994 A1 | 12/2013 | Hutchinson et al. |
| 2014/0065096 A1 | 3/2014 | Ichim et al. |
| 2014/0179558 A1 | 6/2014 | Ido et al. |
| 2014/0199293 A1 | 7/2014 | Sabbadini et al. |

(56) References Cited

U.S. PATENT DOCUMENTS

| | | |
|---|---|---|
| 2014/0199763 A1 | 7/2014 | Dutartre et al. |
| 2014/0205602 A1 | 7/2014 | Long et al. |
| 2014/0294849 A1 | 10/2014 | Larocque et al. |
| 2014/0341978 A1 | 11/2014 | Kim et al. |
| 2014/0363461 A1 | 12/2014 | Bagnoli et al. |
| 2015/0044279 A1 | 2/2015 | Miller et al. |
| 2015/0071948 A1 | 3/2015 | Lazar et al. |
| 2015/0110742 A1 | 4/2015 | Spiegel et al. |
| 2015/0141625 A1 | 5/2015 | Stoermer et al. |
| 2015/0158947 A1 | 6/2015 | Cojocaru et al. |
| 2015/0174268 A1 | 6/2015 | Li |
| 2015/0183881 A1 | 7/2015 | Bedi et al. |
| 2015/0191546 A1 | 7/2015 | Molldrem et al. |
| 2015/0284416 A1 | 10/2015 | Zhao |
| 2015/0299194 A1 | 10/2015 | Hoves et al. |
| 2015/0322155 A1 | 11/2015 | Zhao |
| 2016/0008485 A1 | 1/2016 | Marquette et al. |
| 2016/0015803 A1 | 1/2016 | Kedl |
| 2016/0015821 A1 | 1/2016 | Hubbell et al. |
| 2016/0067351 A1 | 3/2016 | Geierstanger et al. |
| 2016/0068533 A1 | 3/2016 | Ferguson et al. |
| 2016/0108123 A1 | 4/2016 | Freeman et al. |
| 2016/0112466 A1 | 4/2016 | Gunnalan et al. |
| 2016/0130348 A1 | 5/2016 | Langermann et al. |
| 2016/0145350 A1 | 5/2016 | Lonberg et al. |
| 2016/0159901 A1 | 6/2016 | Sahin et al. |
| 2016/0194399 A1 | 7/2016 | Irving et al. |
| 2016/0206754 A1 | 7/2016 | Chang et al. |
| 2016/0208020 A1 | 7/2016 | Chang et al. |
| 2016/0208021 A1 | 7/2016 | Chang et al. |
| 2016/0215056 A1 | 7/2016 | Glennie et al. |
| 2016/0279248 A1 | 9/2016 | Hutchinson et al. |
| 2016/0297889 A1 | 10/2016 | Okano et al. |
| 2016/0311903 A1 | 10/2016 | West et al. |
| 2016/0324981 A1 | 11/2016 | Pinkerton et al. |
| 2016/0324983 A1 | 11/2016 | Li |
| 2016/0339109 A1 | 11/2016 | Chang et al. |
| 2016/0339110 A1 | 11/2016 | Chang et al. |
| 2016/0339111 A1 | 11/2016 | Chang et al. |
| 2016/0339115 A1 | 11/2016 | Chang et al. |
| 2016/0339116 A1 | 11/2016 | Chang et al. |
| 2016/0340427 A1 | 11/2016 | Chang et al. |
| 2016/0340430 A1 | 11/2016 | Bedi et al. |
| 2016/0340435 A1 | 11/2016 | Chang et al. |
| 2016/0340439 A1 | 11/2016 | Engleman et al. |
| 2016/0347849 A1 | 12/2016 | Cai et al. |
| 2016/0355587 A1 | 12/2016 | West et al. |
| 2016/0355592 A1 | 12/2016 | Sagert et al. |
| 2016/0355599 A1 | 12/2016 | Sagert et al. |
| 2016/0375148 A1 | 12/2016 | Li |
| 2017/0008971 A1 | 1/2017 | Dennis et al. |
| 2017/0021033 A1 | 1/2017 | Geierstanger et al. |
| 2017/0028079 A1 | 2/2017 | Li |
| 2017/0044259 A1 | 2/2017 | Tipton et al. |
| 2017/0056391 A1 | 3/2017 | Li |
| 2017/0056518 A1 | 3/2017 | Chang et al. |
| 2017/0056519 A1 | 3/2017 | Chang et al. |
| 2017/0073343 A1 | 3/2017 | Galatsis et al. |
| 2017/0073415 A1 | 3/2017 | Urech et al. |
| 2017/0081416 A1 | 3/2017 | Long et al. |
| 2017/0087148 A1 | 3/2017 | Spiegel et al. |
| 2017/0095573 A1 | 4/2017 | Oh et al. |
| 2017/0114137 A1 | 4/2017 | Li |
| 2017/0119790 A1 | 5/2017 | Graversen et al. |
| 2017/0121421 A1 | 5/2017 | Cortez et al. |
| 2017/0145104 A1 | 5/2017 | Wang et al. |
| 2017/0152323 A1 | 6/2017 | Chang et al. |
| 2017/0158770 A1 | 6/2017 | Bedi et al. |
| 2017/0158772 A1 | 6/2017 | Thompson et al. |
| 2017/0173164 A1 | 6/2017 | Wightman |
| 2017/0183408 A1 | 6/2017 | Dimasi |
| 2017/0209574 A1 | 7/2017 | Cao et al. |
| 2017/0216452 A1 | 8/2017 | Ma et al. |
| 2017/0233745 A1 | 8/2017 | Dankers et al. |
| 2017/0290923 A1 | 10/2017 | Li et al. |
| 2017/0298139 A1 | 10/2017 | Thompson et al. |
| 2017/0306038 A1 | 10/2017 | Brogdon et al. |
| 2017/0319712 A1 | 11/2017 | Miller et al. |
| 2017/0368169 A1 | 12/2017 | Loew et al. |
| 2018/0037581 A1 | 2/2018 | McDonald et al. |
| 2018/0044429 A1 | 2/2018 | Keler et al. |
| 2018/0066053 A1 | 3/2018 | Keler et al. |
| 2018/0110874 A1 | 4/2018 | Li |
| 2018/0177887 A1 | 6/2018 | Li |
| 2018/0177888 A1 | 6/2018 | Li |
| 2018/0186792 A1 | 7/2018 | Wightman |
| 2018/0207273 A1 | 7/2018 | Dranoff et al. |
| 2018/0221503 A1 | 8/2018 | Kadiyala et al. |
| 2018/0222982 A1 | 8/2018 | Dranoff et al. |
| 2018/0251557 A1 | 9/2018 | Chui et al. |
| 2018/0258048 A1 | 9/2018 | Coburn et al. |
| 2018/0264133 A1 | 9/2018 | Chang et al. |
| 2018/0273948 A1 | 9/2018 | Kadiyala et al. |
| 2018/0296685 A1 | 10/2018 | Wooster et al. |
| 2018/0303936 A1 | 10/2018 | Cheung et al. |
| 2018/0305357 A1 | 10/2018 | Stoermer et al. |
| 2018/0346572 A1 | 12/2018 | Li |
| 2019/0002583 A1 | 1/2019 | Li |
| 2019/0016808 A1 | 1/2019 | Li |
| 2019/0016819 A1 | 1/2019 | Li |
| 2019/0030182 A1 | 1/2019 | Riggs-Sauthier et al. |
| 2019/0048084 A1 | 2/2019 | Li |
| 2019/0055243 A1 | 2/2019 | Poudel et al. |
| 2019/0055244 A1 | 2/2019 | Young et al. |
| 2019/0055245 A1 | 2/2019 | Poudel et al. |
| 2019/0055246 A1 | 2/2019 | He et al. |
| 2019/0055247 A1 | 2/2019 | He et al. |
| 2019/0062306 A1 | 2/2019 | Coburn et al. |
| 2019/0099415 A1 | 4/2019 | Li |
| 2019/0127367 A1 | 5/2019 | Glick et al. |
| 2019/0151462 A1 | 5/2019 | Coffman et al. |
| 2019/0169164 A1 | 6/2019 | Coburn et al. |
| 2019/0169165 A1 | 6/2019 | Coburn et al. |
| 2019/0202925 A1 | 6/2019 | Thompson |
| 2019/0201334 A1 | 7/2019 | Hakim et al. |
| 2019/0269789 A1 | 9/2019 | Li |
| 2019/0269790 A1 | 9/2019 | Li |
| 2019/0336615 A1 | 11/2019 | Thompson et al. |
| 2019/0352468 A1 | 11/2019 | Andrianov et al. |
| 2019/0374650 A1 | 12/2019 | Moon et al. |
| 2019/0381126 A1 | 12/2019 | Hu et al. |
| 2020/0009262 A1 | 1/2020 | White et al. |
| 2020/0016267 A1 | 1/2020 | Rinaldi et al. |
| 2020/0017501 A1 | 1/2020 | Young et al. |
| 2020/0024279 A1 | 1/2020 | Poudel et al. |
| 2020/0030442 A1 | 1/2020 | Cao |
| 2020/0031798 A1 | 1/2020 | Coburn et al. |
| 2020/0031936 A1 | 1/2020 | Hegde et al. |
| 2020/0038403 A1 | 2/2020 | Poudel et al. |
| 2020/0038519 A1 | 2/2020 | Georges |
| 2020/0039986 A1 | 2/2020 | Poudel et al. |
| 2020/0048254 A1 | 2/2020 | He et al. |
| 2020/0048255 A1 | 2/2020 | Poudel et al. |
| 2020/0048371 A1 | 2/2020 | Mills et al. |
| 2020/0054762 A1 | 2/2020 | Okano et al. |
| 2020/0055851 A1 | 2/2020 | Li et al. |
| 2020/0079860 A1 | 3/2020 | Khalil et al. |
| 2020/0095248 A1 | 3/2020 | He et al. |
| 2020/0108139 A1 | 4/2020 | Levy et al. |
| 2020/0108151 A1 | 4/2020 | Jackson et al. |
| 2020/0113912 A1 | 4/2020 | Odegard et al. |
| 2020/0140547 A1 | 5/2020 | Bedi et al. |
| 2020/0155700 A1 | 5/2020 | Li |
| 2020/0164084 A1 | 5/2020 | Cortez et al. |
| 2020/0179527 A1 | 6/2020 | Li |
| 2020/0190197 A1 | 6/2020 | Calzone et al. |
| 2020/0199242 A1 | 6/2020 | Thompson |
| 2020/0199247 A1 | 6/2020 | Thompson et al. |
| 2020/0206357 A1 | 7/2020 | Alonso et al. |
| 2020/0246478 A1 | 8/2020 | Li |
| 2020/0255429 A1 | 8/2020 | He et al. |
| 2020/0276327 A1 | 9/2020 | Li |
| 2020/0291028 A1 | 9/2020 | Poudel et al. |
| 2020/0308175 A1 | 10/2020 | Poudel et al. |

(56) References Cited

U.S. PATENT DOCUMENTS

| | | |
|---|---|---|
| 2020/0317672 A1 | 10/2020 | He et al. |
| 2020/0338207 A1 | 10/2020 | Geierstanger et al. |
| 2020/0345860 A1 | 11/2020 | Li |
| 2020/0353093 A1 | 11/2020 | Li |
| 2020/0390899 A1 | 12/2020 | Ackerman et al. |
| 2020/0392137 A1 | 12/2020 | He et al. |
| 2020/0405813 A1 | 12/2020 | Yam et al. |
| 2021/0017172 A1 | 1/2021 | Ahmad et al. |
| 2021/0017274 A1 | 1/2021 | Miao et al. |
| 2021/0040216 A1 | 2/2021 | Chui et al. |
| 2021/0053979 A1 | 2/2021 | Purandare et al. |

FOREIGN PATENT DOCUMENTS

| | | |
|---|---|---|
| EP | 1689846 B1 | 3/2013 |
| EP | 2674170 A | 12/2013 |
| GB | 2097790 A | 11/1982 |
| JP | 2003-535907 A | 12/2003 |
| JP | 2013-535508 A | 9/2013 |
| WO | WO 90/14844 A2 | 12/1990 |
| WO | WO 00/75605 A1 | 12/2000 |
| WO | WO 00/76518 A1 | 12/2000 |
| WO | WO 00/76519 A1 | 12/2000 |
| WO | WO 01/97843 A2 | 12/2001 |
| WO | WO 02/46749 A2 | 6/2002 |
| WO | WO 03/043572 A2 | 5/2003 |
| WO | WO 2004/028539 A2 | 4/2004 |
| WO | WO 2004/053057 A2 | 6/2004 |
| WO | WO 2004/053452 A2 | 6/2004 |
| WO | WO 2004/058759 A1 | 7/2004 |
| WO | WO 2004/108072 A2 | 12/2004 |
| WO | WO 2005/001022 A2 | 1/2005 |
| WO | WO 2005/003064 A2 | 1/2005 |
| WO | WO 2005/003065 A2 | 1/2005 |
| WO | WO 2005/016275 A2 | 2/2005 |
| WO | WO 2005/018555 A2 | 3/2005 |
| WO | WO 2005/020999 A1 | 3/2005 |
| WO | WO 2005/051324 A2 | 6/2005 |
| WO | WO 2005/094531 A2 | 10/2005 |
| WO | WO 2005/110013 A2 | 11/2005 |
| WO | WO 2005/123080 A2 | 12/2005 |
| WO | WO 2006/028545 A2 | 3/2006 |
| WO | WO 2006/074003 A2 | 7/2006 |
| WO | WO 2006/091394 A2 | 8/2006 |
| WO | WO 2006/091720 A2 | 8/2006 |
| WO | WO 2007/048122 A1 | 4/2007 |
| WO | WO 2007/100634 A2 | 9/2007 |
| WO | WO 2008/009894 A2 | 1/2008 |
| WO | WO 2009/085262 A1 | 7/2009 |
| WO | WO 2010/132622 A2 | 11/2010 |
| WO | WO 2012/021834 A1 | 2/2012 |
| WO | WO 2012/170072 A1 | 12/2012 |
| WO | WO 2012170072 | 12/2012 |
| WO | WO 2013/067597 A1 | 5/2013 |
| WO | WO 2013/105013 A1 | 7/2013 |
| WO | WO 2013/166110 A1 | 11/2013 |
| WO | WO 2013/180811 A1 | 12/2013 |
| WO | WO 2014/012479 A1 | 1/2014 |
| WO | WO 2014/161887 A1 | 10/2014 |
| WO | WO 2015/082905 A1 | 6/2015 |
| WO | WO 2015/095418 | 6/2015 |
| WO | WO 2015/103987 A1 | 7/2015 |
| WO | WO 2015/103989 A1 | 7/2015 |
| WO | WO 2015/103990 A1 | 7/2015 |
| WO | WO 2015/112749 A2 | 7/2015 |
| WO | WO 2015/143091 A1 | 9/2015 |
| WO | WO 2015/151078 A2 | 10/2015 |
| WO | WO 2015/151080 A2 | 10/2015 |
| WO | WO 2015/151081 A2 | 10/2015 |
| WO | WO 2015/155753 A2 | 10/2015 |
| WO | WO 2015/187637 A1 | 12/2015 |
| WO | WO 2016/004875 A1 | 1/2016 |
| WO | WO 2016/004876 A1 | 1/2016 |
| WO | WO 2016/032009 | 3/2016 |
| WO | WO 2016/034085 A1 | 3/2016 |
| WO | WO 2016/055812 A1 | 4/2016 |
| WO | WO 2016/057618 A1 | 4/2016 |
| WO | WO 2016/059622 A2 | 4/2016 |
| WO | WO 2016/064749 A2 | 4/2016 |
| WO | WO 2016/085967 A1 | 6/2016 |
| WO | WO 2016/112870 A1 | 7/2016 |
| WO | WO 2016/118754 A1 | 7/2016 |
| WO | WO 2016/141890 A1 | 9/2016 |
| WO | WO 2016/149201 A2 | 9/2016 |
| WO | WO 2016/150899 A2 | 9/2016 |
| WO | WO 2016/187122 A1 | 11/2016 |
| WO | WO 2016/187656 A1 | 12/2016 |
| WO | WO 2016/198470 A2 | 12/2016 |
| WO | WO 2016/203025 A1 | 12/2016 |
| WO | WO 2016/205551 A2 | 12/2016 |
| WO | WO 2016/205566 A1 | 12/2016 |
| WO | WO 2017/019894 A1 | 2/2017 |
| WO | WO 2017/019896 A1 | 2/2017 |
| WO | WO 2017/019897 A1 | 2/2017 |
| WO | WO 2017/021791 A1 | 2/2017 |
| WO | WO 2017/023779 A1 | 2/2017 |
| WO | WO 2017/024296 A1 | 2/2017 |
| WO | WO 2017/040233 A1 | 3/2017 |
| WO | WO 2017/040234 A1 | 3/2017 |
| WO | WO 2017/044803 A1 | 3/2017 |
| WO | WO 2017/058996 A1 | 4/2017 |
| WO | WO 2017/072662 A1 | 5/2017 |
| WO | WO 2017/083525 A1 | 5/2017 |
| WO | WO 2017/087280 | 5/2017 |
| WO | WO 2017/100305 A2 | 6/2017 |
| WO | WO 2017/106656 A1 | 6/2017 |
| WO | WO 2017/118405 A1 | 7/2017 |
| WO | WO 2017/118406 A1 | 7/2017 |
| WO | WO 2017/118407 A1 | 7/2017 |
| WO | WO 2017/180834 A1 | 10/2017 |
| WO | WO 2017/184746 A1 | 10/2017 |
| WO | WO 2017/210246 A2 | 12/2017 |
| WO | WO 2018/009916 A1 | 1/2018 |
| WO | WO 2018/046460 A1 | 3/2018 |
| WO | WO 2018/078620 A1 | 5/2018 |
| WO | WO 2018/112108 A1 | 6/2018 |
| WO | WO 2018/119474 A2 | 6/2018 |
| WO | WO 2018/119475 A1 | 6/2018 |
| WO | WO 2018/132496 A1 | 7/2018 |
| WO | WO 2018/140831 A2 | 8/2018 |
| WO | WO 2018/144955 A1 | 8/2018 |
| WO | WO 2018/152396 A1 | 8/2018 |
| WO | WO 2018/156617 A2 | 8/2018 |
| WO | WO 2018/166529 A1 | 9/2018 |
| WO | WO 2018/170179 A1 | 9/2018 |
| WO | WO 2018/175854 A1 | 9/2018 |
| WO | WO 2018/176159 A1 | 10/2018 |
| WO | WO 2018/187515 A1 | 10/2018 |
| WO | WO 2018/191746 A1 | 10/2018 |
| WO | WO 2018/195283 A1 | 10/2018 |
| WO | WO 2018/196823 A1 | 11/2018 |
| WO | WO 2018/198091 A1 | 11/2018 |
| WO | WO 2018/218215 A1 | 11/2018 |
| WO | WO 2018/227018 A1 | 12/2018 |
| WO | WO 2018/227023 A1 | 12/2018 |
| WO | WO 2018/232725 A1 | 12/2018 |
| WO | WO 2019/023622 A1 | 1/2019 |
| WO | WO 2019/084060 A1 | 5/2019 |
| WO | WO 2019/099412 A1 | 5/2019 |
| WO | WO 2019/118884 A1 | 6/2019 |
| WO | WO 2019/192454 A1 | 10/2019 |
| WO | WO 2019/222676 A1 | 11/2019 |
| WO | WO 2019/236567 A2 | 12/2019 |
| WO | WO 2020/023680 A1 | 1/2020 |
| WO | WO 2020/047187 A1 | 3/2020 |
| WO | WO 2020/051356 A1 | 3/2020 |
| WO | WO 2020/056008 A1 | 3/2020 |
| WO | WO 2020/056192 A1 | 3/2020 |
| WO | WO 2020/056194 A1 | 3/2020 |
| WO | WO 2020/056198 A2 | 3/2020 |
| WO | WO 2020/089811 A1 | 5/2020 |
| WO | WO 2020/123425 A1 | 6/2020 |
| WO | WO 2020/139618 A1 | 7/2020 |
| WO | WO 2020/141221 A1 | 7/2020 |

(56) References Cited

FOREIGN PATENT DOCUMENTS

| WO | WO 2020/168017 A1 | 8/2020 |
|---|---|---|
| WO | WO 2020/190690 A1 | 9/2020 |
| WO | WO 2020/190731 A1 | 9/2020 |
| WO | WO 2020/190734 A1 | 9/2020 |
| WO | WO 2020/190760 A1 | 9/2020 |
| WO | WO 2020/252015 A1 | 12/2020 |
| WO | WO 2020/252294 A1 | 12/2020 |
| WO | WO 2020/257235 A1 | 12/2020 |
| WO | WO 2020/257407 A1 | 12/2020 |
| WO | WO 2021/030665 A1 | 2/2021 |

OTHER PUBLICATIONS

Altin et al., "Targeting dentritic cells with antigen-containing liposomes: antitumor immunity," *Expert Opinion on Biological Therapy*, 4(11): 1735-47 (2004).
Andreu et al., "FcRγ Activation Regulates Inflammation-Associated Squamous Carcinogenesis," *Cancer Cell*, 17(2): 121-134 (2017).
Barbuto et al., "Induction of innate and adaptive immunity by delivery of poly dA:dT to dentritic cells," *Nature Chemical Biology*, 9: 250-56 (2013).
Beesu et al., "Identification of High-Potency Human TLR8 and Dual TLR7/TLR8 Agonists in Pyrimidine-2,4-diamines," *Journal of Medicinal Chemistry*, 60(5): 2084-98 (2017).
Bensinger et al., "A phase 1 study of lucatumumab, a fully human anti-CD40 antagonist monoclonal antibody administered intravenously to patients with relapsed or refractory multiple myeloma," *British Journal of Haematology*, 159: 58-66 (2012).
Borghaei et al., "Immunotherapy of cancer," *European Journal of Pharmacolog*, 625: 41-54 (2009).
Brunswick et al., "Surface immunoglobulin crosslinking activates a tyrosine kinase pathway in B cells that is independent of protein kinase C," *Proc. Natl. Acad. Sci. USA*, 88: 1311-14 (1991).
Chabre et al., "Design and creativity in synthesis of multivalent neoglycoconjugates," *Advances in carbohydrate chemistry and biochemistr*, 2(63): 165-393 (2010).
Cross et al., "Gene Therapy for Cancer Treatment: Past, Present and Future," *Clinical Medicine and Research*, 4(3): 218-27 (2006).
DeVisser et al., "De novo carcinogenesis promoted by chronic inflammation is B lymphocyte dependent," *Cancer Cell*, 7: 411-23 (2005).
Ducancel et al., "Molecular engineering of antibodies for therapeutic and diagnostic purposes," *mAbs*, 4(4):445-57 (2012).
Elluru et al., "Regulation of Human Dendritic Cell Functions by Natural Anti-CD40 Antibodies," *Methods in Molecular Biology (The TNF Superfamily: Methods and Protocols)*, 1155: 47-54 (2014).
Esteva et al., "CD40 signaling predicts response to preoperative trastuzumab and concomitant paclitaxel followed by 5-fluorouracil, epirubicin, and cyclophosphamide in HER-2-overexpressing breast cancer," *Breast Cancer Research*, 9: R87 (2007).
Eurasian Patent Office, Office Action in Eurasian Patent Application No. 201990092 (dated Dec. 9, 2019).
European Patent Office, Partial Supplementary European Search Report in European Patent Application No. 15740815.4 (dated Sep. 13, 2017).
European Patent Office, Extended European Search Report in European Patent Application No. 15740815.4 (dated Jan. 9, 2018).
European Patent Office, International Search Report in International Patent Application No. PCT/US2017/066220 (dated Mar. 9, 2018).
European Patent Office, Written Opinion in International Patent Application No. PCT/US2017/066220 (dated Mar. 9, 2018).
Fiaux, "Development of New Anticancer Agents based on a—Mannosida se Inhibition," Thèse No. 3793, Jun. 1, 2007.
Fong et al., "Dendritic Cells in Cancer Immunotherapy," *Annu. Rev. Immunol.*, 18:245-73 (2000).
Fong et al., "Dendritic Cells Injected Via Different Routes Induce Immunity in Cancer Patients," *J. Immunol.*, 166(6): 4254-59 (2001).
Friedberg et al., "Combination immunotherapy with a CpG oligonucleotide (1018 ISS) and rituximab in patients with non-Hodgkin lymphoma: increased interferon-α/β-inducable gene expression, without significant toxicity," *Blood*, 105(2): 489-95 (2005).
Gadd et al., "Targeted Activation of Toll-Like Receptors: Conjugation of a Toll-Like Receptor 7 Agonist to a Monoclonal Antibody Maintains Antigen Binding and Specificity," *Bioconjugate Chemistry*, 26: 1743-52 (2015).
Gavino et al., "Identification and expression profiling of a human C-type lectin, structurally homologous to mouse dectin-2," *Experimental dermatology*, 14(4): 281-288 (2005).
Gerber-Lemaire et al., "Studies toward new anti-cancer strategies based on alpha-mannosidase inhibition," *CHIMIA International Journal for Chemistry*, 64(9): 634-639 (2010).
Gilboa, "DC-based cancer vaccines," *The Journal of Clinical Investigation*, 117(5): 1195-1203 (2007).
Gladue et al., "The CD40 agonist antibody of CP-870,893 enhances dendritic cell and B-cell activity and promotes anti-tumor efficacy in SCID-hu mice," *Cancer Immunol. Immunother.*, 60(7): 1009-17 (2011).
Goldwater et al., "A Phase 1, Randomized Ascending Single-Dose Study of Antagonist Anti-Human CD40 ASKP1240 in Healthy Subjects," *American Journal of Transplantation*, 13: 1040-46 (2013).
Hamblett et al., "Altering Antibody-Drug Conjugate Binding to the Neonatal Fc Receptor Impacts Efficacy and Tolerability," *Molecular Pharmaceutics*, 13: 2387-96 (2016).
Houot et al., "Targeting immune effector cells to promote antibody-induced cytotoxicity in cancer immunotherapy," *Trends in Immunology*, 32(11): 510-16 (2011).
Hsu et al., "Vaccination of patients with B-cell lymphoma using autologous antigen-pulsed dendritic cells," *Nat. Med.*, 2(1): 52-8 (1996).
Ishikawa et al., "Identification of Distinct Ligands for the C-type Lectin Receptors Mincle and Dectin-2 in the Pathogenic Fungus Malassezia," *Cell Host & Microbe*, 13: 477-88 (2013).
Jain et al., "Engineering antibodies for clinical applications," *TRENDS in Biotechnology*, 25(7): 307-16 (2007).
Jefferis et al., "Human immunoglobulin allotypes," *mAbs*, 1(4): 332-38 (2009).
Jiang et al., "A Novel Peptide Isolated from a Phage Display Peptide Library with Trastuzumab Can Mimic Antigen Epitope of HER-2," *The Journal of Biological Chemistry*, 280(6): 4656-62 (2005).
Kalinski et al., "Dentritic cells in cancer immunotherapy: vaccines and combination immunotherapies," *Expert Rev. Vaccines*, 12(3): 285-95 (2013).
Kato et al., "Selective and Efficient Gene Delivery of CD4O-Ligand by a Fiber-Modified Adenovirus Vector with Specific Antibody to Human Leukemia and Myeloma," *Blood*, 104(11): 5263 (2004).
Kerscher et al., "The Dectin-2 family of C-type lectin-like receptors: an update," *International Immunology*, 25(5): 271-77 (2013).
Khalil et al., "Anti-CD40 agonist antibodies: preclinical and clinical experience," *Update Cancer Ther.*, 2(2): 61-65 (2007).
Khong et al., "The Use of Agonistic Anti-CD40 Therapy in Treatments for Cancer," *International Reviews of Immunology*, 31: 246-66 (2012).
Khong et al., "Agonistic Anti-CD40 Antibody Therapy is Effective Against Postoperative Cancer Recurrence and Metastasis in a Murine Tumor Model," *J. Immunother.*, 36(7): 365-72 (2013).
Kim et al., "Anti-cancer effect and structural characterization of endo-polysaccharide from cultivated mycelia of *Inonotus obliquus*," *Life Sciences*, 79: 72-80 (2006).
Kim et al., "Fcγ receptors enable anticancer action of proapoptotic and immune-modulatory antibodies," *J. Exp. Med.*, 210(9): 1647-51 (2013).
Kimura et al., "The Innate Immune Receptor Dectin-2 Mediates the Phagocytosis of Cancer Cells by Kupffer Cells for the Suppression of Liver Metastasis," *PNAS*, 113(49): 14097-14102 (2016).
Kokatla et al., "Structure-Based Design of Novel Human Toll-Like Receptor 8 Agonists," *ChemMedChem*, 9: 719-723 (2014).
Kramer et al., "Chemically tunable mucin chimeras assembled on living cells," PNAS, 112(41): 12574-12579 (2018).
Krieg, "Toll-like receptor 9 (TLR9) agonists in the treatment of cancer," *Oncogene*, 27: 161-67 (2008).
Kurts et al., "Cross-priming in health and disease," *Nat. Rev. Immunol.*, 10(6): 403-14 (2010).

(56) References Cited

OTHER PUBLICATIONS

Kwekkeboom, "Modulation of Dentritic Cells and Regulatory T Cells by Naturally Occurring Antibodies," *Naturally Occurring Antibodies* (*Nabs*), Chapter 10, Landes Bioscience and Springer Science+Business Media, pp. 133-144 (2012).
Li et al., "Generation of tumor-targeted antibody-CpG conjugates," *Journal of Immunological Methods*, 389: 45-51 (2013).
Lim et al., "TLR3 agonists improve the immunostimulatory potential of cetuximab against EGFR+ head and neck cancer cells," *Oncolmmunology*, 2(6): e24677-3-e24677-10 (2013).
Loskog et al., "CD40L—A Multipotent Molecule for Tumor Therapy," *Endocrine, Metabolic & Immune Disorders—Drug Targets*, 7: 23-28 (2007).
Lu et al., "1-Deoxymannojirimycin, the α1,2-mannosidase inhibitor, induced cellular endoplasmic reticulum stress in human hepatocarcinoma cell 7721," *Biochemical and Biophysical Research Communications*, 344: 221-25 (2006).
Lu et al., "Site-specific Antibody-polymer Conjugates for siRNA Delivery," *J. Am. Chem. Soc.*, 135(37): 13885-891 (2013).
Mantovani et al., "Macrophages, innate immunity and cancer: balance, tolerance, and diversity," *Current opinion in immunology*, 22(2): 231-237 (2010).
McDonagh et al., "Engineered anti-CD70 antibody-drug conjugate with increased therapeutic index," *Mol. Cancer. Ther.*, 7(9): 2913-23 (2008).
McGreal et al., "The carbohydrate-recognition domain of Dectin-2 is a C-type lectin with specificity for high mannose," *Glycobiology*, 16(5): 422-30 (2006).
Melief, "Cancer Immunotherapy by Dendritic Cells," *Immunity*, 29: 372-83 (2008).
Moga et al., "NK cells stimulated with IL-15 or CpG ODN enhance rituximab-dependent cellular cytotoxicity against B-cell lymphoma," *Experimental Hematology*, 36: 69-77 (2008).
Mohrbacher et al., "Synergy of CD40L and IL2 Fusion Antibodies in Killing of Malignant B Cells," *Blood*, p. 55b, Abstract #3398 (1999).
Müller et al., "Trastuzumab emtansine (T-DM1) renders HER2+ breast cancer highly susceptible to CTLA-4/PD-1 blockade," *Science Translational Medicine*, 7(315): 5-13 (2015).
Nunez-Prado et al., "The coming of age of engineered multivalent antibodies," *Drug discovery today*, 20(5): 588-594 (2015).
Palucka et al., "Dendritic-Cell-Based Therapeutic Cancer Vaccines," *Immunity*, 39: 38-48 (2013).
Park et al., "The Therapeutic Effect of Anti-HER2/neu Antibody Depends on Both Innate and Adaptive Immunity," *Cancer Cell*, 18(2): 160-170 (2010).
Pincetic et al., "Type I and type II Fc receptors regulate innate and adaptive immunity," *Nature immunology*, 15: 707-716 (2014).
Presta, "Engineering of therapeutic antibodies to minimize immunogenicity and optimize function," *Advanced Drug Delivery Reviews*, 58: 640-56 (2006).
Rafiq et al., "Immune complex-mediated antigen presentation induces tumor immunity," *The Journal of Clinical Investigation*, 110(1): 71-79 (2002).
Riemer et al., "Matching of trastuzumab (Herceptin®) epitope mimics onto the surface of Her-2/neu—a new method of epitope definition," *Mol. Immunol.* 42: 1121-24 (2005).
Rycyzyn et al., "The Use of an Anti-CD40 Agonist Monoclonal Antibody During Immunizations Enhances Hybridoma Generation," *Hybridoma*, 27(1): 25-30 (2008).
Sato et al., "Dectin-2 is a Pattern Recognition Receptor for Fungi That Couples with the Fc Receptor γ Chain to Induce Innate Immune Responses," *The Journal of Biological Chemistry*, 281(50): 38854-66 (2006).
Schuurhuis et al., "Immune Complex-Loaded Dendritic Cells are Superior to Soluble Immune Complexes as Antitumor Vaccine," *J. Immunol.*, 176(8): 4573-80 (2006).
Shoenfeld et al., "Gamma-globulin inhibits tumor spread in mice," *International Immunology*, 11(8): 1247-51 (1999).

Spitzer et al., "Systemic Immunity is Required for Effective Cancer Immunotherapy," *Cell*, 168: 1-16 (2017).
Steinman et al., "Taking dendritic cells into medicine," *Nature*, 449(7161): 419-26 (2007).
Suzuki et al., "Antitumor Activity of Polysaccharides. II. Growth-Inhibitory Activity of Mannan Fractions Isolated From Several Species of Yeasts Against Sarcoma-180 Solid Tumor," *GANN*, 60: 65-69 (1969).
Tham et al., "Melanoma-initiating cells exploit M2 macrophage TGFβ and arginase pathway for survival and proliferation," *Oncotarget*, 5(23): 12027-42 (2014).
Trombetta et al., "Cell Biology of Antigen Processing In Vitro and In Vivo," *Annu. Rev. Immunol.*, 23: 975-1028 (2005).
Tseng et al., "Anti-CD47 antibody-mediated phagocytosis of cancer by macrophages primes an effective antitumor T-cell response," *Proc. Natl. Acad. Sci. U.S.A.*, 110(27): 11103-08 (2013).
Vacchelli et al., "Toll-like receptor agonists for cancer therapy," *OncoImmunology*, 2(8): e25238-1-e25238-14 (2013).
Van Berkel et al., "Rapid production of recombinant human IgG with improved ADCC effector function in a transient expression system," *Biotechnology and bioengineering*, 105(2): 350-357 (2010).
Vonderheide et al., "Agonistic CD40 antibodies and cancer therapy," *Clin. Cancer Res.*, 19(5): 1035-43 (2013).
Wakim et al., "High dose intravenous immunoglobulin in atopic dermatitis and hyper-IgE syndrome," *Ann. Allergy Asthma Immunol.*, 81: 153-8 (1998).
Wang et al., "Effective antibody therapy induces host-protective antitumor immunity that is augmented by TLR4 agonist treatment," *Cancer Immunol. Immunother.*, 61: 49-61 (2012).
Wang et al., "Antigen targeting to dendritic cells with bispecific antibodies," *Journal of Immunological Methods*, 306: 80-92 (2005).
Warren et al., "Synergism Between Cytosine-Guanine Oligodeoxynucleotides and Monoclonal Antibody in the Treatment of Lymphoma," *Seminars in Oncology*, 29(1, Suppl. 2): 93-97 (2002).
Willimsky et al., "Immunogenicity of premalignant lesions is the primary cause of general cytotoxic T lymphocyte unresponsiveness," *The Journal of Experimental Medicine*, 205(7): 1687-1700 (2008).
Wooldridge et al., "T-cell activation induced by anti-CD3 x anti-B-cell lymphoma monoclonal antibody is enhanced by pretreatment of lymphoma cells with soluble CD40 ligand," *Cancer Immunol. Immunother.*, 45(3-4): 174-9 (1997).
Yan et al., "Targeting C-type lectin receptors for cancer immunity," *Frontiers in Immunology*, 6(408): 1-9 (2015).
Yang et al., "M-CSF cooperating with NFκB induces macrophage transformation from M1 to M2 by upregulating c-Jun," *Cancer Biology & Therapy*, 15(1): 99-107 (2014).
Zhou et al., "Development of a simple and rapid method for producing nonfucosylated oligomannose containing antibodies with increased effector function," *Biotechnology and bioengineering*, 99(3): 652-665 (2008).
Zhou et al., "N-Carboxyanhydride Polymerization of Glycopolypeptides That Activate Antigen-Presenting Cells through Dectin-1 and Dectin-2," *Angew. Chem. Int. Ed.*, 57: 3137-3142 (2018).
U.S. Appl. No. 16/723,276, filed Dec. 20, 2019, David Y. Jackson (first named inventor).
European Patent Office, Extended European Search Report in European Patent Application No. 17825059.3, dated Mar. 19, 2020.
Schwenk et al., "IgG2 Antibodies against a Clinical Grade *Plasmodium falciparum* CSP Vaccine Antigen Associate with Protection against Transgenic Sporozoite Challenge in Mice," *PLoS One*, 9(10):e111020 (2014).
Yao et al., "Methods to Design and Synthesize Antibody-Drug Conjugates (ADCs)," *International Journal of Molecular Sciences*, 17, 194 (2016).
Ackerman, "Antibody-Adjuvant Conjugates Elicit Robust Myeloid Activation and Durable Anti-Tumor Immunity—A Dissertation Submitted to the Department of Bioengineering and a Committee on Graduate Studies of Stanford University in Partial Fulfillment of the Requirements for the Degree of Doctor of Philosophy," http://purl.stanford.edu/xf251nx6820 (2018).

(56) References Cited

OTHER PUBLICATIONS

Ackerman et al., "HER2-Targeting TLR7/8 immune-stimulating antibody conjugates elicit robust myeloid activation and anti-tumor immune responses in a TLR- and FcR-dependent manner," Poster Presented at Society for Immunotherapy of Cancer (2019).
Ackerman et al., "TLR7/8 immune stimulating antibody conjugates elicit robust myeloid activation and durable anti-tumor immunity," Poster Presented at American Association for Cancer Research (2019).
Ackerman et al., "Covalent attachment of a TLR7/8 agonist to tumor-targeting antibodies drives potent anti-tumor efficacy by synergistically activating FcγR- and TLR-signaling and enables safe systemic administration," Poster Presented at Society for Immunotherapy of Cancer (2020).
Ackerman et al., "Immune-stimulating antibody conjugates elicit robust myeloid activation and durable antitumor immunity," Nature Cancer, 2: 18-33 (2021).
Castiglia et al., "Labelling techniques of biomolecules for targeted radiotherapy—Final report of a co-ordinated research project—1998-2002," IAEA-TECDOC-1359, International Atomic Energy Agency (IAEA) (Jul. 2003).
Crudo et al., "Labeling of the anti-melanoma 14f7 monoclonal antibody with rhenium-188-MAG$_3$ chelate: Conjugation optimization, in vitro stability and animal studies," J. Radioanal. Nucl., 261(2): 337-342 (2004).
Dumbrava et al., "Phase 1/2 study of novel HER2-targeting, TLR7/8 immune-stimulating antibody conjugate (ISAC) BDC-1001 as a single agent and in combination with an immune checkpoint inhibitor in patients with advanced HER2-expressing solid tumors," Poster Presented at San Antonio Breast Cancer Symposium (2020).
Fritzberg et al., "Specific and stable labeling of antibodies with technetium-99m with a diamide dithiolate chelating agent," Proc. Natl. Acad. Sci. USA, 85: 4025-4029 (1988).
Leblanc et al., "Systemically administered HER2-targeted ISACs provoke a rapid, local response that engages the innate and adaptive arms of the immune system to eradicate tumors in preclinical models," Poster Presented at Society for Immunotherapy of Cancer (2020).
Nagengast et al., "In Vivo VEGF Imaging with Radiolabeled Bevacizumab in a Human Ovarian Tumor Xenograft," J. Nucl. Med., 48: 1313-1319 (2007).
Perk et al., "$^{89}$Zr as a PET Surrogate Radioisotope for Scouting Biodistribution of the Therapeutic Radiometals $^{90}$Y and $^{177}$Lu in Tumor-Bearing Nude Mice After Coupling to the Internalizing Antibody Cetuximab," J. Nucl. Med., 46: 1898-1906 (2005).
Pham et al., "Tuning a Protein-Labeling Reaction to Achieve Highly Site Selective Lysine Conjugation," ChemBioChem, 19: 799-804 (2018).
Quanta Biodesign, Ltd., "TFP Esters Have More Hydrolytic Stability and Greater Reactivity Than NHS Esters," Flyer (2014).
Sharma et al., "Phase 1/2 study of novel HER2-targeting, TLR7/8 immune-stimulating antibody conjugate (ISAC) BDC-1001 with or without immune checkpoint inhibitor in patients with advanced HER2-expressing solid tumors," Poster Presented at Society for Immunotherapy of Cancer (2020).
Somlai et al., "Synthesis and Use of Pentafluorophenyl 6-(Biotinylamido)hexanoate—An Alternative Reagent for Labelling of Proteins with Biotin Moiety," Z. Naturforsch, 48b: 511-516 (1993).
Thermo Fisher Scientific Inc., "Thermo Scientific Avidin-Biotin Technical Handbook," www.thermo.com/perbio (2009).
Van Gog et al., "Monoclonal Antibodies Labeled with Rhenium-186 Using the MAG3 Chelate: Relationship between the Number of Chelated Groups and Biodistribution Characteristics," J. Nucl. Med., 37: 352-362 (1996).
Verel et al., "$^{89}$Zr Immuno-PET: Comprehensive Procedures for the Production of $^{89}$Zr-Labeled Monoclonal Antibodies," J. Nucl. Med., 44: 1271-1281 (2003).
Visser et al., "Labeling of Monoclonal Antibodies with Rhenium-186 Using the MAG3 Chelate for Radioimmunotherapy of Cancer: A Technical Protocol," J. Nucl. Med., 34: 1953-1963 (1993).
Vrouenraets et al., "Development of meta-Tetrahydroxyphenylchlorin-Monoclonal Antibody Conjugates for Photoimmunotherapy," Cancer Research, 59: 1505-1513 (1999).
Vrouenraets et al., "Targeting of Aluminum (Iii) Phtalocyanine Tetrasulfonate by Use of Internalizing Monoclonal Antibodies: Improved Efficacy in Photodynamic Therapy," Cancer Research, 61: 1970-1975 (2001).
Vrouenraets et al., "Targeting of a Hydrophilic Photosensitizer by Use of Internalizing Monoclonal Antibodies: A New Possibility for Use in Photodynamic Therapy," Int. J. Cancer, 88: 108-114 (2000).
Zambianchi et al., "Microwave-Assisted Synthesis of Thlophene Fluorophores, Labeling and Multilabeling of Monoclonal Antibodies, and Long Lasting Staining of Fixed Cells," J. Am. Chem. Soc., 131: 10892-10900 (2009).
Abes et al. (2010) "Long-lasting antitumor protection by anti-CD20 antibody through cellular immune response" Blood 116(6): 926-934.
Blumhagen et al., "Alternative pre-mRNA splicing of Toll-like receptor signaling components in peripheral blood mononuclear cells from patients with ARDS," Am. J. Physiol. Lung Cell. Mol. Physiol., 313(5):L930-L939 (2017).
Carmi et al. (2015) "Allogeneic IgG combined with dendritic cell stimuli induce antitumour T-cell immunity" ePub 521(7550): 99-104.
European Patent Office, Examination Report in European Patent Application No. 15740815.4, dated Aug. 18, 2020.
Hirano et al., "Inhibition of human breast carcinoma growth by a soluble recombinant human CD40 ligand," Blood, 93(9):2999-3007 (1999).
Hudziak et al., "p185HER2 monoclonal antibody has antiproliferative effects in vitro and sensitizes human breast tumor cells to tumor necrosis factor," Mol. Cell. Biol., 9(3):1165-1172 (1989).
Palucka et al., "Cancer Immunotherapy via dendritic cells," Nature Reviews/Cancer, 12:265-277 (2012).
Pinzon-Charry et al., "The key role of CD40 ligand is overcoming tumor-induced dendritic cell dysfunction," Breast Cancer Res., 8(1):402 (2006).
Poon et al., "Preclinical safety profile of trastuzumab emtansine (T-DM1): mechanism of action of its cytotoxic component retained with improved tolerability," Toxicol. Appl. Pharmacol., 273(2):298-313 (2013).
Schettini et al., "Intratumoral delivery of CpG-conjugated anti-MUC1 antibody enhances NK cell anti-tumor activity," Cancer Immunology, 61(11):2055-2065 (2012).
Shi et al., "Engagement of immune effector cells by trastuzumab induces HER2/ERBB2 downregulation in cancer cells through STAT1 activation," Breast Cancer Research, 16:R33 (2014), http://breast-cancer-research.com/content/16/2/R33.
Shukla et al. (2011) "Toward self-adjuvanting subunit vaccines: Model peptide and protein antigens incorporating covalently bound toll-like receptor-7 agonistic imidazoquinolines" Bioorganic & Medicinal Chemistry Letters 21(11): 3232-3236.
Stancovski et al., "Mechanistic aspects of the opposing effects of monoclonal antibodies to the ERBB2 receptor on tumor growth," Proc. Natl. Acad. Sci. USA, 88(19):8691-8695 (1991).
Turpin et al., "The ErbB2ΔEx16 splice variant is a major oncogenic driver in breast cancer that promotes a pro-metastatic tumor microenvironment," Oncogene, 35(47):6053-6054 (2016).
Wingett et al., "CD40 is functionally expressed on human breast carcinomas: variable inducibility by cytokines and enhancement of Fas-mediated apoptosis," Breast Cancer Res. Treat., 50(1):27-36 (1998).
Sancho D et al., "Signaling by Myeloid C-Type Lectin Receptors in Immunity and Homeostasis", Annual Review Of Immunology, Annual Reviews Inc, vol. 30, Jan. 1, 2012 (Jan. 1, 2012), pp. 491-529.
Upchurch Katherine C et al., "Preclinical 9-15 Assessment of the Effectiveness of alpha-Dectin-1-Pam3 Conjugate in Controlling T(H)2 Responses", Journal of Allergy and Clinical Immunology, &

(56) References Cited

OTHER PUBLICATIONS

Annual Meeting of the American-Academy-of-Allergy-Asthma-and-Immunology (Aaaai); Houston, TX, USA; Feb. 1, 2015, vol. 135, No. 2, Suppl . S.
Vasso Apostolopoulos et al: "Targeting 9-15 Antigens to Dendritic Cell Receptors for Vaccine Development", Journal of Drug Delivery, vol. 23, No. 7, Jan. 1, 2013 (Jan. 1, 2013), pp. 1739-22.

* cited by examiner

FIG. 8A
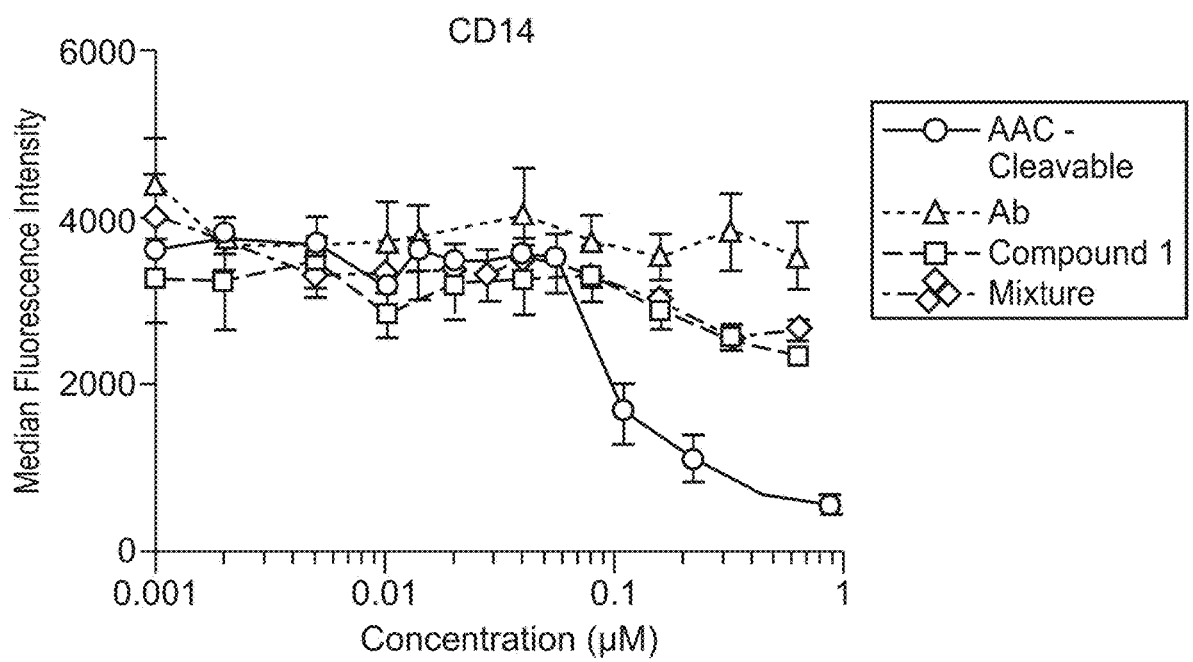
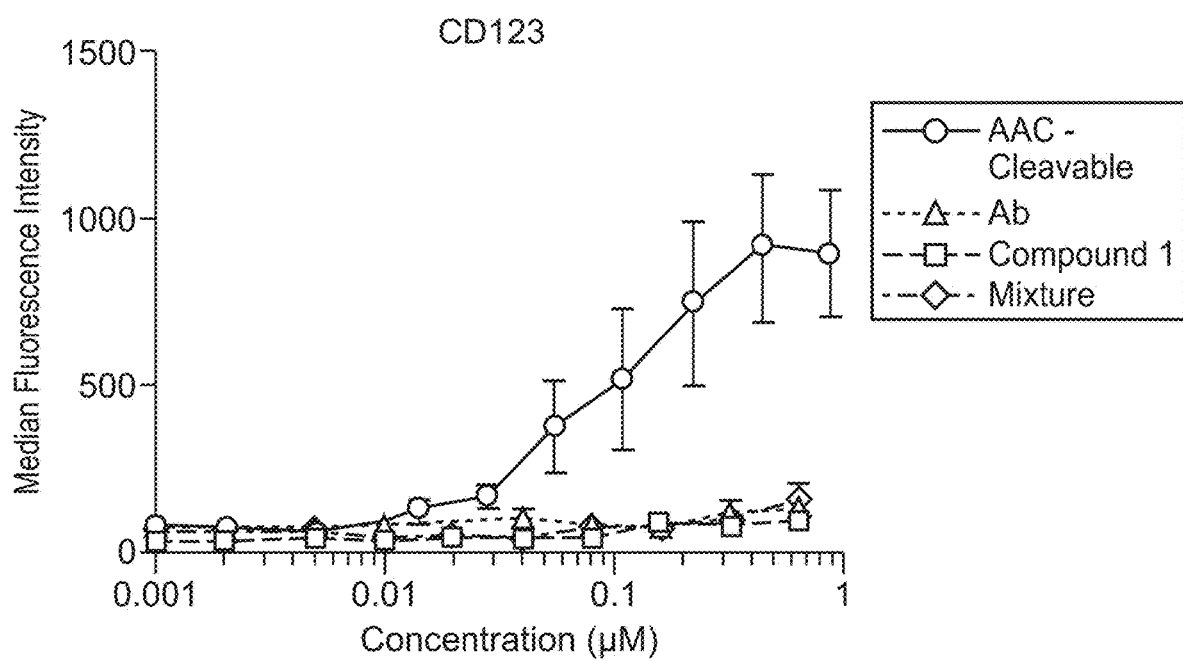

FIG. 8B
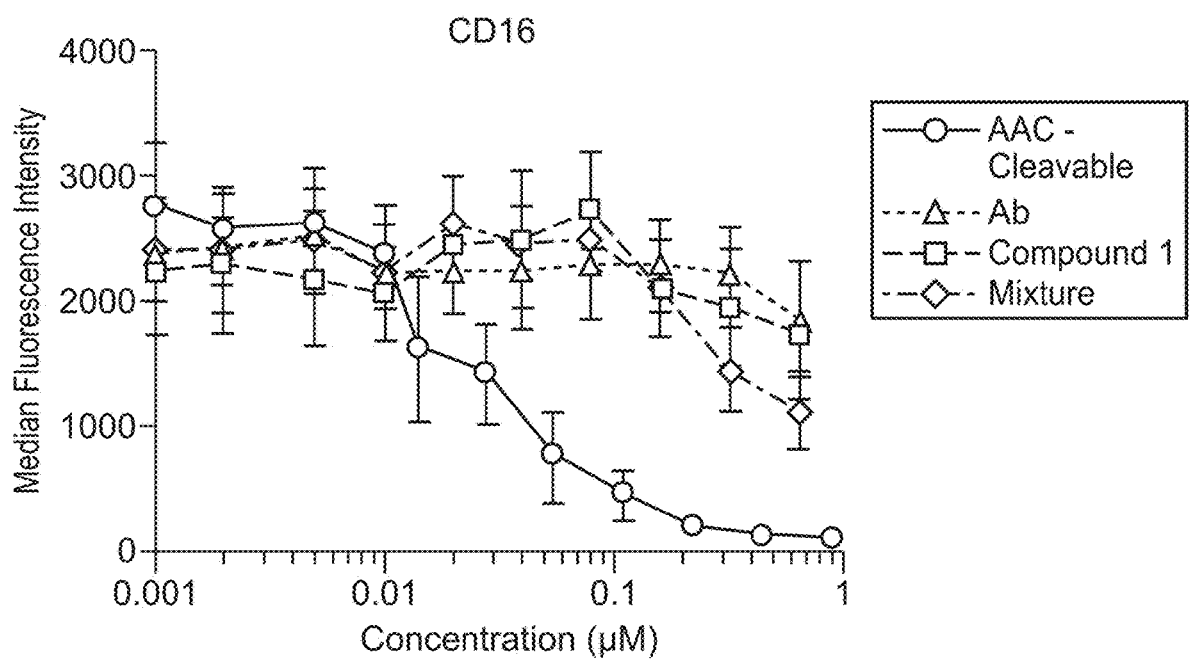
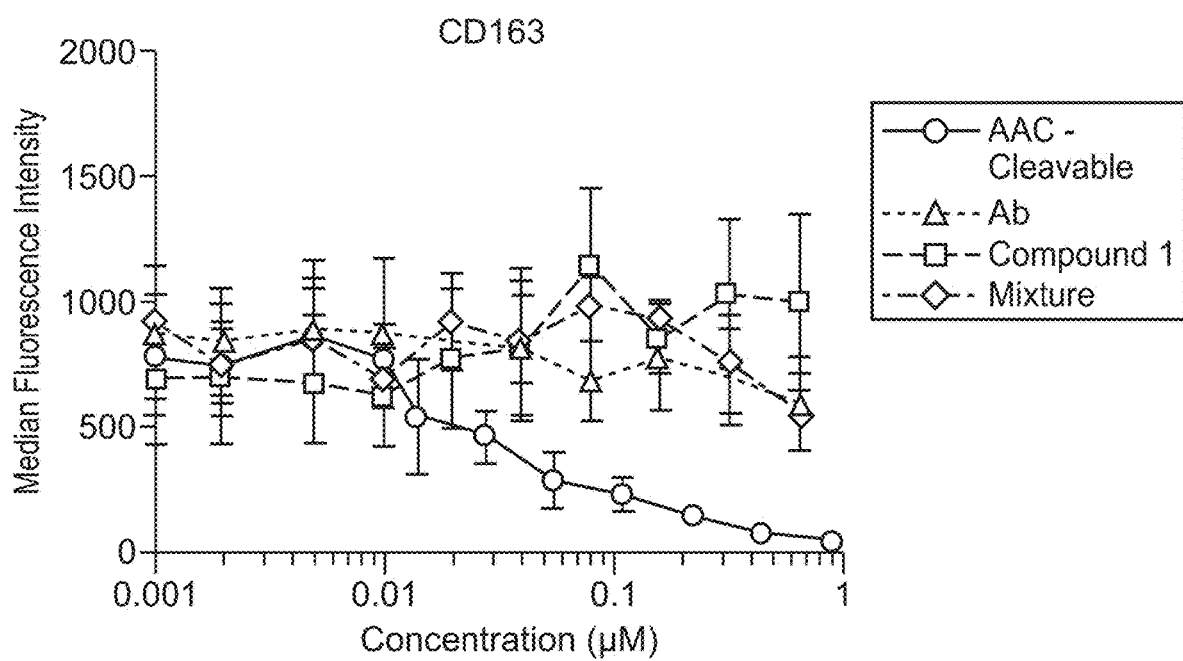

FIG. 8C
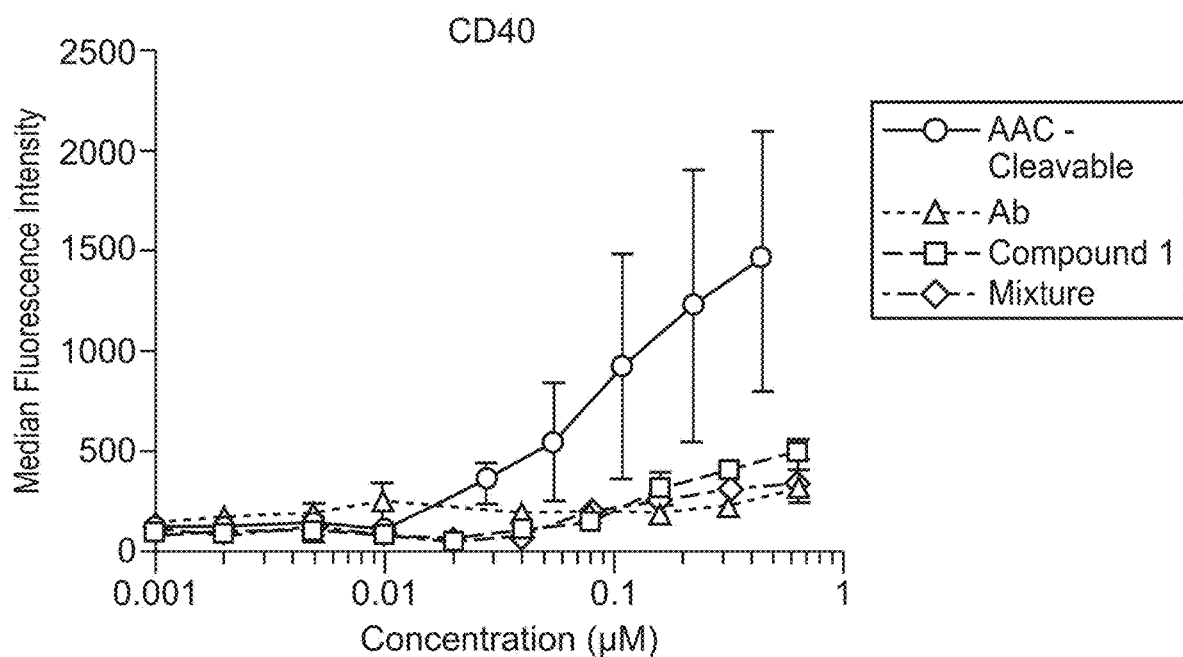
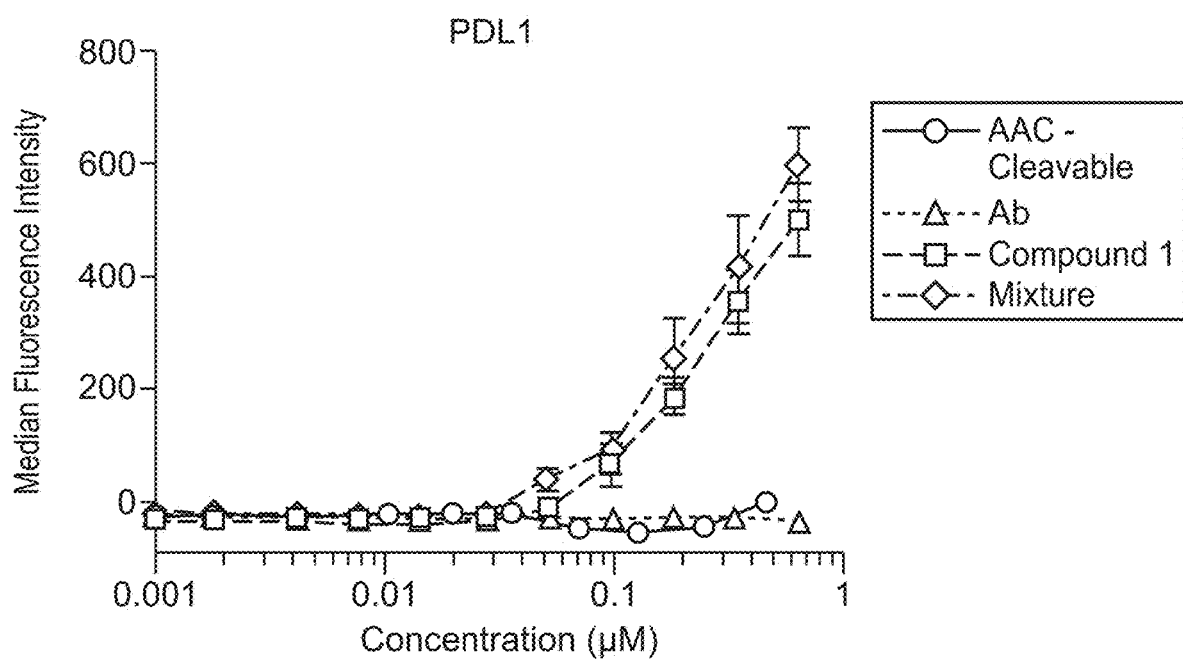

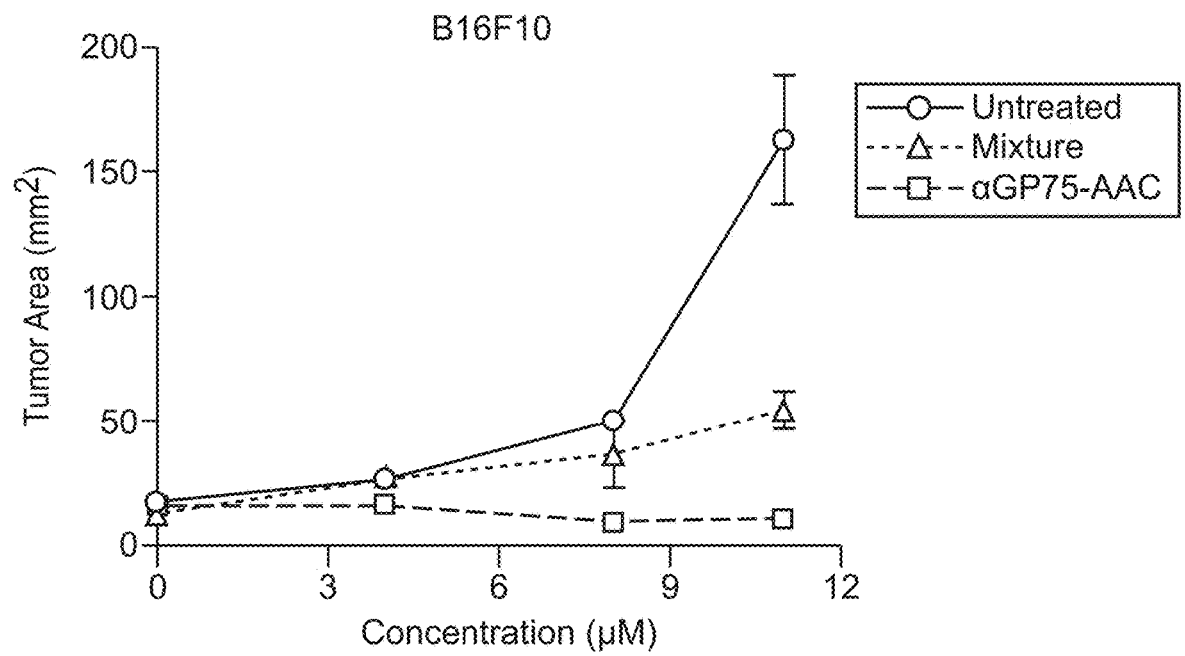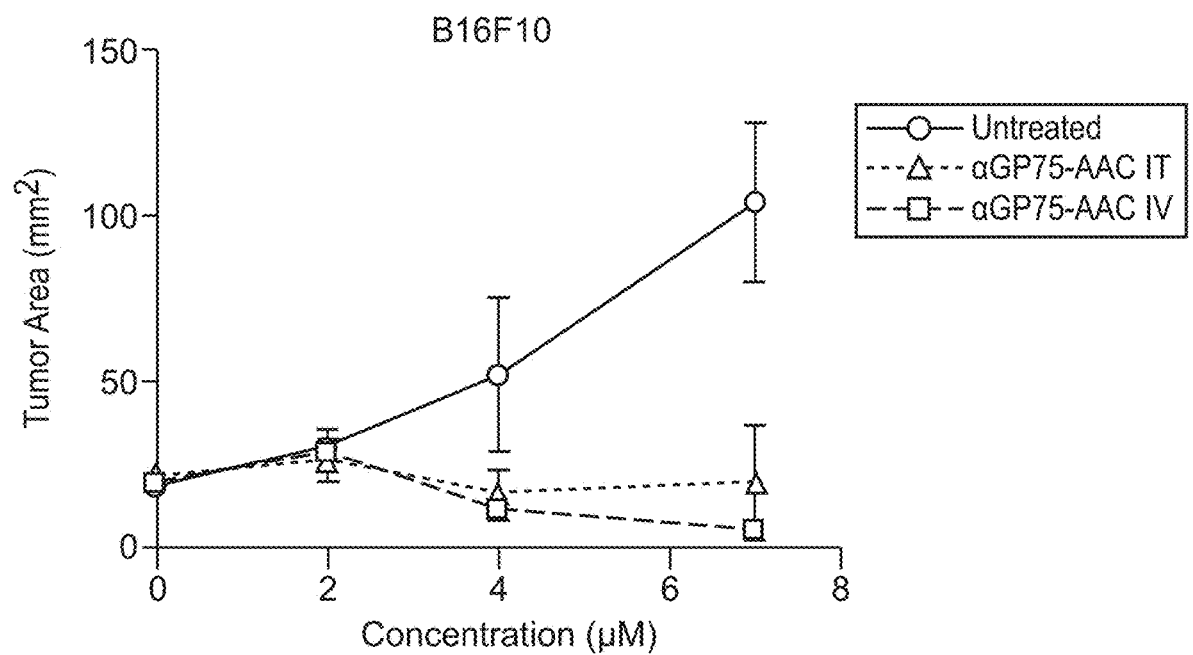

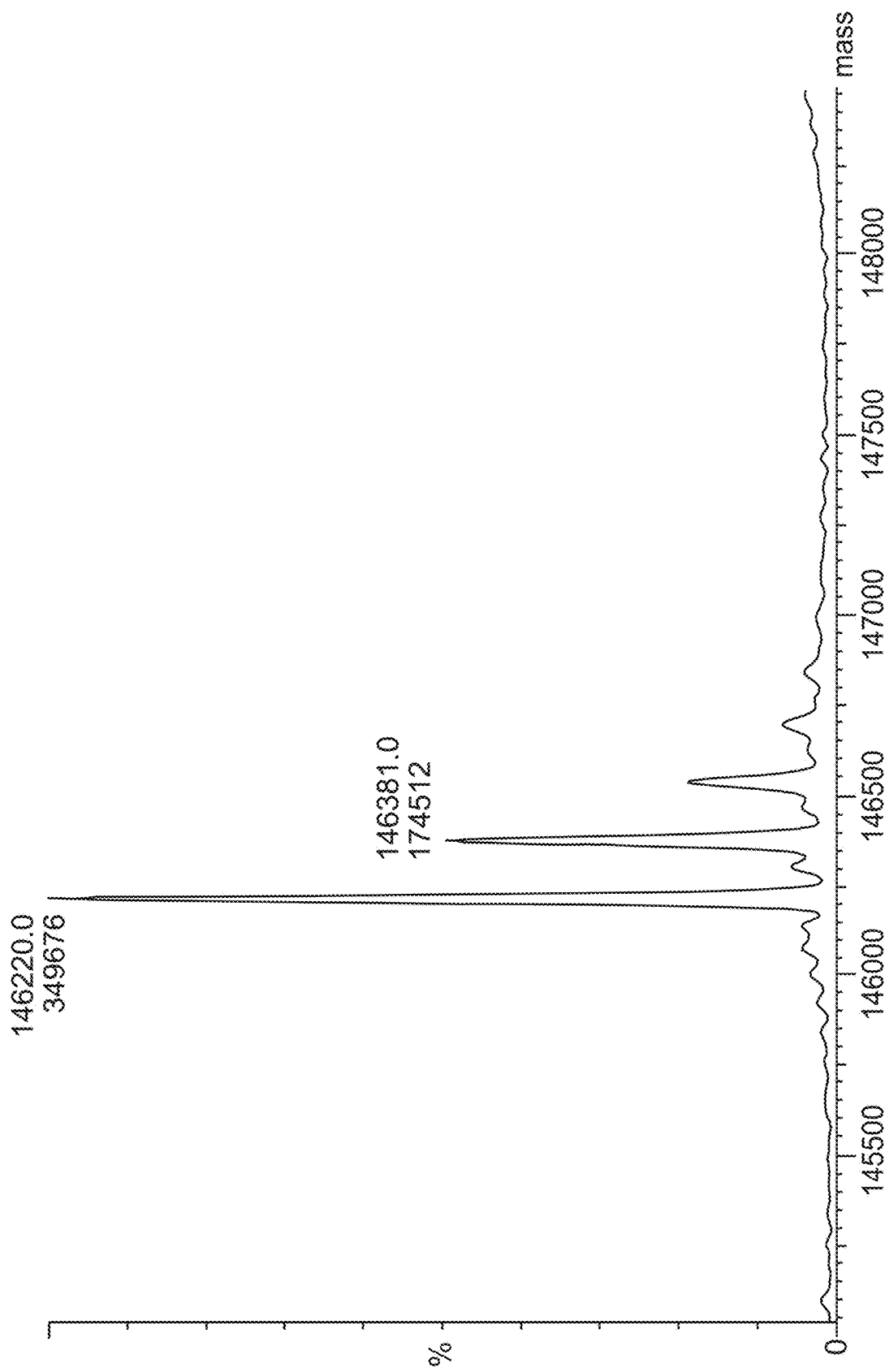

CL413 – Conjugation via First Lysine Residue

CL413 – Conjugation via Second Lysine Residue

CL413 - Conjugation via Third Lysine Residue

CL413 - Conjugation via Fourth Lysine Residue

CL413 - Conjugation via Primary Amine

CL419 - Conjugation via Terminal Amine
CL419 - Conjugation via Amine

CL553 - Conjugation via Secondary Amine

CL553 - Conjugation via Secondary Amine

CL553 - Conjugation via Primary Amine

CL553 - Conjugation via Secondary Amine

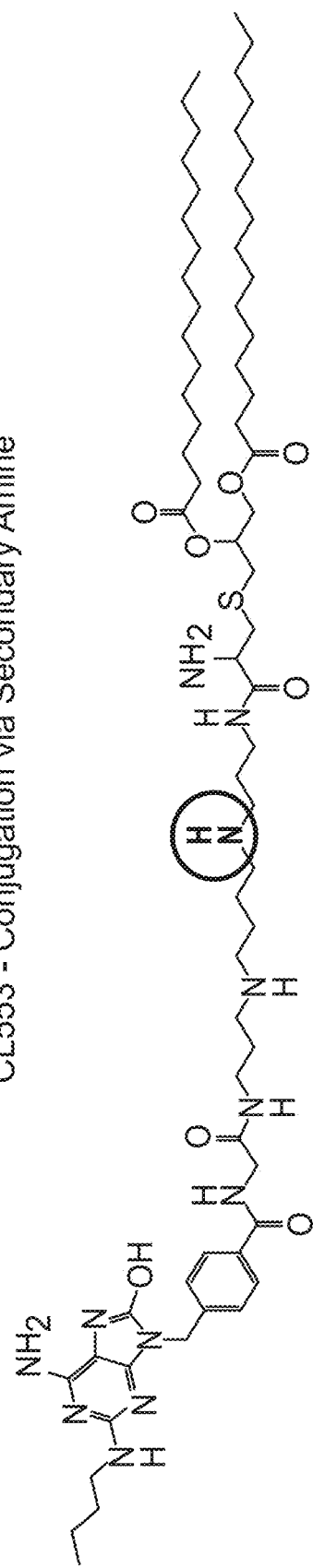
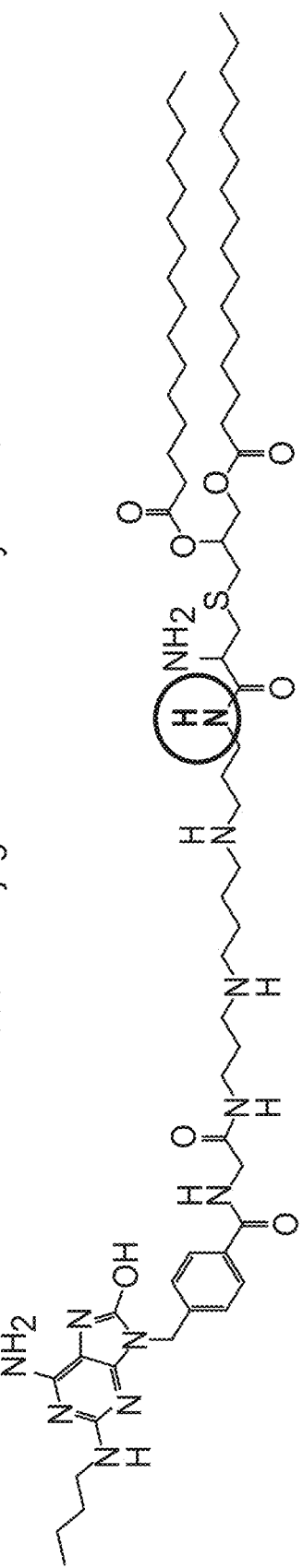
FIG. 22M
CL553 - Conjugation via Secondary Amine

FIG. 22N
CL572 - Conjugation via Primary Amine
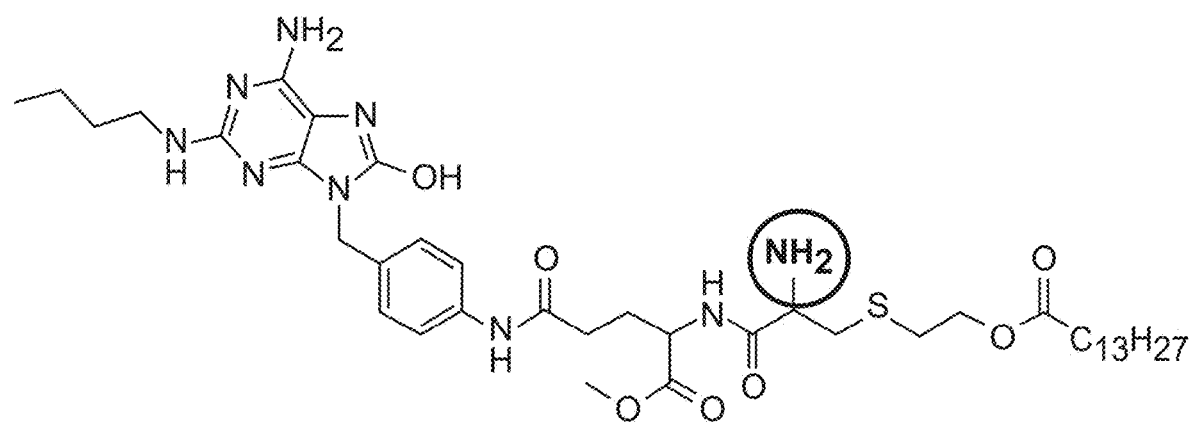
CL572 - Conjugation via Carboxylate
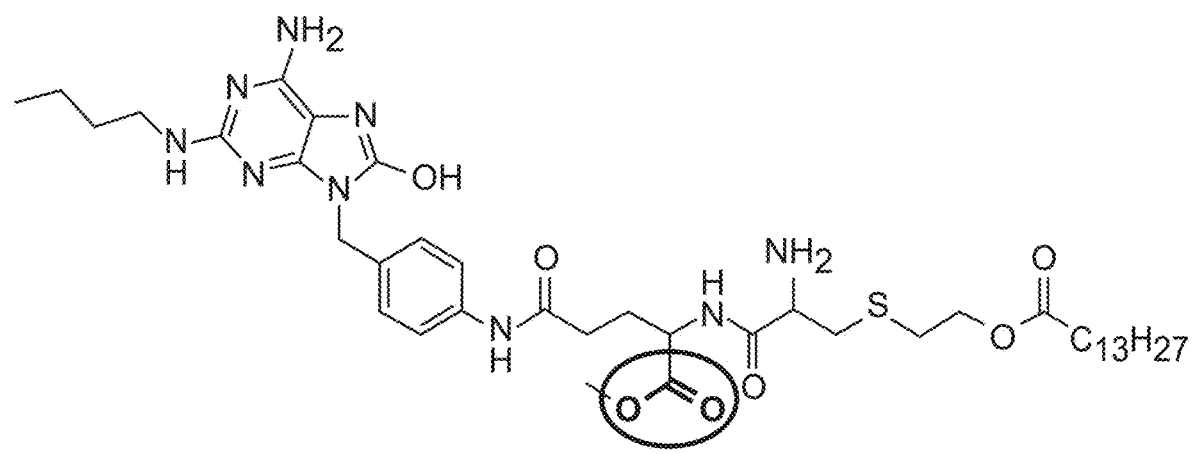

Pam2CSK4 - Conjugation via Terminal Carboxylic Acid

Pam2CSK4 - Conjugation via Addition of Terminal Thiol

Pam2CSK4 - Conjugation via Second Lysine Residue

Pam2CSK4 - Conjugation via Third Lysine Residue

Pam2CSK4 - Conjugation via Terminal Lysine Residue

Pam3CSK4 - Conjugation via Terminal Carboxylic Acid

Pam3CSK4 - Conjugation via Addition of Terminal Thiol

Pam3CSK4 - Conjugation via Second Lysine Residue

Pam3CSK4 - Conjugation via Third Lysine Residue

Pam3CSK4 - Conjugation via Terminal Lysine Residue

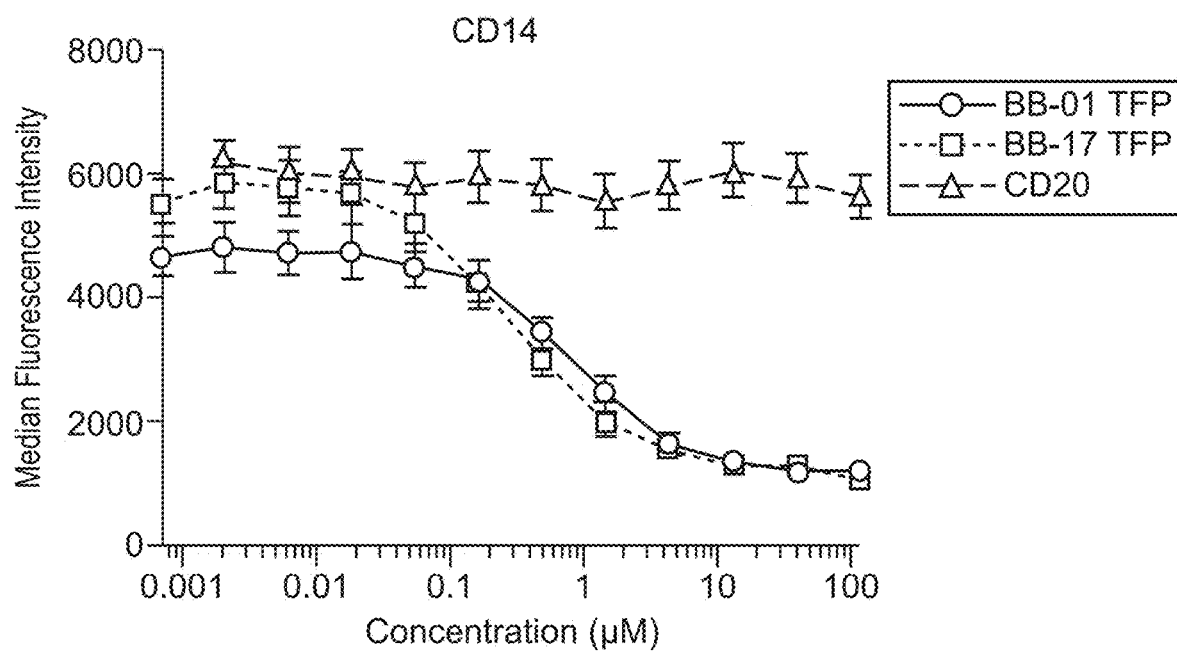
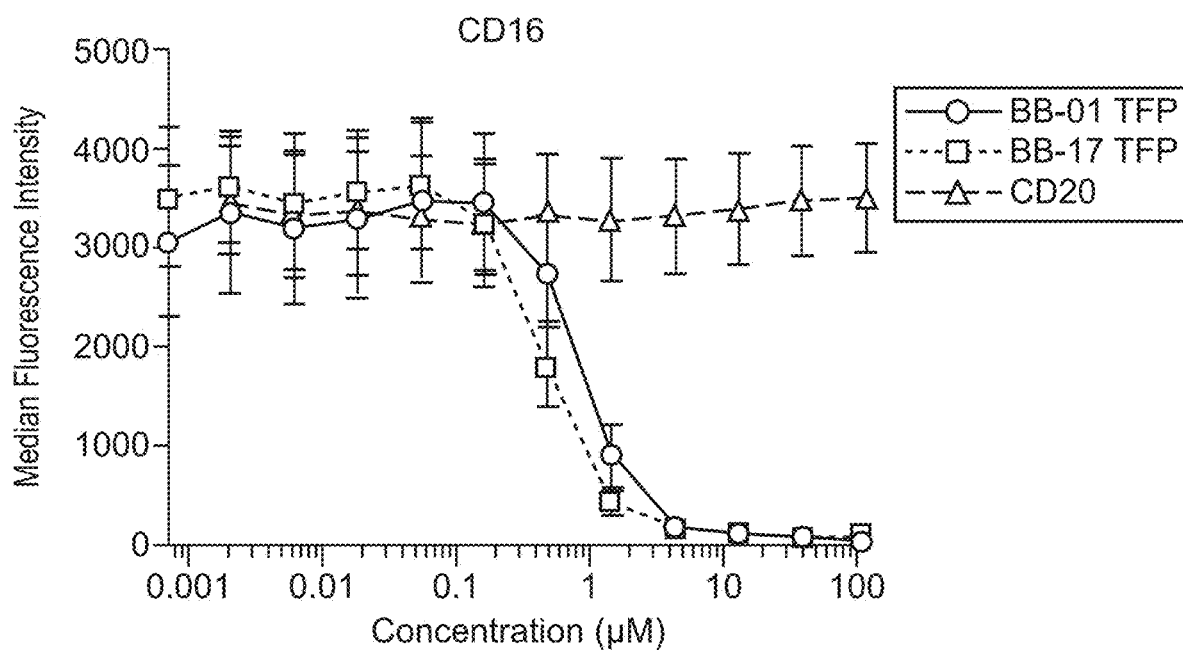

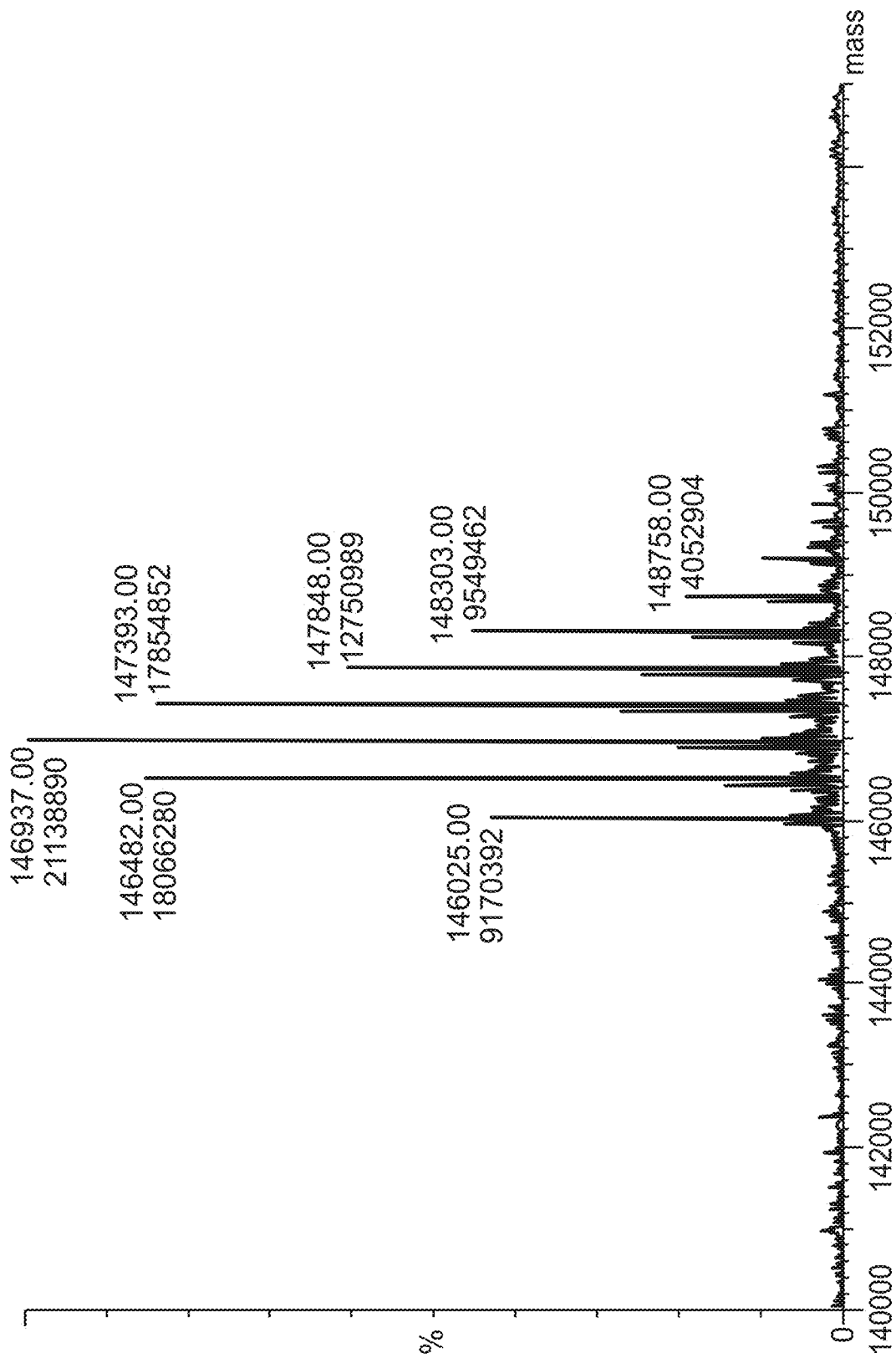

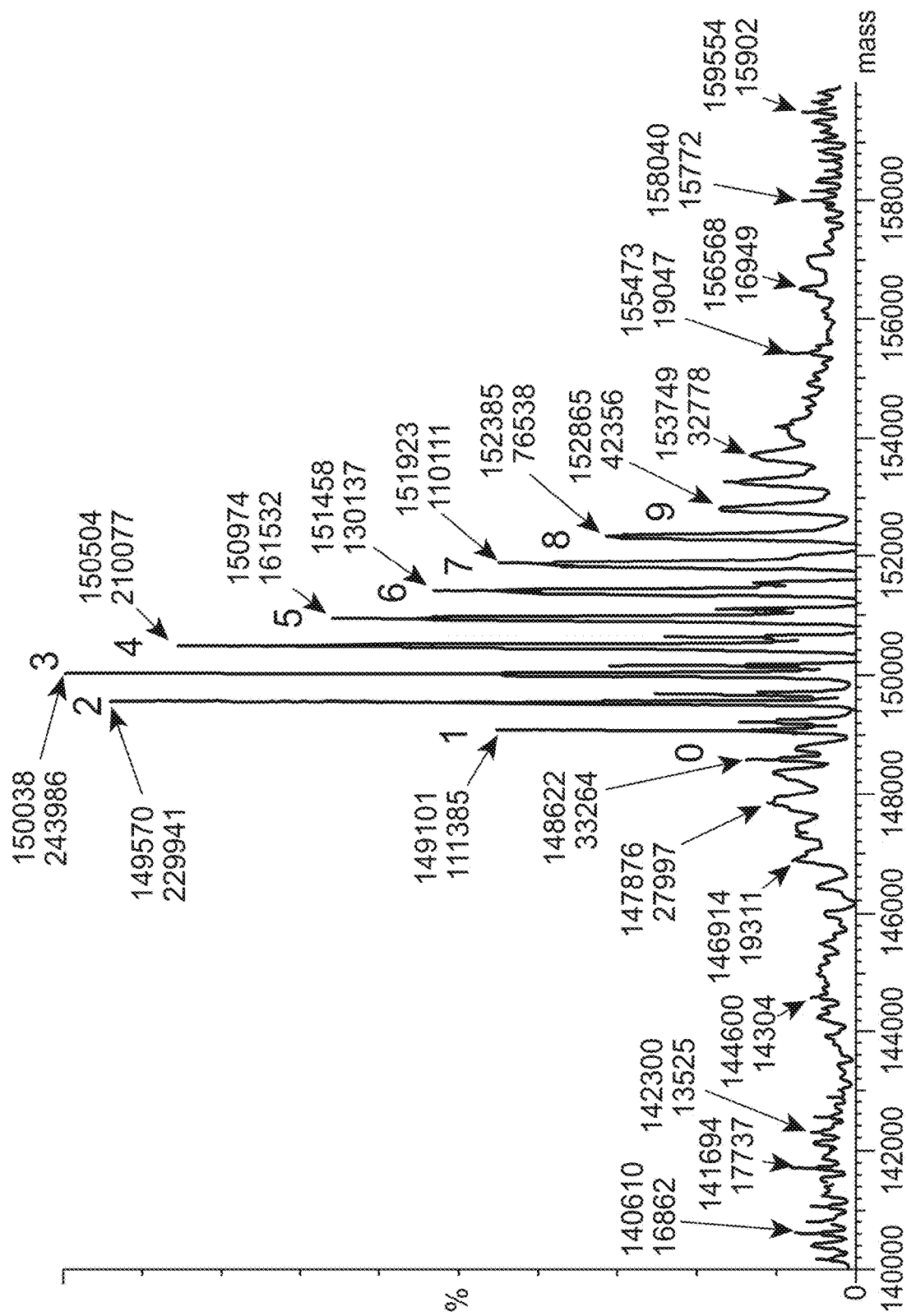

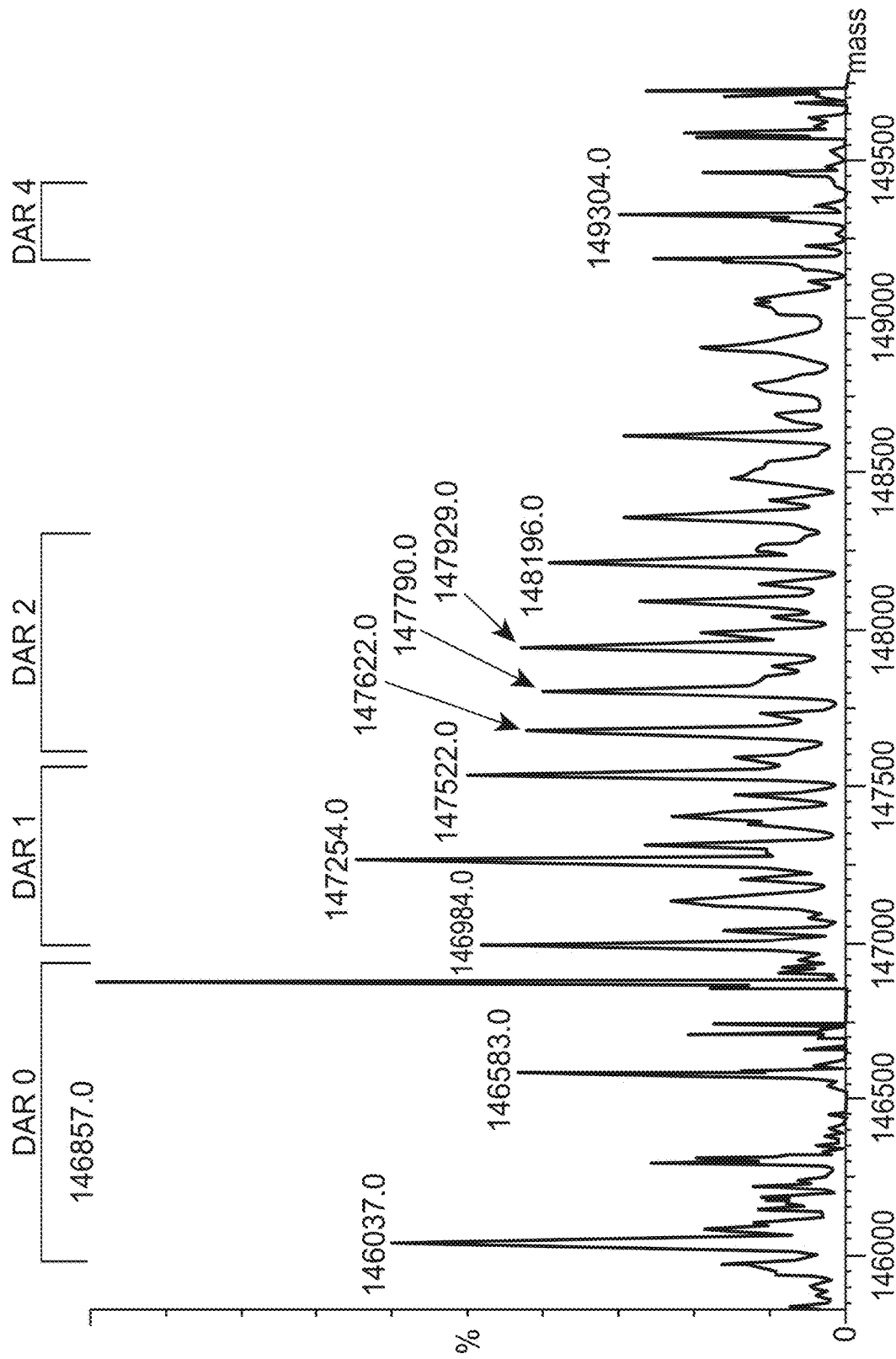

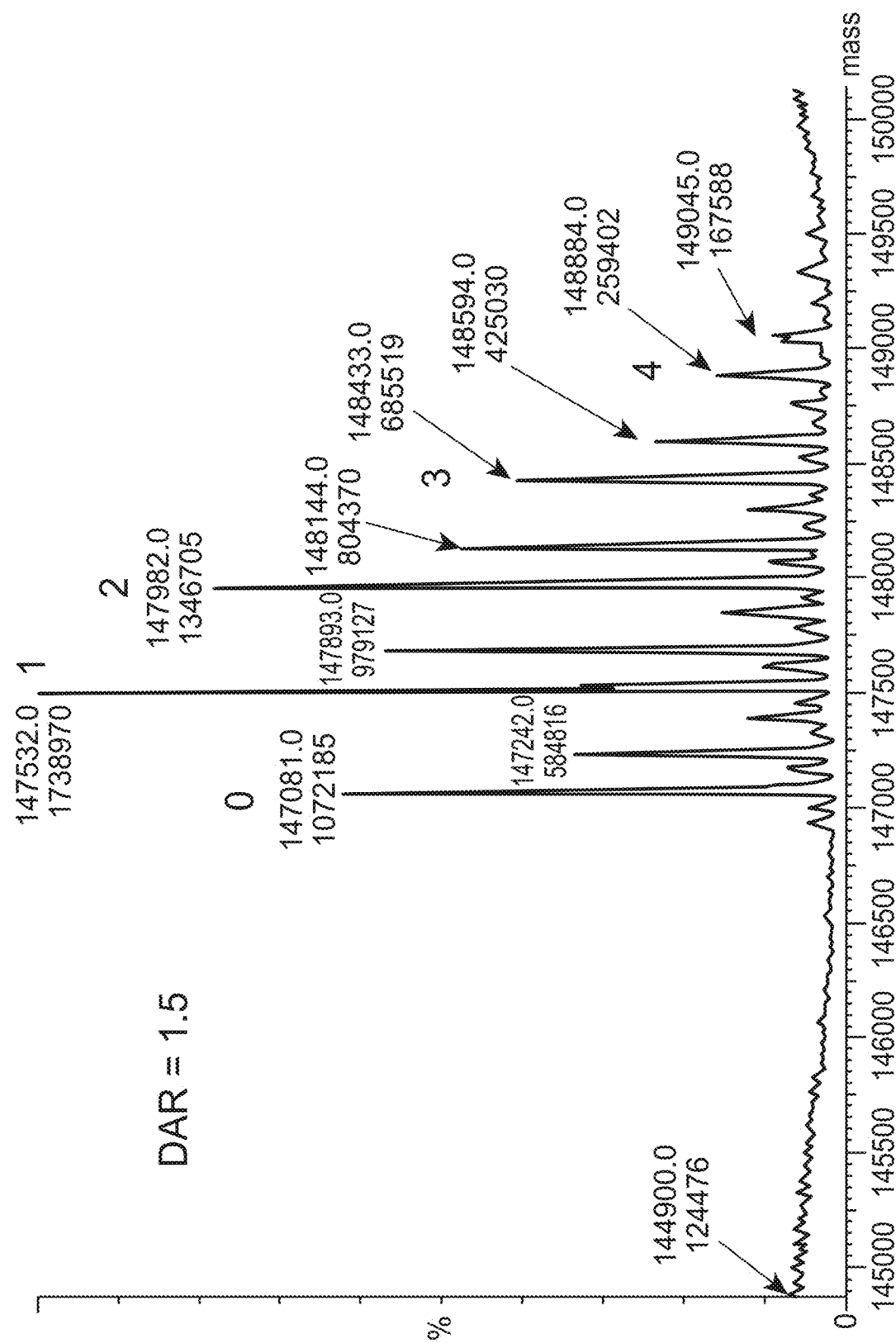

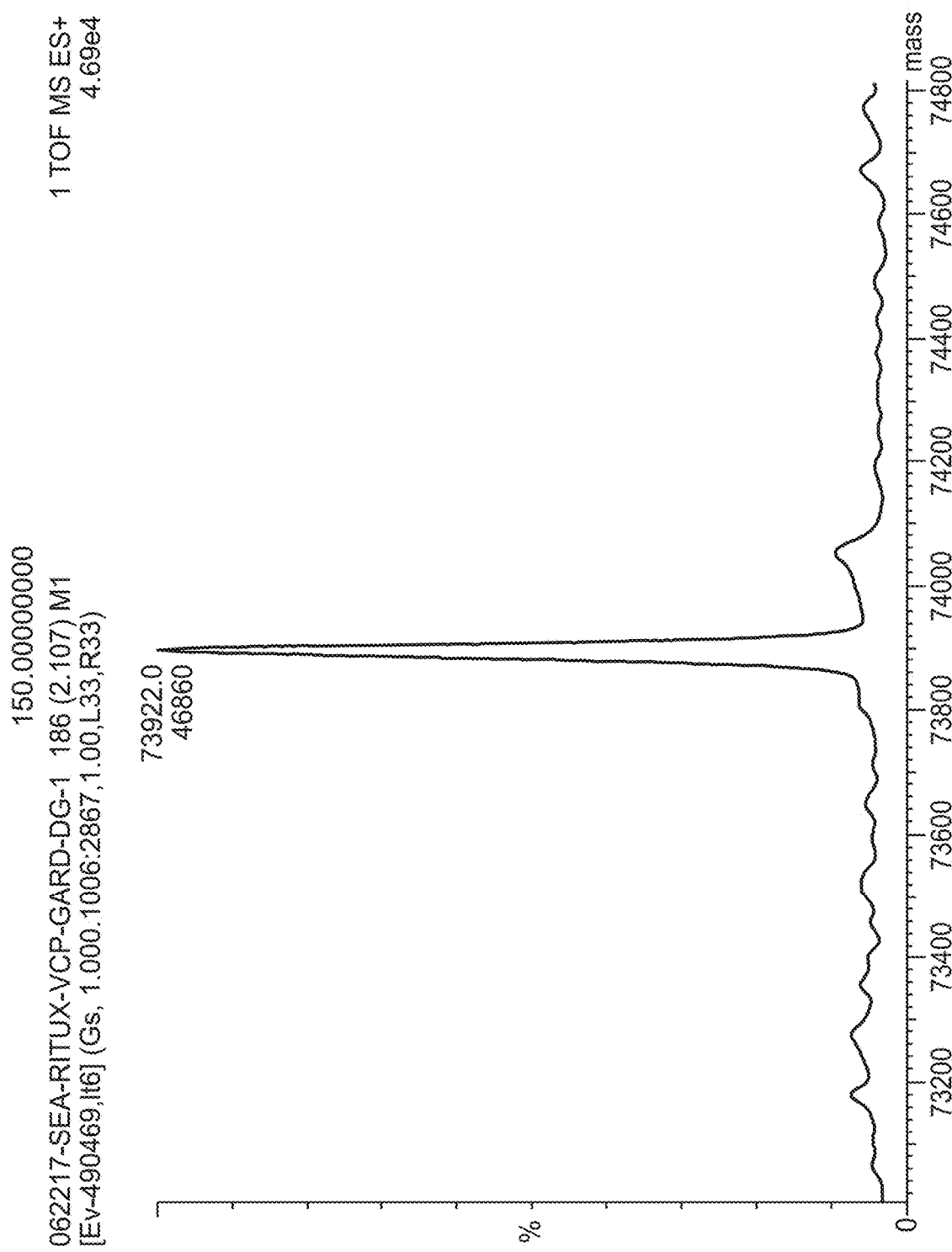

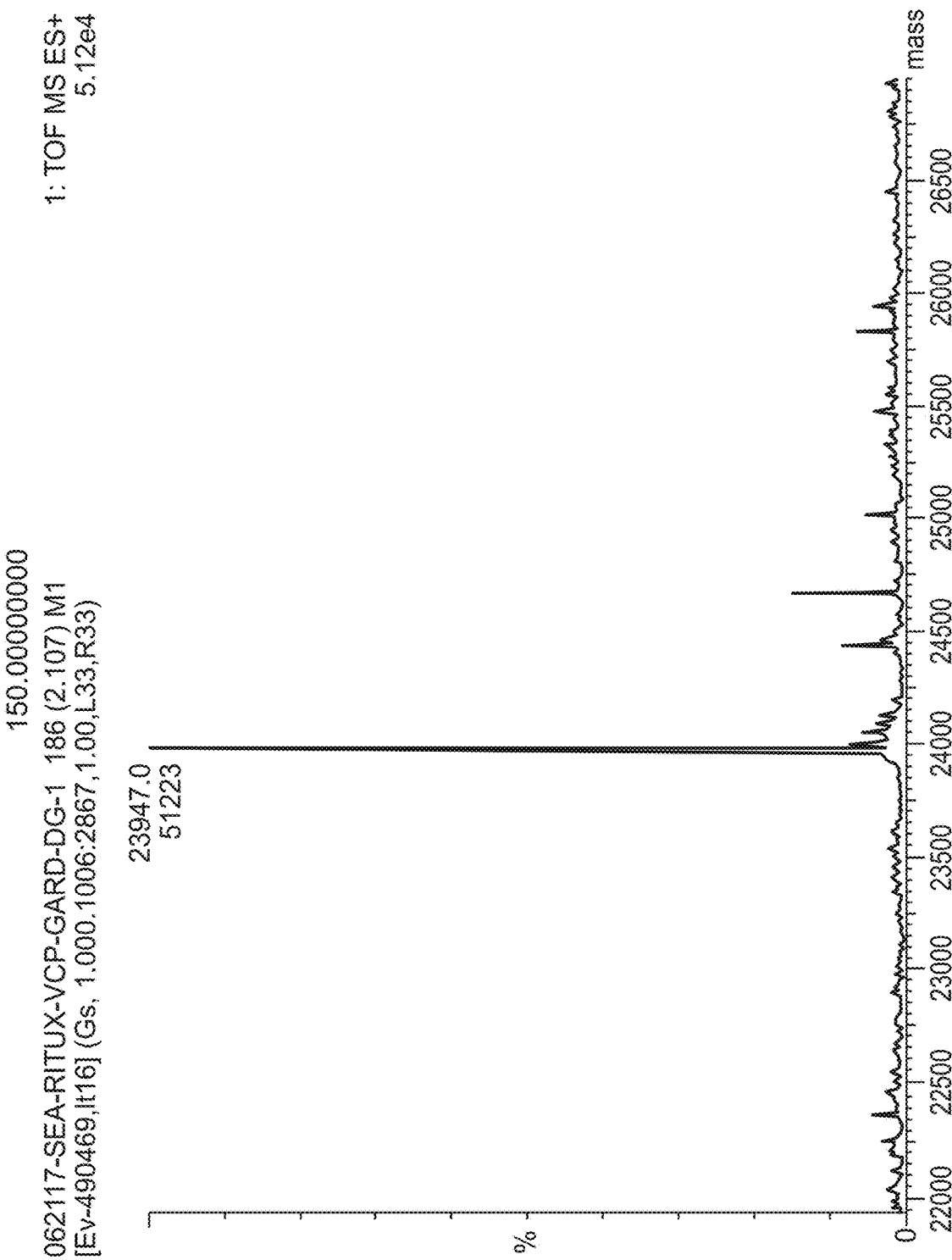

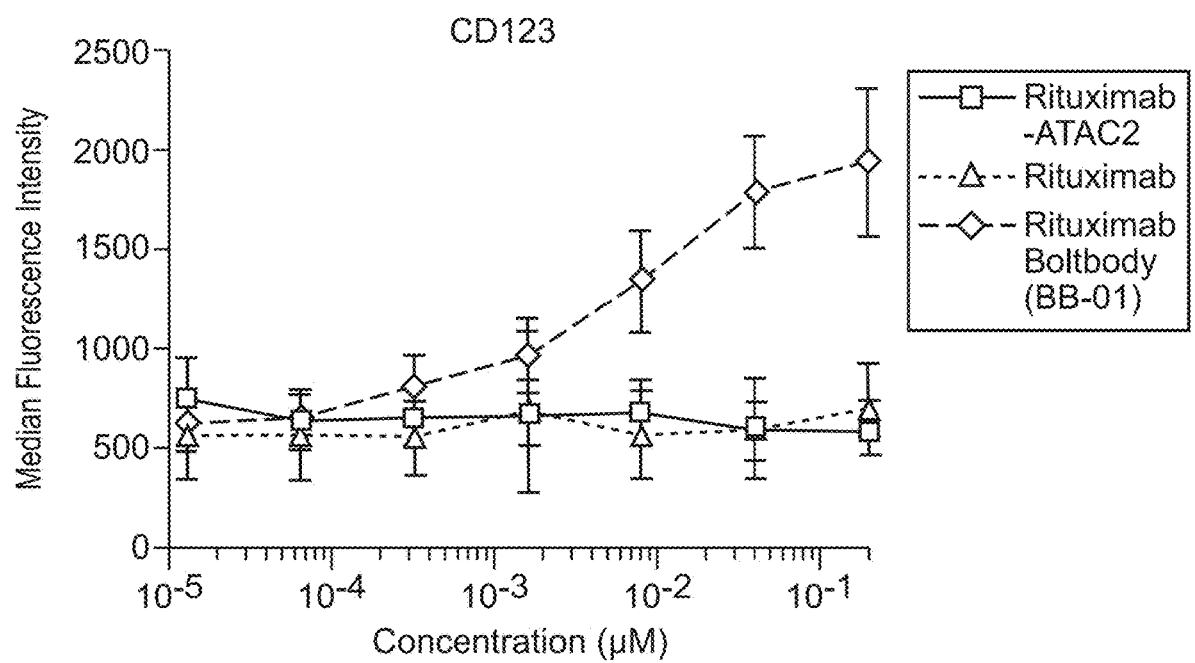

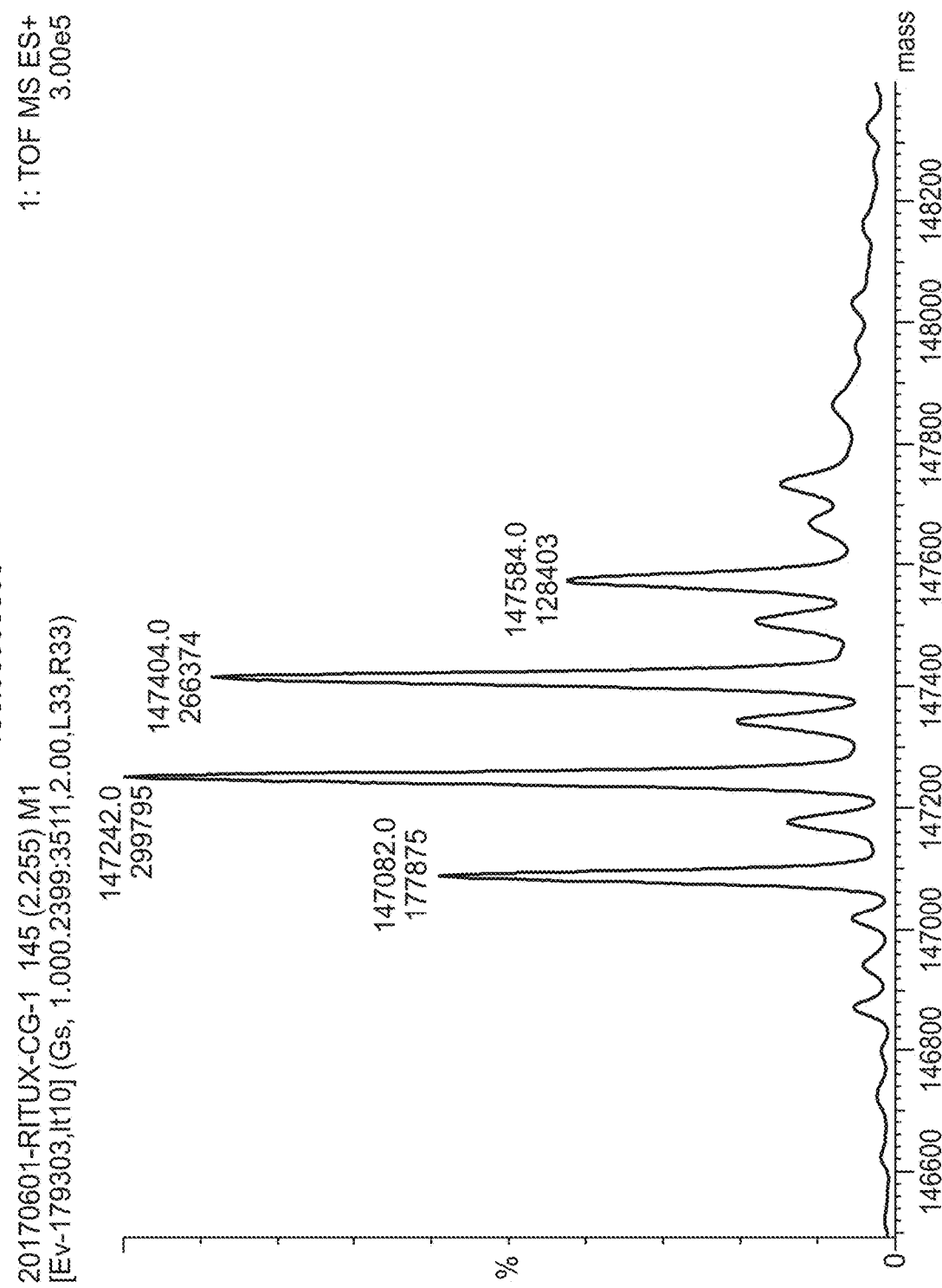

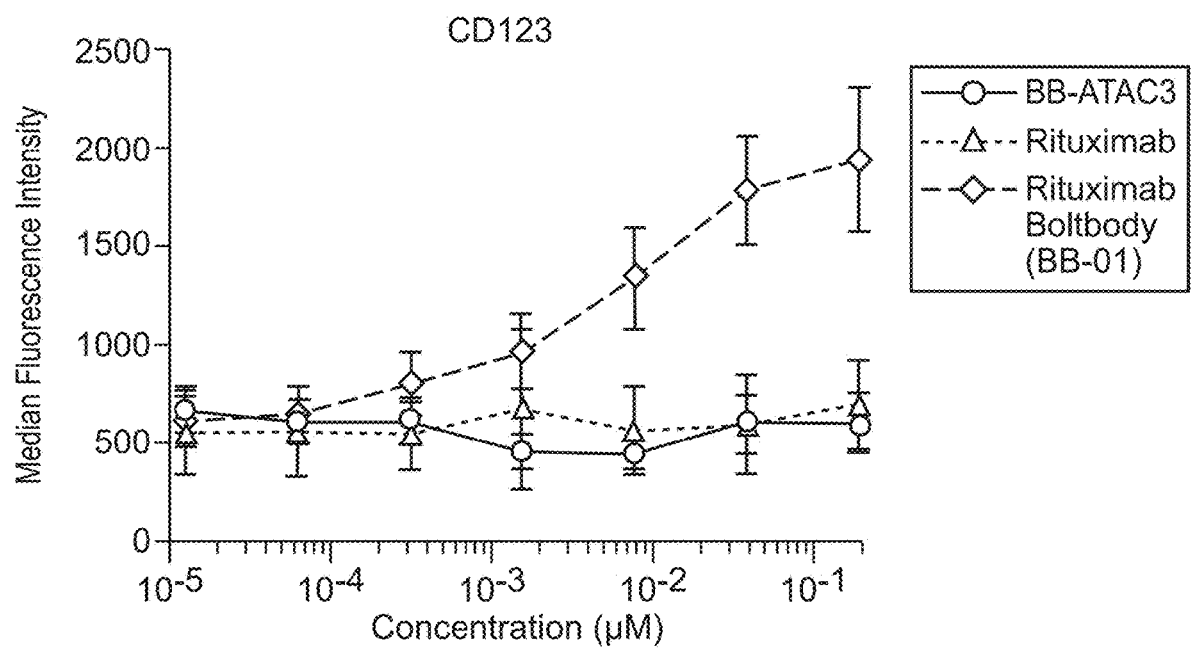

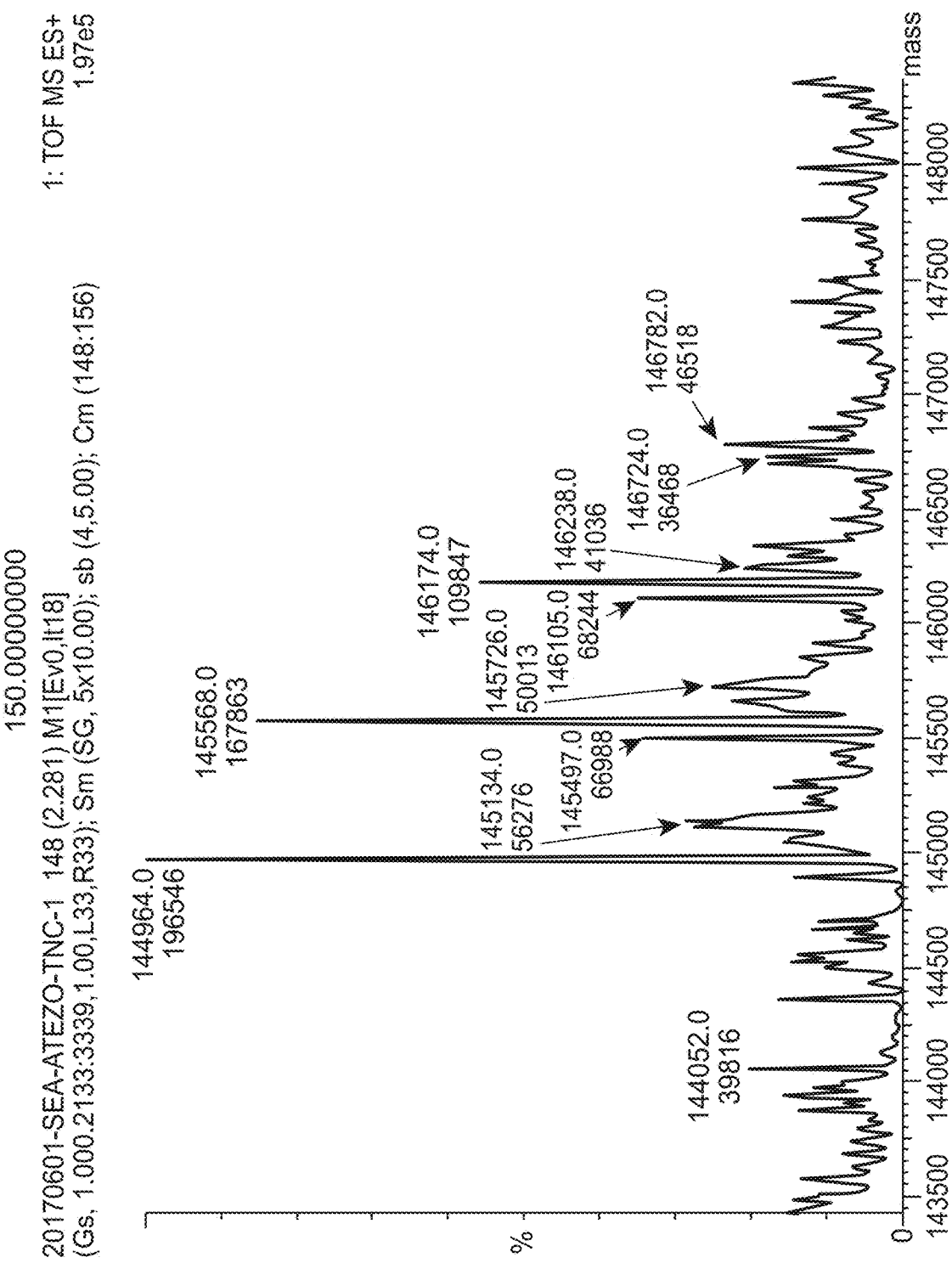

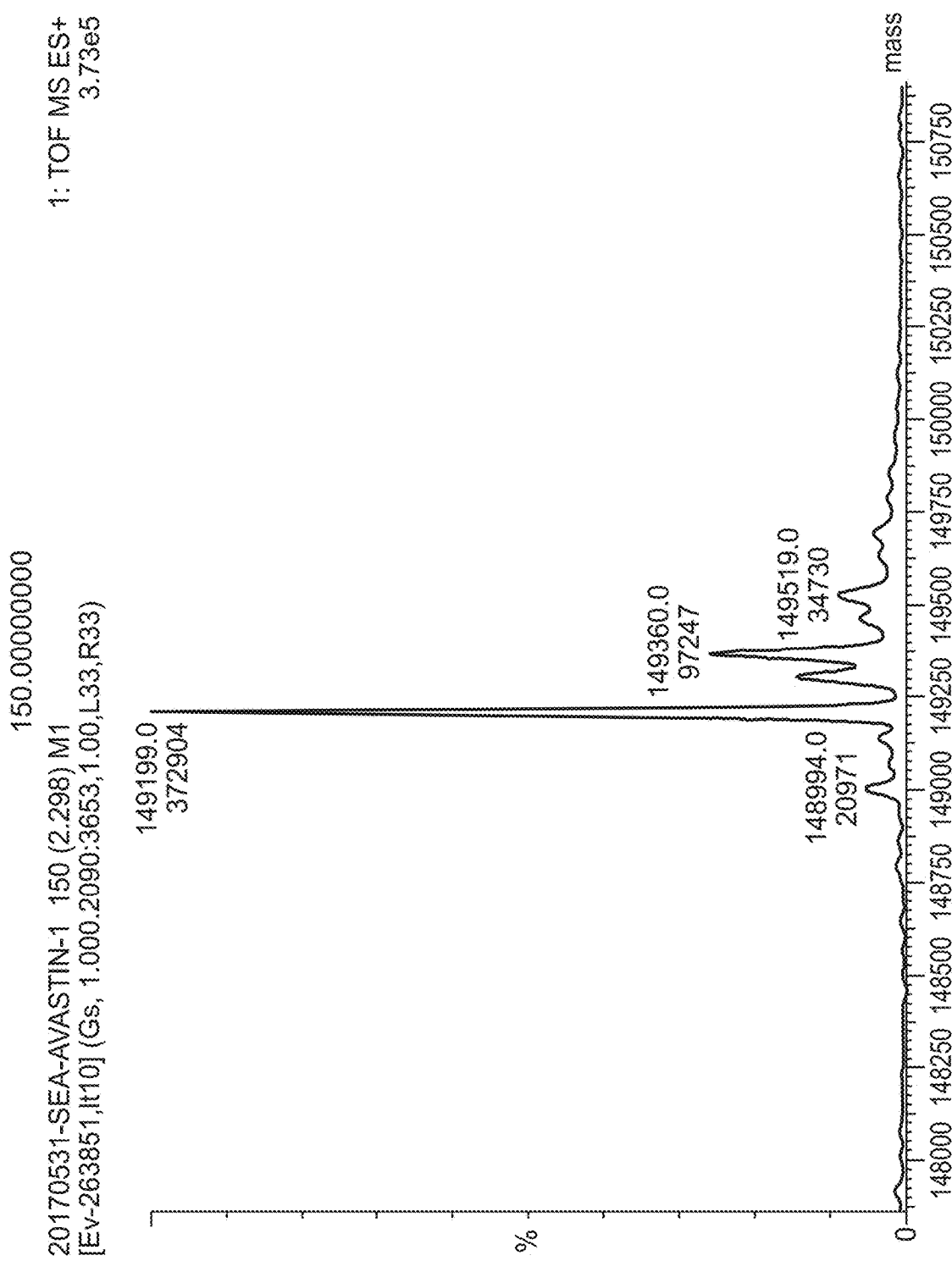

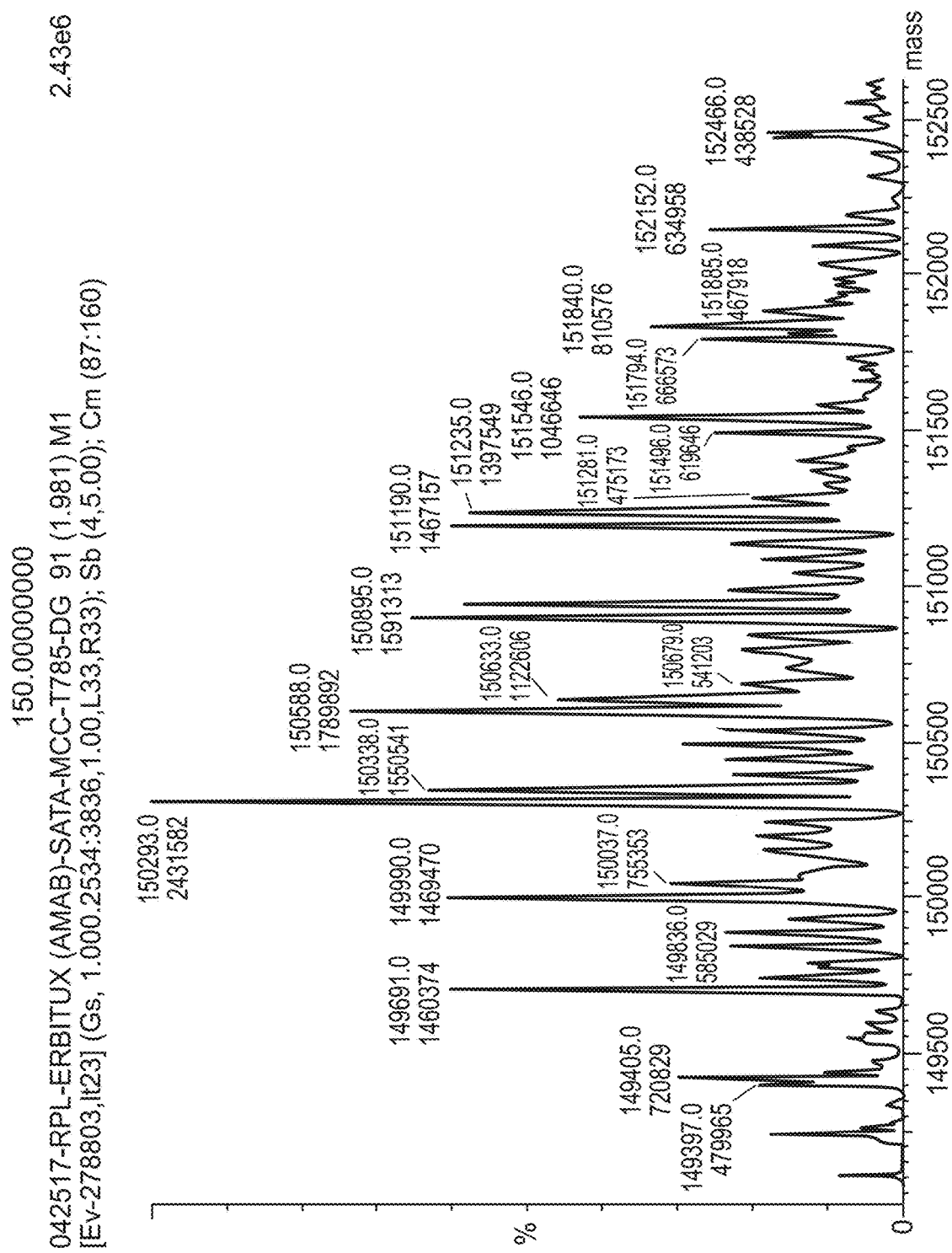

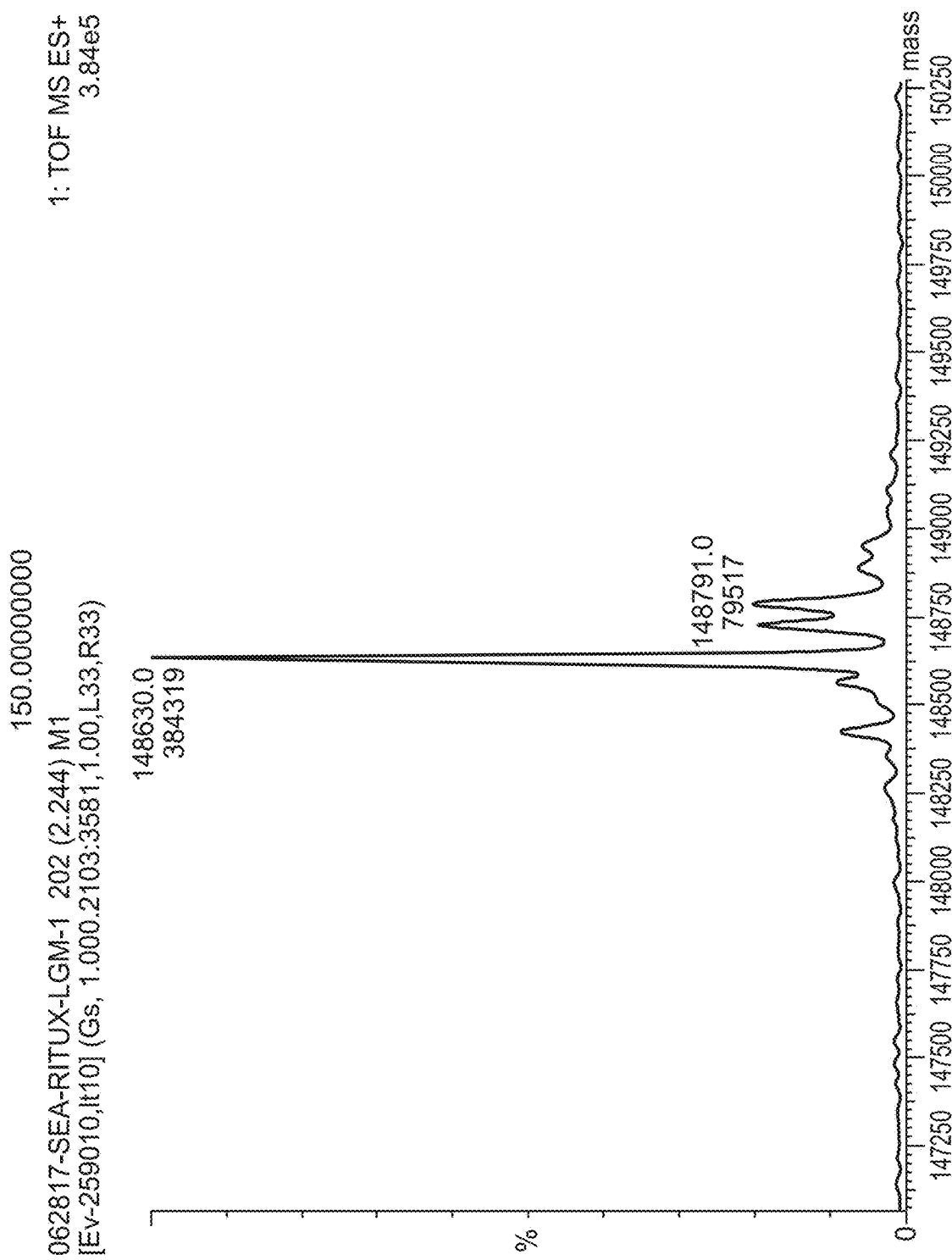


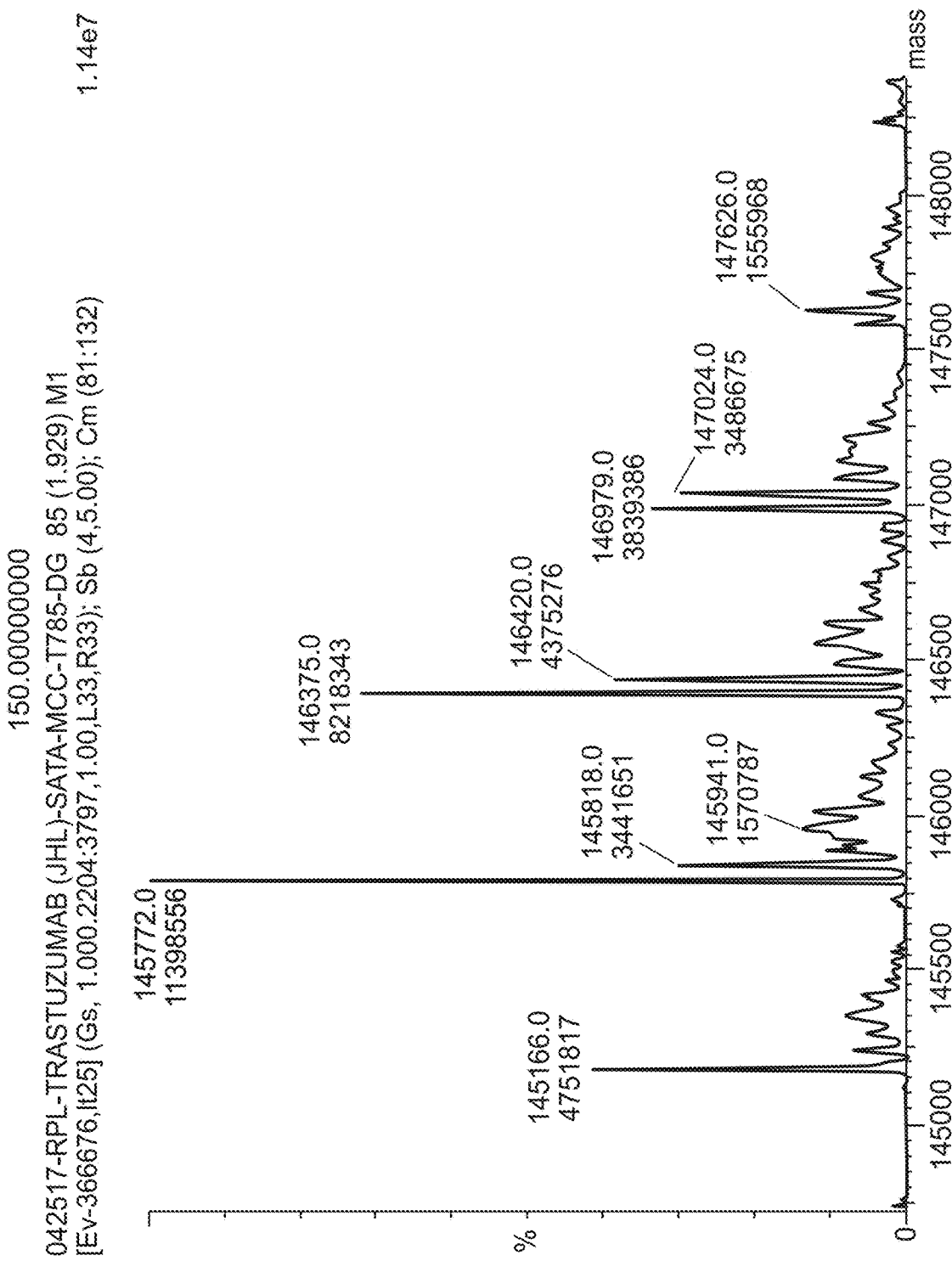

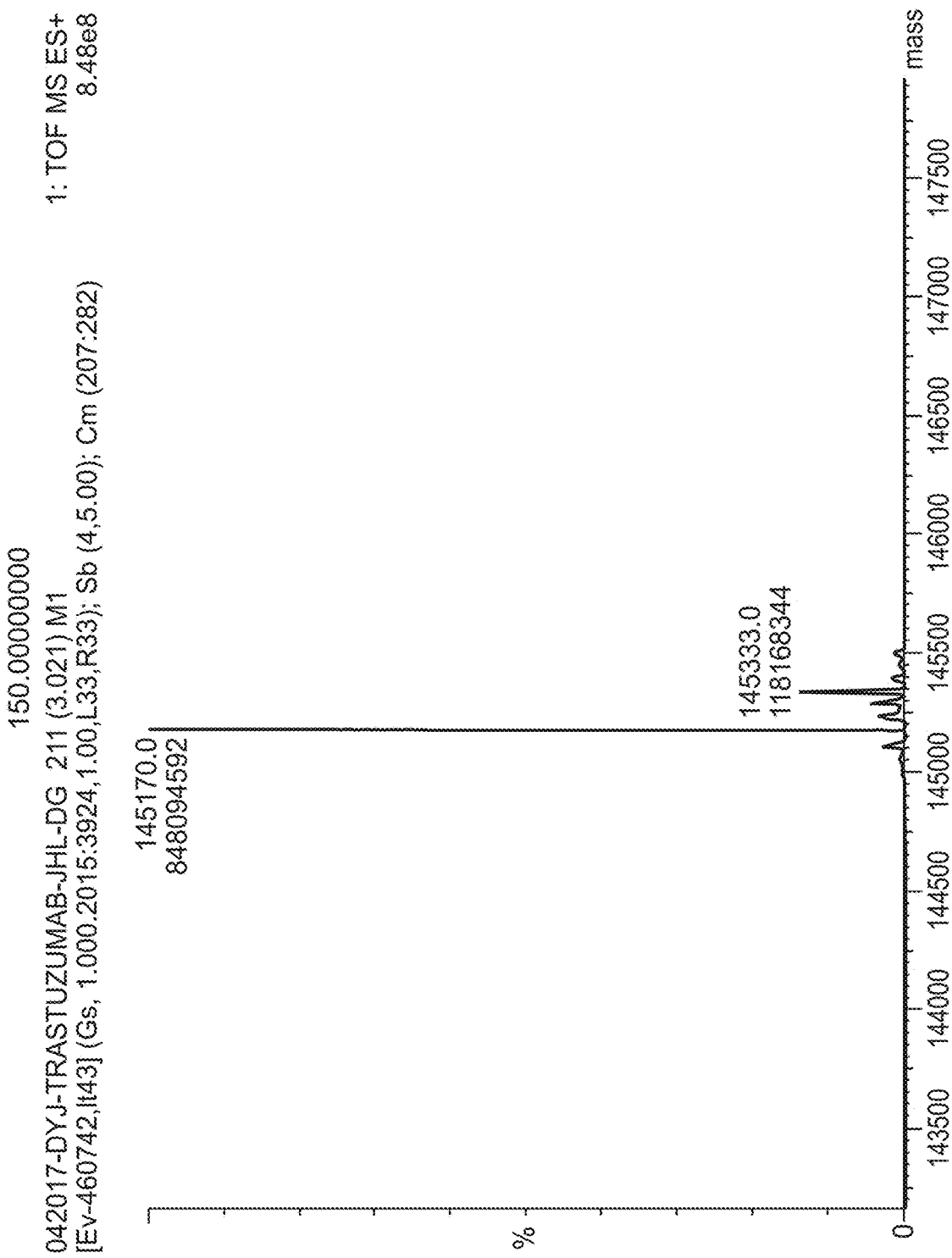

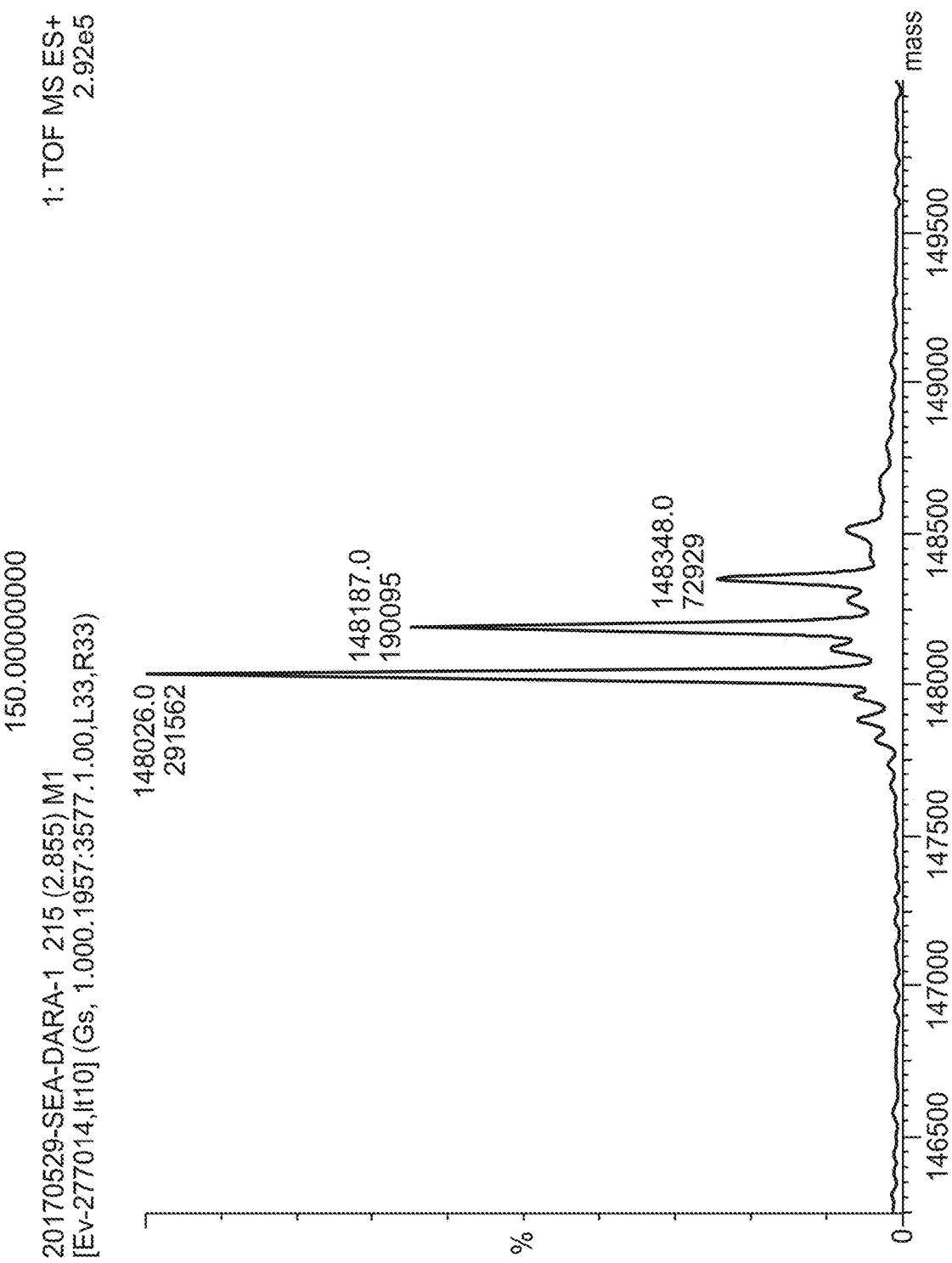

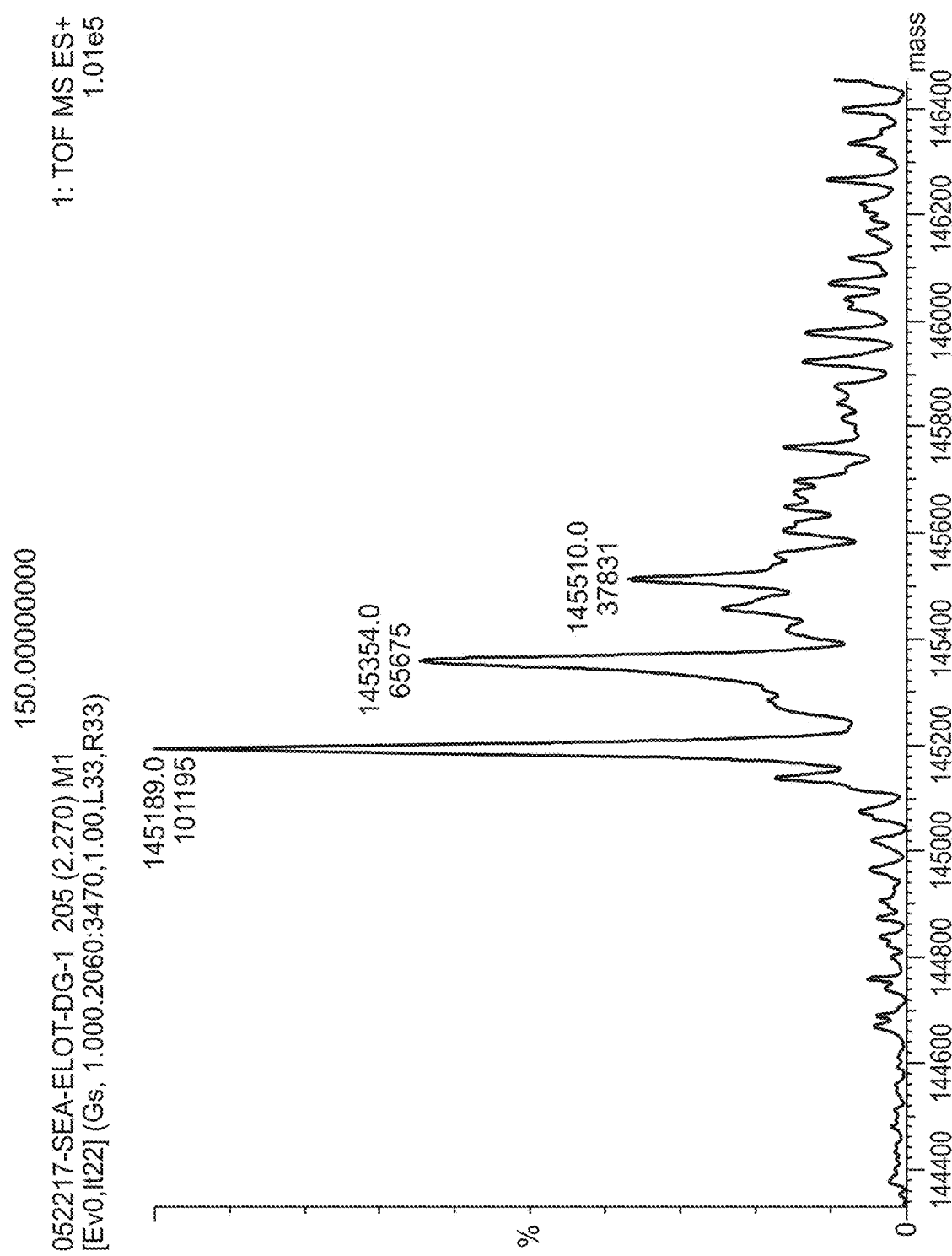

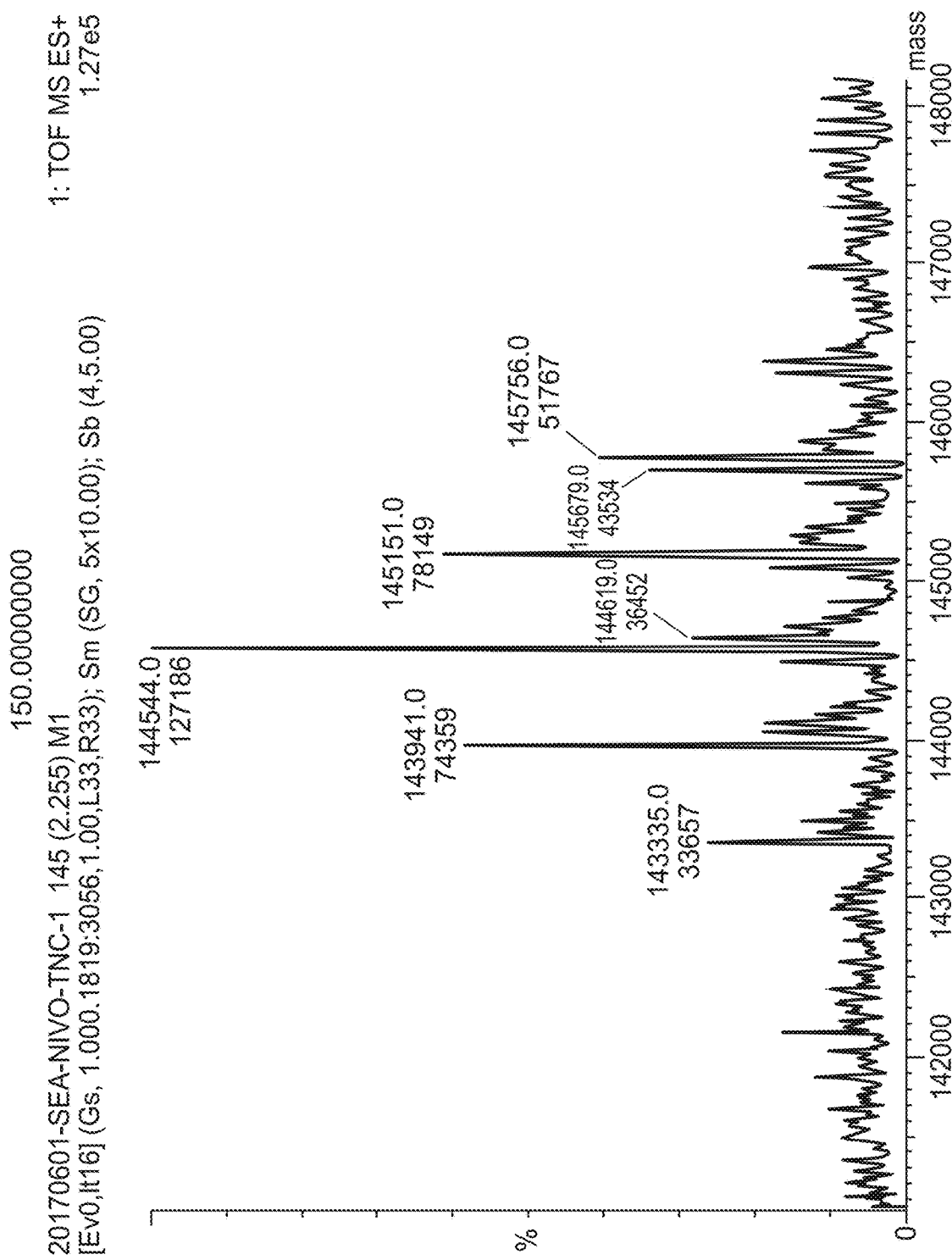

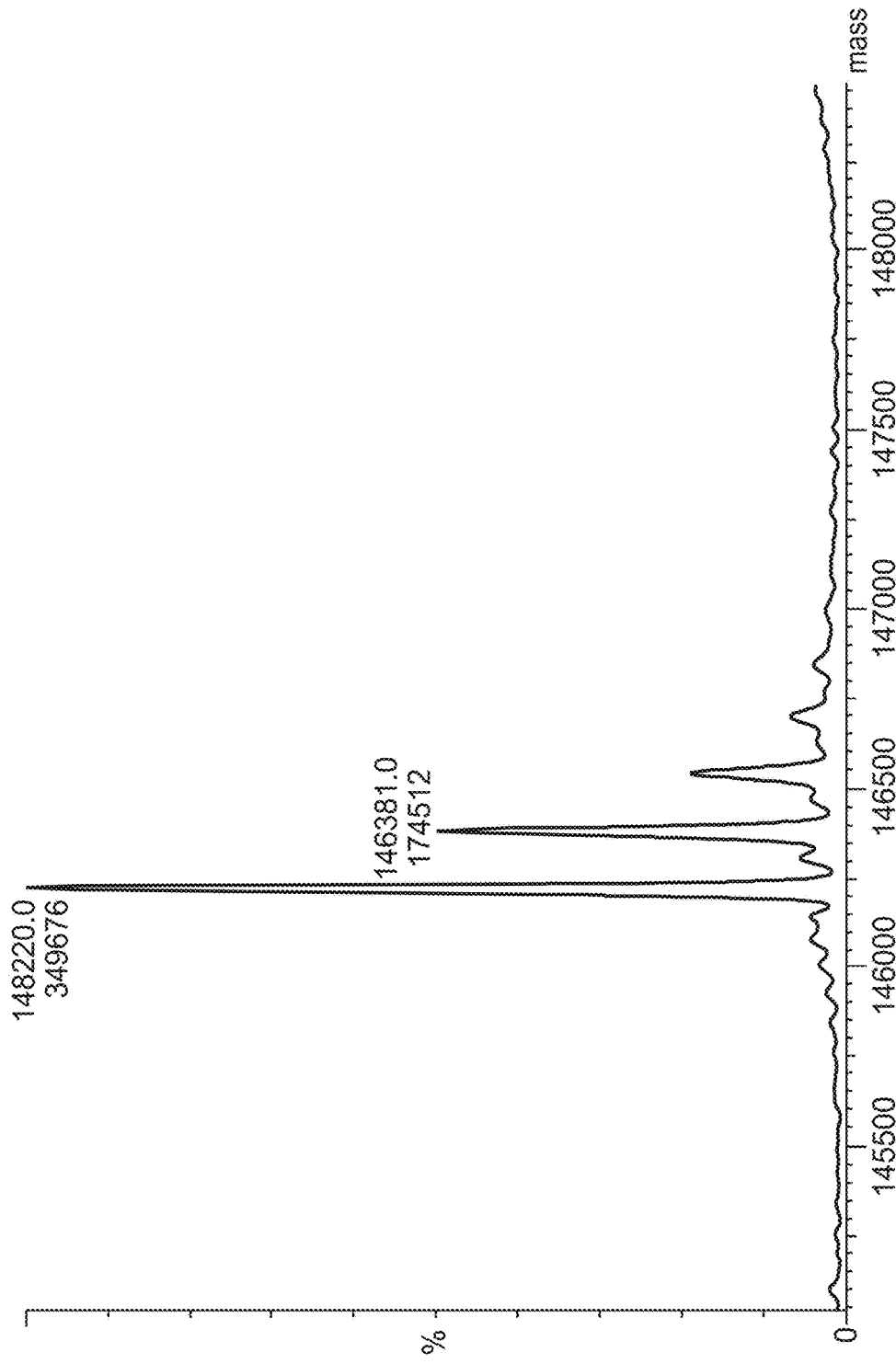

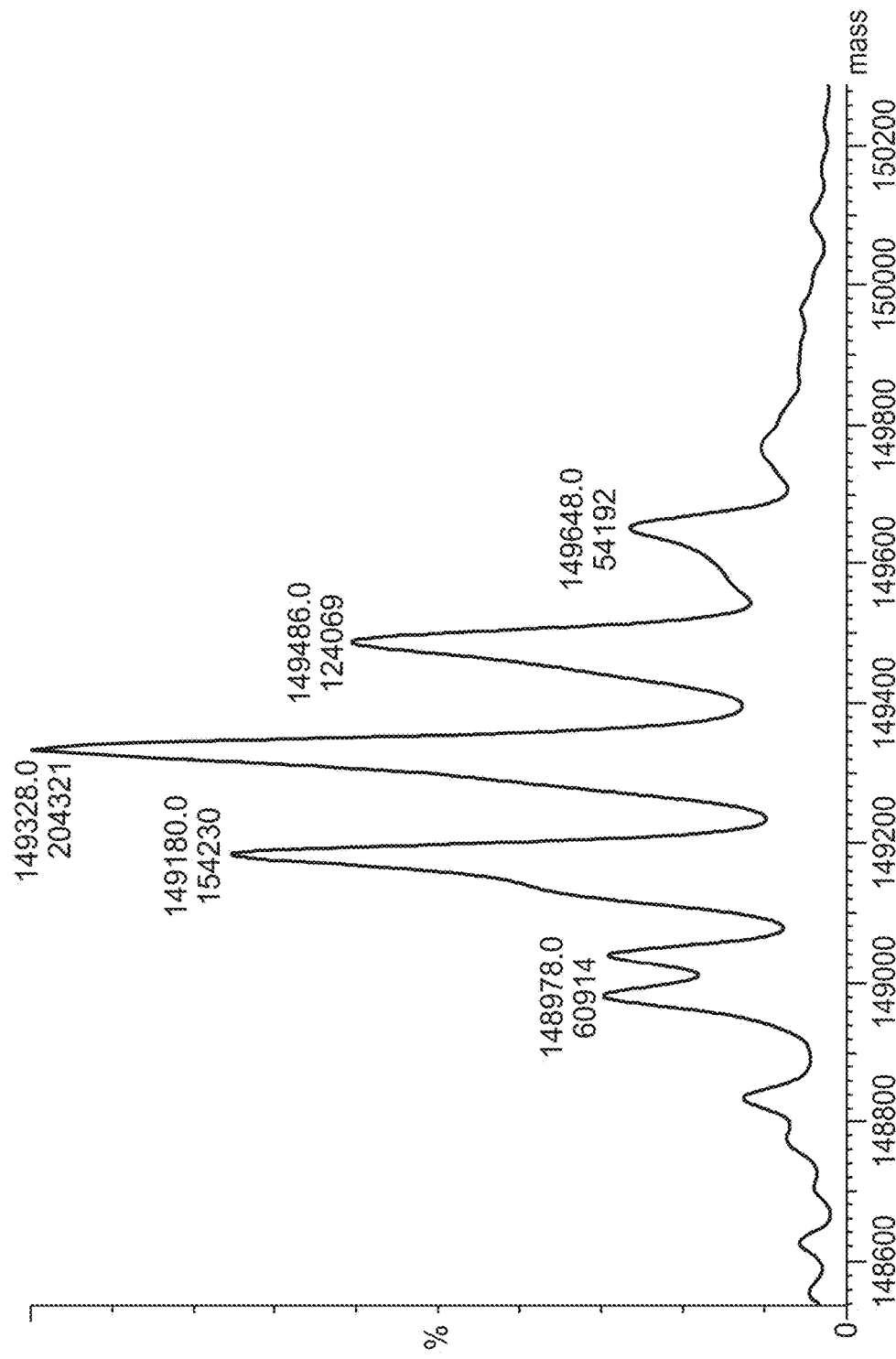

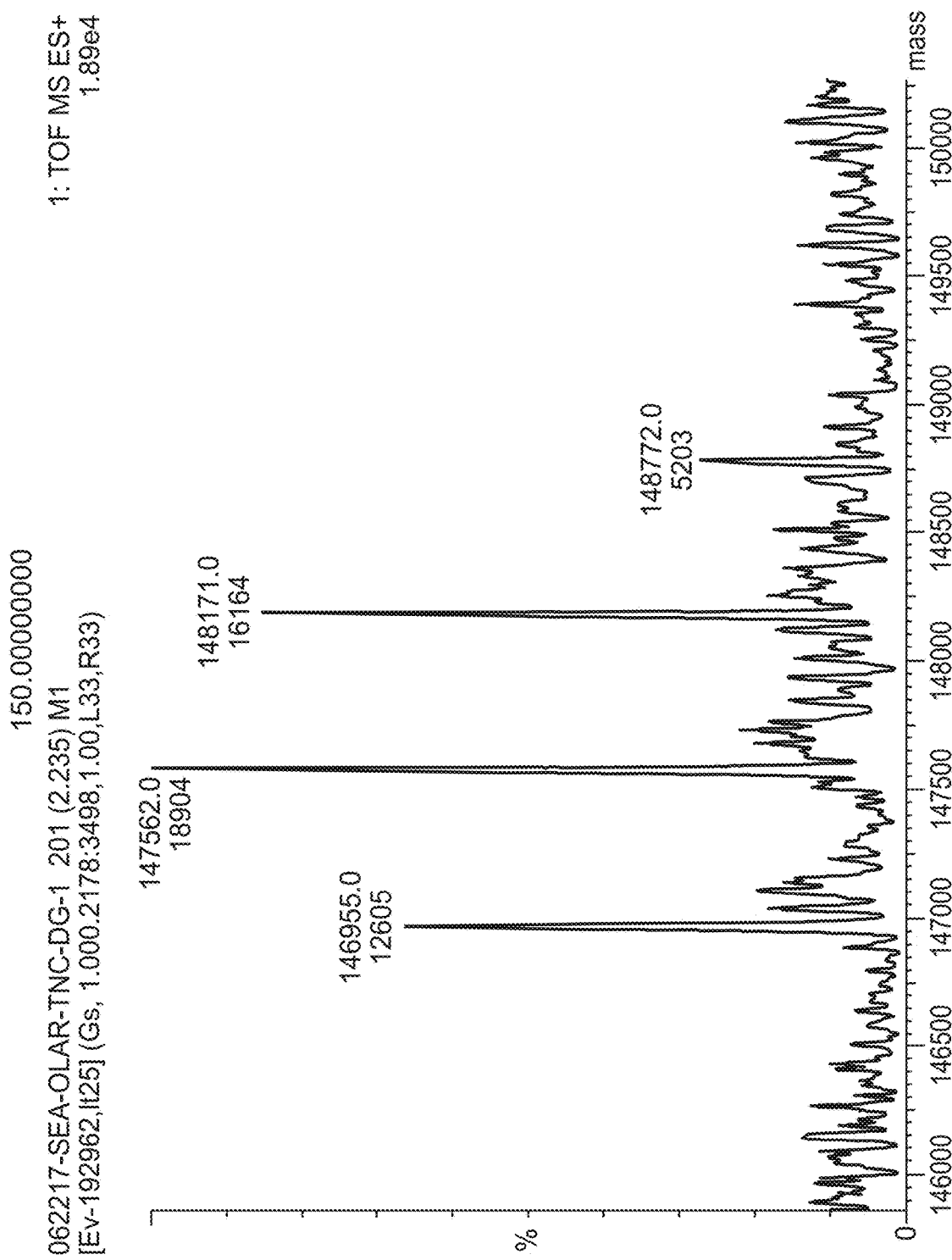

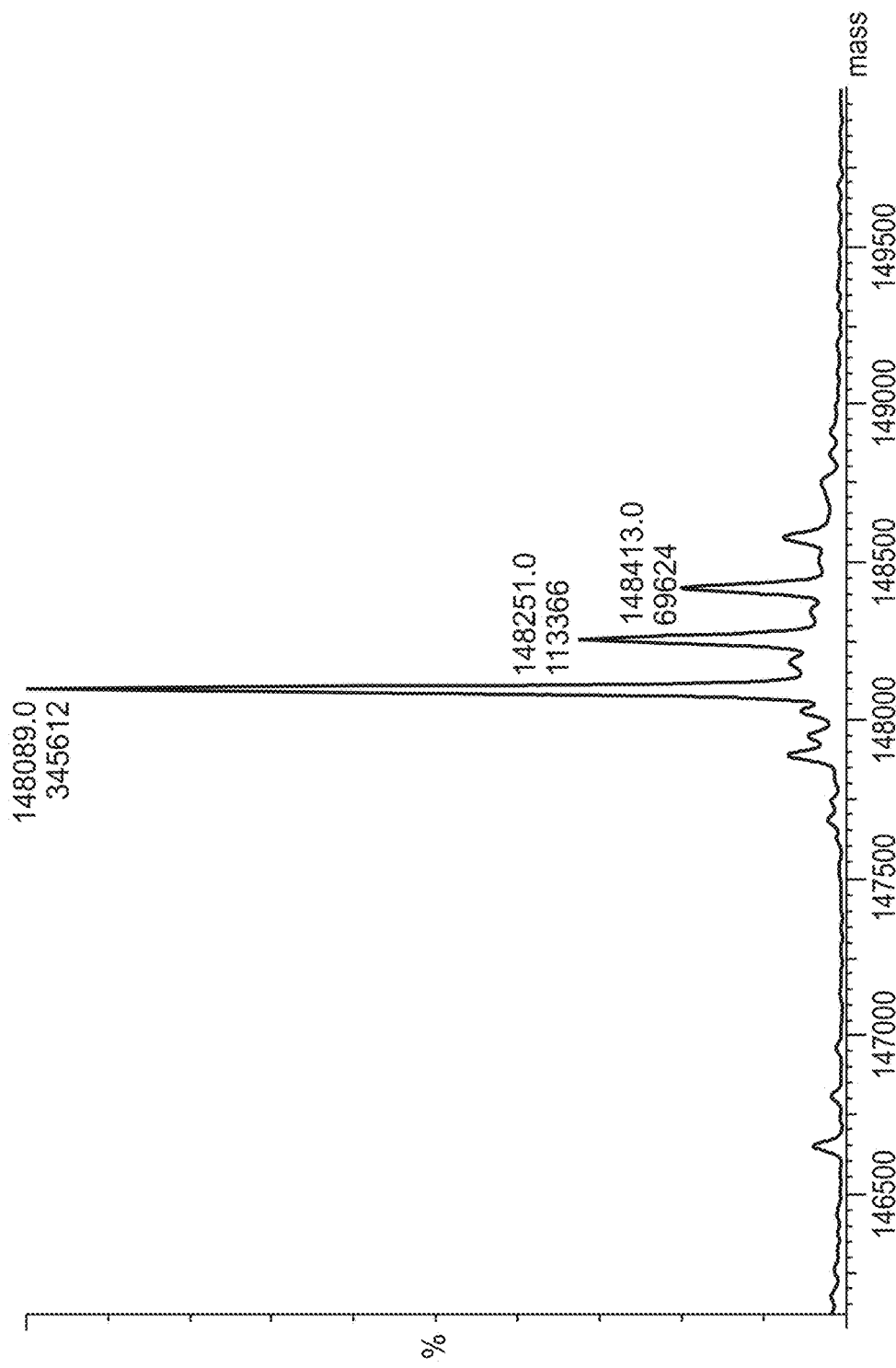

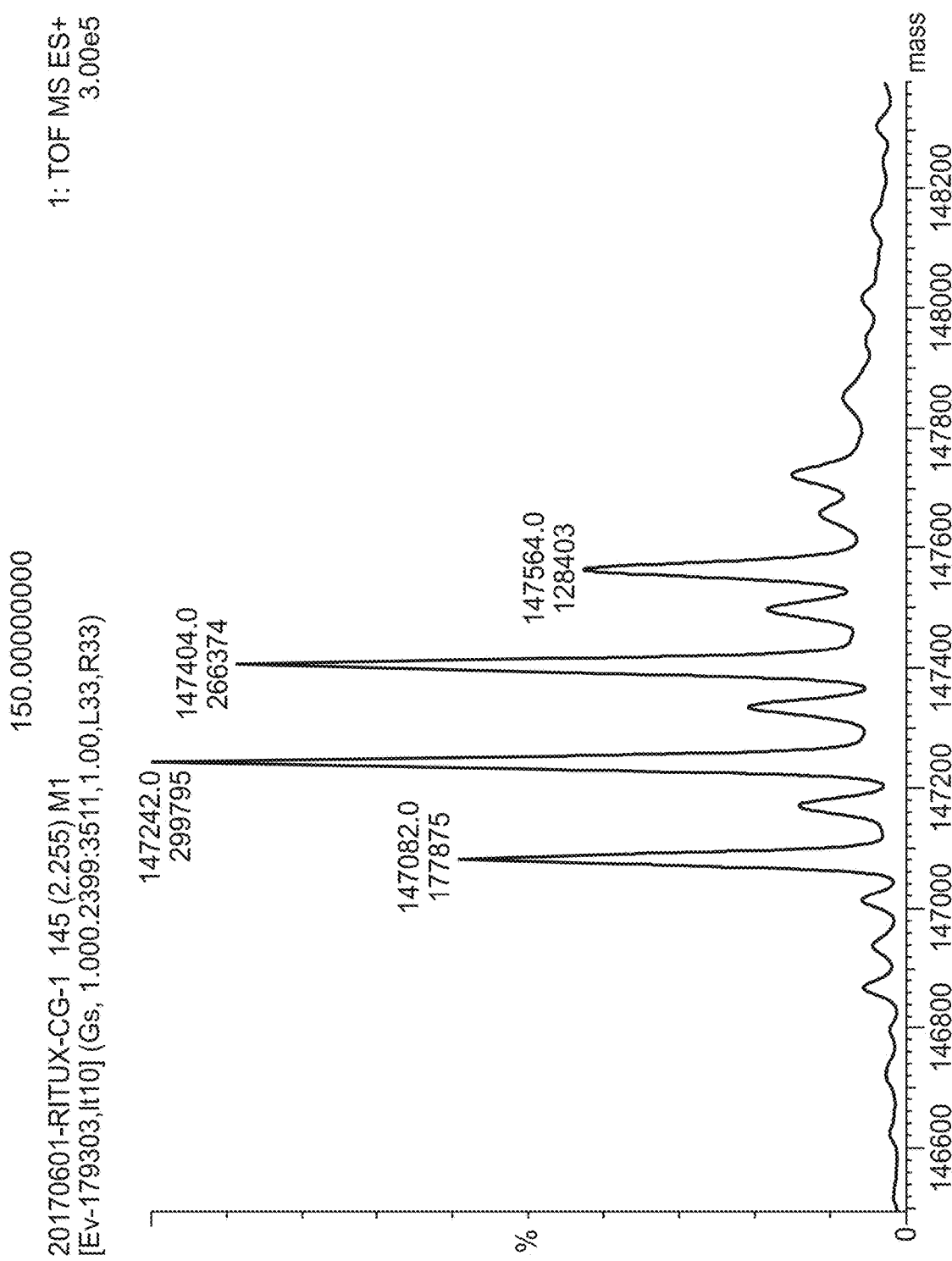

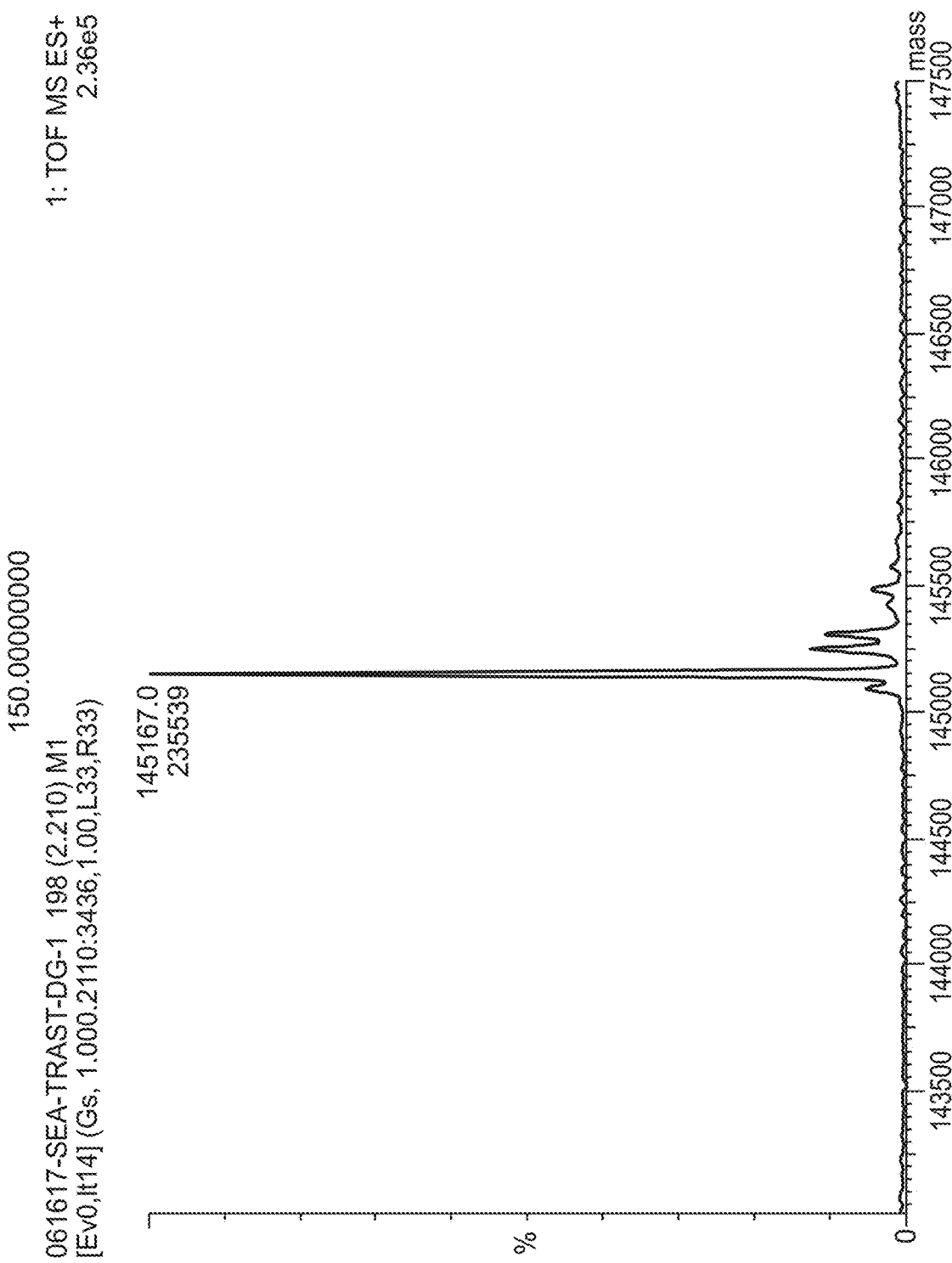

Trastuzumab - CD123

Trastuzumab - HLA-DR

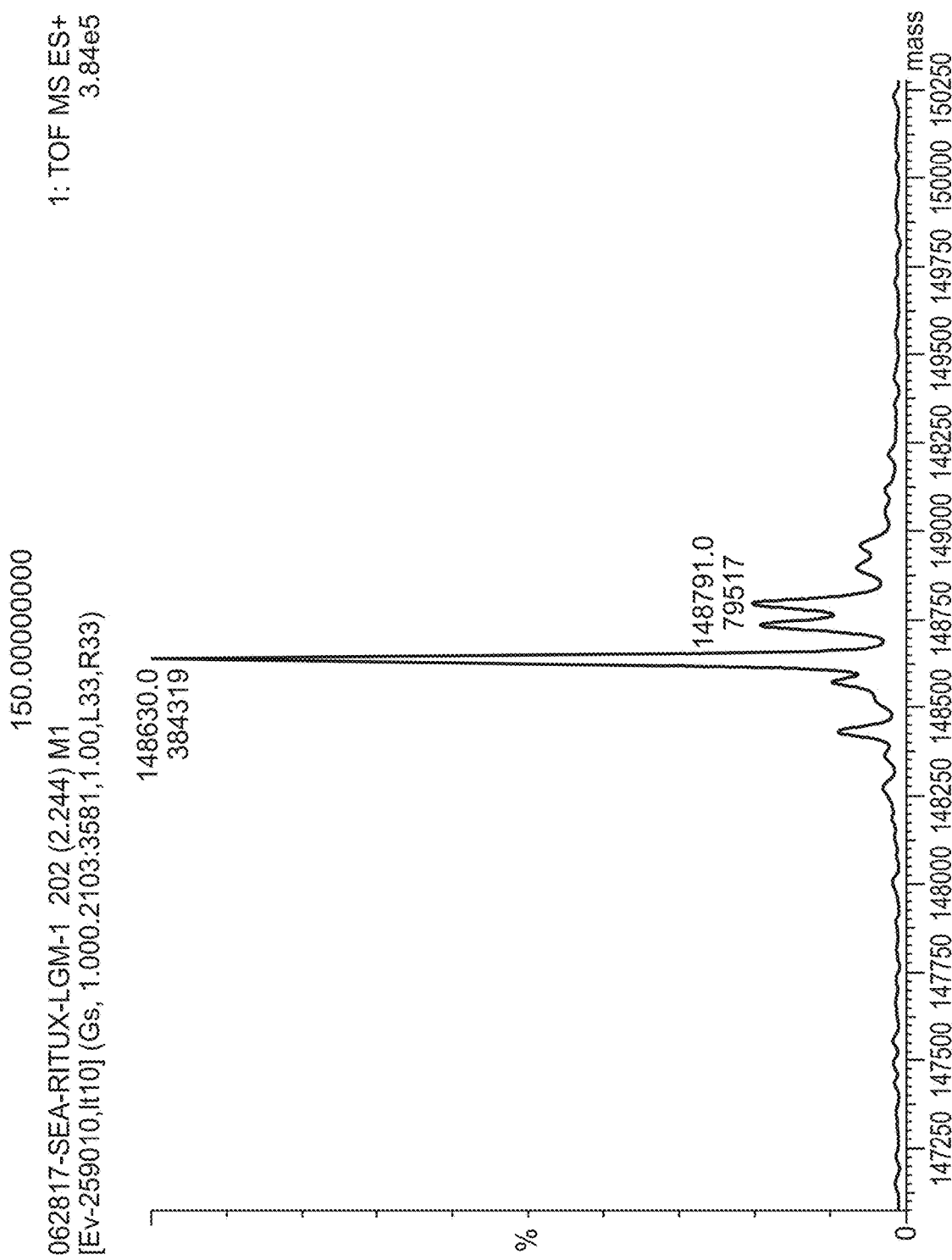

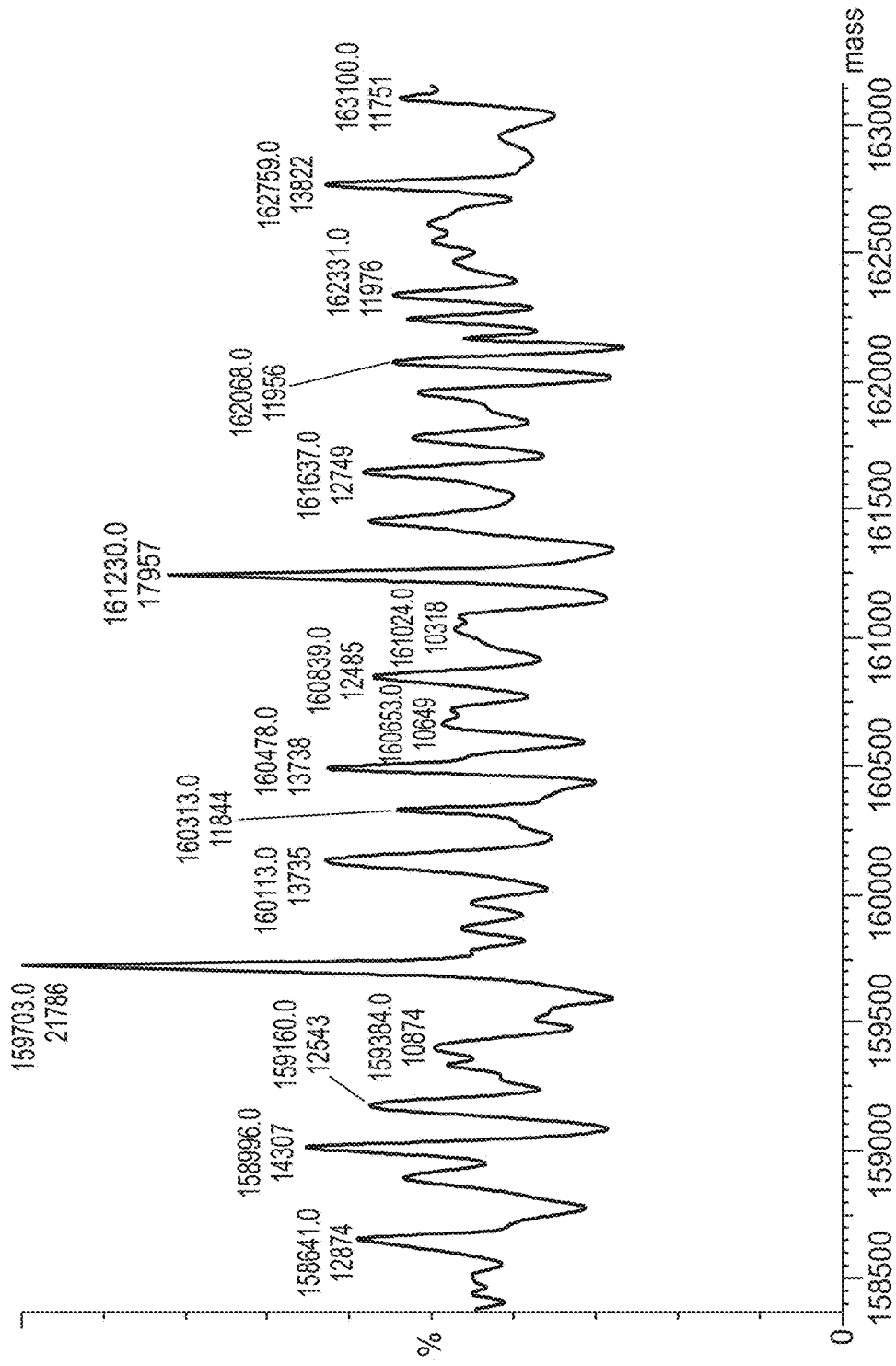


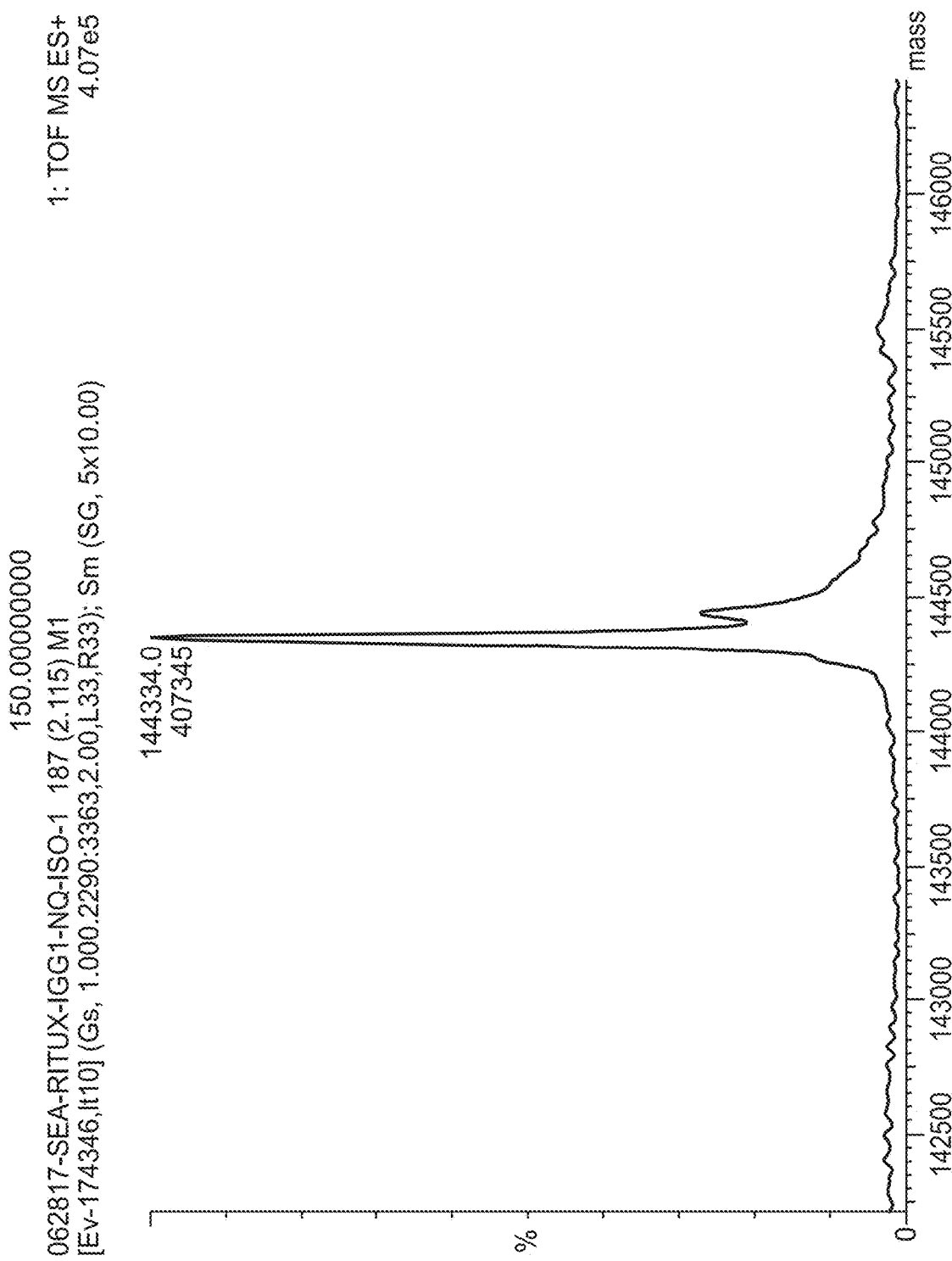

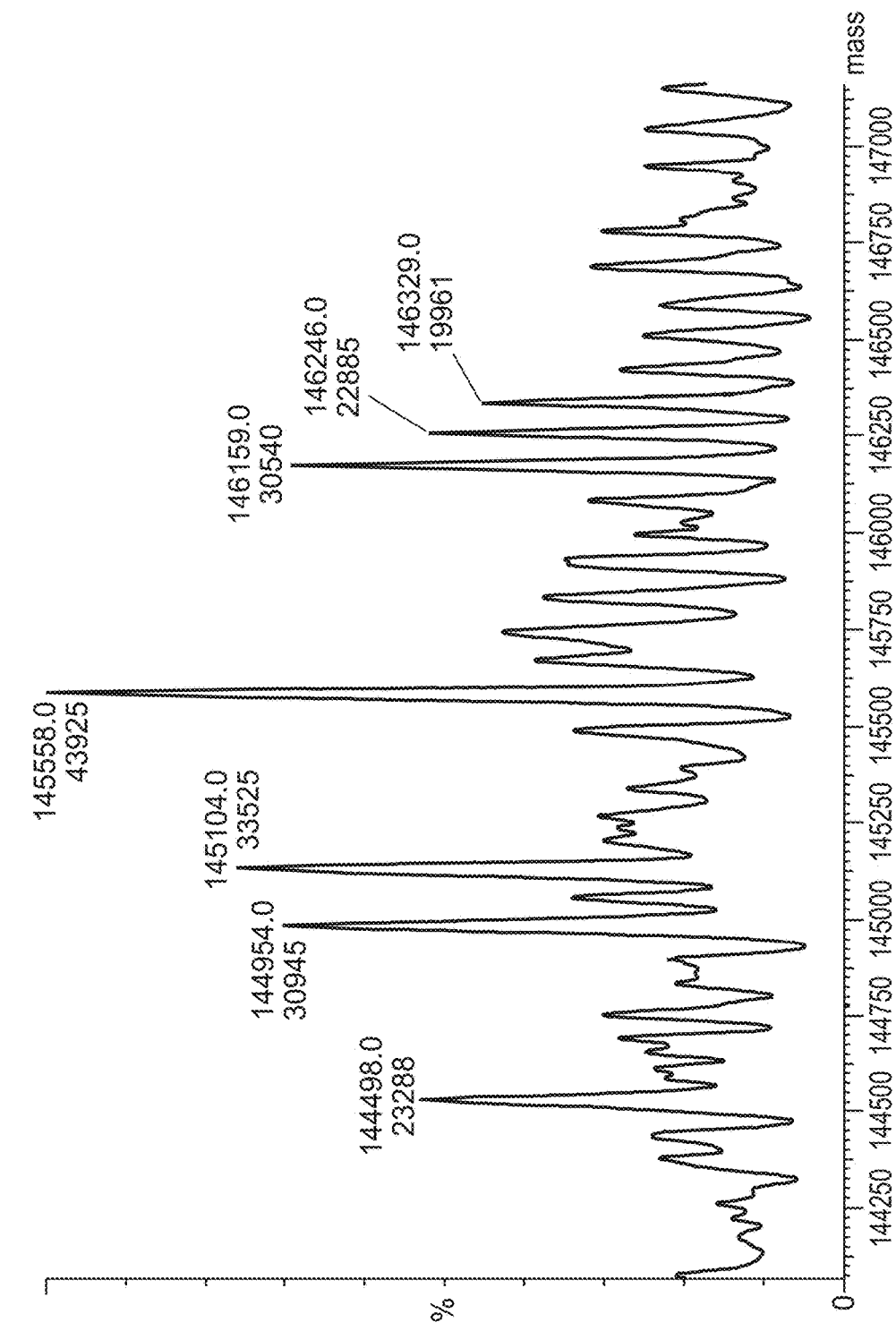

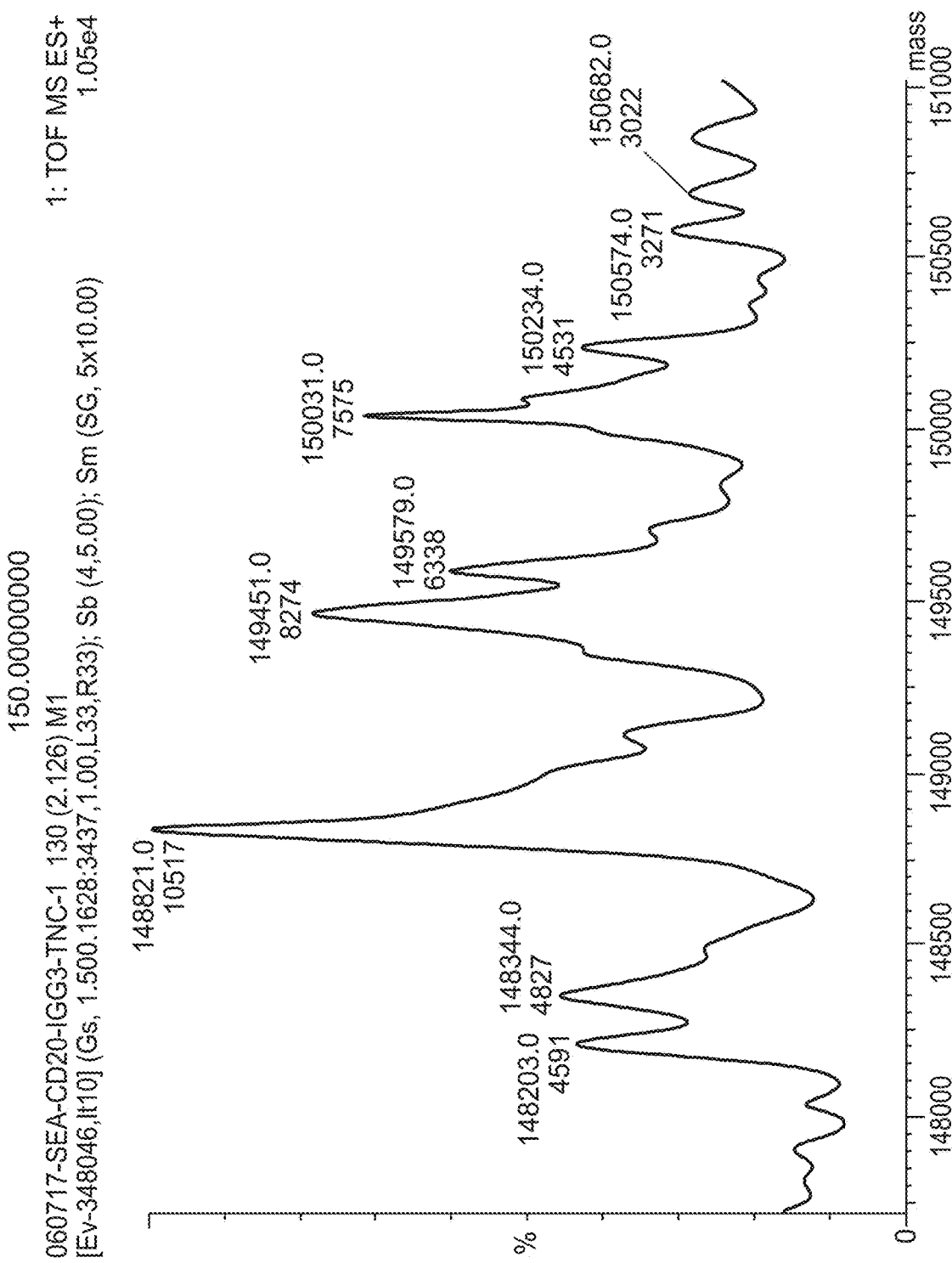

FIG. 95

| Name | CD14 | | CD40 | | CD86 | |
|---|---|---|---|---|---|---|
| | EC50 (nM) | Fold Change | EC50 (nM) | Fold Change | EC50 (nM) | Fold Change |
| BB-IgG1 | 1.86 | 5.05 | 4.41 | 2.20 | 4.19 | 2.11 |
| BB-IgG1 AF | 0.40 | 4.31 | 0.86 | 1.66 | 1.01 | 1.38 |
| BB-IgG2 | 3.54 | 2.43 | 13.93 | 1.89 | 4.55 | 1.93 |
| BB-IgG3 | 3.20 | 4.07 | 21.81 | 1.72 | 11.53 | 1.56 |
| BB-IgG4 | 4.65 | 4.05 | 6.61 | 1.50 | 15.63 | 1.75 |

*Values with Rituximab with 1:5 dilution series
*Fold Change calculated at 200nM relative to naked antibody

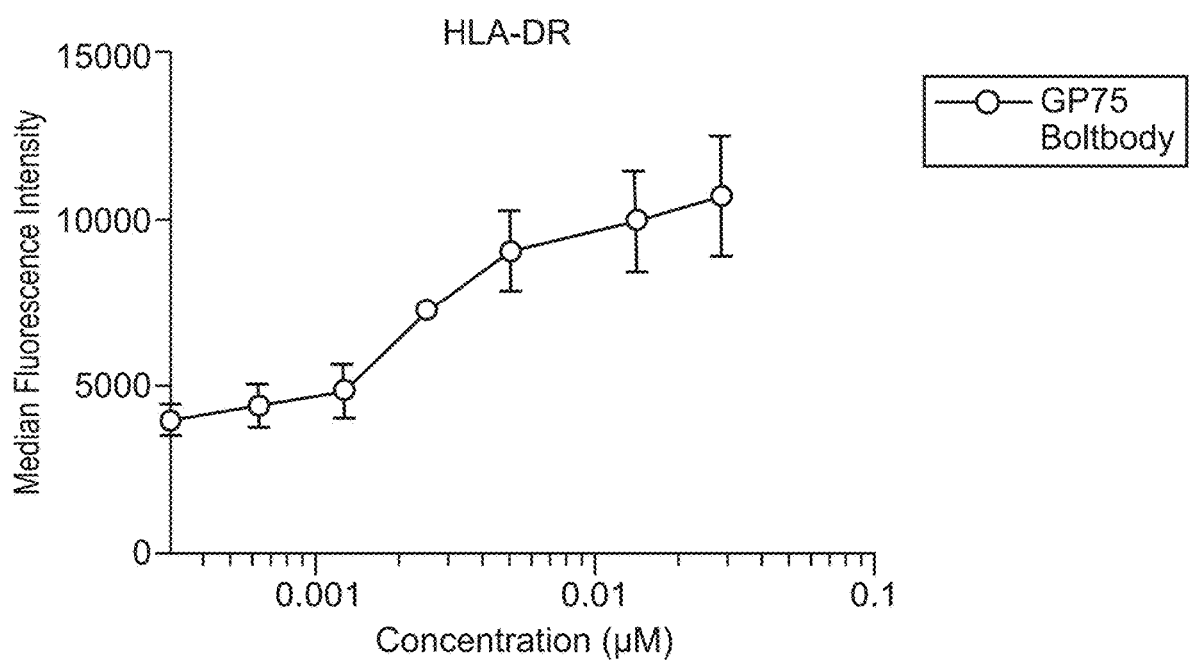

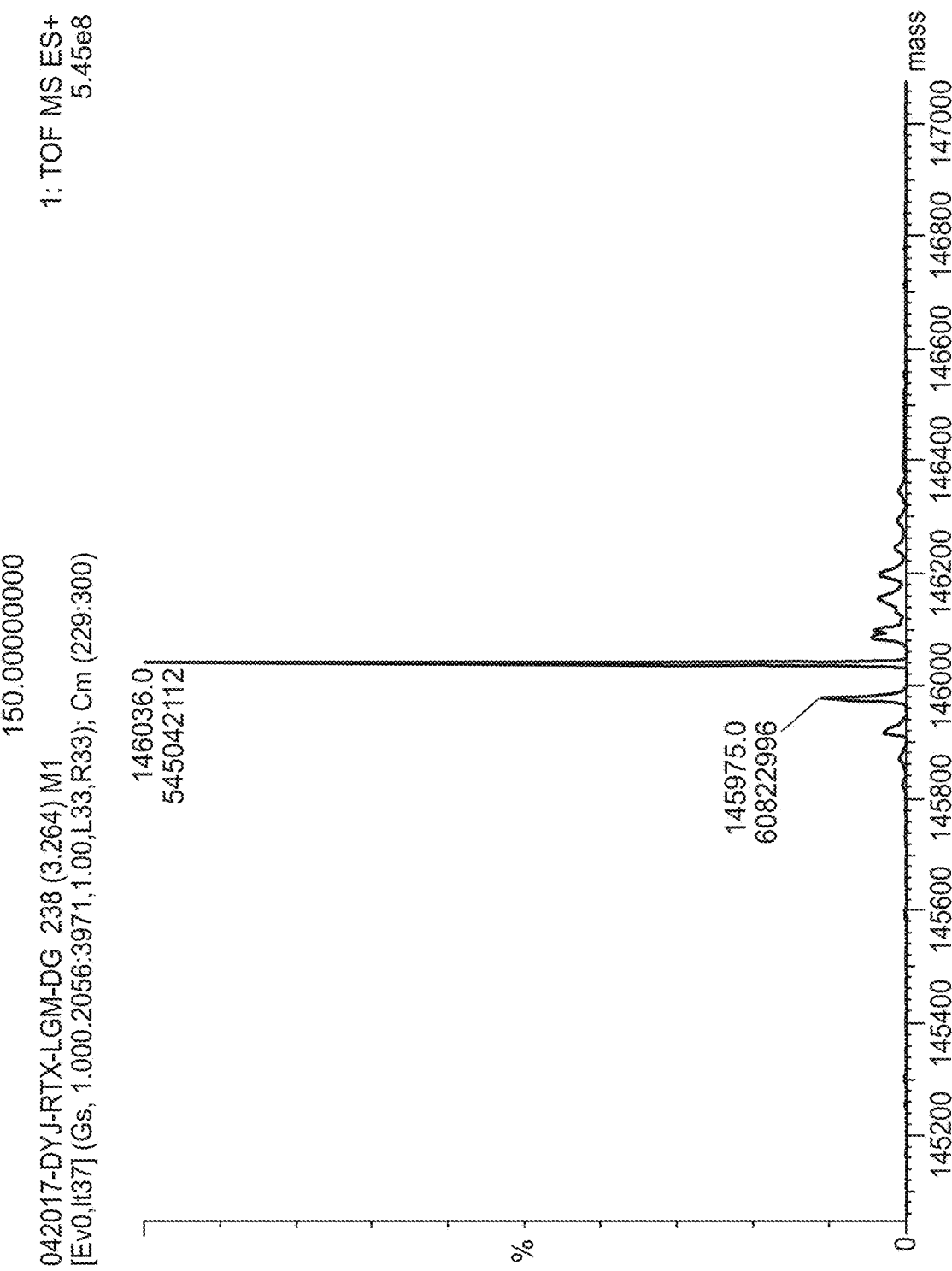

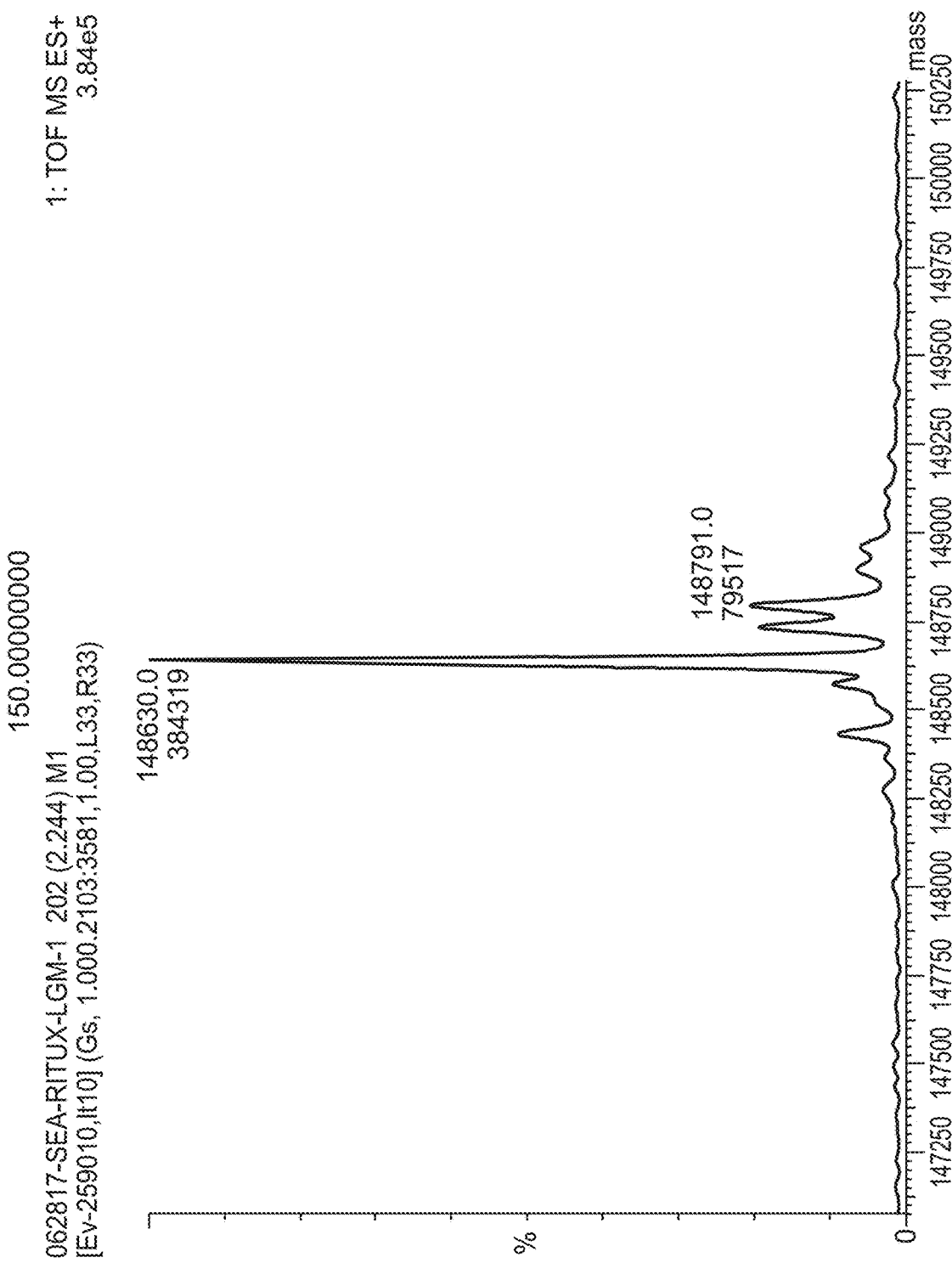

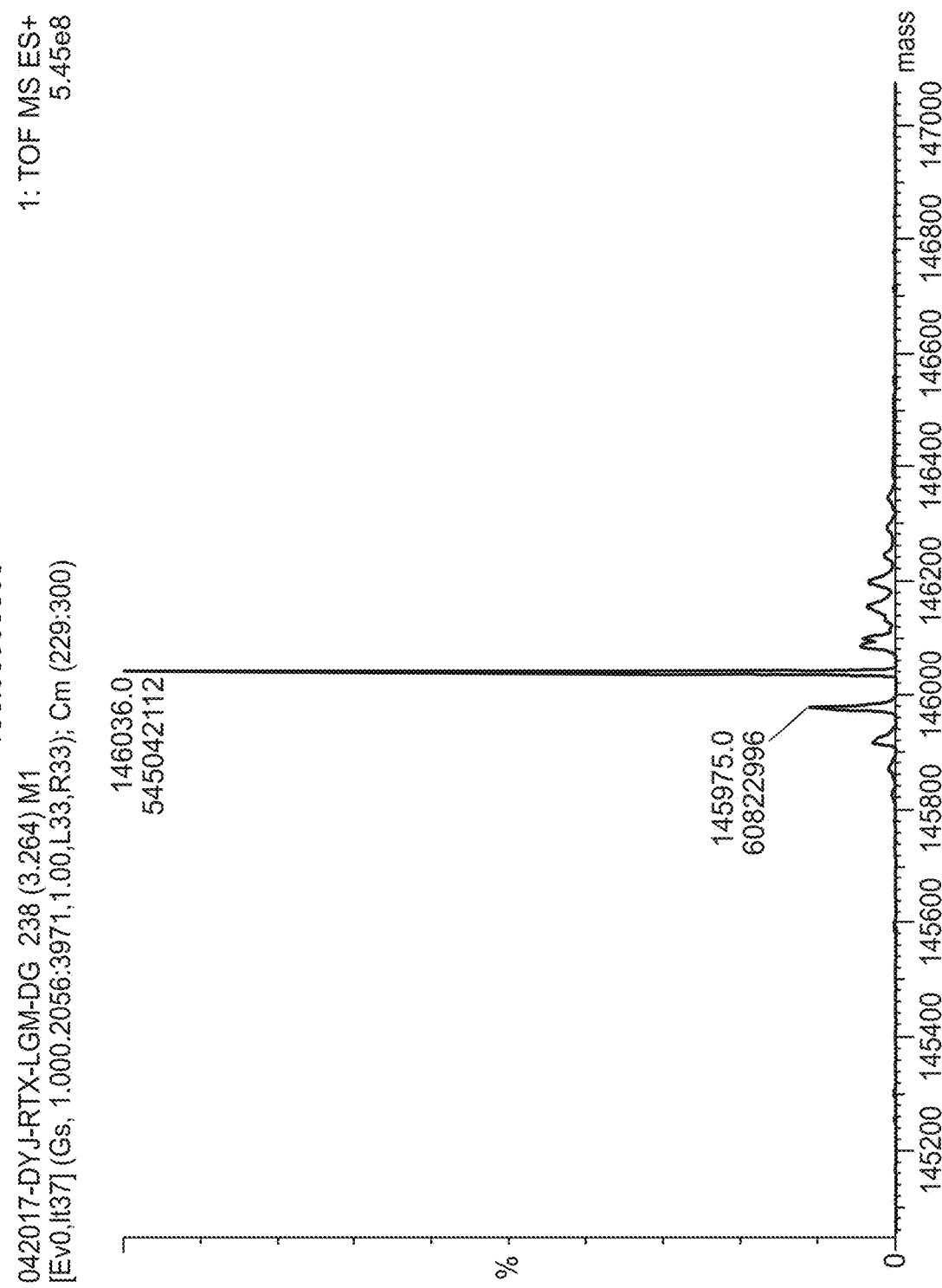

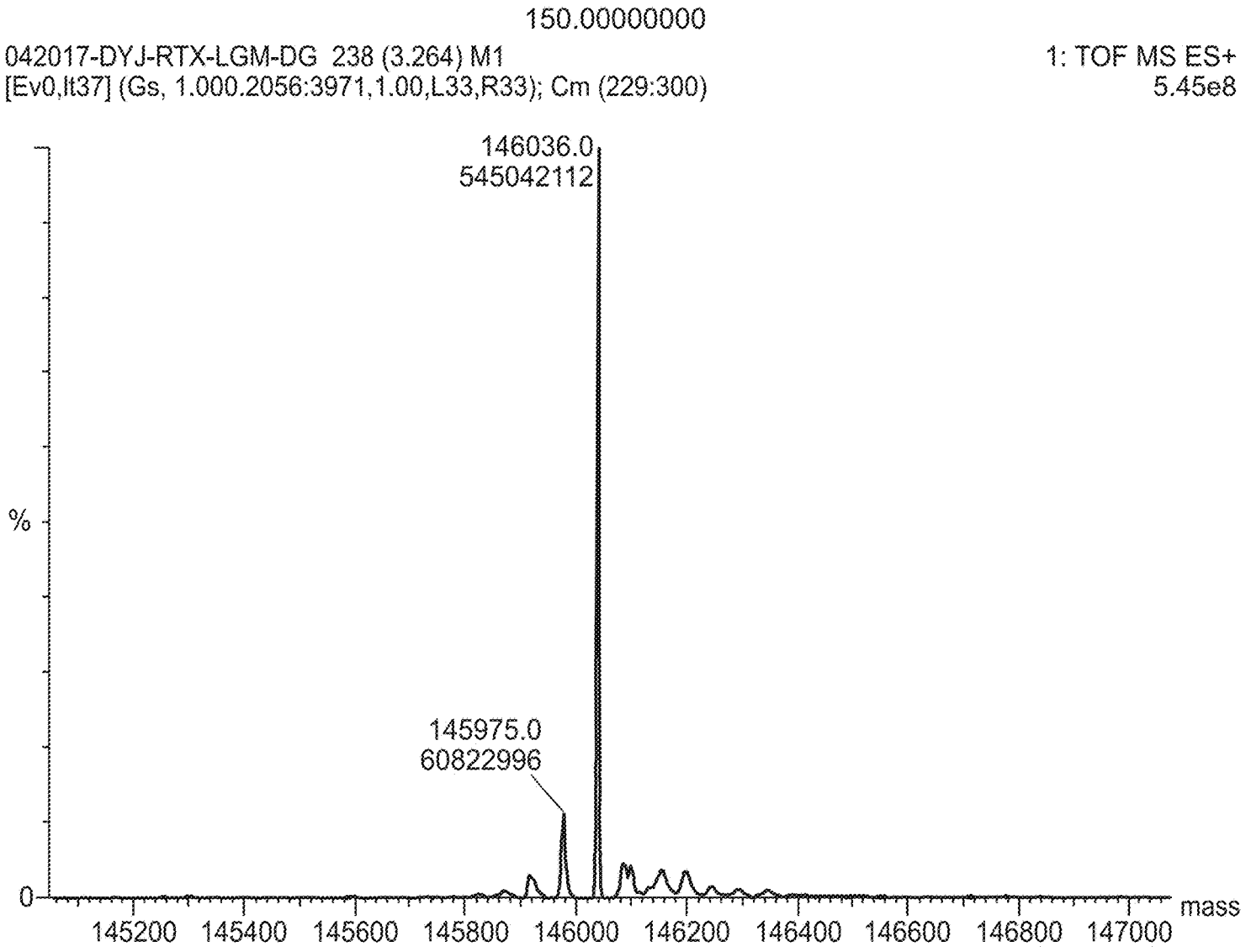

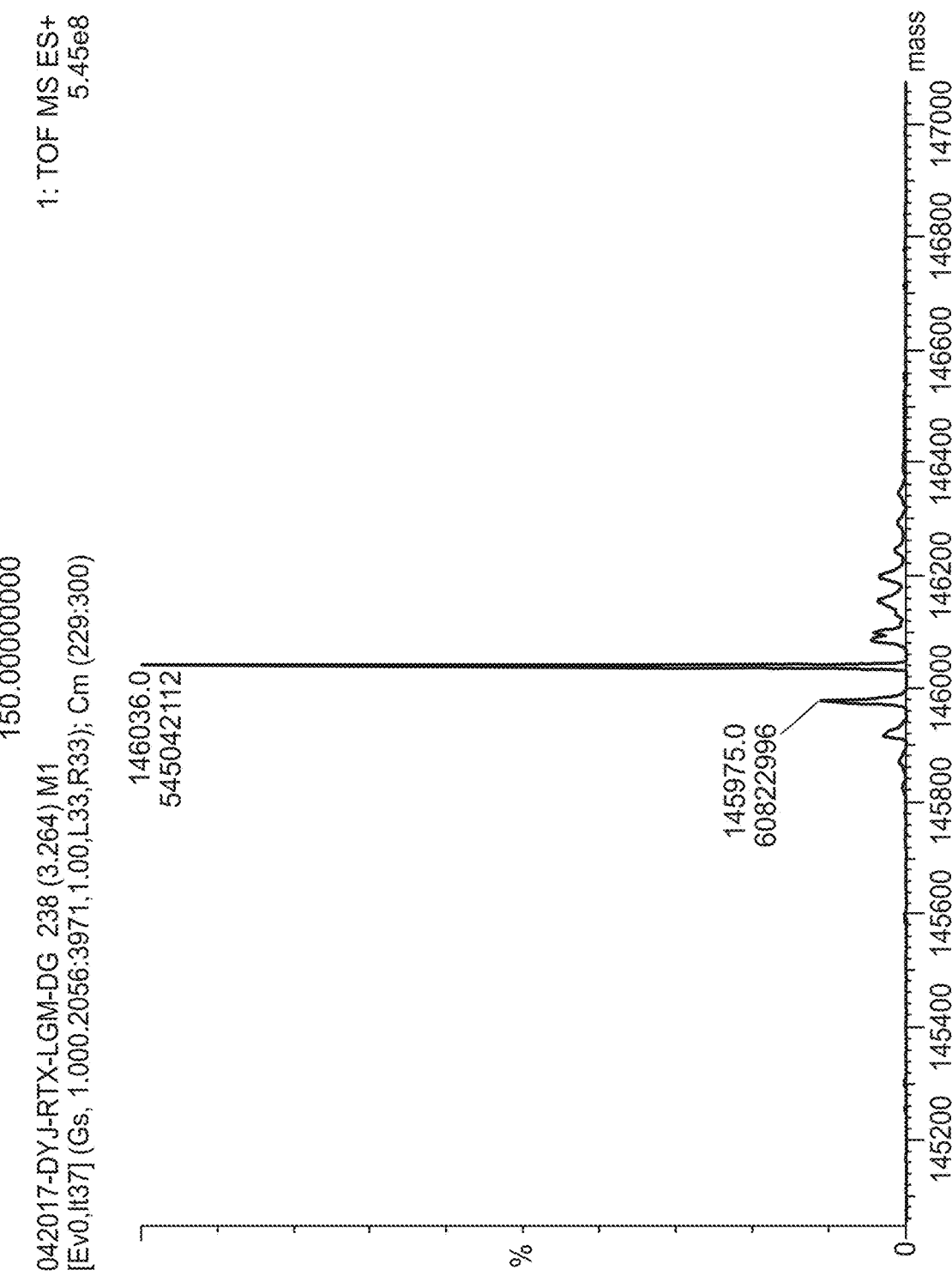

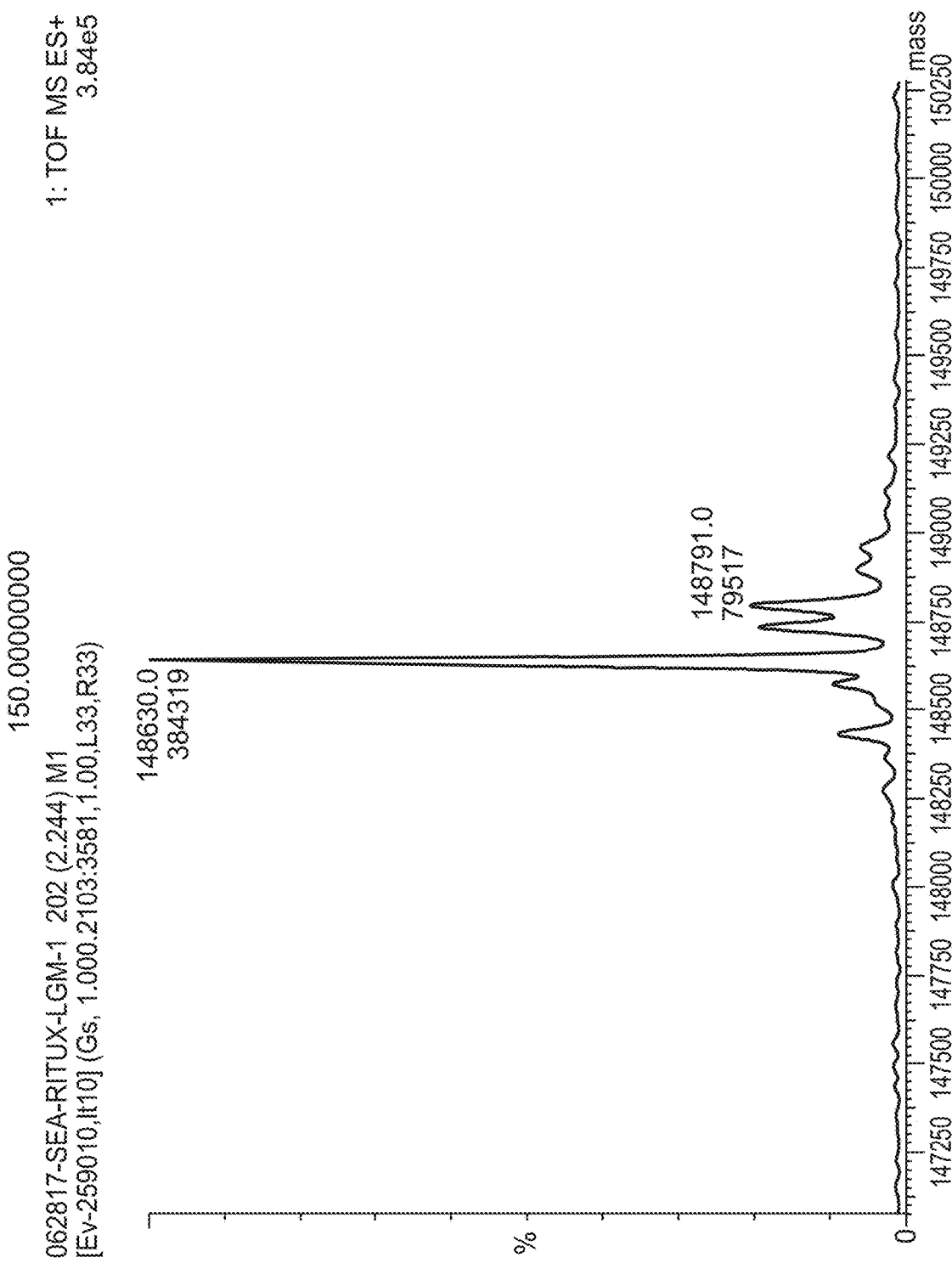

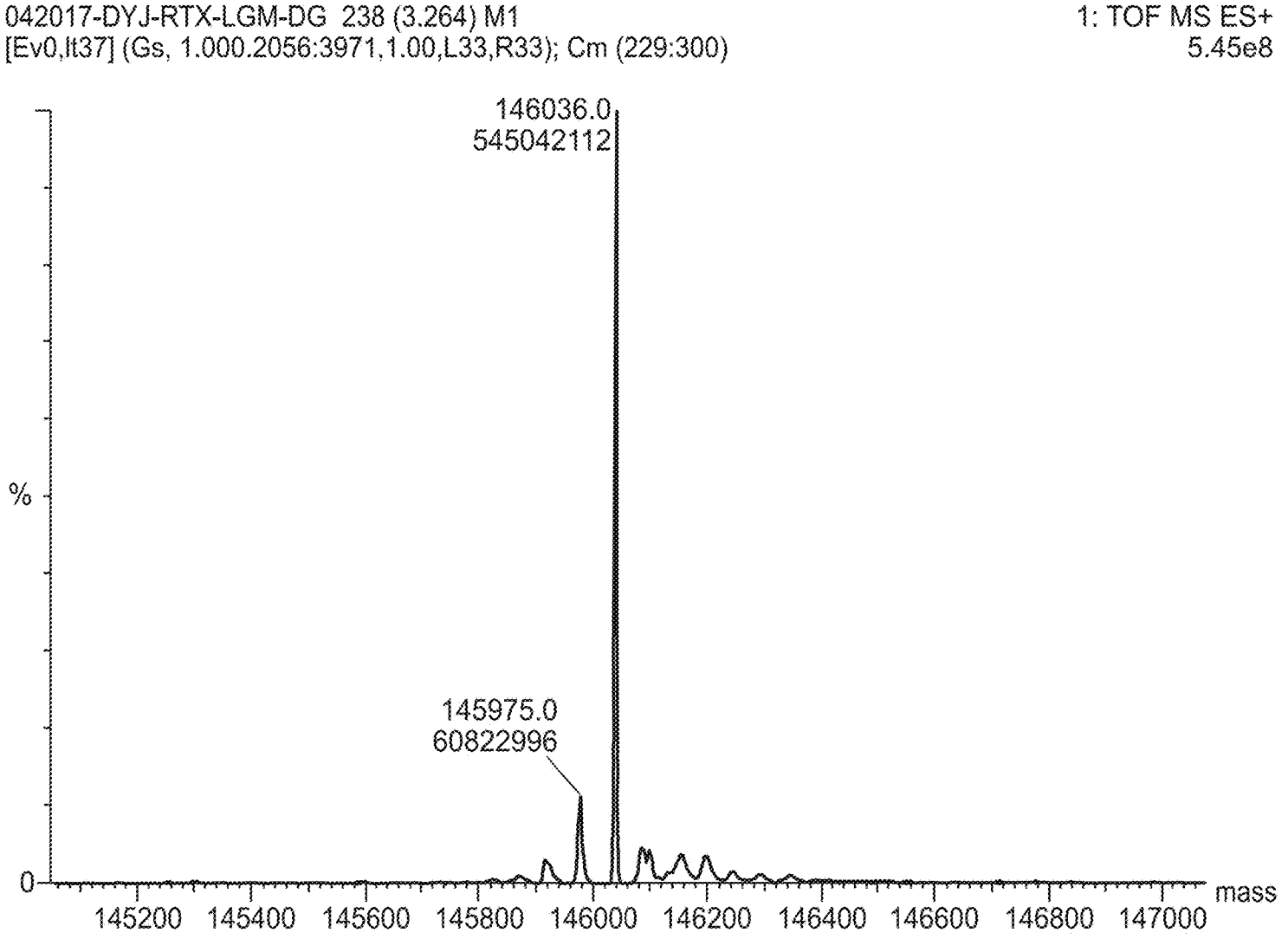

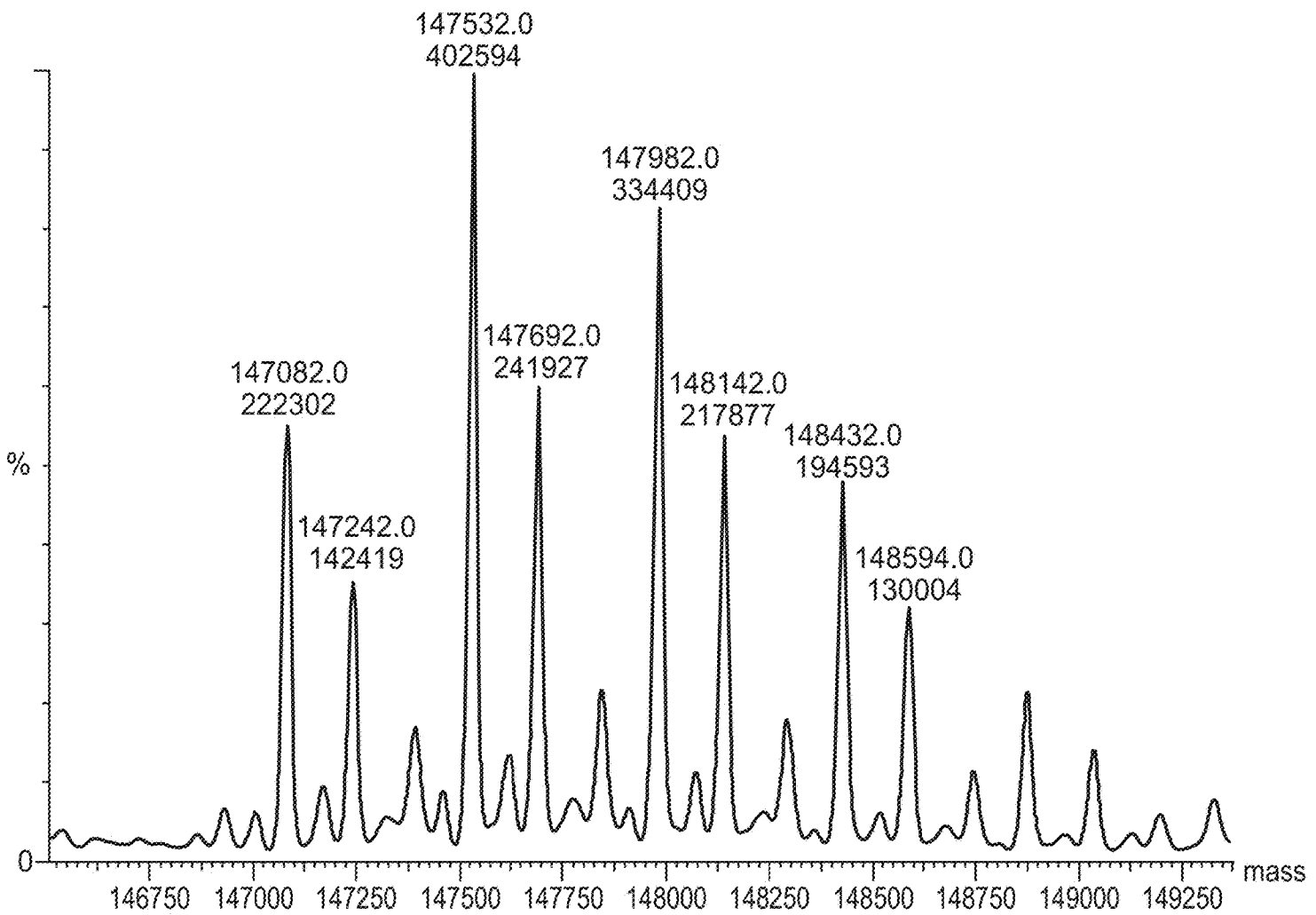

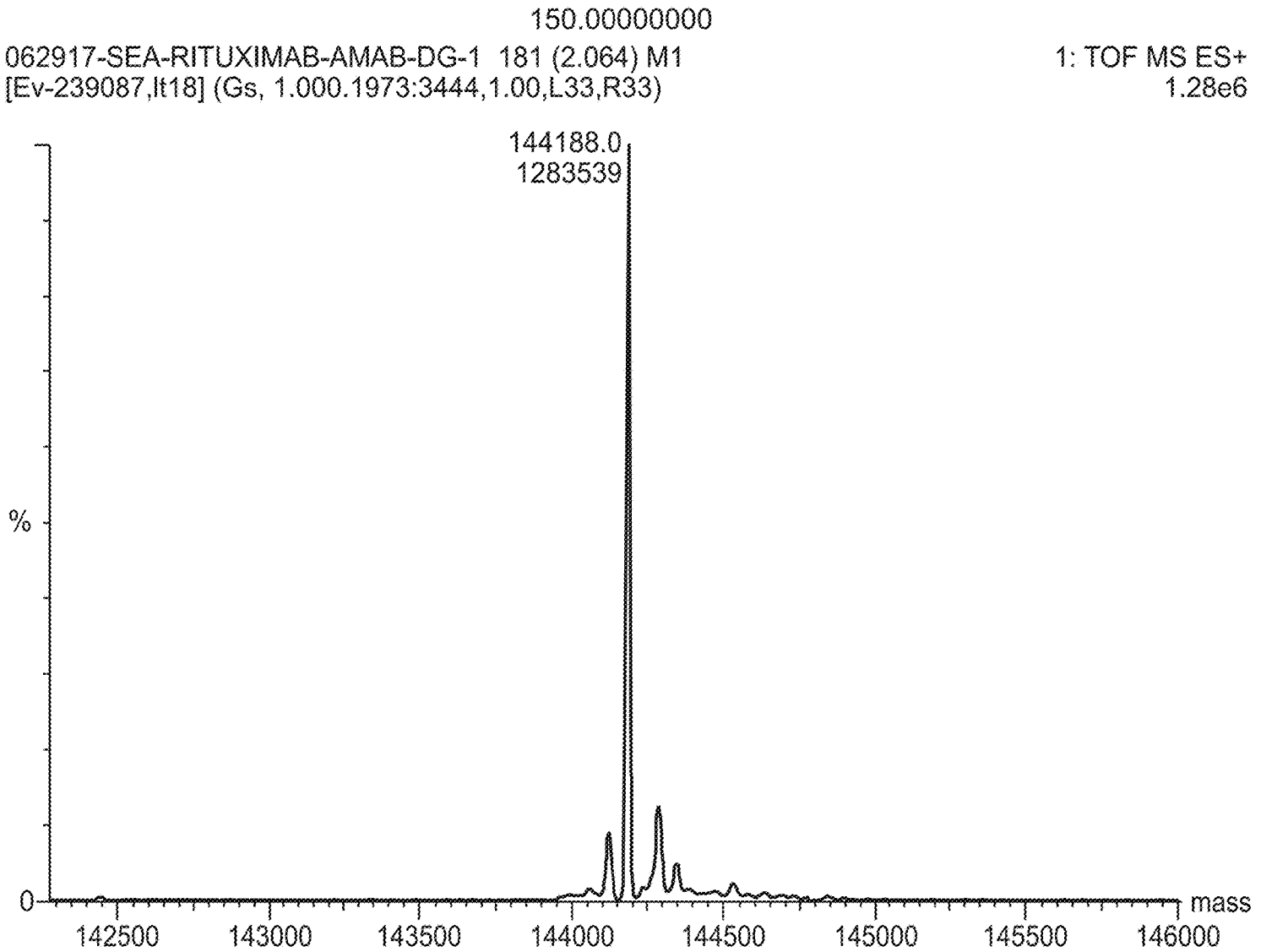

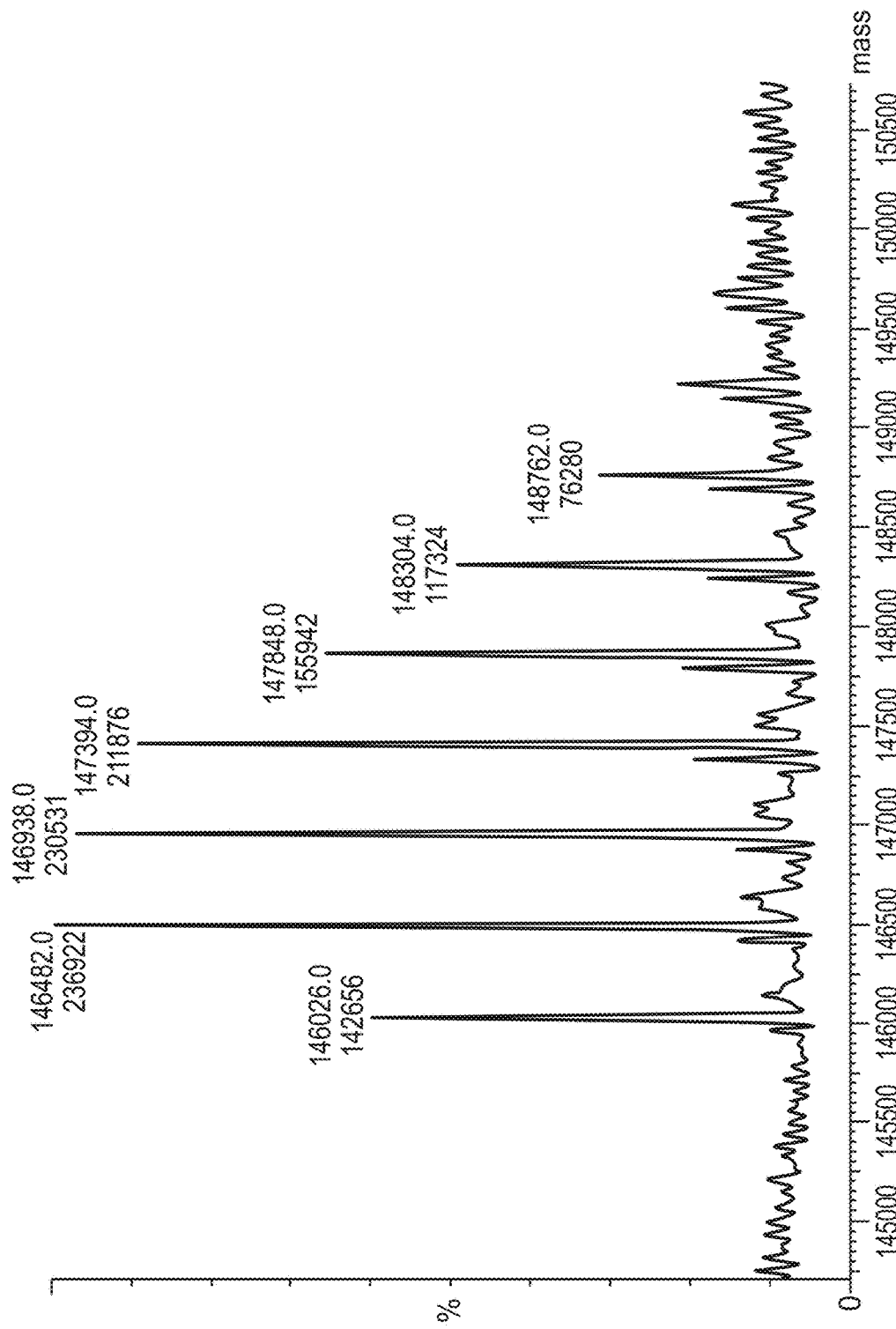

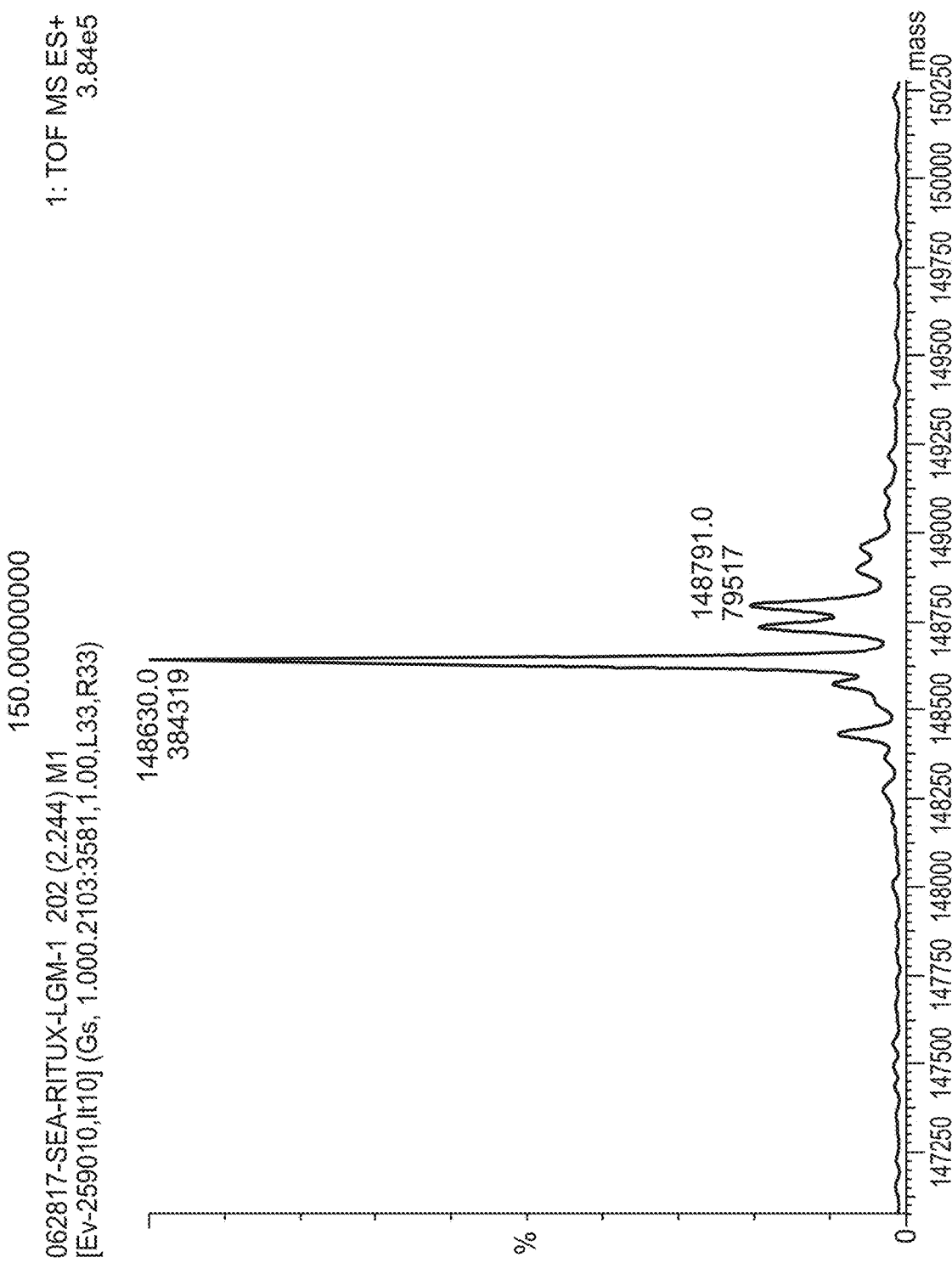

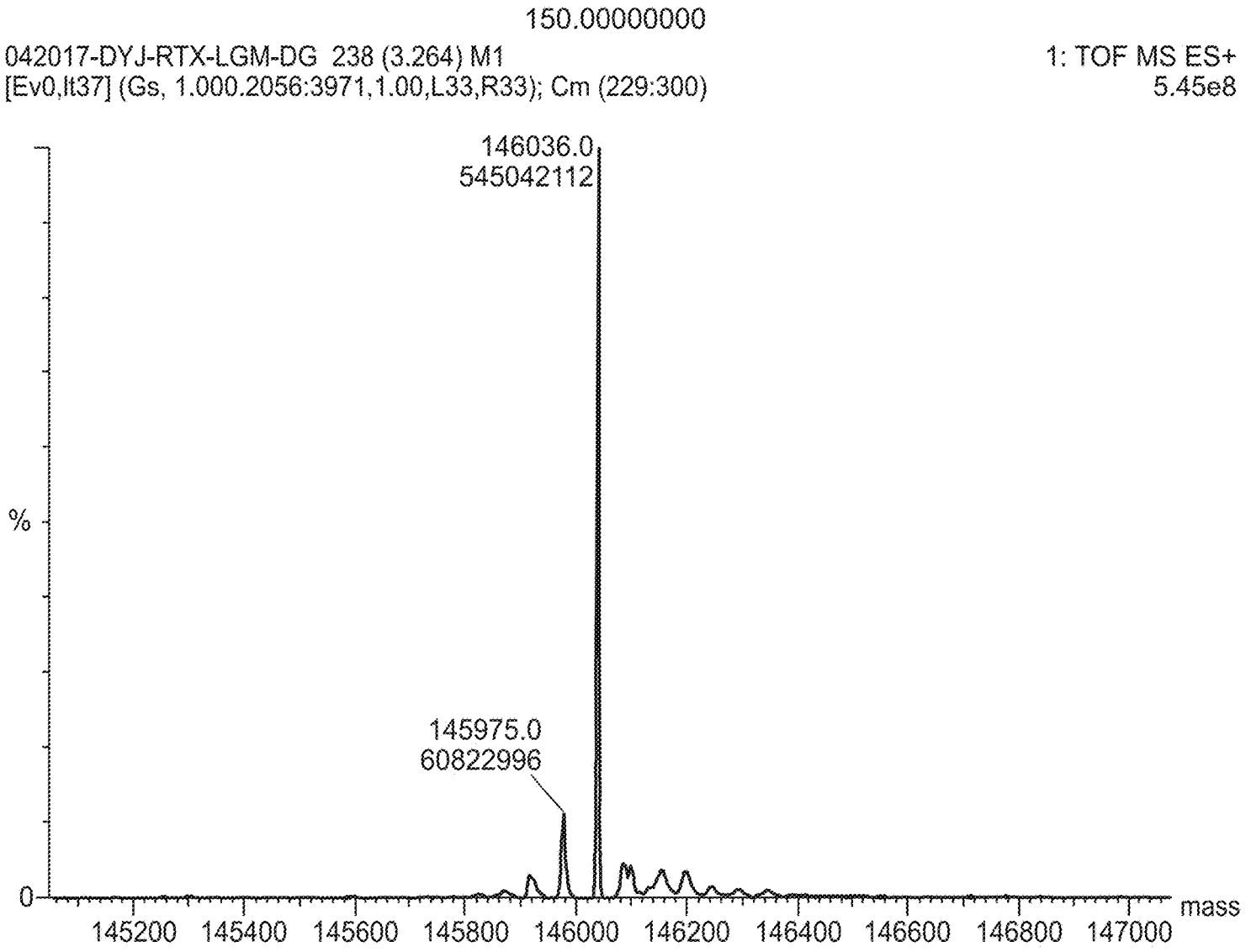


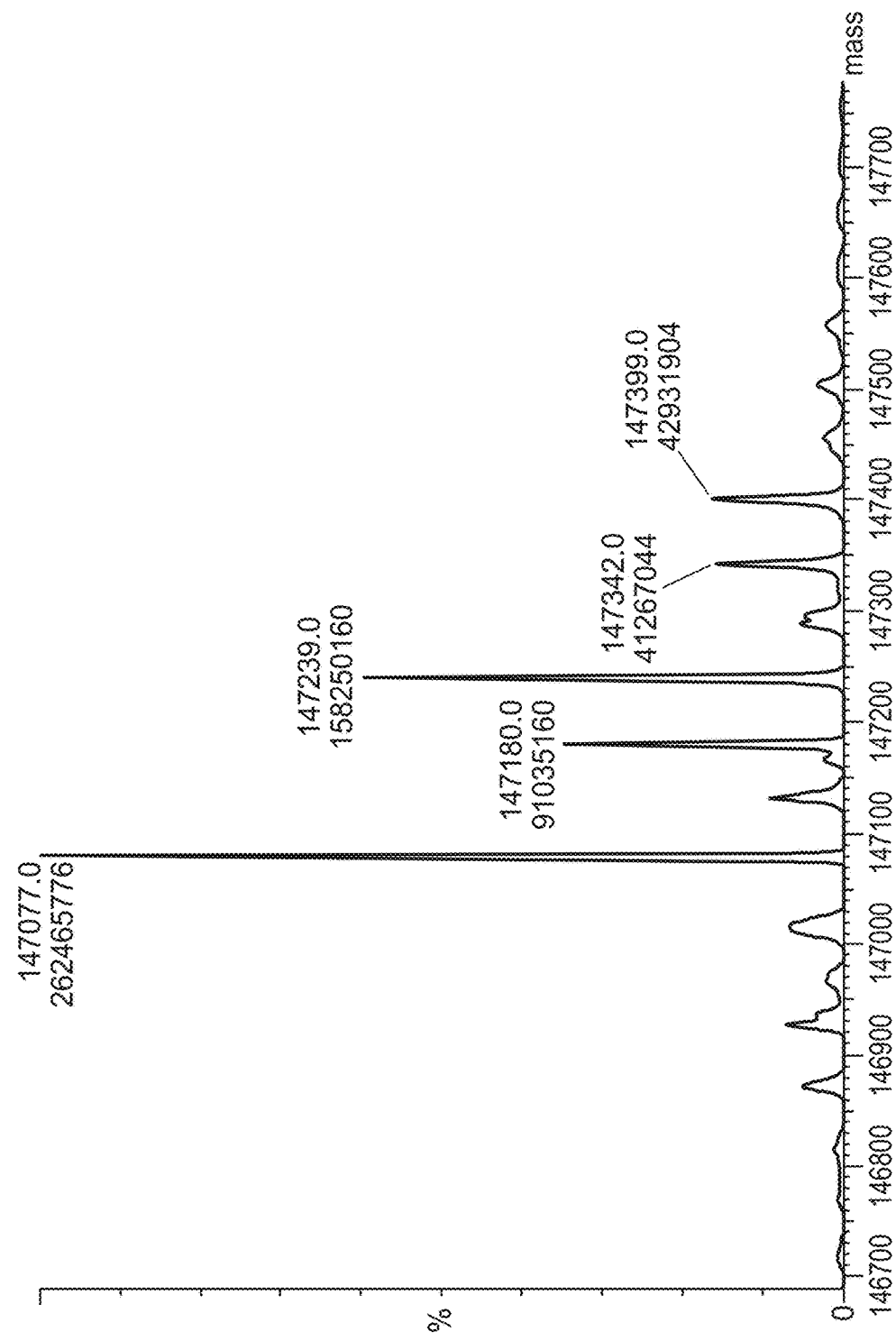

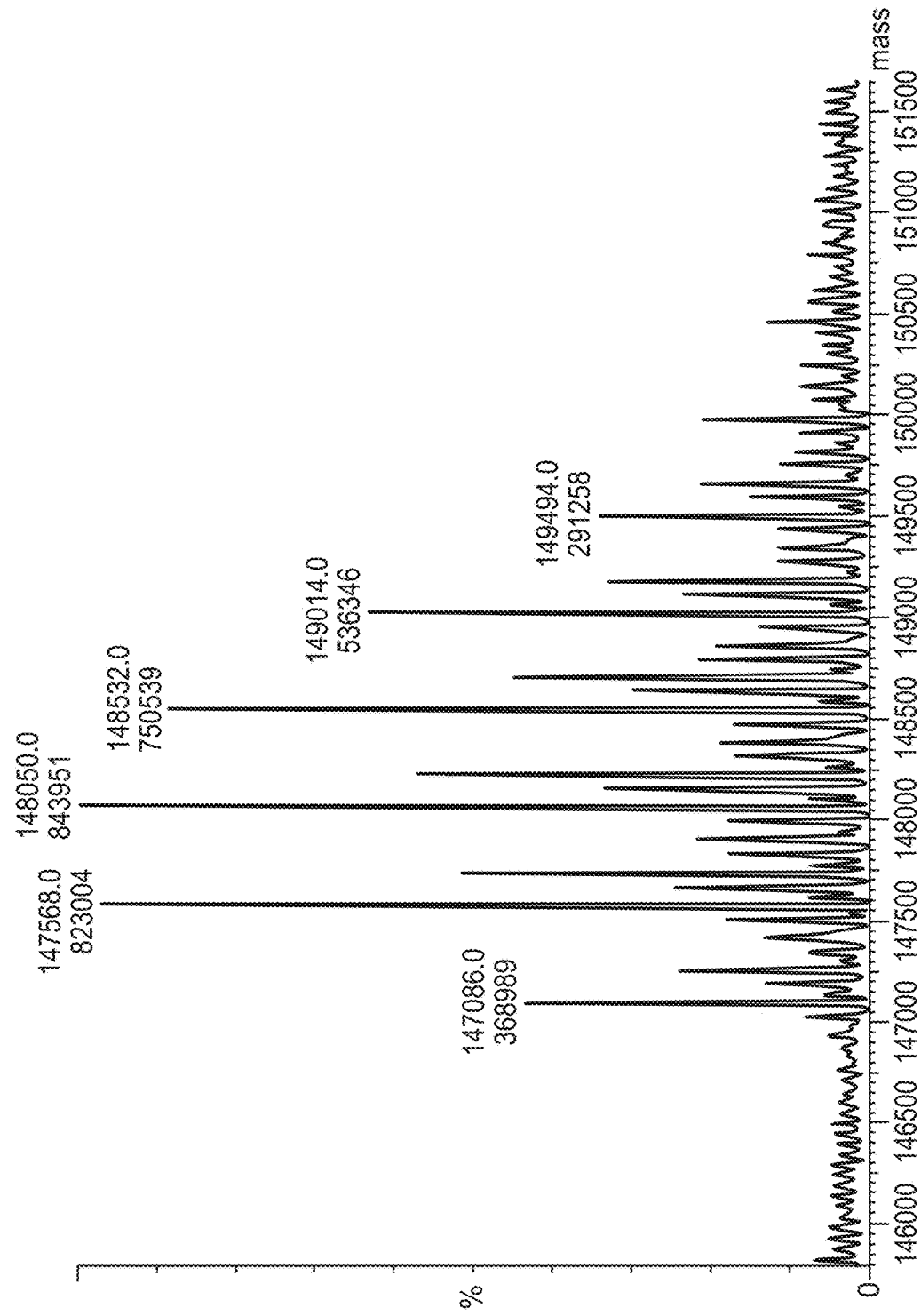

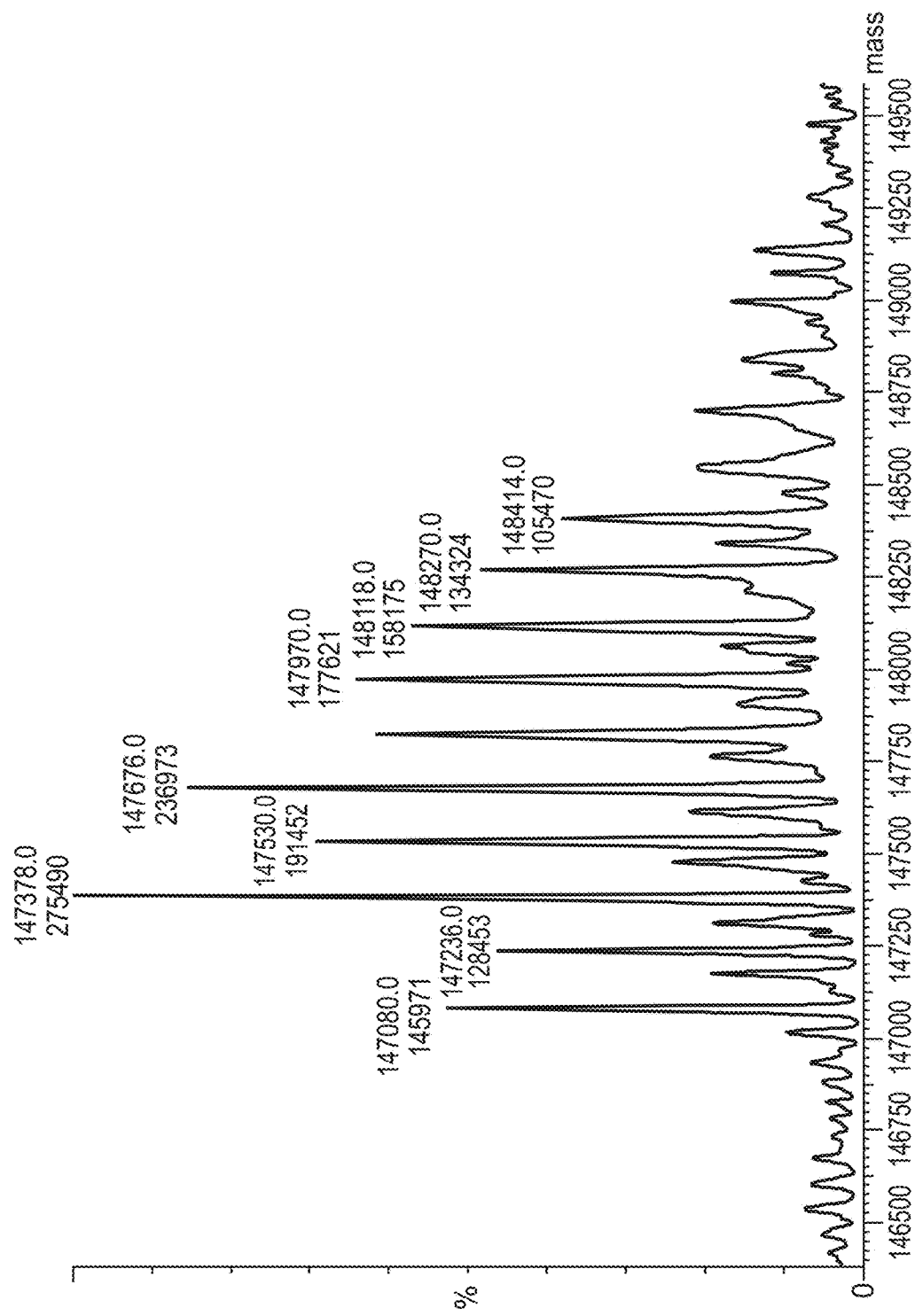

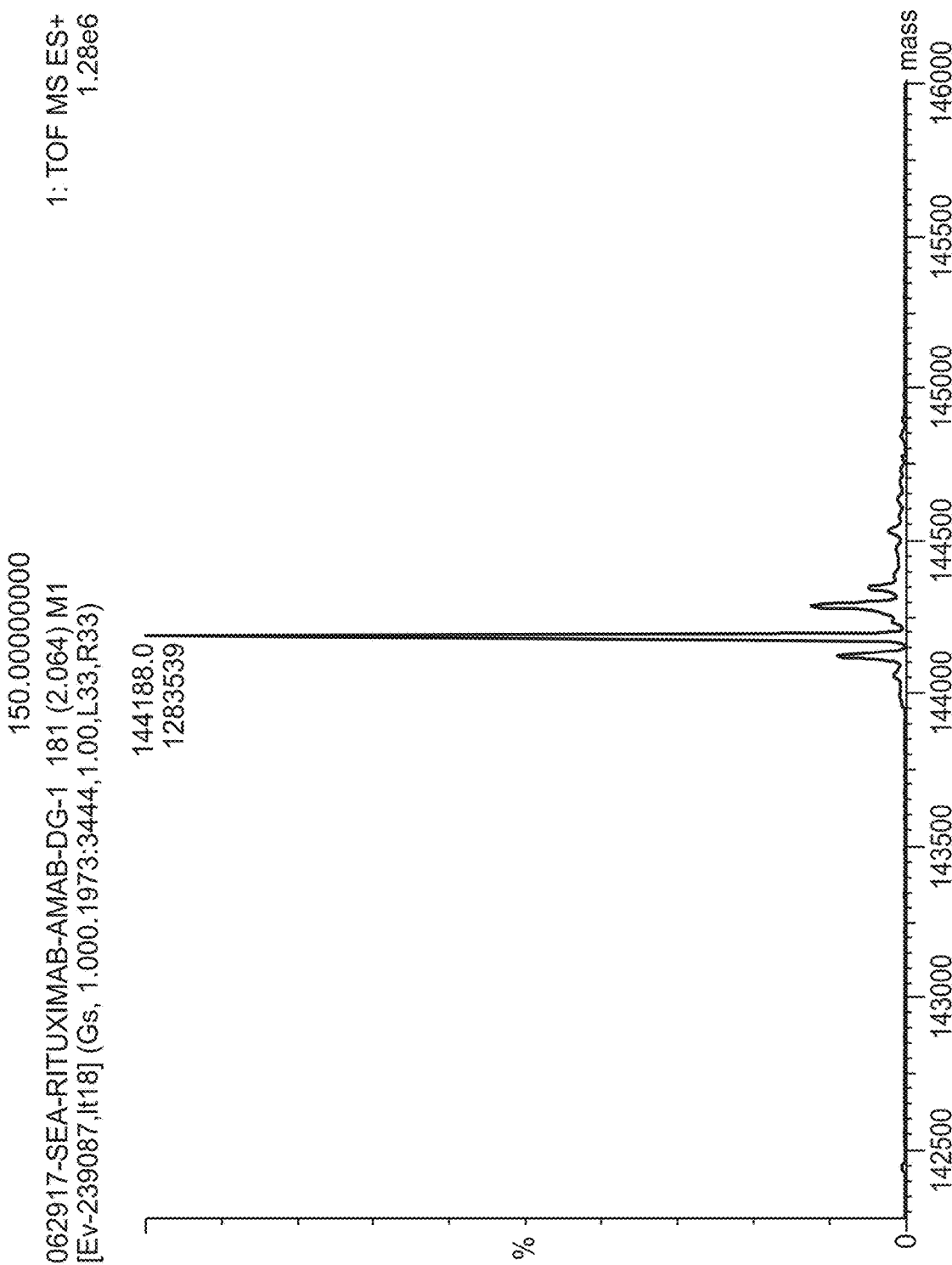

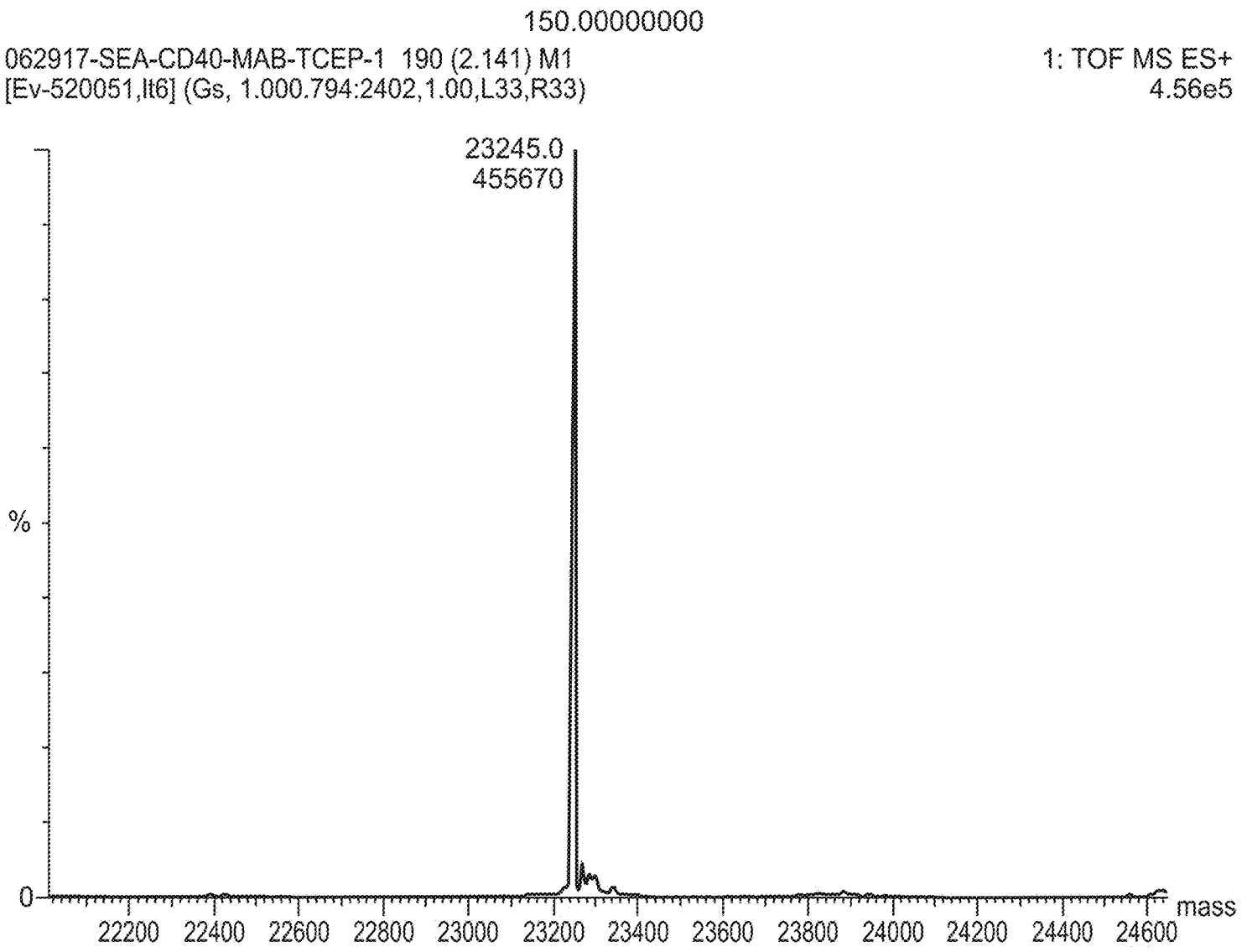

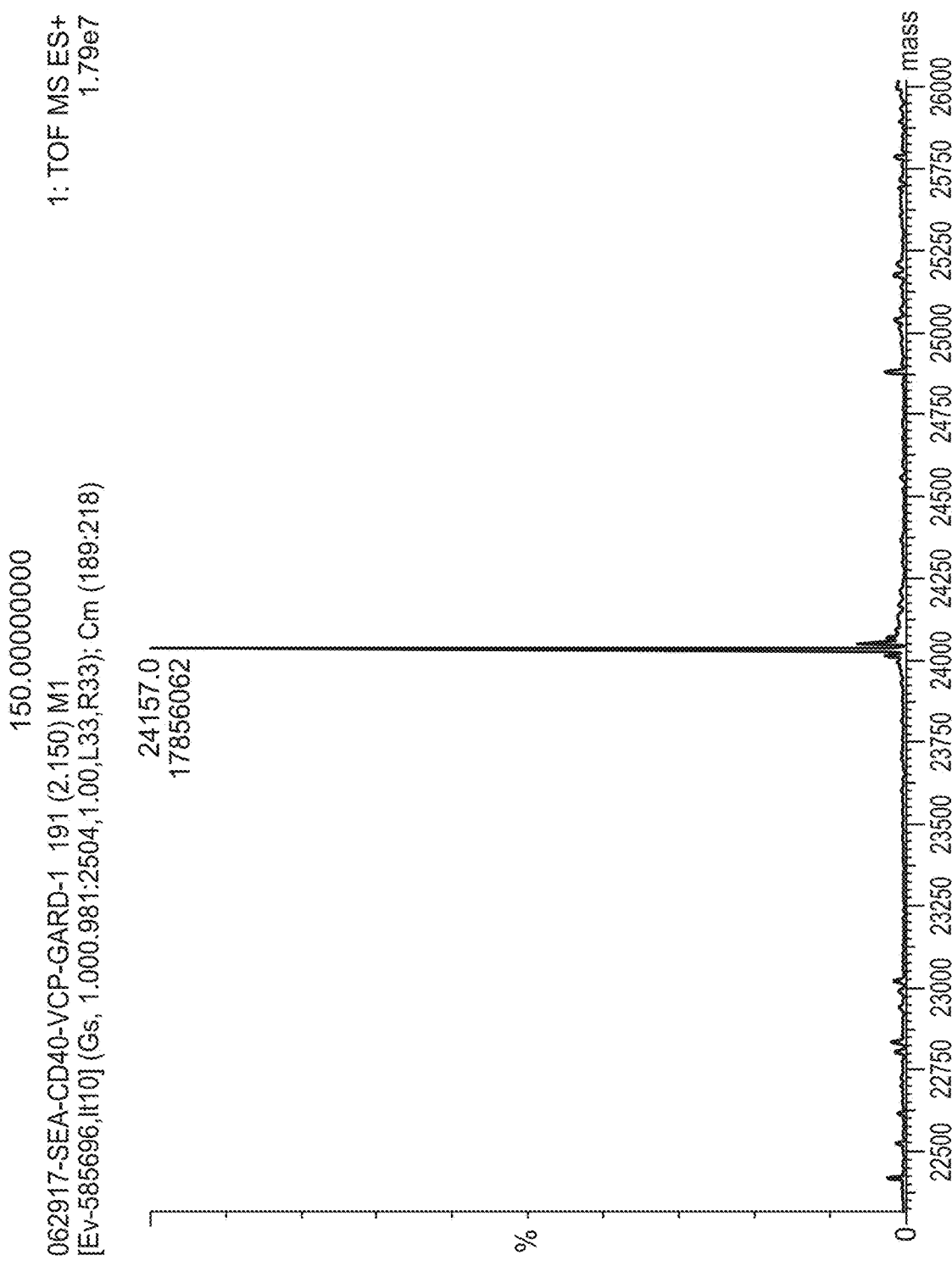

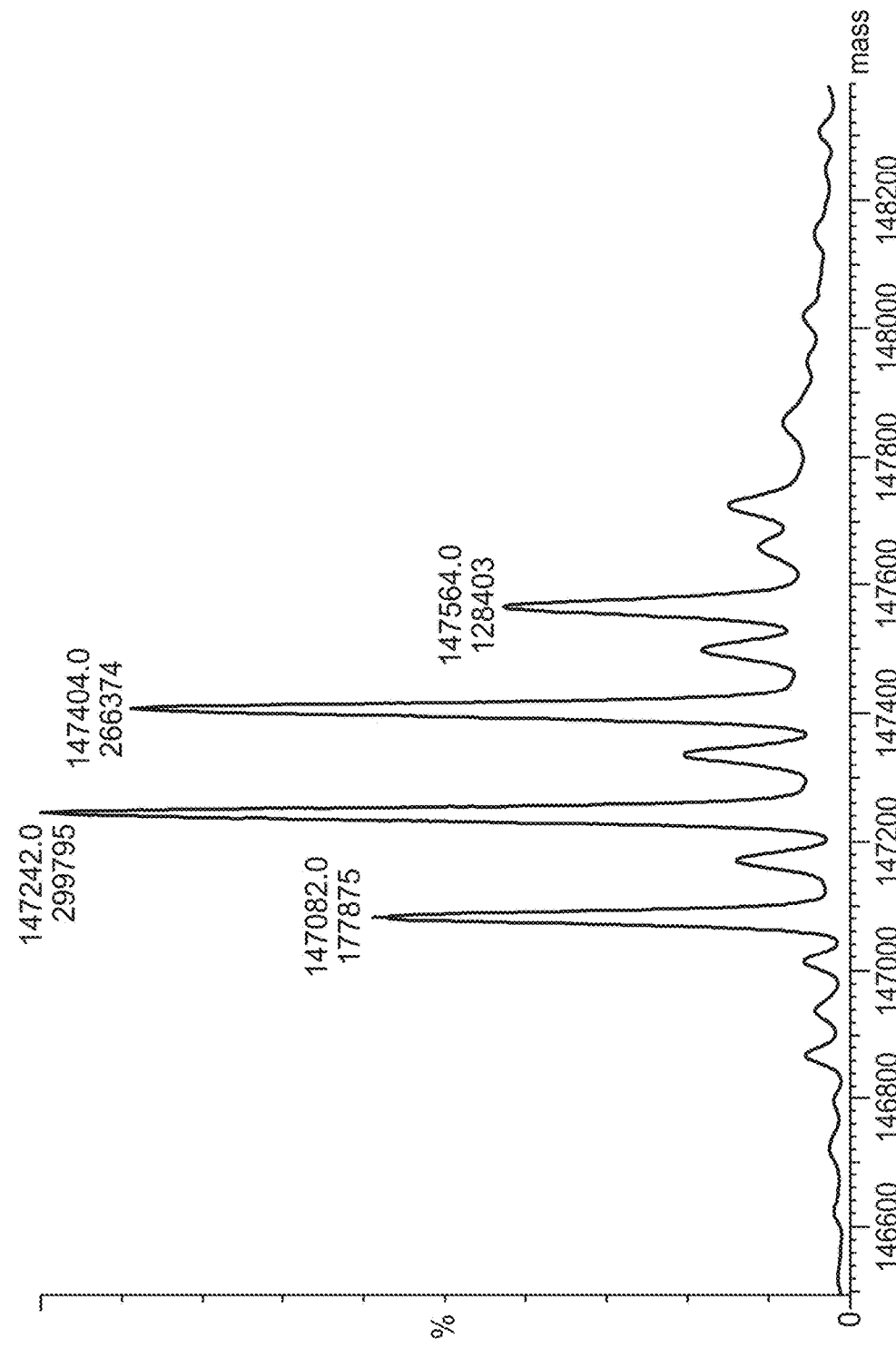

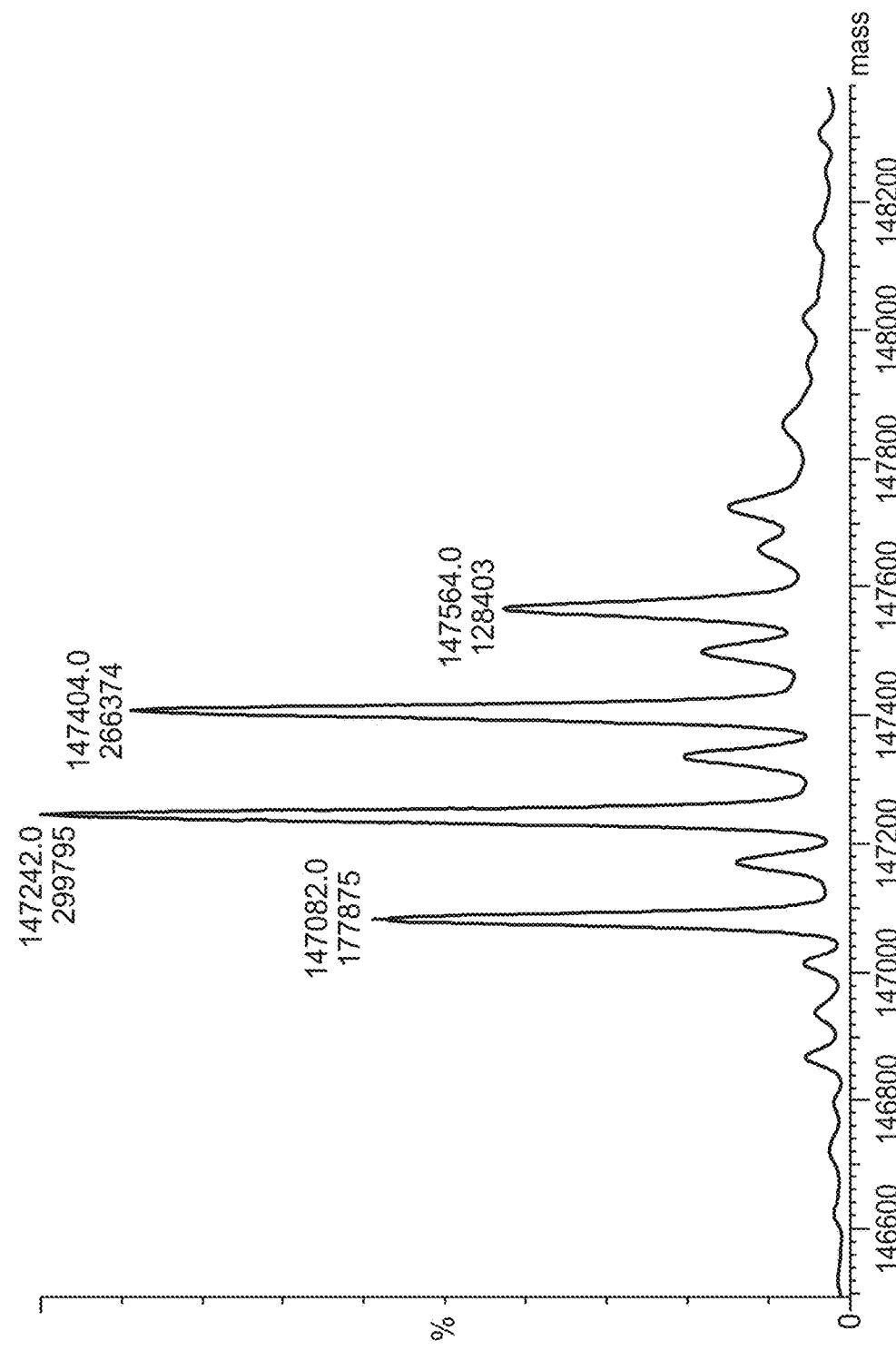

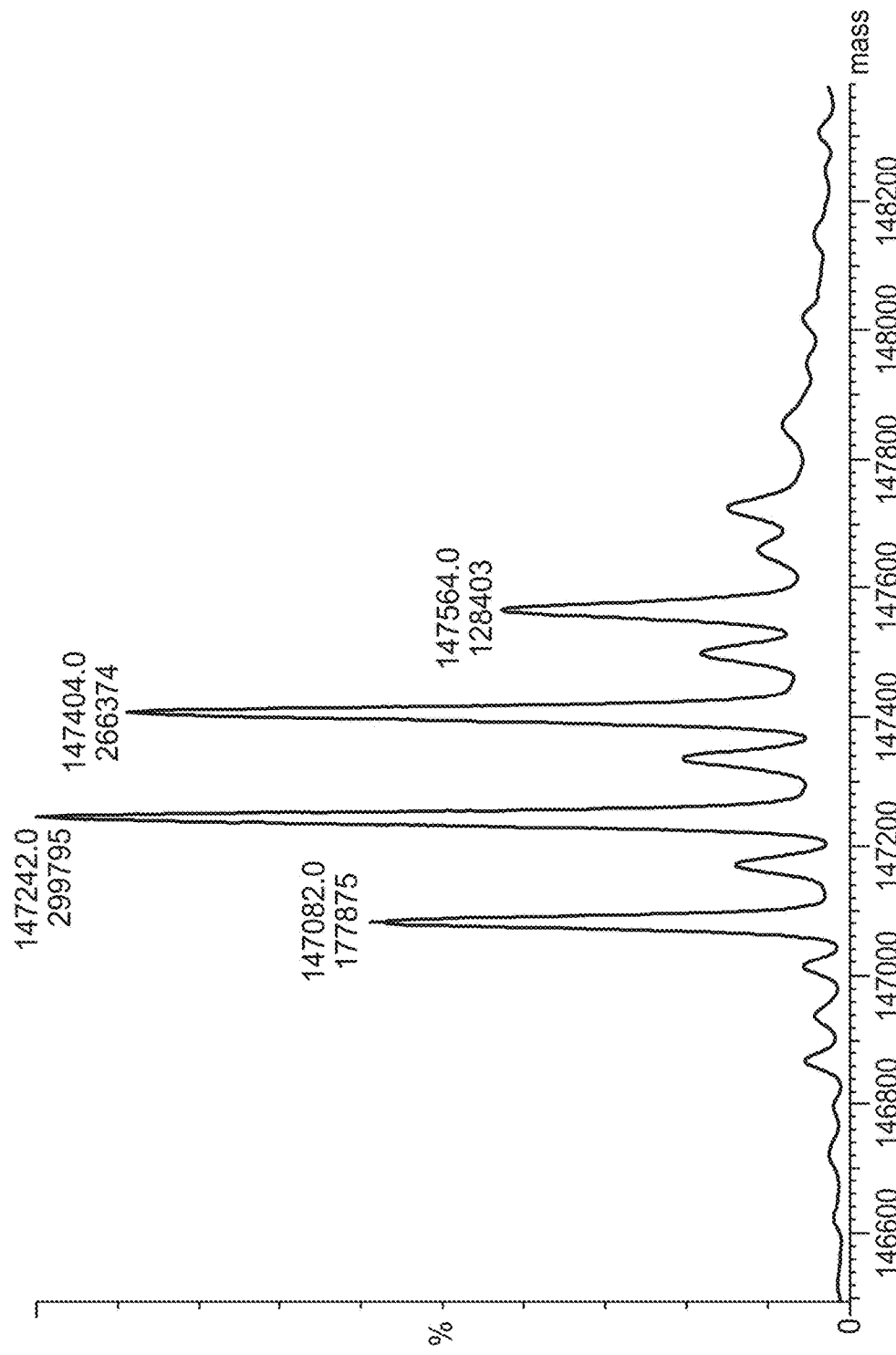

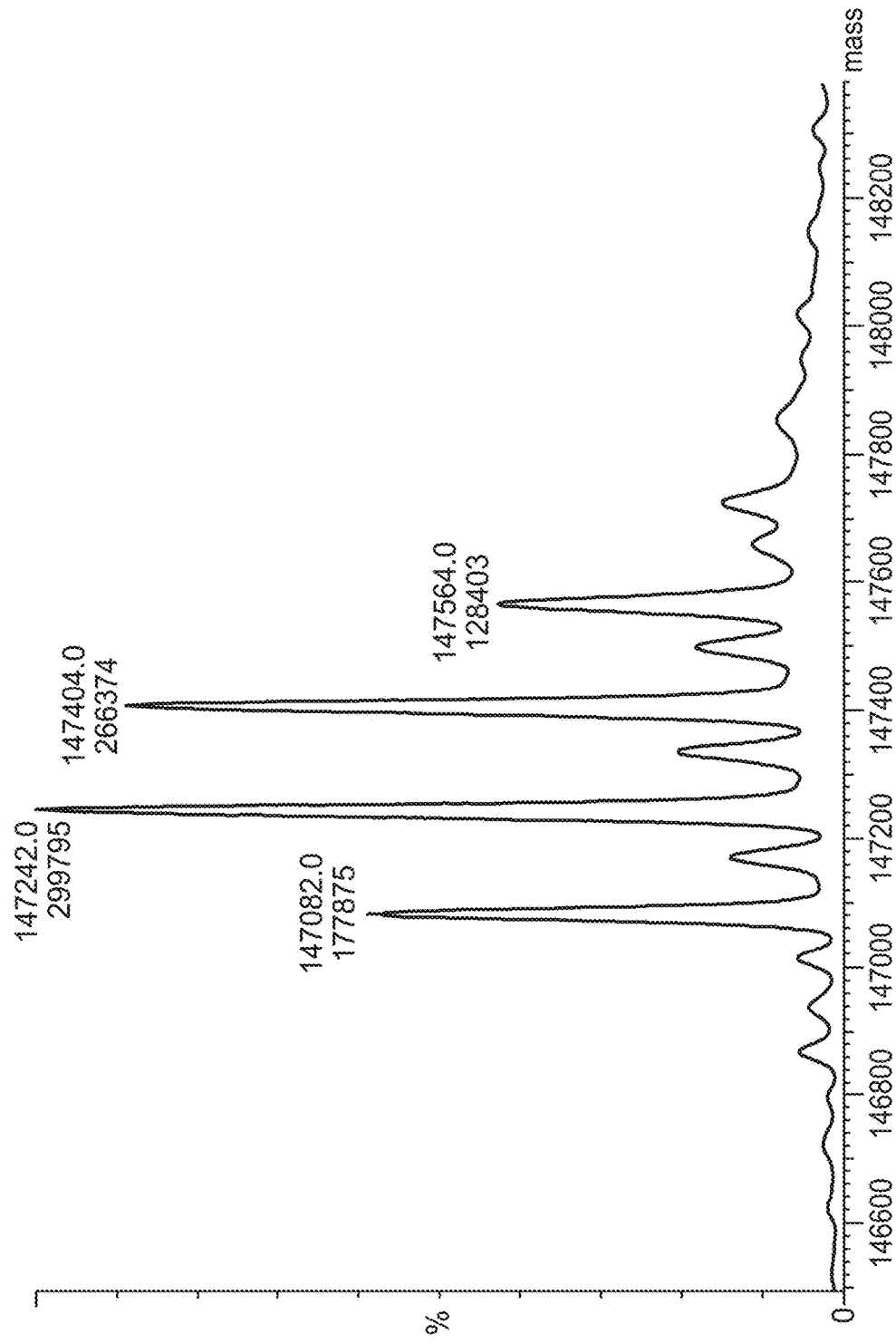

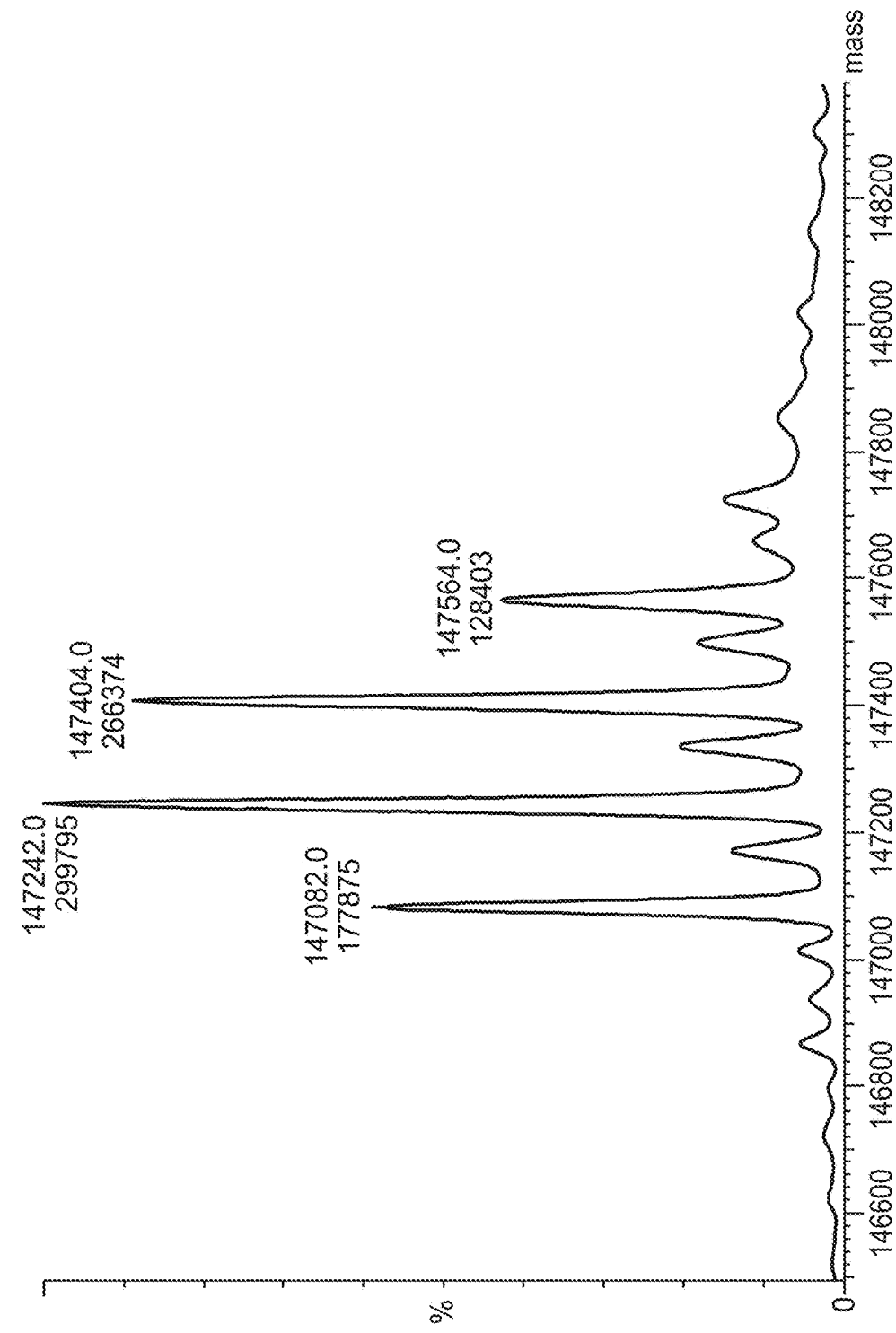

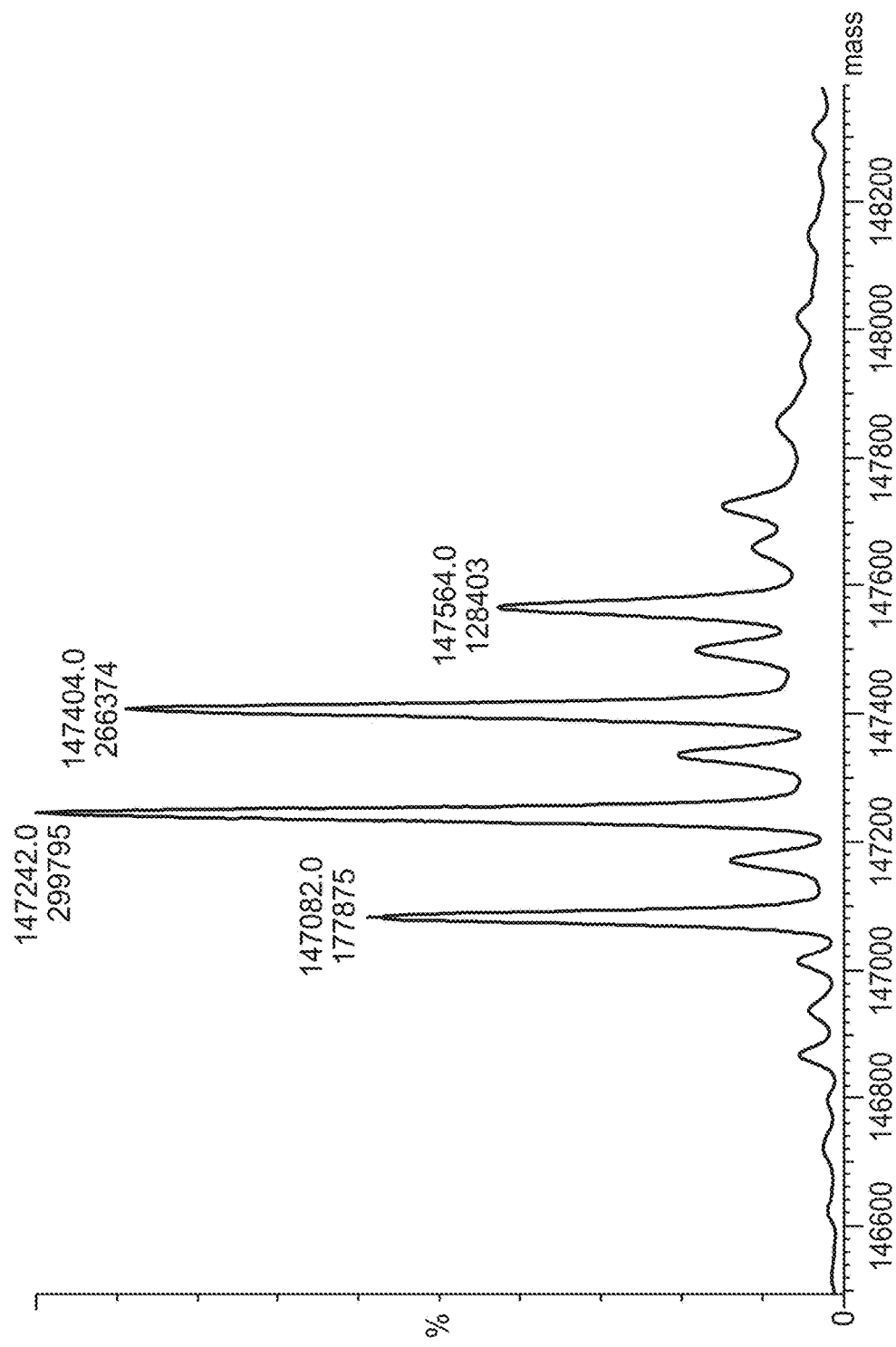

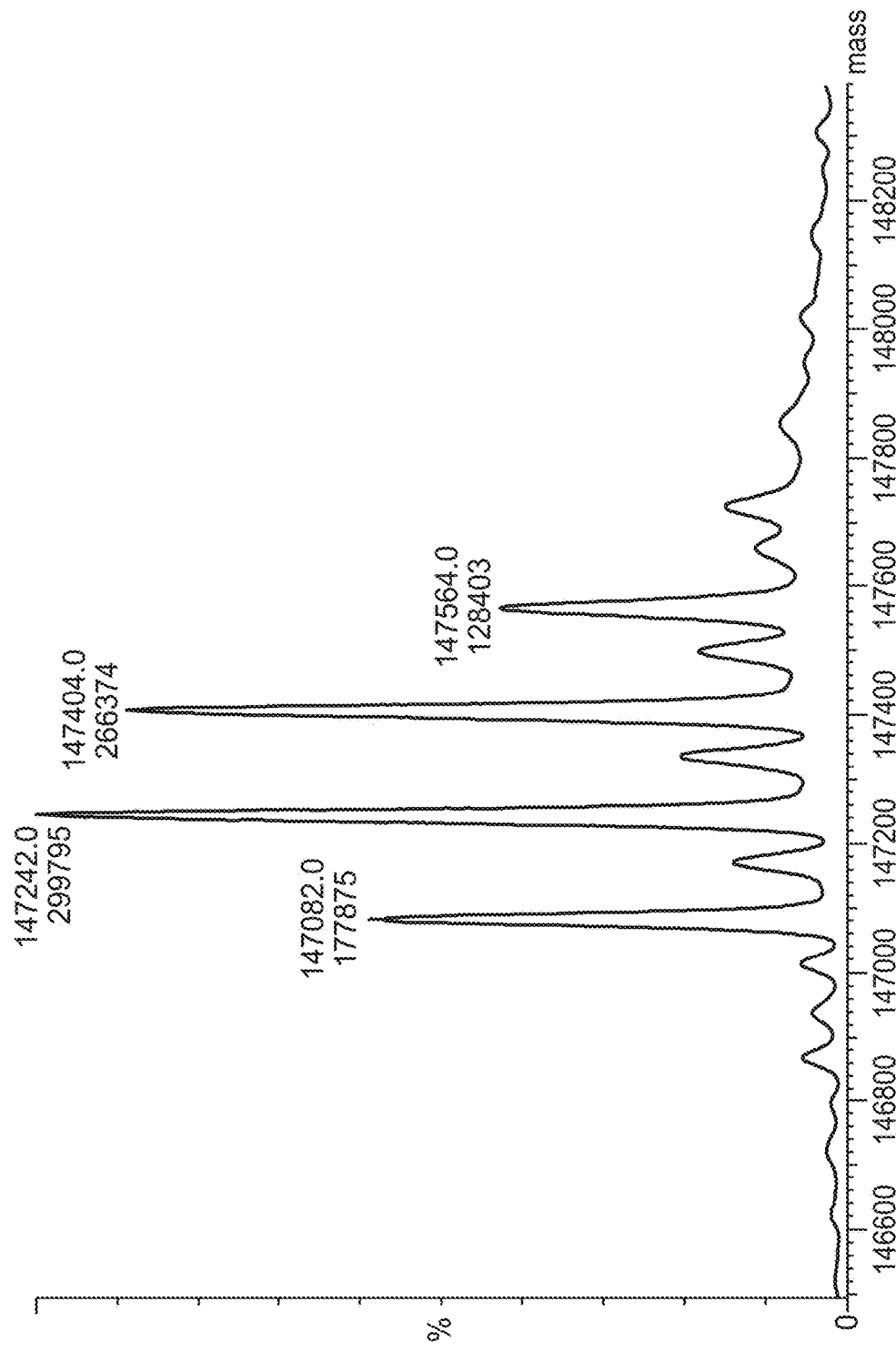

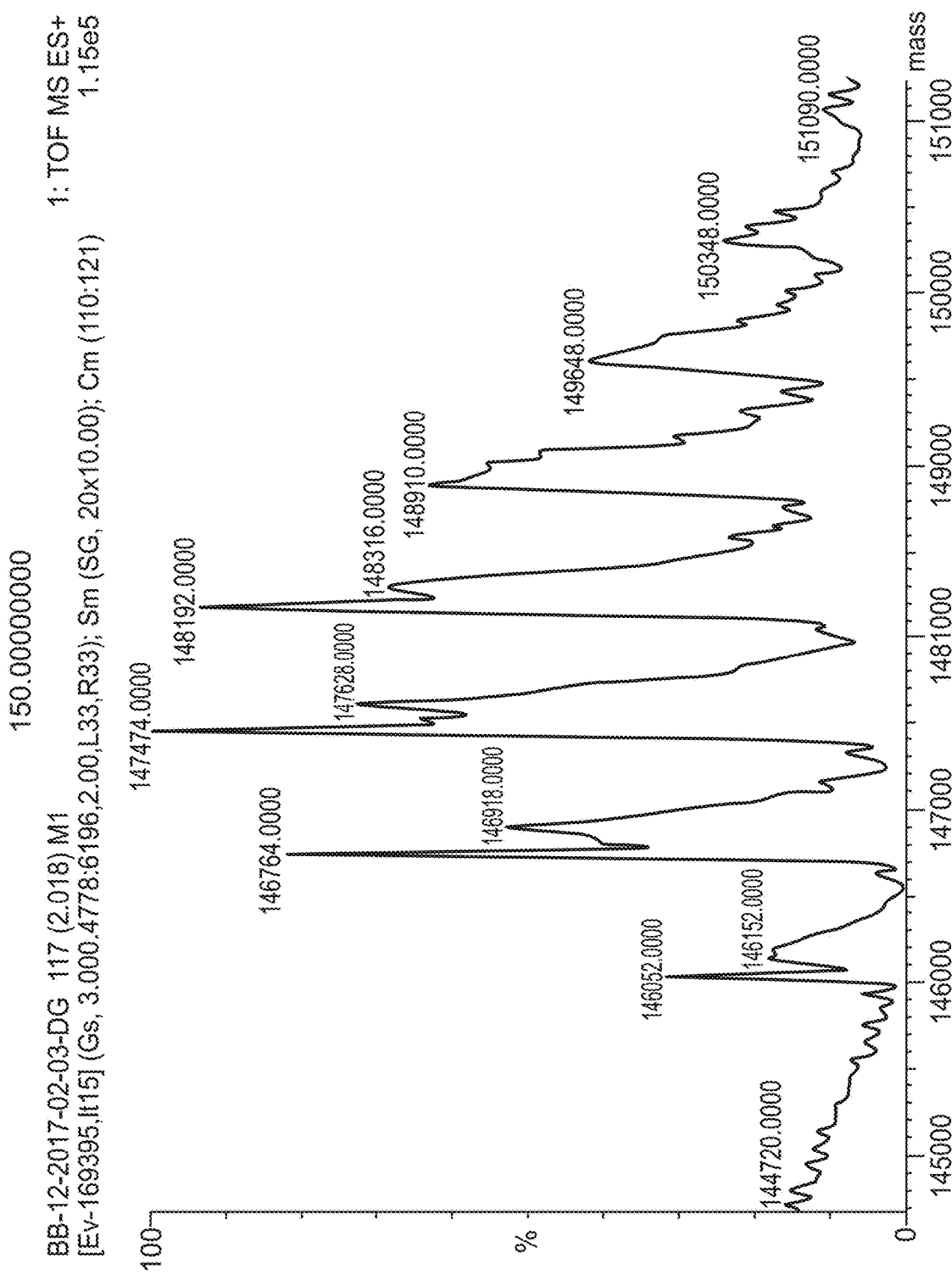

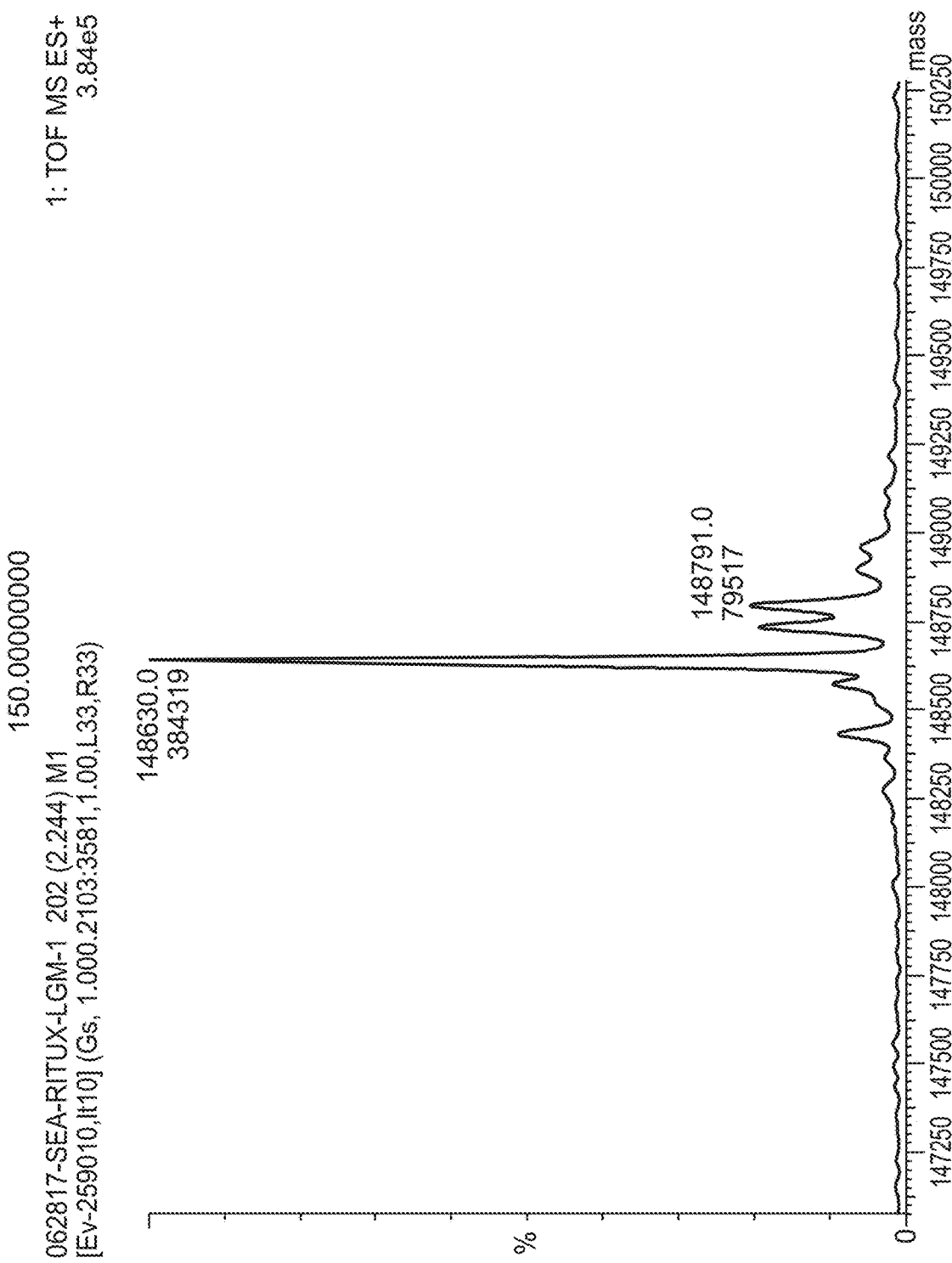

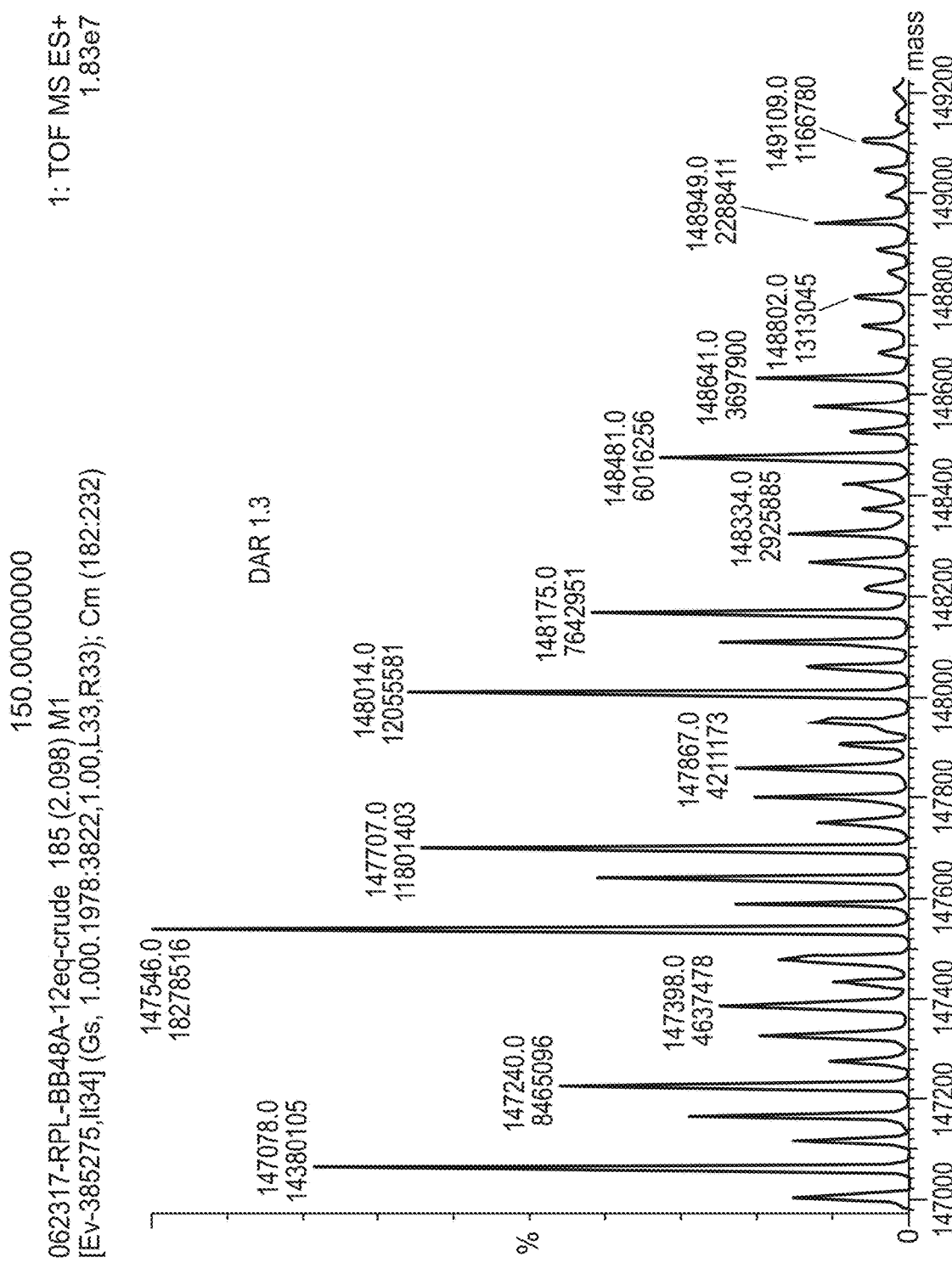

FIG. 138A

Heavy_withRituxInsert

```
1         10        20        30        40        50
|         |         |         |         |         |
GGATCTGCGATCGCTCCGGTGCCCGTCAGTGGGCAGAGCGCACATCGCCC
ACAGTCCCCGAGAAGTTGGGGGGAGGGGTCGGCAATTGAACGGGTGCCTA
GAGAAGGTGGCGCGGGGTAAACTGGGAAAGTGATGTCGTGTACTGGCTCC
GCCTTTTTCCCGAGGGTGGGGGAGAACCGTATATAAGTGCAGTAGTCGCC
GTGAACGTTCTTTTTCGCAACGGGTTTGCCGCCAGAACACAGCTGAAGCT
TCGAGGGGCTCGCATCTCTCCTTCACGCGCCCGCCGCCCTACCTGAGGCC
GCCATCCACGCCGGTTGAGTCGCGTTCTGCCGCCTCCCGCCTGTGGTGCC
TCCTGAACTGCGTCCGCCGTCTAGGTAAGTTTAAAGCTCAGGTCGAGACC
GGGCCTTTGTCCGGCGCTCCCTTGGAGCCTACCTAGACTCAGCCGGCTCT
CCACGCTTTGCCTGACCCTGCTTGCTCAACTCTACGTCTTTGTTTCGTTT
TCTGTTCTGCGCCGTTACAGATCCAAGCTGTGACCGGCGCCTACCTGAGA
TCACCGGTGAATTCCTGAGATCACCGGCGAAGGAGGGCCACCATGTACAG
GATGCAACTCCTGTCTTGCATTGCACTAAGTCTTGCACTTGTCACGCAGG
TGCAGCTGCAGCAGCCCGGAGCGGAATTGGTGAAGCCAGGCGCTTCCGTG
AAAATGAGTTGCAAGGCCTCCGGATATACCTTTACCTCTTACAACATGCA
TTGGGTGAAACAGACTCCTGGTCGTGGCCTGGAATGGATCGGAGCTATTT
ACCCTGGAAACGGTGACACTTCCTACAACCAGAAATTCAAGGGCAAGGCG
ACCCTGACCGCAGATAAGTCCAGCAGCACCGCCTACATGCAGCTGAGCTC
TCTGACTAGCGAAGACAGCGCTGTCTACTATTGCGCCCGCTCCACTTACT
ACGGCGGTGACTGGTACTTCAACGTGTGGGGGCCGGCACTACCGTGACT
GTGTCTGCGGCTAGCACCAAGGGCCCATCGGTCTTCCCCCTGGCACCCTC
CTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACC
AGCGGCGTGCACACCTTCCCGGCTGTCCTACAGTCCTCAGGACTCTACTC
CCTCAGCAGCGTGGTGACCGTGCCCTCCAGCAGCTTGGGCACCCAGACCT
ACATCTGCAACGTGAATCACAAGCCCAGCAACACCAAGGTGGACAAGAAA
GTTGAGCCCAAATCTTGTGACAAAACTCACACATGCCCACCGTGCCCAGC
ACCTGAACTCCTGGGGGGACCGTCAGTCTTCCTCTTCCCCCCAAAACCCA
AGGACACCCTCATGATCTCCCGGACCCCTGAGGTCACATGCGTGGTGGTG
GACGTGAGCCACGAAGACCCTGAGGTCAAGTTCAACTGGTACGTGGACGG
CGTGGAGGTGCATAATGCCAAGACAAAGCCGCGGGAGGAGCAGTACAACA
GCACGTACCGTGTGGTCAGCGTCCTCACCGTCCTGCACCAGGACTGGCTG
AATGGCAAGGAGTACAAGTGCAAGGTCTCCAACAAAGCCCTCCCAGCCCC
CATCGAGAAAACCATCTCCAAAGCCAAAGGGCAGCCCCGAGAACCACAGG
TGTACACCCTGCCCCCATCCCGGGAGGAGATGACCAAGAACCAGGTCAGC
CTGACCTGCCTGGTCAAAGGCTTCTATCCCAGCGACATCGCCGTGGAGTG
GGAGAGCAATGGGCAGCCGGAGAACAACTACAAGACCACGCCTCCCGTGC
TGGACTCCGACGGCTCCTTCTTCCTCTACAGCAAGCTCACCGTGGACAAG
AGCAGGTGGCAGCAGGGGAACGTCTTCTCATGCTCCGTGATGCATGAGGC
TCTGCACAACCACTACACGCAGAAGAGCCTCTCCCTGTCTCCGGGTAAAT
GAGTCCTAGCTGGCCAGACATGATAAGATACATTGATGAGTTTGGACAAA
CCACAACTAGAATGCAGTGAAAAAATGCTTTATTTGTGAAATTTGTGAT
GCTATTGCTTTATTTGTAACCATTATAAGCTGCAATAAACAAGTTAACAA
CAACAATTGCATTCATTTTATGTTTCAGGTTCAGGGGGAGGTGTGGGAGG
TTTTTTAAAGCAAGTAAAACCTCTACAAATGTGGTATGGAATTAATTCTA
AAATACAGCATAGCAAAACTTTAACCTCCAAATCAAGCCTCTACTTGAAT
CCTTTTCTGAGGGATGAATAAGGCATAGGCATCAGGGGCTGTTGCCAATG
TGCATTAGCTGTTTGCAGCCTCACCTTCTTTCATGGAGTTTAAGATATAG
```

FIG. 138A
(Cont.)

TGTATTTTCCCAAGGTTTGAACTAGCTCTTCATTTCTTTATGTTTTAAAT
GCACTGACCTCCCACATTCCCTTTTTAGTAAAATATTCAGAAATAATTTA
AATACATCATTGCAATGAAAATAAATGTTTTTTATTAGGCAGAATCCAGA
TGCTCAAGGCCCTTCATAATATCCCCAGTTTAGTAGTTGGACTTAGGGA
ACAAAGGAACCTTTAATAGAAATTGGACAGCAAGAAAGCGAGCTTCTAGC
TTATCCTCAGTCCTGCTCCTCTGCCACAAAGTGCACGCAGTTGCCGGCCG
GGTCGCGCAGGGCGAACTCCCGCCCCACGGCTGCTCGCCGATCTCGGTC
ATGGCCGGCCCGGAGGCGTCCGGAAGTTCGTGGACACGACCTCCGACCA
CTCGGCGTACAGCTCGTCCAGGCCGCGCACCCACACCCAGGCCAGGGTGT
TGTCCGGCACCACCTGGTCCTGGACCGCGCTGATGAACAGGGTCACGTCG
TCCCGGACCACACCGGCGAAGTCGTCCTCCACGAAGTCCCGGGAGAACCC
GAGCCGGTCGGTCCAGAACTCGACCGCTCCGGCGACGTCGCGCGCGGTGA
GCACCGGAACGGCACTGGTCAACTTGGCCATGATGGCTCCTCCTGTCAGG
AGAGGAAAGAGAAGAAGGTTAGTACAATTGCTATAGTGAGTTGTATTATA
CTATGCAGATATACTATGCCAATGATTAATTGTCAAACTAGGGCTGCAGG
GTTCATAGTGCCACTTTTCCTGCACTGCCCCATCTCCTGCCCACCCTTTC
CCAGGCATAGACAGTCAGTGACTTACCAAACTCACAGGAGGGAGAAGGCA
GAAGCTTGAGACAGACCCGCGGGACCGCCGAACTGCGAGGGGACGTGGCT
AGGGCGGCTTCTTTTATGGTGCGCCGGCCCTCGGAGGCAGGGCGCTCGGG
GAGGCCTAGCGGCCAATCTGCGGTGGCAGGAGGCGGGGCCGAAGGCCGTG
CCTGACCAATCCGGAGCACATAGGAGTCTCAGCCCCCGCCCCAAAGCAA
GGGAAGTCACGCGCCTGTAGCGCCAGCGTGTTGTGAAATGGGGGCTTGG
GGGGGTTGGGGCCCTGACTAGTCAAAACAAACTCCCATTGACGTCAATGG
GGTGGAGACTTGGAAATCCCCGTGAGTCAAACCGCTATCCACGCCCATTG
ATGTACTGCCAAAACCGCATCATCATGGTAATAGCGATGACTAATACGTA
GATGTACTGCCAAGTAGGAAAGTCCCATAAGGTCATGTACTGGGCATAAT
GCCAGGCGGGCCATTTACCGTCATTGACGTCAATAGGGGGCGTACTTGGC
ATATGATACACTTGATGTACTGCCAAGTGGGCAGTTTACCGTAAATACTC
CACCCATTGACGTCAATGGAAAGTCCCTATTGGCGTTACTATGGGAACAT
ACGTCATTATTGACGTCAATGGGCGGGGGTCGTTGGGCGGTCAGCCAGGC
GGGCCATTTACCGTAAGTTATGTAACGCCTGCAGGTTAATTAAGAACATG
TGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGAC
GCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATC
CGGTAACTATCGTCTTGAGTCCAACCCGGTAAGACACGACTTATCGCCAC
TGGCAGCAGCCACTGGTAACAGGATTAGCAGAGCGAGGTATGTAGGCGGT
GCTACAGAGTTCTTGAAGTGGTGGCCTAACTACGGCTACACTAGAAGAAC
AGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCAC
GTTAAGGGATTTTGGTCATGCTAGTTAATTAACATTTAAATCAGCGGCC
GCAATAAAATATCTTTATTTTCATTACATCTGTGTGTTGGTTTTTTGTGT
GAATCGTAACTAACATACGCTCTCCATCAAAACAAAACGAAACAAAACAA
ACTAGCAAAATAGGCTGTCCCCAGTGCAAGTGCAGGTGCCAGAACATTTC
TCTATCGAA

FIG. 138B

LC-V205C_withRituxInsert

```
1         10        20        30        40        50
|         |         |         |         |         |
GGATCTGCGATCGCTCCGGTGCCCGTCAGTGGGCAGAGCGCACATCGCCC
ACAGTCCCCGAGAAGTTGGGGGGAGGGGTCGGCAATTGAACGGGTGCCTA
GAGAAGGTGGCGCGGGGTAAACTGGGAAAGTGATGTCGTGTACTGGCTCC
GCCTTTTTCCCGAGGGTGGGGGAGAACCGTATATAAGTGCAGTAGTCGCC
GTGAACGTTCTTTTTCGCAACGGGTTTGCCGCCAGAACACAGCTGAAGCT
TCGAGGGGCTCGCATCTCTCCTTCACGCGCCCGCCGCCCTACCTGAGGCC
GCCATCCACGCCGGTTGAGTCGCGTTCTGCCGCCTCCCGCCTGTGGTGCC
TCCTGAACTGCGTCCGCCGTCTAGGTAAGTTTAAAGCTCAGGTCGAGACC
GGGCCTTTGTCCGGCGCTCCCTTGGAGCCTACCTAGACTCAGCCGGCTCT
CCACGCTTTGCCTGACCCTGCTTGCTCAACTCTACGTCTTTGTTTCGTTT
TCTGTTCTGCGCCGTTACAGATCCAAGCTGTGACCGGCGCCTACCTGAGA
TCACCGGTACATGTACAGGATGCAACTCCTGTCTTGCATTGCACTAAGTC
TTGCACTTGTCACGAATTCACAAATCGTCCTCTCCCAGAGCCCCGCAATC
CTGAGCGCCAGCCCCGGGGAGAAGGTGACCATGACCTGCCGCGCCTCTAG
CAGTGTGTCCTACATTCACTGGTTCCAGCAAAAGCCGGGCAGTTCTCCAA
AGCCCTGGATTTATGCCACATCTAACCTGGCCTCTGGGGTGCCAGTTAGG
TTTTCCGGCAGCGGCTCCGGCACATCTTACAGCCTCACCATTTCTAGAGT
TGAGGCAGAGGACGCCGCTACCTATTATTGTCAGCAGTGGACCAGTAACC
CGCCTACCTTTGGAGGCGGCACCAAACTGGAGATTAAACGTACGGTGGCT
GCACCATCTGTCTTCATCTTCCCGCCATCTGATGAGCAGTTGAAATCTGG
AACTGCCTCTGTTGTGTGCCTGCTGAATAACTTCTATCCCAGAGAGGCCA
AAGTACAGTGGAAGGTGGATAACGCCCTCCAATCGGGTAACTCCCAGGAG
AGTGTCACAGAGCAGGACAGCAAGGACAGCACCTACAGCCTCAGCAGCAC
CCTGACGCTGAGCAAAGCAGACTACGAGAAACACAAAGTCTACGCCTGCG
AAGTCACCCATCAGGGCCTGAGCTCGCCCTGCACAAAGAGCTTCAACAGG
GGAGAGTGTTAGAGGGAGCTAGCTCGACATGATAAGATACATTGATGAGT
TTGGACAAACCACAACTAGAATGCAGTGAAAAAATGCTTTATTTGTGAA
ATTTGTGATGCTATTGCTTTATTTGTGAAATTTGTGATGCTATTGCTTTA
TTTGTAACCATTATAAGCTGCAATAAACAAGTTAACAACAACAATTGCAT
TCATTTTATGTTTCAGGTTCAGGGGGAGGTGTGGGAGGTTTTTTAAAGCA
AGTAAAACCTCTACAAATGTGGTATGGAATTAATTCTAAAATACAGCATA
GCAAACTTTAACCTCCAAATCAAGCCTCTACTTGAATCCTTTTCTGAGG
GATGAATAAGGCATAGGCATCAGGGGCTGTTGCCAATGTGCATTAGCTGT
TGCAGCCTCACCTTCTTTCATGGAGTTTAAGATATAGTGTATTTTCCCA
AGGTTTGAACTAGCTCTTCATTTCTTTATGTTTAAATGCACTGACCTCC
CACATTCCCTTTTAGTAAAATATTCAGAAATAATTTAAATACATCATTG
CAATGAAAATAAATGTTTTTTATTAGGCAGAATCCAGATGCTCAAGGCCC
TTCATAATATCCCCCAGTTTAGTAGTTGGACTTAGGGAACAAAGGAACCT
TTAATAGAAATTGGACAGCAAGAAAGCGAGCTTCTAGCTTTAGTTCCTGG
TGTACTTGAGGGGATGAGTTCCTCAATGGTGGTTTTGACCAGCTTGCCA
TTCATCTCAATGAGCACAAAGCAGTCAGGAGCATAGTCAGAGATGAGCTC
```

FIG. 138B (Cont.)

```
TCTGCACATGCCACAGGGGCTGACCACCCTGATGGATCTGTCCACCTCAT
CAGAGTAGGGGTGCCTGACAGCCACAATGGTGTCAAAGTCCTTCTGCCCG
TTGCTCACAGCAGACCCAATGGCAATGGCTTCAGCACAGACAGTGACCCT
GCCAATGTAGGCCTCAATGTGGACAGCAGAGATGATCTCCCCAGTCTTGG
TCCTGATGGCCGCCCGACATGGTGCTTGTTGTCCTCATAGAGCATGGTG
ATCTTCTCAGTGGCGACCTCCACCAGCTCCAGATCCTGCTGAGAGATGTT
GAAGGTCTTCATGATGGCTCCTCCTGTCAGGAGAGGAAAGAGAAGAAGGT
TAGTACAATTGCTATAGTGAGTTGTATTATACTATGCTTATGATTAATTG
TCAAACTAGGGCTGCAGGGTTCATAGTGCCACTTTTCCTGCACTGCCCCA
TCTCCTGCCCACCCTTTCCCAGGCATAGACAGTCAGTGACTTACCAAACT
CACAGGAGGGAGAAGGCAGAAGCTTGAGACAGACCCGCGGGACCGCCGAA
CTGCGAGGGGACGTGGCTAGGGCGGCTTCTTTTATGGTGCGCCGGCCCTC
GGAGGCAGGGCGCTCGGGGAGGCCTAGCGGCCAATCTGCGGTGGCAGGAG
GCGGGGCCGAAGGCCGTGCCTGACCAATCCGGAGCACATAGGAGTCTCAG
CCCCCCGCCCCAAAGCAAGGGGAAGTCACGCGCCTGTAGCGCCAGCGTGT
TGTGAAATGGGGGCTTGGGGGGGTTGGGGCCCTGACTAGTCAAAACAAAC
TCCCATTGACGTCAATGGGGTGGAGACTTGGAAATCCCCGTGAGTCAAAC
CGCTATCCACGCCCATTGATGTACTGCCAAAACCGCATCATCATGGTAAT
AGCGATGACTAATACGTAGATGTACTGCCAAGTAGGAAAGTCCCATAAGG
TCATGTACTGGGCATAATGCCAGGCGGGCCATTTACCGTCATTGACGTCA
ATAGGGGCGTACTTGGCATATGATACACTTGATGTACTGCCAAGTGGGC
AGTTACCGTAAATACTCCACCCATTGACGTCAATGGAAAGTCCCTATTG
GCGTTACTATGGGAACATACGTCATTATTGACGTCAATGGGCGGGGTCG
TTGGGCGGTCAGCCAGGCGGGCCATTTACCGTAAGTTATGTAACGCCTGC
AGGTTAATTAAGAACATGTGAGCAAAAGGCCAGCAAAAGGCCAGGAACCG
TAAAAAGGCCGCGTTGCTGGCGTTTTCCATAGGCTCCGCCCCCTGACG
AGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAA
GACACGACTTATCGCCACTGGCAGCAGCCACTGGTAACAGGATTAGCAGA
GCGAGGTATGTAGGCGGTGCTACAGAGTTCTTGAAGTGGTGGCCTAACTA
CGGCTACACTAGAAGAACAGTATTTGGTATCTGCGCTCTGCTGAAGCCAG
TTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAA
AAAAGGATCTCAAGAAGATCCTTTGATCTTTTCTACGGGTCTGACGCTC
AGTGGAACGAAAACTCACGTTAAGGGATTTTGGTCATGGCTAGTTAATTA
ACATTTAAATCAGCGGCCGCAATAAAATATCTTTATTTTCATTACATCTG
TGTGTTGGTTTTTTGTGTGAATCGTAACTAACATACGCTCTCCATCAAAA
CAAAACGAAACAAAACAAACTAGCAAAATAGGCTGTCCCCAGTGCAAGTG
CAGGTGCCAGAACATTTCTCTATCGAA
```

Scheme 14

Scheme 15

Scheme 16

Scheme 17

Scheme 20

Scheme 21

Scheme 22

Scheme 23

Scheme 24

Scheme 25

Scheme 27

Scheme 28

SEQUENCE LISTING

```
<160> NUMBER OF SEQ ID NOS: 4

<210> SEQ ID NO 1
<211> LENGTH: 4859
<212> TYPE: DNA
<213> ORGANISM: Artificial Sequence
<220> FEATURE:
<223> OTHER INFORMATION: Synthetic sequence

<400> SEQUENCE: 1
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggtga attcctgaga tcaccggcga aggagggcca ccatgtacag     600
gatgcaactc ctgtcttgca ttgcactaag tcttgcactt gtcacgcagg tgcagctgca     660
gcagcccgga gcggaattgg tgaagccagg cgcttccgtg aaaatgagtt gcaaggcctc     720
cggatatacc tttacctctt acaacatgca ttgggtgaaa cagactcctg gtcgtggcct     780
ggaatggatc ggagctattt accctggaaa cggtgacact tcctacaacc agaaattcaa     840
gggcaaggcg accctgaccg cagataagtc cagcagcacc gcctacatgc agctgagctc     900
tctgactagc gaagacagcg ctgtctacta ttgcgcccgc tccacttact acggcggtga     960
ctggtacttc aacgtgtggg gggccggcac taccgtgact gtgtctgcgg ctagcaccaa    1020
gggcccatcg gtcttccccc tggcaccctc ctccaagagc acctctgggg gcacagcggc    1080
cctgggctgc ctggtcaagg actacttccc cgaaccggtg acggtgtcgt ggaactcagg    1140
cgccctgacc agcggcgtgc acaccttccc ggctgtccta cagtcctcag gactctactc    1200
```

```
cctcagcagc gtggtgaccg tgccctccag cagcttgggc acccagacct acatctgcaa    1260
cgtgaatcac aagcccagca acaccaaggt ggacaagaaa gttgagccca aatcttgtga    1320
caaaactcac acatgcccac cgtgcccagc acctgaactc ctggggggac cgtcagtctt    1380
cctcttcccc ccaaaaccca aggacaccct catgatctcc cggaccccctg aggtcacatg    1440 cgtggtggtg gacgtgagcc acgaagaccc tgaggtcaag ttcaactggt acgtggacgg    1500
cgtggaggtg cataatgcca agacaaagcc gcgggaggag cagtacaaca gcacgtaccg    1560
tgtggtcagc gtcctcaccg tcctgcacca ggactggctg aatggcaagg agtacaagtg    1620
caaggtctcc aacaaagccc tcccagcccc catcgagaaa accatctcca aagccaaagg    1680
gcagccccga gaaccacagg tgtacaccct gcccccatcc cggaggagag tgaccaagaa    1740
ccaggtcagc ctgacctgcc tggtcaaagg cttctatccc agcgacatcg ccgtggagtg    1800
ggagagcaat gggcagccgg agaacaacta caagaccacg cctcccgtgc tggactccga    1860
cggctccttc ttcctctaca gcaagctcac cgtggacaag agcaggtggc agcaggggaa    1920
cgtcttctca tgctccgtga tgcatgaggc tctgcacaac cactacacgc agaagagcct    1980
ctccctgtct ccgggtaaat gagtcctagc tggccagaca tgataagata cattgatgag    2040
tttggacaaa ccacaactag aatgcagtga aaaaaatgct ttatttgtga aatttgtgat    2100
gctattgctt tatttgtaac cattataagc tgcaataaac aagttaacaa caacaattgc    2160
attcatttta tgtttcaggt tcaggggggag gtgtgggagg ttttttaaag caagtaaaac    2220
ctctacaaat gtggtatgga attaattcta aaatacagca tagcaaaact ttaacctcca    2280
aatcaagcct ctacttgaat cctttttctga gggatgaata aggcataggc atcagggct    2340 gttgccaatg tgcattagct gtttgcagcc tcaccttctt tcatggagtt taagatatag    2400 tgtatttttcc caaggtttga actagctctt catttcttta tgttttaaat gcactgacct    2460
cccacattcc cttttttagta aaatattcag aaataattta aatacatcat tgcaatgaaa    2520
ataaatgttt tttattaggc agaatccaga tgctcaaggc ccttcataat atcccccagt    2580
ttagtagttg gacttaggga acaaaggaac ctttaataga aattggacag caagaaagcg    2640
agcttctagc ttatcctcag tcctgctcct ctgccacaaa gtgcacgcag ttgccggccg    2700
ggtcgcgcag ggcgaactcc cgcccccacg gctgctcgcc gatctcggtc atggccggcc    2760
cggaggcgtc ccggaagttc gtggacacga cctccgacca ctcggcgtac agctcgtcca    2820
ggccgcgcac ccacacccag gccagggtgt tgtccggcac cacctggtcc tggaccgcgc    2880
tgatgaacag ggtcacgtcg tcccggacca caccggcgaa gtcgtcctcc acgaagtccc    2940
gggagaaccc gagccggtcg gtccagaact cgaccgctcc ggcgacgtcg cgcgcggtga    3000
gcaccggaac ggcactggtc aacttggcca tgatggctcc tcctgtcagg agaggaaaga    3060
gaagaaggtt agtacaattg ctatagtgag ttgtattata ctatgcagat atactatgcc    3120
aatgattaat tgtcaaacta gggctgcagg gttcatagtg ccactttttcc tgcactgccc    3180 catctcctgc ccacccttttc ccaggcatag acagtcagtg acttaccaaa ctcacaggag    3240
ggagaaggca gaagcttgag acagacccgc gggaccgccg aactgcgagg ggacgtggct    3300
agggcggctt cttttatggt gcgccggccc tcggaggcag ggcgctcggg gaggcctagc    3360
ggccaatctg cggtggcagg aggcgggcc gaaggccgtg cctgaccaat ccggagcaca    3420
taggagtctc agccccccgc cccaaagcaa ggggaagtca cgcgcctgta gcgccagcgt    3480
gttgtgaaat ggggggcttgg gggggttggg gccctgacta gtcaaaacaa actcccattg    3540
```

| | |
|---|---|
| acgtcaatgg ggtggagact tggaaatccc cgtgagtcaa accgctatcc acgcccattg | 3600 |
| atgtactgcc aaaaccgcat catcatggta atagcgatga ctaatacgta gatgtactgc | 3660 |
| caagtaggaa agtcccataa ggtcatgtac tgggcataat gccaggcggg ccatttaccg | 3720 |
| tcattgacgt caatagggggg cgtacttggc atatgataca cttgatgtac tgccaagtgg | 3780 |
| gcagtttacc gtaaatactc cacccattga cgtcaatgga aagtccctat tggcgttact | 3840 |
| atgggaacat acgtcattat tgacgtcaat gggcgggggt cgttgggcgg tcagccaggc | 3900 |
| gggccattta ccgtaagtta tgtaacgcct gcaggttaat taagaacatg tgagcaaaag | 3960 |
| gccagcaaaa ggccaggaac cgtaaaaagg ccgcgttgct ggcgtttttc cataggctcc | 4020 |
| gccccctga cgagcatcac aaaaatcgac gctcaagtca gaggtggcga aacccgacag | 4080 |
| gactataaag ataccaggcg tttccccctg gaagctccct cgtgcgctct cctgttccga | 4140 |
| ccctgccgct taccggatac ctgtccgcct ttctcccttc gggaagcgtg gcgctttctc | 4200 |
| atagctcacg ctgtaggtat ctcagttcgg tgtaggtcgt tcgctccaag ctgggctgtg | 4260 |
| tgcacgaacc ccccgttcag cccgaccgct gcgccttatc cggtaactat cgtcttgagt | 4320 |
| ccaacccggt aagacacgac ttatcgccac tggcagcagc cactggtaac aggattagca | 4380 |
| gagcgaggta tgtaggcggt gctacagagt tcttgaagtg gtggcctaac tacggctaca | 4440 |
| ctagaagaac agtatttggt atctgcgctc tgctgaagcc agttaccttc ggaaaaagag | 4500 |
| ttggtagctc ttgatccggc aaacaaacca ccgctggtag cggtggtttt tttgtttgca | 4560 |
| agcagcagat tacgcgcaga aaaaaggat ctcaagaaga tcctttgatc ttttctacgg | 4620 |
| ggtctgacgc tcagtggaac gaaaactcac gttaagggat tttggtcatg ctagttaat | 4680 |
| taacatttaa atcagcggcc gcaataaaat atctttattt tcattacatc tgtgtgttgg | 4740 |
| ttttttgtgt gaatcgtaac taacatacgc tctccatcaa aacaaaacga aacaaaacaa | 4800 |
| actagcaaaa taggctgtcc ccagtgcaag tgcaggtgcc agaacatttc tctatcgaa | 4859 |

<210> SEQ ID NO 2
<211> LENGTH: 4177
<212> TYPE: DNA
<213> ORGANISM: Artificial Sequence
<220> FEATURE:
<223> OTHER INFORMATION: Synthetic sequence

<400> SEQUENCE: 2

| | |
|---|---|
| ggatctgcga tcgctccggt gcccgtcagt gggcagagcg cacatcgccc acagtccccg | 60 |
| agaagttggg gggaggggtc ggcaattgaa cgggtgccta gagaaggtgg cgcggggtaa | 120 |
| actgggaaag tgatgtcgtg tactggctcc gcctttttcc cgagggtggg ggagaaccgt | 180 |
| atataagtgc agtagtcgcc gtgaacgttc ttttcgcaa cgggtttgcc gccagaacac | 240 |
| agctgaagct tcgaggggct cgcatctctc cttcacgcgc ccgccgccct acctgaggcc | 300 |
| gccatccacg ccggttgagt cgcgttctgc cgcctcccgc ctgtggtgcc tcctgaactg | 360 |
| cgtccgccgt ctaggtaagt ttaaagctca ggtcgagacc gggcctttgt ccggcgctcc | 420 |
| cttggagcct acctagactc agccggctct ccacgctttg cctgaccctg cttgctcaac | 480 |
| tctacgtctt tgtttcgttt tctgttctgc gccgttacag atccaagctg tgaccggcgc | 540 |
| ctacctgaga tcaccggtac atgtacagga tgcaactcct gtcttgcatt gcactaagtc | 600 |
| ttgcacttgt cacgaattca caaatcgtcc tctcccagag cccgcaatc ctgagcgcca | 660 |
| gccccgggga gaaggtgacc atgacctgcc gcgcctctag cagtgtgtcc tacattcact | 720 |
| ggttccagca aaagccgggc agttctccaa agccctggat ttatgccaca tctaacctgg | 780 |

```
cctctggggt gccagttagg ttttccggca gcggctccgg cacatcttac agcctcacca    840
tttctagagt tgaggcagag gacgccgcta cctattattg tcagcagtgg accagtaacc    900
cgcctacctt tggaggcggc accaaactgg agattaaacg tacggtggct gcaccatctg    960
tcttcatctt cccgccatct gatgagcagt tgaaatctgg aactgcctct gttgtgtgcc   1020
tgctgaataa cttctatccc agagaggcca agtacagtg gaaggtggat aacgccctcc    1080
aatcgggtaa ctcccaggag agtgtcacag agcaggacag caaggacagc acctacagcc   1140
tcagcagcac cctgacgctg agcaaagcag actacgagaa acacaaagtc tacgcctgcg   1200
aagtcaccca tcagggcctg agctcgccct gcacaaagag cttcaacagg ggagagtgtt   1260
agagggagct agctcgacat gataagatac attgatgagt ttggacaaac cacaactaga   1320
atgcagtgaa aaaaatgctt tatttgtgaa atttgtgatg ctattgcttt atttgtgaaa   1380
tttgtgatgc tattgcttta tttgtaacca ttataagctg caataaacaa gttaacaaca   1440
acaattgcat tcattttatg tttcaggttc agggggaggt gtgggaggtt ttttaaagca   1500
agtaaaacct ctacaaatgt ggtatggaat taattctaaa atacagcata gcaaaacttt   1560
aacctccaaa tcaagcctct acttgaatcc ttttctgagg gatgaataag gcataggcat   1620
caggggctgt tgccaatgtg cattagctgt ttgcagcctc accttctttc atggagttta   1680
agatatagtg tattttccca aggtttgaac tagctcttca tttctttatg ttttaaatgc   1740
actgacctcc cacattccct ttttagtaaa atattcagaa ataatttaaa tacatcattg   1800
caatgaaaat aaatgttttt tattaggcag aatccagatg ctcaaggccc ttcataatat   1860
cccccagttt agtagttgga cttagggaac aaaggaacct taatagaaa ttggacagca    1920
agaaagcgag cttctagctt tagttcctgg tgtacttgag ggggatgagt tcctcaatgg   1980
tggttttgac cagcttgcca ttcatctcaa tgagcacaaa gcagtcagga gcatagtcag   2040
agatgagctc tctgcacatg ccacaggggc tgaccaccct gatggatctg tccacctcat   2100
cagagtaggg gtgcctgaca gccacaatgg tgtcaaagtc cttctgcccg ttgctcacag   2160
cagacccaat ggcaatggct tcagcacaga cagtgaccct gccaatgtag gcctcaatgt   2220
ggacagcaga gatgatctcc ccagtcttgg tcctgatggc cgccccgaca tggtgcttgt   2280
tgtcctcata gagcatggtg atcttctcag tggcgacctc caccagctcc agatcctgct   2340
gagagatgtt gaaggtcttc atgatggctc ctcctgtcag gagaggaaag agaagaaggt   2400
tagtacaatt gctatagtga gttgtattat actatgctta tgattaattg tcaaactagg   2460
gctgcagggt tcatagtgcc acttttcctg cactgcccca tctcctgccc acccttttccc   2520
aggcatagac agtcagtgac ttaccaaact cacaggaggg agaaggcaga agcttgagac   2580
agacccgcgg gaccgccgaa ctgcgagggg acgtggctag gcggcttct tttatggtgc    2640
gccggccctc ggaggcaggg cgctcgggga ggcctagcgg ccaatctgcg gtggcaggag   2700
gcggggccga aggccgtgcc tgaccaatcc ggagcacata ggagtctcag ccccccgccc   2760
caaagcaagg ggaagtcacg cgcctgtagc gccagcgtgt tgtgaaatgg gggcttgggg   2820
gggttggggc cctgactagt caaaacaaac tcccattgac gtcaatgggg tggagacttg   2880
gaaatccccg tgagtcaaac cgctatccac gcccattgat gtactgccaa accgcatca    2940
tcatggtaat agcgatgact aatacgtaga tgtactgcca agtaggaaag tcccataagg   3000
tcatgtactg ggcataatgc caggcggcc atttaccgtc attgacgtca atagggggcg    3060
tacttggcat atgatacact tgatgtactg ccaagtgggc agtttaccgt aaatactcca   3120
```

-continued

```
cccattgacg tcaatggaaa gtccctattg gcgttactat gggaacatac gtcattattg    3180
acgtcaatgg gcgggggtcg ttgggcggtc agccaggcgg gccatttacc gtaagttatg    3240
taacgcctgc aggttaatta agaacatgtg agcaaaaggc cagcaaaagg ccaggaaccg    3300
taaaaaggcc gcgttgctgg cgttttttcca taggctccgc ccccctgacg agcatcacaa    3360
aaatcgacgc tcaagtcaga ggtggcgaaa cccgacagga ctataaagat accaggcgtt    3420
tccccctgga agctccctcg tgcgctctcc tgttccgacc ctgccgctta ccggatacct    3480
gtccgccttt ctcccttcgg gaagcgtggc gctttctcat agctcacgct gtaggtatct    3540
cagttcggtg taggtcgttc gctccaagct gggctgtgtg cacgaacccc ccgttcagcc    3600
cgaccgctgc gccttatccg gtaactatcg tcttgagtcc aacccggtaa gacacgactt    3660
atcgccactg gcagcagcca ctggtaacag gattagcaga gcgaggtatg taggcggtgc    3720
tacagagttc ttgaagtggt ggcctaacta cggctacact agaagaacag tatttggtat    3780
ctgcgctctg ctgaagccag ttaccttcgg aaaaagagtt ggtagctctt gatccggcaa    3840
acaaaccacc gctggtagcg gtggtttttt tgtttgcaag cagcagatta cgcgcagaaa    3900
aaaaggatct caagaagatc ctttgatctt ttctacgggg tctgacgctc agtggaacga    3960
aaactcacgt taagggattt tggtcatggc tagttaatta acatttaaat cagcggccgc    4020
aataaaatat ctttattttc attacatctg tgtgttggtt ttttgtgtga atcgtaacta    4080
acatacgctc tccatcaaaa caaaacgaaa caaaacaaac tagcaaaata ggctgtcccc    4140
agtgcaagtg caggtgccag aacatttctc tatcgaa                             4177
```

<210> SEQ ID NO 3
<211> LENGTH: 19
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: the nucleotide at this position has a 5'
   triphosphate

<400> SEQUENCE: 3
gcaugcgacc ucuguuuga                                                 19

<210> SEQ ID NO 4
<211> LENGTH: 19
<212> TYPE: RNA
<213> ORGANISM: Artificial Sequence
<220> FEATURE:
<223> OTHER INFORMATION: Synthetic sequence

<400> SEQUENCE: 4
ucaaacagag gucgcaugc                                                 19

ANTIBODY ADJUVANT CONJUGATES

CROSS-REFERENCE TO RELATED APPLICATIONS

This patent application is a continuation of co-pending U.S. patent application Ser. No. 16/140,309, filed Sep. 24, 2018, which is a continuation of International Patent Application No. PCT/US2017/041268, filed on Jul. 7, 2017, which claims the benefit of U.S. Provisional Application 62/359,626, filed on Jul. 7, 2016, U.S. Provisional Application 62/359,627, filed on Jul. 7, 2016, U.S. Provisional Application 62/432,530, filed on Dec. 9, 2016, U.S. Provisional Application 62/433,742, filed on Dec. 13, 2016, U.S. Provisional Application 62/522,623, filed on Jun. 20, 2017, and U.S. Provisional Application 62/526,306, filed on Jun. 28, 2017, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: one 13 kilobyte file named "STAN-1340CON-SeqList-ST25.txt," created Mar. 12, 2020.

BACKGROUND OF THE INVENTION

It is now well appreciated that tumor growth necessitates the acquisition of mutations that facilitate immune evasion. Even so, tumorigenesis results in the accumulation of mutated antigens, or neoantigens, that are readily recognized by the host immune system following ex vivo stimulation. Why and how the immune system fails to recognize neoantigens are beginning to be elucidated. Groundbreaking studies by Carmi et al. (*Nature*, 521: 99-104 (2015)) have indicated that immune ignorance can be overcome by delivering neoantigens to activated dendritic cells via antibody-tumor immune complexes. In these studies, simultaneous delivery of tumor binding antibodies and dendritic cell adjuvants via intratumoral injections resulted in robust antitumor immunity. New compositions and methods for the delivery of antibodies and dendritic cell adjuvants are needed in order to reach inaccessible tumors and to expand treatment options for cancer patients and other subjects

BRIEF SUMMARY OF THE INVENTION

In a first aspect, the invention provides an immunoconjugate comprising (a) an antibody construct comprising (i) an antigen binding domain and (ii) an Fc domain, (b) an adjuvant moiety, and (c) a linker, wherein each adjuvant moiety is covalently bonded to the antibody construct via the linker.

In some embodiments, the immunoconjugate has a structure according to Formula I:

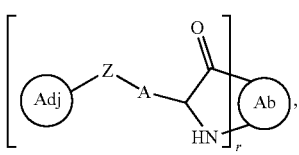

(I)

or a pharmaceutically acceptable salt thereof, wherein Ab is an antibody construct; A is an unmodified amino acid sidechain in the antibody construct or a modified amino acid sidechain in the antibody construct; Z is a linking moiety; Adj is an adjuvant moiety; and subscript r is an integer from 1 to 10.

In a related aspect, the invention provides a composition comprising a plurality of immunoconjugates as described herein.

In another aspect, the invention provides a method for treating cancer. The method includes administering a therapeutically effective amount of an immunoconjugate according to the invention to a subject in need thereof.

BRIEF DESCRIPTION OF THE DRAWINGS

The invention is best understood from the following detailed description when read in conjunction with the accompanying drawings. According to common practice, the various features of the drawings are not to-scale. On the contrary, the dimensions of the various features are arbitrarily expanded or reduced for clarity.

FIG. 8A shows that immunoconjugates with cleavable linkers elicit APC activation and DC differentiation. Human APCs that were ~95% monocytes were stimulated with 2-fold serial dilutions of Rituximab-SATA-SPDP-Compound 1 (Conjugated, cleavable), Rituximab alone (Ab), Compound 1 alone or Rituximab+Compound 1 (Mixture) in the presence of CFSE-labeled tumor cells. The immunoconjugate (AAC—cleavable) had a drug to antibody ratio (DAR) of 1.4 as confirmed by MALDI-TOF. After 18 hours, CD19– human APCs (CD14 and CD123) were analyzed via flow cytometry; n=3.

FIG. 8B shows that immunoconjugates (AACs) with cleavable linkers elicit APC activation and DC differentiation. Human APCs that were ~95% monocytes were stimulated with 2-fold serial dilutions of Rituximab-SATA-SPDP-Compound 1 (Conjugated, cleavable), Rituximab alone (Ab), Compound 1 alone or Rituximab+Compound 1 (Mixture) in the presence of CFSE-labeled tumor cells. The immunoconjugates (AAC—Cleavable) had a drug to antibody ratio (DAR) of 1.4 as confirmed by MALDI-TOF. After 18 hours, CD19– human APCs (CD16 and CD163) were analyzed via flow cytometry; n=3.

FIG. 8C shows that immunoconjugates with cleavable linkers elicit APC activation and DC differentiation. Human APCs that were ~95% monocytes were stimulated with 2-fold serial dilutions of Rituximab-SATA-SPDP-Compound 1 (Conjugated, cleavable), Rituximab alone (Ab), Compound 1 alone or Rituximab+Compound 1 (Mixture) in the presence of CFSE-labeled tumor cells. Immunoconjugates (AAC—Cleavable) had a drug to antibody ratio (DAR) of 1.4 as confirmed by MALDI-TOF. After 18 hours, CD19– human APCs (CD40 and PDL1) were analyzed via flow cytometry; n=3.

FIG. 9A shows that antibody-adjuvant conjugates reduce tumors in vivo. C57BL/6 mice with B 16F10 tumors in the right flank were injected intratumorally with PBS (Untreated), uGP75+Compound 1 (Mixture) or uGP75-SATA-SMCC-Compound 1 (uGP75-immunoconjugate).

FIG. 9B shows that αGP75-immunoconjugate reduces tumors in vivo when administered via intratumoral (IT) or intravenous (IV) injection.

FIG. 12A shows the analysis of nivolumab via LC-MS.

FIG. 22M shows the structure of adjuvant CL553 and the circle indicates a position on the adjuvant where it could be conjugated to the linker, specifically, another secondary amine of the adjuvant.

FIG. 22N shows the structure of adjuvant CL553 and the circle indicates a position on the adjuvant where it could be conjugated to the linker, specifically, another secondary amine of the adjuvant.

FIG. 38A shows BB-01 and BB-17 synthesized using the ester method elicits myeloid activation as indicated by CD14 downregulation while the control does not. CD20 is the unconjugated monoclonal antibody used as a control.

FIG. 38B shows BB-01 and BB-17 synthesized using the ester method elicits myeloid activation as indicated by CD16 downregulation while the control does not. CD20 is the unconjugated monoclonal antibody used as a control.

FIG. 41B shows a liquid chromatography-mass spectrometry analysis of immunoconjugate BB-26 synthesized using the ester method.

FIG. 43B shows a liquid chromatography-mass spectrometry analysis of immunoconjugate BB-36 synthesized using the ester method.

FIG. 45A shows a liquid chromatography-mass spectrometry analysis of IRM1 conjugate following overnight deglycosylation with PNGase F.

FIG. 47B shows a liquid chromatography-mass spectrometry analysis of immunoconjugate BB-24 synthesized using the ester method.

FIG. 48A shows a size-exclusion chromatography analysis of immunoconjugate BB-37 synthesized using the ester method.

FIG. 48B shows a liquid chromatography-mass spectrometry analysis of immunoconjugate BB-37 synthesized using the ester method.

FIG. 49A shows a size-exclusion chromatography analysis of immunoconjugate BB-42 synthesized using the ester method.

FIG. 49B shows a liquid chromatography-mass spectrometry analysis of immunoconjugate BB-42 synthesized using the ester method.

FIG. 50 shows a liquid chromatography-mass spectrometry analysis of immunoconjugate BB-43 synthesized using the ester method.

FIG. 51 shows a liquid chromatography-mass spectrometry analysis of immunoconjugate BB-44 synthesized using the ester method.

FIG. 52A shows that BB-14 elicits myeloid activation as indicated by CD14 downregulation while the control does not. CD20 is the unconjugated monoclonal antibody used as a control.

FIG. 52B shows that BB-14 elicits myeloid activation as indicated by CD40 upregulation while the control does not. CD20 is the unconjugated monoclonal antibody used as a control.

FIG. 52C shows that BB-14 elicits myeloid activation as indicated by CD86 upregulation while the control does not. CD20 is the unconjugated monoclonal antibody used as a control.

FIG. 52D shows that BB-14 elicits myeloid activation as indicated by HLA-DR upregulation while the control does do not. CD20 is the unconjugated monoclonal antibody used as a control.

FIG. 53A shows that BB-15 elicits myeloid activation as indicated by CD14 downregulation while the control does not. CD20 is the unconjugated monoclonal antibody used as a control.

FIG. 53B shows that BB-15 elicits myeloid activation as indicated by CD40 upregulation while the control does not. CD20 is the unconjugated monoclonal antibody used as a control.

Figure 53A:
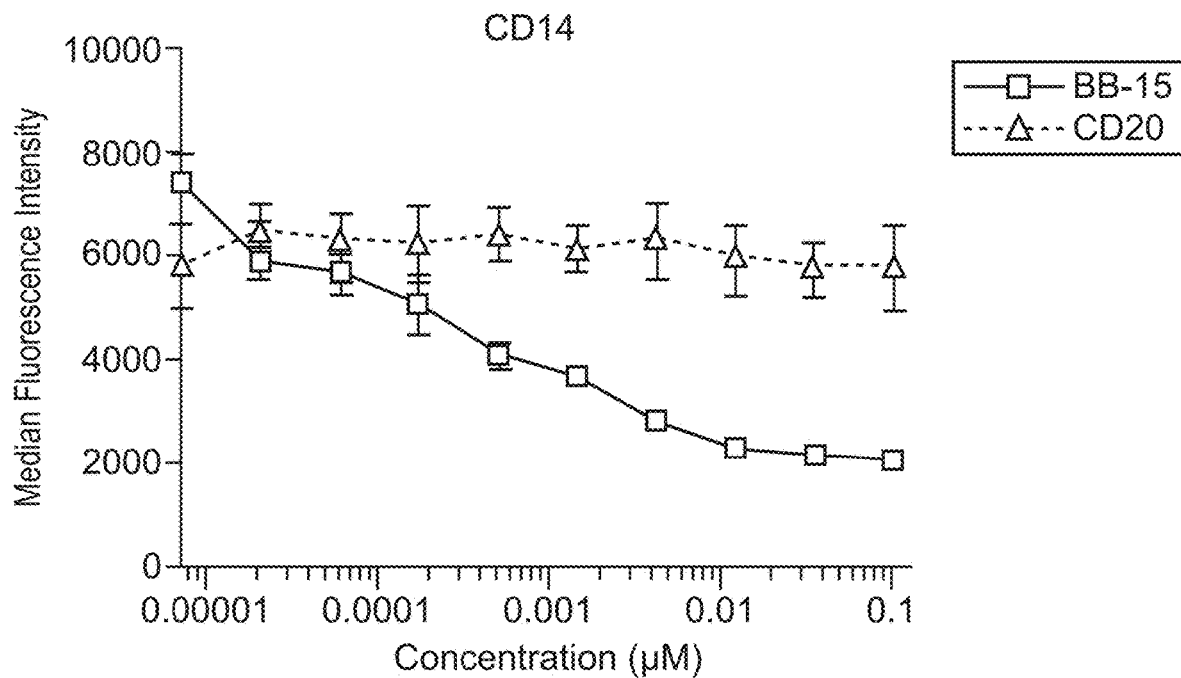
Figure 53B:
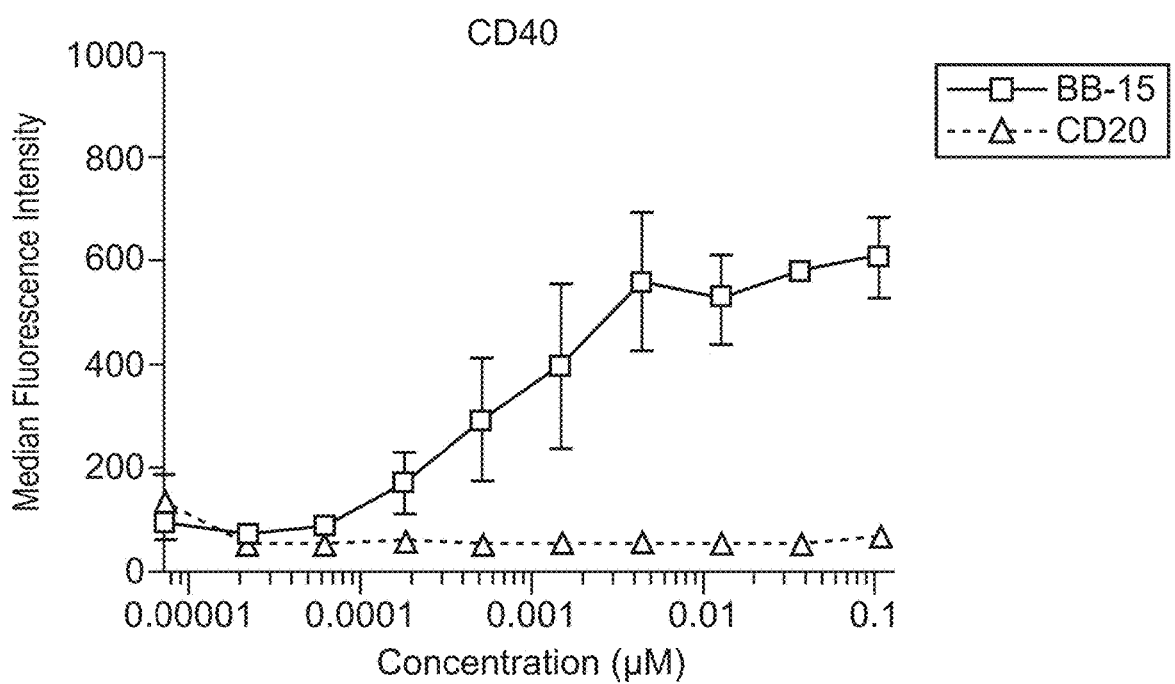
Figure 53C:
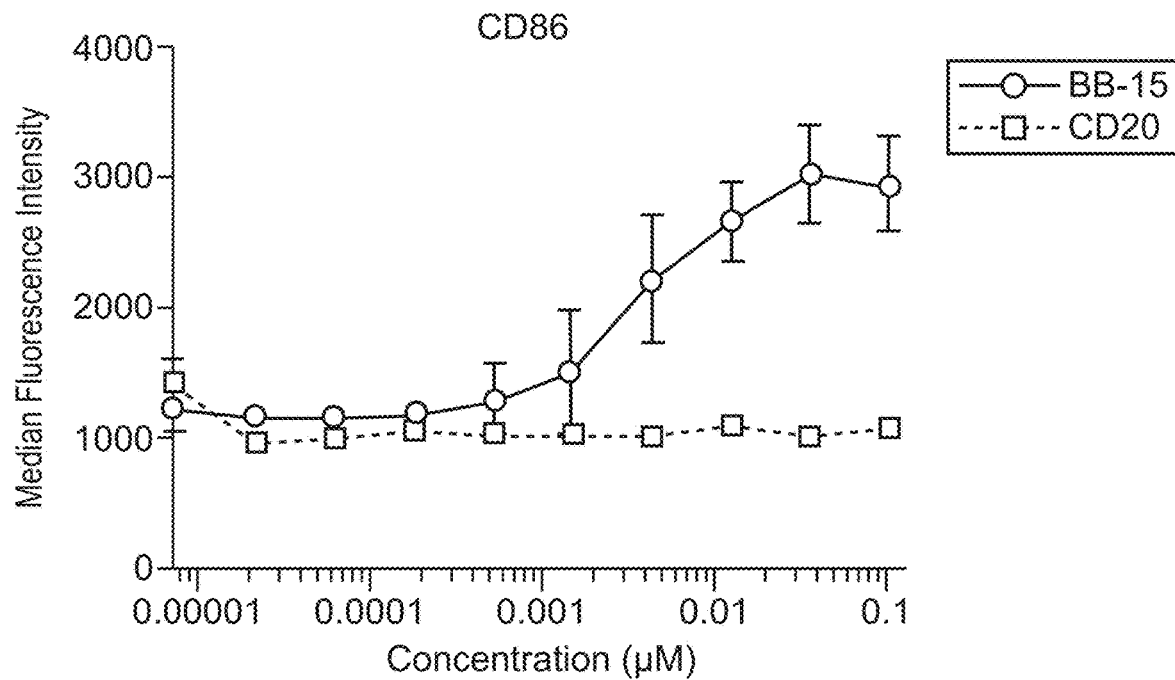

FIG. 53C shows that BB-15 elicits myeloid activation as indicated by CD86 upregulation while the control does not. CD20 is the unconjugated monoclonal antibody used as a control.

Figure 53D:
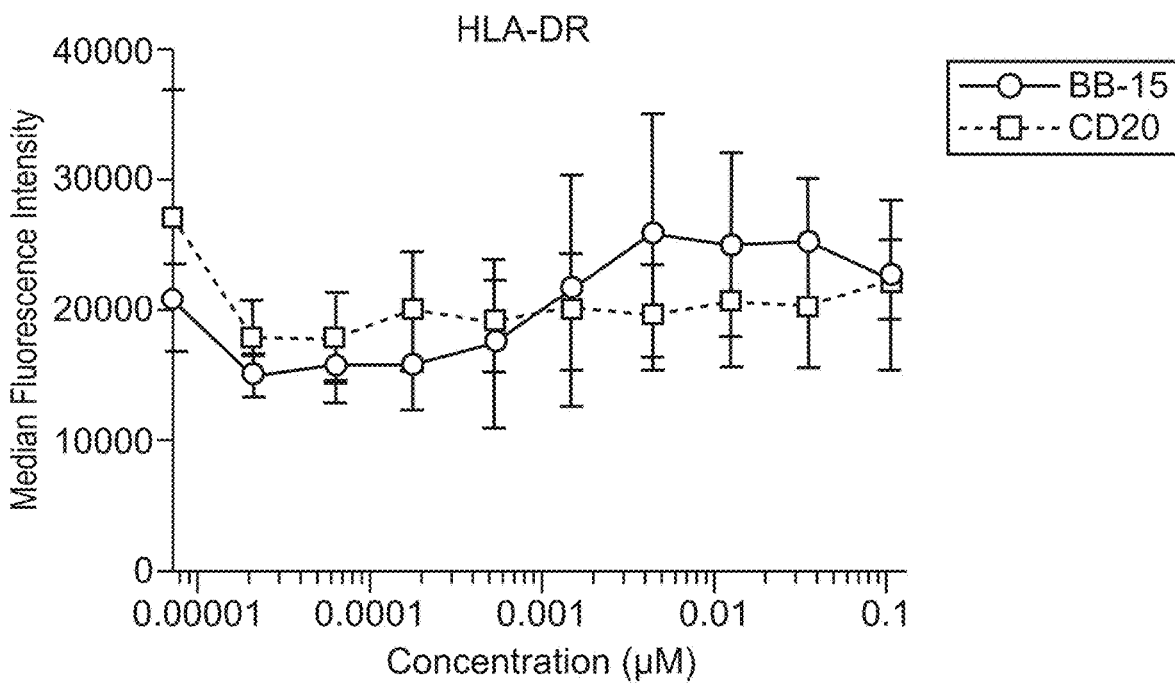

FIG. 53D shows that BB-27 elicits myeloid activation as indicated by HLA-DR upregulation while the control does do not. CD20 is the unconjugated monoclonal antibody used as a control.

Figure 54A:
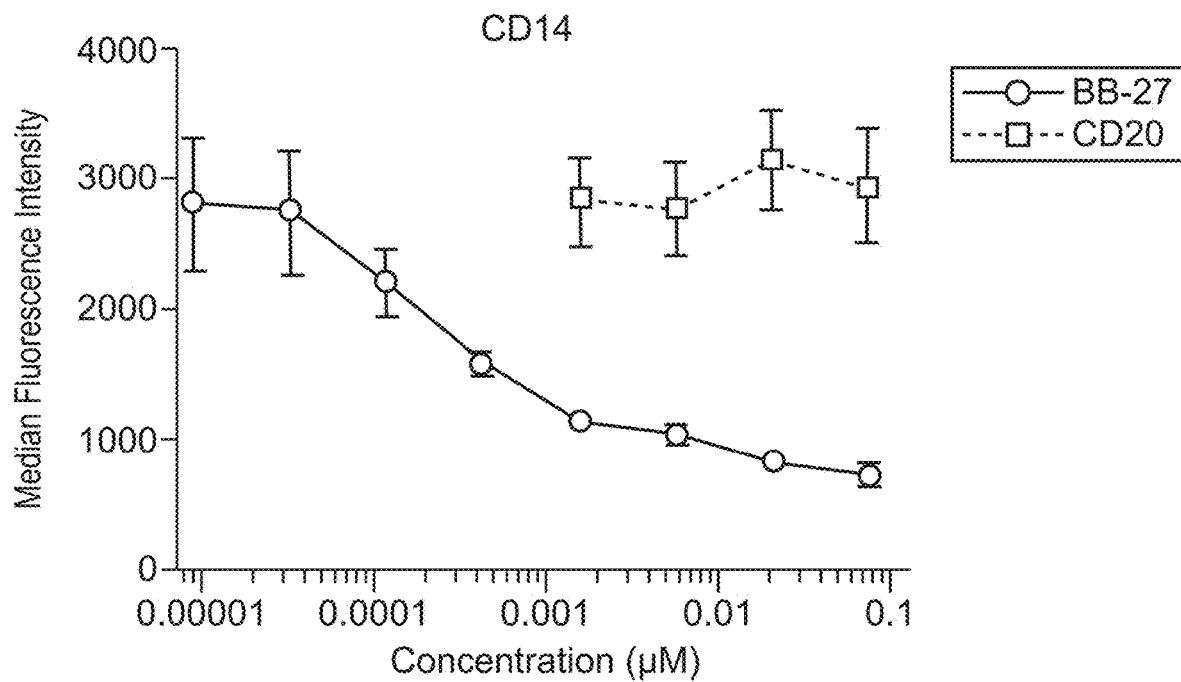

FIG. 54A shows that BB-27 elicits myeloid activation as indicated by CD14 downregulation while the control does not. CD20 is the unconjugated monoclonal antibody used as a control.

Figure 54B:
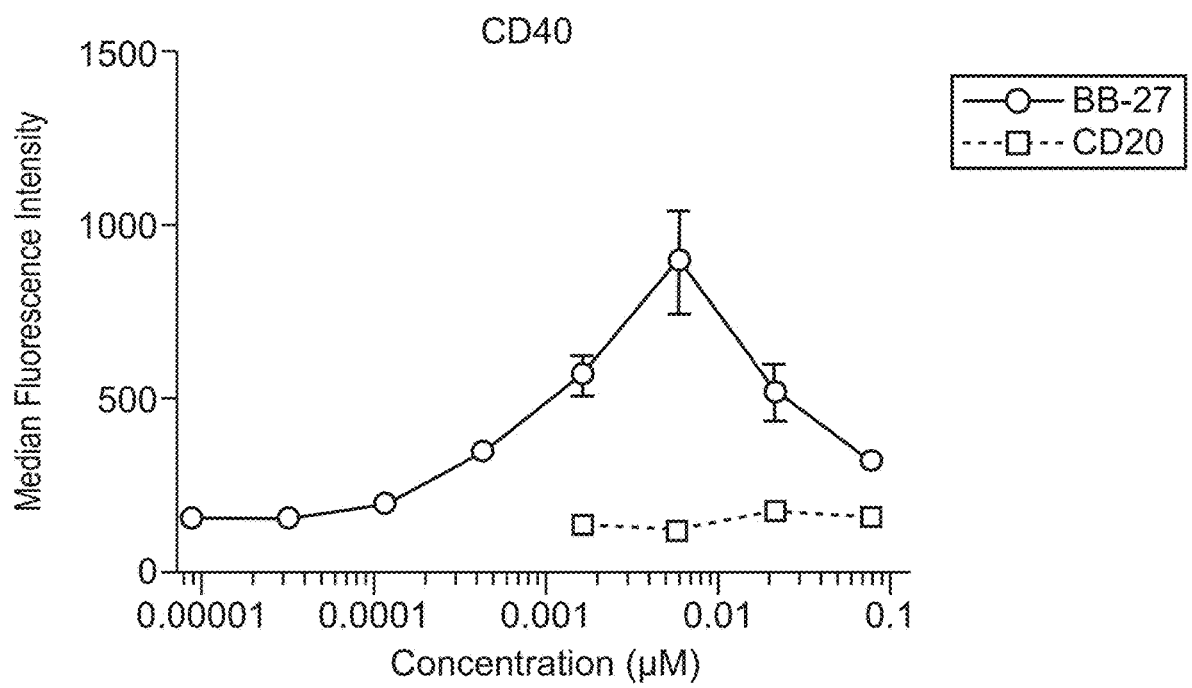

FIG. 54B shows that BB-27 elicits myeloid activation as indicated by CD40 upregulation while the control does not. CD20 is the unconjugated monoclonal antibody used as a control.

Figure 54C:
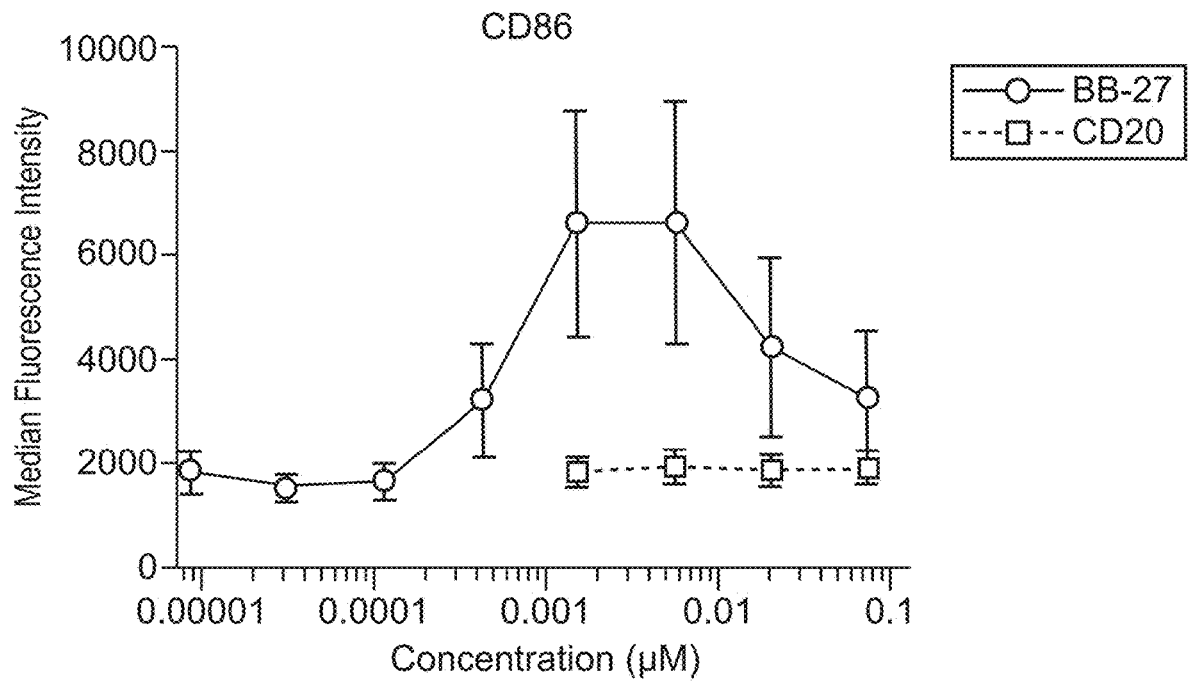

FIG. 54C shows that BB-27 elicits myeloid activation as indicated by CD86 upregulation while the control does not. CD20 is the unconjugated monoclonal antibody used as a control.

Figure 54D:
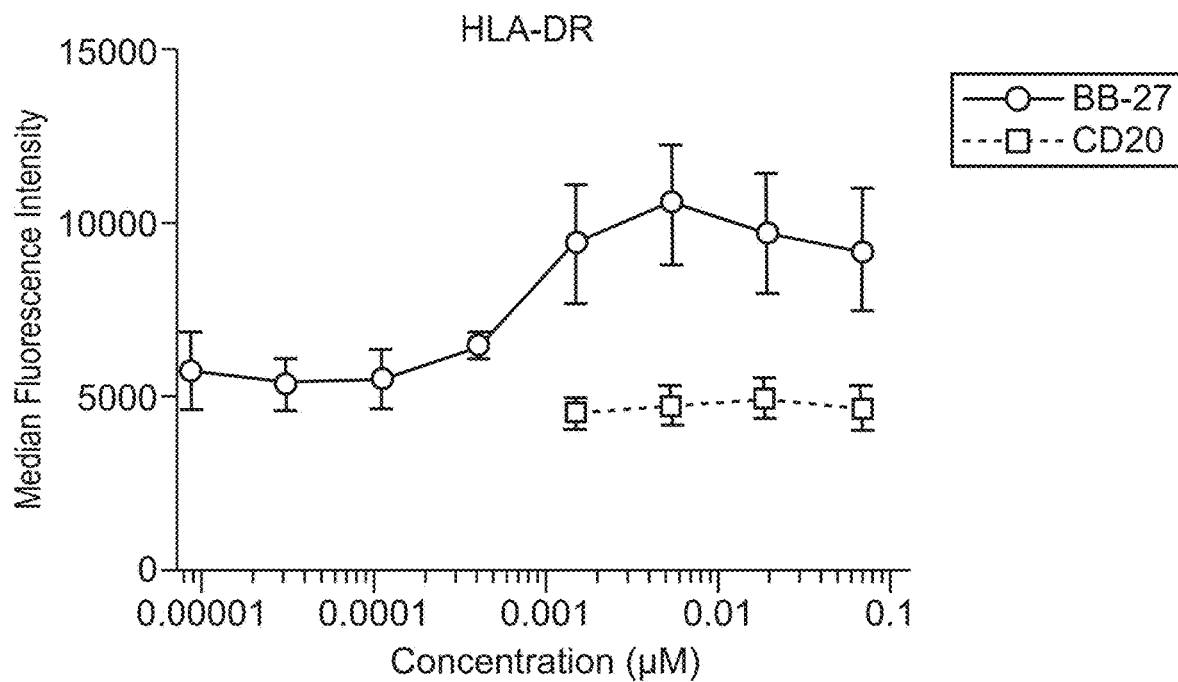

FIG. 54D shows that BB-27 elicits myeloid activation as indicated by HLA-DR upregulation while the control does do not. CD20 is the unconjugated monoclonal antibody used as a control.

Figure 55A:
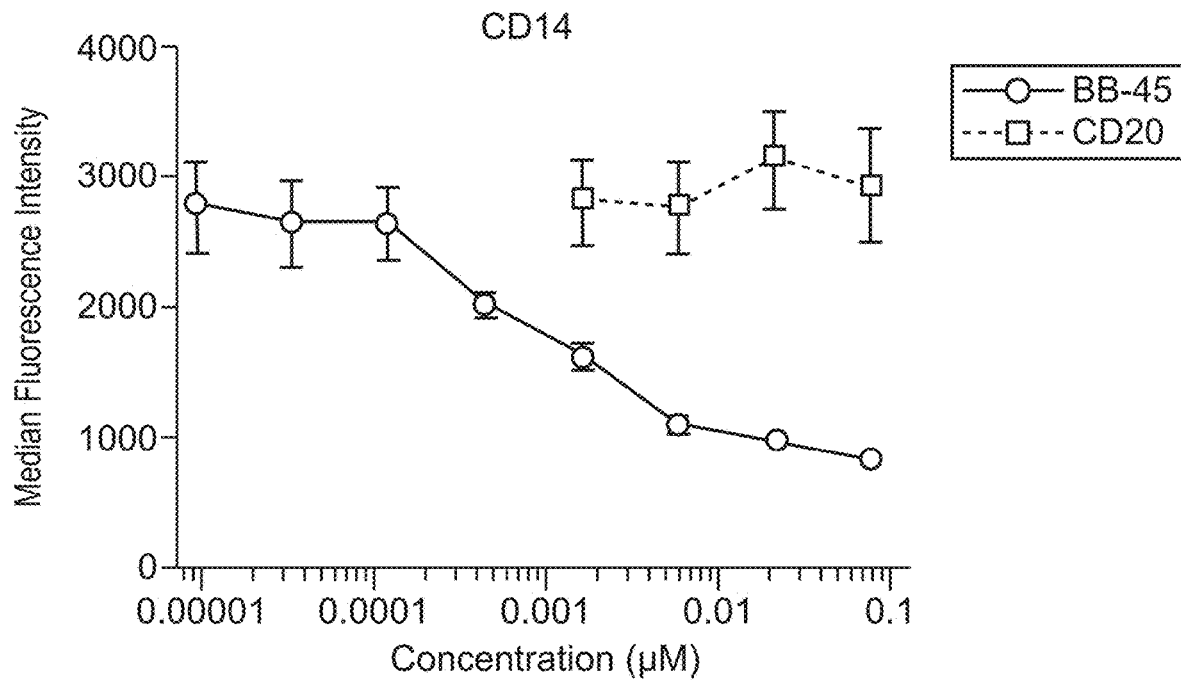

FIG. 55A shows that BB-45 elicits myeloid activation as indicated by CD14 downregulation while the control does not. CD20 is the unconjugated monoclonal antibody used as a control.

Figure 55B:
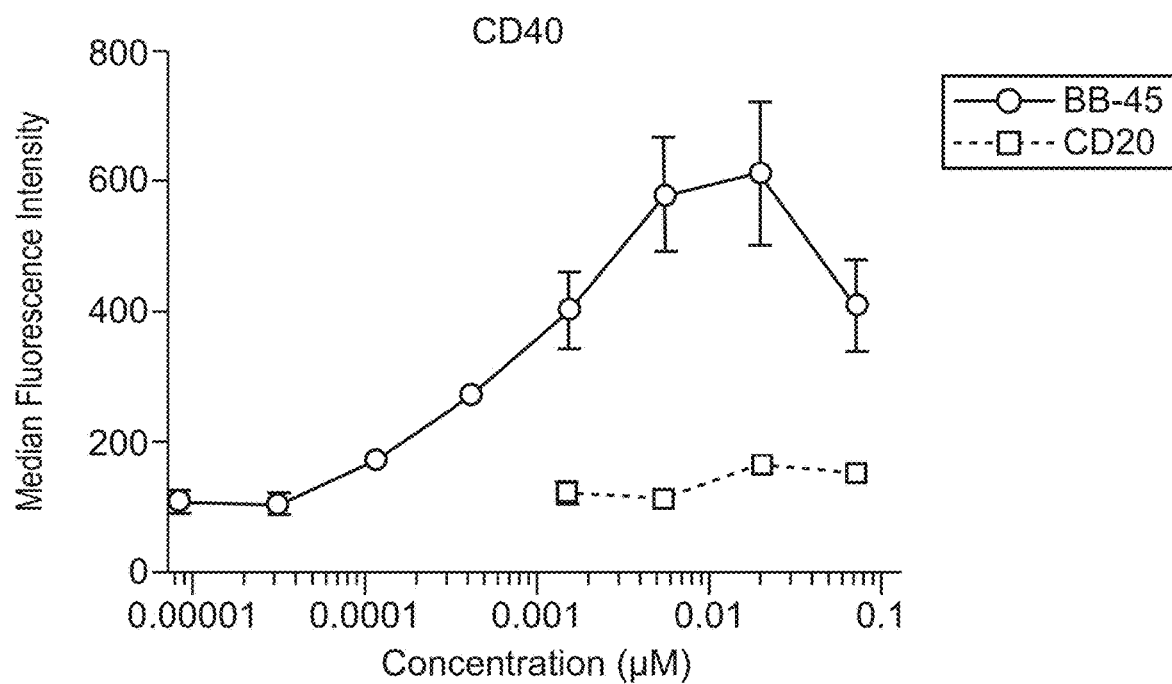

FIG. 55B shows that BB-45 elicits myeloid activation as indicated by CD40 upregulation while the control does not. CD20 is the unconjugated monoclonal antibody used as a control.

Figure 55C:
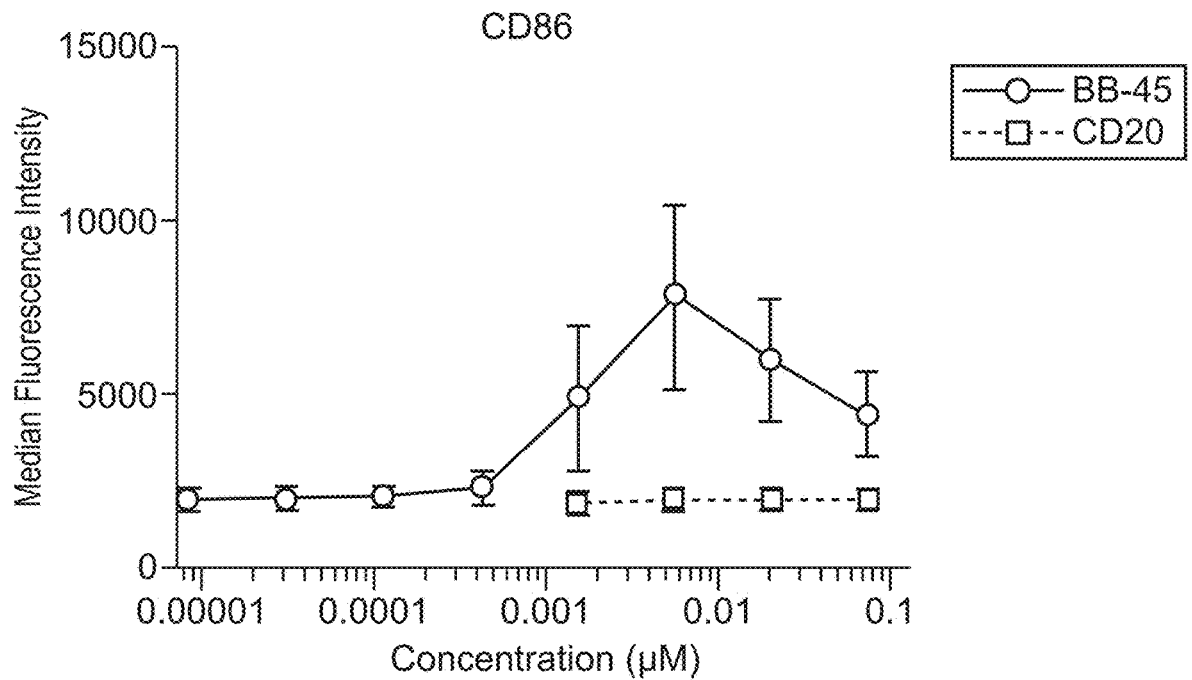

FIG. 55C shows that BB-45 elicits myeloid activation as indicated by CD86 upregulation while the control does not. CD20 is the unconjugated monoclonal antibody used as a control.

Figure 55D:
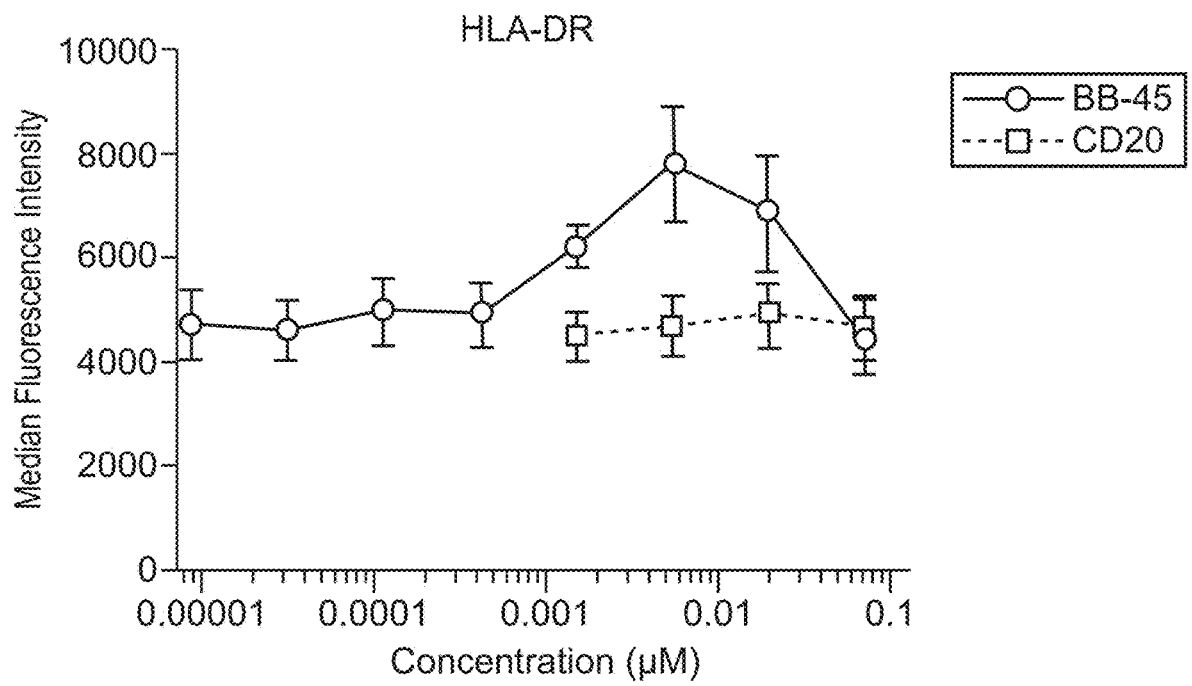

FIG. 55D shows that BB-45 elicits myeloid activation as indicated by HLA-DR upregulation while the control does do not. CD20 is the unconjugated monoclonal antibody used as a control.

Figure 56A:
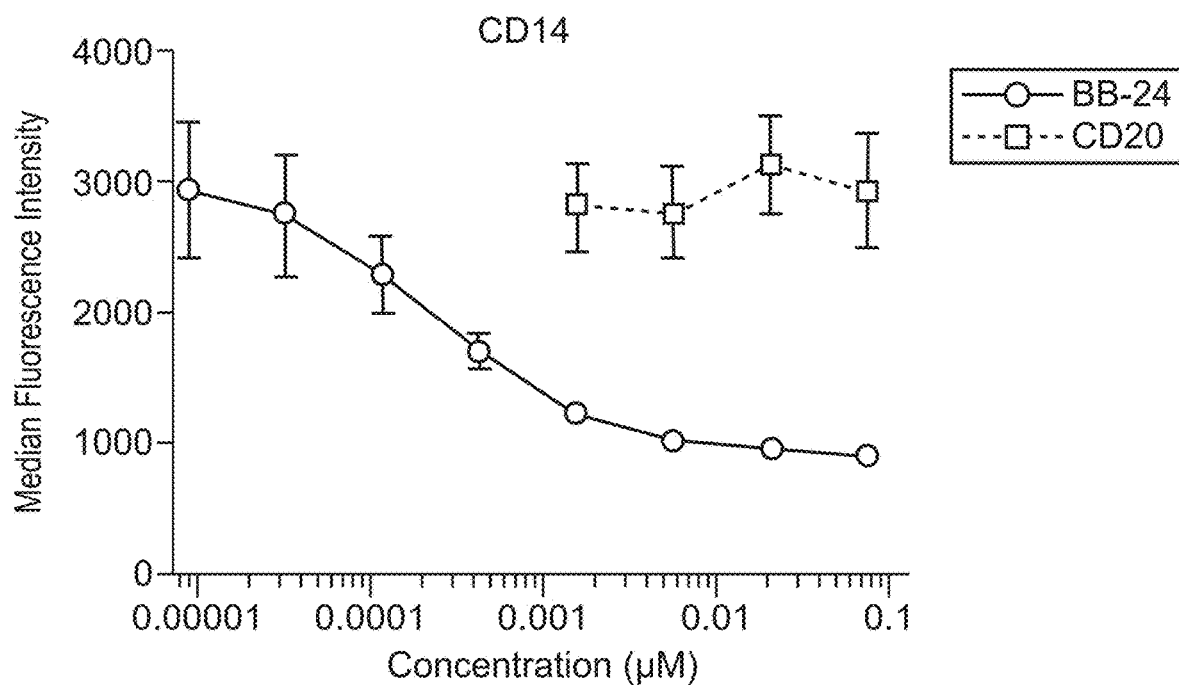

FIG. 56A shows that BB-24 elicits myeloid activation as indicated by CD14 downregulation while the control does not. CD20 is the unconjugated monoclonal antibody used as a control.

Figure 56B:
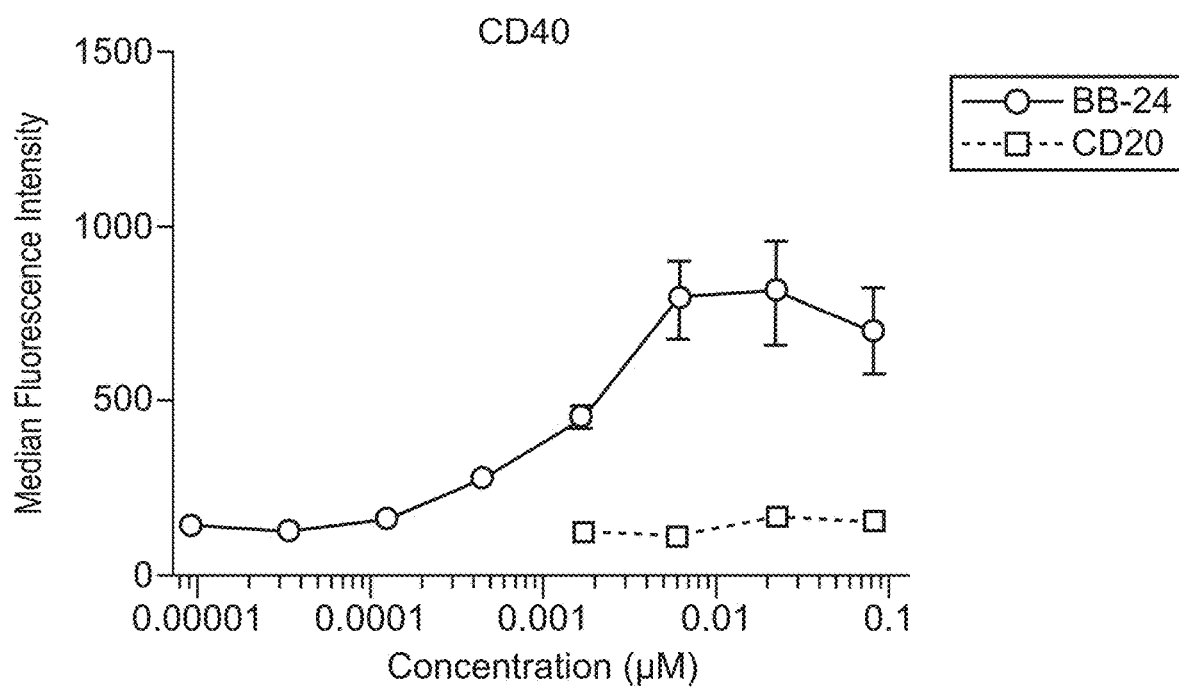

FIG. 56B shows that BB-24 elicits myeloid activation as indicated by CD40 upregulation while the control does not. CD20 is the unconjugated monoclonal antibody used as a control.

Figure 56C:
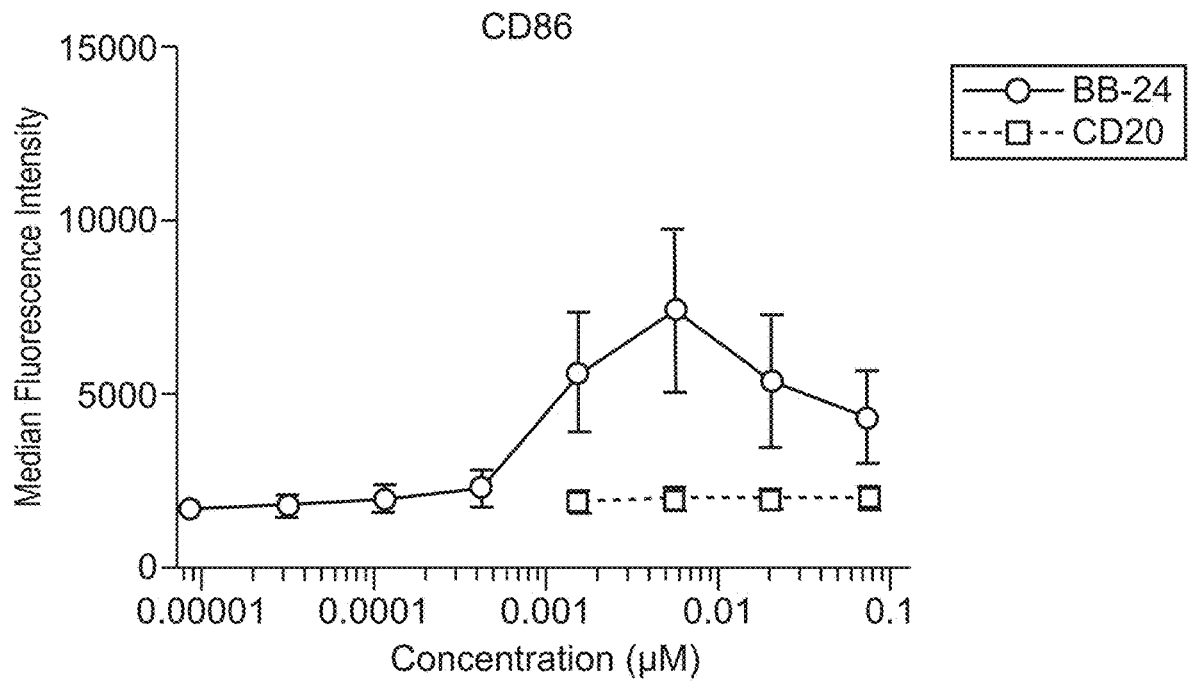

FIG. 56C shows that BB-24 elicits myeloid activation as indicated by CD86 upregulation while the control does not. CD20 is the unconjugated monoclonal antibody used as a control.

Figure 56D:
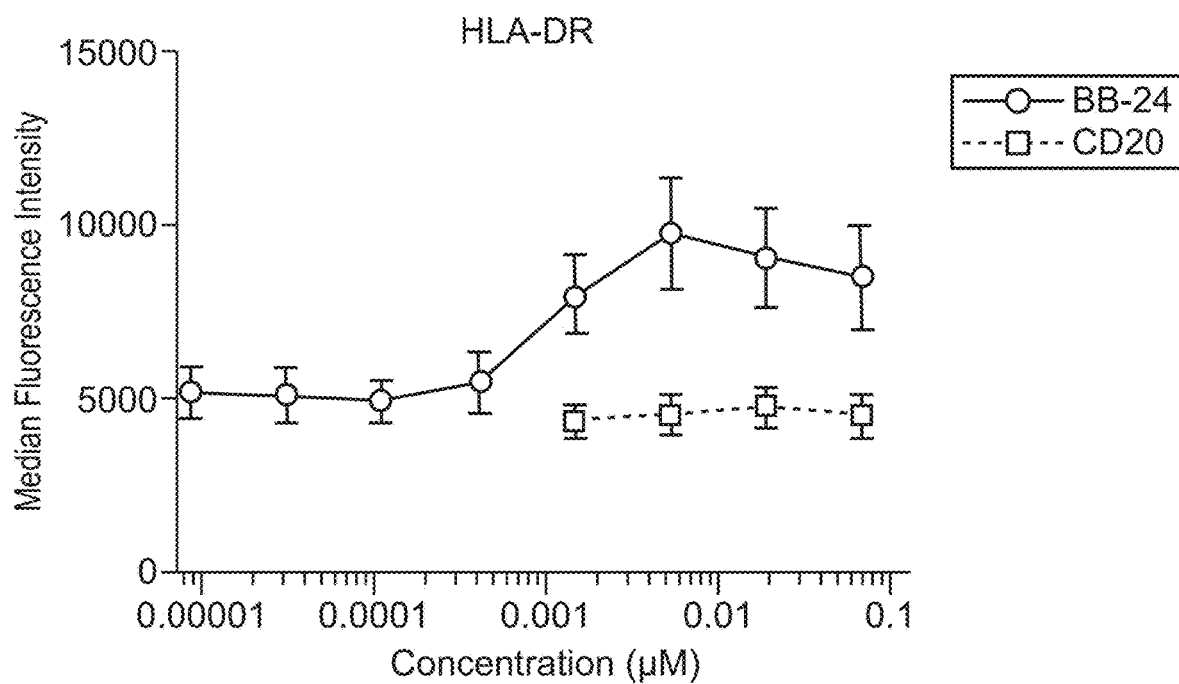

FIG. 56D shows that BB-24 elicits myeloid activation as indicated by HLA-DR upregulation while the control does do not. CD20 is the unconjugated monoclonal antibody used as a control.

Figure 57:
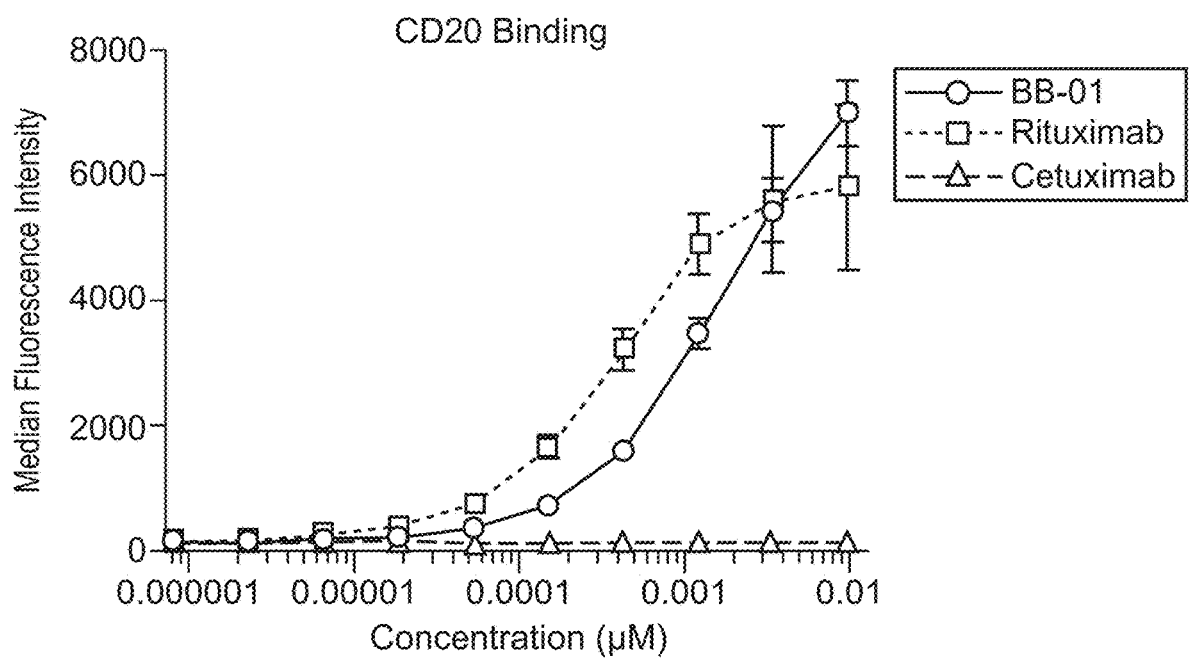

FIG. 57 shows BB-01 binding to CD20 Toledo cells, which are a cell line used as a model system for studying non-Hodgkin lymphomas. BB-01 had stronger binding than the antibodies rituximab or cetuximab.

Figure 58:
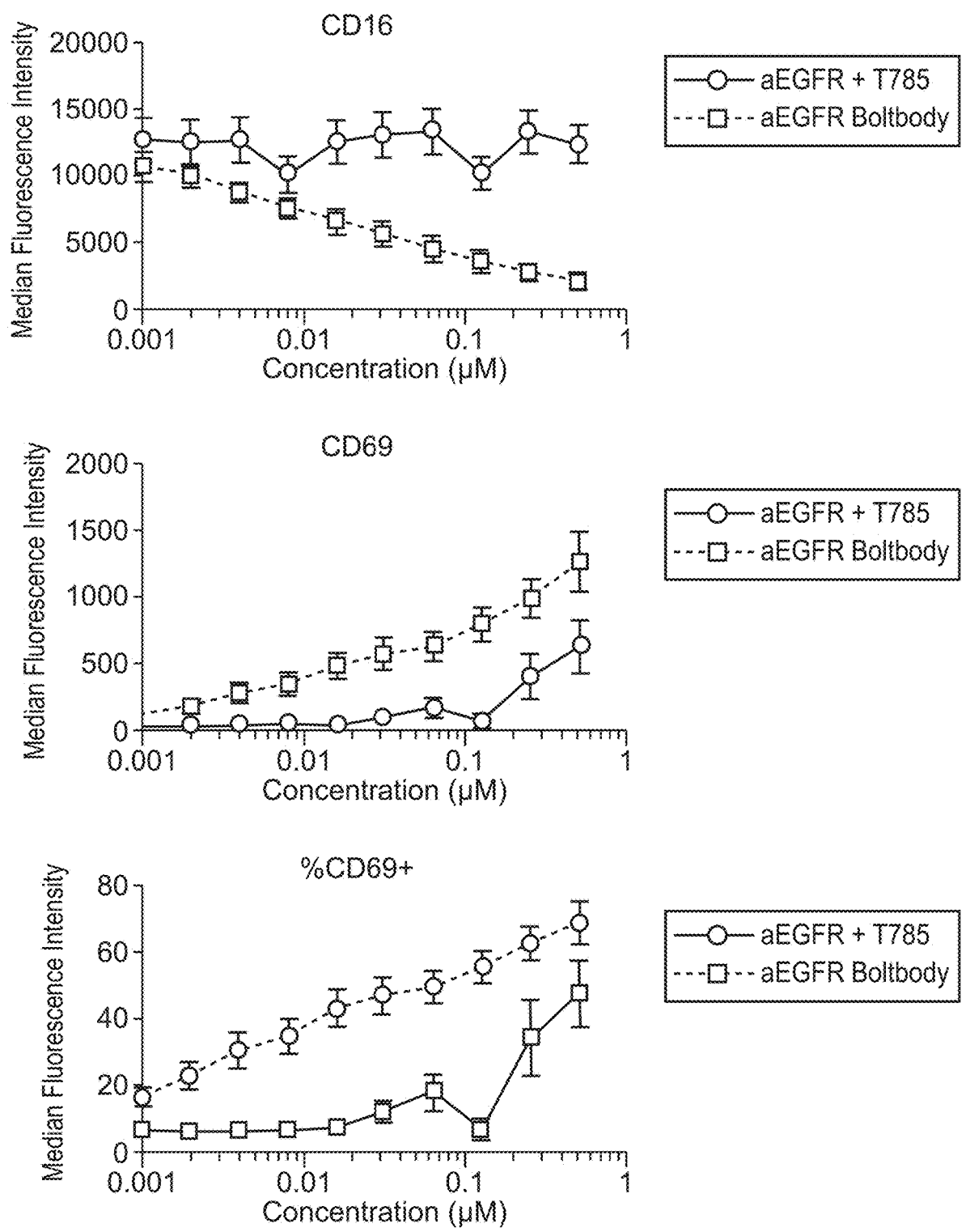

FIG. 58 shows aEGFR immunoconjugate with Compound 1 (aEGFR Boltbody) was more effective than the mixture of antibody and adjuvant at activating NK cells. PBMCs were activated with the immunoconjugate or the mixture for 18 hours. NK cells were gated according to lineage negative (CD3, CD19, CD14 negative) and CD56 positive.

Figure 59:
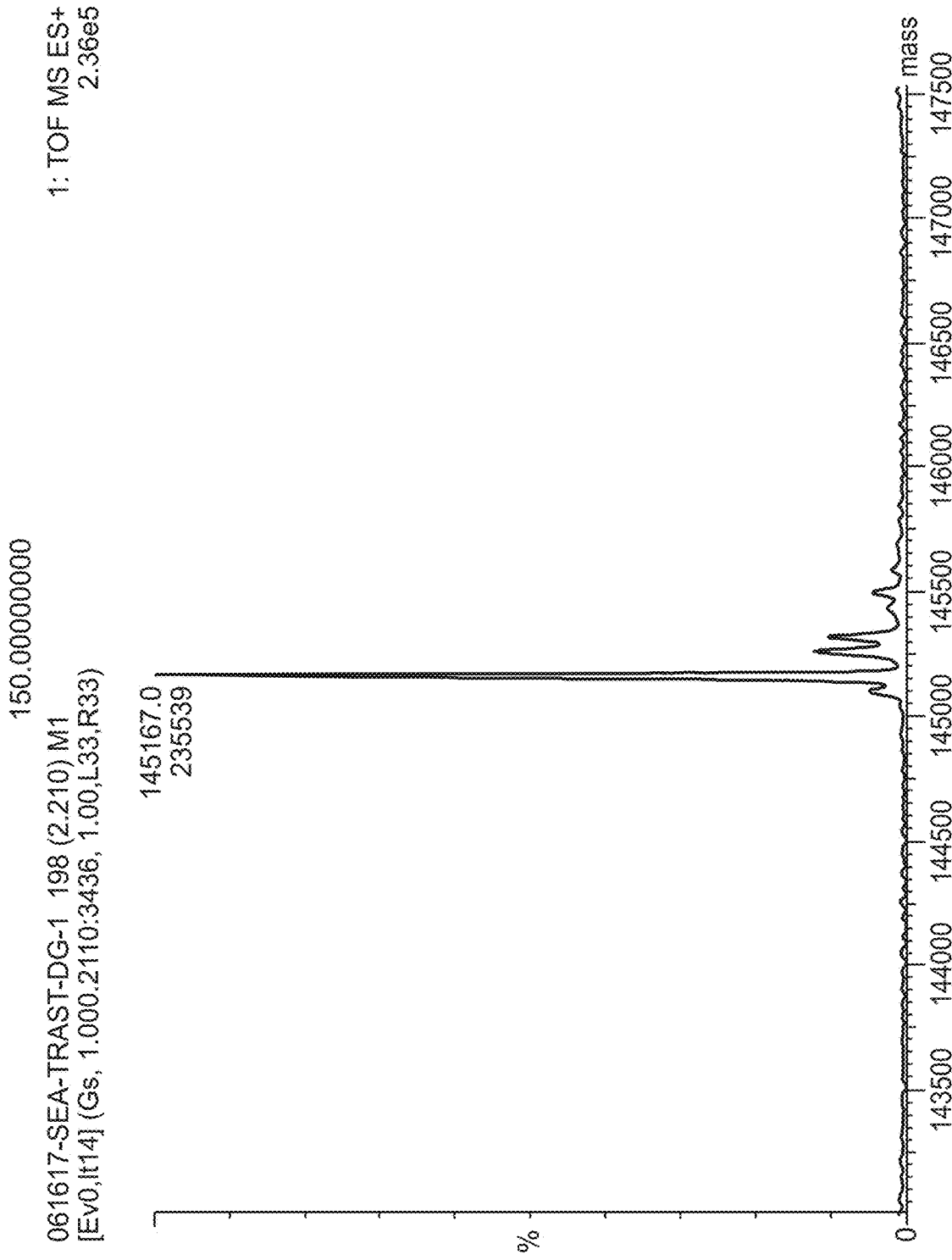

FIG. 59 shows the analysis of a comparative immunoconjugate via LC-MS (DG). This comparative conjugate was prepared with trastuzumab and a noncleavable maleimide-PEG4 linker containing a pentafluorophenyl group with gardiquimod (see US 2017/0158772, paragraph 0275, description of immunoconjugate ATAC3).

Figure 60:
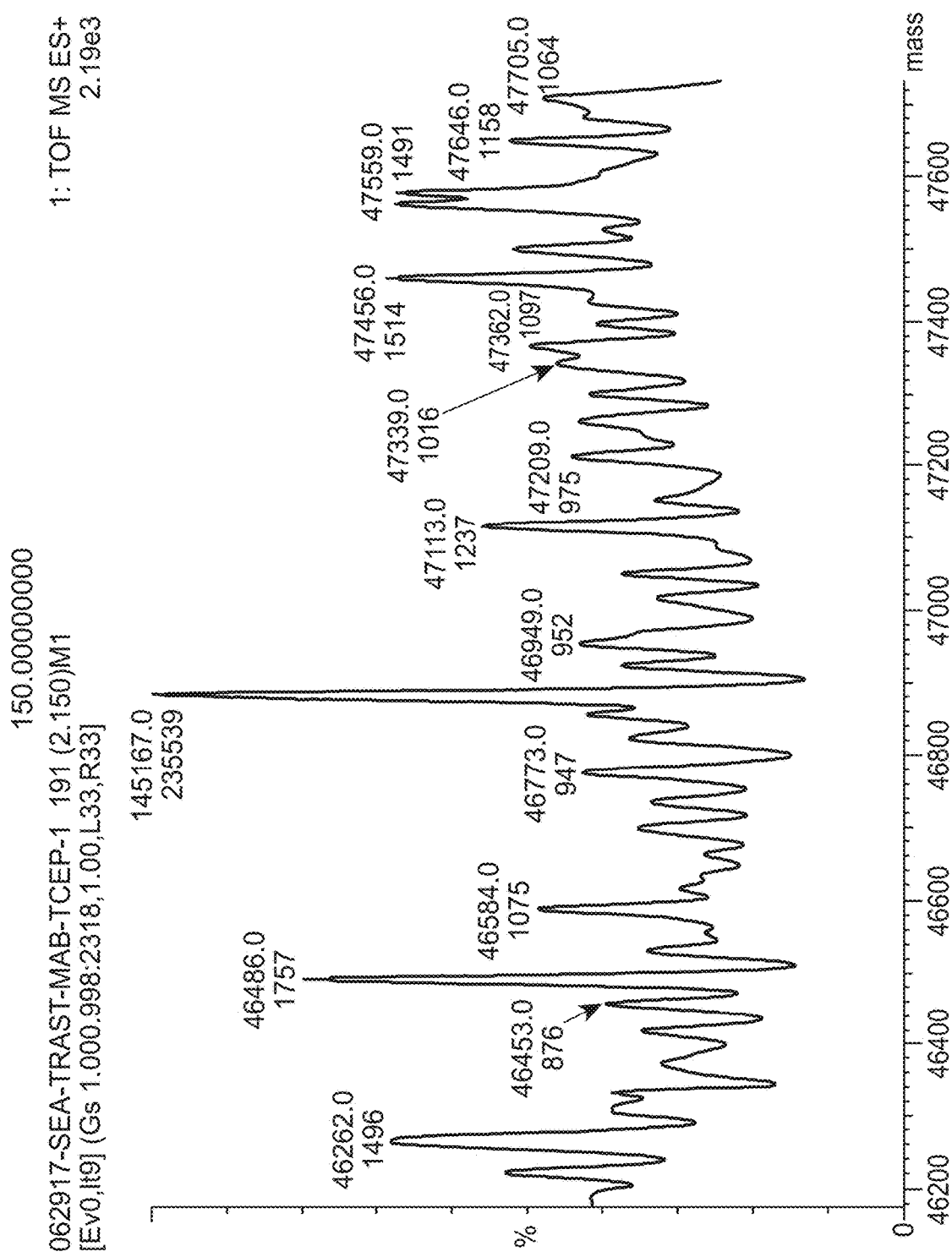

FIG. 60 shows the analysis of a comparative immunoconjugate via LC-MS (heavy chain). This comparative conjugate was prepared with trastuzumab and a noncleavable maleimide-PEG4 linker containing a pentafluorophenyl group with gardiquimod (see US 2017/0158772, paragraph 0275, description of immunoconjugate ATAC3).

Figure 61:
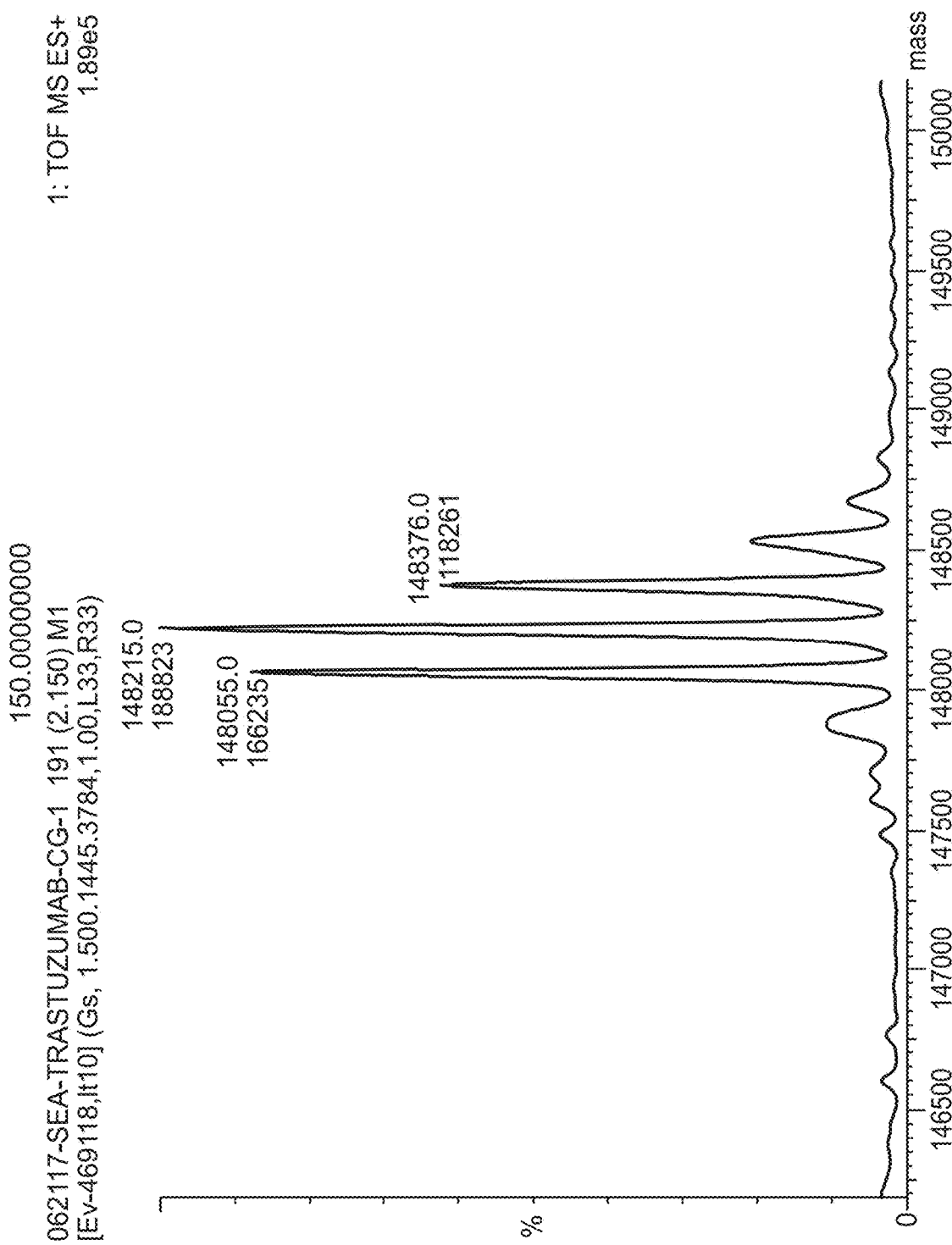

FIG. 61 shows the analysis of a comparative immunoconjugate via LC-MS. This comparative conjugate was prepared with trastuzumab and a noncleavable maleimide-PEG4 linker containing a pentafluorophenyl group with gardiquimod (see US 2017/0158772, paragraph 0275, description of immunoconjugate ATAC3).

Figure 62:
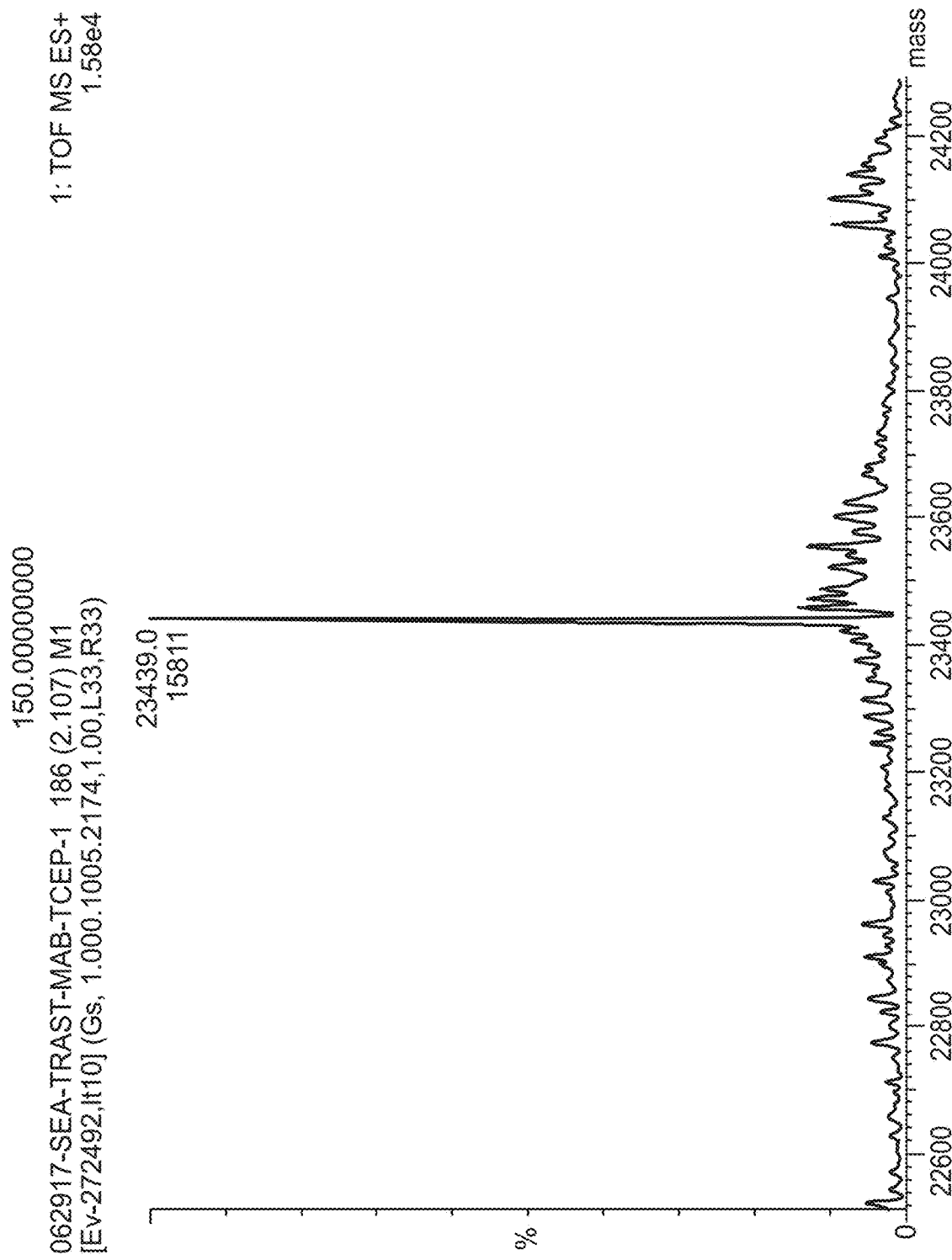

FIG. 62 shows the analysis of a comparative immunoconjugate via LC-MS (light chain). This comparative conjugate was prepared with trastuzumab and a noncleavable maleimide-PEG4 linker containing a pentafluorophenyl group with gardiquimod (see US 2017/0158772, paragraph 0275, description of immunoconjugate ATAC3).

Figure 63:
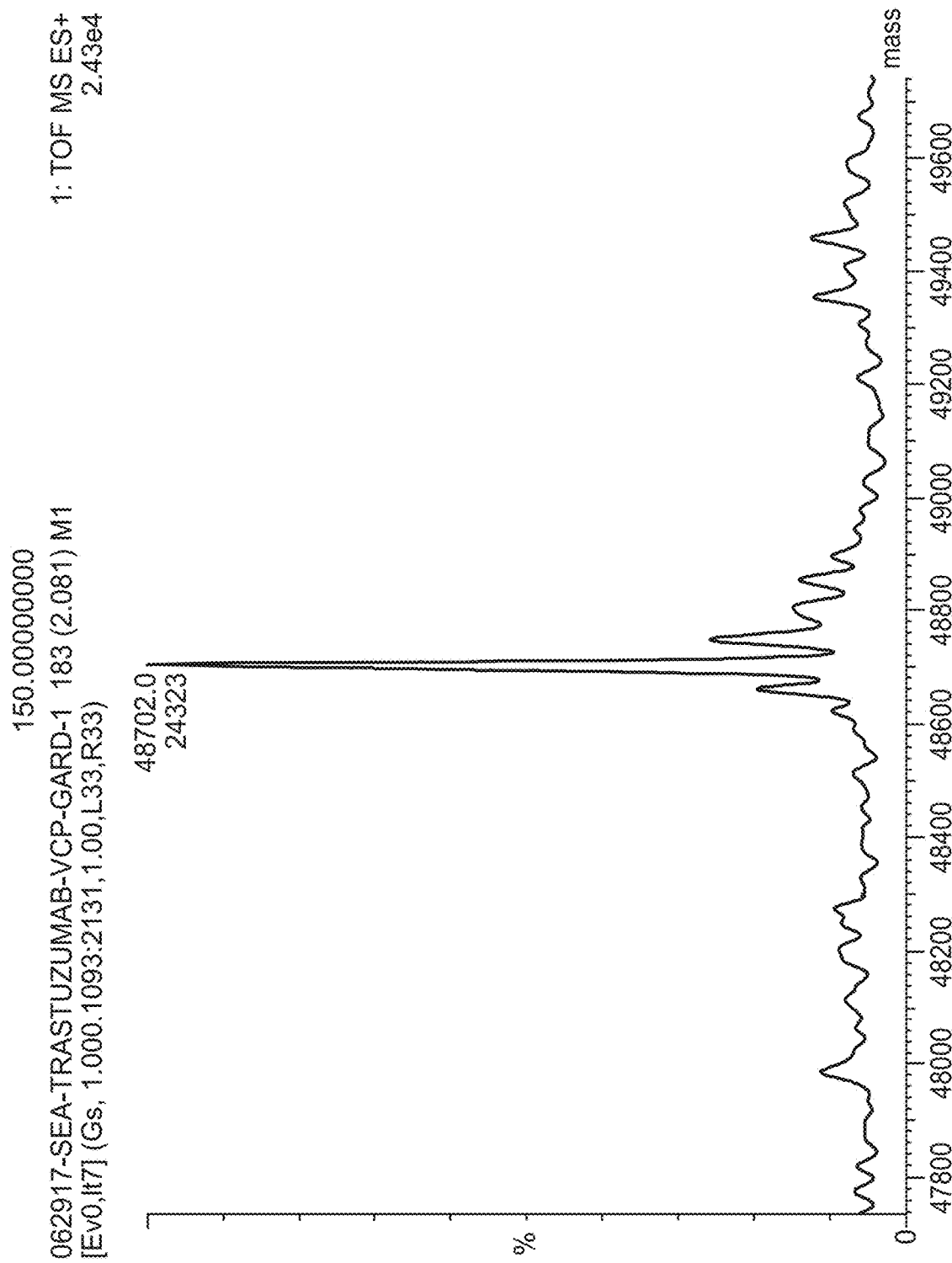

FIG. 63 shows the analysis of a comparative immunoconjugate via LC-MS (DG, heavy chain). This comparative conjugate was prepared with trastuzumab and a noncleavable maleimide-PEG4 linker containing a pentafluorophenyl group with gardiquimod (see US 2017/0158772, paragraph 0275, description of immunoconjugate ATAC3).

Figure 64:
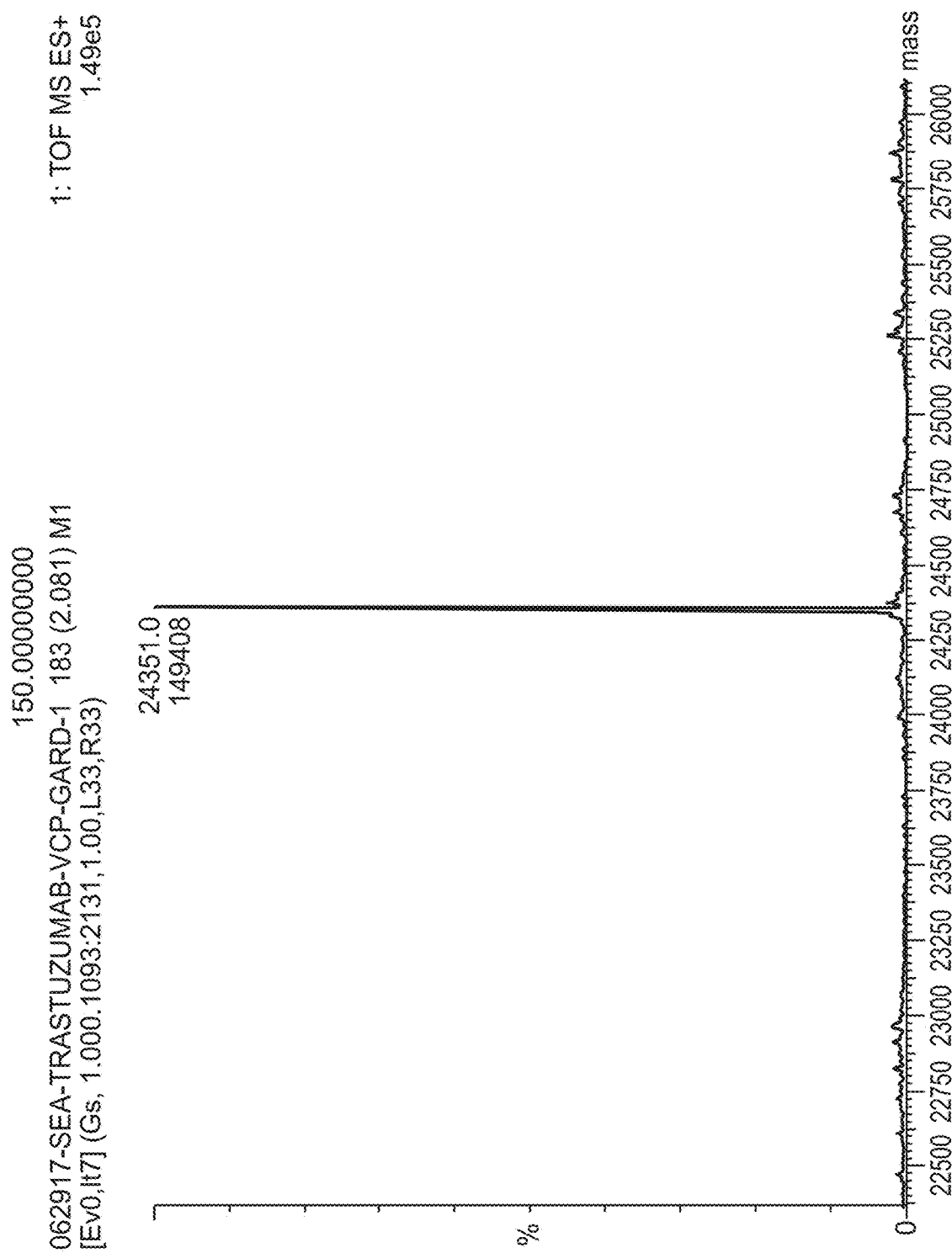

FIG. 64 shows the analysis of a comparative immunoconjugate via LC-MS (DG, light chain). This comparative conjugate was prepared with trastuzumab and a noncleavable maleimide-PEG4 linker containing a pentafluorophenyl group with gardiquimod (see US 2017/0158772, paragraph 0275, description of immunoconjugate ATAC3).

Figure 65:
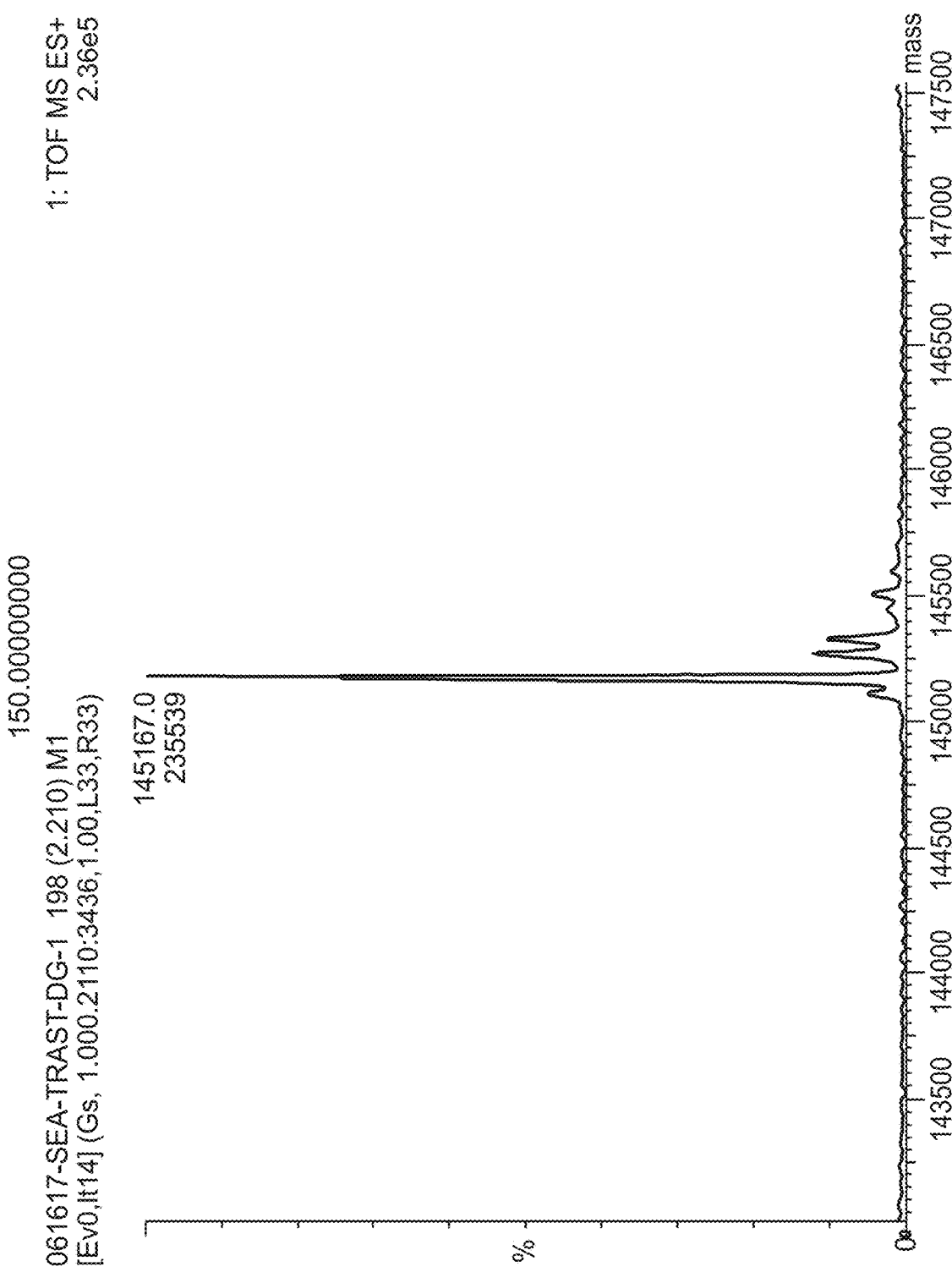

FIG. 65 shows the analysis of a comparative immunoconjugate via LC-MS (DG). This comparative conjugate was prepared with trastuzumab and a cleavable valine-citrulline linker containing a PABA group with succinamide (see US 2017/0158772, paragraph 0275, description of immunoconjugate ATAC2).

Figure 66:
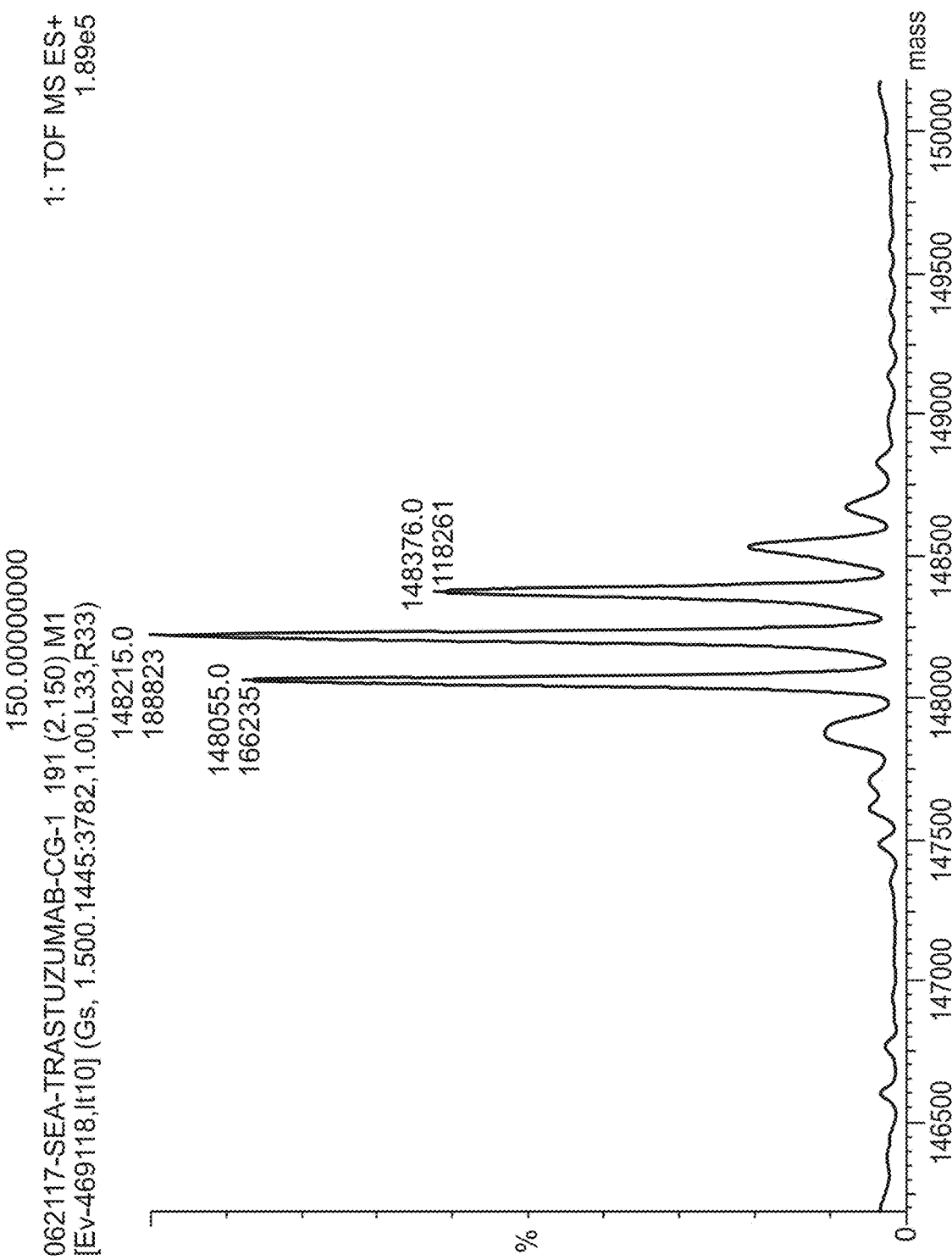

FIG. 66 shows the analysis of a comparative immunoconjugate via LC-MS. This comparative conjugate was prepared with trastuzumab and a cleavable valine-citrulline linker containing a PABA group with succinamide (see US 2017/0158772, paragraph 0275, description of immunoconjugate ATAC2).

Figure 67A:
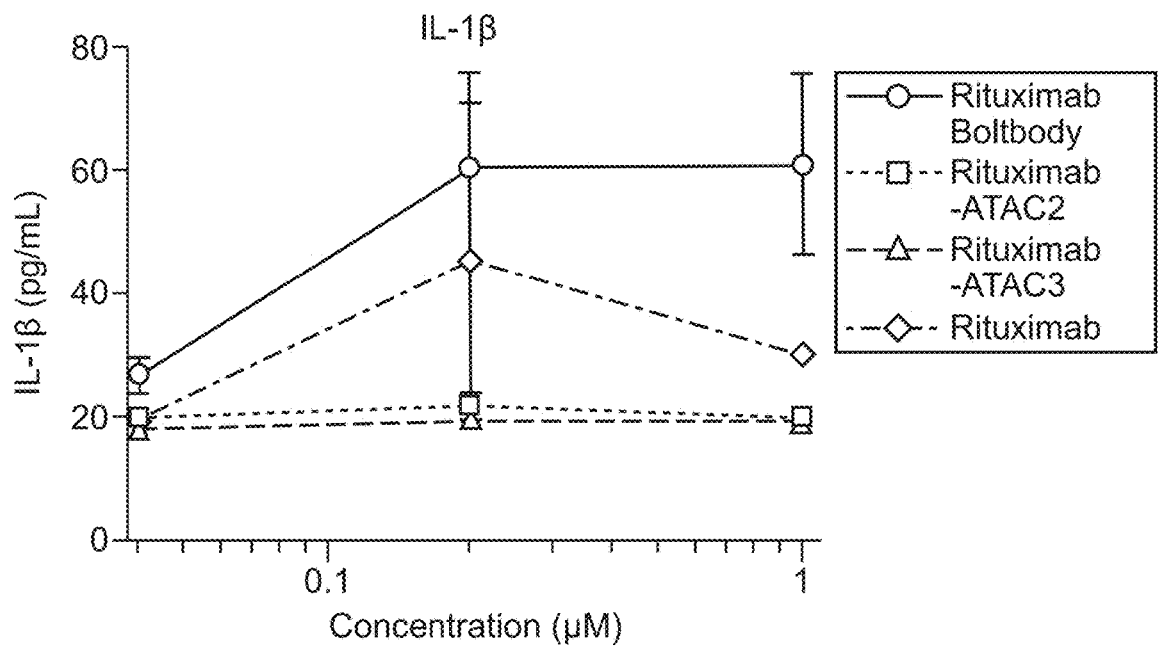

FIG. 67A shows that the rituximab immunoconjugate produced according to the BB-01 SATA method (Rituximab Boltbody) elicits superior IL-1β secretion from myeloid cells as compared to unconjugated rituximab (Roche) as well as equimolar concentrations of comparative conjugates prepared with rituximab and either a valine-citruline-PABC or a maleimide-PEG4 linker, both containing a pentafluorophenyl group with gardiquimod (Rituximab-ATAC2, Rituximab-ATAC3 respectively; US 2017/0158772) following 18 hours of stimulation.

Figure 67B:
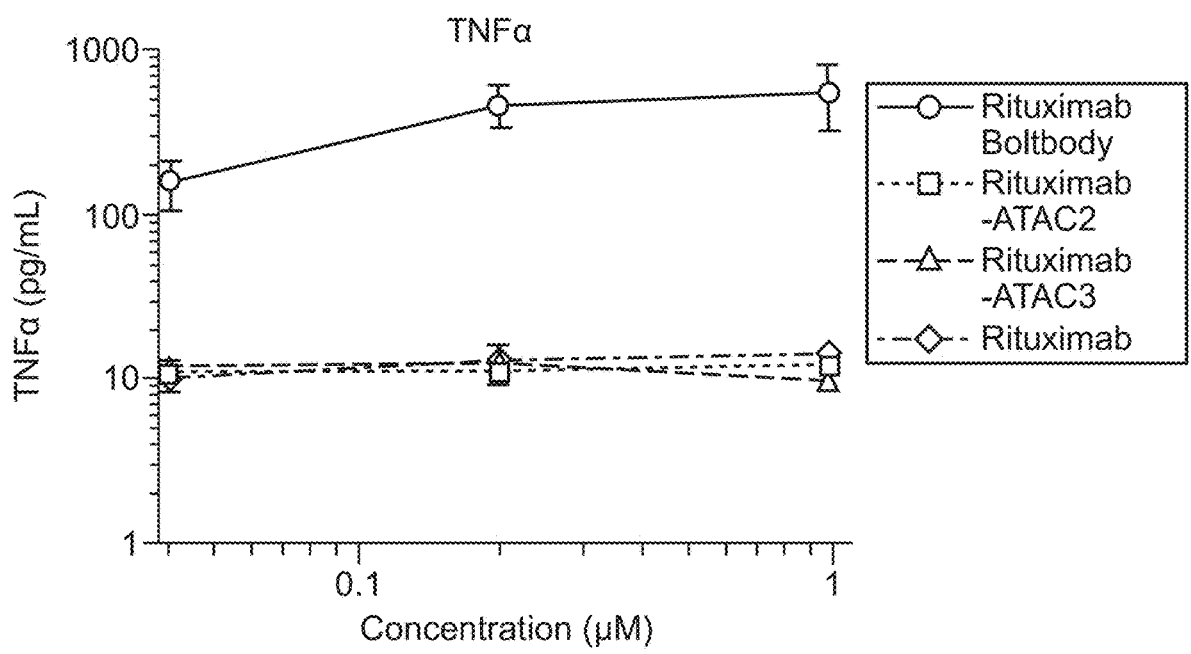

FIG. 67B shows that the rituximab immunoconjugate produced according to the BB-01 SATA method (Rituximab Boltbody) elicits superior TNFα secretion from myeloid cells as compared to unconjugated rituximab (Roche) as well as equimolar concentrations of comparative conjugates prepared with rituximab and either a valine-citruline-PABC or a maleimide-PEG4 linker, both containing a pentafluorophenyl group with gardiquimod (Rituximab-ATAC2, Rituximab-ATAC3 respectively; US 2017/0158772) following 18 hours of stimulation.

Figure 67C:
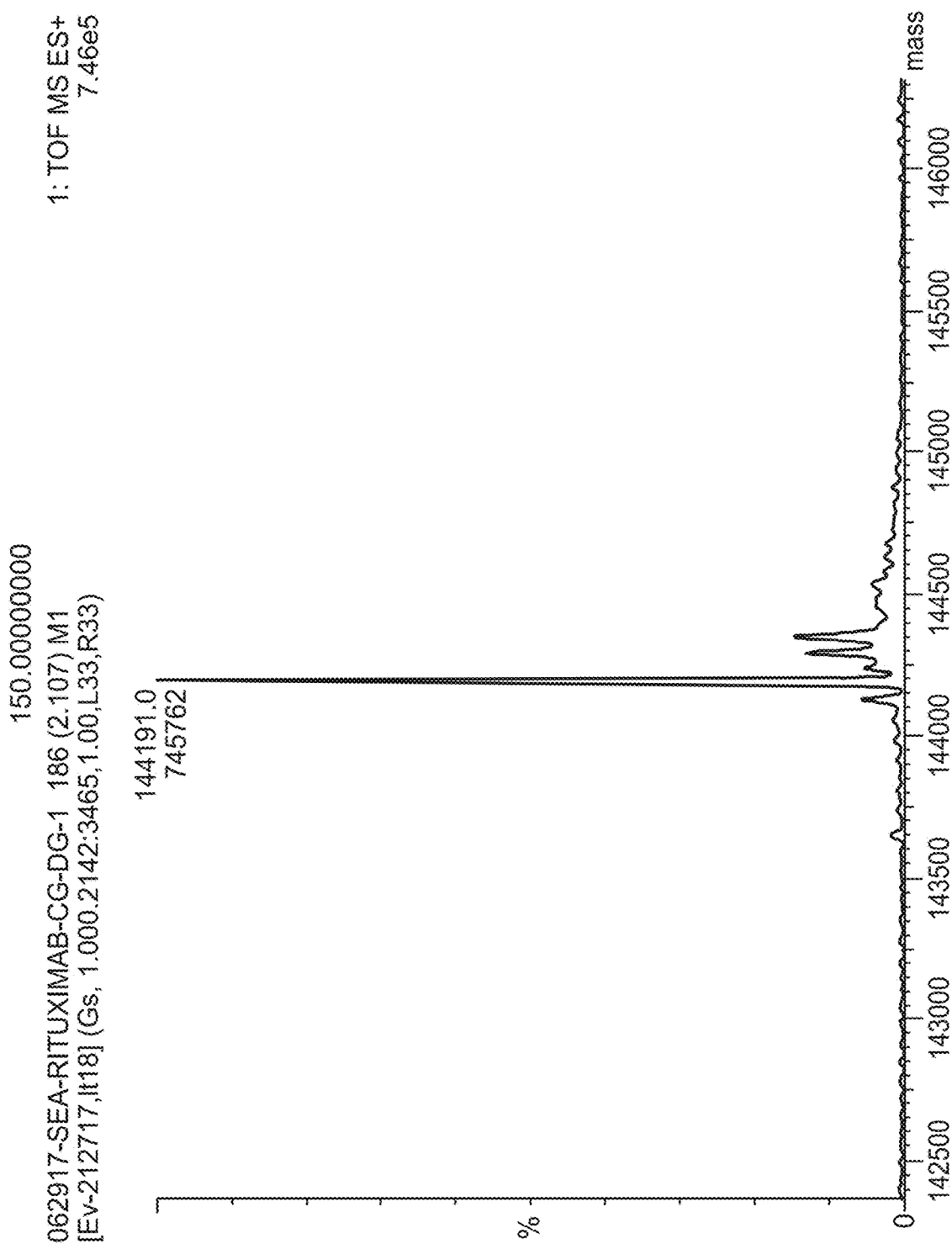

FIG. 67C shows a liquid chromatography-mass spectrometry analysis of unconjugated rituximab (Roche) that was utilized to produce the rituximab immunoconjugate according to the BB-01 conjugation method or the rituximab immunoconjugates according to the methods described in US 2017/0158772 following overnight deglycosylation with PNGase F.

Figure 67D:
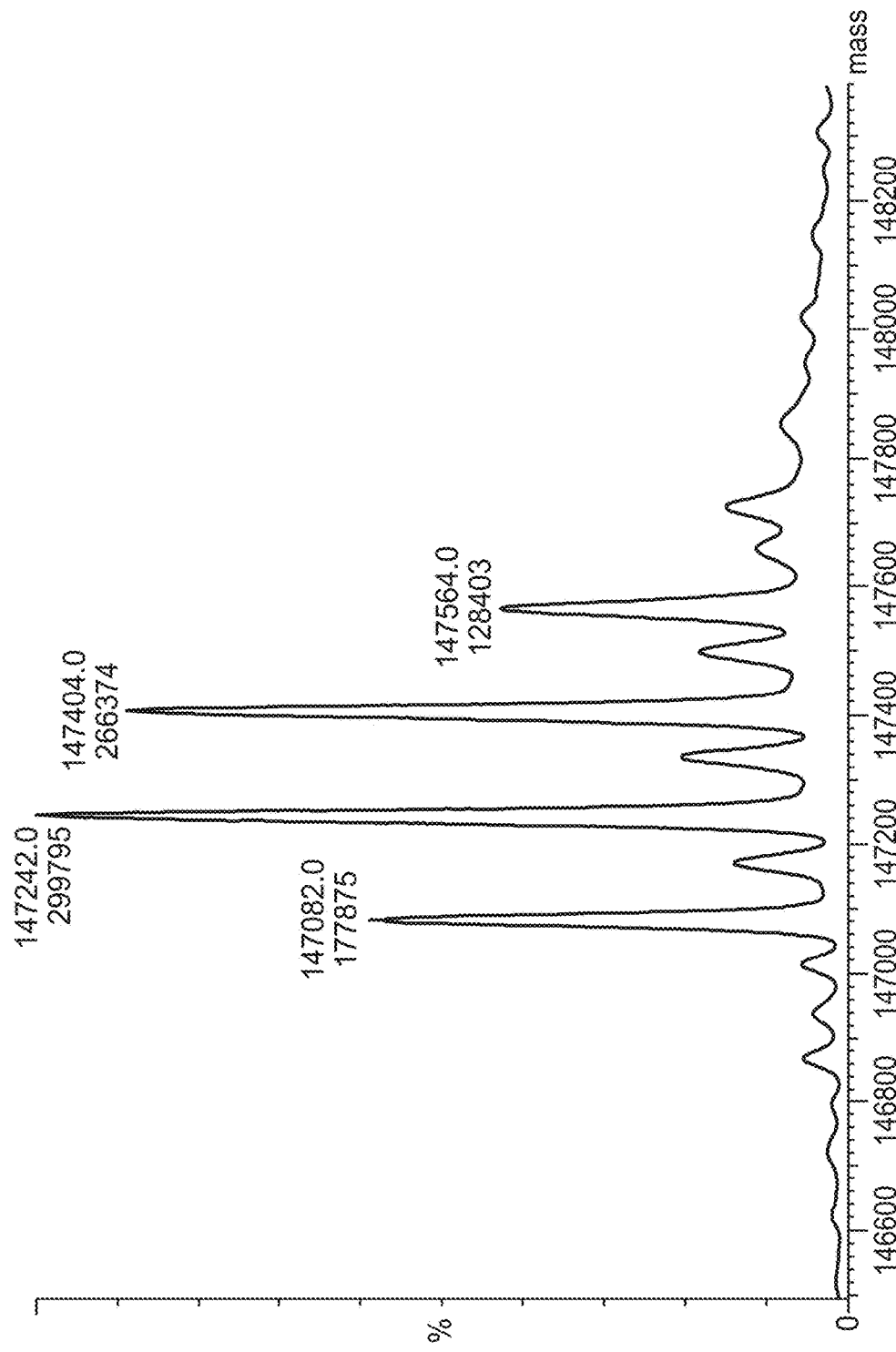

FIG. 67D shows a liquid chromatography-mass spectrometry analysis of unconjugated rituximab (Roche) that was utilized to produce the rituximab immunoconjugate according to the BB-01 conjugation method or the rituximab immunoconjugates according to the methods described in US 2017/0158772.

FIG. 67E shows a liquid chromatography-mass spectrometry analysis of the ipsilateral heavy-light chain of the rituximab immunoconjugate produced using a valine-citruline-PABC linker as described in US 2017/0158772 following overnight deglycosylation with PNGase F.

FIG. 67F shows a liquid chromatography-mass spectrometry analysis of the light chain of the rituximab immunoconjugate produced using a valine-citruline-PABC linker as described in US 2017/0158772 following overnight deglycosylation with PNGase F.

FIG. 67G shows that the rituximab with valine-citruline-PABC linker immunoconjugate produced according to the methods described in US 2017/0158772 (Ritux-ATAC2) fails to elicit CD 123 upregulation on myeloid cells following 18 hours of stimulation. FIG. 67G also shows that the BB-01 immunoconjugate produced according to the SATA method [Rituximab Boltbody (BB-01)] is superior at eliciting CD123 upregulation as compared to Ritux-ATAC2 and equimolar concentrations of unconjugated rituximab (Roche).

Figure 67H:
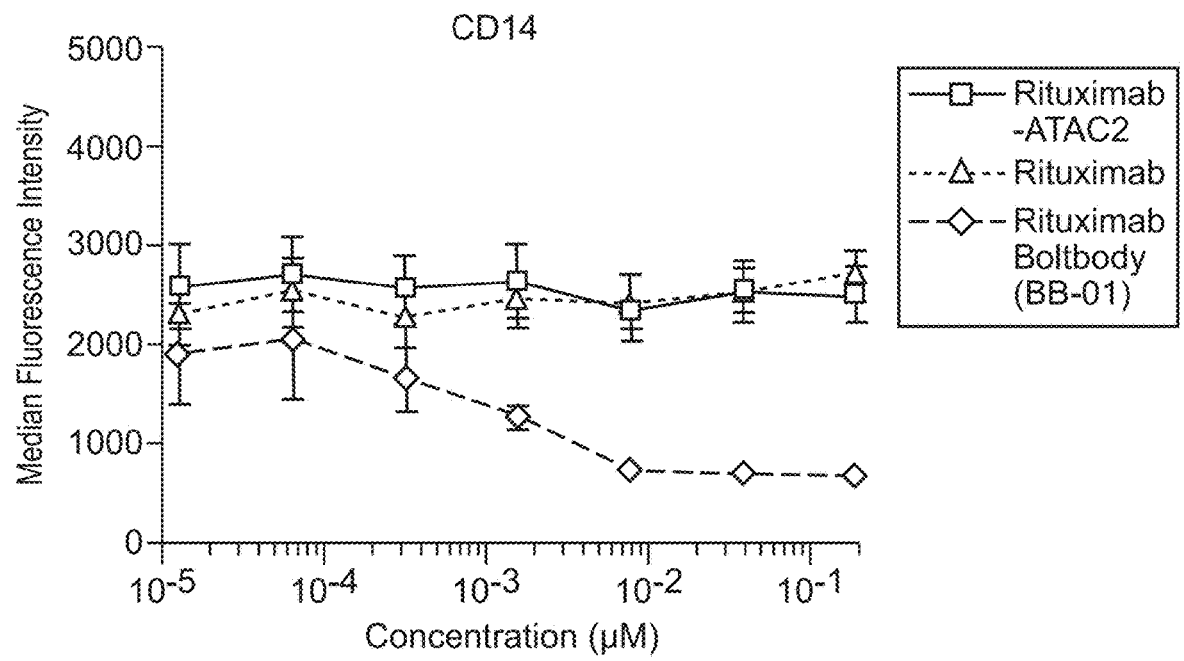

FIG. 67H shows that the rituximab with valine-citruline-PABC linker immunoconjugate produced according to the methods described in US 2017/0158772 (Ritux-ATAC2) fails to elicit CD14 downregulation on myeloid cells following 18 hours of stimulation. FIG. 67H also shows that the BB-01 immunoconjugate produced according to the SATA method [Rituximab Boltbody (BB-01)] is superior at eliciting CD14 downregulation as compared to Ritux-ATAC2 and equimolar concentrations of unconjugated rituximab (Roche).

Figure 67I:
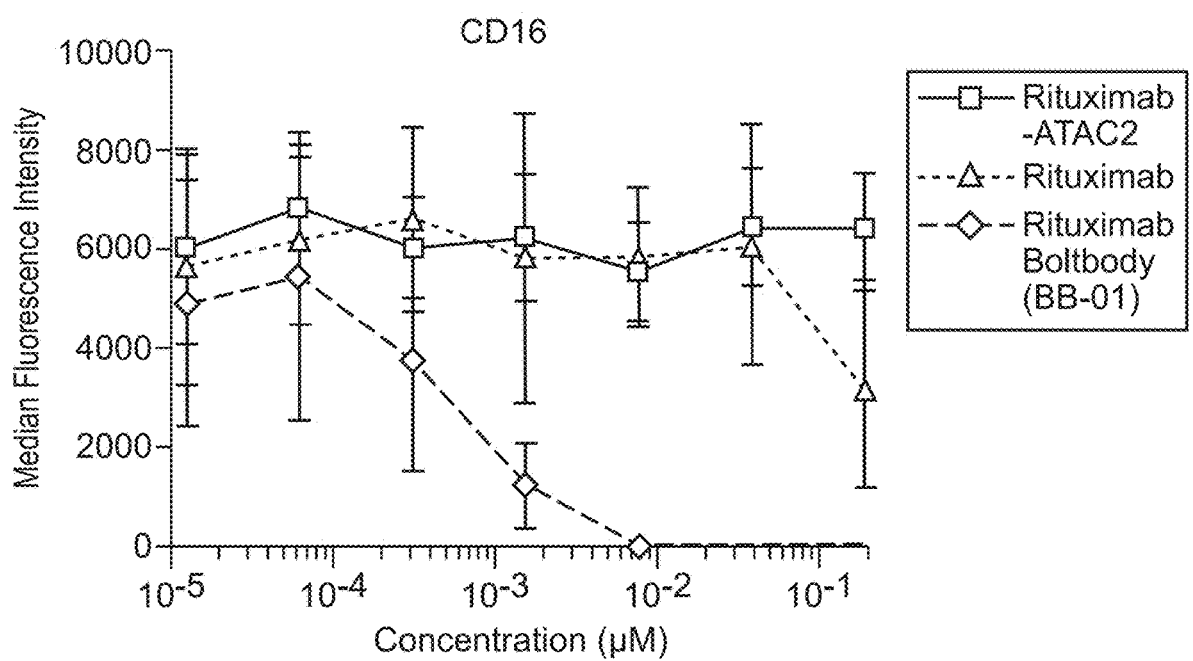

FIG. 67I shows that the BB-01 immunoconjugate produced according to the SATA method [Rituximab Boltbody (BB-01)] is superior at eliciting CD16 downregulation on myeloid cells as compared to the rituximab with valine-citruline-PABC linker immunoconjugate produced according to the methods described in US 2017/0158772 (Ritux-ATAC2) and equimolar concentrations of unconjugated rituximab (Roche).

Figure 67J:
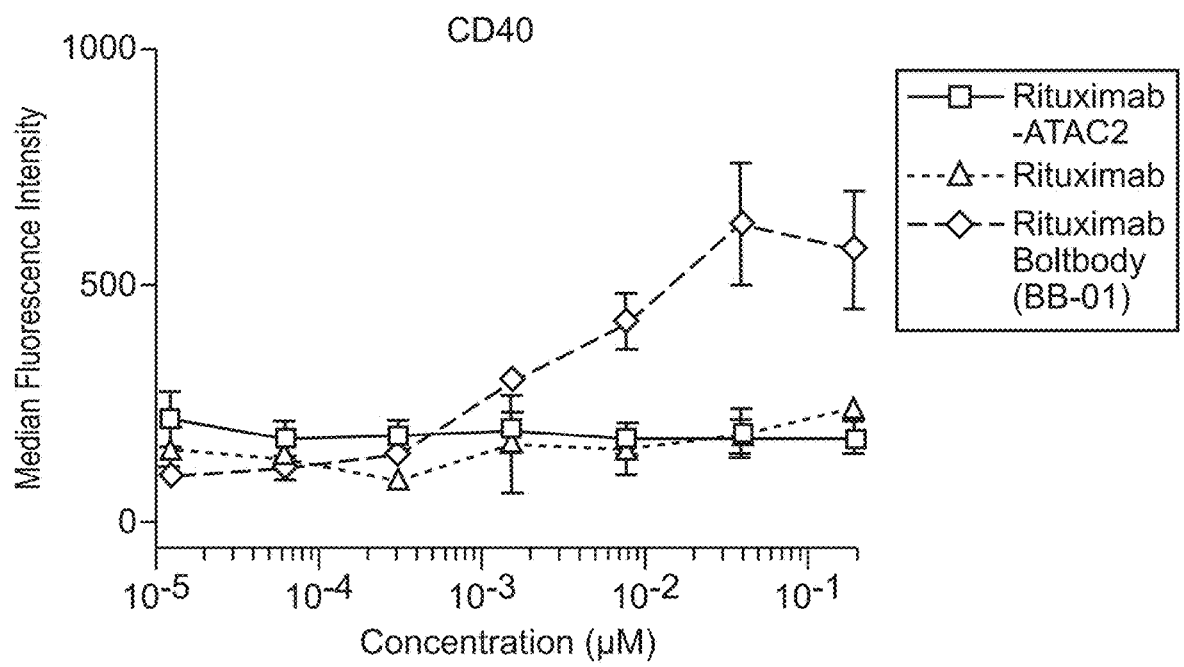

FIG. 67J shows that the rituximab with valine-citruline-PABC linker immunoconjugate produced according to the methods described in US 2017/0158772 (Ritux-ATAC2) fails to elicit CD40 upregulation on myeloid cells following 18 hours of stimulation. FIG. 67J also shows that the BB-01 immunoconjugate produced according to the SATA method [Rituximab Boltbody (BB-01)] is superior at eliciting CD40 upregulation as compared to Ritux-ATAC2 and equimolar concentrations of unconjugated rituximab (Roche).

Figure 67K:
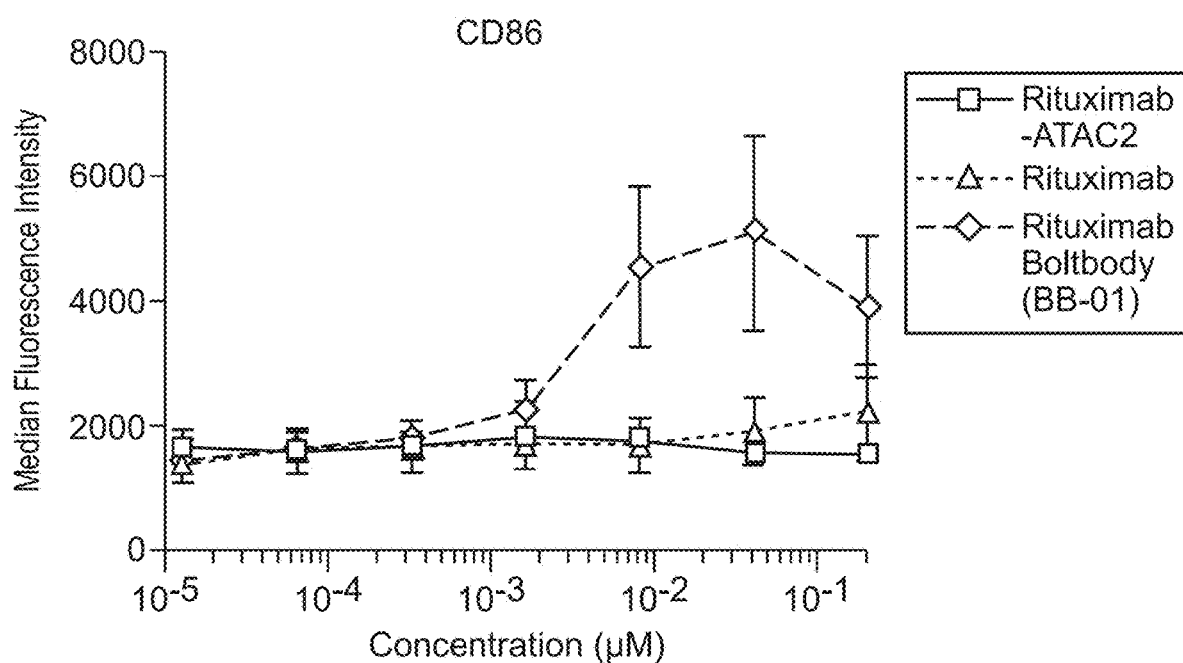

FIG. 67K shows that the BB-01 immunoconjugate produced according to the SATA method [Rituximab Boltbody (BB-01)] is superior at eliciting CD86 upregulation on myeloid cells as compared to the rituximab with valine-citruline-PABC linker immunoconjugate produced according to the methods described in US 2017/0158772 (Ritux-ATAC2) and equimolar concentrations of unconjugated rituximab (Roche).

Figure 67L:
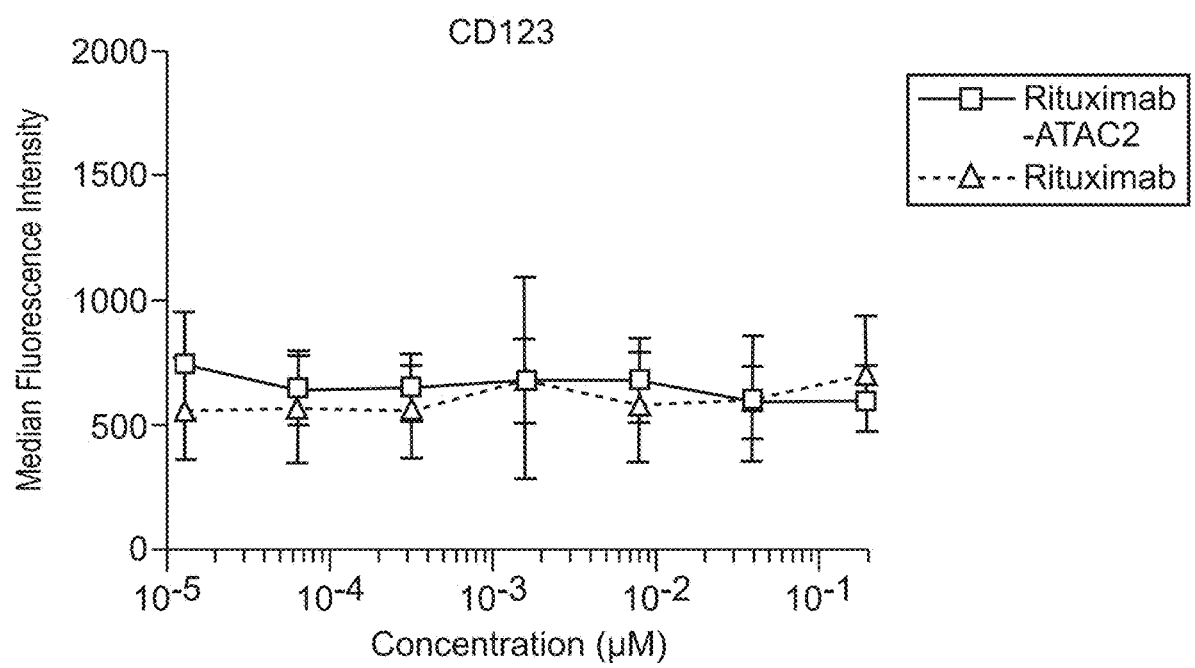

FIG. 67L shows CD123 expression on myeloid cells following 18 hours of stimulation with the rituximab with valine-citruline-PABC linker immunoconjugate produced according to the methods described in US 2017/0158772 (Ritux-ATAC2) as compared to unconjugated rituximab (Roche).

Figure 67M:
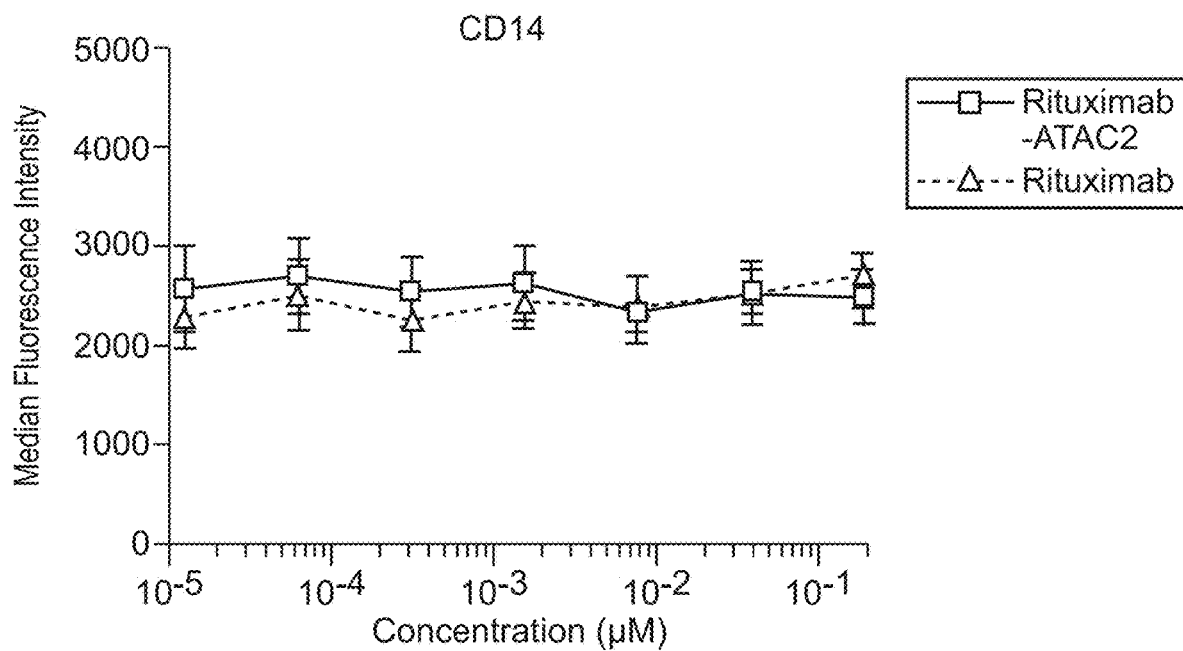

FIG. 67M shows CD14 expression on myeloid cells following 18 hours of stimulation with the rituximab with valine-citruline-PABC linker immunoconjugate produced according to the methods described in US 2017/0158772 (Ritux-ATAC2) as compared to unconjugated rituximab (Roche).

Figure 67N:
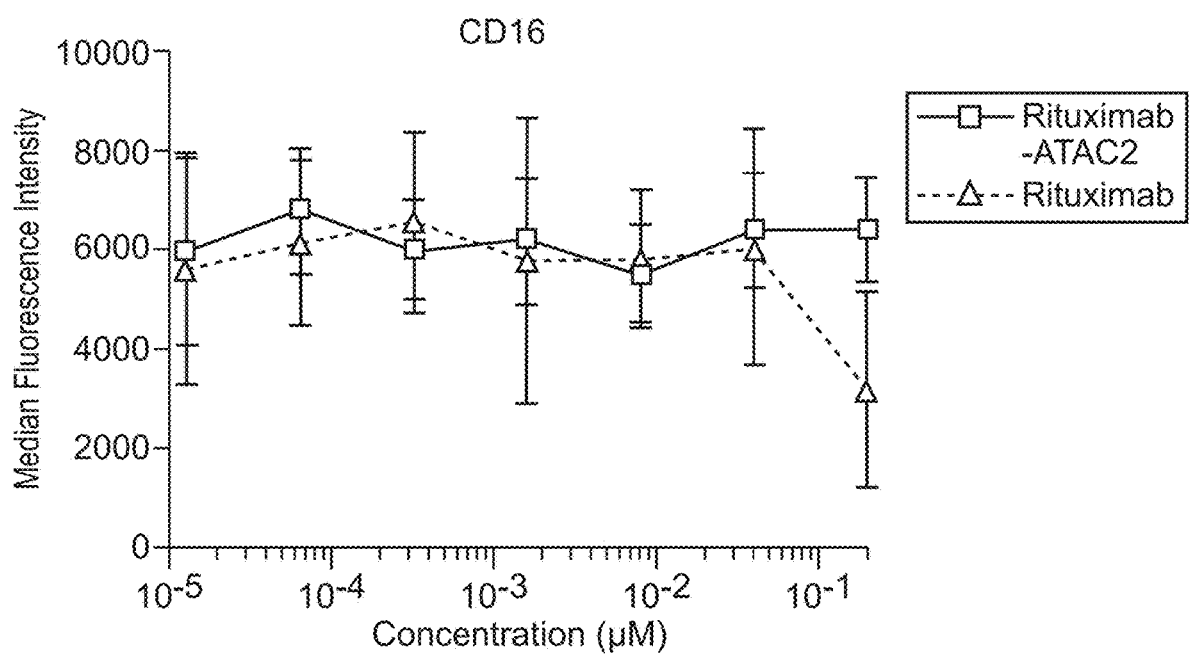

FIG. 67N shows CD16 expression on myeloid cells following 18 hours of stimulation with the rituximab with valine-citruline-PABC linker immunoconjugate produced according to the methods described in US 2017/0158772 (Ritux-ATAC2) as compared to unconjugated rituximab (Roche).

Figure 67O:
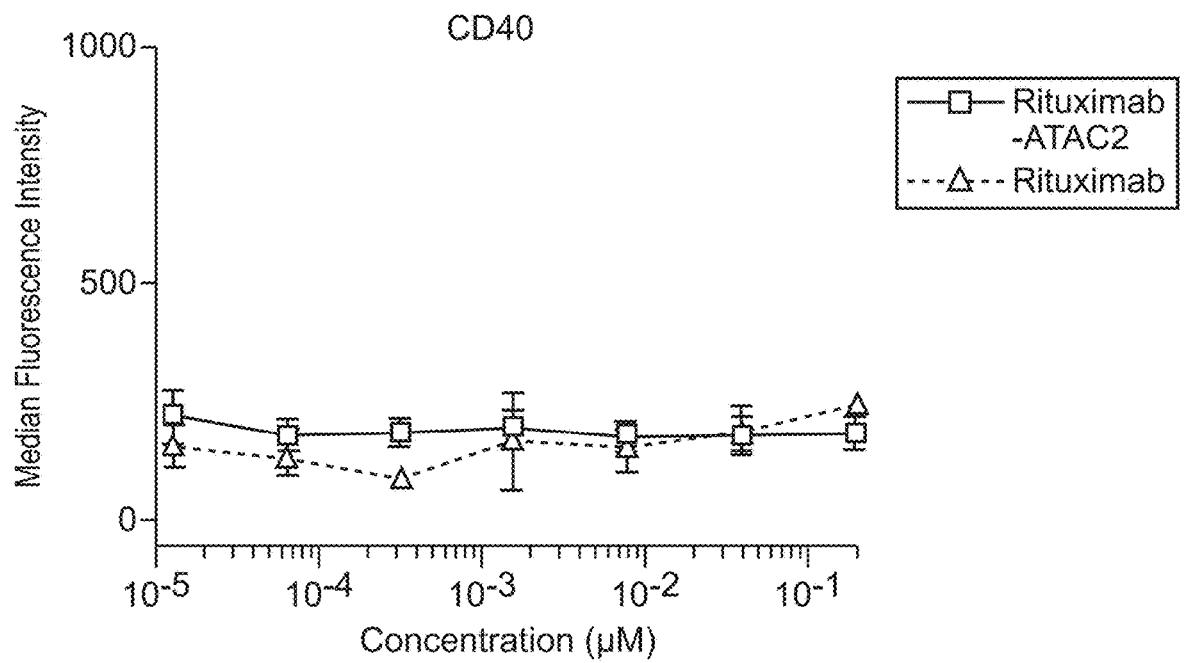

FIG. 67O shows CD40 expression on myeloid cells following 18 hours of stimulation with the rituximab with valine-citruline-PABC linker immunoconjugate produced according to the methods described in US 2017/0158772 (Ritux-ATAC2) as compared to unconjugated rituximab (Roche).

Figure 67P:
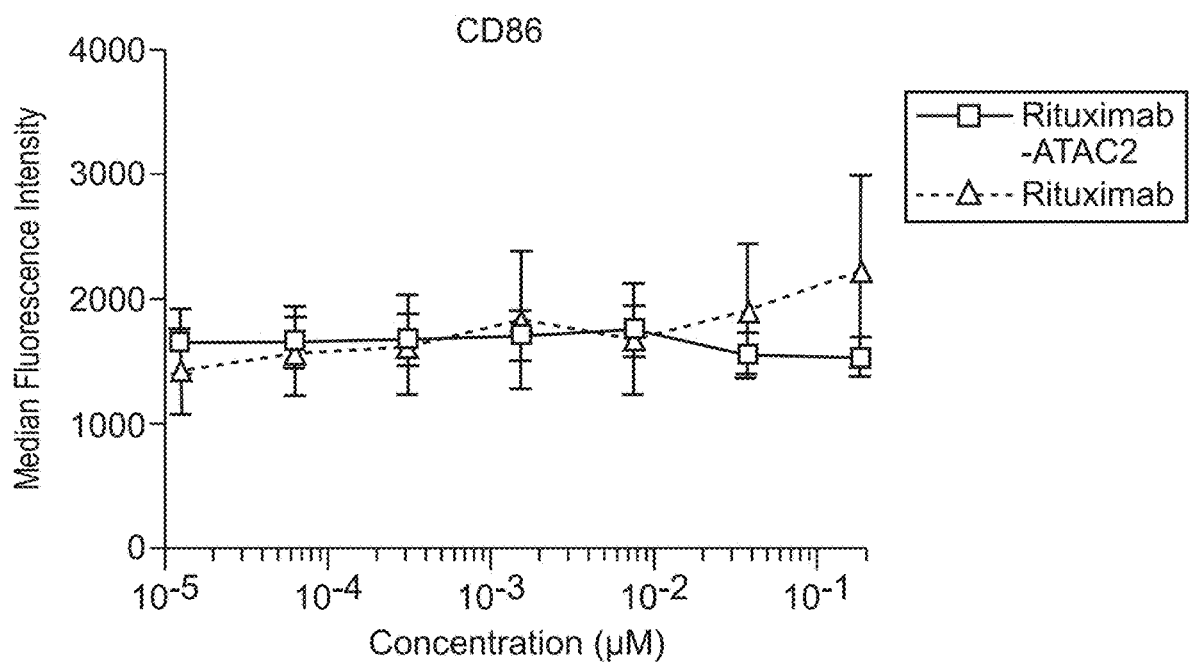

FIG. 67P shows CD86 expression on myeloid cells following 18 hours of stimulation with the rituximab with valine-citruline-PABC linker immunoconjugate produced according to the methods described in US 2017/0158772 (Ritux-ATAC2) as compared to unconjugated rituximab (Roche).

Figure 68A:
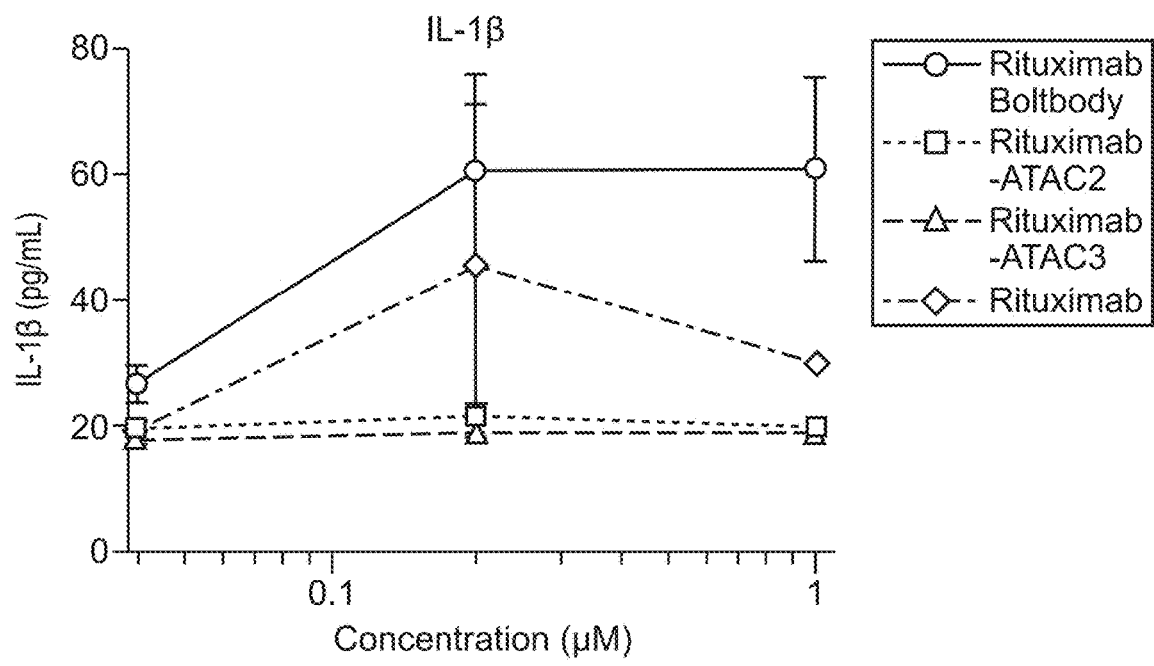

FIG. 68A shows that the rituximab immunoconjugate produced according to the BB-01 SATA method (Rituximab Boltbody) elicits superior IL-1$\beta$ secretion from myeloid cells as compared to unconjugated rituximab (Roche) as well as equimolar concentrations of comparative conjugates prepared with rituximab and either a valine-citruline-PABC or a maleimide-PEG4 linker, both containing a pentafluorophenyl group with gardiquimod (Rituximab-ATAC2, Rituximab-ATAC3 respectively; US 2017/0158772) following 18 hours of stimulation.

Figure 68B:
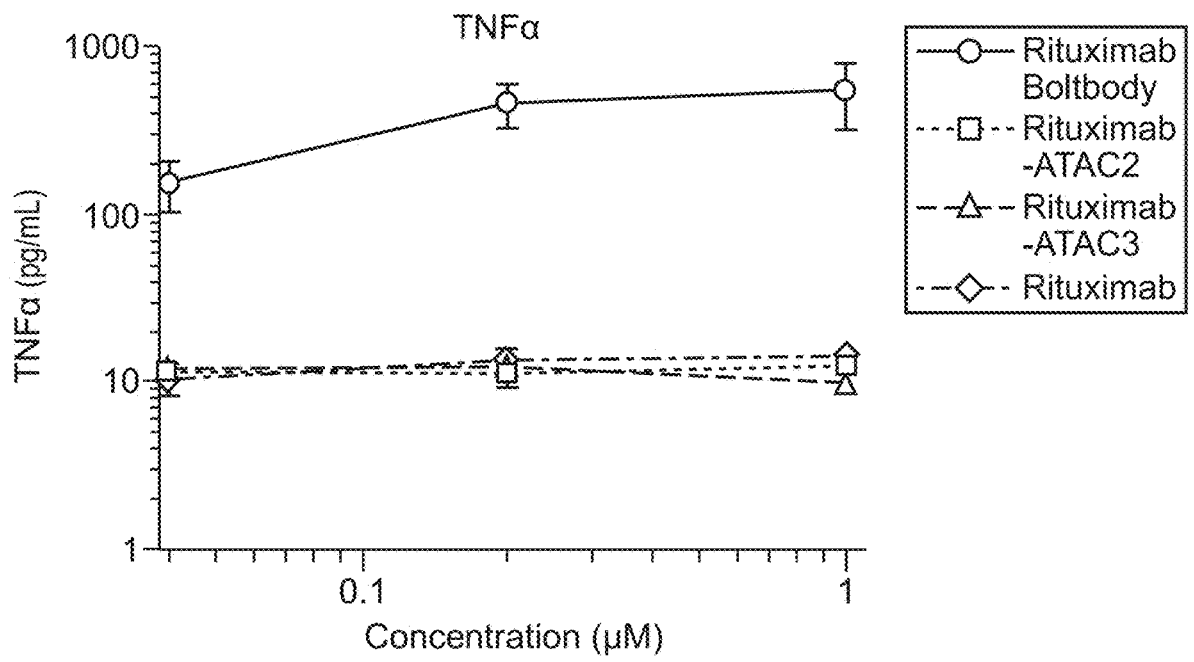

FIG. 68B shows that the rituximab immunoconjugate produced according to the BB-01 SATA method (Rituximab Boltbody) elicits superior TNF$\alpha$ secretion from myeloid cells as compared to unconjugated rituximab (Roche) as well as equimolar concentrations of comparative conjugates prepared with rituximab and either a valine-citruline-PABC or a maleimide-PEG4 linker, both containing a pentafluorophenyl group with gardiquimod (Rituximab-ATAC2, Rituximab-ATAC3 respectively; US 2017/0158772) following 18 hours of stimulation.

Figure 68C:
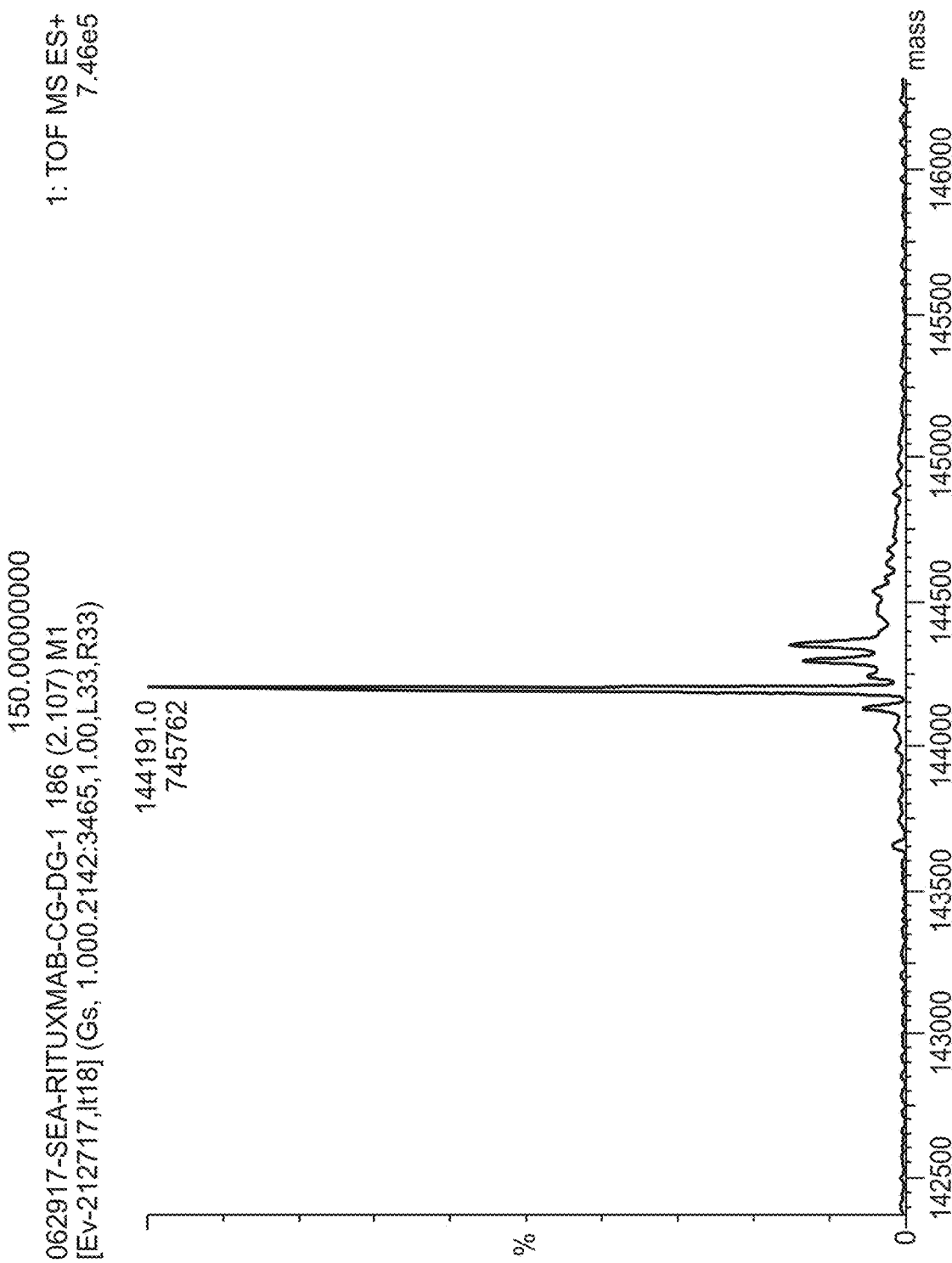

FIG. 68C shows a liquid chromatography-mass spectrometry analysis of unconjugated rituximab (Roche) that was utilized to produce the rituximab immunoconjugate according to the BB-01 conjugation method or the rituximab immunoconjugates according to the methods described in US 2017/0158772 following overnight deglycosylation with PNGase F.

FIG. 68D shows a liquid chromatography-mass spectrometry analysis of unconjugated rituximab (Roche) that was utilized to produce the rituximab immunoconjugate according to the BB-01 conjugation method or the rituximab immunoconjugates according to the methods described in US 2017/0158772.

Figure 68E:
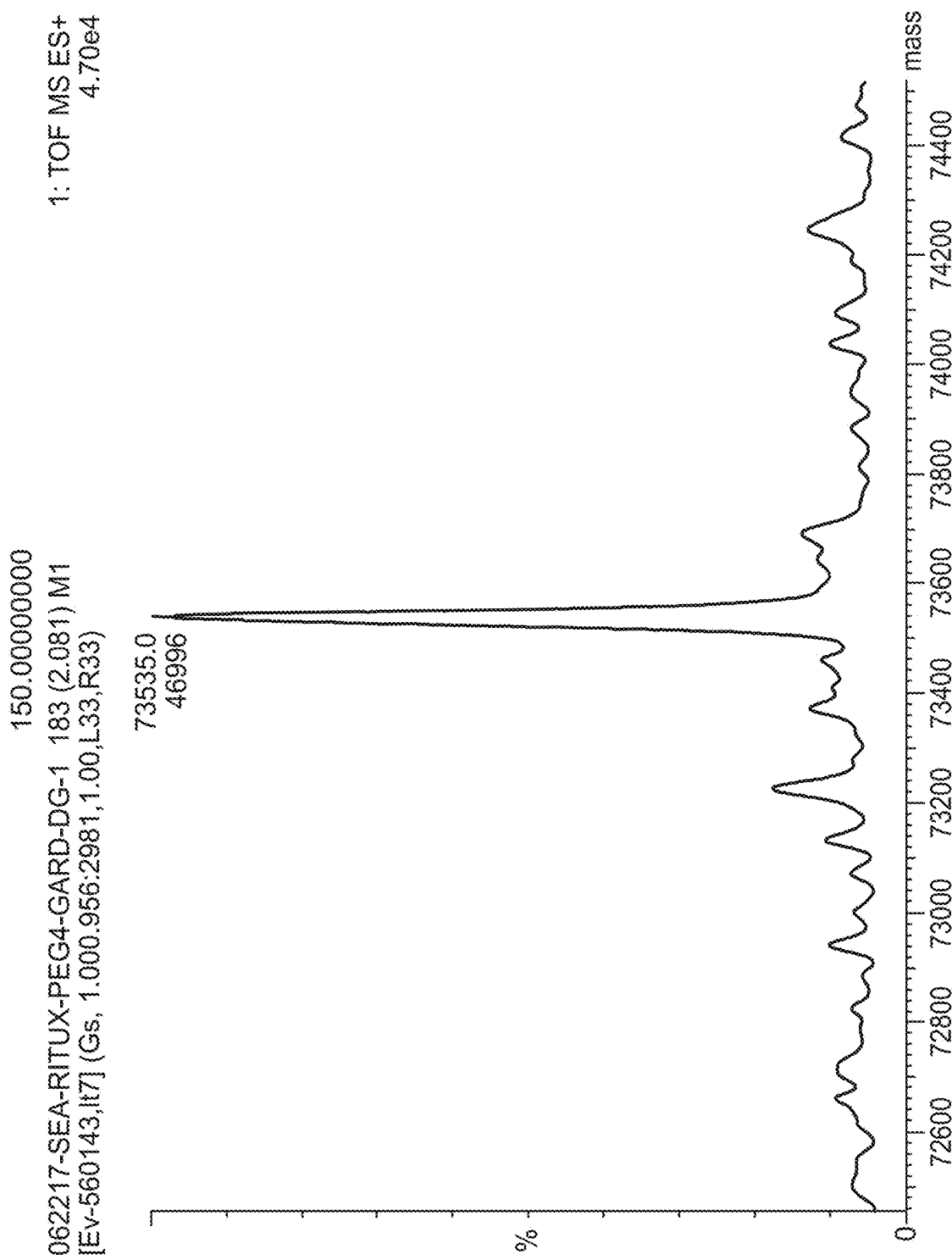

FIG. 68E shows a liquid chromatography-mass spectrometry analysis of the ipsilateral heavy-light chain of the rituximab immunoconjugate produced using a maleimide-PEG4 linker as described in US 2017/0158772 following overnight deglycosylation with PNGase F.

Figure 68F:
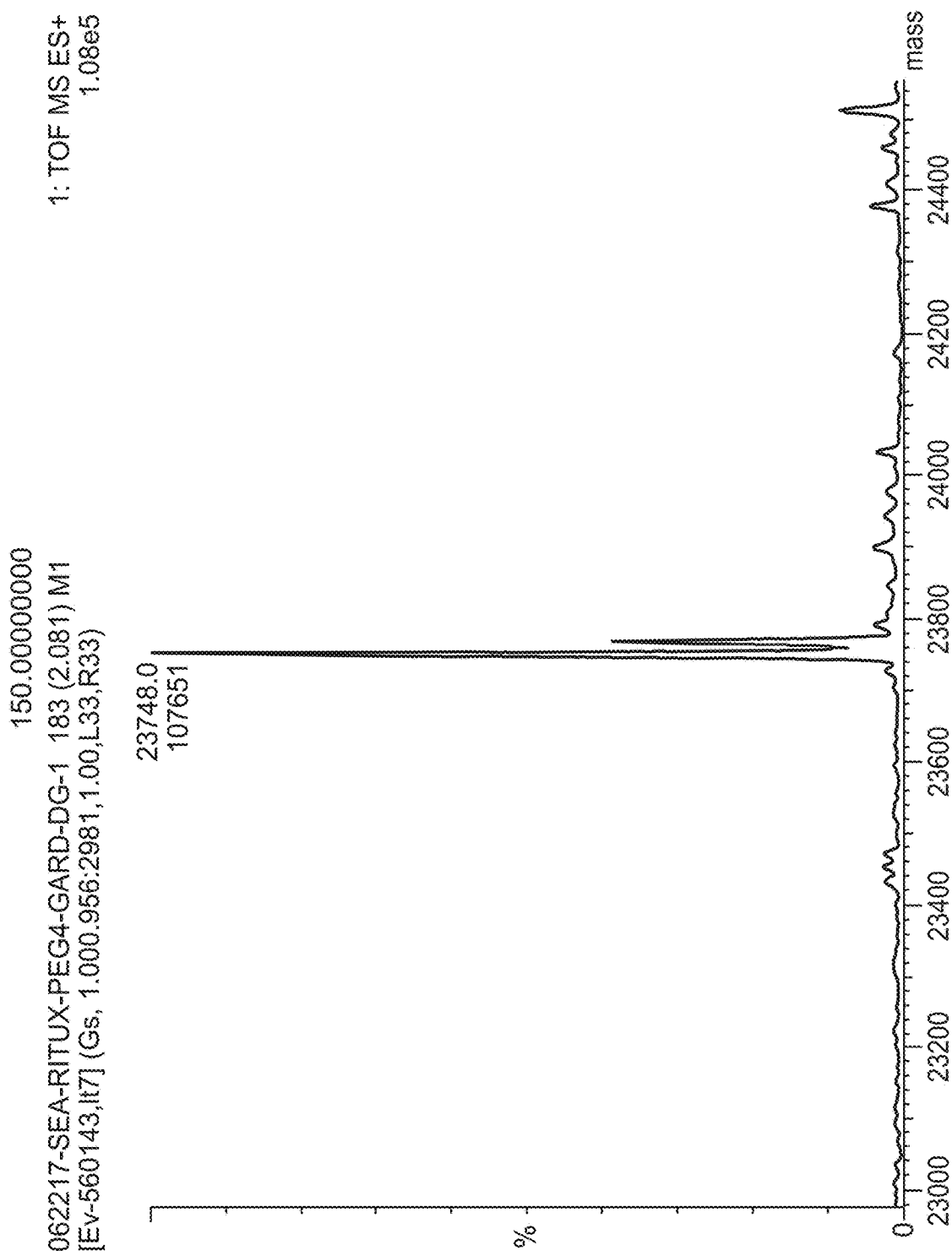

FIG. 68F shows a liquid chromatography-mass spectrometry analysis of the light chain of the rituximab immunoconjugate produced using a maleimide-PEG4 linker as described in US 2017/0158772 following overnight deglycosylation with PNGase F.

FIG. 68G shows that the rituximab with maleimide-PEG4 linker immunoconjugate produced according to the methods described in US 2017/0158772 (Ritux-ATAC3) fails to elicit CD123 upregulation on myeloid cells following 18 hours of stimulation. FIG. 68G also shows that the BB-01 immunoconjugate produced according to the SATA method [Rituximab Boltbody (BB-01)] is superior at eliciting CD123 upregulation as compared to Ritux-ATAC3 and equimolar concentrations of unconjugated rituximab (Roche).

Figure 68H:
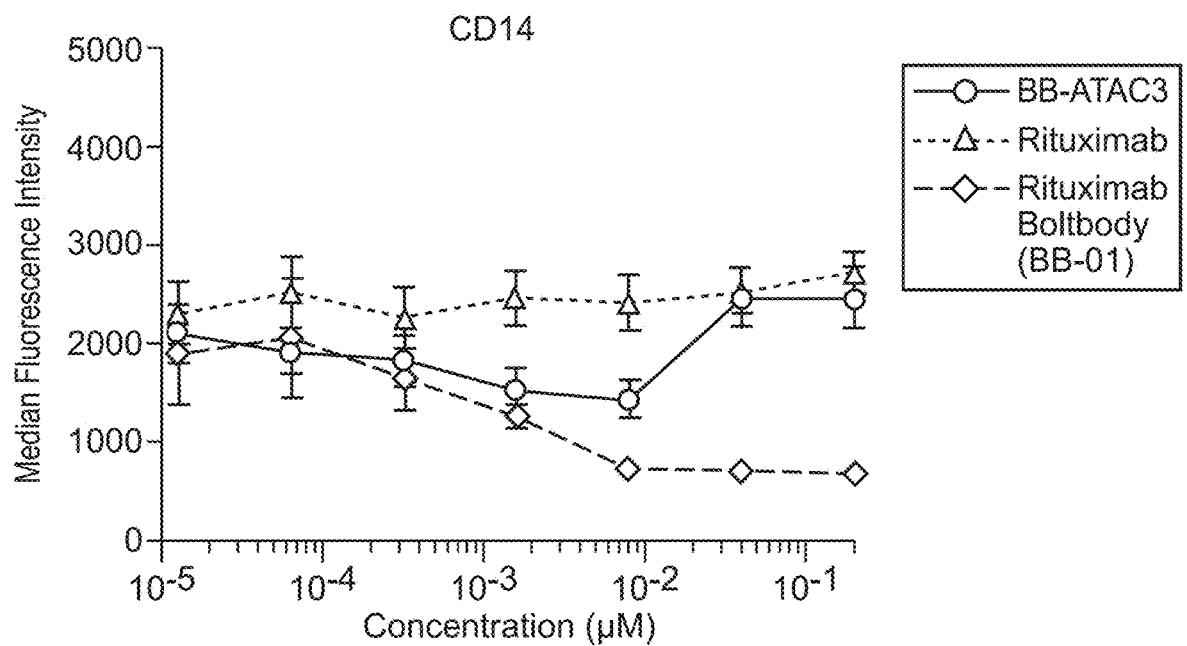

FIG. 68H shows that the BB-01 immunoconjugate produced according to the SATA method [Rituximab Boltbody (BB-01)] is superior at eliciting CD14 downregulation on myeloid cells as compared to the rituximab with maleimide-PEG4 linker immunoconjugate produced according to the methods described in US 2017/0158772 (Ritux-ATAC3) and equimolar concentrations of unconjugated rituximab (Roche) following 18 hours of stimulation.

Figure 68I:
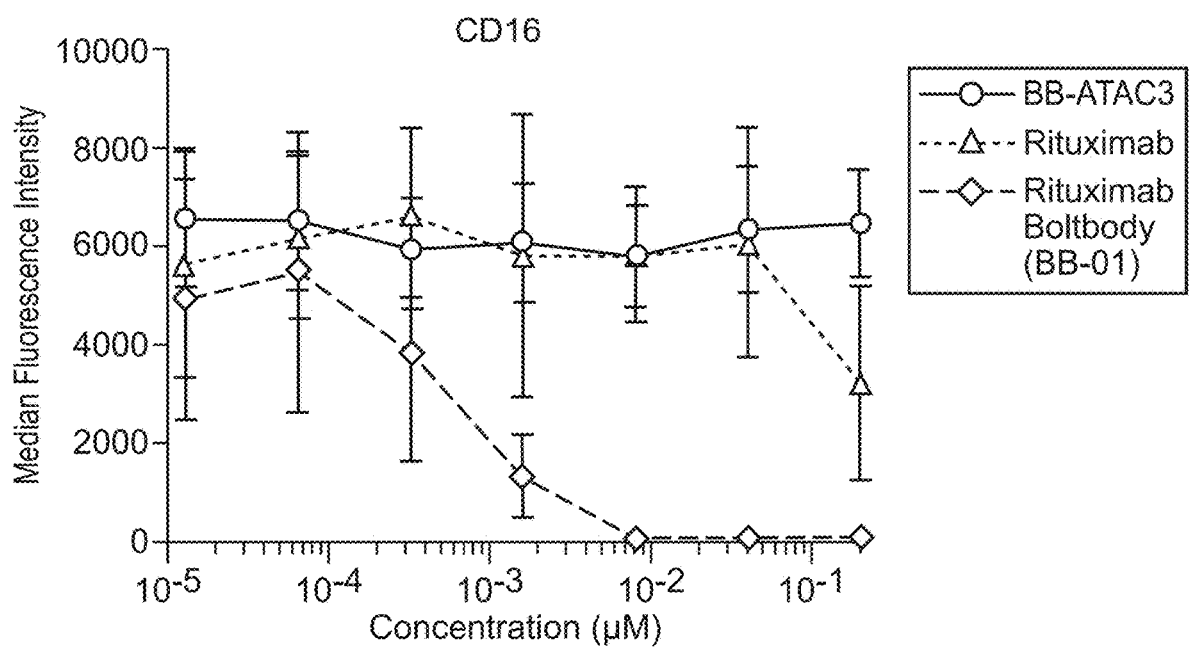

FIG. 68I shows that the rituximab with maleimide-PEG4 linker immunoconjugate produced according to the methods described in US 2017/0158772 (Ritux-ATAC3) fails to elicit CD16 downregulation on myeloid cells following 18 hours of stimulation. FIG. 68I also shows that the BB-01 immunoconjugate produced according to the SATA method [Rituximab Boltbody (BB-01)] is superior at eliciting CD40 upregulation as compared to Ritux-ATAC2 and equimolar concentrations of unconjugated rituximab (Roche).

Figure 68J:
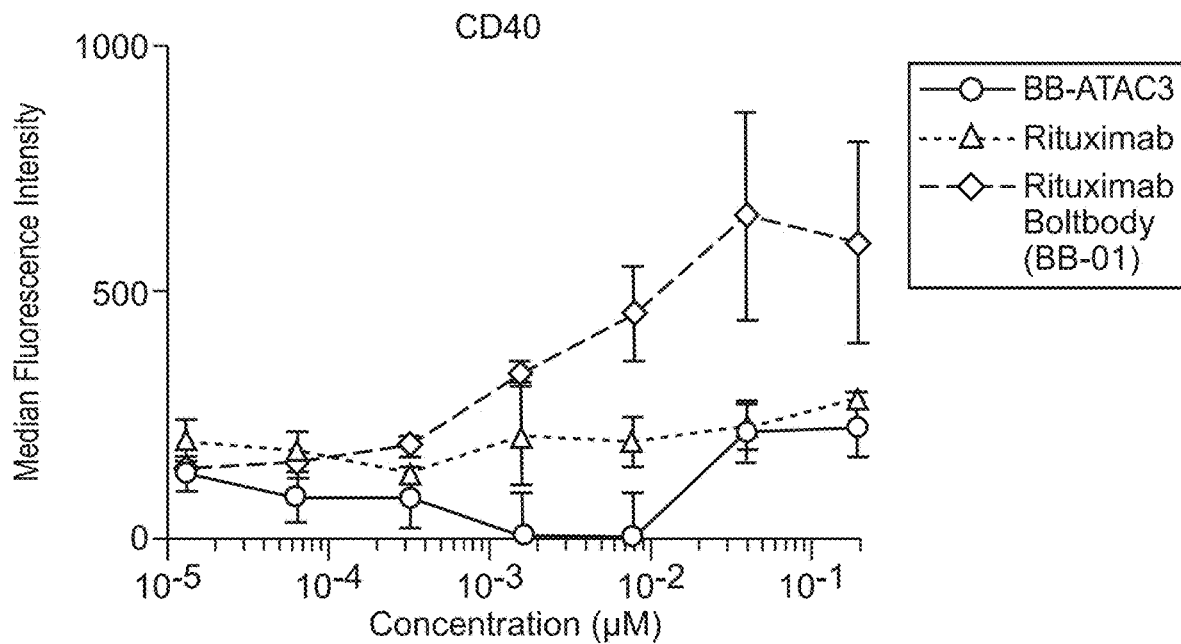

FIG. 68J shows that the rituximab with maleimide-PEG4 linker immunoconjugate produced according to the methods described in US 2017/0158772 (Ritux-ATAC3) fails to elicit CD40 upregulation on myeloid cells following 18 hours of stimulation. FIG. 68J also shows that the BB-01 immunoconjugate produced according to the SATA method [Rituximab Boltbody (BB-01)] is superior at eliciting CD40 upregulation as compared to Ritux-ATAC2 and equimolar concentrations of unconjugated rituximab (Roche).

Figure 68K:
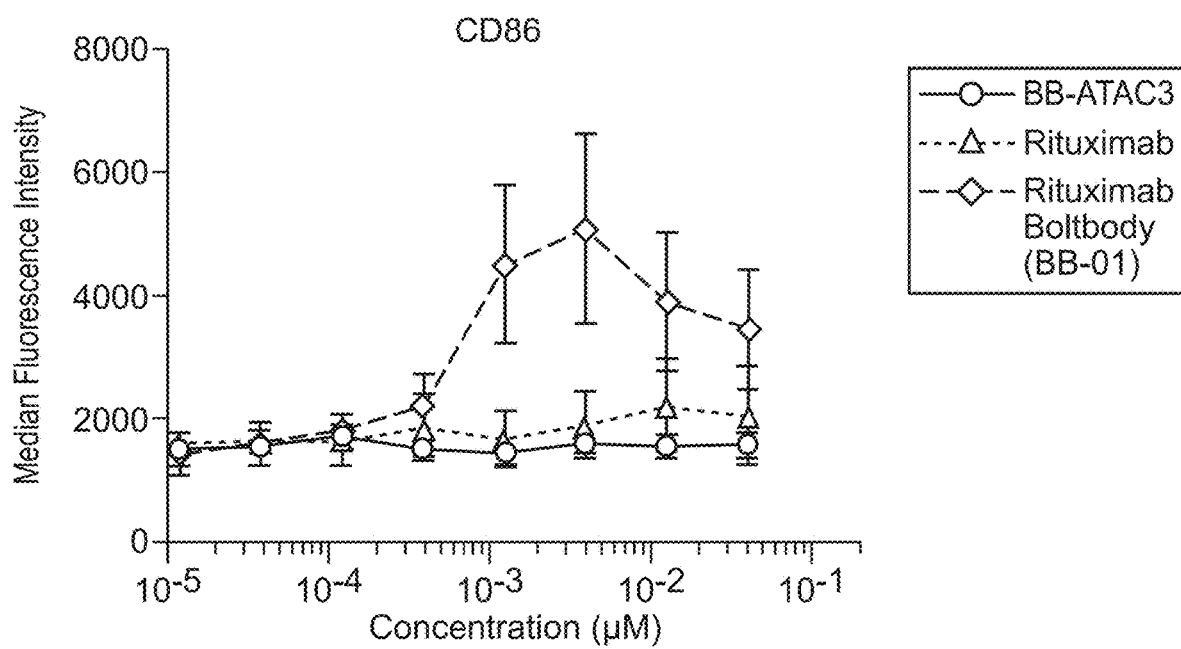

FIG. 68K shows that the rituximab with maleimide-PEG4 linker immunoconjugate produced according to the methods described in US 2017/0158772 (Ritux-ATAC3) fails to elicit CD86 upregulation on myeloid cells following 18 hours of stimulation. FIG. 68J also shows that the BB-01 immunoconjugate produced according to the SATA method [Rituximab Boltbody (BB-01)] is superior at eliciting CD86 upregulation as compared to Ritux-ATAC2 and equimolar concentrations of unconjugated rituximab (Roche).

Figure 68L:
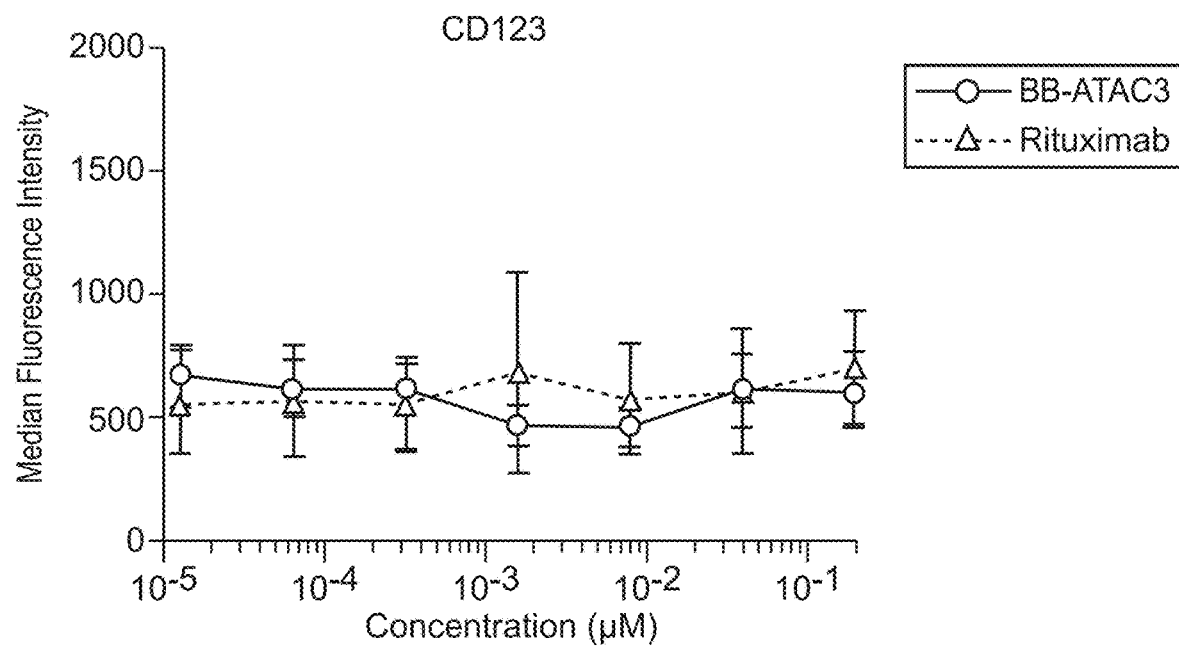

FIG. 68L shows CD123 expression on myeloid cells following 18 hours of stimulation with the rituximab with maleimide-PEG4 linker immunoconjugate produced according to the methods described in US 2017/0158772 (Ritux-ATAC3) as compared to unconjugated rituximab (Roche).

Figure 68M:
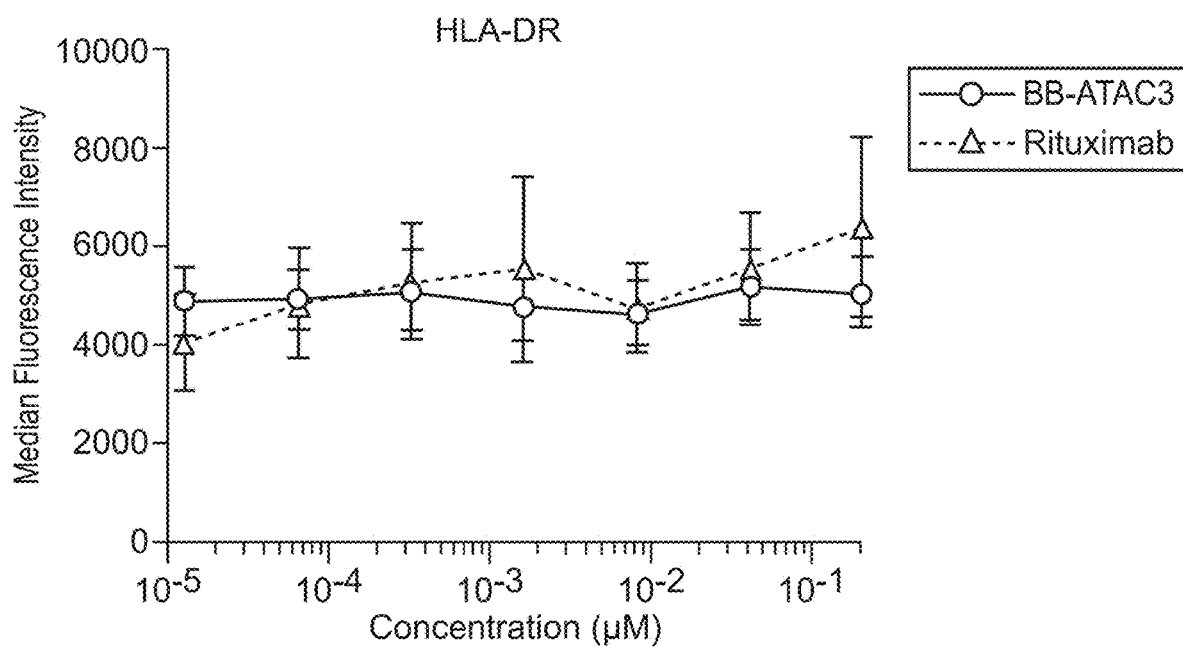

FIG. 68M shows HLA-DR expression on myeloid cells following 18 hours of stimulation with the rituximab with maleimide-PEG4 linker immunoconjugate produced according to the methods described in US 2017/0158772 (Ritux-ATAC3) as compared to unconjugated rituximab (Roche).

Figure 68N:
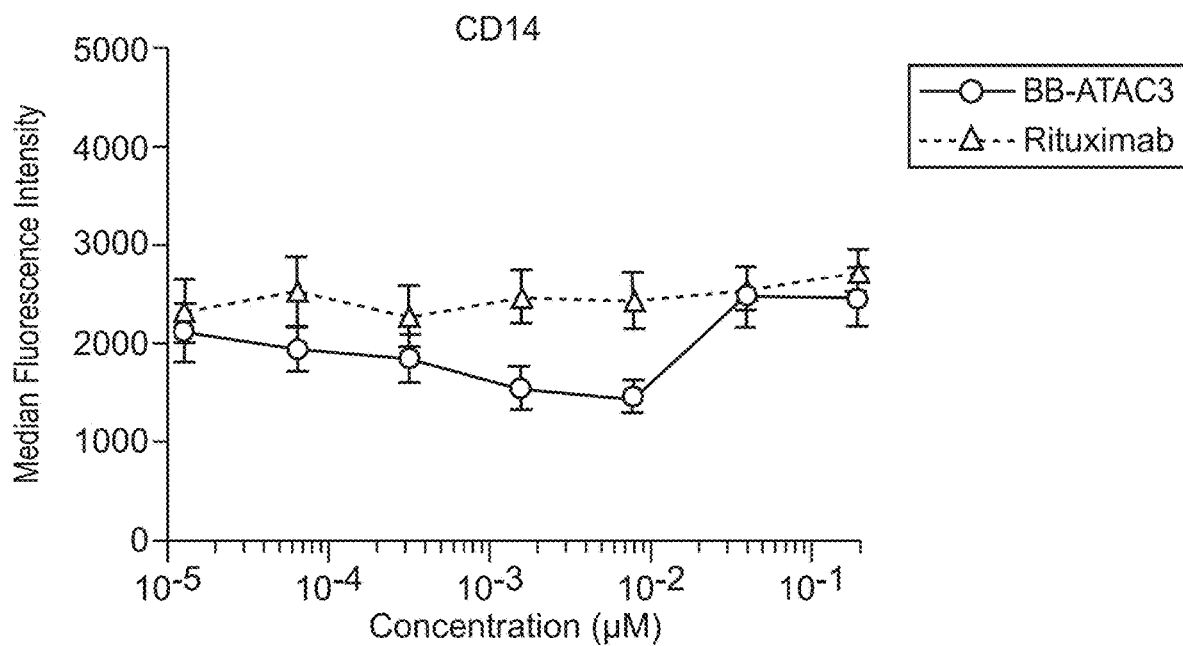

FIG. 68N shows CD14 expression on myeloid cells following 18 hours of stimulation with the rituximab with maleimide-PEG4 linker immunoconjugate produced according to the methods described in US 2017/0158772 (Ritux-ATAC3) as compared to unconjugated rituximab (Roche)

Figure 68O:
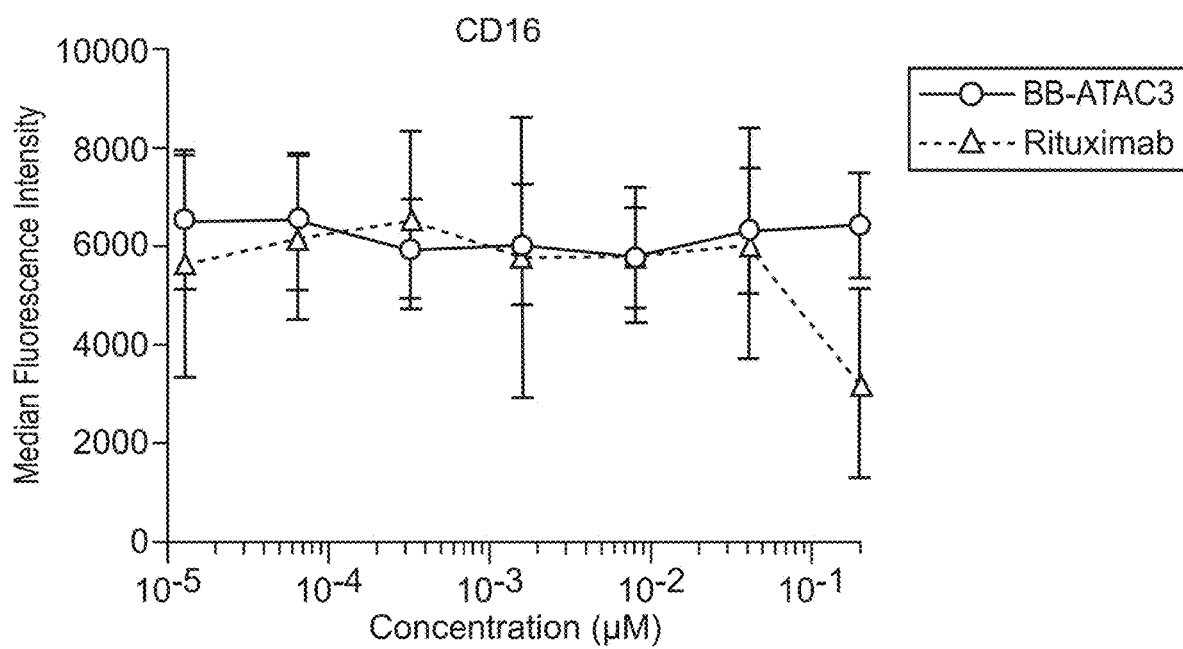

FIG. 68O shows CD16 expression on myeloid cells following 18 hours of stimulation with the rituximab with maleimide-PEG4 linker immunoconjugate produced according to the methods described in US 2017/0158772 (Ritux-ATAC3) as compared to unconjugated rituximab (Roche).

Figure 68P:
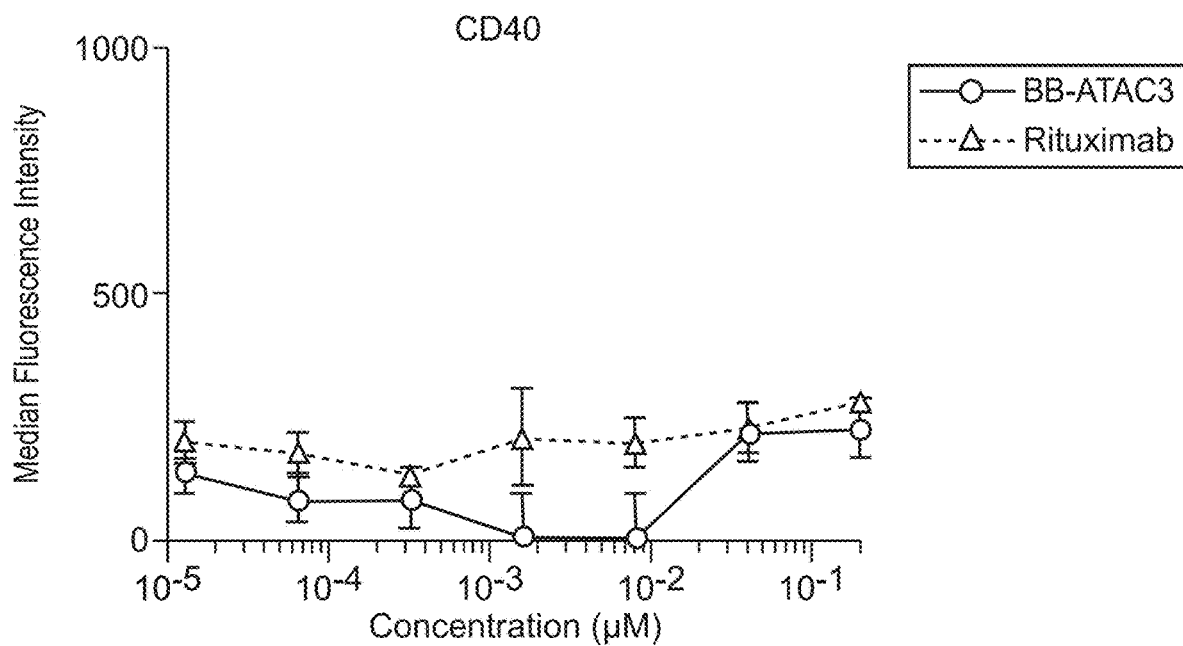

FIG. 68P shows CD40 expression on myeloid cells following 18 hours of stimulation with the rituximab with maleimide-PEG4 linker immunoconjugate produced according to the methods described in US 2017/0158772 (Ritux-ATAC3) as compared to unconjugated rituximab (Roche).

Figure 68Q:
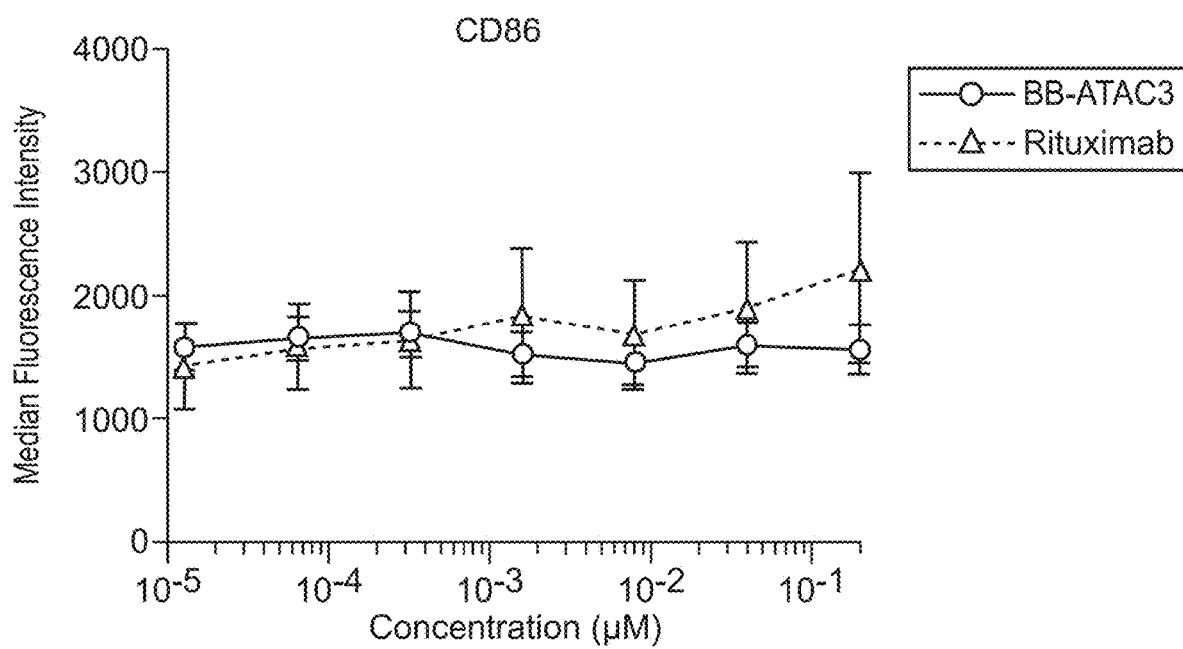

FIG. 68Q shows CD86 expression on myeloid cells following 18 hours of stimulation with the rituximab with maleimide-PEG4 linker immunoconjugate produced according to the methods described in US 2017/0158772 (Ritux-ATAC3) as compared to unconjugated rituximab (Roche).

Figure 69A:
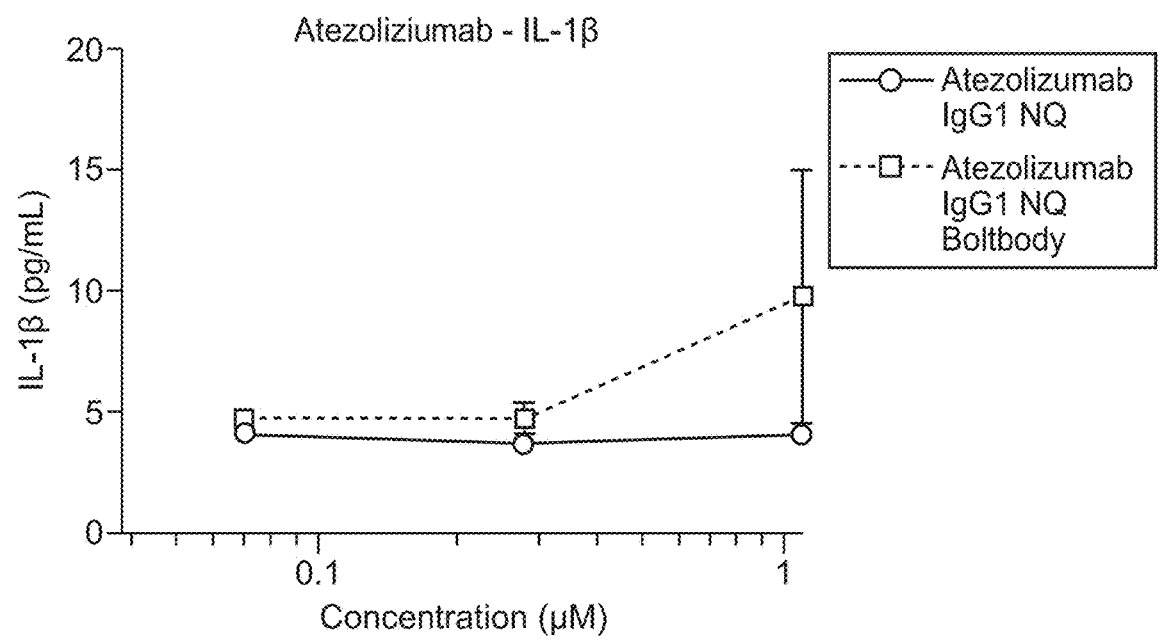

FIG. 69A shows that the atezolizumab immunoconjugate produced according to the BB-01 method (Atezolizumab IgG1 NQ Boltbody) elicits superior IL-10 secretion from myeloid cells as compared to equimolar concentrations of unconjugated atezolizumab (Roche) following 18 hours of stimulation.

Figure 69B:
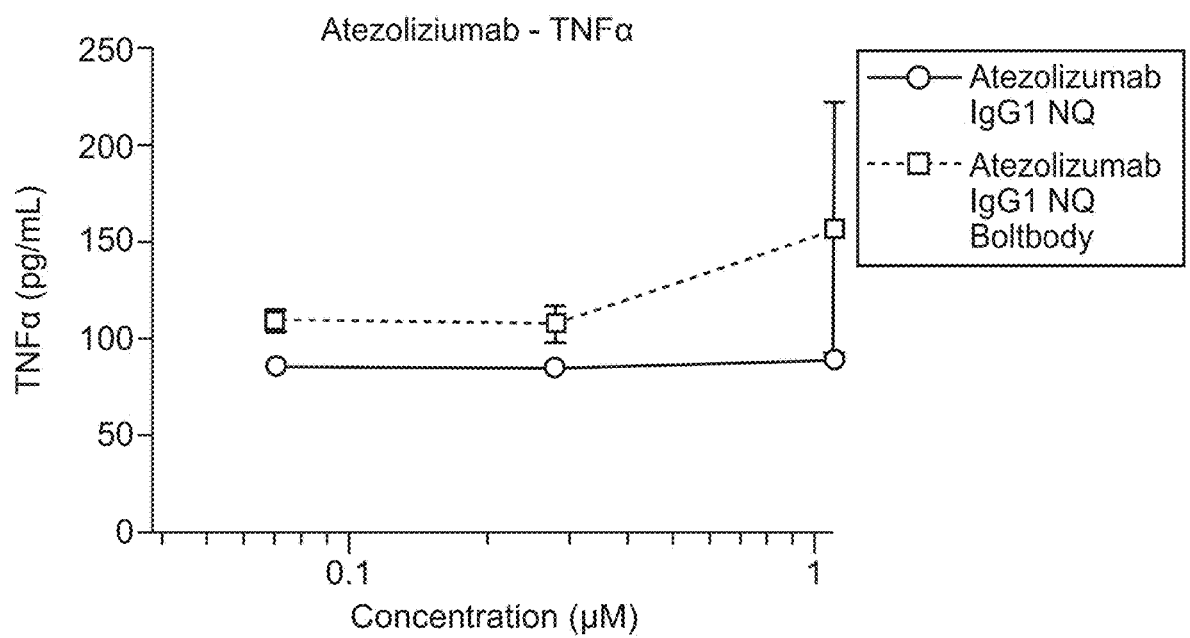

FIG. 69B shows that the atezolizumab immunoconjugate produced according to the BB-01 method (Atezolizumab IgG1 NQ Boltbody) elicits superior TNFα secretion from myeloid cells as compared to equimolar concentrations of unconjugated atezolizumab (Roche) following 18 hours of stimulation.

FIG. 69C shows a liquid chromatography-mass spectrometry analysis of the atezolizumab immunoconjugate produced according to the BB-01 conjugation method following overnight deglycosylation with PNGase F.

Figure 69D:
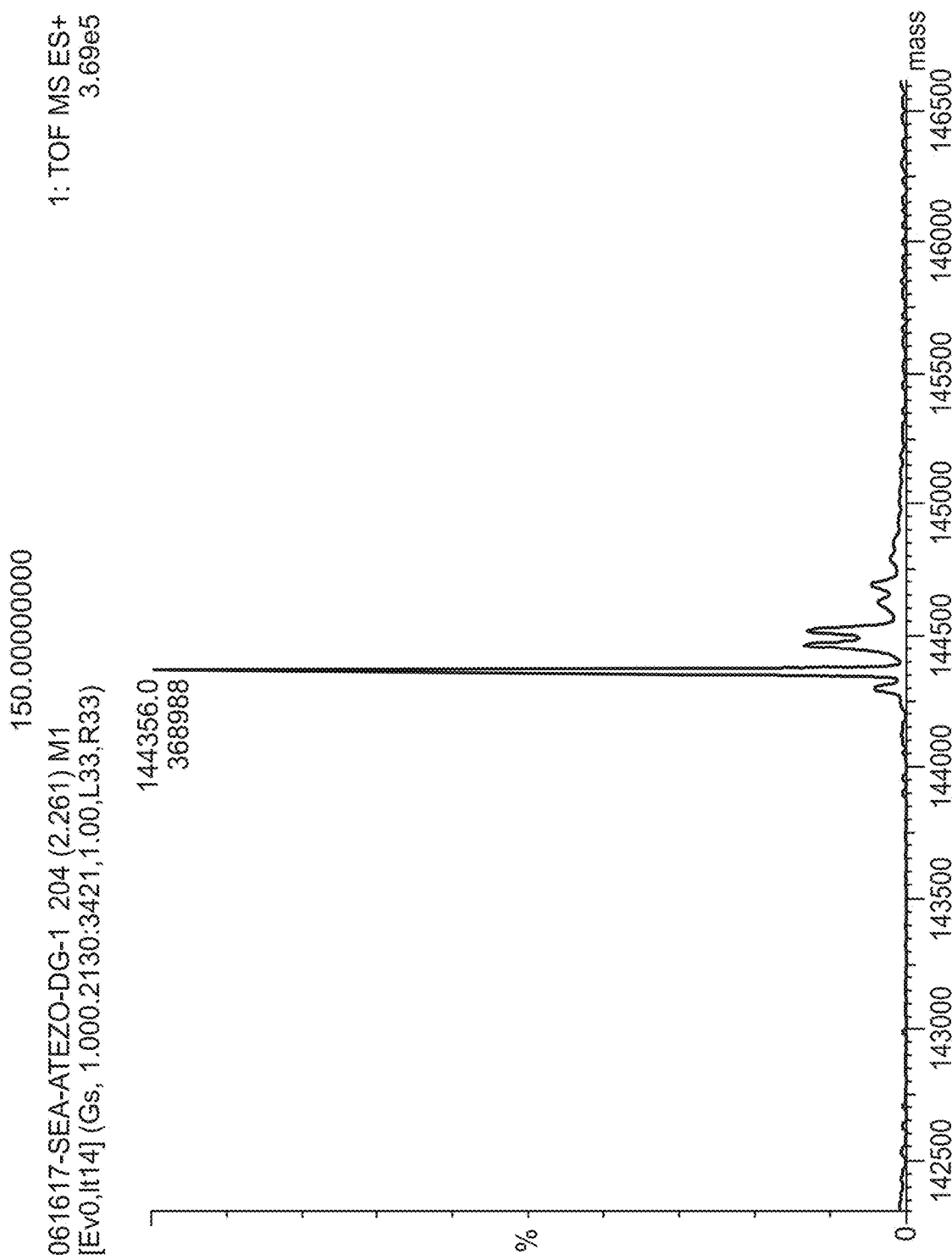

FIG. 69D shows a liquid chromatography-mass spectrometry analysis of unconjugated atezolizumab (Roche) that was utilized to produce the atezolizumab immunoconjugate according to the BB-01 conjugation method following overnight deglycosylation with PNGase F.

Figure 69E:
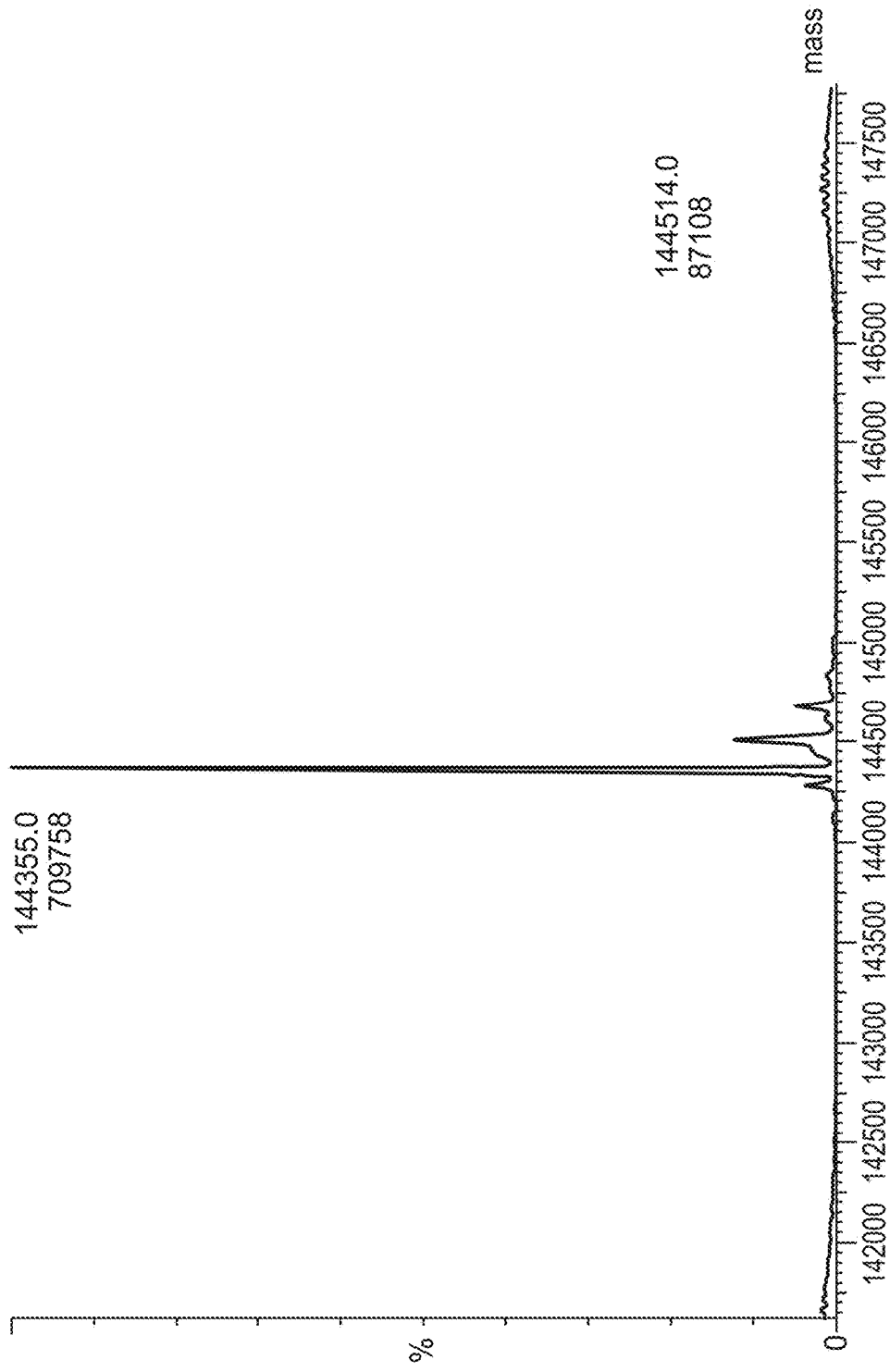

FIG. 69E shows a liquid chromatography-mass spectrometry analysis of unconjugated atezolizumab (Roche) that was utilized to produce the atezolizumab immunoconjugate according to the BB-01 method.

Figure 69F:
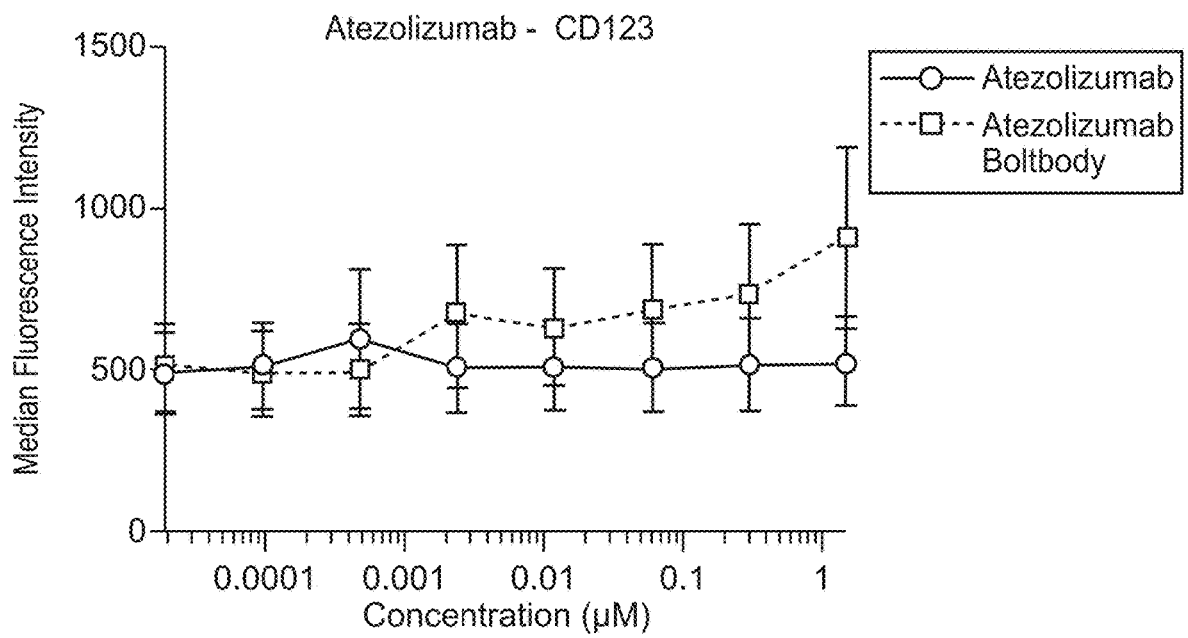

FIG. 69F shows CD123 expression on myeloid cells following 18 hours of stimulation with the atezolizumab immunoconjugate produced according to the BB-01 method (Atezolizumab Boltbody) as compared to unconjugated atezolizumab (Roche).

Figure 69G:
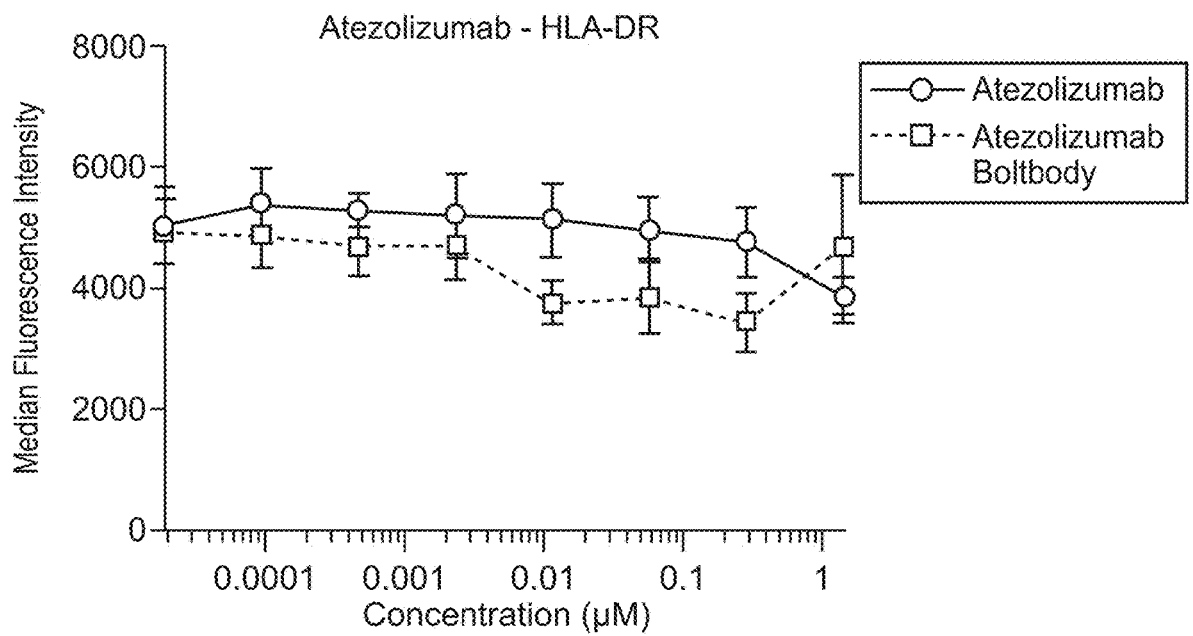

FIG. 69G shows HLA-DR expression on myeloid cells following 18 hours of stimulation with the atezolizumab immunoconjugate produced according to the BB-01 method (Atezolizumab Boltbody) as compared to unconjugated atezolizumab (Roche).

Figure 69H:
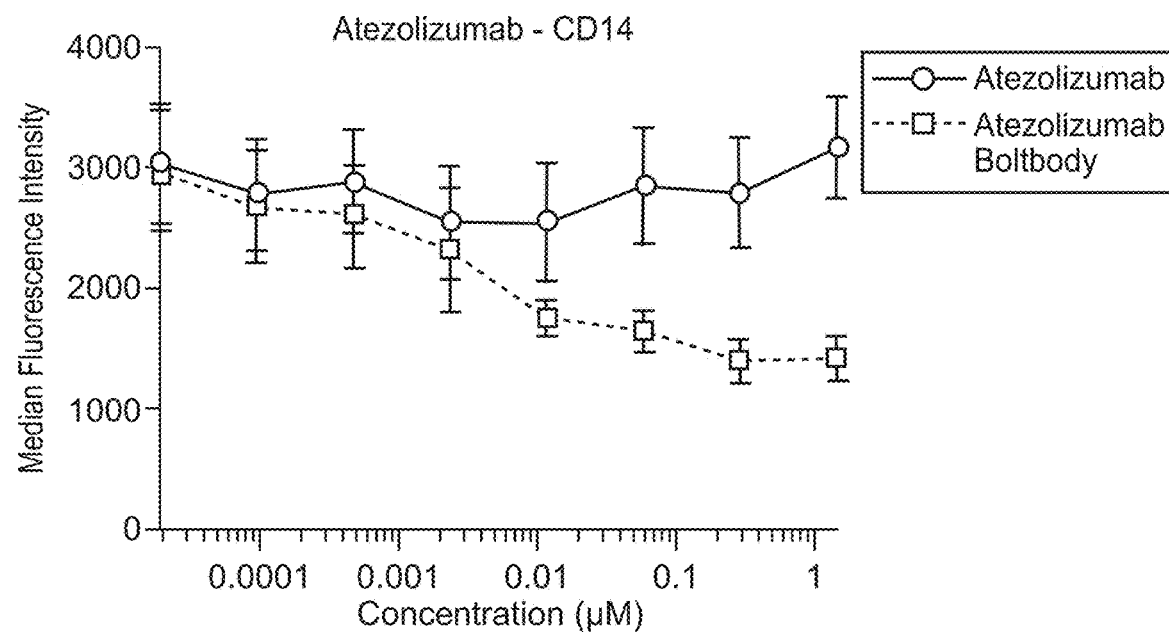

FIG. 69H shows that the atezolizumab immunoconjugate produced according to the BB-01 method (Atezolizumab Boltbody) is superior at eliciting CD14 downregulation on myeloid cells as compared to the unconjugated atezolizumab (Roche) following 18 hours of stimulation.

Figure 69I:
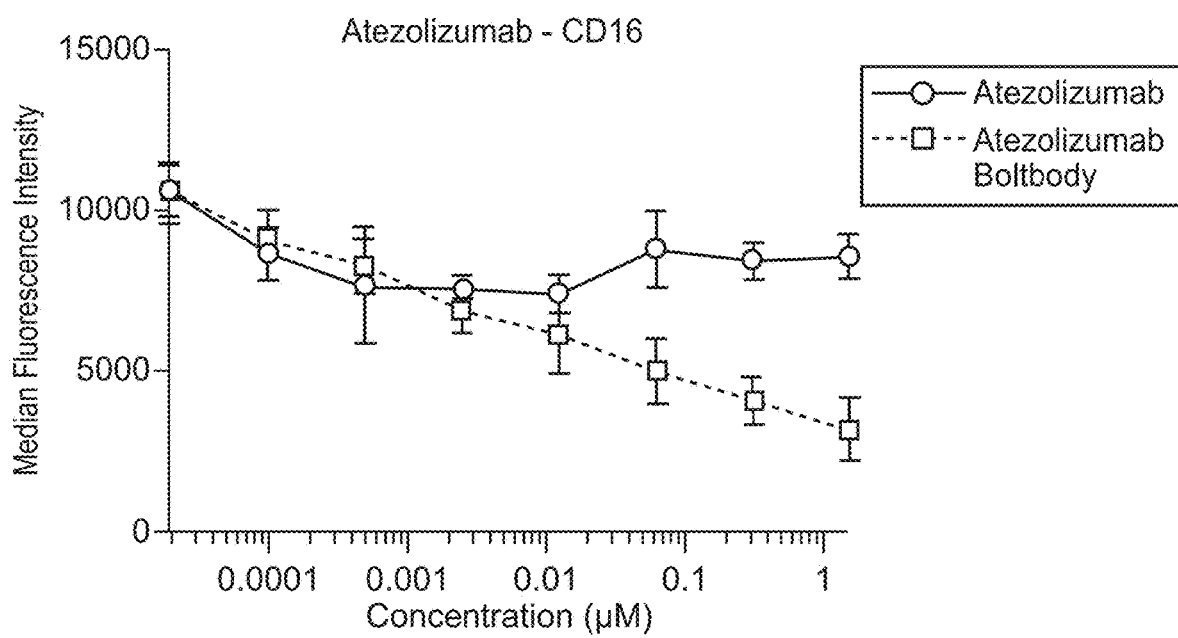

FIG. 69I shows that the atezolizumab immunoconjugate produced according to the BB-01 method (Atezolizumab Boltbody) is superior at eliciting CD16 downregulation on myeloid cells as compared to the unconjugated atezolizumab (Roche) following 18 hours of stimulation.

Figure 69J:
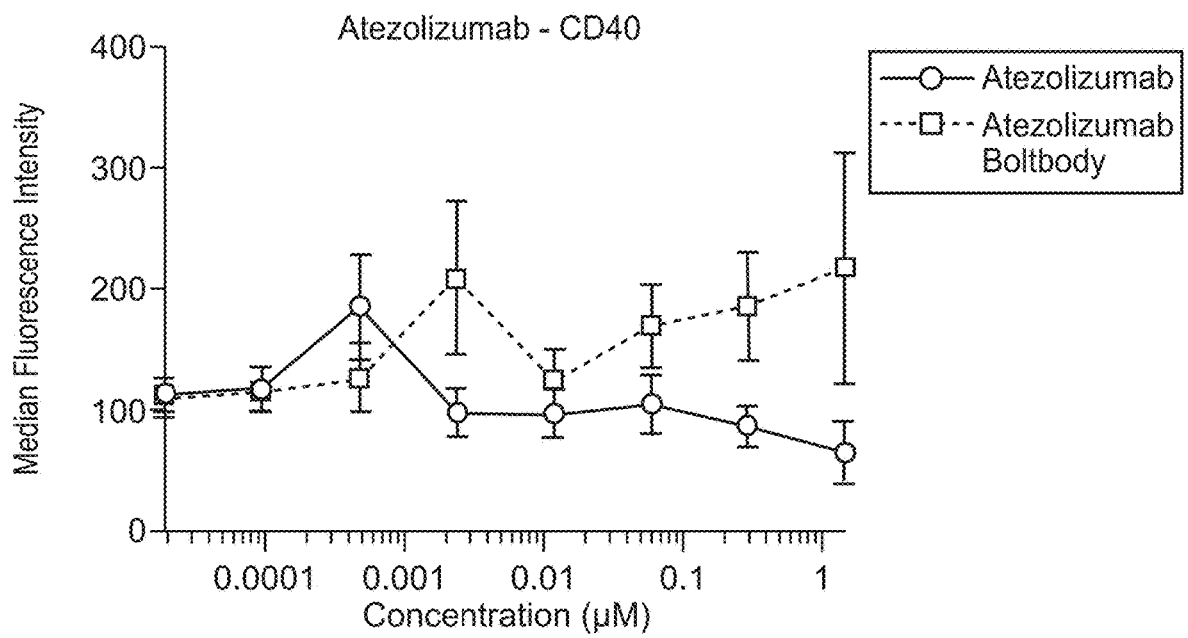

FIG. 69J shows that the atezolizumab immunoconjugate produced according to the BB-01 method (Atezolizumab Boltbody) is superior at eliciting CD40 upregulation on myeloid cells as compared to the unconjugated atezolizumab (Roche) following 18 hours of stimulation.

Figure 69K:
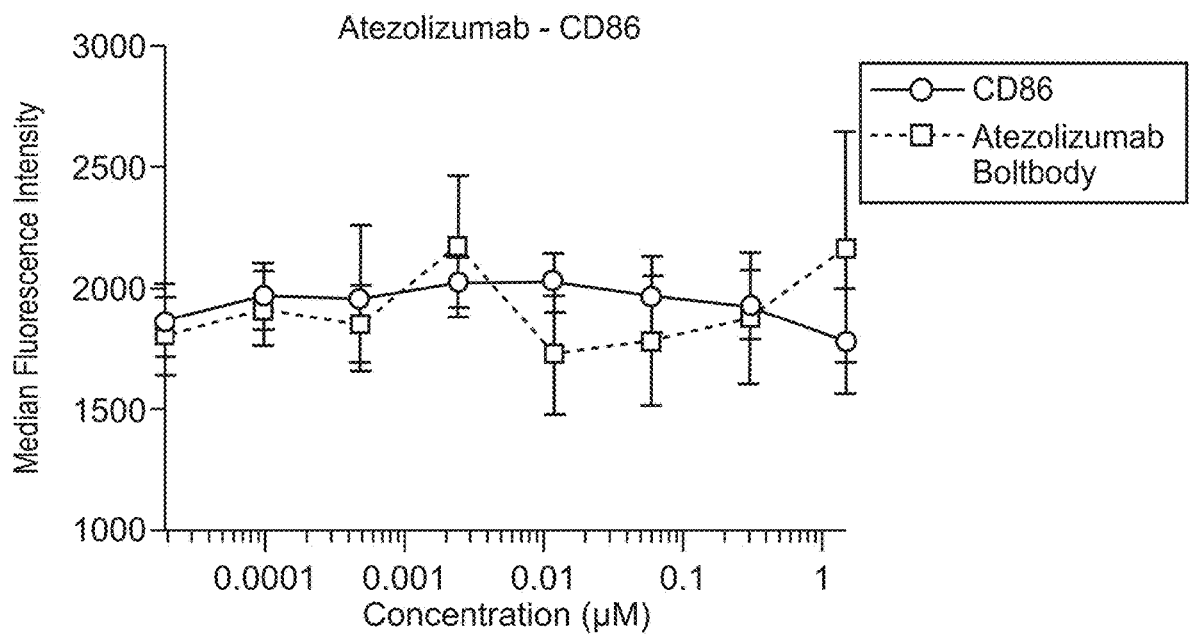

FIG. 69K shows CD86 expression on myeloid cells following 18 hours of stimulation with the atezolizumab immunoconjugate produced according to the BB-01 method (Atezolizumab Boltbody) as compared to unconjugated atezolizumab (Roche).

Figure 70A:
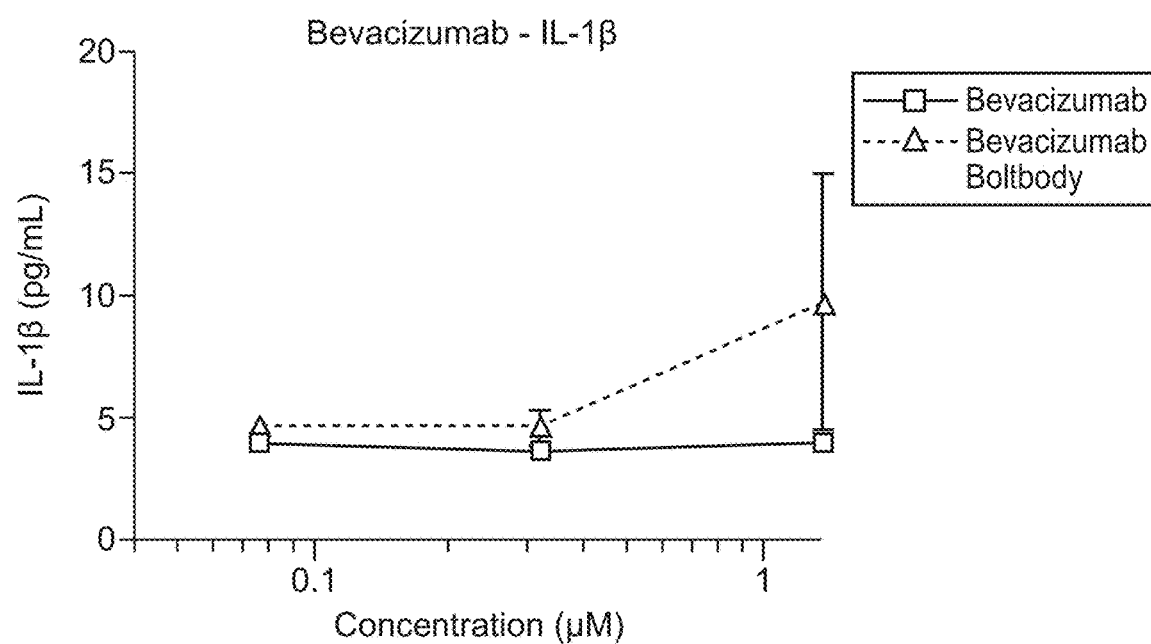

FIG. 70A shows that the bevacizumab immunoconjugate produced according to the BB-01 method (Bevacizumab Boltbody) elicits superior IL-1β secretion from myeloid cells as compared to equimolar concentrations of unconjugated bevacizumab (Roche) following 18 hours of stimulation.

Figure 70B:
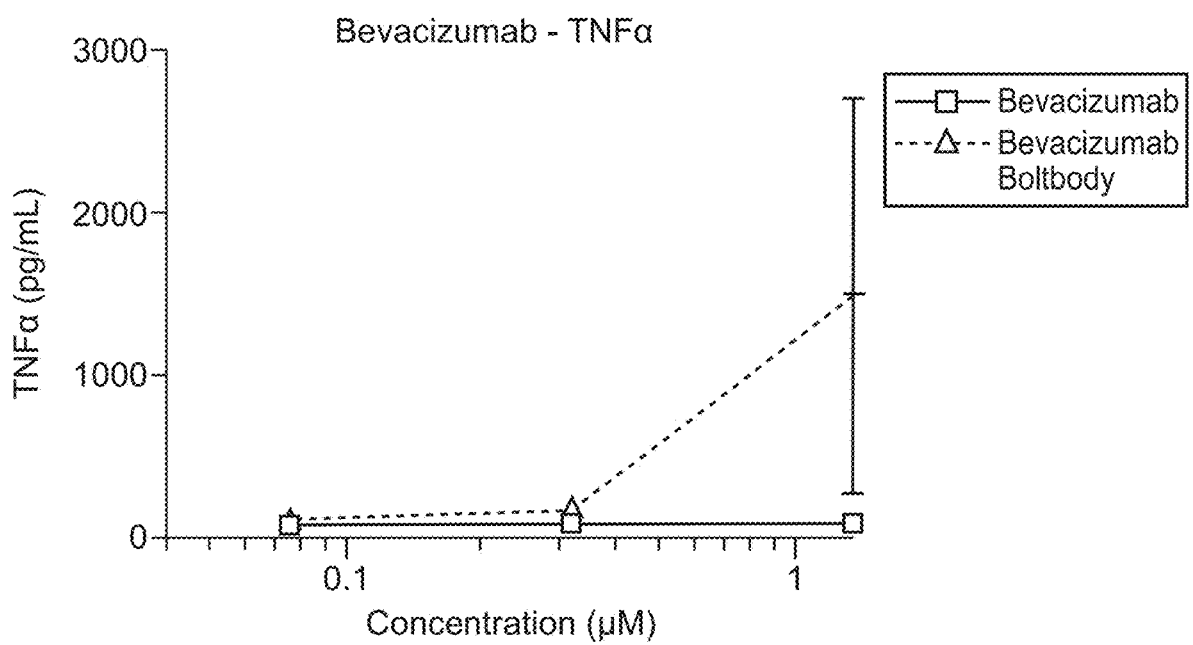

FIG. 70B shows that the bevacizumab immunoconjugate produced according to the BB-01 method (Bevacizumab Boltbody) elicits superior TNFα secretion from myeloid cells as compared to equimolar concentrations of unconjugated bevacizumab (Roche) following 18 hours of stimulation.

Figure 70C:
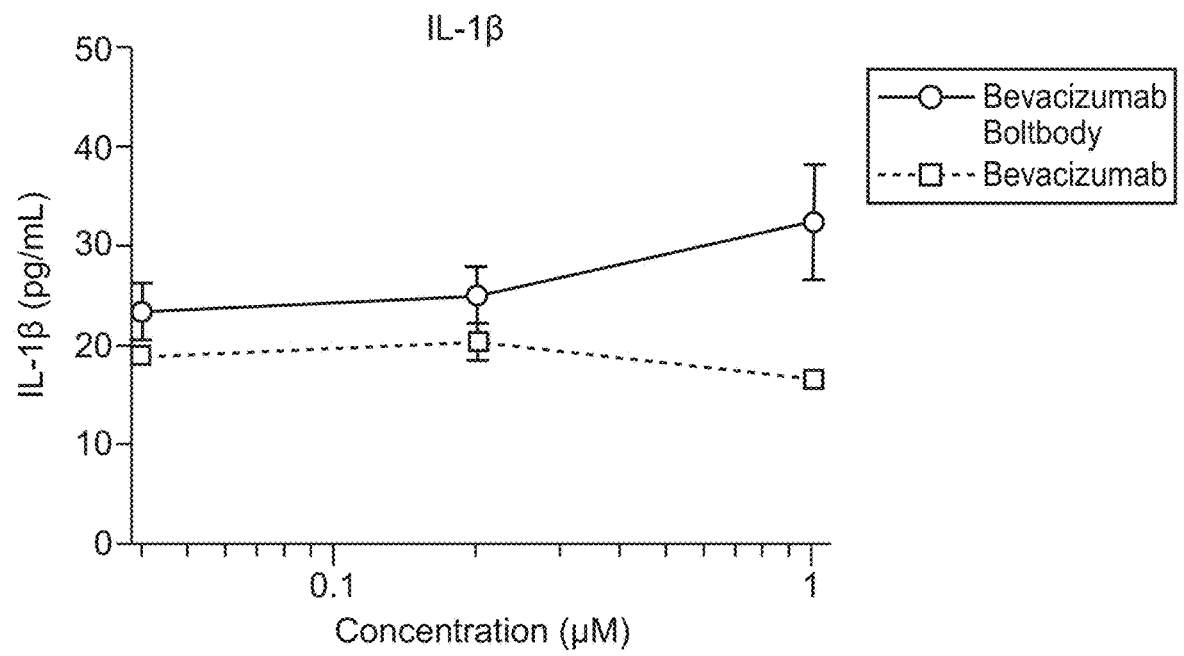

FIG. 70C shows that the bevacizumab immunoconjugate produced according to the BB-01 method (Bevacizumab Boltbody) elicits superior IL-1β secretion from myeloid cells as compared to equimolar concentrations of unconjugated bevacizumab (Roche) following 36 hours of stimulation.

Figure 70D:
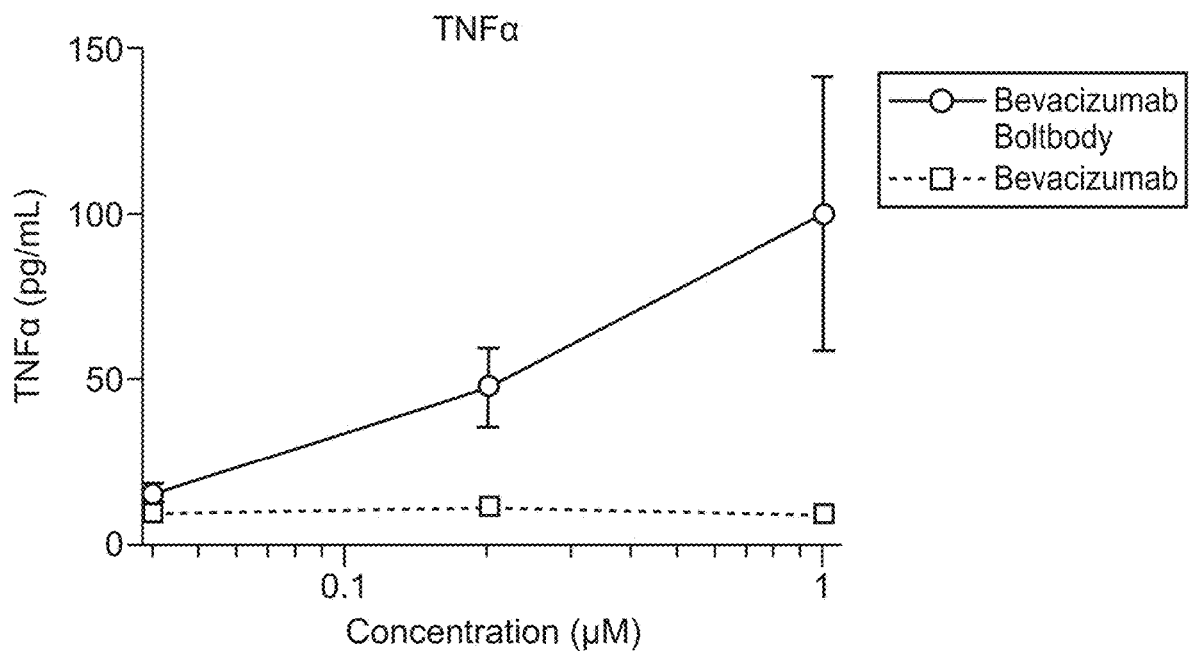

FIG. 70D shows that the bevacizumab immunoconjugate produced according to the BB-01 method (Bevacizumab Boltbody) elicits superior TNFα secretion from myeloid cells as compared to equimolar concentrations of unconjugated bevacizumab (Roche) following 36 hours of stimulation.

Figure 70E:
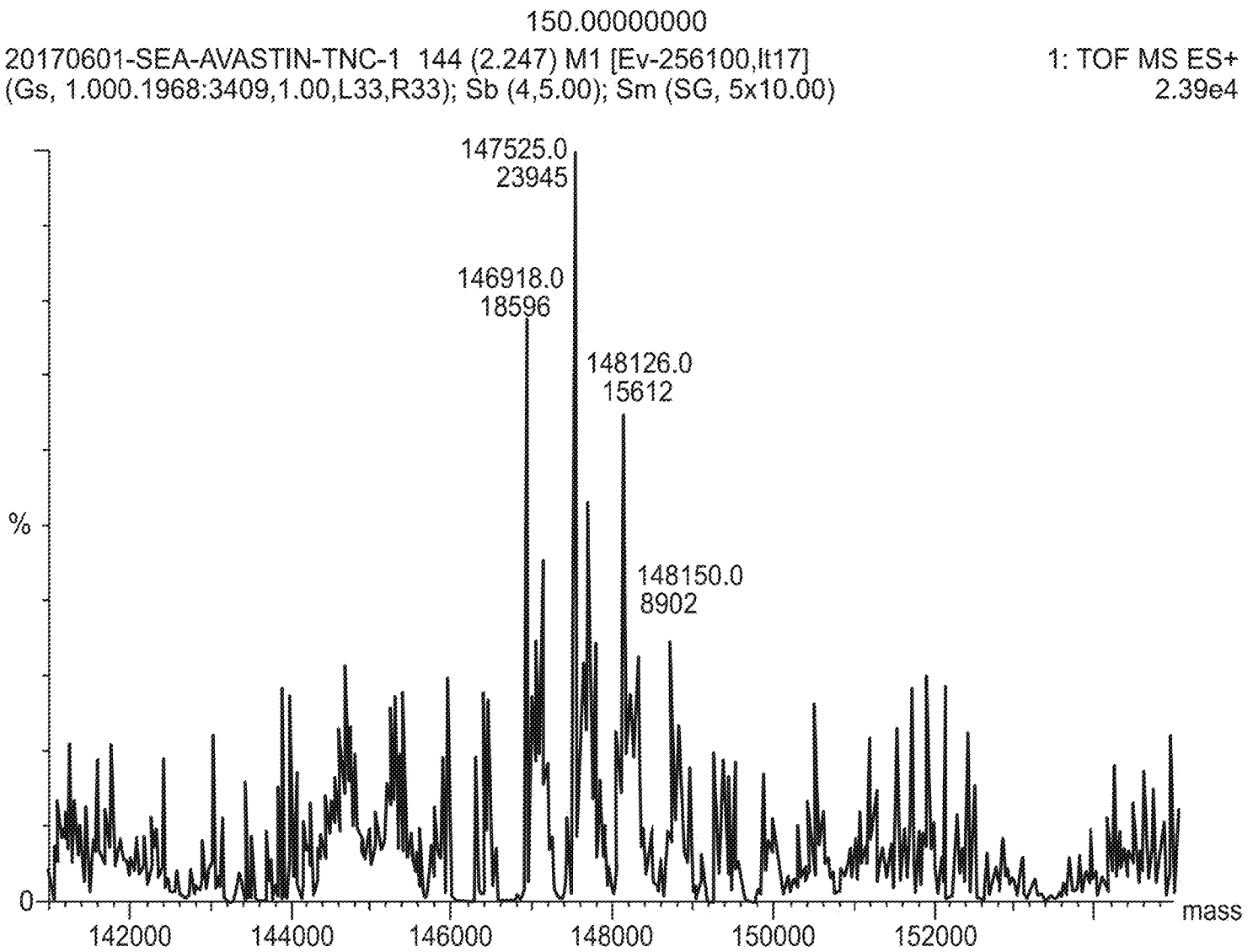

FIG. 70E shows a liquid chromatography-mass spectrometry analysis of the bevacizumab immunoconjugate produced according to the BB-01 conjugation method following overnight deglycosylation with PNGase F.

Figure 70F:
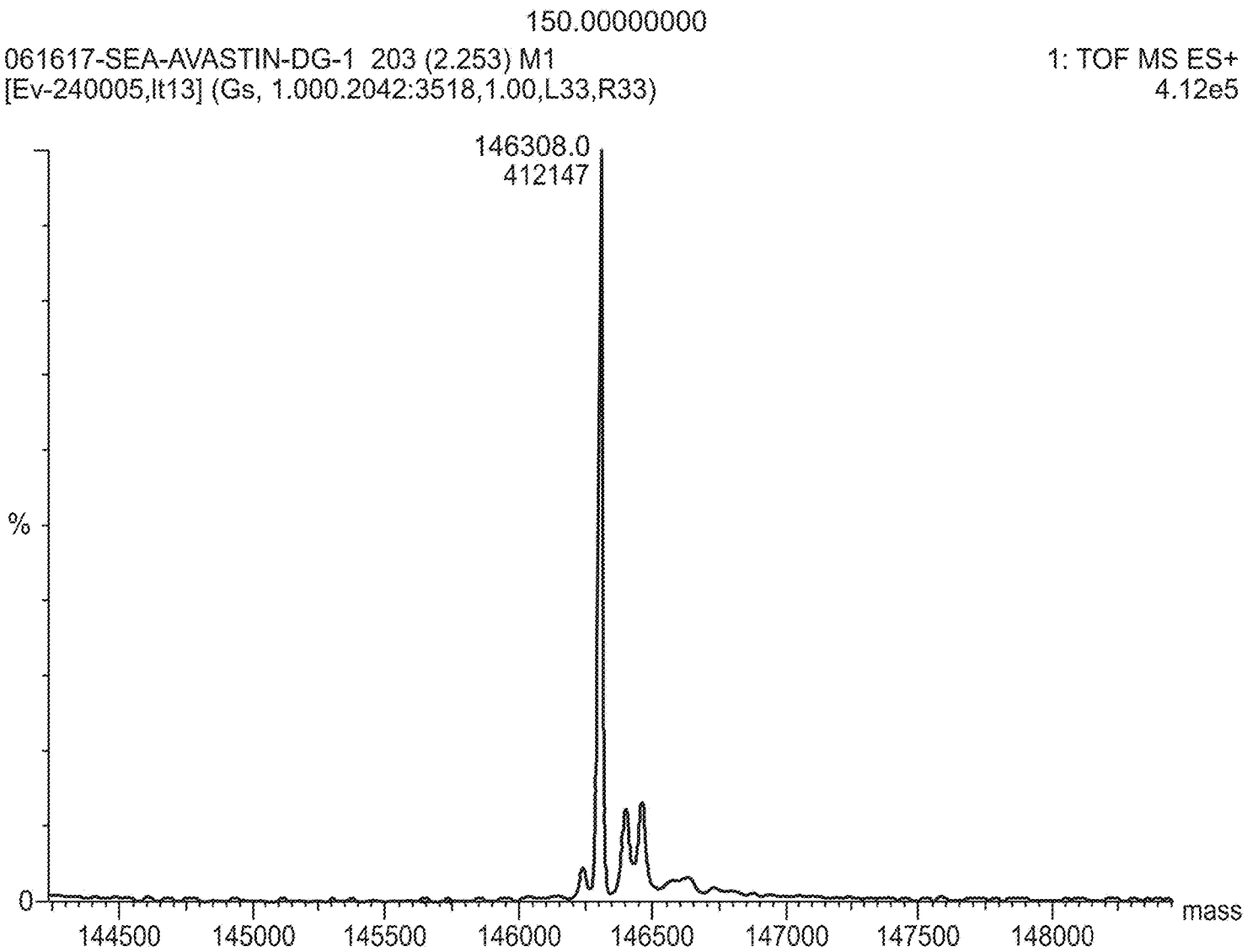

FIG. 70F shows a liquid chromatography-mass spectrometry analysis of unconjugated bevacizumab (Roche) that was utilized to produce the bevacizumab immunoconjugate according to the BB-01 conjugation method following overnight deglycosylation with PNGase F.

FIG. 70G shows a liquid chromatography-mass spectrometry analysis of unconjugated bevacizumab (Roche) that was utilized to produce the bevacizumab immunoconjugate according to the BB-01 method.

Figure 70H:
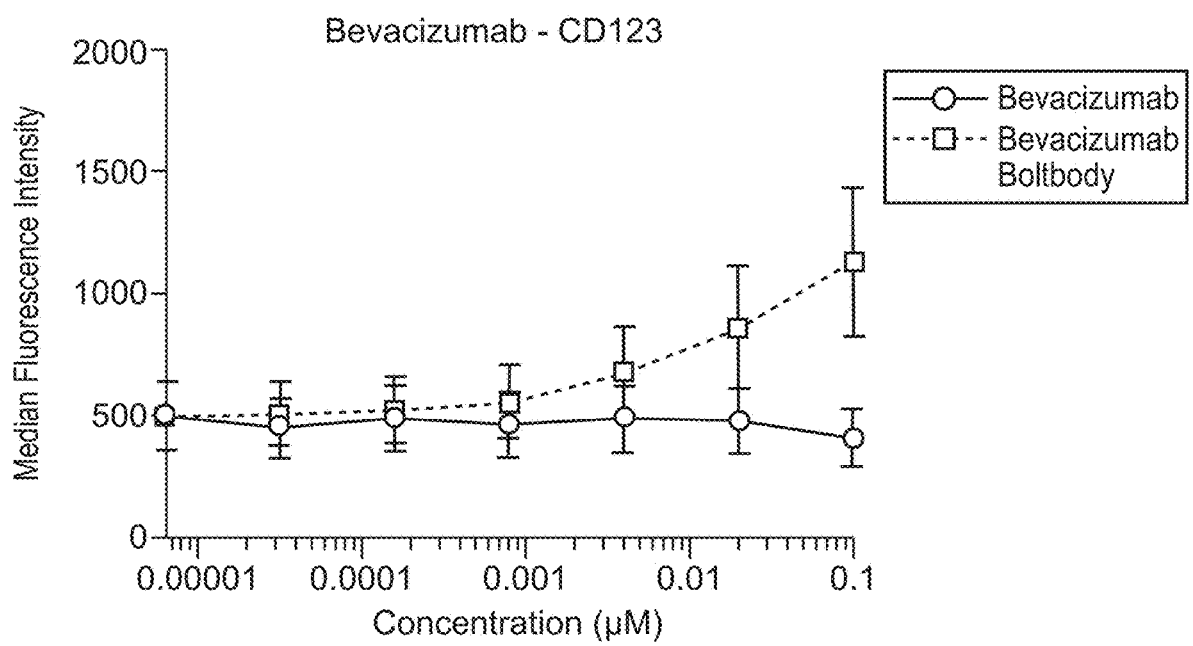

FIG. 70H shows that the bevacizumab immunoconjugate produced according to the BB-01 method (Bevacizumab Boltbody) is superior at eliciting CD123 upregulation on myeloid cells as compared to the unconjugated bevacizumab (Roche) following 18 hours of stimulation.

Figure 70I:
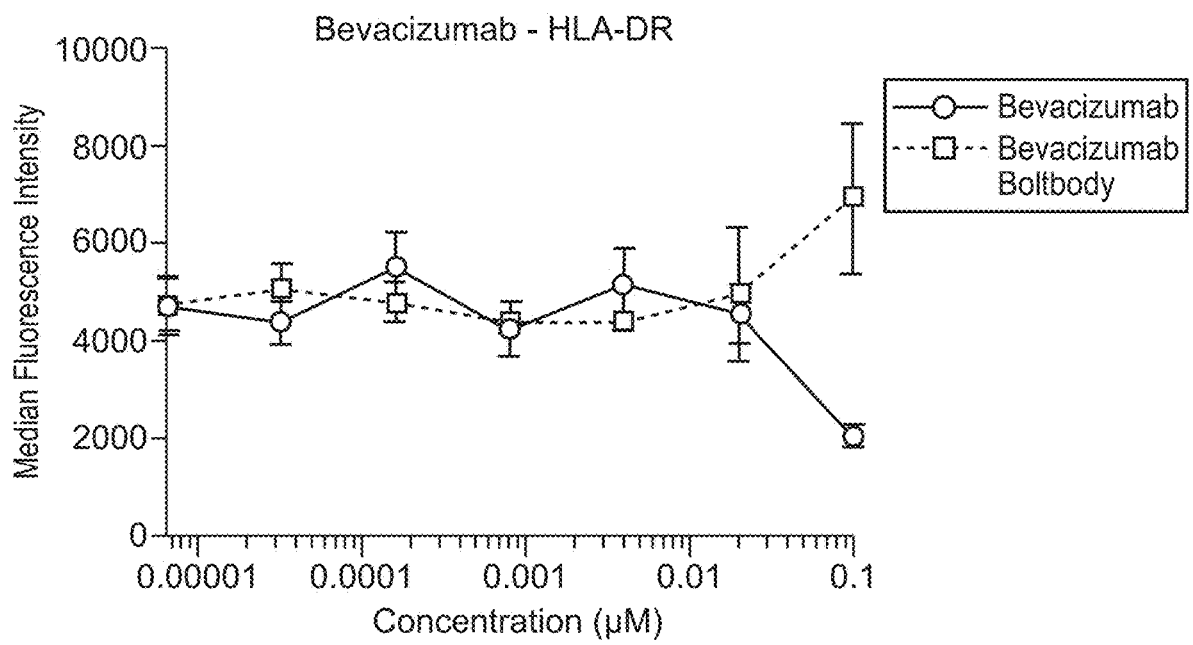

FIG. 70I shows HLA-DR expression on myeloid cells following 18 hours of stimulation with the bevacizumab immunoconjugate produced according to the BB-01 method (Bevacizumab Boltbody) as compared to unconjugated bevacizumab (Roche).

Figure 70J:
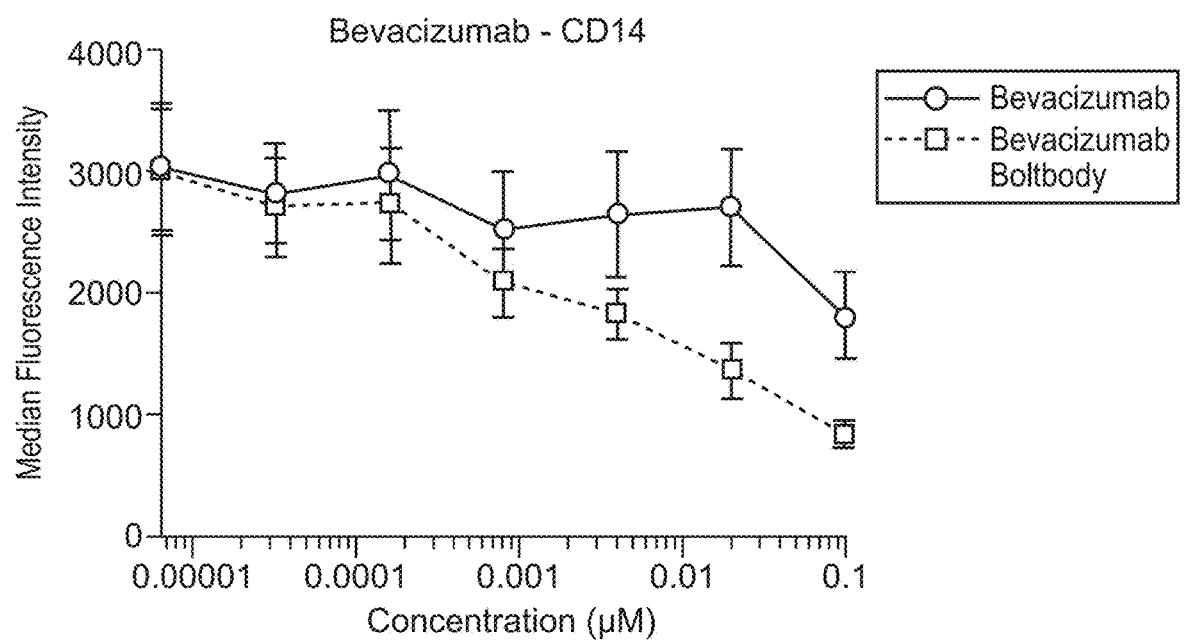

FIG. 70J shows that the bevacizumab immunoconjugate produced according to the BB-01 method (Bevacizumab Boltbody) is superior at eliciting CD14 downregulation on myeloid cells as compared to the unconjugated bevacizumab (Roche) following 18 hours of stimulation.

Figure 70K:
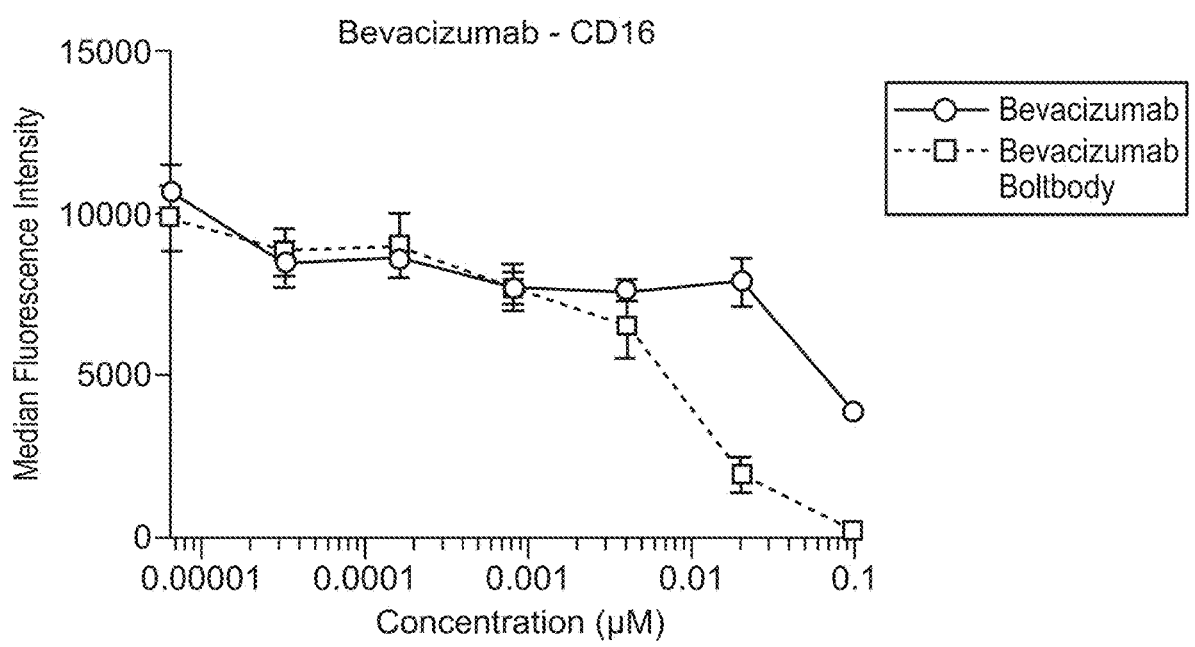

FIG. 70K shows that the bevacizumab immunoconjugate produced according to the BB-01 method (Bevacizumab Boltbody) is superior at eliciting CD16 downregulation on myeloid cells as compared to the unconjugated bevacizumab (Roche) following 18 hours of stimulation.

Figure 70L:
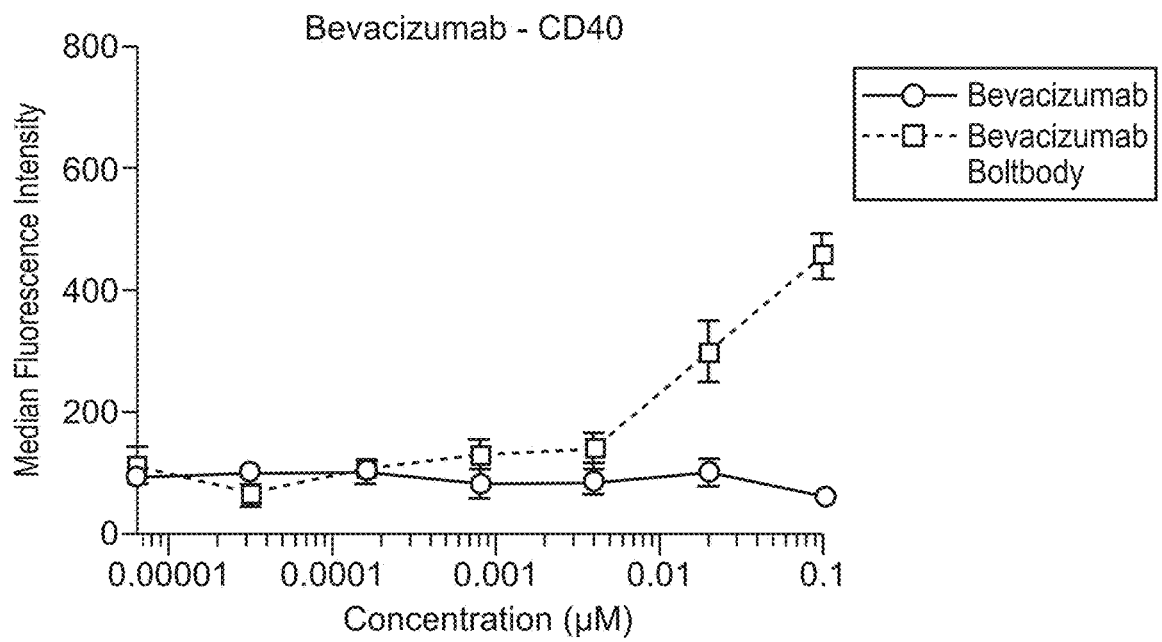

FIG. 70L shows that the bevacizumab immunoconjugate produced according to the BB-01 method (Bevacizumab Boltbody) is superior at eliciting CD40 upregulation on myeloid cells as compared to the unconjugated bevacizumab (Roche) following 18 hours of stimulation.

Figure 70M:
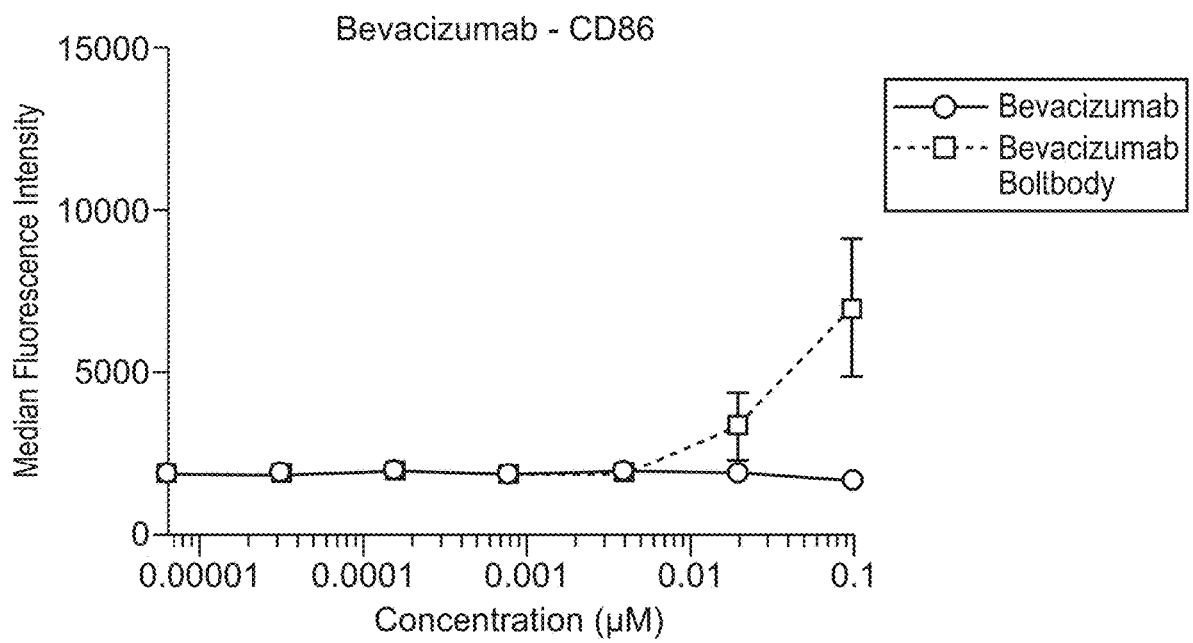

FIG. 70M shows that the bevacizumab immunoconjugate produced according to the BB-01 method (Bevacizumab Boltbody) is superior at eliciting CD86 upregulation on myeloid cells as compared to the unconjugated bevacizumab (Roche) following 18 hours of stimulation.

Figure 71B:
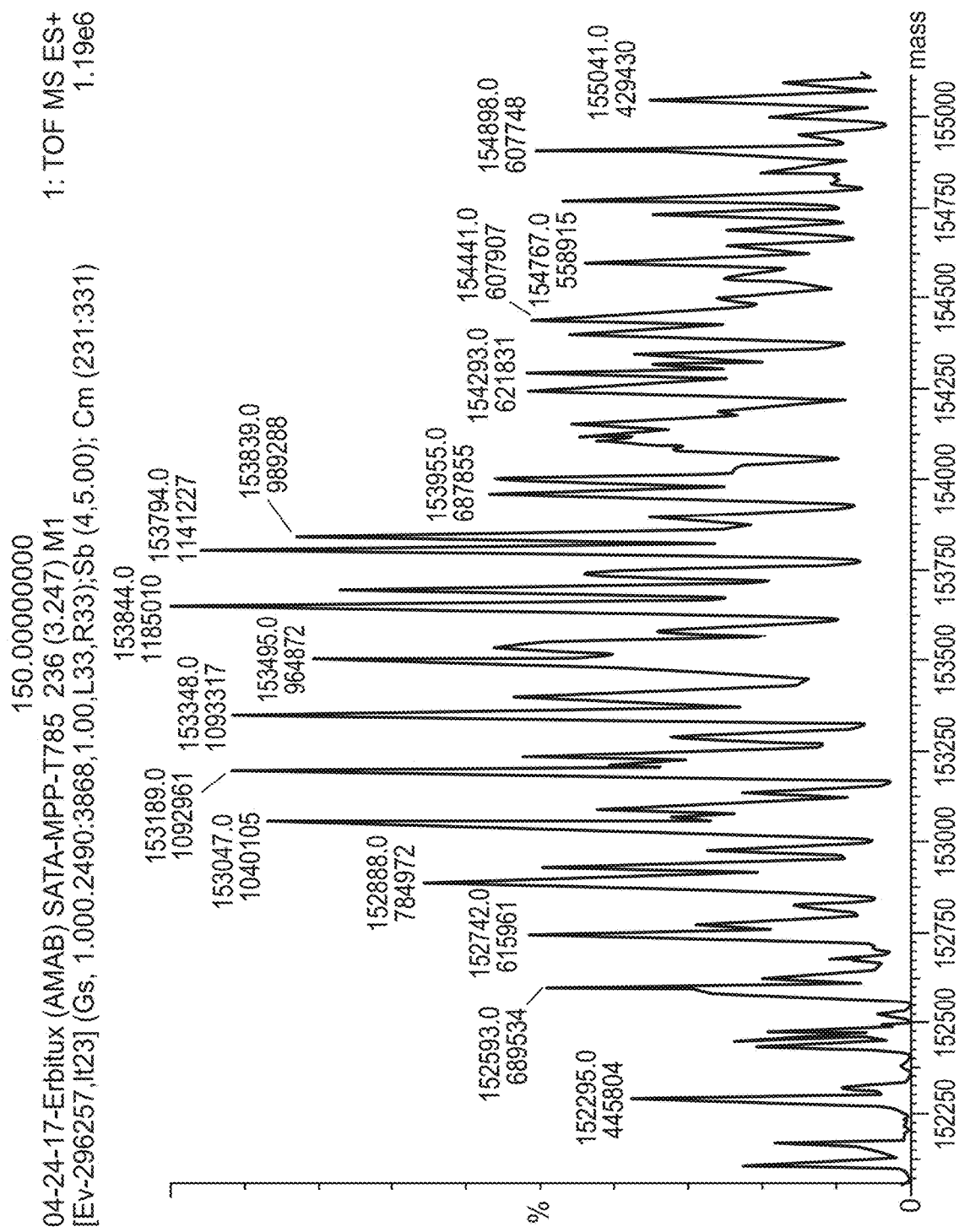
Figure 71C:
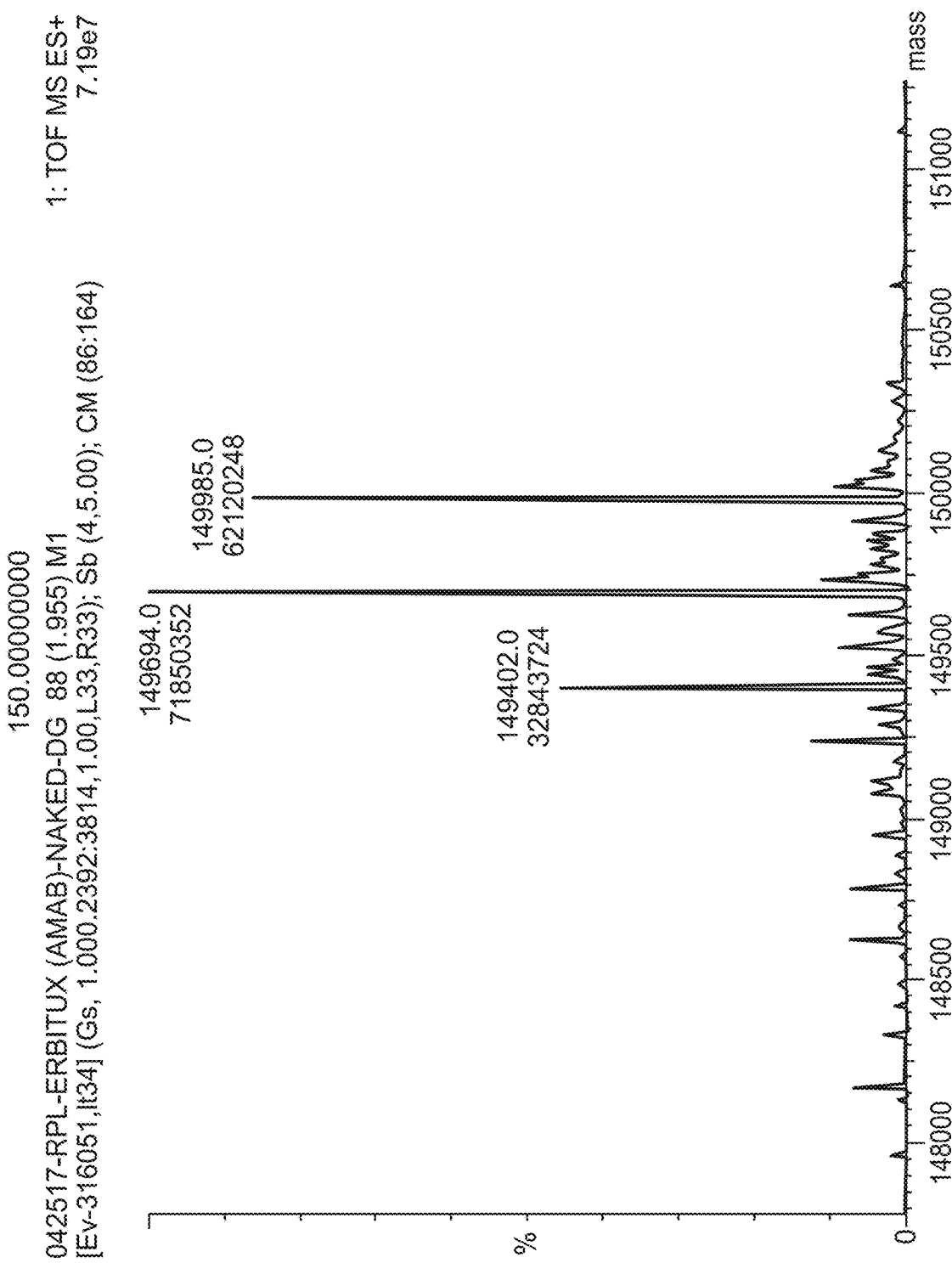
Figure 71D:
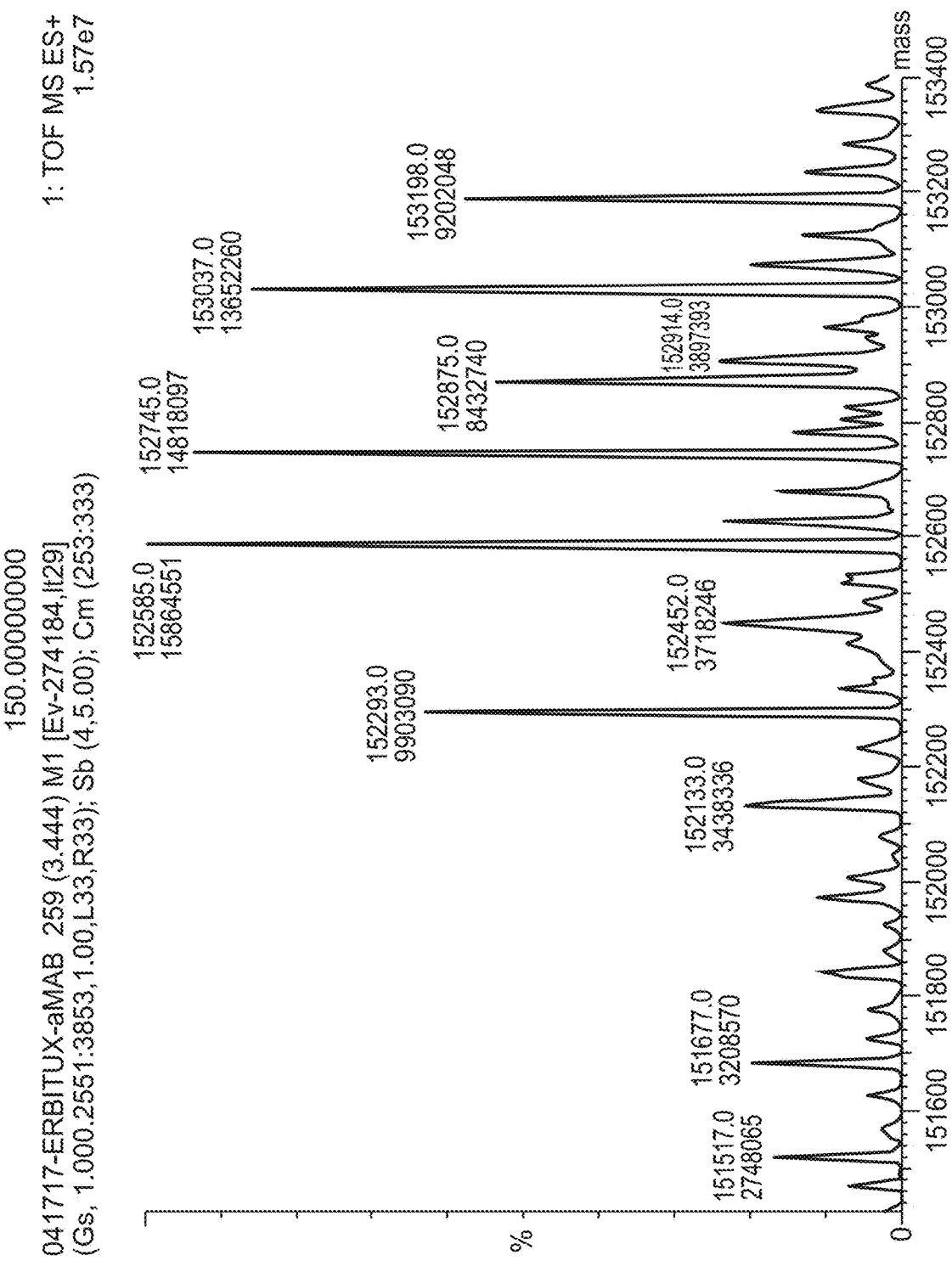
Figure 71E:
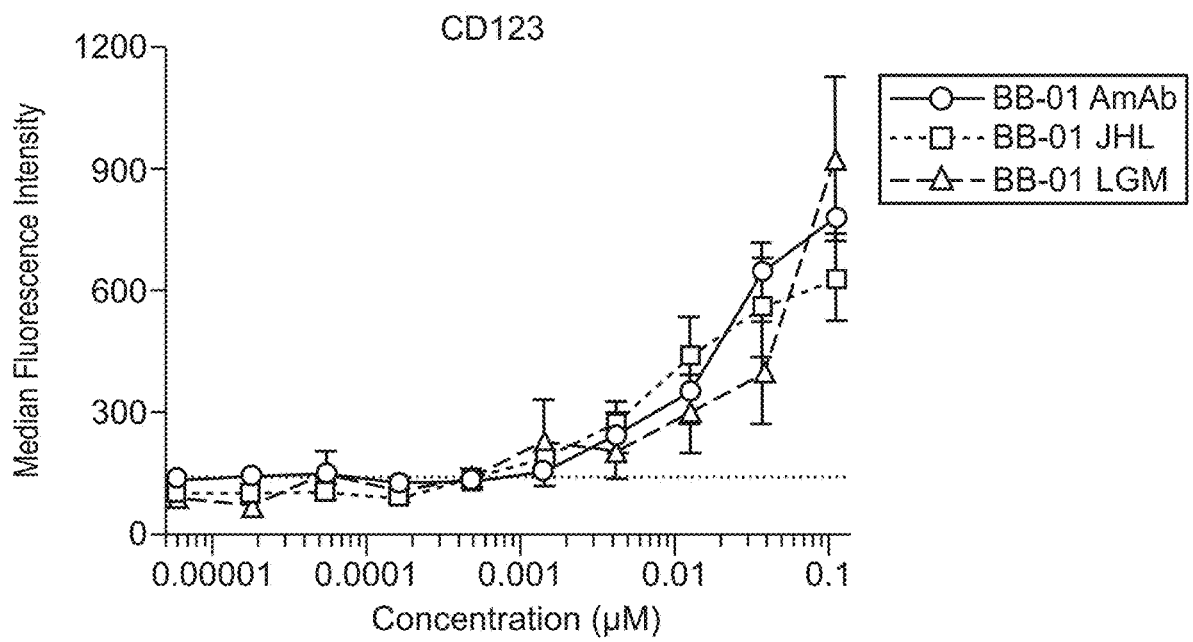
Figure 71F:
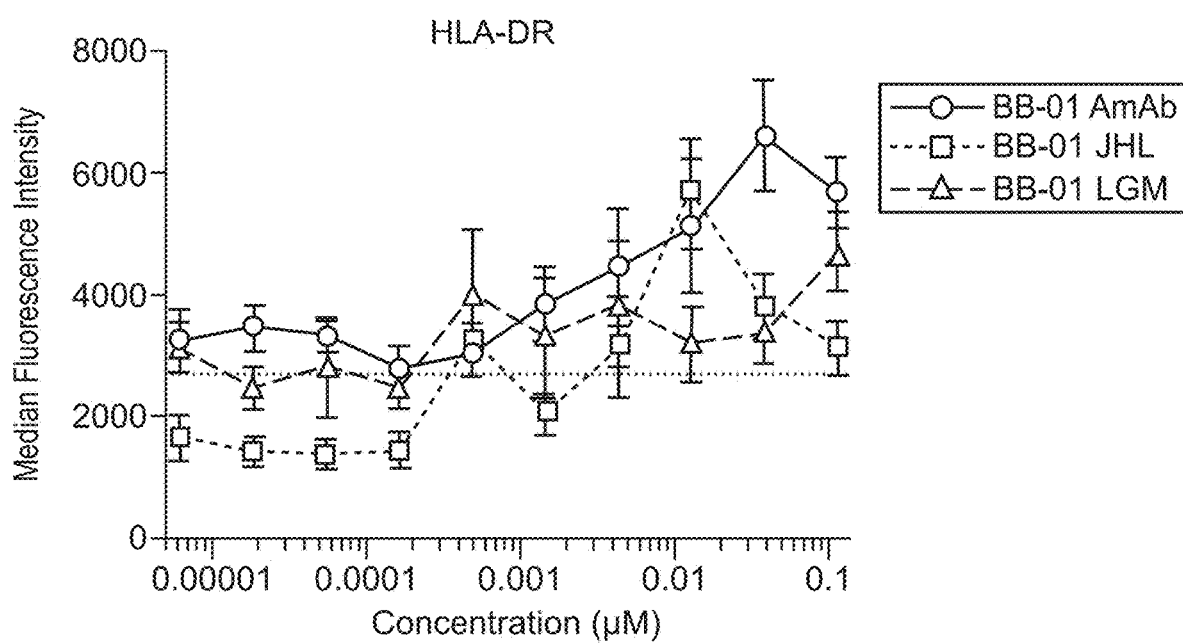
Figure 71G:
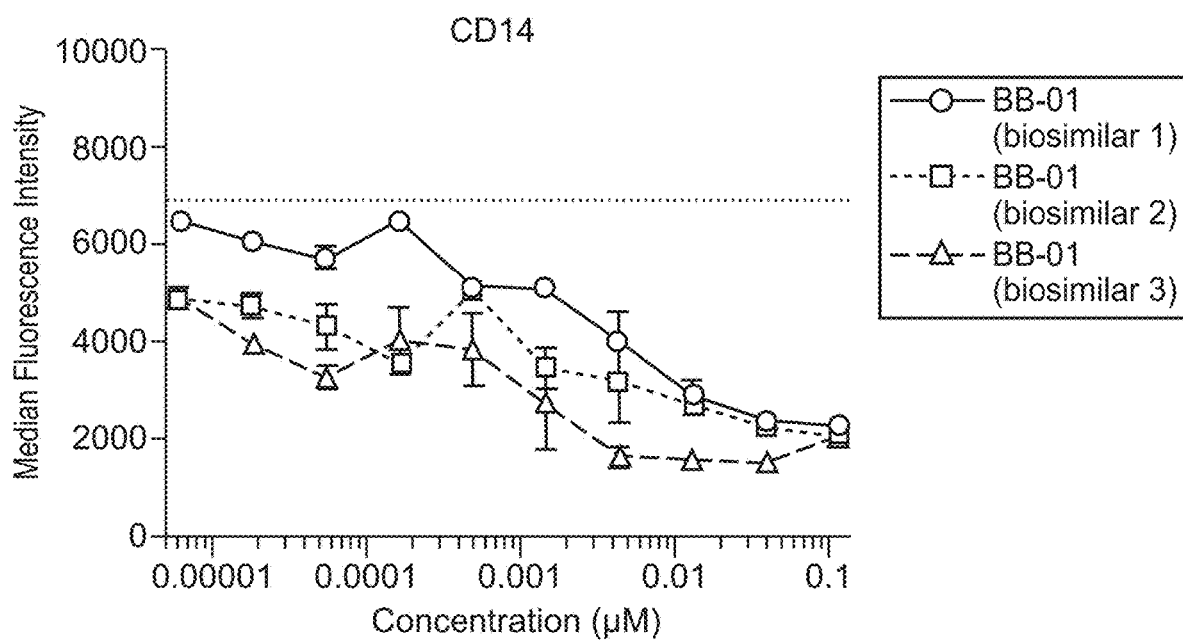
Figure 71H:
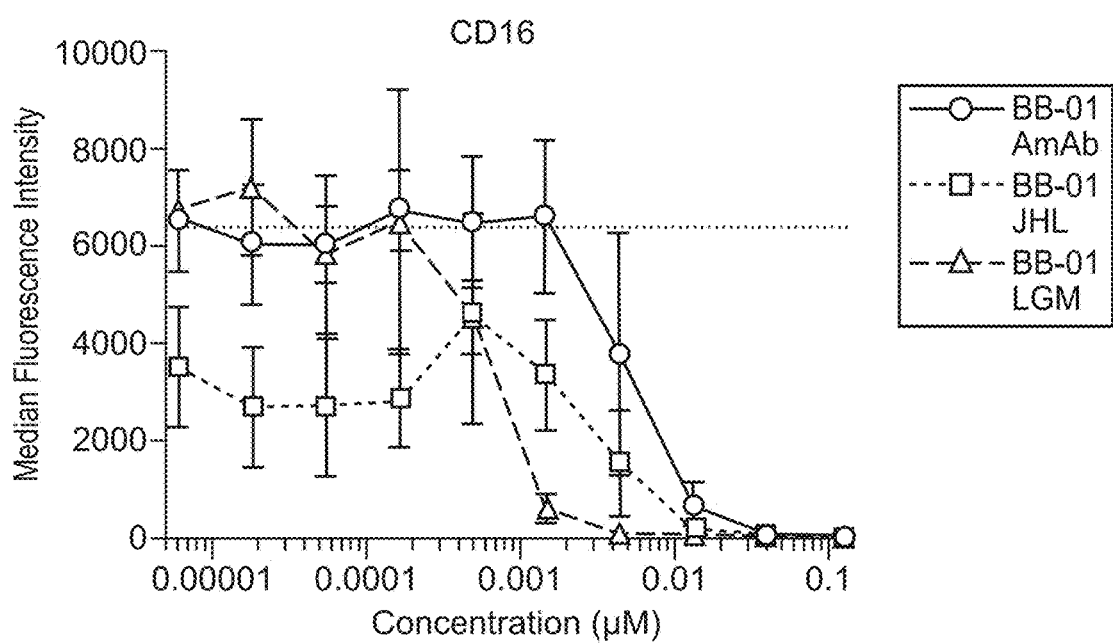
Figure 71I:
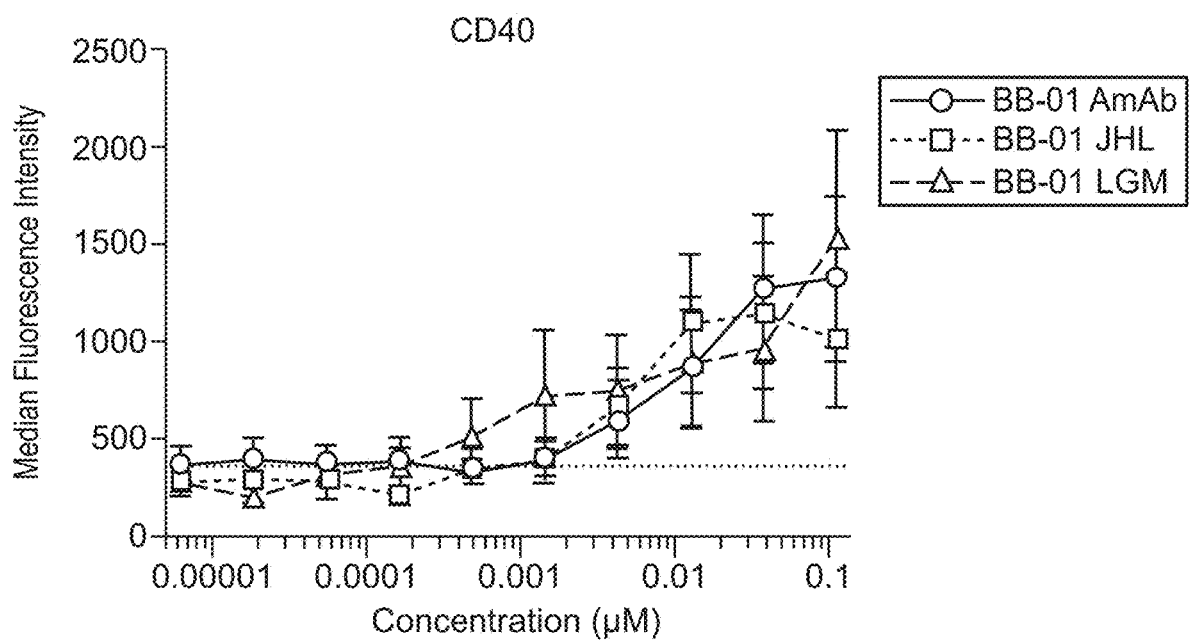
Figure 71J:
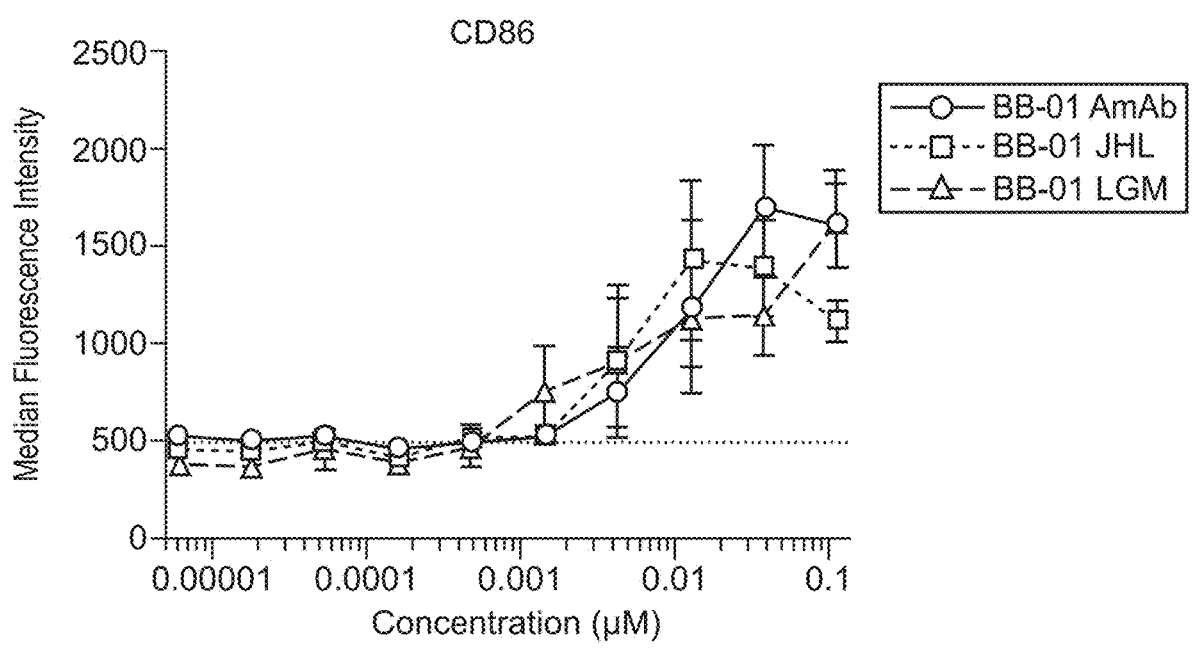
Figure 71K:
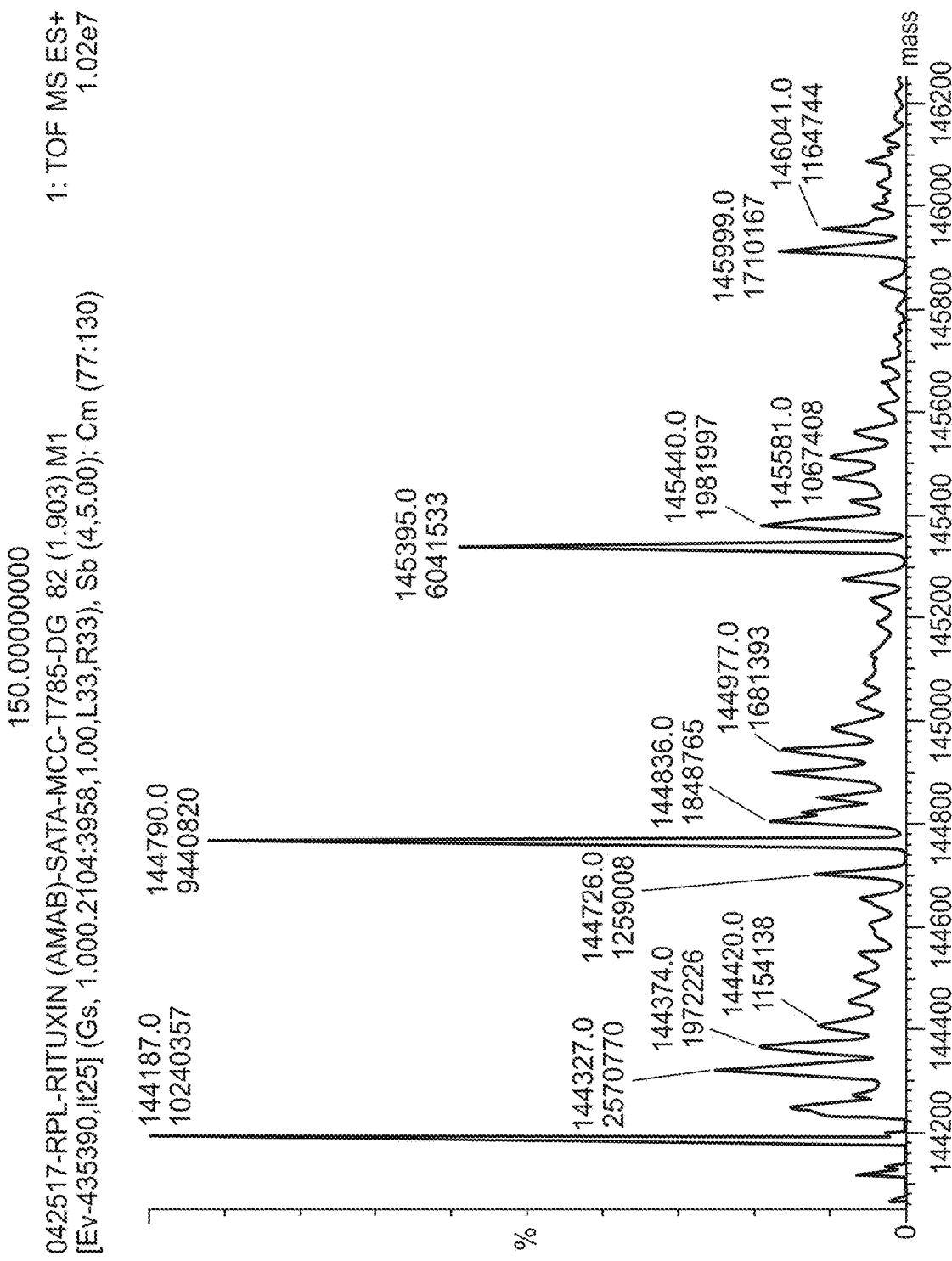
Figure 71L:
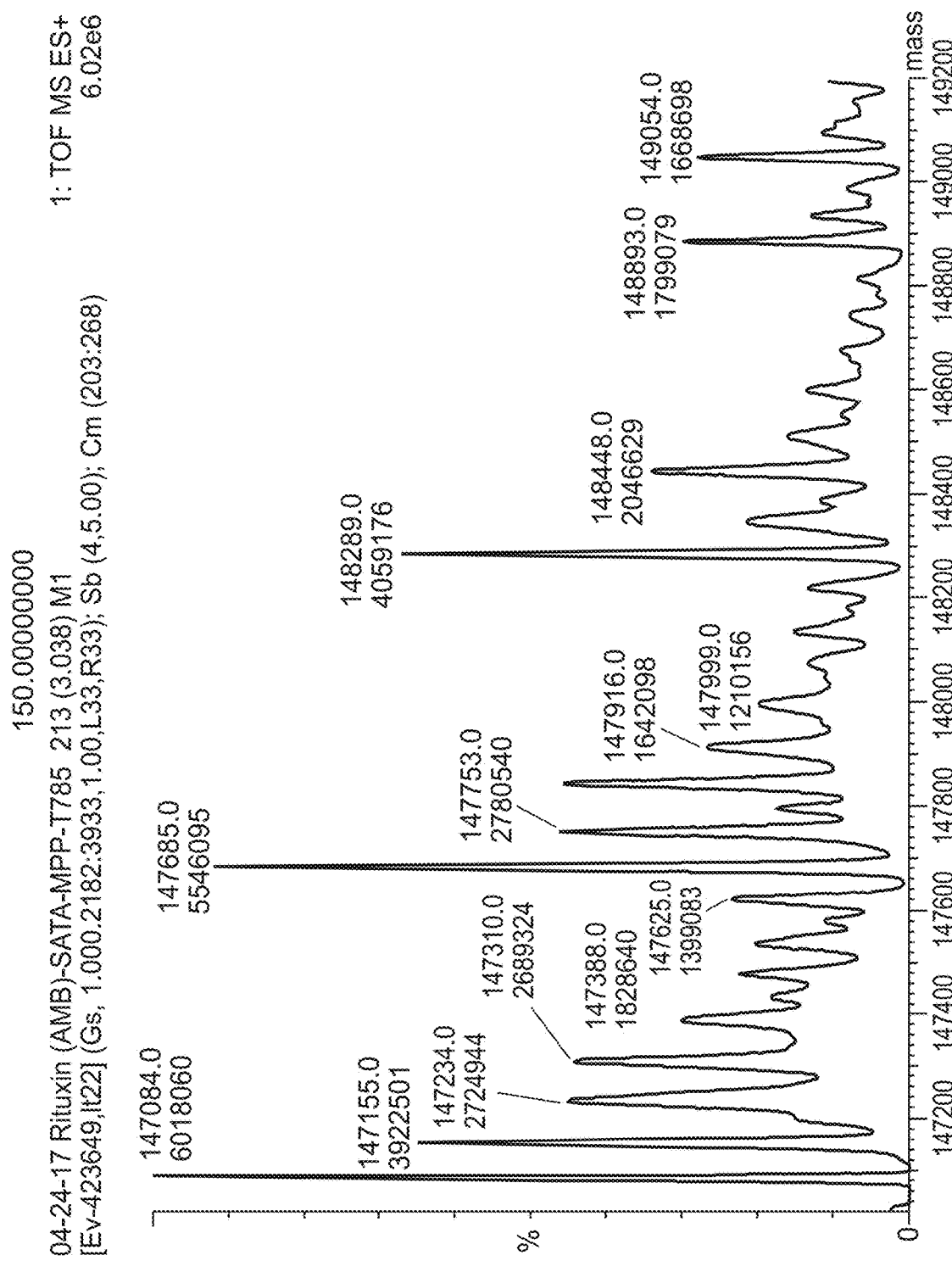
Figure 71M:
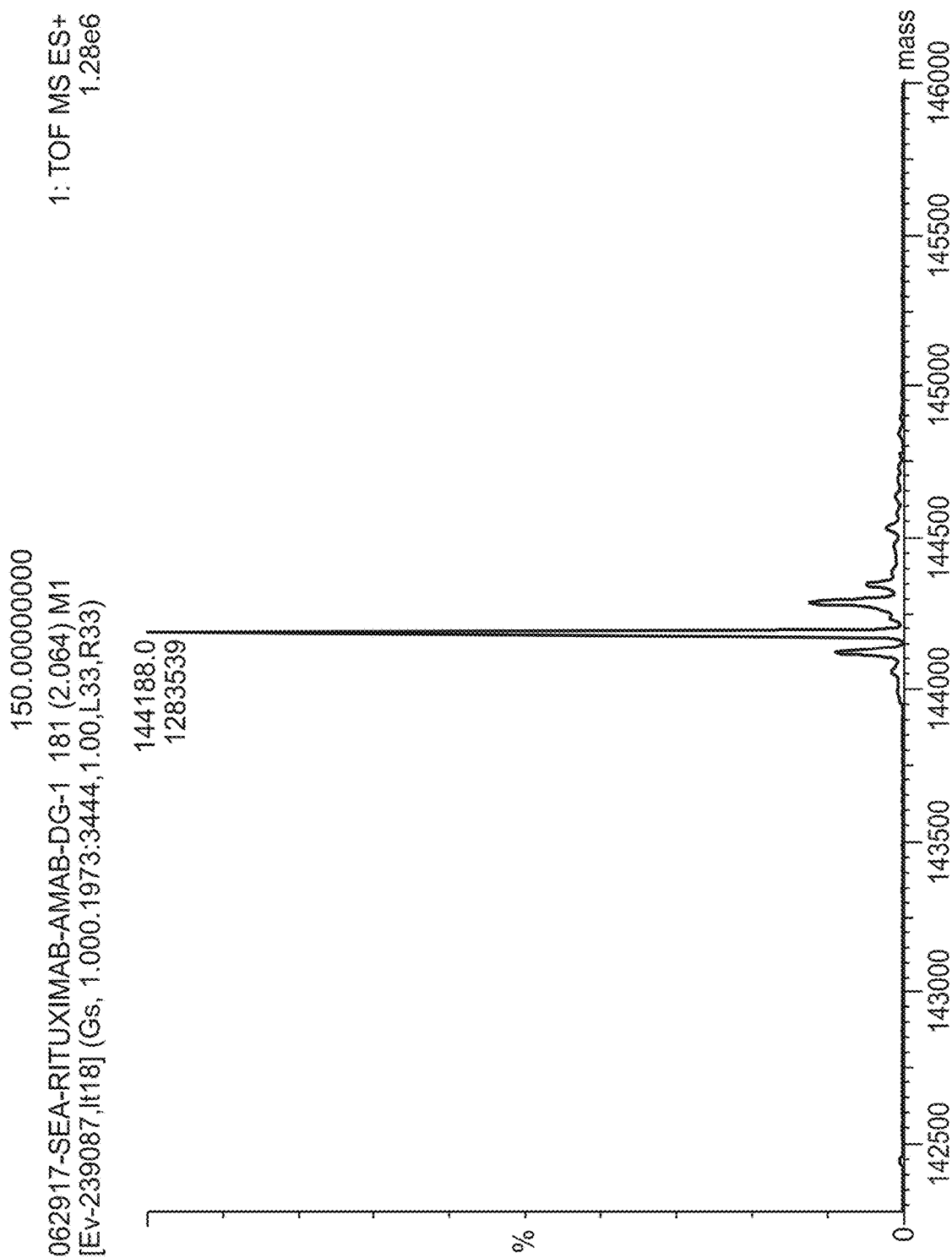
Figure 71N:
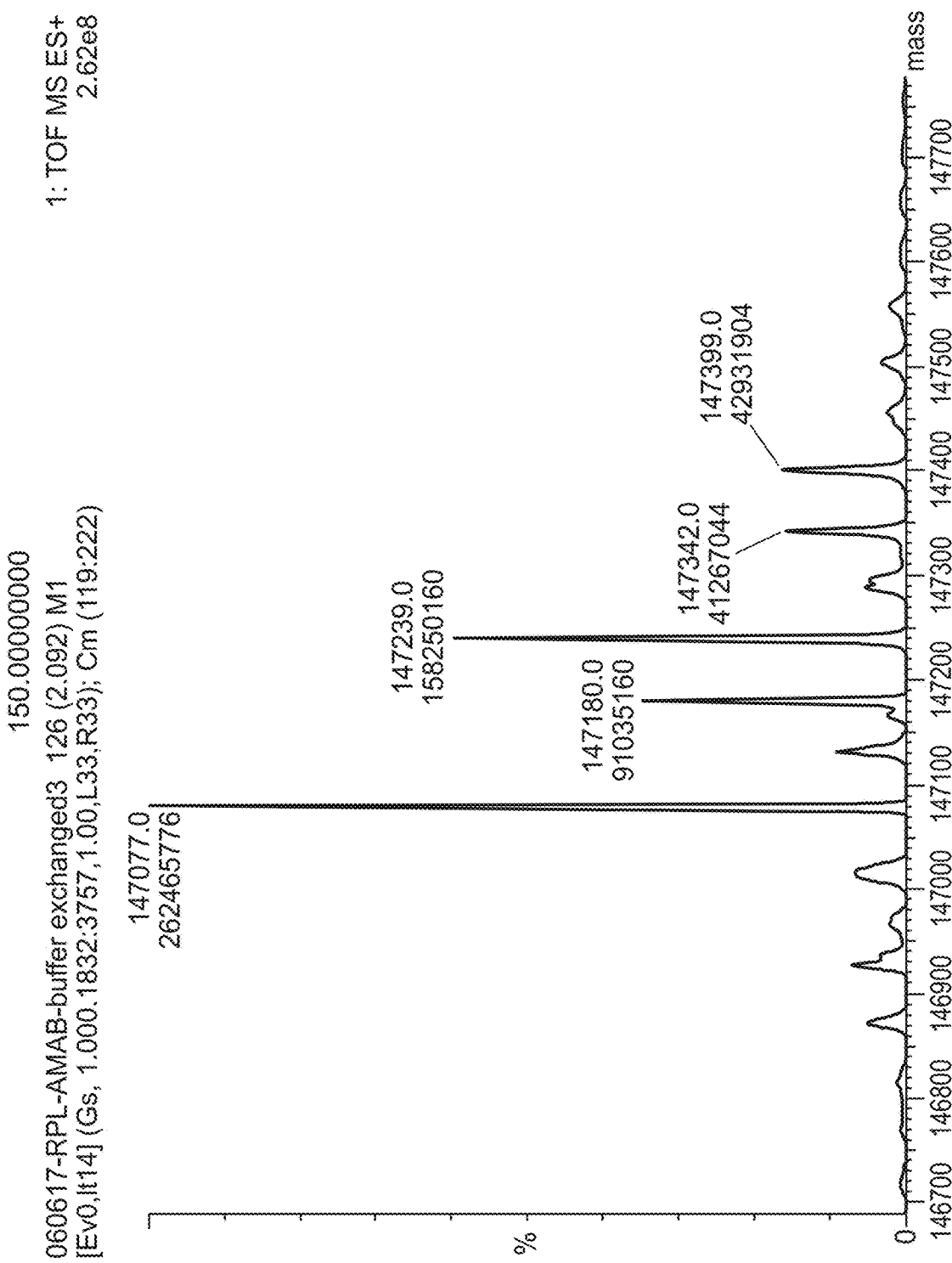
Figure 71O:
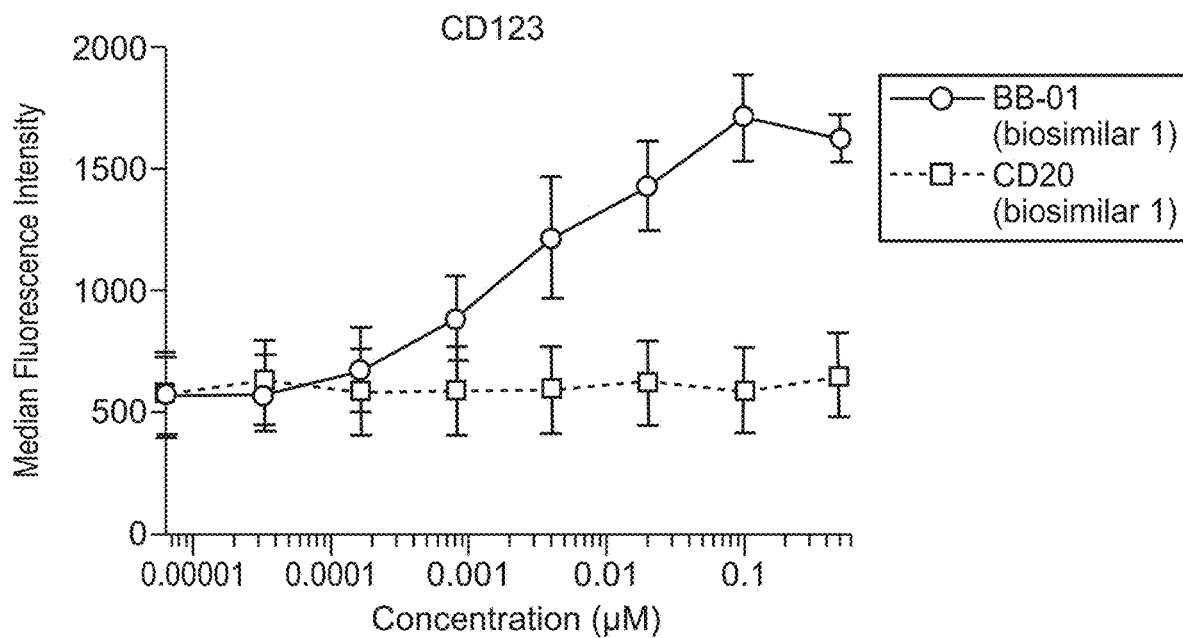
Figure 71P:
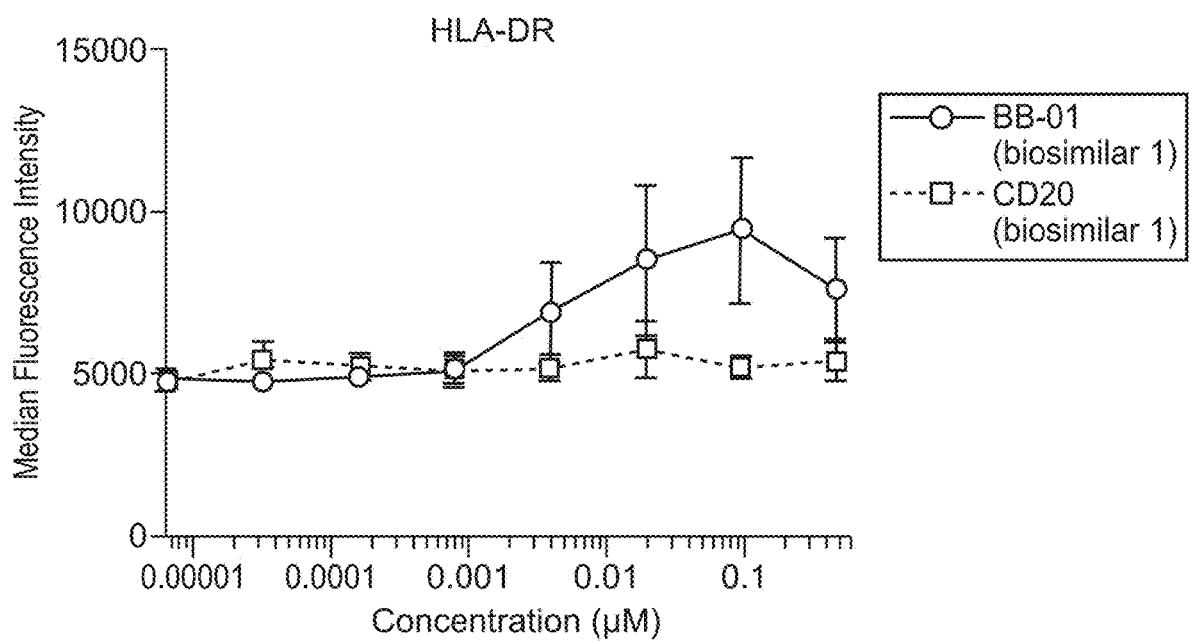
Figure 71Q:
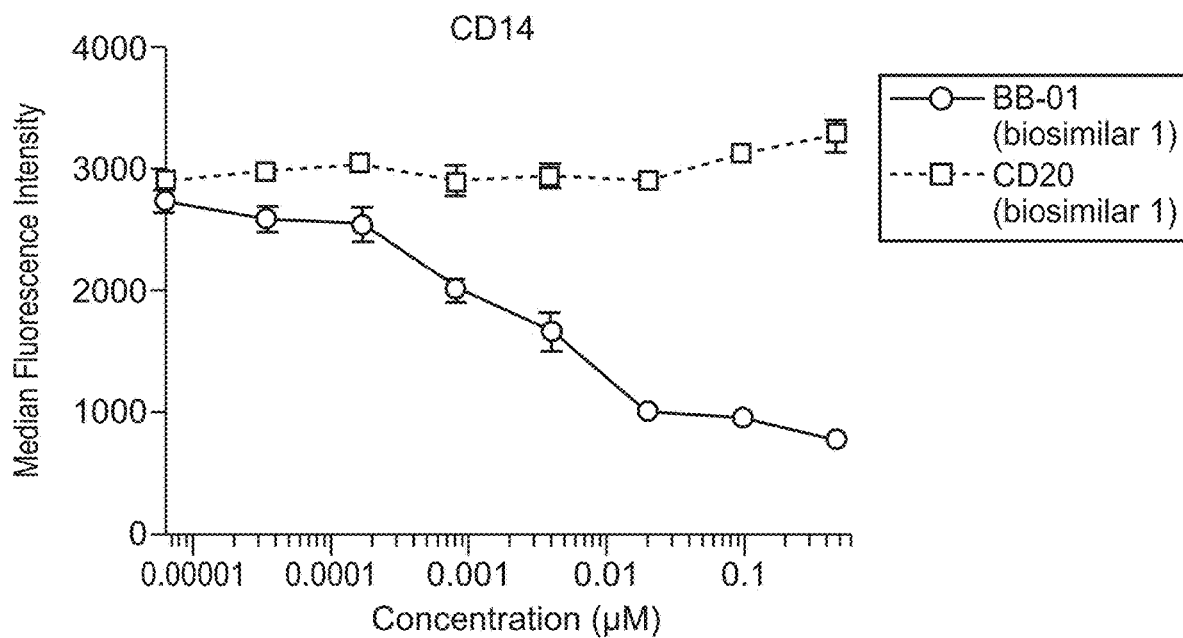
Figure 71R:
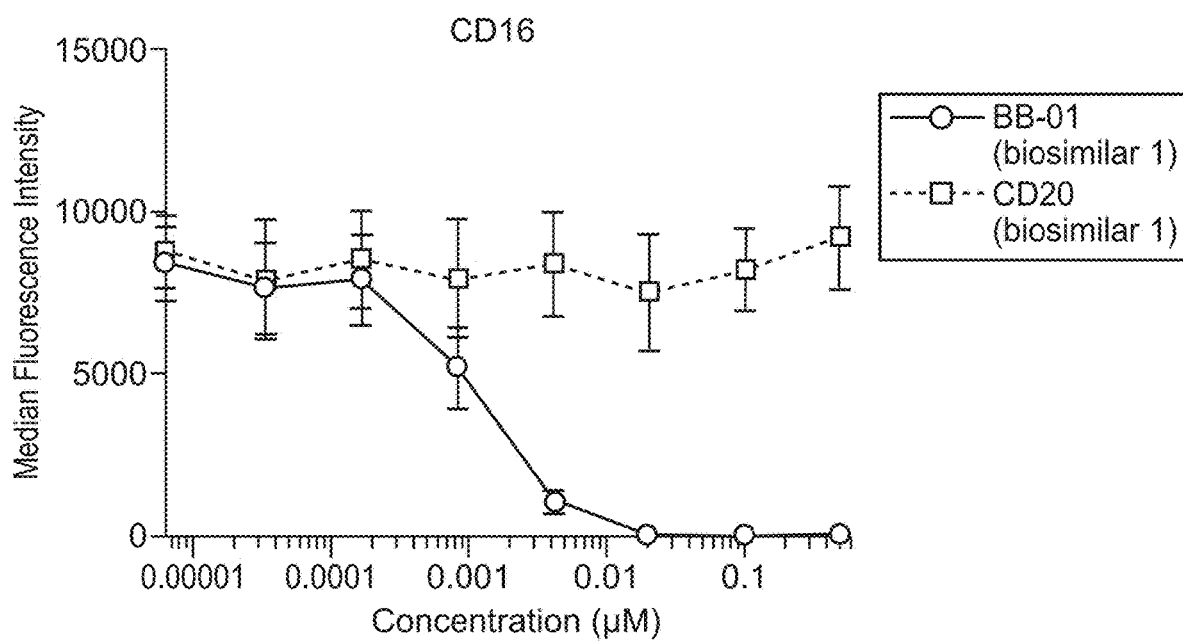
Figure 71S:
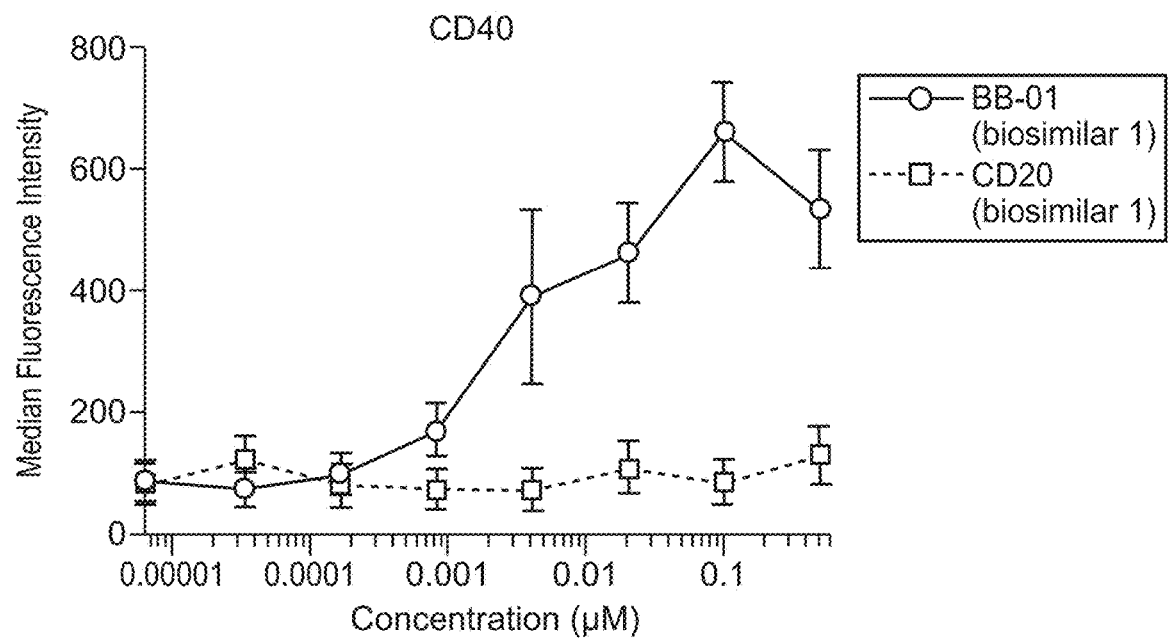
Figure 71T:
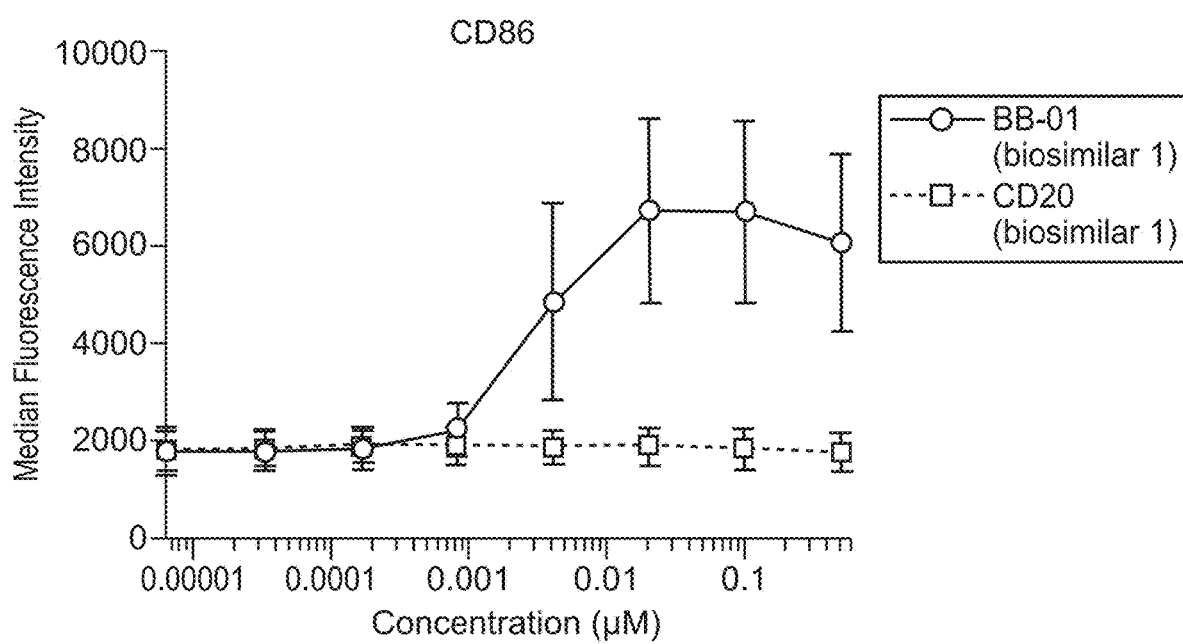
Figure 71U:
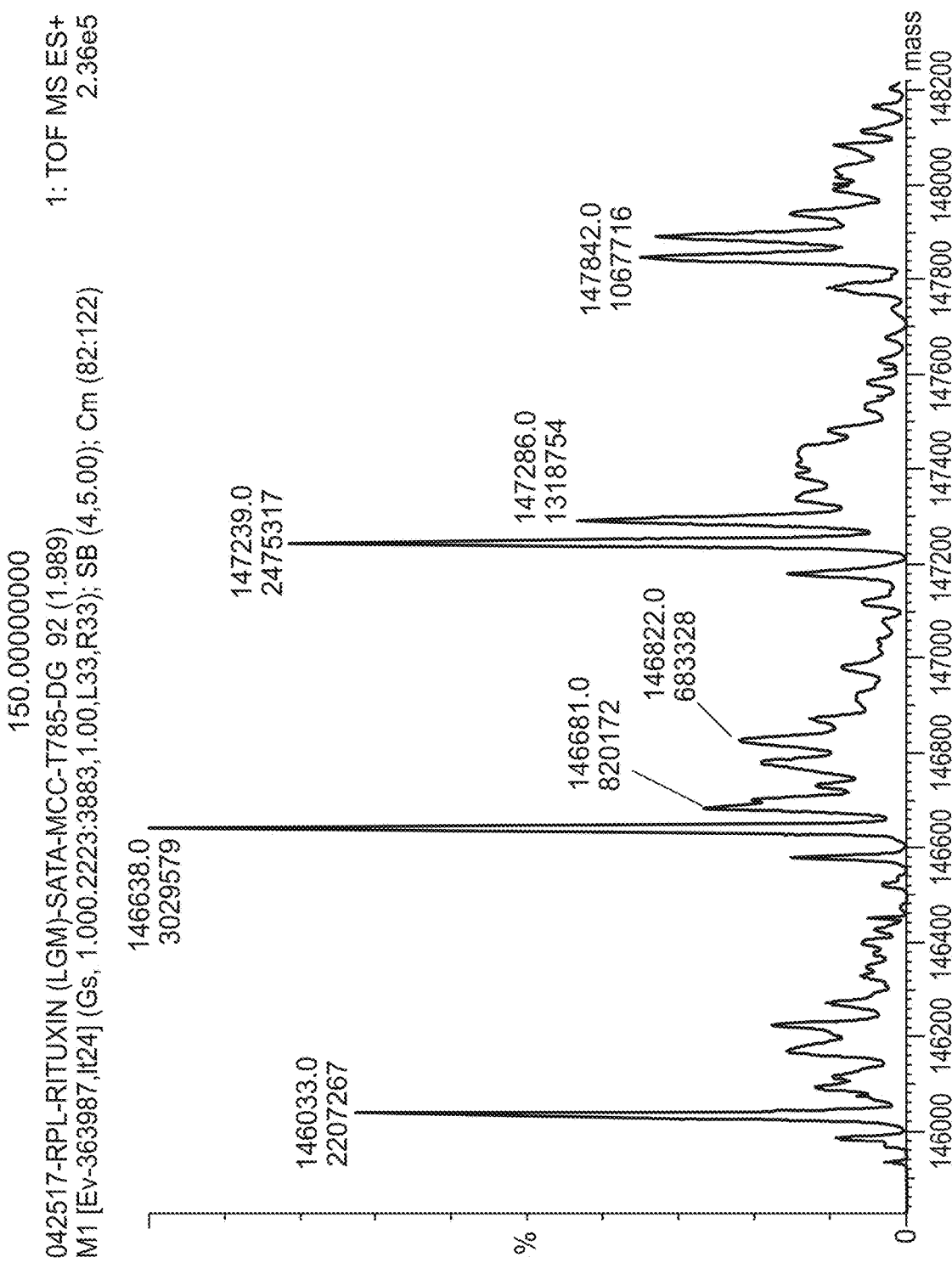
Figure 71V:
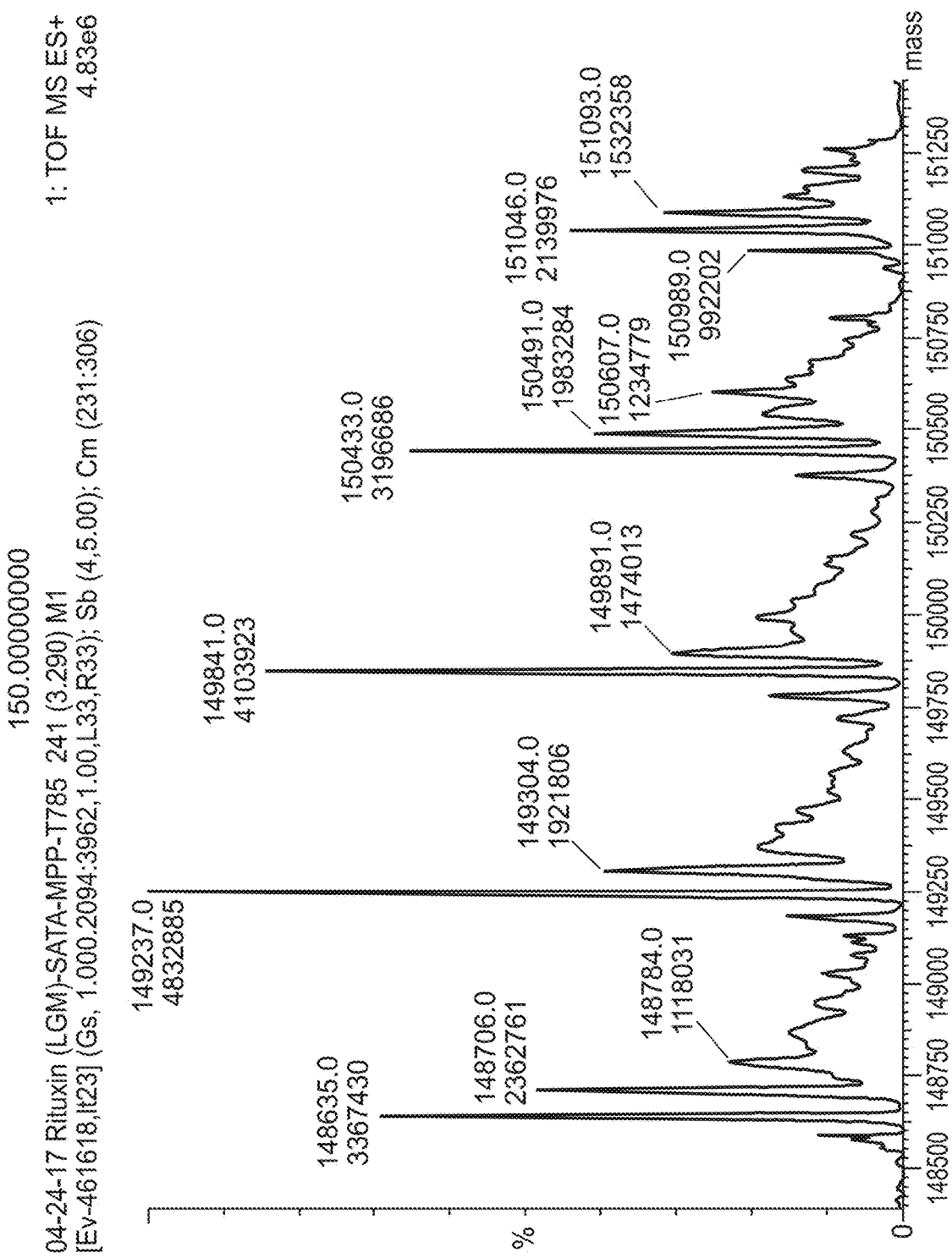
Figure 71W:
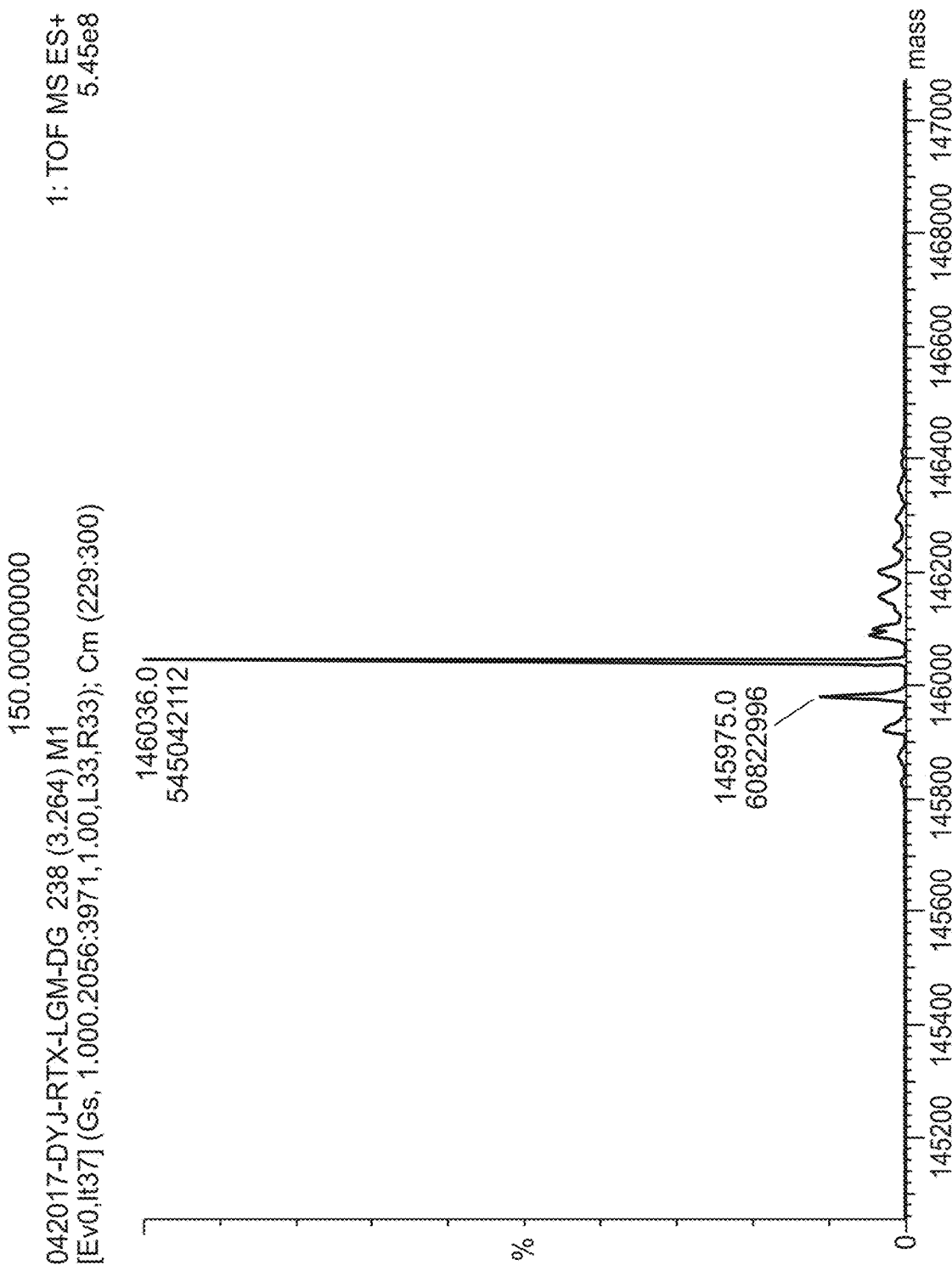
Figure 71Y:
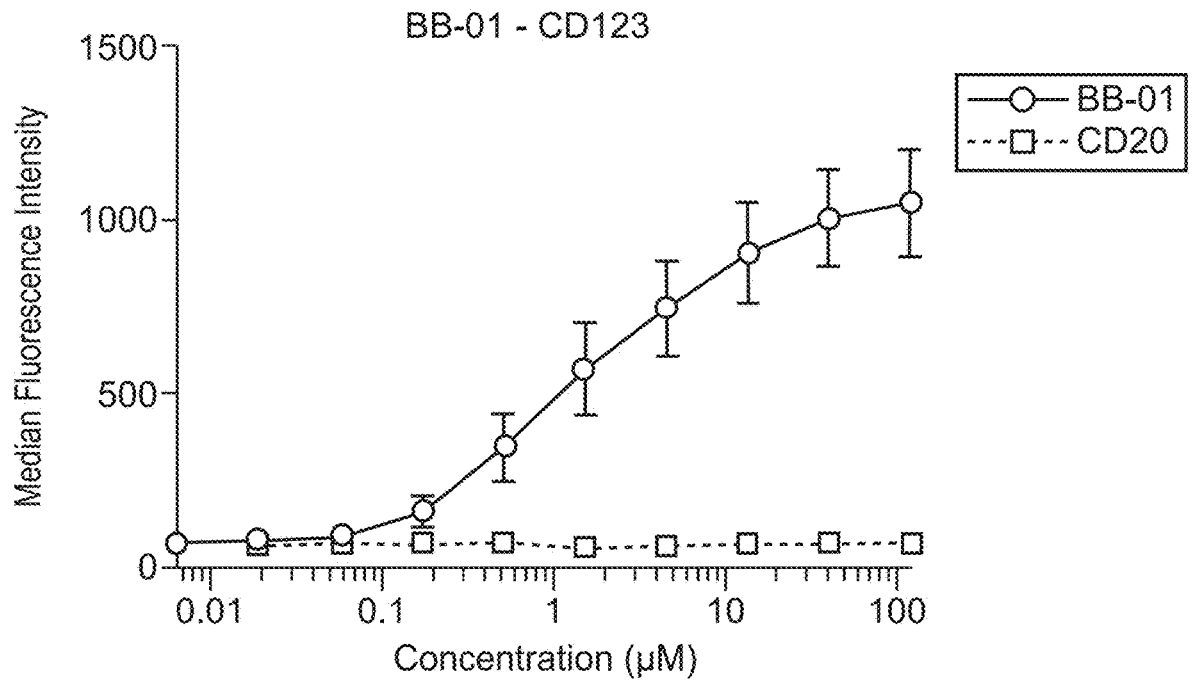
Figure 71Z:
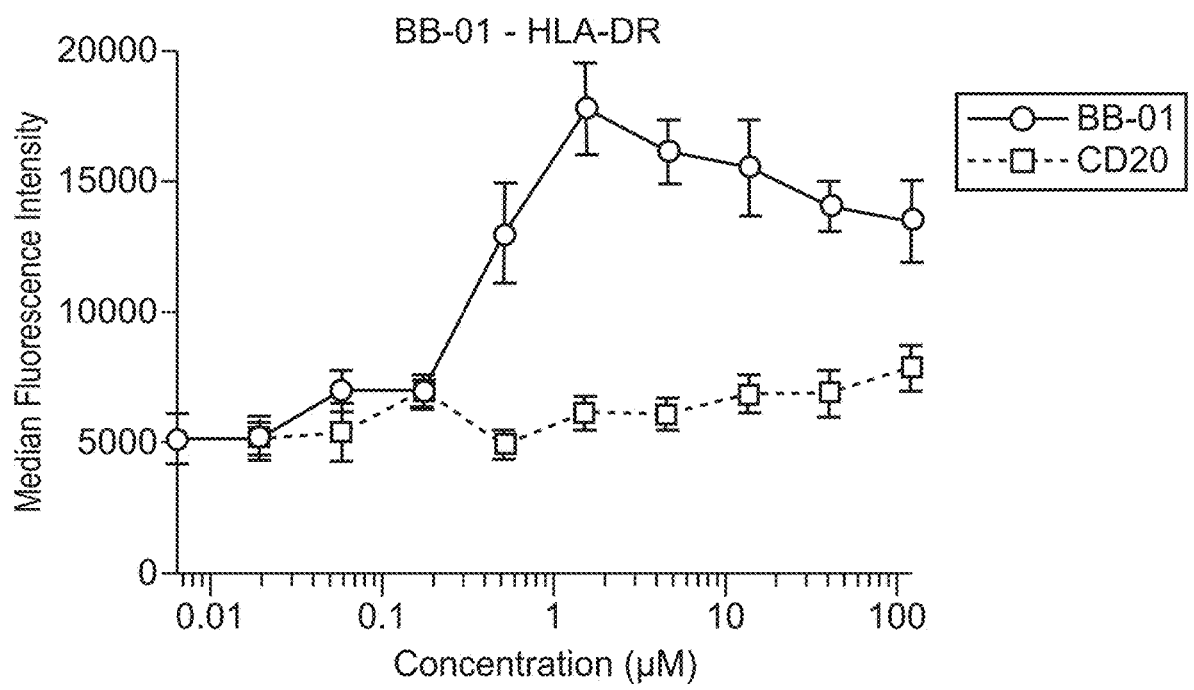
Figure 71A:
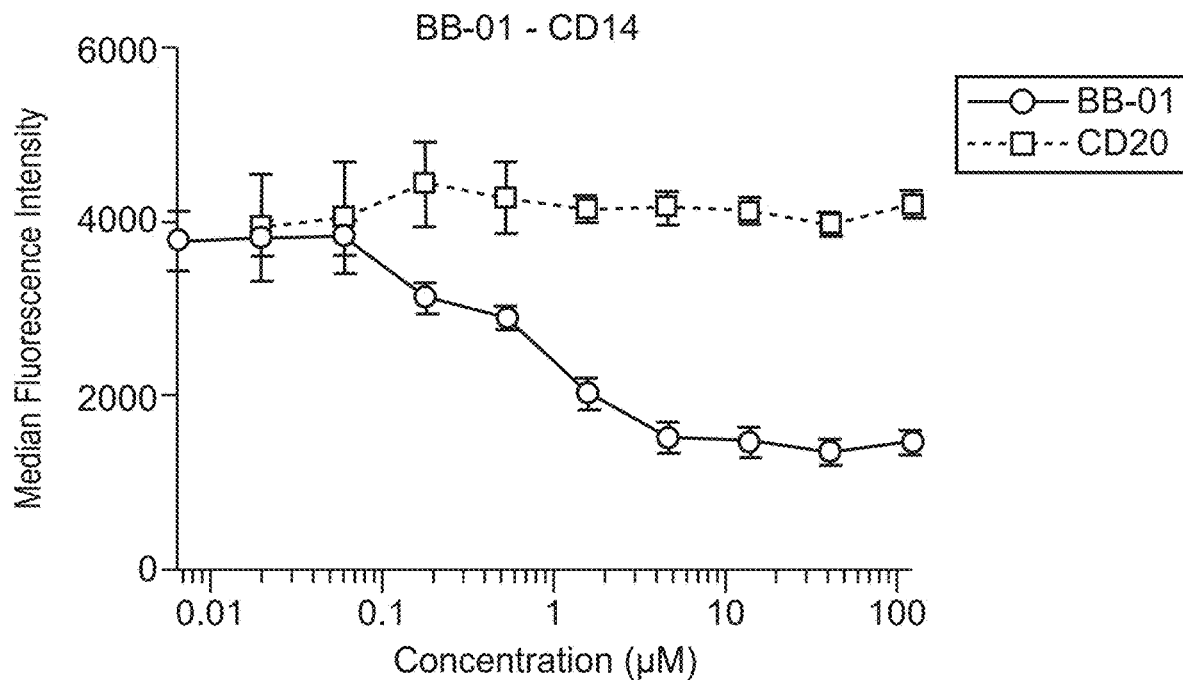
Figure 71A:
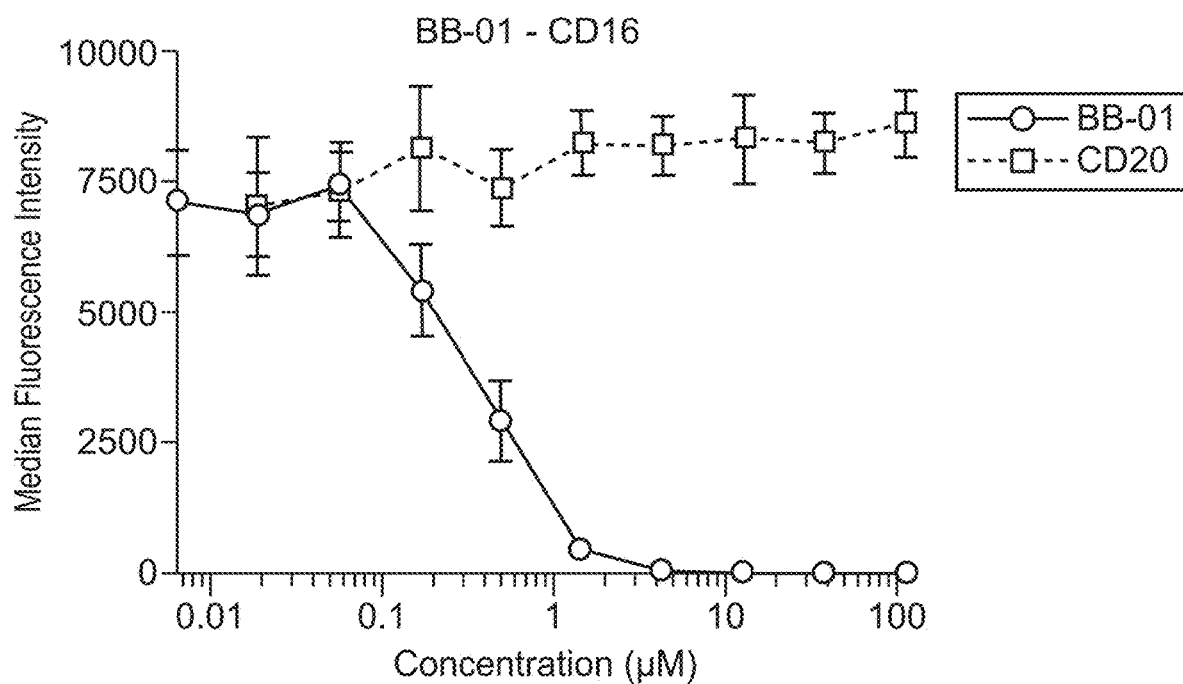
Figure 71A:
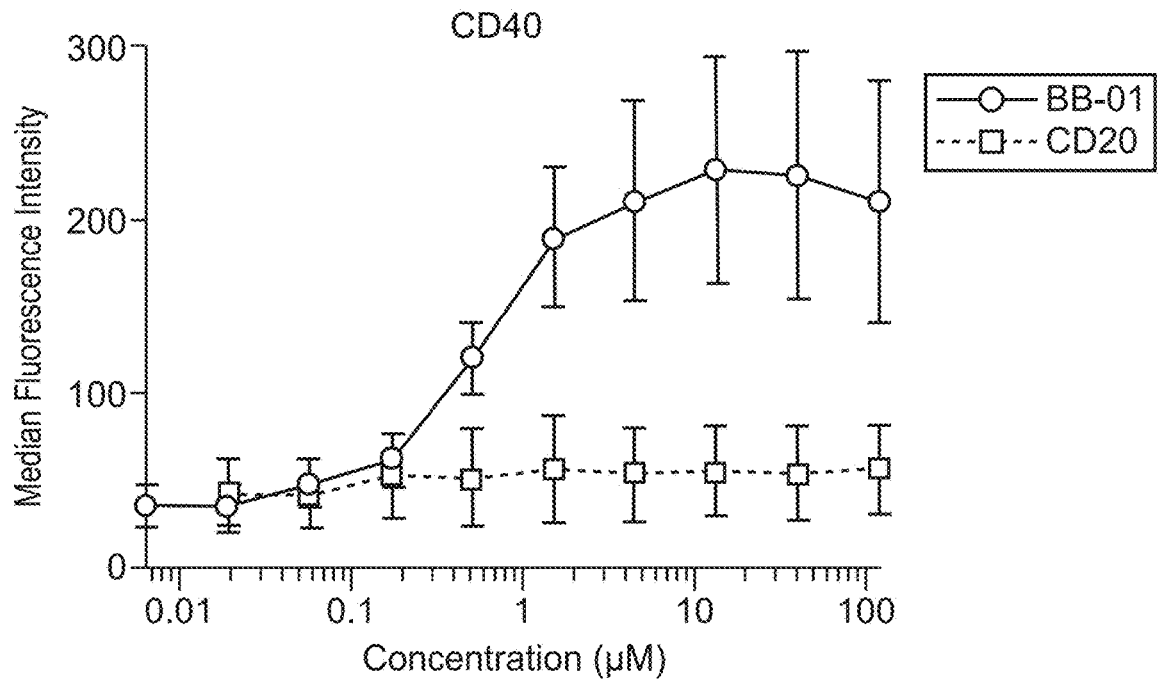
Figure 71A:
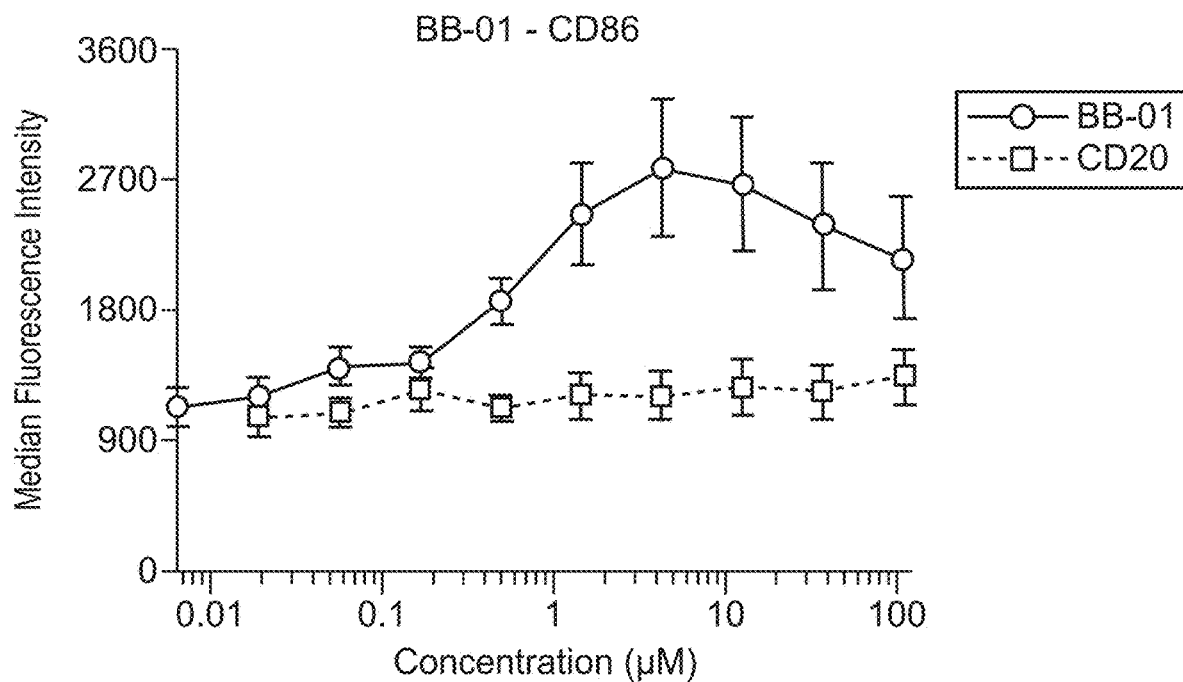
Figure 71A:
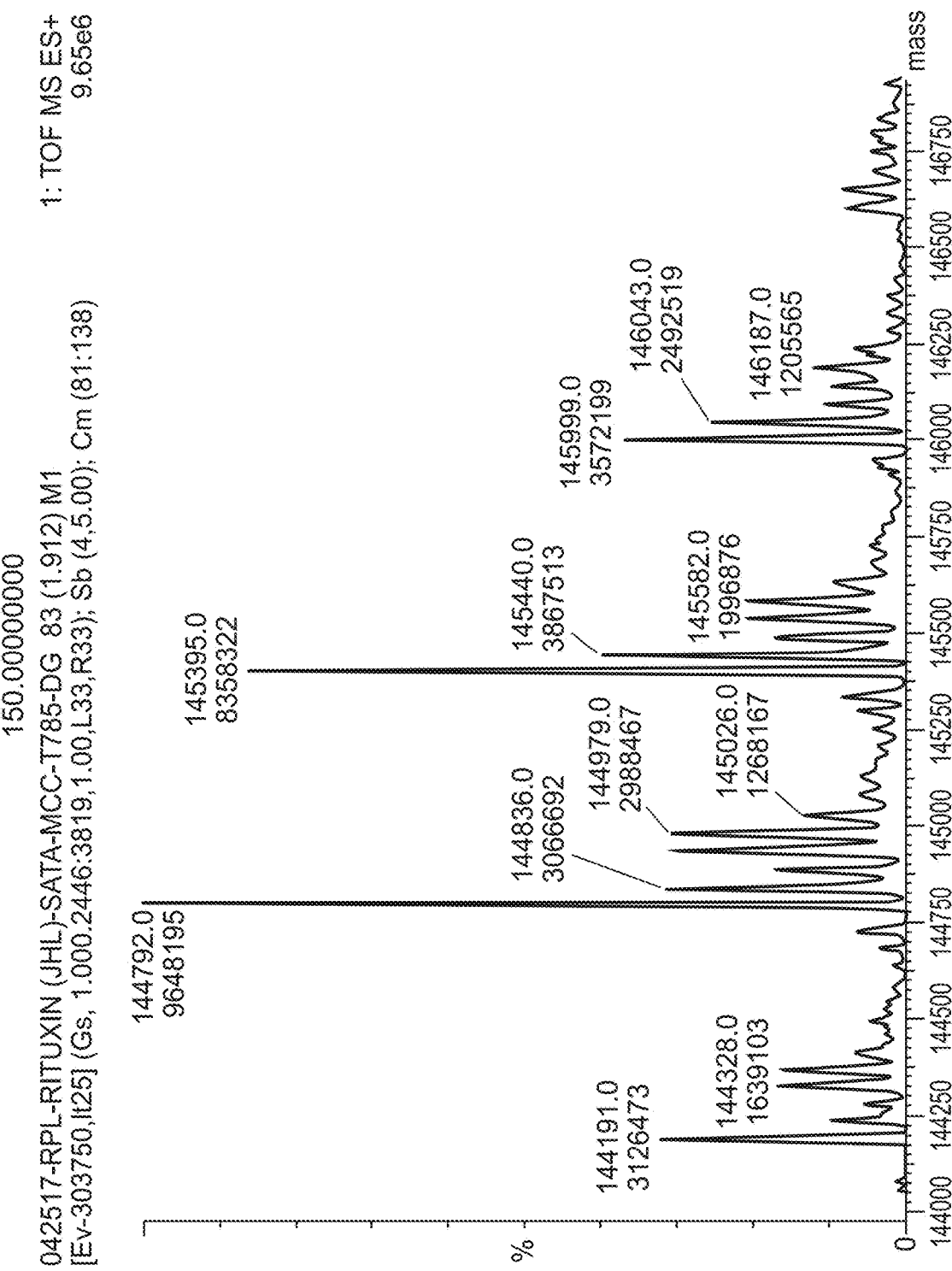
Figure 71A:
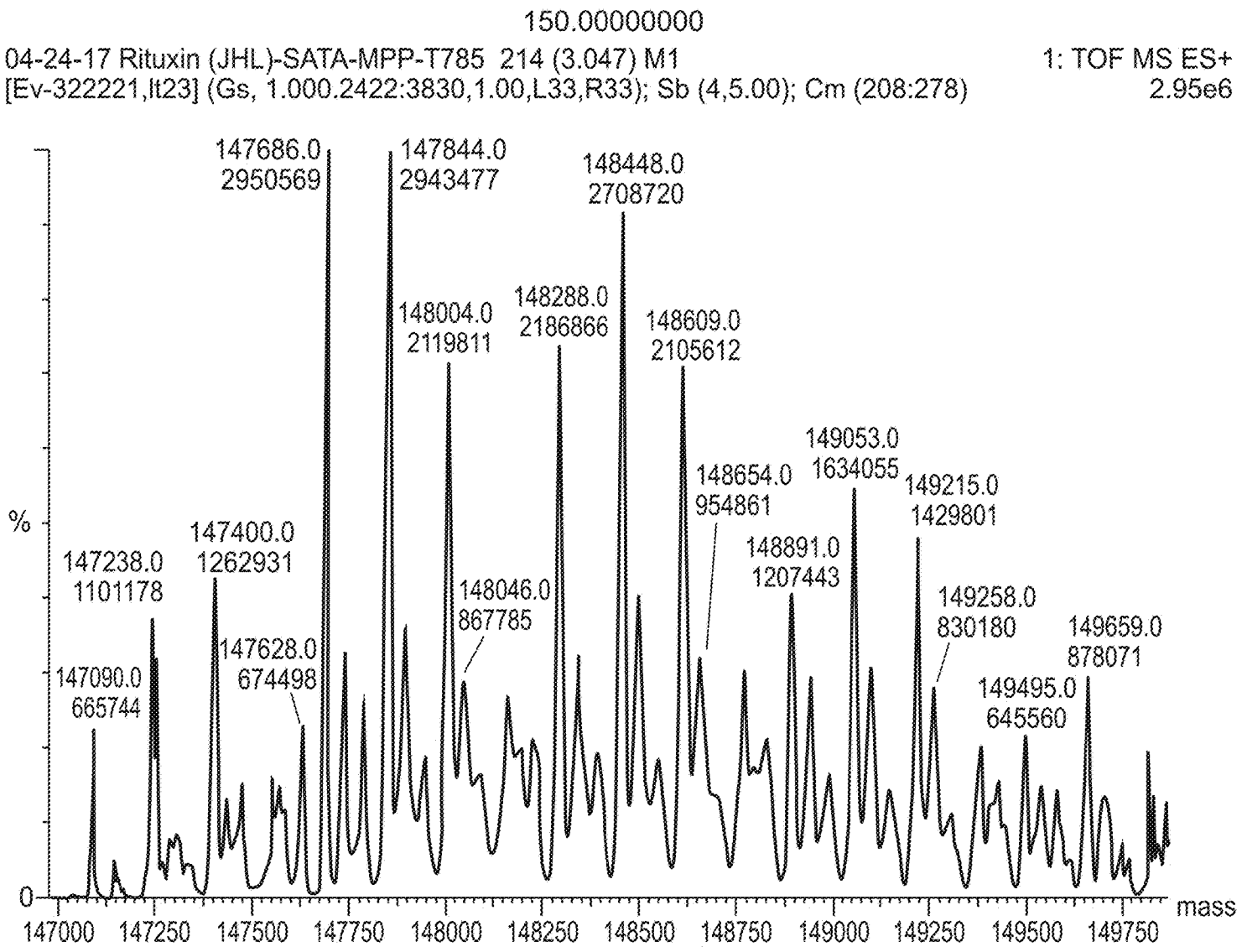
Figure 71A:
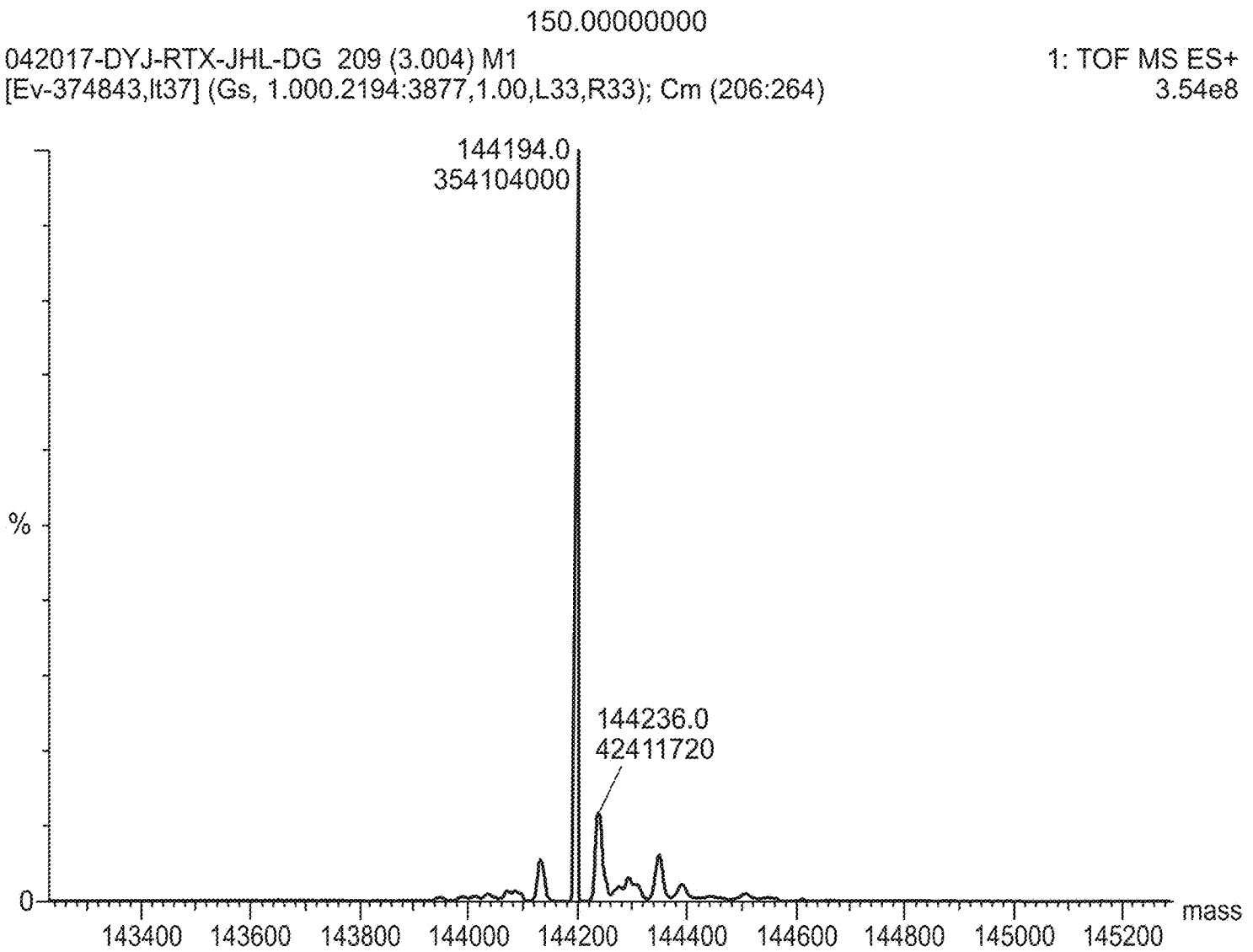
Figure 71A:
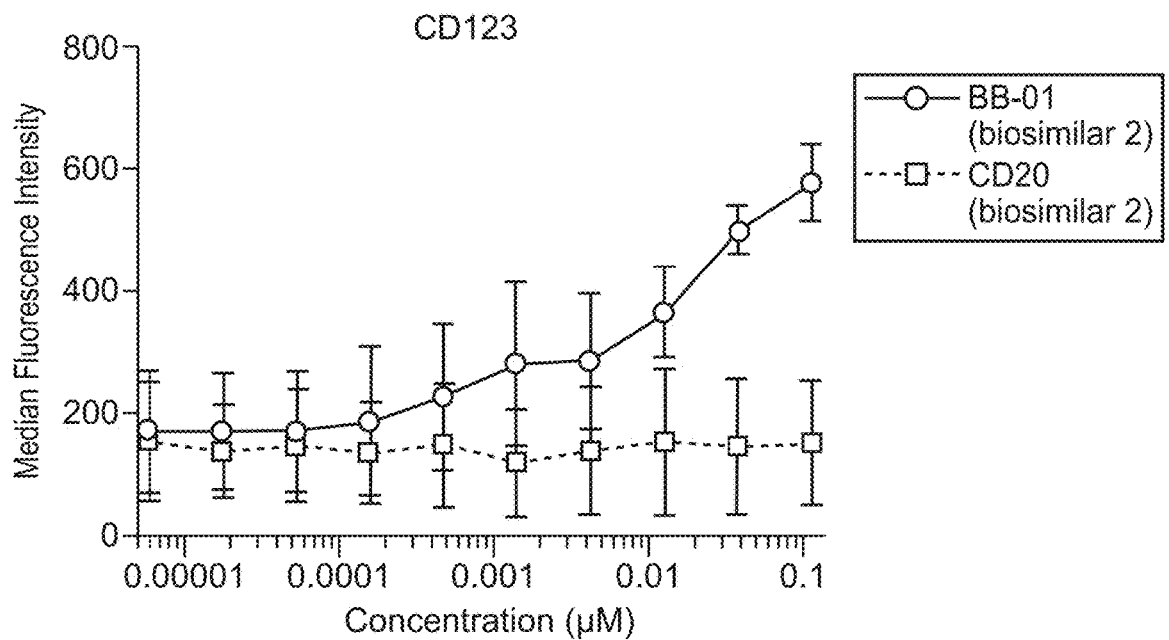
Figure 71A:
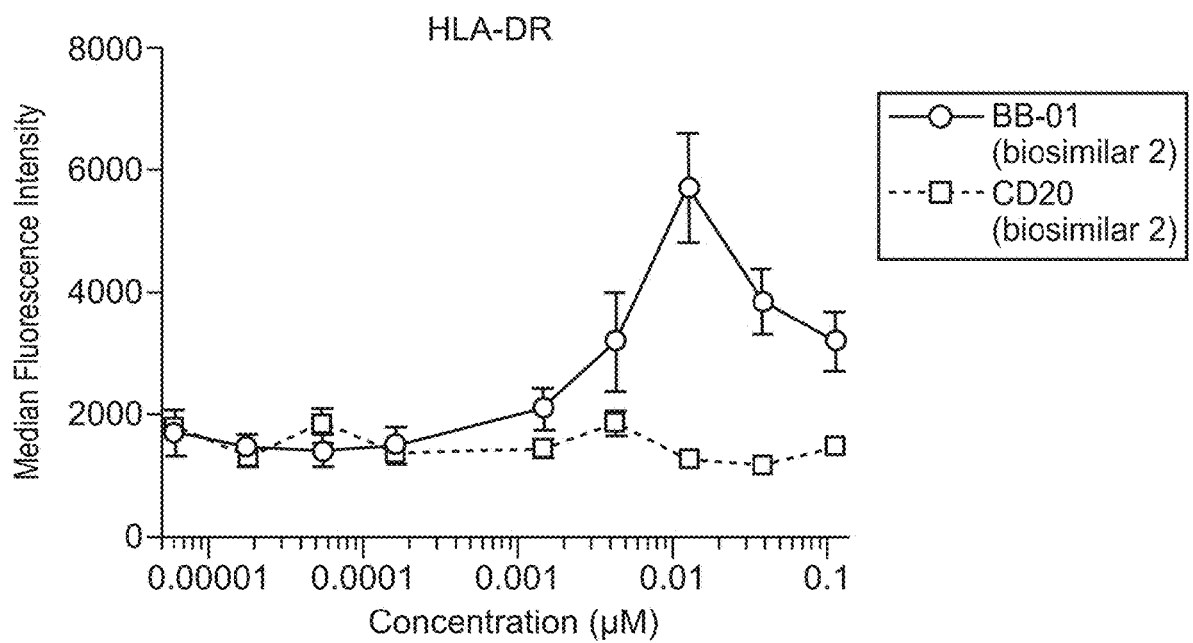
Figure 71A:
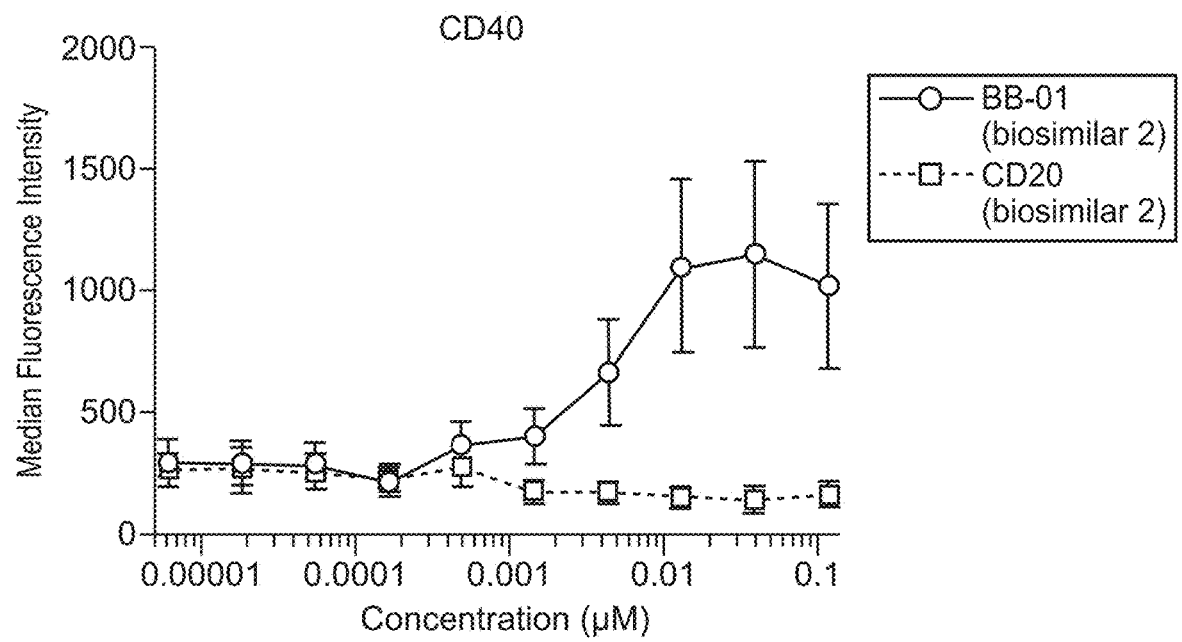
Figure 71A:
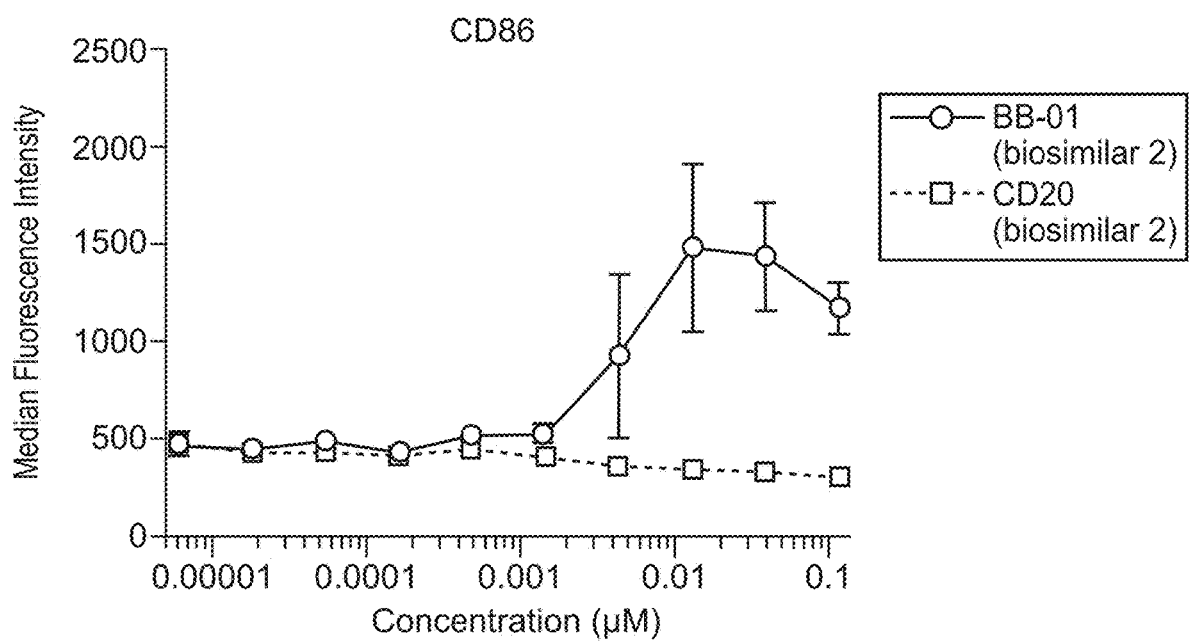
Figure 71A:
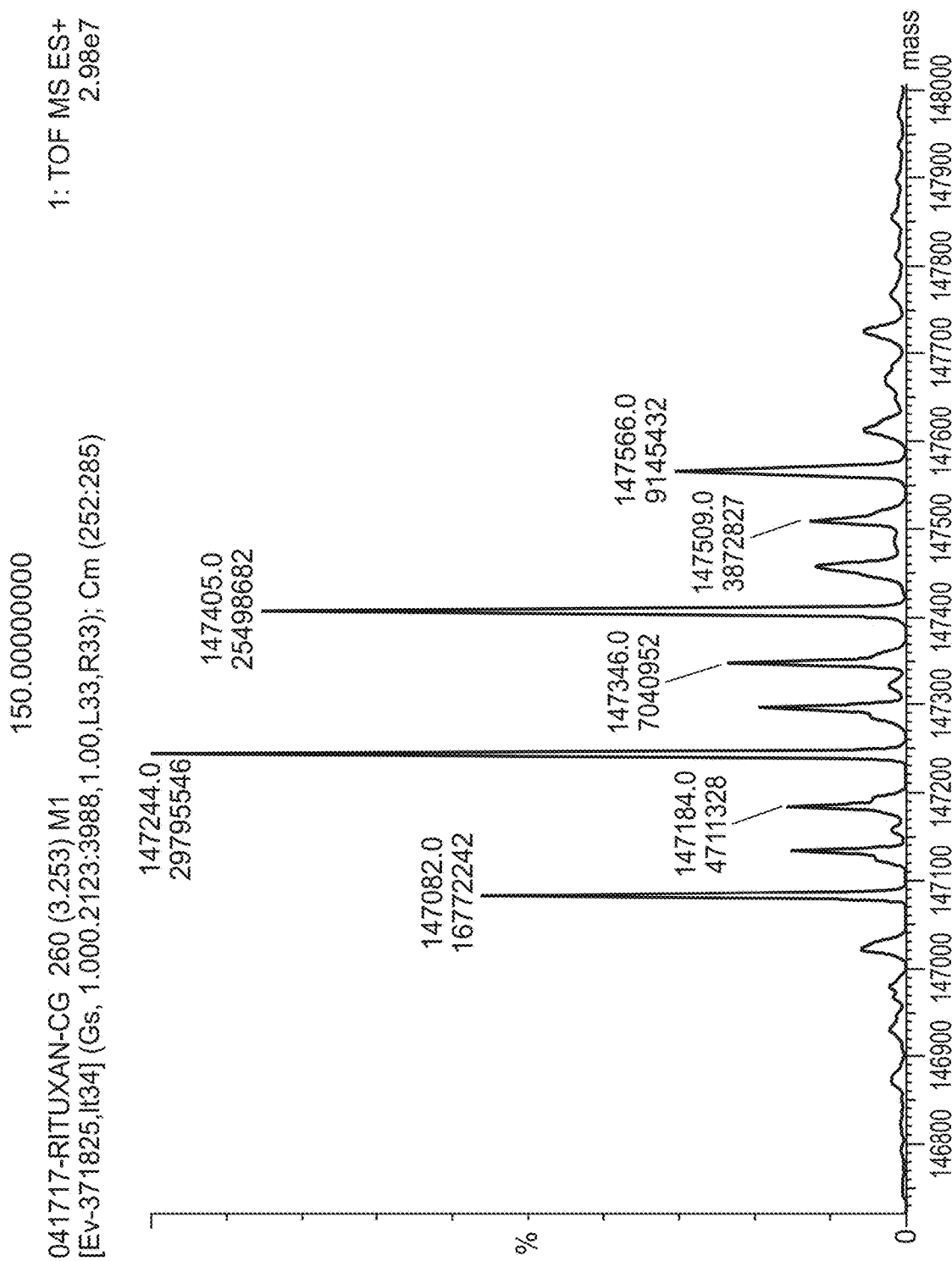
Figure 71A:
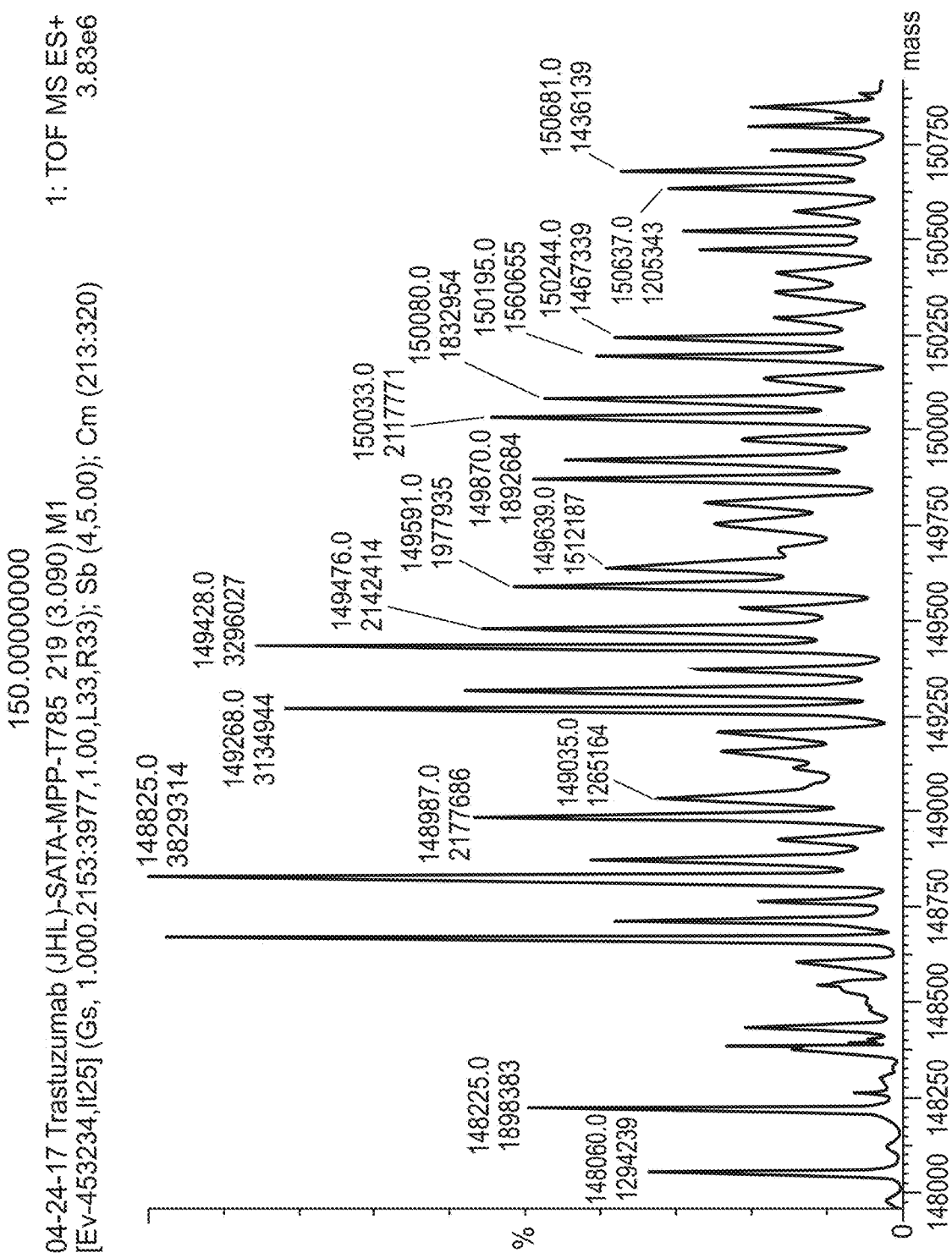
Figure 71A:
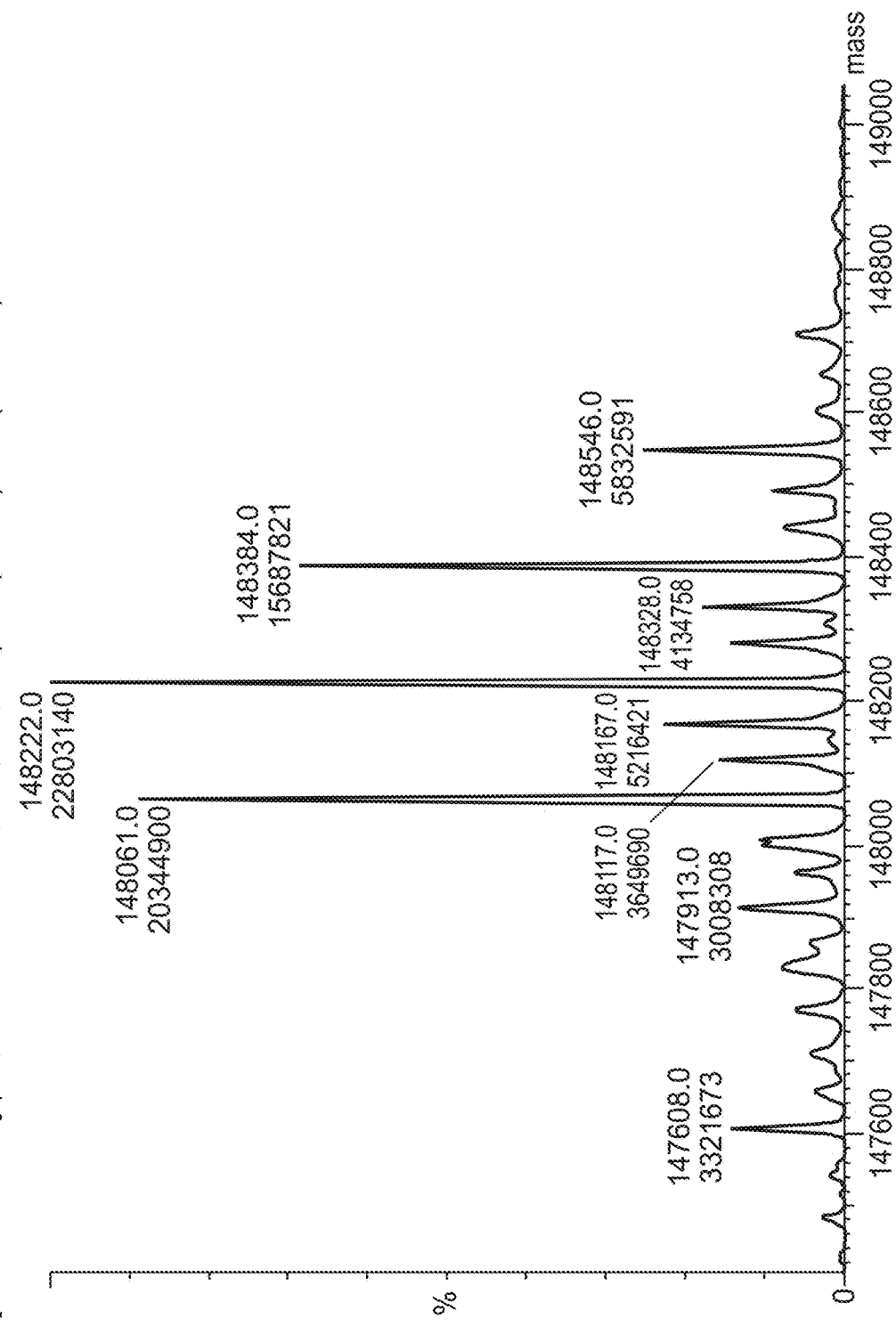
Figure 71A:
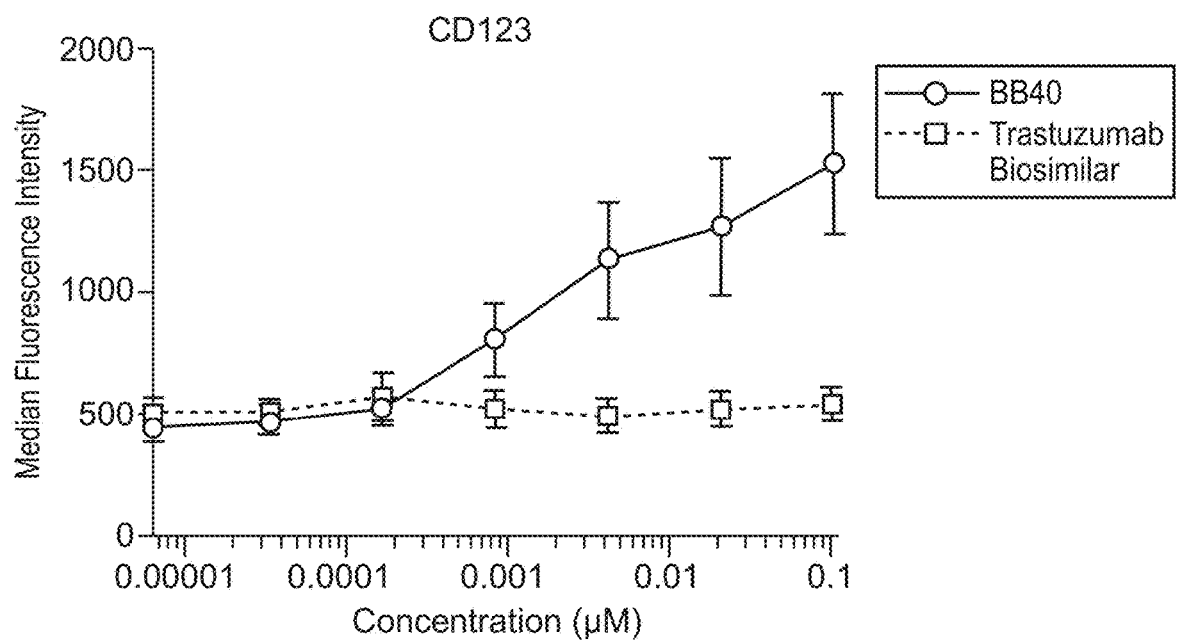
Figure 71A:
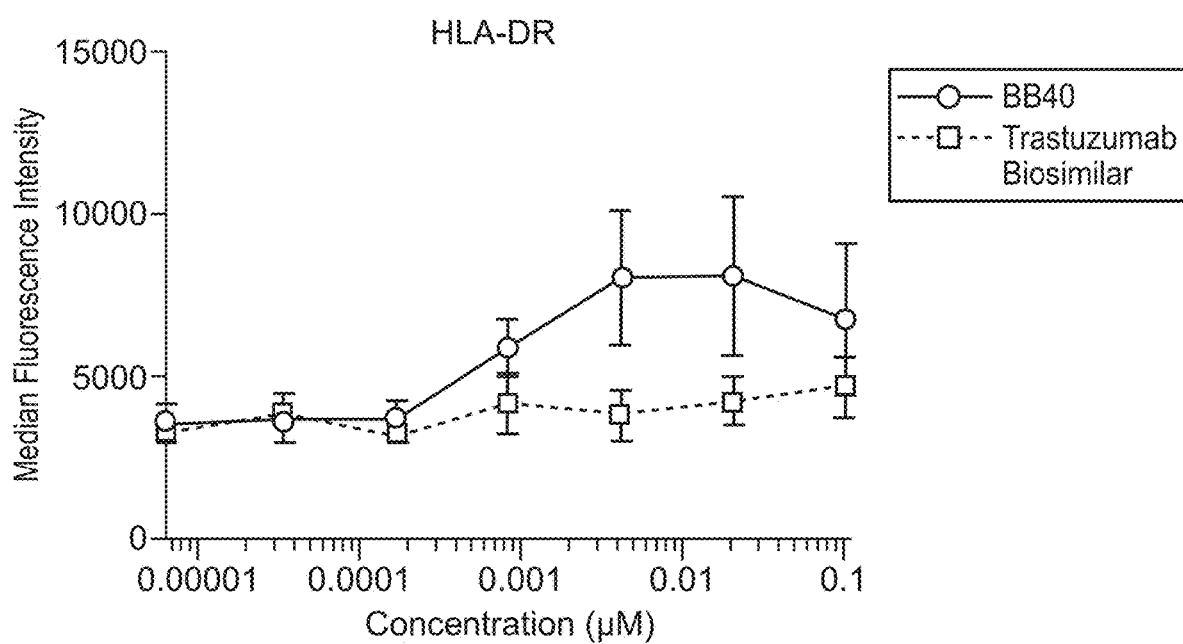
Figure 71A:
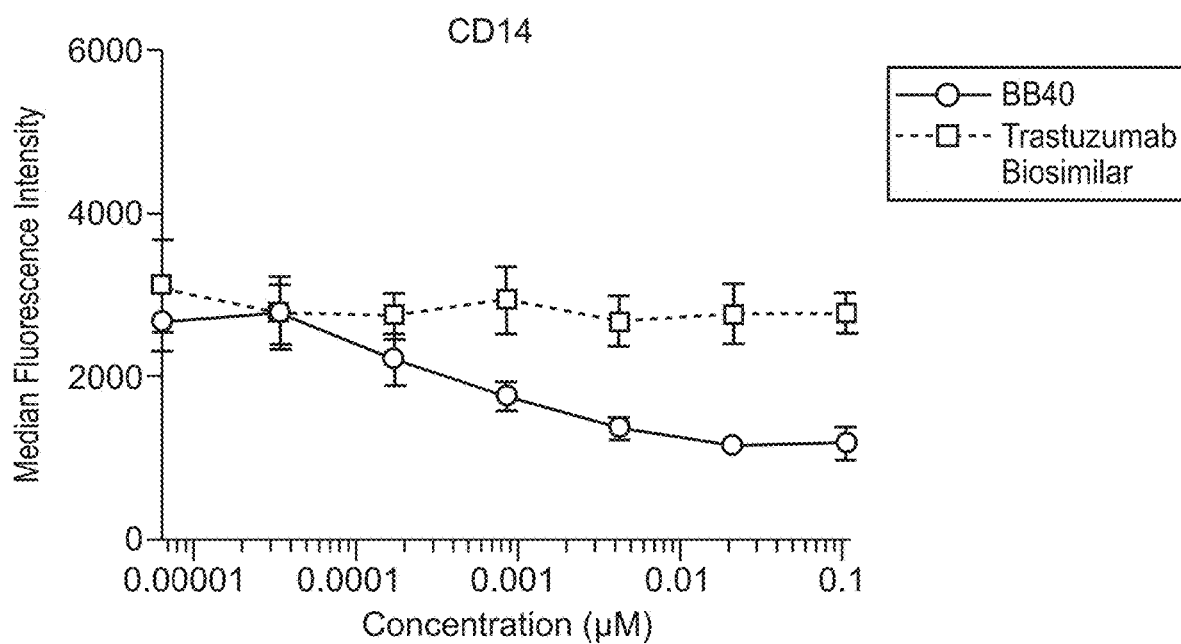
Figure 71A:
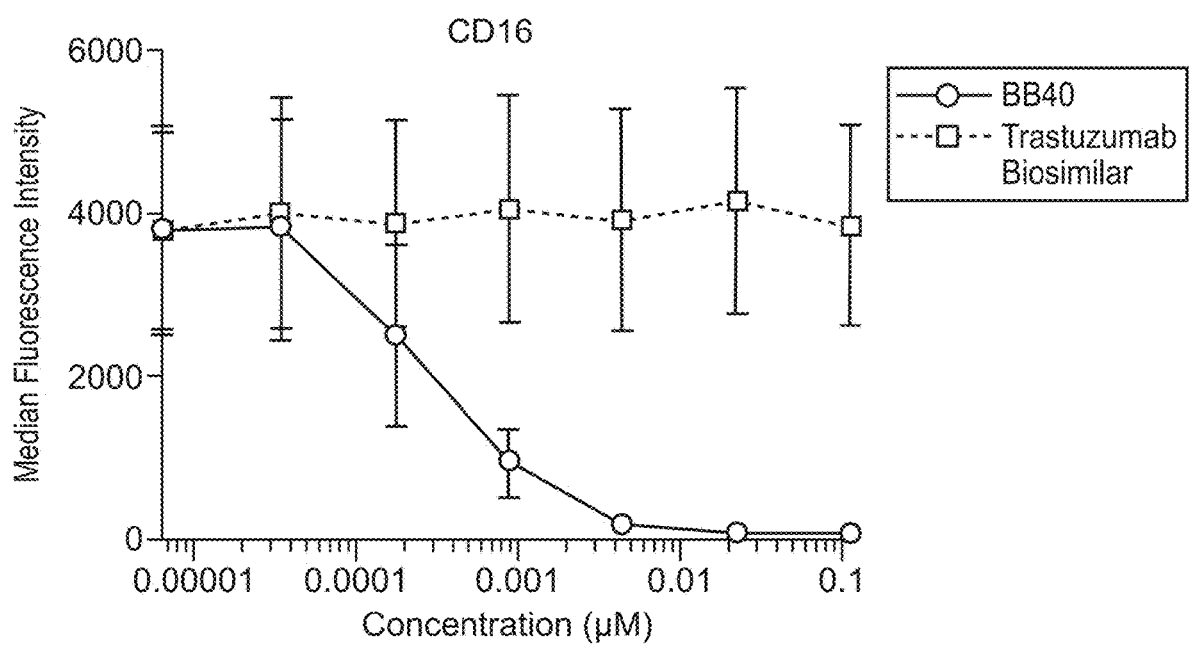
Figure 71A:
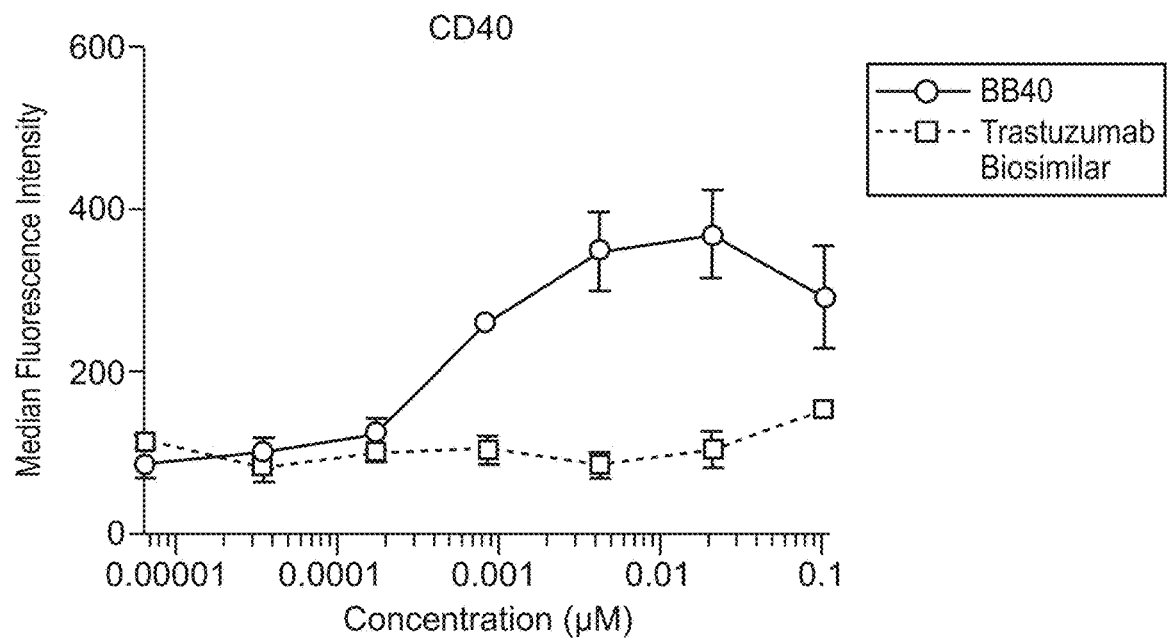
Figure 71A:
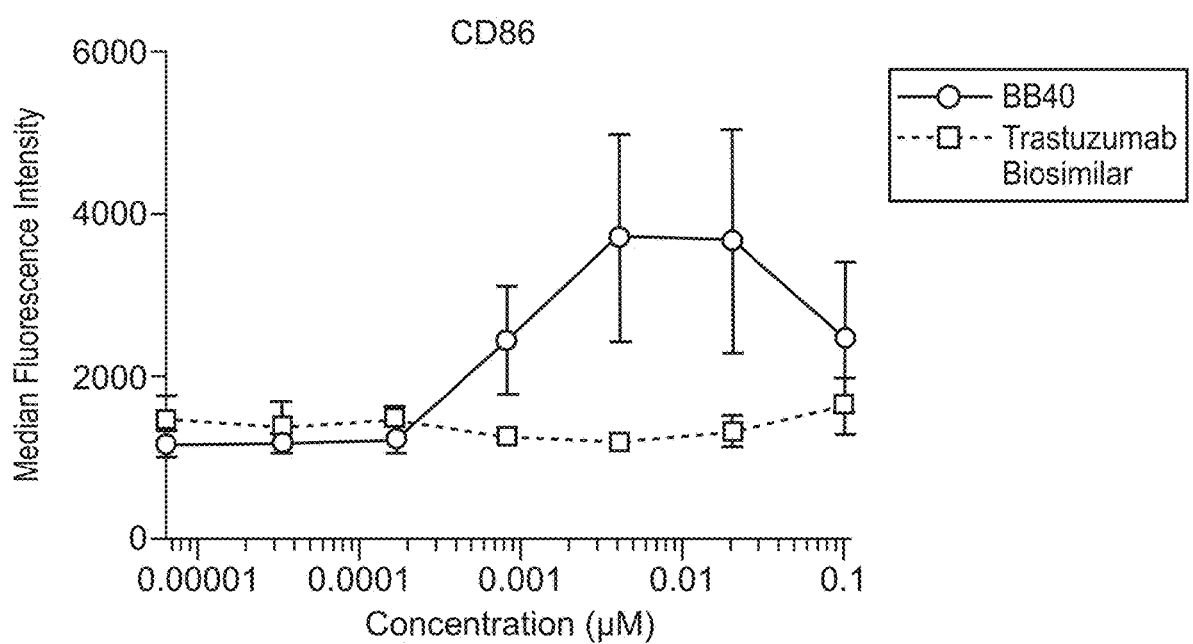

FIG. 71A shows a liquid chromatography-mass spectrometry analysis of the cetuximab immunoconjugate produced according to the BB-01 conjugation method from the cetuximab biosimilar (Alphamab) following overnight deglycosylation with PNGase F.

FIG. 71B shows a liquid chromatography-mass spectrometry analysis of the cetuximab immunoconjugate produced according to the BB-01 conjugation method.

FIG. 71C shows a liquid chromatography-mass spectrometry analysis of unconjugated cetuximab biosimilar (Alphamab) that was utilized to produce the cetuximab immunoconjugate according to the BB-01 method following overnight deglycosylation with PNGase F.

FIG. 71D shows a liquid chromatography-mass spectrometry analysis of unconjugated cetuximab biosimilar (Alphamab) that was utilized to produce the cetuximab immunoconjugate according to the BB-01 conjugation method.

FIG. 71E shows that the rituximab immunoconjugates produced according to the BB-01 method from rituximab biosimilars (AmAb, Alphamab; JHL, JHL Biotech; LGM, LGM Pharma) elicit comparable CD123 upregulation on myeloid cells following 18 hours of stimulation. The dashed line indicates the level of expression on unstimulated myeloid cells cultured for 18 hours.

FIG. 71F shows that the rituximab immunoconjugates produced according to the BB-01 method from rituximab biosimilars (AmAb, Alphamab; JHL, JHL Biotech; LGM, LGM Pharma) elicit comparable HLA-DR expression on myeloid cells following 18 hours of stimulation. The dashed line indicates the level of expression on unstimulated myeloid cells cultured for 18 hours.

FIG. 71G shows that the rituximab immunoconjugates produced according to the BB-01 method from rituximab biosimilars (biosimilar 1, Alphamab; biosimilar 2, JHL Biotech; biosimilar 3, LGM Pharma) elicit comparable CD14 downregulation on myeloid cells following 18 hours of stimulation. The dashed line indicates the level of expression on unstimulated myeloid cells cultured for 18 hours.

FIG. 71H shows that the rituximab immunoconjugates produced according to the BB-01 method from rituximab biosimilars (AmAb, Alphamab; JHL, JHL Biotech; LGM, LGM Pharma) elicit comparable CD16 downregulation on myeloid cells following 18 hours of stimulation. The dashed line indicates the level of expression on unstimulated myeloid cells cultured for 18 hours.

FIG. 71I shows that the rituximab immunoconjugates produced according to the BB-01 method from rituximab biosimilars (AmAb, Alphamab; JHL, JHL Biotech; LGM, LGM Pharma) elicit comparable CD40 upregulation on myeloid cells following 18 hours of stimulation. The dashed line indicates the level of expression on unstimulated myeloid cells cultured for 18 hours.

FIG. 71J shows that the rituximab immunoconjugates produced according to the BB-01 method from rituximab biosimilars (AmAb, Alphamab; JHL, JHL Biotech; LGM, LGM Pharma) elicit comparable CD86 upregulation on myeloid cells following 18 hours of stimulation. The dashed line indicates the level of expression on unstimulated myeloid cells cultured for 18 hours.

FIG. 71K shows a liquid chromatography-mass spectrometry analysis of the rituximab immunoconjugate produced according to the BB-01 conjugation method from the rituximab biosimilar (Alphamab) following overnight deglycosylation with PNGase F.

FIG. 71L shows a liquid chromatography-mass spectrometry analysis of the rituximab immunoconjugate produced according to the BB-01 conjugation method from the rituximab biosimilar (Alphamab).

FIG. 71M shows a liquid chromatography-mass spectrometry analysis of an unconjugated rituximab biosimilar (Alphamab) that was utilized to produce the rituximab biosimilar immunoconjugate according to the BB-01 method following overnight deglycosylation with PNGase F.

FIG. 71N shows a liquid chromatography-mass spectrometry analysis of an unconjugated rituximab biosimilar (Alphamab) that was utilized to produce the rituximab biosimilar immunoconjugate according to the BB-01 method.

FIG. 71O shows that the rituximab biosimilar immunoconjugate produced according to the BB-01 method from a rituximab biosimilar [BB-01 (biosimilar 1)] is superior at eliciting CD123 upregulation on myeloid cells as compared to the corresponding unconjugated rituximab biosimilar [(CD20 (biosimilar 1), Alphamab] following 18 hours of stimulation.

FIG. 71P shows that the rituximab biosimilar immunoconjugate produced according to the BB-01 method from a rituximab biosimilar [BB-01 (biosimilar 1)] is superior at eliciting HLA-DR upregulation on myeloid cells as compared to the corresponding unconjugated rituximab biosimilar [(CD20 (biosimilar 1), Alphamab] following 18 hours of stimulation.

FIG. 71Q shows that the rituximab biosimilar immunoconjugate produced according to the BB-01 method from a rituximab biosimilar [BB-01 (biosimilar 1)] is superior at eliciting CD14 downregulation on myeloid cells as compared to the corresponding unconjugated rituximab biosimilar [(CD20 (biosimilar 1), Alphamab] following 18 hours of stimulation.

FIG. 71R shows that the rituximab biosimilar immunoconjugate produced according to the BB-01 method from a rituximab biosimilar [BB-01 (biosimilar 1)] is superior at eliciting CD16 downregulation on myeloid cells as compared to the corresponding unconjugated rituximab biosimilar [(CD20 (biosimilar 1), Alphamab] following 18 hours of stimulation.

FIG. 71S shows that the rituximab biosimilar immunoconjugate produced according to the BB-01 method from a rituximab biosimilar [BB-01 (biosimilar 1)] is superior at eliciting CD40 upregulation on myeloid cells as compared to the corresponding unconjugated rituximab biosimilar [(CD20 (biosimilar 1), Alphamab] following 18 hours of stimulation.

FIG. 71T shows that the rituximab biosimilar immunoconjugate produced according to the BB-01 method from a rituximab biosimilar [BB-01 (biosimilar 1)] is superior at eliciting CD86 upregulation on myeloid cells as compared to the corresponding unconjugated rituximab biosimilar [(CD20 (biosimilar 1), Alphamab] following 18 hours of stimulation.

FIG. 71U shows a liquid chromatography-mass spectrometry analysis of the rituximab immunoconjugate produced according to the BB-01 conjugation method from the rituximab biosimilar (LGM Pharma) following overnight deglycosylation with PNGase F.

FIG. 71V shows a liquid chromatography-mass spectrometry analysis of the rituximab immunoconjugate produced according to the BB-01 conjugation method from the rituximab biosimilar (LGM Pharma).

FIG. 71W shows a liquid chromatography-mass spectrometry analysis of an unconjugated rituximab biosimilar (LGM Pharma) that was utilized to produce the rituximab biosimilar immunoconjugate according to the BB-01 method following overnight deglycosylation with PNGase F.

FIG. 71X shows a liquid chromatography-mass spectrometry analysis of an unconjugated rituximab biosimilar (LGM Pharma) that was utilized to produce the rituximab biosimilar immunoconjugate according to the BB-01 method.

FIG. 71Y shows that the rituximab biosimilar immunoconjugate produced according to the BB-01 method from a rituximab biosimilar (BB-01) is superior at eliciting CD123 upregulation on myeloid cells as compared to the corresponding unconjugated rituximab biosimilar (CD20, LGM Pharma) following 18 hours of stimulation.

FIG. 71Z shows that the rituximab biosimilar immunoconjugate produced according to the BB-01 method from a rituximab biosimilar (BB-01) is superior at eliciting HLA-DR upregulation on myeloid cells as compared to the corresponding unconjugated rituximab biosimilar (CD20, LGM Pharma) following 18 hours of stimulation.

FIG. 71AA shows that the rituximab biosimilar immunoconjugate produced according to the BB-01 method from a rituximab biosimilar (BB-01) is superior at eliciting CD14 downregulation on myeloid cells as compared to the corresponding unconjugated rituximab biosimilar (CD20, LGM Pharma) following 18 hours of stimulation.

FIG. 71AB shows that the rituximab biosimilar immunoconjugate produced according to the BB-01 method from a rituximab biosimilar (BB-01) is superior at eliciting CD16 downregulation on myeloid cells as compared to the corresponding unconjugated rituximab biosimilar (CD20, LGM Pharma) following 18 hours of stimulation.

FIG. 71AC shows that the rituximab biosimilar immunoconjugate produced according to the BB-01 method from a rituximab biosimilar (BB-01) is superior at eliciting CD40 upregulation on myeloid cells as compared to the corresponding unconjugated rituximab biosimilar (CD20, LGM Pharma) following 18 hours of stimulation.

FIG. 71AD shows that the rituximab biosimilar immunoconjugate produced according to the BB-01 method from a rituximab biosimilar (BB-01) is superior at eliciting CD86 upregulation on myeloid cells as compared to the corresponding unconjugated rituximab biosimilar (CD20, LGM Pharma) following 18 hours of stimulation.

FIG. 71AE shows a liquid chromatography-mass spectrometry analysis of the rituximab immunoconjugate produced according to the BB-01 conjugation method from the rituximab biosimilar (JHL Biotech) following overnight deglycosylation with PNGase F.

FIG. 71AF shows a liquid chromatography-mass spectrometry analysis of the rituximab immunoconjugate produced according to the BB-01 conjugation method from the rituximab biosimilar (JHL Biotech).

FIG. 71AG shows a liquid chromatography-mass spectrometry analysis of an unconjugated rituximab biosimilar (JHL Biotech) that was utilized to produce the rituximab biosimilar immunoconjugate according to the BB-01 method following overnight deglycosylation with PNGase F.

FIG. 71AH shows a liquid chromatography-mass spectrometry analysis of an unconjugated rituximab biosimilar (JHL Biotech) that was utilized to produce the rituximab biosimilar immunoconjugate according to the BB-01 method.

FIG. 71AI shows that the rituximab biosimilar immunoconjugate produced according to the BB-01 method from a rituximab biosimilar [BB-01 (biosimilar 2)] is superior at eliciting CD123 upregulation on myeloid cells as compared to the corresponding unconjugated rituximab biosimilar [(CD20 (biosimilar 2), JHL Biotech] following 18 hours of stimulation.

FIG. 71AJ shows that the rituximab biosimilar immunoconjugate produced according to the BB-01 method from a rituximab biosimilar [BB-01 (biosimilar 2)] is superior at eliciting HLA-DR upregulation on myeloid cells as compared to the corresponding unconjugated rituximab biosimilar [(CD20 (biosimilar 2), JHL Biotech] following 18 hours of stimulation.

FIG. 71AK shows that the rituximab biosimilar immunoconjugate produced according to the BB-01 method from a rituximab biosimilar [BB-01 (biosimilar 2)] is superior at eliciting CD40 upregulation on myeloid cells as compared to the corresponding unconjugated rituximab biosimilar [(CD20 (biosimilar 2), JHL Biotech] following 18 hours of stimulation.

FIG. 71AL shows that the rituximab biosimilar immunoconjugate produced according to the BB-01 method from a rituximab biosimilar [BB-01 (biosimilar 2)] is superior at eliciting CD86 upregulation on myeloid cells as compared to the corresponding unconjugated rituximab biosimilar [(CD20 (biosimilar 2), JHL Biotech] following 18 hours of stimulation.

FIG. 71AM shows a liquid chromatography-mass spectrometry analysis of unconjugated rituximab (Roche).

FIG. 71AN shows a liquid chromatography-mass spectrometry analysis of the trastuzumab immunoconjugate produced according to the BB-01 conjugation method from the trastuzumab biosimilar (JHL Biotech) following overnight deglycosylation with PNGase F.

FIG. 71AO shows a liquid chromatography-mass spectrometry analysis of the trastuzumab immunoconjugate produced according to the BB-01 conjugation method from the trastuzumab biosimilar (JHL Biotech).

FIG. 71AP shows a liquid chromatography-mass spectrometry analysis of an unconjugated trastuzumab biosimilar (JHL Biotech) that was utilized to produce the trastuzumab biosimilar immunoconjugate according to the BB-01 method following overnight deglycosylation with PNGase F.

FIG. 71AQ shows a liquid chromatography-mass spectrometry analysis of an unconjugated trastuzumab biosimilar (JHL Biotech) that was utilized to produce the trastuzumab biosimilar immunoconjugate according to the BB-01 method.

FIG. 71AR shows that the trastuzumab biosimilar immunoconjugate produced according to the BB-01 method from a trastuzumab biosimilar (BB-40) is superior at eliciting CD123 upregulation on myeloid cells as compared to the corresponding unconjugated trastuzumab biosimilar [Trastuzumab (JHL), JHL Biotech) following 18 hours of stimulation.

FIG. 71AS shows that the trastuzumab biosimilar immunoconjugate produced according to the BB-01 method from a trastuzumab biosimilar (BB-40) is superior at eliciting HLA-DR upregulation on myeloid cells as compared to the corresponding unconjugated trastuzumab biosimilar [Trastuzumab (JHL), JHL Biotech) following 18 hours of stimulation.

FIG. 71AT shows that the trastuzumab biosimilar immunoconjugate produced according to the BB-01 method from a trastuzumab biosimilar (BB-40) is superior at eliciting CD14 downregulation on myeloid cells as compared to the corresponding unconjugated trastuzumab biosimilar [Trastuzumab (JHL), JHL Biotech) following 18 hours of stimulation.

FIG. 71AU shows that the trastuzumab biosimilar immunoconjugate produced according to the BB-01 method from a trastuzumab biosimilar (BB-40) is superior at eliciting CD16 downregulation on myeloid cells as compared to the corresponding unconjugated trastuzumab biosimilar [Trastuzumab (JHL), JHL Biotech) following 18 hours of stimulation.

FIG. 71AV shows that the trastuzumab biosimilar immunoconjugate produced according to the BB-01 method from a trastuzumab biosimilar (BB-40) is superior at eliciting CD40 upregulation on myeloid cells as compared to the corresponding unconjugated trastuzumab biosimilar [Trastuzumab (JHL), JHL Biotech) following 18 hours of stimulation.

FIG. 71AW shows that the trastuzumab biosimilar immunoconjugate produced according to the BB-01 method from a trastuzumab biosimilar (BB-40) is superior at eliciting CD86 upregulation on myeloid cells as compared to the corresponding unconjugated trastuzumab biosimilar [Trastuzumab (JHL), JHL Biotech) following 18 hours of stimulation.

Figure 72A:
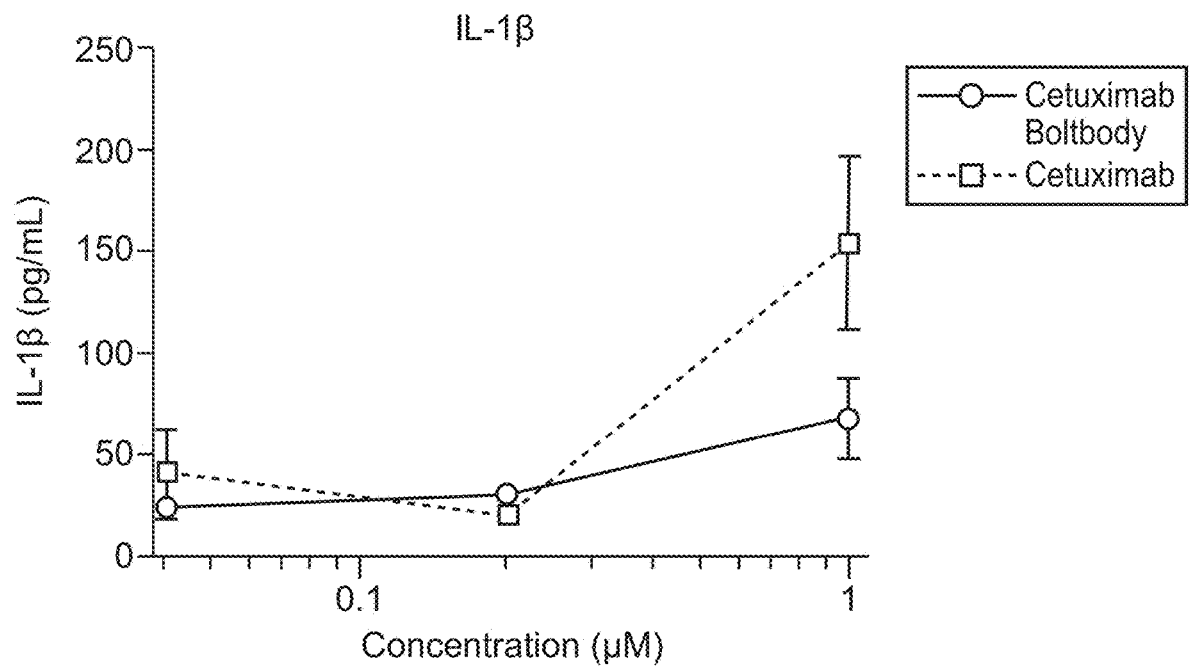

FIG. 72A shows that the cetuximab immunoconjugate produced according to the BB-01 method (Cetuximab Boltbody) elicits superior IL-1β secretion from myeloid cells as compared to equimolar concentrations of unconjugated cetuximab (Imclone/Lilly) following 18 hours of stimulation.

Figure 72B:
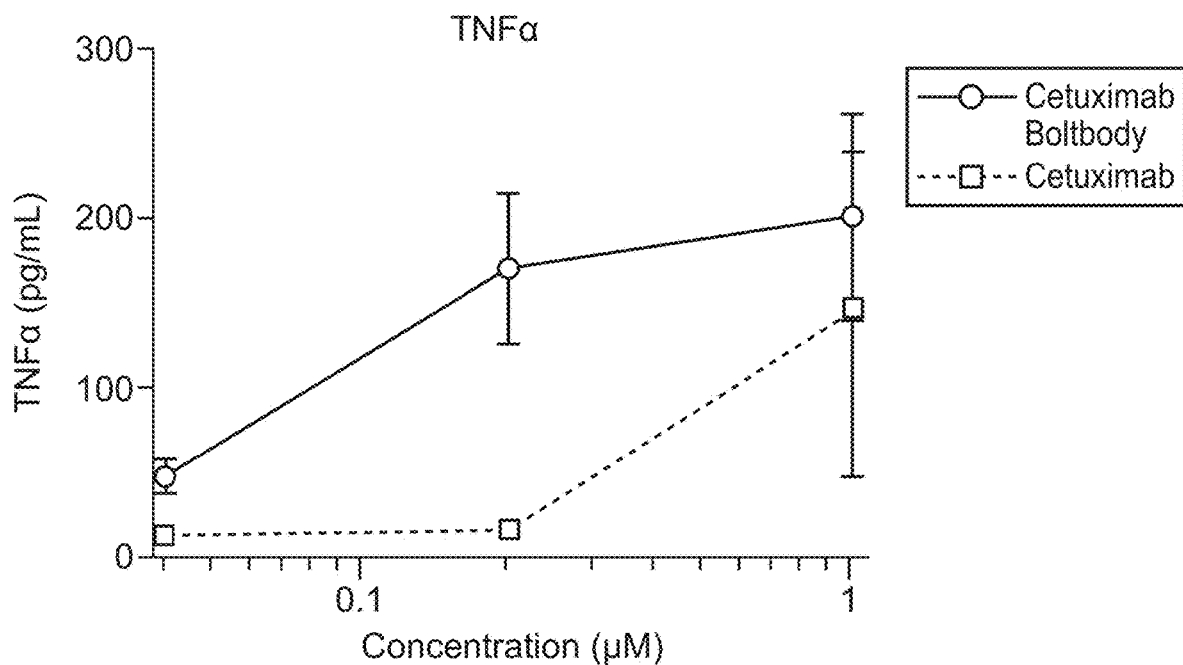

FIG. 72B shows that the cetuximab immunoconjugate produced according to the BB-01 method (Cetuximab Boltbody) elicits superior TNFα secretion from myeloid cells as compared to equimolar concentrations of unconjugated cetuximab (Imclone/Lilly) following 18 hours of stimulation.

Figure 72C:
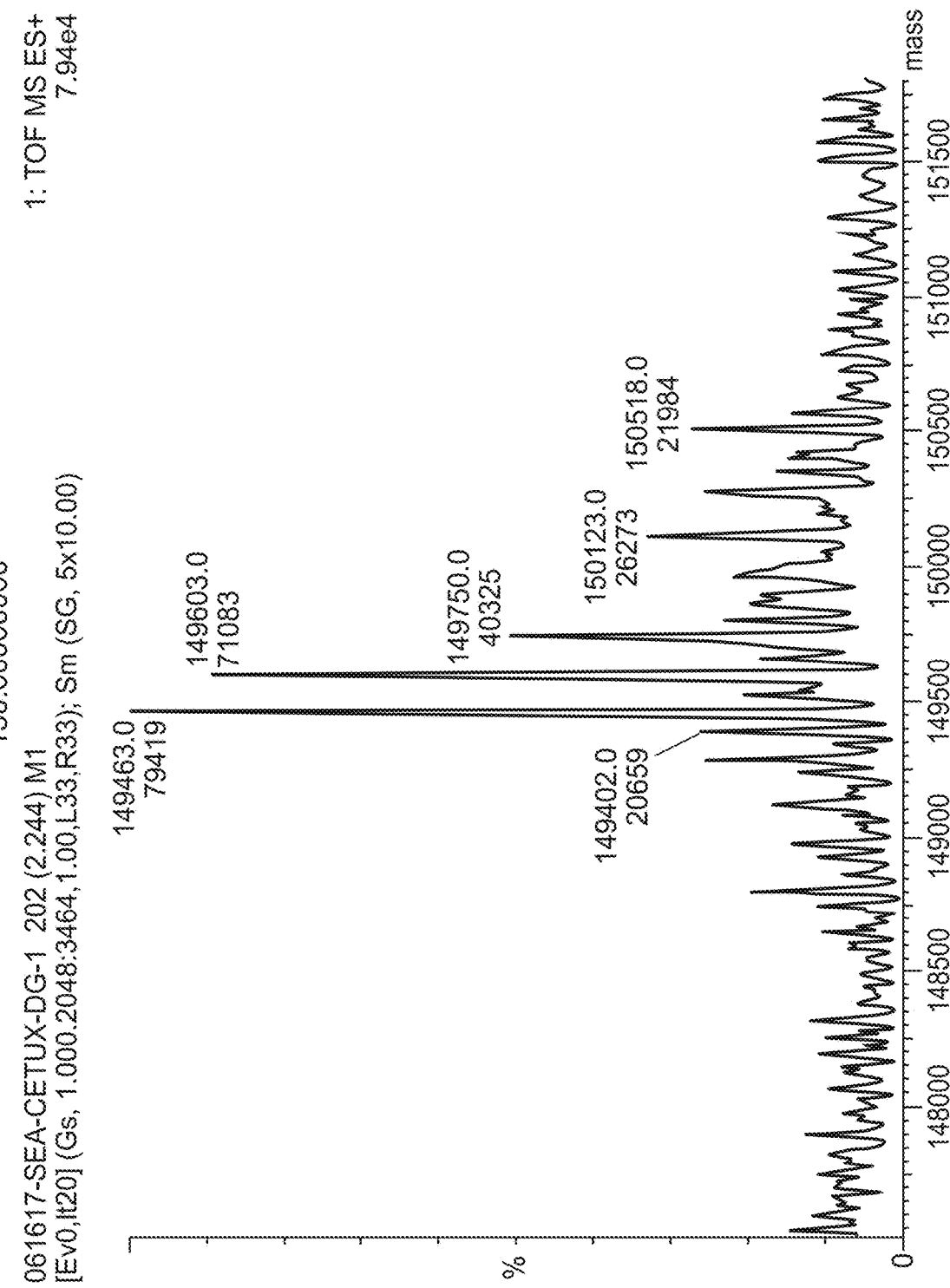

FIG. 72C shows a liquid chromatography-mass spectrometry analysis of unconjugated cetuximab (Imclone/Lilly) that was utilized to produce the cetuximab immunoconjugate according to the BB-01 conjugation method following overnight deglycosylation with PNGase F.

Figure 72D:
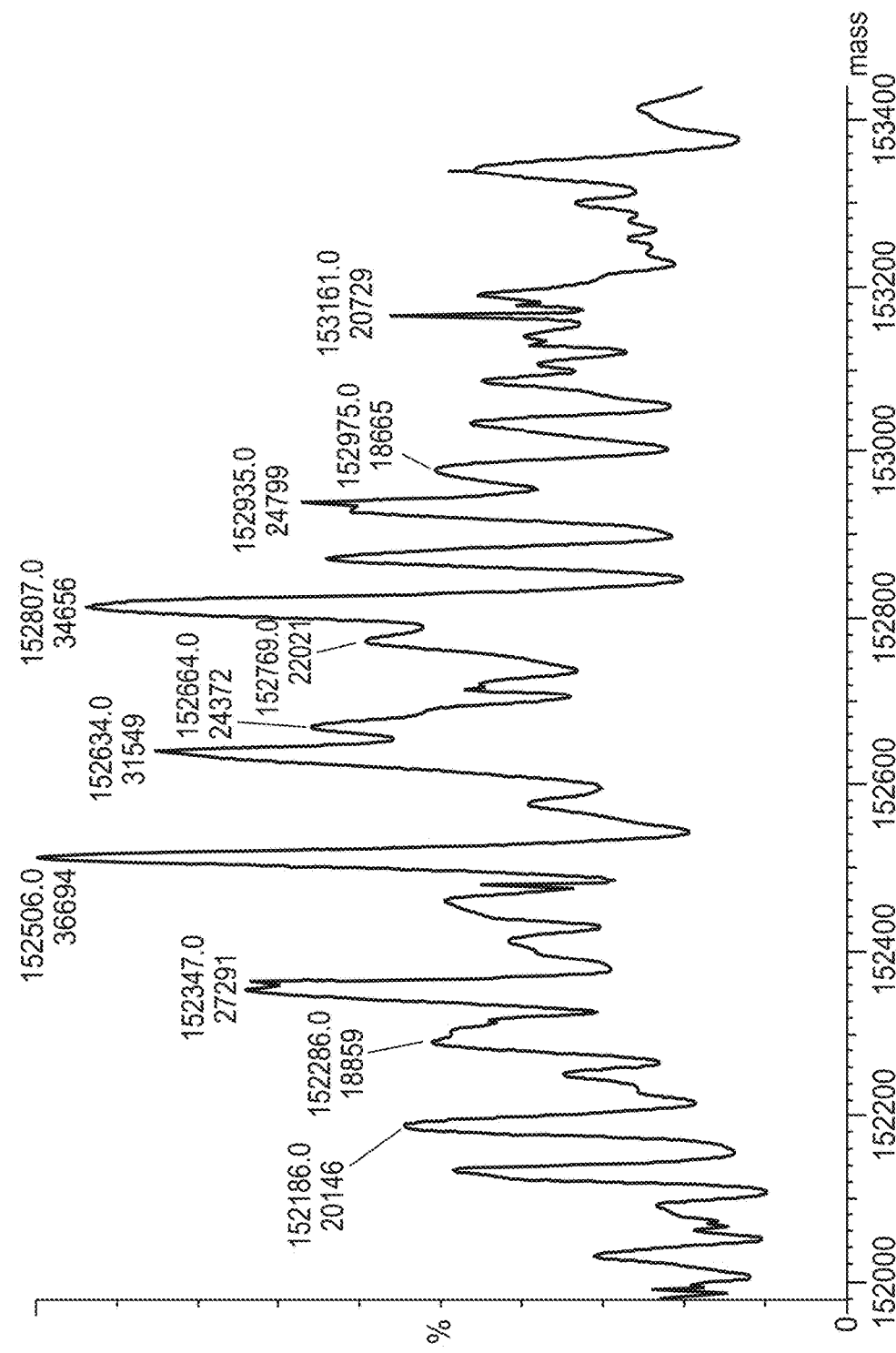

FIG. 72D shows a liquid chromatography-mass spectrometry analysis of unconjugated cetuximab (Imclone/Lilly) that was utilized to produce the cetuximab immunoconjugate according to the BB-01 conjugation method.

Figure 72E:
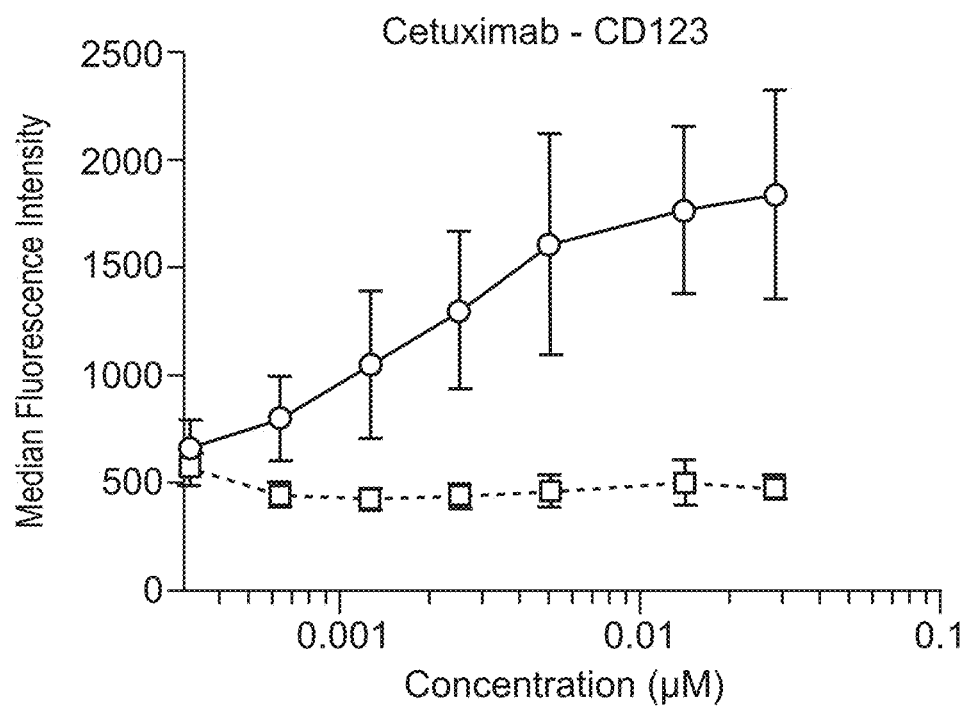

FIG. 72E shows that the cetuximab immunoconjugate produced according to the BB-01 method (closed circles, red) is superior at eliciting CD123 upregulation on myeloid cells as compared to the unconjugated cetuximab (closed squares, black; Imclone/Lilly) following 18 hours of stimulation.

Figure 72F:
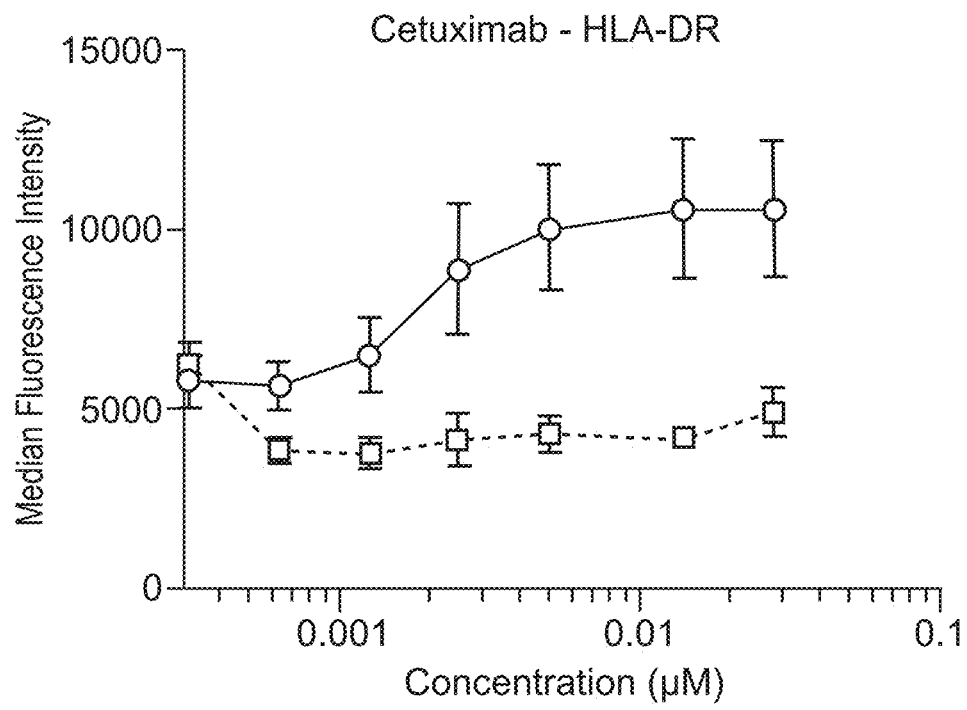

FIG. 72F shows that the cetuximab immunoconjugate produced according to the BB-01 method (closed circles, red) is superior at eliciting HLA-DR upregulation on myeloid cells as compared to the unconjugated cetuximab (closed squares, black; Imclone/Lilly) following 18 hours of stimulation.

Figure 72G:
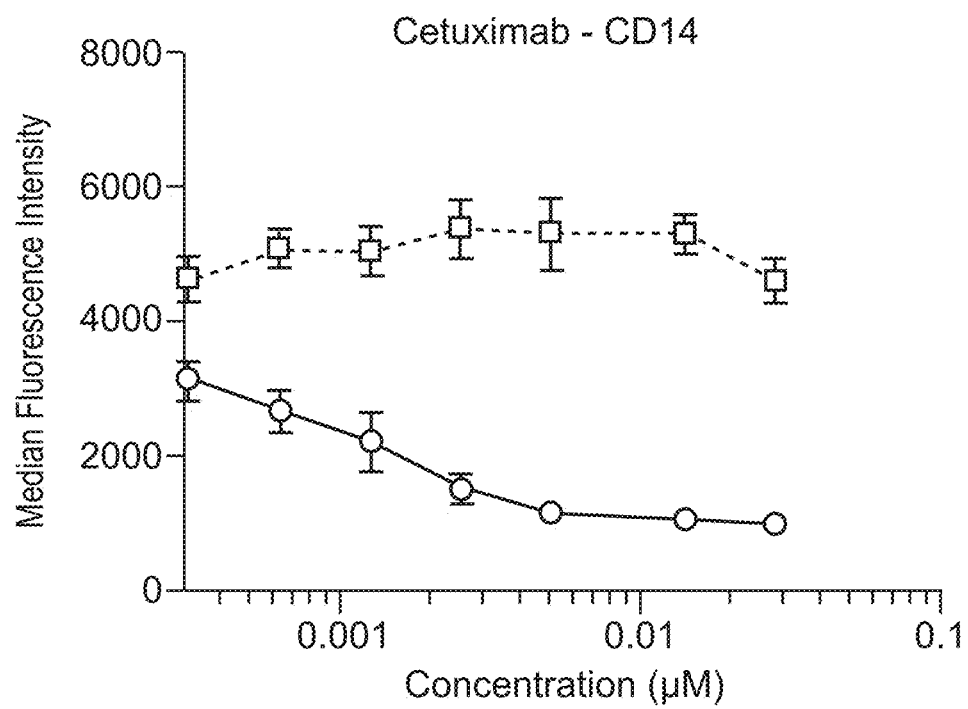

FIG. 72G shows that the cetuximab immunoconjugate produced according to the BB-01 method (closed circles, red) is superior at eliciting CD14 downregulation on myeloid cells as compared to the unconjugated cetuximab (closed squares, black; Imclone/Lilly) following 18 hours of stimulation.

Figure 72H:
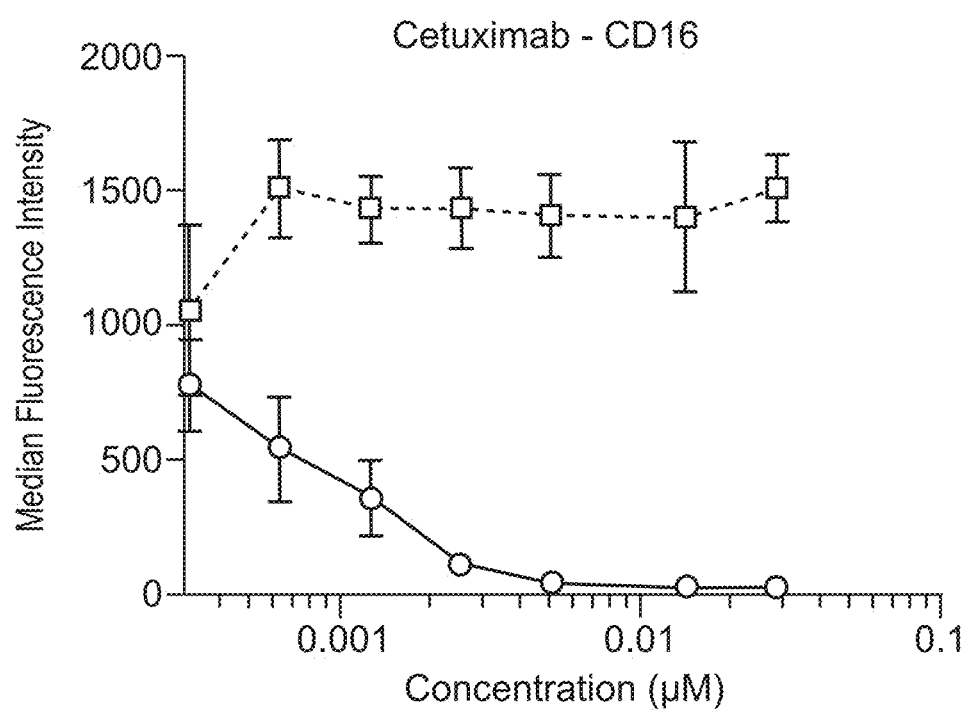

FIG. 72H shows that the cetuximab immunoconjugate produced according to the BB-01 method (closed circles, red) is superior at eliciting CD16 downregulation on myeloid cells as compared to the unconjugated cetuximab (closed squares, black; Imclone/Lilly) following 18 hours of stimulation.

Figure 72I:
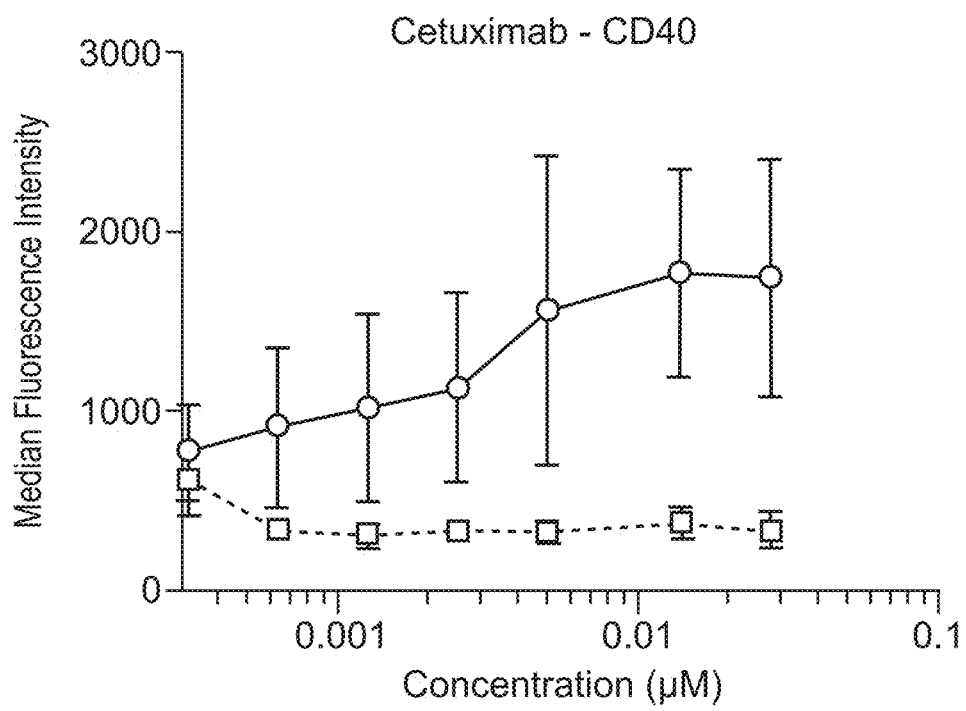

FIG. 72I shows that the cetuximab immunoconjugate produced according to the BB-01 method (closed circles, red) is superior at eliciting CD40 upregulation on myeloid cells as compared to the unconjugated cetuximab (closed squares, black; Imclone/Lilly) following 18 hours of stimulation.

Figure 72J:
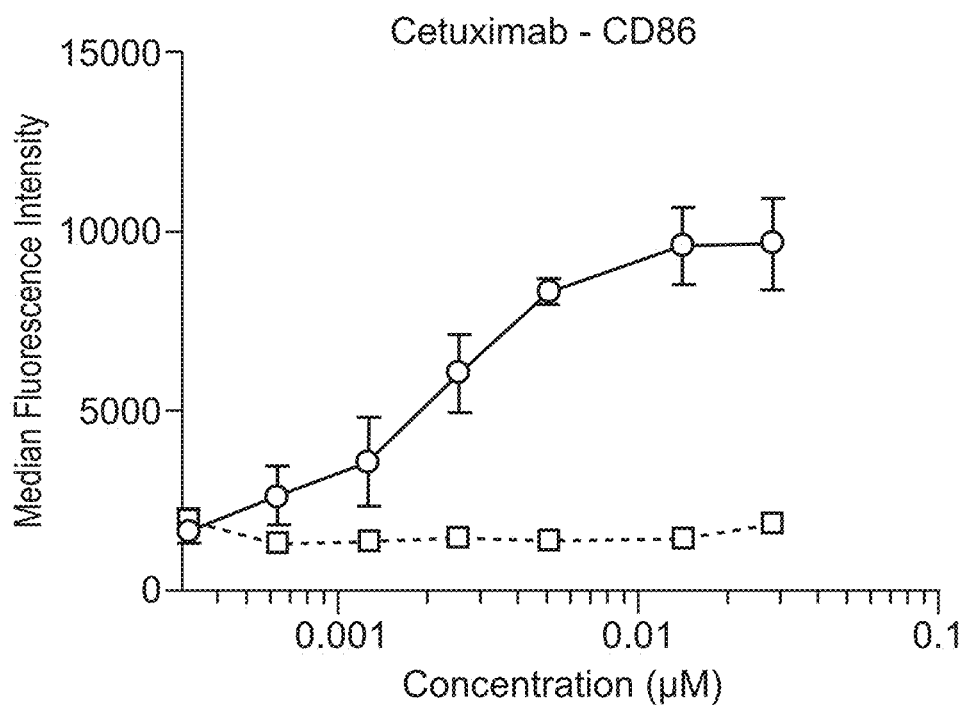

FIG. 72J shows that the cetuximab immunoconjugate produced according to the BB-01 method (closed circles, red) is superior at eliciting CD86 upregulation on myeloid cells as compared to the unconjugated cetuximab (closed squares, black; Imclone/Lilly) following 18 hours of stimulation.

Figure 73A:
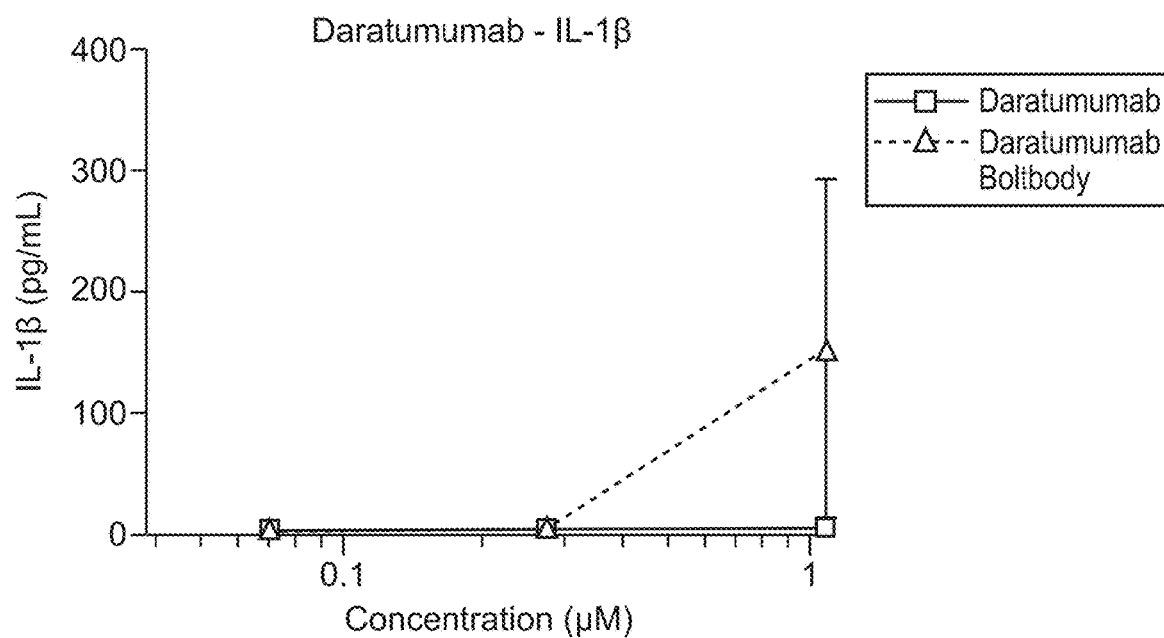

FIG. 73A shows that the daratumumab immunoconjugate produced according to the BB-01 method (Daratumumab Boltbody) elicits superior IL-11 secretion from myeloid cells as compared to equimolar concentrations of unconjugated daratumumab (Genmab/Janssen Biotech) following 18 hours of stimulation.

Figure 73B:
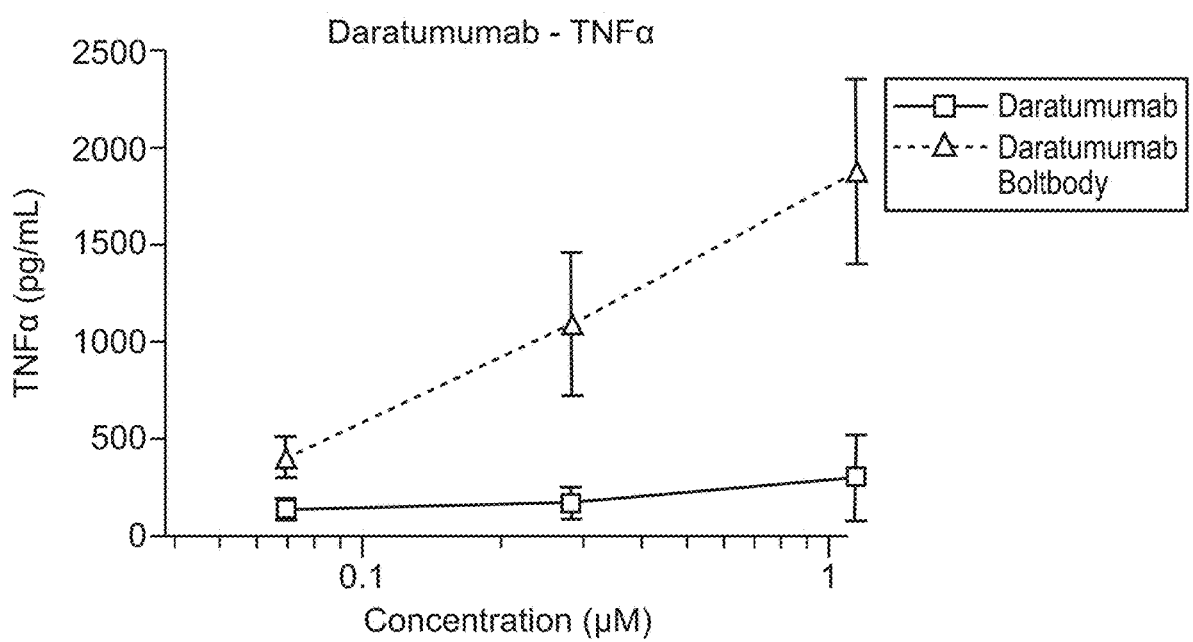

FIG. 73B shows that the daratumumab immunoconjugate produced according to the BB-01 method (Daratumumab Boltbody) elicits superior TNFα secretion from myeloid cells as compared to equimolar concentrations of unconjugated daratumumab (Genmab/Janssen Biotech) following 18 hours of stimulation.

Figure 73C:
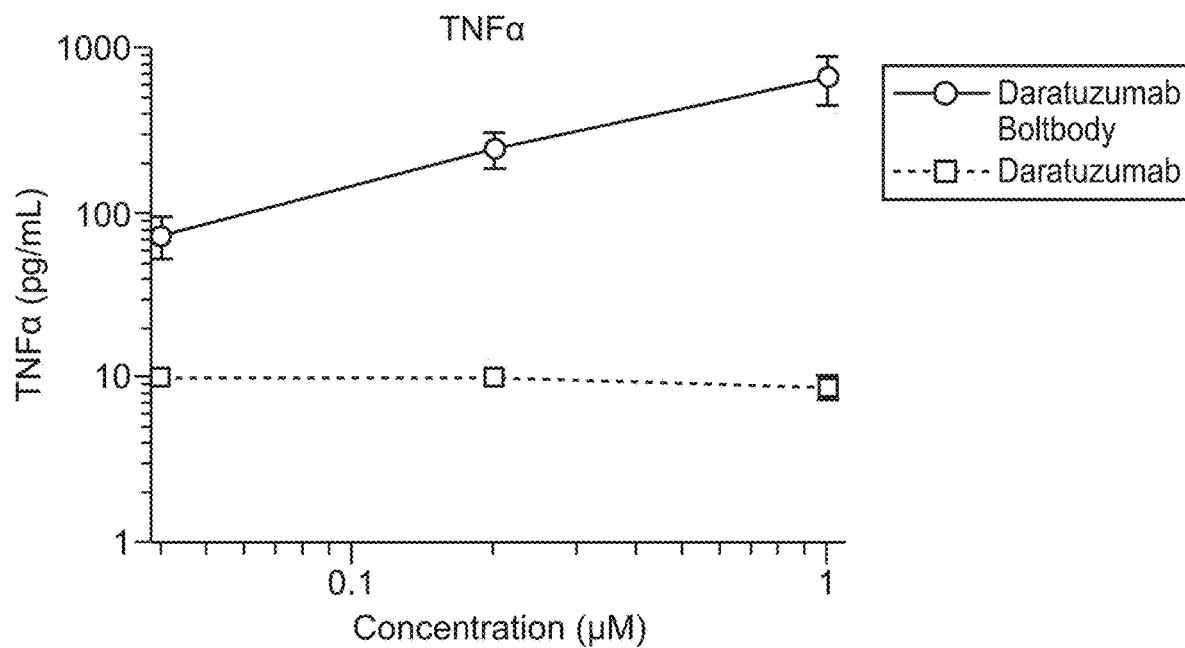

FIG. 73C shows that the daratumumab immunoconjugate produced according to the BB-01 method (Daratuzumab [sic] Boltbody) elicits superior TNFα secretion from myeloid cells as compared to equimolar concentrations of unconjugated daratumumab (Daratuzumab [sic], Genmab/Janssen Biotech) following 36 hours of stimulation.

Figure 73D:
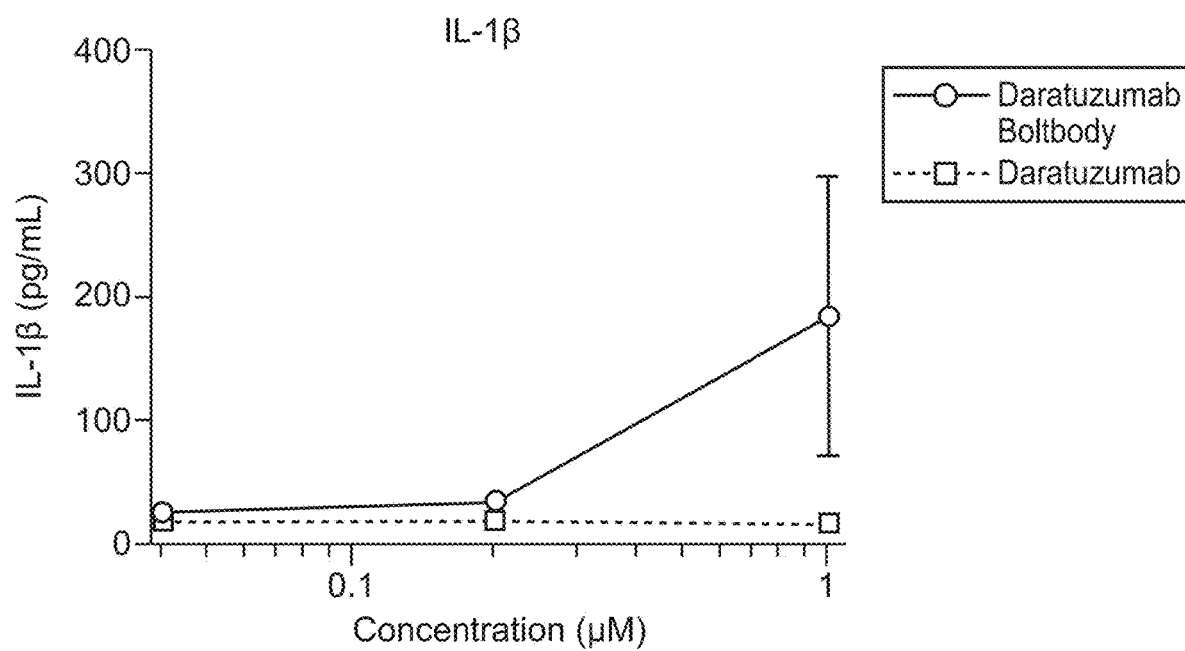

FIG. 73D shows that the daratumumab immunoconjugate produced according to the BB-01 method (Daratuzumab [sic] Boltbody) elicits superior IL-11 secretion from myeloid cells as compared to equimolar concentrations of unconjugated daratumumab (Daratuzumab [sic], Genmab/Janssen Biotech) following 36 hours of stimulation.

Figure 73E:
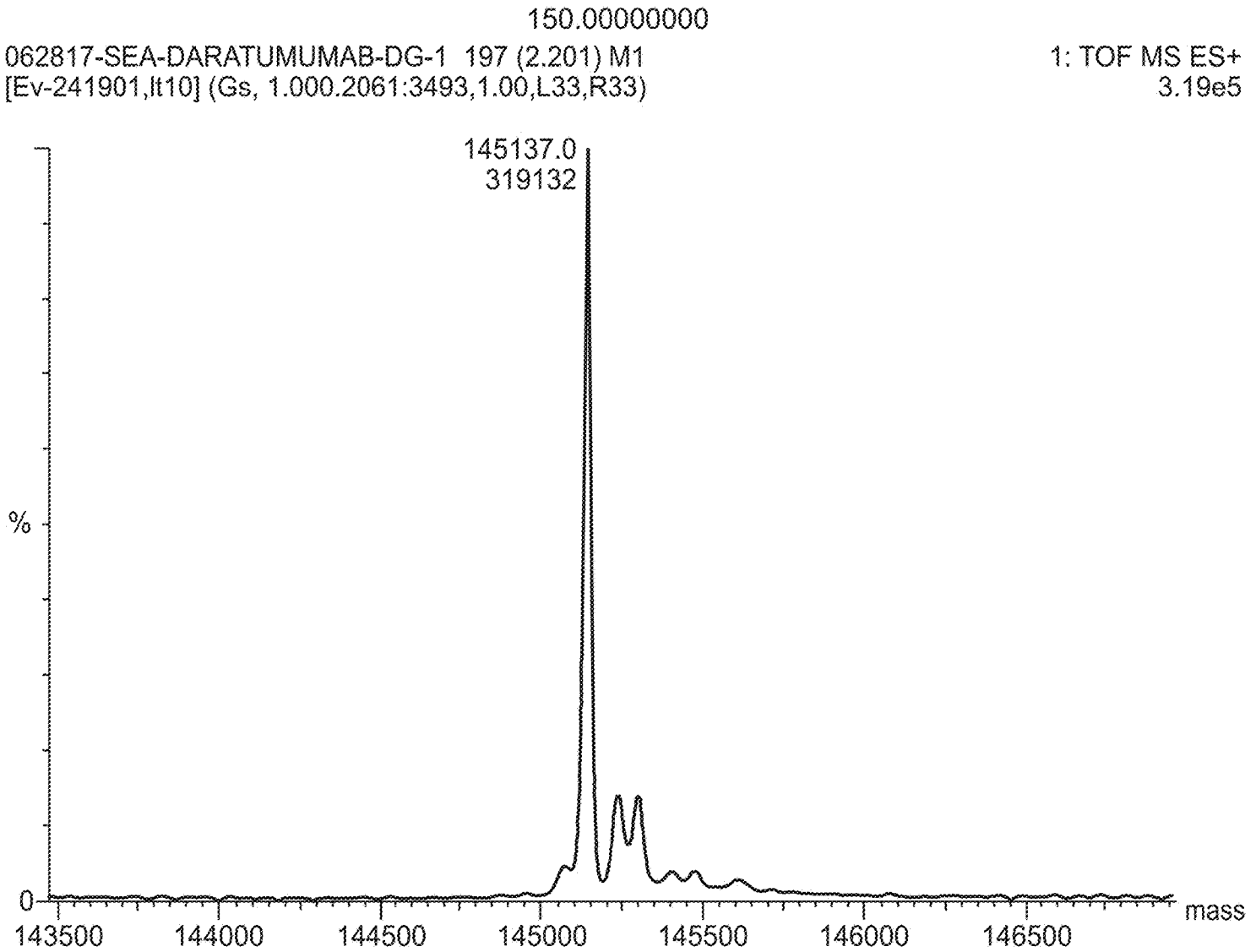

FIG. 73E shows a liquid chromatography-mass spectrometry analysis of unconjugated daratumumab (Genmab/Janssen Biotech) that was utilized to produce the daratumumab immunoconjugate according to the BB-01 method following overnight deglycosylation with PNGase F.

Figure 73F:
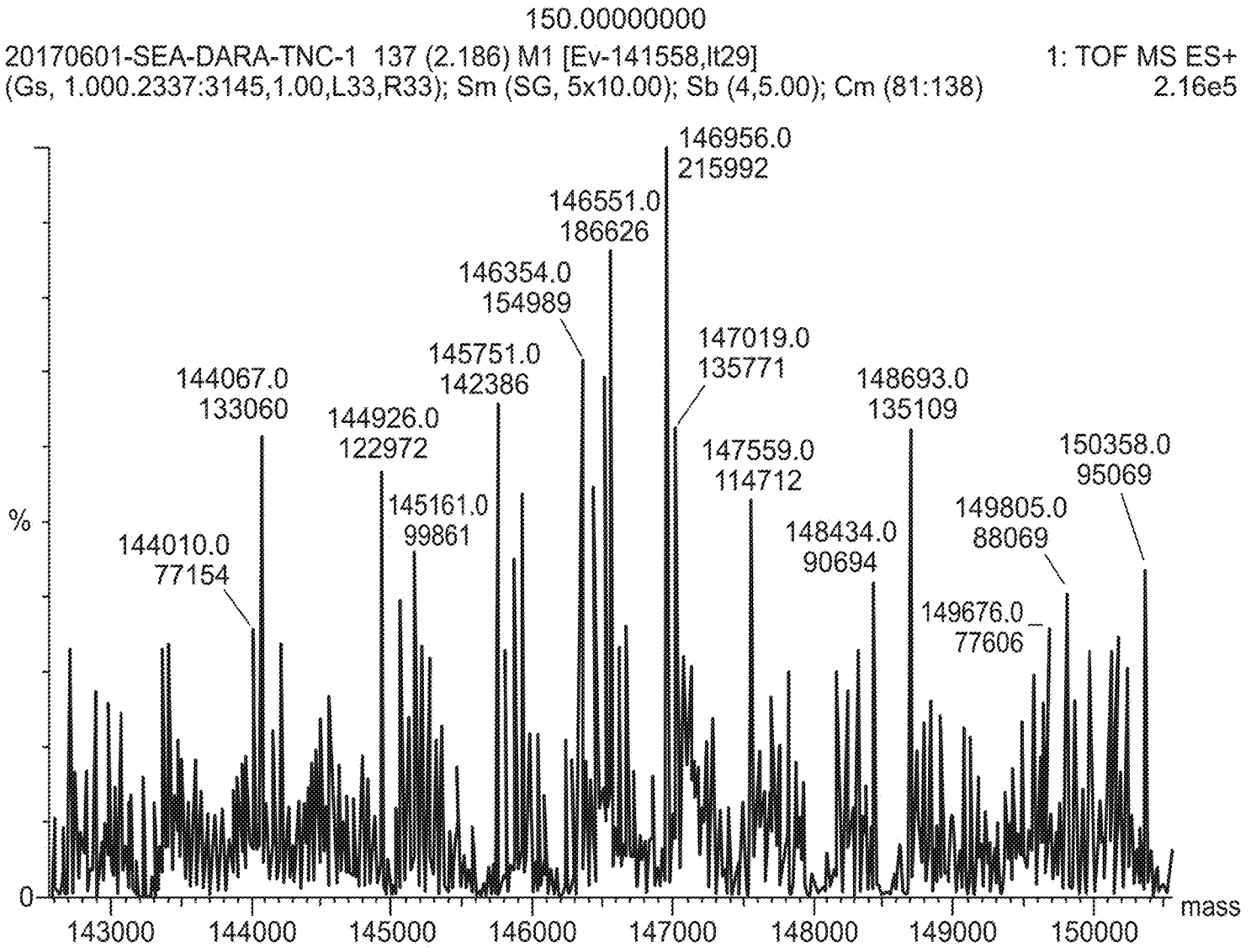

FIG. 73F shows a liquid chromatography-mass spectrometry analysis of the daratumumab immunoconjugate produced according to the BB-01 method following overnight deglycosylation with PNGase F.

FIG. 73G shows a liquid chromatography-mass spectrometry analysis of unconjugated daratumumab (Genmab/Janssen Biotech) that was utilized to produce the daratumumab immunoconjugate according to the BB-01 method.

Figure 73H:
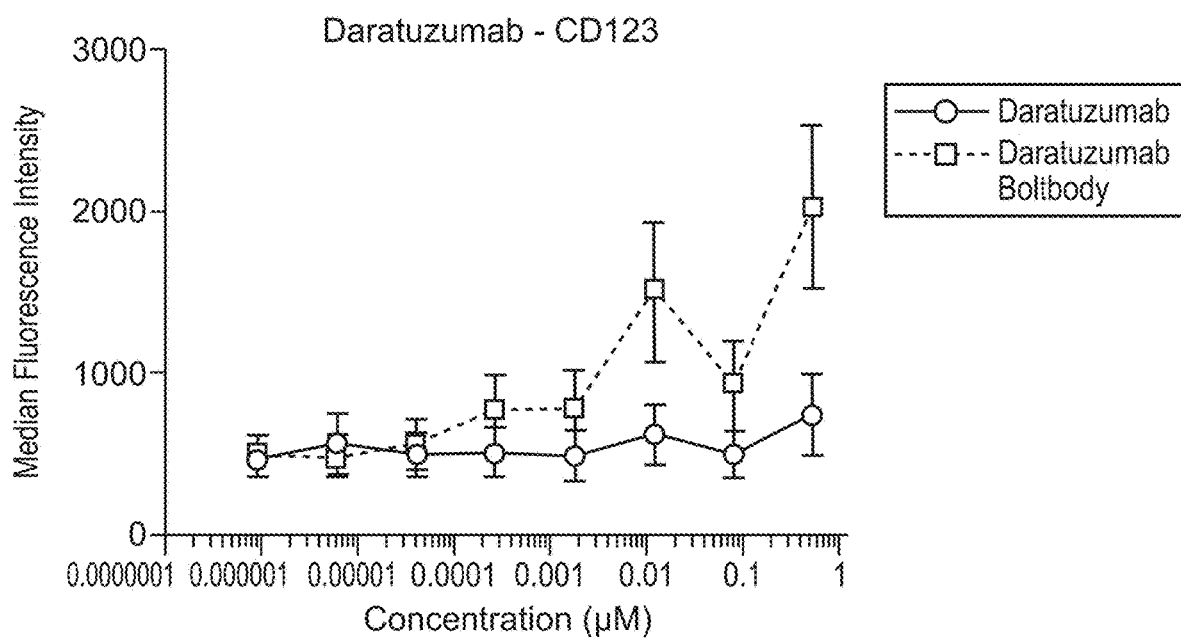

FIG. 73H shows that the daratumumab immunoconjugate produced according to the BB-01 method (Daratuzumab [sic] Boltbody) is superior at eliciting CD123 upregulation on myeloid cells as compared to the unconjugated daratumumab (Daratuzumab [sic], Genmab/Janssen Biotech) following 18 hours of stimulation.

Figure 73I:
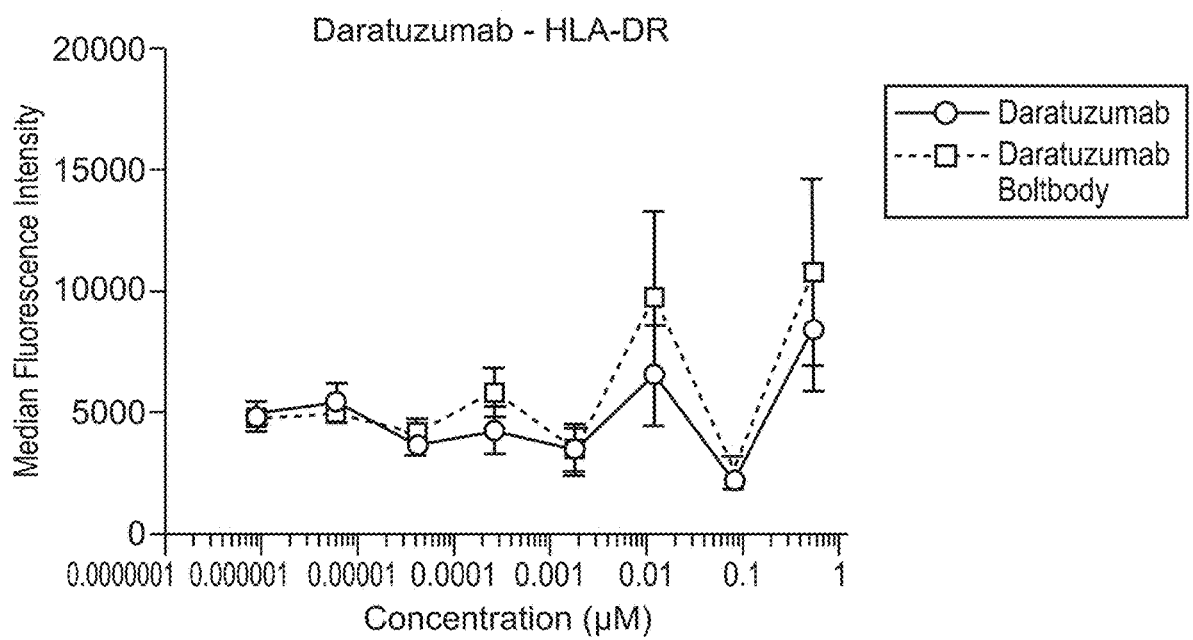

FIG. 73I shows HLA-DR expression on myeloid cells following 18 hours of stimulation with the daratumumab immunoconjugate produced according to the BB-01 method (Daratumumab Boltbody) as compared to unconjugated daratumumab (Genmab/Janssen Biotech).

Figure 73J:
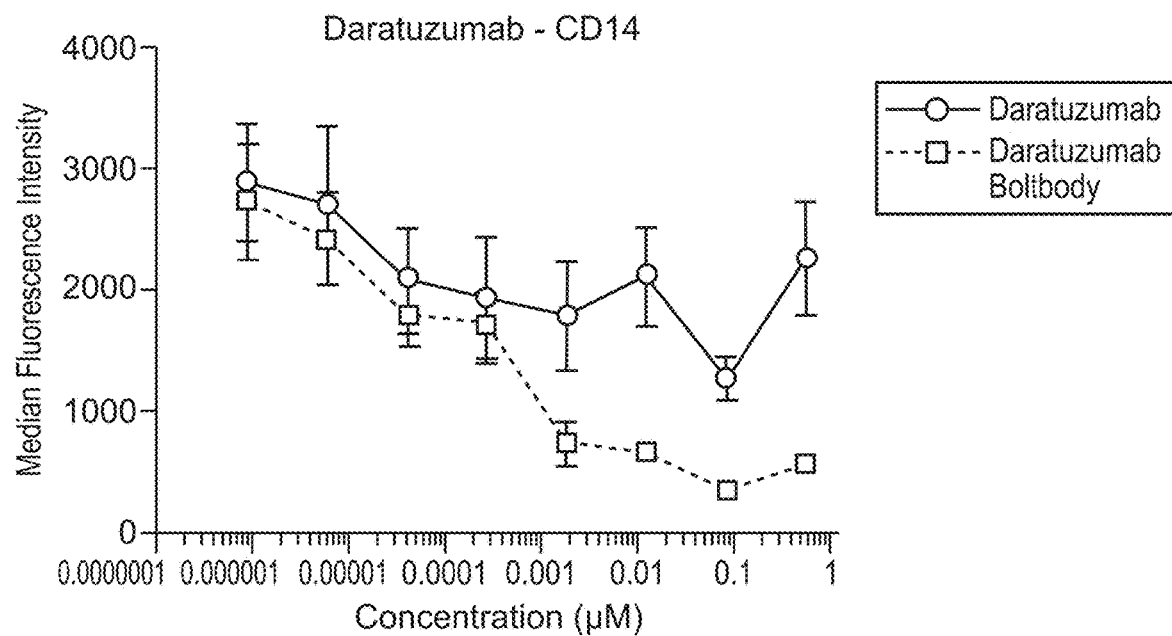

FIG. 73J shows that the daratumumab immunoconjugate produced according to the BB-01 method (Daratuzumab [sic] Boltbody) is superior at eliciting CD14 downregulation on myeloid cells as compared to the unconjugated daratumumab (Daratuzumab [sic], Genmab/Janssen Biotech) following 18 hours of stimulation.

Figure 73K:
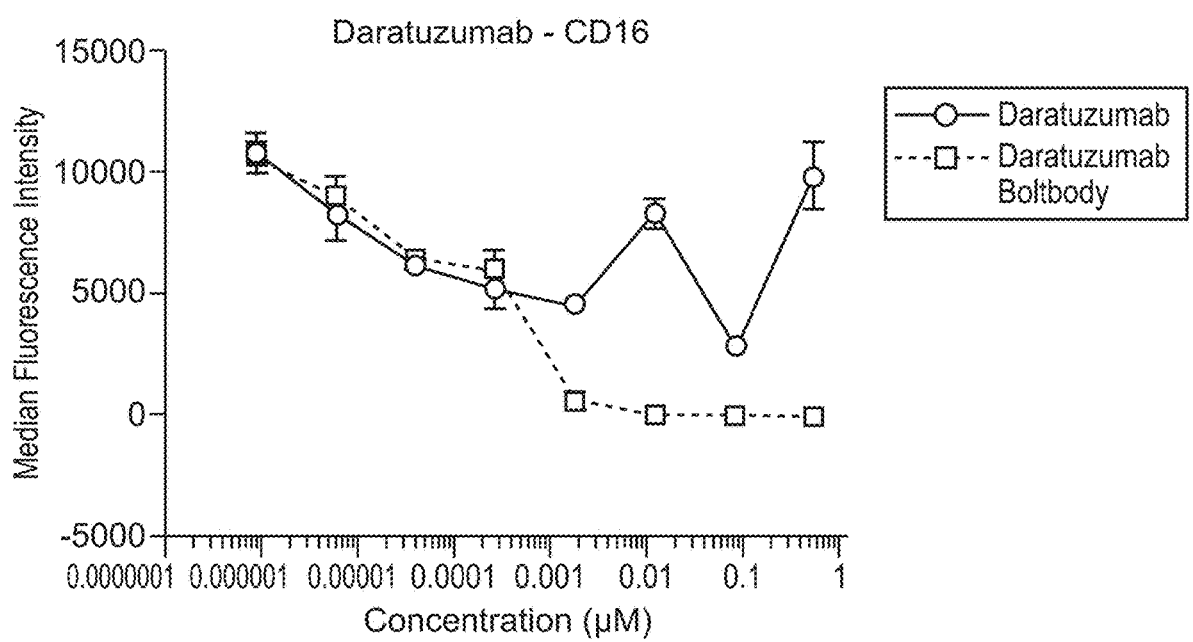

FIG. 73K shows that the daratumumab immunoconjugate produced according to the BB-01 method (Daratuzumab [sic] Boltbody) is superior at eliciting CD16 downregulation on myeloid cells as compared to the unconjugated daratumumab (Daratuzumab [sic], Genmab/Janssen Biotech) following 18 hours of stimulation.

Figure 73L:
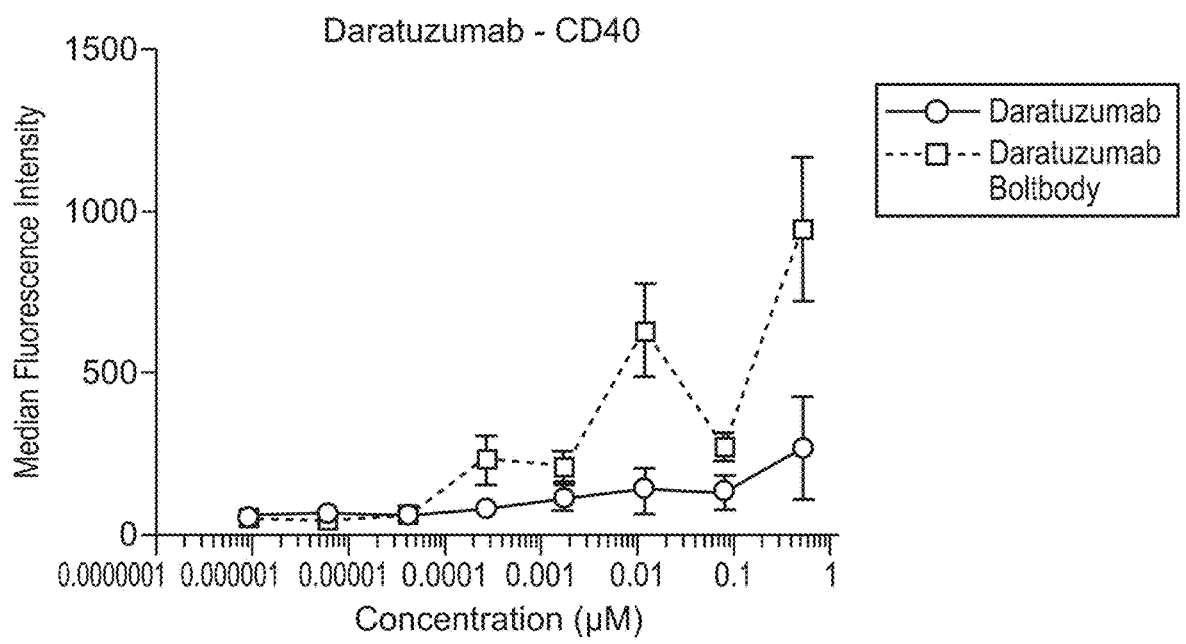

FIG. 73L shows that the daratumumab immunoconjugate produced according to the BB-01 method (Daratuzumab [sic] Boltbody) is superior at eliciting CD40 upregulation on myeloid cells as compared to the unconjugated daratumumab (Daratuzumab [sic], Genmab/Janssen Biotech) following 18 hours of stimulation.

Figure 73M:
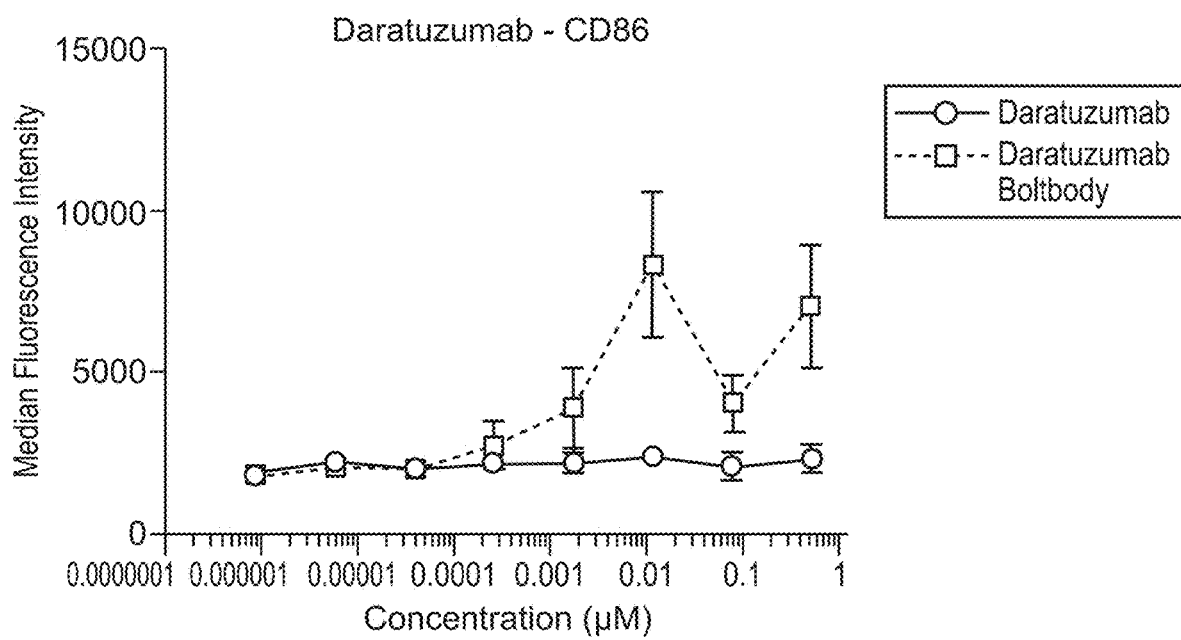

FIG. 73M shows that the daratumumab immunoconjugate produced according to the BB-01 method (Daratuzumab [sic] Boltbody) is superior at eliciting CD86 upregulation on myeloid cells as compared to the unconjugated daratumumab (Daratuzumab [sic], Genmab/Janssen Biotech) following 18 hours of stimulation.

Figure 74A:
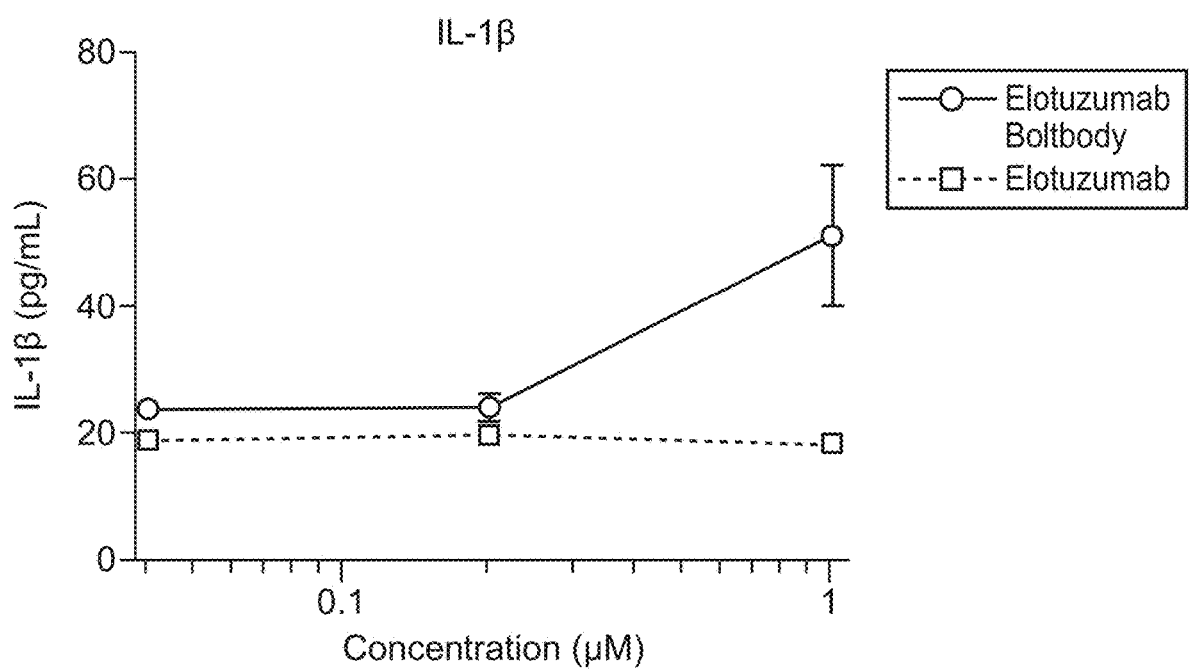

FIG. 74A shows that the elotuzumab immunoconjugate produced according to the BB-01 method (Elotuzumab Boltbody) elicits superior IL-1β secretion from myeloid cells as compared to equimolar concentrations of unconjugated elotuzumab (BMS) following 36 hours of stimulation.

Figure 74B:
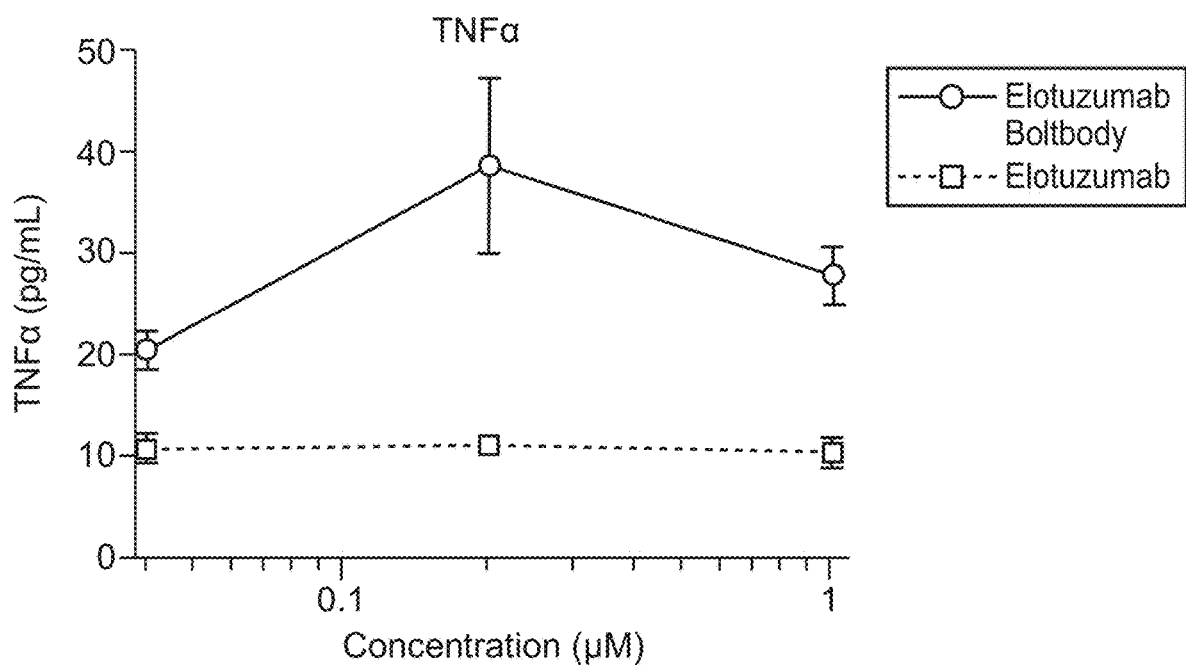

FIG. 74B shows that the elotuzumab immunoconjugate produced according to the BB-01 method (Elotuzumab Boltbody) elicits superior TNFα secretion from myeloid cells as compared to equimolar concentrations of unconjugated elotuzumab (BMS) following 36 hours of stimulation.

Figure 74C:
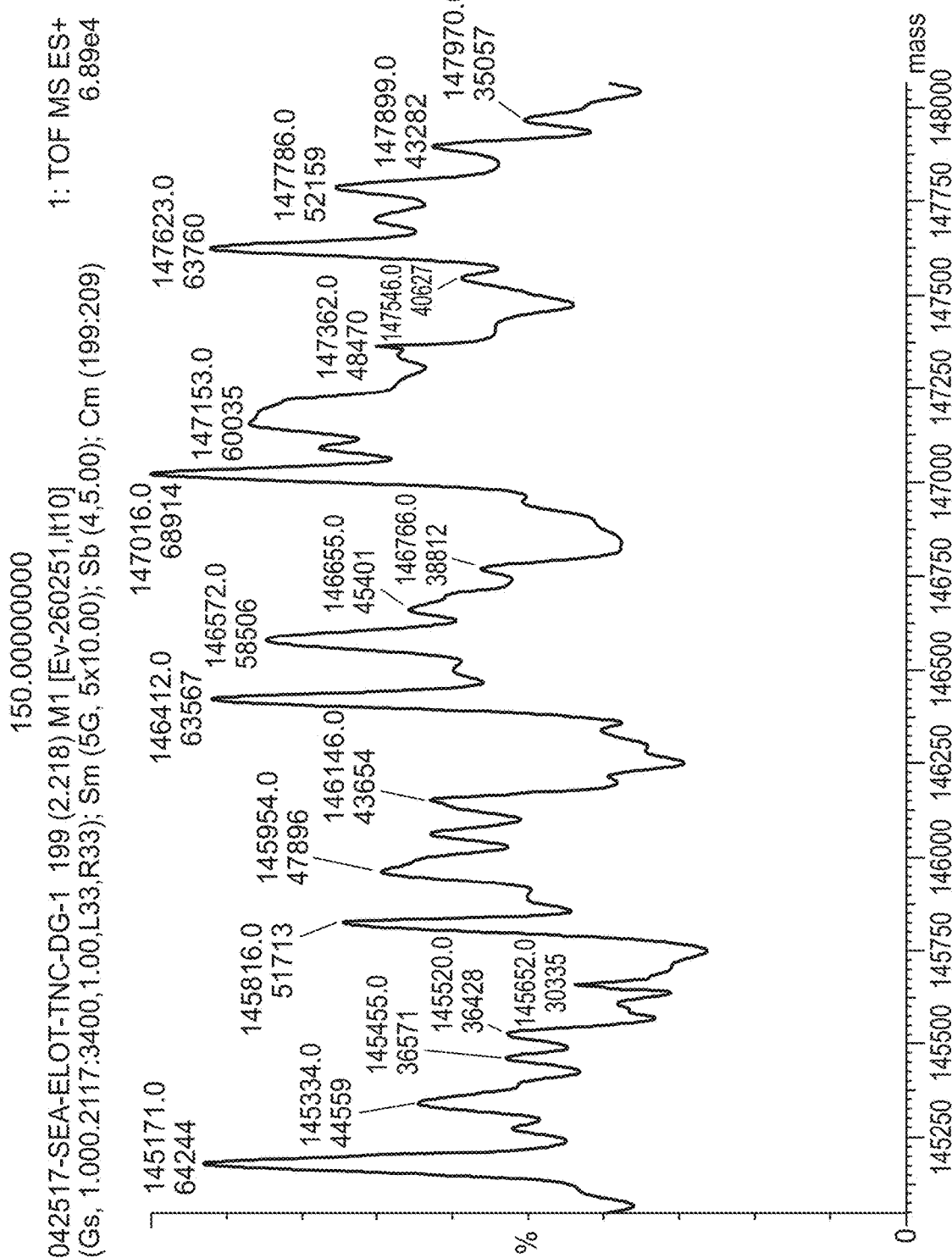

FIG. 74C shows a liquid chromatography-mass spectrometry analysis of the elotuzumab immunoconjugate produced according to the BB-01 conjugation method following overnight deglycosylation with PNGase F.

FIG. 74D shows a liquid chromatography-mass spectrometry analysis of unconjugated elotuzumab (BMS) that was utilized to produce the elotuzumab immunoconjugate according to the BB-01 conjugation method following overnight deglycosylation with PNGase F.

Figure 74E:
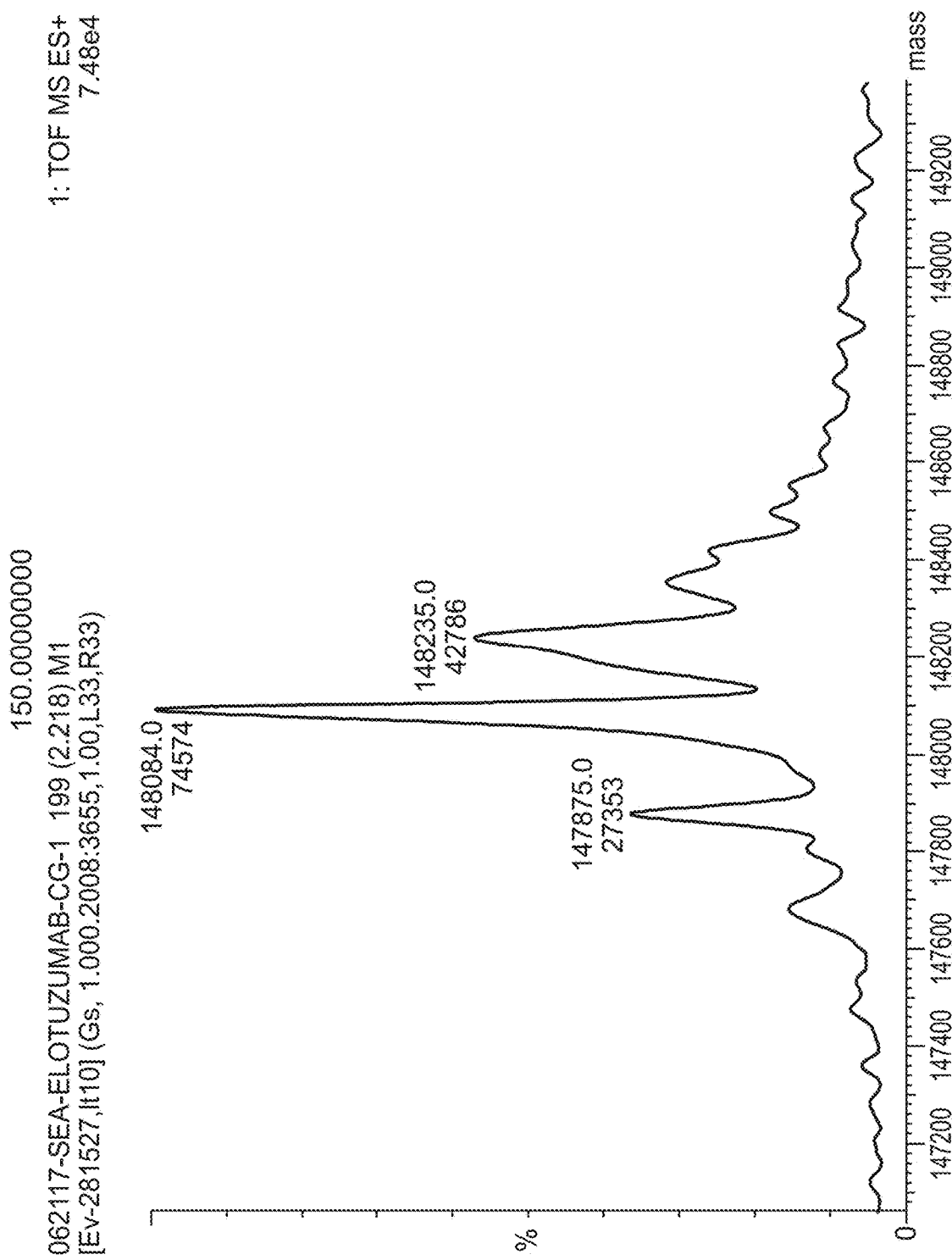

FIG. 74E shows a liquid chromatography-mass spectrometry analysis of unconjugated elotuzumab (BMS) that was utilized to produce the elotuzumab immunoconjugate according to the BB-01 method.

Figure 74F:
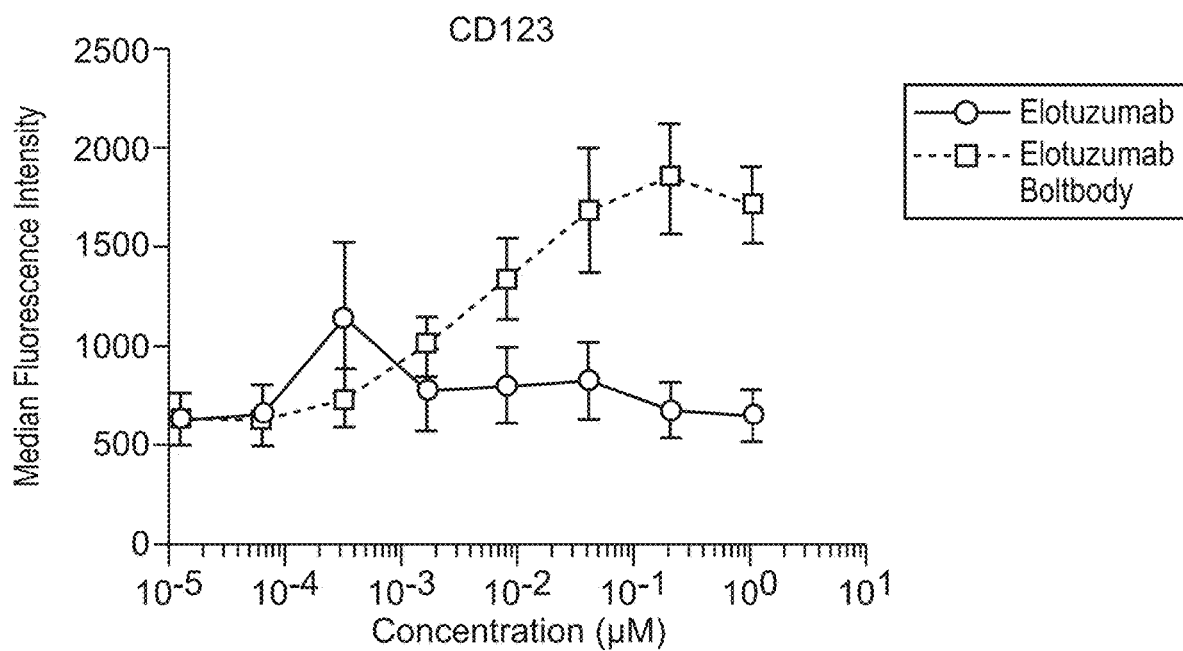

FIG. 74F shows that the elotuzumab immunoconjugate produced according to the BB-01 method (Elotuzumab Boltbody) is superior at eliciting CD123 upregulation on myeloid cells as compared to the unconjugated elotuzumab (BMS) following 18 hours of stimulation.

Figure 74G:
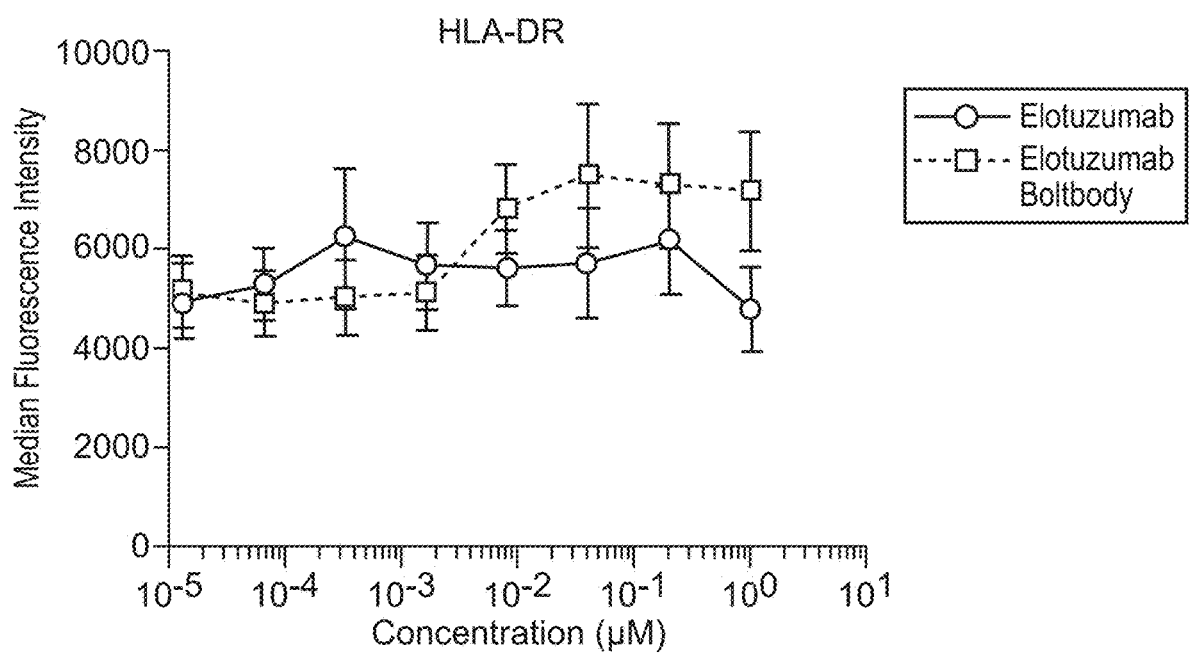

FIG. 74G shows that the elotuzumab immunoconjugate produced according to the BB-01 method (Elotuzumab Boltbody) is superior at eliciting HLA-DR upregulation on myeloid cells as compared to the unconjugated elotuzumab (BMS) following 18 hours of stimulation.

Figure 74H:
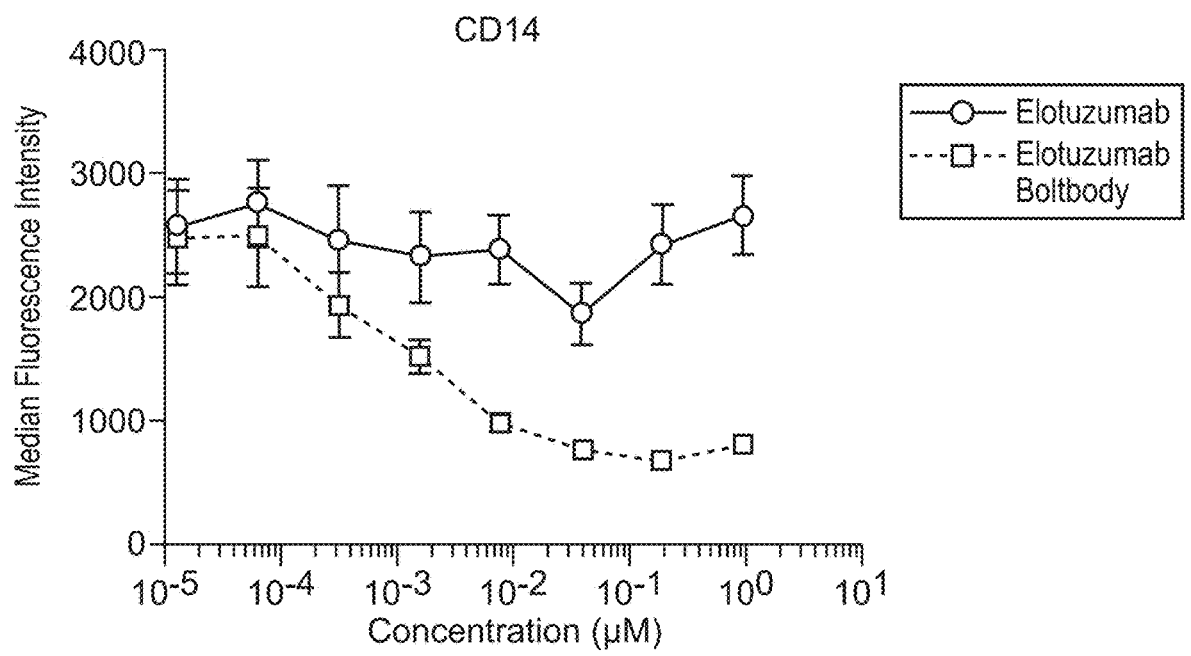

FIG. 74H shows that the elotuzumab immunoconjugate produced according to the BB-01 method (Elotuzumab Boltbody) is superior at eliciting CD14 downregulation on myeloid cells as compared to the unconjugated elotuzumab (BMS) following 18 hours of stimulation.

Figure 74I:
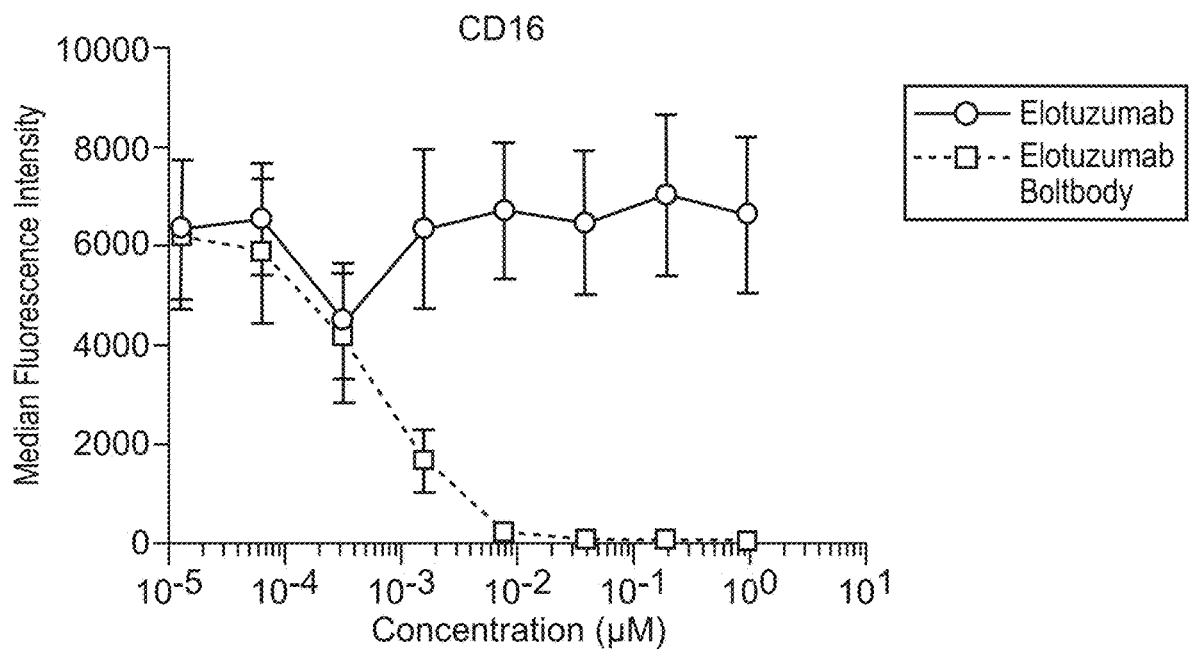

FIG. 74I shows that the elotuzumab immunoconjugate produced according to the BB-01 method (Elotuzumab Boltbody) is superior at eliciting CD16 downregulation on myeloid cells as compared to the unconjugated elotuzumab (BMS) following 18 hours of stimulation.

Figure 74J:
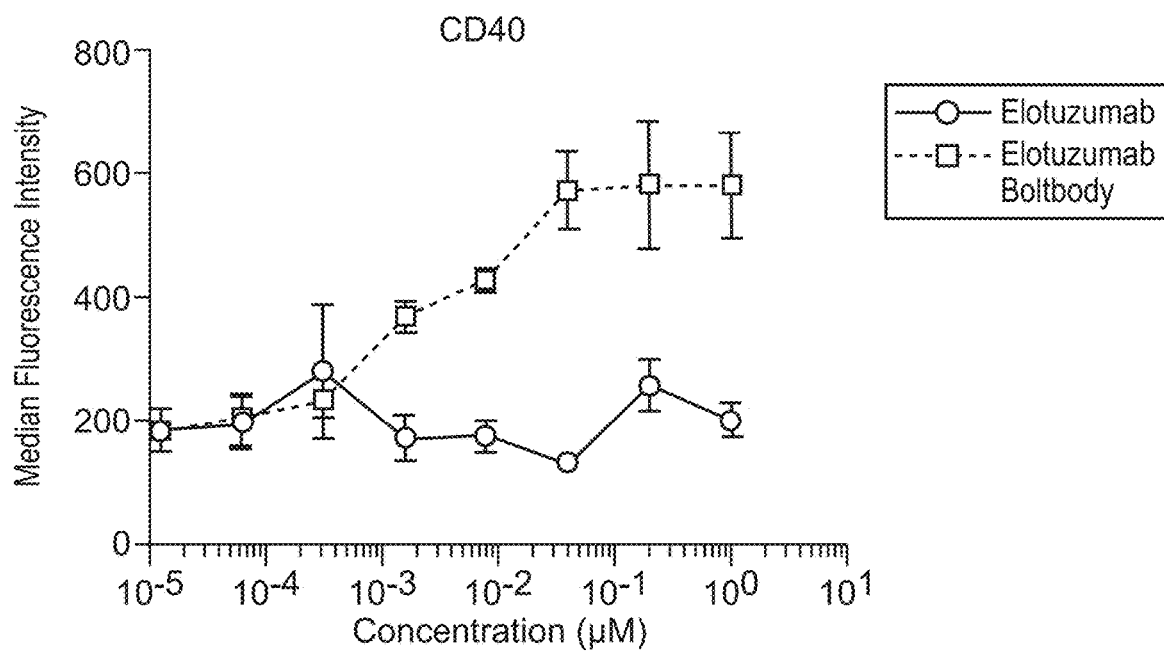

FIG. 74J shows that the elotuzumab immunoconjugate produced according to the BB-01 method (Elotuzumab Boltbody) is superior at eliciting CD40 upregulation on myeloid cells as compared to the unconjugated elotuzumab (BMS) following 18 hours of stimulation.

Figure 74K:
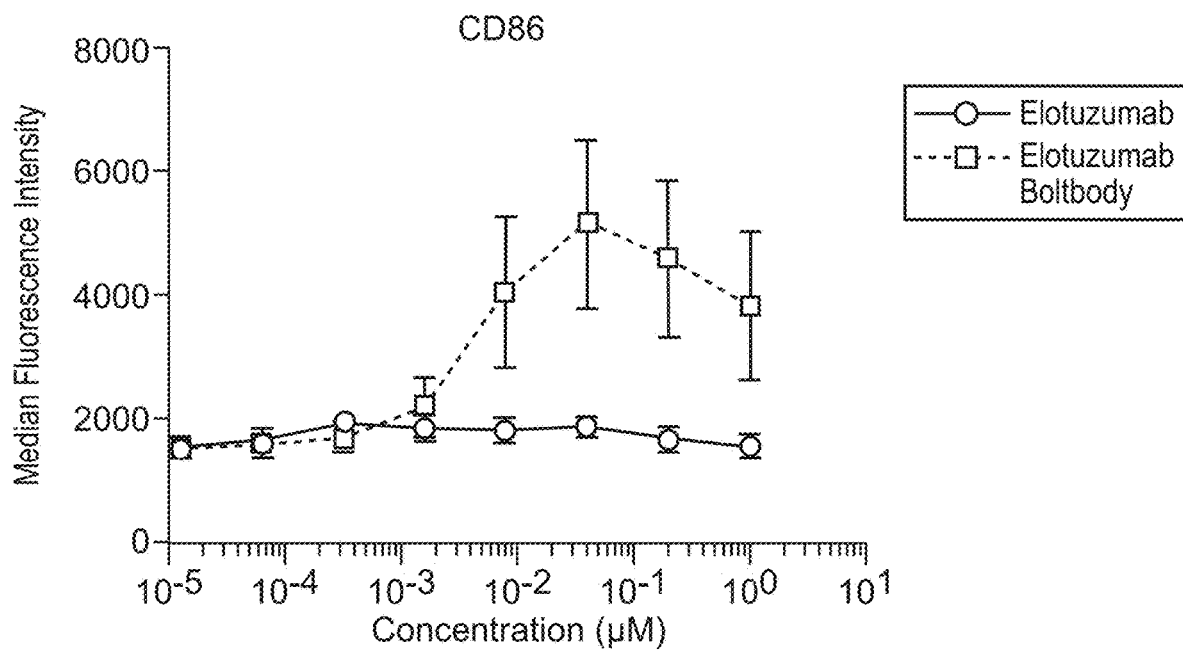

FIG. 74K shows that the elotuzumab immunoconjugate produced according to the BB-01 method (Elotuzumab Boltbody) is superior at eliciting CD86 upregulation on myeloid cells as compared to the unconjugated elotuzumab (BMS) following 18 hours of stimulation.

Figure 75A:
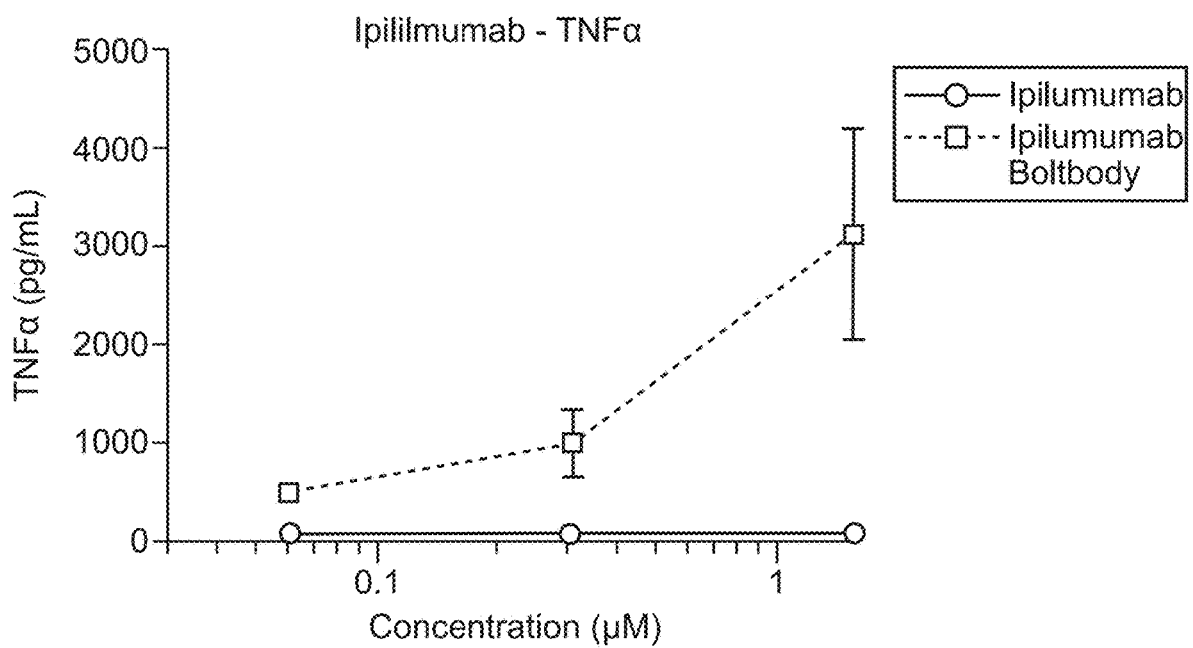

FIG. 75A shows that the ipilimumab immunoconjugate produced according to the BB-01 method (Ipilimumab Boltbody) elicits superior TNFα secretion from myeloid cells as compared to equimolar concentrations of unconjugated ipilimumab (BMS) following 36 hours of stimulation.

Figure 75B:
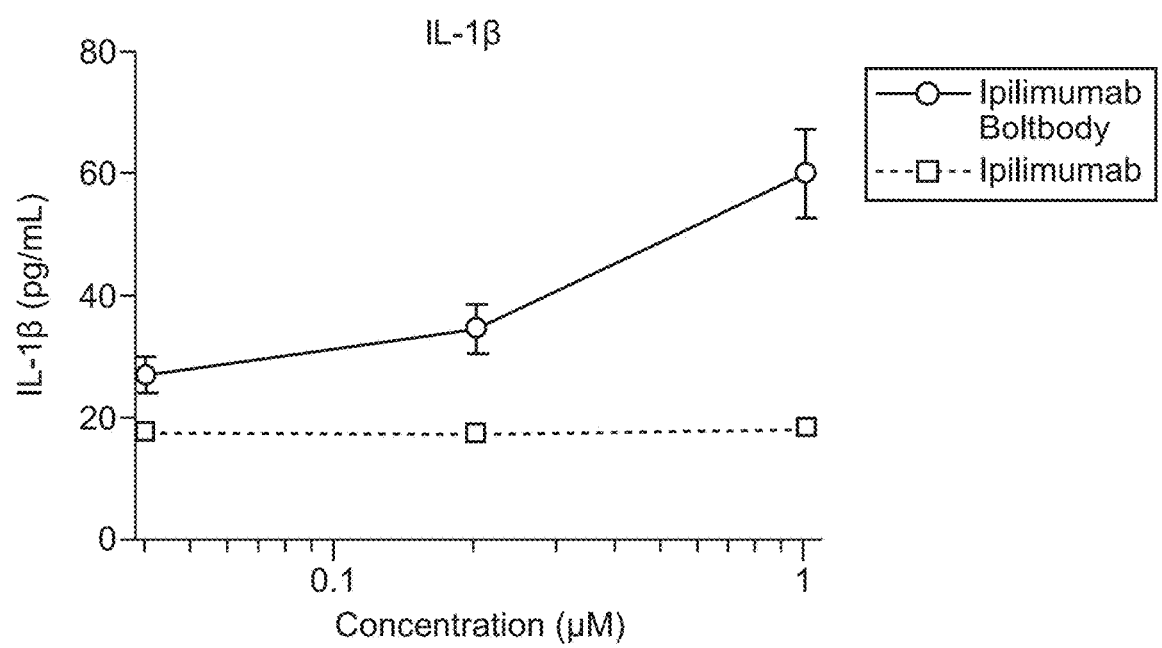

FIG. 75B shows that the ipilimumab immunoconjugate produced according to the BB-01 method (Ipilimumab Boltbody) elicits superior IL-1β secretion from myeloid cells as compared to equimolar concentrations of unconjugated ipilimumab (BMS) following 18 hours of stimulation.

Figure 75C:
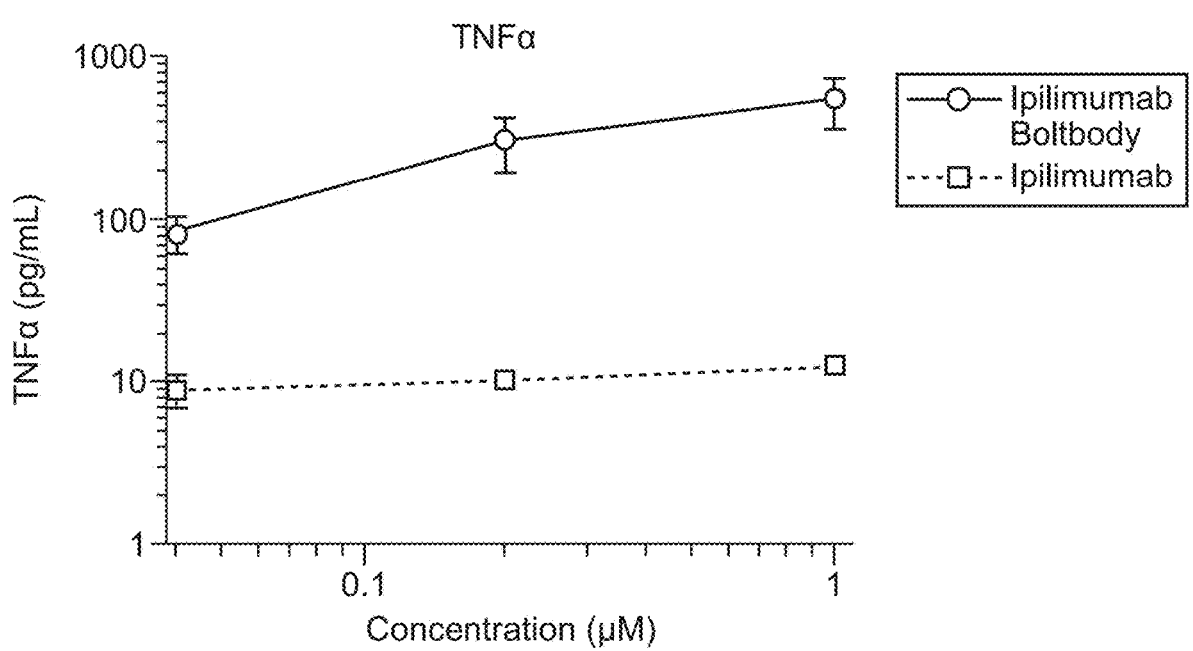

FIG. 75C shows that the ipilimumab immunoconjugate produced according to the BB-01 method (Ipilimumab Boltbody) elicits superior TNFα secretion from myeloid cells as compared to equimolar concentrations of unconjugated ipilimumab (BMS) following 18 hours of stimulation.

Figure 75D:
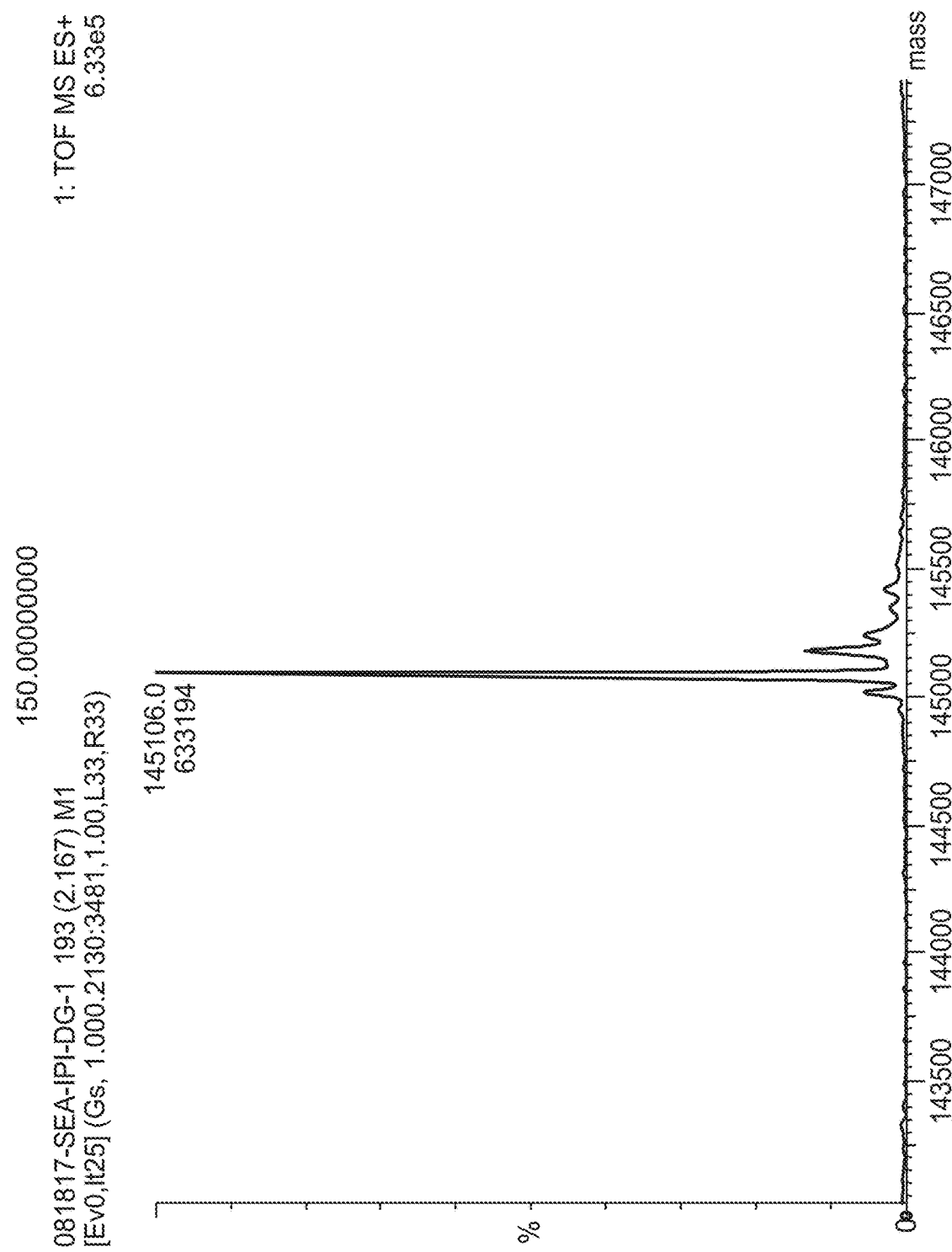

FIG. 75D shows a liquid chromatography-mass spectrometry analysis of unconjugated ipilimumab (BMS) that was utilized to produce the ipilimumab immunoconjugate according to the BB-01 conjugation method following overnight deglycosylation with PNGase F.

Figure 75E:
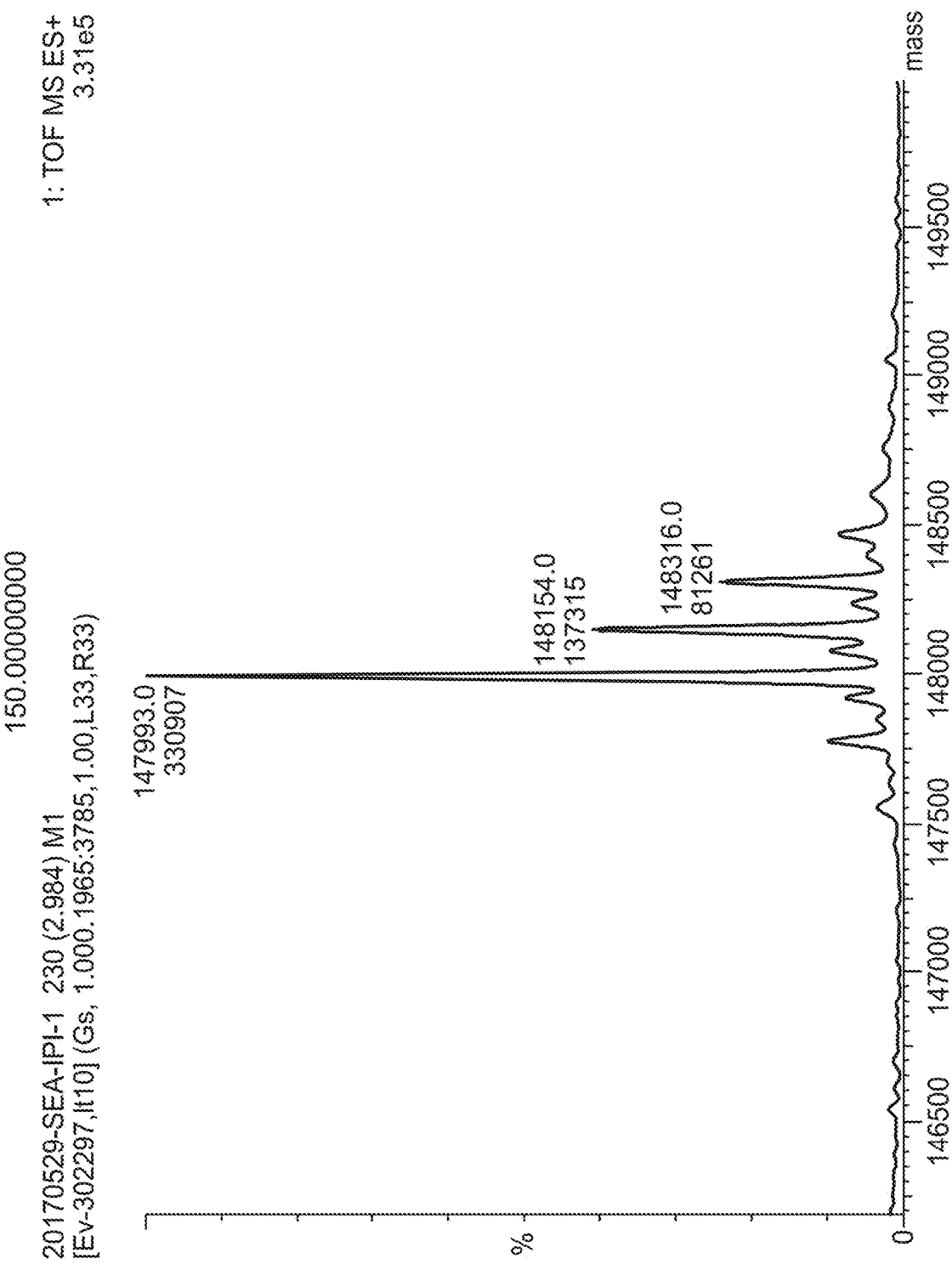

FIG. 75E shows a liquid chromatography-mass spectrometry analysis of unconjugated ipilimumab (BMS) that was utilized to produce the ipilimumab immunoconjugate according to the BB-01 method.

Figure 75F:
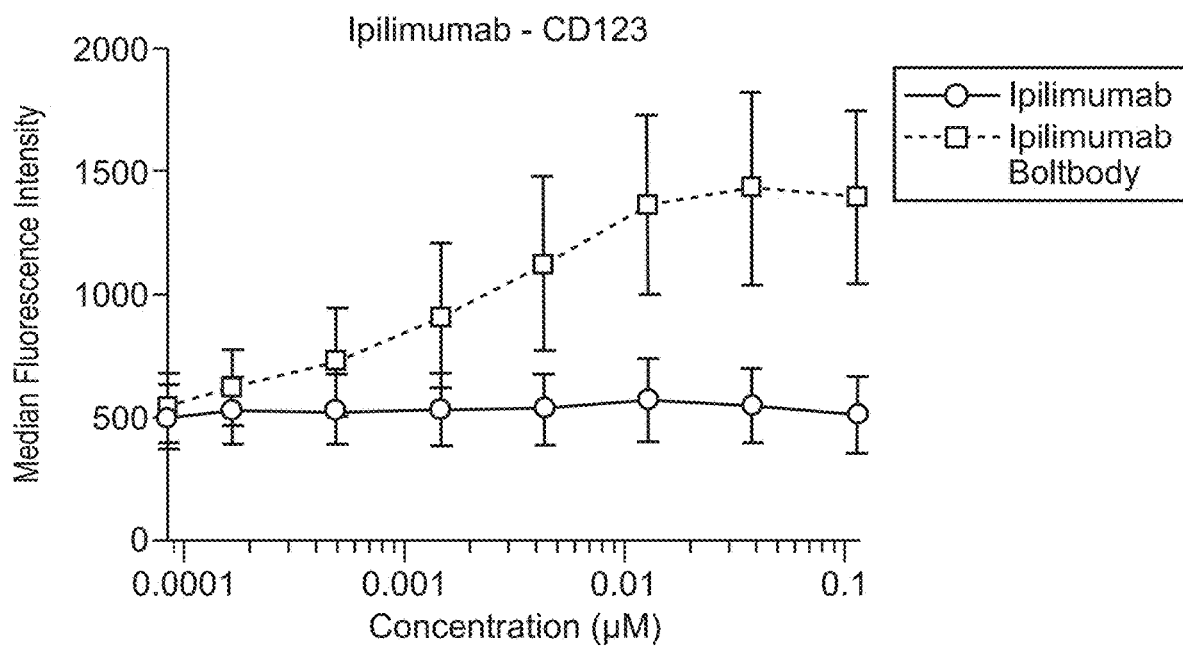

FIG. 75F shows that the ipilimumab immunoconjugate produced according to the BB-01 method (Ipilimumab Boltbody) is superior at eliciting CD123 upregulation on myeloid cells as compared to the unconjugated ipilimumab (BMS) following 18 hours of stimulation.

Figure 75G:
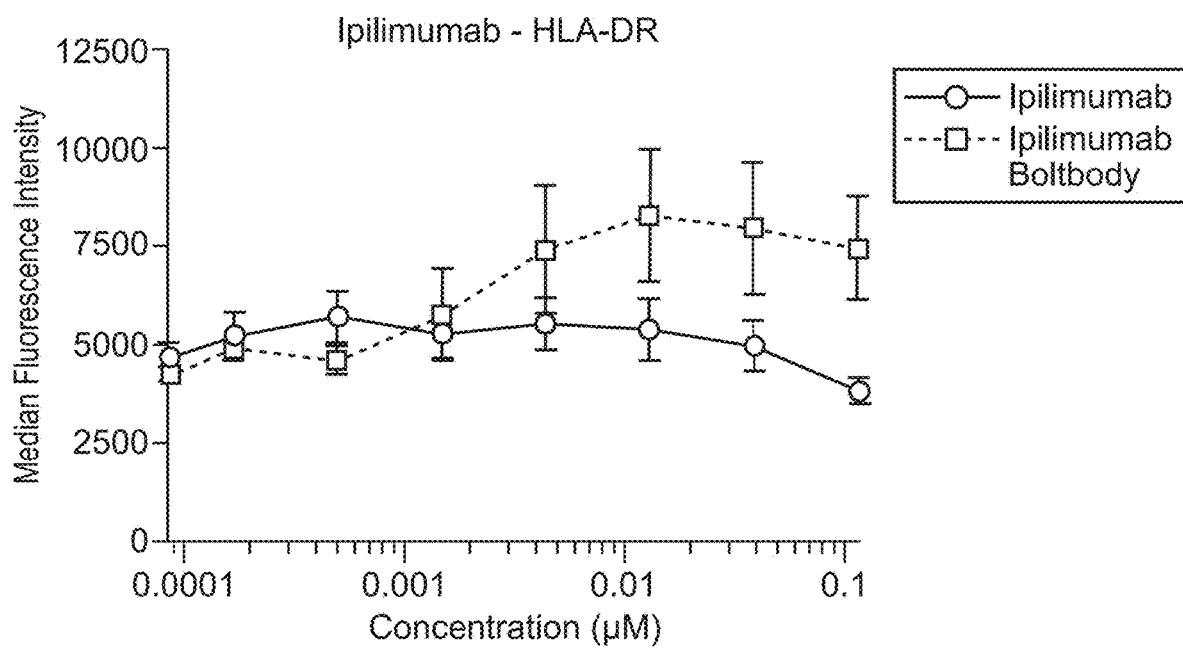

FIG. 75G shows that the ipilimumab immunoconjugate produced according to the BB-01 method (Ipilimumab Boltbody) is superior at eliciting HLA-DR upregulation on myeloid cells as compared to the unconjugated ipilimumab (BMS) following 18 hours of stimulation.

Figure 75H:
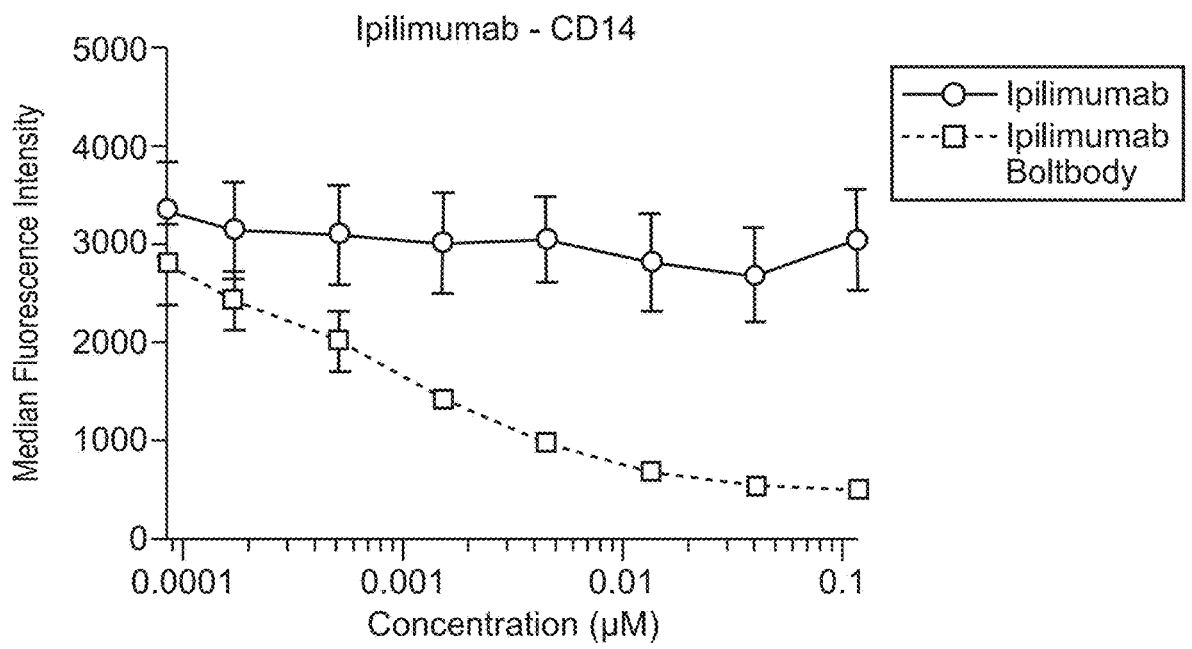

FIG. 75H shows that the ipilimumab immunoconjugate produced according to the BB-01 method (Ipilimumab Boltbody) is superior at eliciting CD14 downregulation on myeloid cells as compared to the unconjugated ipilimumab (BMS) following 18 hours of stimulation.

Figure 75I:
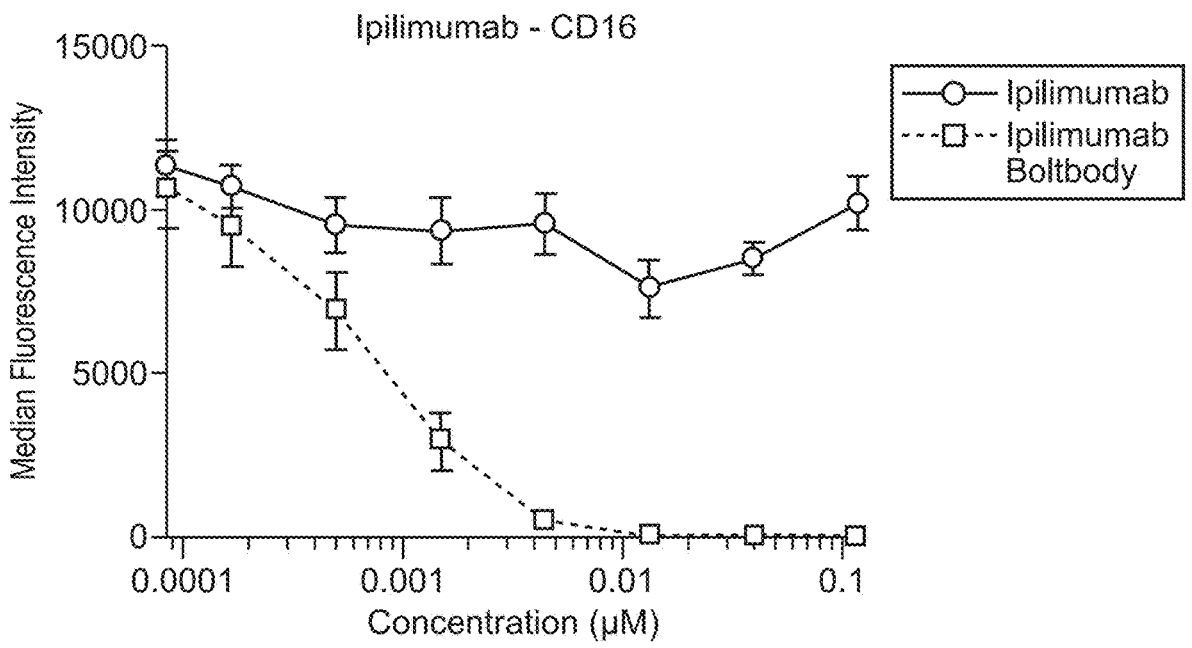

FIG. 75I shows that the ipilimumab immunoconjugate produced according to the BB-01 method (Ipilimumab Boltbody) is superior at eliciting CD16 downregulation on myeloid cells as compared to the unconjugated ipilimumab (BMS) following 18 hours of stimulation.

Figure 75J:
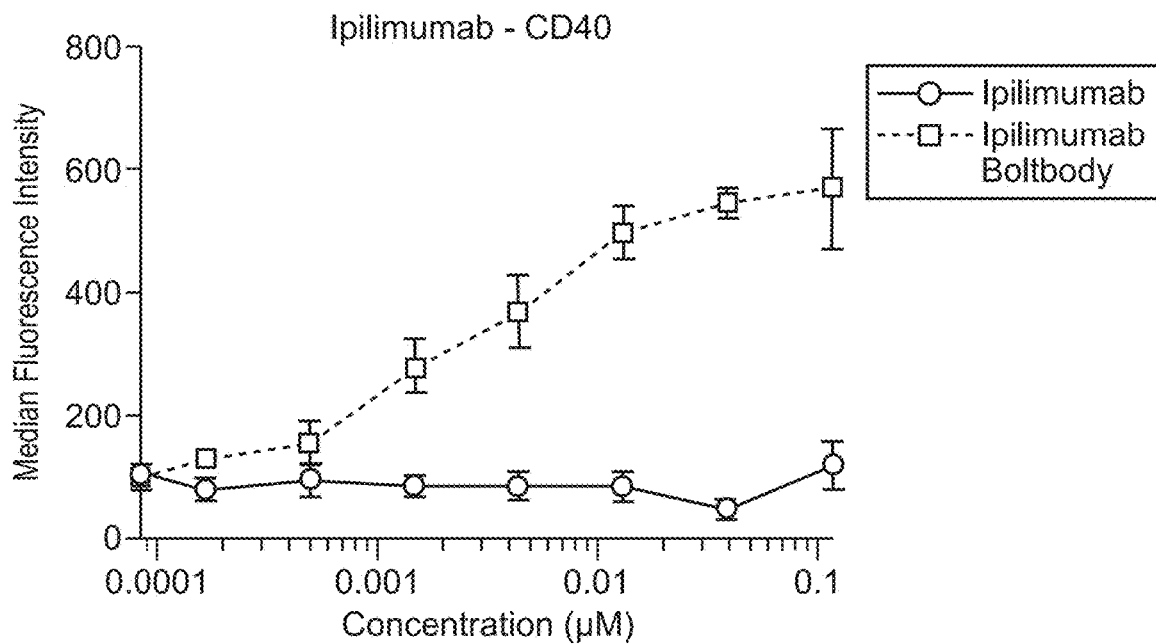

FIG. 75J shows that the ipilimumab immunoconjugate produced according to the BB-01 method (Ipilimumab Boltbody) is superior at eliciting CD40 upregulation on myeloid cells as compared to the unconjugated ipilimumab (BMS) following 18 hours of stimulation.

Figure 75K:
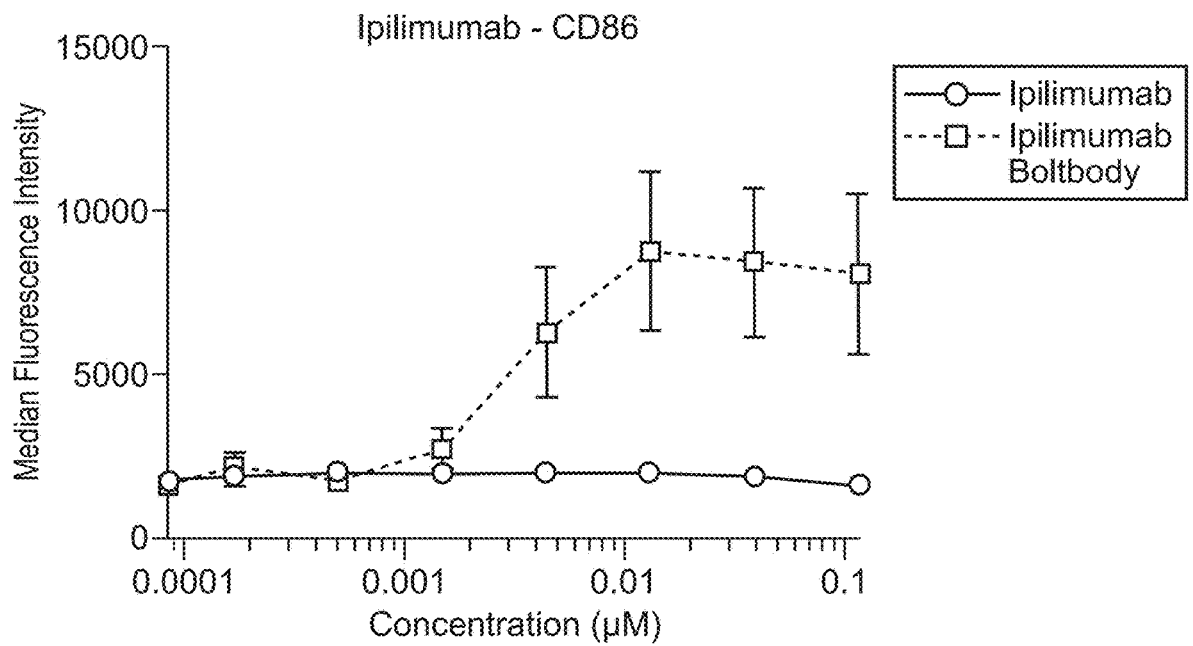

FIG. 75K shows that the ipilimumab immunoconjugate produced according to the BB-01 method (Ipilimumab Boltbody) is superior at eliciting CD86 upregulation on myeloid cells as compared to the unconjugated ipilimumab (BMS) following 18 hours of stimulation.

Figure 76A:
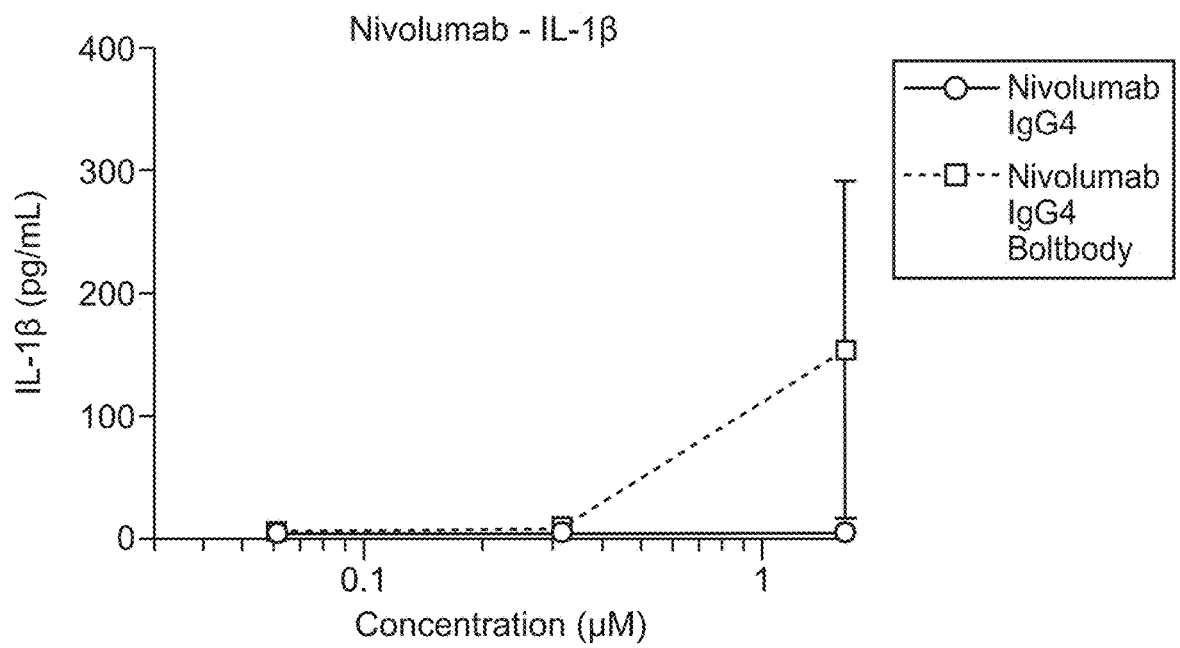

FIG. 76A shows that the nivolumab immunoconjugate produced according to the BB-01 method (Nivolumab IgG4 Boltbody) elicits superior IL-1β secretion from myeloid cells as compared to equimolar concentrations of unconjugated nivolumab (Nivolumab IgG4, BMS) following 18 hours of stimulation.

Figure 76B:
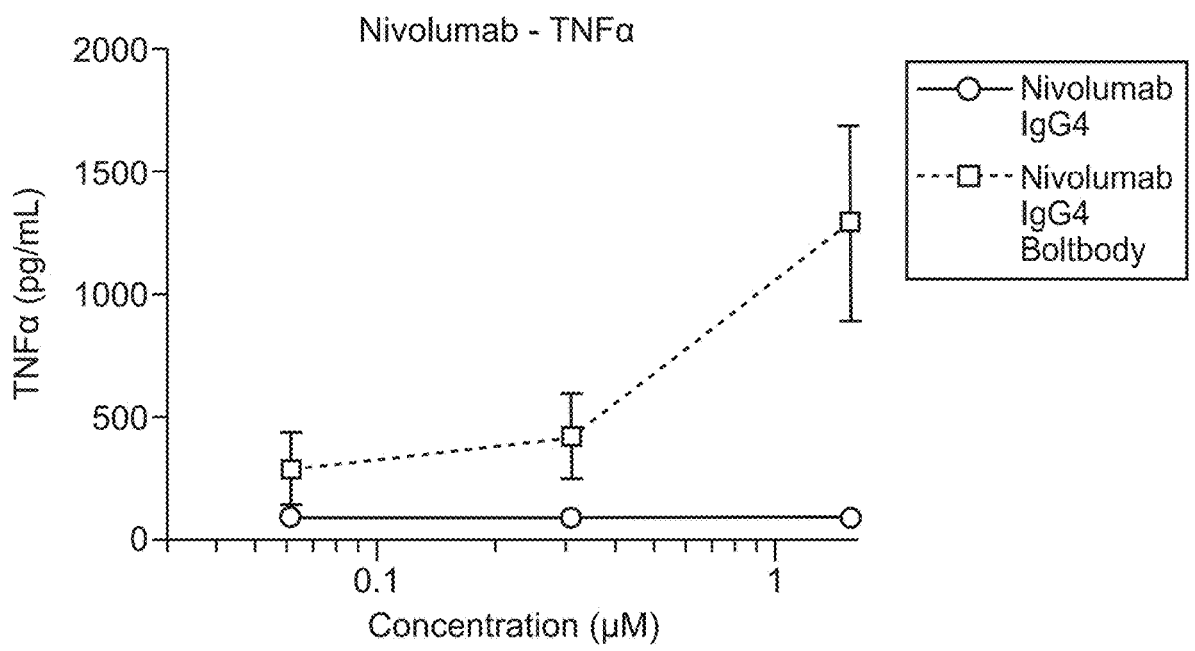

FIG. 76B shows that the nivolumab immunoconjugate produced according to the BB-01 method (Nivolumab IgG4 Boltbody) elicits superior TNFα secretion from myeloid cells as compared to equimolar concentrations of unconjugated nivolumab (Nivolumab IgG4, BMS) following 18 hours of stimulation.

Figure 76C:
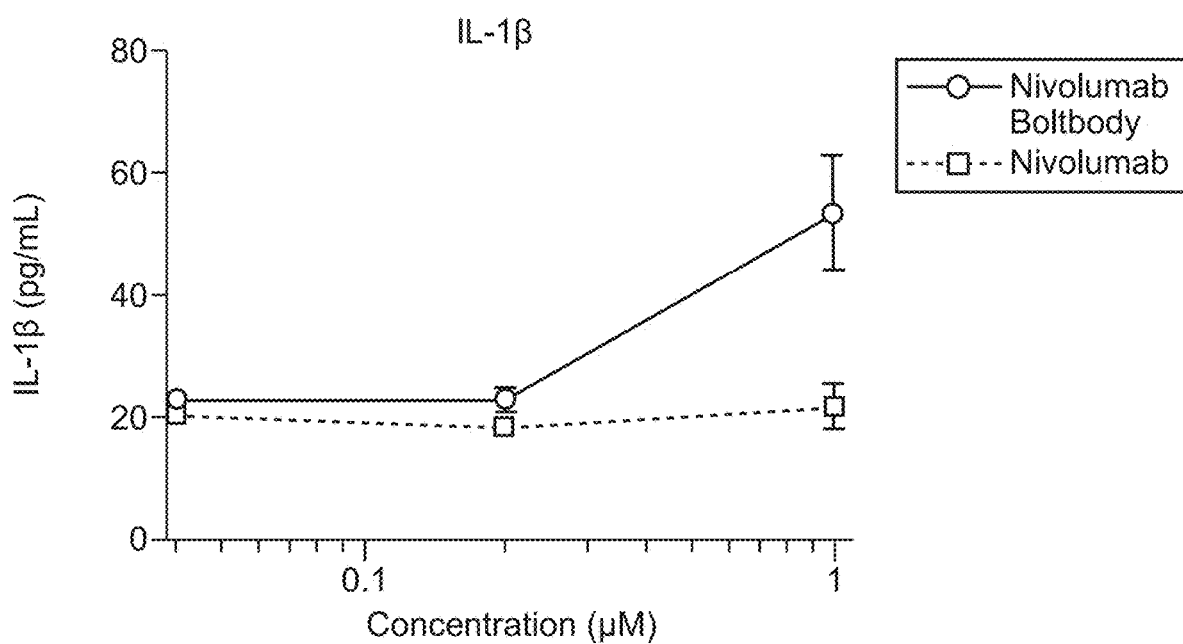

FIG. 76C shows that the nivolumab immunoconjugate produced according to the BB-01 method (Nivolumab IgG4 Boltbody) elicits superior IL-1β secretion from myeloid cells as compared to equimolar concentrations of unconjugated nivolumab (Nivolumab IgG4, BMS) following 36 hours of stimulation.

Figure 76D:
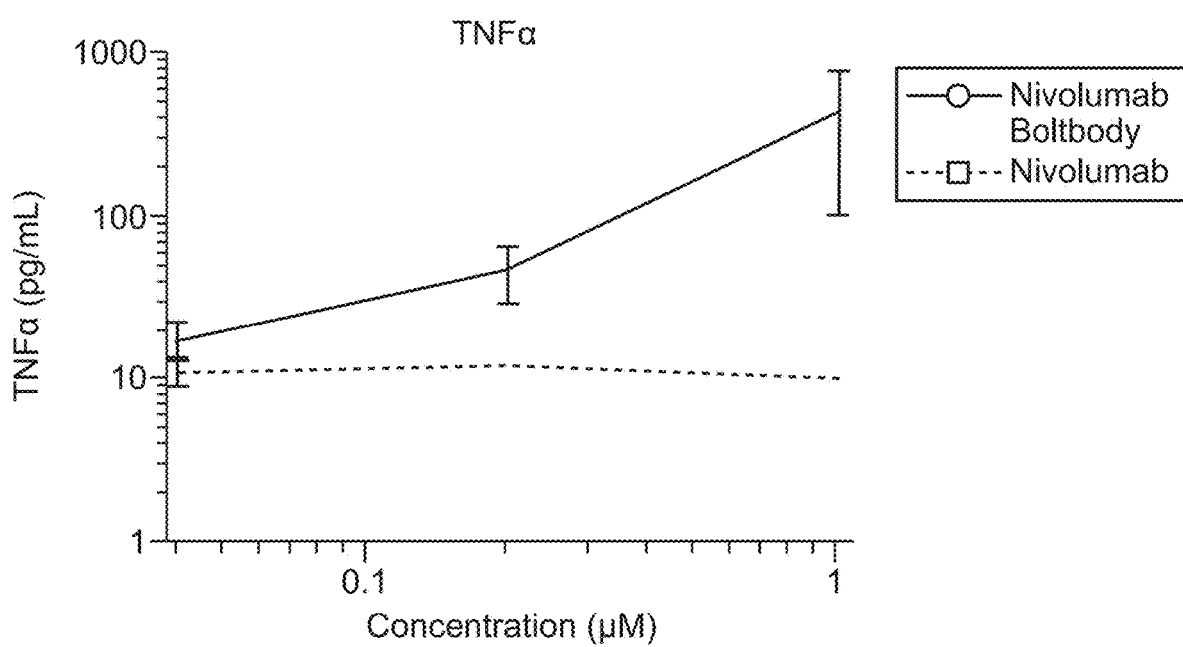

FIG. 76D shows that the nivolumab immunoconjugate produced according to the BB-01 method (Nivolumab IgG4 Boltbody) elicits superior TNFα secretion from myeloid cells as compared to equimolar concentrations of unconjugated nivolumab (Nivolumab IgG4, BMS) following 36 hours of stimulation.

FIG. 76E shows a liquid chromatography-mass spectrometry analysis of the nivolumab immunoconjugate produced according to the BB-01 conjugation method following overnight deglycosylation with PNGase F.

Figure 76F:
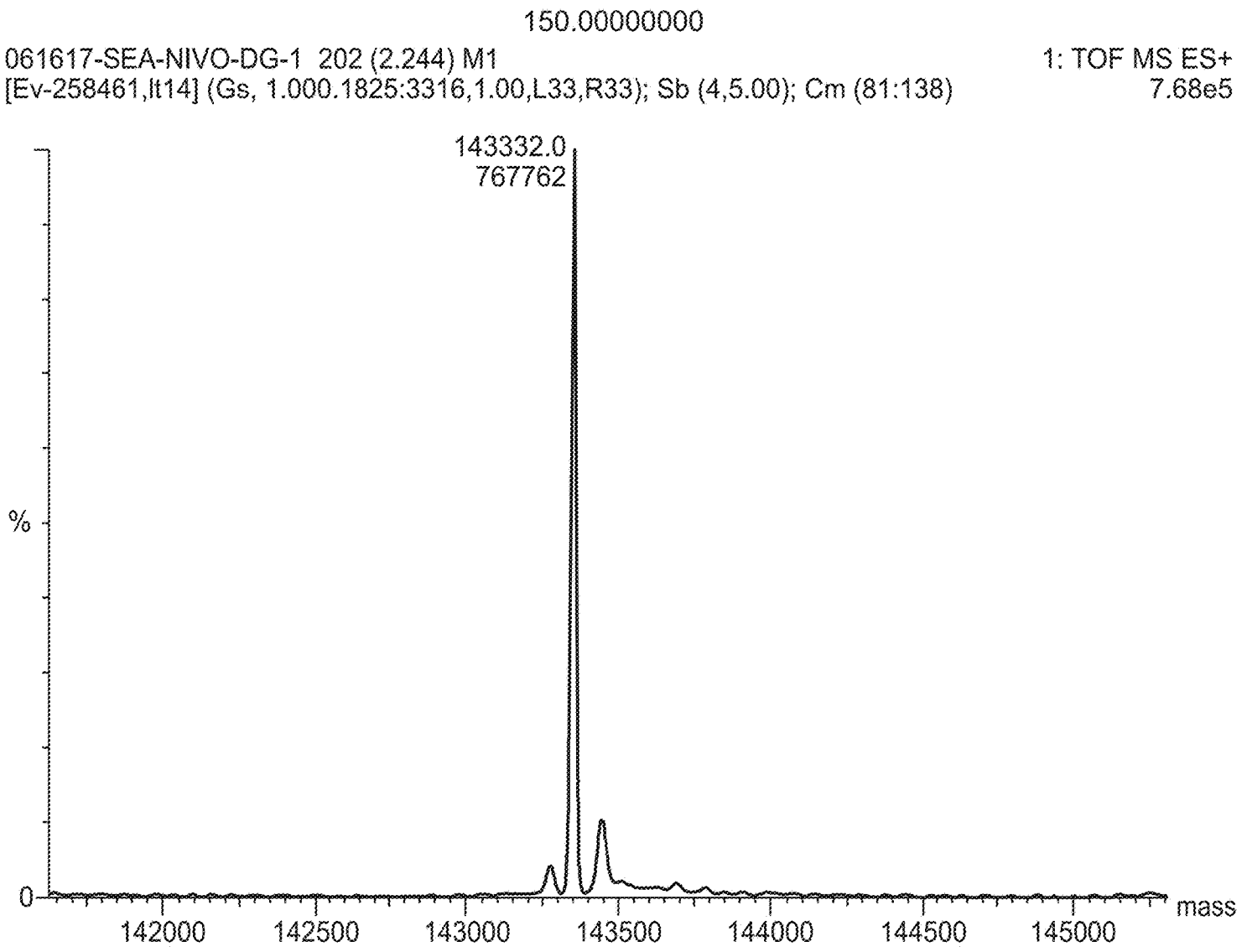

FIG. 76F shows a liquid chromatography-mass spectrometry analysis of unconjugated nivolumab (BMS) that was utilized to produce the nivolumab immunoconjugate according to the BB-01 conjugation method following overnight deglycosylation with PNGase F.

FIG. 76G shows a liquid chromatography-mass spectrometry analysis of unconjugated nivolumab (BMS) that was utilized to produce the nivolumab immunoconjugate according to the BB-01 method.

Figure 76H:
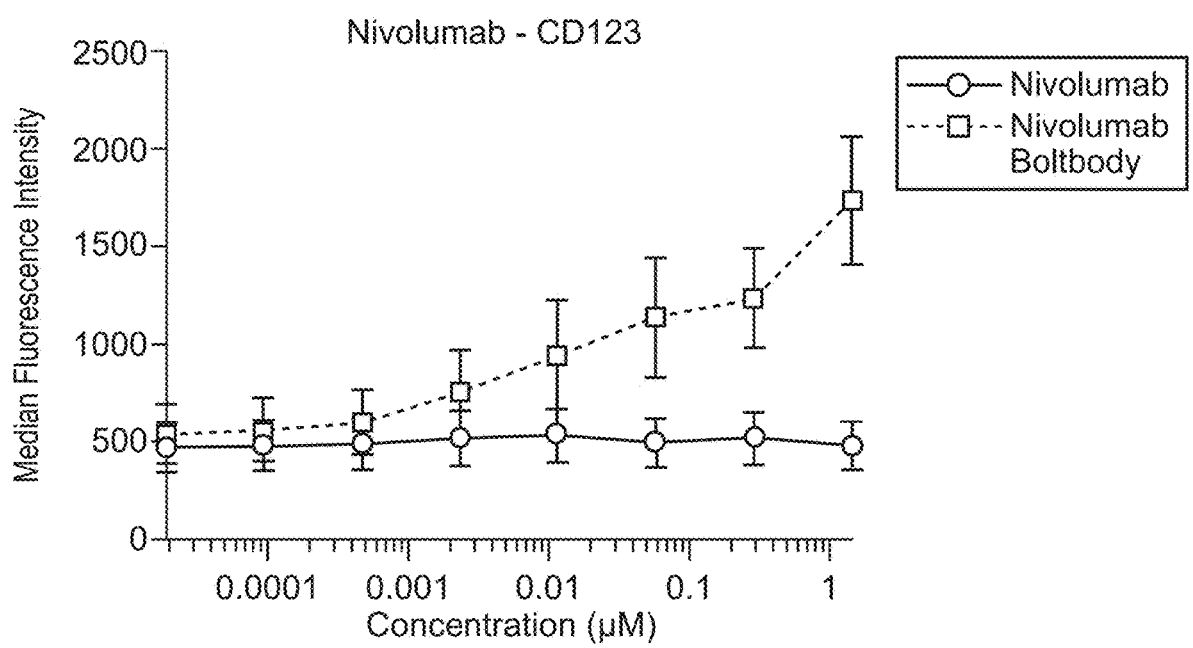

FIG. 76H shows that the nivolumab immunoconjugate produced according to the BB-01 method (Nivolumab Boltbody) is superior at eliciting CD123 upregulation on myeloid cells as compared to the unconjugated nivolumab (BMS) following 18 hours of stimulation.

Figure 76I:
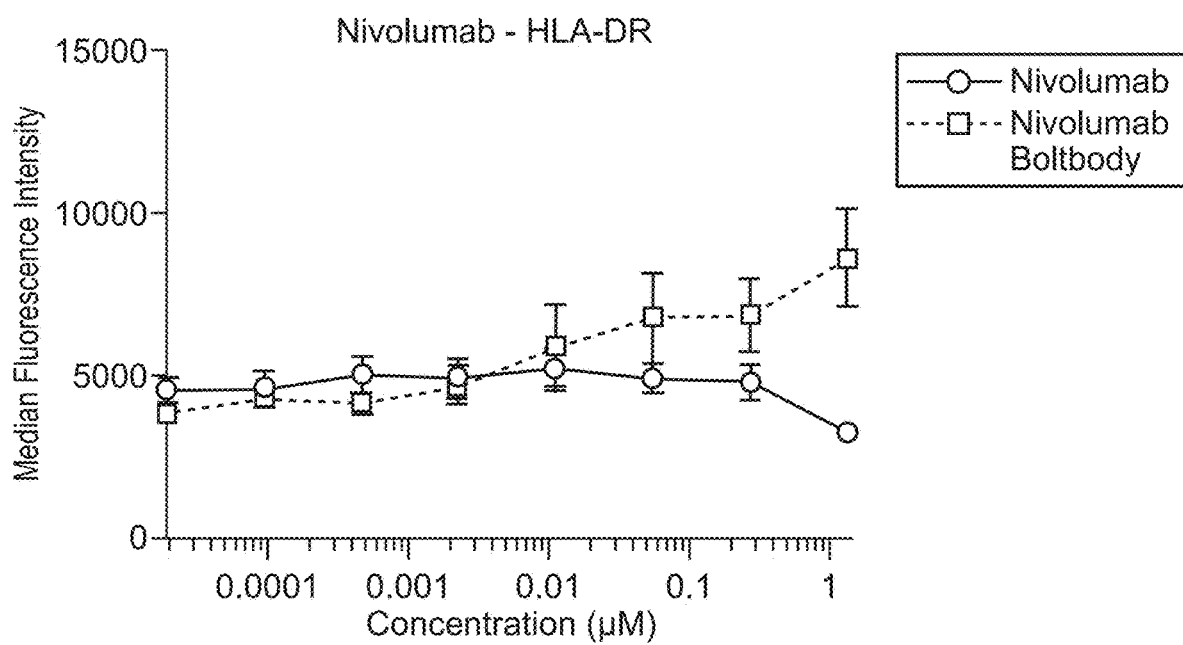

FIG. 76I shows HLA-DR expression on myeloid cells following 18 hours of stimulation with the nivolumab immunoconjugate produced according to the BB-01 method (Nivolumab Boltbody) as compared to unconjugated nivolumab (BMS).

Figure 76J:
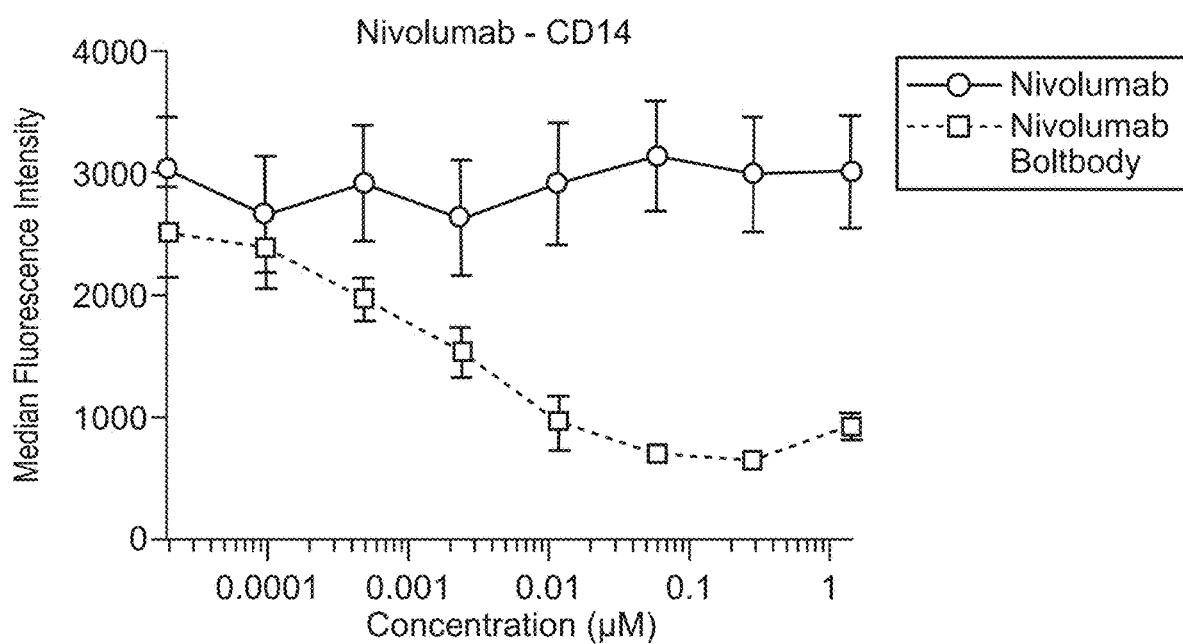

FIG. 76J shows that the nivolumab immunoconjugate produced according to the BB-01 method (Nivolumab Boltbody) is superior at eliciting CD14 downregulation on myeloid cells as compared to the unconjugated nivolumab (BMS) following 18 hours of stimulation.

Figure 76K:
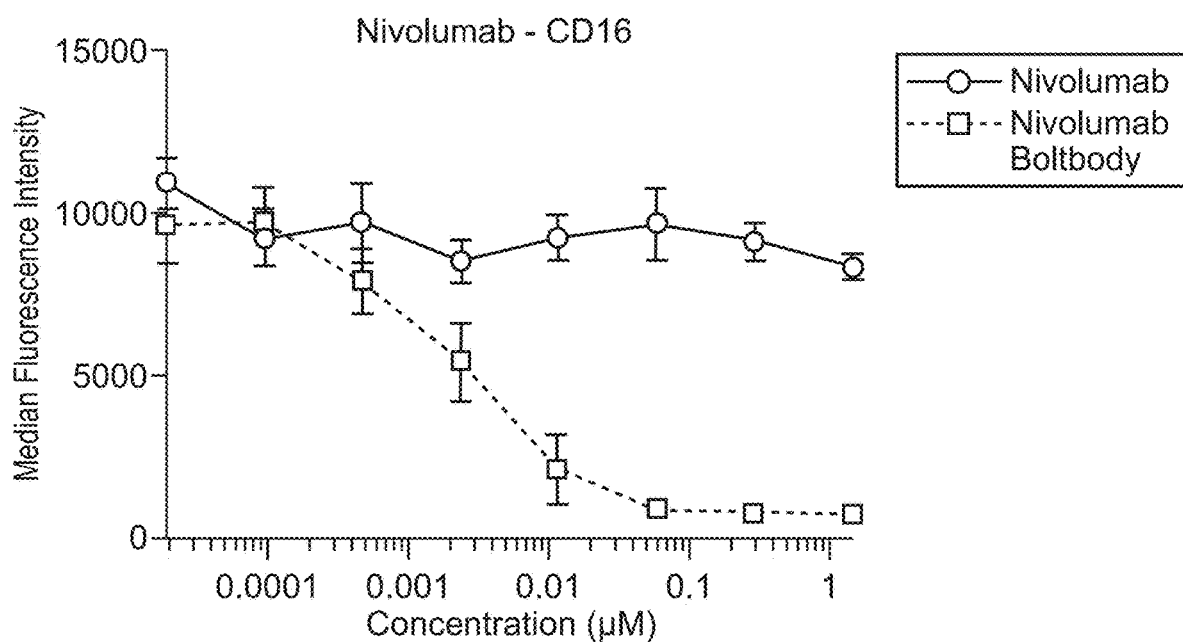

FIG. 76K shows that the nivolumab immunoconjugate produced according to the BB-01 method (Nivolumab Boltbody) is superior at eliciting CD16 downregulation on myeloid cells as compared to the unconjugated nivolumab (BMS) following 18 hours of stimulation.

Figure 76L:
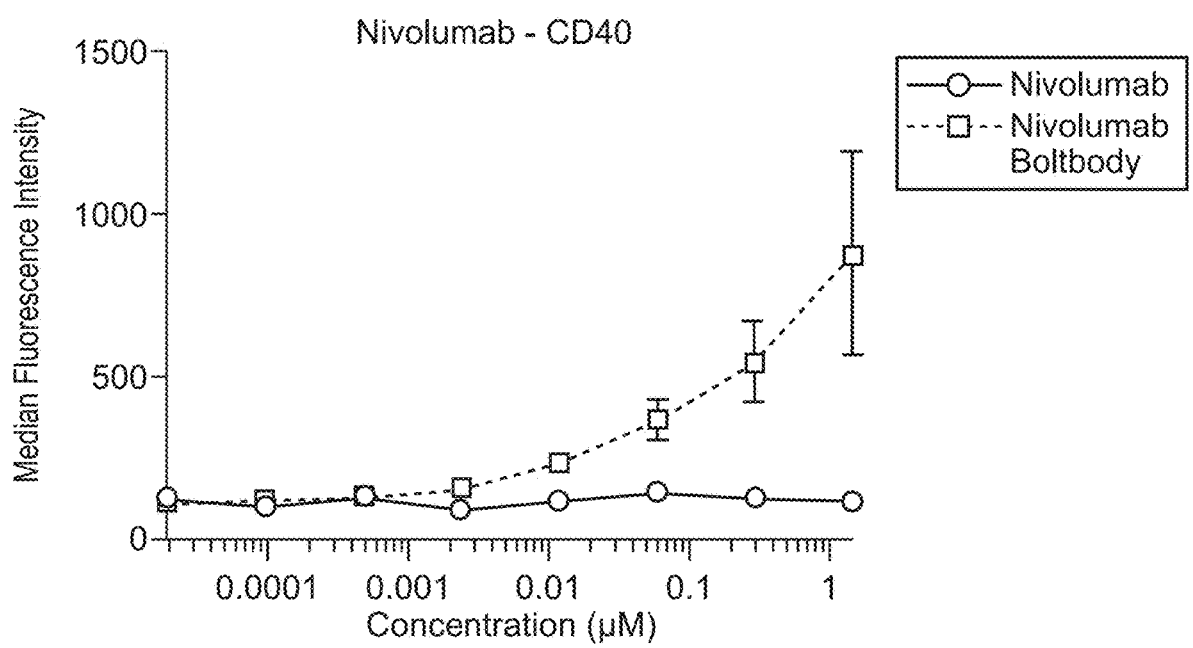

FIG. 76L shows that the nivolumab immunoconjugate produced according to the BB-01 method (Nivolumab Boltbody) is superior at eliciting CD40 upregulation on myeloid cells as compared to the unconjugated nivolumab (BMS) following 18 hours of stimulation.

Figure 76M:
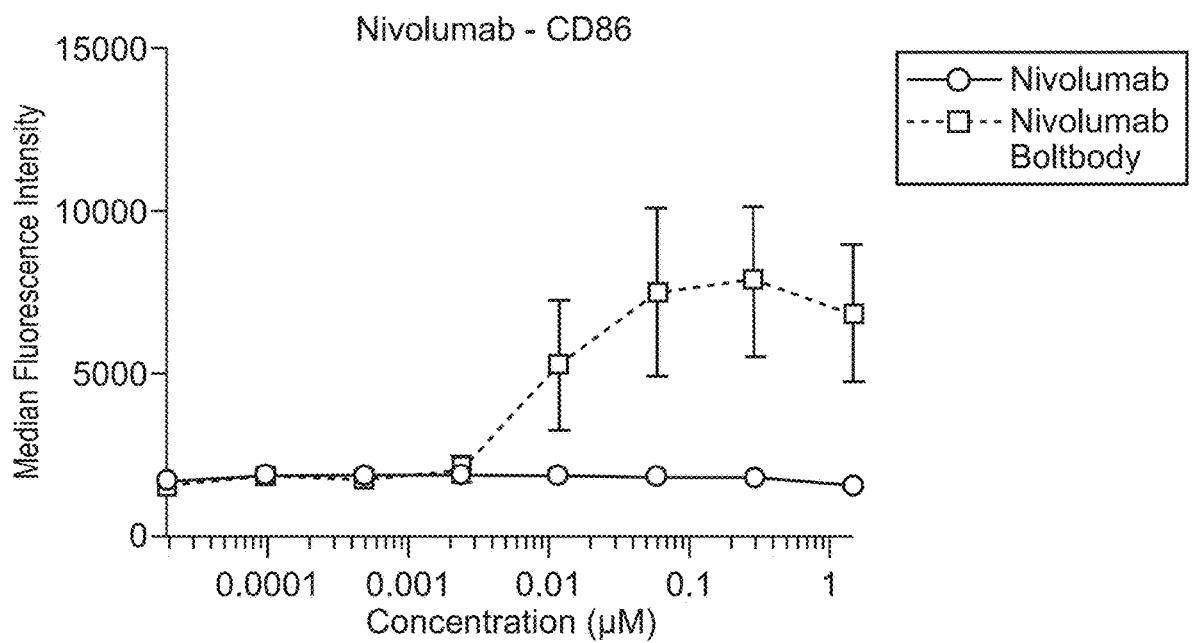

FIG. 76M shows that the nivolumab immunoconjugate produced according to the BB-01 method (Nivolumab Boltbody) is superior at eliciting CD86 upregulation on myeloid cells as compared to the unconjugated nivolumab (BMS) following 18 hours of stimulation.

Figure 77A:
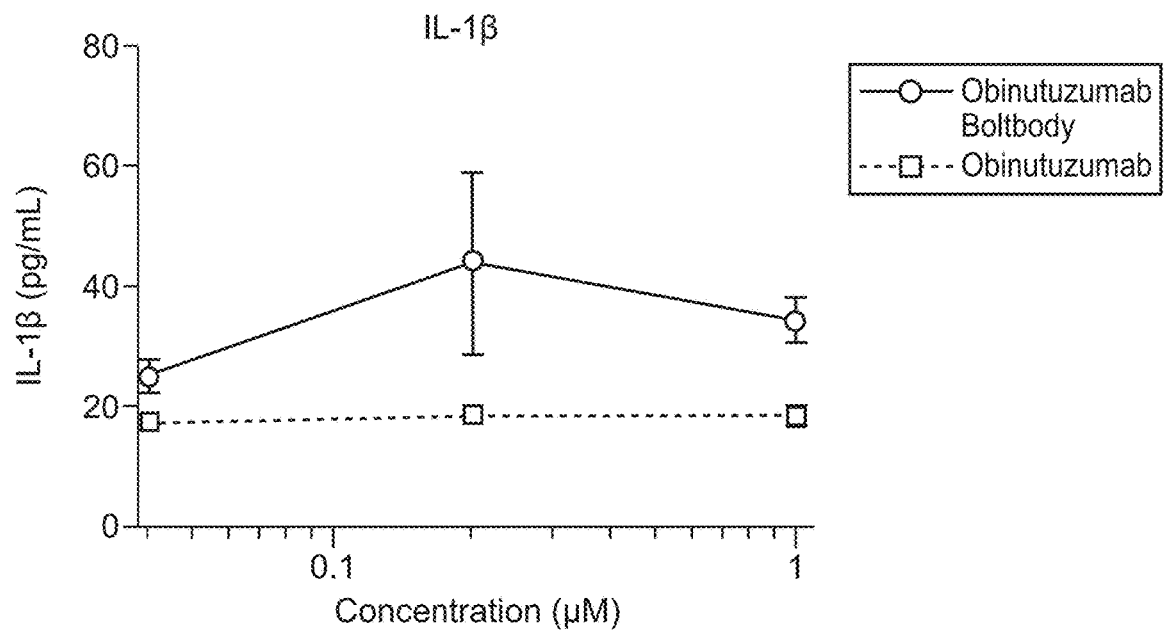

FIG. 77A shows that the obinutuzumab immunoconjugate produced according to the BB-01 method (Obinutuzumab Boltbody) elicits superior IL-10 secretion from myeloid cells as compared to equimolar concentrations of unconjugated obinutuzumab (Roche) following 36 hours of stimulation.

Figure 77B:
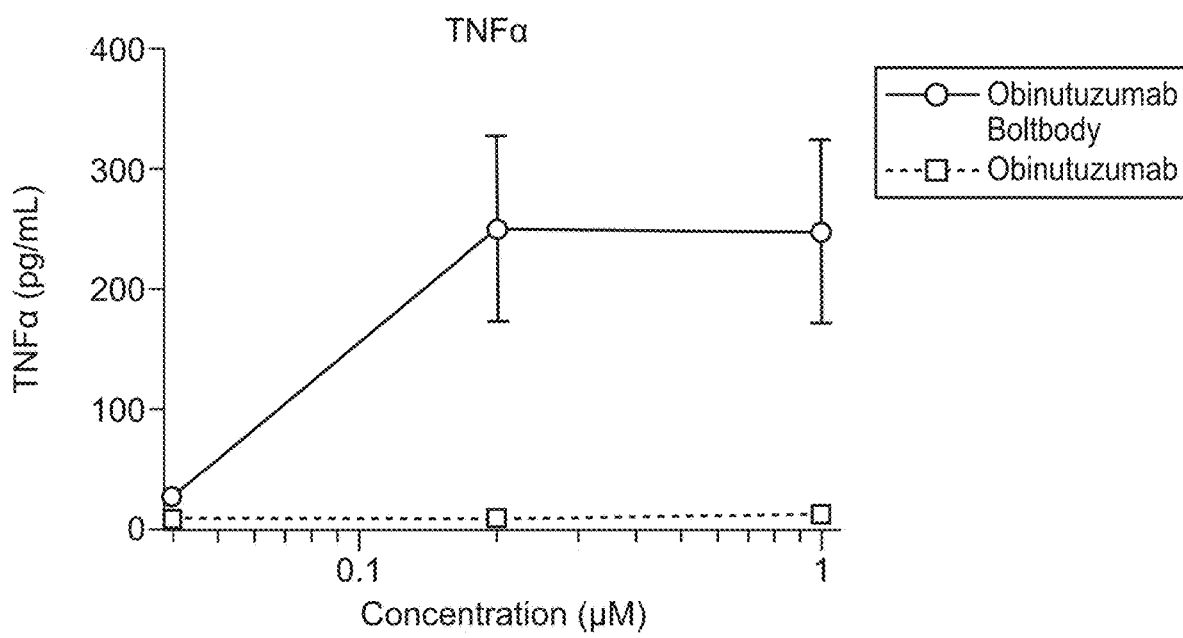

FIG. 77B shows that the obinutuzumab immunoconjugate produced according to the BB-01 method (Obinutuzumab Boltbody) elicits superior TNFα secretion from myeloid cells as compared to equimolar concentrations of unconjugated obinutuzumab (Roche) following 36 hours of stimulation.

Figure 77C:
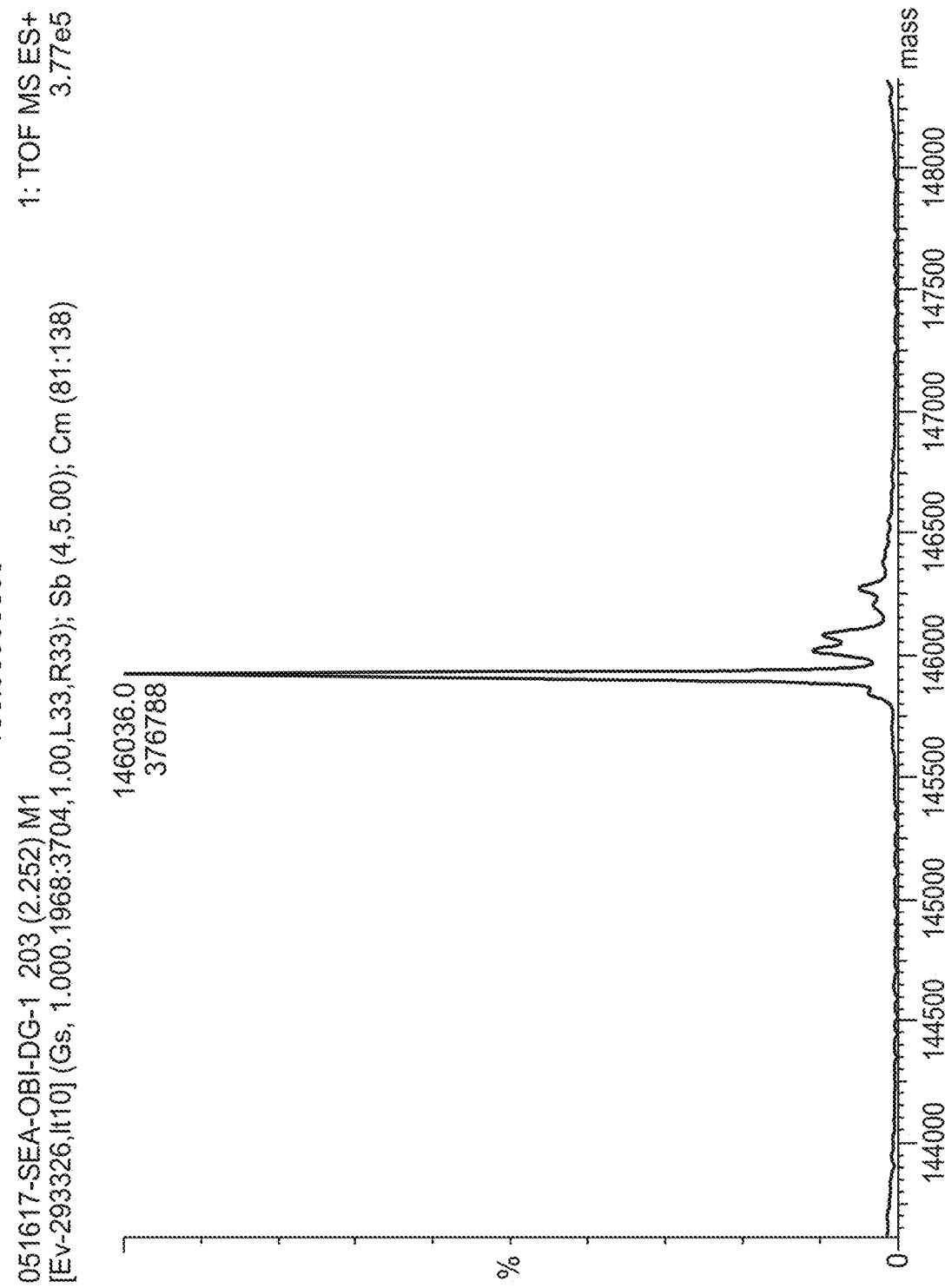

FIG. 77C shows a liquid chromatography-mass spectrometry analysis of unconjugated obinutuzumab (Roche) that was utilized to produce the obinutuzumab immunoconjugate according to the BB-01 conjugation method following overnight deglycosylation with PNGase F.

FIG. 77D shows a liquid chromatography-mass spectrometry analysis of unconjugated obinutuzumab (Roche) that was utilized to produce the obinutuzumab immunoconjugate according to the BB-01 conjugation method.

Figure 77E:
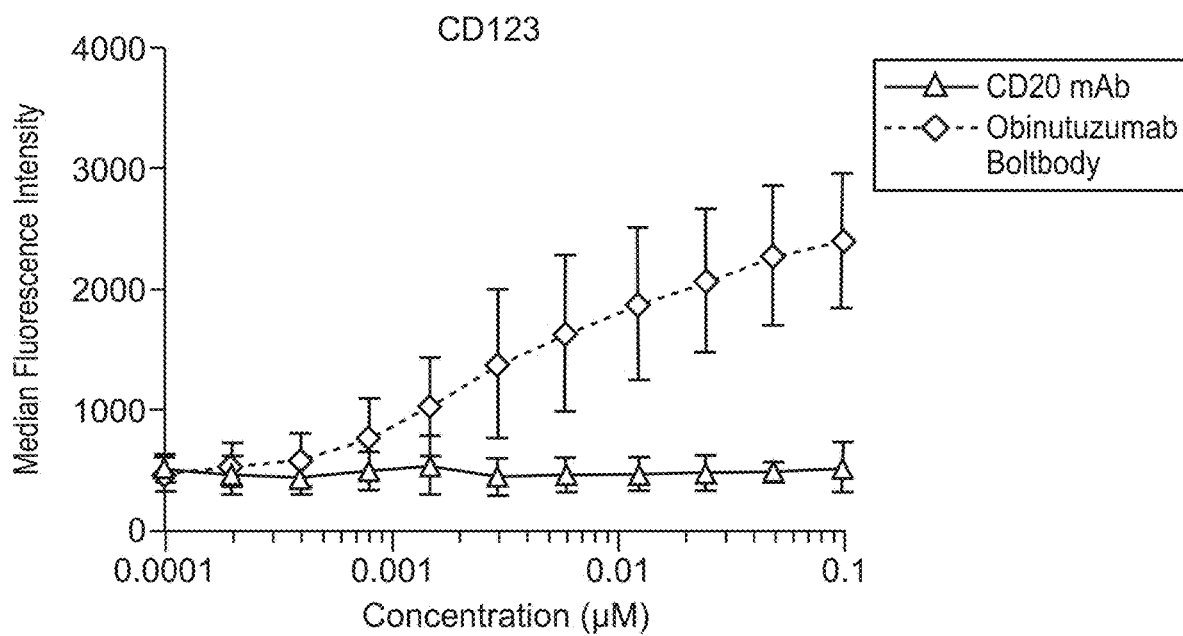

FIG. 77E shows that the obinutuzumab immunoconjugate produced according to the BB-01 method (Obinutuzumab Boltbody) is superior at eliciting CD123 upregulation on myeloid cells as compared to the unconjugated CD20 mAb (Roche) following 18 hours of stimulation.

Figure 77F:
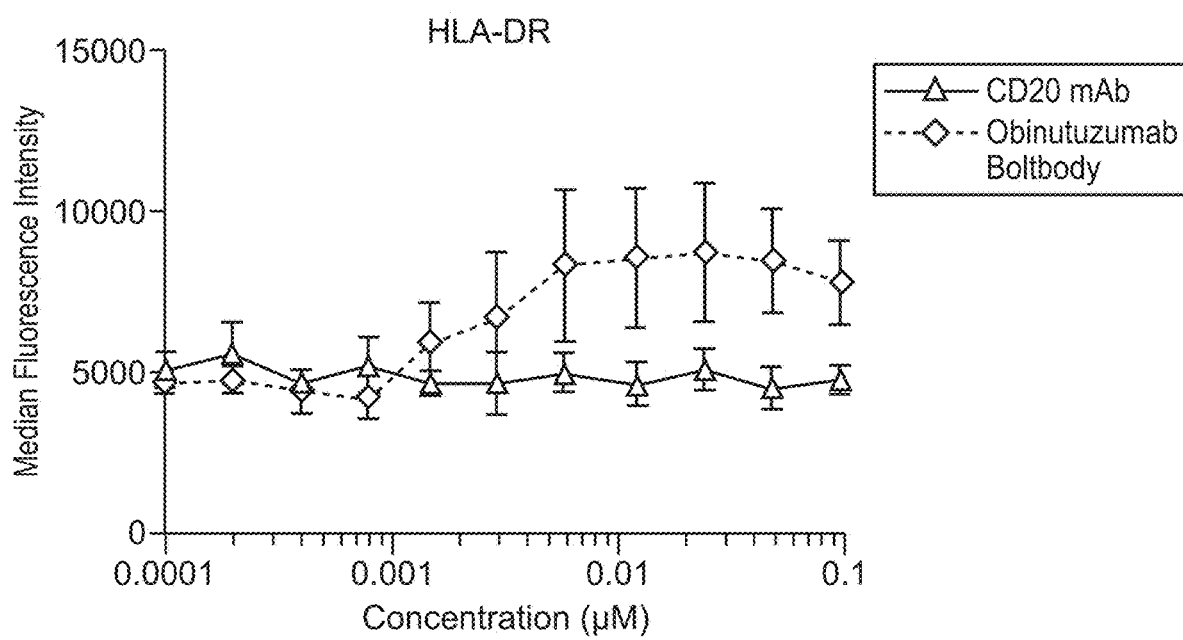

FIG. 77F shows HLA-DR expression on myeloid cells following 18 hours of stimulation with the obinutuzumab immunoconjugate produced according to the BB-01 method (Obinutuzumab Boltbody) as compared to unconjugated CD20 mAb (Roche).

Figure 77G:
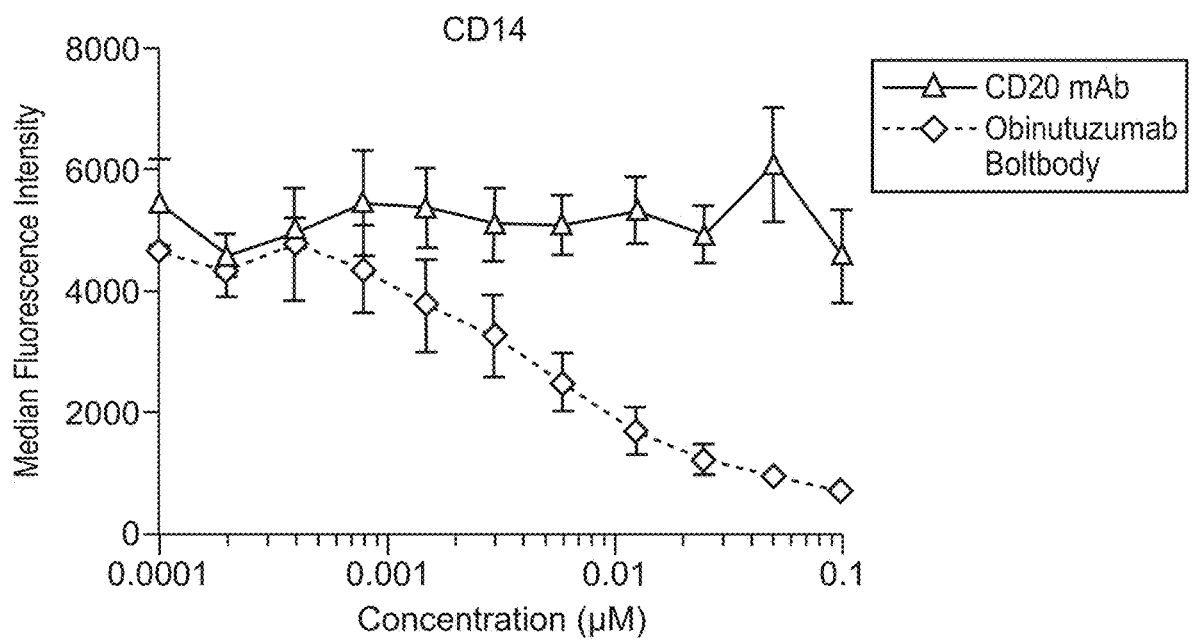

FIG. 77G shows that the obinutuzumab immunoconjugate produced according to the BB-01 method (Obinutuzumab Boltbody) is superior at eliciting CD14 downregulation on myeloid cells as compared to the unconjugated CD20 mAb (Roche) following 18 hours of stimulation.

Figure 77H:
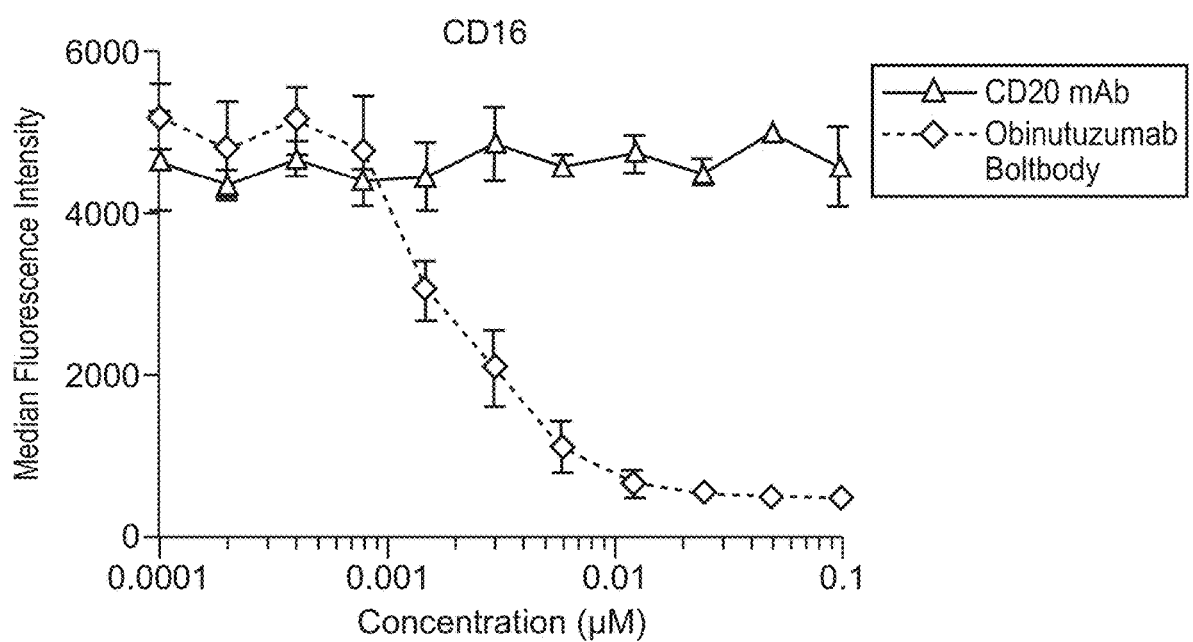

FIG. 77H shows that the obinutuzumab immunoconjugate produced according to the BB-01 method (Obinutuzumab Boltbody) is superior at eliciting CD16 downregulation on myeloid cells as compared to the unconjugated CD20 mAb (Roche) following 18 hours of stimulation.

Figure 77I:
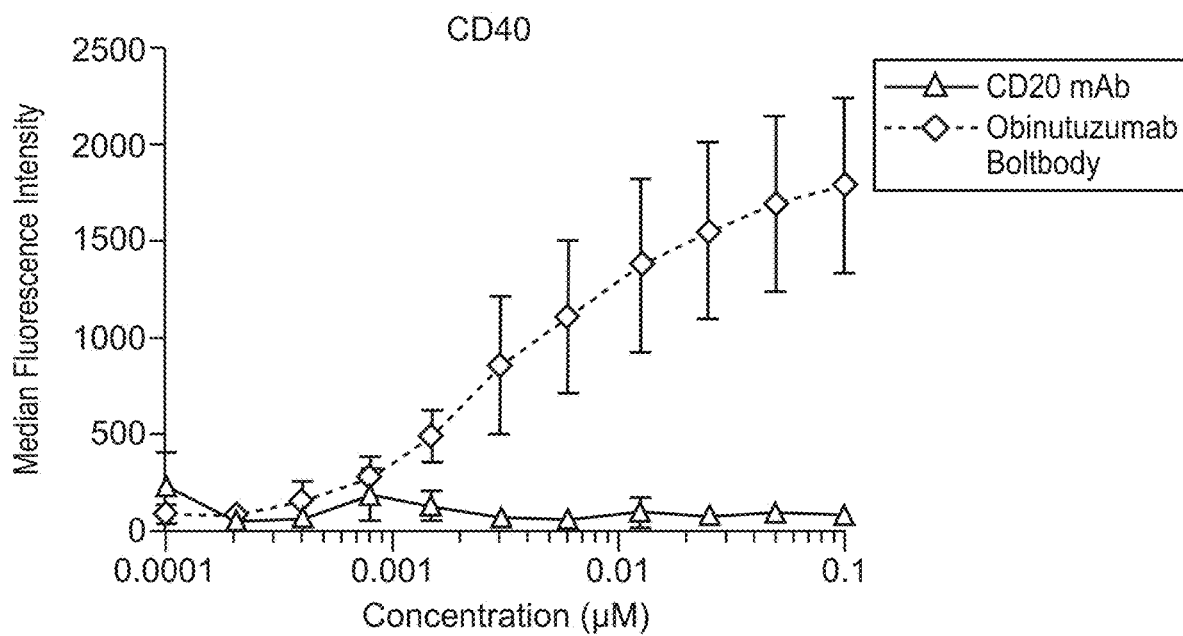

FIG. 77I shows that the obinutuzumab immunoconjugate produced according to the BB-01 method (Obinutuzumab Boltbody) is superior at eliciting CD40 upregulation on myeloid cells as compared to the unconjugated CD20 mAb (Roche) following 18 hours of stimulation.

Figure 77J:
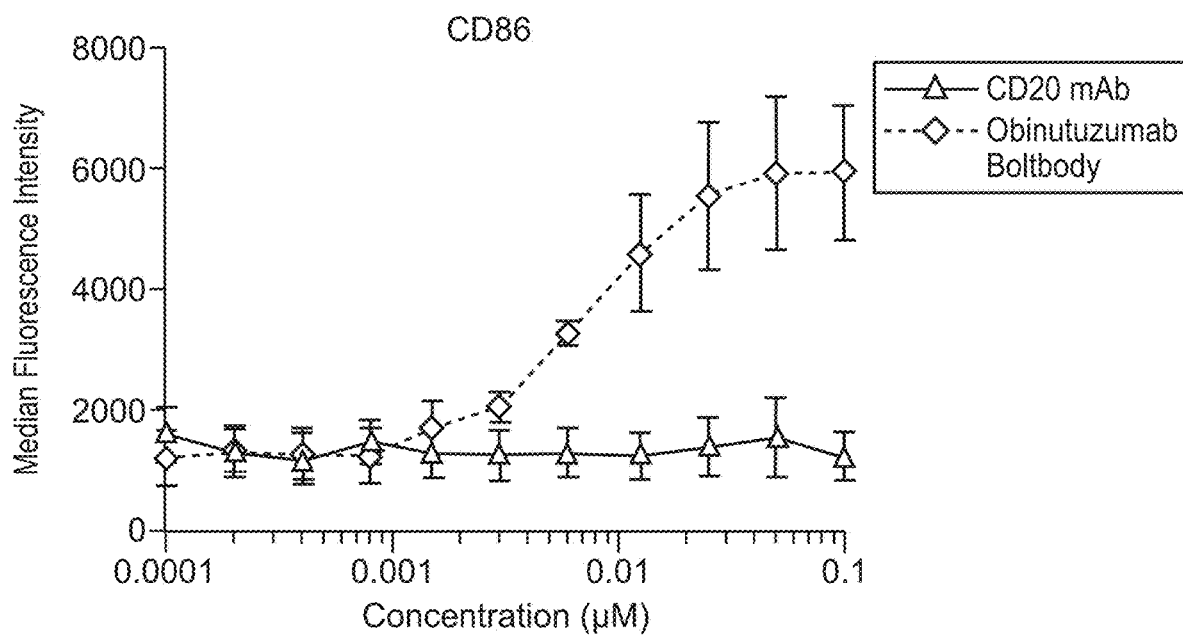

FIG. 77J shows that the obinutuzumab immunoconjugate produced according to the BB-01 method (Obinutuzumab Boltbody) is superior at eliciting CD86 upregulation on myeloid cells as compared to the unconjugated CD20 mAb (Roche) following 18 hours of stimulation.

Figure 78A:
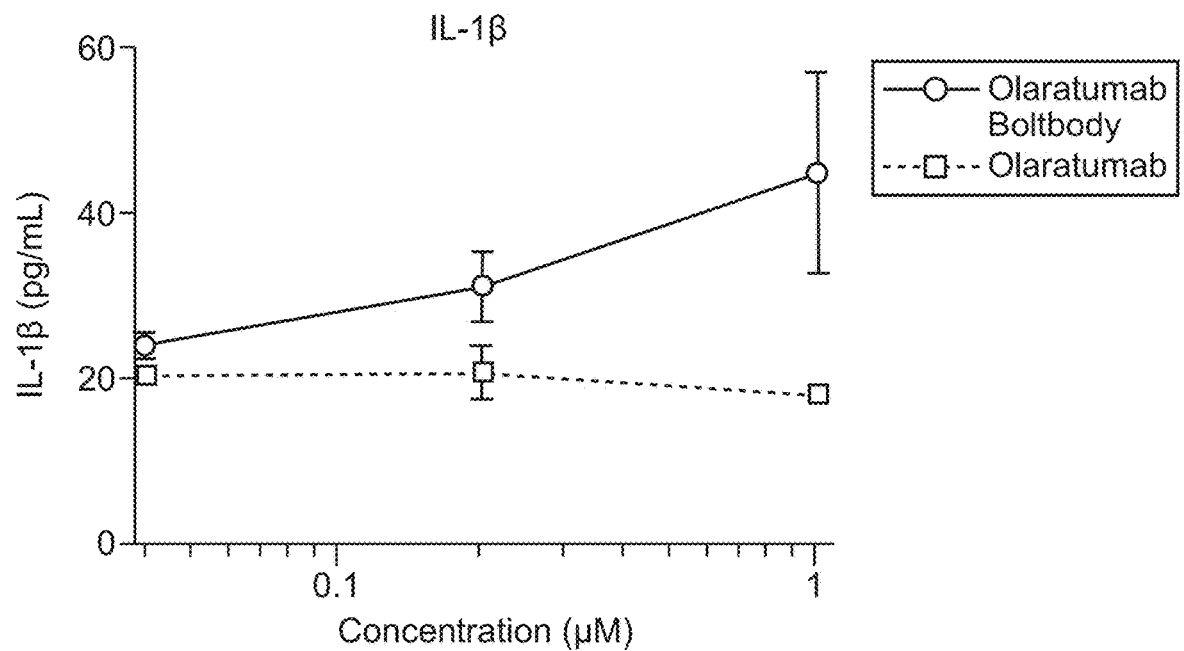

FIG. 78A shows that the olaratumab immunoconjugate produced according to the BB-01 method (Olaratumab Boltbody) elicits superior IL-1β secretion from myeloid cells as compared to equimolar concentrations of unconjugated olaratumab (Lilly) following 36 hours of stimulation.

Figure 78B:
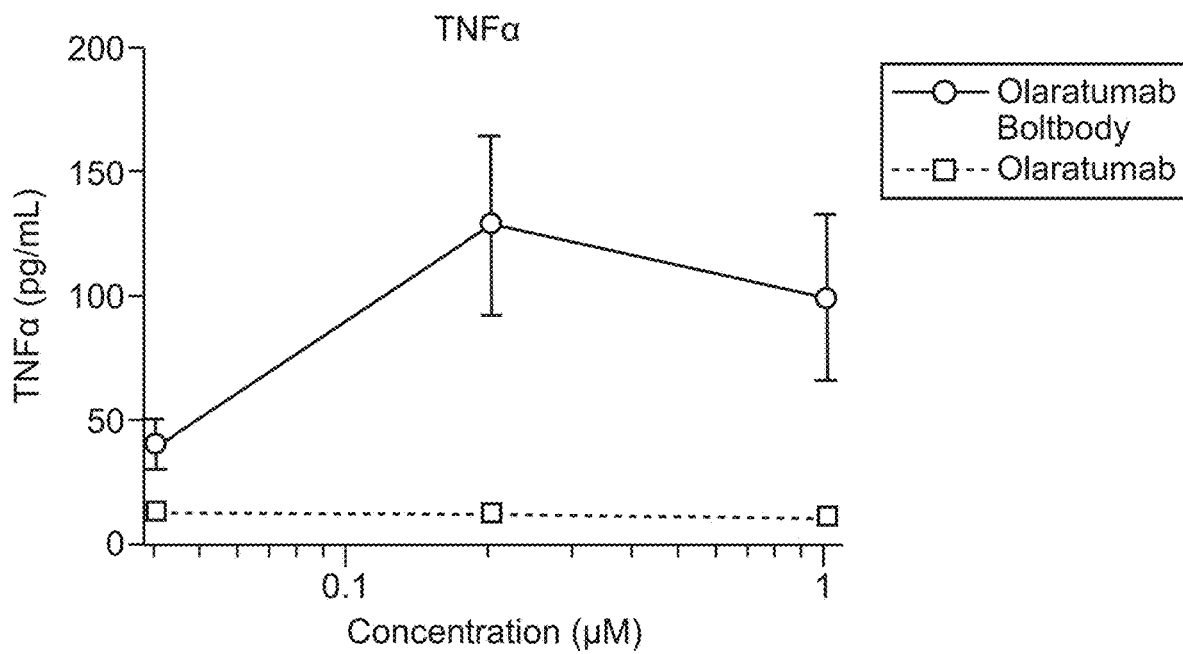

FIG. 78B shows that the olaratumab immunoconjugate produced according to the BB-01 method (Olaratumab Boltbody) elicits superior TNFα secretion from myeloid cells as compared to equimolar concentrations of unconjugated olaratumab (Lilly) following 36 hours of stimulation.

FIG. 78C shows a liquid chromatography-mass spectrometry analysis of the olaratumab immunoconjugate produced according to the BB-01 conjugation method following overnight deglycosylation with PNGase F.

Figure 78D:
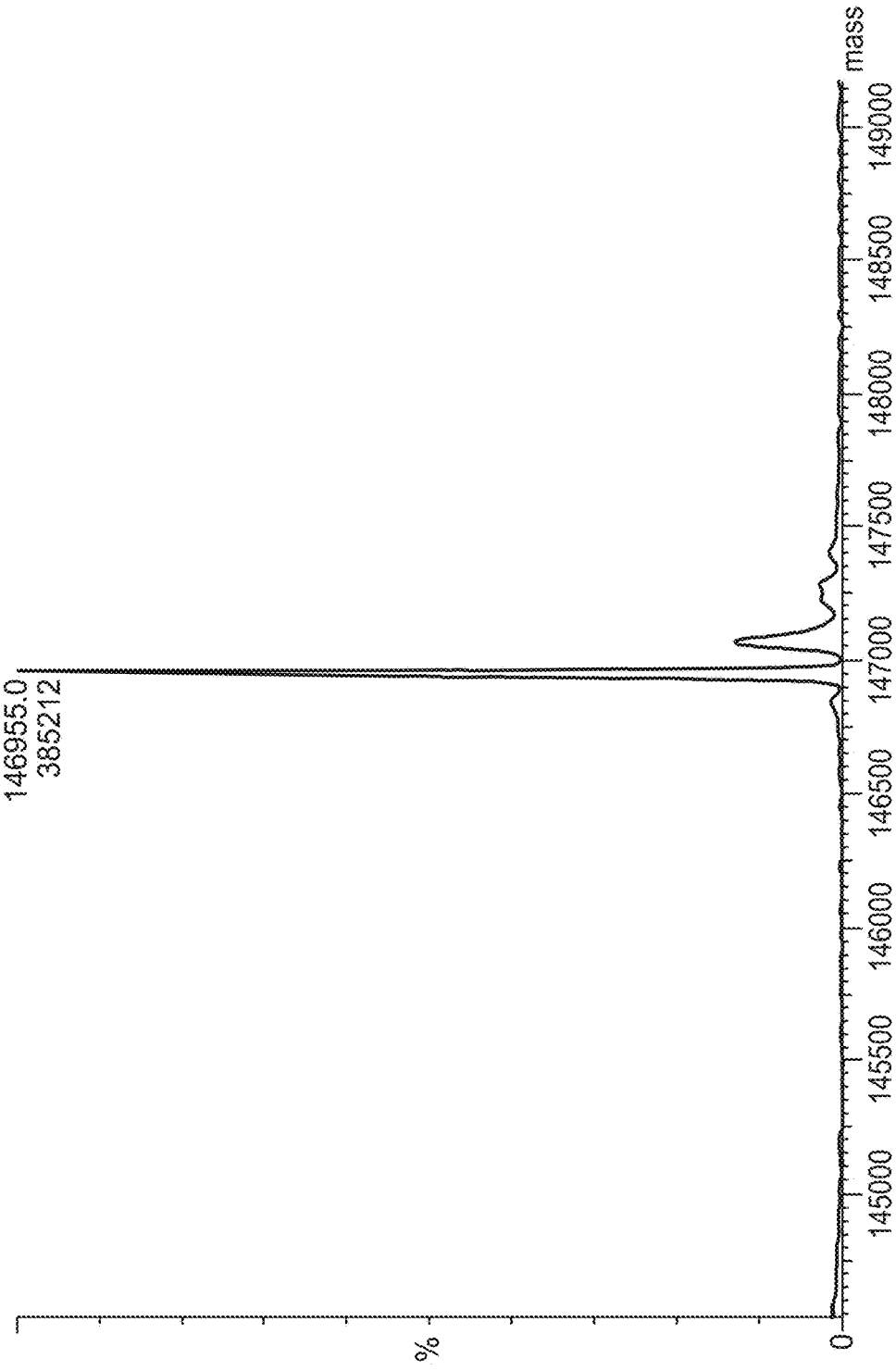

FIG. 78D shows a liquid chromatography-mass spectrometry analysis of unconjugated olaratumab (Lilly) that was utilized to produce the olaratumab immunoconjugate according to the BB-01 conjugation method following overnight deglycosylation with PNGase F.

Figure 78E:
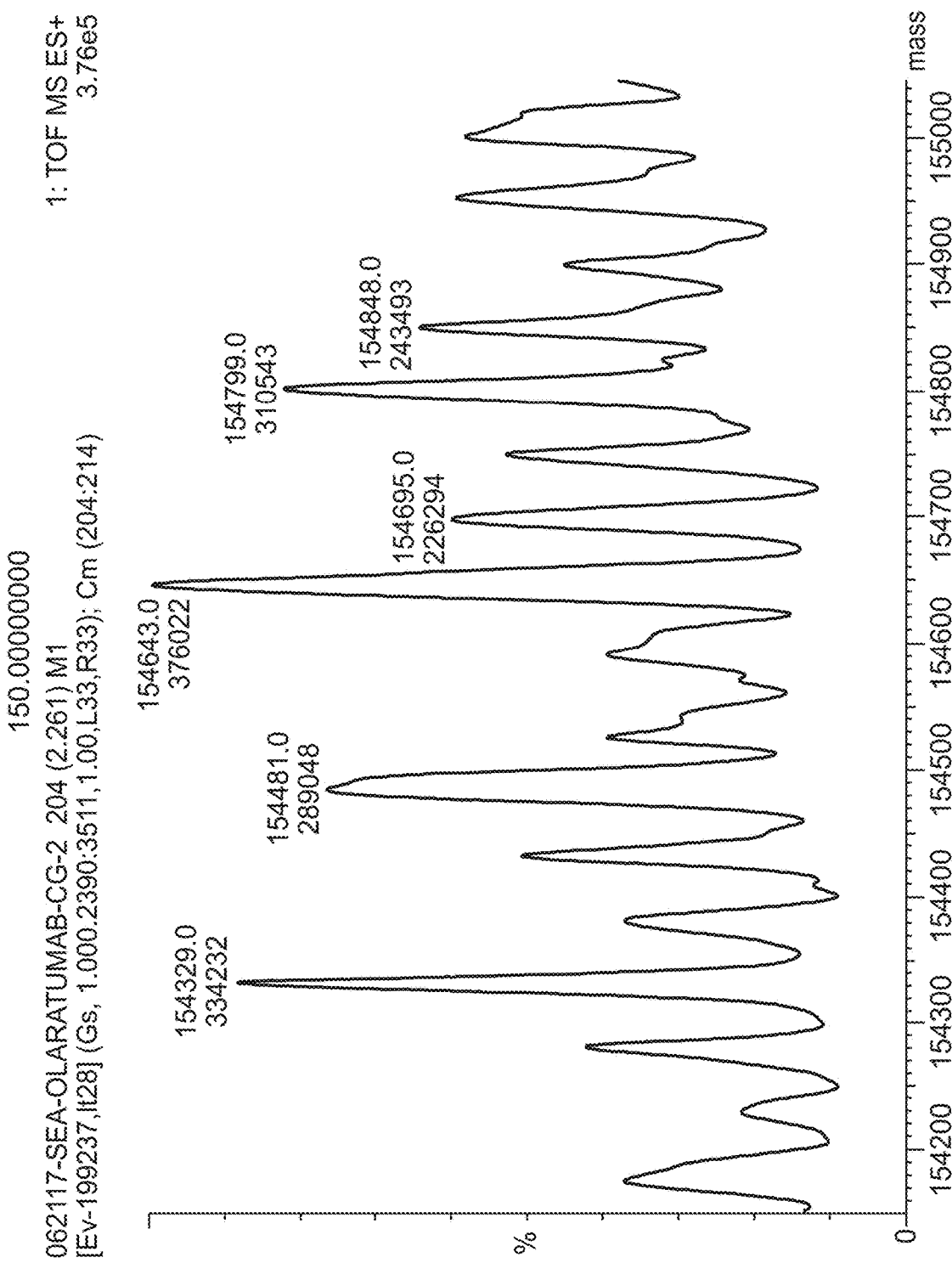

FIG. 78E shows a liquid chromatography-mass spectrometry analysis of unconjugated olaratumab (Lilly) that was utilized to produce the olaratumab immunoconjugate according to the BB-01 conjugation method.

Figure 78F:
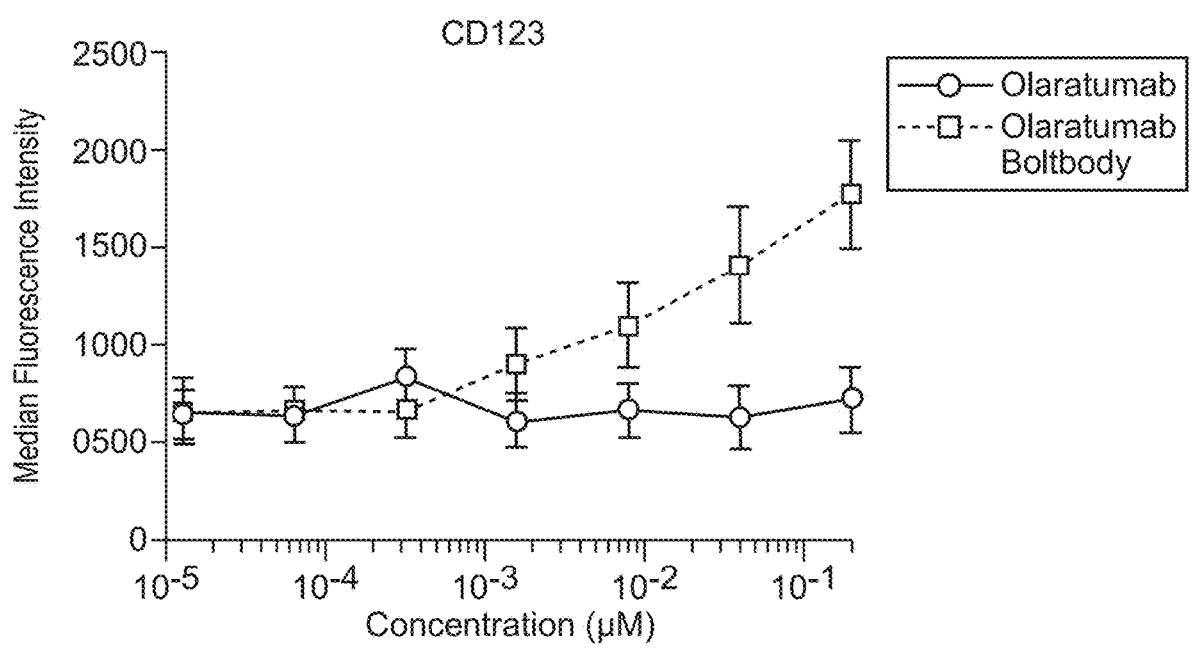

FIG. 78F shows that the olaratumab immunoconjugate produced according to the BB-01 method (Olaratumab Boltbody) is superior at eliciting CD123 upregulation on myeloid cells as compared to the unconjugated olaratumab (Lilly) following 18 hours of stimulation.

Figure 78G:
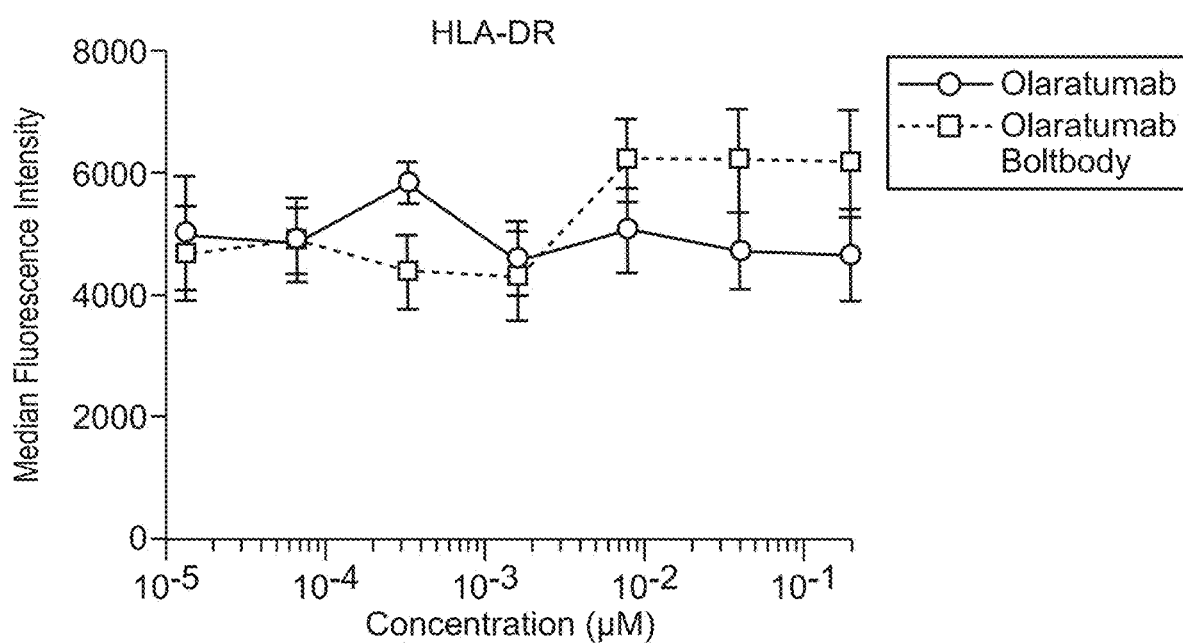

FIG. 78G shows that the olaratumab immunoconjugate produced according to the BB-01 method (Olaratumab Boltbody) is superior at eliciting HLA-DR upregulation on myeloid cells as compared to the unconjugated olaratumab (Lilly) following 18 hours of stimulation.

Figure 78H:
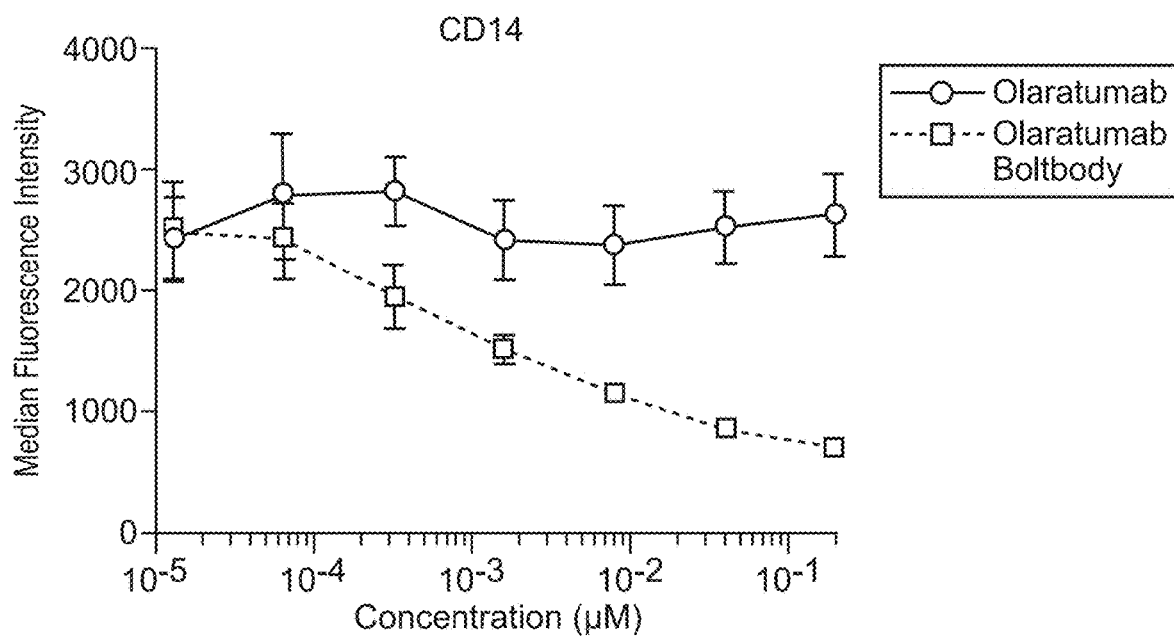

FIG. 78H shows that the olaratumab immunoconjugate produced according to the BB-01 method (Olaratumab Boltbody) is superior at eliciting CD14 downregulation on myeloid cells as compared to the unconjugated olaratumab (Lilly) following 18 hours of stimulation.

Figure 78I:
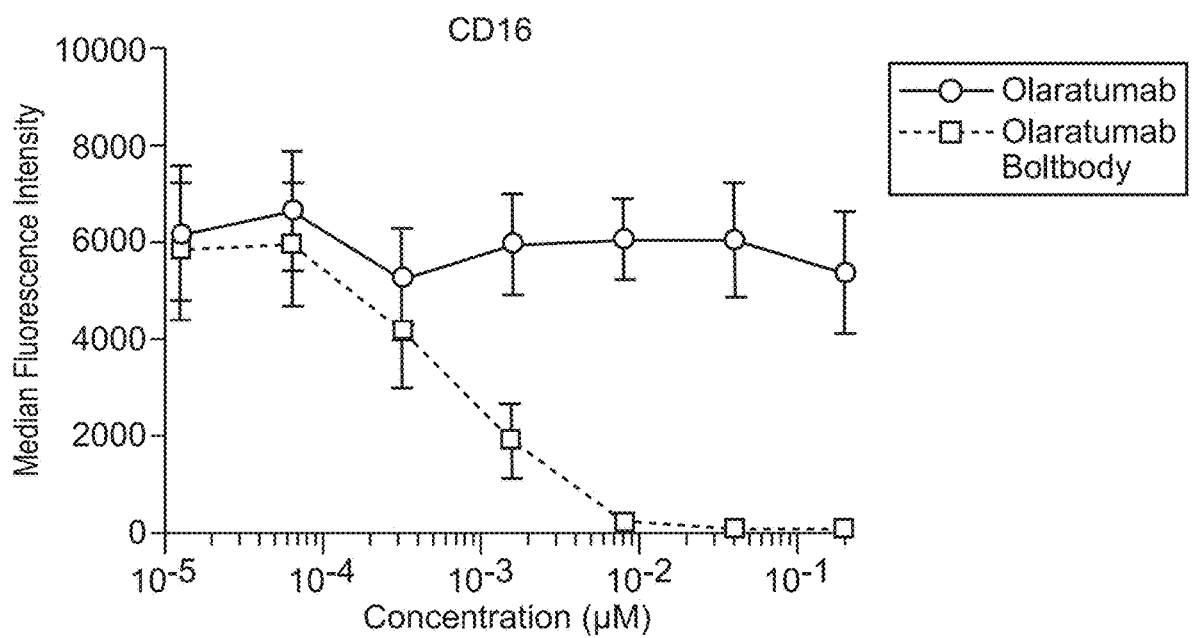

FIG. 78I shows that the olaratumab immunoconjugate produced according to the BB-01 method (Olaratumab Boltbody) is superior at eliciting CD16 downregulation on myeloid cells as compared to the unconjugated olaratumab (Lilly) following 18 hours of stimulation.

Figure 78J:
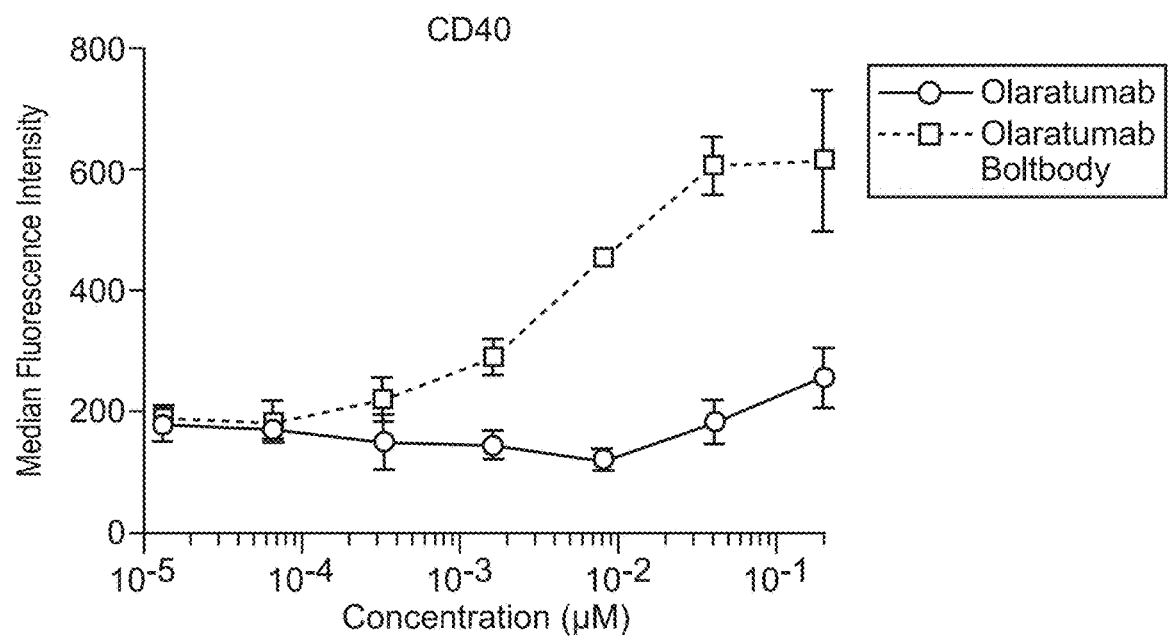

FIG. 78J shows that the olaratumab immunoconjugate produced according to the BB-01 method (Olaratumab Boltbody) is superior at eliciting CD40 upregulation on myeloid cells as compared to the unconjugated olaratumab (Lilly) following 18 hours of stimulation.

Figure 78K:
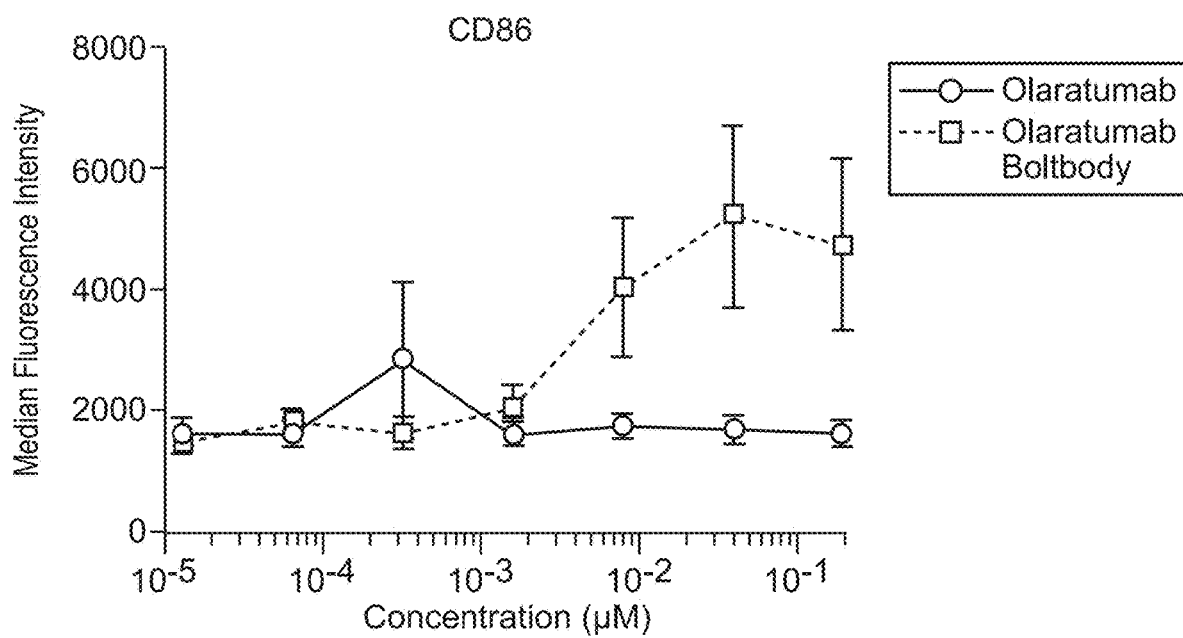

FIG. 78K shows that the olaratumab immunoconjugate produced according to the BB-01 method (Olaratumab Boltbody) is superior at eliciting CD86 upregulation on myeloid cells as compared to the unconjugated olaratumab (Lilly) following 18 hours of stimulation.

Figure 79A:
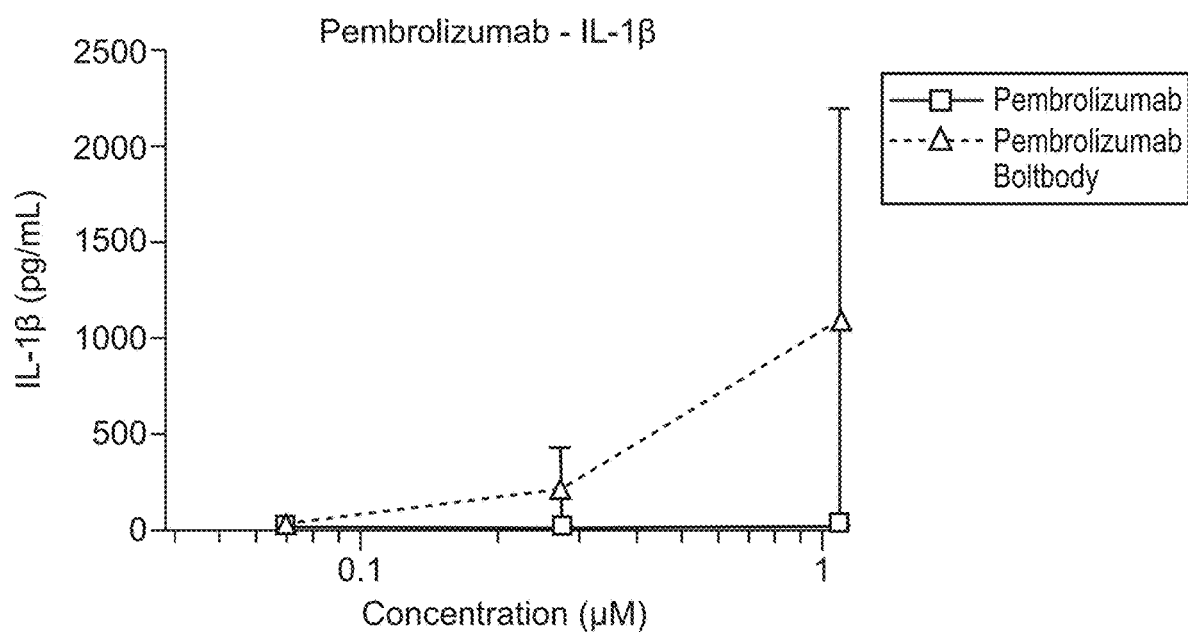

FIG. 79A shows that the pembrolizumab immunoconjugate produced according to the BB-01 method (Pembrolizumab Boltbody) elicits superior IL-1β secretion from myeloid cells as compared to equimolar concentrations of unconjugated pembrolizumab (Merck) following 36 hours of stimulation.

Figure 79B:
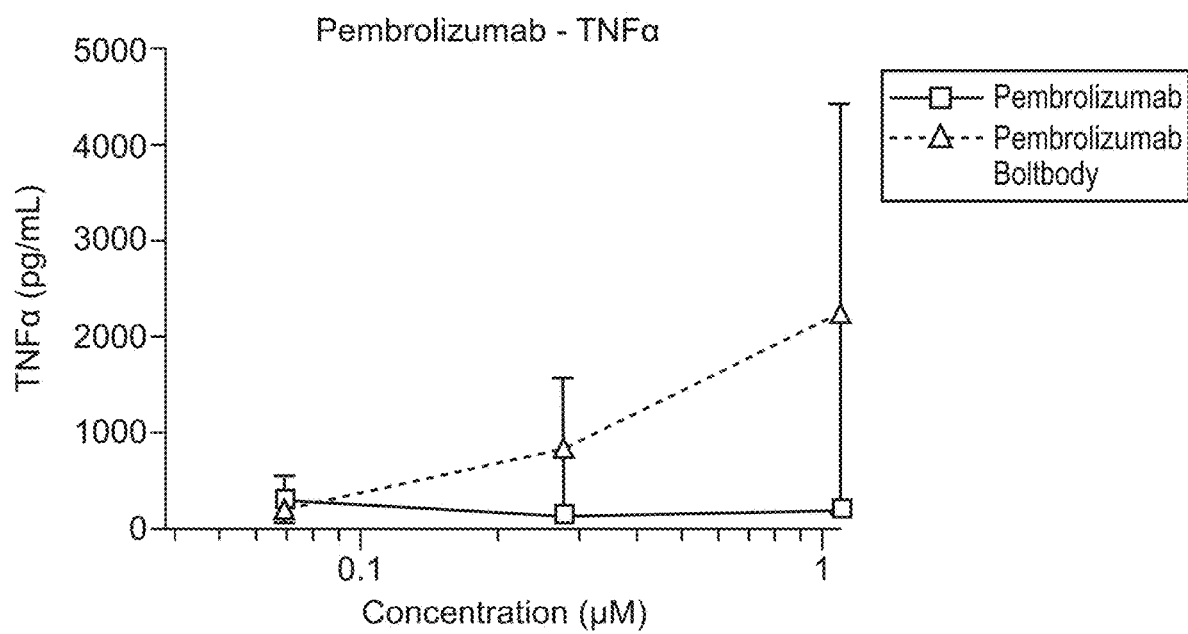

FIG. 79B shows that the pembrolizumab immunoconjugate produced according to the BB-01 method (Pembrolizumab Boltbody) elicits superior TNFα secretion from myeloid cells as compared to equimolar concentrations of unconjugated pembrolizumab (Merck) following 36 hours of stimulation.

Figure 79C:
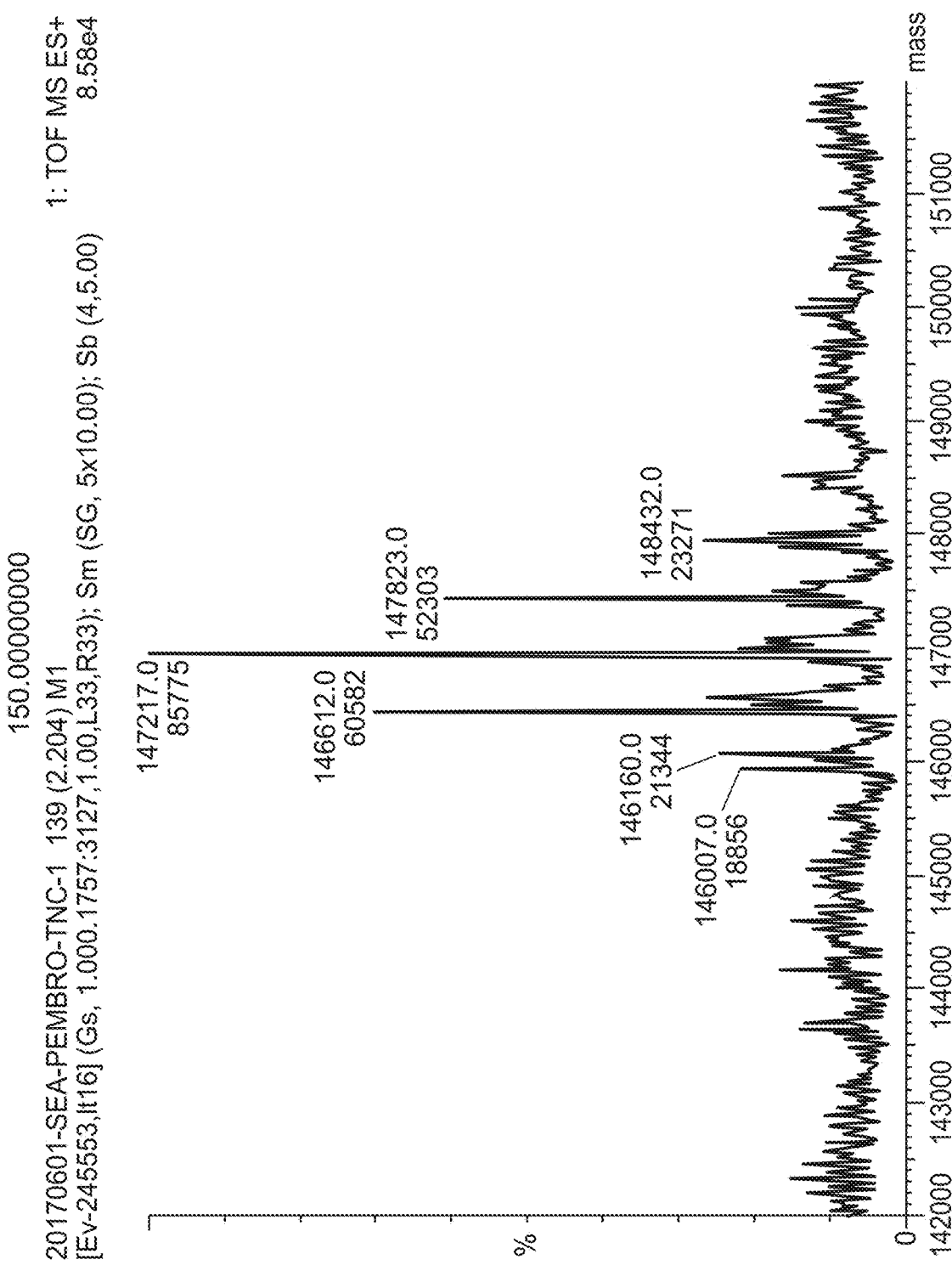

FIG. 79C shows a liquid chromatography-mass spectrometry analysis of the pembrolizumab immunoconjugate produced according to the BB-01 conjugation method following overnight deglycosylation with PNGase F.

Figure 79D:
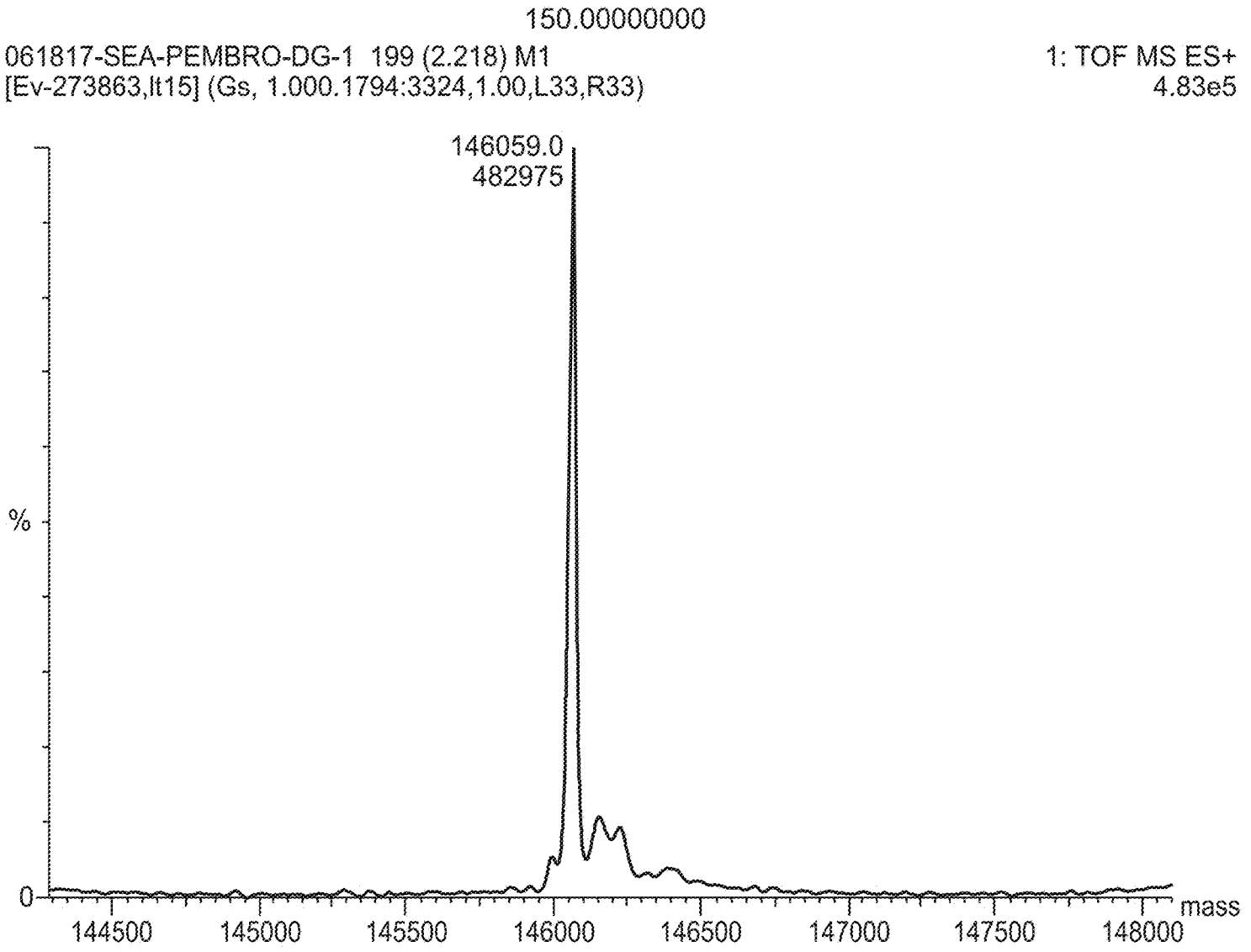

FIG. 79D shows a liquid chromatography-mass spectrometry analysis of unconjugated pembrolizumab (Merck) that was utilized to produce the pembrolizumab immunoconjugate according to the BB-01 conjugation method following overnight deglycosylation with PNGase F.

Figure 79E:
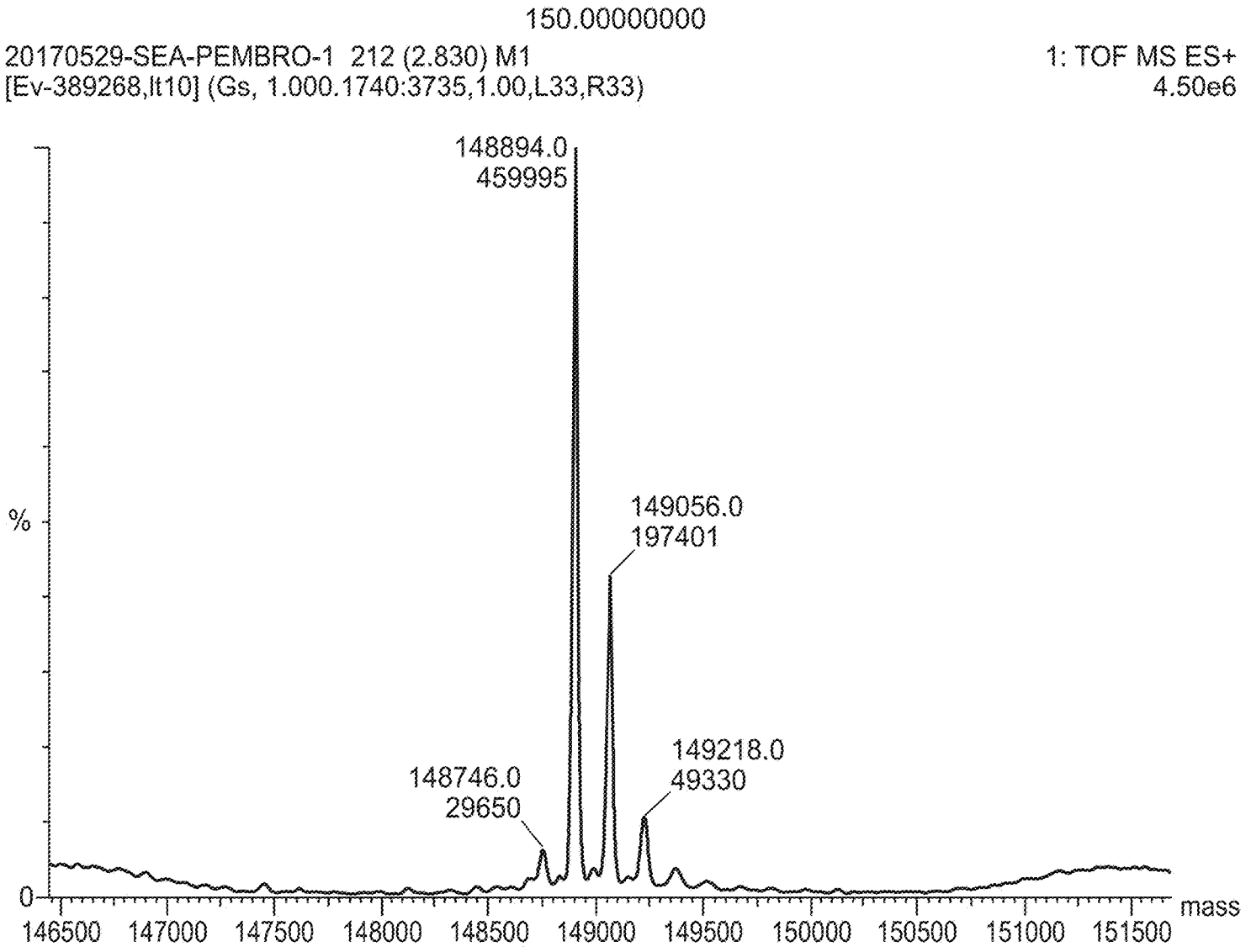

FIG. 79E shows a liquid chromatography-mass spectrometry analysis of unconjugated pembrolizumab (Merck) that was utilized to produce the pembrolizumab immunoconjugate according to the BB-01 conjugation method.

Figure 79F:
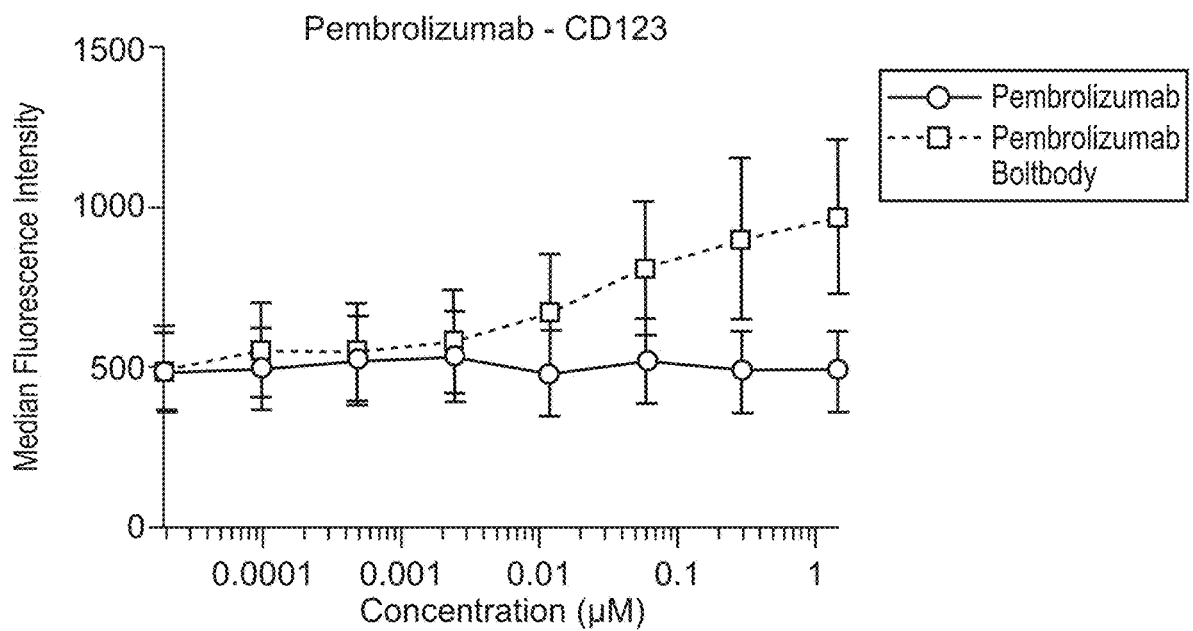

FIG. 79F shows that the pembrolizumab immunoconjugate produced according to the BB-01 method (Pembrolizumab Boltbody) is superior at eliciting CD123 upregulation on myeloid cells as compared to the unconjugated pembrolizumab (Merck) following 18 hours of stimulation.

Figure 79G:
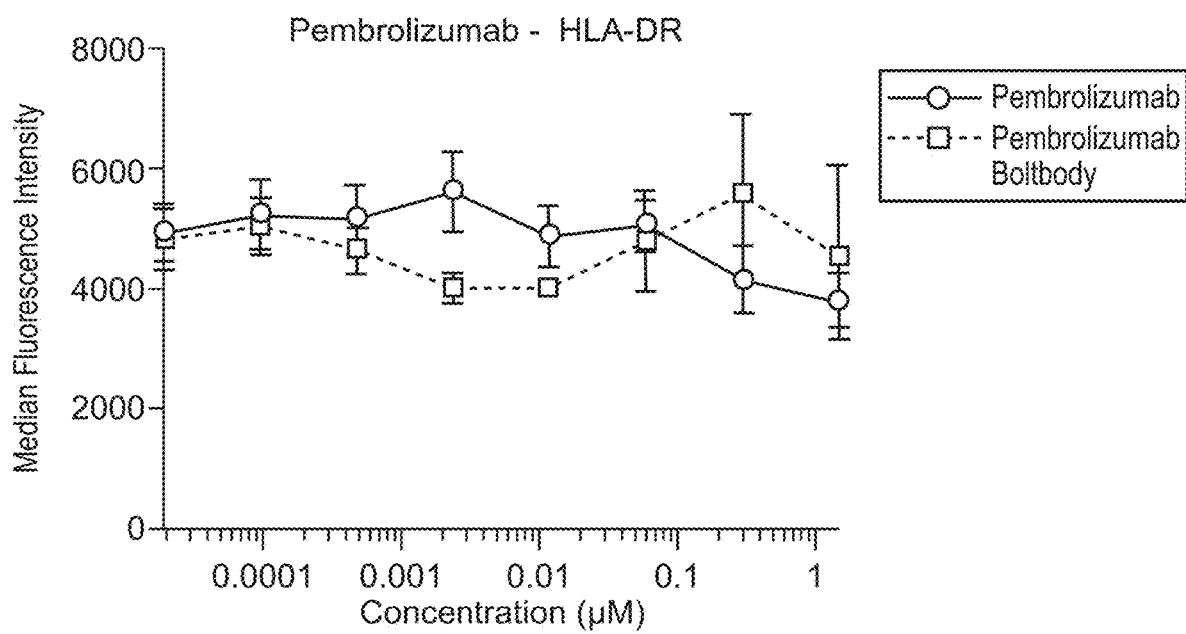

FIG. 79G shows that the pembrolizumab immunoconjugate produced according to the BB-01 method (Pembrolizumab Boltbody) is superior at eliciting HLA-DR upregulation on myeloid cells as compared to the unconjugated pembrolizumab (Merck) following 18 hours of stimulation.

Figure 79H:
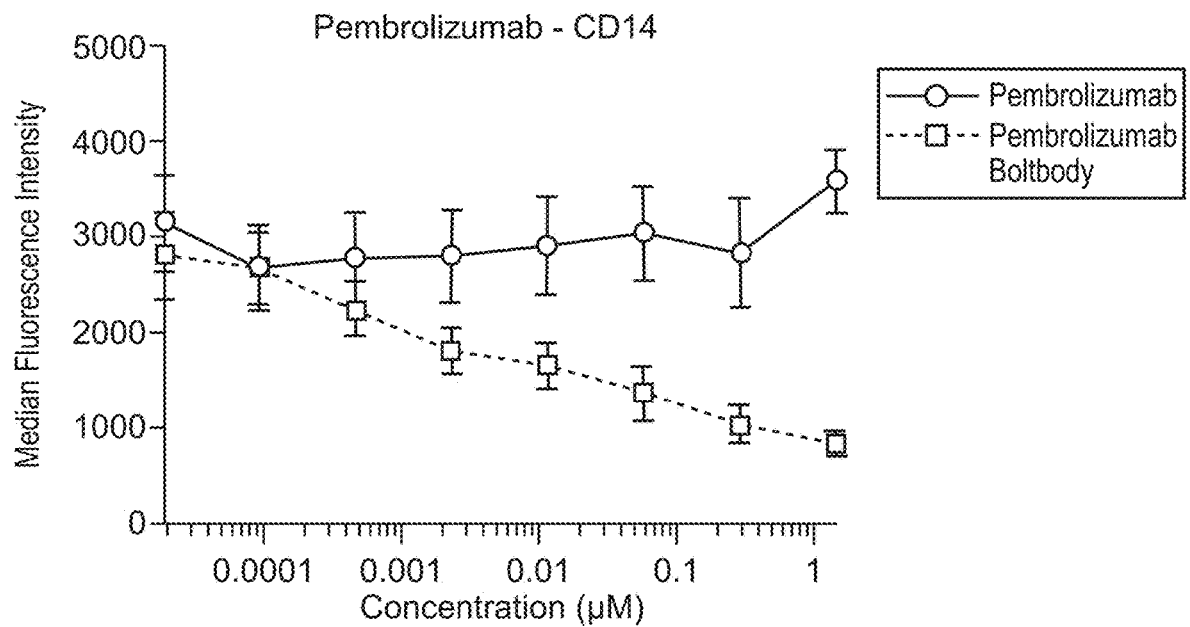

FIG. 79H shows that the pembrolizumab immunoconjugate produced according to the BB-01 method (Pembrolizumab Boltbody) is superior at eliciting CD14 downregulation on myeloid cells as compared to the unconjugated pembrolizumab (Merck) following 18 hours of stimulation.

Figure 79I:
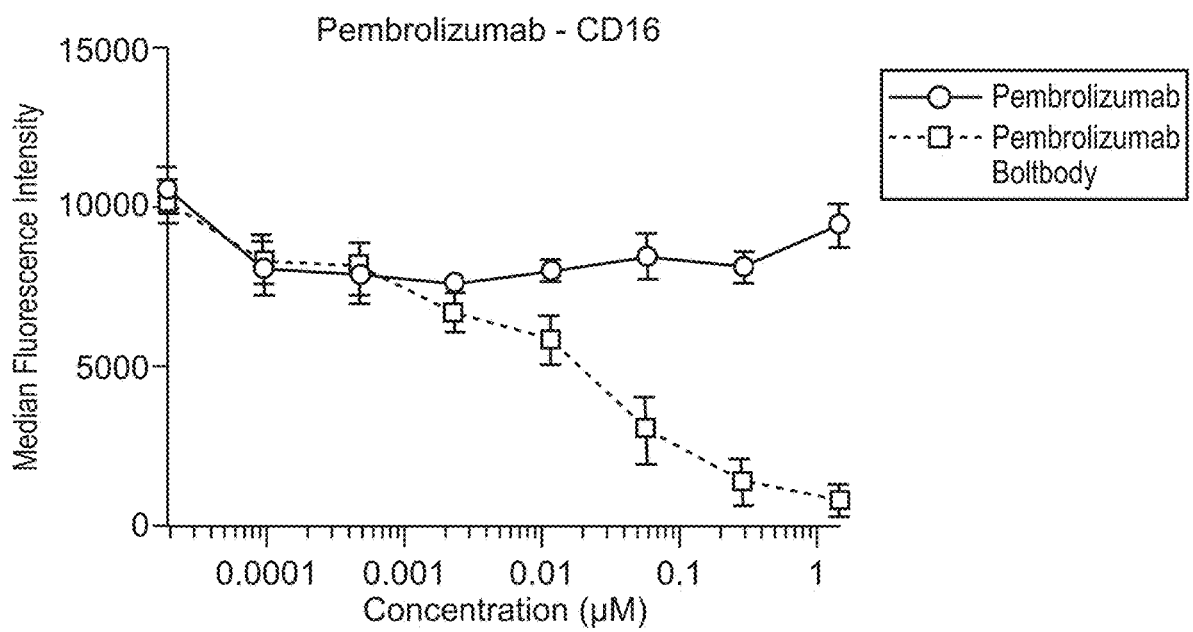

FIG. 79I shows that the pembrolizumab immunoconjugate produced according to the BB-01 method (Pembrolizumab Boltbody) is superior at eliciting CD16 downregulation on myeloid cells as compared to the unconjugated pembrolizumab (Merck) following 18 hours of stimulation.

Figure 79J:
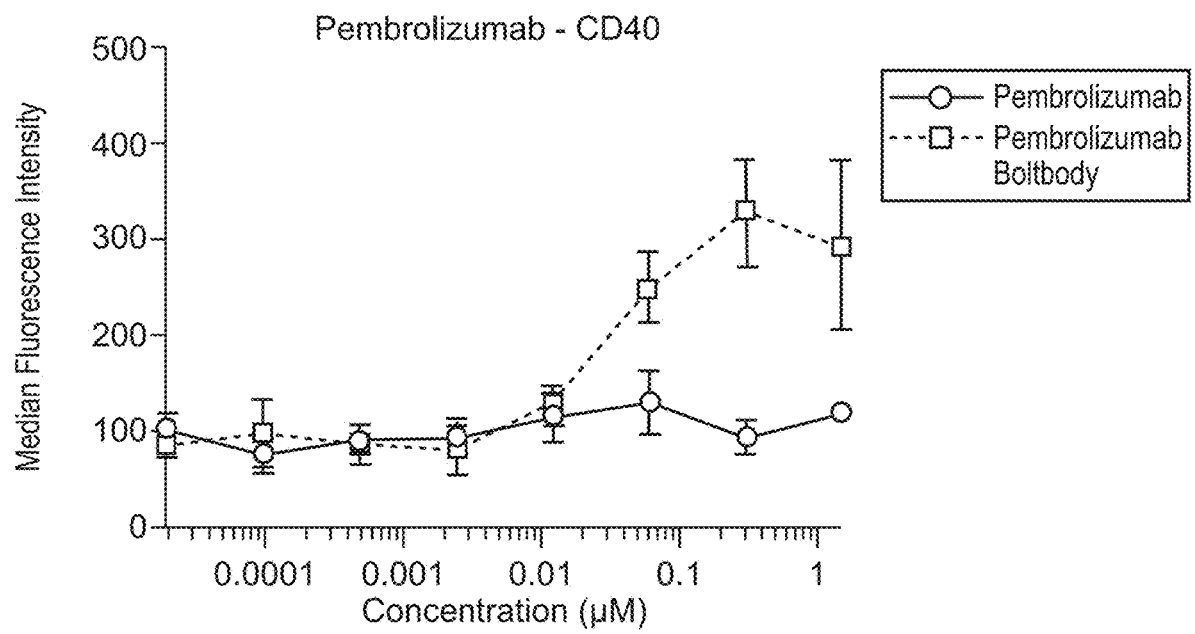

FIG. 79J shows that the pembrolizumab immunoconjugate produced according to the BB-01 method (Pembrolizumab Boltbody) is superior at eliciting CD40 upregulation on myeloid cells as compared to the unconjugated pembrolizumab (Merck) following 18 hours of stimulation.

Figure 79K:
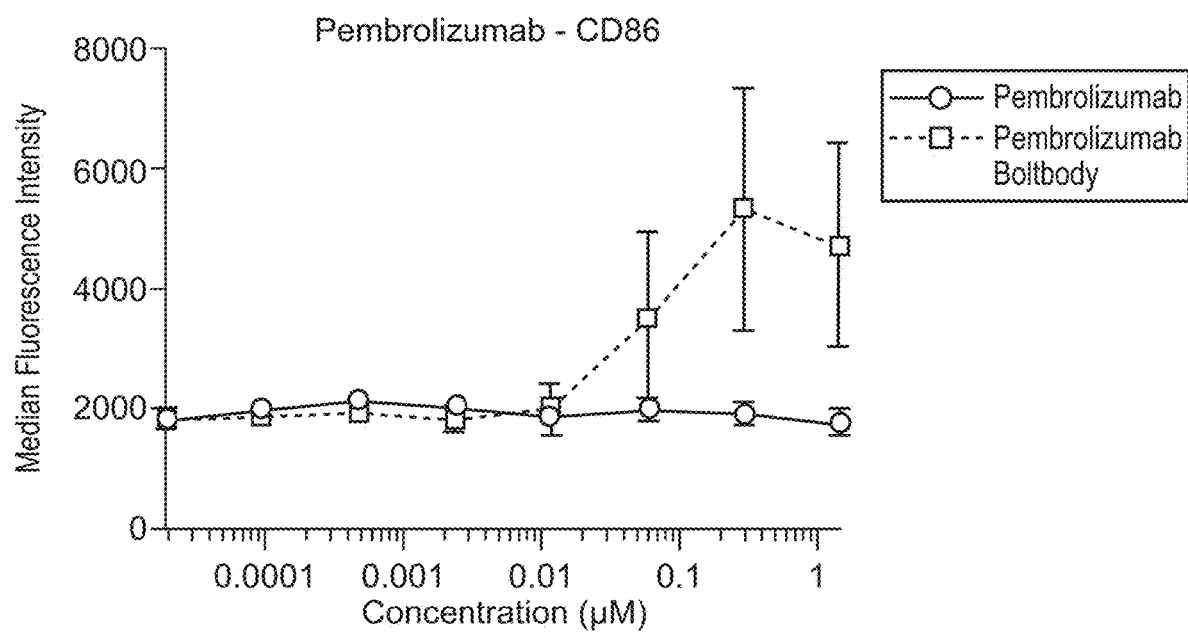

FIG. 79K shows that the pembrolizumab immunoconjugate produced according to the BB-01 method (Pembrolizumab Boltbody) is superior at eliciting CD86 upregulation on myeloid cells as compared to the unconjugated pembrolizumab (Merck) following 18 hours of stimulation.

Figure 80A:
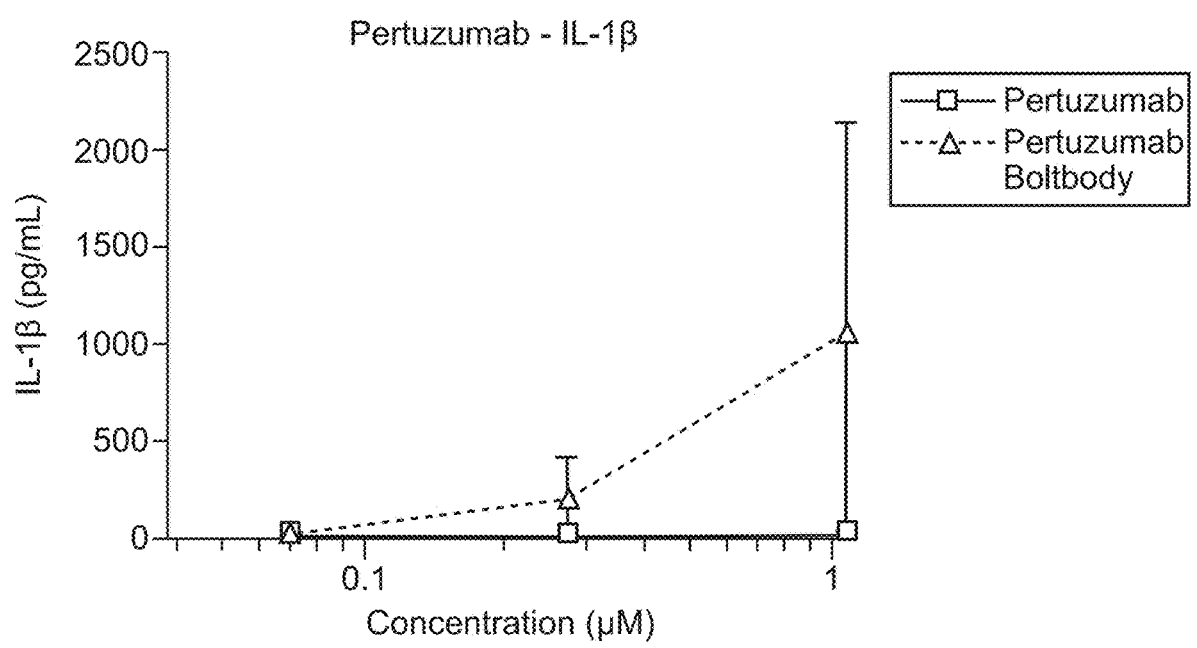

FIG. 80A shows that the pertuzumab immunoconjugate produced according to the BB-01 method (Pertuzumab Boltbody) elicits superior IL-10 secretion from myeloid cells as compared to equimolar concentrations of unconjugated pertuzumab (Roche) following 18 hours of stimulation.

Figure 80B:
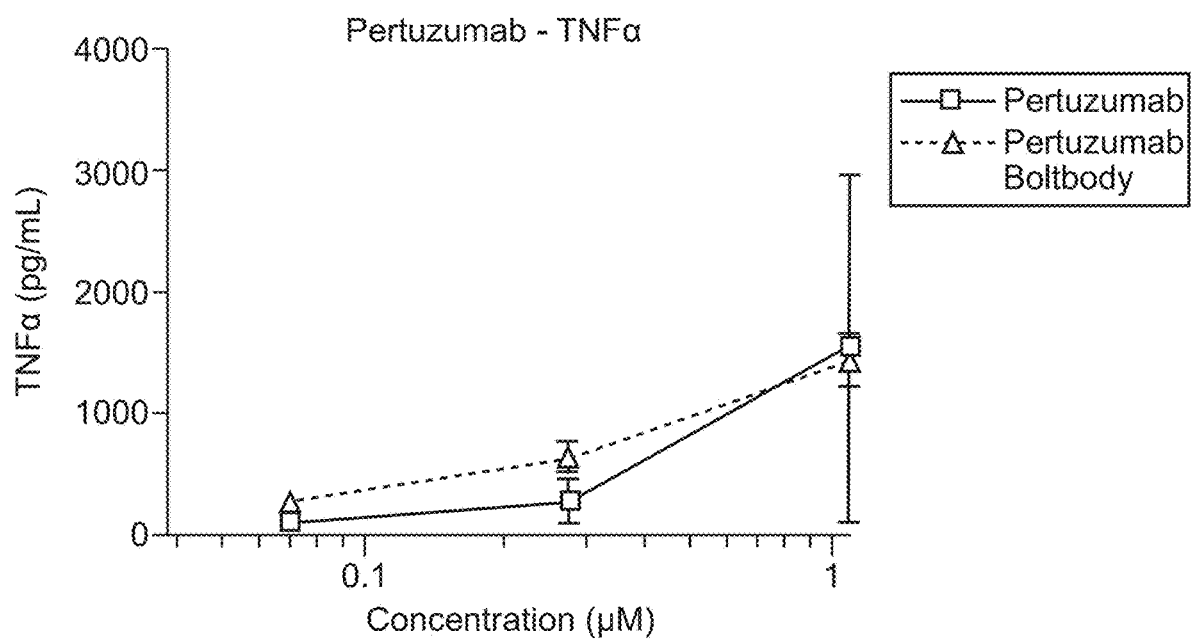

FIG. 80B shows that the pertuzumab immunoconjugate produced according to the BB-01 method (Pertuzumab Boltbody) elicits superior TNFα secretion from myeloid cells as compared to equimolar concentrations of unconjugated pertuzumab (Roche) following 18 hours of stimulation.

Figure 80C:
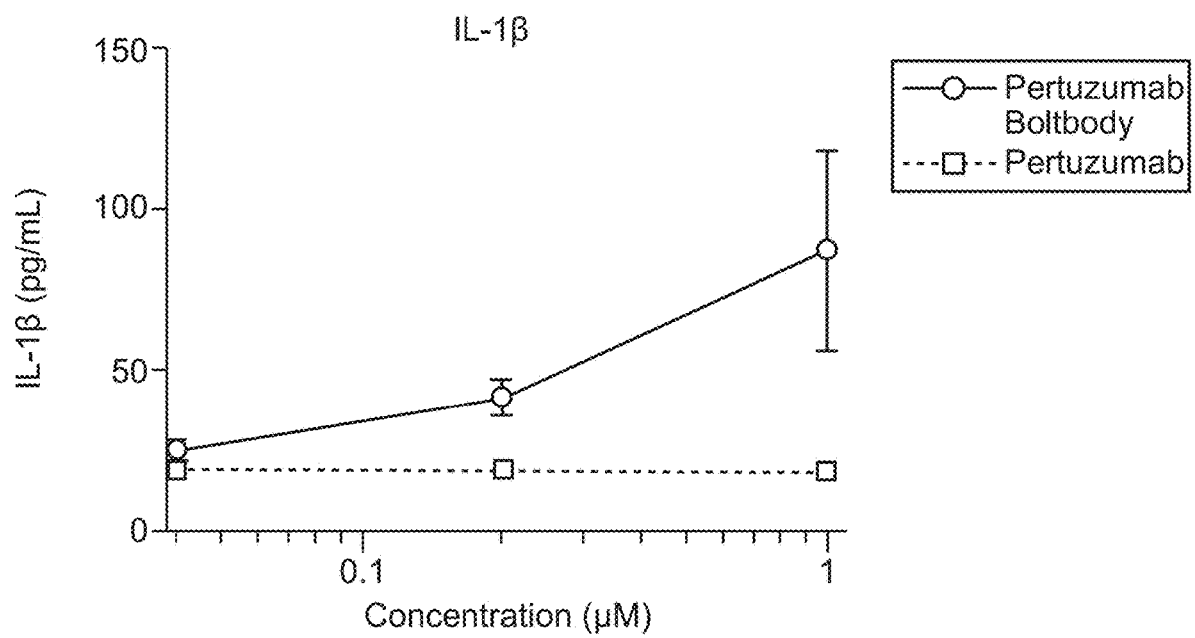

FIG. 80C shows that the pertuzumab immunoconjugate produced according to the BB-01 method (Pertuzumab Boltbody) elicits superior IL-10 secretion from myeloid cells as compared to equimolar concentrations of unconjugated pertuzumab (Roche) following 36 hours of stimulation.

Figure 80D:
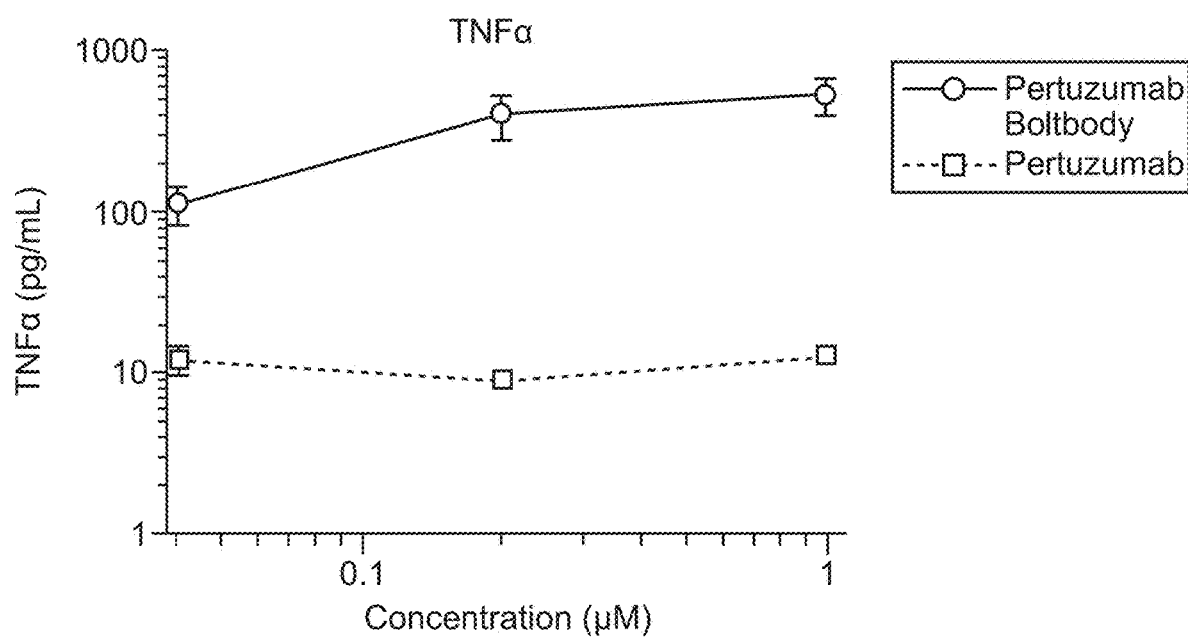

FIG. 80D shows that the pertuzumab immunoconjugate produced according to the BB-01 method (Pertuzumab Boltbody) elicits superior TNFα secretion from myeloid cells as compared to equimolar concentrations of unconjugated pertuzumab (Roche) following 36 hours of stimulation.

Figure 80E:
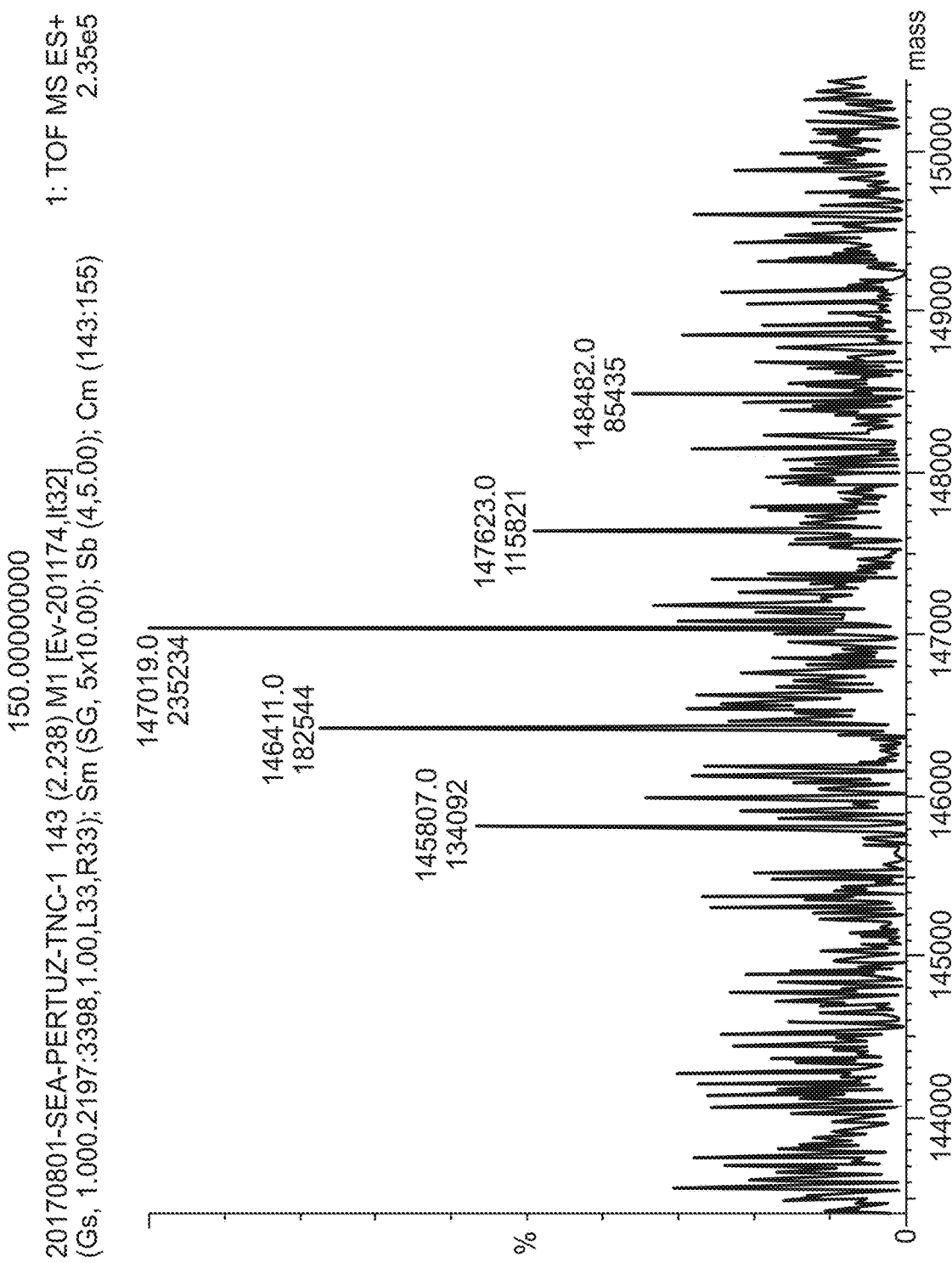

FIG. 80E shows a liquid chromatography-mass spectrometry analysis of the pertuzumab immunoconjugate produced according to the BB-01 conjugation method following overnight deglycosylation with PNGase F.

Figure 80F:
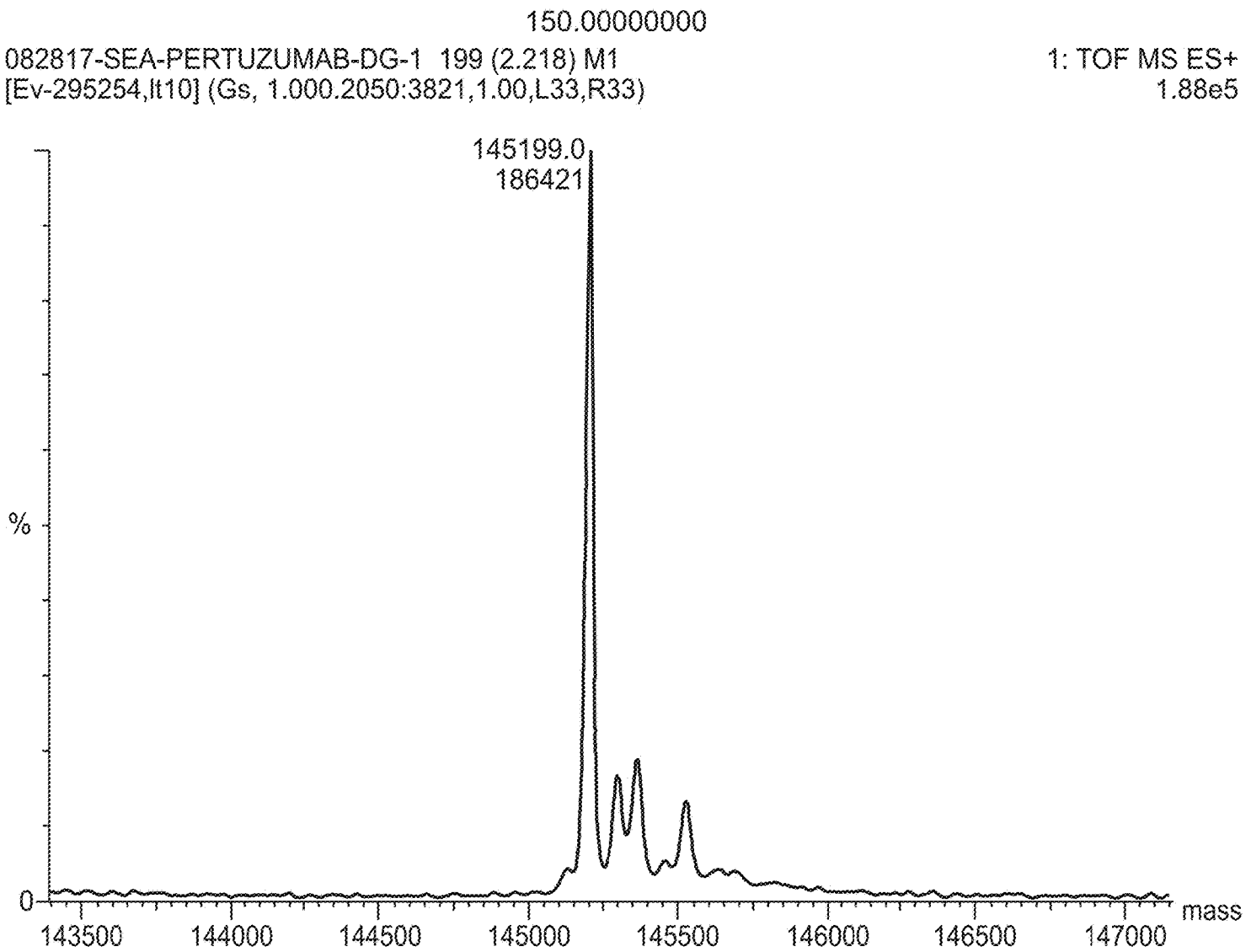

FIG. 80F shows a liquid chromatography-mass spectrometry analysis of unconjugated pertuzumab (Roche) that was utilized to produce the pertuzumab immunoconjugate according to the BB-01 conjugation method following overnight deglycosylation with PNGase F.

FIG. 80G shows a liquid chromatography-mass spectrometry analysis of unconjugated pertuzumab (Roche) that was utilized to produce the pertuzumab immunoconjugate according to the BB-01 conjugation method.

Figure 80H:
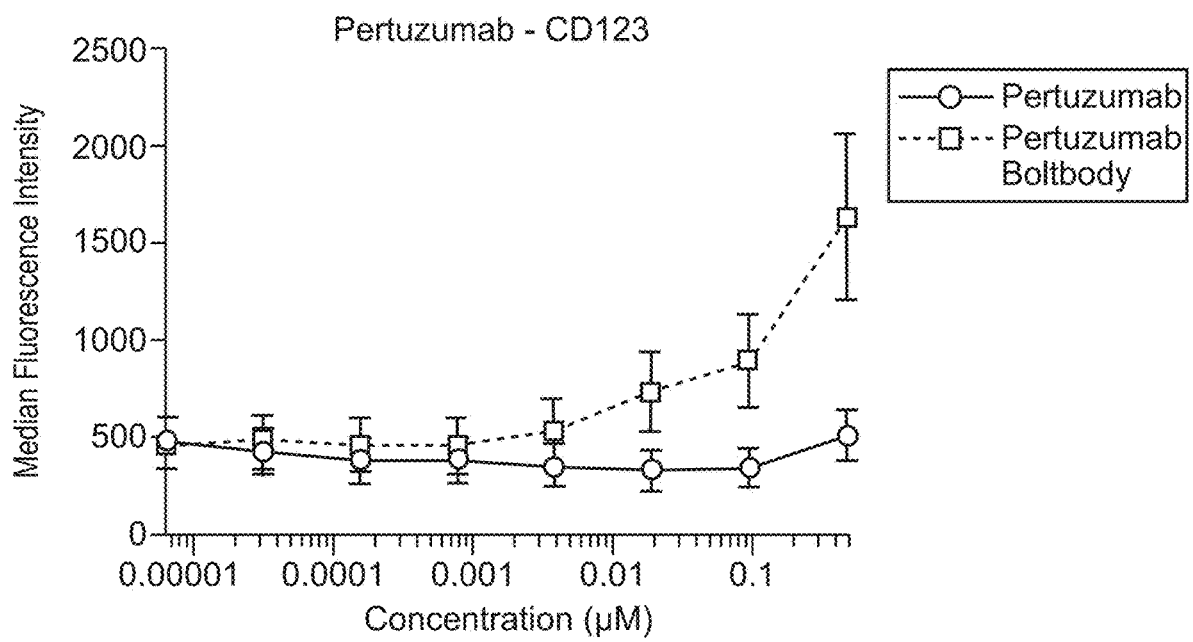

FIG. 80H shows that the pertuzumab immunoconjugate produced according to the BB-01 method (Pertuzumab Boltbody) is superior at eliciting CD123 upregulation on myeloid cells as compared to the unconjugated pertuzumab (Roche) following 18 hours of stimulation.

Figure 80I:
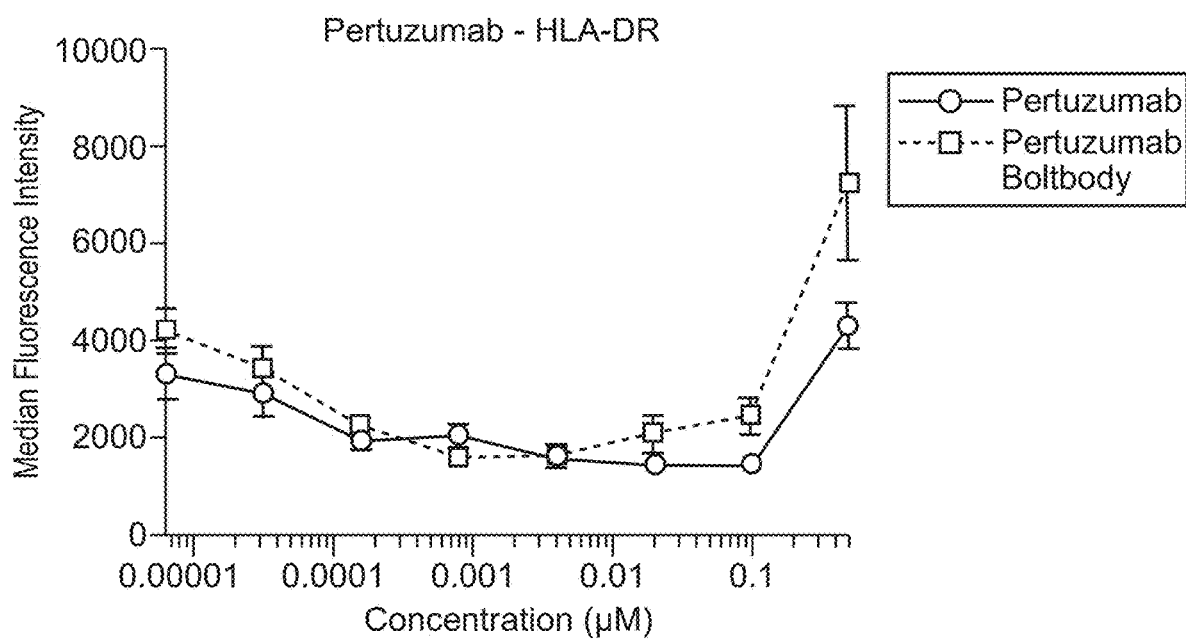

FIG. 80I shows that the pertuzumab immunoconjugate produced according to the BB-01 method (Pertuzumab Boltbody) is superior at eliciting HLA-DR upregulation on myeloid cells as compared to the unconjugated pertuzumab (Roche) following 18 hours of stimulation.

Figure 80J:
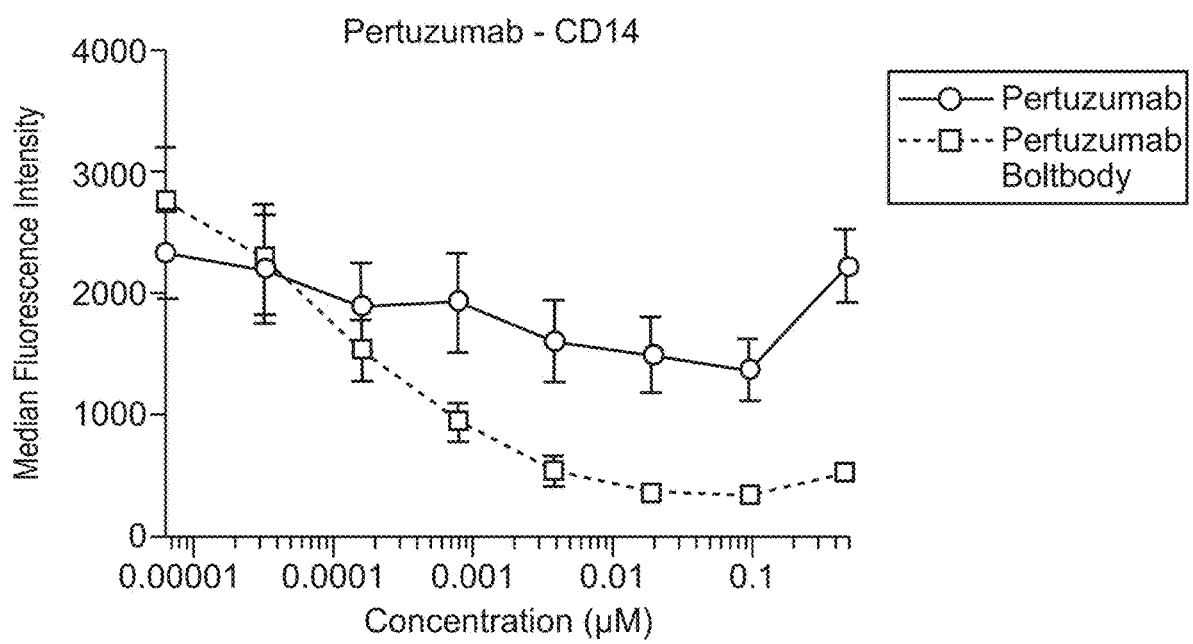

FIG. 80J shows that the pertuzumab immunoconjugate produced according to the BB-01 method (Pertuzumab Boltbody) is superior at eliciting CD14 downregulation on myeloid cells as compared to the unconjugated pertuzumab (Roche) following 18 hours of stimulation.

Figure 80K:
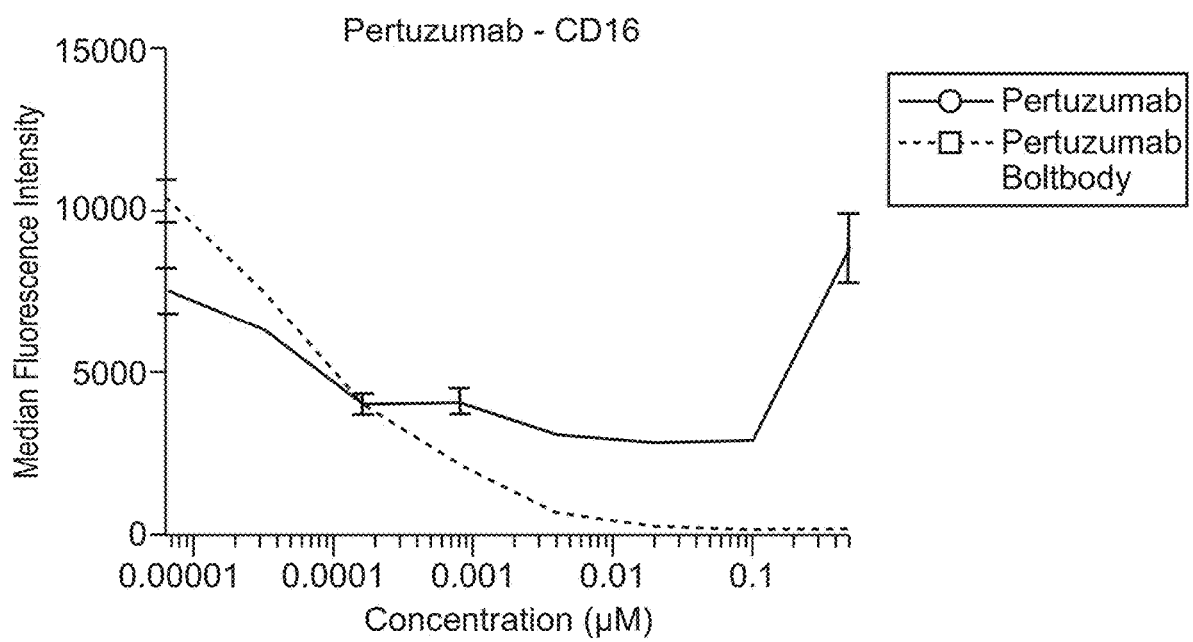

FIG. 80K shows that the pertuzumab immunoconjugate produced according to the BB-01 method (Pertuzumab Boltbody) is superior at eliciting CD16 downregulation on myeloid cells as compared to the unconjugated pertuzumab (Roche) following 18 hours of stimulation.

Figure 80L:
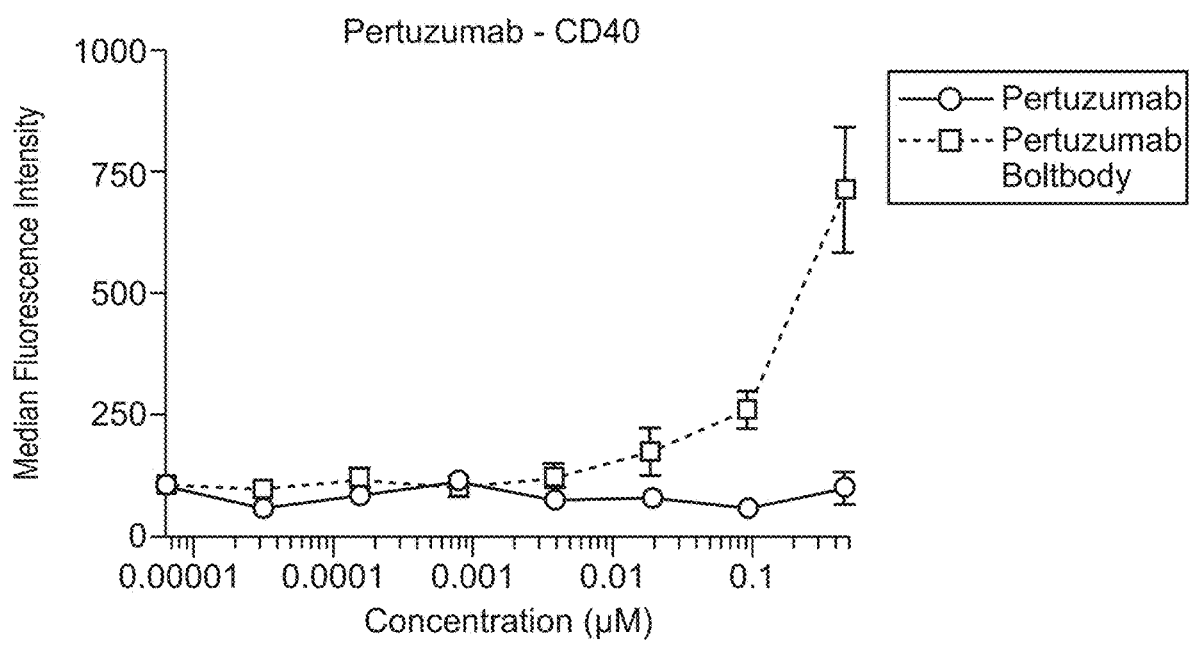

FIG. 80L shows that the pertuzumab immunoconjugate produced according to the BB-01 method (Pertuzumab Boltbody) is superior at eliciting CD40 upregulation on myeloid cells as compared to the unconjugated pertuzumab (Roche) following 18 hours of stimulation.

Figure 80M:
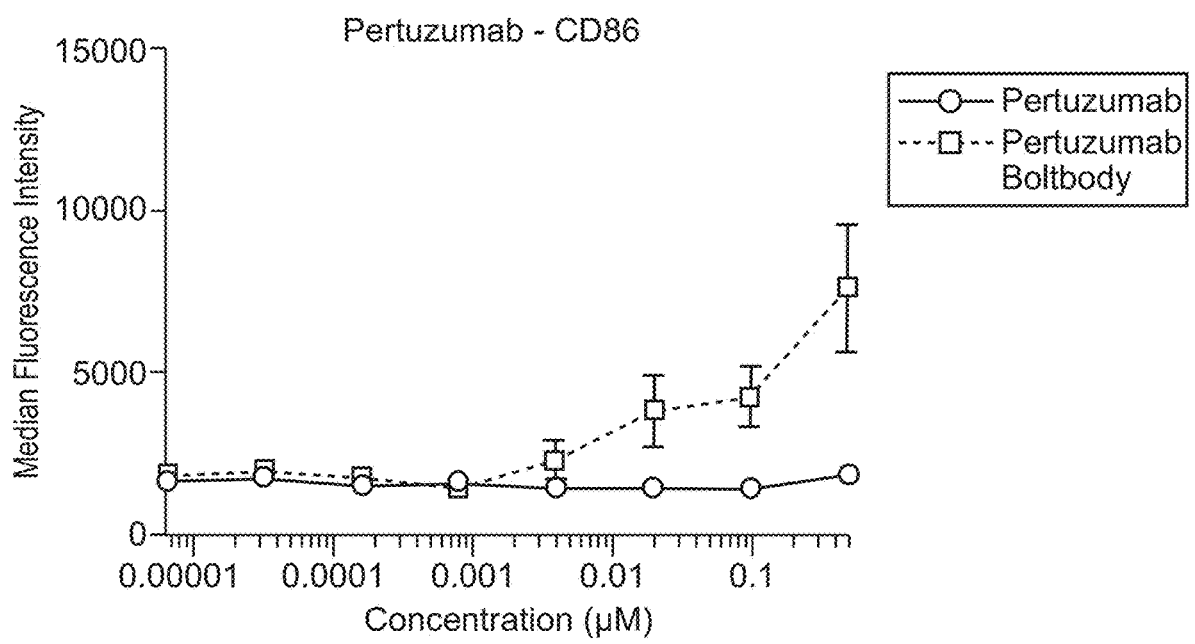

FIG. 80M shows that the pertuzumab immunoconjugate produced according to the BB-01 method (Pertuzumab Boltbody) is superior at eliciting CD86 upregulation on myeloid cells as compared to the unconjugated pertuzumab (Roche) following 18 hours of stimulation.

Figure 81A:
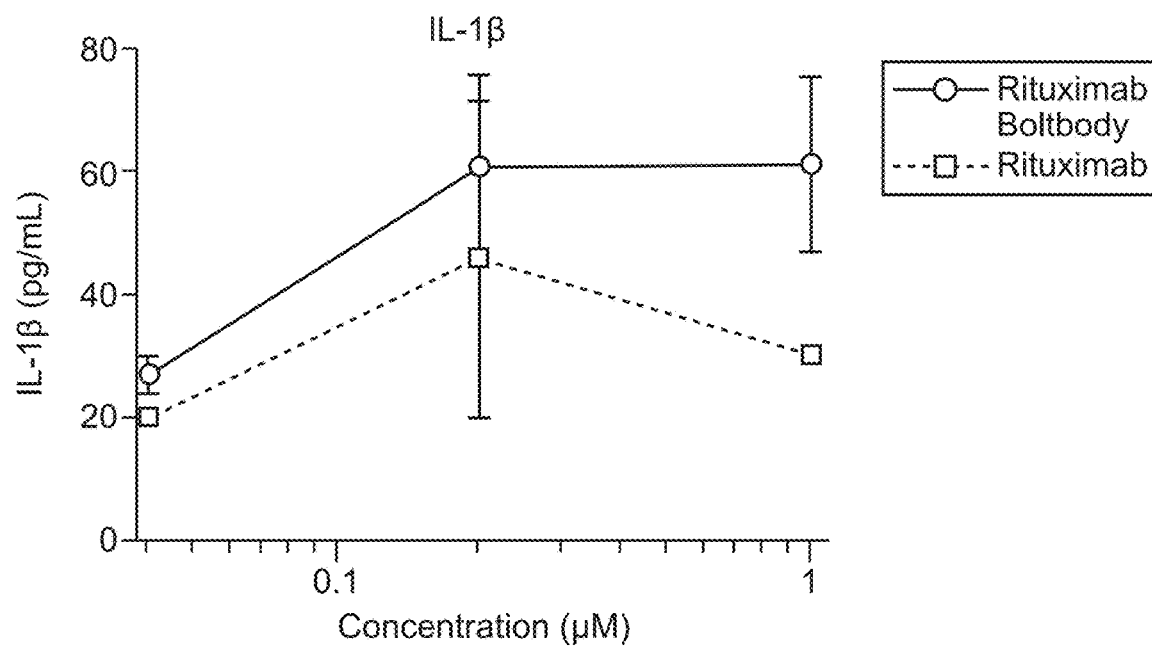

FIG. 81A shows that the rituximab immunoconjugate produced according to the BB-01 method (Rituximab Boltbody) elicits superior IL-1β secretion from myeloid cells as compared to equimolar concentrations of unconjugated rituximab (Roche) following 36 hours of stimulation.

Figure 81B:
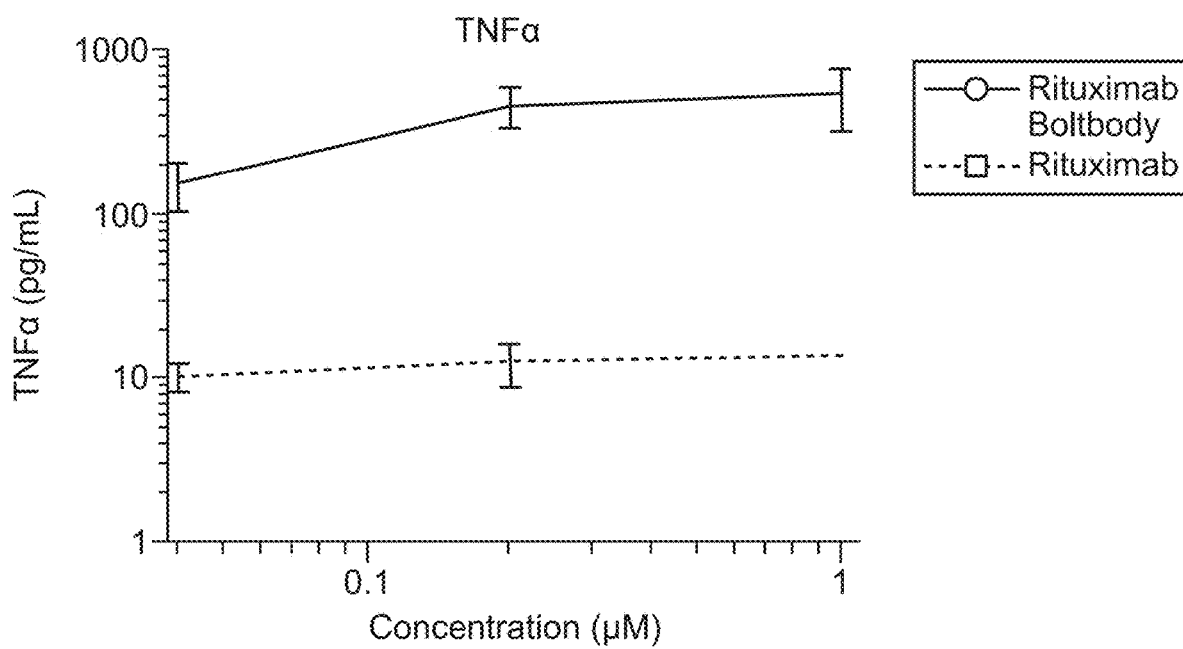

FIG. 81B shows that the rituximab immunoconjugate produced according to the BB-01 method (Rituximab Boltbody) elicits superior TNFα secretion from myeloid cells as compared to equimolar concentrations of unconjugated rituximab (Roche) following 36 hours of stimulation.

Figure 81C:
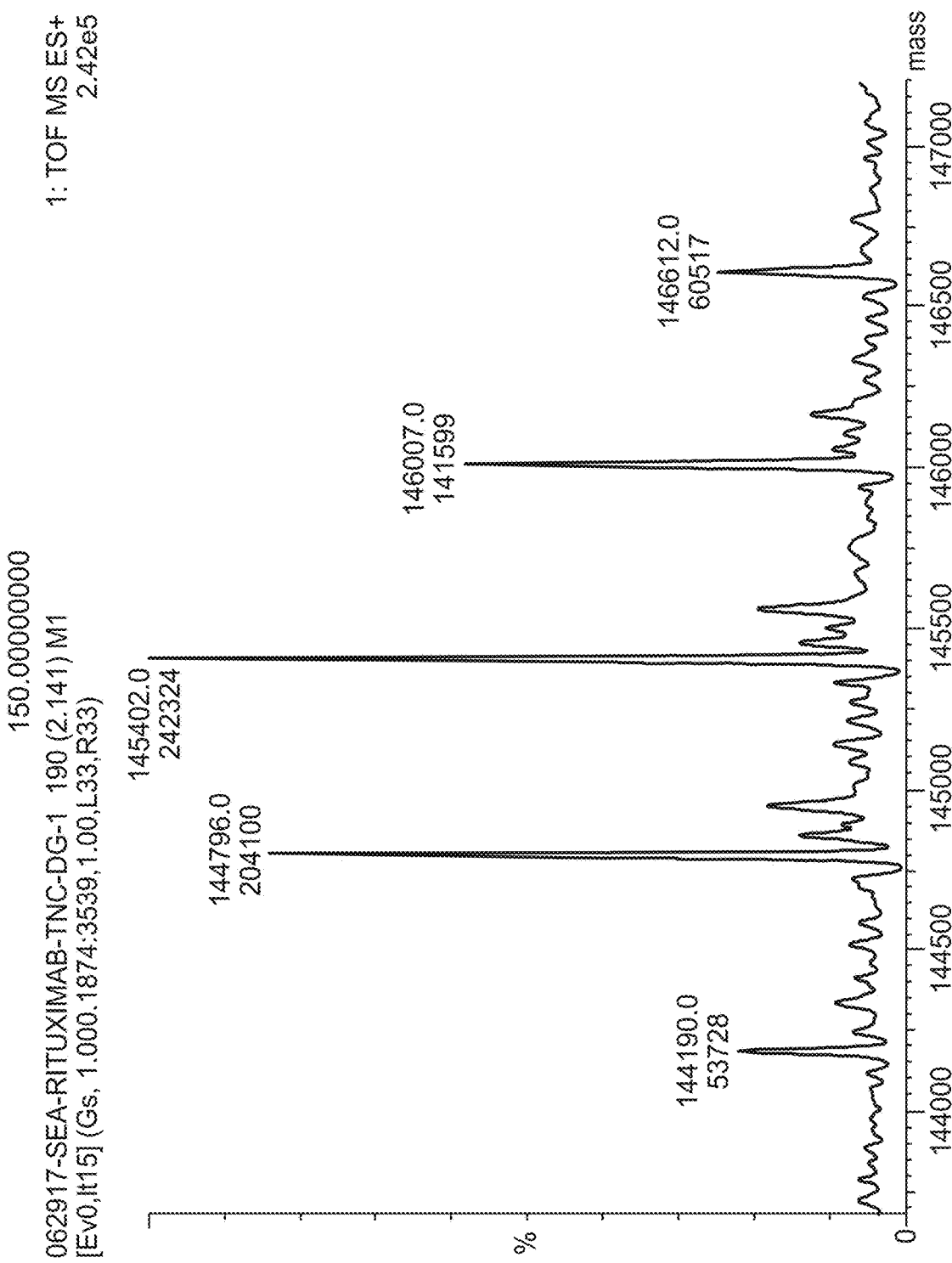

FIG. 81C shows a liquid chromatography-mass spectrometry analysis of the rituximab immunoconjugate produced according to the BB-01 conjugation method following overnight deglycosylation with PNGase F.

Figure 81D:
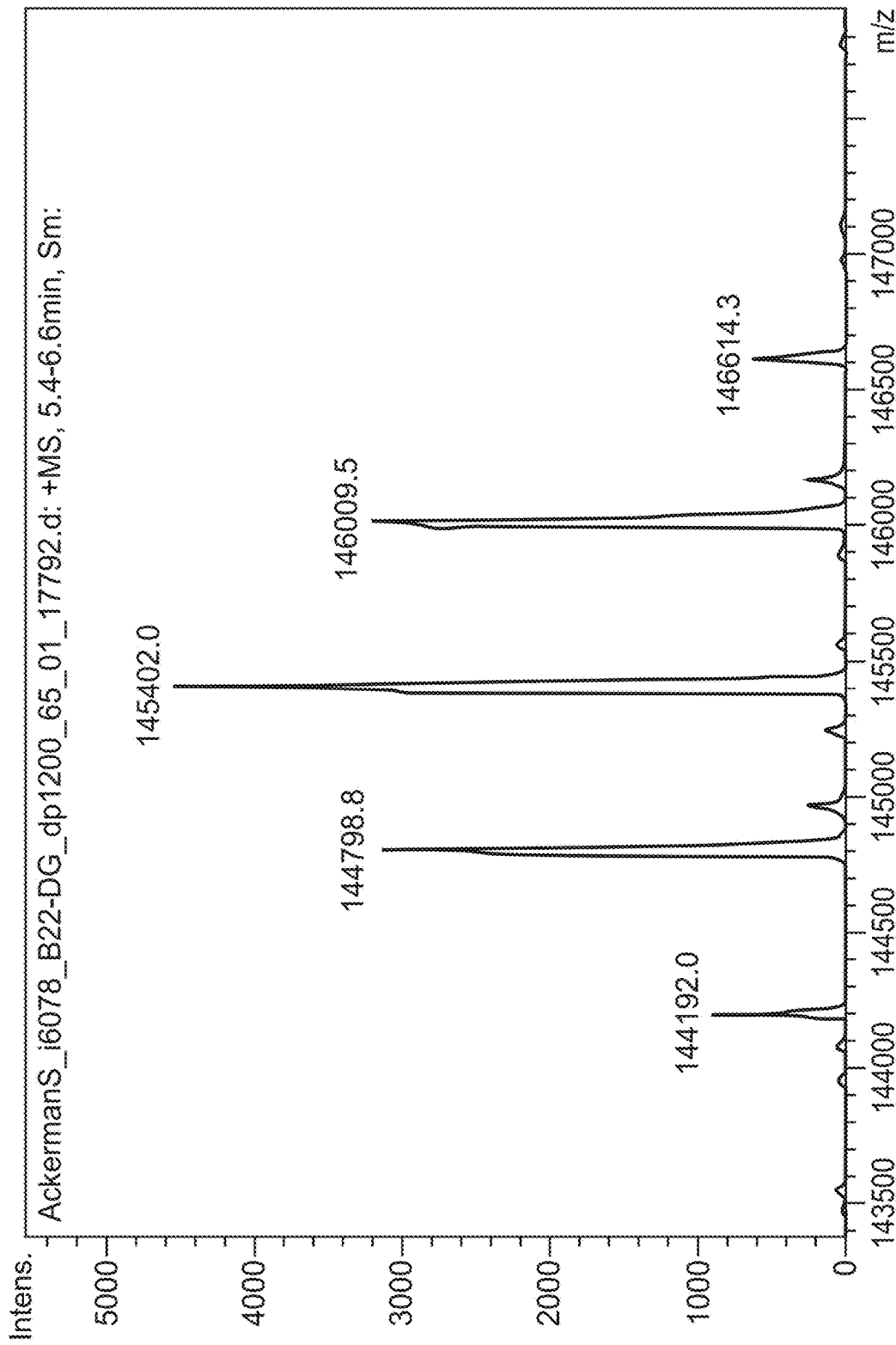

FIG. 81D shows a liquid chromatography-mass spectrometry analysis of the rituximab immunoconjugate produced according to the BB-01 conjugation method following overnight deglycosylation with PNGase F.

Figure 81E:
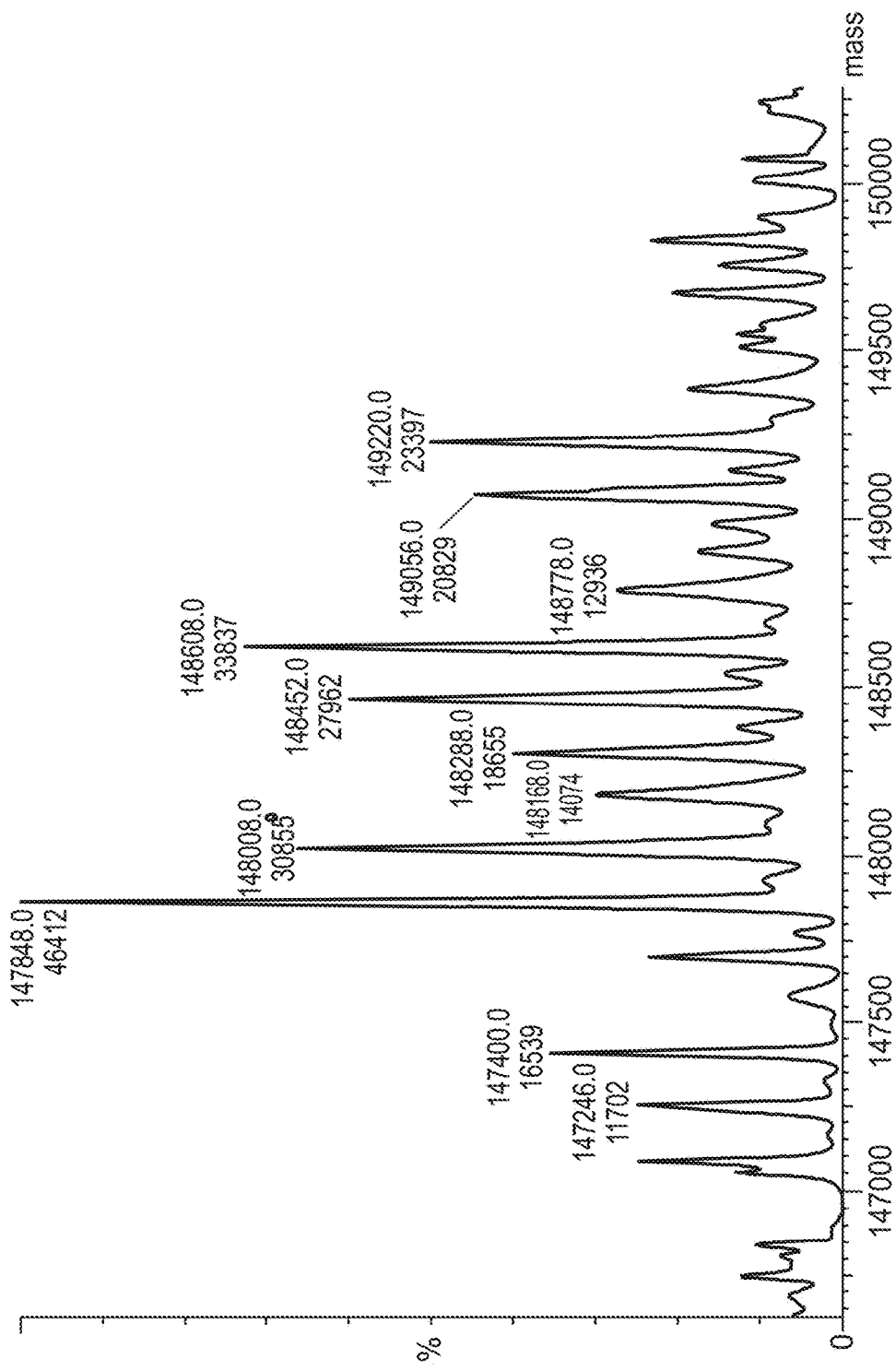

FIG. 81E shows a liquid chromatography-mass spectrometry analysis of the rituximab immunoconjugate produced according to the BB-01 conjugation method.

Figure 81F:
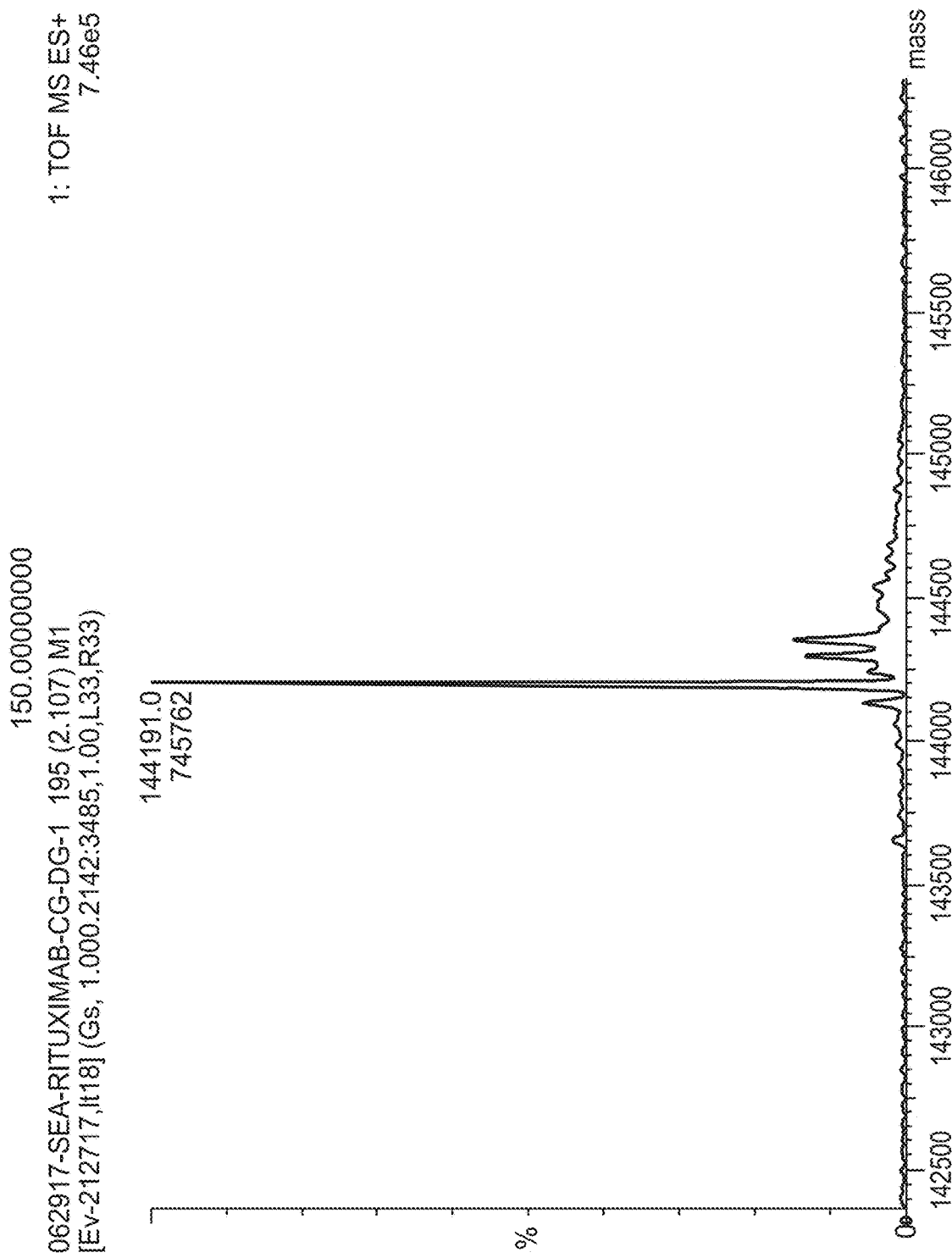

FIG. 81F shows a liquid chromatography-mass spectrometry analysis of unconjugated rituximab (Roche) that was utilized to produce the rituximab immunoconjugate according to the BB-01 conjugation method following overnight deglycosylation with PNGase F.

FIG. 81G shows a liquid chromatography-mass spectrometry analysis of unconjugated rituximab (Roche) that was utilized to produce the rituximab immunoconjugate according to the BB-01 conjugation method.

Figure 81H:
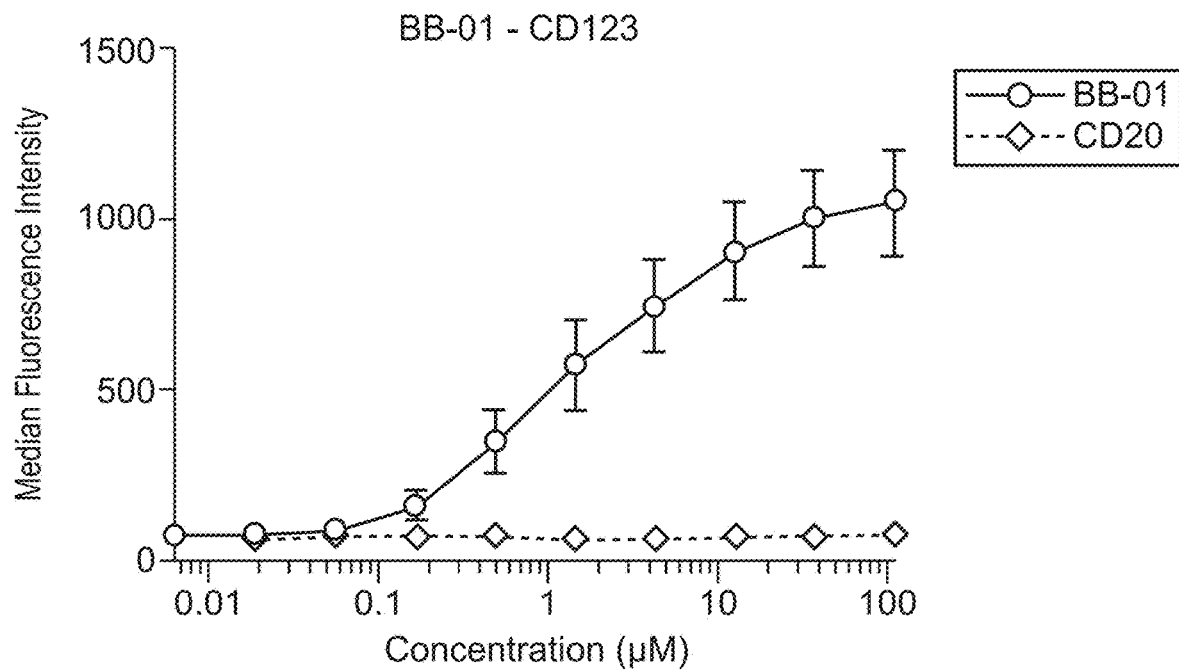

FIG. 81H shows that the rituximab immunoconjugate produced according to the BB-01 method (BB-01) is superior at eliciting CD123 upregulation on myeloid cells as compared to the unconjugated rituximab (CD20, Roche) following 18 hours of stimulation.

Figure 81I:
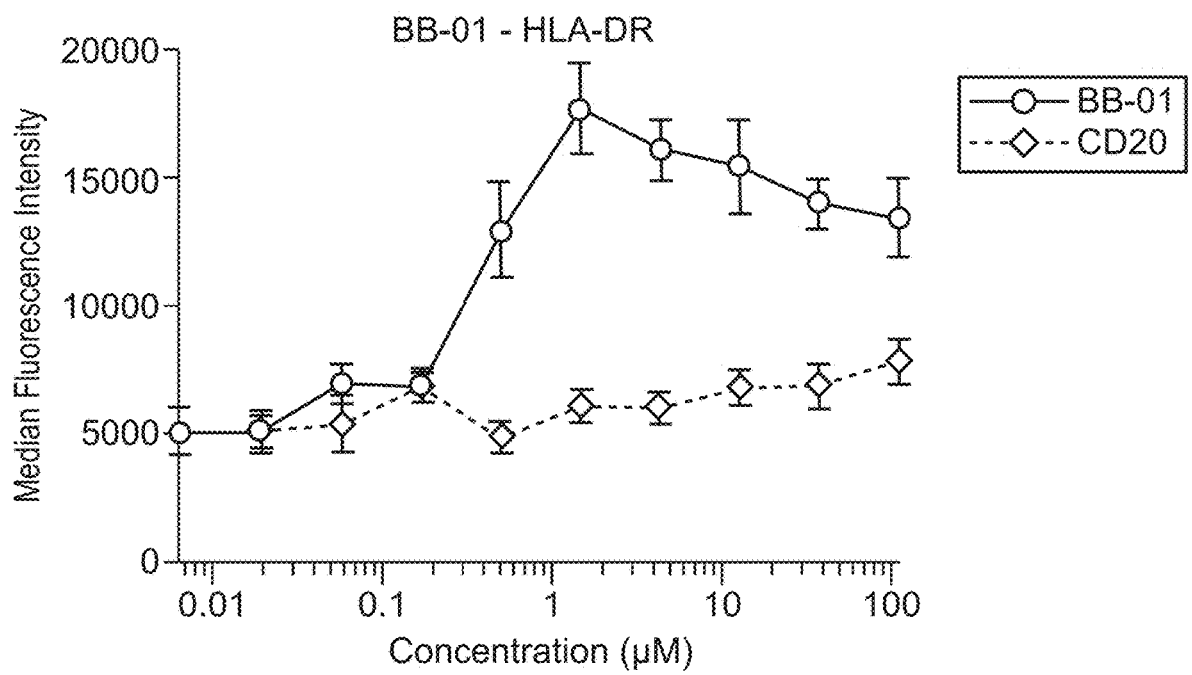

FIG. 81I shows that the rituximab immunoconjugate produced according to the BB-01 method (BB-01) is superior at eliciting HLA-DR upregulation on myeloid cells as compared to the unconjugated rituximab (CD20, Roche) following 18 hours of stimulation.

Figure 81J:
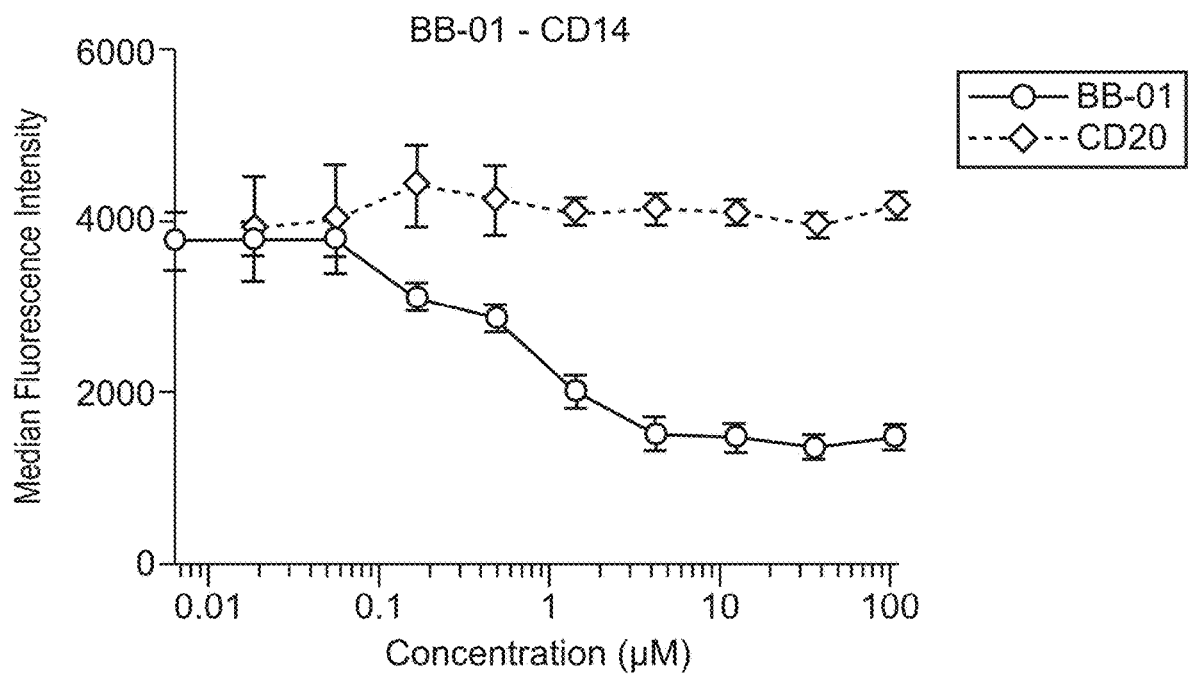

FIG. 81J shows that the rituximab immunoconjugate produced according to the BB-01 method (BB-01) is superior at eliciting CD14 downregulation on myeloid cells as compared to the unconjugated rituximab (CD20, Roche) following 18 hours of stimulation.

Figure 81K:
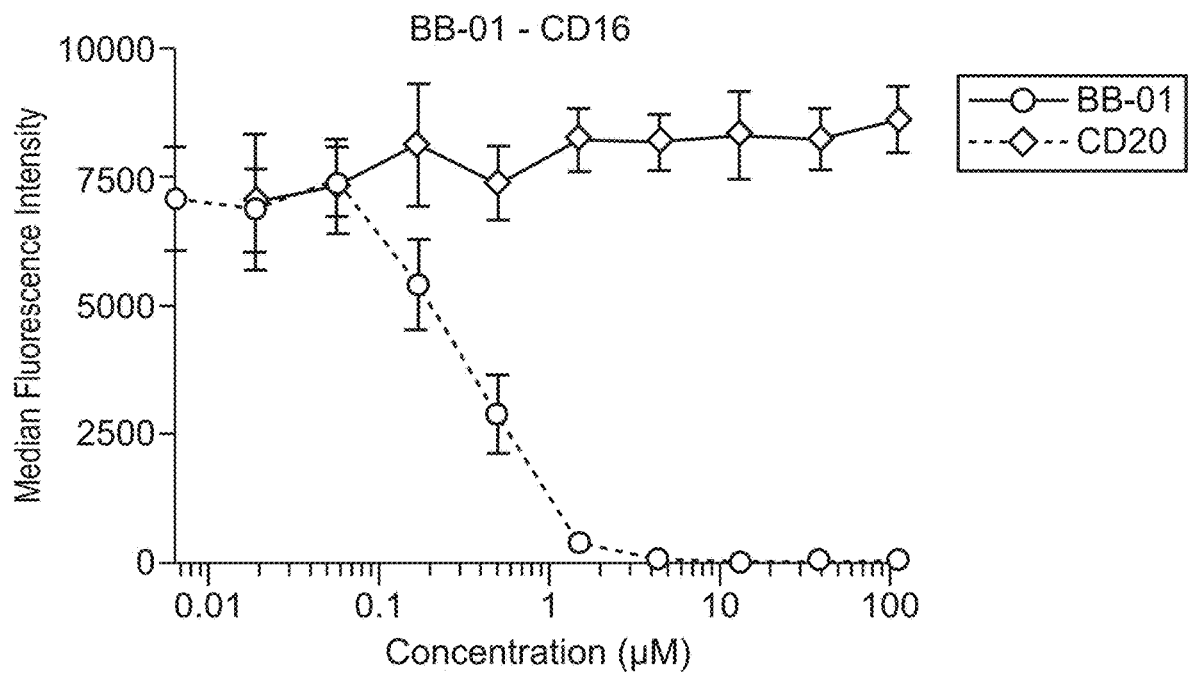

FIG. 81K shows that the rituximab immunoconjugate produced according to the BB-01 method (BB-01) is superior at eliciting CD16 downregulation on myeloid cells as compared to the unconjugated rituximab (CD20, Roche) following 18 hours of stimulation.

Figure 81L:
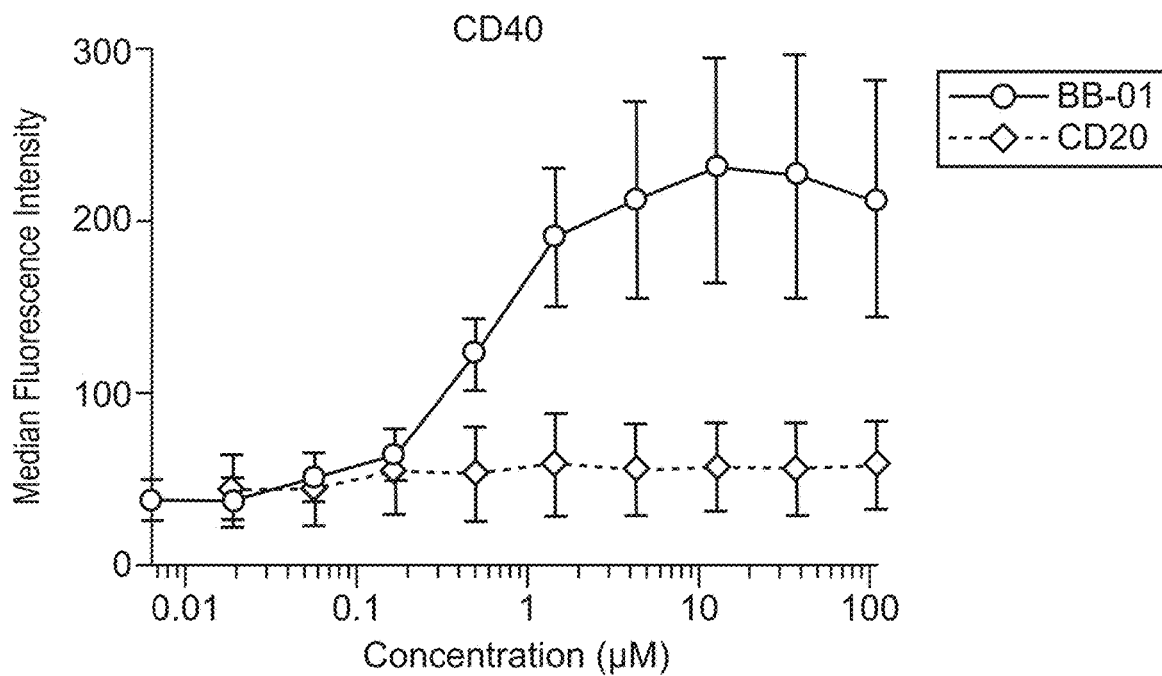

FIG. 81L shows that the rituximab immunoconjugate produced according to the BB-01 method (BB-01) is superior at eliciting CD40 upregulation on myeloid cells as compared to the unconjugated rituximab (CD20, Roche) following 18 hours of stimulation.

Figure 81M:
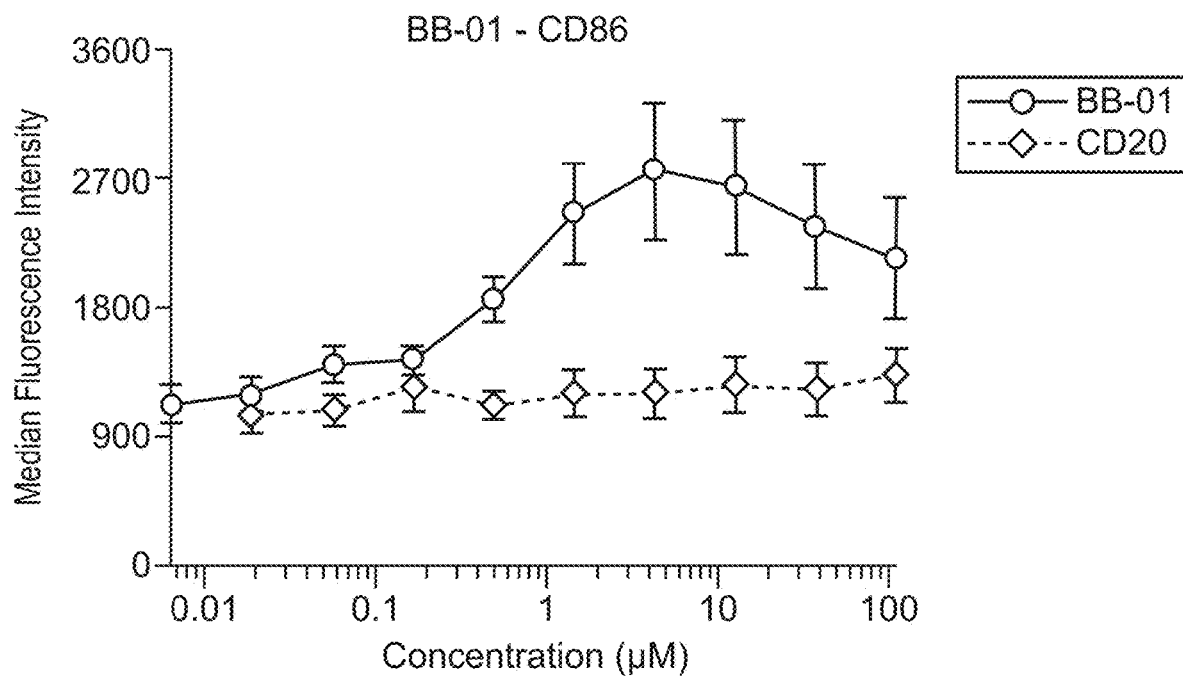

FIG. 81M shows that the rituximab immunoconjugate produced according to the BB-01 method (BB-01) is superior at eliciting CD86 upregulation on myeloid cells as compared to the unconjugated rituximab (CD20, Roche) following 18 hours of stimulation.

Figure 82A:
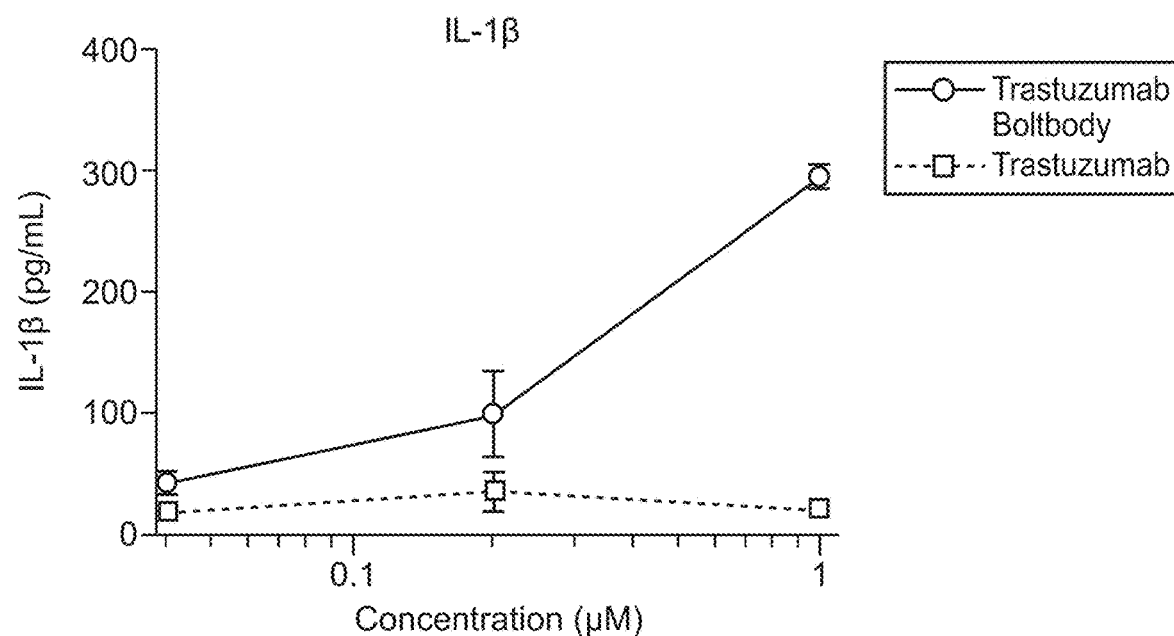

FIG. 82A shows that the trastuzumab immunoconjugate produced according to the BB-01 method (Trastuzumab Boltbody) elicits superior IL-1β secretion from myeloid cells as compared to equimolar concentrations of unconjugated trastuzumab (Roche) following 36 hours of stimulation.

Figure 82B:
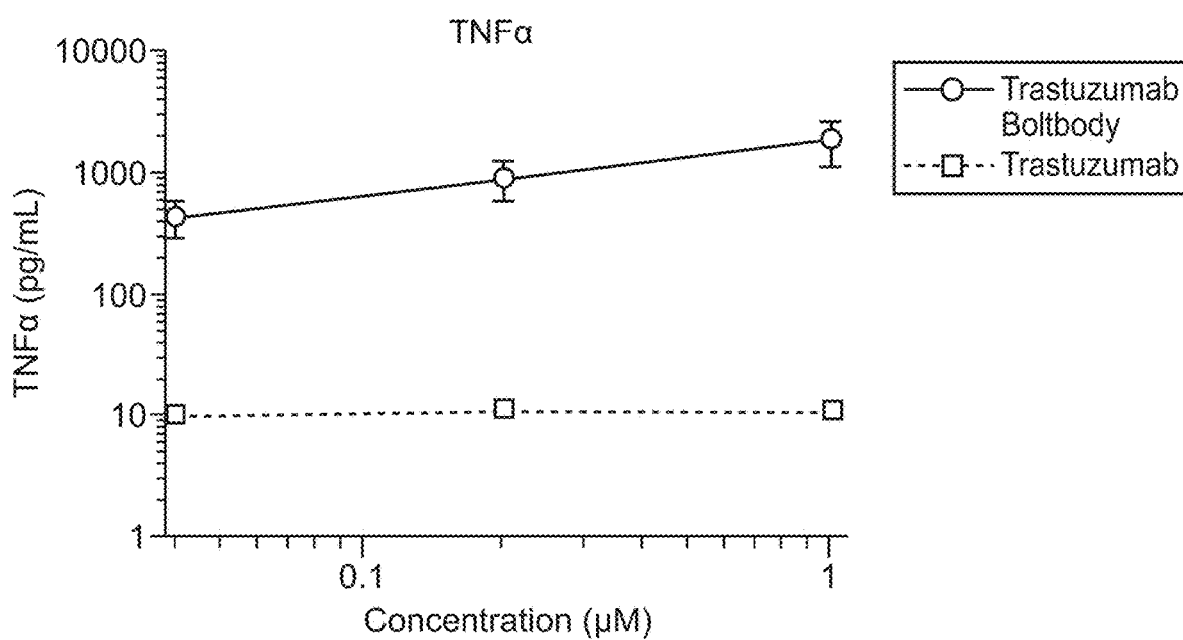

FIG. 82B shows that the trastuzumab immunoconjugate produced according to the BB-01 method (Trastuzumab Boltbody) elicits superior TNFα secretion from myeloid cells as compared to equimolar concentrations of unconjugated trastuzumab (Roche) following 36 hours of stimulation.

Figure 82C:
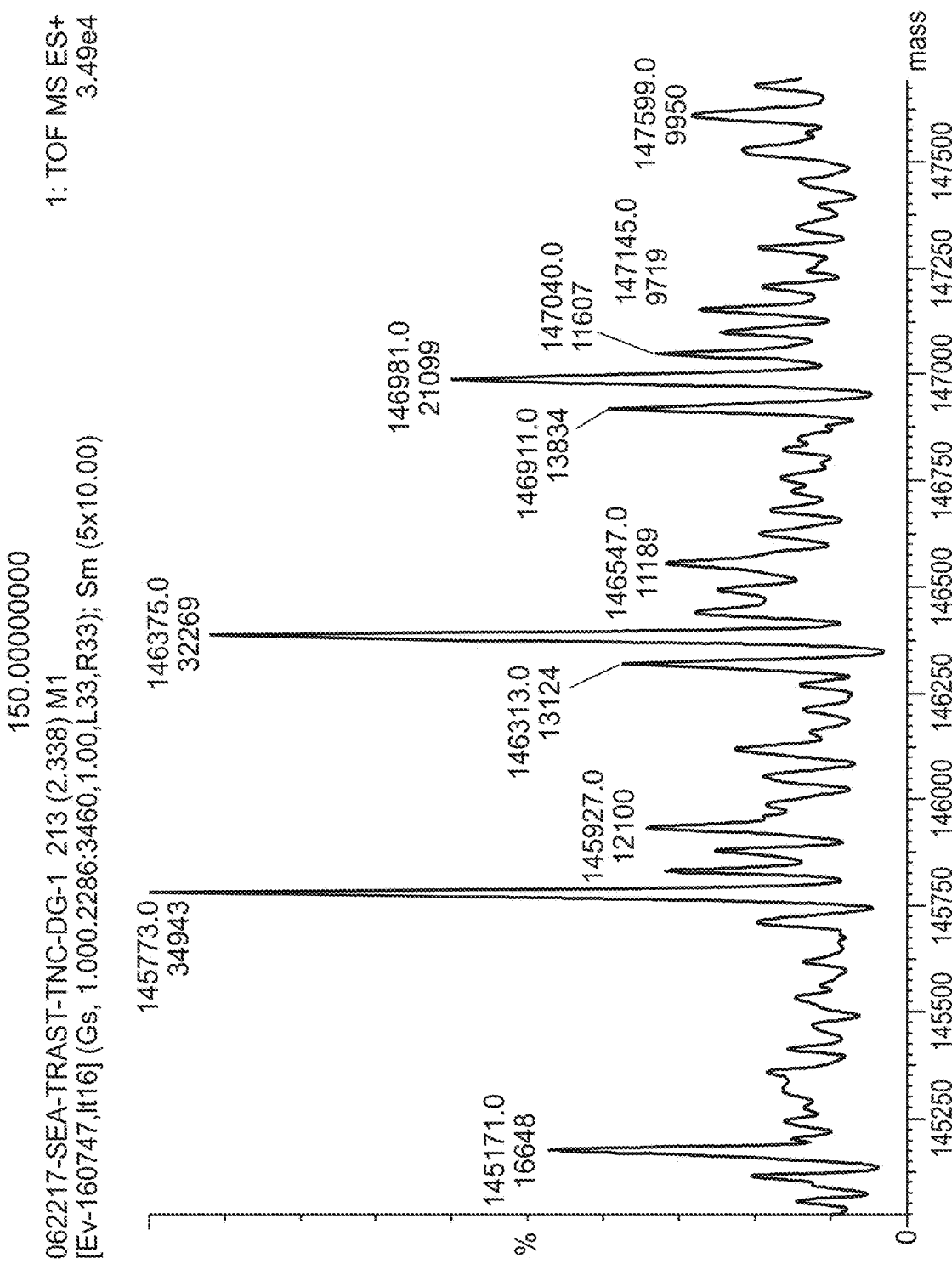

FIG. 82C shows a liquid chromatography-mass spectrometry analysis of the trastuzumab immunoconjugate produced according to the BB-01 conjugation method following overnight deglycosylation with PNGase F.

FIG. 82D shows a liquid chromatography-mass spectrometry analysis of unconjugated trastuzumab (Roche) that was utilized to produce the trastuzumab immunoconjugate according to the BB-01 conjugation method following overnight deglycosylation with PNGase F.

Figure 82E:
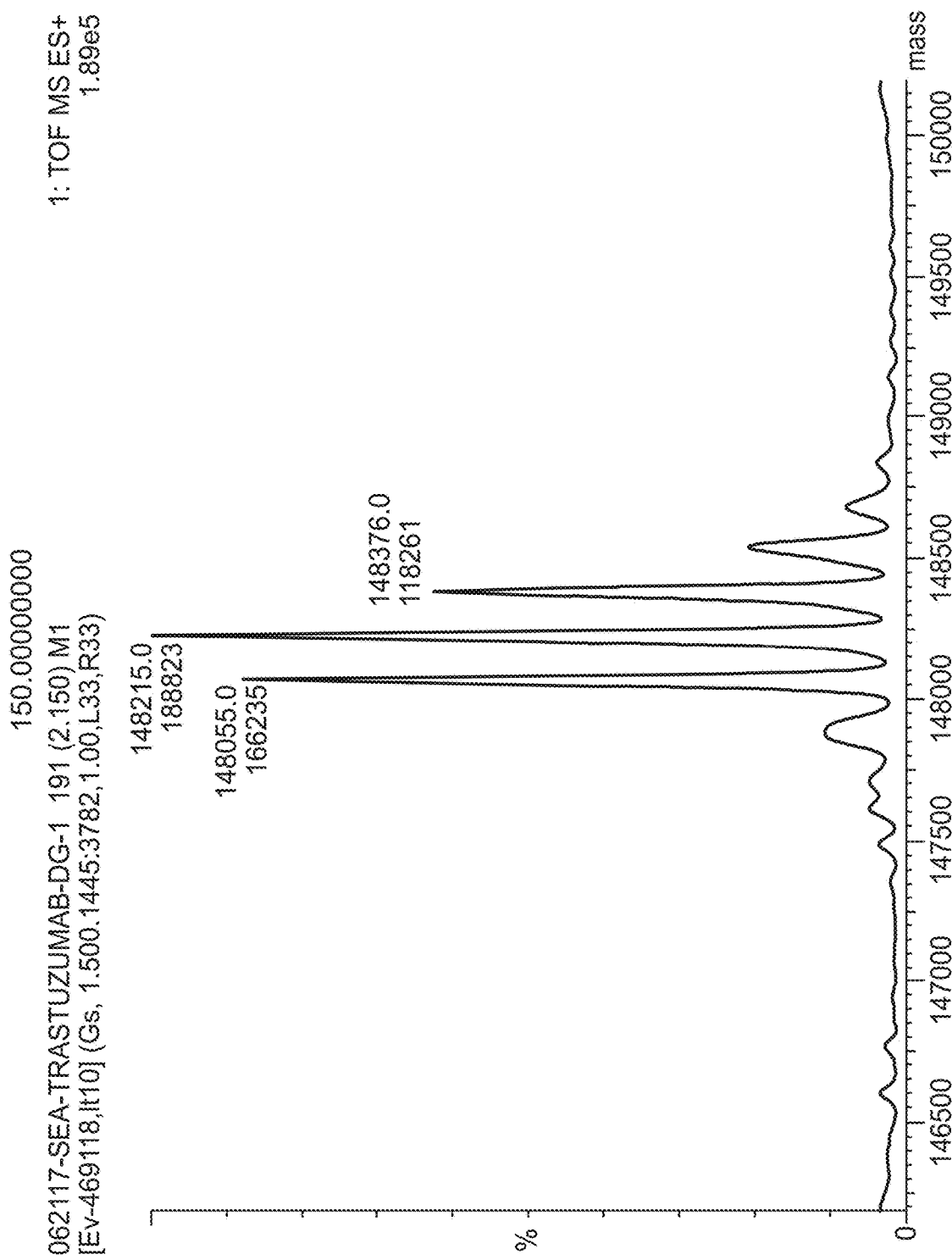

FIG. 82E shows a liquid chromatography-mass spectrometry analysis of unconjugated trastuzumab (Roche) that was utilized to produce the trastuzumab immunoconjugate according to the BB-01 conjugation method.

Figure 82F:
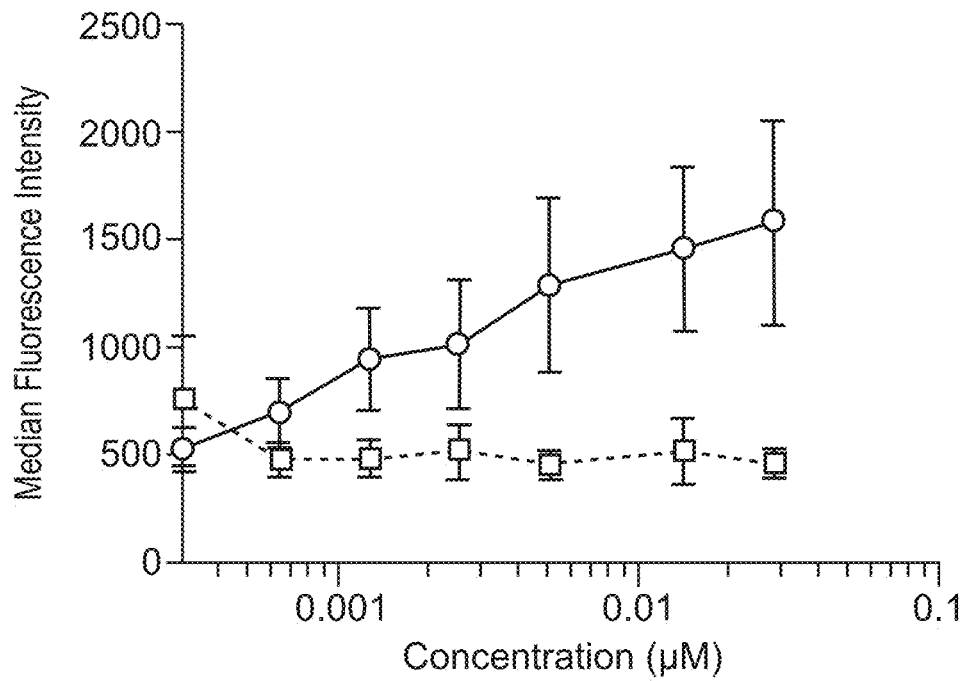

FIG. 82F shows that the trastuzumab immunoconjugate produced according to the BB-01 method (closed circles, red) is superior at eliciting CD123 upregulation on myeloid cells as compared to the unconjugated trastuzumab (closed squares, black; Roche) following 18 hours of stimulation.

Figure 82G:
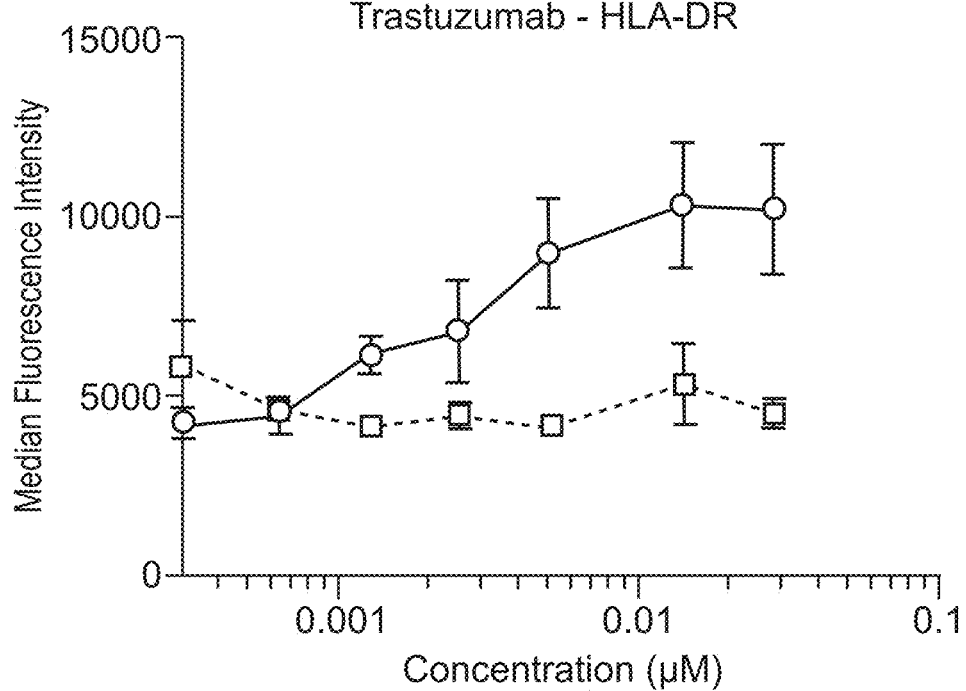

FIG. 82G shows that the trastuzumab immunoconjugate produced according to the BB-01 method (closed circles, red) is superior at eliciting HLA-DR upregulation on myeloid cells as compared to the unconjugated trastuzumab (closed squares, black; Roche) following 18 hours of stimulation.

Figure 82H:
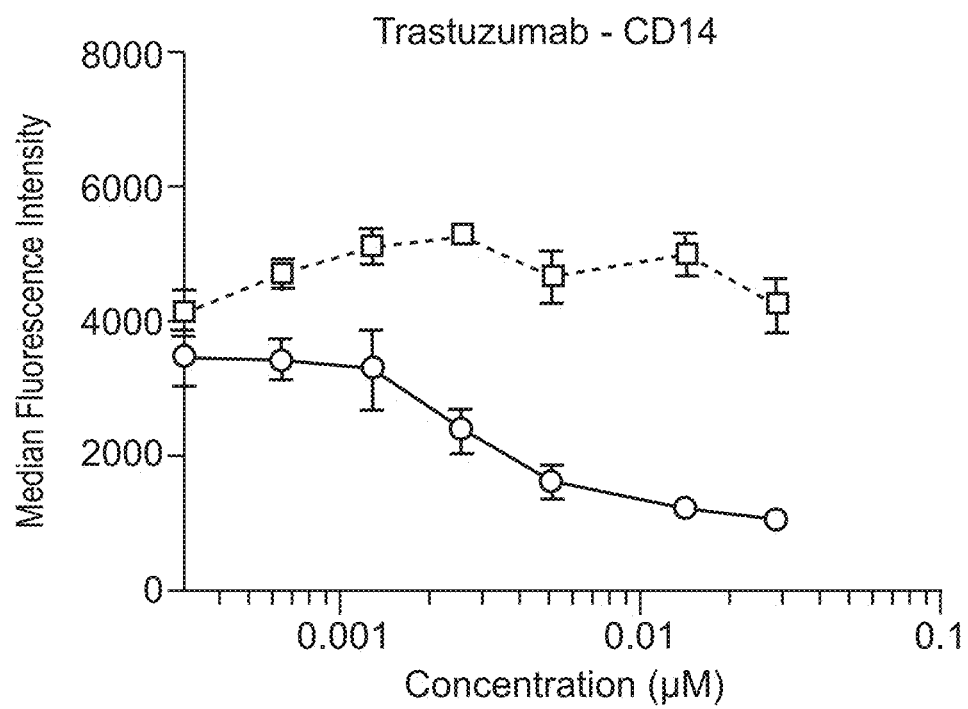

FIG. 82H shows that the trastuzumab immunoconjugate produced according to the BB-01 method (closed circles, red) is superior at eliciting CD14 downregulation on myeloid cells as compared to the unconjugated trastuzumab (closed squares, black; Roche) following 18 hours of stimulation.

Figure 82I:
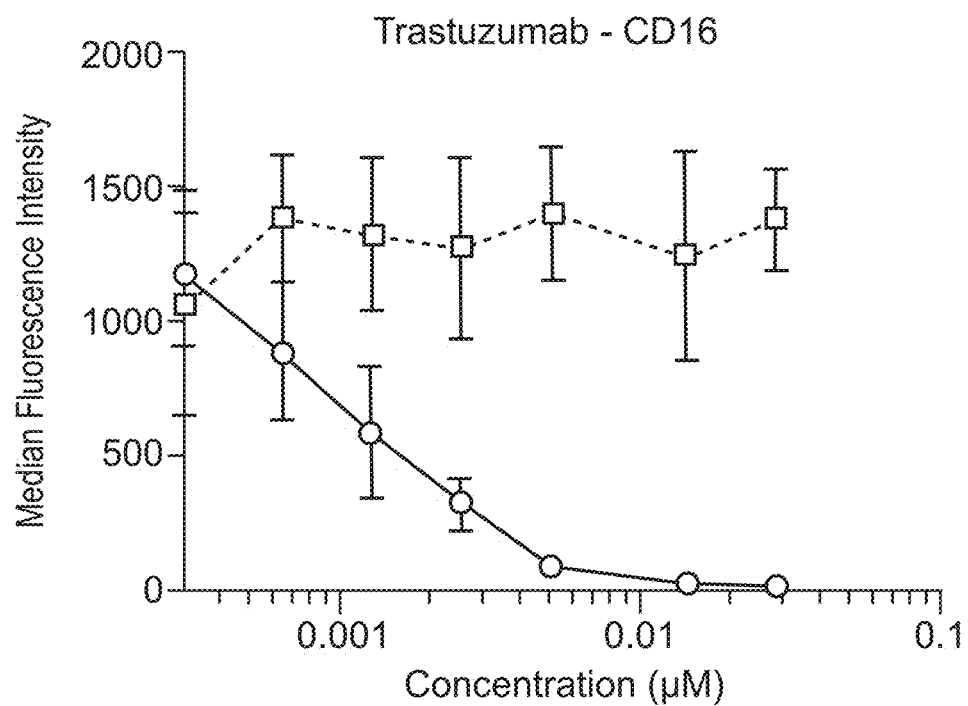

FIG. 82I shows that the trastuzumab immunoconjugate produced according to the BB-01 method (closed circles, red is superior at eliciting CD16 downregulation on myeloid cells as compared to the unconjugated trastuzumab (closed squares, black; Roche) following 18 hours of stimulation.

Figure 82J:
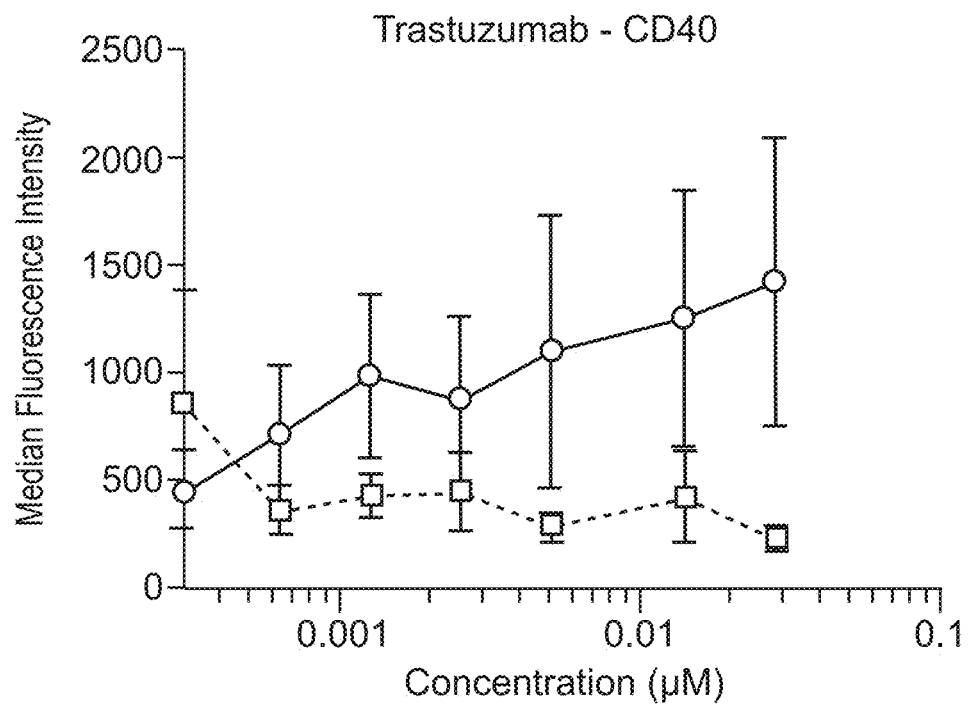

FIG. 82J shows that the trastuzumab immunoconjugate produced according to the BB-01 method (closed circles, red) is superior at eliciting CD40 upregulation on myeloid cells as compared to the unconjugated trastuzumab (closed squares, black; Roche) following 18 hours of stimulation.

Figure 82K:
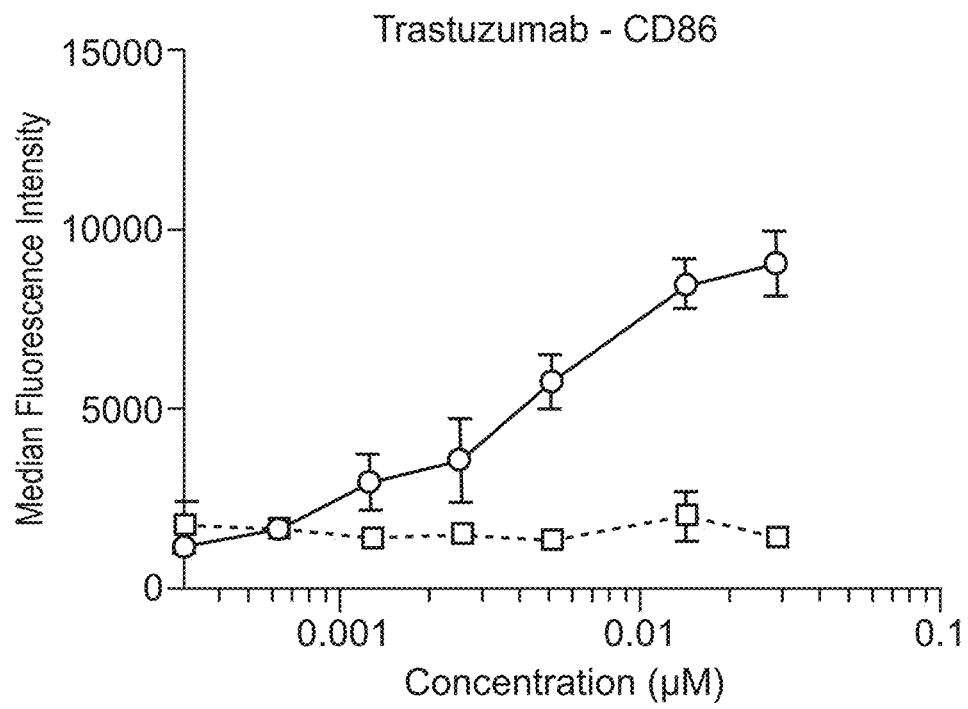

FIG. 82K shows that the trastuzumab immunoconjugate produced according to the BB-01 method (closed circles, red) is superior at eliciting CD86 upregulation on myeloid cells as compared to the unconjugated trastuzumab (closed squares, black; Roche) following 18 hours of stimulation.

Figure 83A:
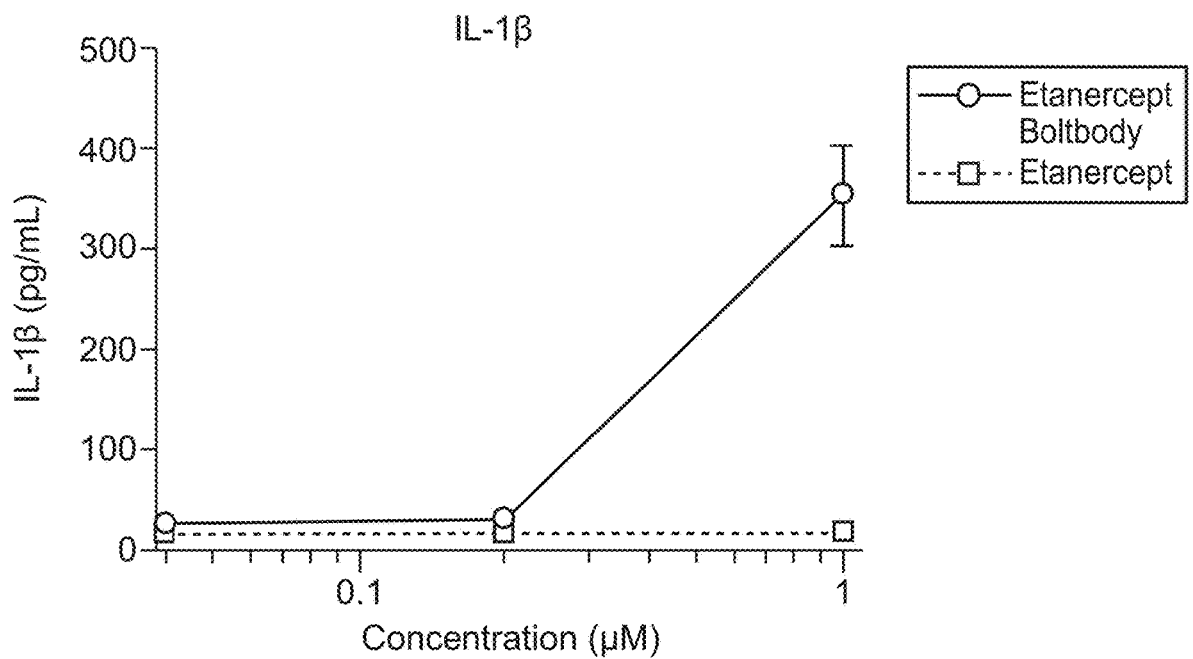

FIG. 83A shows that the etanercept immunoconjugate produced according to the BB-01 method (Etanercept Boltbody) elicits superior IL-10 secretion from myeloid cells as compared to equimolar concentrations of unconjugated etanercept (Amgen) following 36 hours of stimulation.

Figure 83B:
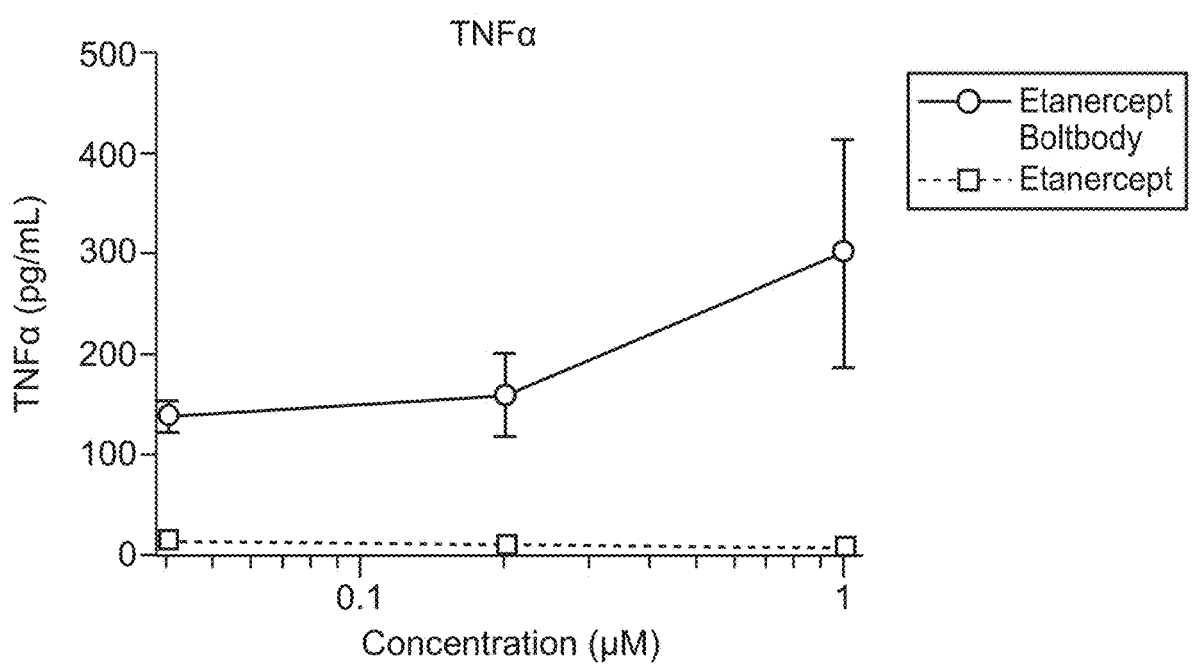

FIG. 83B shows that the etanercept immunoconjugate produced according to the BB-01 method (Etanercept Boltbody) elicits superior TNFα secretion from myeloid cells as compared to equimolar concentrations of unconjugated etanercept (Amgen) following 36 hours of stimulation.

Figure 83C:
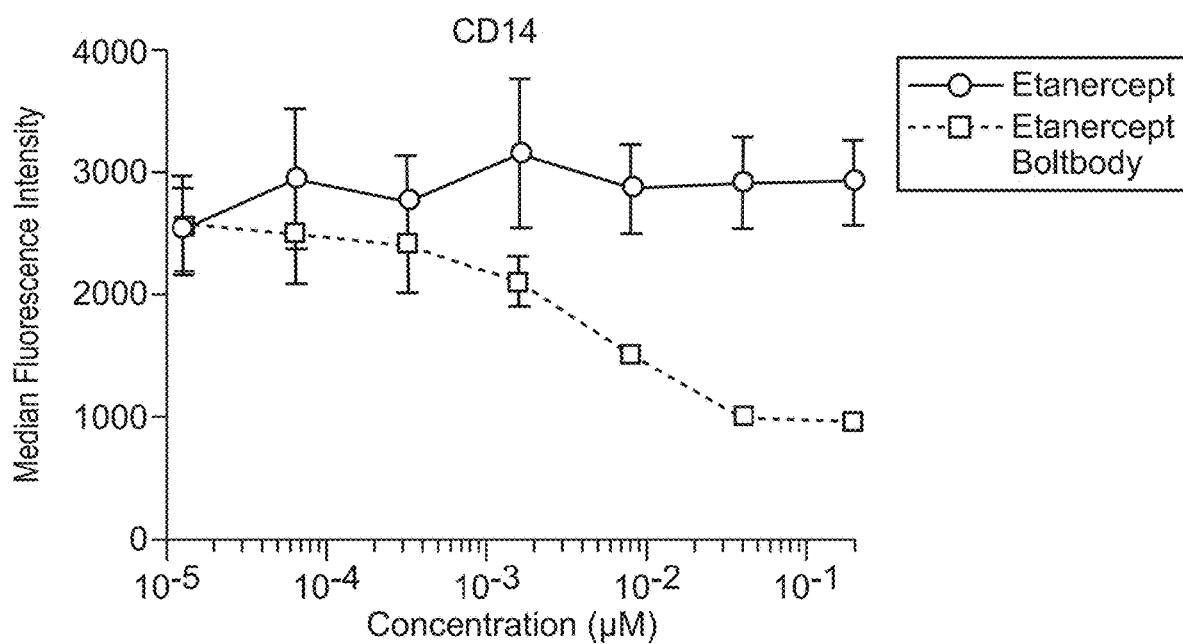

FIG. 83C shows that the etanercept immunoconjugate produced according to the BB-01 method (Etanercept Boltbody) is superior at eliciting CD14 downregulation on myeloid cells as compared to the unconjugated etanercept (Amgen) following 18 hours of stimulation.

Figure 83D:
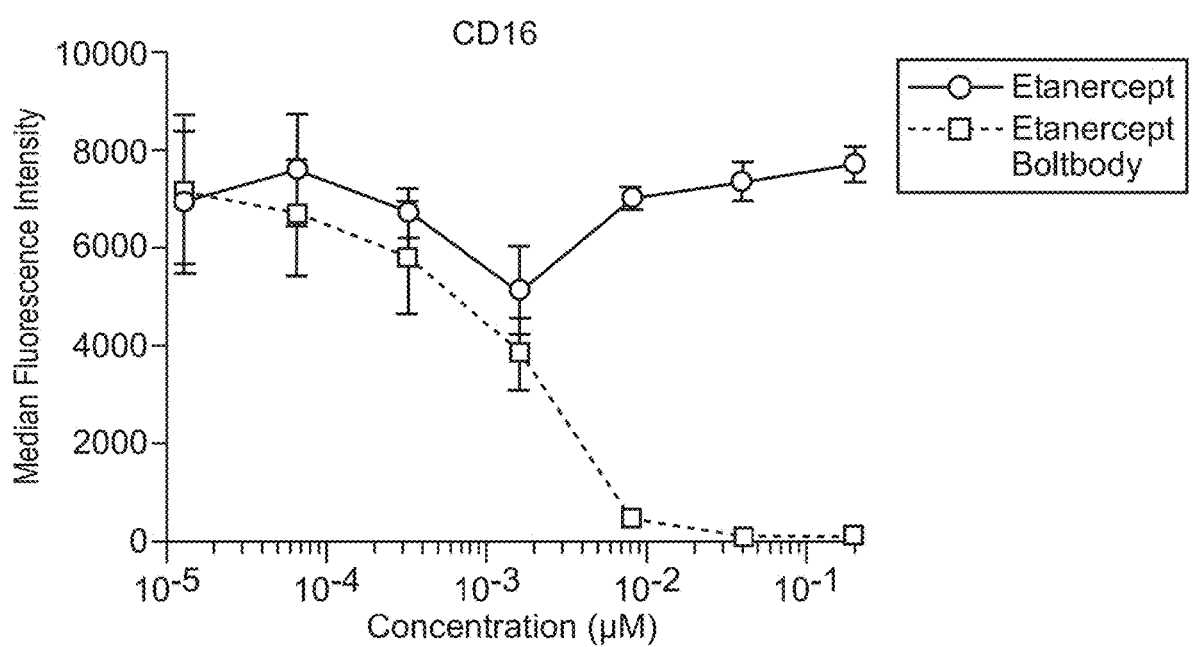

FIG. 83D shows that the etanercept immunoconjugate produced according to the BB-01 method (Etanercept Boltbody is superior at eliciting CD16 downregulation on myeloid cells as compared to the unconjugated etanercept (Amgen) following 18 hours of stimulation.

Figure 83E:
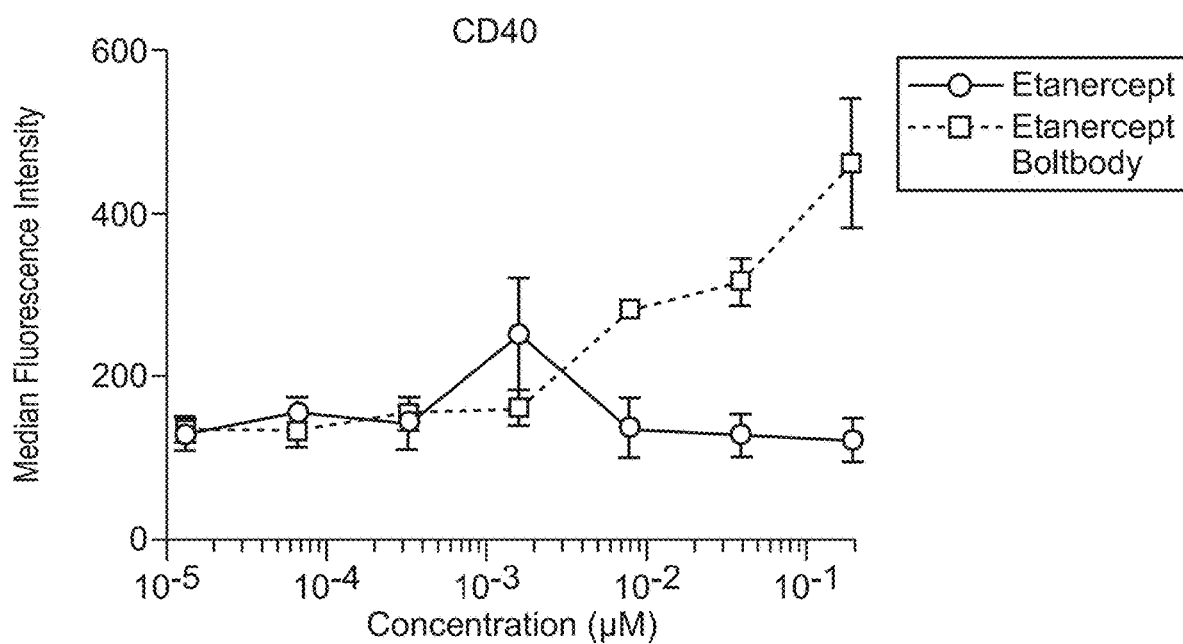

FIG. 83E shows that the etanercept immunoconjugate produced according to the BB-01 method (Etanercept Boltbody) is superior at eliciting CD40 upregulation on myeloid cells as compared to the unconjugated etanercept (Amgen) following 18 hours of stimulation.

Figure 83F:
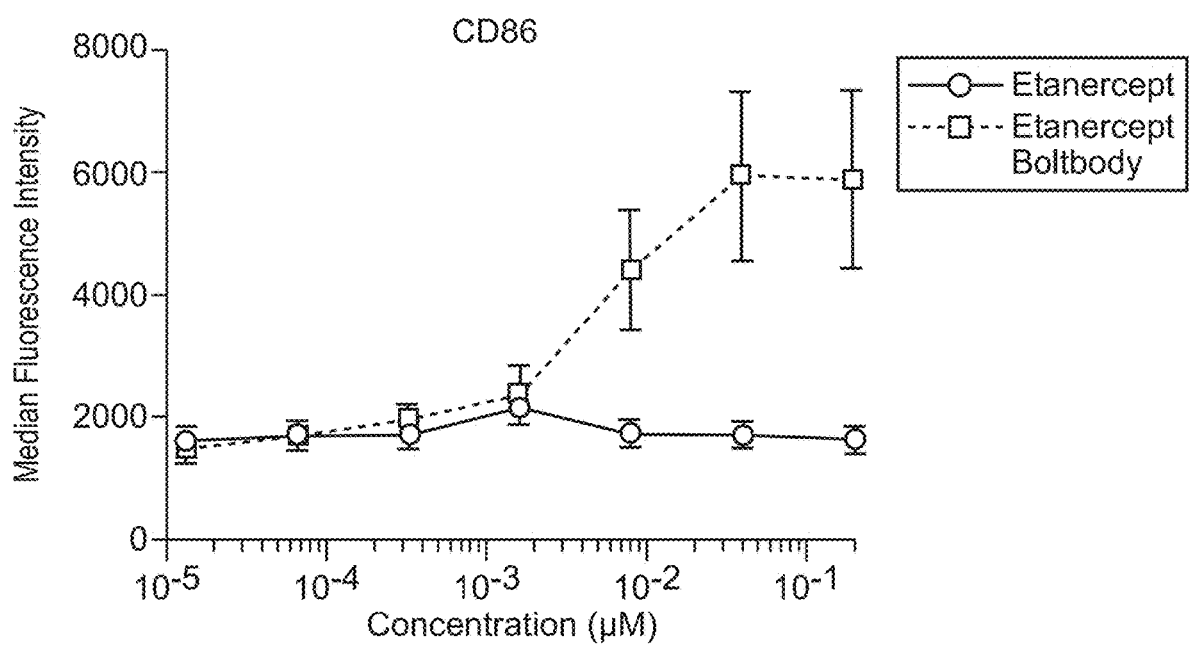

FIG. 83F shows that the etanercept immunoconjugate produced according to the BB-01 method (Etanercept Boltbody) is superior at eliciting CD86 upregulation on myeloid cells as compared to the unconjugated etanercept (Amgen) following 18 hours of stimulation.

Figure 83G:
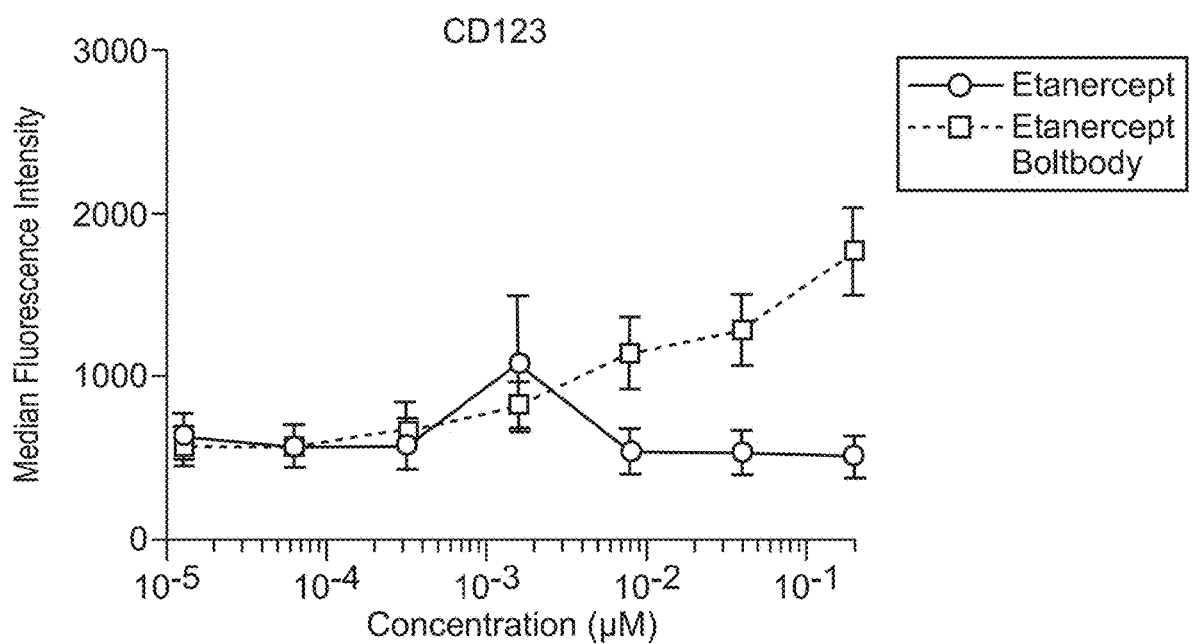

FIG. 83G shows that the etanercept immunoconjugate produced according to the BB-01 method (Etanercept Boltbody) is superior at eliciting CD123 upregulation on myeloid cells as compared to the unconjugated etanercept (Amgen) following 18 hours of stimulation.

Figure 83H:
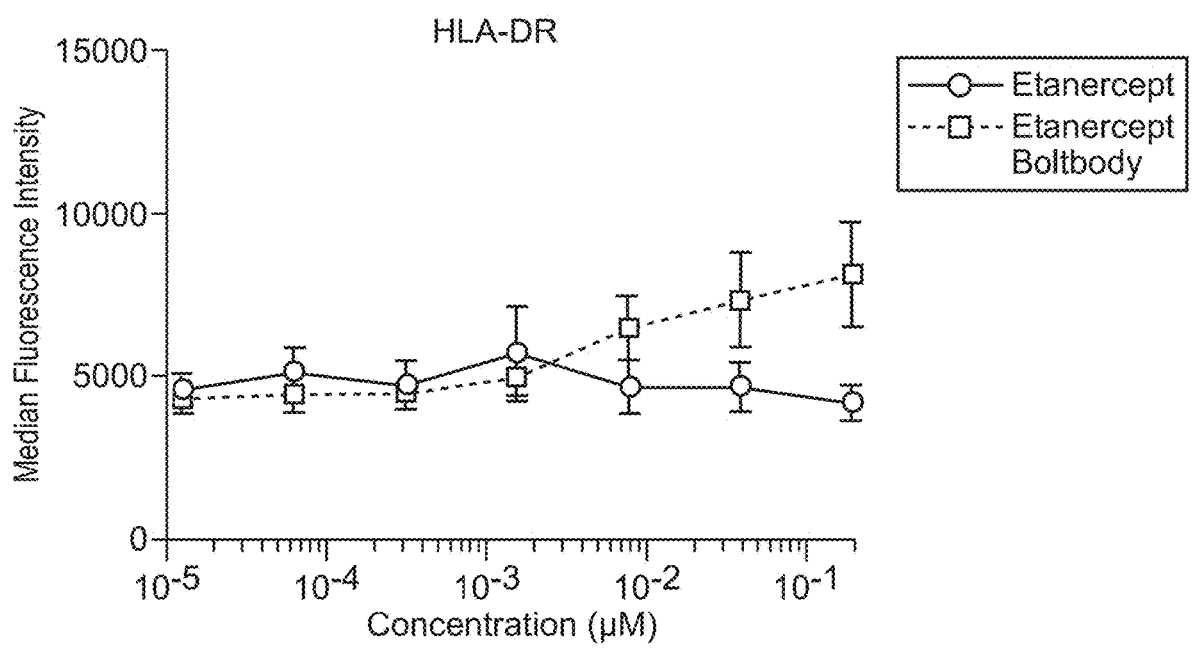

FIG. 83H shows that the etanercept immunoconjugate produced according to the BB-01 method (Etanercept Boltbody) is superior at eliciting HLA-DR upregulation on myeloid cells as compared to the unconjugated etanercept (Amgen) following 18 hours of stimulation.

Figure 84A:
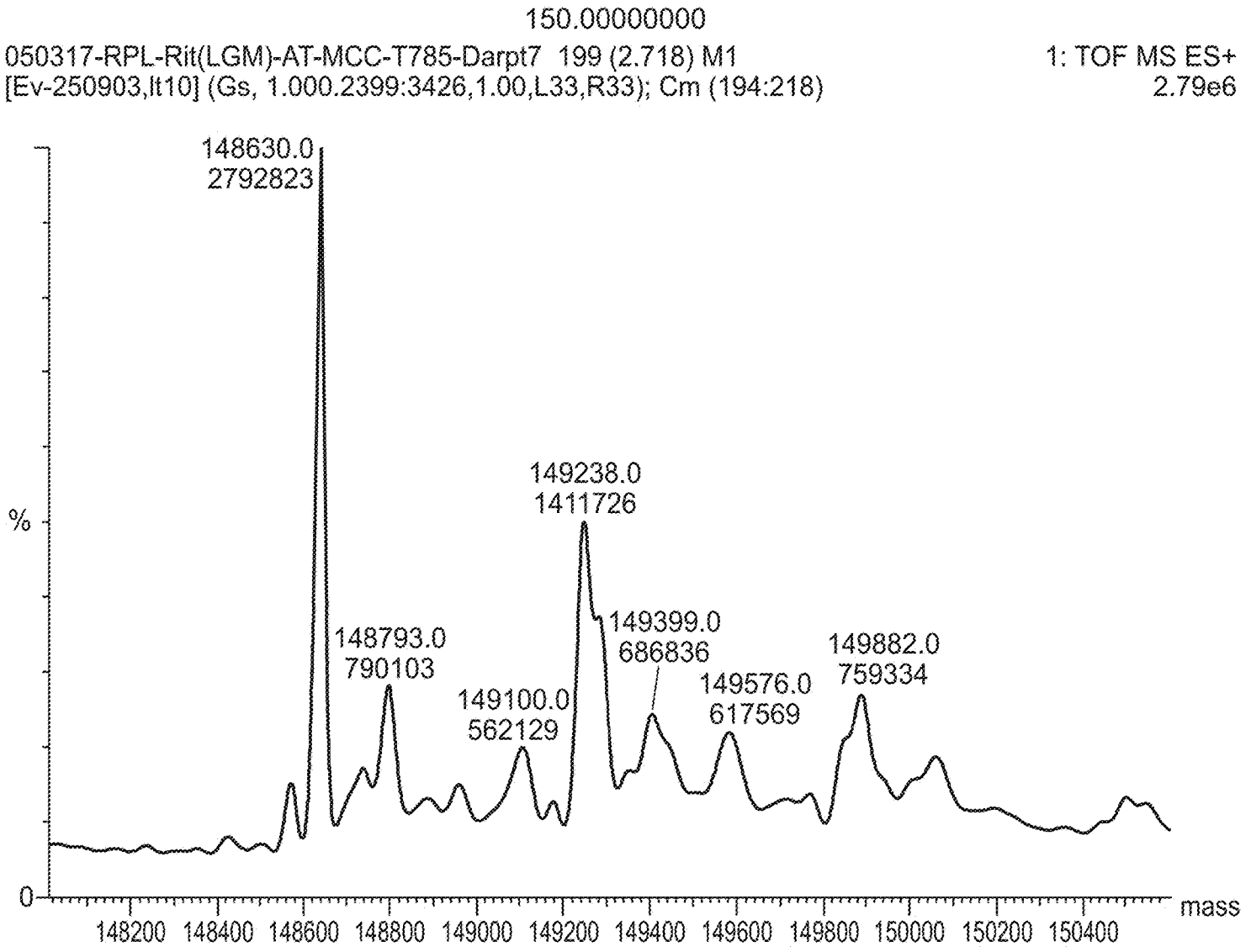

FIG. 84A shows a liquid chromatography-mass spectrometry analysis of the rituximab immunoconjugate produced according to the BB-01 conjugation method from the rituximab biosimilar (LGM Pharma). The calculated DAR is 0.7.

Figure 84B:
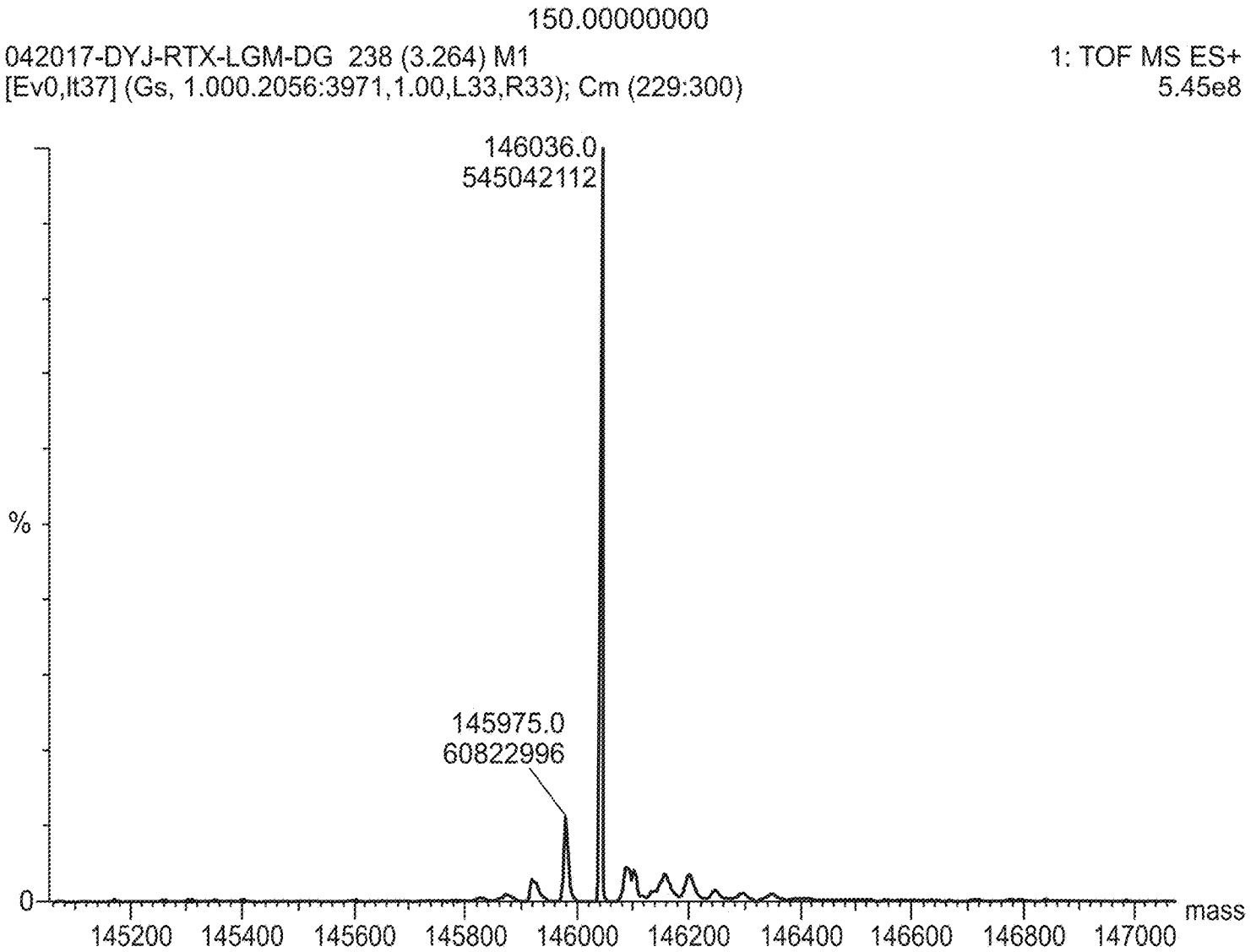

FIG. 84B shows a liquid chromatography-mass spectrometry analysis of unconjugated rituximab biosimilar (LGM Pharma) that was utilized to produce the rituximab immunoconjugate according to the BB-01 conjugation method following overnight deglycosylation with PNGase F.

Figure 84C:
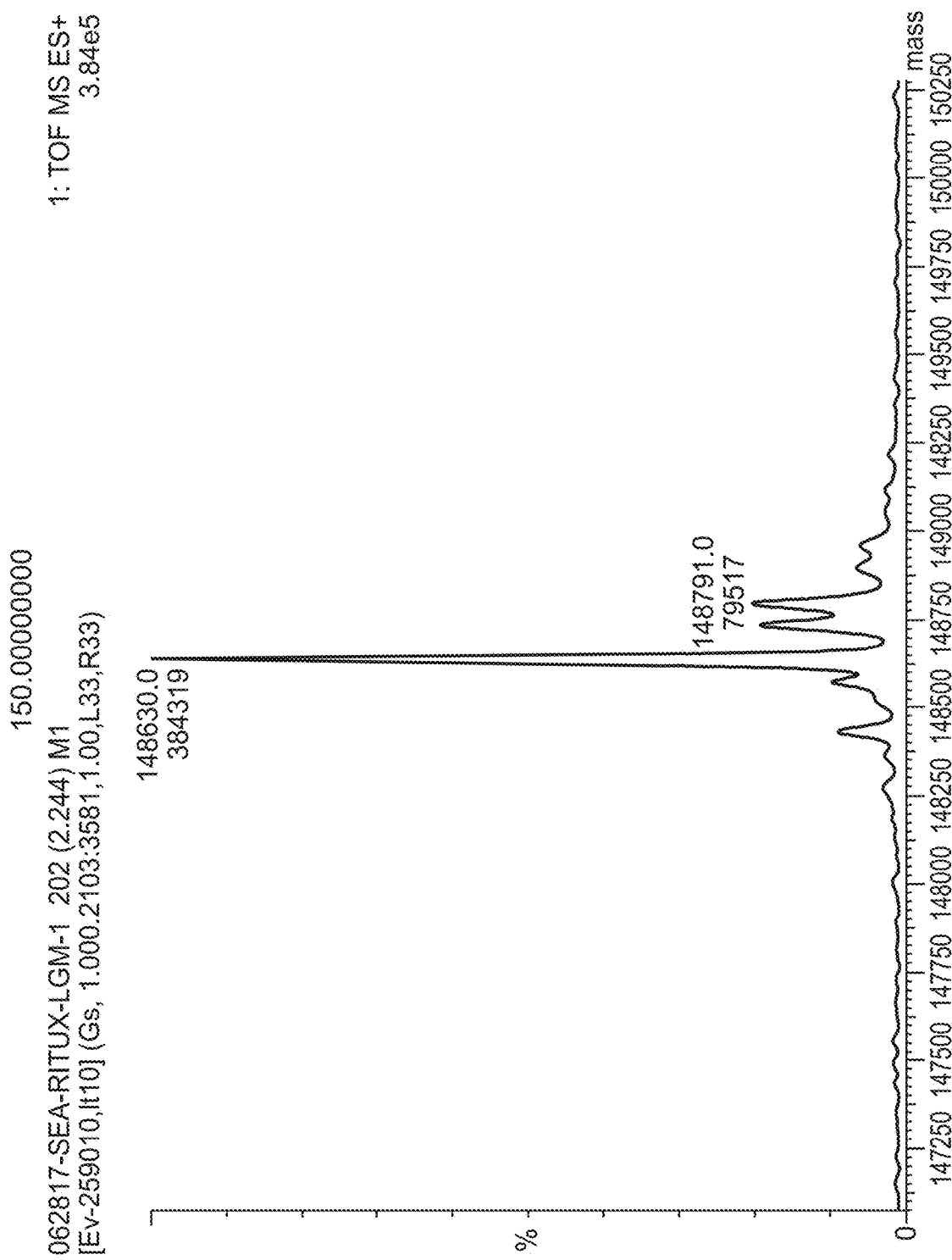

FIG. 84C shows a liquid chromatography-mass spectrometry analysis of unconjugated rituximab (LGM Pharma) that was utilized to produce the rituximab immunoconjugate according to the BB-01 conjugation method.

Figure 84D:
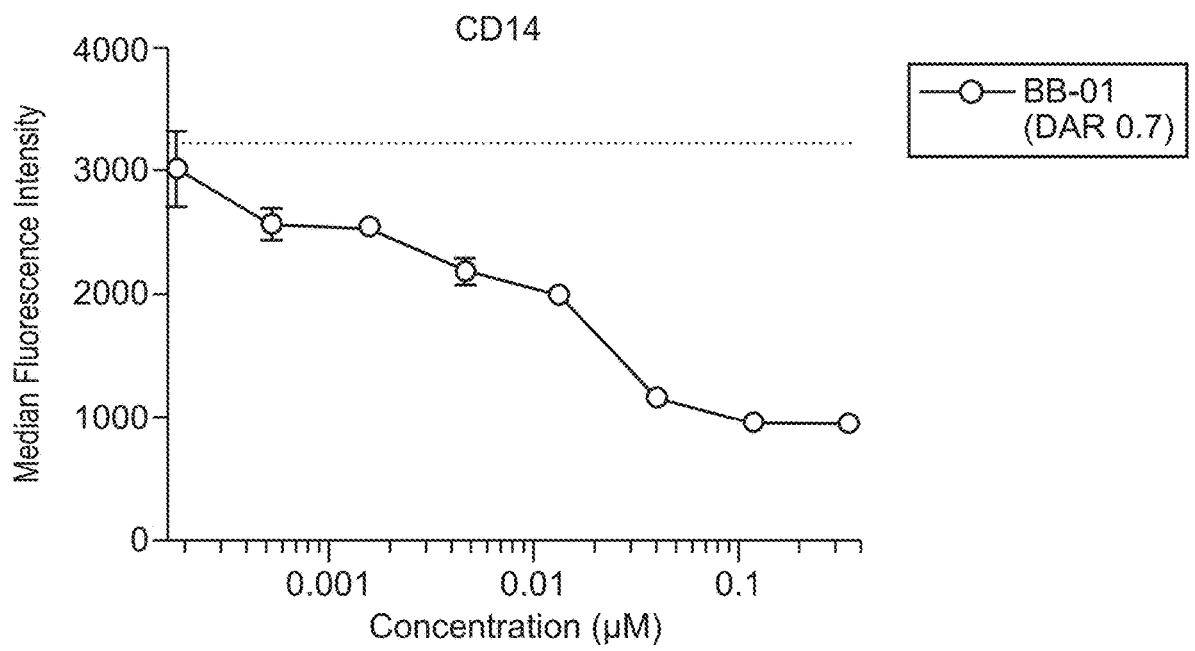

FIG. 84D shows CD14 expression on myeloid cells following 18 hours of stimulation with the rituximab immunoconjugate produced according to the BB-01 method [BB-01 (DAR 0.7)]. The dashed line indicates the level of expression on unstimulated myeloid cells cultured for 18 hours.

Figure 84E:
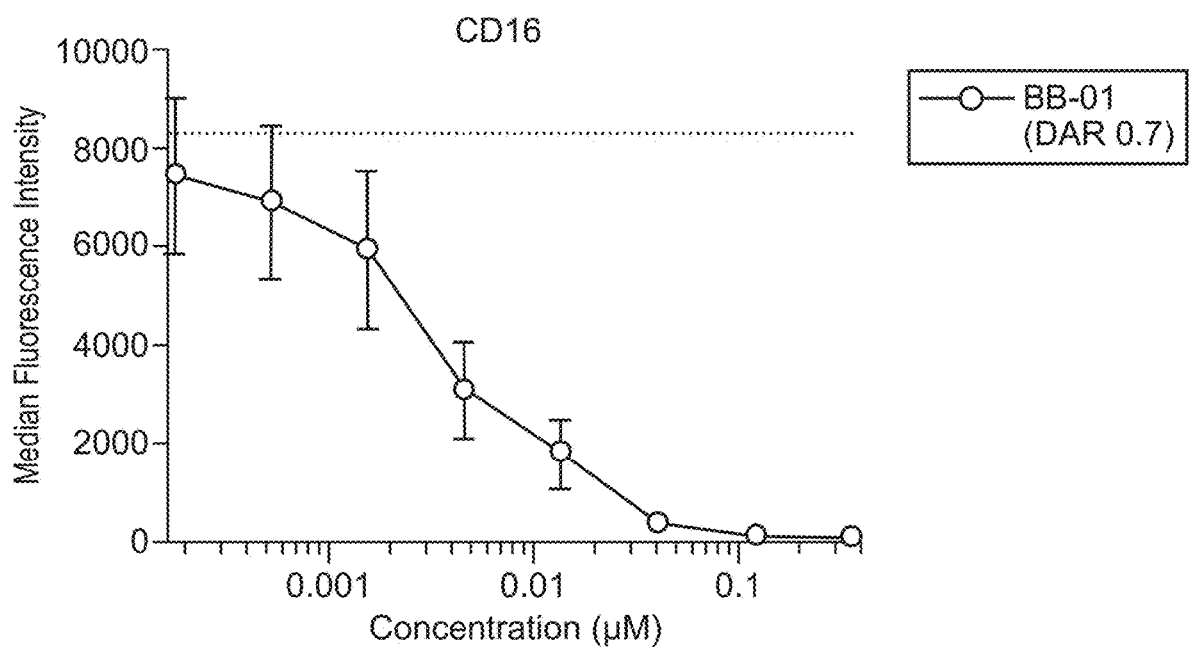

FIG. 84E shows CD16 expression on myeloid cells following 18 hours of stimulation with the rituximab immunoconjugate produced according to the BB-01 method [BB- 01 (DAR 0.7)]. The dashed line indicates the level of expression on unstimulated myeloid cells cultured for 18 hours.

Figure 84F:
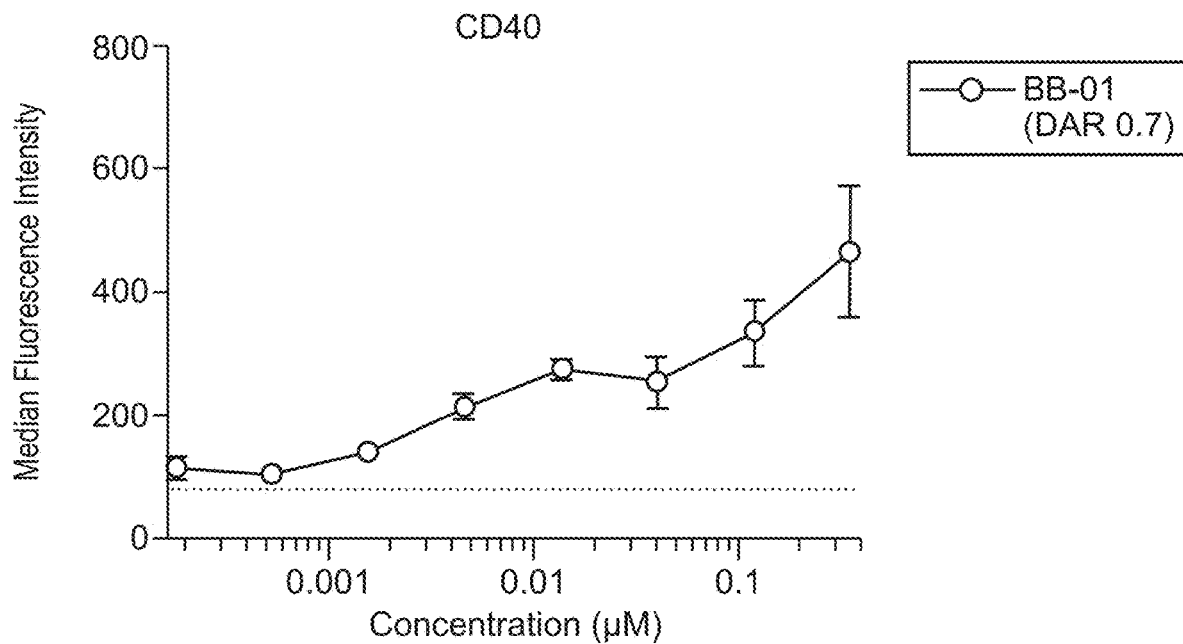

FIG. 84F shows CD40 expression on myeloid cells following 18 hours of stimulation with the rituximab immunoconjugate produced according to the BB-01 method [BB-01 (DAR 0.7)]. The dashed line indicates the level of expression on unstimulated myeloid cells cultured for 18 hours.

Figure 84G:
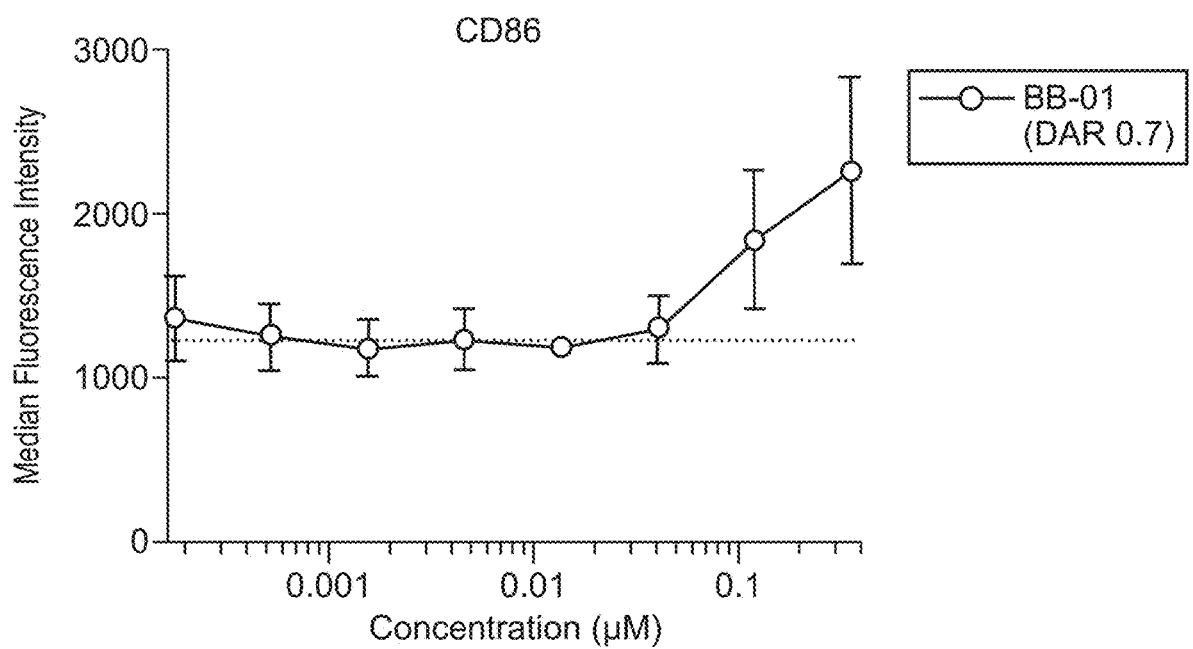

FIG. 84G shows CD86 expression on myeloid cells following 18 hours of stimulation with the rituximab immunoconjugate produced according to the BB-01 method [BB-01 (DAR 0.7)]. The dashed line indicates the level of expression on unstimulated myeloid cells cultured for 18 hours.

Figure 84H:
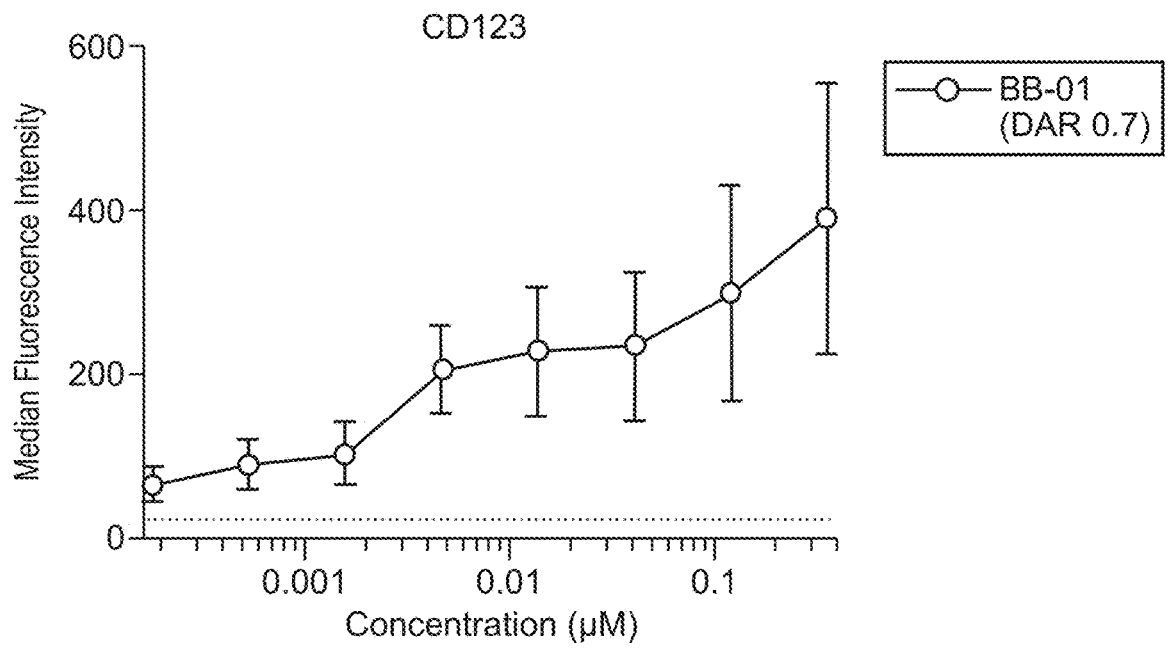

FIG. 84H shows CD123 expression on myeloid cells following 18 hours of stimulation with the rituximab immunoconjugate produced according to the BB-01 method [BB-01 (DAR 0.7)]. The dashed line indicates the level of expression on unstimulated myeloid cells cultured for 18 hours.

Figure 84I:
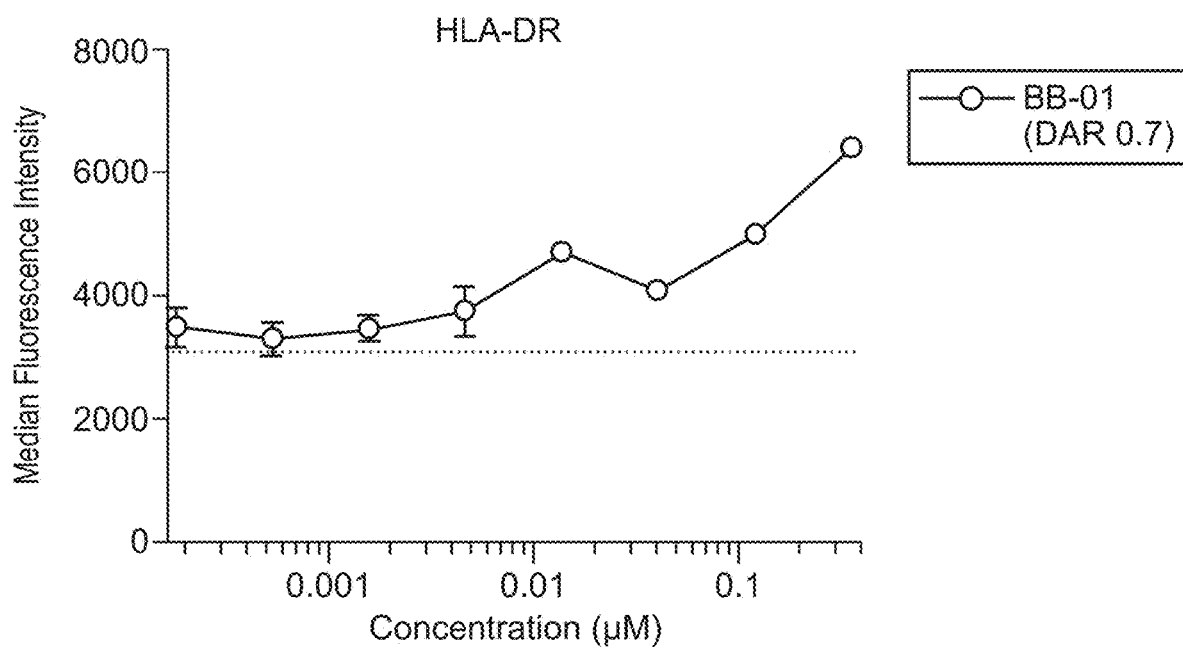

FIG. 84I shows HLA-DR expression on myeloid cells following 18 hours of stimulation with the rituximab immunoconjugate produced according to the BB-01 method [BB-01 (DAR 0.7)]. The dashed line indicates the level of expression on unstimulated myeloid cells cultured for 18 hours.

Figure 85A:
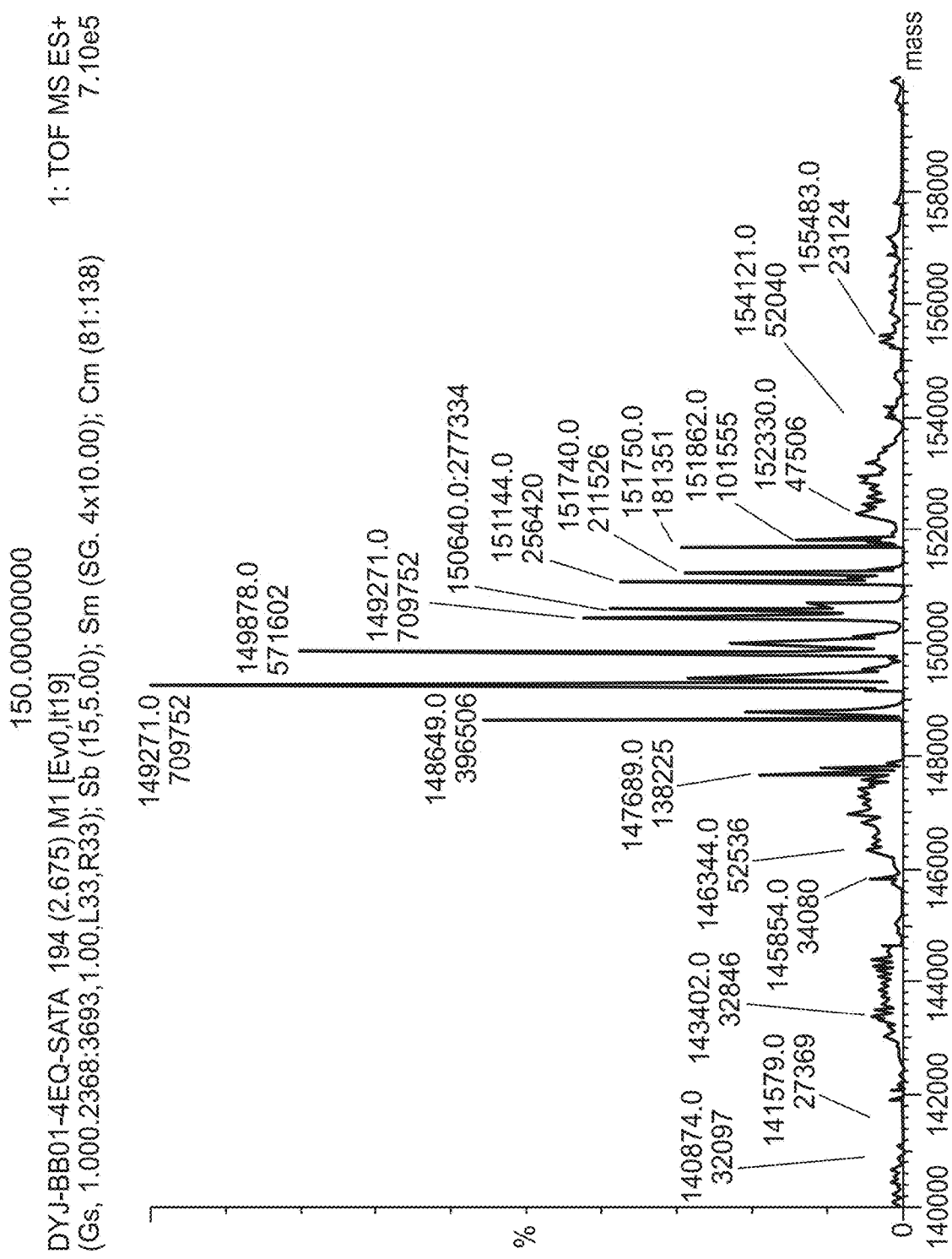

FIG. 85A shows a liquid chromatography-mass spectrometry analysis of the rituximab immunoconjugate produced according to the BB-01 conjugation method from the rituximab biosimilar (LGM Pharma). The calculated DAR is 1.6.

Figure 85B:
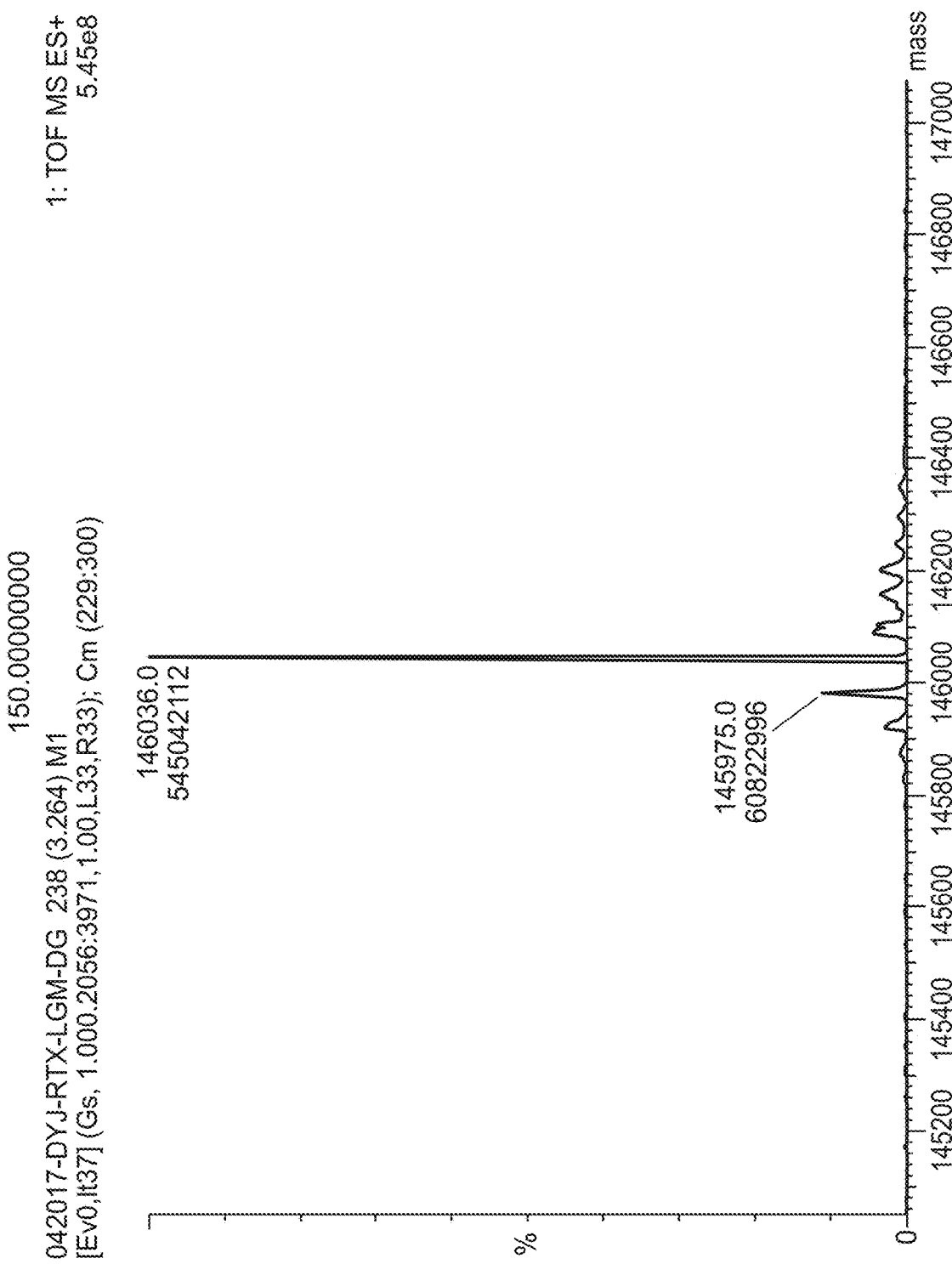

FIG. 85B shows a liquid chromatography-mass spectrometry analysis of unconjugated rituximab biosimilar (LGM Pharma) that was utilized to produce the rituximab immunoconjugate according to the BB-01 conjugation method following overnight deglycosylation with PNGase F.

Figure 85C:
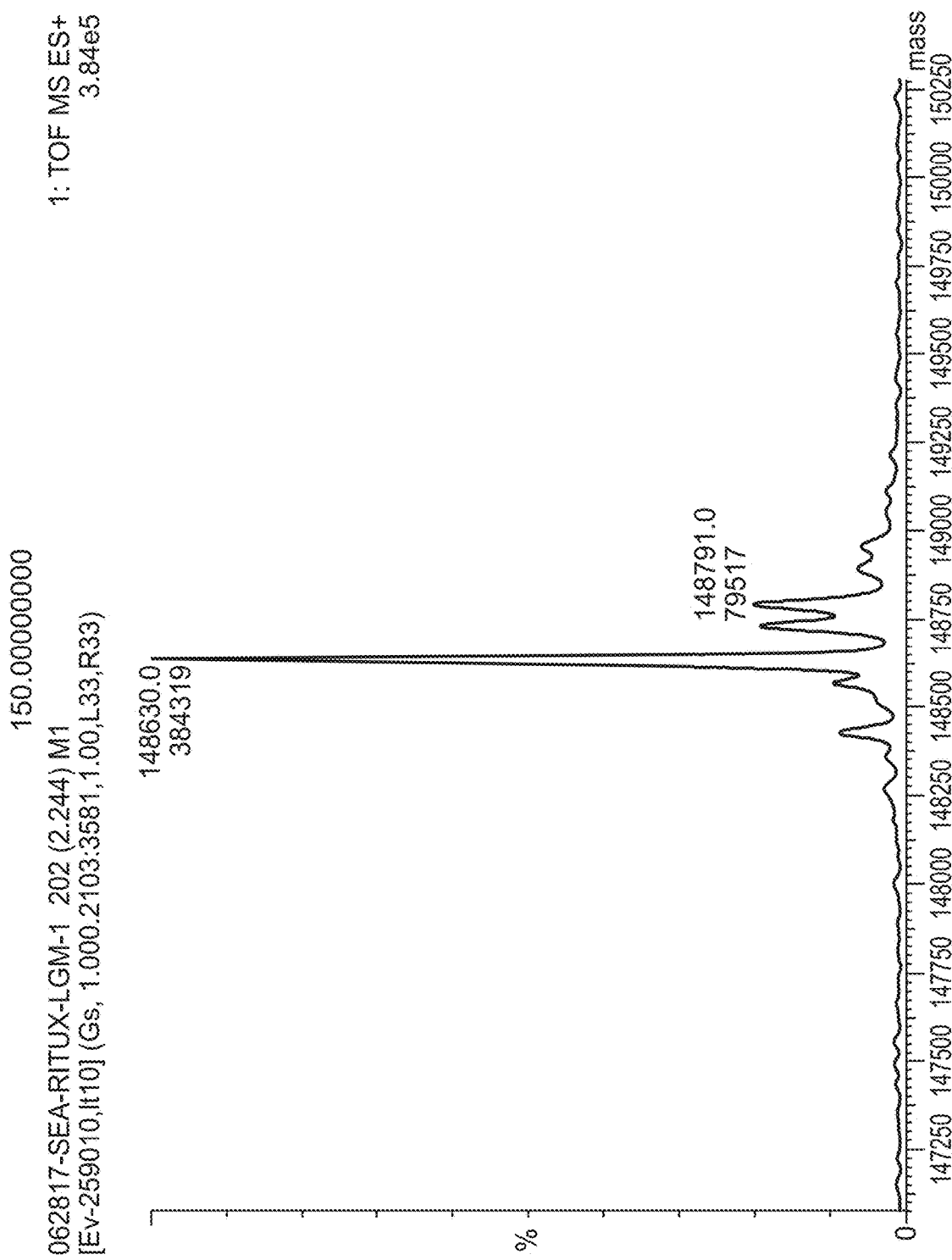

FIG. 85C shows a liquid chromatography-mass spectrometry analysis of unconjugated rituximab (LGM Pharma) that was utilized to produce the rituximab immunoconjugate according to the BB-01 conjugation method.

Figure 85D:
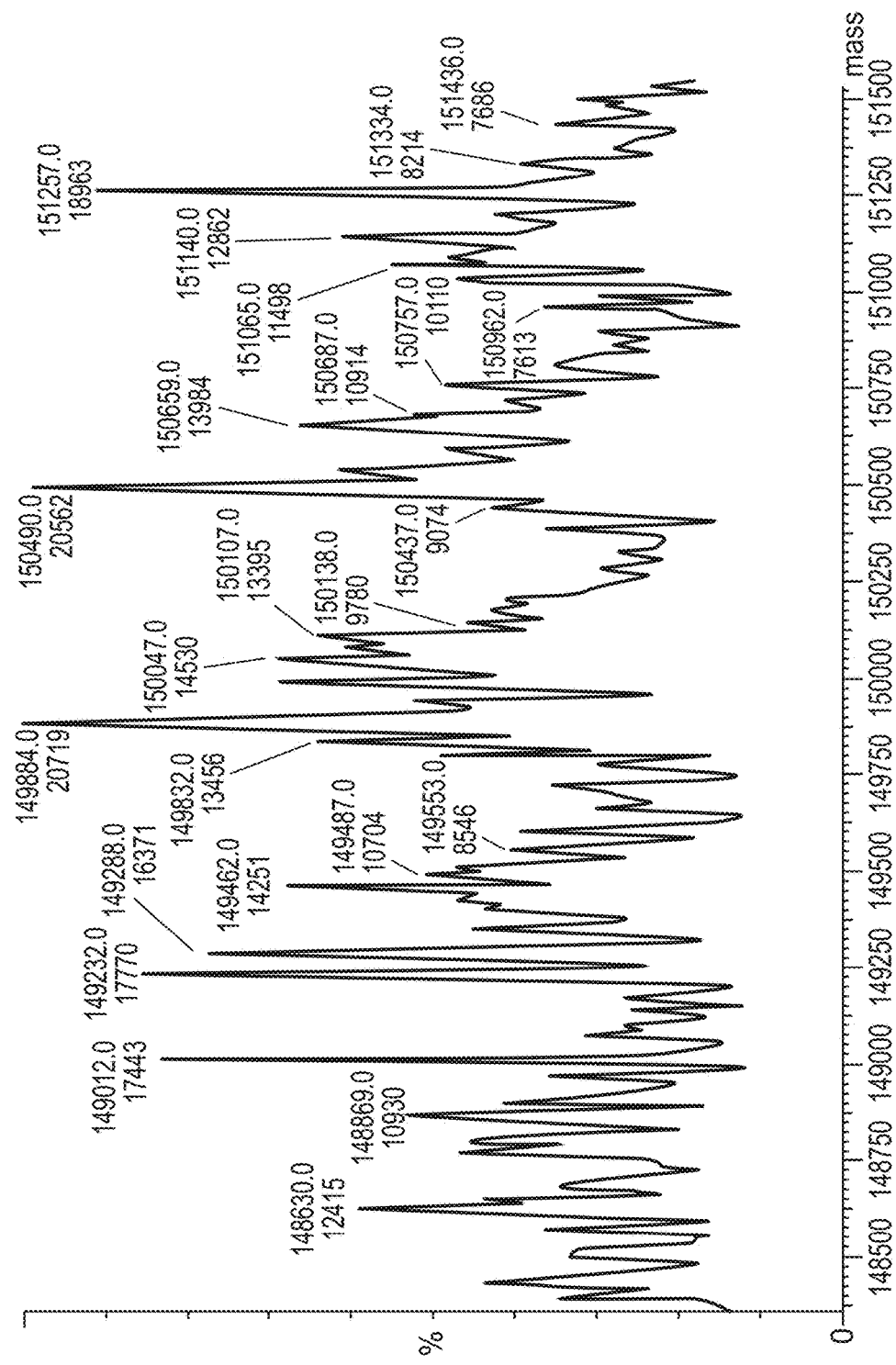

FIG. 85D shows a liquid chromatography-mass spectrometry analysis of unconjugated rituximab (LGM Pharma) that was utilized to produce the rituximab immunoconjugate according to the BB-01 conjugation method.

Figure 85E:
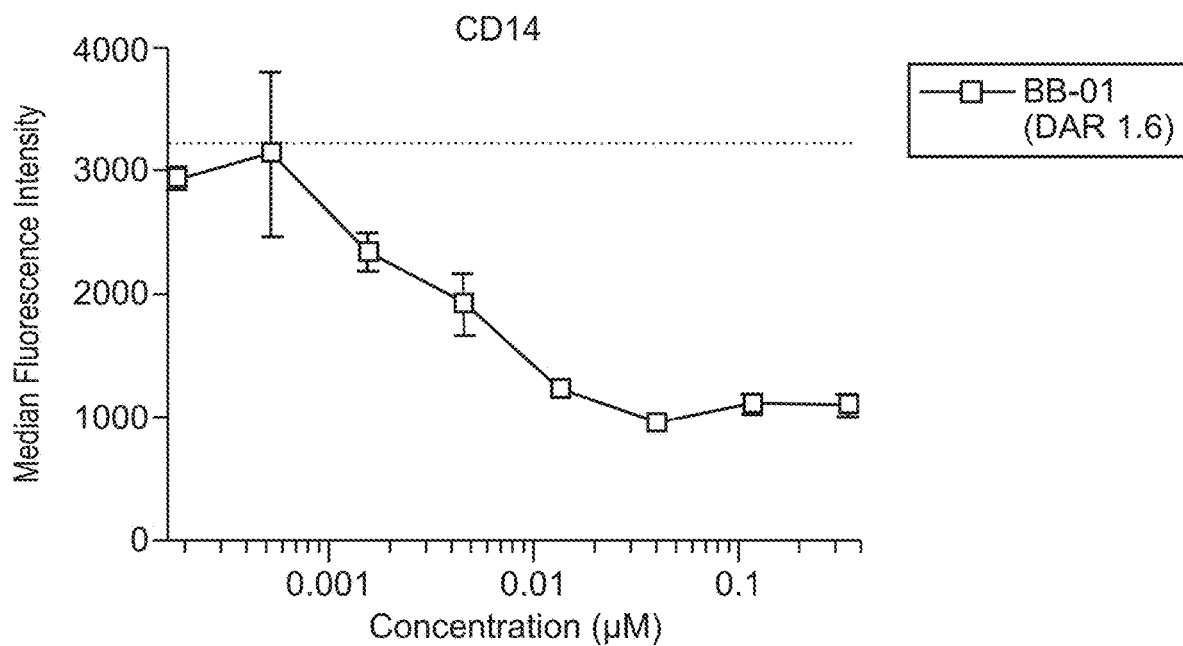

FIG. 85E shows CD14 expression on myeloid cells following 18 hours of stimulation with the rituximab immunoconjugate produced according to the BB-01 method [BB-01 (DAR 1.6)]. The dashed line indicates the level of expression on unstimulated myeloid cells cultured for 18 hours.

Figure 85F:
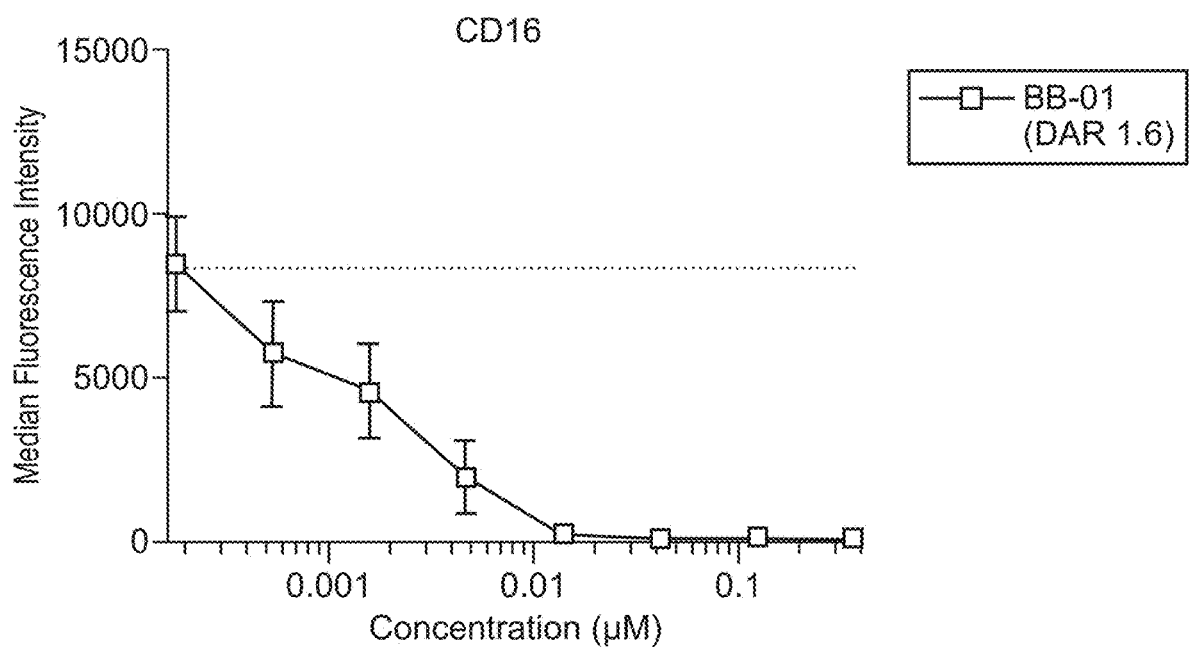

FIG. 85F shows CD16 expression on myeloid cells following 18 hours of stimulation with the rituximab immunoconjugate produced according to the BB-01 method [BB-01 (DAR 1.6)]. The dashed line indicates the level of expression on unstimulated myeloid cells cultured for 18 hours.

Figure 85G:
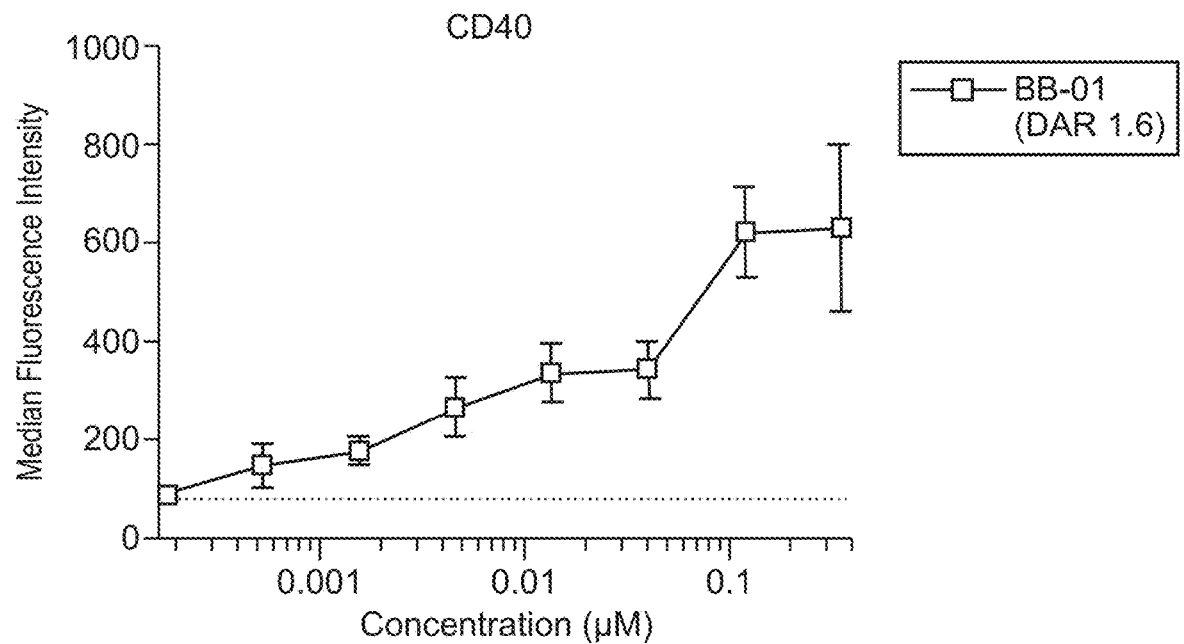

FIG. 85G shows CD40 expression on myeloid cells following 18 hours of stimulation with the rituximab immunoconjugate produced according to the BB-01 method [BB-01 (DAR 1.6)]. The dashed line indicates the level of expression on unstimulated myeloid cells cultured for 18 hours.

Figure 85H:
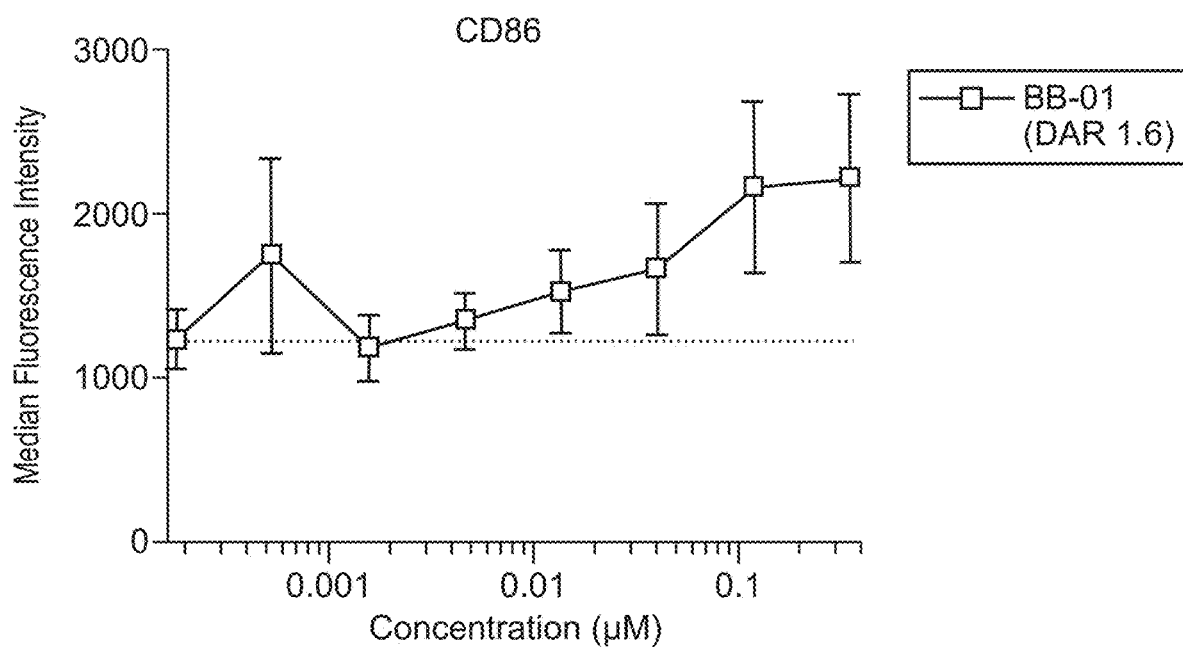

FIG. 85H shows CD86 expression on myeloid cells following 18 hours of stimulation with the rituximab immunoconjugate produced according to the BB-01 method [BB-01 (DAR 1.6)]. The dashed line indicates the level of expression on unstimulated myeloid cells cultured for 18 hours.

Figure 85I:
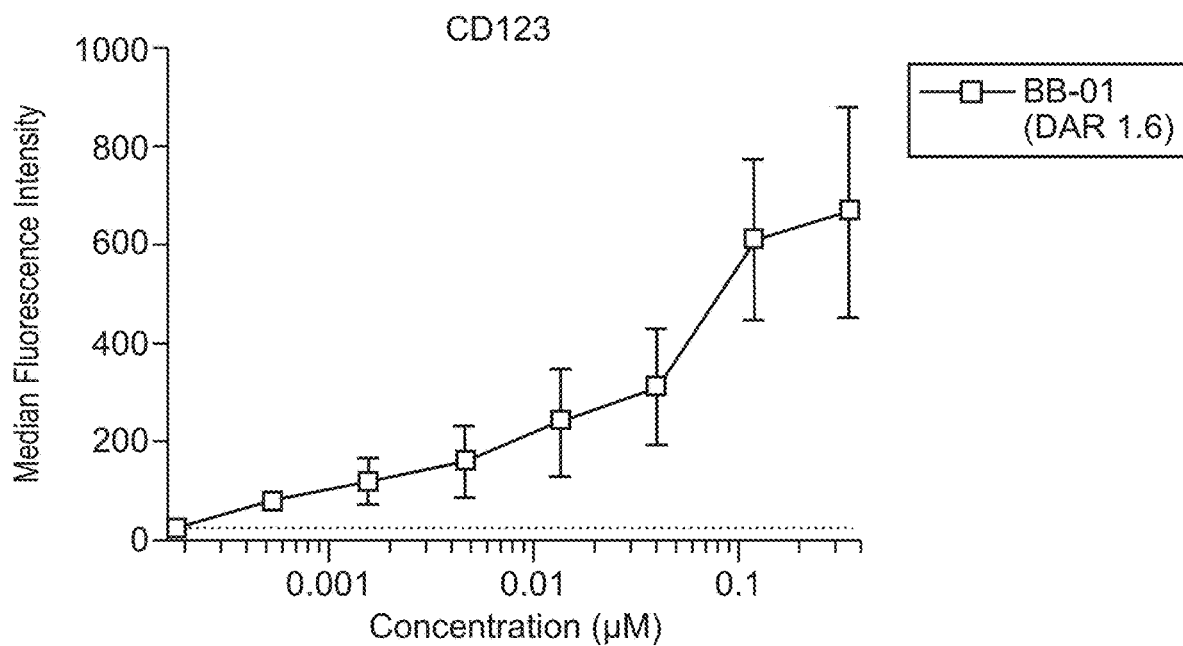

FIG. 85I shows CD123 expression on myeloid cells following 18 hours of stimulation with the rituximab immunoconjugate produced according to the BB-01 method [BB-01 (DAR 1.6)]. The dashed line indicates the level of expression on unstimulated myeloid cells cultured for 18 hours.

Figure 85J:
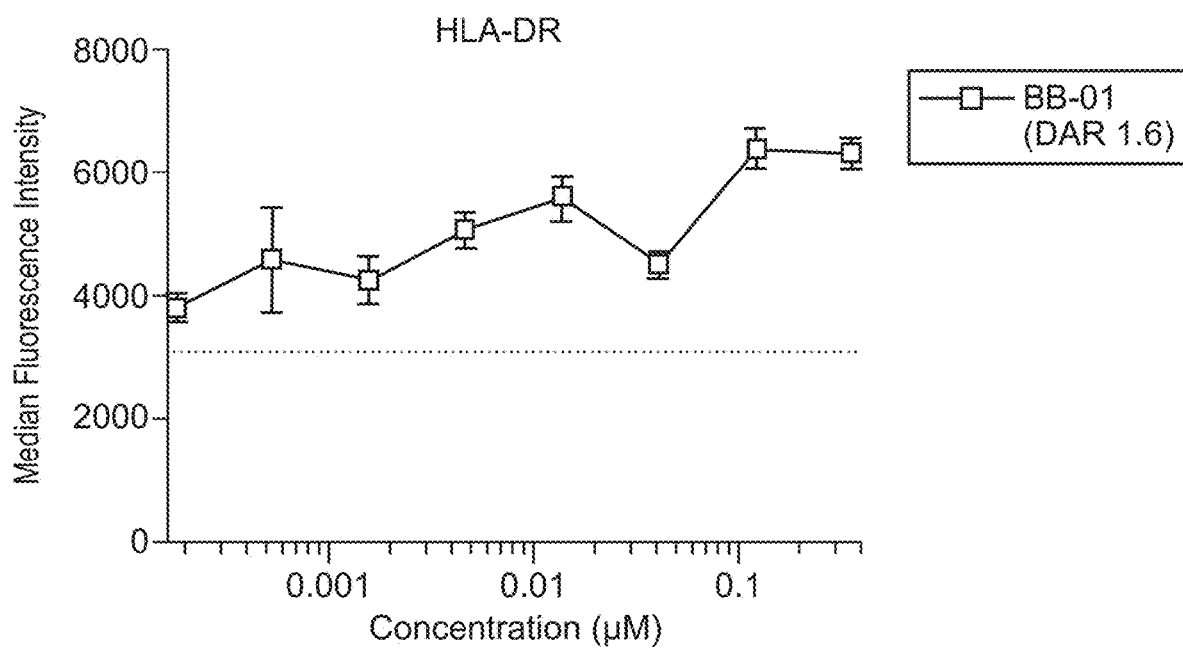

FIG. 85J shows HLA-DR expression on myeloid cells following 18 hours of stimulation with the rituximab immunoconjugate produced according to the BB-01 method [BB-01 (DAR 1.6)]. The dashed line indicates the level of expression on unstimulated myeloid cells cultured for 18 hours.

Figure 86A:
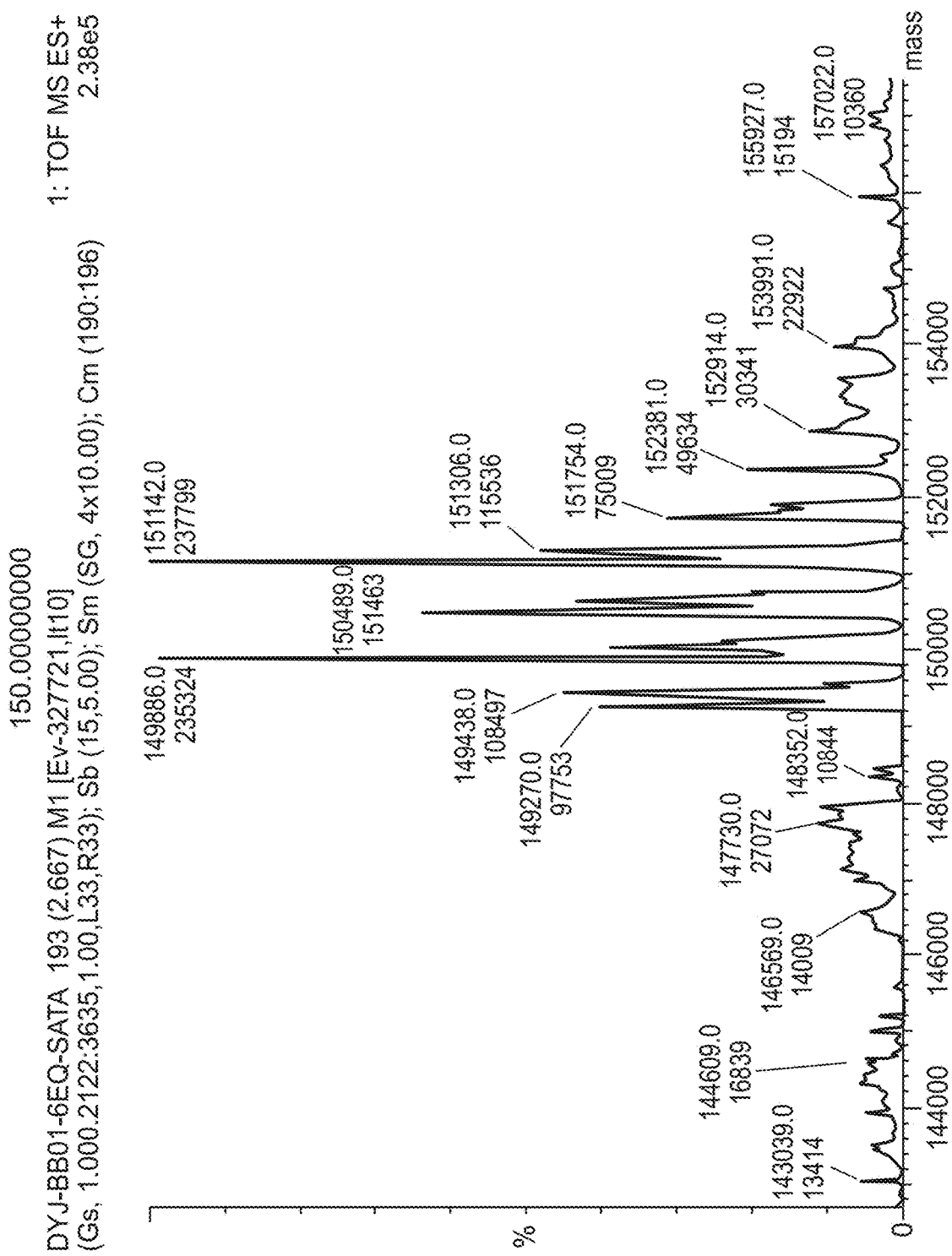

FIG. 86A shows a liquid chromatography-mass spectrometry analysis of the rituximab immunoconjugate produced according to the BB-01 conjugation method from the rituximab biosimilar (LGM Pharma). The calculated DAR is 2.5.

Figure 86B:
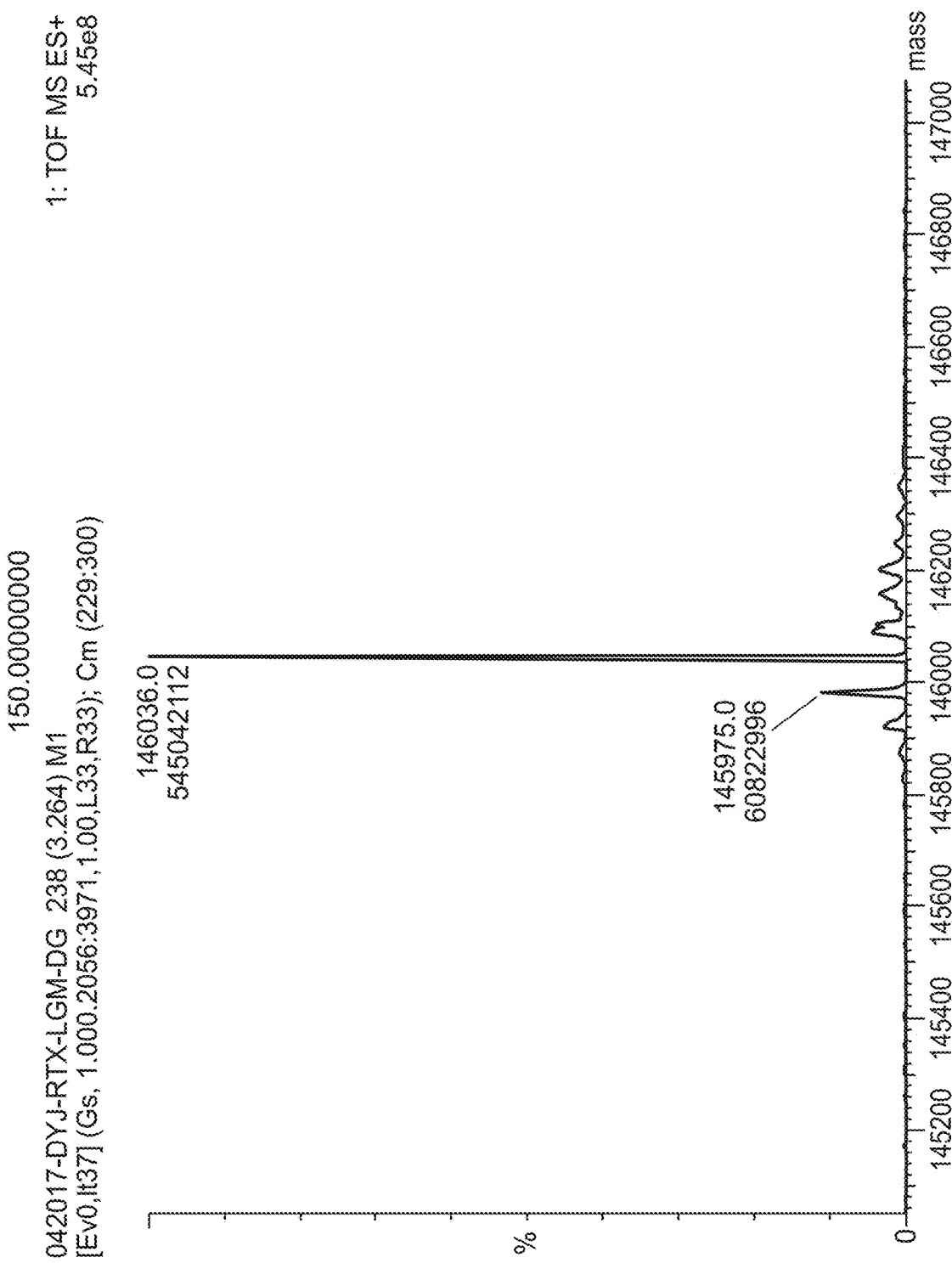

FIG. 86B shows a liquid chromatography-mass spectrometry analysis of unconjugated rituximab biosimilar (LGM Pharma) that was utilized to produce the rituximab immunoconjugate according to the BB-01 conjugation method following overnight deglycosylation with PNGase F.

FIG. 86C shows a liquid chromatography-mass spectrometry analysis of unconjugated rituximab (LGM Pharma) that was utilized to produce the rituximab immunoconjugate according to the BB-01 conjugation method.

Figure 86D:
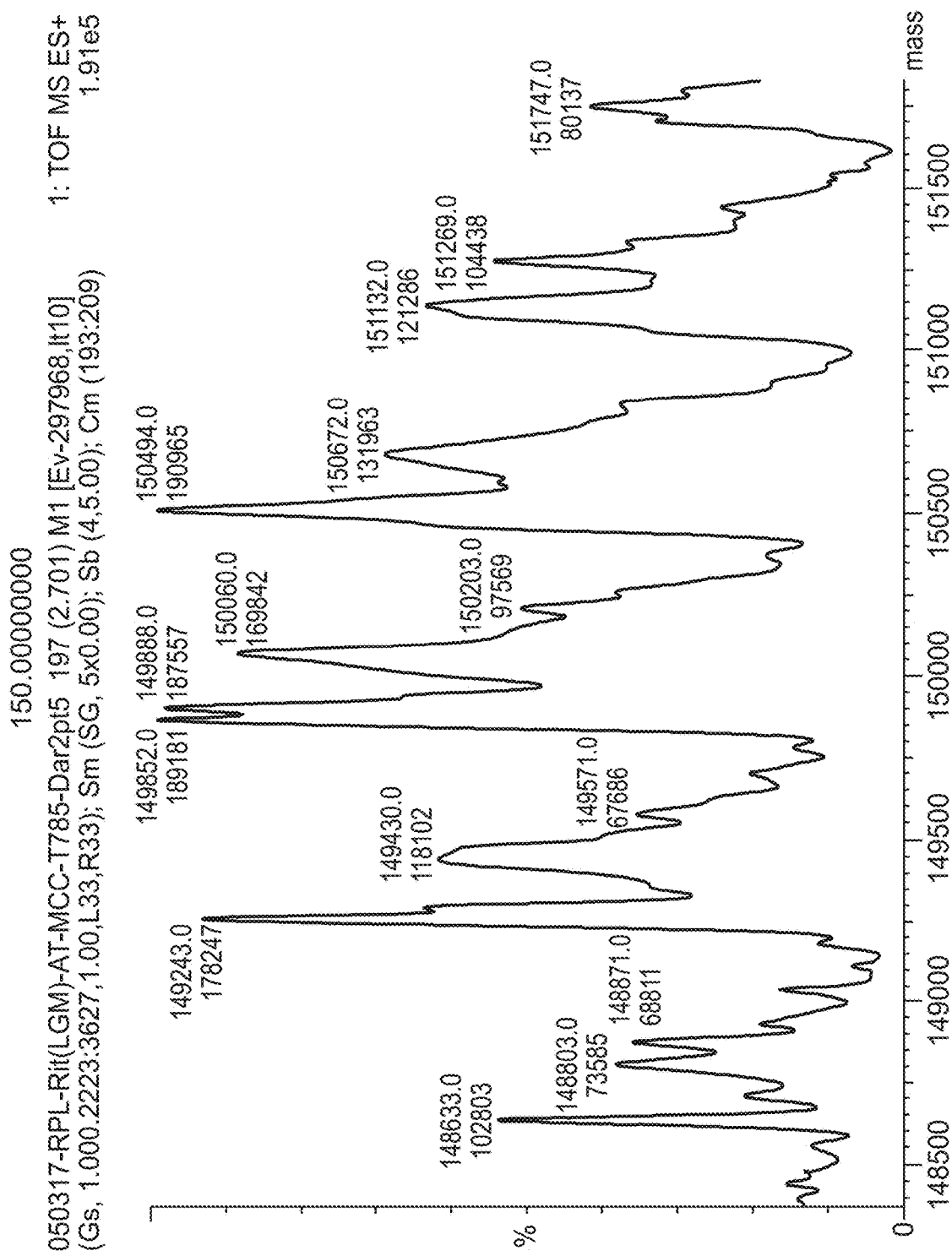

FIG. 86D shows a liquid chromatography-mass spectrometry analysis of the rituximab immunoconjugate produced according to the BB-01 conjugation method from the rituximab biosimilar (LGM Pharma). The calculated DAR is 2.5.

Figure 86E:
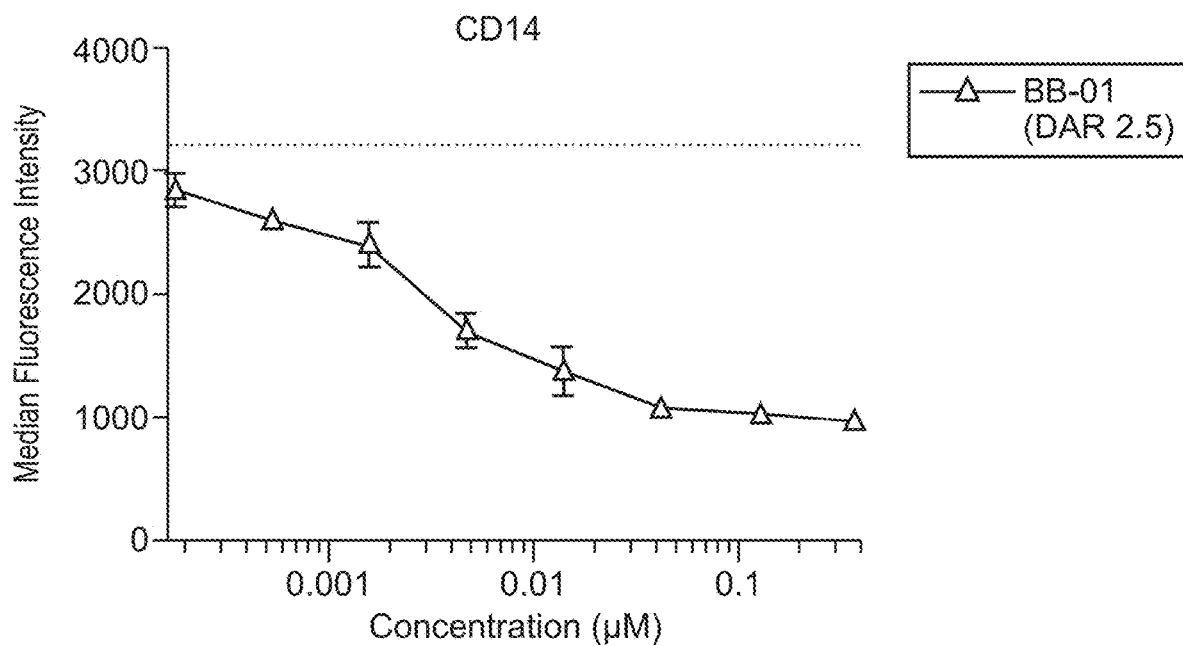

FIG. 86E shows CD14 expression on myeloid cells following 18 hours of stimulation with the rituximab immunoconjugate produced according to the BB-01 method [BB-01 (DAR 2.5)]. The dashed line indicates the level of expression on unstimulated myeloid cells cultured for 18 hours.

Figure 86F:
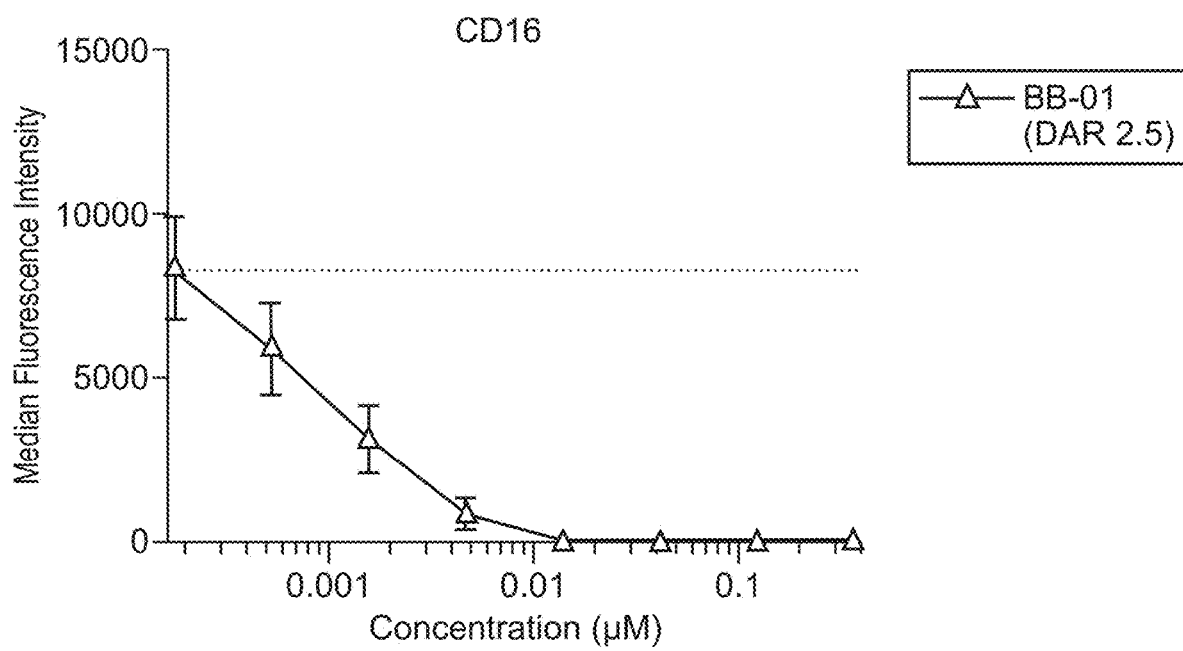

FIG. 86F shows CD16 expression on myeloid cells following 18 hours of stimulation with the rituximab immunoconjugate produced according to the BB-01 method [BB-01 (DAR 2.5)]. The dashed line indicates the level of expression on unstimulated myeloid cells cultured for 18 hours.

Figure 86G:
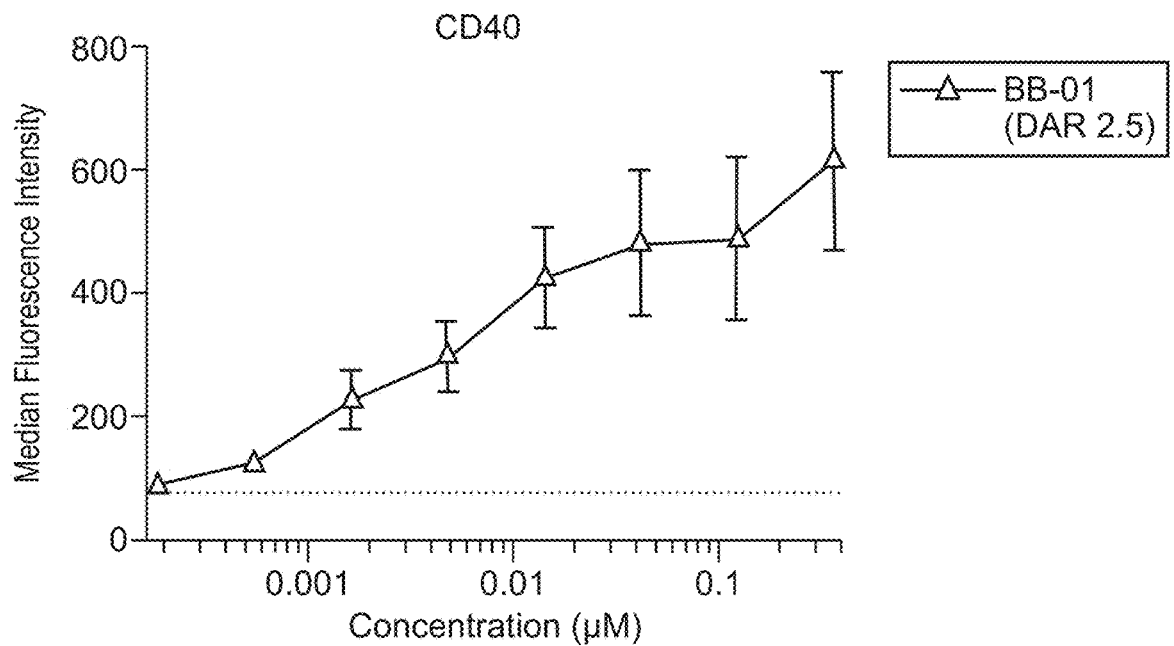

FIG. 86G shows CD40 expression on myeloid cells following 18 hours of stimulation with the rituximab immunoconjugate produced according to the BB-01 method [BB-01 (DAR 2.5)]. The dashed line indicates the level of expression on unstimulated myeloid cells cultured for 18 hours.

Figure 86H:
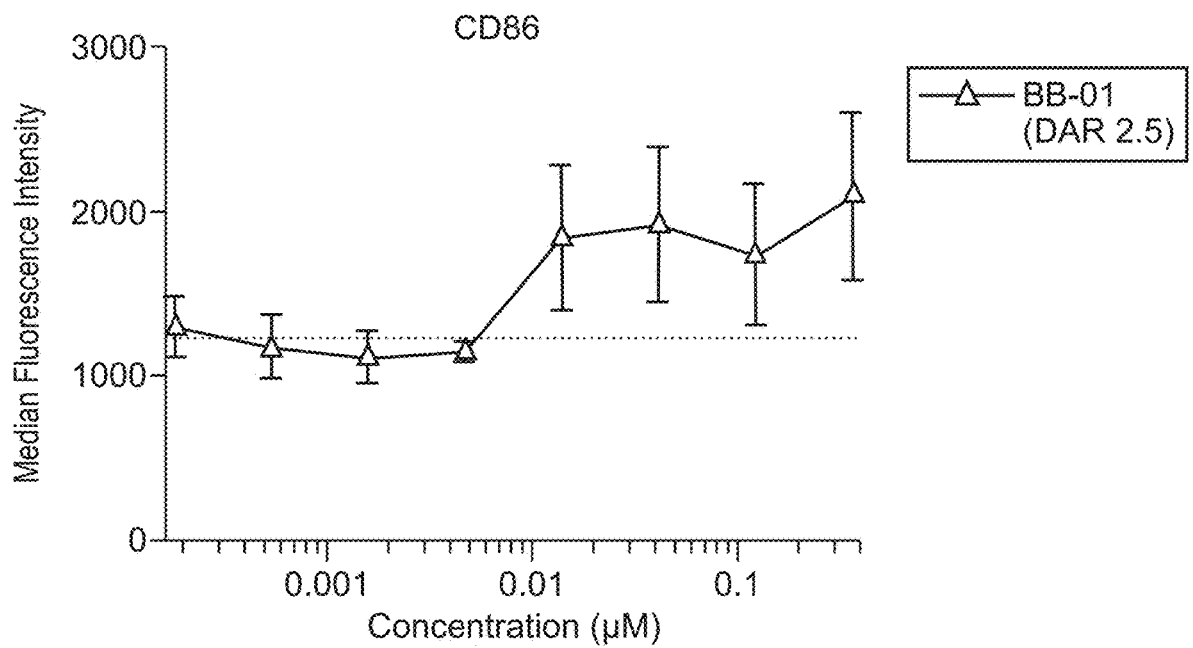

FIG. 86H shows CD86 expression on myeloid cells following 18 hours of stimulation with the rituximab immunoconjugate produced according to the BB-01 method [BB-01 (DAR 2.5)]. The dashed line indicates the level of expression on unstimulated myeloid cells cultured for 18 hours.

Figure 86I:
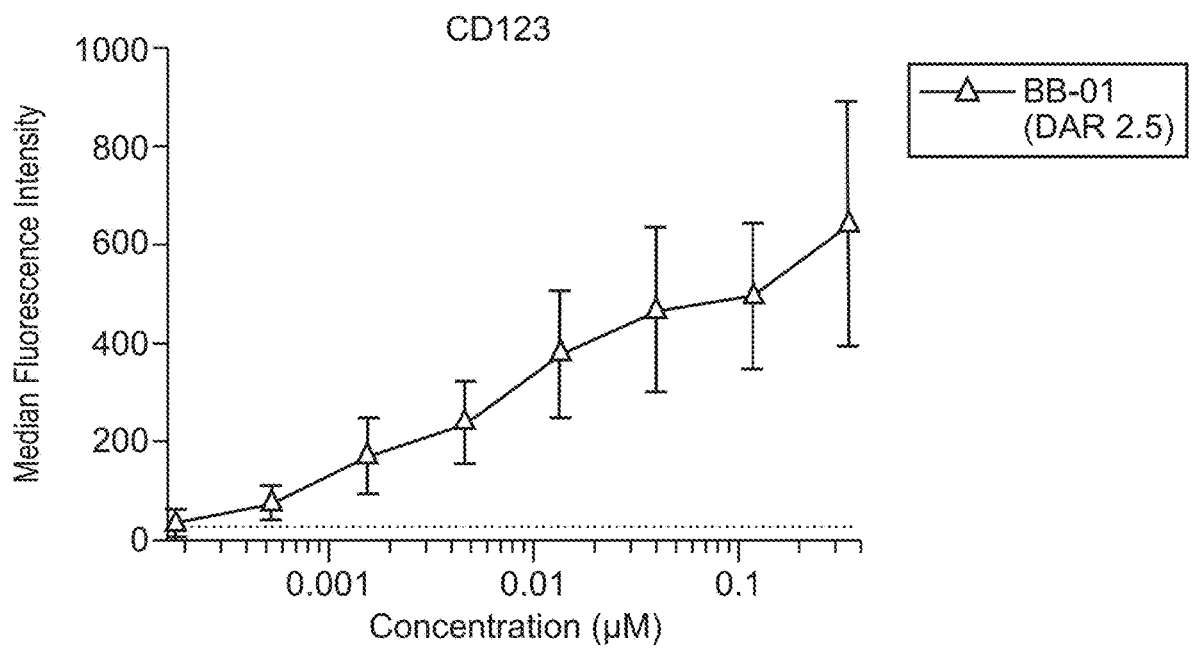

FIG. 86I shows CD123 expression on myeloid cells following 18 hours of stimulation with the rituximab immunoconjugate produced according to the BB-01 method [BB-01 (DAR 1.6)]. The dashed line indicates the level of expression on unstimulated myeloid cells cultured for 18 hours.

Figure 86J:
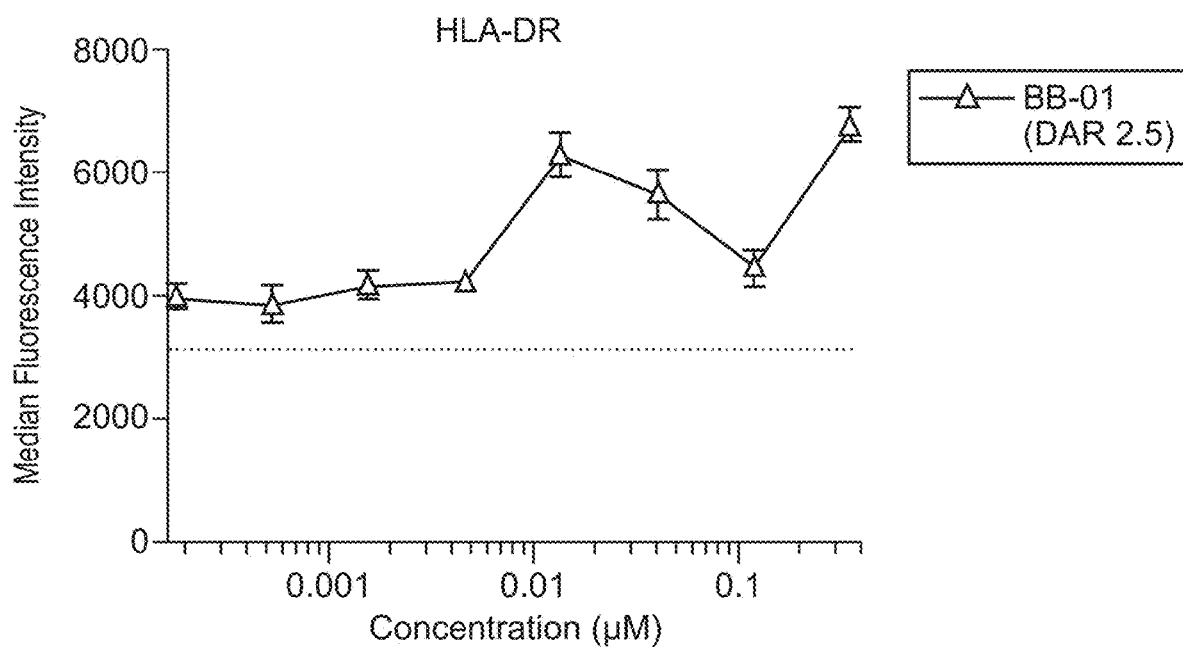

FIG. 86J shows HLA-DR expression on myeloid cells following 18 hours of stimulation with the rituximab immunoconjugate produced according to the BB-01 method [BB- 01 (DAR 1.6)]. The dashed line indicates the level of expression on unstimulated myeloid cells cultured for 18 hours.

Figure 87A:
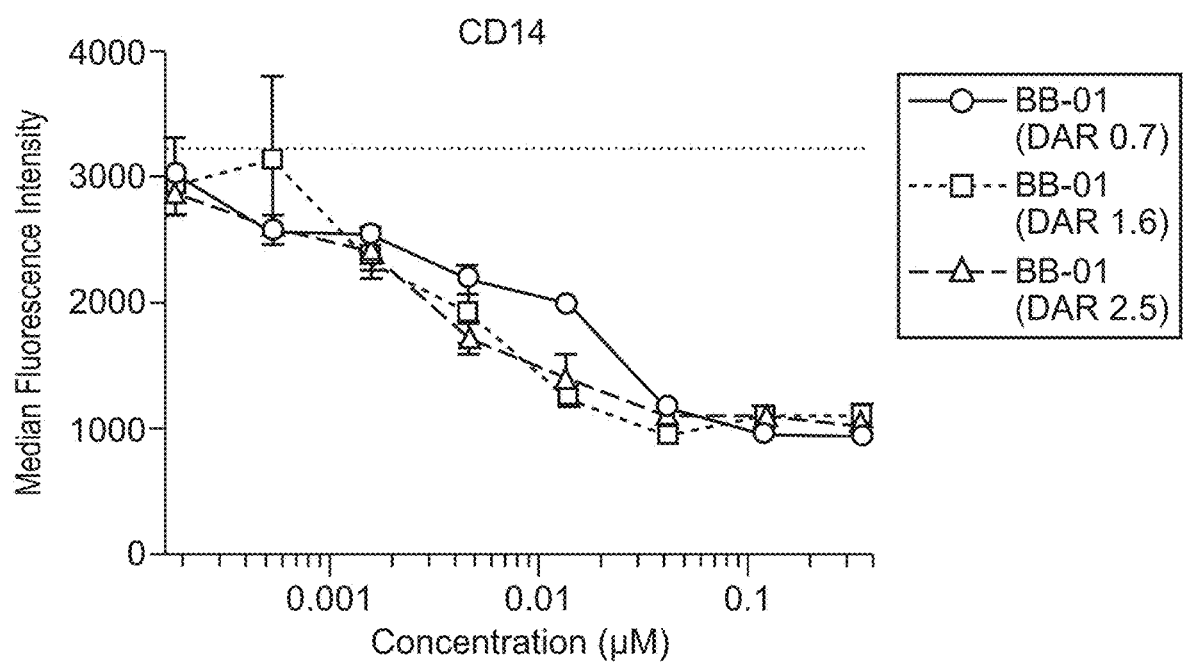

FIG. 87A shows that the rituximab immunoconjugates of varying DAR, all produced according to the BB-01 method from the rituximab biosimilar (LGM Pharma) elicit comparable CD14 downregulation on myeloid cells following 18 hours of stimulation. The dashed line indicates the level of expression on unstimulated myeloid cells cultured for 18 hours.

Figure 87B:
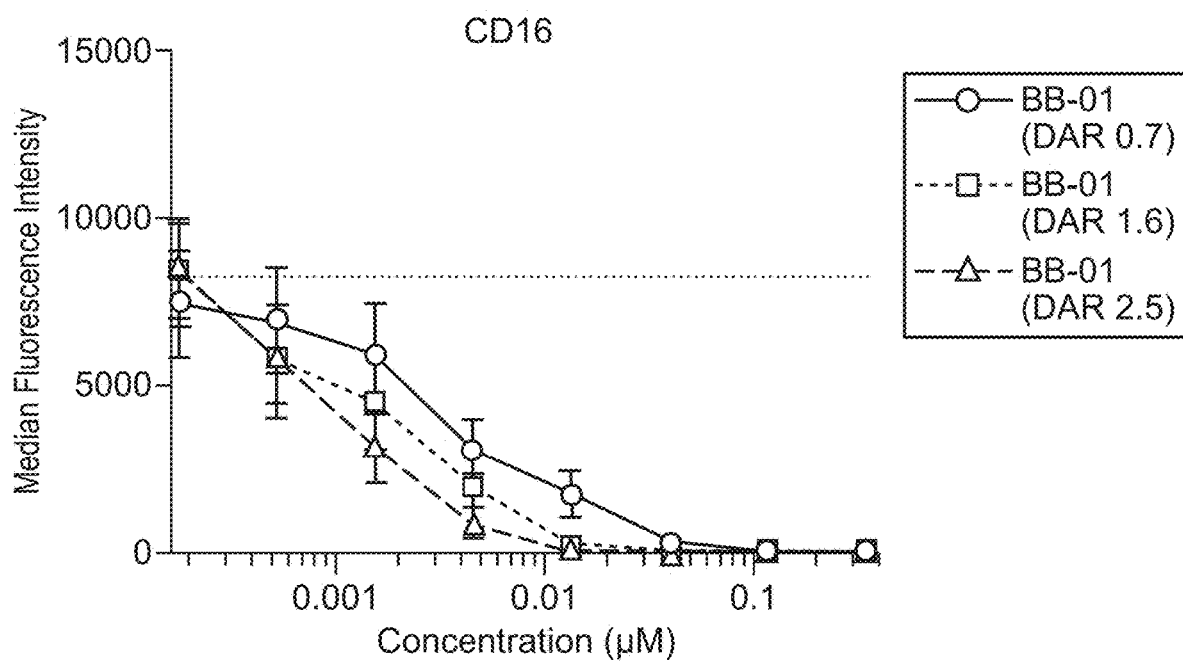

FIG. 87B shows that the rituximab immunoconjugates of varying DAR, all produced according to the BB-01 method from the rituximab biosimilar (LGM Pharma) elicit comparable CD16 downregulation on myeloid cells following 18 hours of stimulation. The dashed line indicates the level of expression on unstimulated myeloid cells cultured for 18 hours.

Figure 87C:
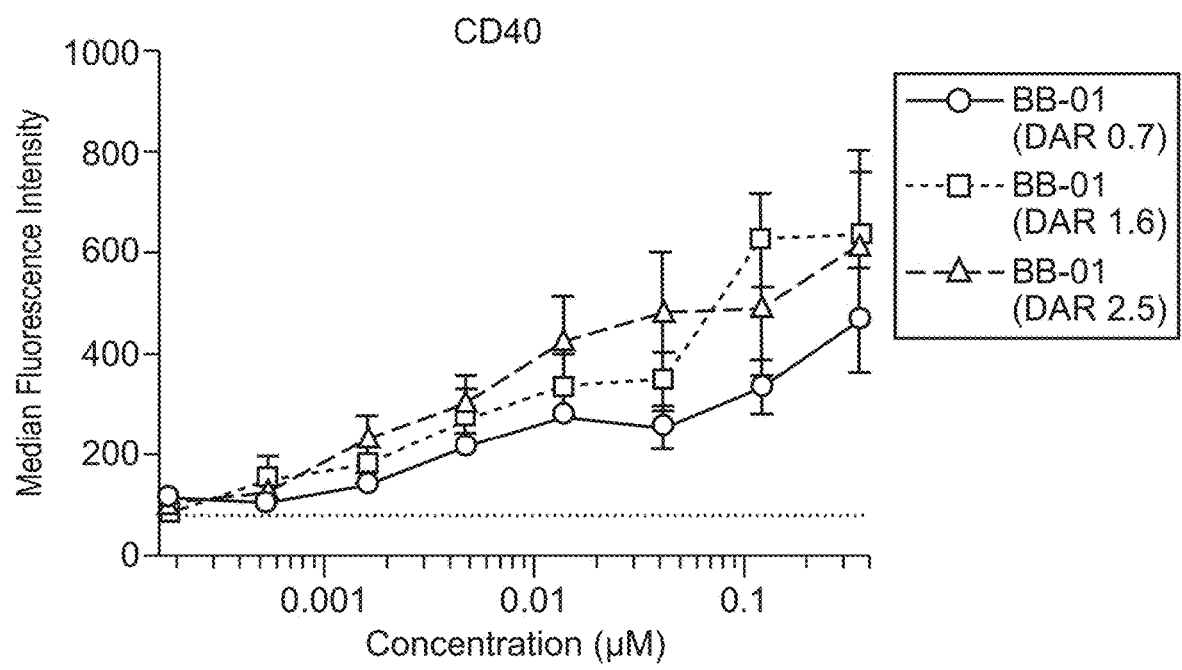

FIG. 87C shows that the rituximab immunoconjugates of varying DAR, all produced according to the BB-01 method from the rituximab biosimilar (LGM Pharma) elicit comparable CD40 upregulation on myeloid cells following 18 hours of stimulation. The dashed line indicates the level of expression on unstimulated myeloid cells cultured for 18 hours.

Figure 87D:
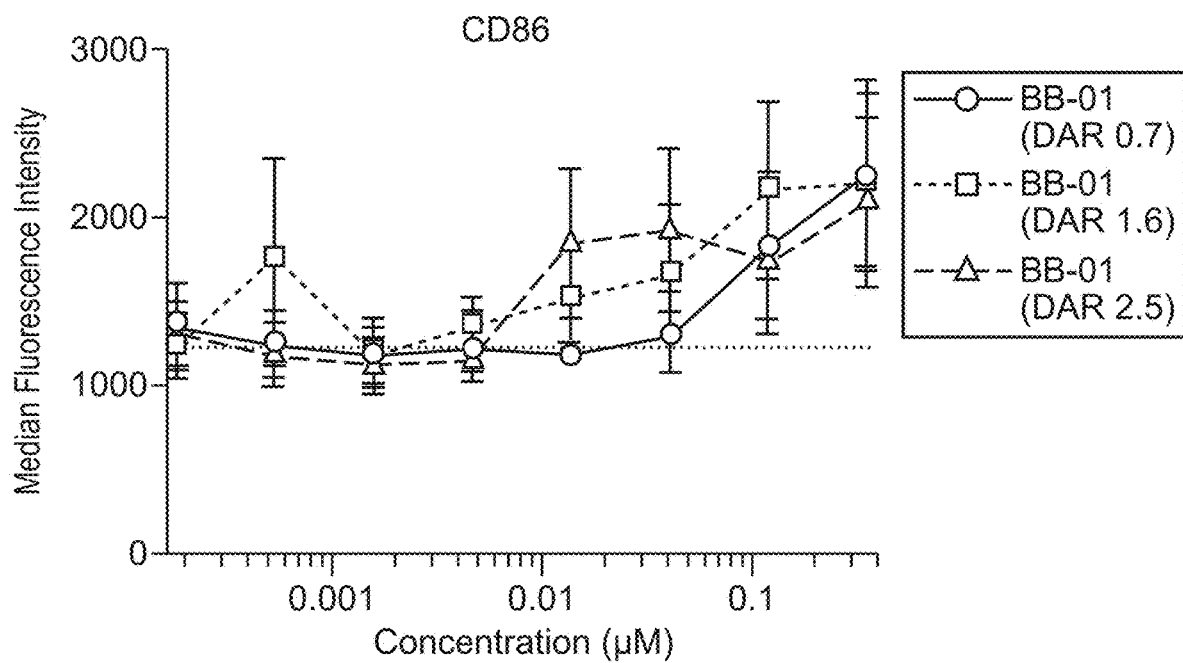

FIG. 87D shows that the rituximab immunoconjugates of varying DAR, all produced according to the BB-01 method from the rituximab biosimilar (LGM Pharma) elicit comparable CD86 upregulation on myeloid cells following 18 hours of stimulation. The dashed line indicates the level of expression on unstimulated myeloid cells cultured for 18 hours.

Figure 87E:
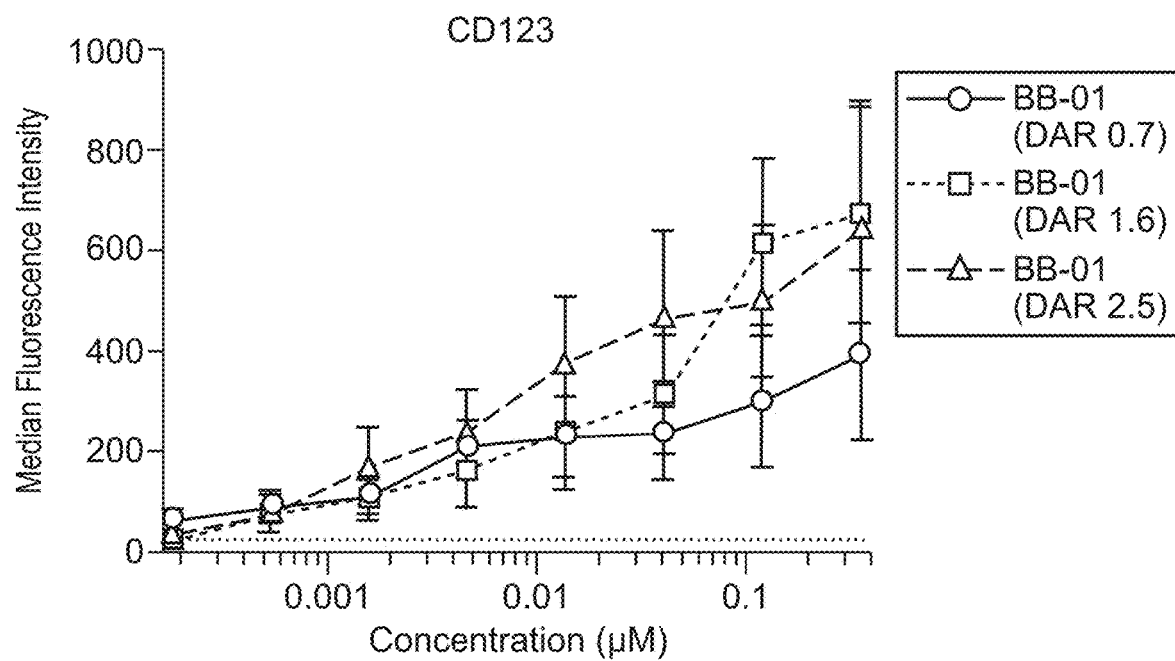

FIG. 87E shows that the rituximab immunoconjugates of varying DAR, all produced according to the BB-01 method from the rituximab biosimilar (LGM Pharma) elicit comparable CD123 upregulation on myeloid cells following 18 hours of stimulation. The dashed line indicates the level of expression on unstimulated myeloid cells cultured for 18 hours.

Figure 87F:
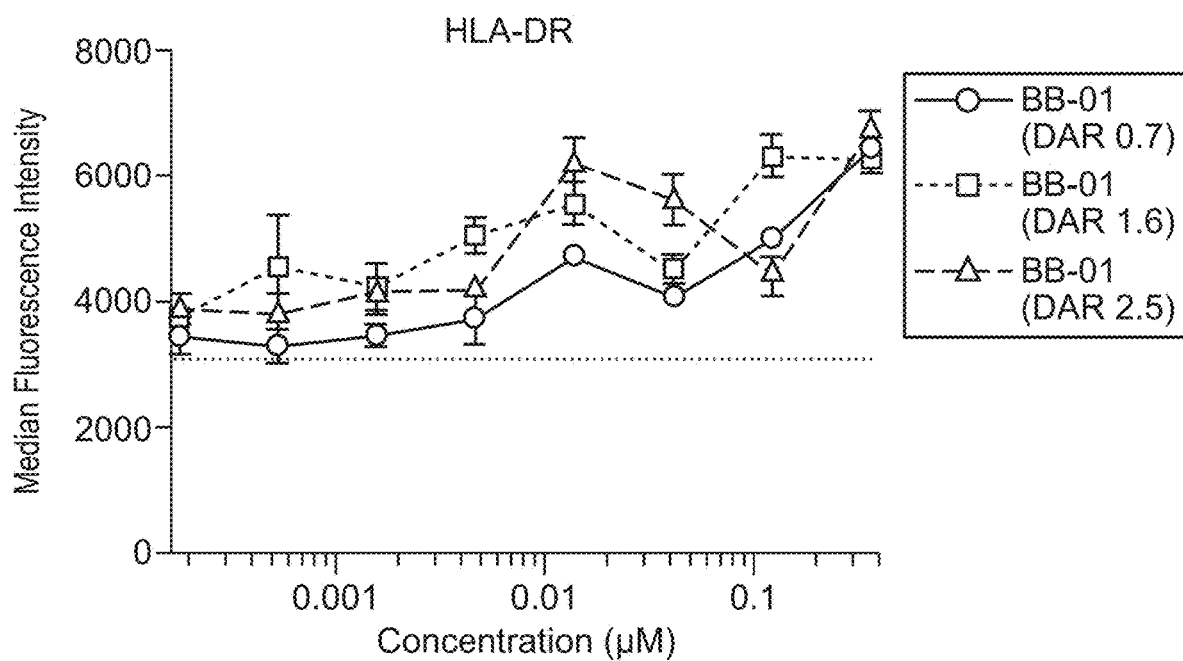

FIG. 87F shows that the rituximab immunoconjugates of varying DAR, all produced according to the BB-01 method from the rituximab biosimilar (LGM Pharma) elicit comparable HLA-DR upregulation on myeloid cells following 18 hours of stimulation. The dashed line indicates the level of expression on unstimulated myeloid cells cultured for 18 hours.

Figure 88A:
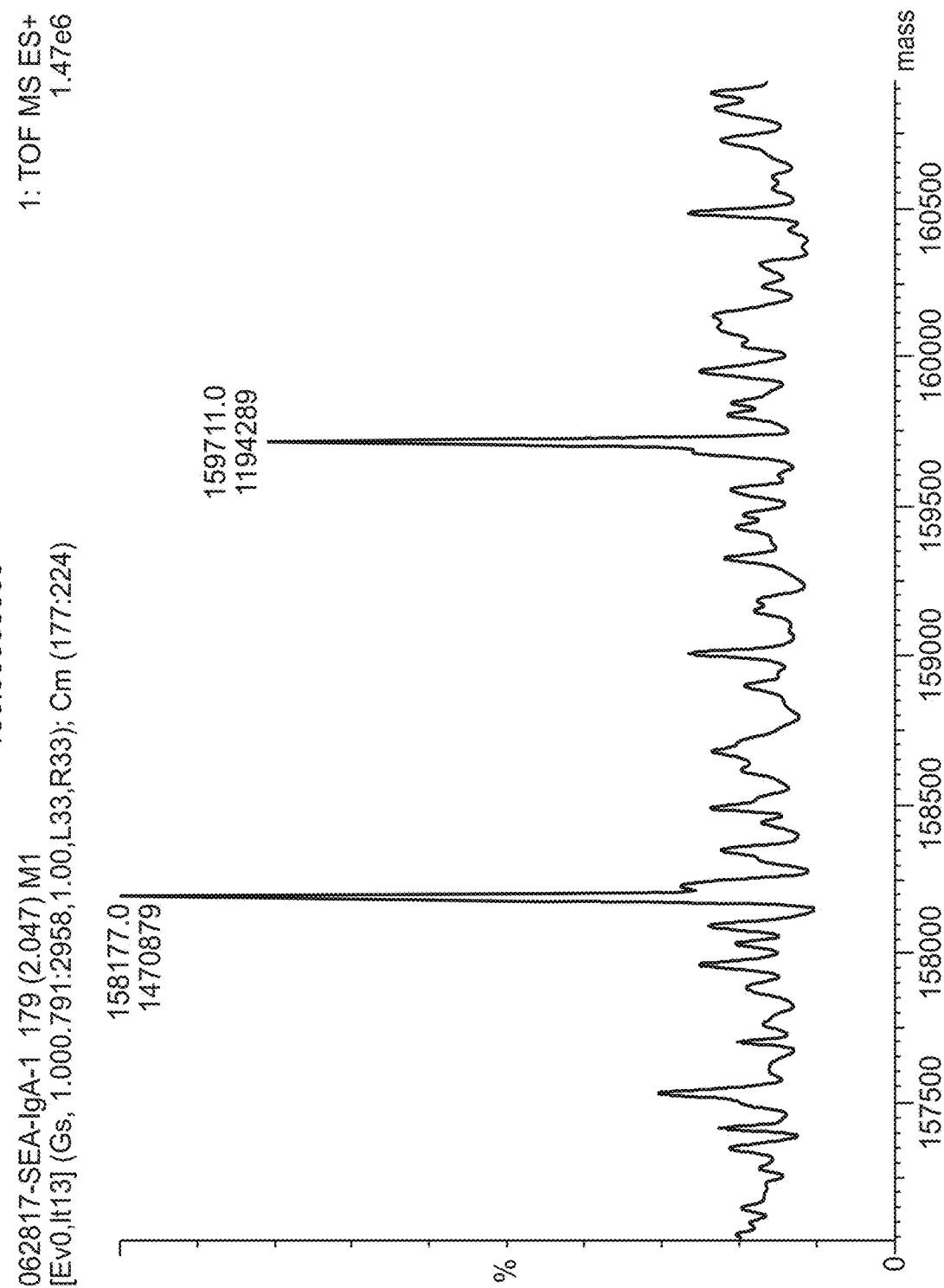

FIG. 88A shows a liquid chromatography-mass spectrometry analysis of unconjugated rituximab IgA2 (Invivogen, hcd20-mab7) that was utilized to produce the rituximab immunoconjugate according to the BB-01 conjugation method following overnight deglycosylation with PNGase F.

FIG. 88B shows a liquid chromatography-mass spectrometry analysis of the rituximab IgA2 immunoconjugate produced according to the BB-01 conjugation method following overnight deglycosylation with PNGase F.

Figure 88C:
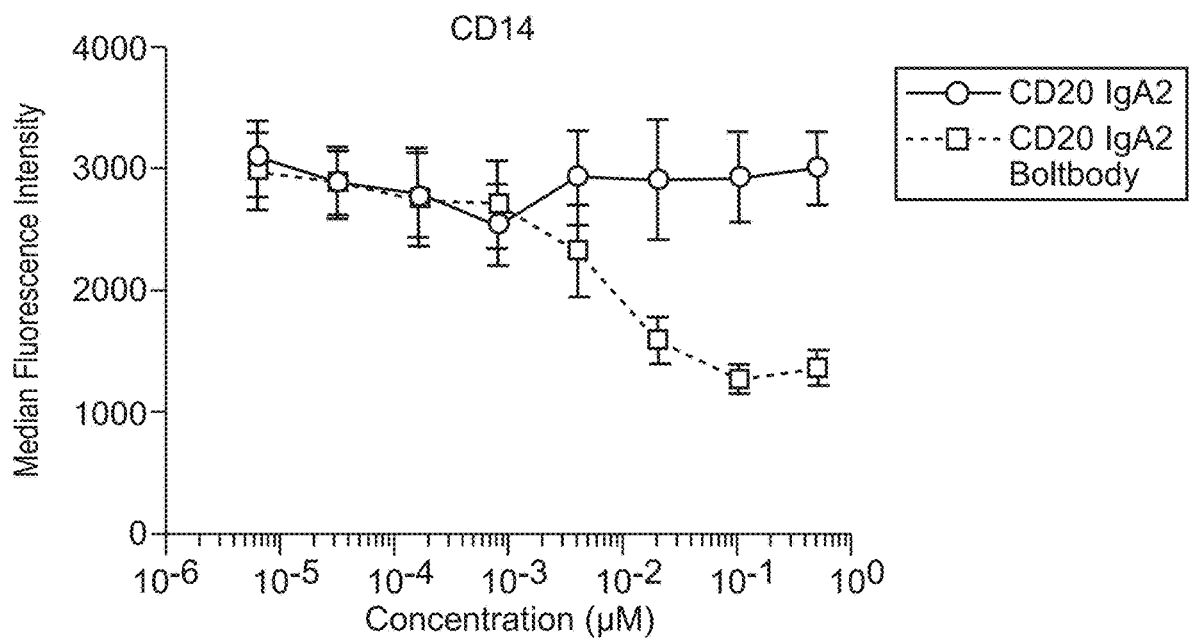

FIG. 88C shows that the rituximab IgA2 immunoconjugate produced according to the BB-01 method (CD20 IgA2 Boltbody) is superior at eliciting CD14 downregulation on myeloid cells as compared to the unconjugated rituximab (CD20 IgA2; Invivogen, hcd20-mac7) following 18 hours of stimulation.

Figure 88D:
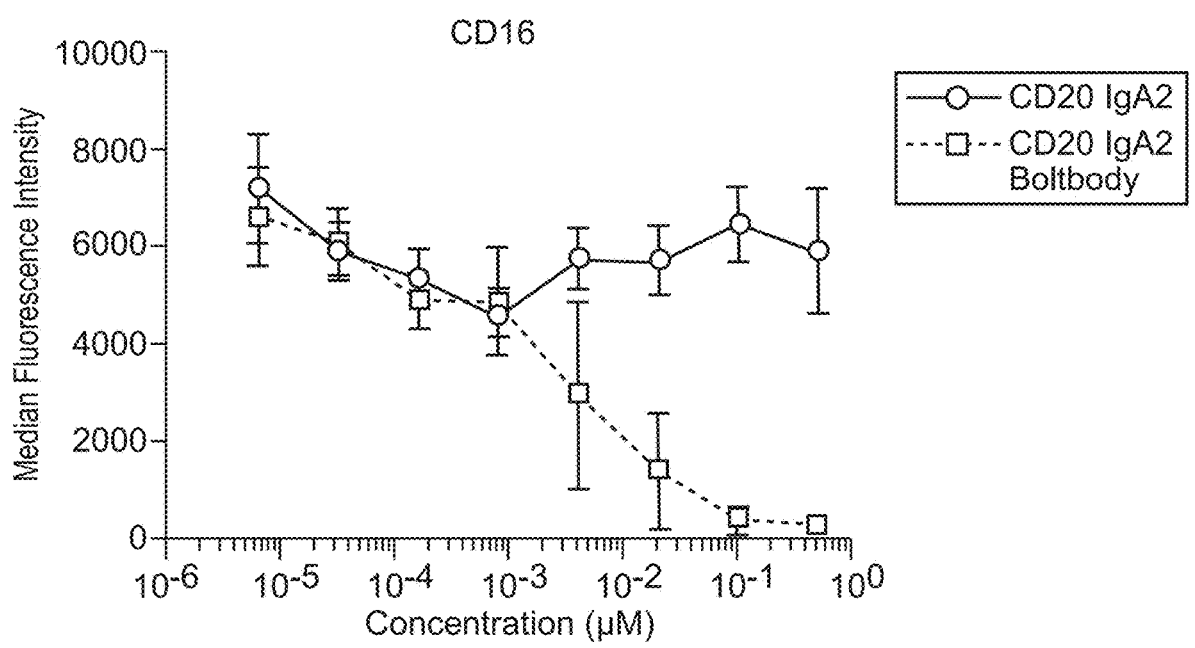

FIG. 88D shows that the rituximab IgA2 immunoconjugate produced according to the BB-01 method (CD20 IgA2 Boltbody) is superior at eliciting CD16 downregulation on myeloid cells as compared to the unconjugated rituximab (CD20 IgA2; Invivogen, hcd20-mac7) following 18 hours of stimulation.

Figure 88E:
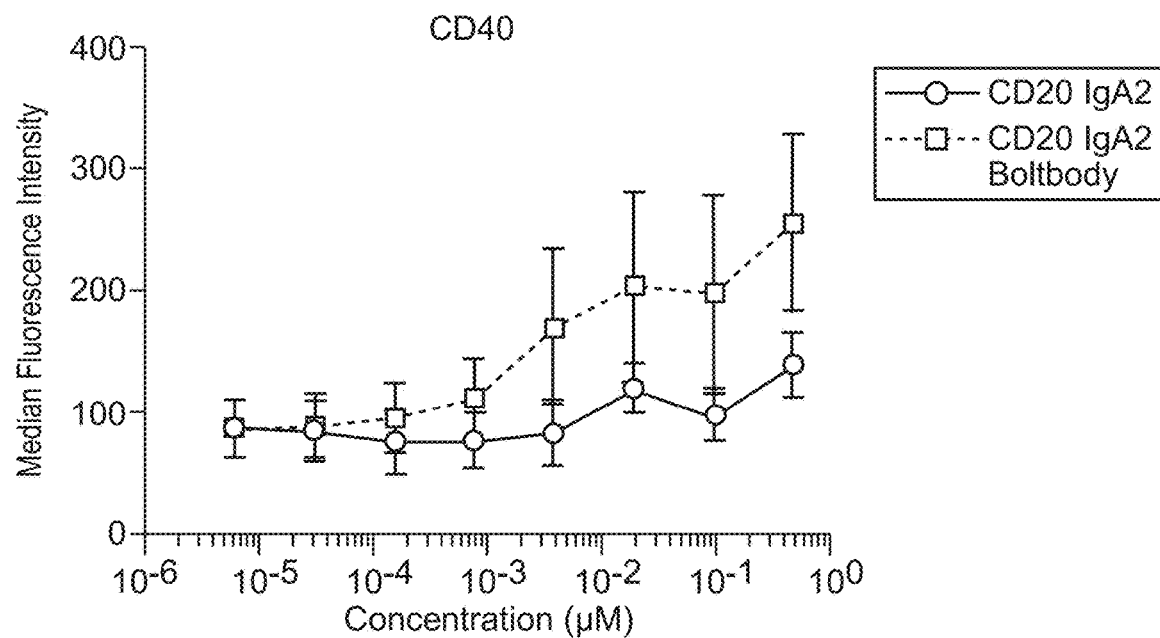

FIG. 88E shows that the rituximab IgA2 immunoconjugate produced according to the BB-01 method (CD20 IgA2 Boltbody) is superior at eliciting CD40 upregulation on myeloid cells as compared to the unconjugated rituximab (CD20 IgA2; Invivogen, hcd20-mac7) following 18 hours of stimulation.

Figure 88F:
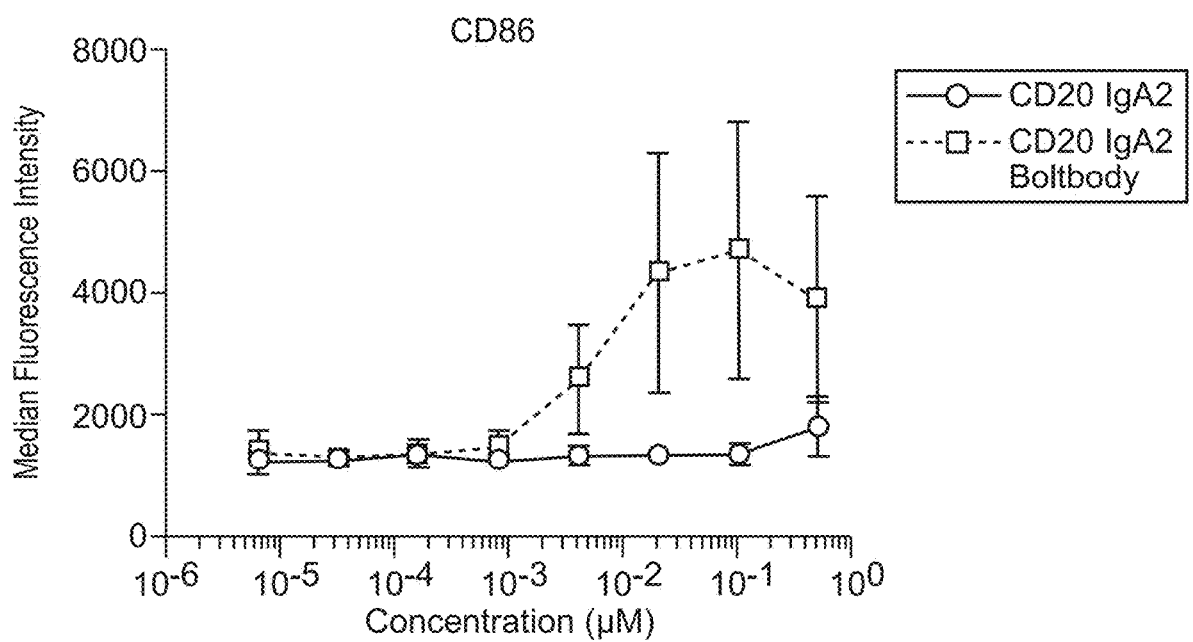

FIG. 88F shows that the rituximab IgA2 immunoconjugate produced according to the BB-01 method (CD20 IgA2 Boltbody) is superior at eliciting CD86 upregulation on myeloid cells as compared to the unconjugated rituximab (CD20 IgA2; Invivogen, hcd20-mac7) following 18 hours of stimulation.

Figure 88G:
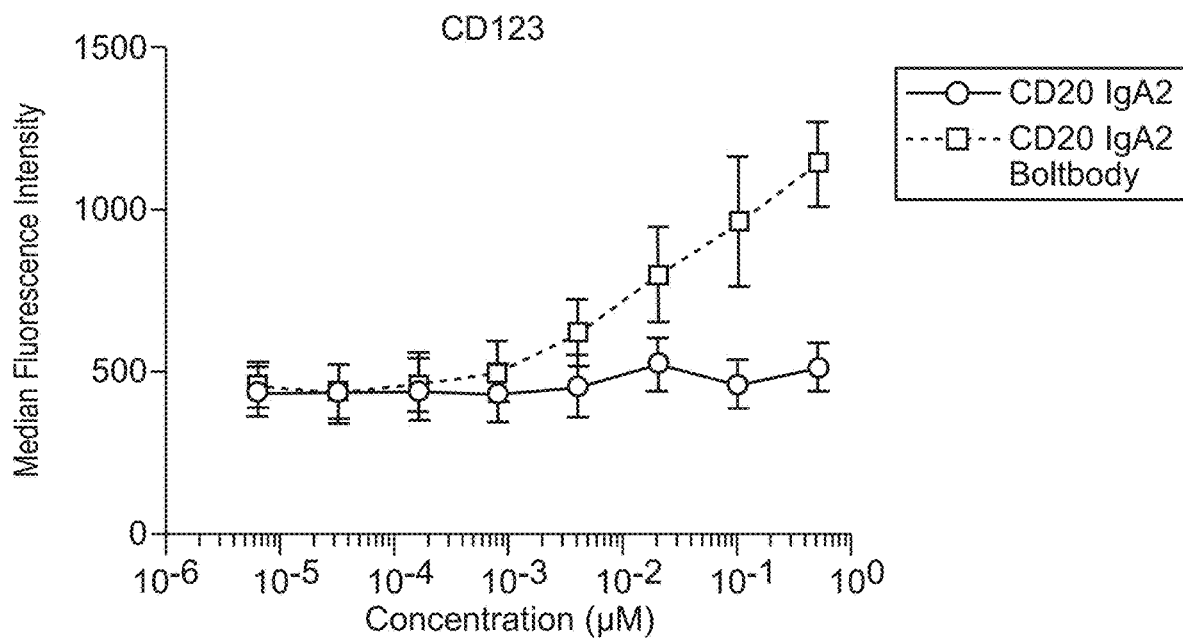

FIG. 88G shows that the rituximab IgA2 immunoconjugate produced according to the BB-01 method (CD20 IgA2 Boltbody) is superior at eliciting CD123 upregulation on myeloid cells as compared to the unconjugated rituximab (CD20 IgA2; Invivogen, hcd20-mac7) following 18 hours of stimulation.

Figure 88H:
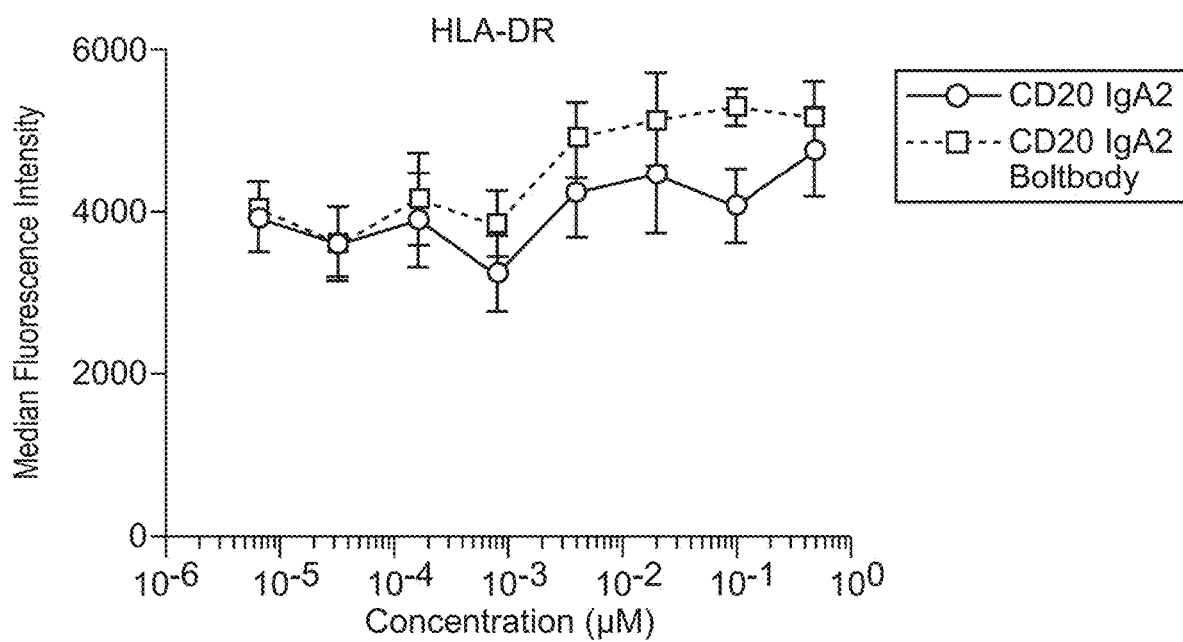

FIG. 88H shows that the rituximab IgA2 immunoconjugate produced according to the BB-01 method (CD20 IgA2 Boltbody) is superior at eliciting HLA-DR upregulation on myeloid cells as compared to the unconjugated rituximab (CD20 IgA2; Invivogen, hcd20-mac7) following 18 hours of stimulation.

Figure 89A:
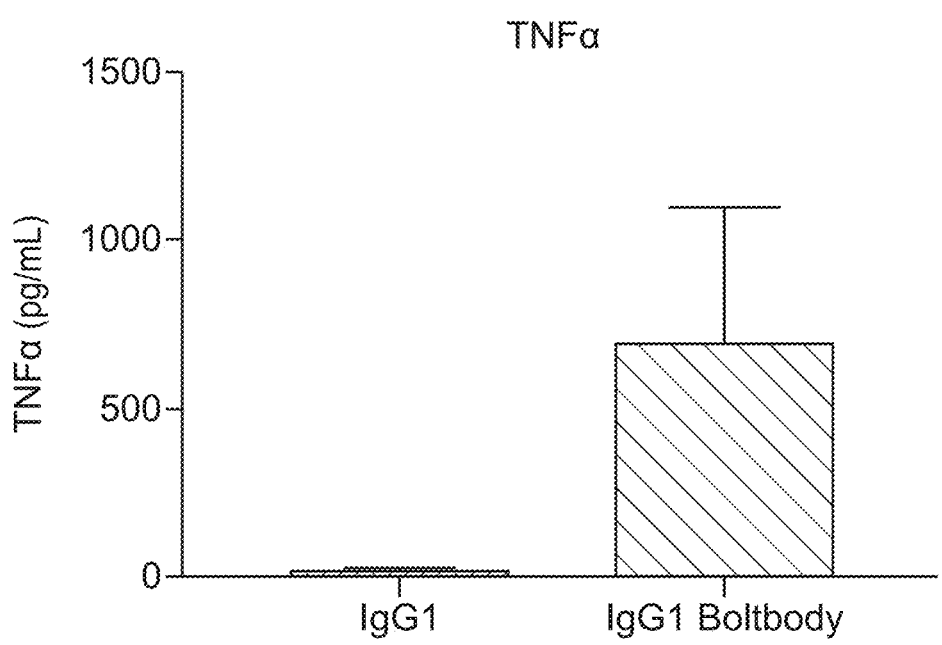

FIG. 89A shows that the rituximab IgG1 immunoconjugate produced according to the BB-01 method (IgG1 Boltbody) elicits superior TNFα secretion from myeloid cells as compared to equimolar concentrations (0.2 µM) of unconjugated rituximab (IgG; Invivogen, hcd20-mab1) following 36 hours of stimulation.

Figure 89B:
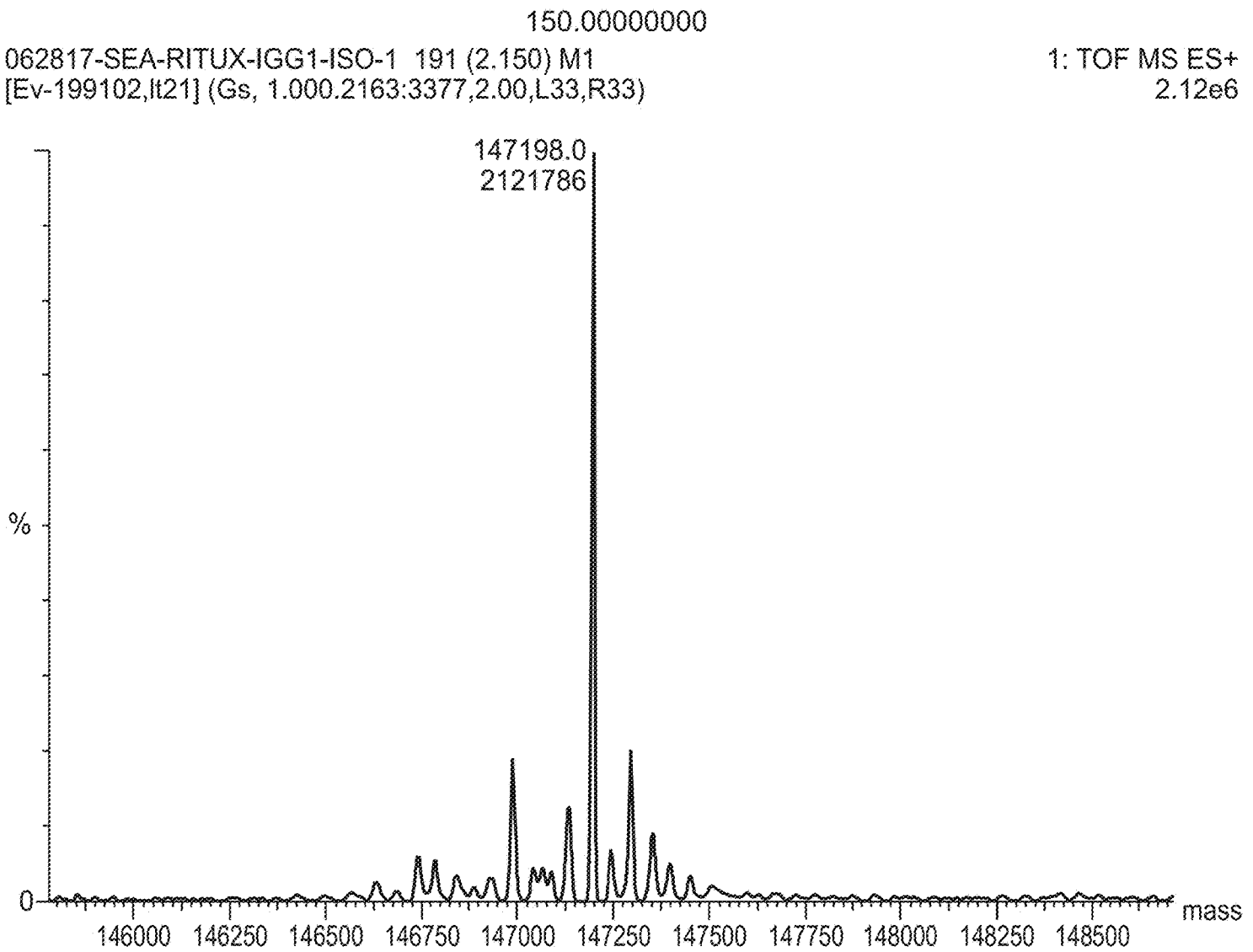

FIG. 89B shows a liquid chromatography-mass spectrometry analysis of unconjugated rituximab IgG1 (Invivogen, hcd20-mab1) that was utilized to produce the rituximab immunoconjugate according to the BB-01 conjugation method.

Figure 89C:
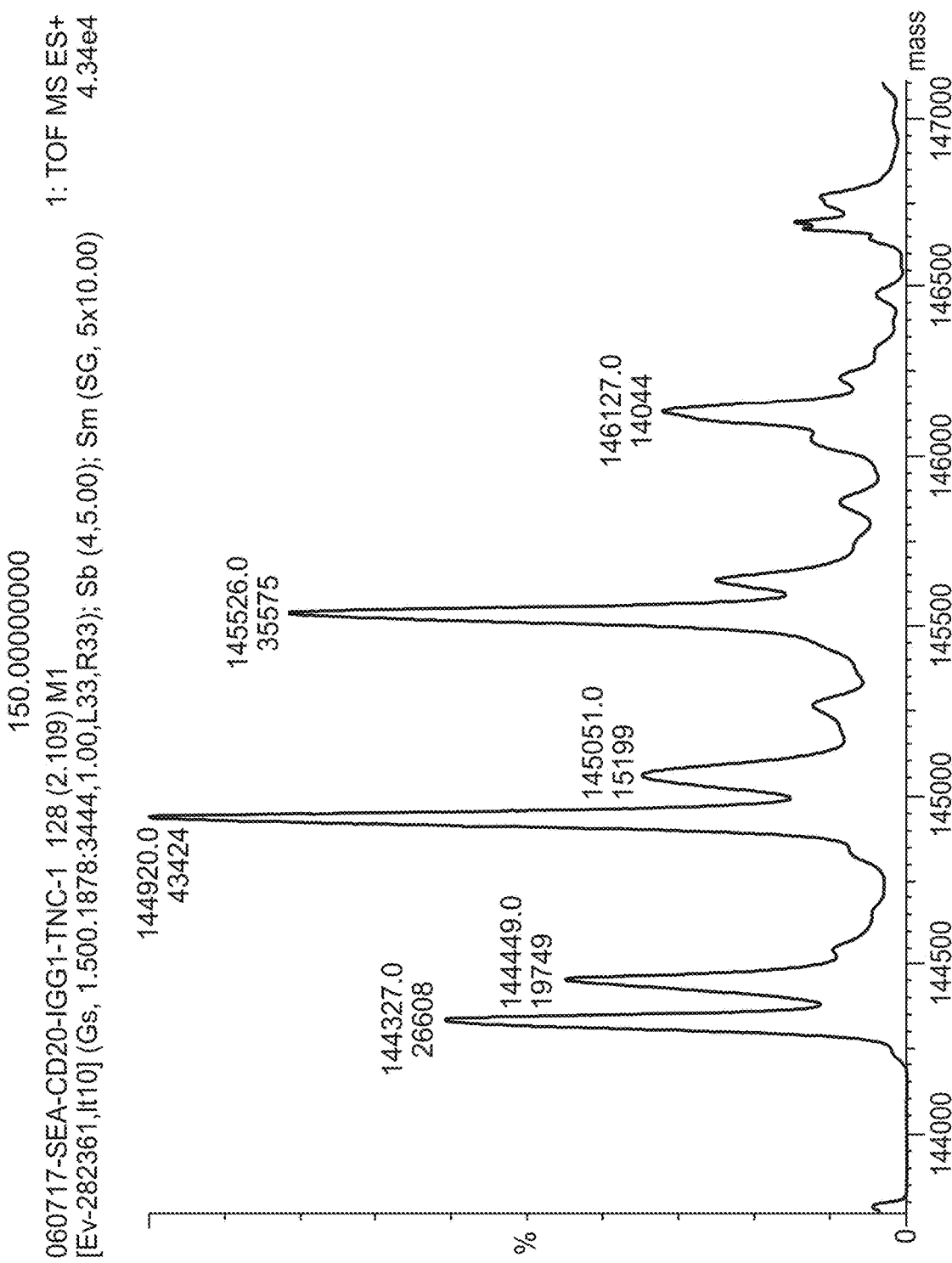

FIG. 89C shows a liquid chromatography-mass spectrometry analysis of the rituximab IgG1 immunoconjugate produced according to the BB-01 conjugation method.

Figure 89D:
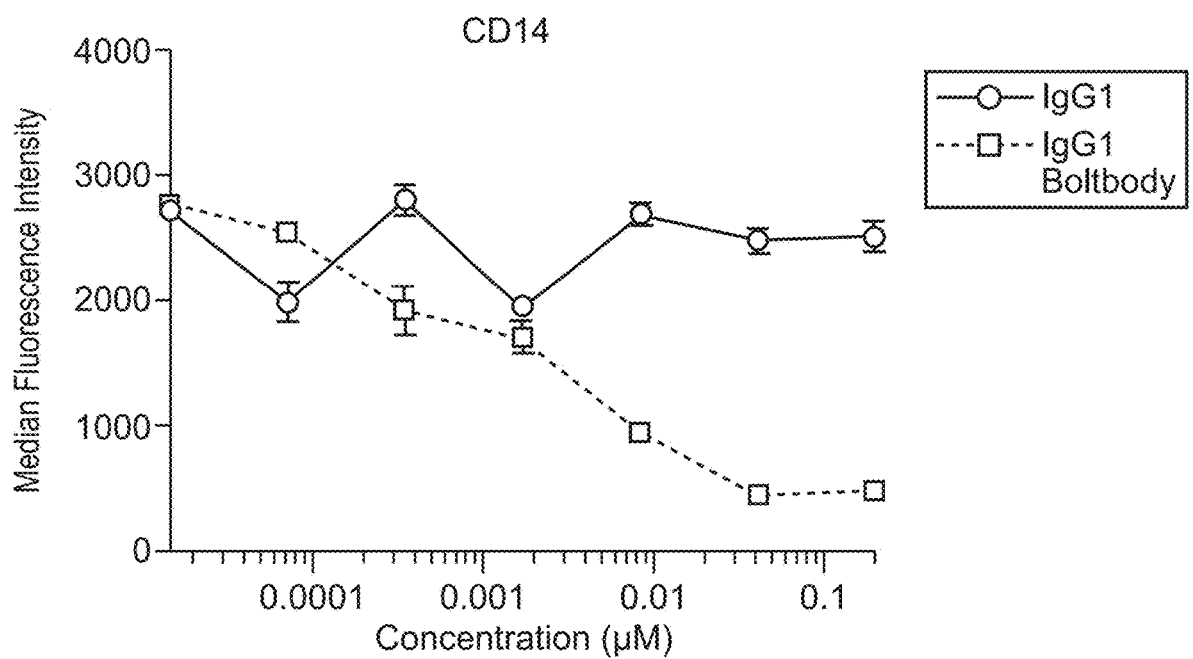

FIG. 89D shows that the rituximab IgG1 immunoconjugate produced according to the BB-01 method (CD20 IgG1 Boltbody) is superior at eliciting CD14 downregulation on myeloid cells as compared to the unconjugated rituximab (CD20 IgG1; Invivogen, hcd20-mab1) following 18 hours of stimulation.

Figure 89E:
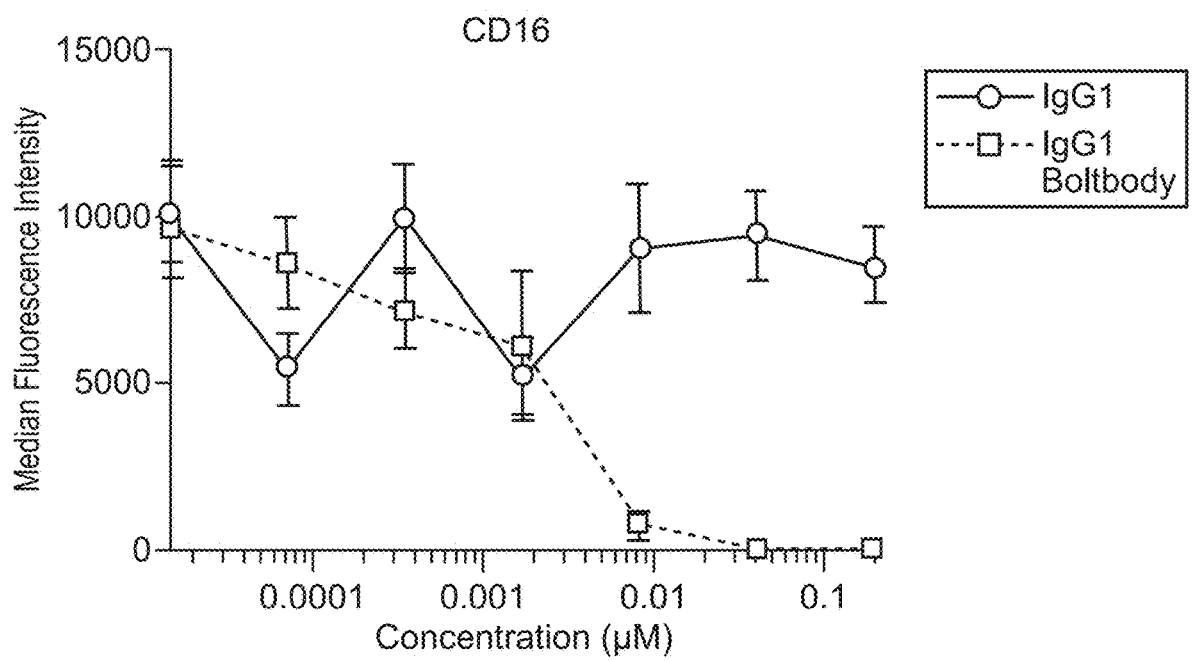

FIG. 89E shows that the rituximab IgG1 immunoconjugate produced according to the BB-01 method (CD20 IgG1 Boltbody) is superior at eliciting CD16 downregulation on myeloid cells as compared to the unconjugated rituximab (CD20 IgG1; Invivogen, hcd20-mab1) following 18 hours of stimulation.

Figure 89F:
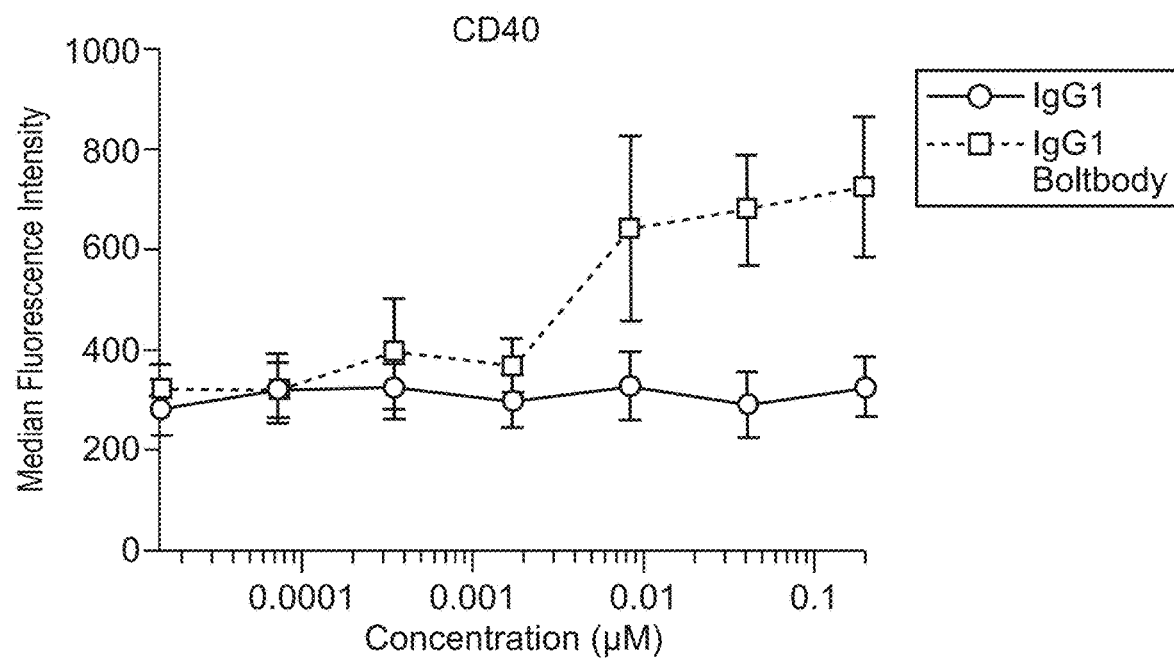

FIG. 89F shows that the rituximab IgG1 immunoconjugate produced according to the BB-01 method (CD20 IgG1 Boltbody) is superior at eliciting CD40 upregulation on myeloid cells as compared to the unconjugated rituximab (CD20 IgG1; Invivogen, hcd20-mab1) following 18 hours of stimulation.

Figure 89G:
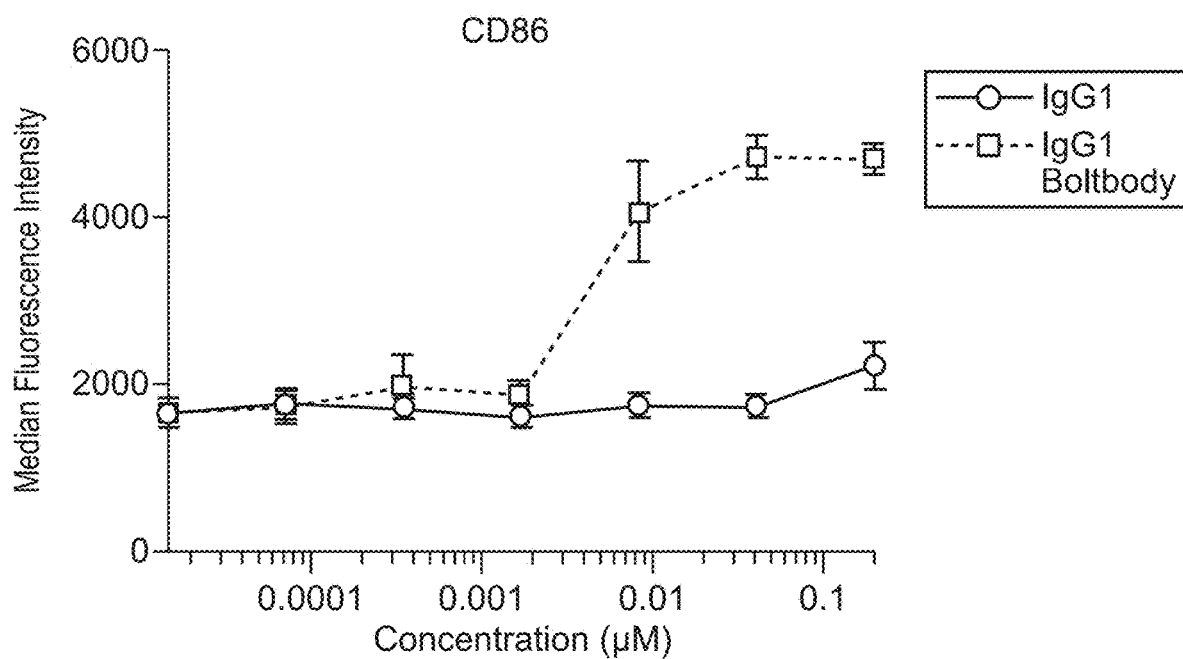

FIG. 89G shows that the rituximab IgG1 immunoconjugate produced according to the BB-01 method (CD20 IgG1 Boltbody) is superior at eliciting CD86 upregulation on myeloid cells as compared to the unconjugated rituximab (CD20 IgG1; Invivogen, hcd20-mab1) following 18 hours of stimulation.

Figure 89H:
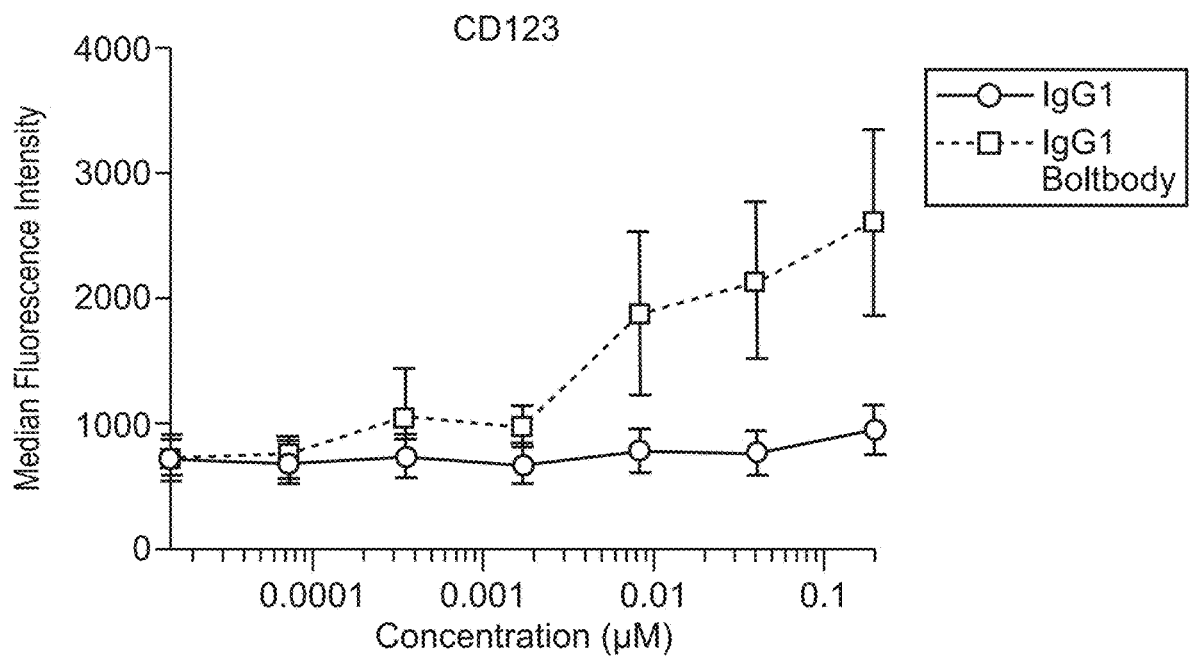

FIG. 89H shows that the rituximab IgG1 immunoconjugate produced according to the BB-01 method (CD20 IgG1 Boltbody) is superior at eliciting CD123 upregulation on myeloid cells as compared to the unconjugated rituximab (CD20 IgG; Invivogen, hcd20-mab1) following 18 hours of stimulation.

Figure 89I:
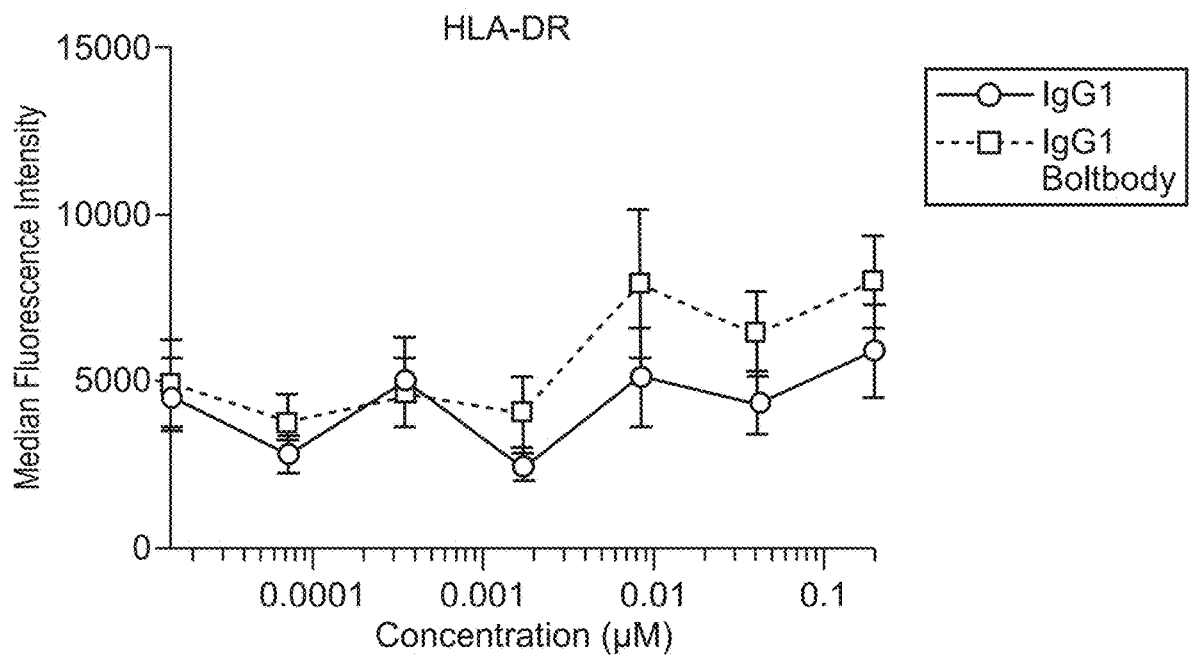

FIG. 89I shows that the rituximab IgG1 immunoconjugate produced according to the BB-01 method (CD20 IgG1 Boltbody) is superior at eliciting HLA-DR upregulation on myeloid cells as compared to the unconjugated rituximab (CD20 IgG; Invivogen, hcd20-mab1) following 18 hours of stimulation.

Figure 90A:
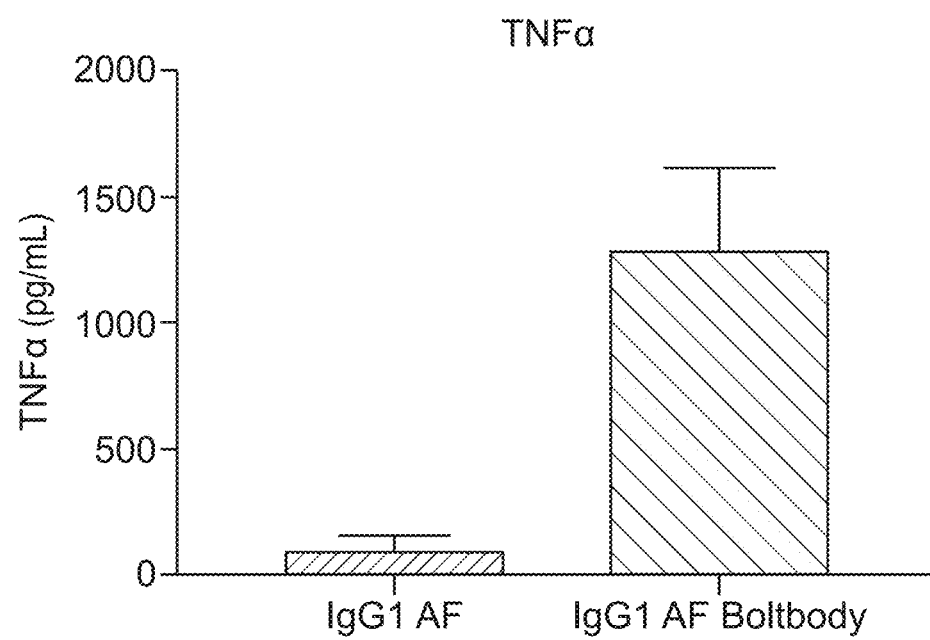

FIG. 90A shows that the rituximab afucosylated IgG1 immunoconjugate produced according to the BB-01 method (IgG1 AF Boltbody) elicits superior TNFα secretion from myeloid cells as compared to equimolar concentrations (0.2 μM) of unconjugated rituximab (IgG1 AF; Invivogen, hcd20-mab13) following 18 hours of stimulation.

FIG. 90B shows a liquid chromatography-mass spectrometry analysis of unconjugated rituximab IgG1 (Invivogen, hcd20-mab13) that was utilized to produce the rituximab immunoconjugate according to the BB-01 conjugation method.

Figure 90C:
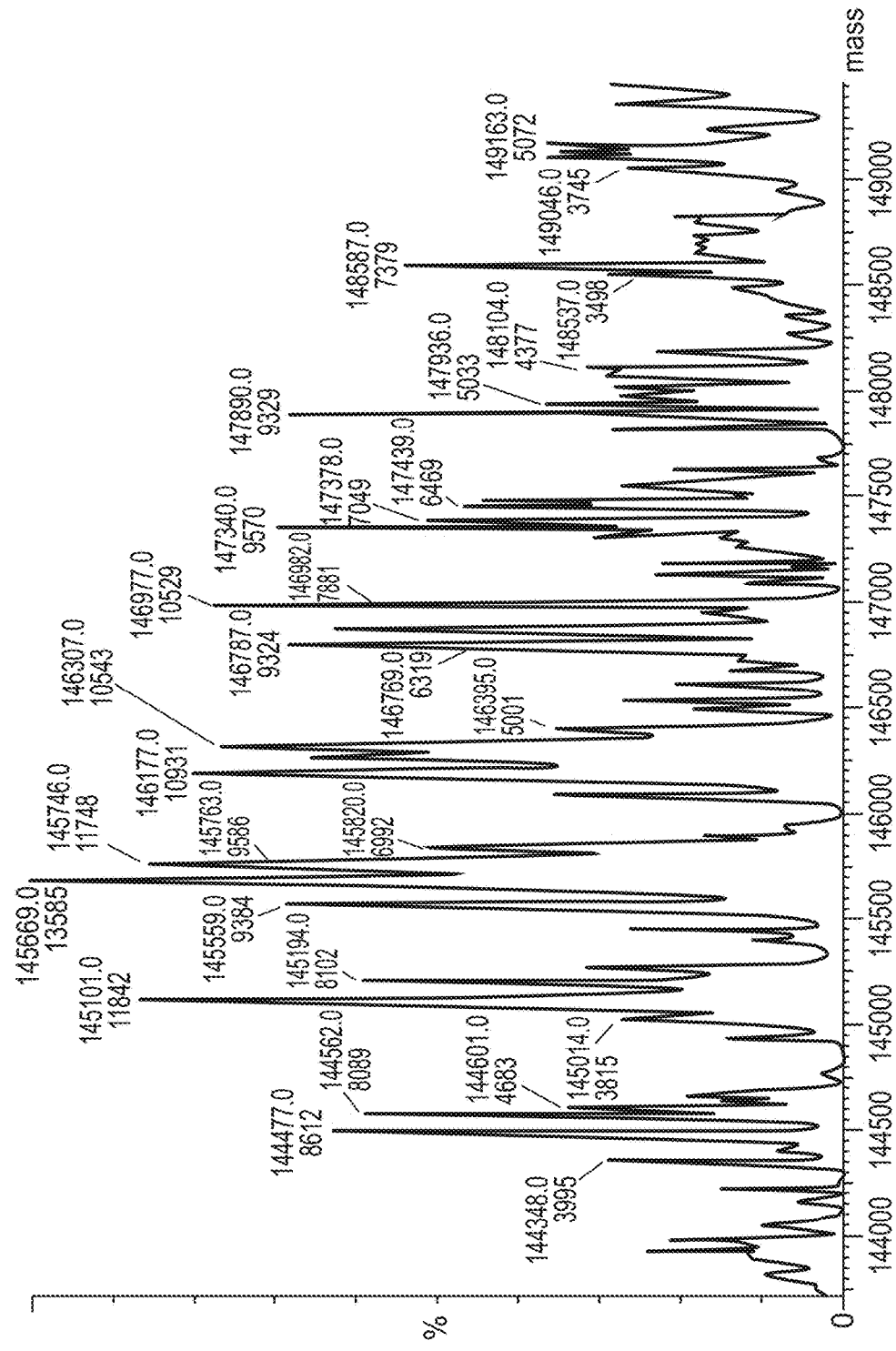

FIG. 90C shows a liquid chromatography-mass spectrometry analysis of the rituximab IgG1 immunoconjugate produced according to the BB-01 conjugation method.

Figure 90D:
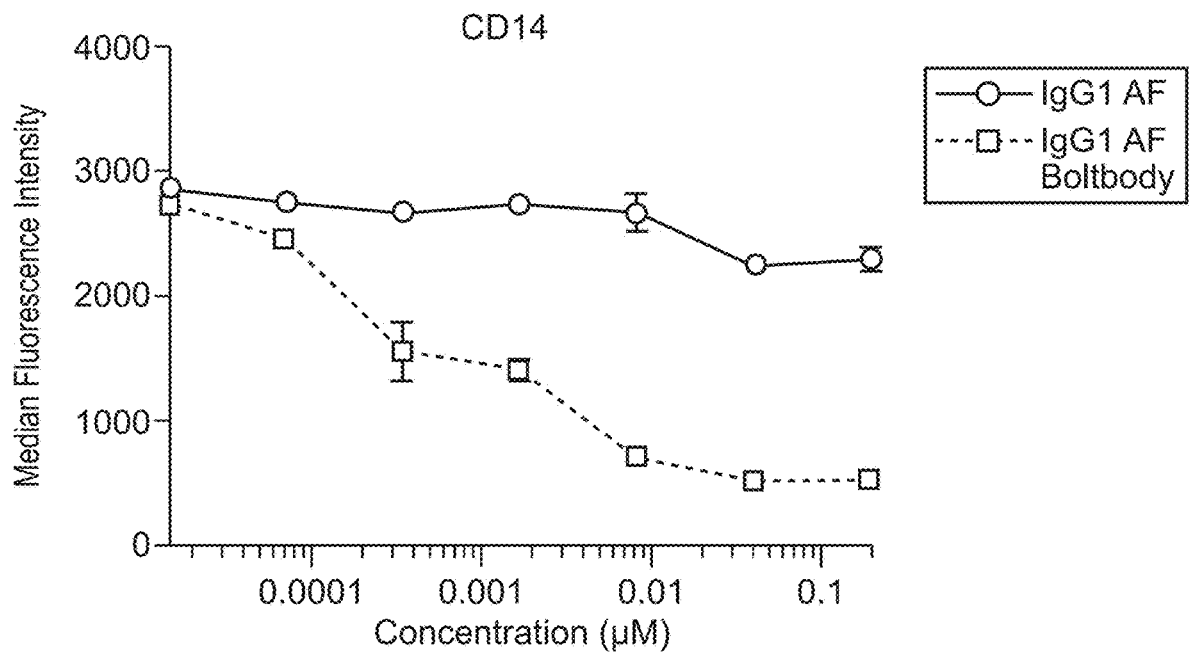

FIG. 90D shows that the rituximab IgG1 AF immunoconjugate produced according to the BB-01 method (IgG1 AF Boltbody) is superior at eliciting CD14 downregulation on myeloid cells as compared to the unconjugated rituximab (IgG1 AF; Invivogen, hcd20-mab13) following 18 hours of stimulation.

Figure 90E:
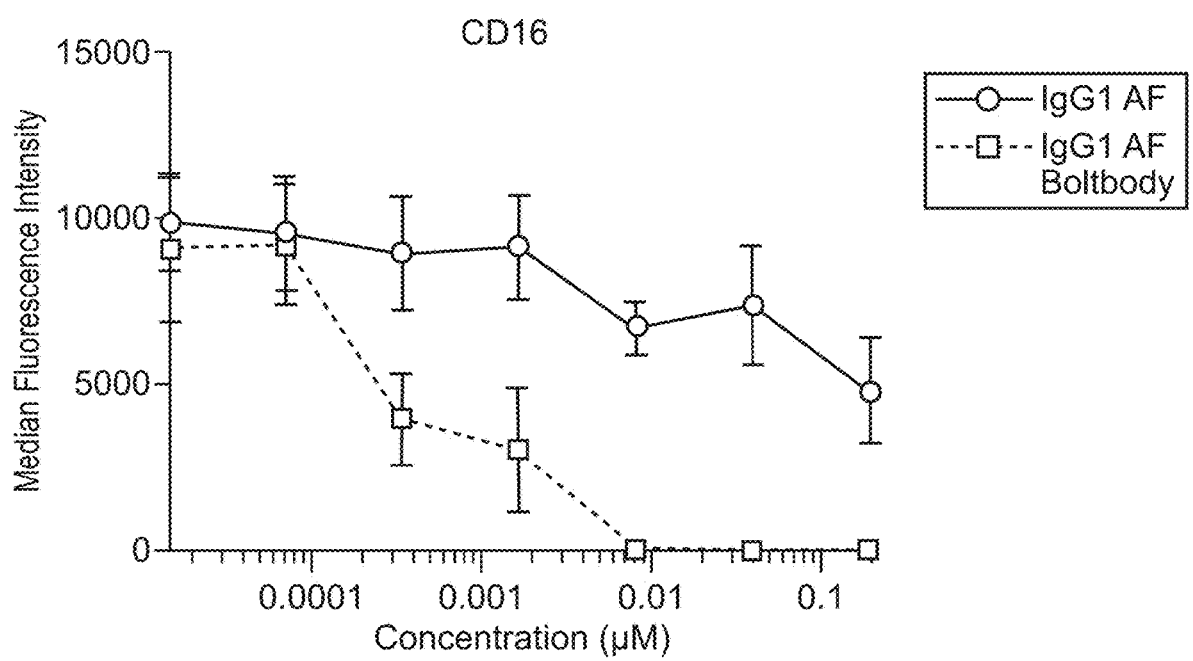

FIG. 90E shows that the rituximab IgG1 immunoconjugate produced according to the BB-01 method (IgG1 AF Boltbody) is superior at eliciting CD16 downregulation on myeloid cells as compared to the unconjugated rituximab (IgG1 AF; Invivogen, hcd20-mab13) following 18 hours of stimulation.

Figure 90F:
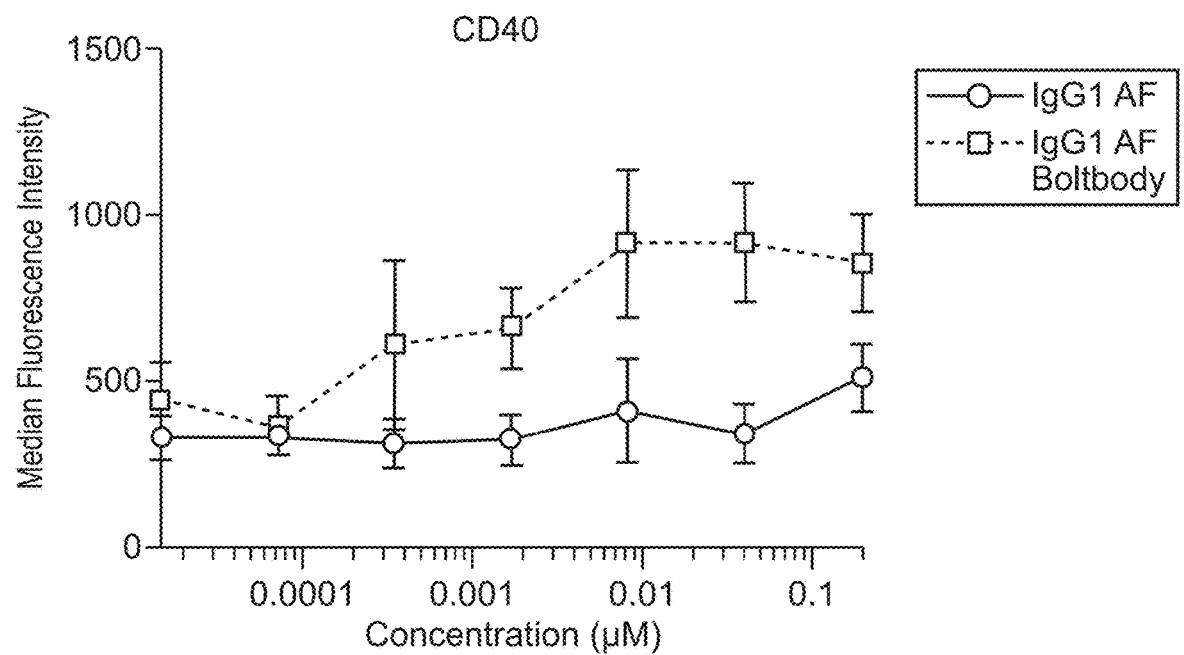

FIG. 90F shows that the rituximab IgG1 immunoconjugate produced according to the BB-01 method (IgG1 AF Boltbody) is superior at eliciting CD40 upregulation on myeloid cells as compared to the unconjugated rituximab (IgG1 AF; Invivogen, hcd20-mab13) following 18 hours of stimulation.

Figure 90G:
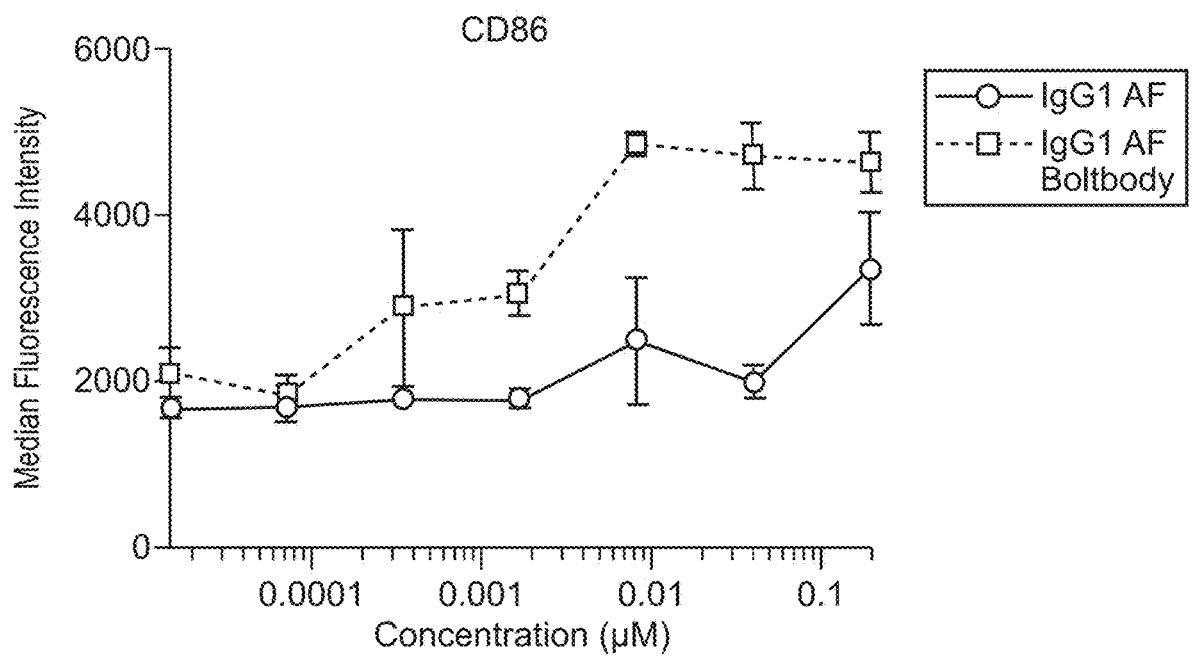

FIG. 90G shows that the rituximab IgG1 immunoconjugate produced according to the BB-01 method (IgG1 AF Boltbody) is superior at eliciting CD86 upregulation on myeloid cells as compared to the unconjugated rituximab (IgG1 AF; Invivogen, hcd20-mab13) following 18 hours of stimulation.

Figure 90H:
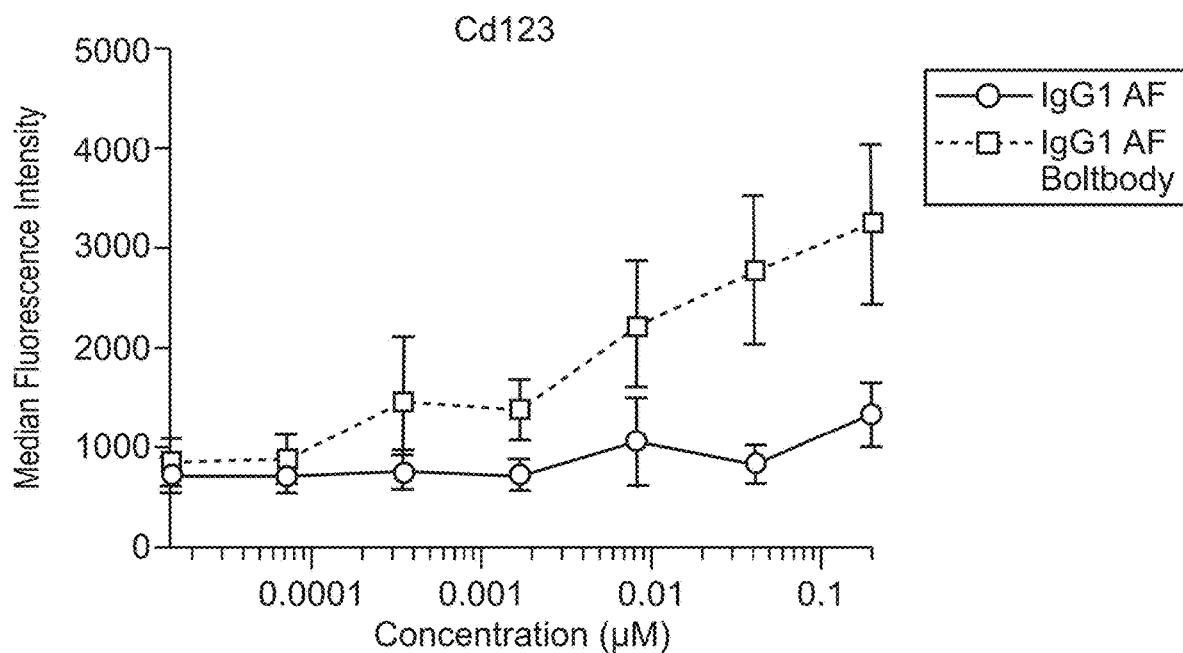

FIG. 90H shows that the rituximab IgG1 immunoconjugate produced according to the BB-01 method (IgG1 AF Boltbody) is superior at eliciting CD123 upregulation on myeloid cells as compared to the unconjugated rituximab (IgG1 AF; Invivogen, hcd20-mab13) following 18 hours of stimulation.

Figure 90I:
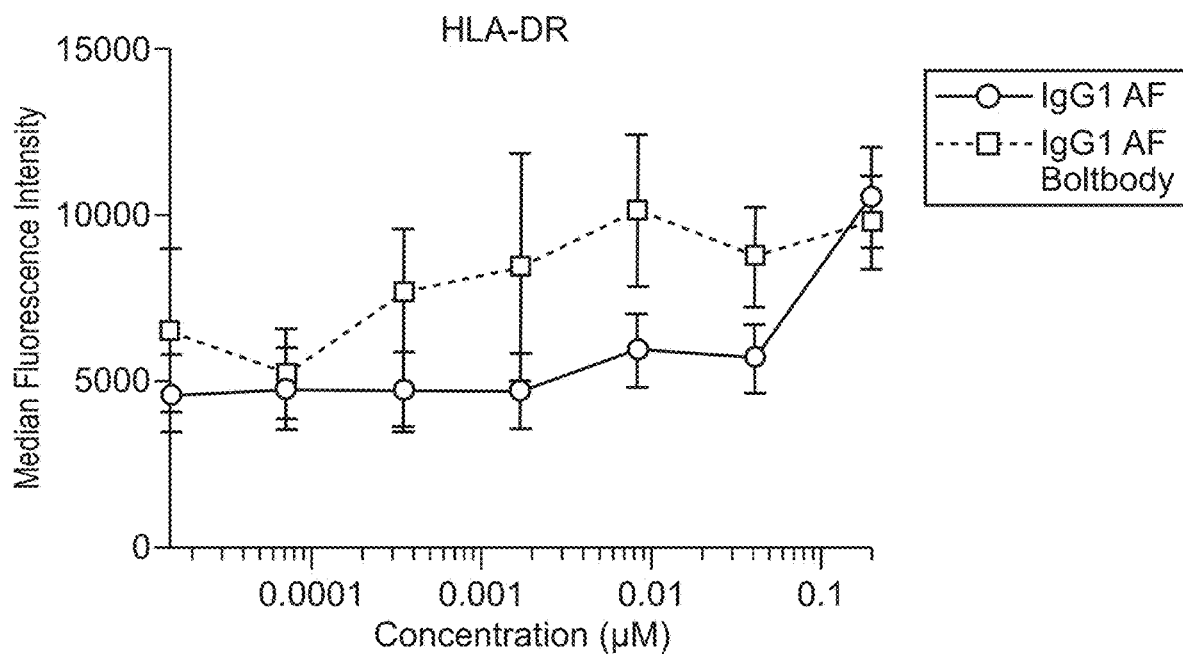

FIG. 90I shows that the rituximab IgG1 immunoconjugate produced according to the BB-01 method (IgG1 AF Boltbody) is superior at eliciting HLA-DR upregulation on myeloid cells as compared to the unconjugated rituximab (IgG1 AF; Invivogen, hcd20-mab13) following 18 hours of stimulation.

Figure 91A:
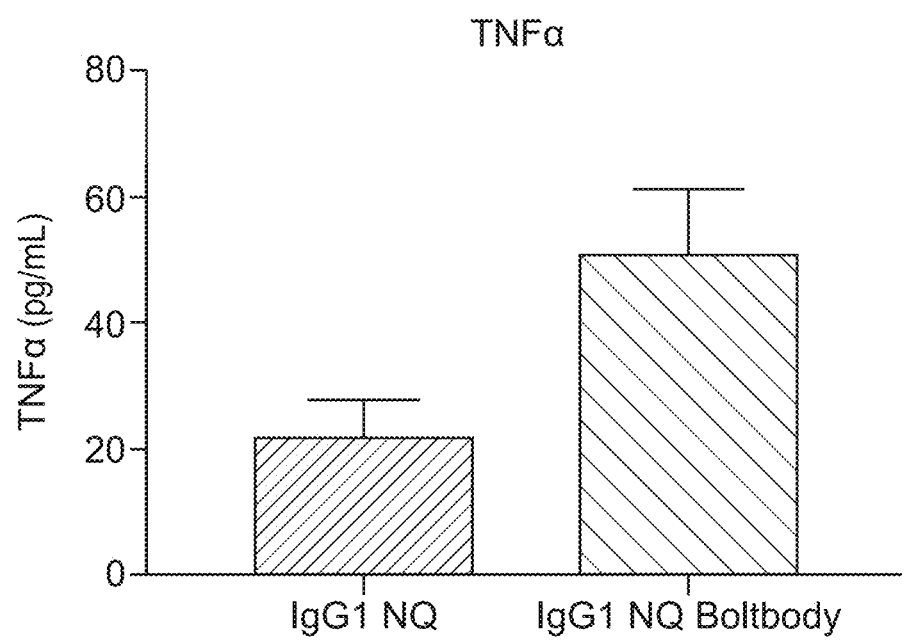

FIG. 91A shows that the rituximab N297Q mutant IgG1 immunoconjugate produced according to the BB-01 method (IgG1 NQ Boltbody) elicits superior TNFαsecretion from myeloid cells as compared to equimolar concentrations (0. μM) of unconjugated rituximab (IgG1 NQ; Invivogen, hcd20-mab12) following 36 hours of stimulation.

FIG. 91B shows a liquid chromatography-mass spectrometry analysis of unconjugated rituximab IgG1 (Invivogen, hcd20-mab12) that was utilized to produce the rituximab immunoconjugate according to the BB-01 conjugation method.

FIG. 91C shows a liquid chromatography-mass spectrometry analysis of the rituximab IgG1 immunoconjugate produced according to the BB-01 conjugation method.

Figure 91D:
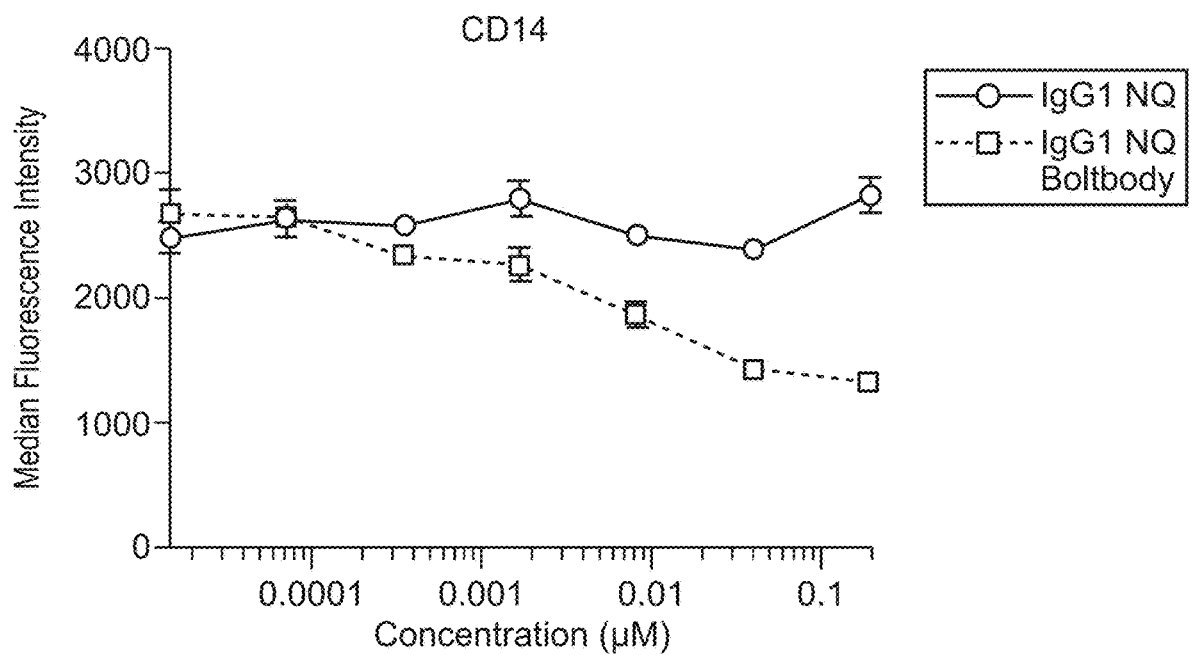

FIG. 91D shows CD14 expression on myeloid cells following 18 hours of stimulation with the rituximab N297Q mutant IgG1 immunoconjugate produced according to the BB-01 method (IgG1 NQ Boltbody) as compared to unconjugated rituximab IgG1 (Invivogen, hcd20-mab12).

Figure 91E:
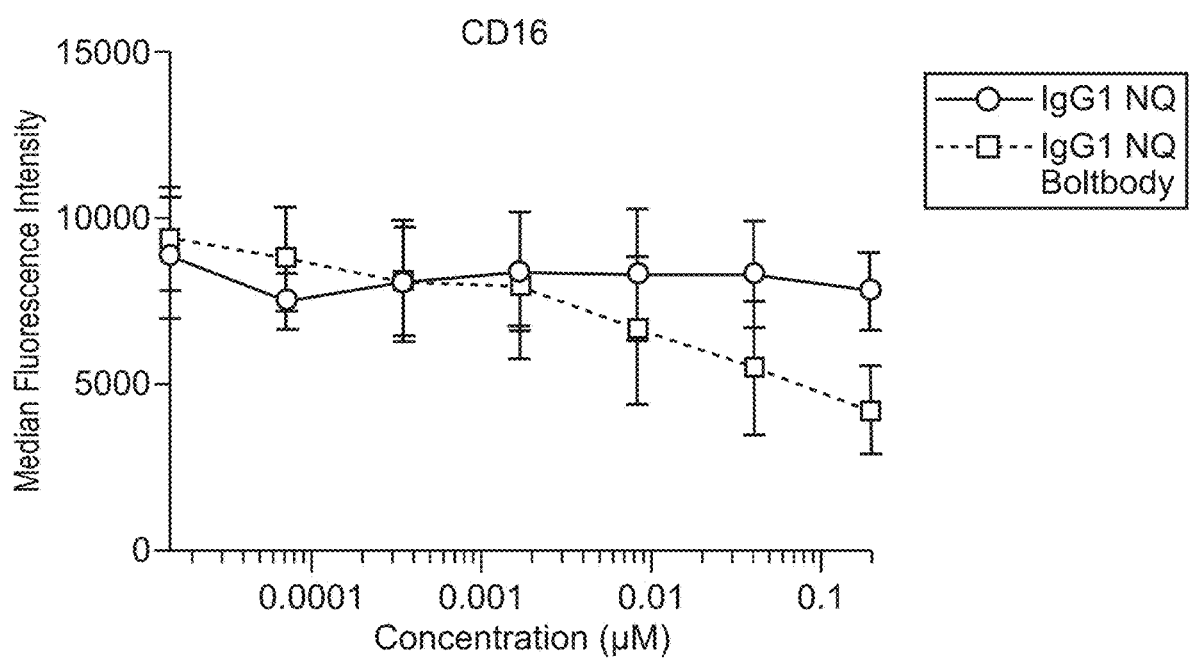

FIG. 91E shows CD16 expression on myeloid cells following 18 hours of stimulation with the rituximab N297Q mutant IgG1 immunoconjugate produced according to the BB-01 method (IgG1 NQ Boltbody) as compared to unconjugated rituximab IgG1 (Invivogen, hcd20-mab12).

Figure 91F:
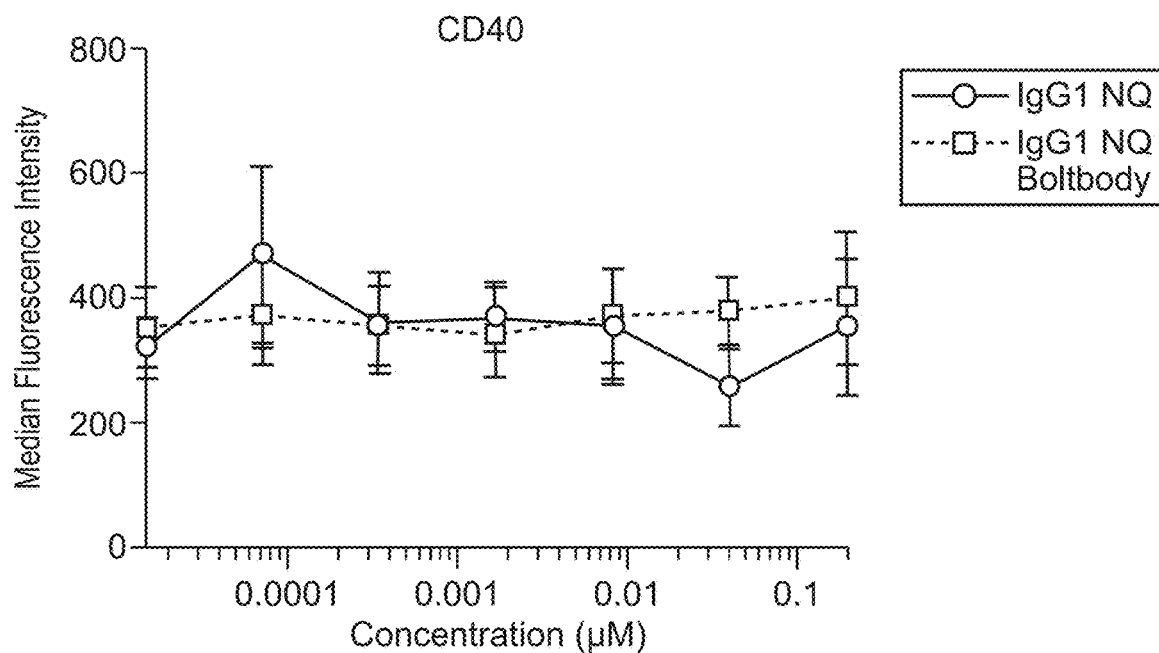

FIG. 91F shows CD40 expression on myeloid cells following 18 hours of stimulation with the rituximab N297Q mutant IgG1 immunoconjugate produced according to the BB-01 method (IgG1 NQ Boltbody) as compared to unconjugated rituximab IgG1 (Invivogen, hcd20-mab12).

Figure 91G:
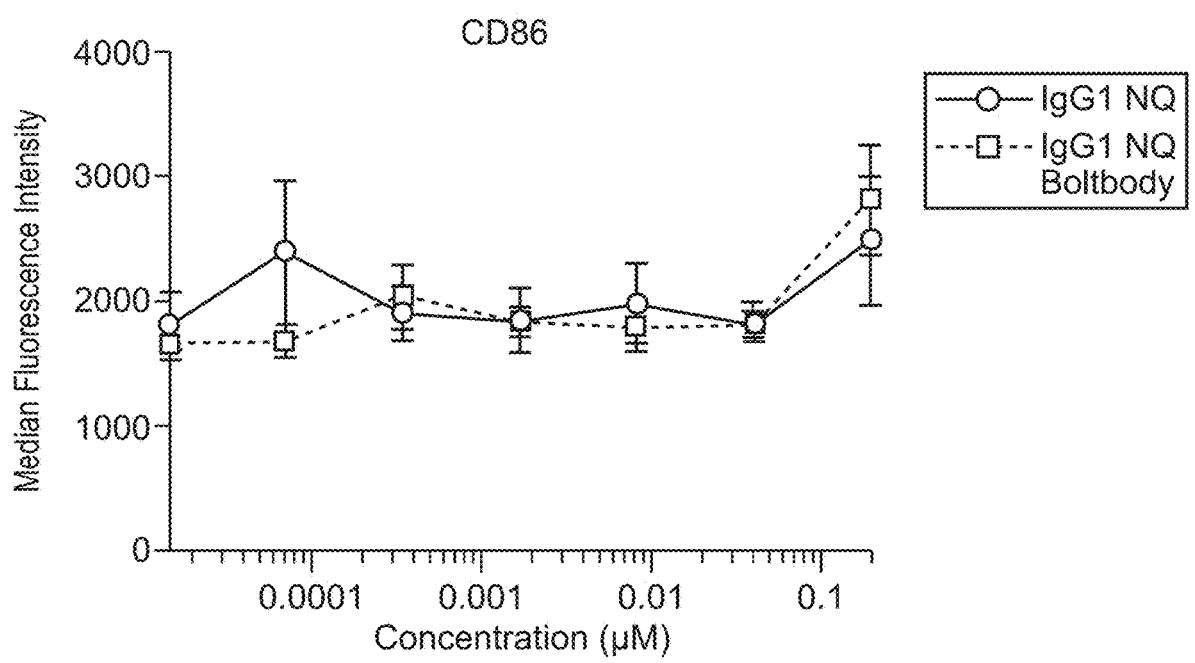

FIG. 91G shows CD86 expression on myeloid cells following 18 hours of stimulation with the rituximab N297Q mutant IgG1 immunoconjugate produced according to the BB-01 method (IgG1 NQ Boltbody) as compared to unconjugated rituximab IgG1 (Invivogen, hcd20-mab12).

Figure 91H:
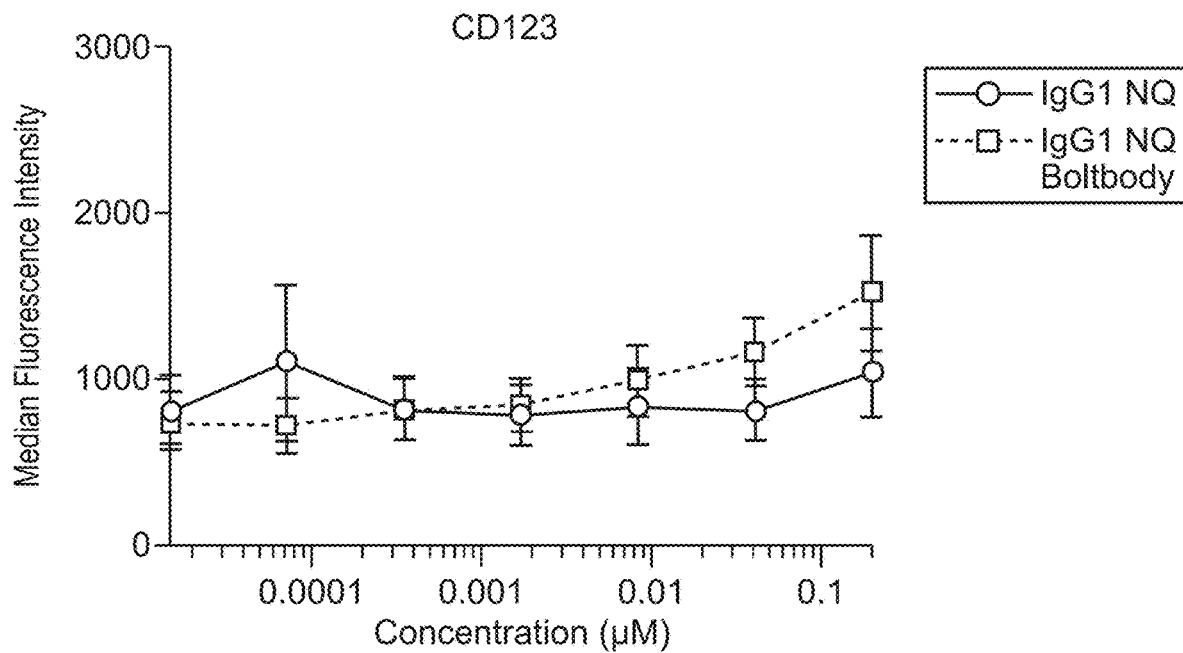

FIG. 91H shows CD123 expression on myeloid cells following 18 hours of stimulation with the rituximab N297Q mutant IgG1 immunoconjugate produced according to the BB-01 method (IgG1 NQ Boltbody) as compared to unconjugated rituximab IgG1 (Invivogen, hcd20-mab12).

Figure 91I:
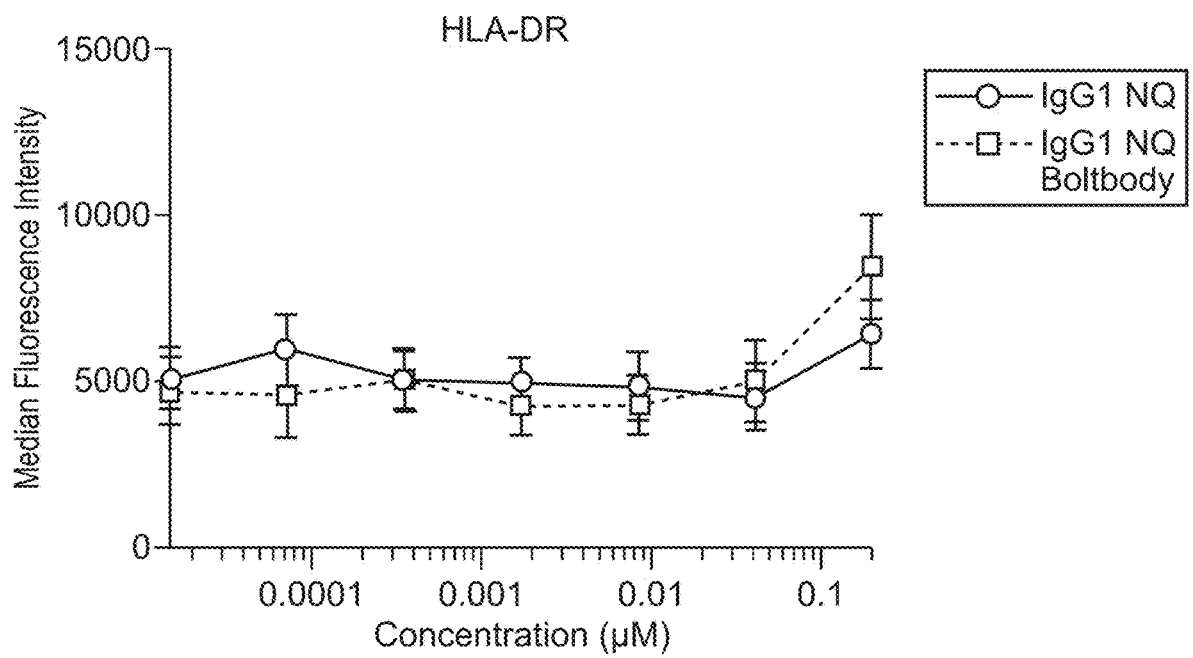

FIG. 91I shows HLA-DR expression on myeloid cells following 18 hours of stimulation with the rituximab N297Q mutant IgG1 immunoconjugate produced according to the BB-01 method (IgG1 NQ Boltbody) as compared to unconjugated rituximab IgG1 (Invivogen, hcd20-mab12).

Figure 92A:
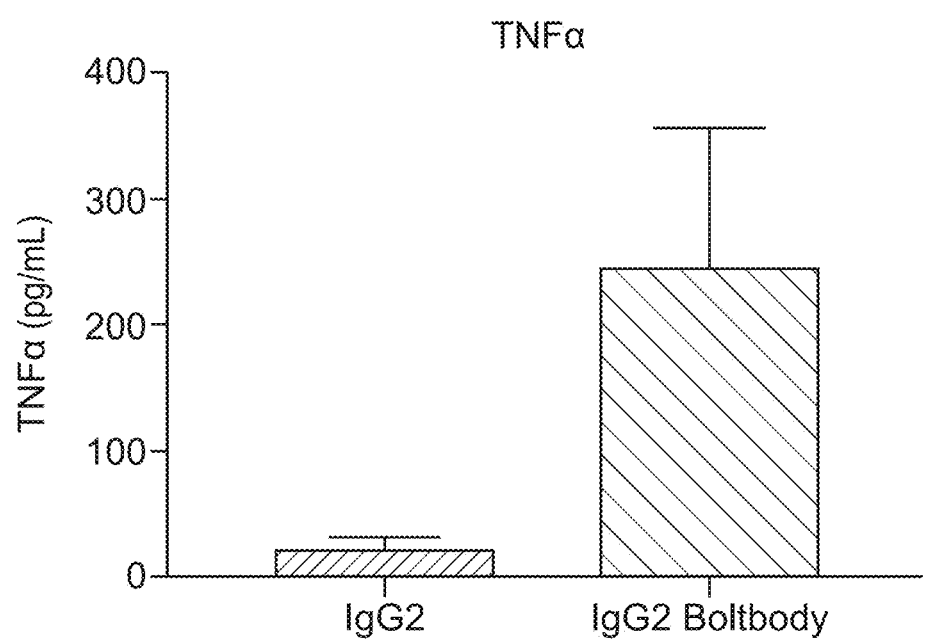

FIG. 92A shows that the rituximab IgG2 immunoconjugate produced according to the BB-01 method (IgG2 Boltbody) elicits superior TNFα secretion from myeloid cells as compared to equimolar concentrations (0.2 μM) of unconjugated rituximab (IgG2; Invivogen, hcd20-mab2) following 18 hours of stimulation.

Figure 92B:
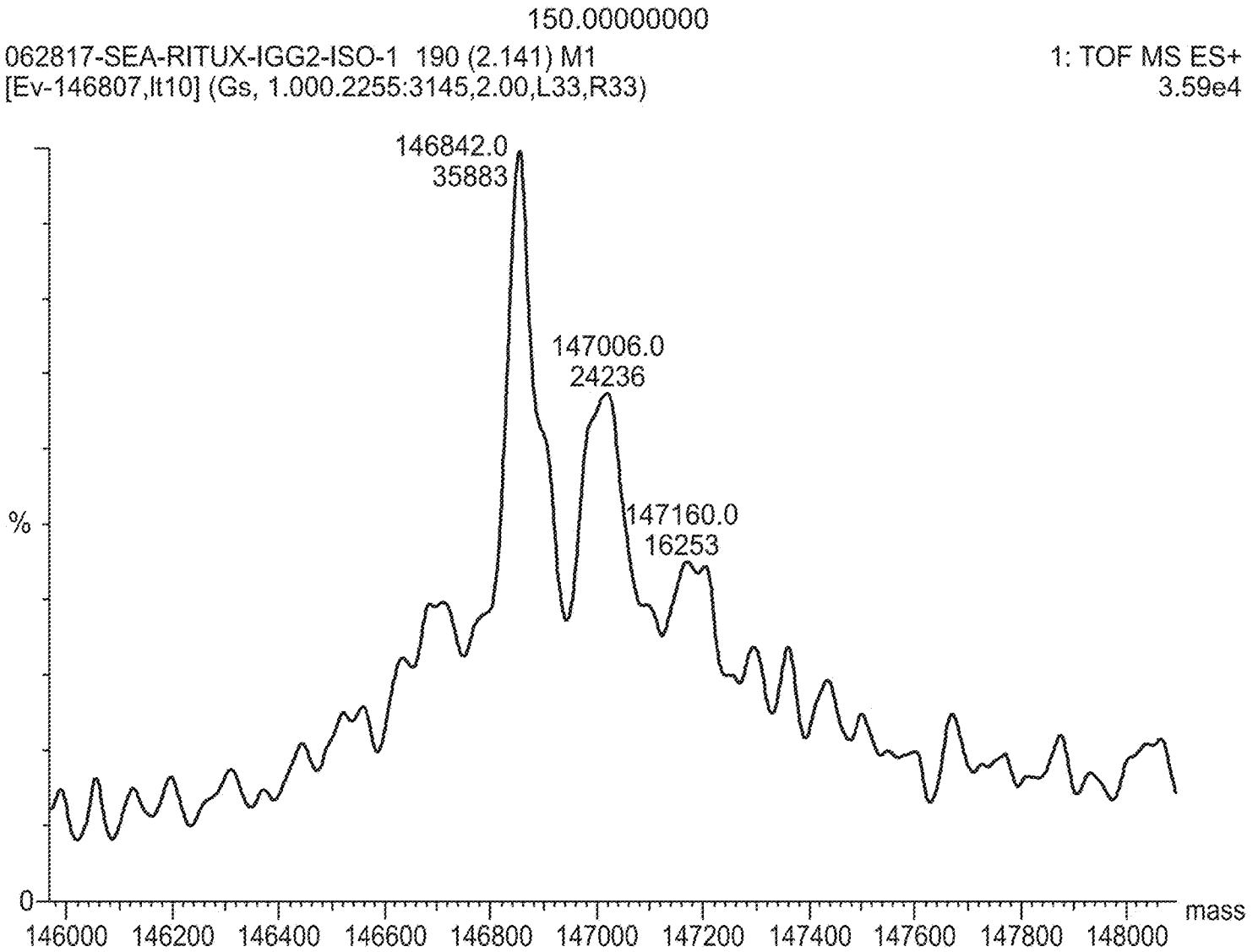

FIG. 92B shows a liquid chromatography-mass spectrometry analysis of unconjugated rituximab IgG2 (Invivogen, hcd20-mab2) that was utilized to produce the rituximab immunoconjugate according to the BB-01 conjugation method.

Figure 92C:
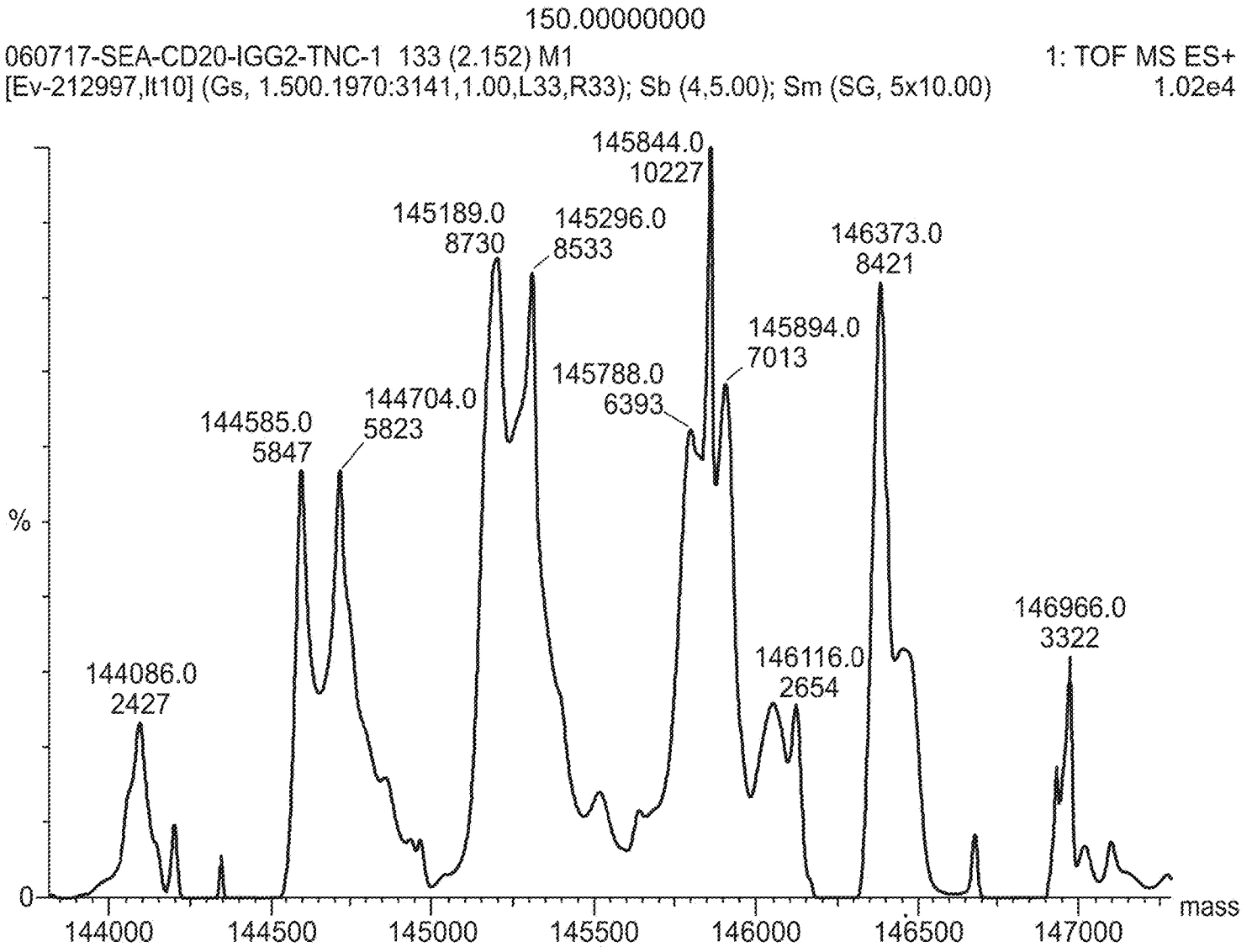

FIG. 92C shows a liquid chromatography-mass spectrometry analysis of the rituximab IgG2 immunoconjugate produced according to the BB-01 conjugation method.

Figure 92D:
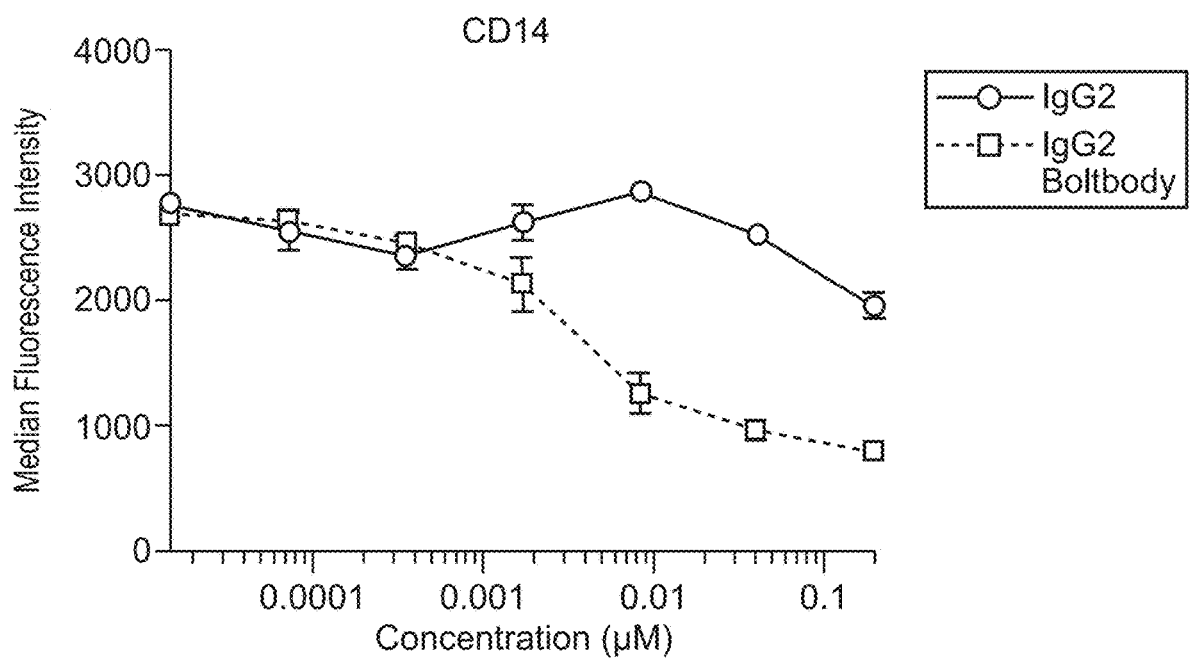

FIG. 92D shows that the rituximab IgG2 immunoconjugate produced according to the BB-01 method (IgG2 Boltbody) is superior at eliciting CD14 downregulation on myeloid cells as compared to the unconjugated rituximab (IgG2; Invivogen, hcd20-mab2) following 18 hours of stimulation.

Figure 92E:
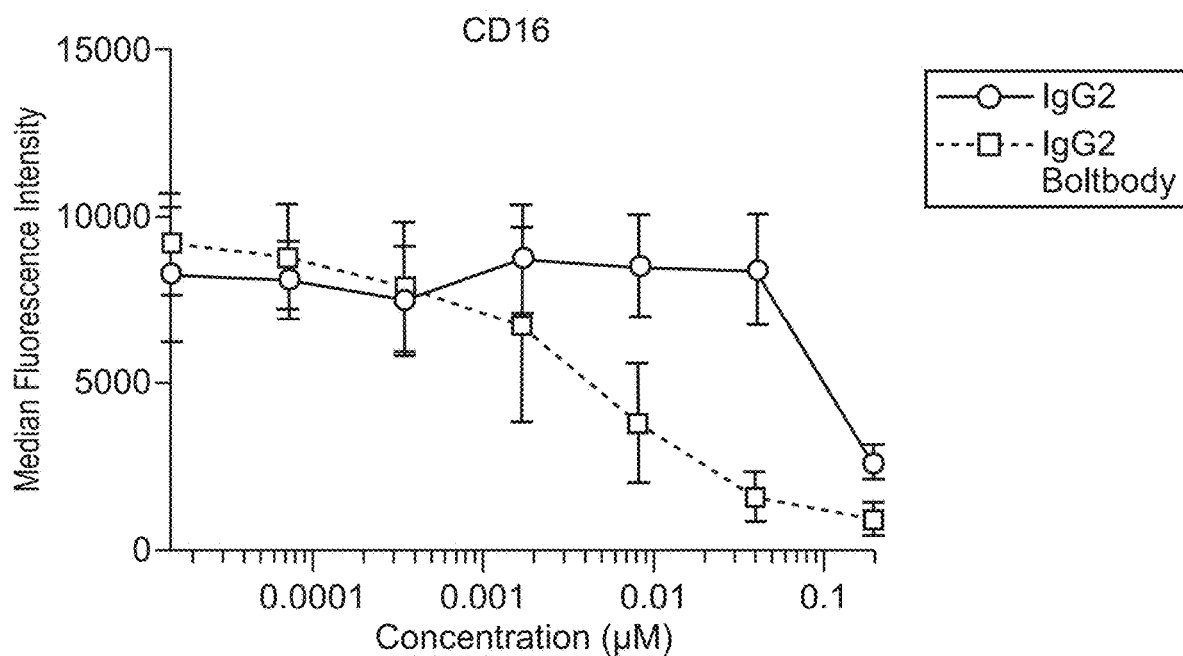

FIG. 92E shows that the rituximab IgG2 immunoconjugate produced according to the BB-01 method (IgG2 Boltbody) is superior at eliciting CD16 downregulation on myeloid cells as compared to the unconjugated rituximab (IgG2; Invivogen, hcd20-mab2) following 18 hours of stimulation.

Figure 92F:
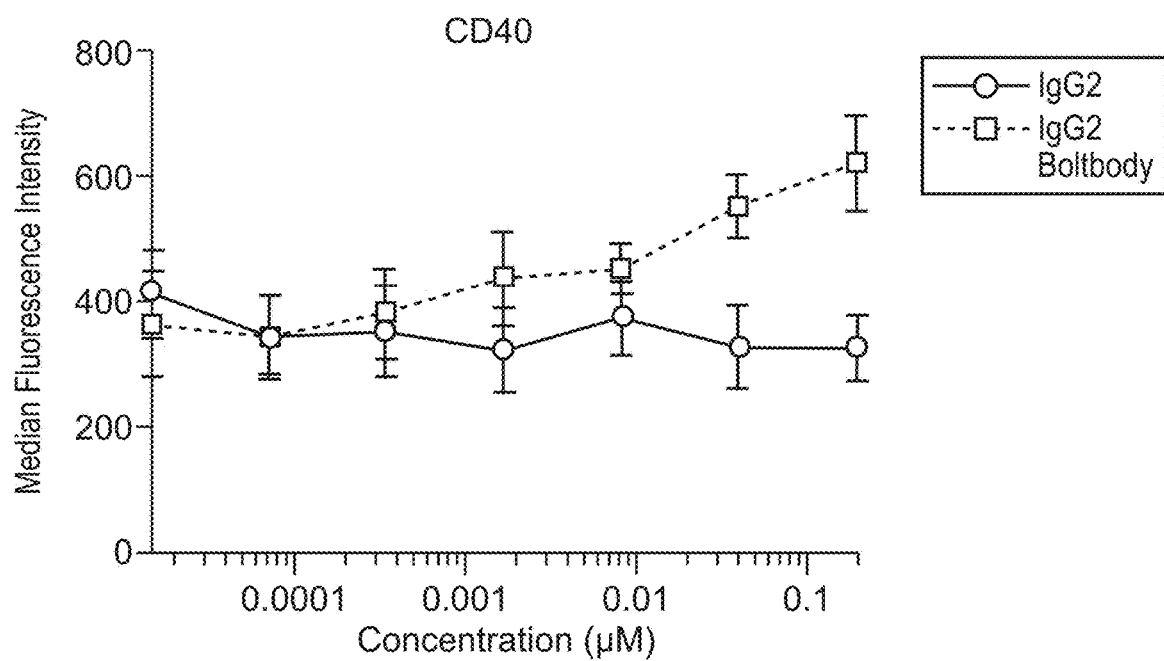

FIG. 92F shows that the rituximab IgG2 immunoconjugate produced according to the BB-01 method (IgG2 Boltbody) is superior at eliciting CD40 upregulation on myeloid cells as compared to the unconjugated rituximab (IgG2; Invivogen, hcd20-mab2) following 18 hours of stimulation.

Figure 92G:
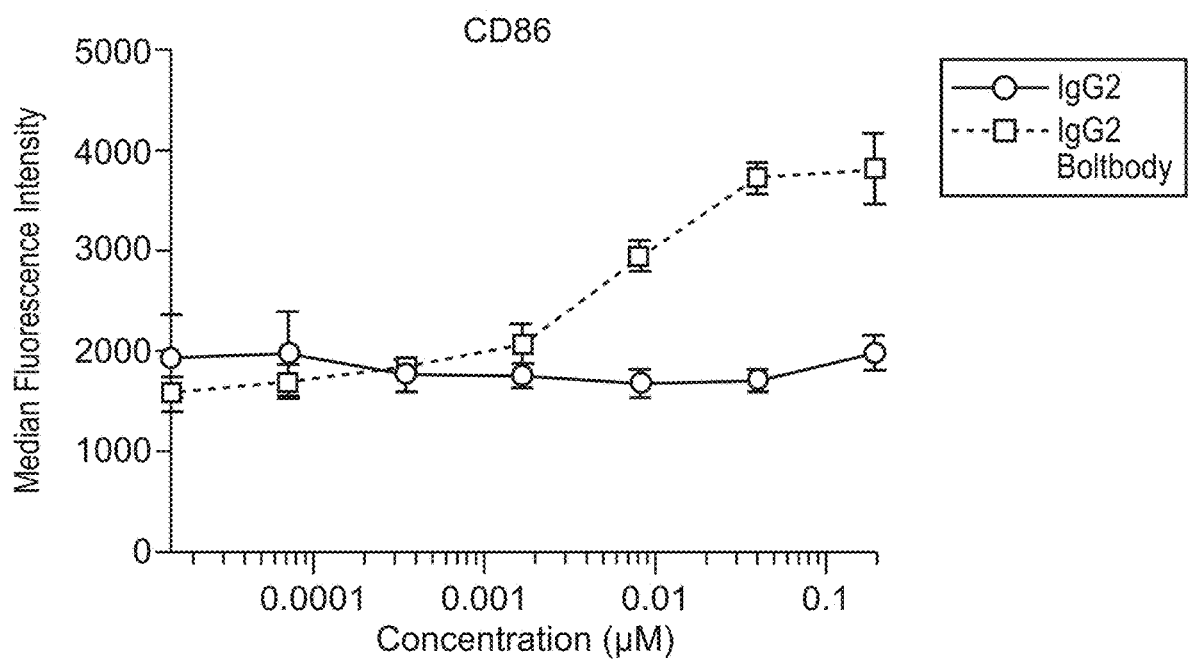

FIG. 92G shows that the rituximab IgG2 immunoconjugate produced according to the BB-01 method (IgG2 Boltbody) is superior at eliciting CD86 upregulation on myeloid cells as compared to the unconjugated rituximab (IgG2; Invivogen, hcd20-mab2) following 18 hours of stimulation.

Figure 92H:
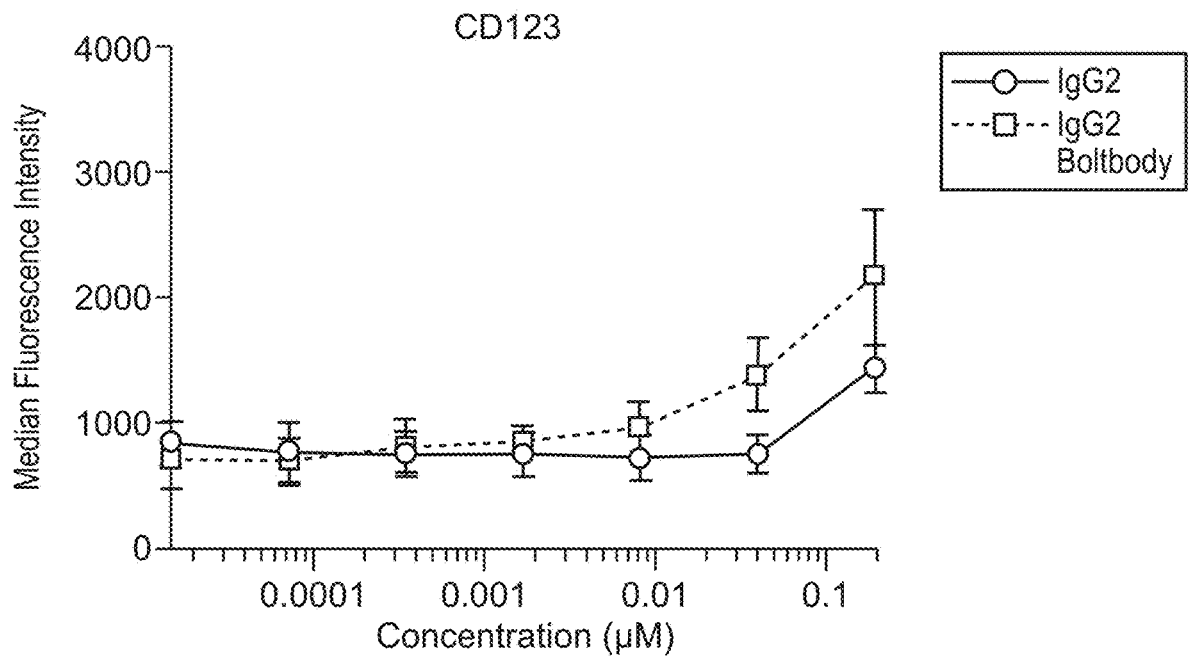

FIG. 92H shows that the rituximab IgG2 immunoconjugate produced according to the BB-01 method (IgG2 Boltbody) is superior at eliciting CD123 upregulation on myeloid cells as compared to the unconjugated rituximab (IgG2; Invivogen, hcd20-mab2) following 18 hours of stimulation.

Figure 92I:
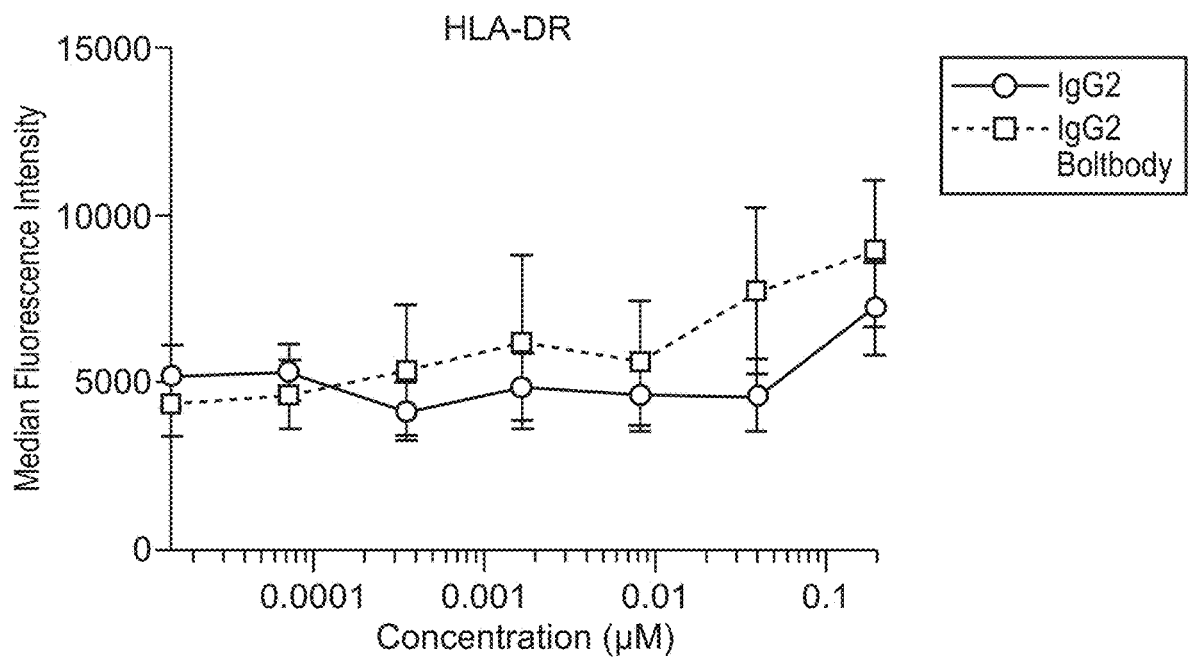

FIG. 92I shows that the rituximab IgG2 immunoconjugate produced according to the BB-01 method (IgG2 Boltbody) is superior at eliciting HLA-DR upregulation on myeloid cells as compared to the unconjugated rituximab (IgG2; Invivogen, hcd20-mab2) following 18 hours of stimulation.

Figure 93A:
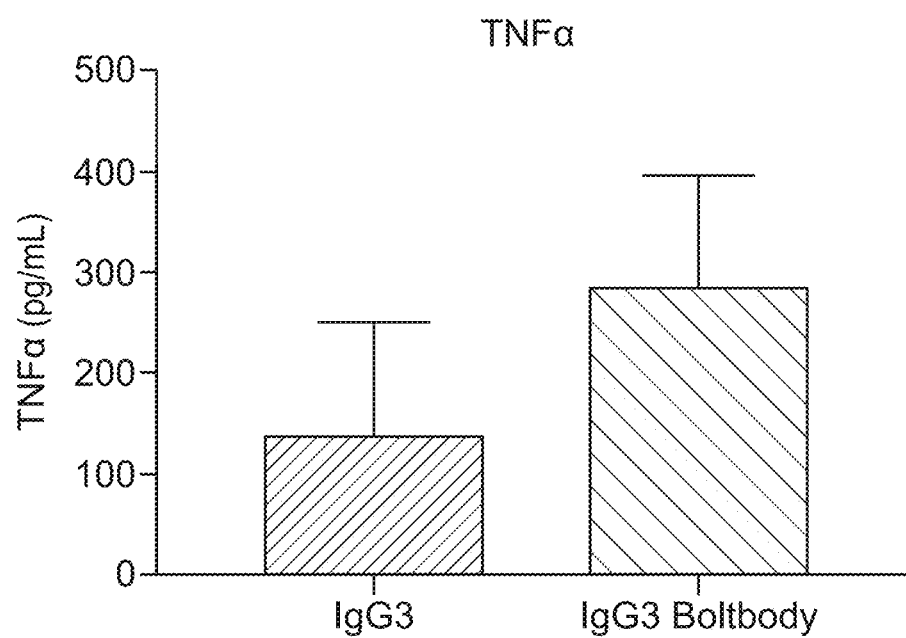

FIG. 93A shows that the rituximab IgG3 immunoconjugate produced according to the BB-01 method (IgG3 Boltbody) elicits superior TNFα secretion from myeloid cells as compared to equimolar concentrations (0.2 µM) of unconjugated rituximab (IgG3; Invivogen, hcd20-mab3) following 18 hours of stimulation.

Figure 93B:
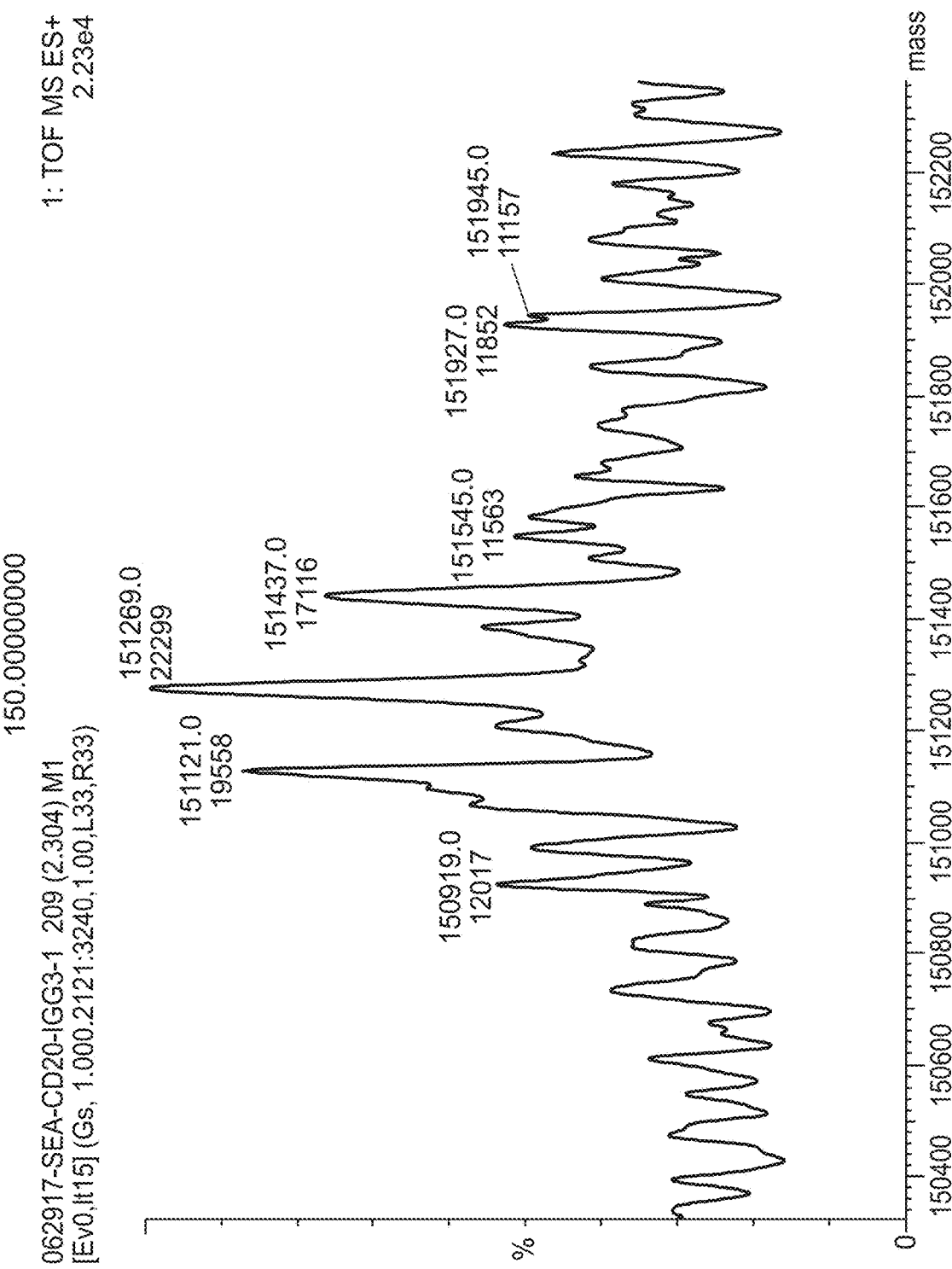

FIG. 93B shows a liquid chromatography-mass spectrometry analysis of unconjugated rituximab IgG3 (Invivogen, hcd20-mab3) that was utilized to produce the rituximab immunoconjugate according to the BB-01 conjugation method.

FIG. 93C shows a liquid chromatography-mass spectrometry analysis of the rituximab IgG3 immunoconjugate produced according to the BB-01 conjugation method.

Figure 93D:
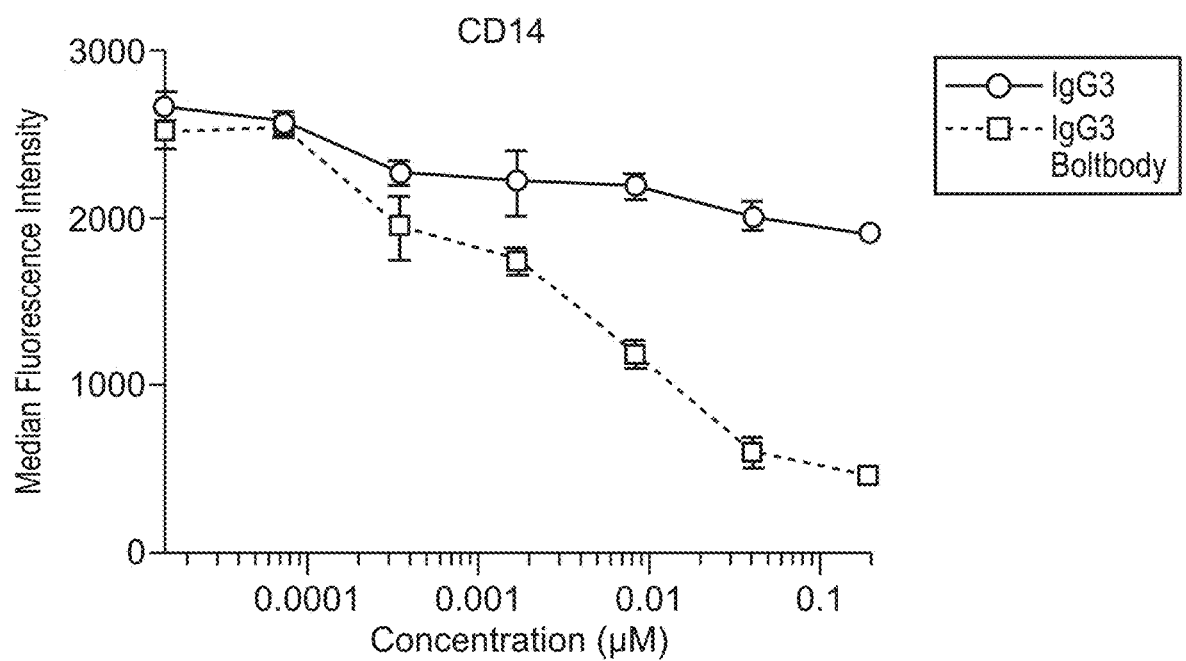

FIG. 93D shows that the rituximab IgG3 immunoconjugate produced according to the BB-01 method (IgG3 Boltbody) is superior at eliciting CD14 downregulation on myeloid cells as compared to the unconjugated rituximab (IgG3; Invivogen, hcd20-mab3) following 18 hours of stimulation.

Figure 93E:
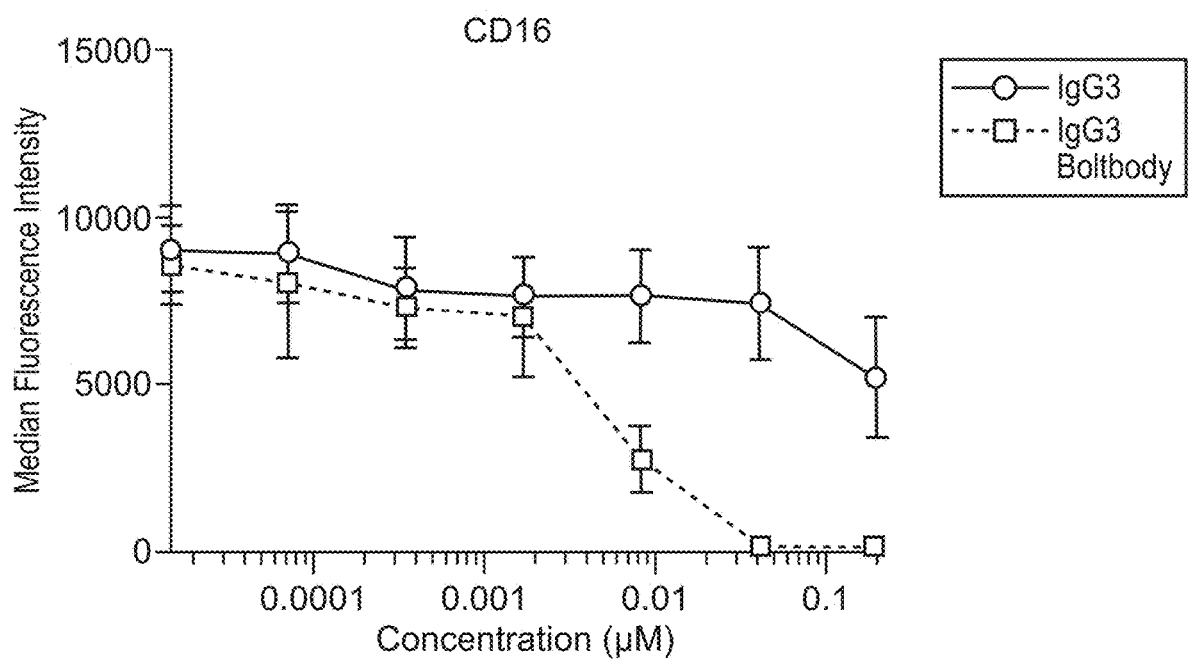

FIG. 93E shows that the rituximab IgG3 immunoconjugate produced according to the BB-01 method (IgG3 Boltbody) is superior at eliciting CD16 downregulation on myeloid cells as compared to the unconjugated rituximab (IgG3; Invivogen, hcd20-mab3) following 18 hours of stimulation.

Figure 93F:
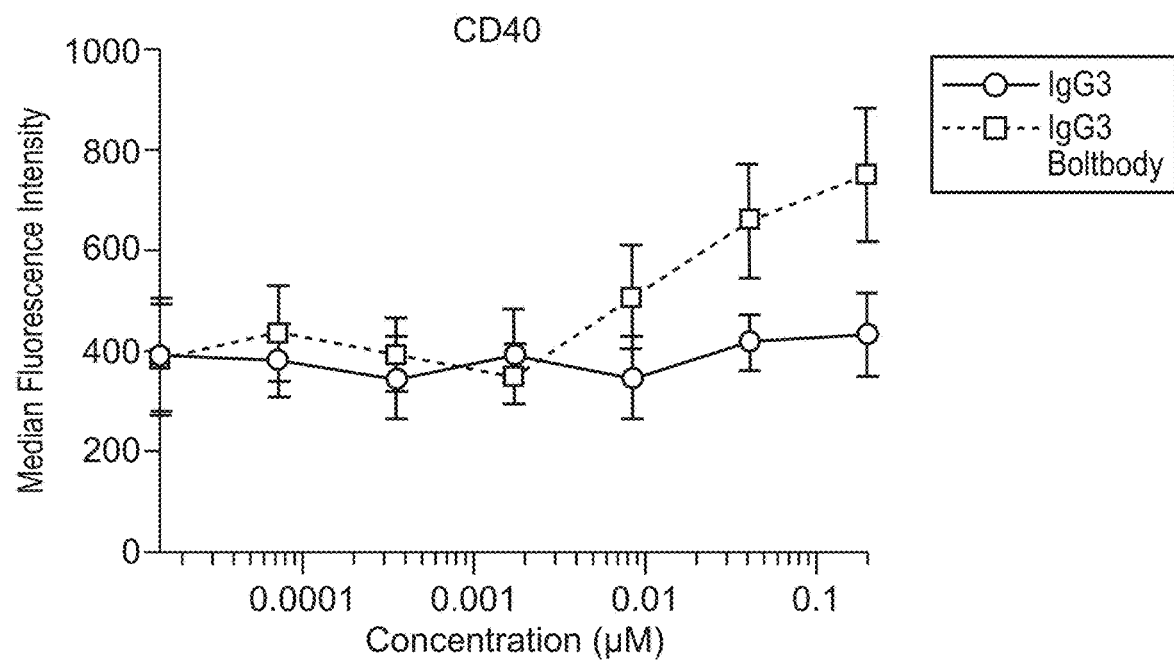

FIG. 93F shows that the rituximab IgG3 immunoconjugate produced according to the BB-01 method (IgG3 Boltbody) is superior at eliciting CD40 upregulation on myeloid cells as compared to the unconjugated rituximab (IgG3; Invivogen, hcd20-mab3) following 18 hours of stimulation.

Figure 93G:
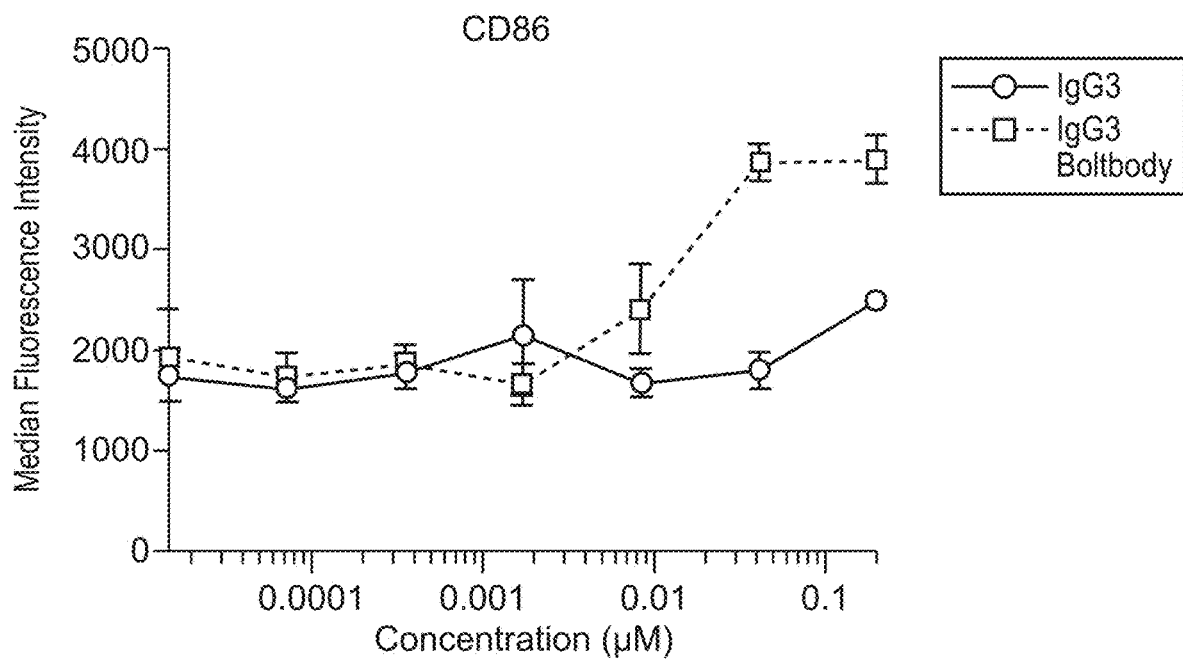

FIG. 93G shows that the rituximab IgG3 immunoconjugate produced according to the BB-01 method (IgG3 Boltbody) is superior at eliciting CD86 upregulation on myeloid cells as compared to the unconjugated rituximab (IgG3; Invivogen, hcd20-mab3) following 18 hours of stimulation.

Figure 93H:
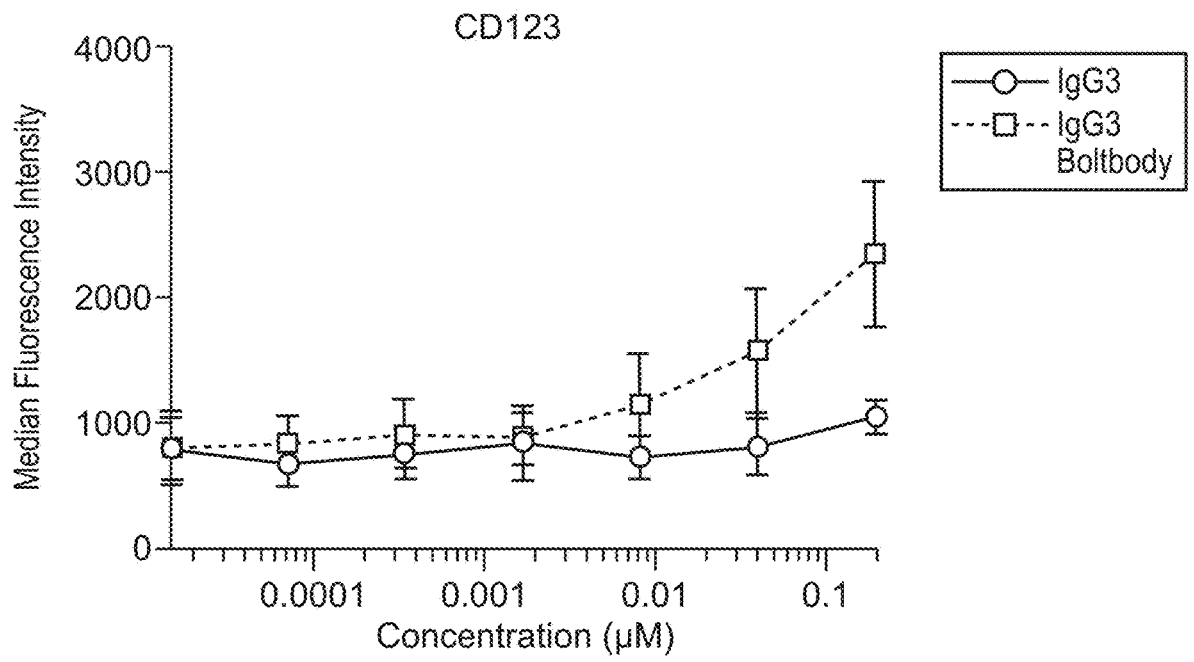

FIG. 93H shows that the rituximab IgG3 immunoconjugate produced according to the BB-01 method (IgG3 Boltbody) is superior at eliciting CD123 upregulation on myeloid cells as compared to the unconjugated rituximab (IgG3; Invivogen, hcd20-mab3) following 18 hours of stimulation.

Figure 93I:
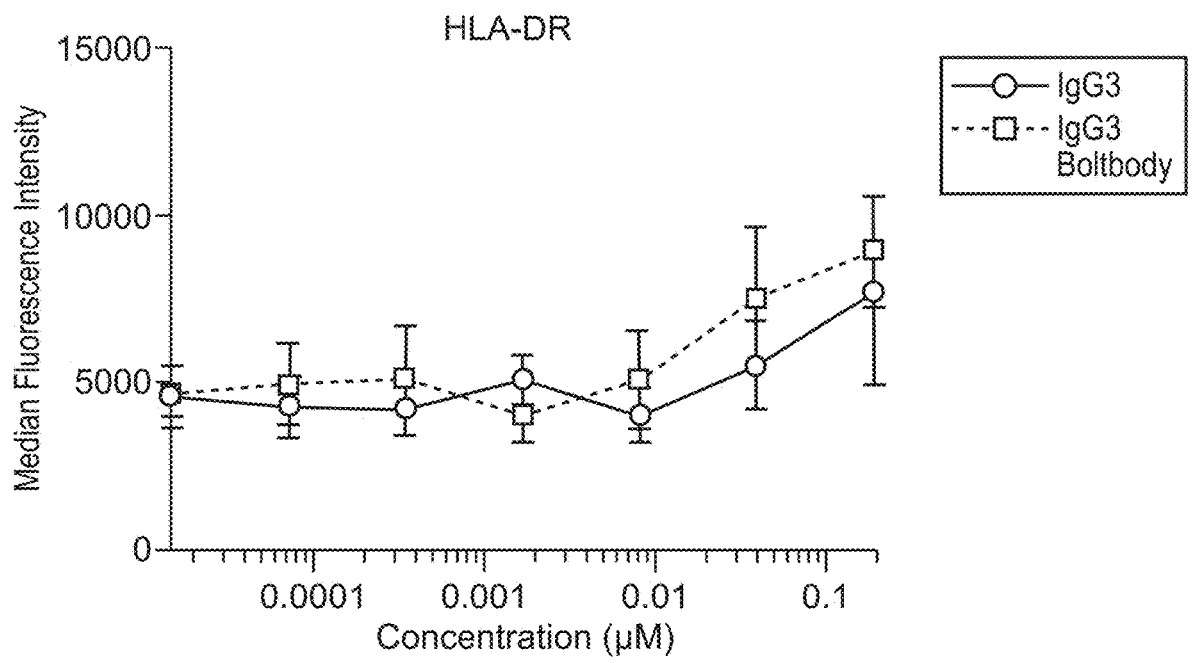

FIG. 93I shows that the rituximab IgG3 immunoconjugate produced according to the BB-01 method (IgG3 Boltbody) is superior at eliciting HLA-DR upregulation on myeloid cells as compared to the unconjugated rituximab (IgG3; Invivogen, hcd20-mab3) following 18 hours of stimulation.

Figure 94A:
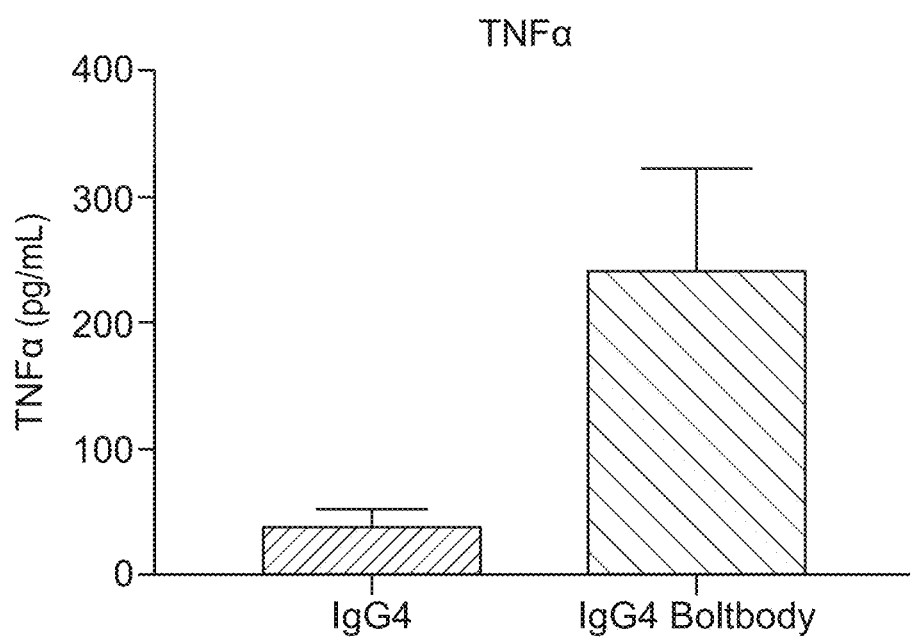

FIG. 94A shows that the rituximab IgG4 immunoconjugate produced according to the BB-01 method (IgG4 Boltbody) elicits superior TNFα secretion from myeloid cells as compared to equimolar concentrations (0.2 µM) of unconjugated rituximab (IgG4; Invivogen, hcd20-mab4) following 18 hours of stimulation.

Figure 94B:
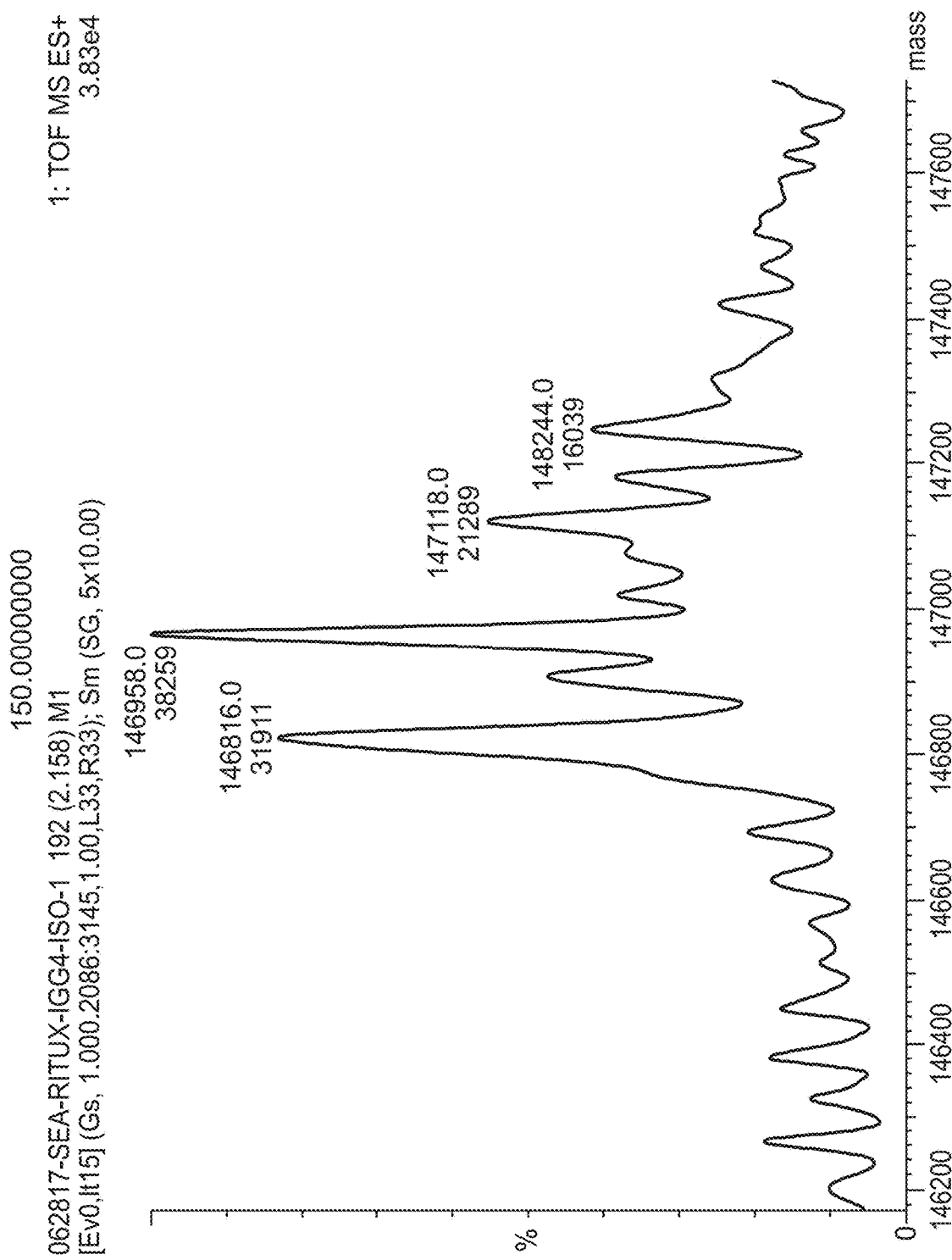

FIG. 94B shows a liquid chromatography-mass spectrometry analysis of unconjugated rituximab IgG4 (Invivogen, hcd20-mab4) that was utilized to produce the rituximab immunoconjugate according to the BB-01 conjugation method.

Figure 94C:
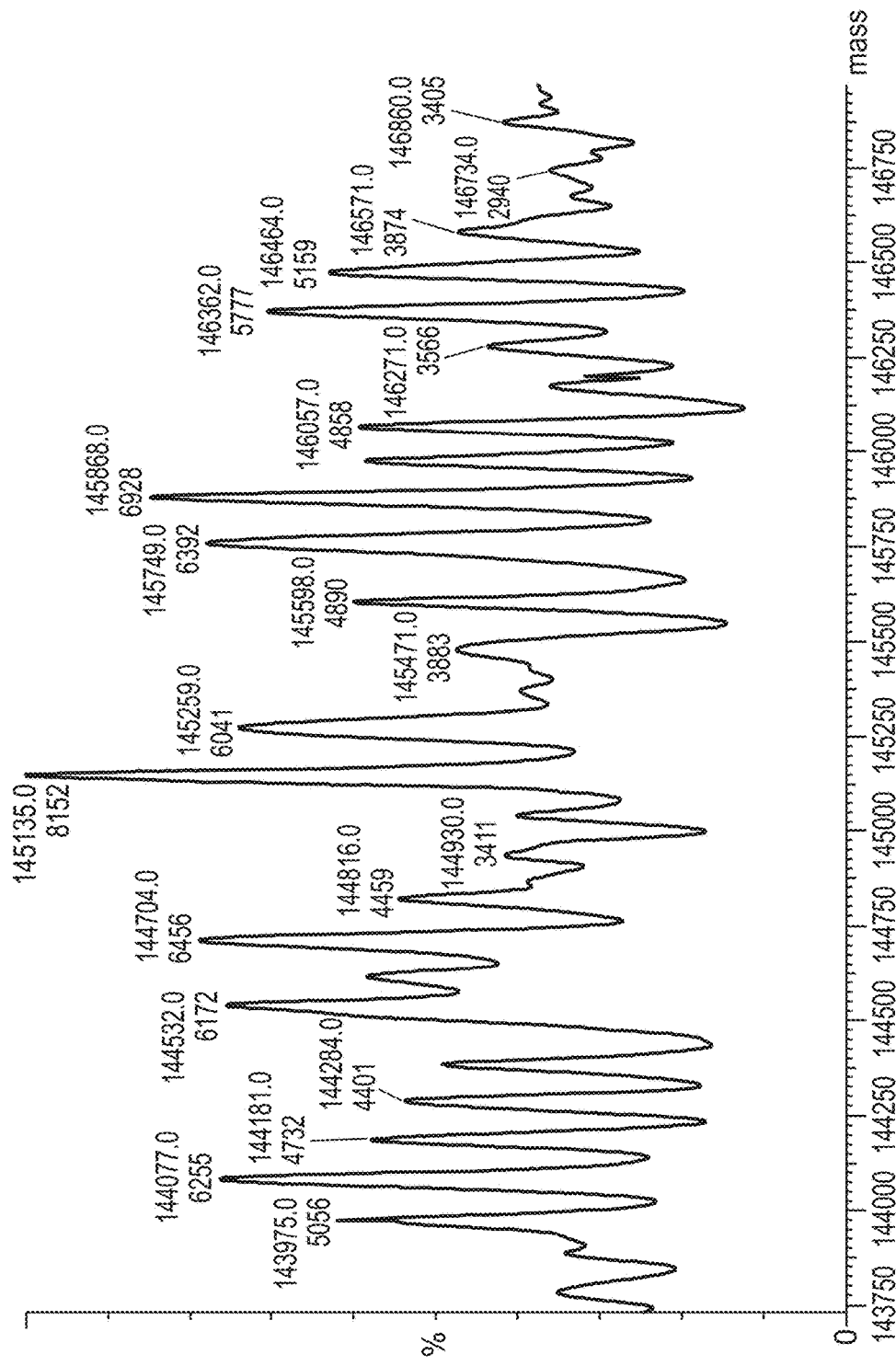

FIG. 94C shows a liquid chromatography-mass spectrometry analysis of the rituximab IgG4 immunoconjugate produced according to the BB-01 conjugation method.

Figure 94D:
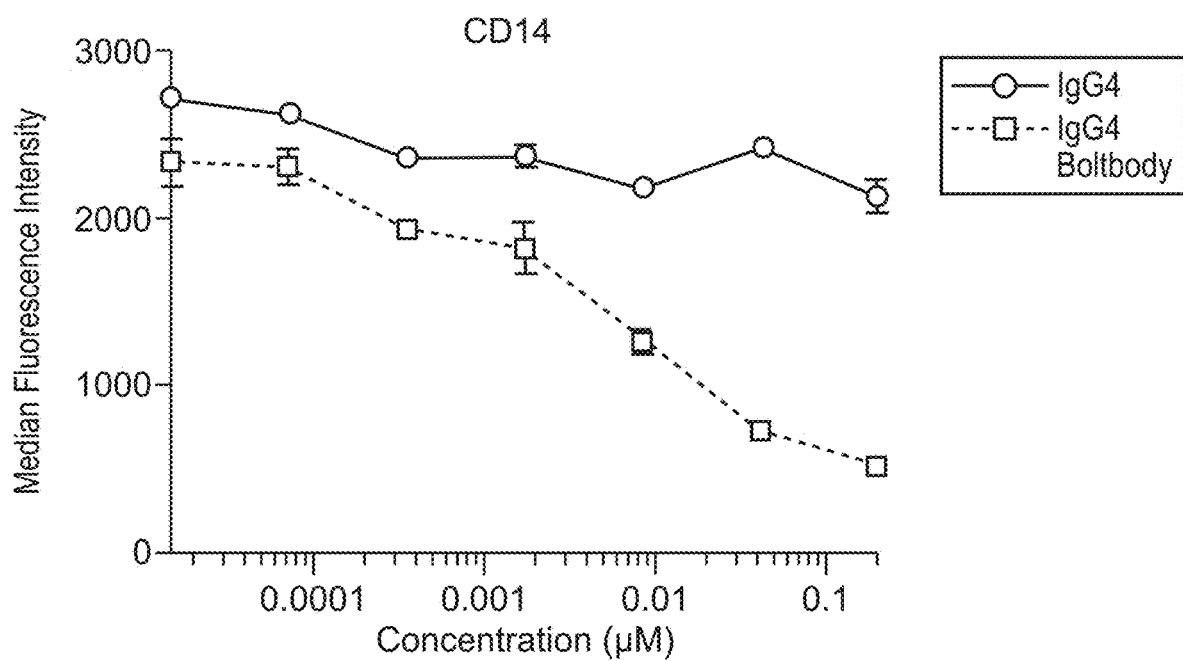

FIG. 94D shows that the rituximab IgG4 immunoconjugate produced according to the BB-01 method (IgG4 Boltbody) is superior at eliciting CD14 downregulation on myeloid cells as compared to the unconjugated rituximab (IgG4; Invivogen, hcd20-mab4) following 18 hours of stimulation.

Figure 94E:
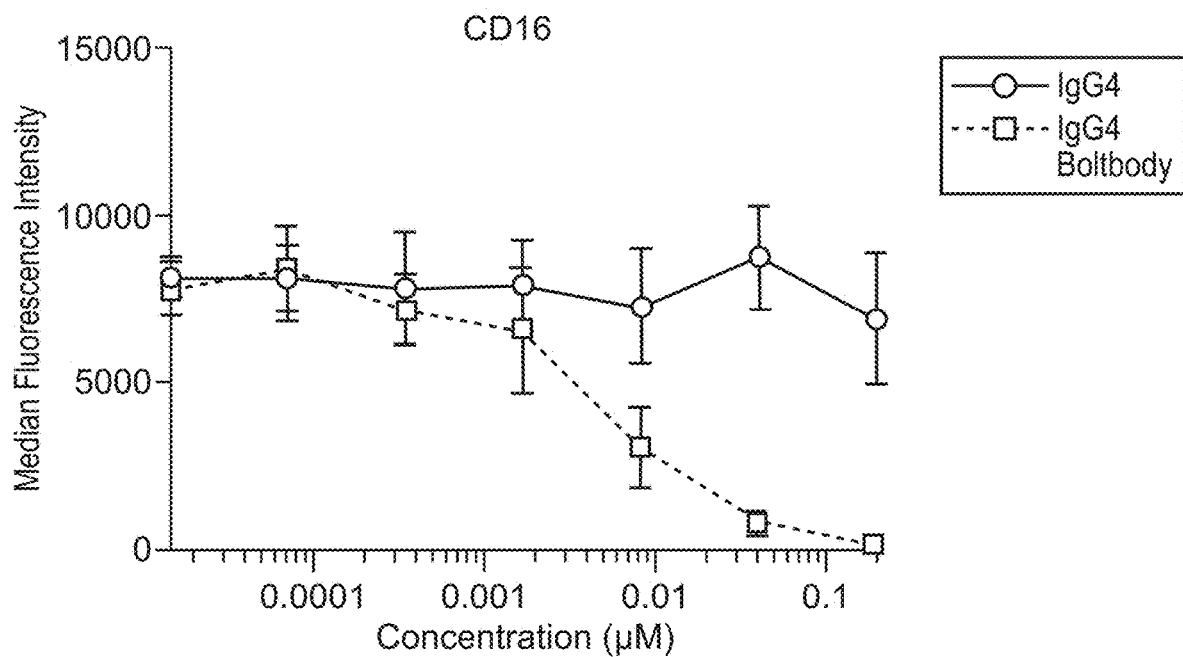

FIG. 94E shows that the rituximab IgG4 immunoconjugate produced according to the BB-01 method (IgG4 Boltbody) is superior at eliciting CD16 downregulation on myeloid cells as compared to the unconjugated rituximab (IgG4; Invivogen, hcd20-mab4) following 18 hours of stimulation.

Figure 94F:
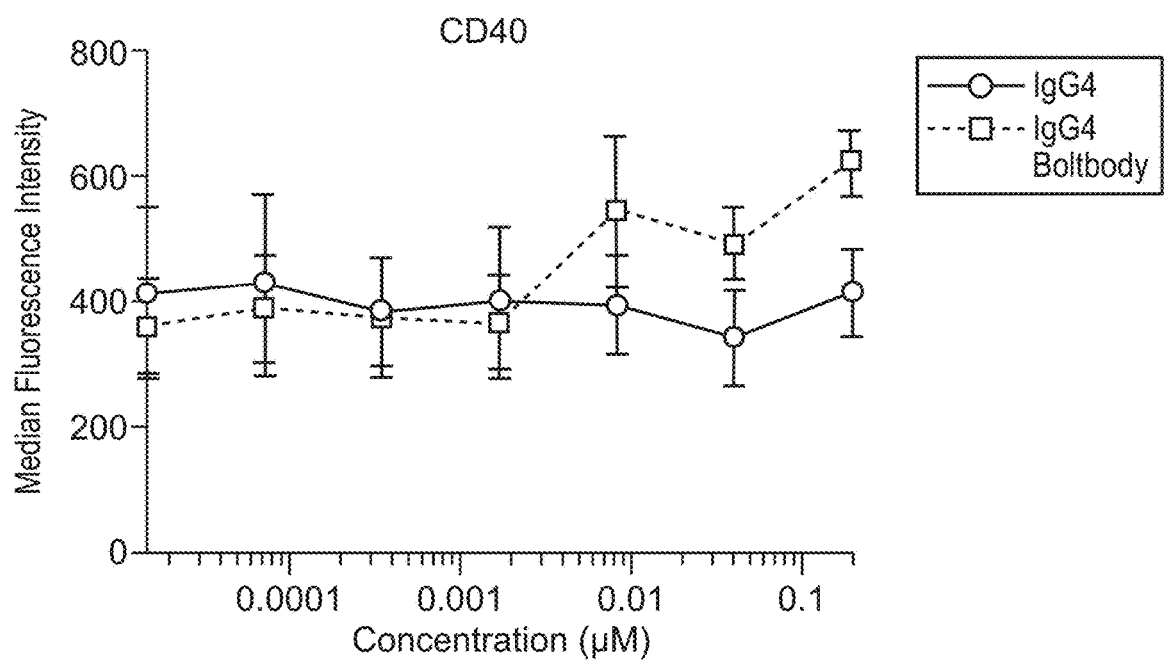

FIG. 94F shows that the rituximab IgG4 immunoconjugate produced according to the BB-01 method (IgG4 Boltbody) is superior at eliciting CD40 upregulation on myeloid cells as compared to the unconjugated rituximab (IgG4; Invivogen, hcd20-mab4) following 18 hours of stimulation.

Figure 94G:
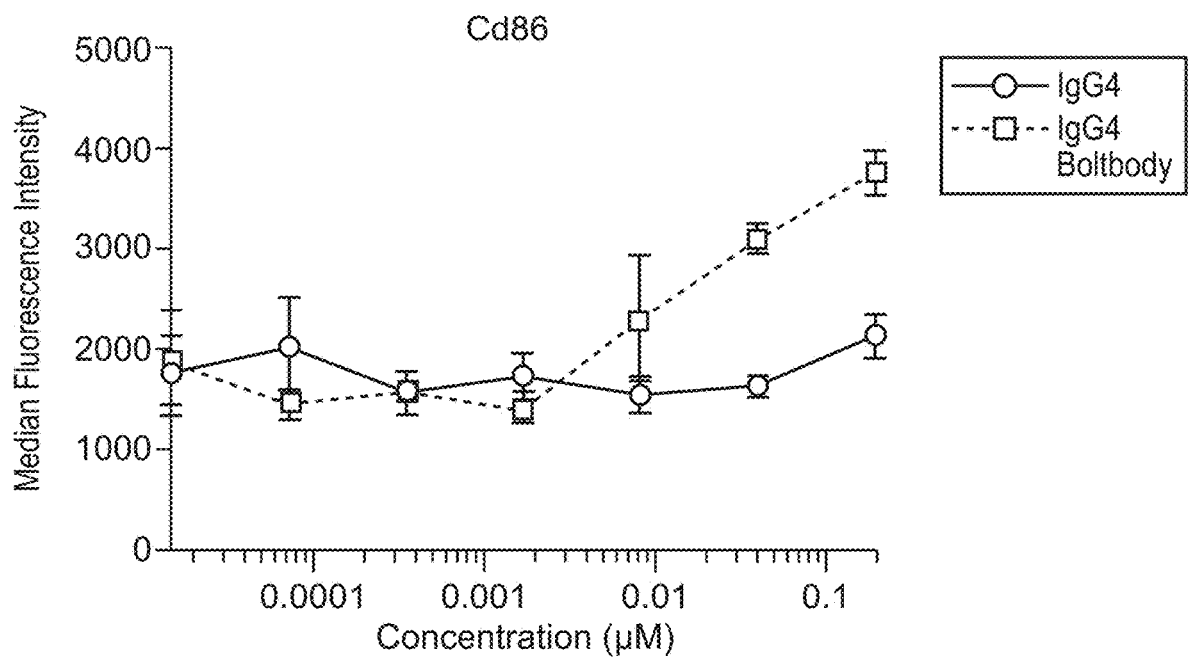

FIG. 94G shows that the rituximab IgG4 immunoconjugate produced according to the BB-01 method (IgG4 Boltbody) is superior at eliciting CD86 upregulation on myeloid cells as compared to the unconjugated rituximab (IgG4; Invivogen, hcd20-mab4) following 18 hours of stimulation.

Figure 94H:
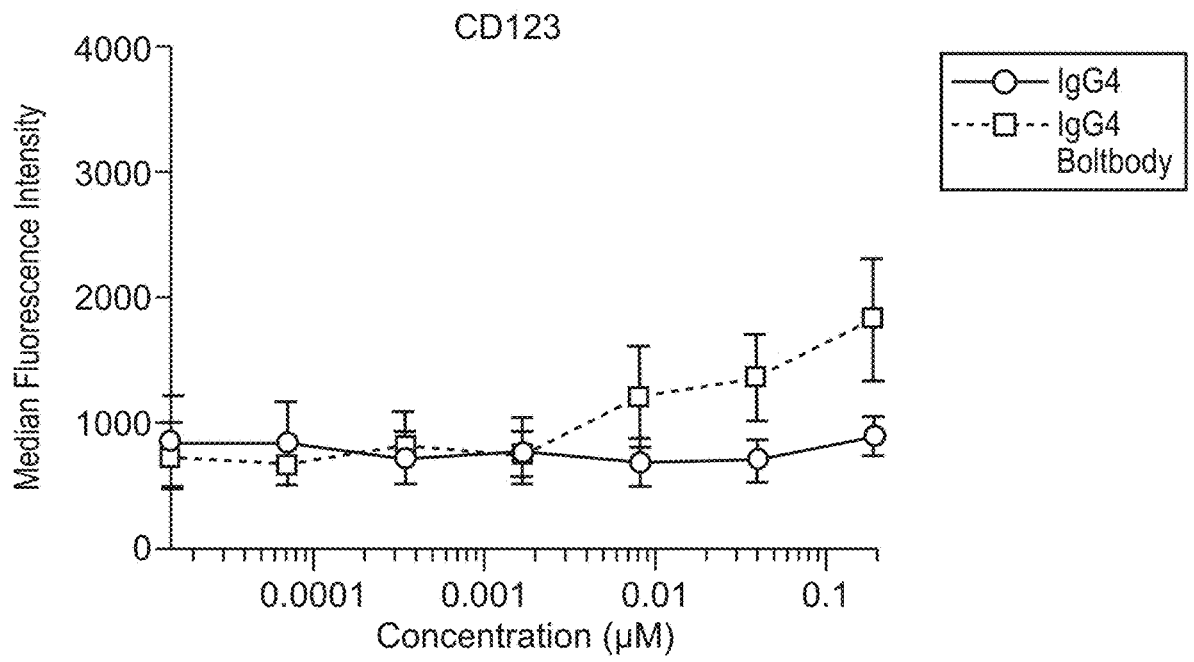

FIG. 94H shows that the rituximab IgG4 immunoconjugate produced according to the BB-01 method (IgG4 Boltbody) is superior at eliciting CD123 upregulation on myeloid cells as compared to the unconjugated rituximab (IgG4; Invivogen, hcd20-mab4) following 18 hours of stimulation.

Figure 94I:
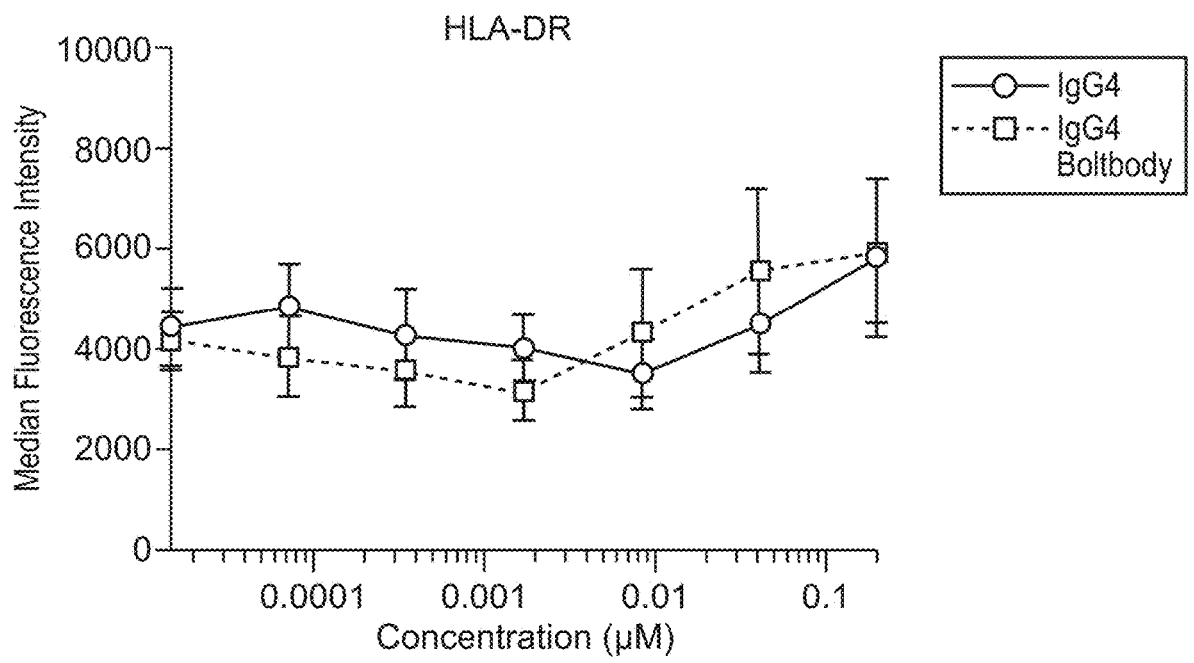

FIG. 94I shows that the rituximab IgG4 immunoconjugate produced according to the BB-01 method (IgG4 Boltbody) is superior at eliciting HLA-DR upregulation on myeloid cells as compared to the unconjugated rituximab (IgG4; Invivogen, hcd20-mab4) following 18 hours of stimulation.

FIG. 95 is a table that lists the EC50 values and fold-changes of CD14, CD40, and CD86 expression for IgG1 Boltbody (BB-IgG1), IgG1 AF Boltbody (BB-IgG1 AF), IgG2 Boltbody (BB-IgG2), IgG3 Boltbody (BB-IgG3), and IgG4 Boltbody (BB-IgG4) referenced in FIGS. 89, 90, 92, 93, and 94 respectively. EC50 values were computed based on dose-response curves generated from 5-fold serial dilutions. All fold-changes were calculated relative to the respective naked antibody at the indicated concentration.

Figure 96A:
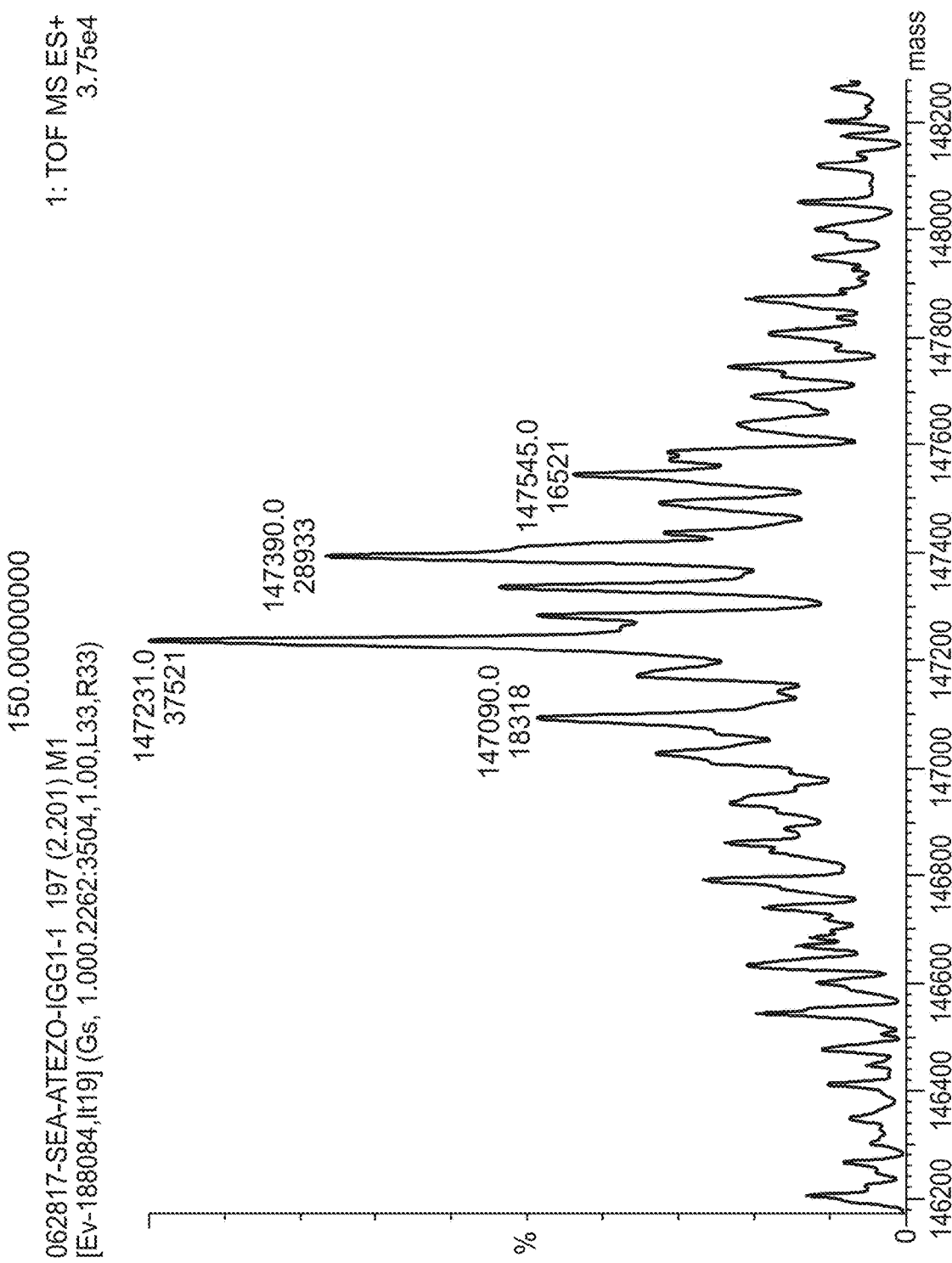

FIG. 96A shows a liquid chromatography-mass spectrometry analysis of unconjugated atezolizumab IgG1 isotype variant (Invivogen, hpd11-mab1) that was utilized to produce the atezolizumab immunoconjugate according to the BB-01 conjugation method.

Figure 96B:
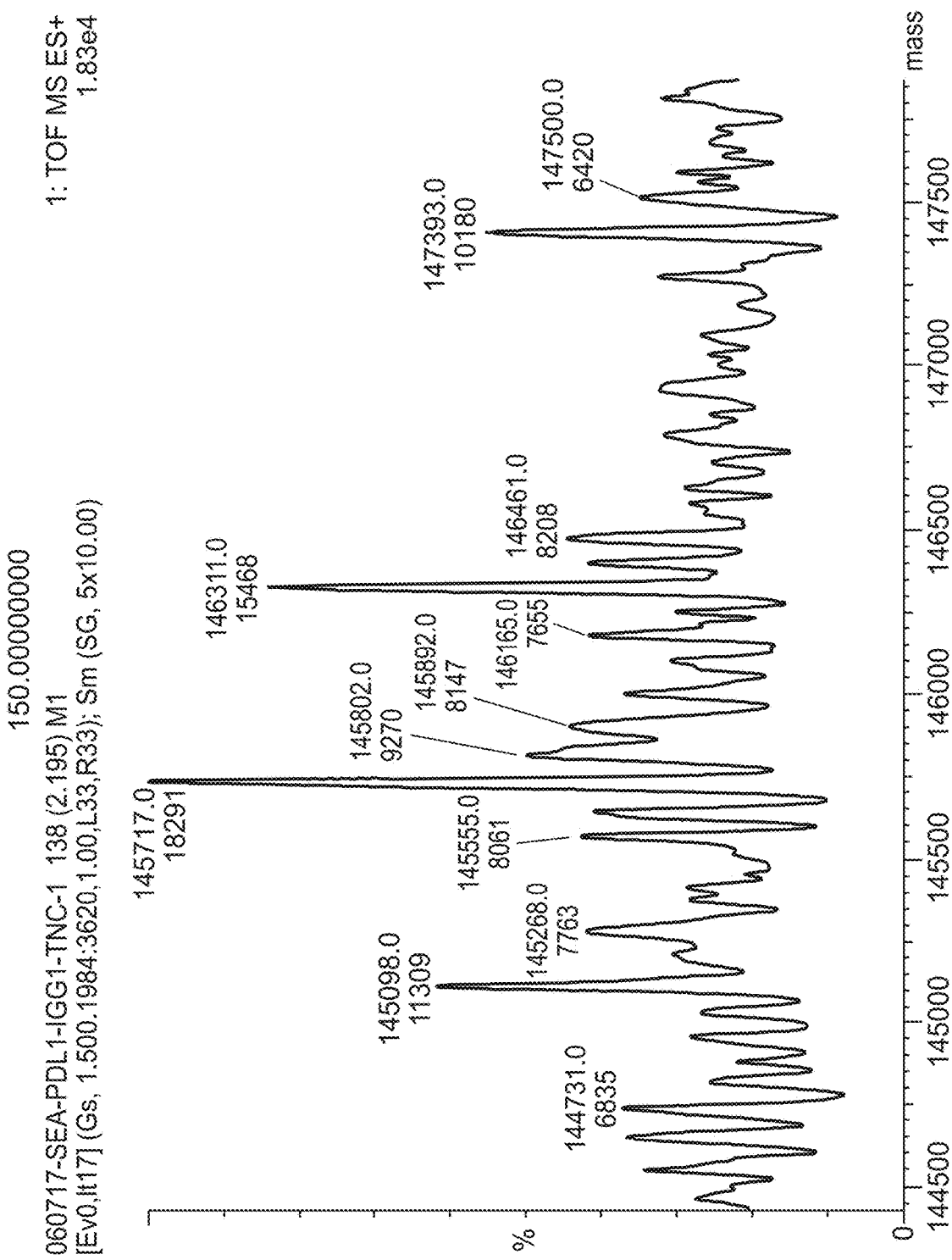

FIG. 96B shows a liquid chromatography-mass spectrometry analysis of the atezolizumab IgG1 isotype variant immunoconjugate produced according to the BB-01 conjugation method.

Figure 96C:
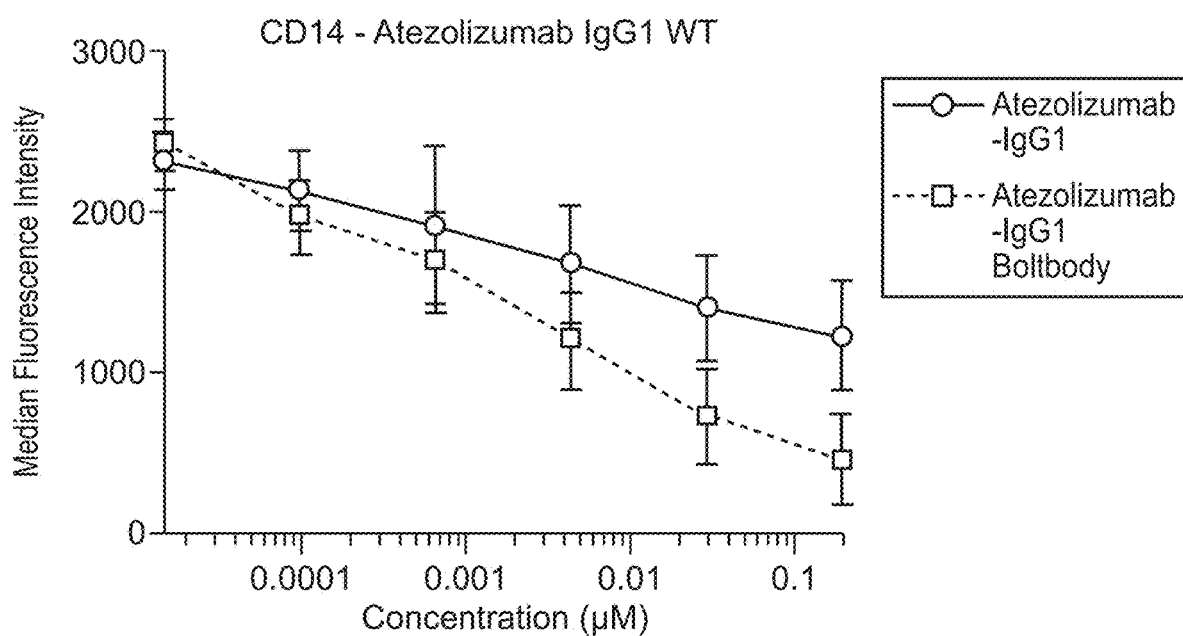

FIG. 96C shows CD14 expression on myeloid cells following 18 hours of stimulation with the atezolizumab IgG1 isotype variant immunoconjugate produced according to the BB-01 method (Atezolizumab—IgG1 Boltbody) as compared to unconjugated atezolizumab (Atezolizumab—IgG; Invivogen, hpd11-mab1).

Figure 96D:
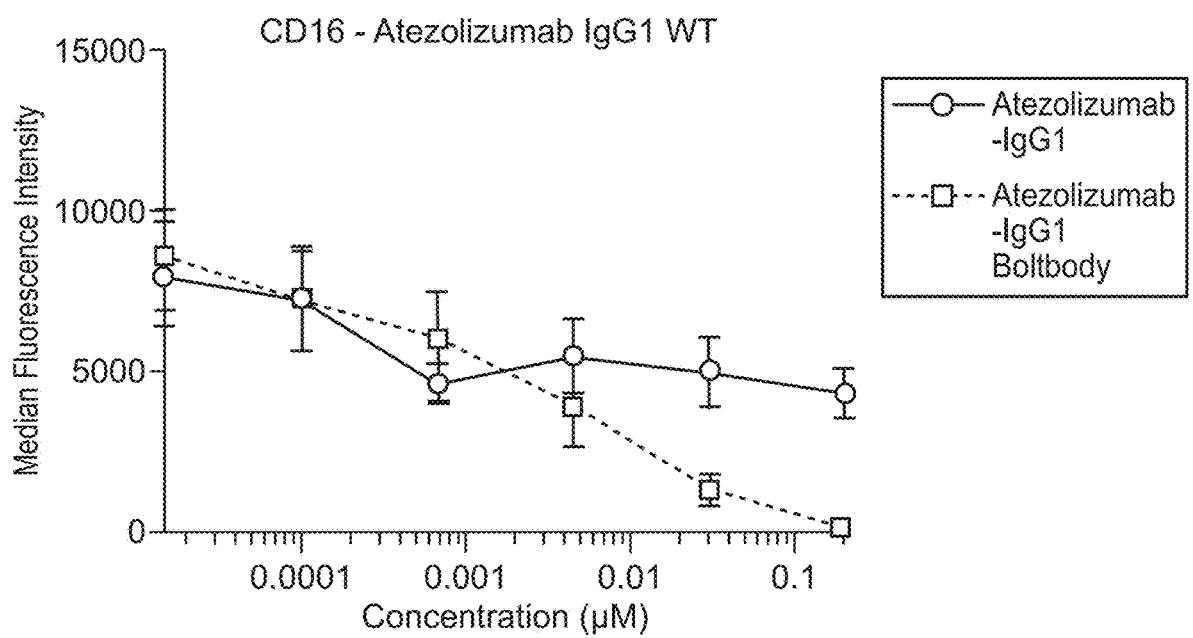

FIG. 96D shows CD16 expression on myeloid cells following 18 hours of stimulation with the atezolizumab IgG1 isotype variant immunoconjugate produced according to the BB-01 method (Atezolizumab—IgG1 Boltbody) as compared to unconjugated atezolizumab (Atezolizumab—IgG; Invivogen, hpd11-mab1).

Figure 96E:
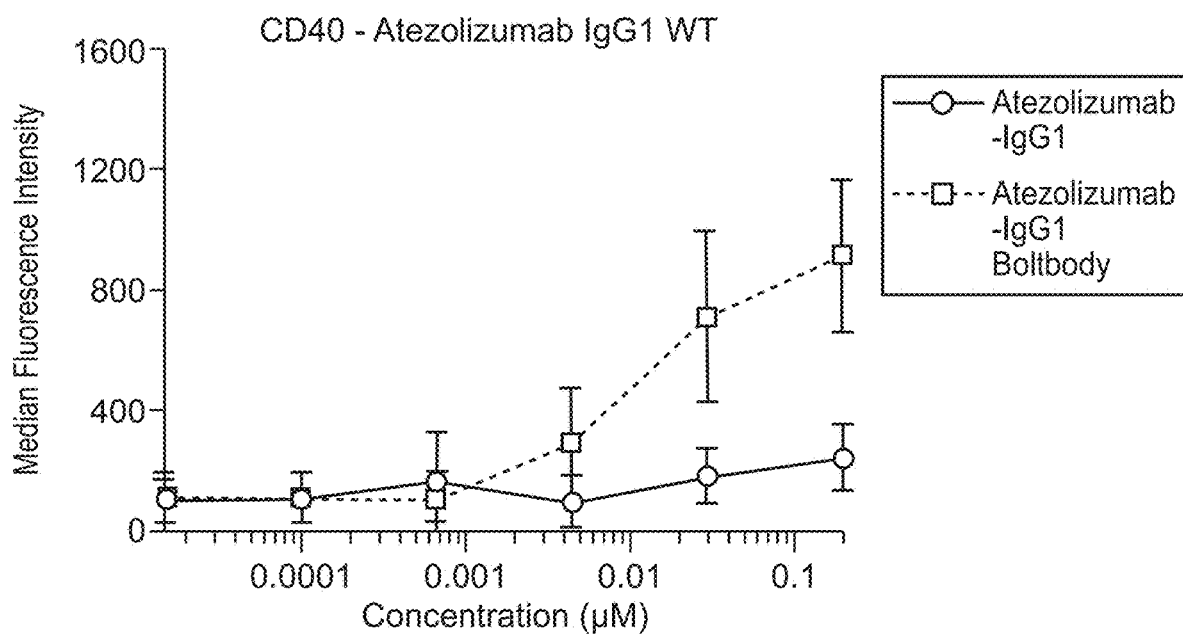

FIG. 96E shows CD40 expression on myeloid cells following 18 hours of stimulation with the atezolizumab IgG1 isotype variant immunoconjugate produced according to the BB-01 method (Atezolizumab—IgG1 Boltbody) as compared to unconjugated atezolizumab (Atezolizumab—IgG1; Invivogen, hpd11-mab1).

Figure 96F:
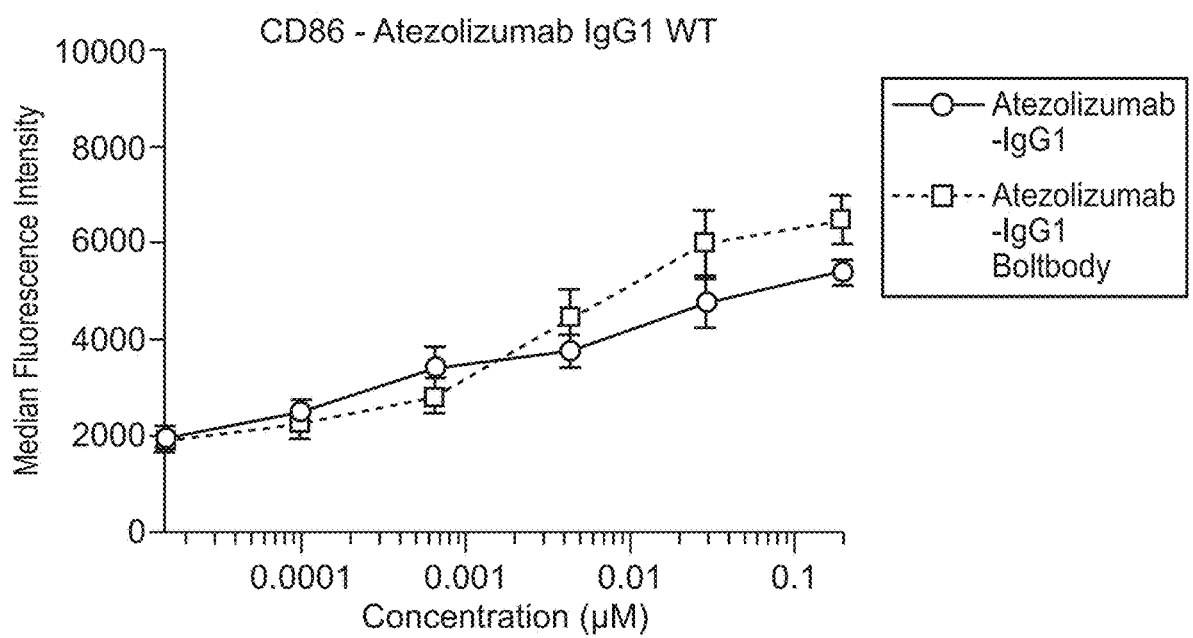

FIG. 96F shows CD86 expression on myeloid cells following 18 hours of stimulation with the atezolizumab IgG1 isotype variant immunoconjugate produced according to the BB-01 method (Atezolizumab—IgG1 Boltbody) as compared to unconjugated atezolizumab (Atezolizumab—IgG; Invivogen, hpd11-mab1).

Figure 96G:
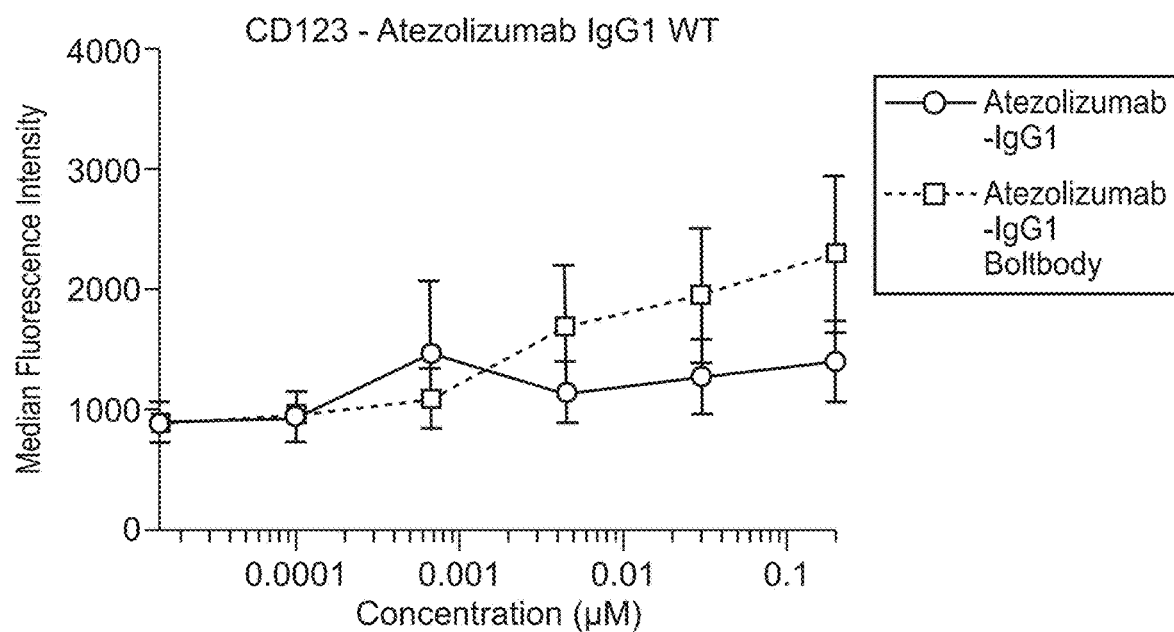

FIG. 96G shows CD123 expression on myeloid cells following 18 hours of stimulation with the atezolizumab IgG1 isotype variant immunoconjugate produced according to the BB-01 method (Atezolizumab—IgG1 Boltbody) as compared to unconjugated atezolizumab (Atezolizumab—IgG1; Invivogen, hpd11-mab1).

Figure 96H:
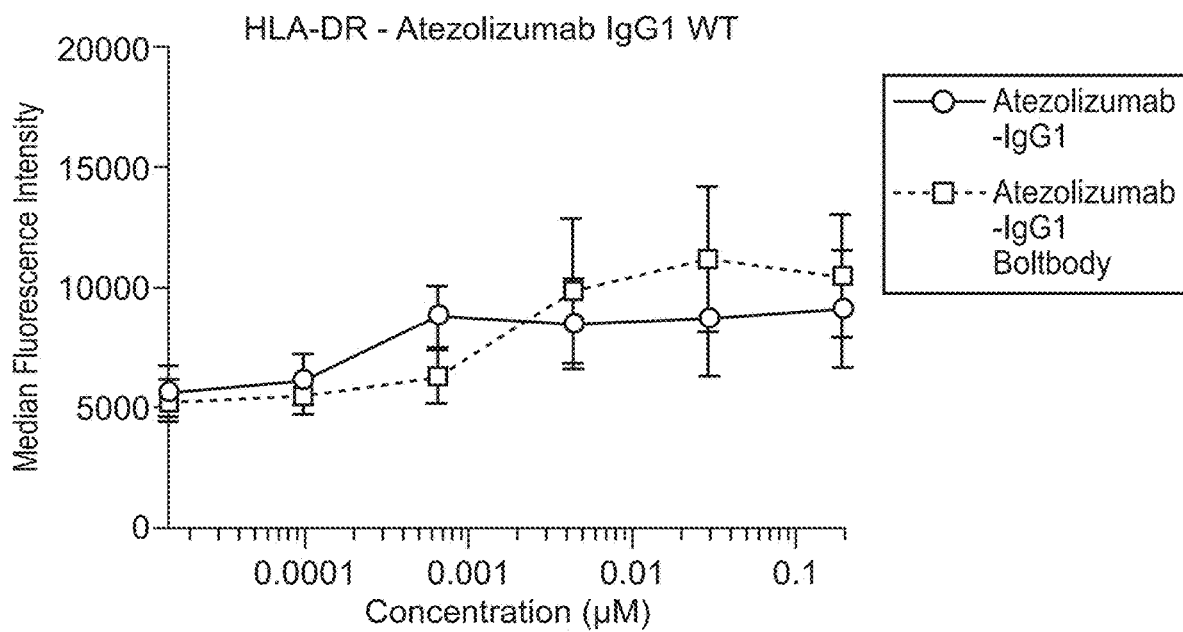

FIG. 96H shows HLA-DR expression on myeloid cells following 18 hours of stimulation with the atezolizumab IgG1 isotype variant immunoconjugate produced according to the BB-01 method (Atezolizumab—IgG1 Boltbody) as compared to unconjugated atezolizumab (Atezolizumab—IgG1; Invivogen, hpd11-mab1).

Figure 97A:
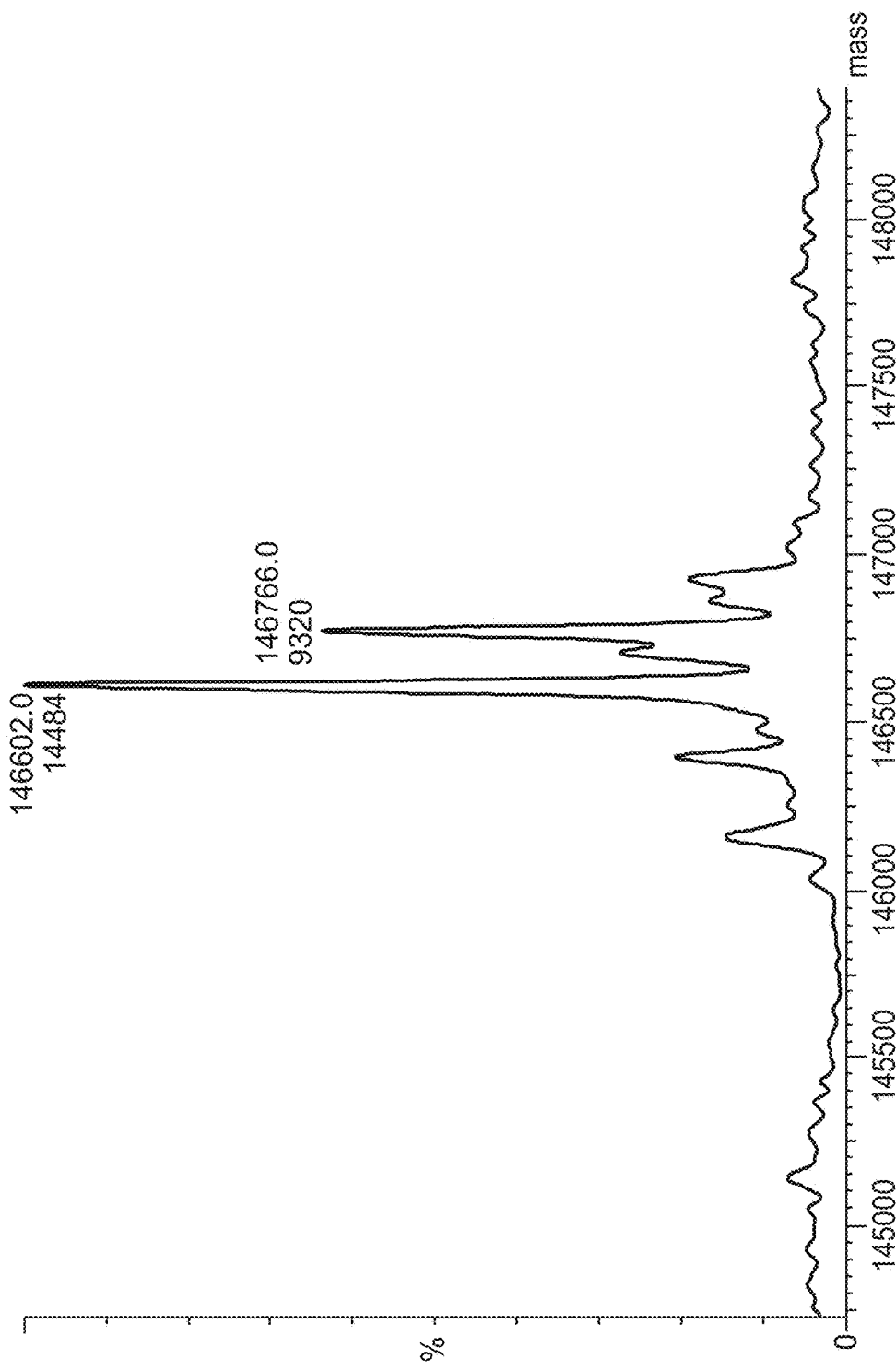

FIG. 97A shows a liquid chromatography-mass spectrometry analysis of unconjugated nivolumab IgG1 isotype variant (Invivogen, hpd1ni-mab1) that was utilized to produce the nivolumab immunoconjugate according to the BB-01 conjugation method.

Figure 97B:
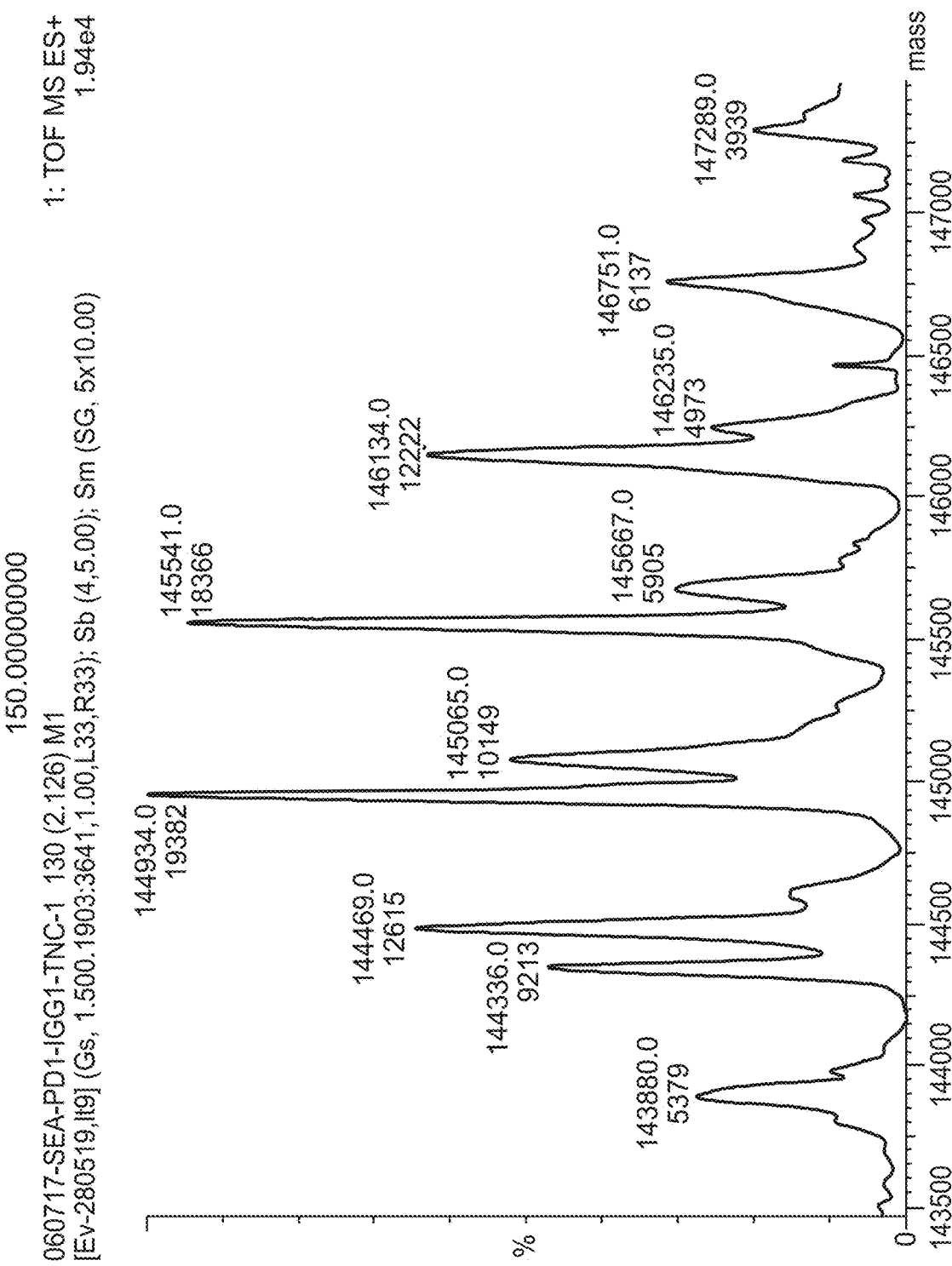

FIG. 97B shows a liquid chromatography-mass spectrometry analysis of the nivolumab IgG1 isotype variant immunoconjugate produced according to the BB-01 conjugation method.

Figure 97C:
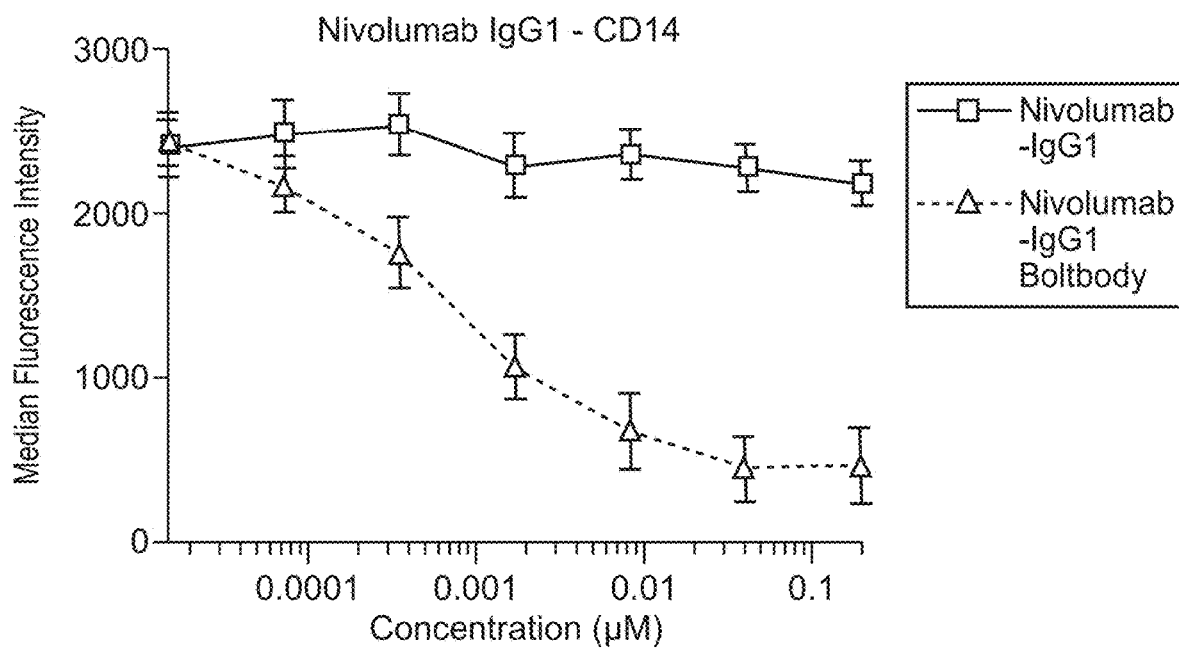

FIG. 97C shows CD14 expression on myeloid cells following 18 hours of stimulation with the nivolumab IgG1 isotype variant immunoconjugate produced according to the BB-01 method (Nivolumab—IgG1 Boltbody) as compared to unconjugated nivolumab (Nivolumab—IgG; Invivogen, hpd1ni-mab1).

Figure 97D:
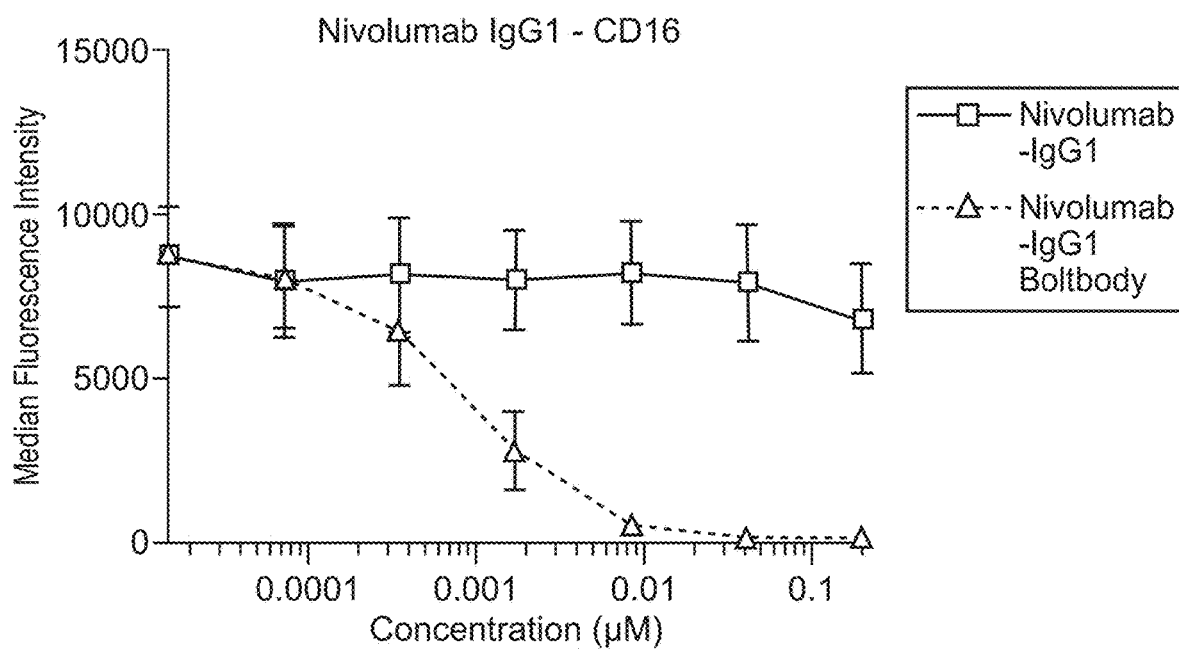

FIG. 97D shows CD16 expression on myeloid cells following 18 hours of stimulation with the nivolumab IgG1 isotype variant immunoconjugate produced according to the BB-01 method (Nivolumab—IgG1 Boltbody) as compared to unconjugated nivolumab (Nivolumab—IgG1; Invivogen, hpd1ni-mab1).

Figure 97E:
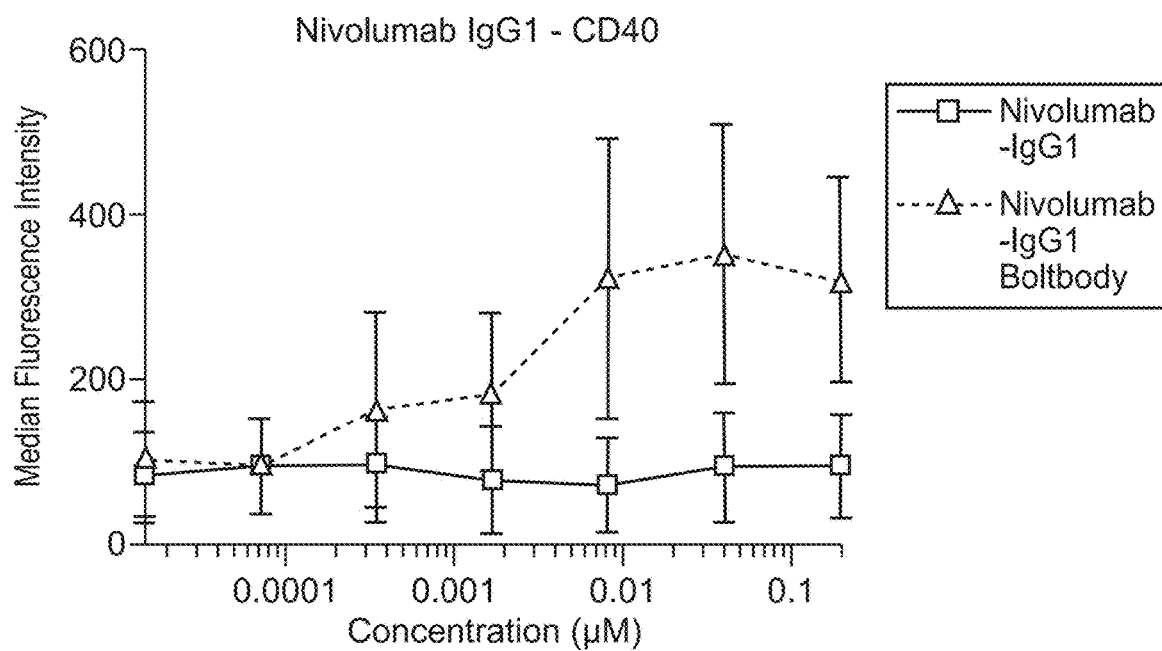

FIG. 97E shows CD40 expression on myeloid cells following 18 hours of stimulation with the nivolumab IgG1 isotype variant immunoconjugate produced according to the BB-01 method (Nivolumab—IgG1 Boltbody) as compared to unconjugated nivolumab (Nivolumab—IgG1; Invivogen, hpd1ni-mab1).

Figure 97F:
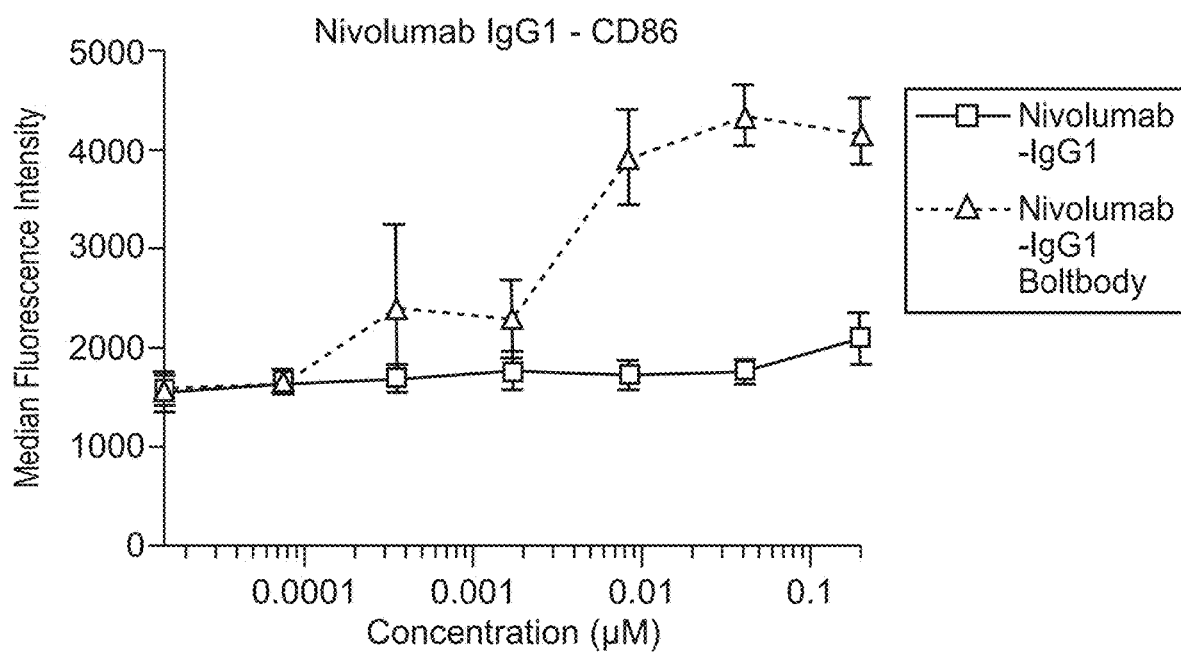

FIG. 97F shows CD86 expression on myeloid cells following 18 hours of stimulation with the nivolumab IgG1 isotype variant immunoconjugate produced according to the BB-01 method (Nivolumab—IgG1 Boltbody) as compared to unconjugated nivolumab (Nivolumab—IgG1; Invivogen, hpd1ni-mab1).

Figure 97G:
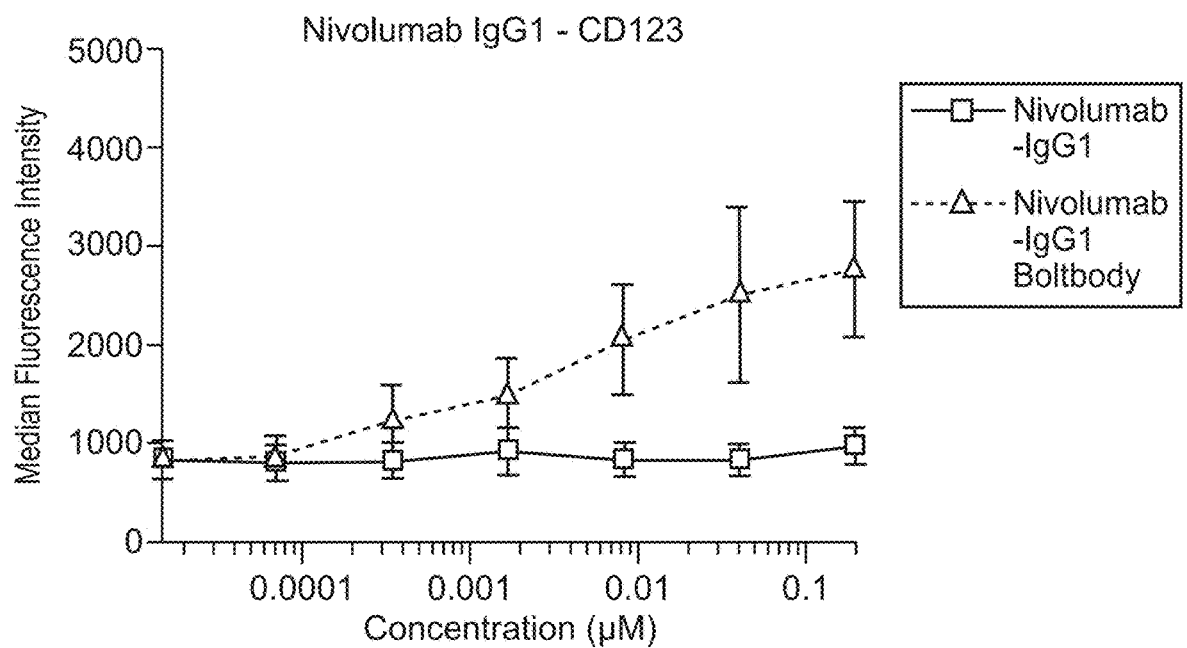

FIG. 97G shows CD123 expression on myeloid cells following 18 hours of stimulation with the nivolumab IgG1 isotype variant immunoconjugate produced according to the BB-01 method (Nivolumab—IgG1 Boltbody) as compared to unconjugated nivolumab (Nivolumab—IgG1; Invivogen, hpd1ni-mab1).

Figure 97H:
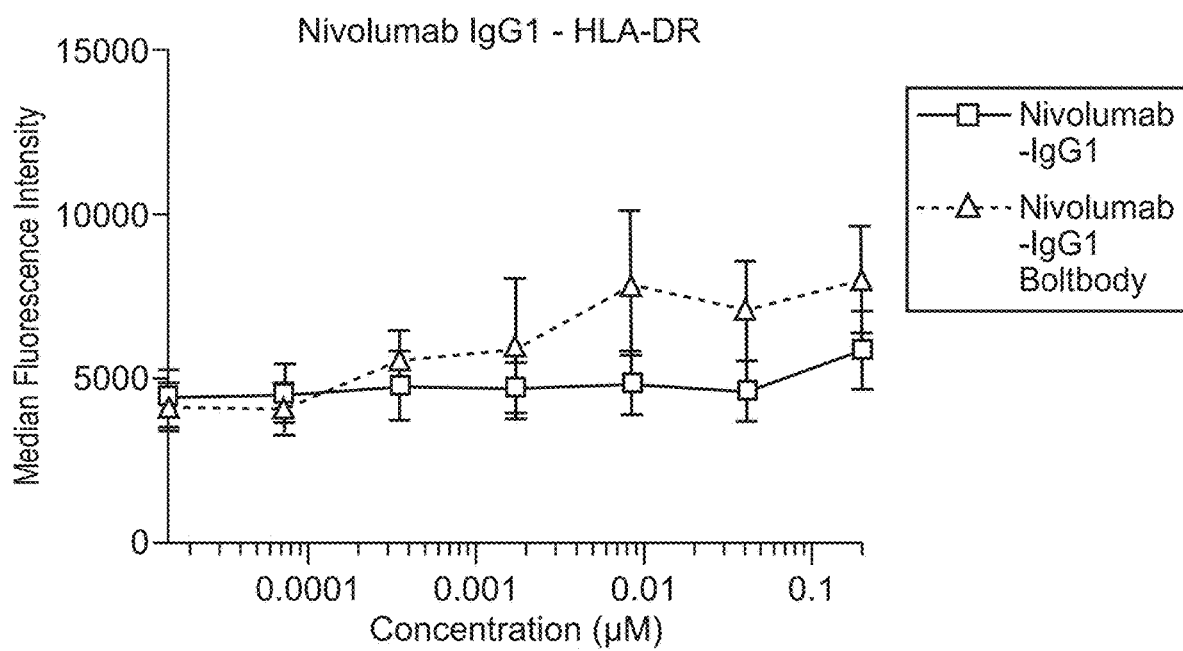

FIG. 97H shows HLA-DR expression on myeloid cells following 18 hours of stimulation with the nivolumab IgG1 isotype variant immunoconjugate produced according to the BB-01 method (Nivolumab—IgG1 Boltbody) as compared to unconjugated nivolumab (Nivolumab—IgG1; Invivogen, hpd1ni-mab1).

Figure 98A:
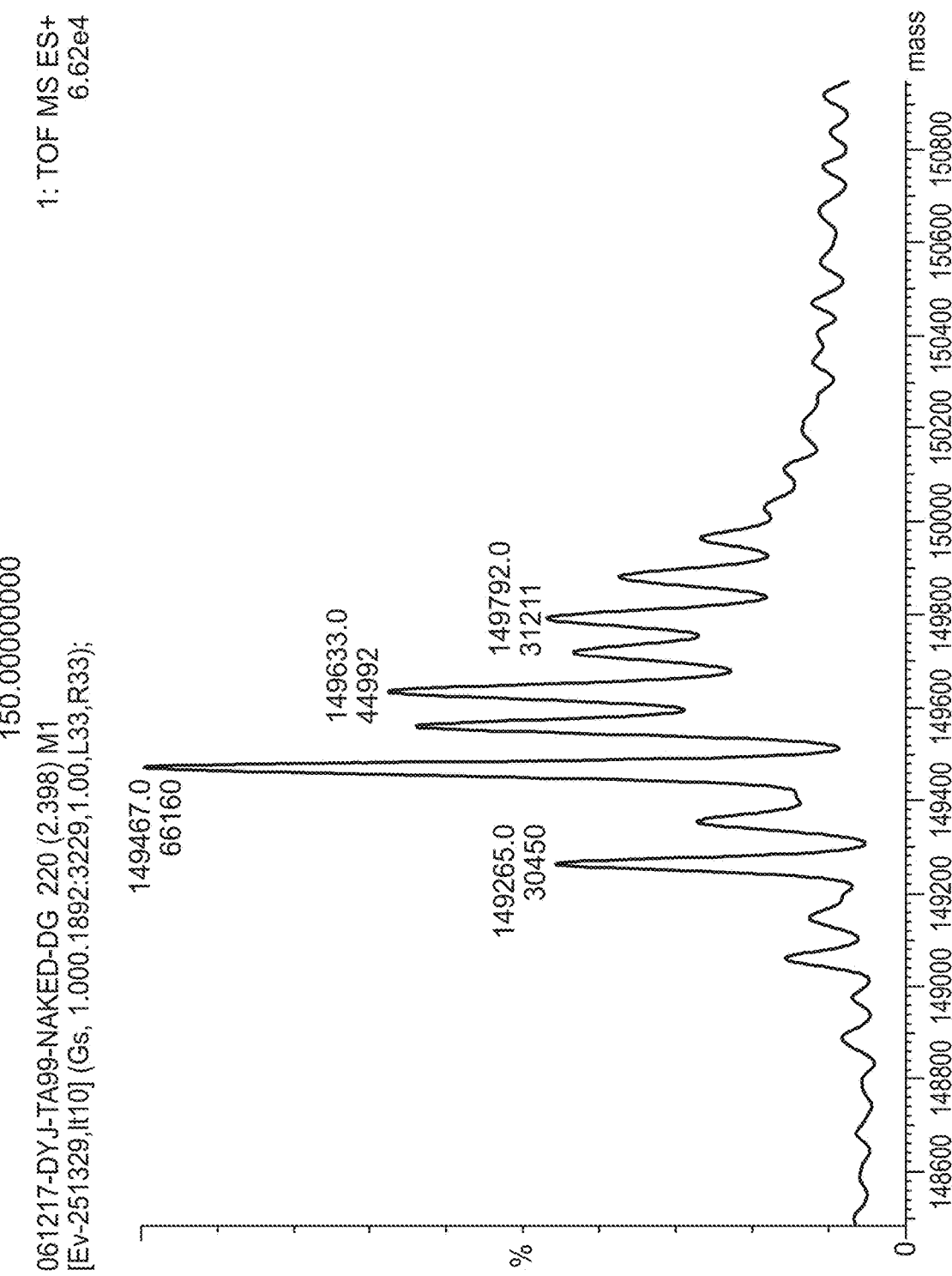

FIG. 98A shows a liquid chromatography-mass spectrometry analysis of unconjugated anti-gp75 mAb (BioXcell, TA99-BE0151) that was utilized to produce the anti-gp75 mAb immunoconjugate according to the BB-01 conjugation method following overnight deglycosylation with PNGase F.

Figure 98B:
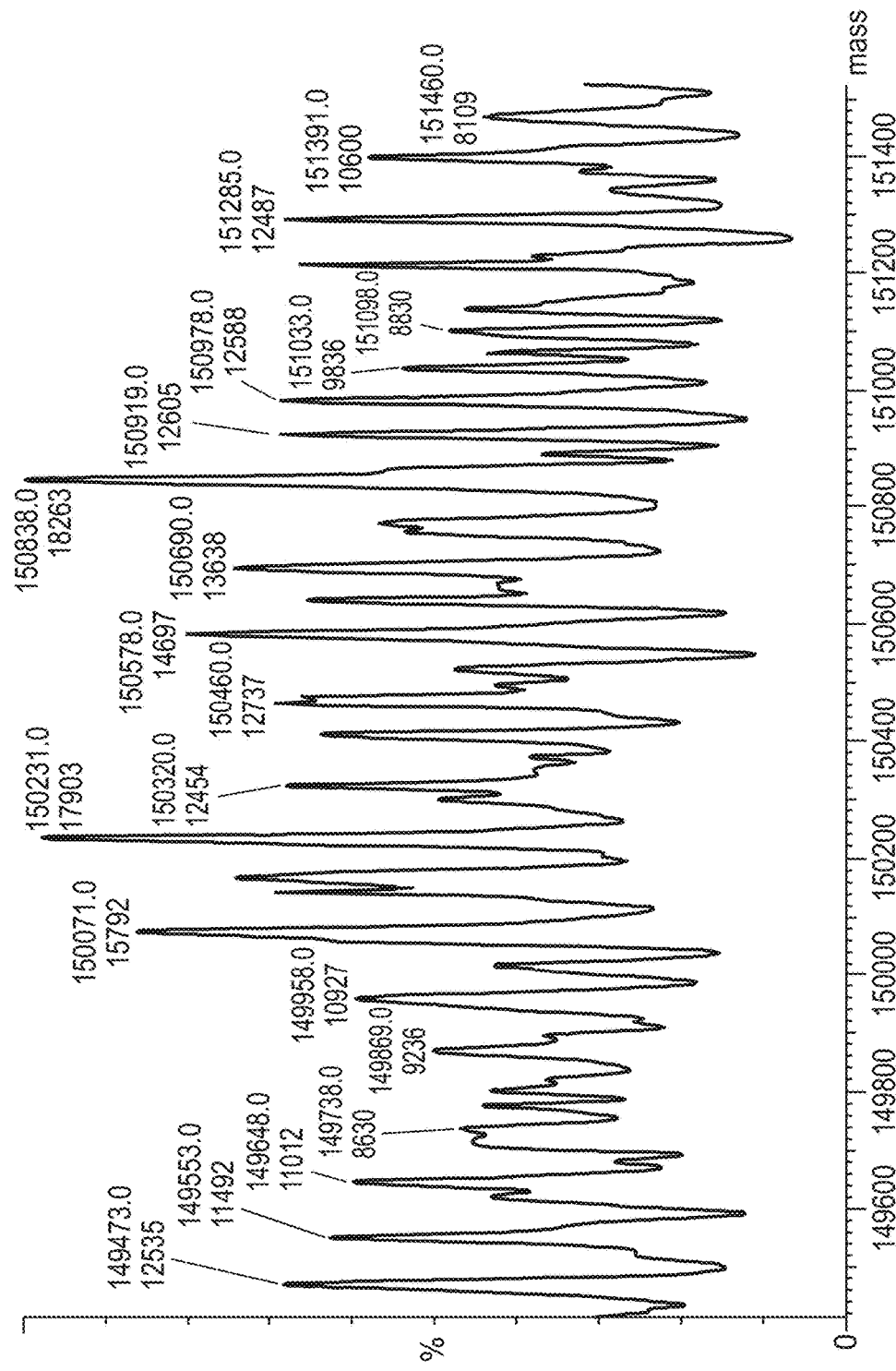

FIG. 98B shows a liquid chromatography-mass spectrometry analysis of the anti-gp75 mAb immunoconjugate produced according to the BB-01 conjugation method following overnight deglycosylation with PNGase F.

Figure 98C:
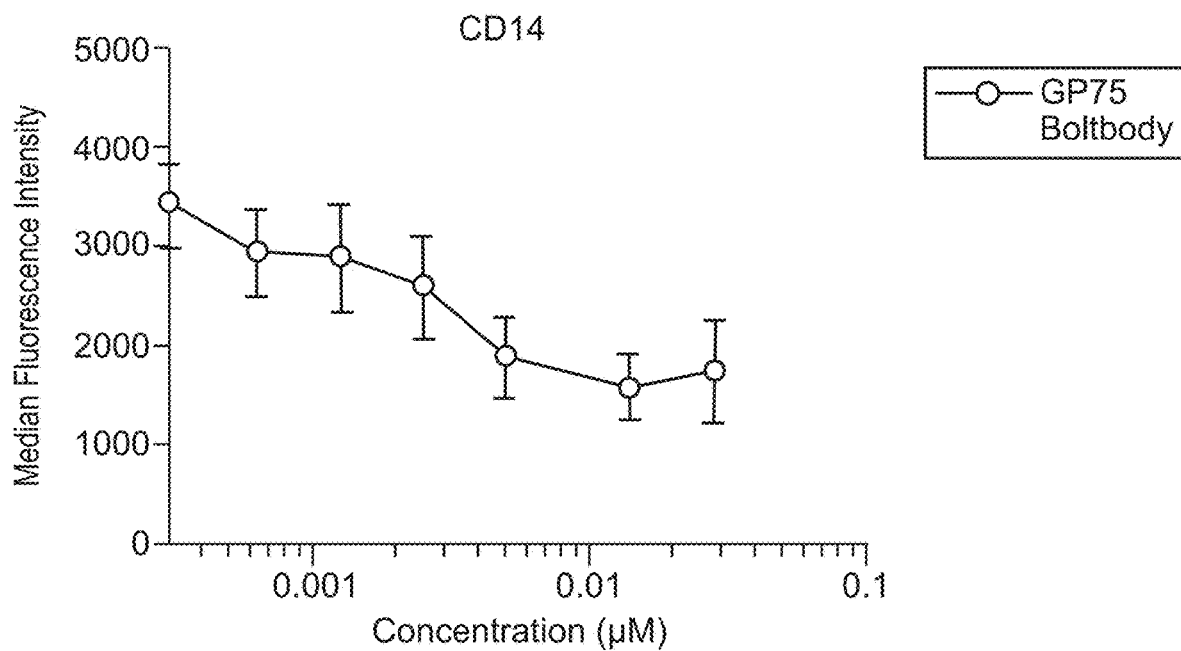

FIG. 98C shows CD14 expression on myeloid cells following 18 hours of stimulation with the anti-gp75 mAb immunoconjugate produced according to the BB-01 method (GP75 Boltbody.

Figure 98D:
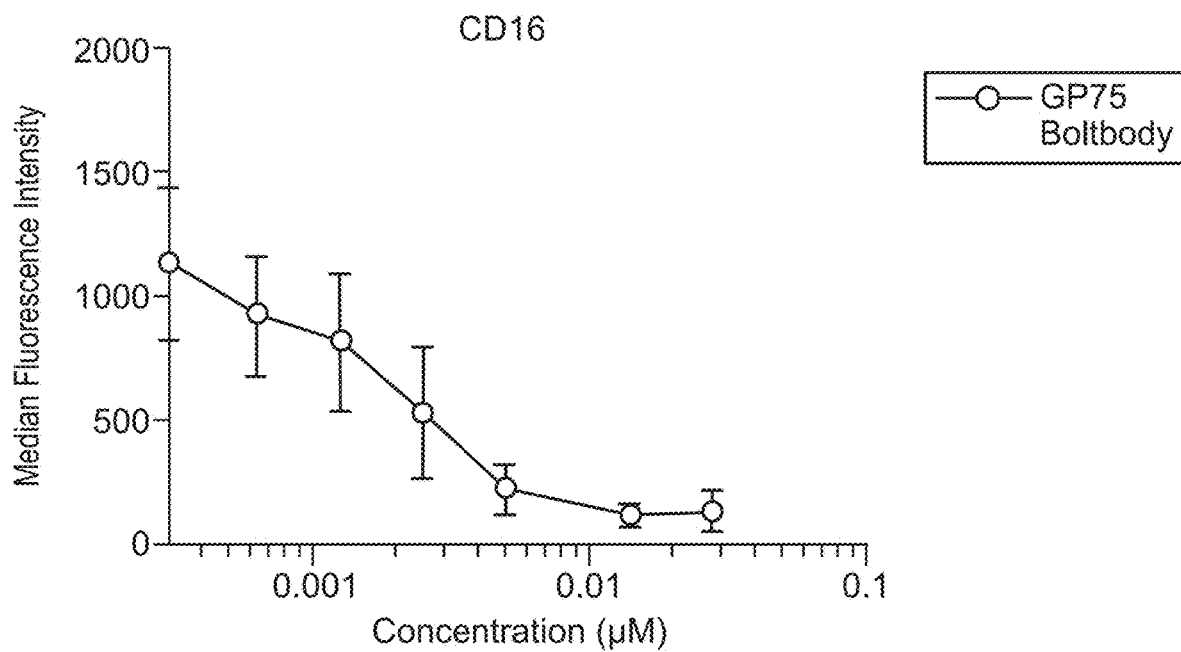

FIG. 98D shows CD16 expression on myeloid cells following 18 hours of stimulation with the anti-gp75 mAb immunoconjugate produced according to the BB-01 method (GP75 Boltbody).

Figure 98E:
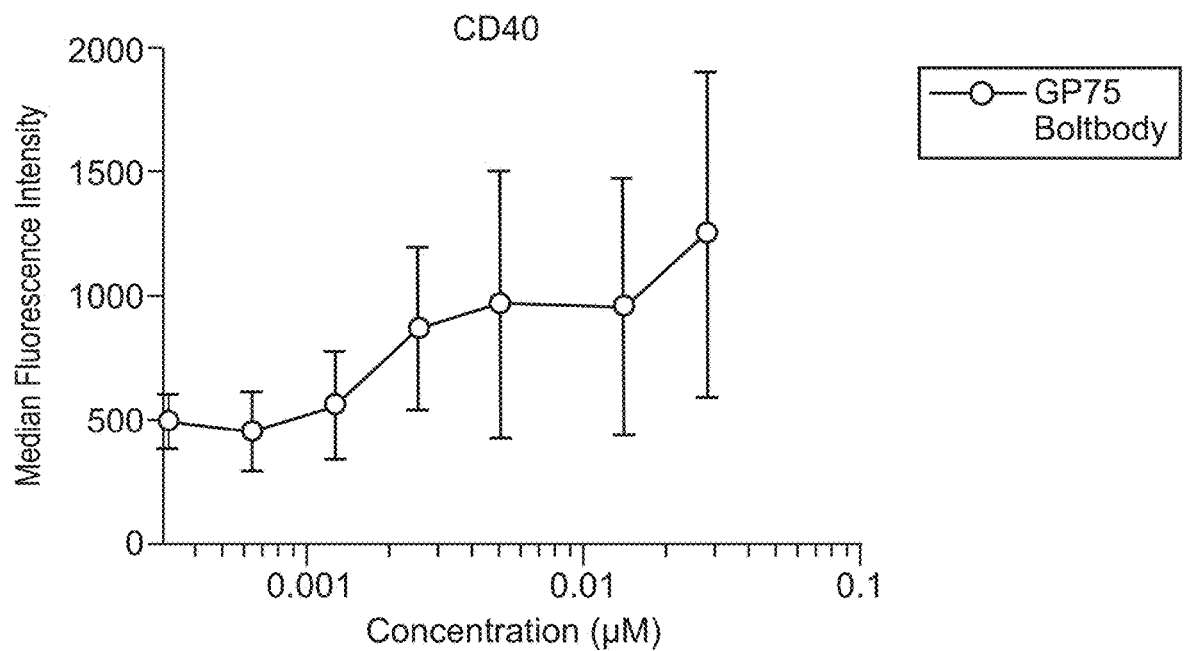

FIG. 98E shows CD40 expression on myeloid cells following 18 hours of stimulation with the anti-gp75 mAb immunoconjugate produced according to the BB-01 method (GP75 Boltbody.

Figure 98F:
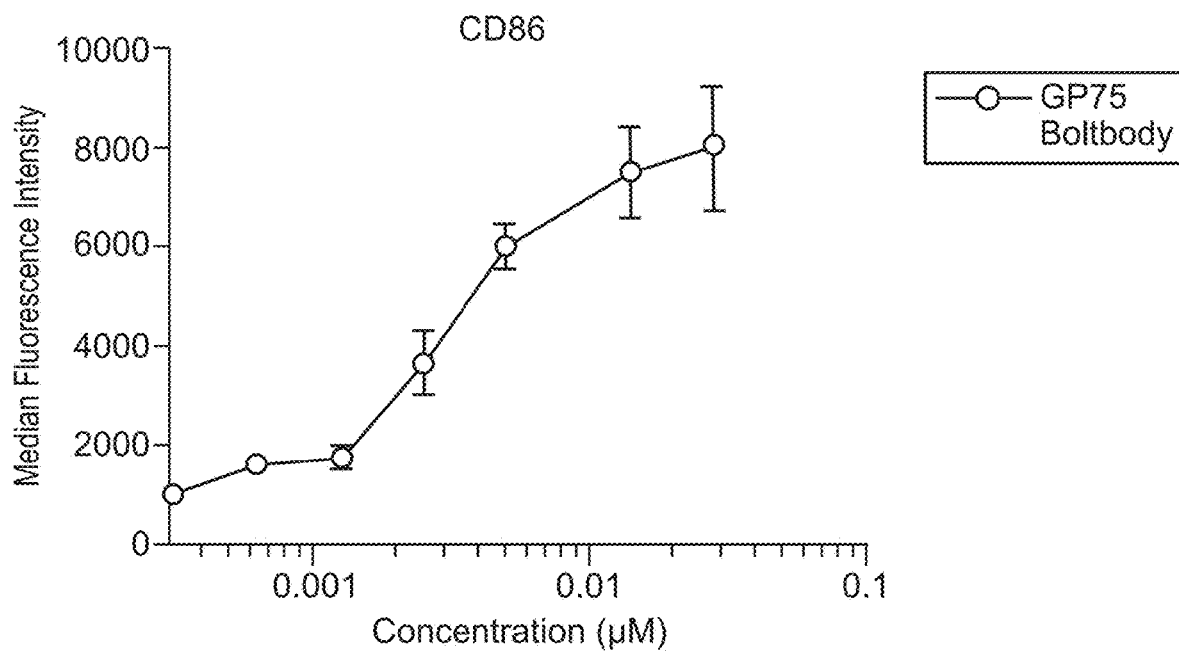

FIG. 98F shows CD86 expression on myeloid cells following 18 hours of stimulation with the anti-gp75 mAb immunoconjugate produced according to the BB-01 method (GP75 Boltbody).

FIG. 98G shows HLA-DR expression on myeloid cells following 18 hours of stimulation with the anti-gp75 mAb immunoconjugate produced according to the BB-01 method (GP75 Boltbody).

FIG. 99A shows a liquid chromatography-mass spectrometry analysis of the unconjugated rituximab biosimilar (CD20, LGM Pharma) that was utilized to produce the rituximab immunoconjugate according to the BB-03 conjugation method following overnight deglycosylation with PNGase F.

Figure 99B:
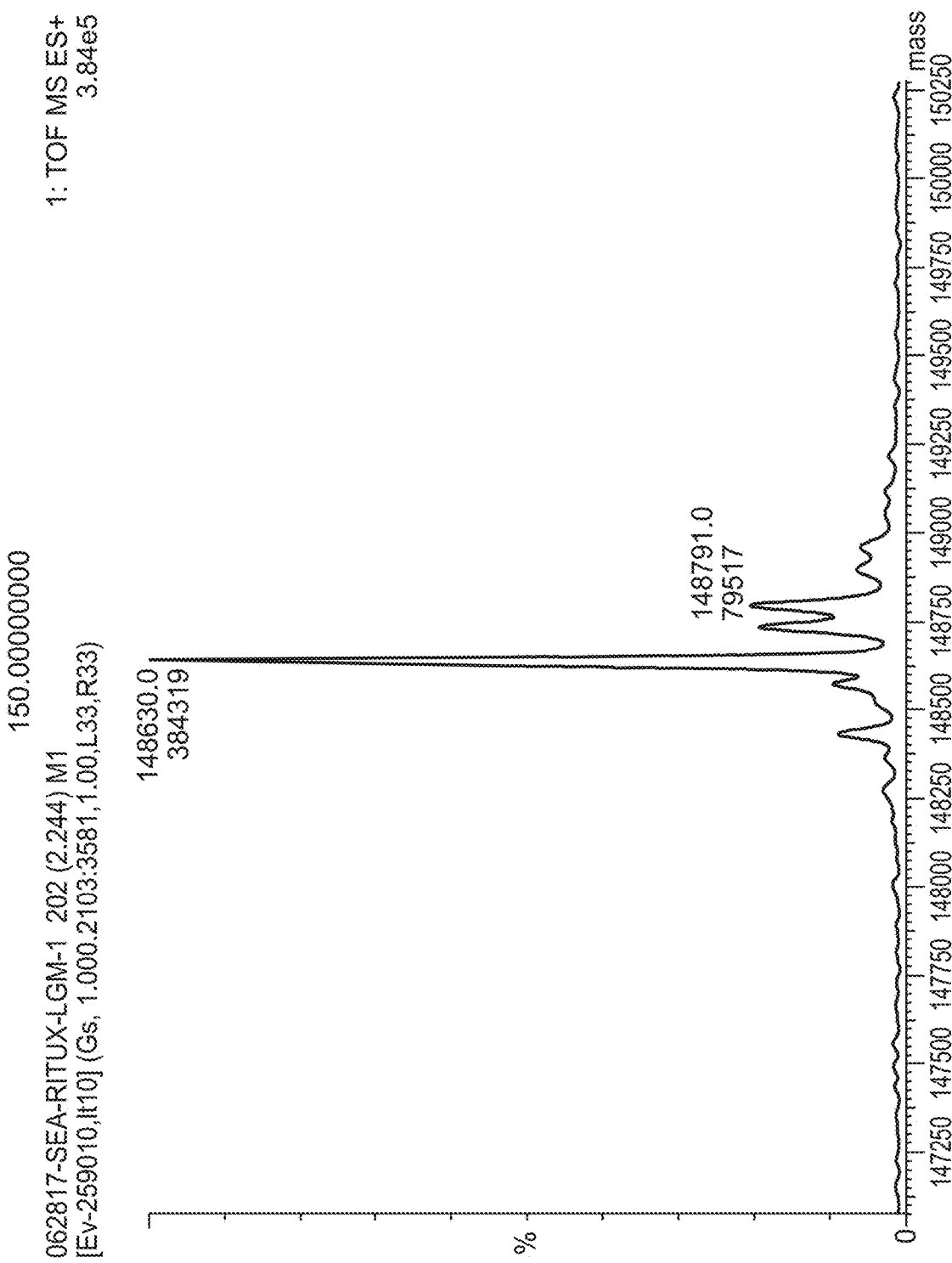

FIG. 99B shows a liquid chromatography-mass spectrometry analysis of the unconjugated rituximab biosimilar (CD20, LGM Pharma) that was utilized to produce the rituximab immunoconjugate according to the BB-03 conjugation method.

Figure 99C:
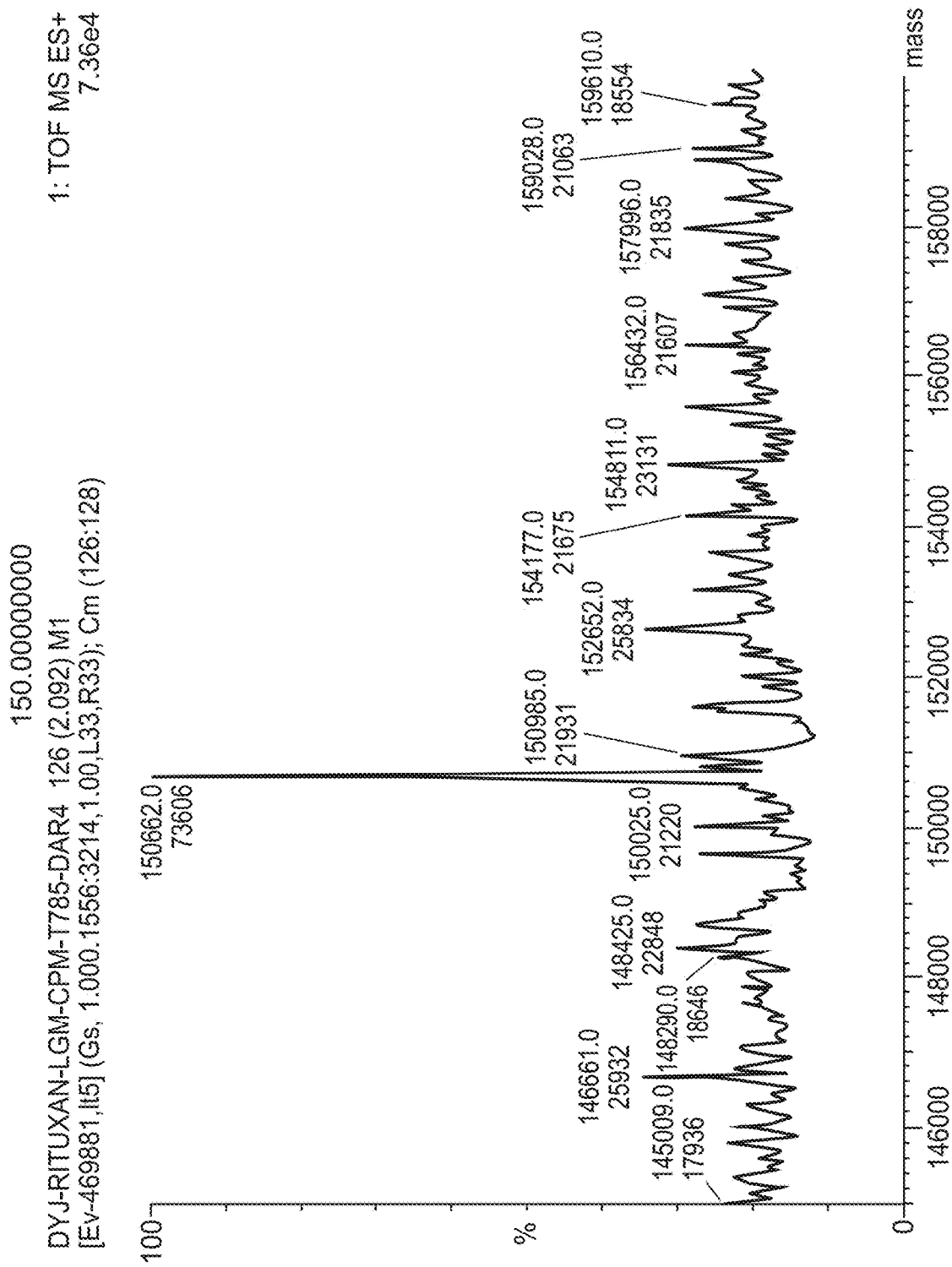

FIG. 99C shows a liquid chromatography-mass spectrometry analysis of the BB-03 immunoconjugate produced according to the BB-03 conjugation method.

Figure 99D:
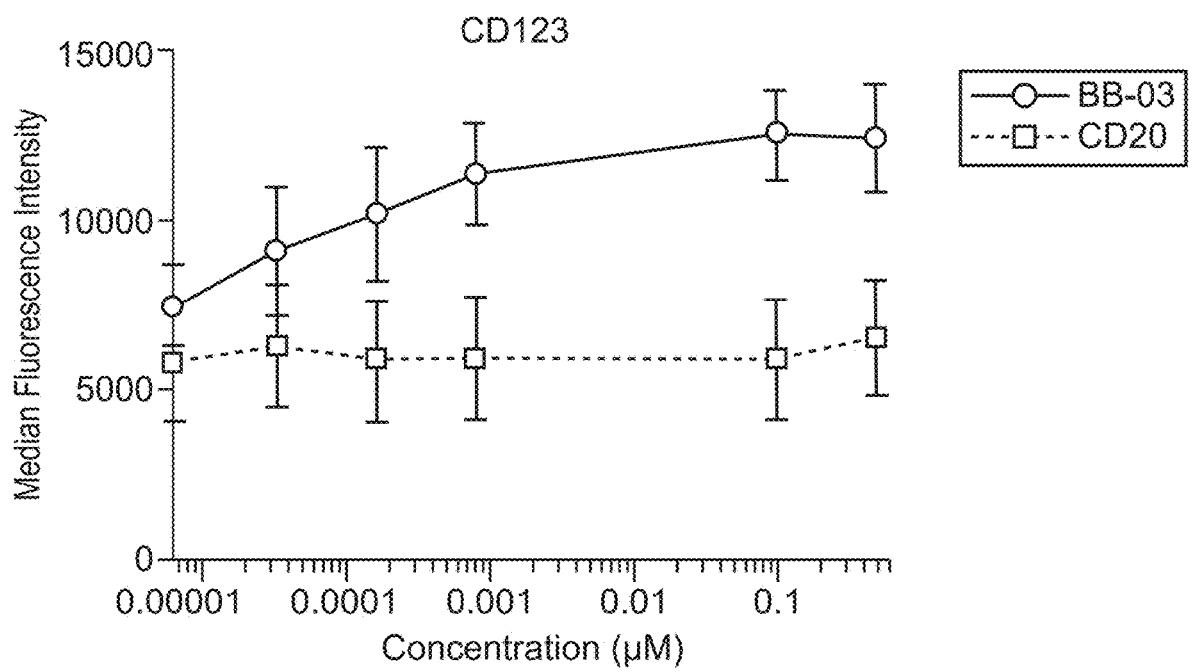

FIG. 99D shows that the BB-03 immunoconjugate produced according to the BB-03 method (BB-03) is superior at eliciting CD123 upregulation on myeloid cells as compared to the unconjugated rituximab biosimilar (CD20; LGM Pharma) following 18 hours of stimulation.

Figure 99E:
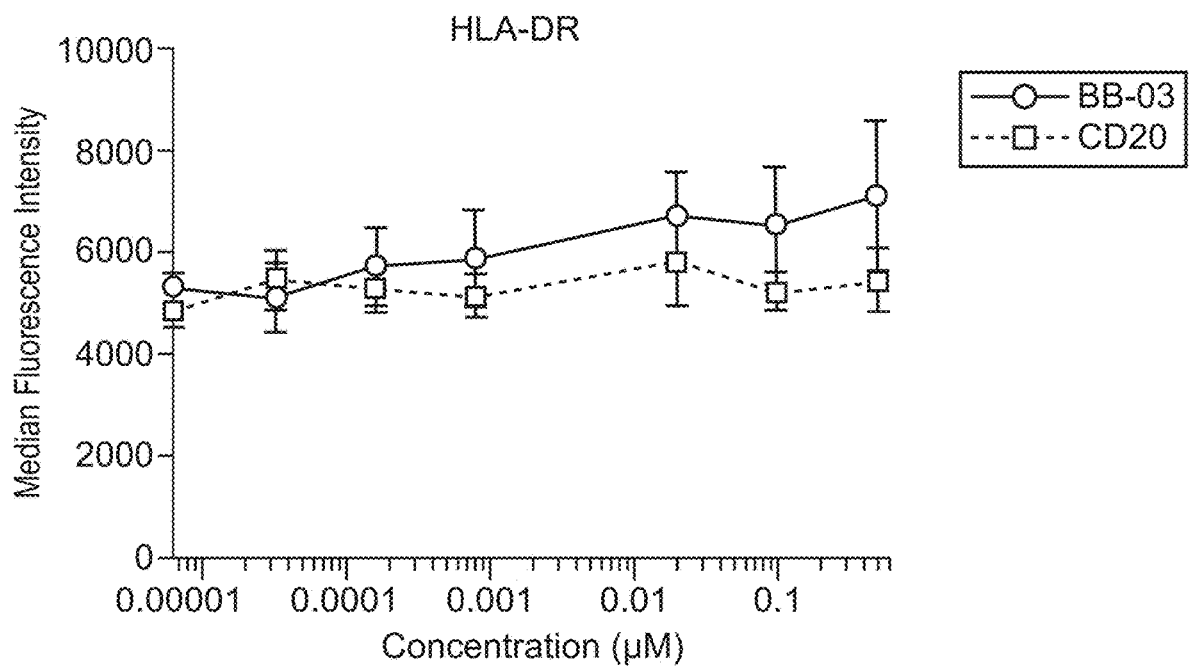

FIG. 99E shows that the BB-03 immunoconjugate produced according to the BB-03 method (BB-03) is superior at eliciting HLA-DR upregulation on myeloid cells as compared to the unconjugated rituximab biosimilar (CD20; LGM Pharma) following 18 hours of stimulation.

Figure 99F:
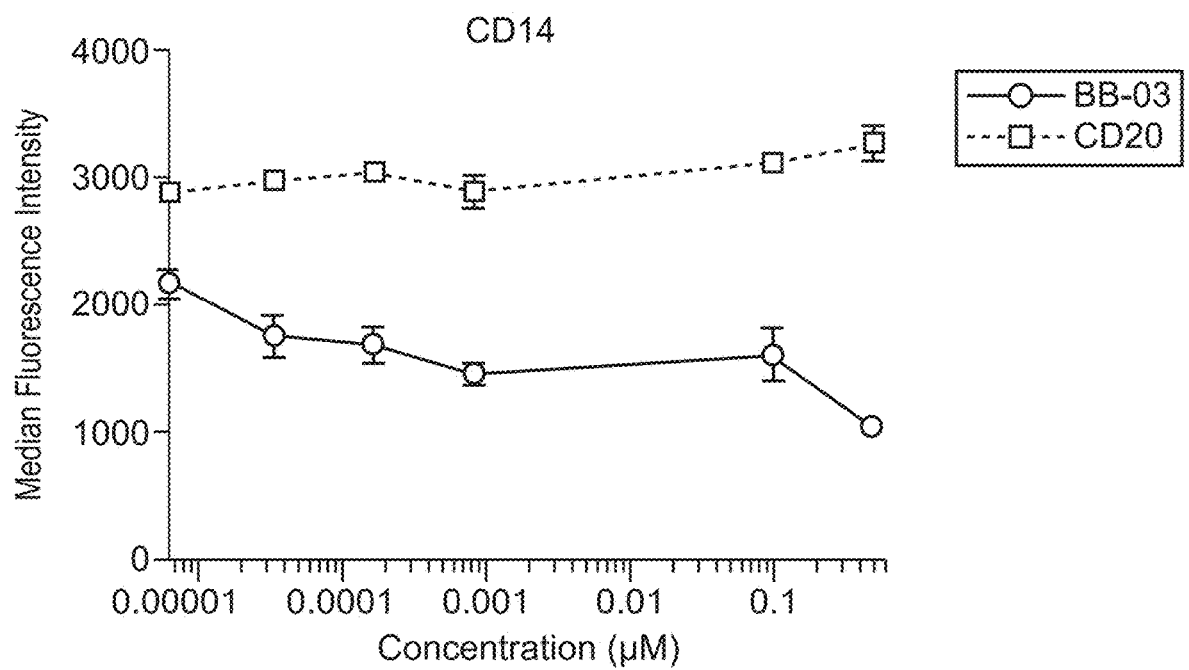

FIG. 99F shows that the BB-03 immunoconjugate produced according to the BB-03 method (BB-03) is superior at eliciting CD14 downregulation on myeloid cells as compared to the unconjugated rituximab biosimilar (CD20; LGM Pharma) following 18 hours of stimulation.

Figure 99G:
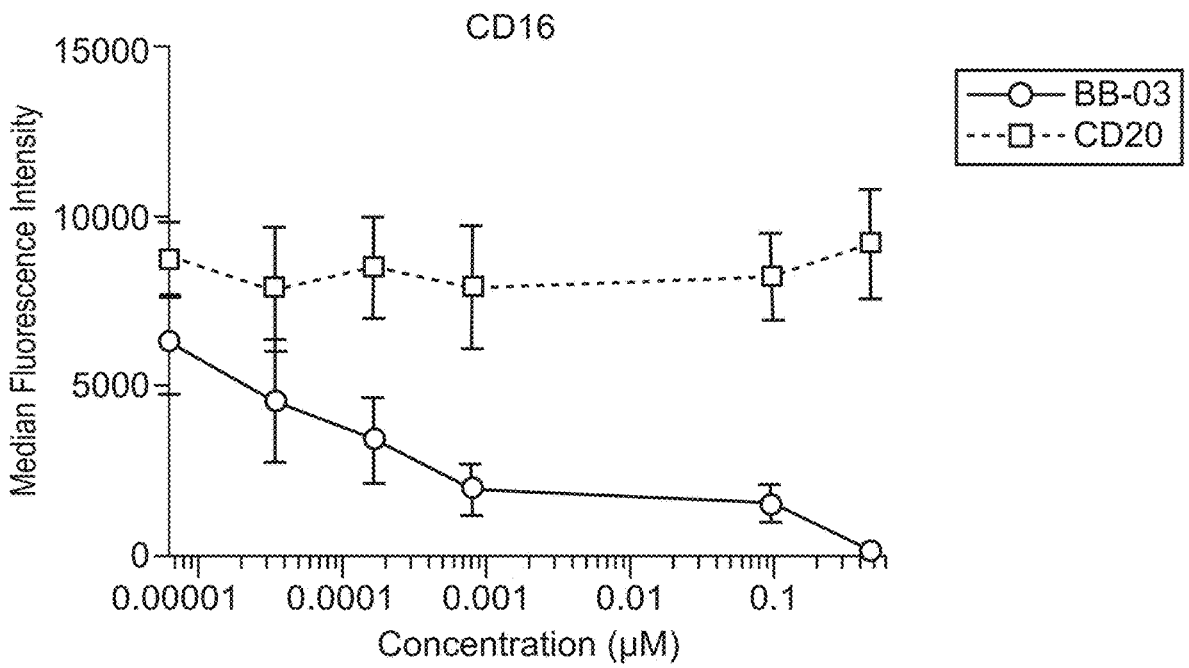

FIG. 99G shows that the BB-03 immunoconjugate produced according to the BB-03 method (BB-03) is superior at eliciting CD16 downregulation on myeloid cells as compared to the unconjugated rituximab biosimilar (CD20; LGM Pharma) following 18 hours of stimulation.

Figure 99H:
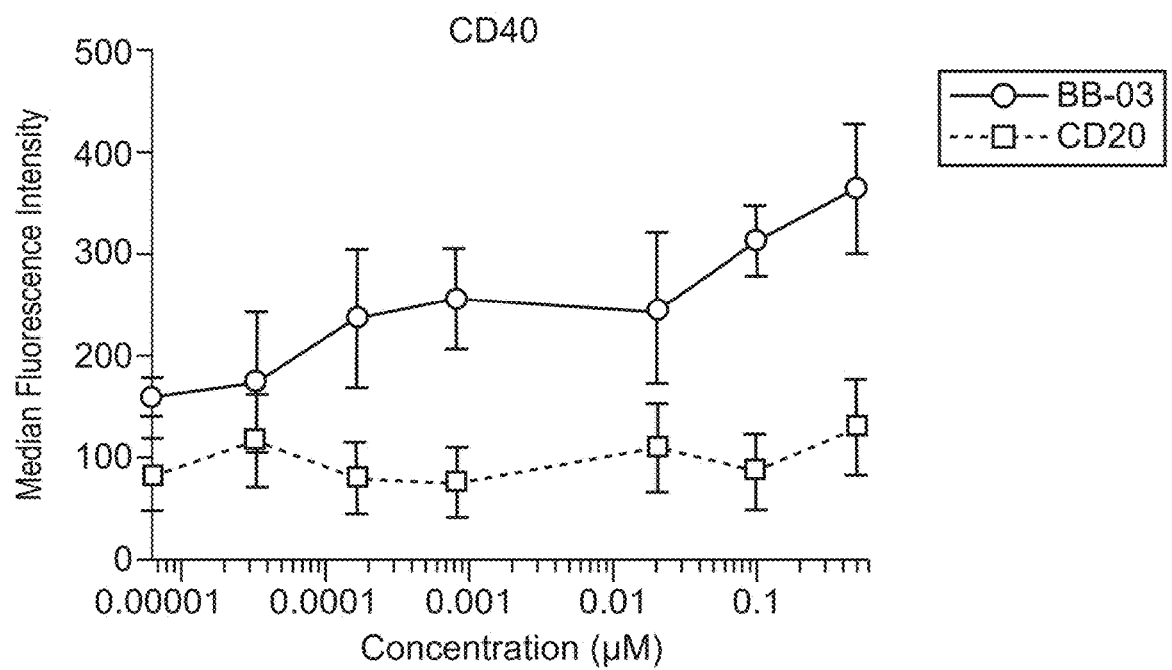

FIG. 99H shows that the BB-03 immunoconjugate produced according to the BB-03 method (BB-03) is superior at eliciting CD40 upregulation on myeloid cells as compared to the unconjugated rituximab biosimilar (CD20; LGM Pharma) following 18 hours of stimulation.

Figure 99I:
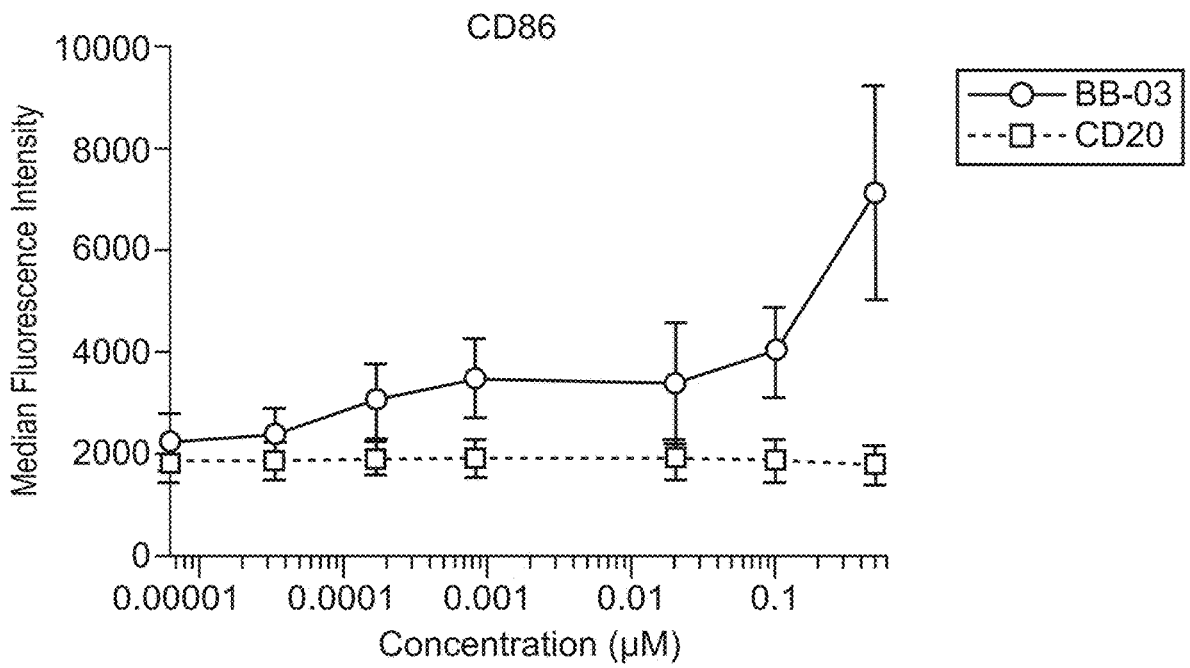

FIG. 99I shows that the BB-03 immunoconjugate produced according to the BB-03 method (BB-03) is superior at eliciting CD86 upregulation on myeloid cells as compared to the unconjugated rituximab biosimilar (CD20; LGM Pharma) following 18 hours of stimulation.

Figure 100A:
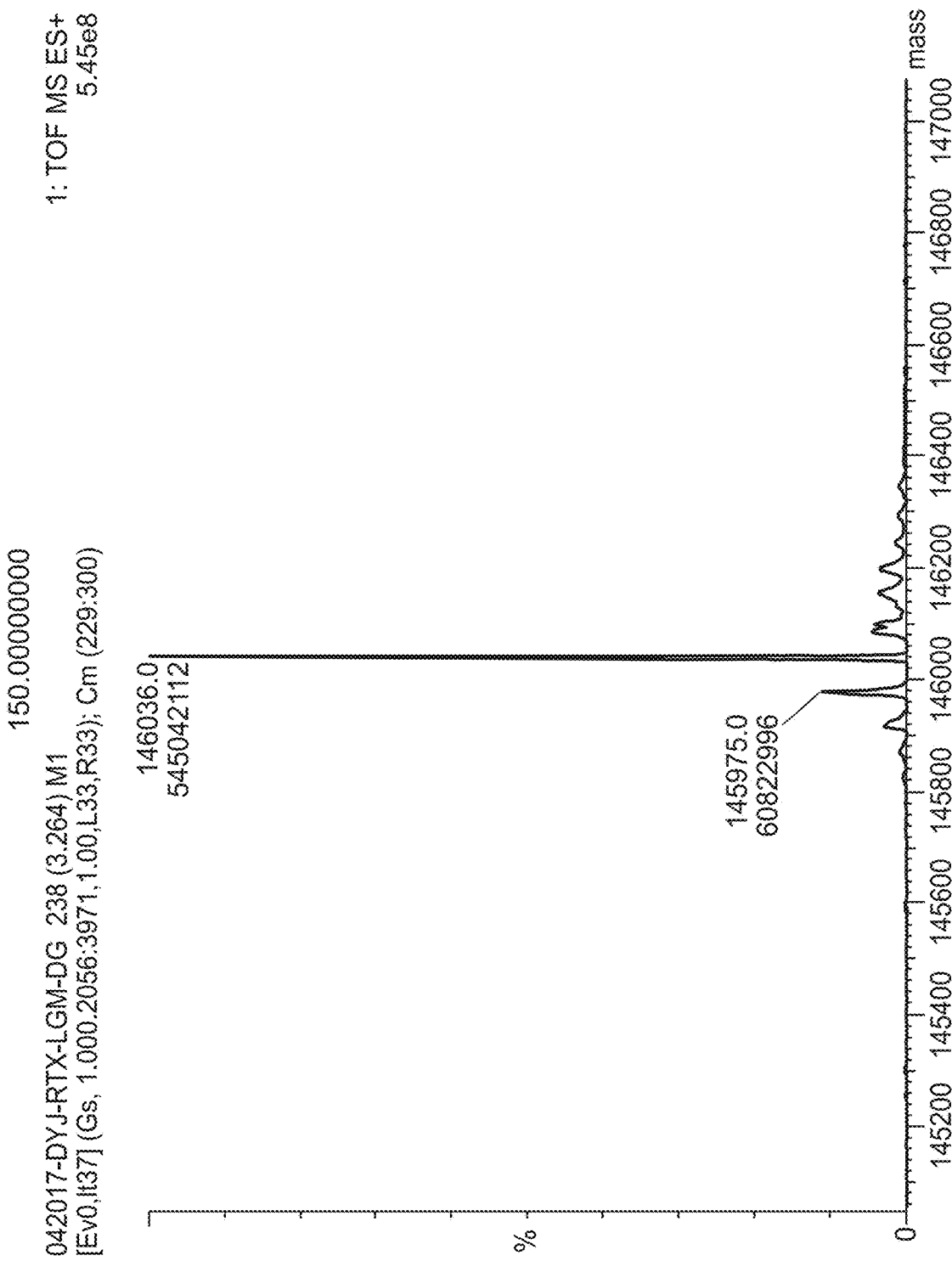

FIG. 100A shows a liquid chromatography-mass spectrometry analysis of the unconjugated rituximab biosimilar (CD20, LGM Pharma) that was utilized to produce the rituximab immunoconjugate according to the BB-05 conjugation method following overnight deglycosylation with PNGase F.

Figure 100B:
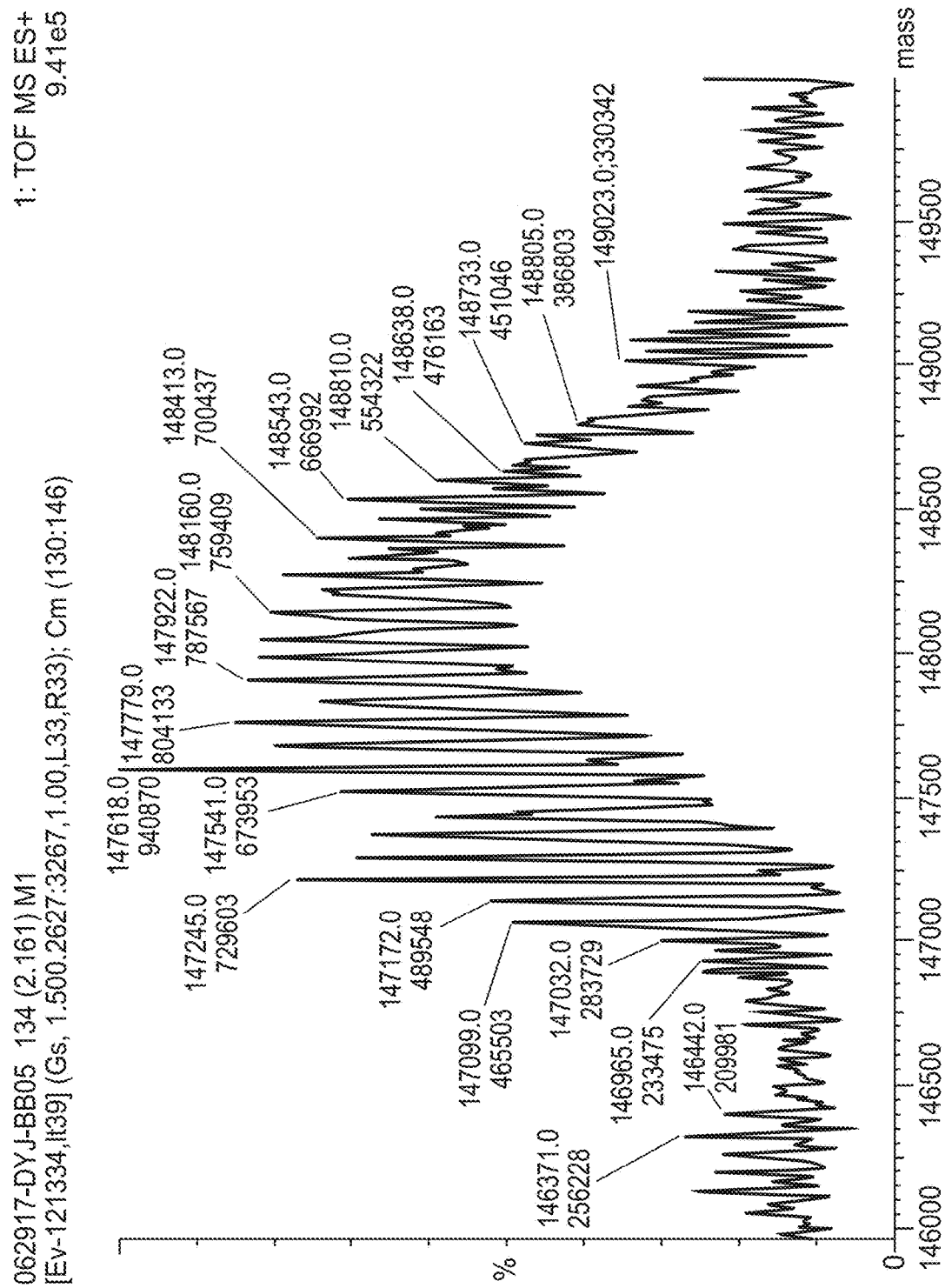

FIG. 100B shows a liquid chromatography-mass spectrometry analysis of the BB-05 immunoconjugate produced according to the BB-05 conjugation method following overnight deglycosylation with PNGase F.

FIG. 100C shows a liquid chromatography-mass spectrometry analysis of the unconjugated rituximab biosimilar (CD20, LGM Pharma) that was utilized to produce the rituximab immunoconjugate according to the BB-05 conjugation method.

Figure 100D:
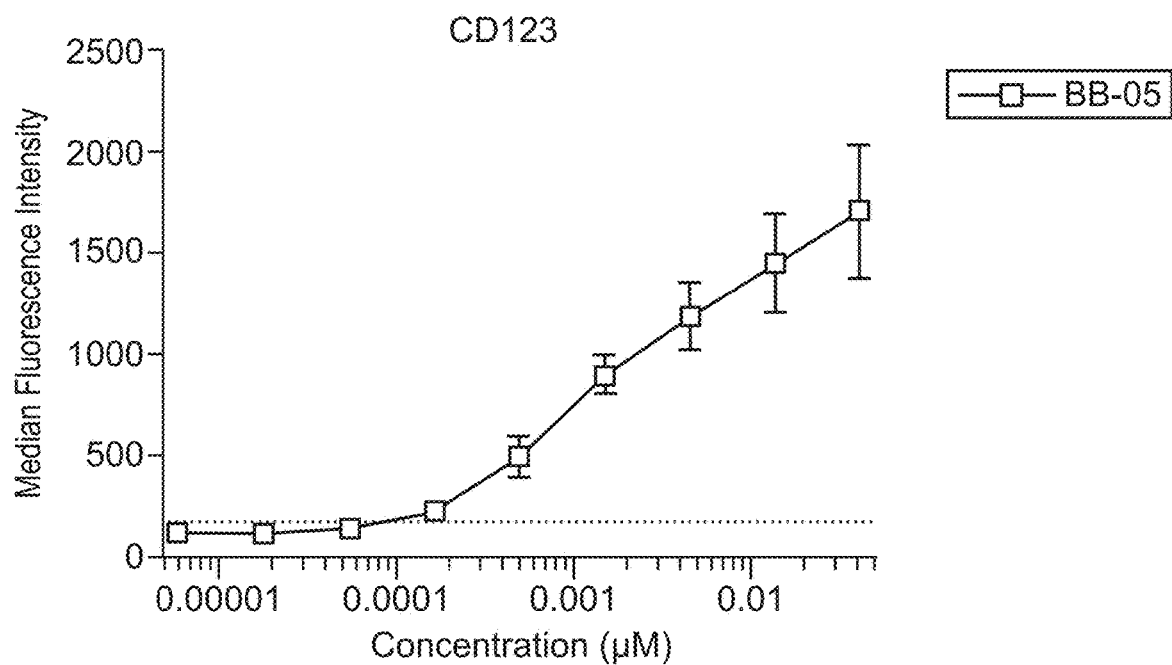

FIG. 100D shows CD123 expression on myeloid cells following 18 hours of stimulation with the BB-05 immunoconjugate produced according to the BB-05 method (BB-05). The dashed line indicates the level of expression on unstimulated myeloid cells cultured for 18 hours.

Figure 100E:
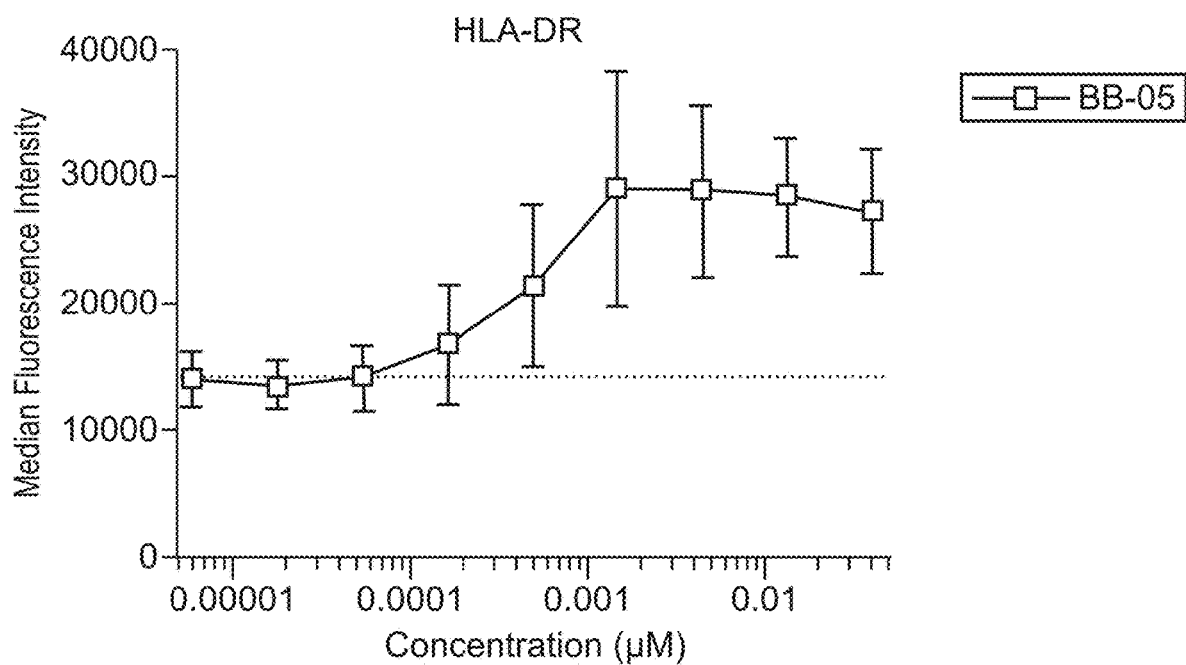

FIG. 100E shows HLA-DR expression on myeloid cells following 18 hours of stimulation with the BB-05 immunoconjugate produced according to the BB-05 method (BB-05). The dashed line indicates the level of expression on unstimulated myeloid cells cultured for 18 hours.

Figure 100F:
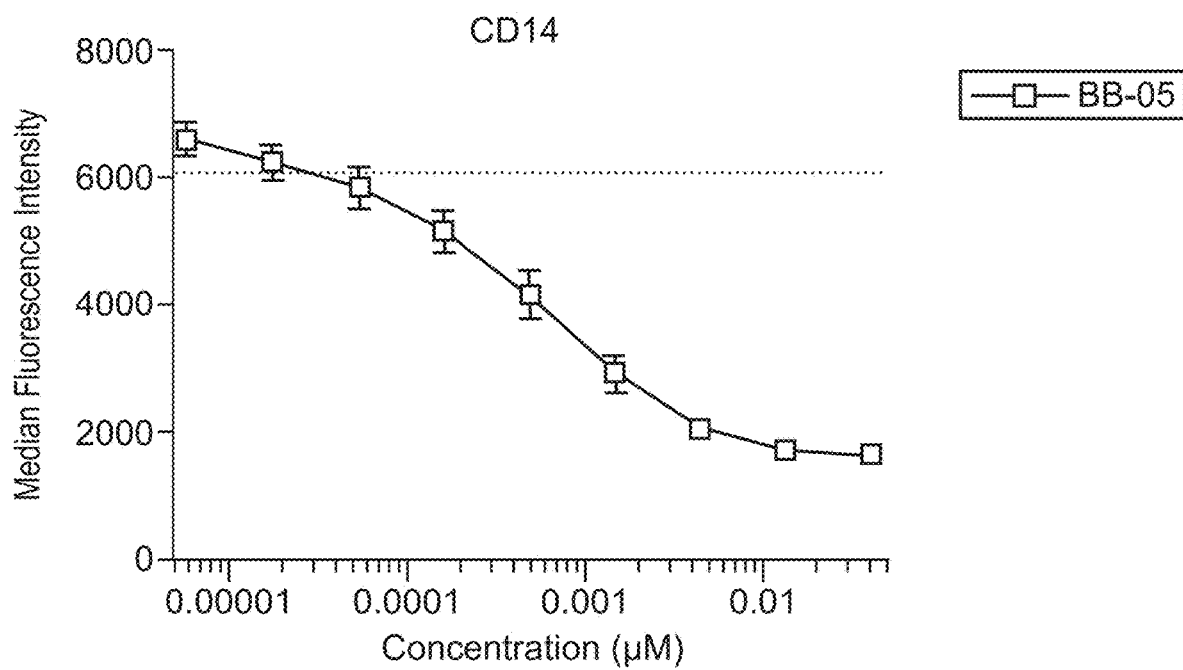

FIG. 100F shows CD14 expression on myeloid cells following 18 hours of stimulation with the BB-05 immunoconjugate produced according to the BB-05 method (BB-05). The dashed line indicates the level of expression on unstimulated myeloid cells cultured for 18 hours.

Figure 100G:
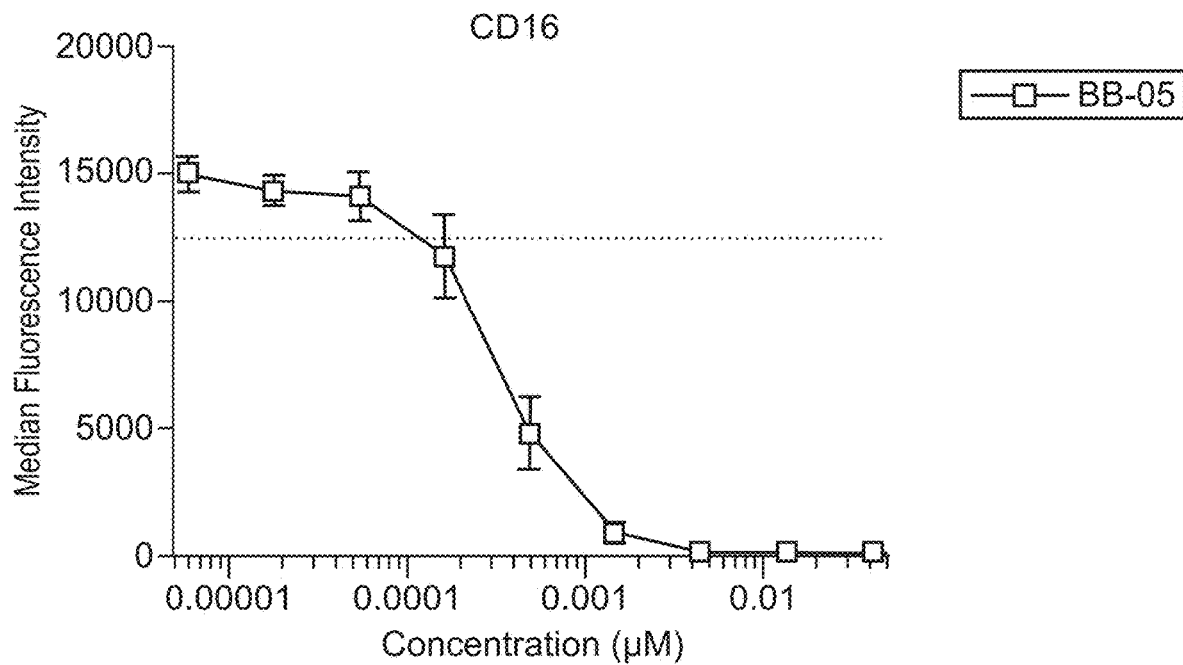

FIG. 100G shows CD16 expression on myeloid cells following 18 hours of stimulation with the BB-05 immunoconjugate produced according to the BB-05 method (BB-05). The dashed line indicates the level of expression on unstimulated myeloid cells cultured for 18 hours.

Figure 100H:
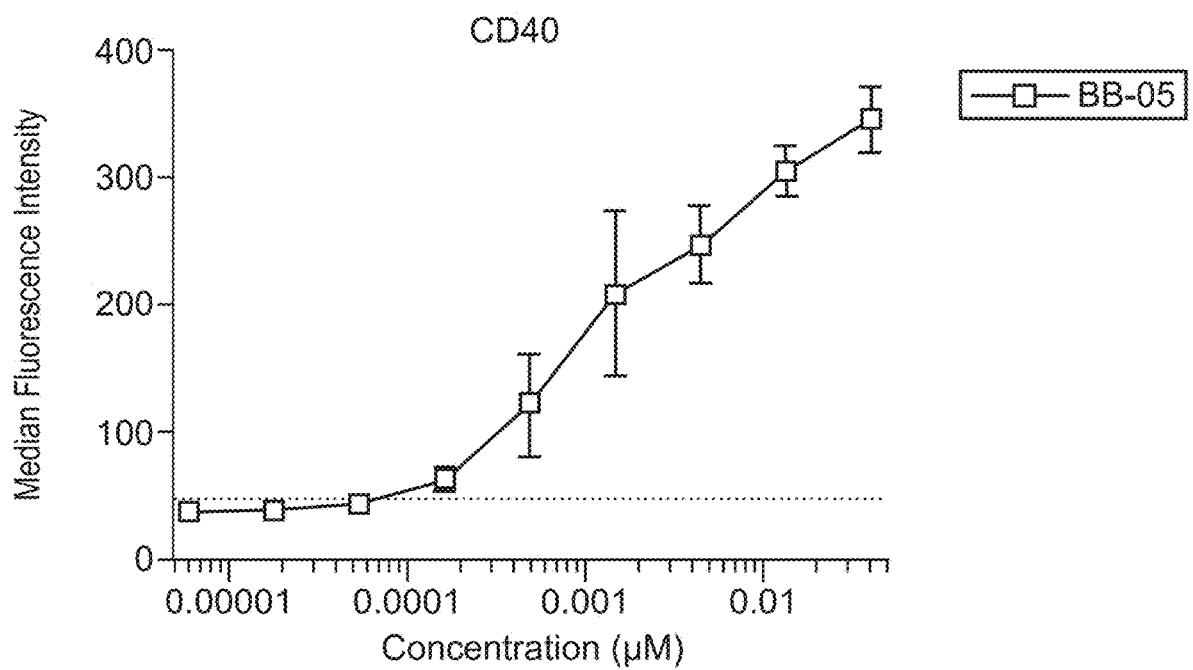

FIG. 100H shows CD40 expression on myeloid cells following 18 hours of stimulation with the BB-05 immunoconjugate produced according to the BB-05 method (BB-05). The dashed line indicates the level of expression on unstimulated myeloid cells cultured for 18 hours.

Figure 100I:
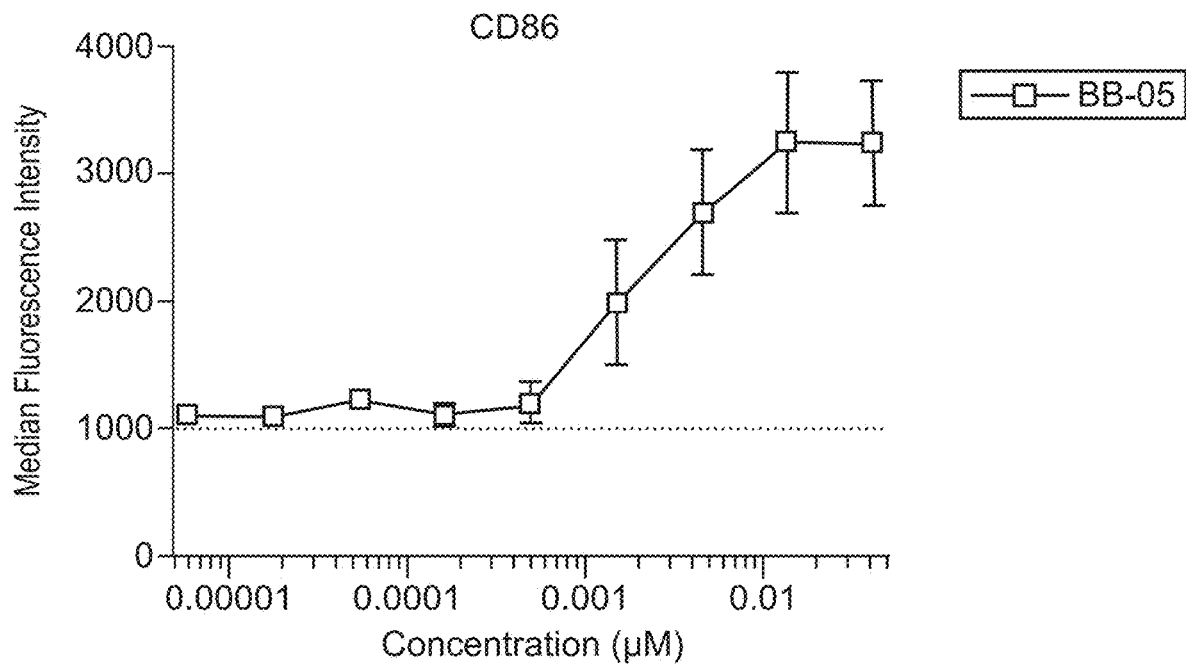

FIG. 100I shows CD86 expression on myeloid cells following 18 hours of stimulation with the BB-05 immunoconjugate produced according to the BB-05 method (BB-05). The dashed line indicates the level of expression on unstimulated myeloid cells cultured for 18 hours.

FIG. 101A shows a liquid chromatography-mass spectrometry analysis of the unconjugated rituximab biosimilar (CD20, LGM Pharma) that was utilized to produce the rituximab immunoconjugate according to the BB-06 conjugation method following overnight deglycosylation with PNGase F.

Figure 101B:
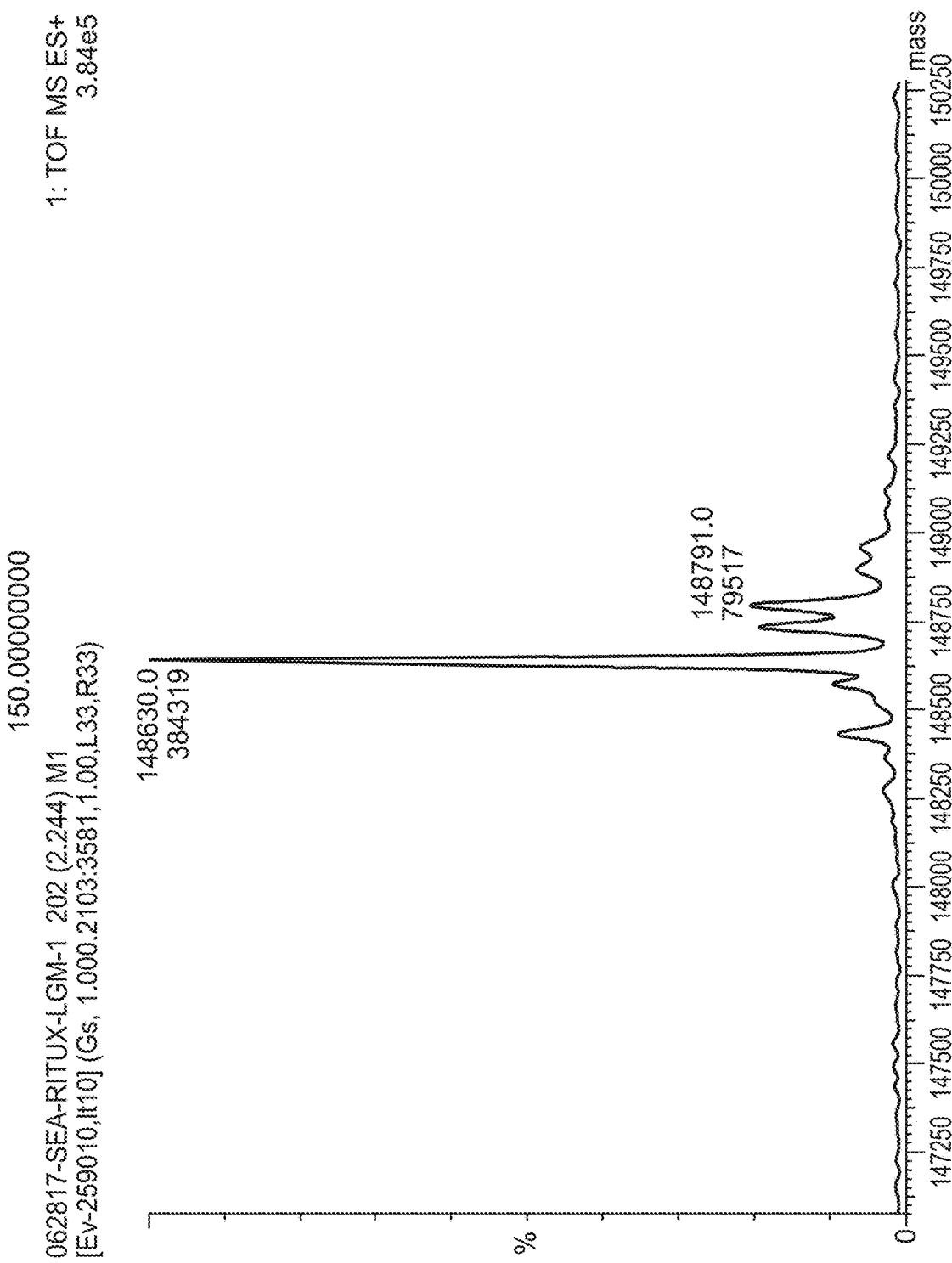

FIG. 101B shows a liquid chromatography-mass spectrometry analysis of the unconjugated rituximab biosimilar (CD20, LGM Pharma) that was utilized to produce the rituximab immunoconjugate according to the BB-06 conjugation method.

Figure 101C:
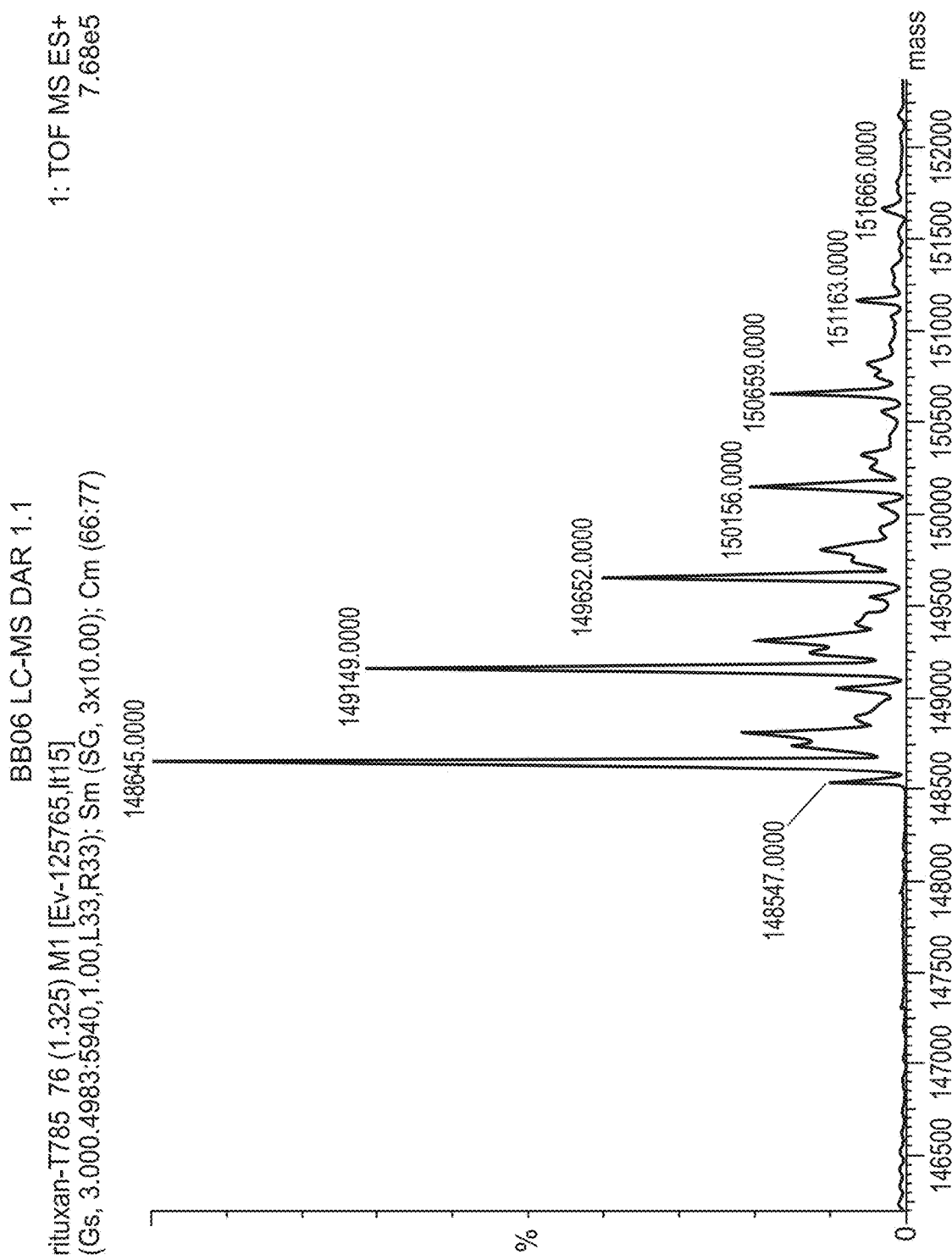

FIG. 101C shows a liquid chromatography-mass spectrometry analysis of the BB-06 immunoconjugate produced according to the BB-06 conjugation method.

Figure 102A:
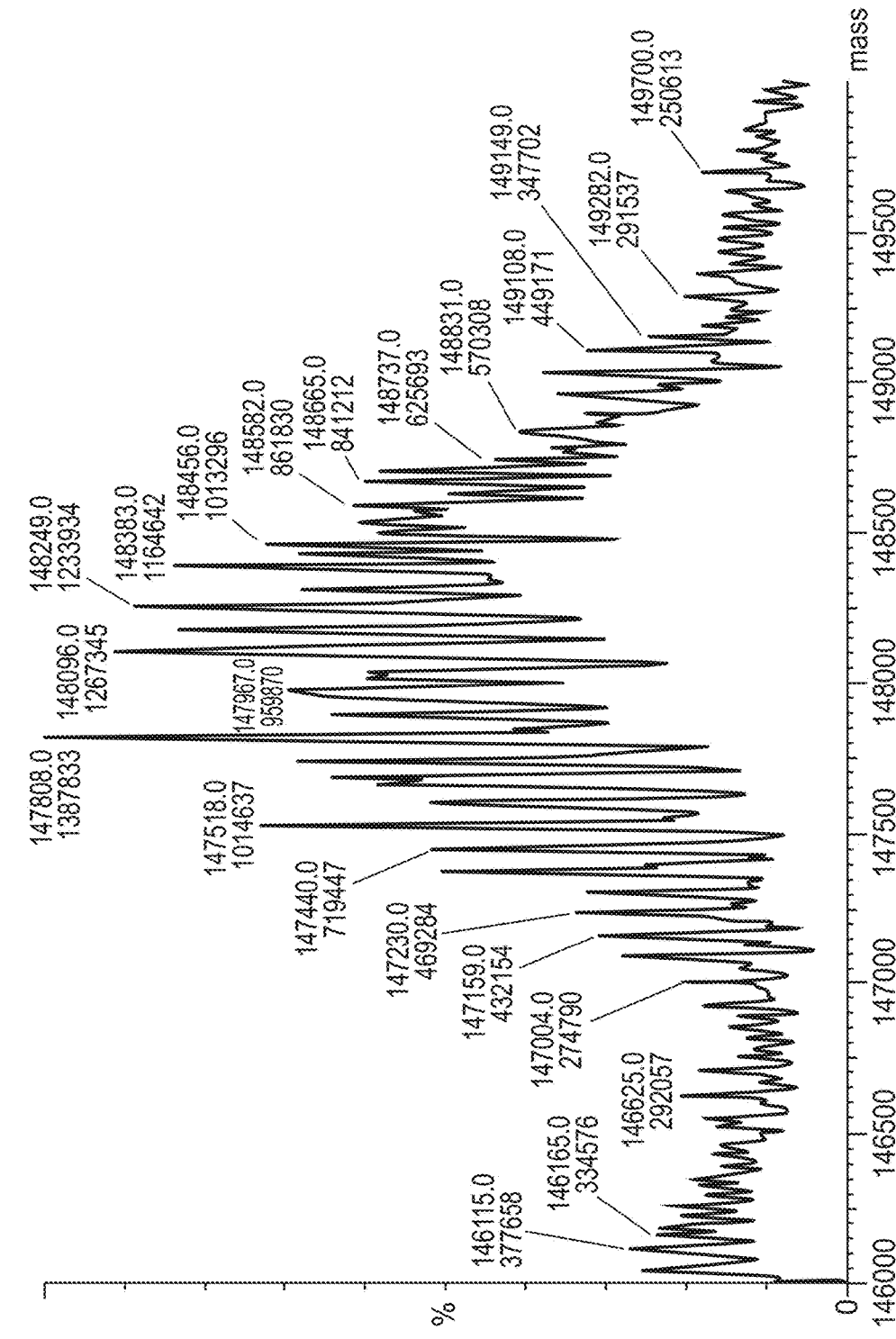

FIG. 102A shows a liquid chromatography-mass spectrometry analysis of the BB-07 immunoconjugate produced according to the BB-07 conjugation method following overnight deglycosylation with PNGase F.

Figure 102B:
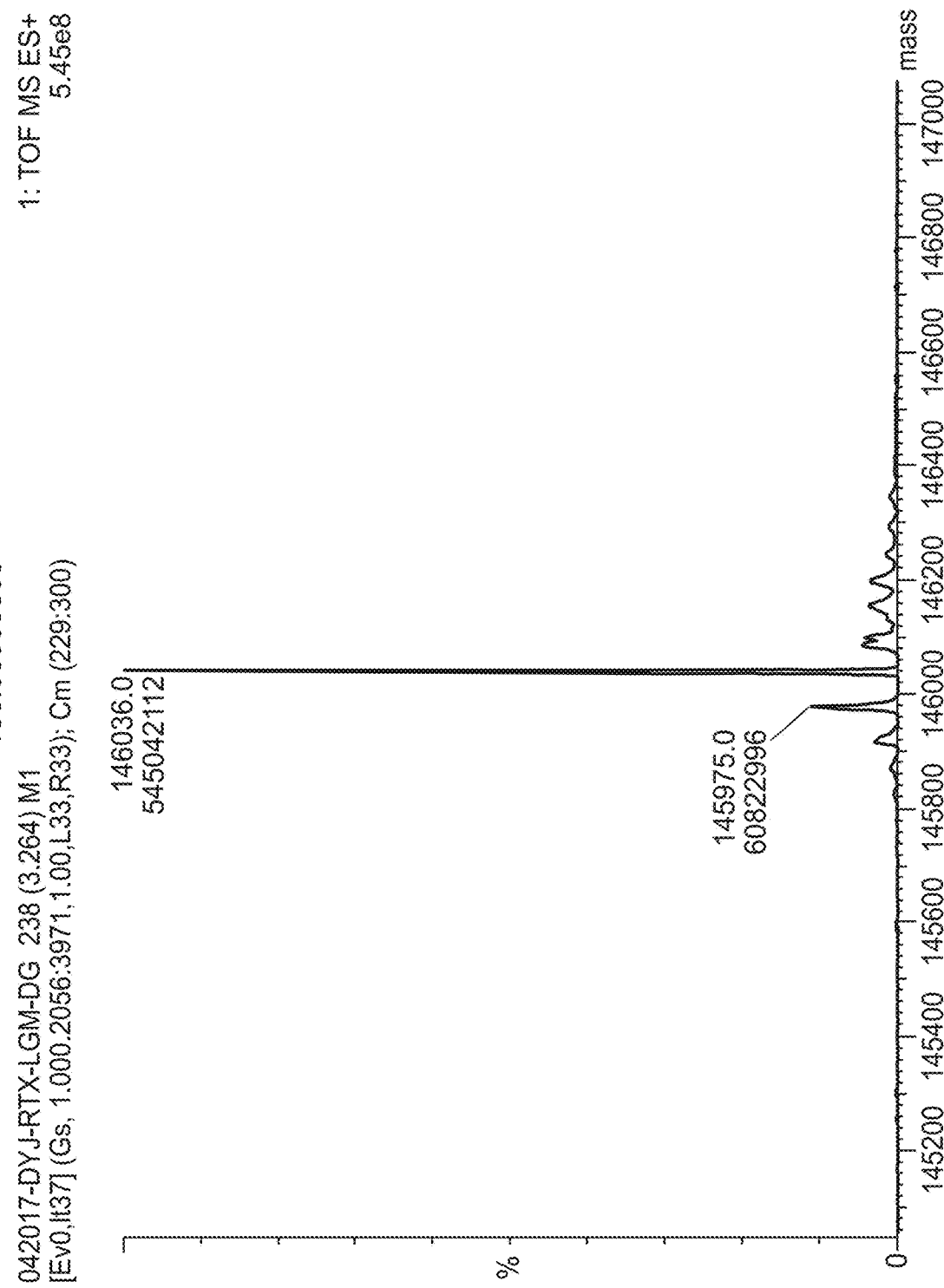

FIG. 102B shows a liquid chromatography-mass spectrometry analysis of the unconjugated rituximab biosimilar (CD20, LGM Pharma) that was utilized to produce the rituximab immunoconjugate according to the BB-07 conjugation method following overnight deglycosylation with PNGase F.

Figure 102C:
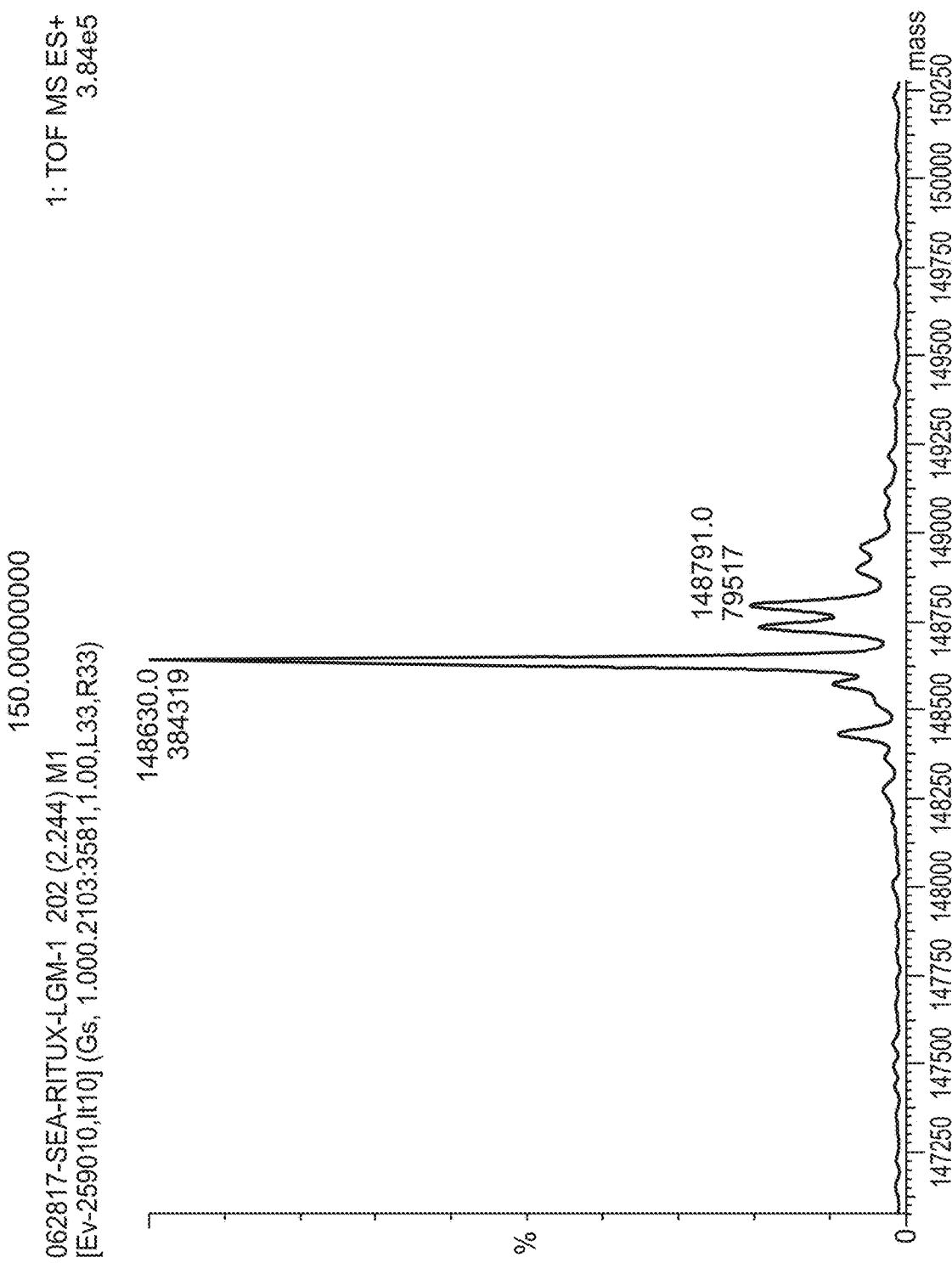

FIG. 102C shows a liquid chromatography-mass spectrometry analysis of the unconjugated rituximab biosimilar (CD20, LGM Pharma) that was utilized to produce the rituximab immunoconjugate according to the BB-07 conjugation method.

Figure 102D:
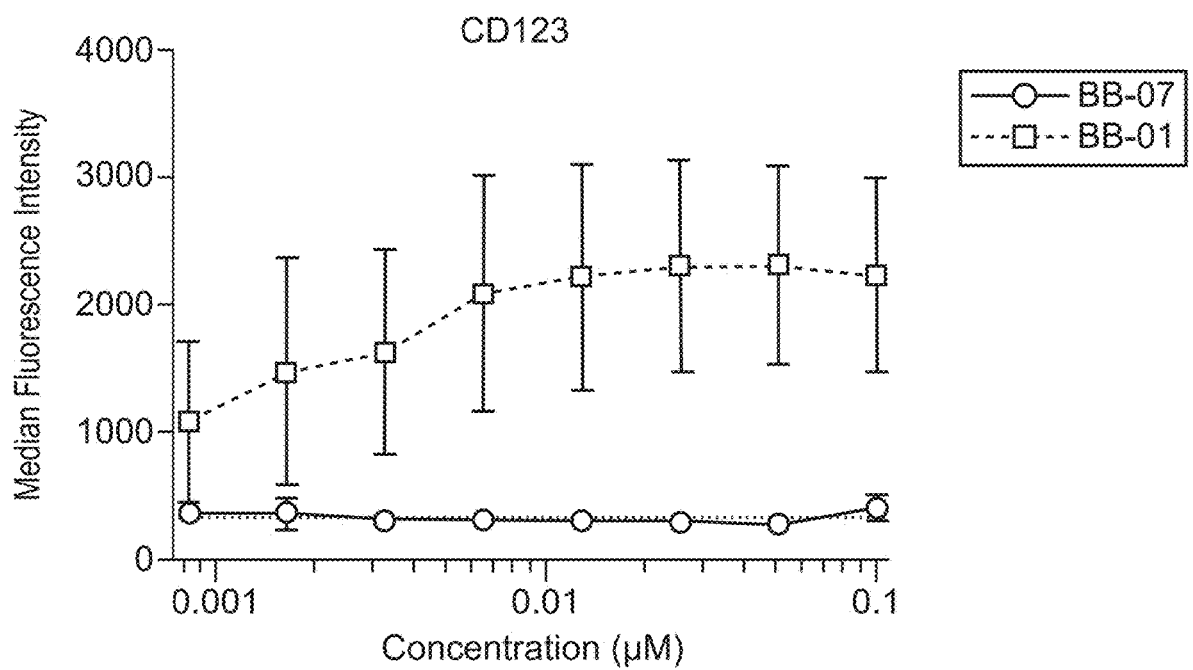

FIG. 102D shows CD123 expression on myeloid cells following 18 hours of stimulation with the BB-07 immunoconjugate produced according to the BB-07 method (BB-07). The dashed line indicates the level of expression on unstimulated myeloid cells cultured for 18 hours. FIG. 102D also compares BB-07 to the BB-01 immunoconjugate produced according to the BB-01 conjugation method (BB-01).

Figure 102E:
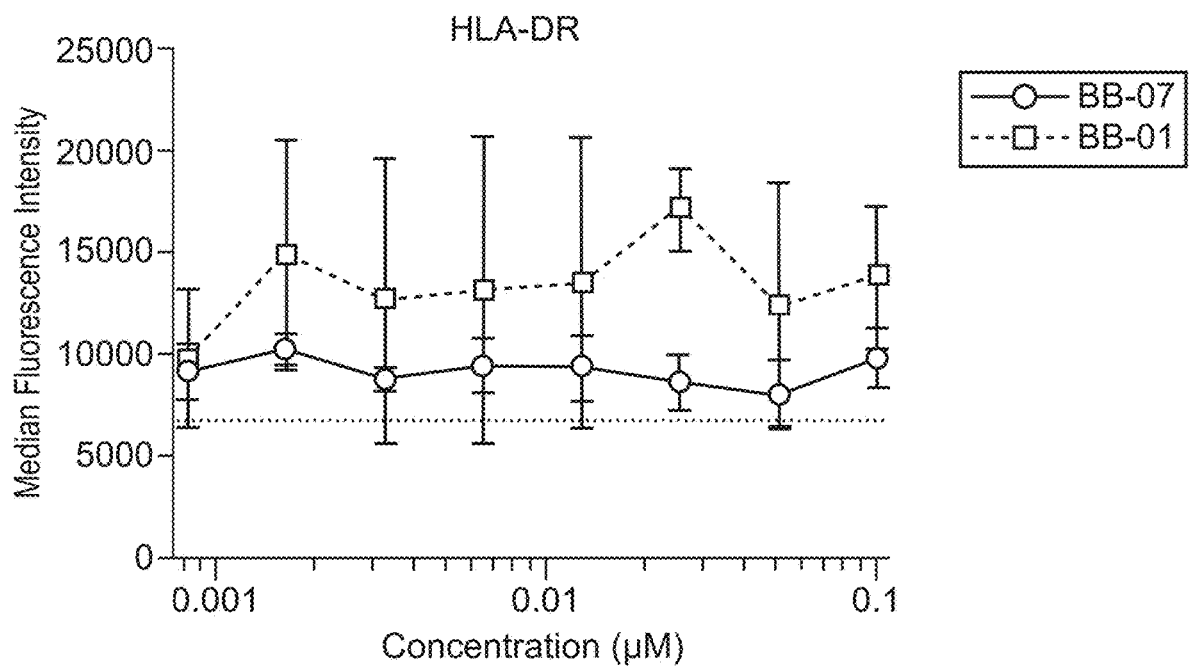

FIG. 102E shows HLA-DR expression on myeloid cells following 18 hours of stimulation with the BB-07 immunoconjugate produced according to the BB-07 method (BB-07). The dashed line indicates the level of expression on unstimulated myeloid cells cultured for 18 hours. FIG. 102E also compares BB-07 to the BB-01 immunoconjugate produced according to the BB-01 conjugation method (BB-01).

Figure 102F:
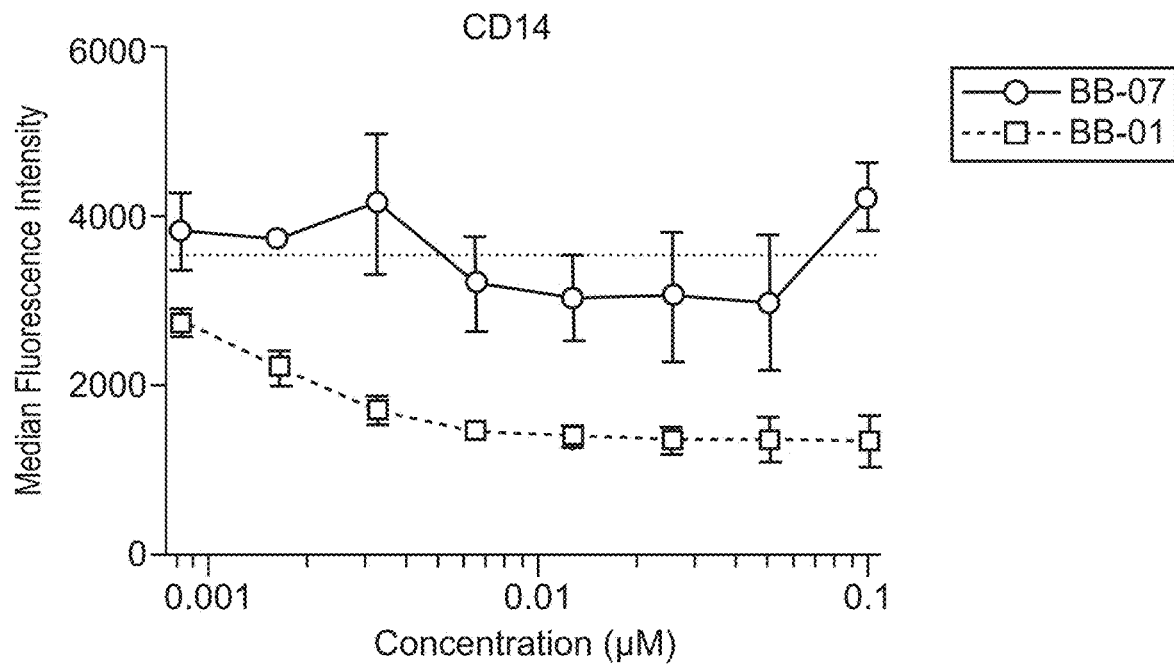

FIG. 102F shows CD14 expression on myeloid cells following 18 hours of stimulation with the BB-07 immunoconjugate produced according to the BB-07 method (BB-07). The dashed line indicates the level of expression on unstimulated myeloid cells cultured for 18 hours. FIG. 102F also compares BB-07 to the BB-01 immunoconjugate produced according to the BB-01 conjugation method (BB-01).

Figure 102G:
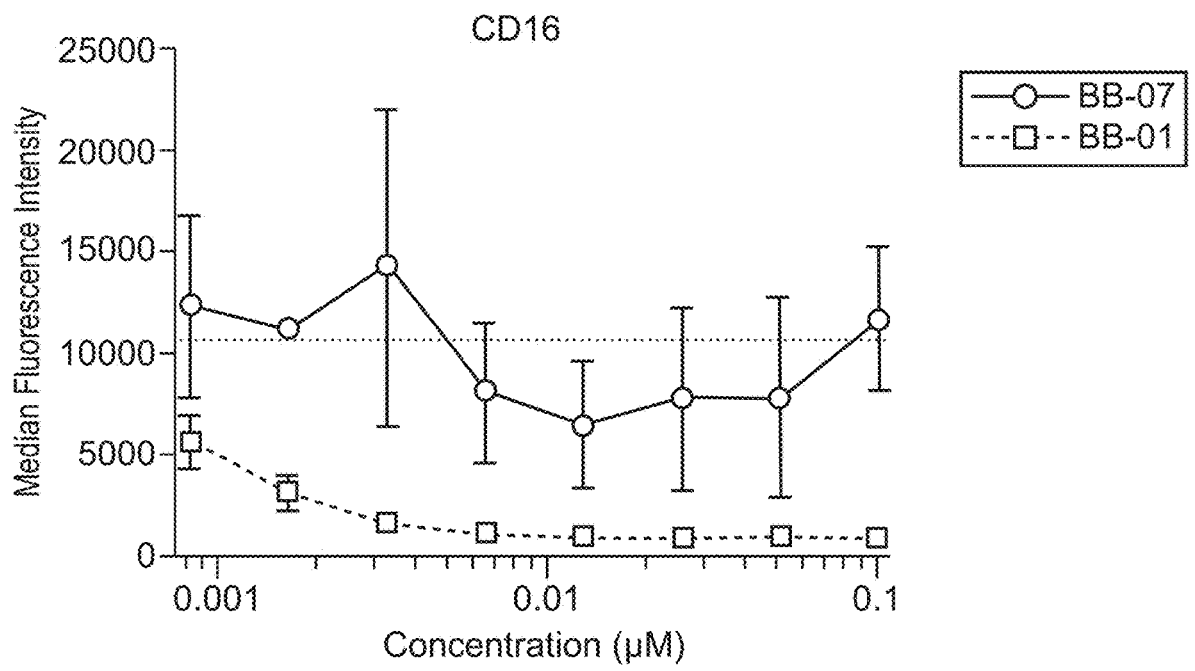

FIG. 102G shows CD16 expression on myeloid cells following 18 hours of stimulation with the BB-07 immunoconjugate produced according to the BB-07 method (BB-07). The dashed line indicates the level of expression on unstimulated myeloid cells cultured for 18 hours. FIG. 102G also compares BB-07 to the BB-01 immunoconjugate produced according to the BB-01 conjugation method (BB-01).

Figure 102H:
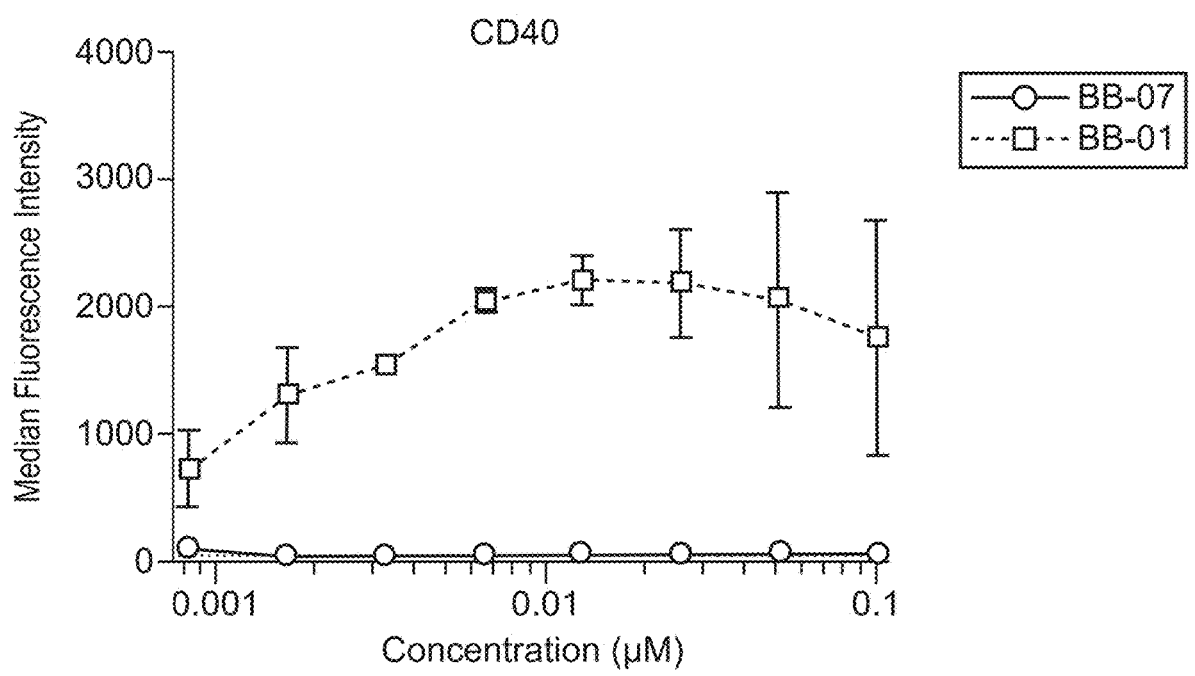

FIG. 102H shows CD40 expression on myeloid cells following 18 hours of stimulation with the BB-07 immunoconjugate produced according to the BB-07 method (BB-07). The dashed line indicates the level of expression on unstimulated myeloid cells cultured for 18 hours. FIG. 102H also compares BB-07 to the BB-01 immunoconjugate produced according to the BB-01 conjugation method (BB-01).

Figure 102I:
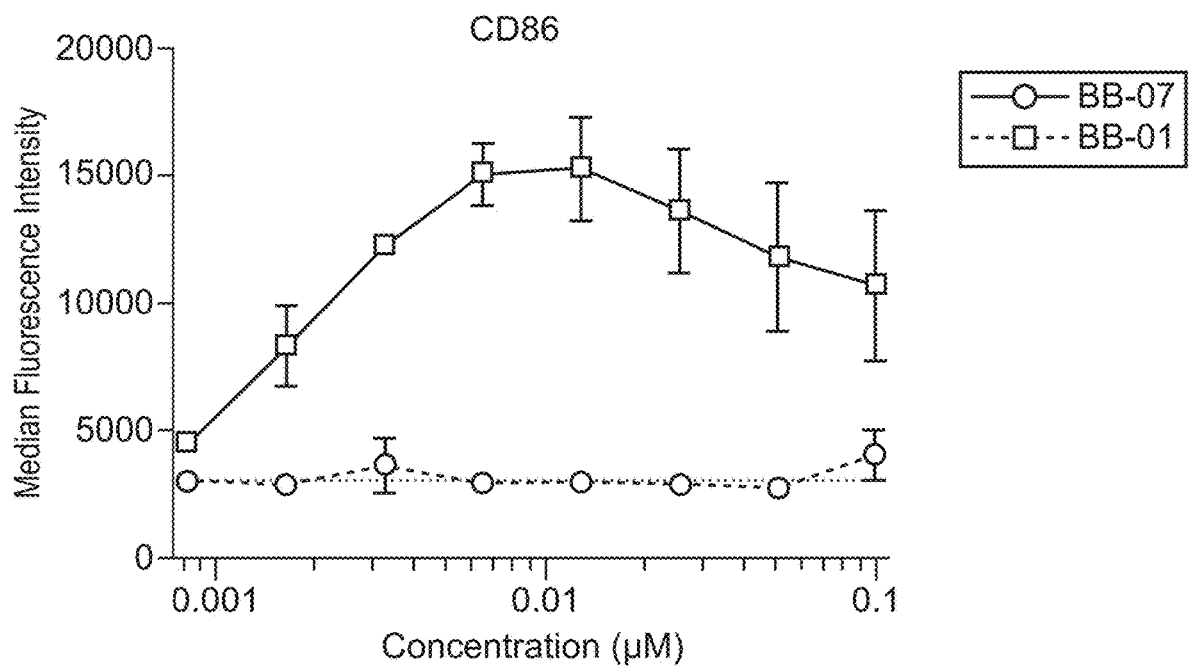

FIG. 102I shows CD86 expression on myeloid cells following 18 hours of stimulation with the BB-07 immunoconjugate produced according to the BB-07 method (BB-07). The dashed line indicates the level of expression on unstimulated myeloid cells cultured for 18 hours. FIG. 102I also compares BB-07 to the BB-01 immunoconjugate produced according to the BB-01 conjugation method (BB-01).

Figure 102J:
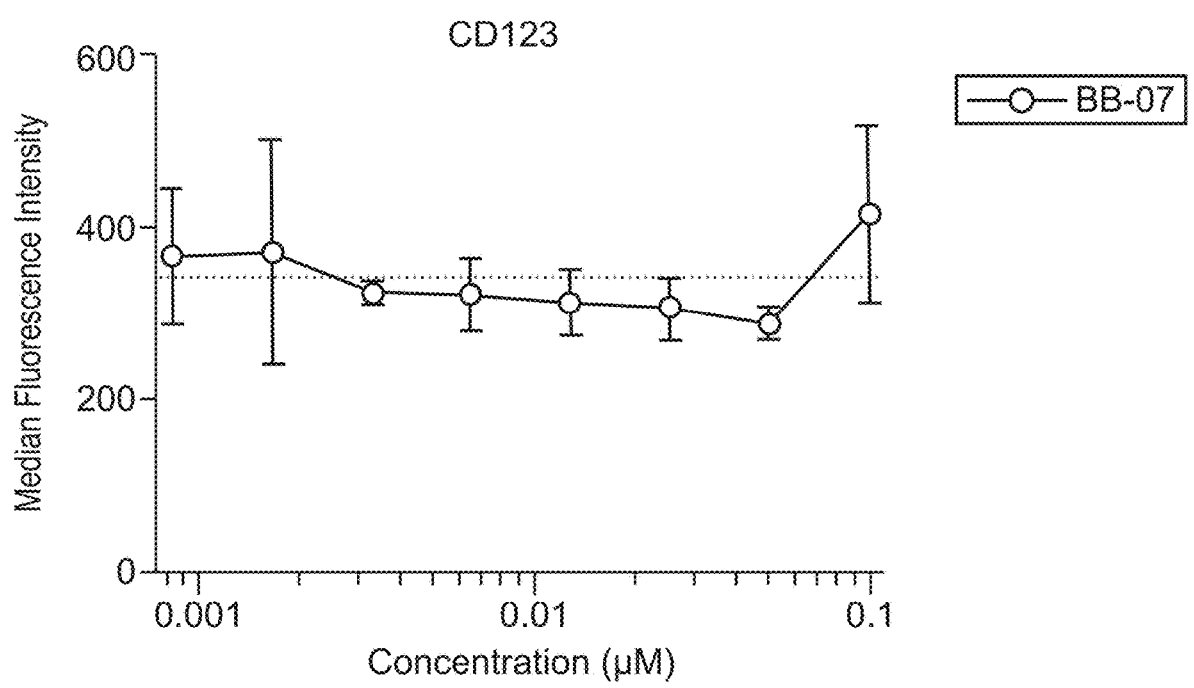

FIG. 102J shows CD123 expression on myeloid cells following 18 hours of stimulation with the BB-07 immunoconjugate produced according to the BB-07 method (BB-07). The dashed line indicates the level of expression on unstimulated myeloid cells cultured for 18 hours.

Figure 102K:
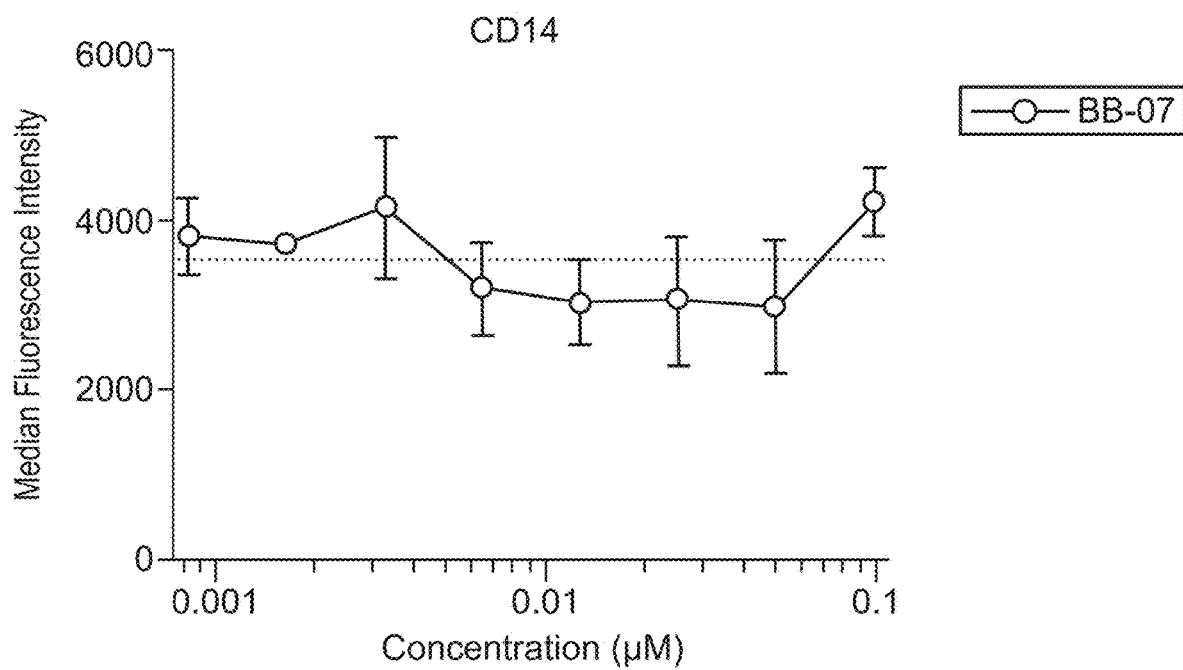

FIG. 102K shows CD14 expression on myeloid cells following 18 hours of stimulation with the BB-07 immunoconjugate produced according to the BB-07 method (BB-07). The dashed line indicates the level of expression on unstimulated myeloid cells cultured for 18 hours.

Figure 102L:
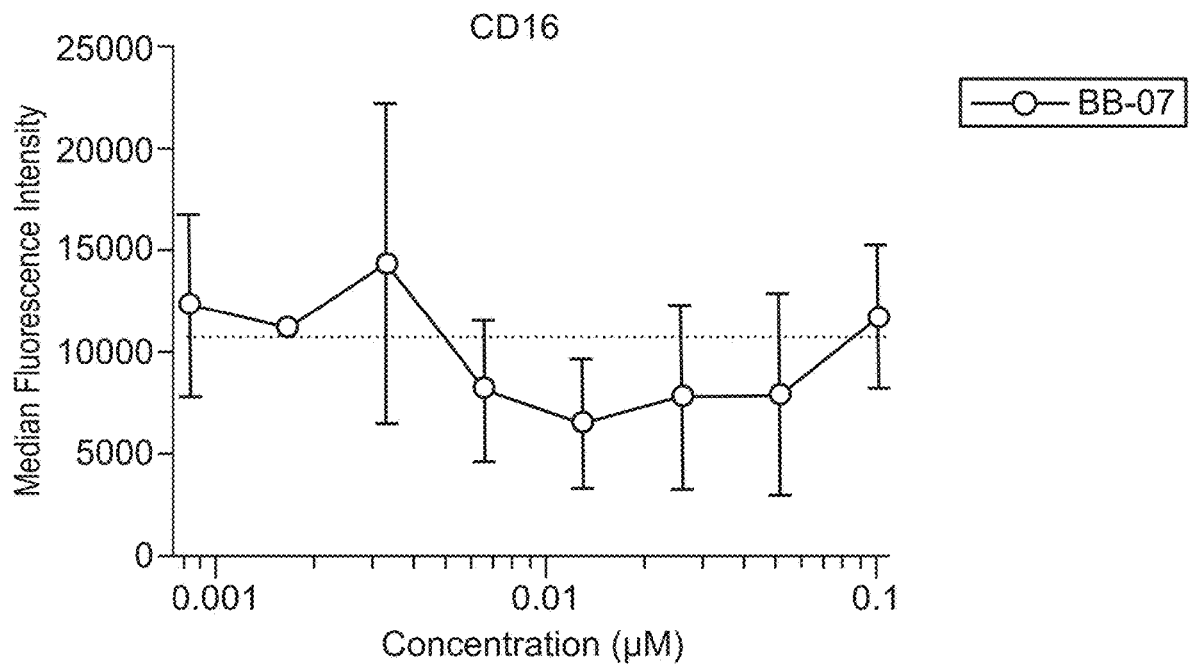

FIG. 102L shows CD16 expression on myeloid cells following 18 hours of stimulation with the BB-07 immunoconjugate produced according to the BB-07 method (BB-07). The dashed line indicates the level of expression on unstimulated myeloid cells cultured for 18 hours.

Figure 102M:
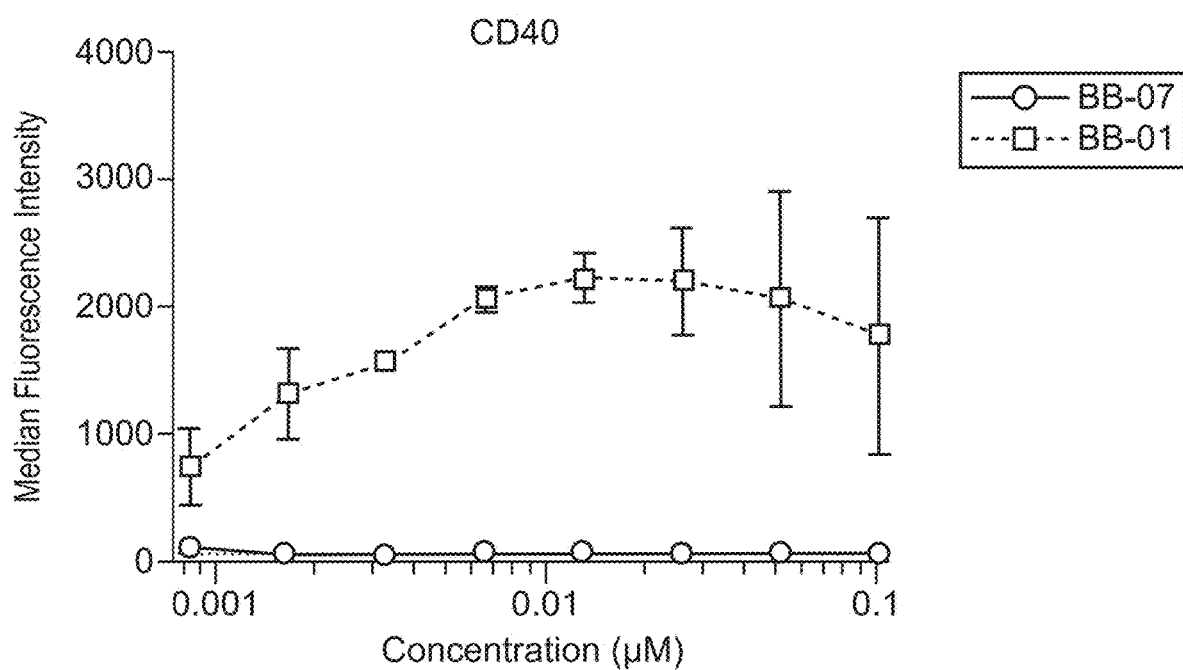

FIG. 102M shows CD40 expression on myeloid cells following 18 hours of stimulation with the BB-07 immunoconjugate produced according to the BB-07 method (BB-07). The dashed line indicates the level of expression on unstimulated myeloid cells cultured for 18 hours. FIG. 102M also compares BB-07 to the BB-01 immunoconjugate produced according to the BB-01 conjugation method (BB-01).

Figure 102N:
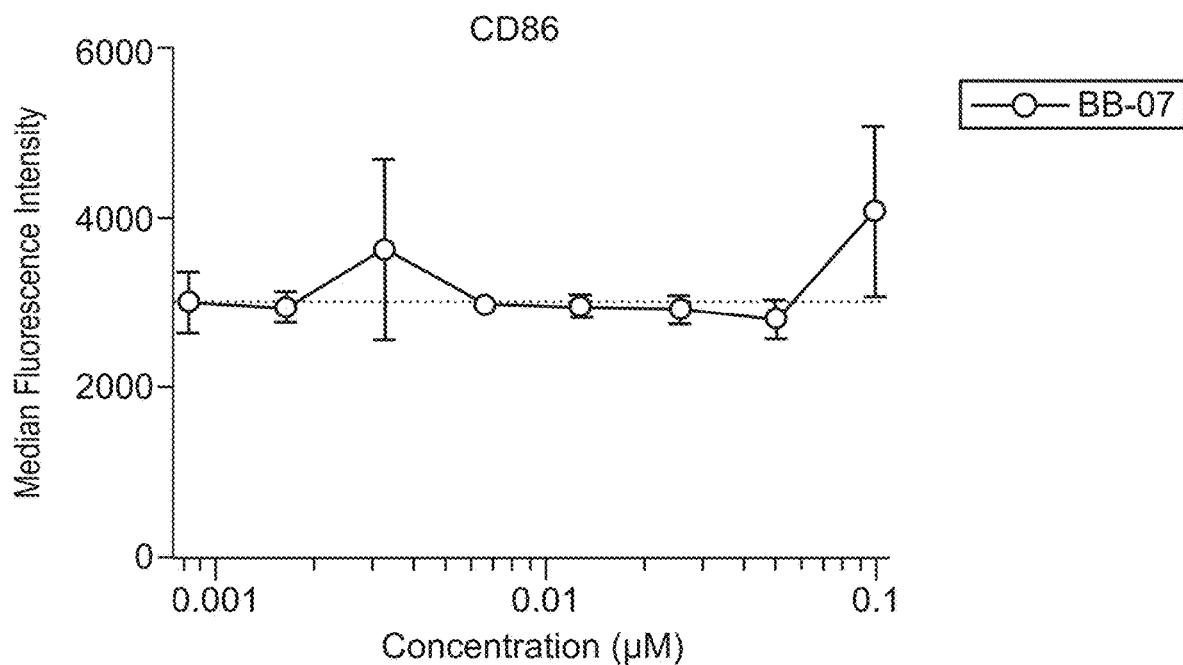

FIG. 102N shows CD86 expression on myeloid cells following 18 hours of stimulation with the BB-07 immunoconjugate produced according to the BB-07 method (BB-07). The dashed line indicates the level of expression on unstimulated myeloid cells cultured for 18 hours.

FIG. 103A shows a liquid chromatography-mass spectrometry analysis of the unconjugated rituximab biosimilar (CD20, LGM Pharma) that was utilized to produce the rituximab immunoconjugate according to the BB-11 conjugation method following overnight deglycosylation with PNGase F.

Figure 103B:
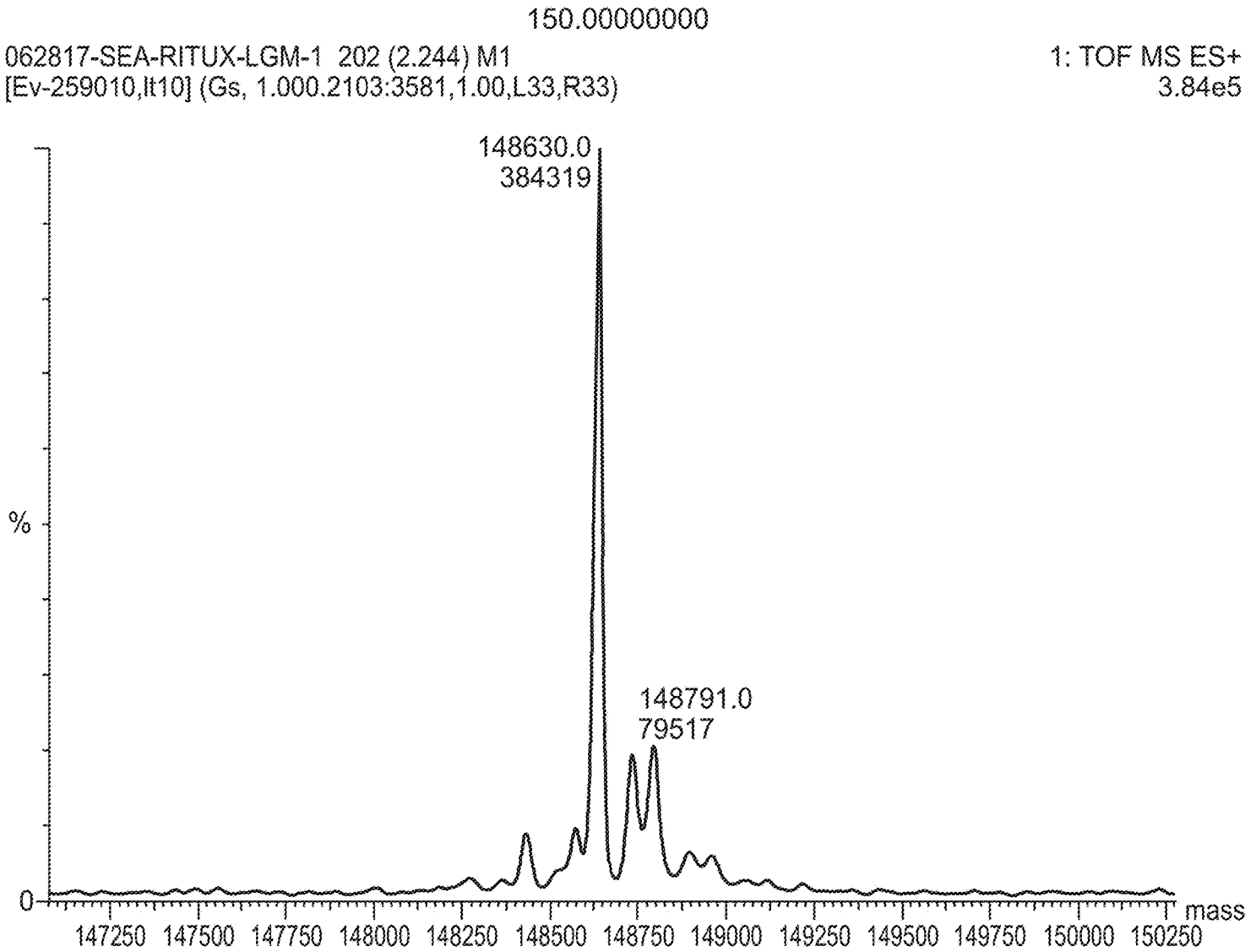

FIG. 103B shows a liquid chromatography-mass spectrometry analysis of the unconjugated rituximab biosimilar (CD20, LGM Pharma) that was utilized to produce the rituximab immunoconjugate according to the BB-11 conjugation method.

Figure 103C:
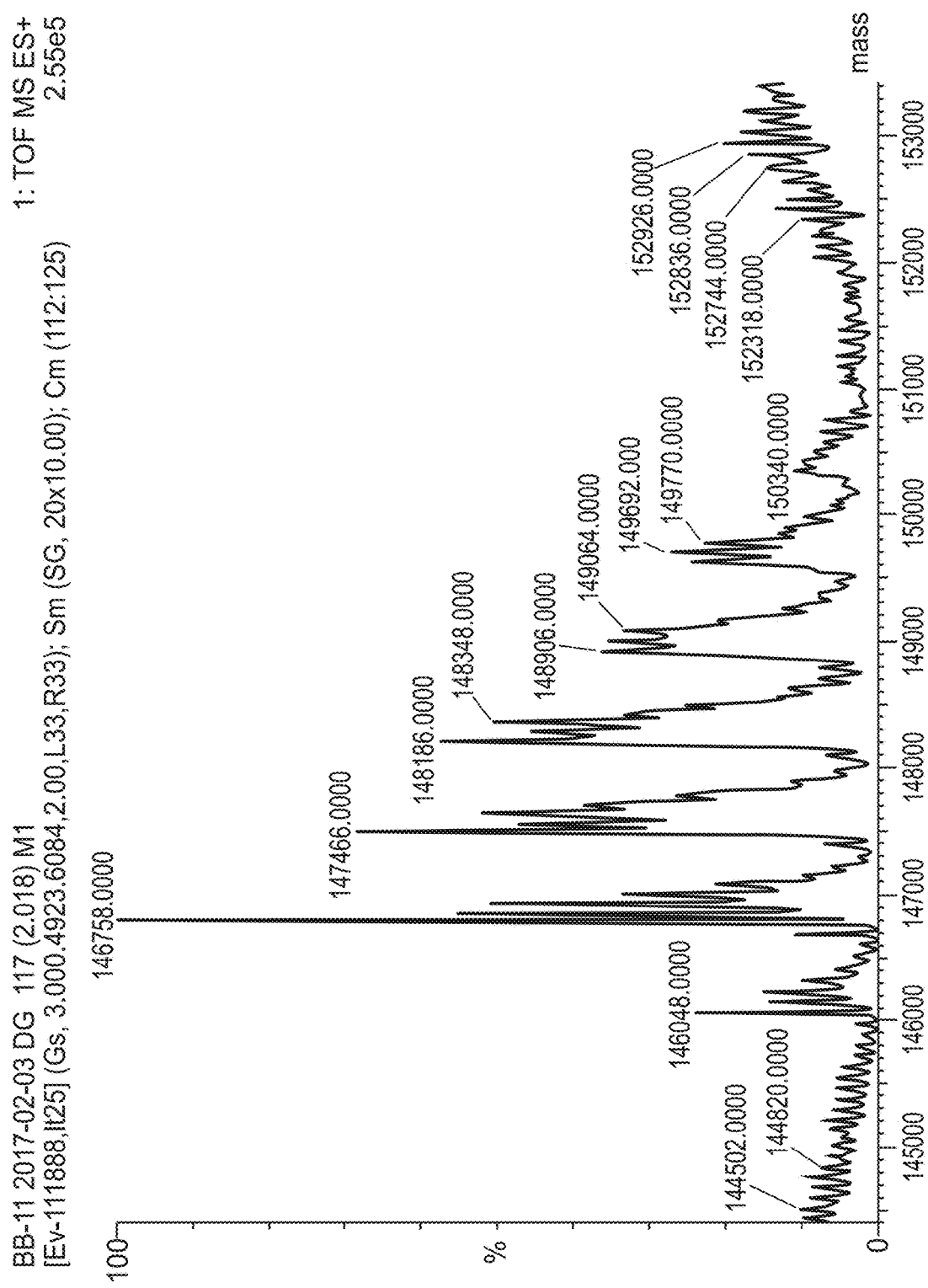

FIG. 103C shows a liquid chromatography-mass spectrometry analysis of the BB-11 immunoconjugate produced according to the BB-11 conjugation method following overnight deglycosylation with PNGase F.

Figure 103D:
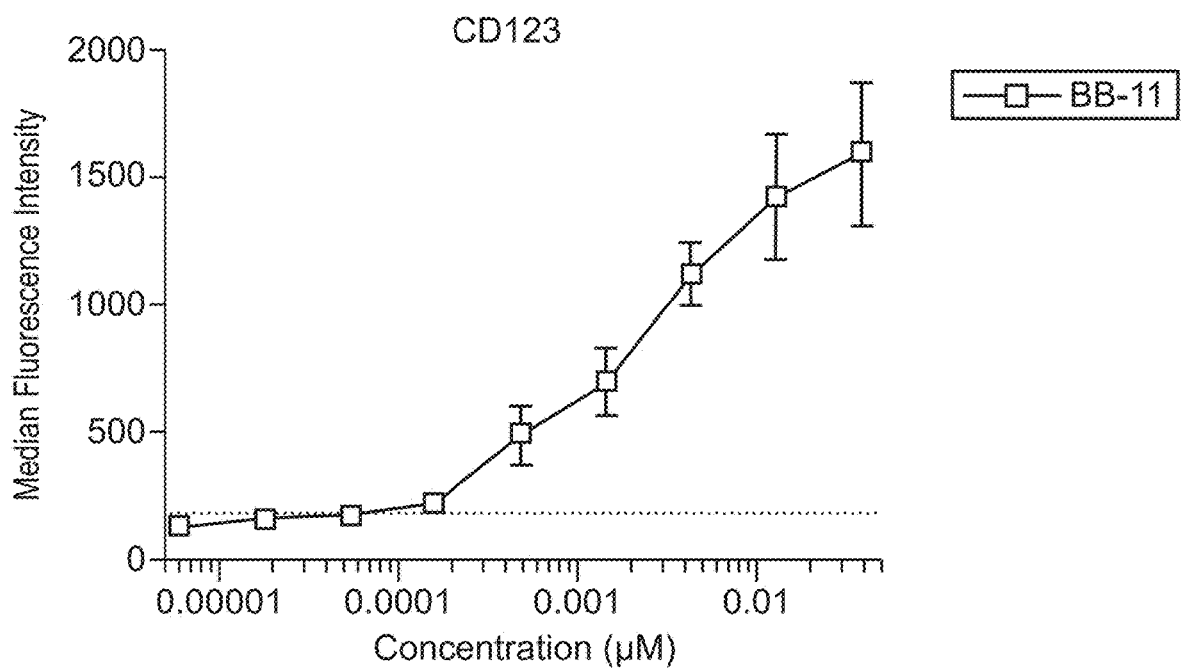

FIG. 103D shows CD123 expression on myeloid cells following 18 hours of stimulation with the BB-11 immunoconjugate produced according to the BB-11 method (BB-11). The dashed line indicates the level of expression on unstimulated myeloid cells cultured for 18 hours.

Figure 103E:
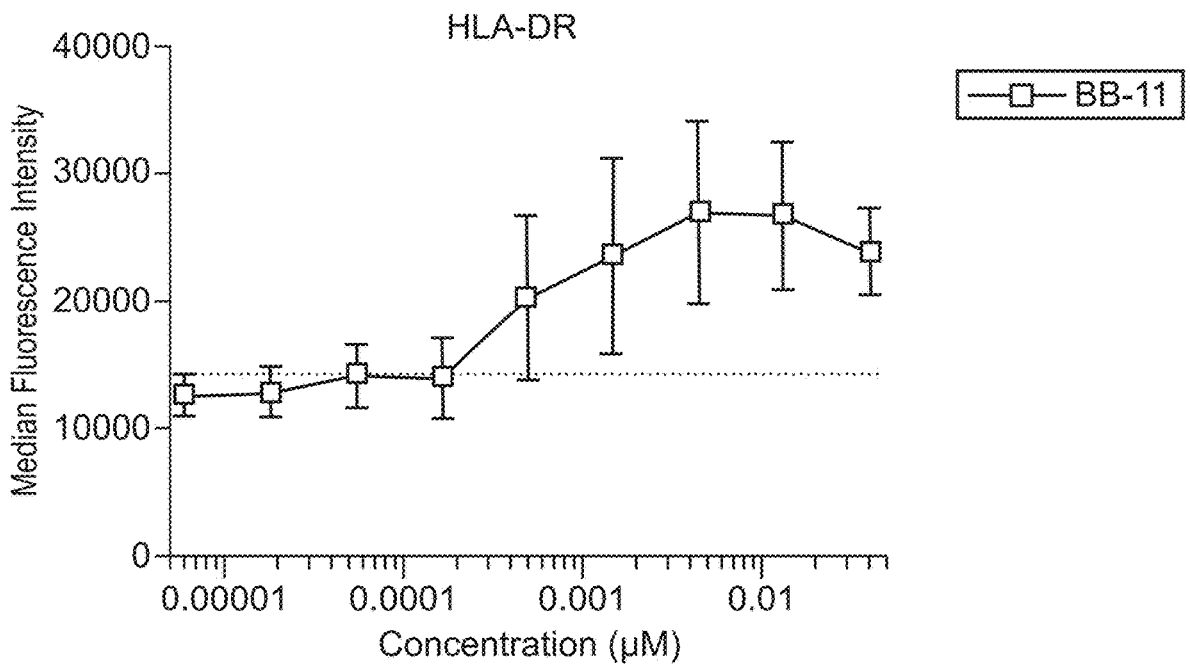

FIG. 103E shows HLA-DR expression on myeloid cells following 18 hours of stimulation with the BB-11 immunoconjugate produced according to the BB-11 method (BB-11). The dashed line indicates the level of expression on unstimulated myeloid cells cultured for 18 hours.

Figure 103F:
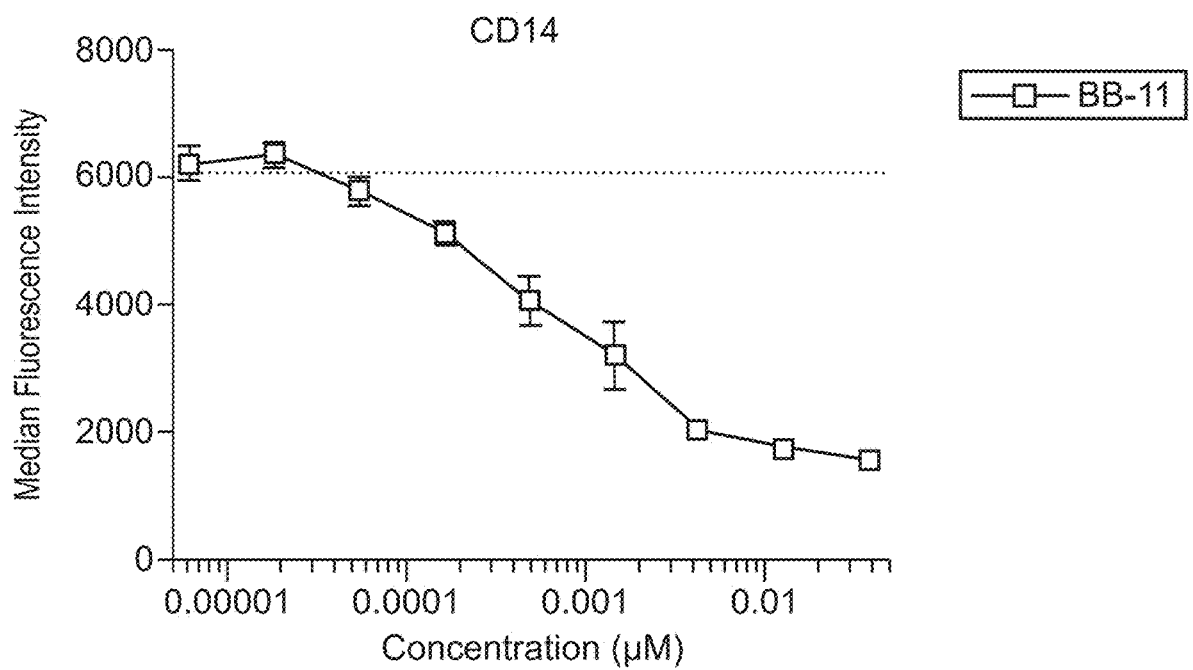

FIG. 103F shows CD14 expression on myeloid cells following 18 hours of stimulation with the BB-11 immunoconjugate produced according to the BB-11 method (BB-11). The dashed line indicates the level of expression on unstimulated myeloid cells cultured for 18 hours.

Figure 103G:
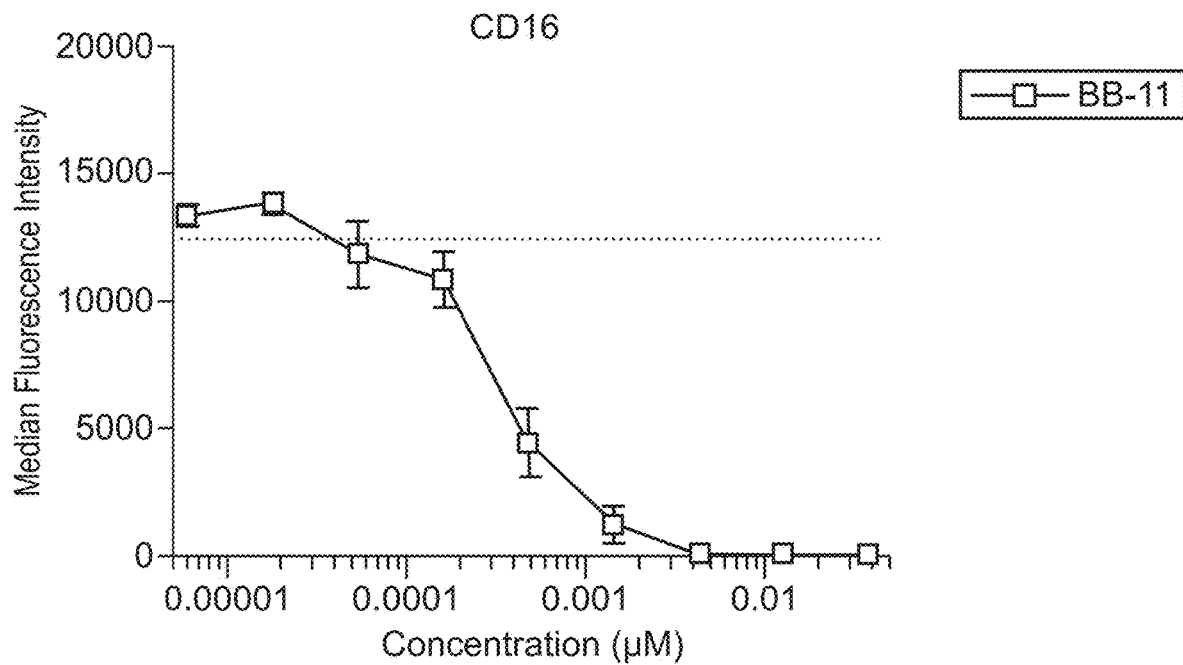

FIG. 103G shows CD16 expression on myeloid cells following 18 hours of stimulation with the BB-11 immunoconjugate produced according to the BB-11 method (BB-11). The dashed line indicates the level of expression on unstimulated myeloid cells cultured for 18 hours.

Figure 103H:
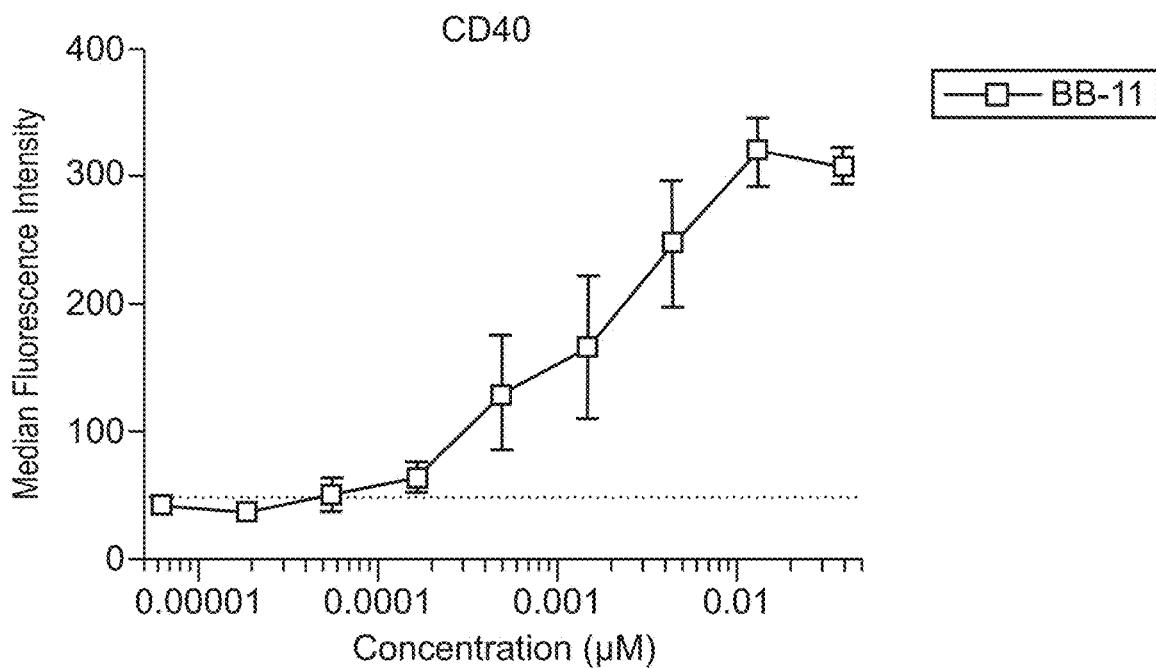

FIG. 103H shows CD40 expression on myeloid cells following 18 hours of stimulation with the BB-11 immunoconjugate produced according to the BB-11 method (BB-11). The dashed line indicates the level of expression on unstimulated myeloid cells cultured for 18 hours.

Figure 103I:
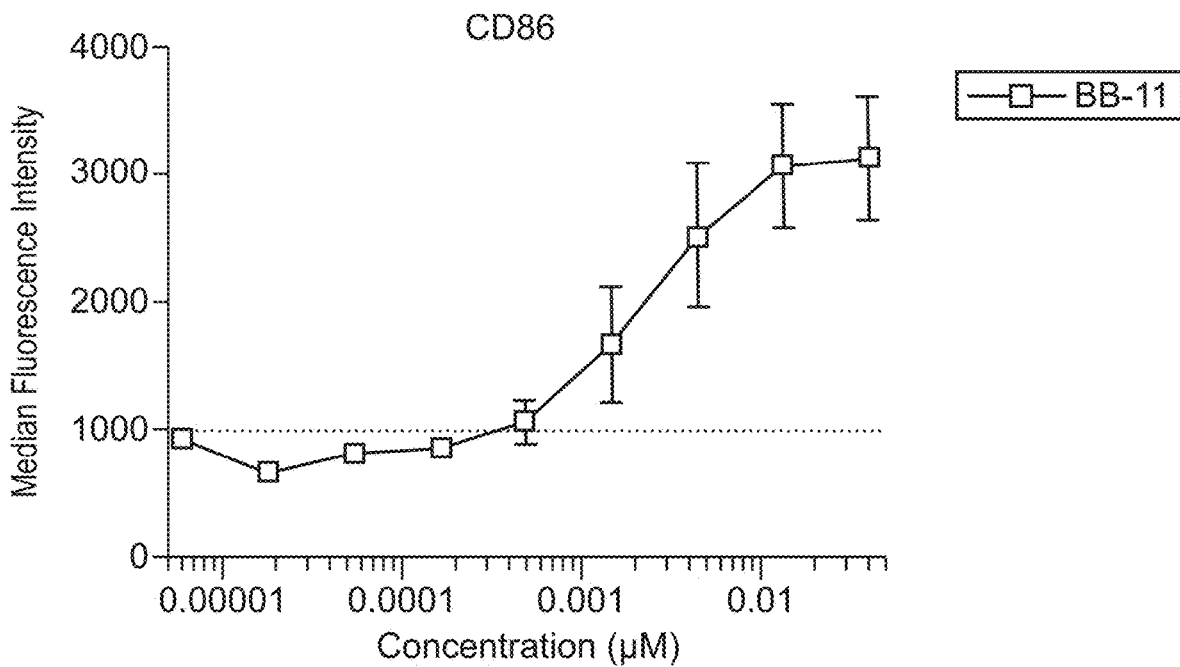

FIG. 103I shows CD86 expression on myeloid cells following 18 hours of stimulation with the BB-11 immunoconjugate produced according to the BB-11 method (BB-11). The dashed line indicates the level of expression on unstimulated myeloid cells cultured for 18 hours.

Figure 104A:
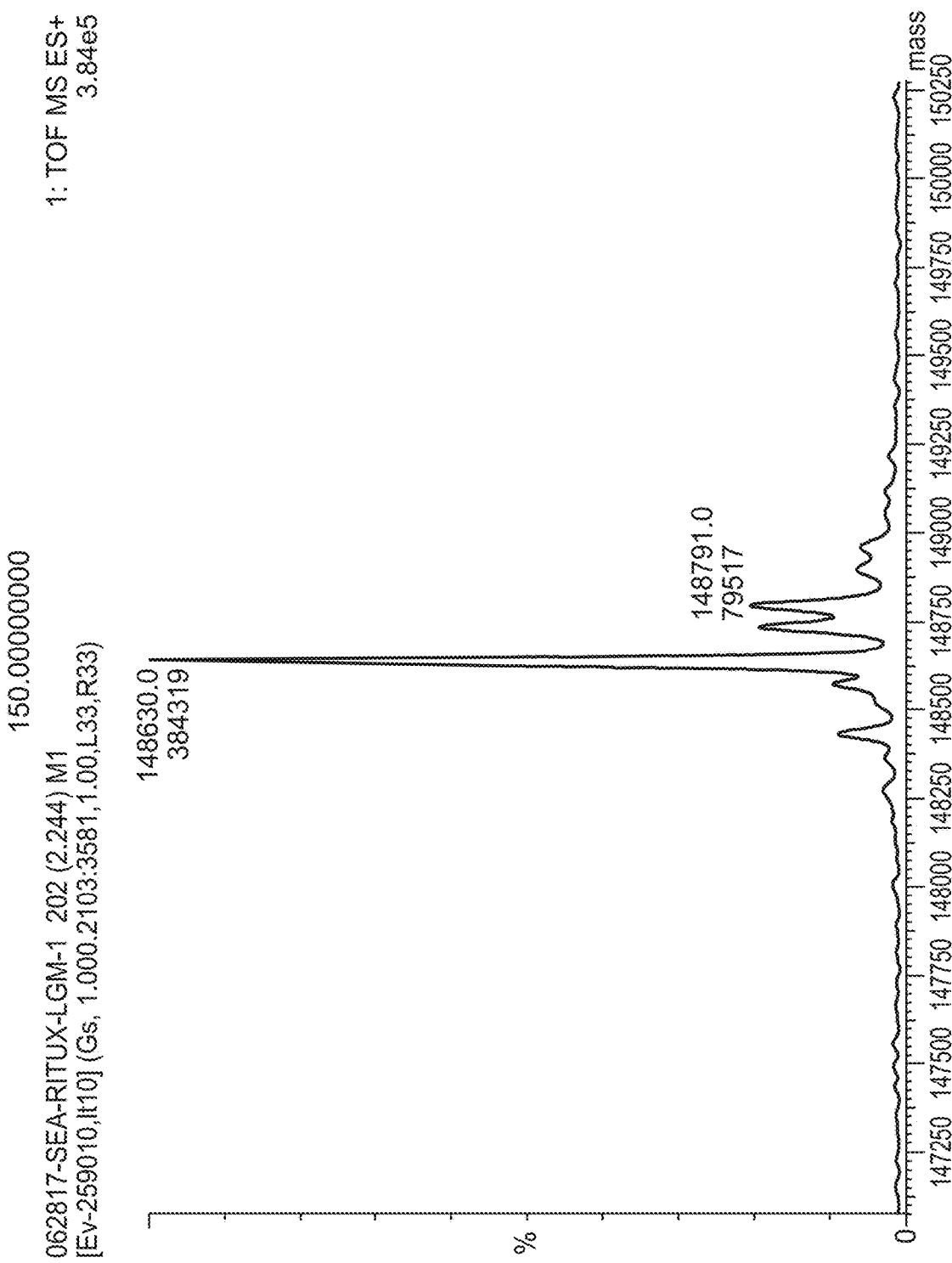

FIG. 104A shows a liquid chromatography-mass spectrometry analysis of the unconjugated rituximab biosimilar (CD20, LGM Pharma) that was utilized to produce the rituximab immunoconjugate according to the BB-14 PFP conjugation method.

Figure 104B:
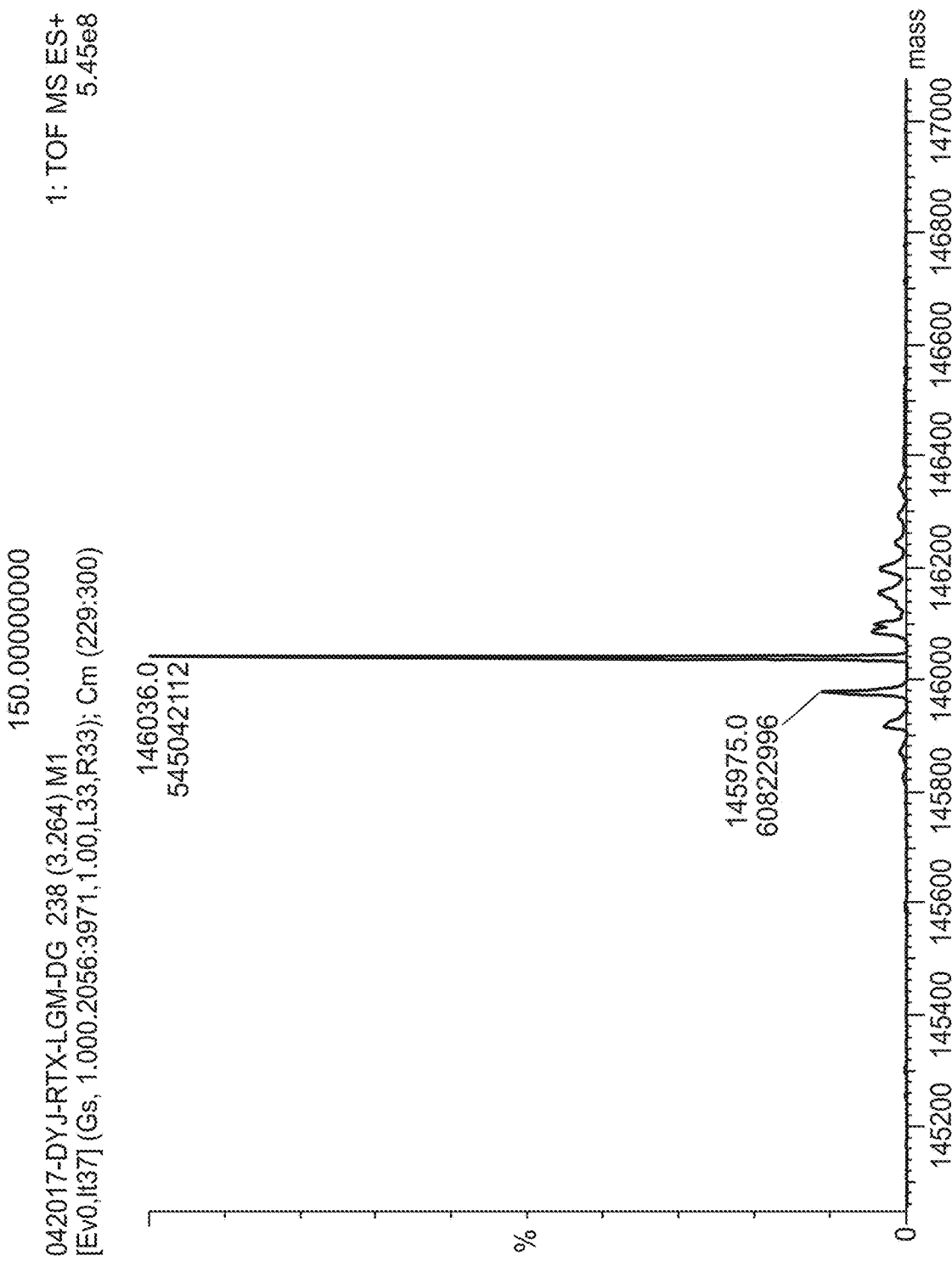

FIG. 104B shows a liquid chromatography-mass spectrometry analysis of the unconjugated rituximab biosimilar (CD20, LGM Pharma) that was utilized to produce the rituximab immunoconjugate according to the BB-14 PFP conjugation method following overnight deglycosylation with PNGase F.

Figure 104C:
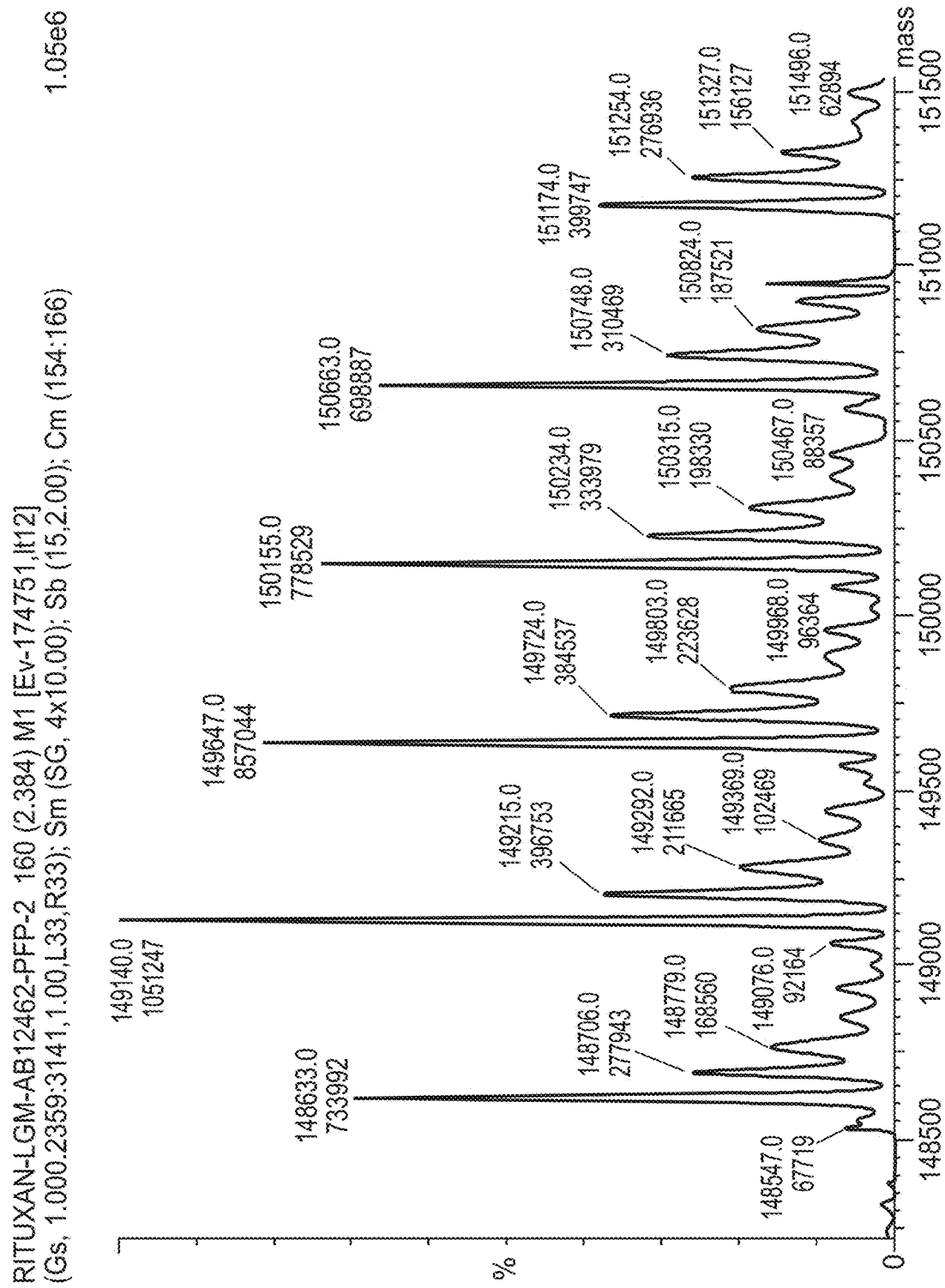

FIG. 104C shows a liquid chromatography-mass spectrometry analysis of the BB-14 immunoconjugate produced according to the BB-14 PFP conjugation method.

Figure 104D:
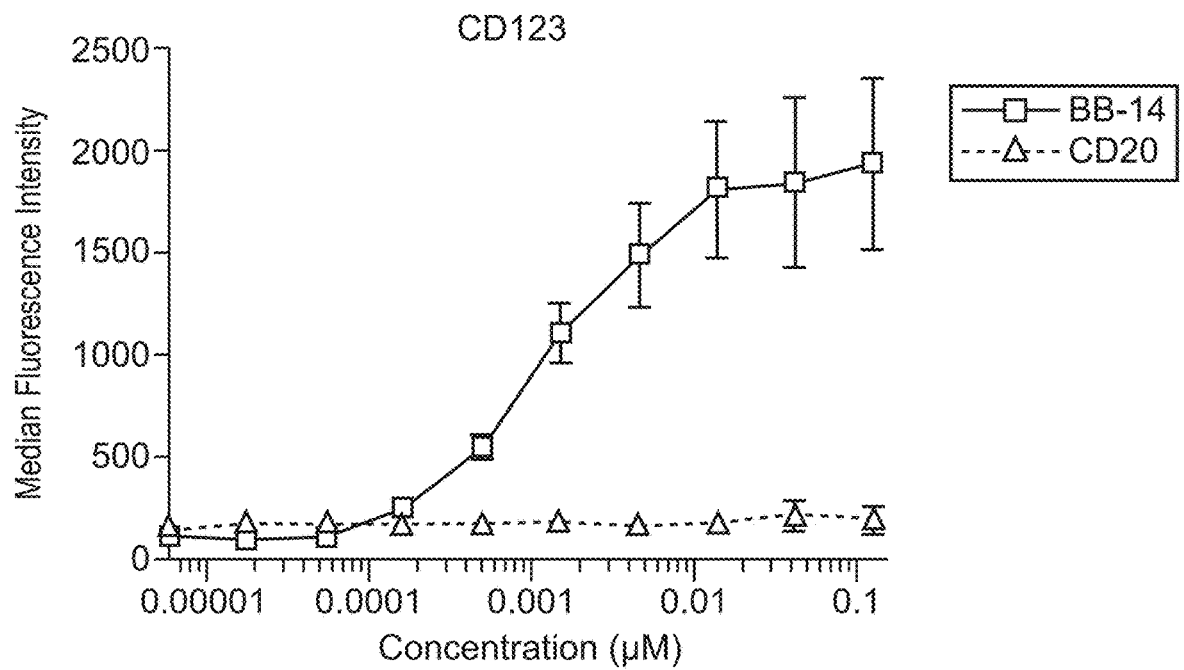

FIG. 104D shows that the rituximab immunoconjugate produced according to the BB-14 PFP conjugation method (BB-14) is superior at eliciting CD123 upregulation on myeloid cells as compared to the unconjugated rituximab (CD20, LGM Pharma) following 18 hours of stimulation.

Figure 104E:
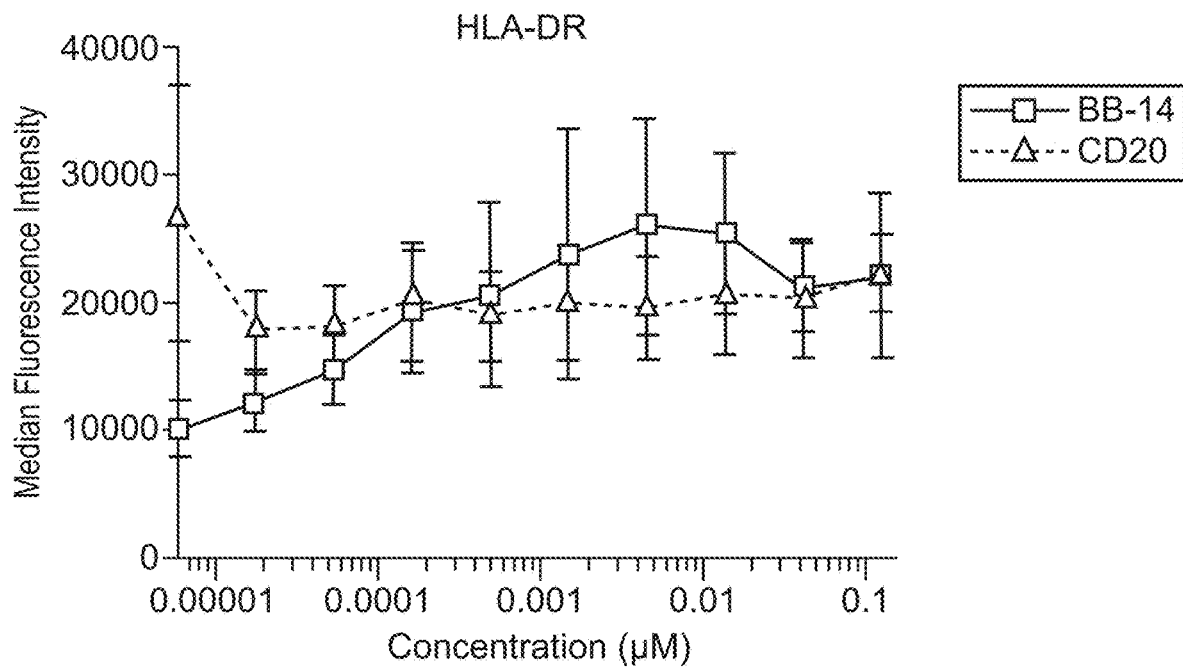

FIG. 104E shows that the rituximab immunoconjugate produced according to the BB-14 PFP conjugation method (BB-14) is superior at eliciting HLA-DR upregulation on myeloid cells as compared to the unconjugated rituximab (CD20, LGM Pharma) following 18 hours of stimulation.

Figure 104F:
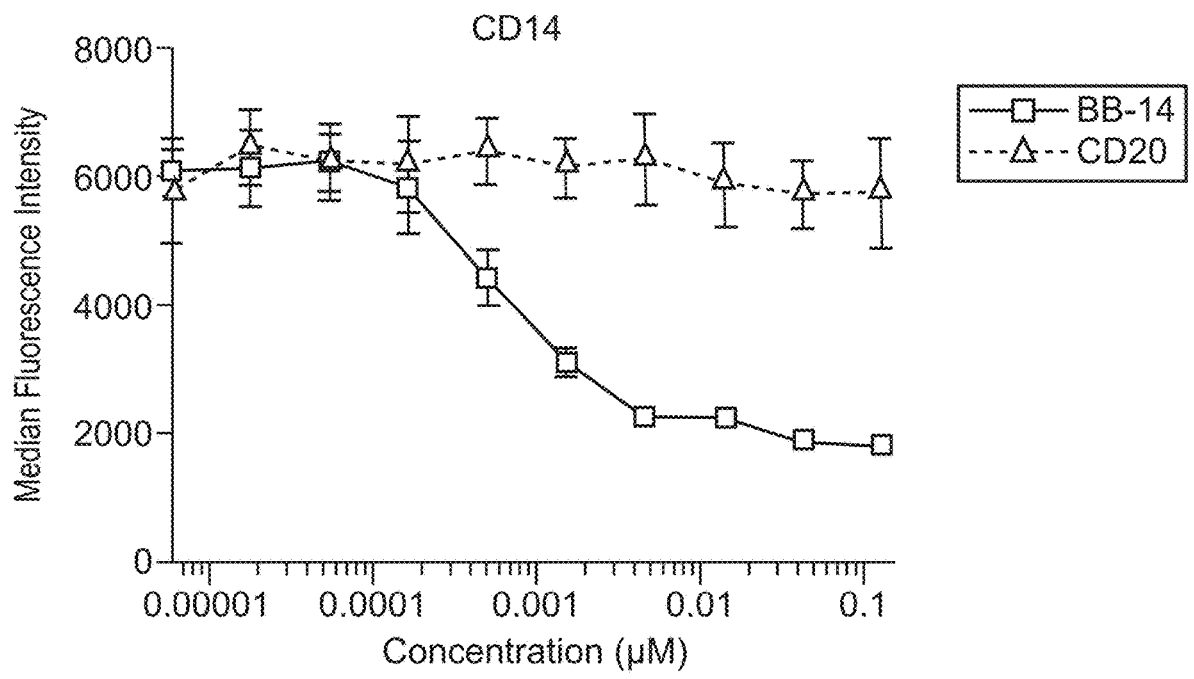

FIG. 104F shows that the rituximab immunoconjugate produced according to the BB-14 PFP conjugation method (BB-14) is superior at eliciting CD14 upregulation on myeloid cells as compared to the unconjugated rituximab (CD20, LGM Pharma) following 18 hours of stimulation.

Figure 104G:
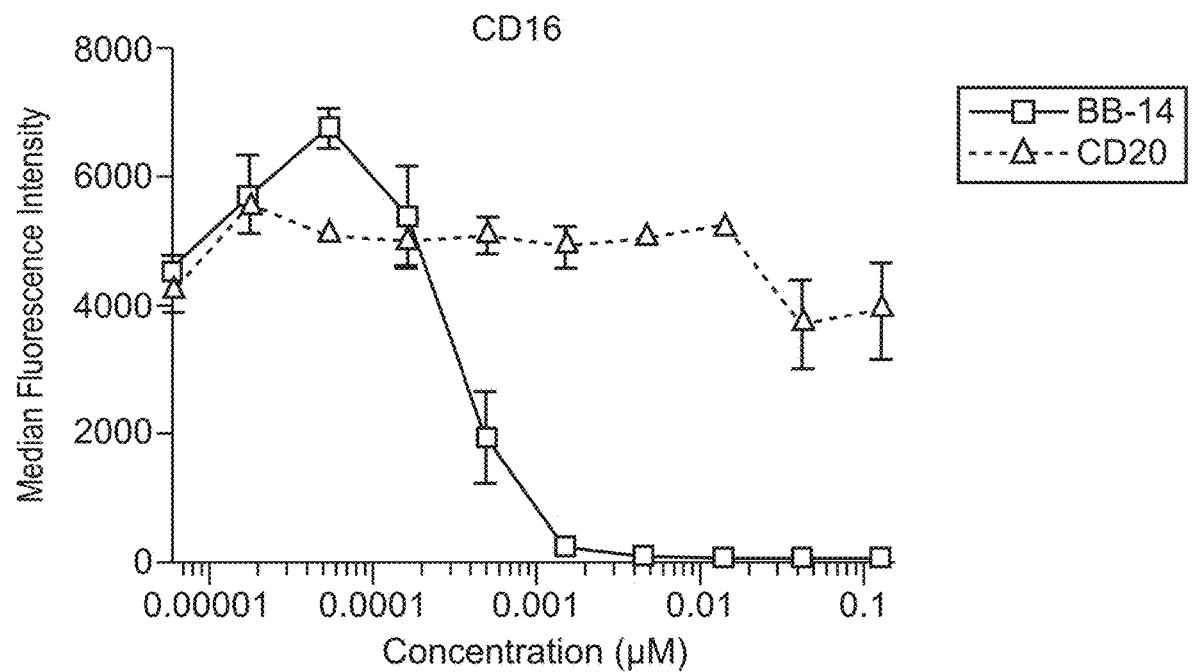

FIG. 104G shows that the rituximab immunoconjugate produced according to the BB-14 PFP conjugation method (BB-14) is superior at eliciting CD16 upregulation on myeloid cells as compared to the unconjugated rituximab (CD20, LGM Pharma) following 18 hours of stimulation.

Figure 104H:
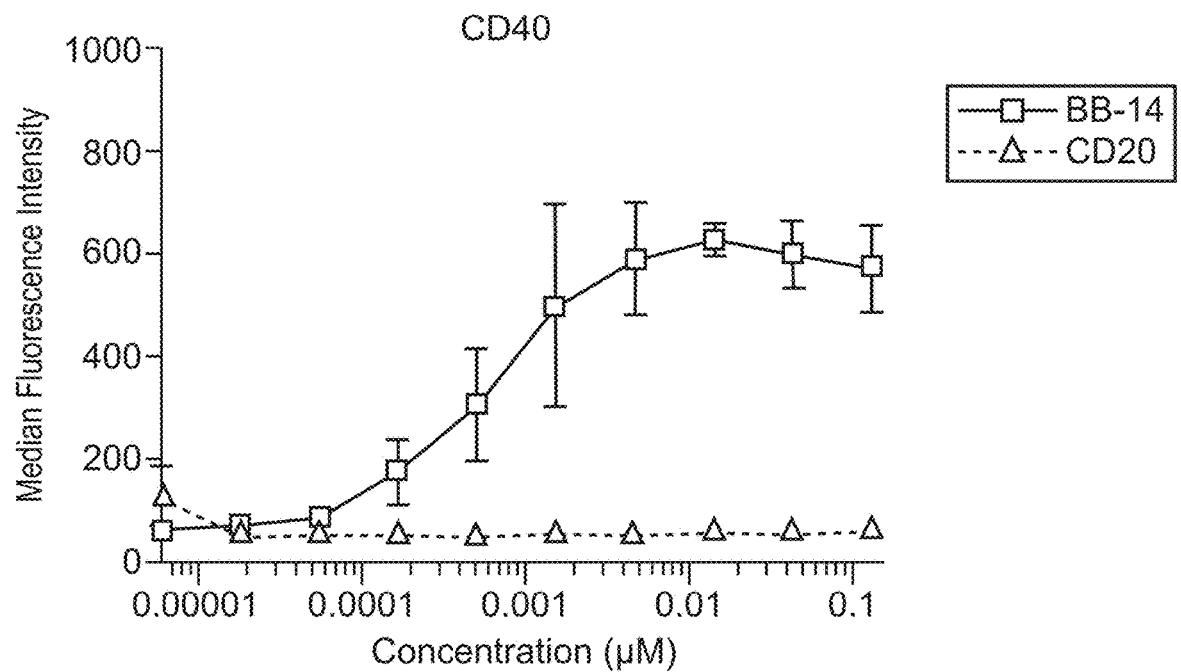

FIG. 104H shows that the rituximab immunoconjugate produced according to the BB-14 PFP conjugation method (BB-14) is superior at eliciting CD40 upregulation on myeloid cells as compared to the unconjugated rituximab (CD20, LGM Pharma) following 18 hours of stimulation.

Figure 104I:
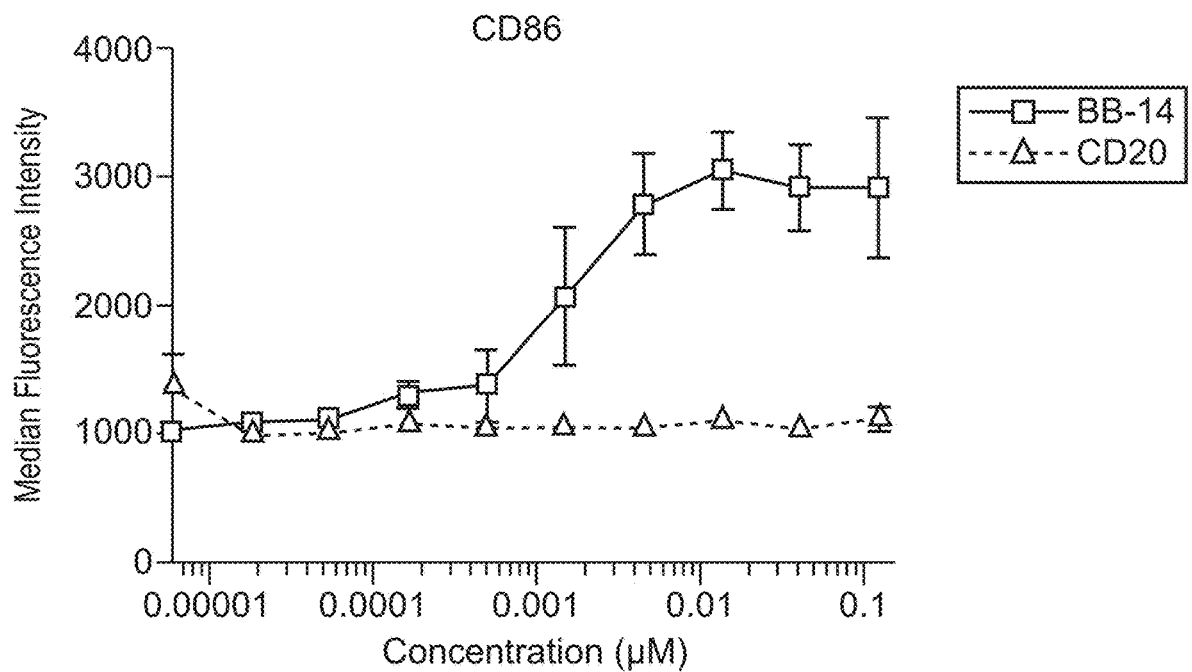

FIG. 104I shows that the rituximab immunoconjugate produced according to the BB-14 PFP conjugation method (BB-14) is superior at eliciting CD86 upregulation on myeloid cells as compared to the unconjugated rituximab (CD20, LGM Pharma) following 18 hours of stimulation.

Figure 105A:
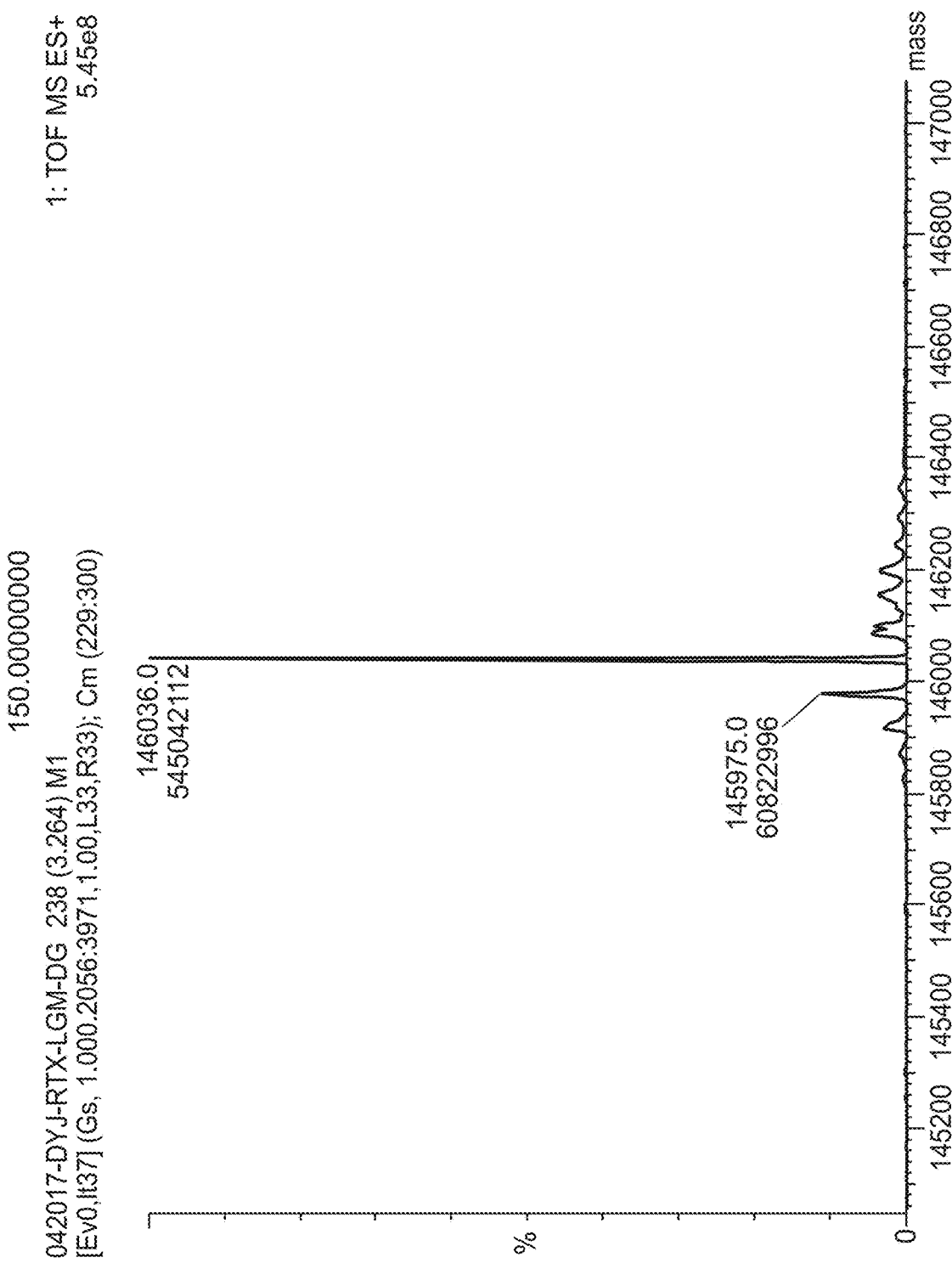

FIG. 105A shows a liquid chromatography-mass spectrometry analysis of the unconjugated rituximab biosimilar (CD20, LGM Pharma) that was utilized to produce the rituximab immunoconjugate according to the BB-15 NHS conjugation method following overnight deglycosylation with PNGase F.

Figure 105B:
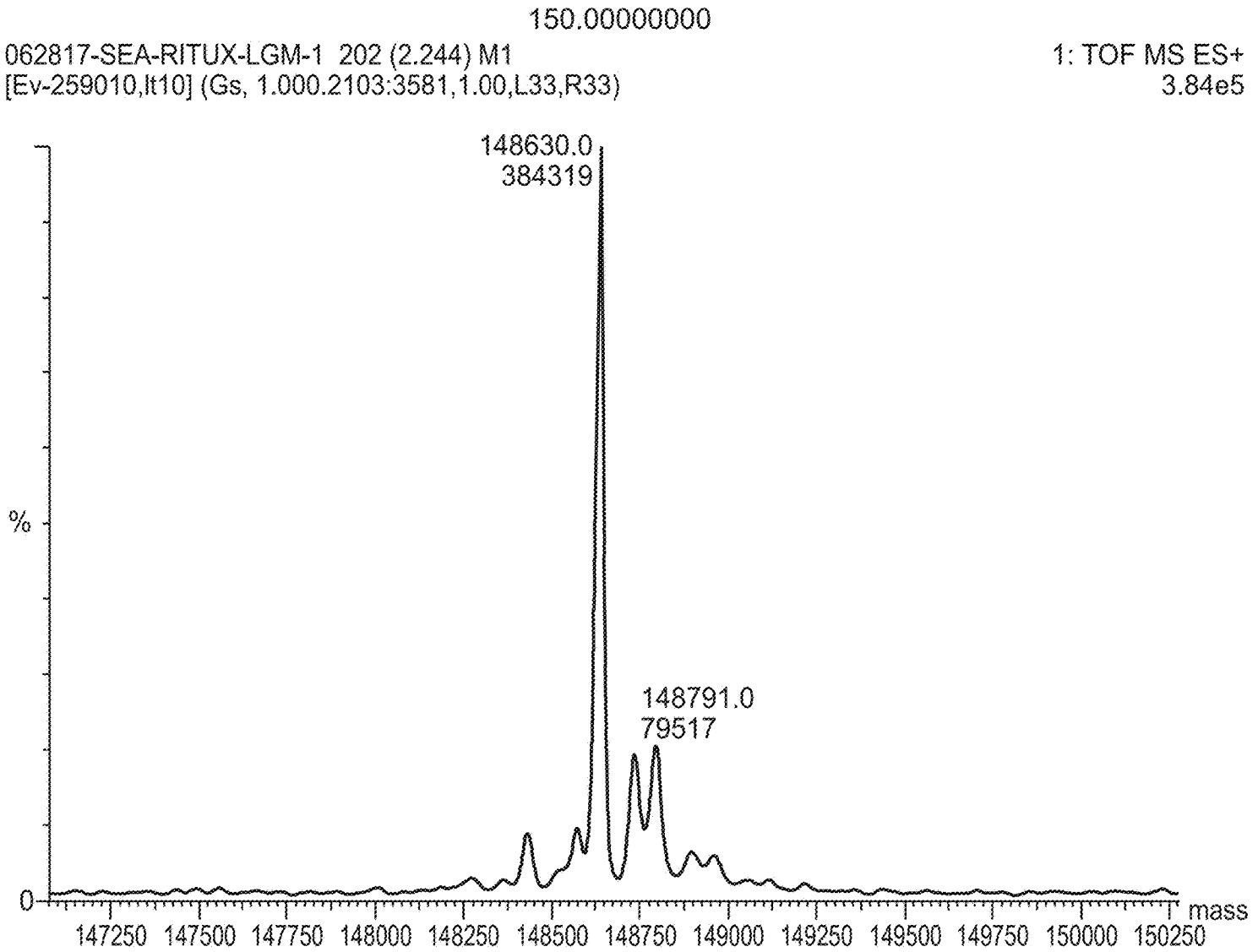

FIG. 105B shows a liquid chromatography-mass spectrometry analysis of the unconjugated rituximab biosimilar (CD20, LGM Pharma) that was utilized to produce the rituximab immunoconjugate according to the BB-15 NHS conjugation method.

Figure 105C:
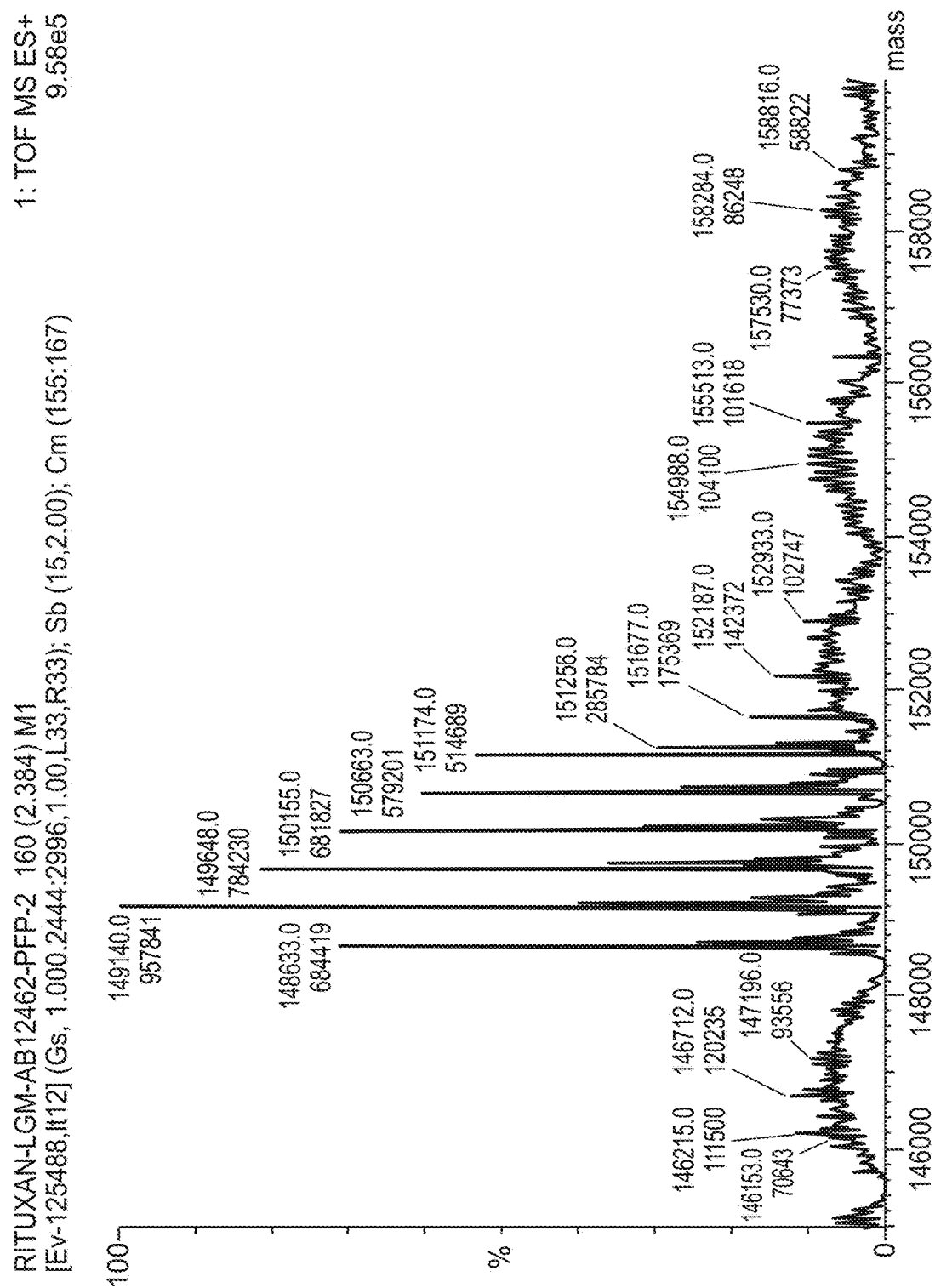

FIG. 105C shows a liquid chromatography-mass spectrometry analysis of the BB-15 immunoconjugate produced according to the BB-15 NHS conjugation method.

Figure 105D:
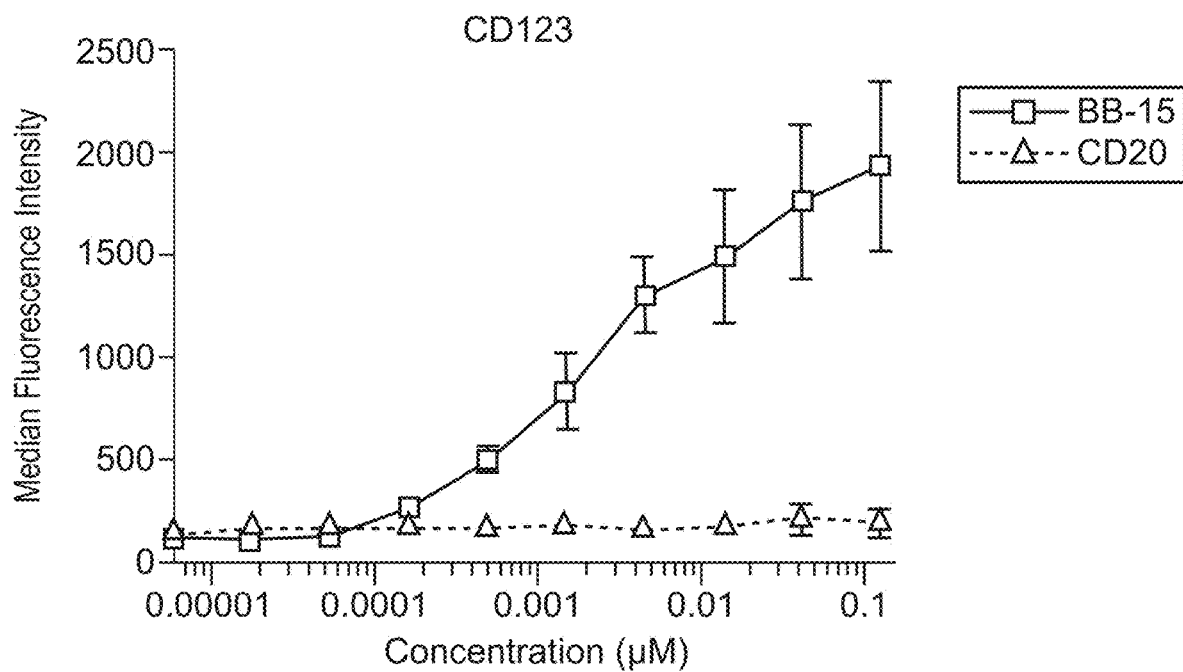

FIG. 105D shows that the rituximab immunoconjugate produced according to the BB-15 NHS conjugation method (BB-15) is superior at eliciting CD123 upregulation on myeloid cells as compared to the unconjugated rituximab (CD20, LGM Pharma) following 18 hours of stimulation.

Figure 105E:
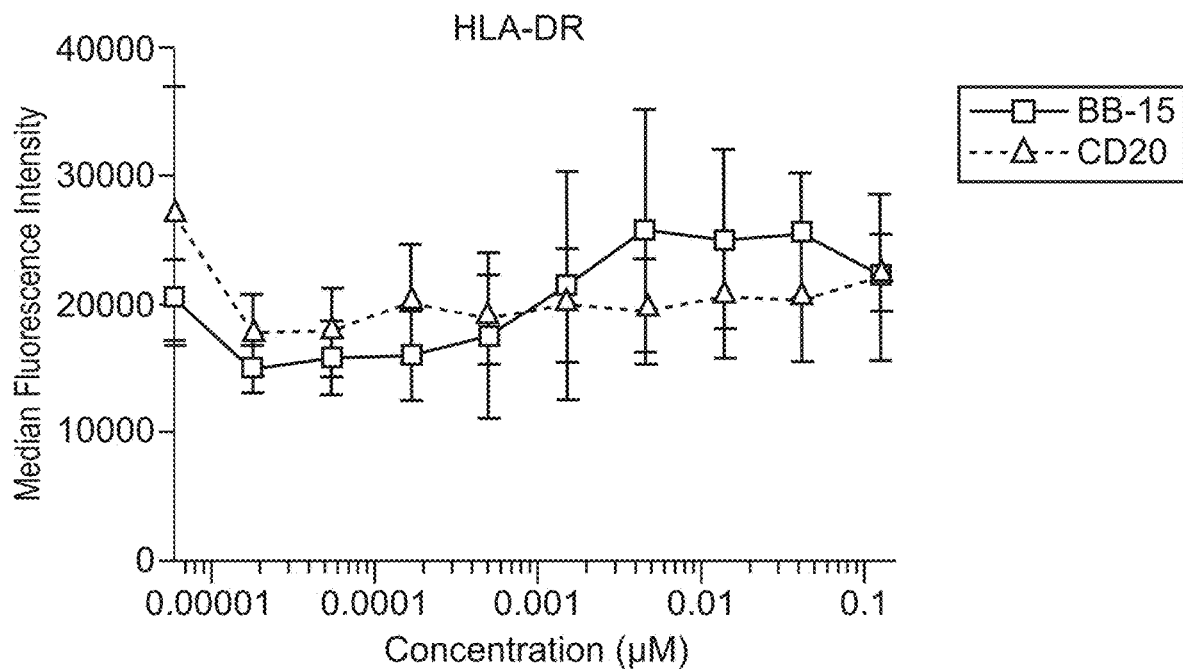

FIG. 105E shows that the rituximab immunoconjugate produced according to the BB-15 NHS conjugation method (BB-15) is superior at eliciting HLA-DR upregulation on myeloid cells as compared to the unconjugated rituximab (CD20, LGM Pharma) following 18 hours of stimulation.

Figure 105F:
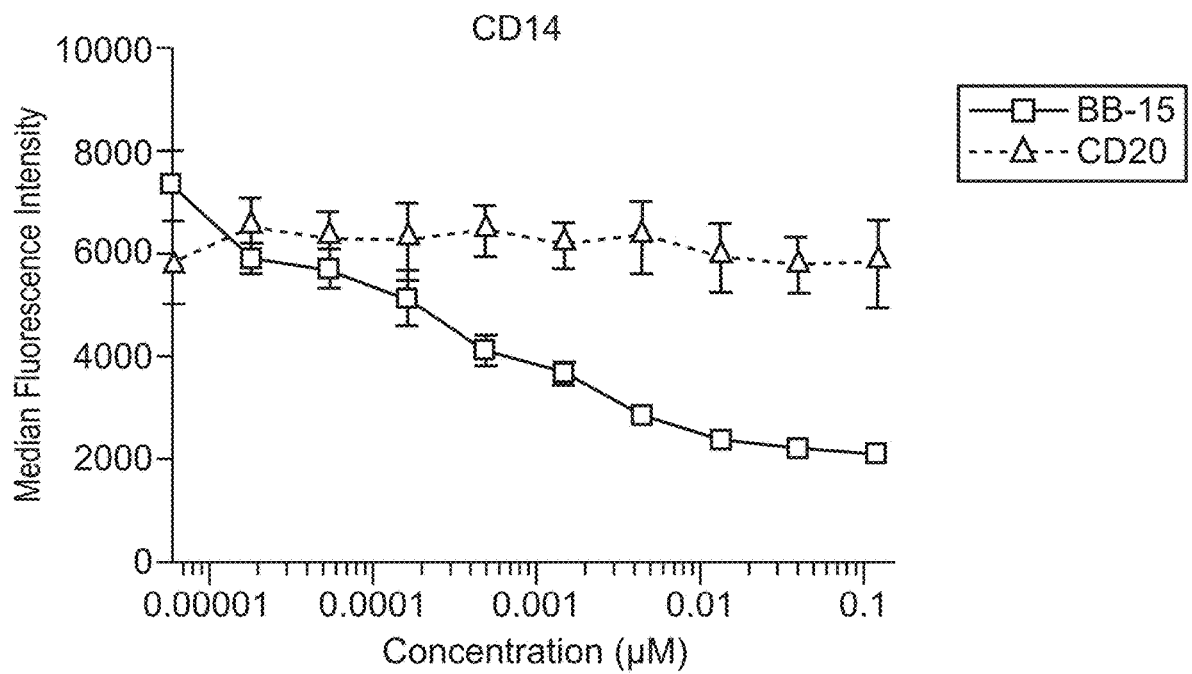

FIG. 105F shows that the rituximab immunoconjugate produced according to the BB-15 NHS conjugation method (BB-15) is superior at eliciting CD14 upregulation on myeloid cells as compared to the unconjugated rituximab (CD20, LGM Pharma) following 18 hours of stimulation.

Figure 105G:
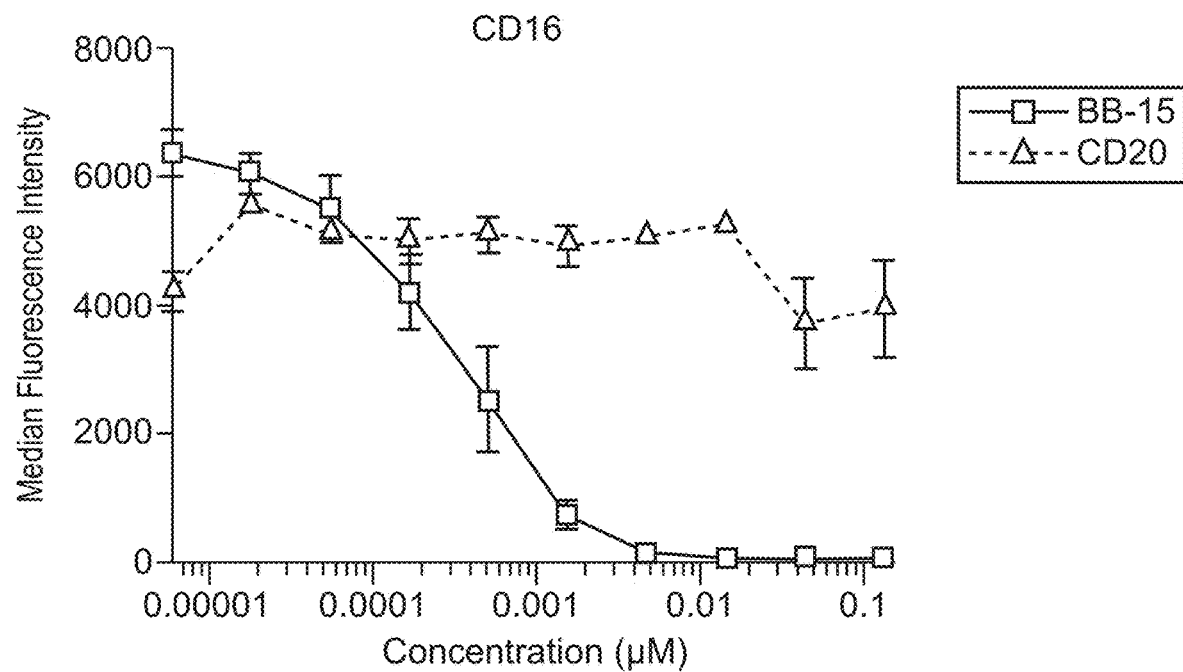

FIG. 105G shows that the rituximab immunoconjugate produced according to the BB-15 NHS conjugation method (BB-15) is superior at eliciting CD16 upregulation on myeloid cells as compared to the unconjugated rituximab (CD20, LGM Pharma) following 18 hours of stimulation.

Figure 105H:
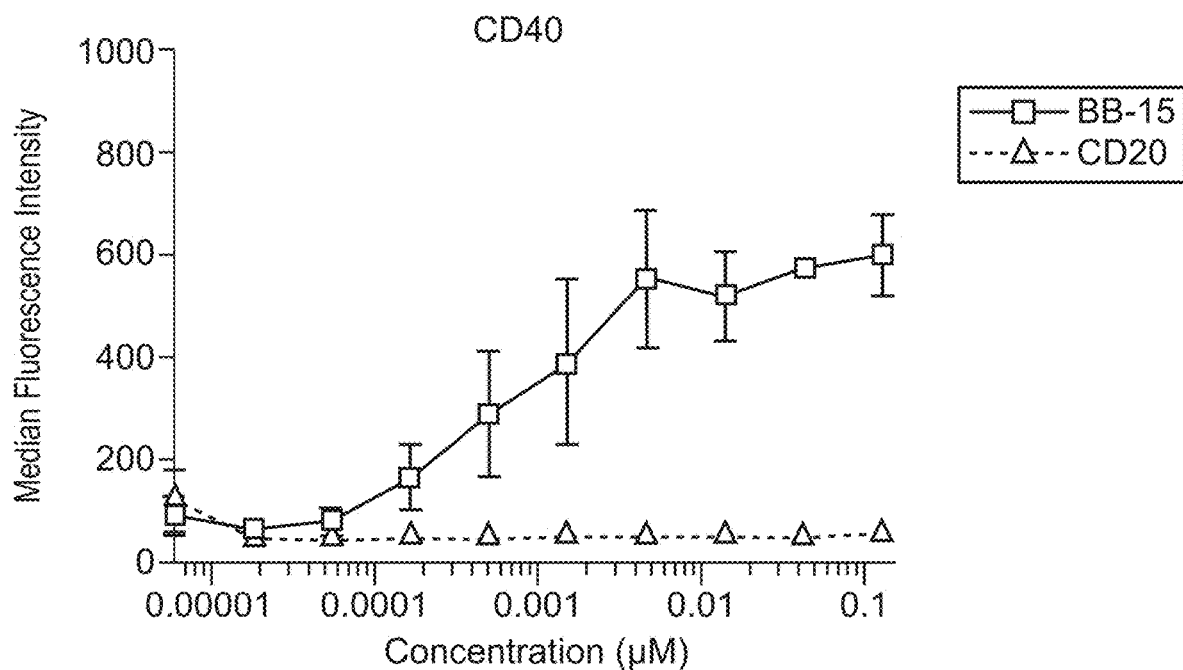

FIG. 105H shows that the rituximab immunoconjugate produced according to the BB-15 NHS conjugation method (BB-15) is superior at eliciting CD40 upregulation on myeloid cells as compared to the unconjugated rituximab (CD20, LGM Pharma) following 18 hours of stimulation.

Figure 105I:
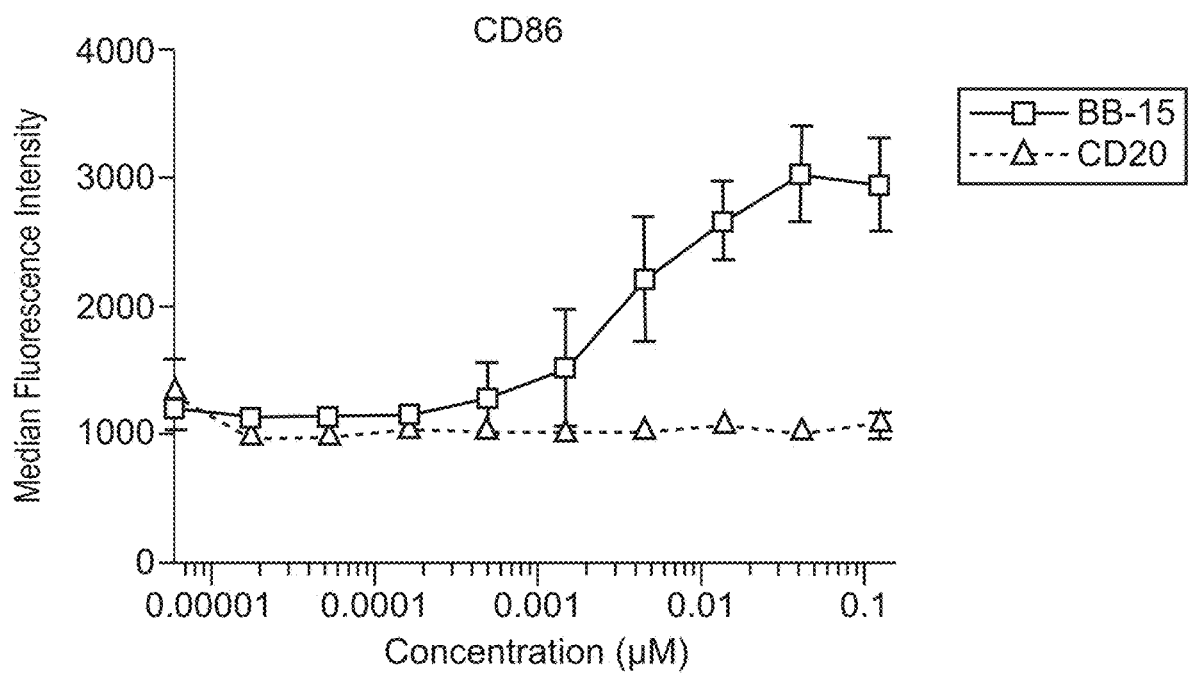

FIG. 105I shows that the rituximab immunoconjugate produced according to the BB-15 NHS conjugation method (BB-15) is superior at eliciting CD86 upregulation on myeloid cells as compared to the unconjugated rituximab (CD20, LGM Pharma) following 18 hours of stimulation.

Figure 106A:
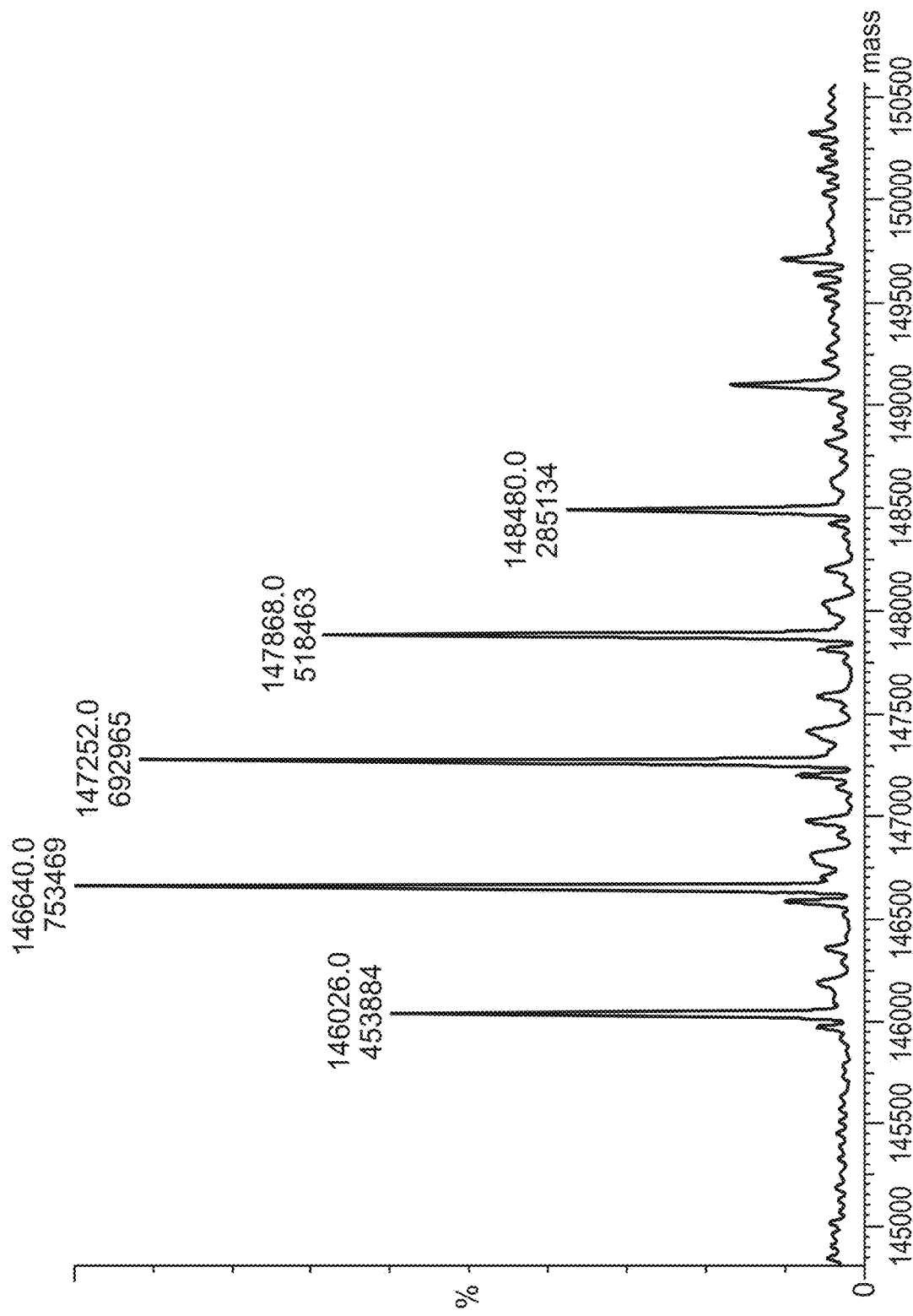

FIG. 106A shows a liquid chromatography-mass spectrometry analysis of the BB-17 immunoconjugate produced according to the BB-17 TFP conjugation method following overnight deglycosylation with PNGase F.

FIG. 106B shows a liquid chromatography-mass spectrometry analysis of the unconjugated rituximab biosimilar (CD20, LGM Pharma) that was utilized to produce the rituximab immunoconjugate according to the BB-17 TFP conjugation method following overnight deglycosylation with PNGase F.

FIG. 106C shows a liquid chromatography-mass spectrometry analysis of the unconjugated rituximab biosimilar (CD20, LGM Pharma) that was utilized to produce the rituximab immunoconjugate according to the BB-17 TFP conjugation method.

Figure 106D:
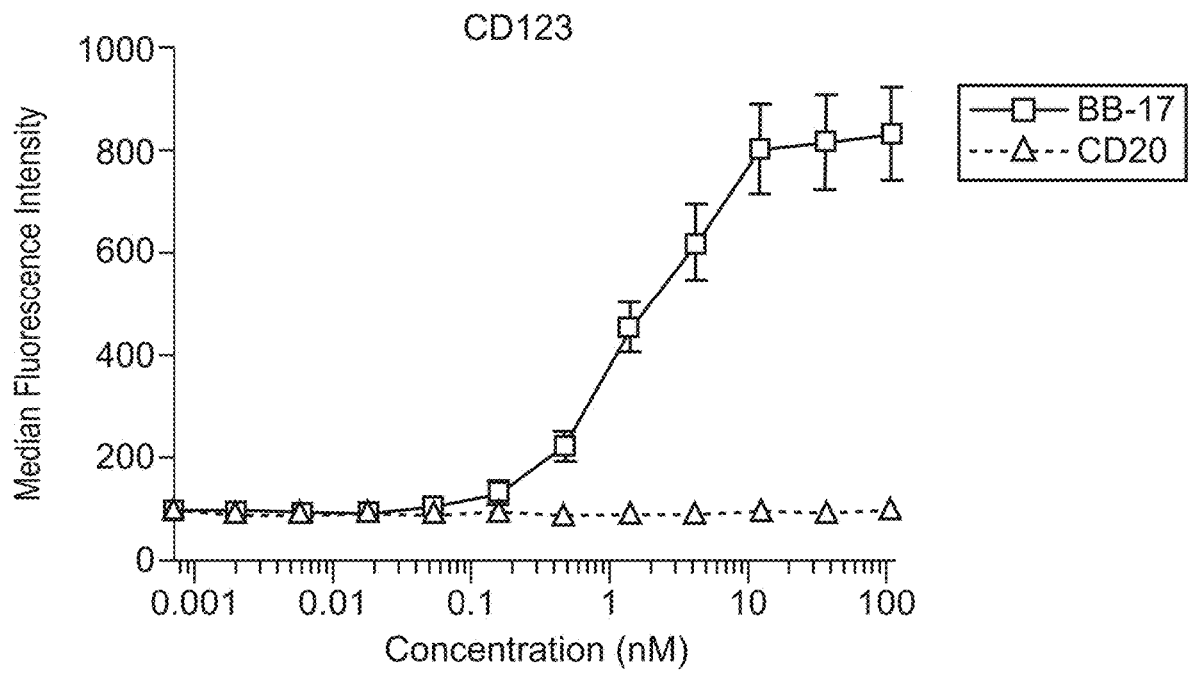

FIG. 106D shows that the rituximab immunoconjugate produced according to the BB-17 TFP conjugation method (BB-17) is superior at eliciting CD123 upregulation on myeloid cells as compared to the unconjugated rituximab (CD20, LGM Pharma) following 18 hours of stimulation.

Figure 106E:
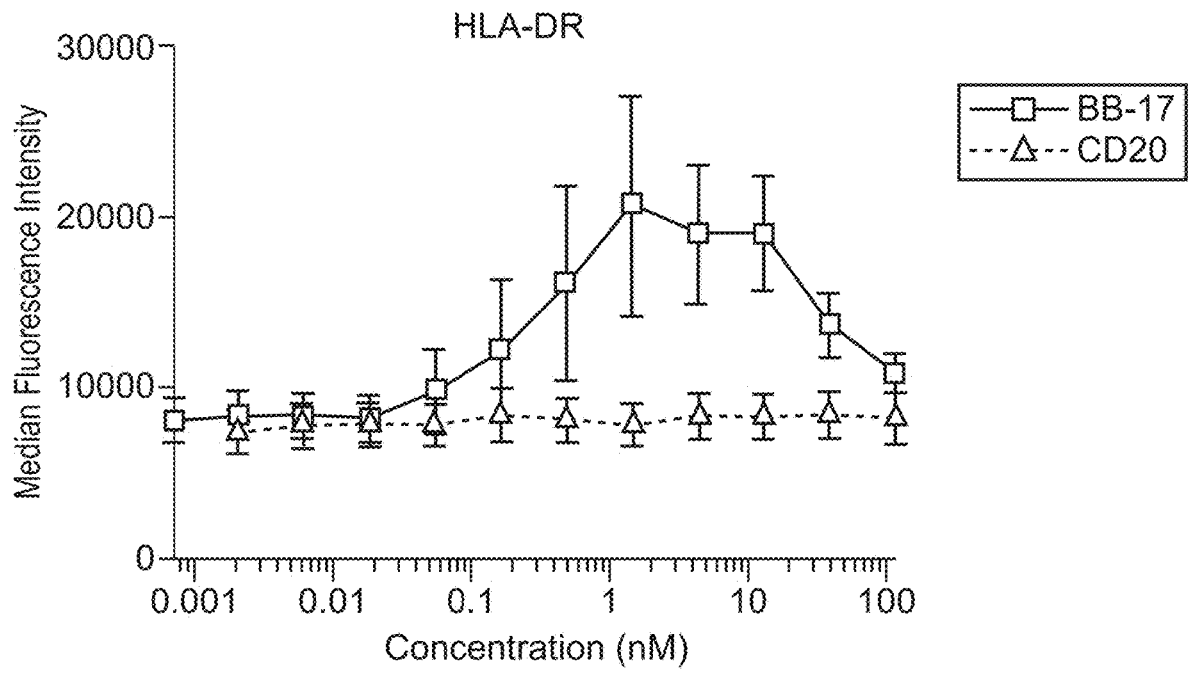

FIG. 106E shows that the rituximab immunoconjugate produced according to the BB-17 TFP conjugation method (BB-17) is superior at eliciting HLA-DR upregulation on myeloid cells as compared to the unconjugated rituximab (CD20, LGM Pharma) following 18 hours of stimulation.

Figure 106F:
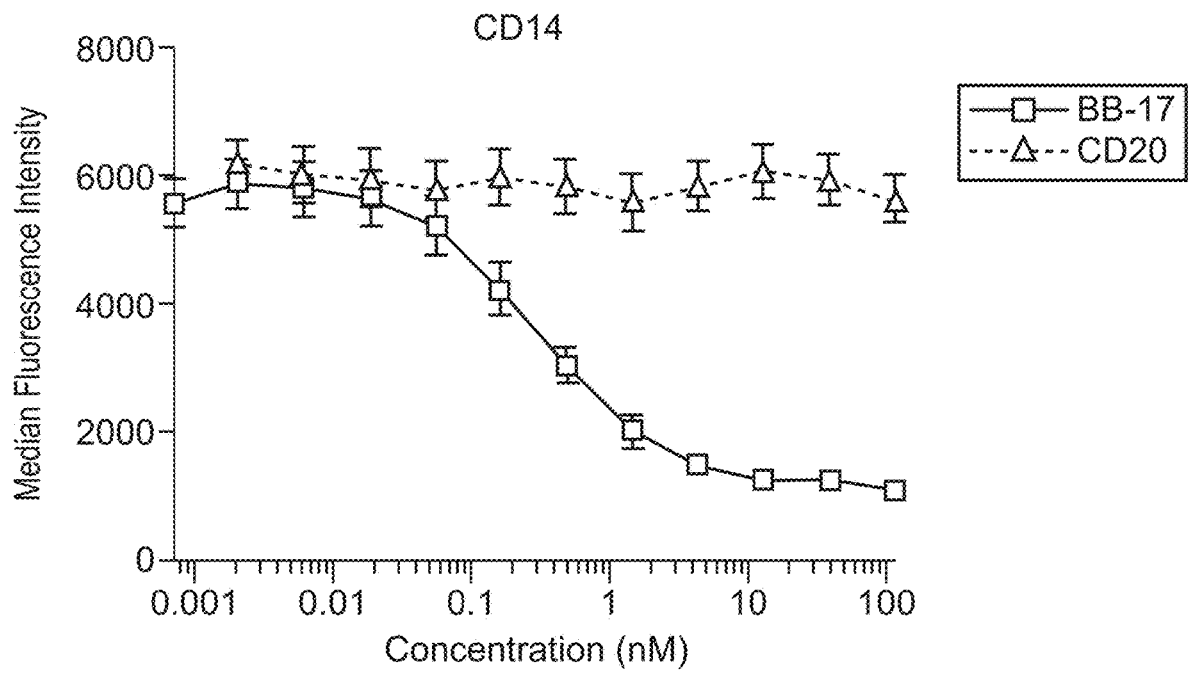

FIG. 106F shows that the rituximab immunoconjugate produced according to the BB-17 TFP conjugation method (BB-17) is superior at eliciting CD14 upregulation on myeloid cells as compared to the unconjugated rituximab (CD20, LGM Pharma) following 18 hours of stimulation.

Figure 106G:
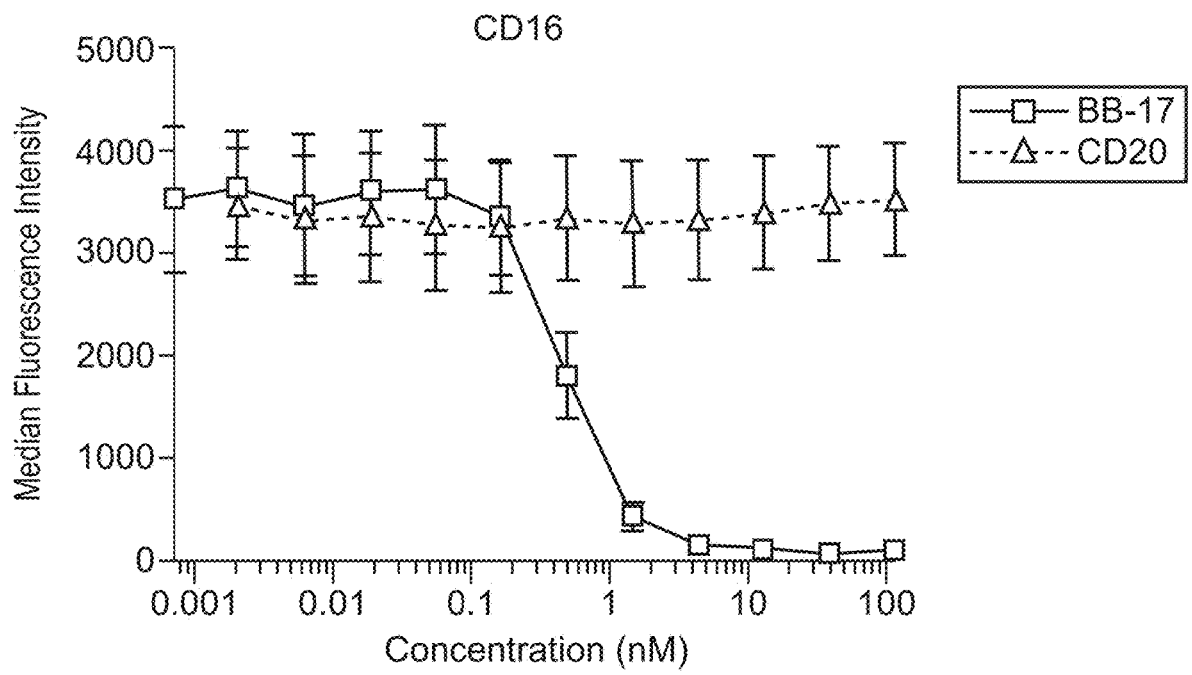

FIG. 106G shows that the rituximab immunoconjugate produced according to the BB-17 TFP conjugation method (BB-17) is superior at eliciting CD16 upregulation on myeloid cells as compared to the unconjugated rituximab (CD20, LGM Pharma) following 18 hours of stimulation.

Figure 106H:
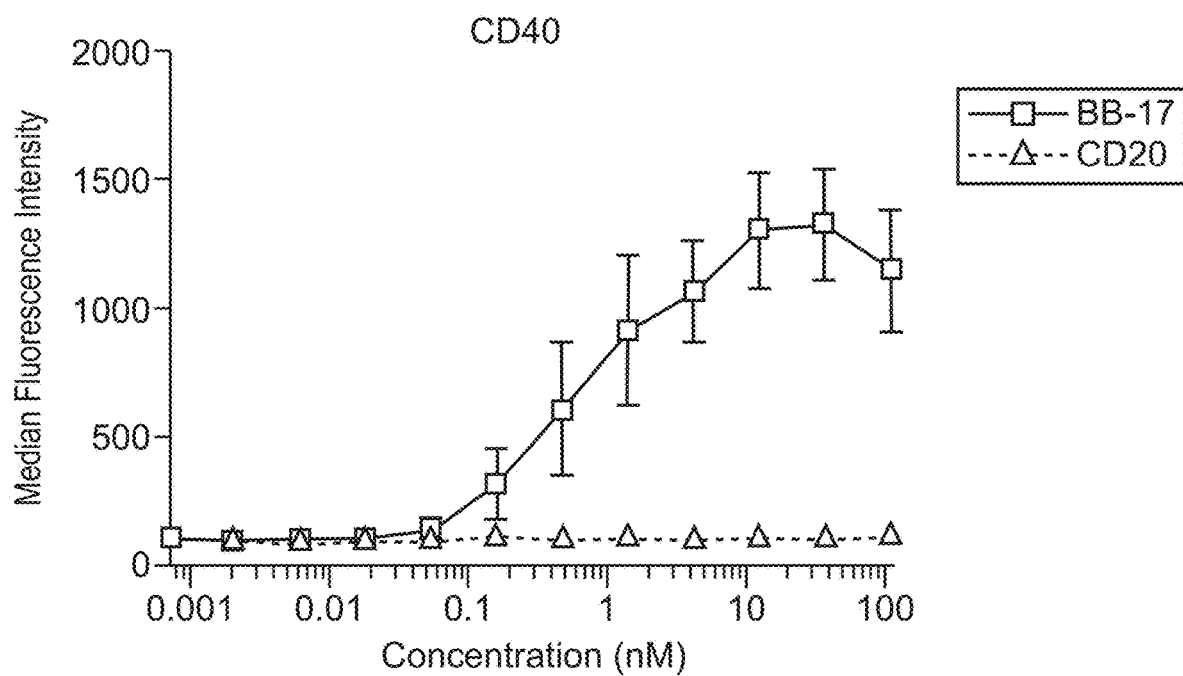

FIG. 106H shows that the rituximab immunoconjugate produced according to the BB-17 TFP conjugation method (BB-17) is superior at eliciting CD40 upregulation on myeloid cells as compared to the unconjugated rituximab (CD20, LGM Pharma) following 18 hours of stimulation.

Figure 106I:
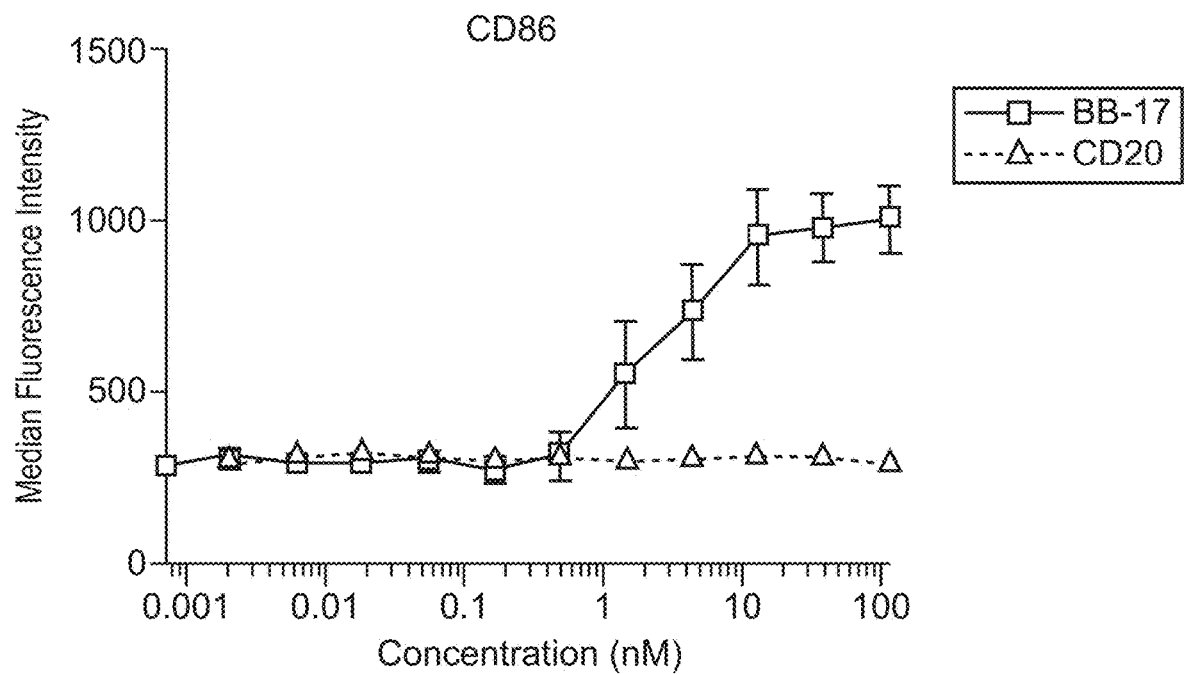

FIG. 106I shows that the rituximab immunoconjugate produced according to the BB-17 TFP conjugation method (BB-17) is superior at eliciting CD86 upregulation on myeloid cells as compared to the unconjugated rituximab (CD20, LGM Pharma) following 18 hours of stimulation.

FIG. 107A shows a liquid chromatography-mass spectrometry analysis of the unconjugated rituximab biosimilar (CD20, LGM Pharma) that was utilized to produce the rituximab immunoconjugate according to the BB-22 SATA conjugation method following overnight deglycosylation with PNGase F.

Figure 107B:
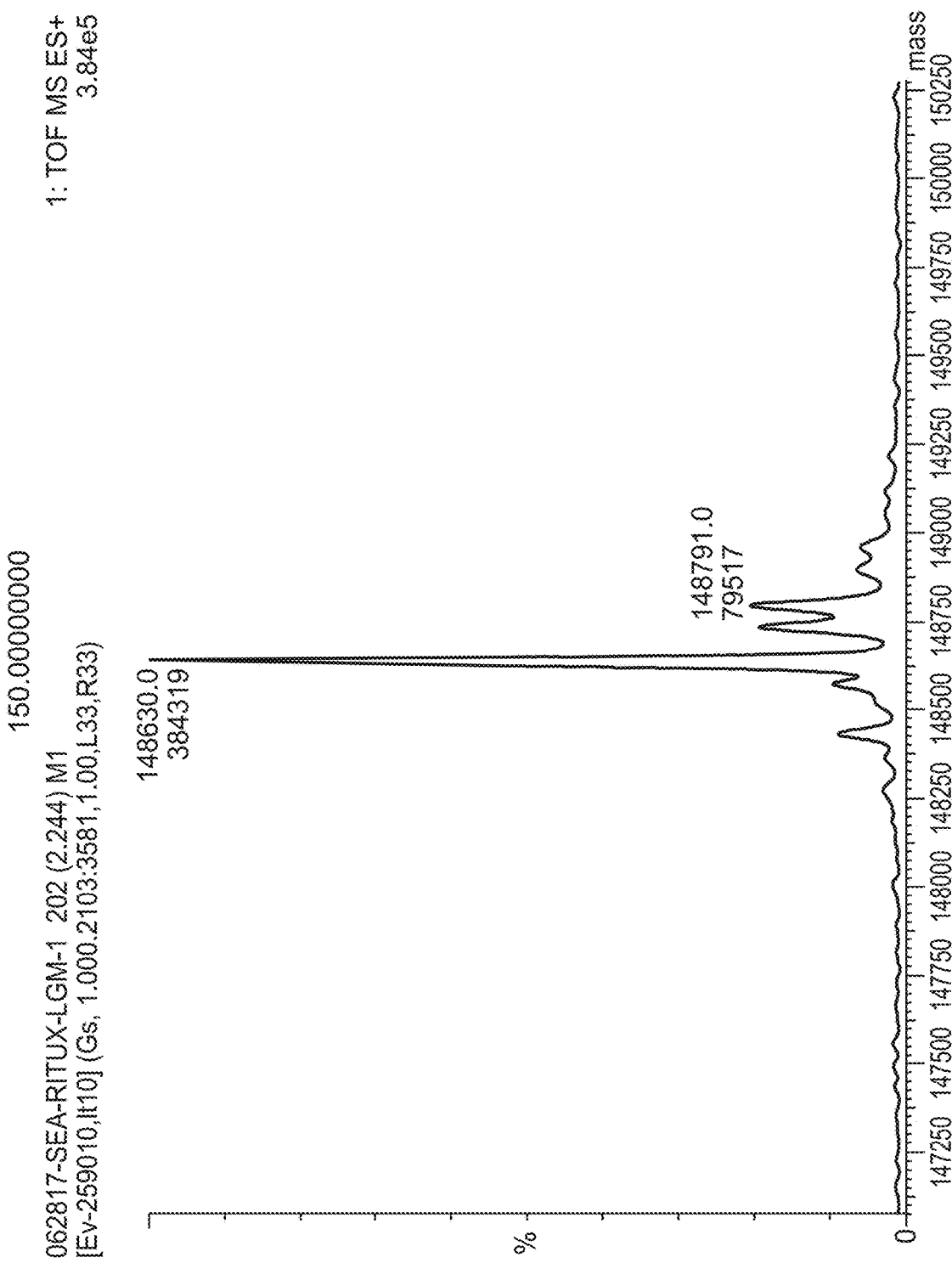

FIG. 107B shows a liquid chromatography-mass spectrometry analysis of the unconjugated rituximab biosimilar (CD20, LGM Pharma) that was utilized to produce the rituximab immunoconjugate according to the BB-22 SATA conjugation method.

Figure 107C:
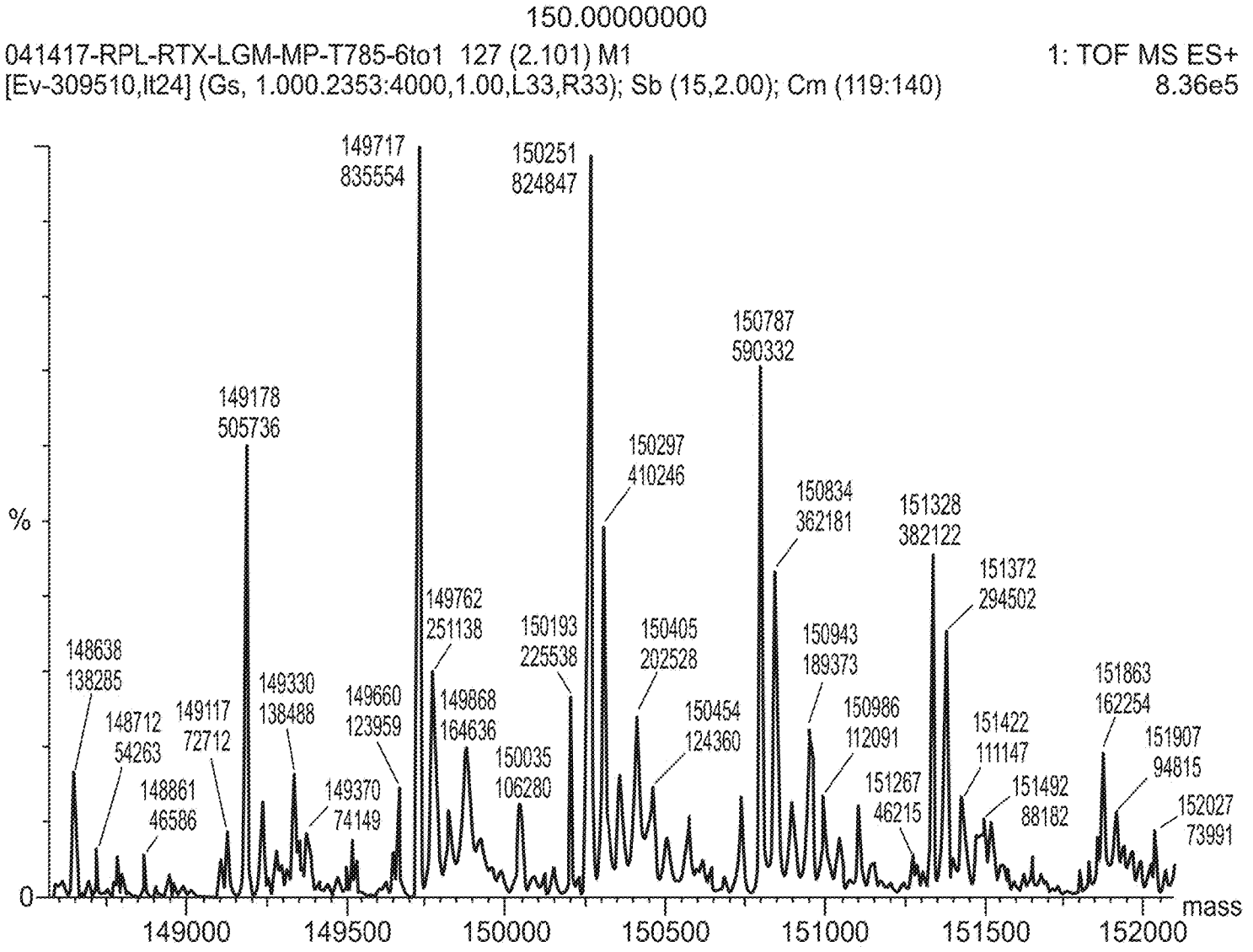

FIG. 107C shows a liquid chromatography-mass spectrometry analysis of the BB-22 immunoconjugate produced according to the BB-22 SATA conjugation method.

FIG. 108A shows a liquid chromatography-mass spectrometry analysis of the BB-24 immunoconjugate produced according to the BB-24 TFP conjugation method.

Figure 108B:
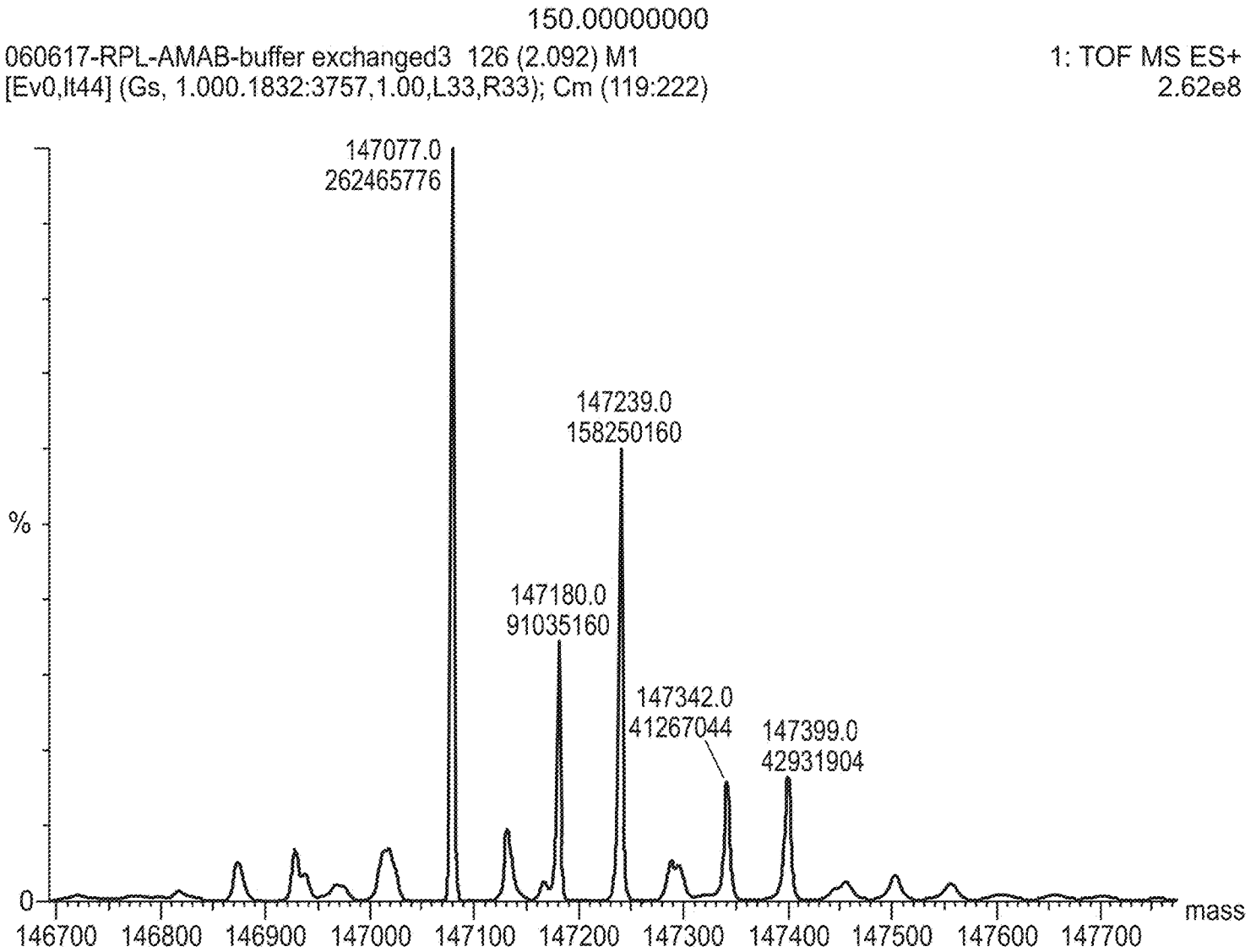

FIG. 108B shows a liquid chromatography-mass spectrometry analysis of the unconjugated rituximab biosimilar (CD20, Alphamab) that was utilized to produce the rituximab immunoconjugate according to the BB-24 TFP conjugation method.

FIG. 108C shows a liquid chromatography-mass spectrometry analysis of the unconjugated rituximab biosimilar (CD20, Alphamab) that was utilized to produce the rituximab immunoconjugate according to the BB-24 TFP conjugation method following overnight deglycosylation with PNGase F.

Figure 108D:
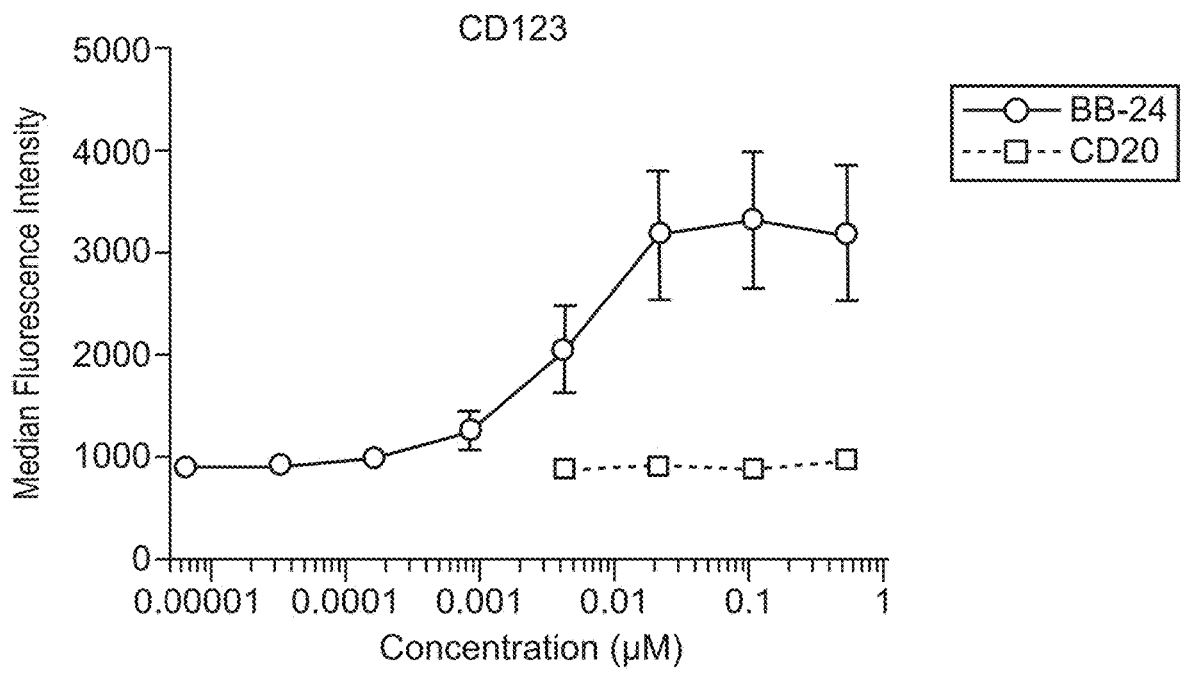

FIG. 108D shows that the rituximab immunoconjugate produced according to the BB-24 TFP conjugation method (BB-24) is superior at eliciting CD123 upregulation on myeloid cells as compared to the unconjugated rituximab (CD20, Alphamab) following 18 hours of stimulation.

Figure 108E:
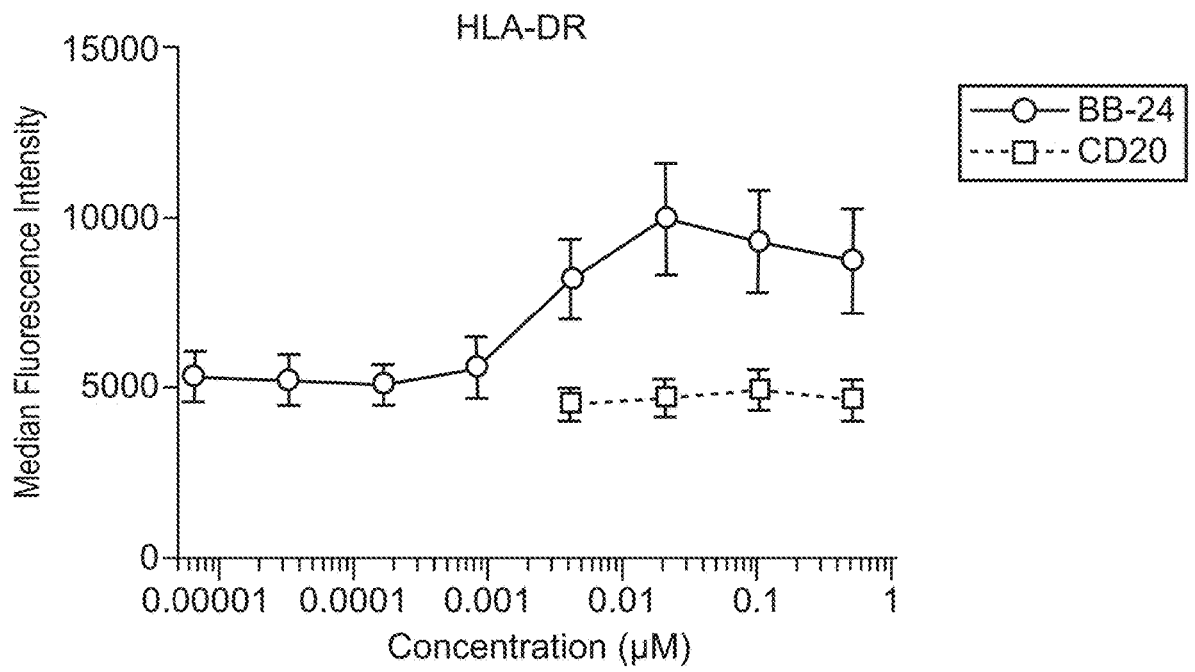

FIG. 108E shows that the rituximab immunoconjugate produced according to the BB-24 TFP conjugation method (BB-24) is superior at eliciting HLA-DR upregulation on myeloid cells as compared to the unconjugated rituximab (CD20, Alphamab) following 18 hours of stimulation.

Figure 108F:
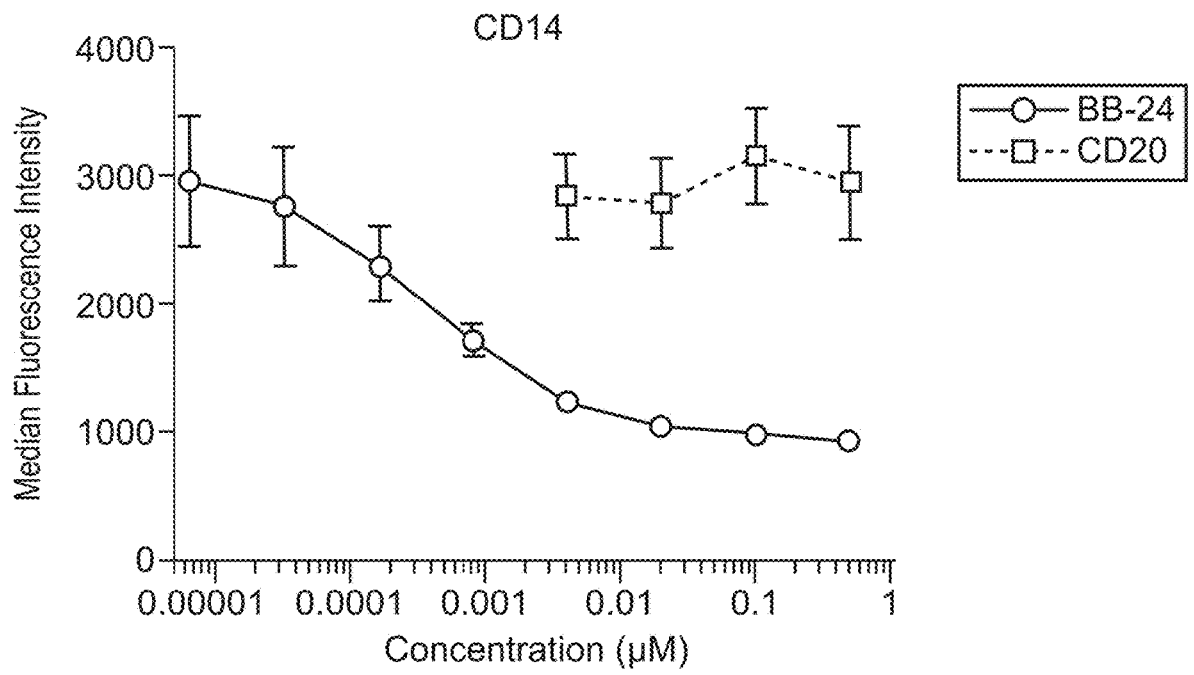

FIG. 108F shows that the rituximab immunoconjugate produced according to the BB-24 TFP conjugation method (BB-24) is superior at eliciting CD14 upregulation on myeloid cells as compared to the unconjugated rituximab (CD20, Alphamab) following 18 hours of stimulation.

Figure 108G:
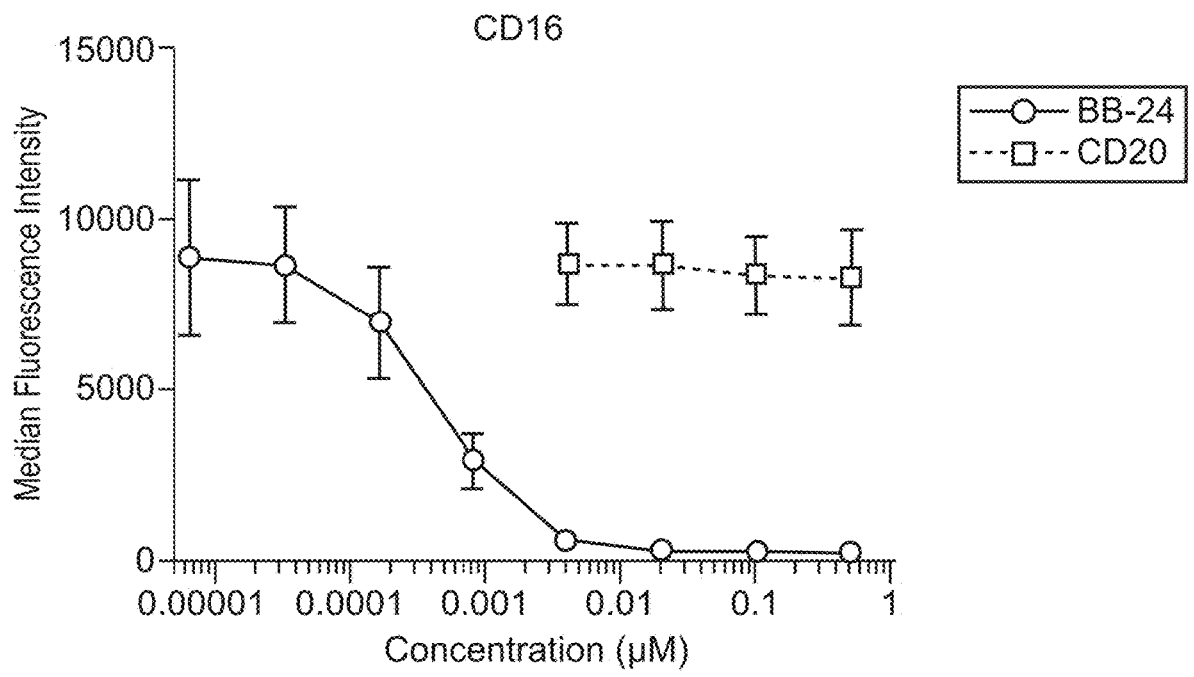

FIG. 108G shows that the rituximab immunoconjugate produced according to the BB-24 TFP conjugation method (BB-24) is superior at eliciting CD16 upregulation on myeloid cells as compared to the unconjugated rituximab (CD20, Alphamab) following 18 hours of stimulation.

Figure 108H:
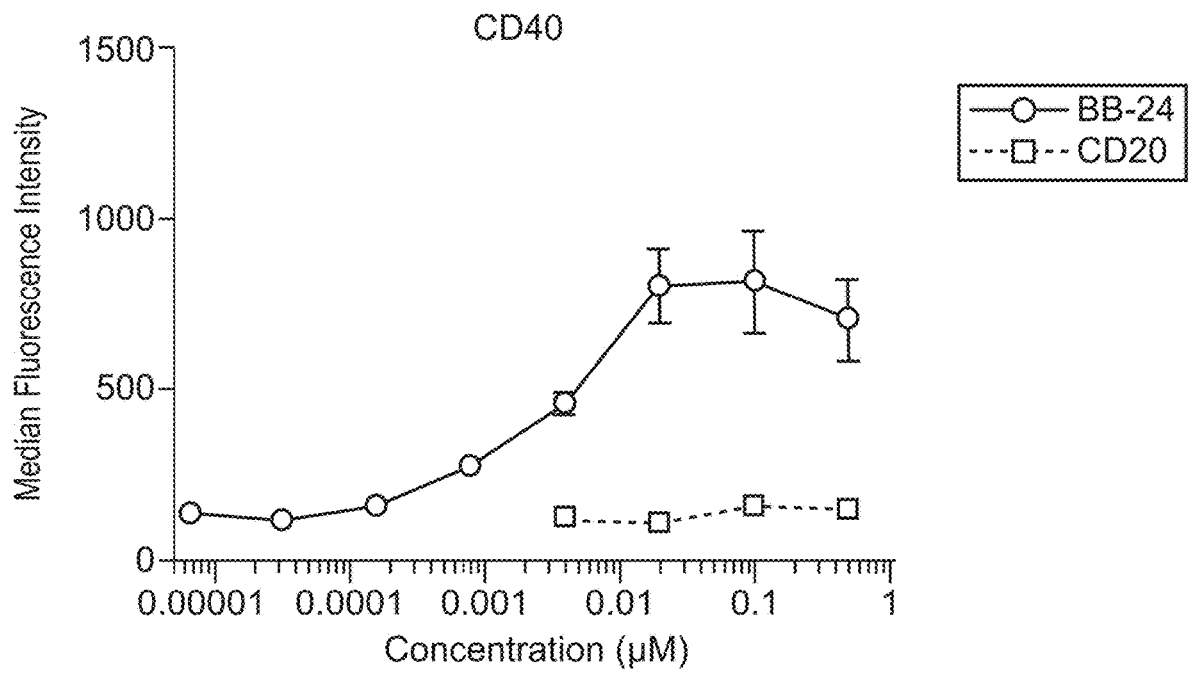

FIG. 108H shows that the rituximab immunoconjugate produced according to the BB-24 TFP conjugation method (BB-24) is superior at eliciting CD40 upregulation on myeloid cells as compared to the unconjugated rituximab (CD20, Alphamab) following 18 hours of stimulation.

Figure 108I:
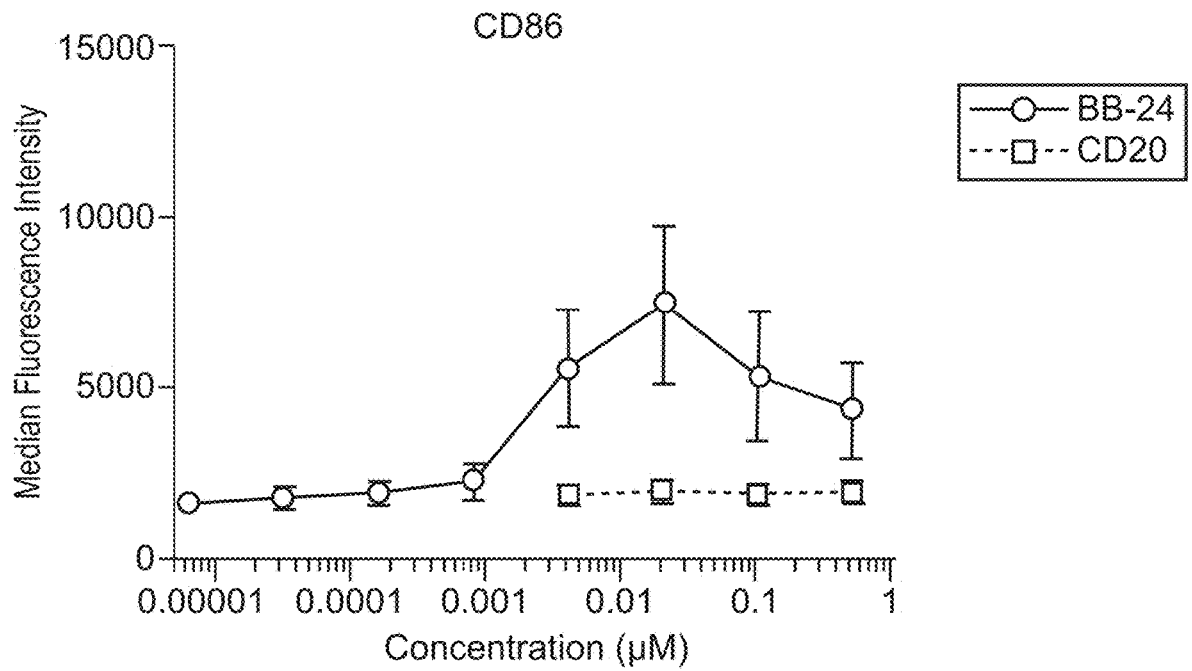

FIG. 108I shows that the rituximab immunoconjugate produced according to the BB-24 TFP conjugation method (BB-24) is superior at eliciting CD86 upregulation on myeloid cells as compared to the unconjugated rituximab (CD20, Alphamab) following 18 hours of stimulation.

FIG. 109A shows a liquid chromatography-mass spectrometry analysis of the BB-26 immunoconjugate produced according to the BB-26 TFP conjugation method following overnight deglycosylation with PNGase F.

Figure 109B:
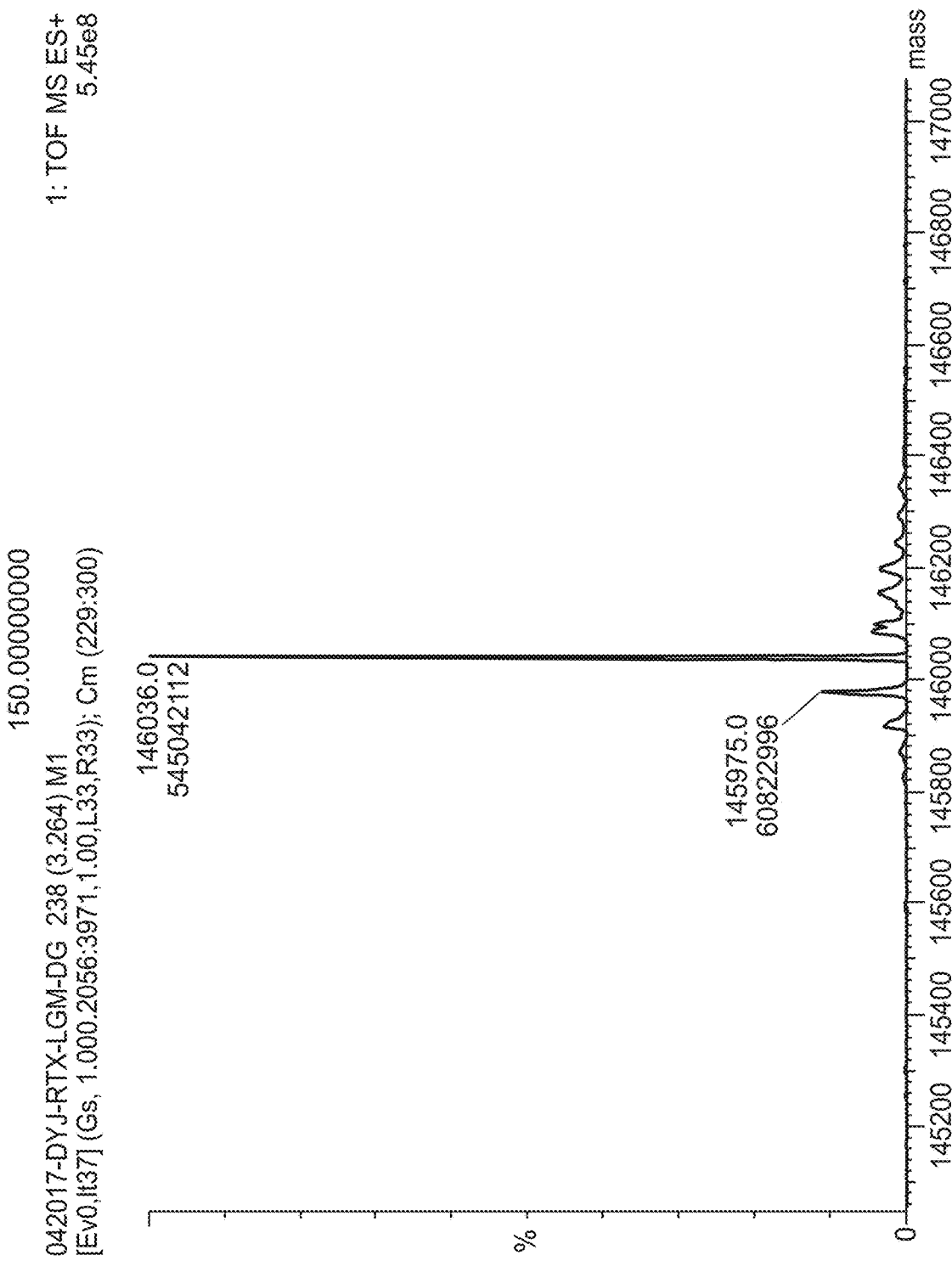

FIG. 109B shows a liquid chromatography-mass spectrometry analysis of the unconjugated rituximab biosimilar (CD20, LGM Pharma) that was utilized to produce the rituximab immunoconjugate according to the BB-26 TFP conjugation method following overnight deglycosylation with PNGase F.

FIG. 109C shows a liquid chromatography-mass spectrometry analysis of the unconjugated rituximab biosimilar (CD20, LGM Pharma) that was utilized to produce the rituximab immunoconjugate according to the BB-26 TFP conjugation method.

Figure 109D:
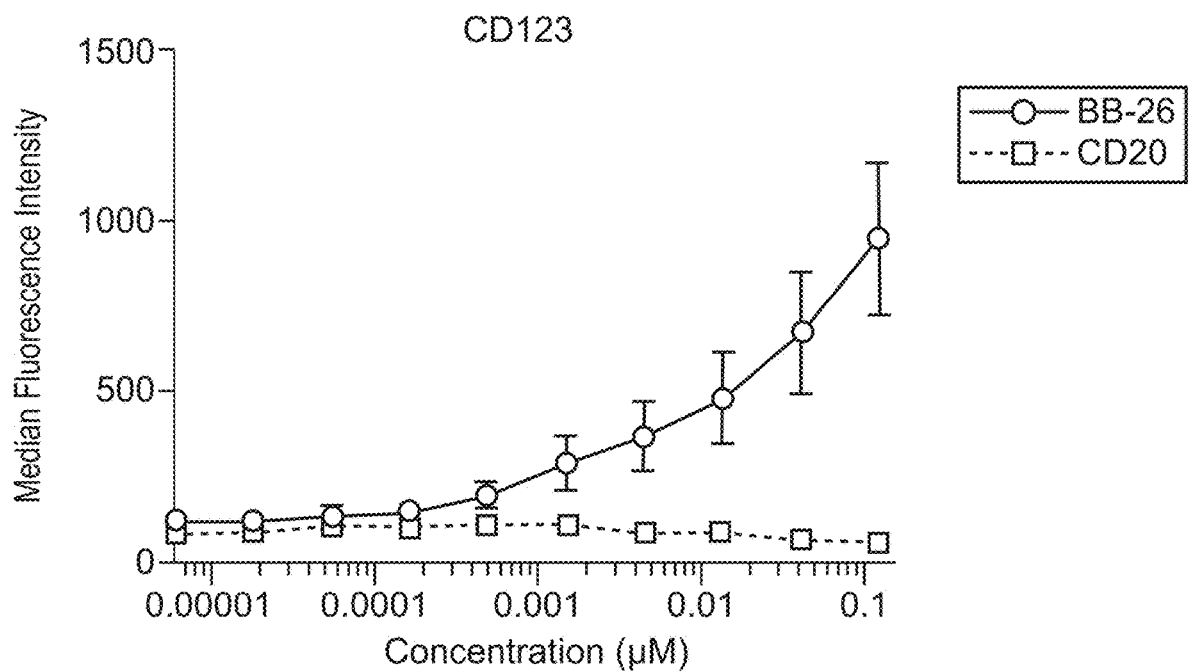

FIG. 109D shows that the rituximab immunoconjugate produced according to the BB-26 TFP conjugation method (BB-26) is superior at eliciting CD123 upregulation on myeloid cells as compared to the unconjugated rituximab (CD20, LGM Pharma) following 18 hours of stimulation.

Figure 109E:
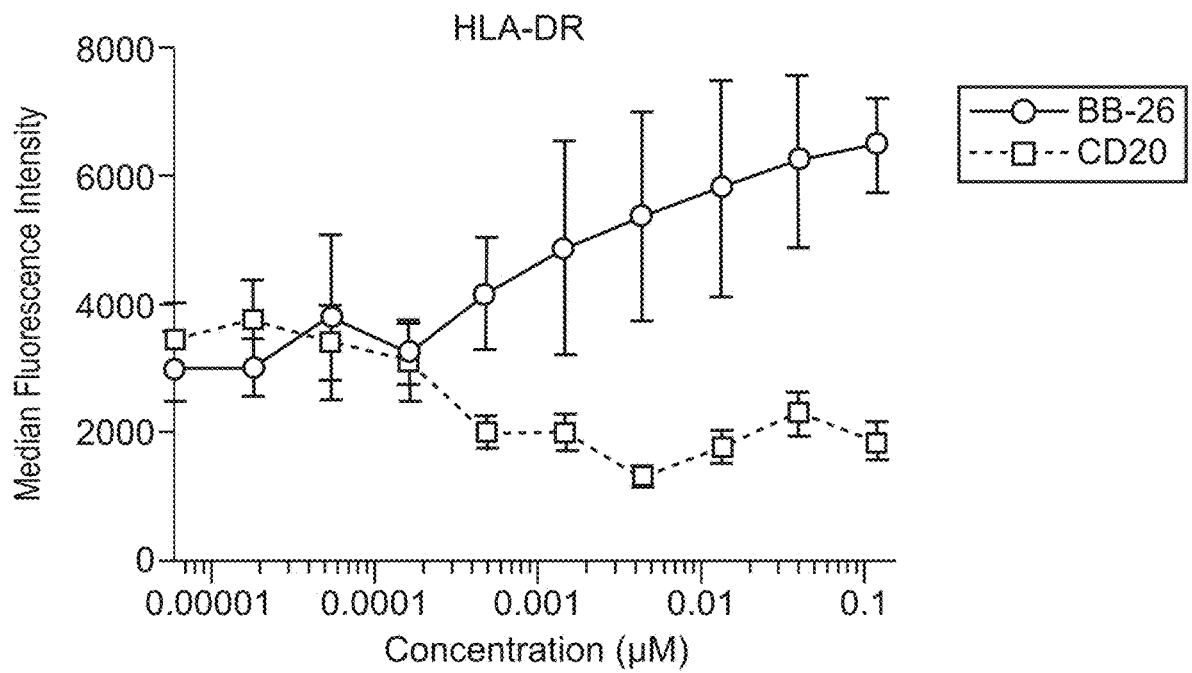

FIG. 109E shows that the rituximab immunoconjugate produced according to the BB-26 TFP conjugation method (BB-26) is superior at eliciting HLA-DR upregulation on myeloid cells as compared to the unconjugated rituximab (CD20, LGM Pharma) following 18 hours of stimulation.

Figure 109F:
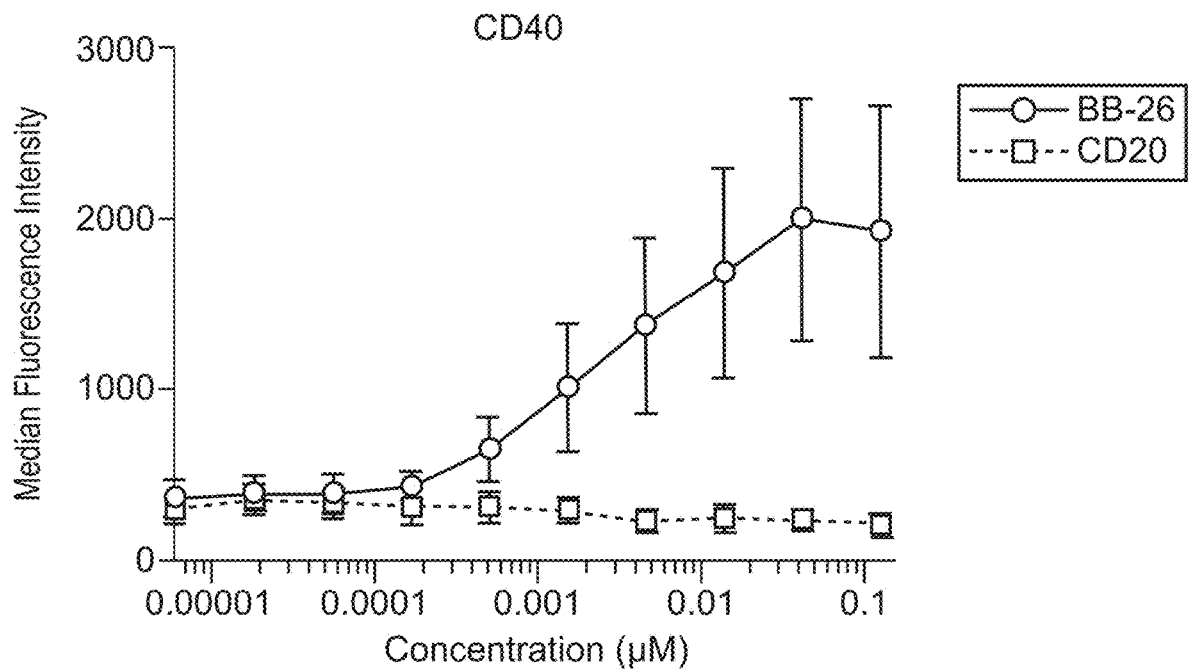

FIG. 109F shows that the rituximab immunoconjugate produced according to the BB-26 TFP conjugation method (BB-26) is superior at eliciting CD40 upregulation on myeloid cells as compared to the unconjugated rituximab (CD20, LGM Pharma) following 18 hours of stimulation.

Figure 109G:
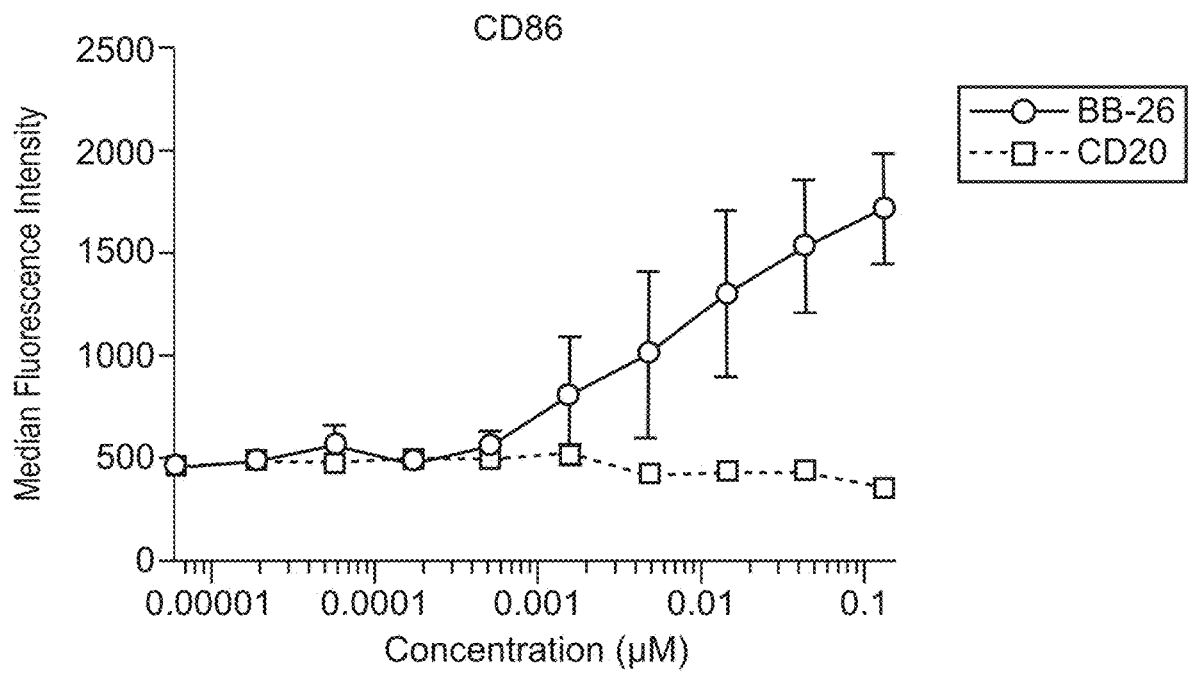

FIG. 109G shows that the rituximab immunoconjugate produced according to the BB-26 TFP conjugation method (BB-26) is superior at eliciting CD86 upregulation on myeloid cells as compared to the unconjugated rituximab (CD20, LGM Pharma) following 18 hours of stimulation.

Figure 110A:
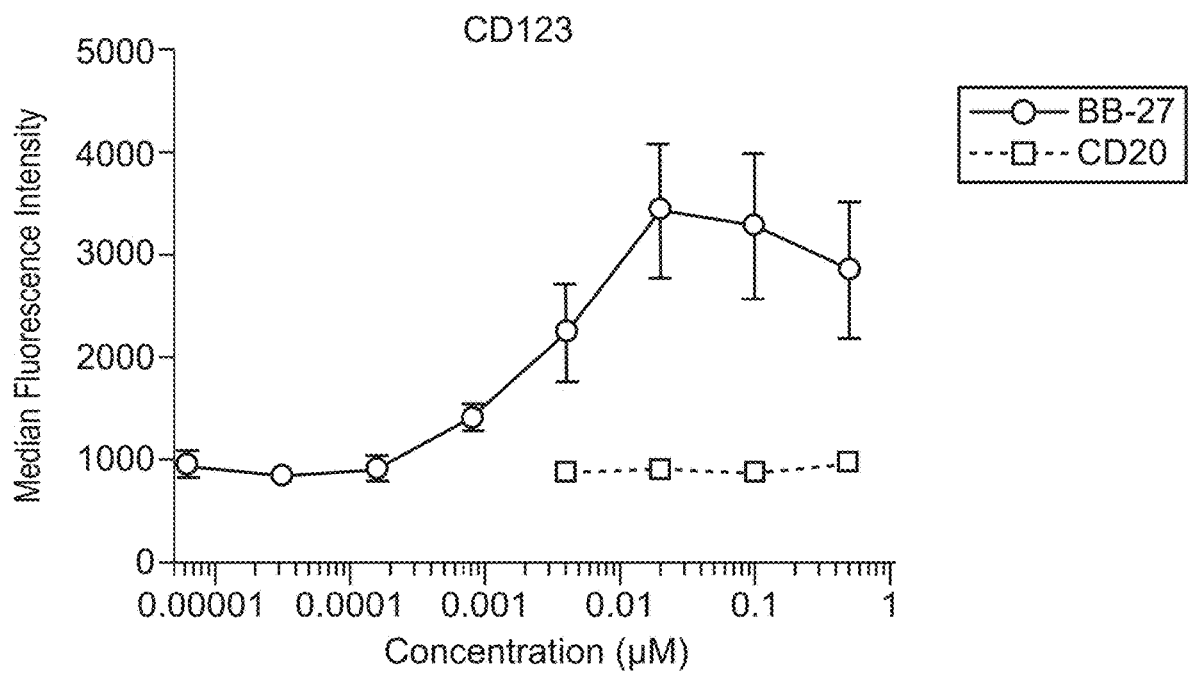

FIG. 110A shows that the rituximab immunoconjugate produced according to the BB-27 TFP conjugation method (BB-27) is superior at eliciting CD123 upregulation on myeloid cells as compared to the unconjugated rituximab (CD20, LGM Pharma) following 18 hours of stimulation.

Figure 110B:
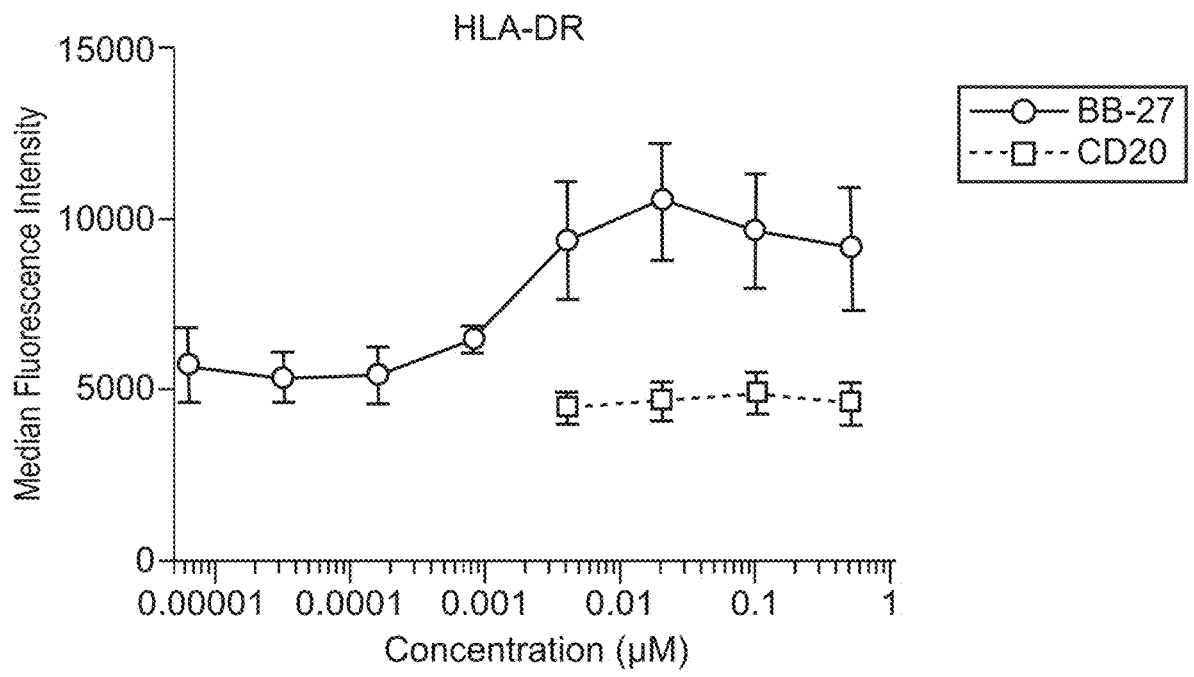

FIG. 110B shows that the rituximab immunoconjugate produced according to the BB-27 TFP conjugation method (BB-27) is superior at eliciting HLA-DR upregulation on myeloid cells as compared to the unconjugated rituximab (CD20, LGM Pharma) following 18 hours of stimulation.

Figure 110C:
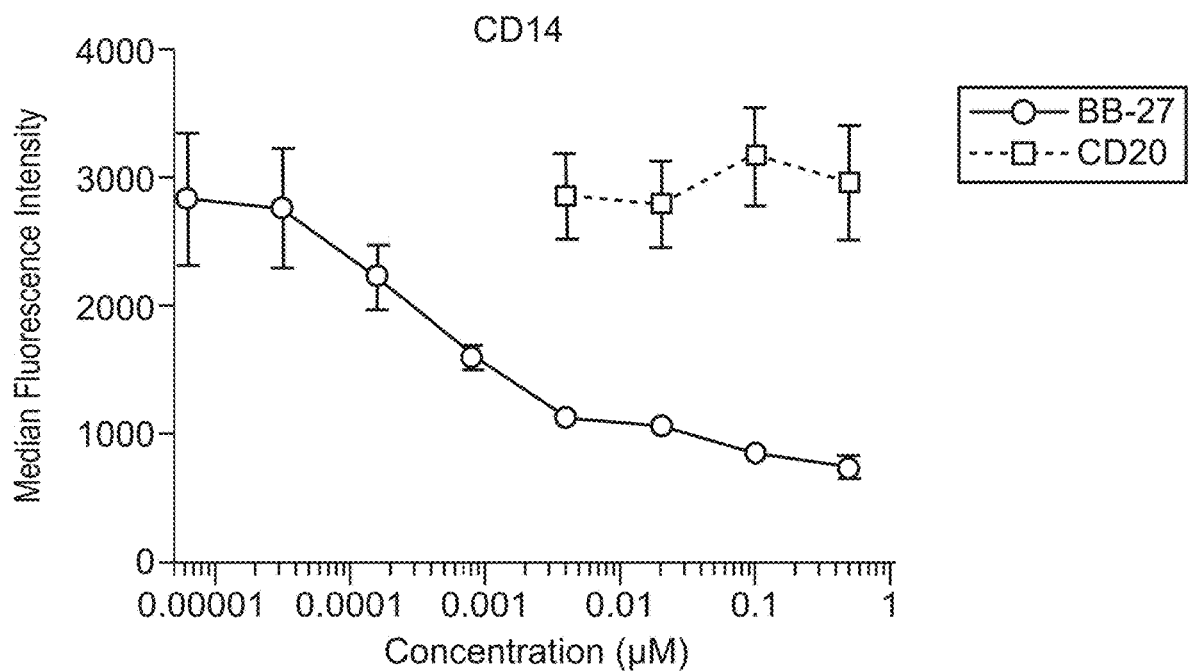

FIG. 110C shows that the rituximab immunoconjugate produced according to the BB-27 TFP conjugation method (BB-27) is superior at eliciting CD14 upregulation on myeloid cells as compared to the unconjugated rituximab (CD20, LGM Pharma) following 18 hours of stimulation.

Figure 110D:
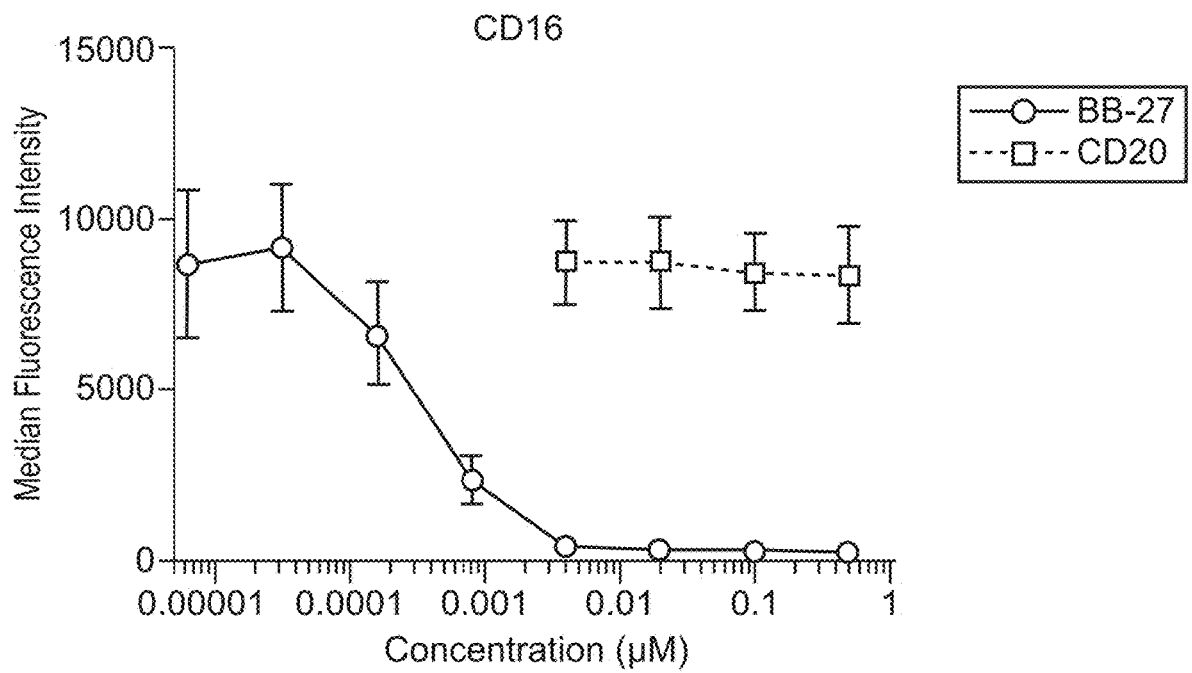

FIG. 110D shows that the rituximab immunoconjugate produced according to the BB-27 TFP conjugation method (BB-27) is superior at eliciting CD16 upregulation on myeloid cells as compared to the unconjugated rituximab (CD20, LGM Pharma) following 18 hours of stimulation.

Figure 110E:
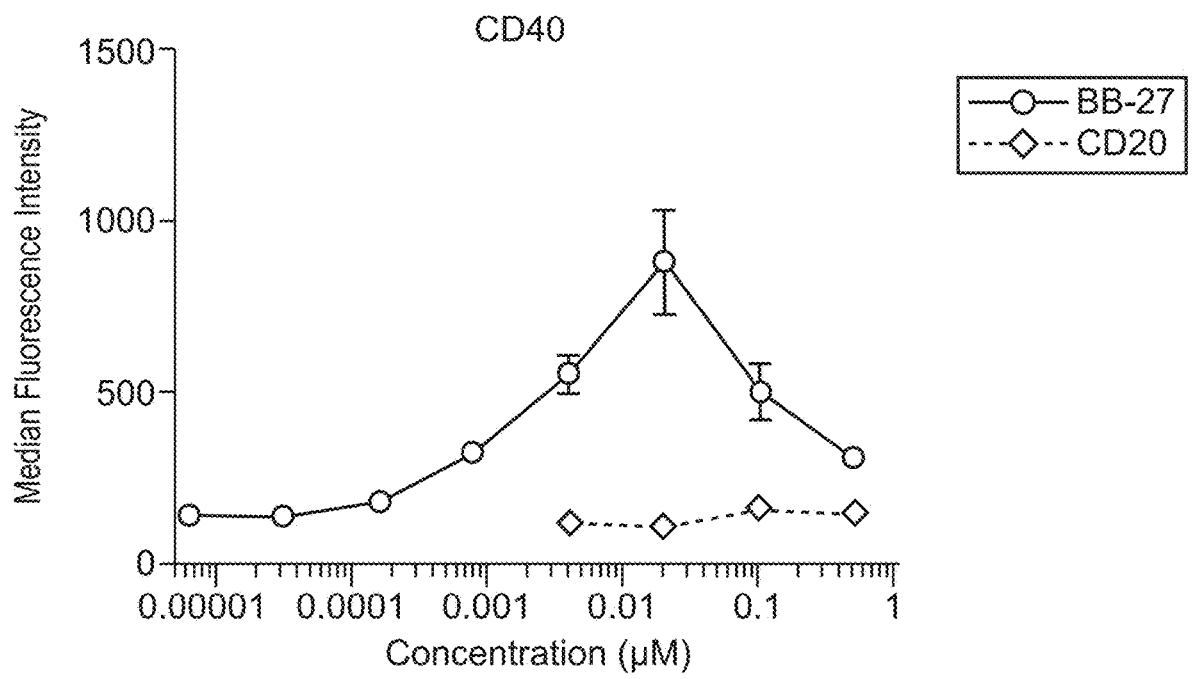

FIG. 110E shows that the rituximab immunoconjugate produced according to the BB-27 TFP conjugation method (BB-27) is superior at eliciting CD40 upregulation on myeloid cells as compared to the unconjugated rituximab (CD20, LGM Pharma) following 18 hours of stimulation.

Figure 110F:
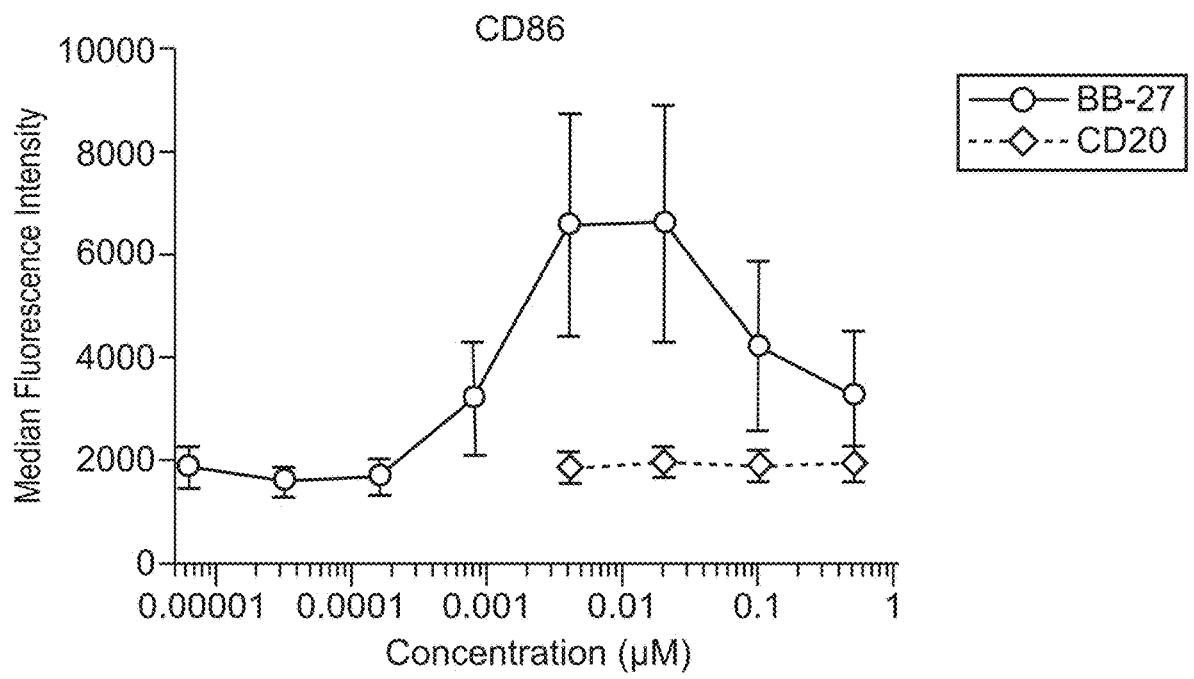

FIG. 110F shows that the rituximab immunoconjugate produced according to the BB-27 TFP conjugation method (BB-27) is superior at eliciting CD86 upregulation on myeloid cells as compared to the unconjugated rituximab (CD20, LGM Pharma) following 18 hours of stimulation.

Figure 110G:
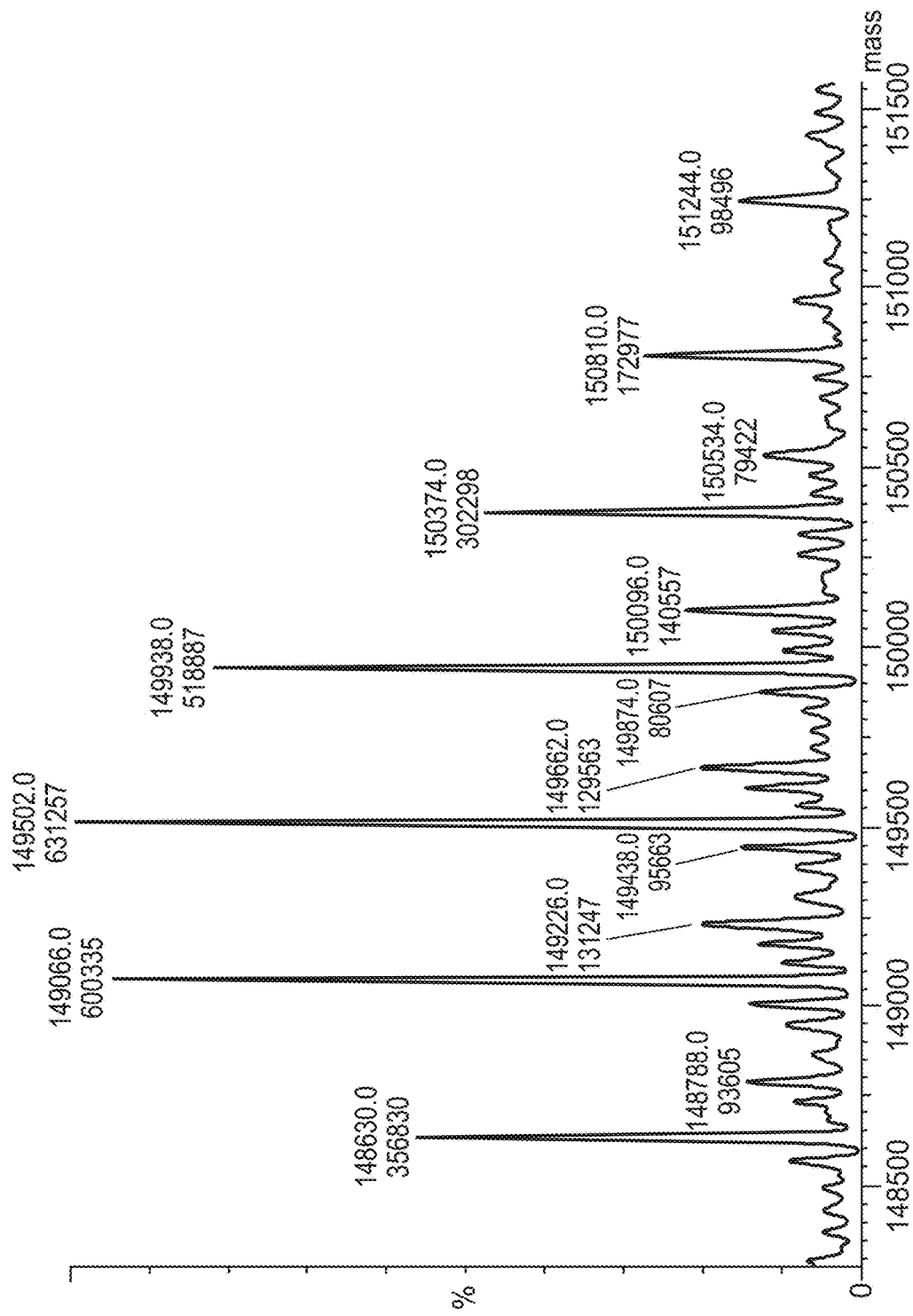

FIG. 110G shows a liquid chromatography-mass spectrometry analysis of the BB-27 immunoconjugate produced according to the BB-27 TFP conjugation method following overnight deglycosylation with PNGase F.

FIG. 110H shows a liquid chromatography-mass spectrometry analysis of the unconjugated rituximab biosimilar (CD20, LGM Pharma) that was utilized to produce the rituximab immunoconjugate according to the BB-27 TFP conjugation method following overnight deglycosylation with PNGase F.

FIG. 110I shows a liquid chromatography-mass spectrometry analysis of the unconjugated rituximab biosimilar (CD20, LGM Pharma) that was utilized to produce the rituximab immunoconjugate according to the BB-27 TFP conjugation method.

Figure 111A:
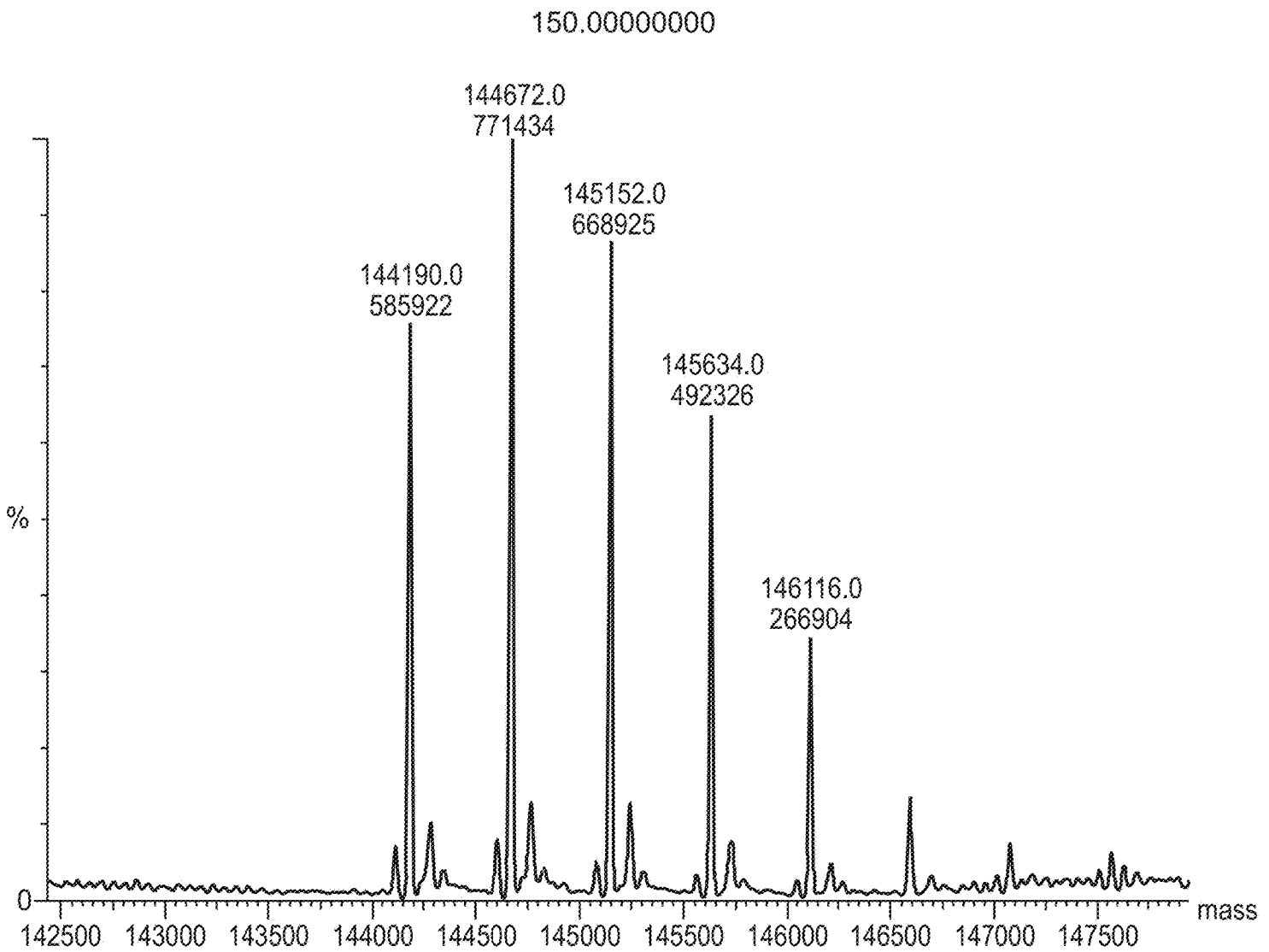

FIG. 111A shows a liquid chromatography-mass spectrometry analysis of the BB-36 immunoconjugate produced according to the BB-36 TFP conjugation method following overnight deglycosylation with PNGase F.

FIG. 111B shows a liquid chromatography-mass spectrometry analysis of the unconjugated rituximab biosimilar (CD20, Alphamab) that was utilized to produce the rituximab immunoconjugate according to the BB-36 TFP conjugation method.

Figure 111C:
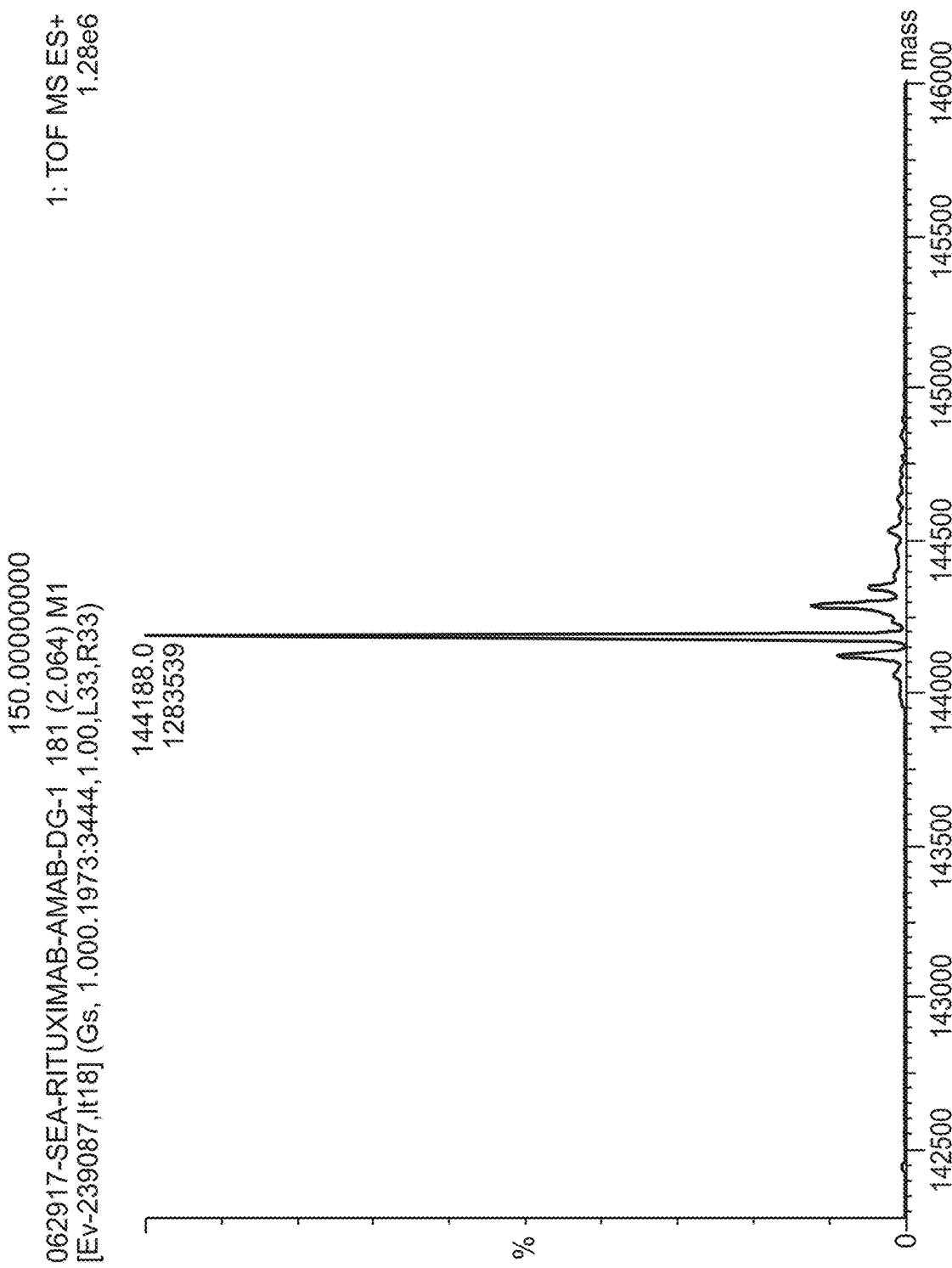

FIG. 111C shows a liquid chromatography-mass spectrometry analysis of the unconjugated rituximab biosimilar (CD20, Alphamab) that was utilized to produce the rituximab immunoconjugate according to the BB-36 TFP conjugation method following overnight deglycosylation with PNGase F.

Figure 111D:
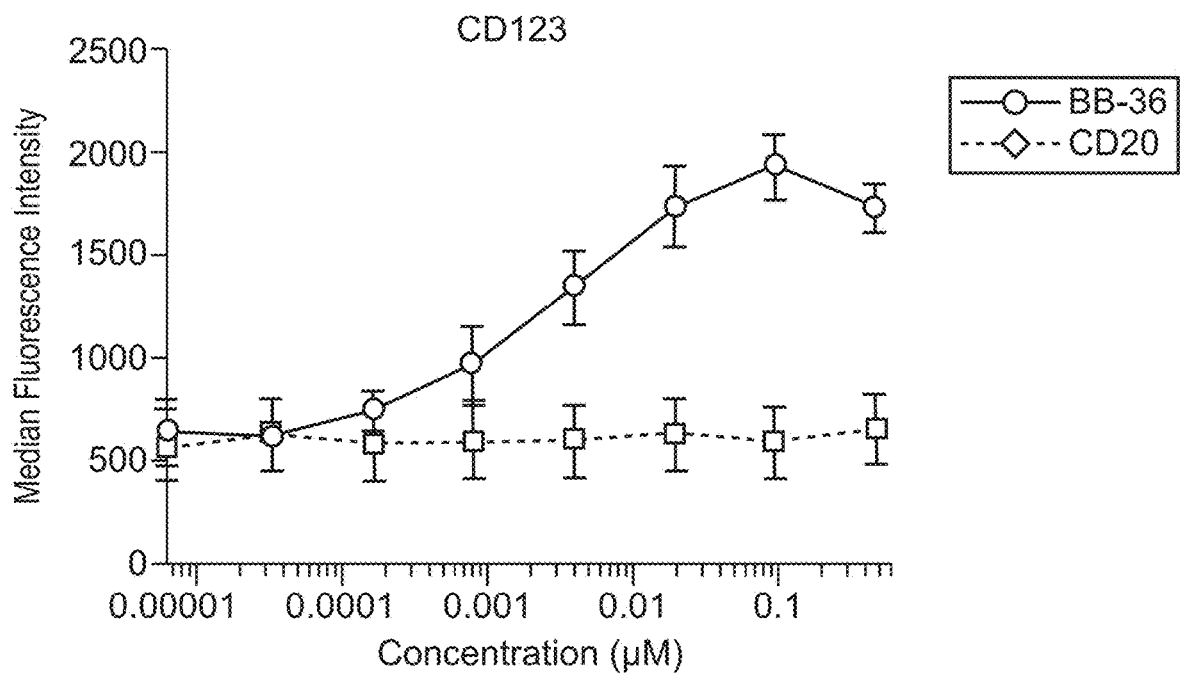

FIG. 111D shows that the rituximab immunoconjugate produced according to the BB-36 TFP conjugation method (BB-36) is superior at eliciting CD123 upregulation on myeloid cells as compared to the unconjugated rituximab (CD20, Alphamab) following 18 hours of stimulation.

Figure 111E:
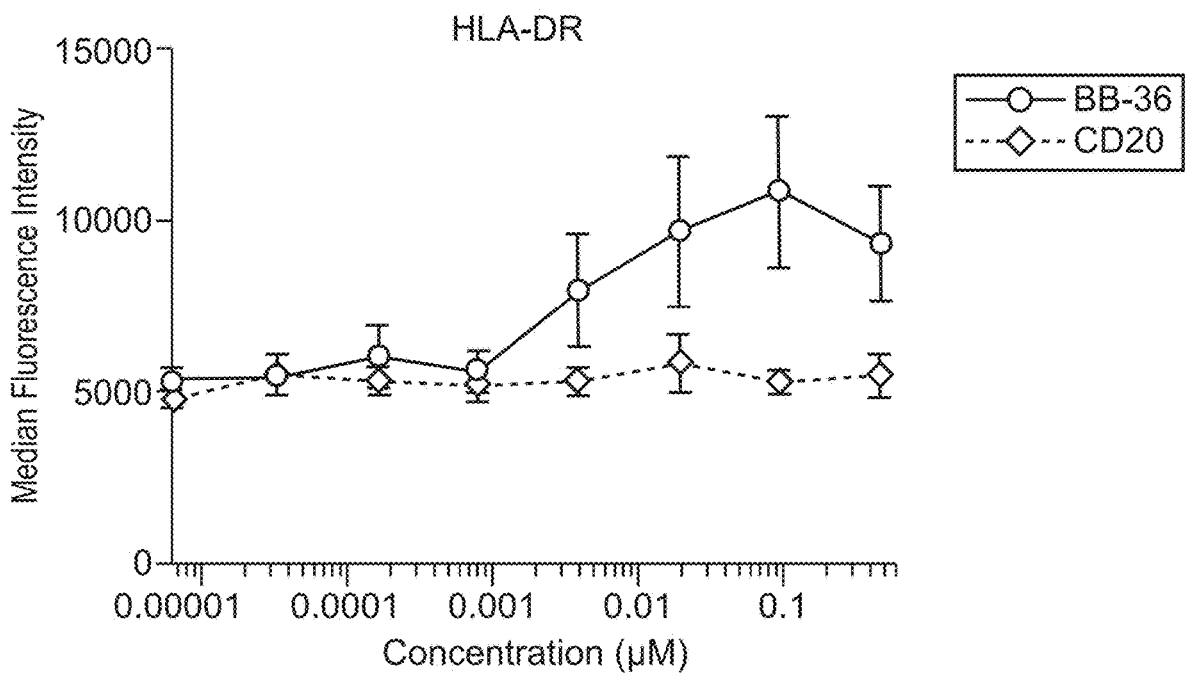

FIG. 111E shows that the rituximab immunoconjugate produced according to the BB-36 TFP conjugation method (BB-36) is superior at eliciting HLA-DR upregulation on myeloid cells as compared to the unconjugated rituximab (CD20, Alphamab) following 18 hours of stimulation.

Figure 111F:
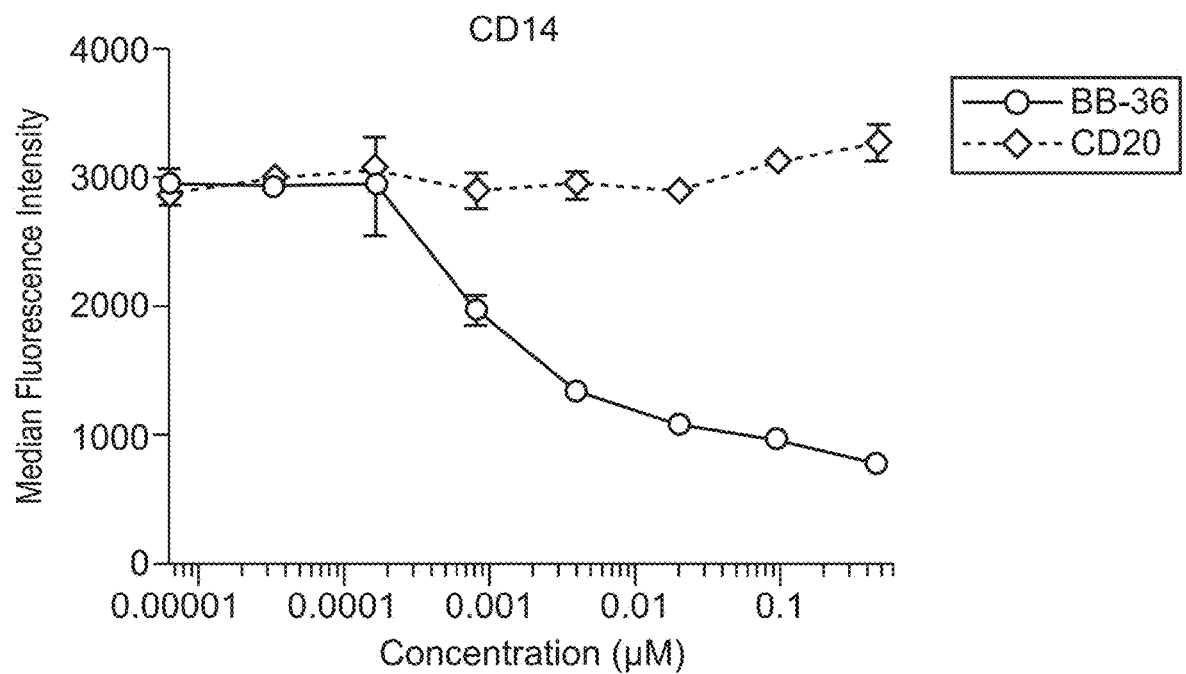

FIG. 111F shows that the rituximab immunoconjugate produced according to the BB-36 TFP conjugation method (BB-36) is superior at eliciting CD14 upregulation on myeloid cells as compared to the unconjugated rituximab (CD20, Alphamab) following 18 hours of stimulation.

Figure 111G:
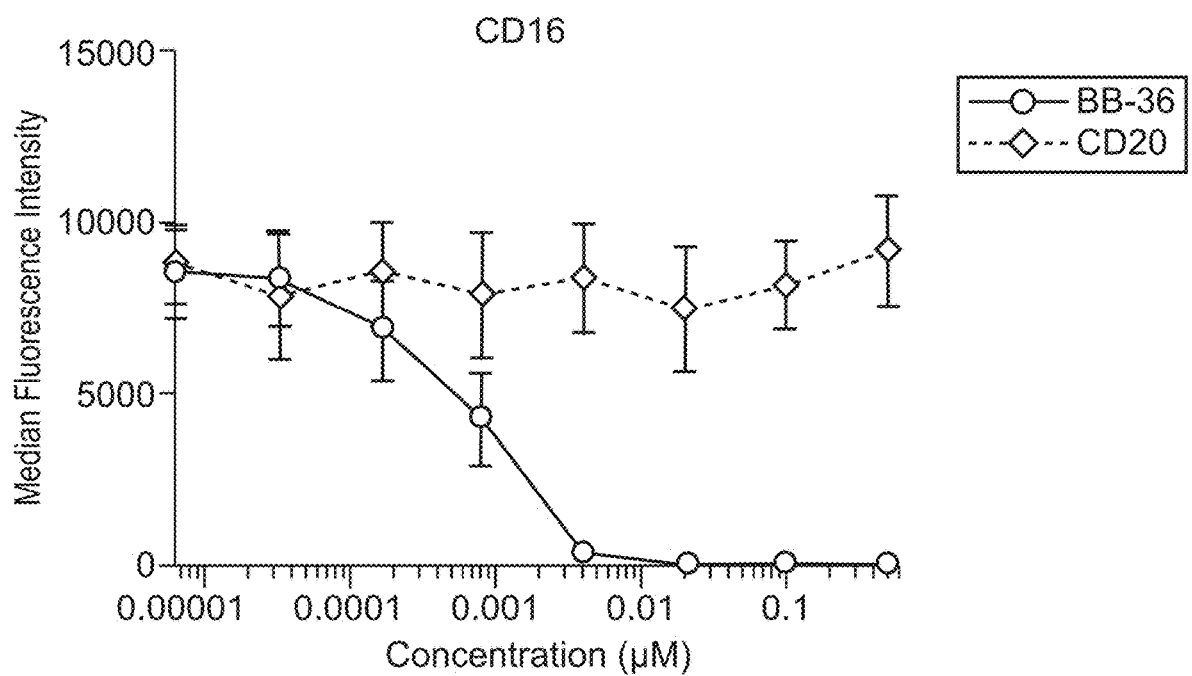

FIG. 111G shows that the rituximab immunoconjugate produced according to the BB-36 TFP conjugation method (BB-36) is superior at eliciting CD16 upregulation on myeloid cells as compared to the unconjugated rituximab (CD20, Alphamab) following 18 hours of stimulation.

Figure 111H:
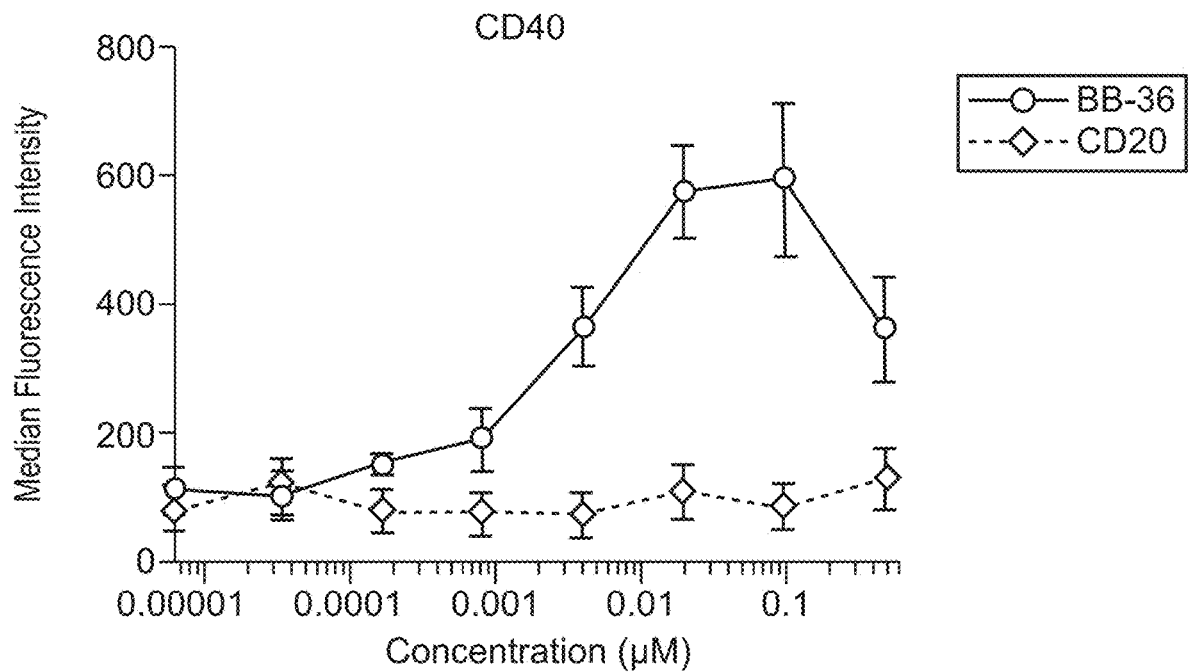

FIG. 111H shows that the rituximab immunoconjugate produced according to the BB-36 TFP conjugation method (BB-36) is superior at eliciting CD40 upregulation on myeloid cells as compared to the unconjugated rituximab (CD20, Alphamab) following 18 hours of stimulation.

Figure 111I:
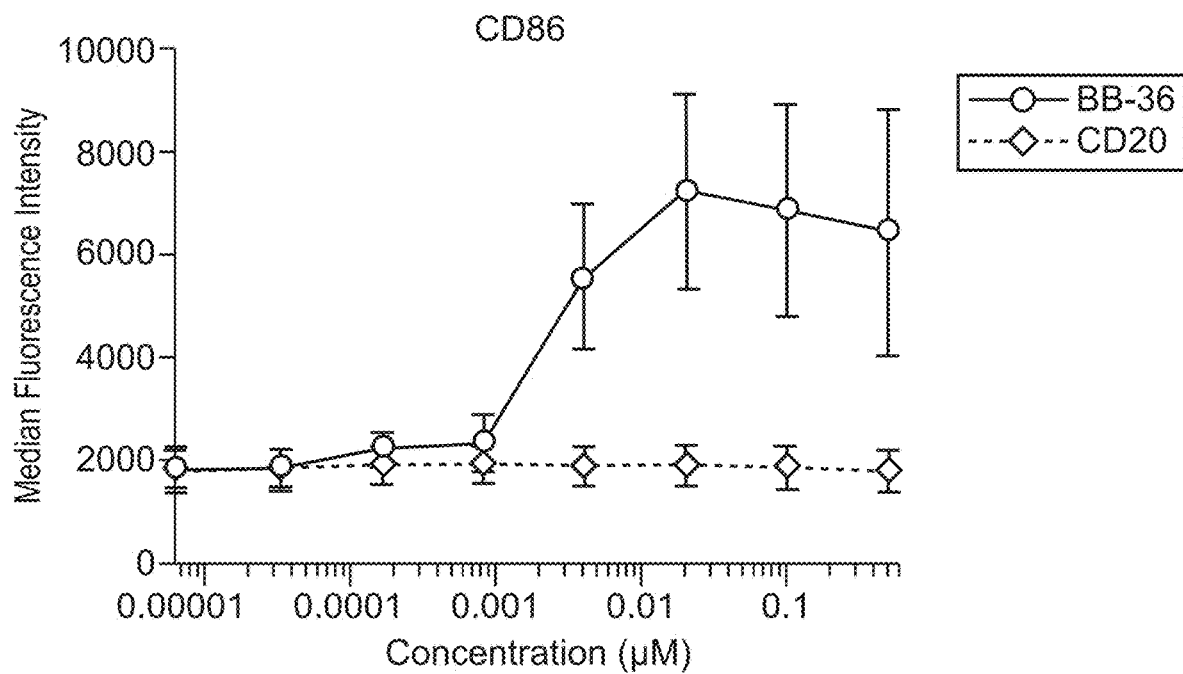

FIG. 111I shows that the rituximab immunoconjugate produced according to the BB-36 TFP conjugation method (BB-36) is superior at eliciting CD86 upregulation on myeloid cells as compared to the unconjugated rituximab (CD20, Alphamab) following 18 hours of stimulation.

FIG. 112A shows a liquid chromatography-mass spectrometry analysis of the BB-37 immunoconjugate produced according to the BB-37 TFP conjugation method.

Figure 112B:
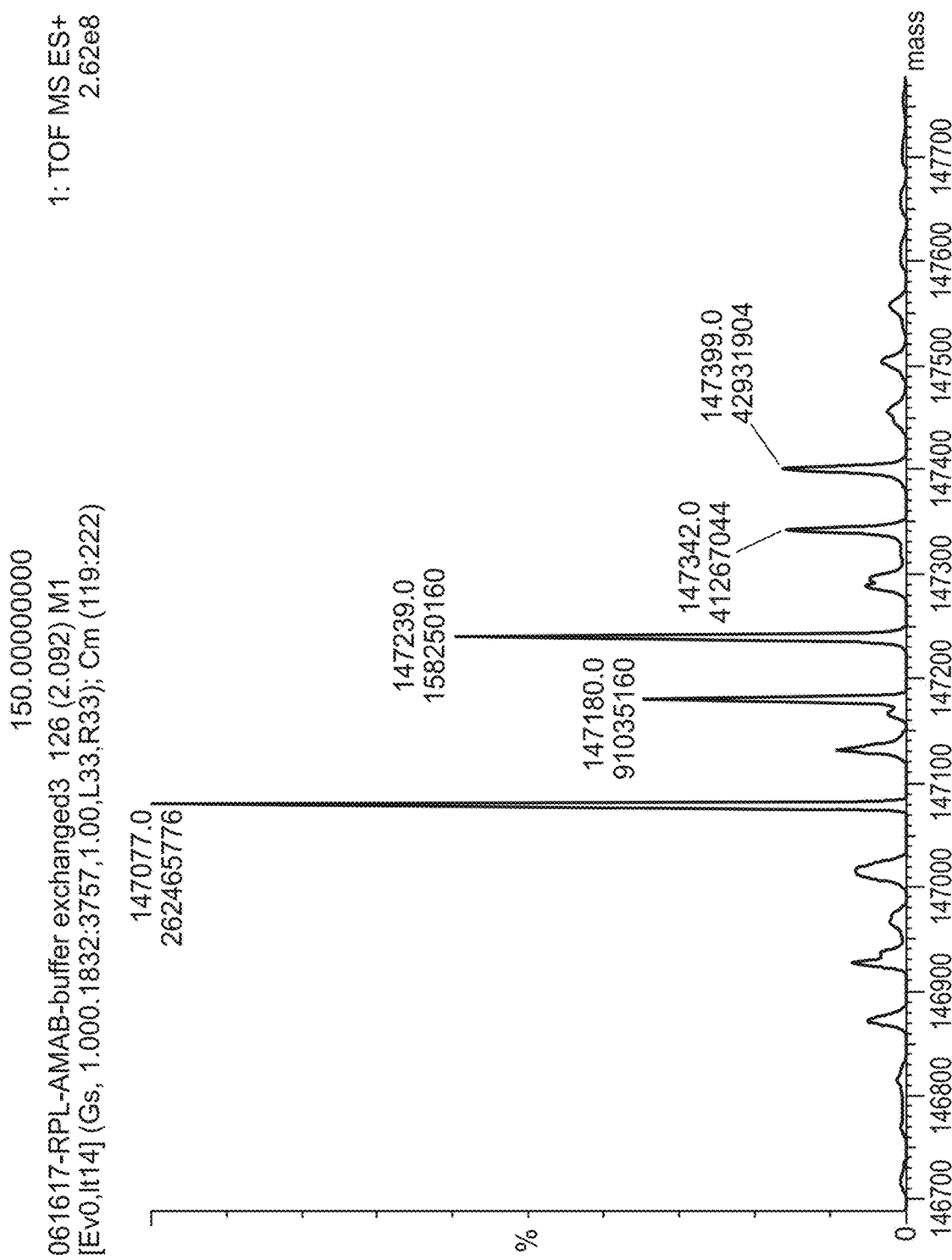

FIG. 112B shows a liquid chromatography-mass spectrometry analysis of the unconjugated rituximab biosimilar (CD20, Alphamab) that was utilized to produce the rituximab immunoconjugate according to the BB-37 TFP conjugation method.

Figure 112C:
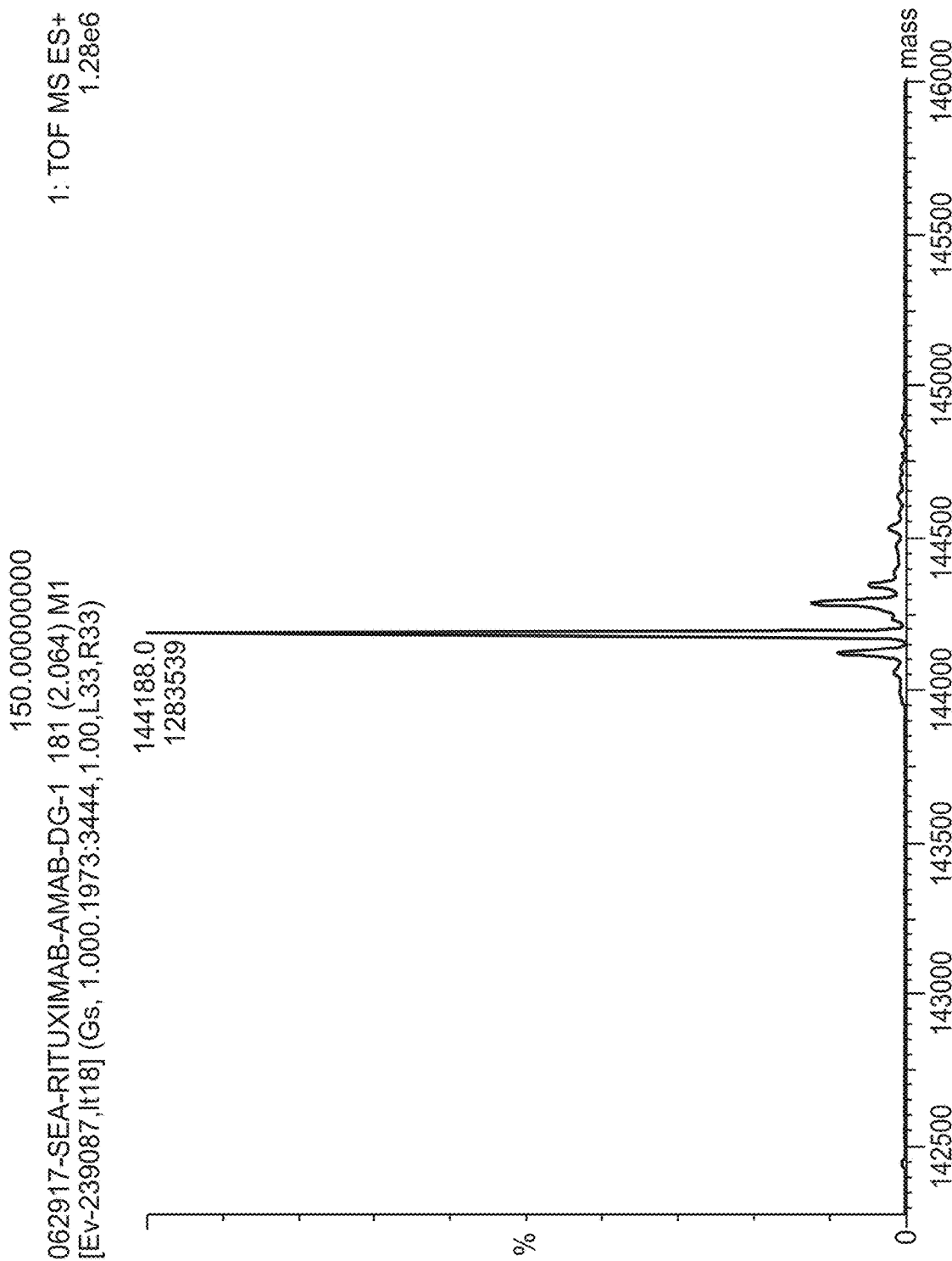

FIG. 112C shows a liquid chromatography-mass spectrometry analysis of the unconjugated rituximab biosimilar (CD20, Alphamab) that was utilized to produce the rituximab immunoconjugate according to the BB-37 TFP conjugation method following overnight deglycosylation with PNGase F.

Figure 112D:
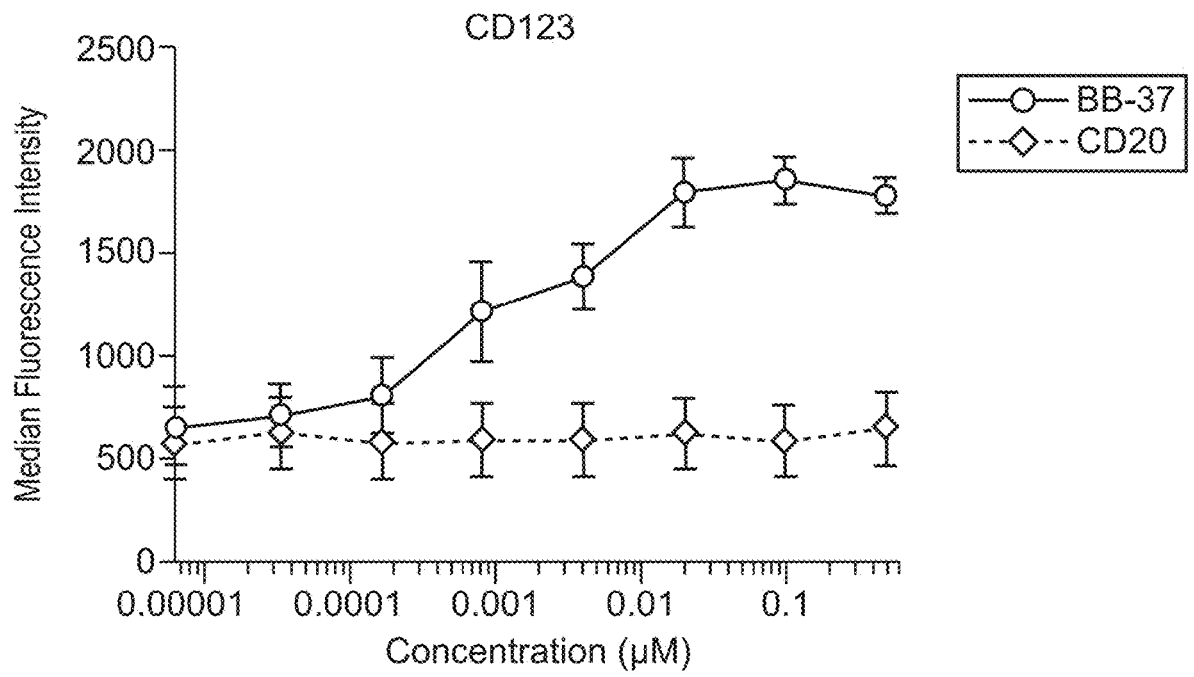

FIG. 112D shows that the rituximab immunoconjugate produced according to the BB-37 TFP conjugation method (BB-37) is superior at eliciting CD123 upregulation on myeloid cells as compared to the unconjugated rituximab (CD20, Alphamab) following 18 hours of stimulation.

Figure 112E:
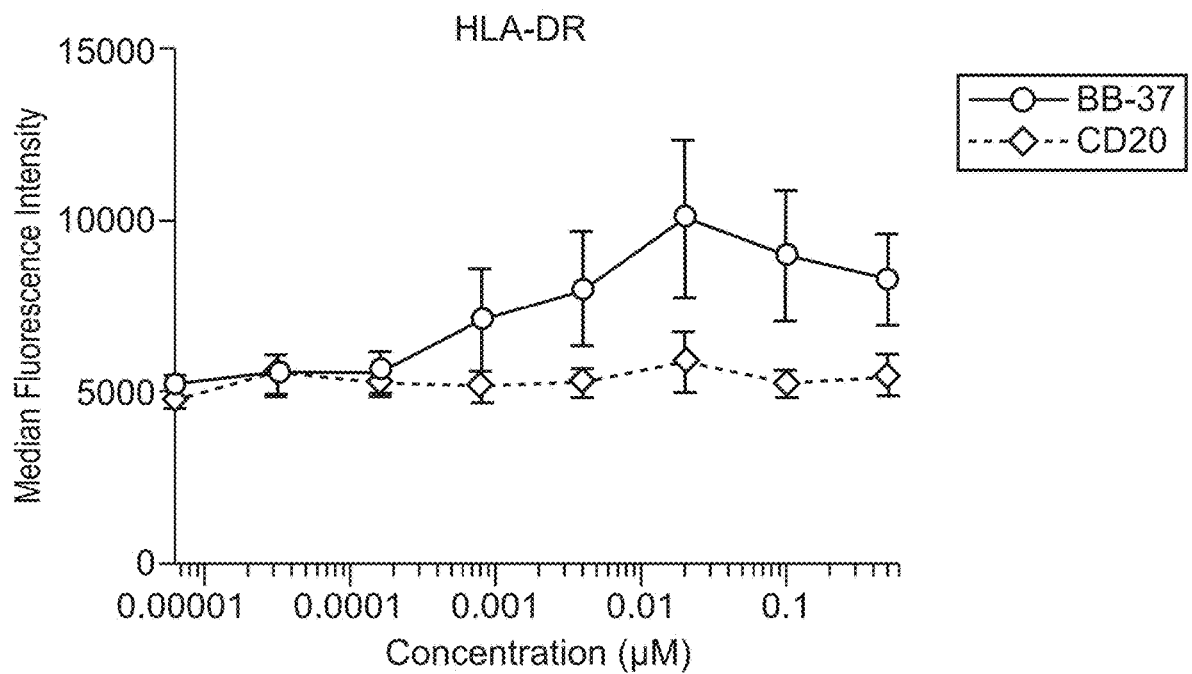

FIG. 112E shows that the rituximab immunoconjugate produced according to the BB-37 TFP conjugation method (BB-37) is superior at eliciting HLA-DR upregulation on myeloid cells as compared to the unconjugated rituximab (CD20, Alphamab) following 18 hours of stimulation.

Figure 112F:
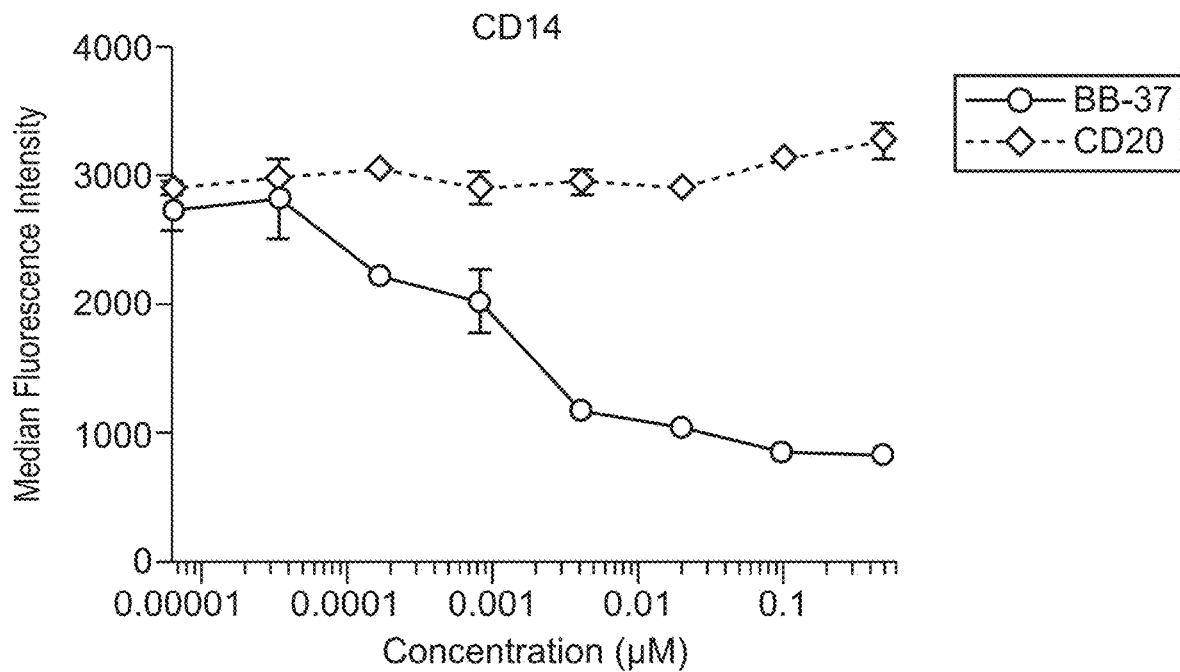

FIG. 112F shows that the rituximab immunoconjugate produced according to the BB-37 TFP conjugation method (BB-37) is superior at eliciting CD14 upregulation on myeloid cells as compared to the unconjugated rituximab (CD20, Alphamab) following 18 hours of stimulation.

Figure 112G:
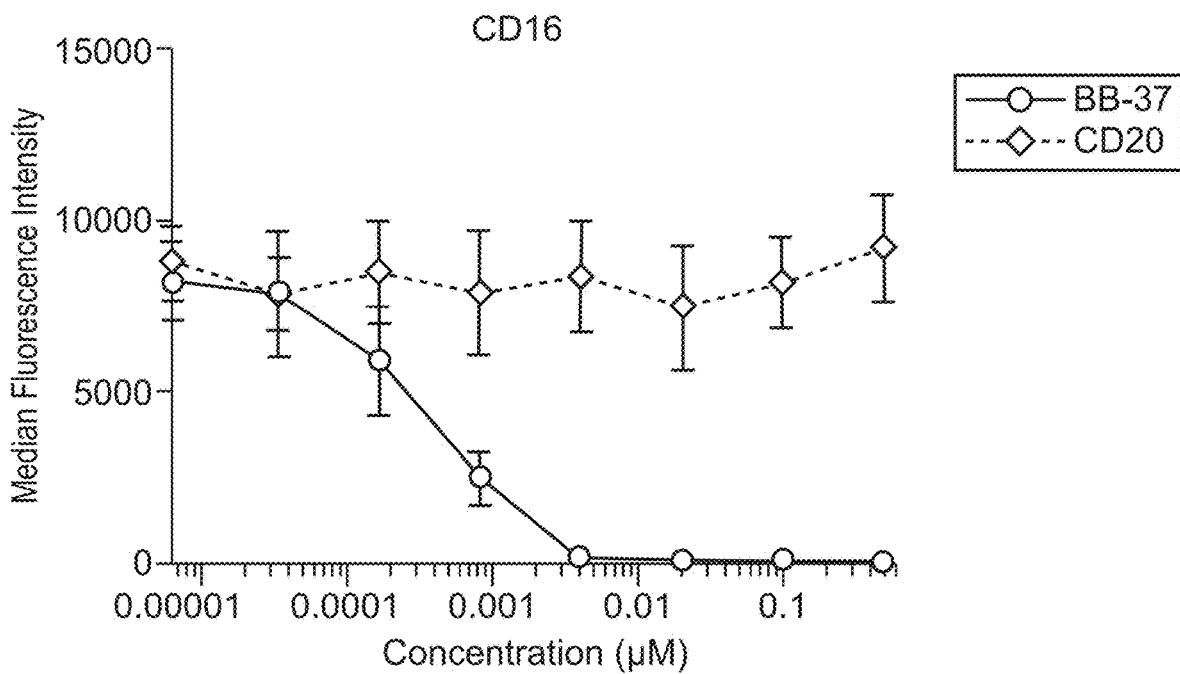

FIG. 112G shows that the rituximab immunoconjugate produced according to the BB-37 TFP conjugation method (BB-37) is superior at eliciting CD16 upregulation on myeloid cells as compared to the unconjugated rituximab (CD20, Alphamab) following 18 hours of stimulation.

Figure 112H:
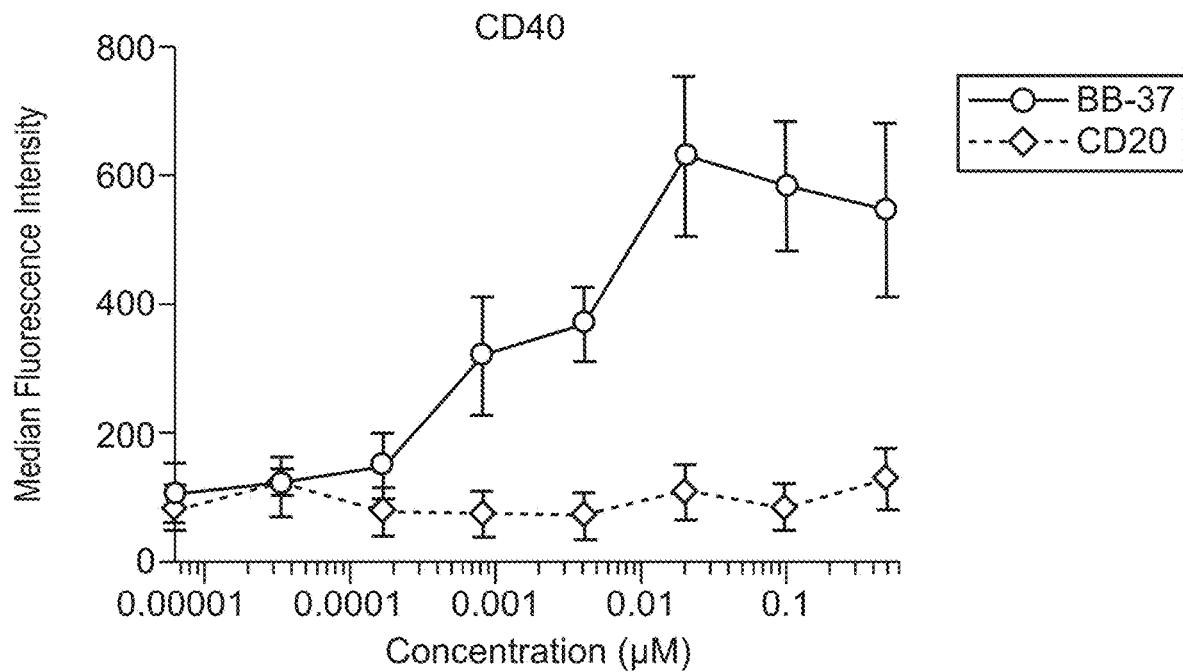

FIG. 112H shows that the rituximab immunoconjugate produced according to the BB-37 TFP conjugation method (BB-37) is superior at eliciting CD40 upregulation on myeloid cells as compared to the unconjugated rituximab (CD20, Alphamab) following 18 hours of stimulation.

Figure 112I:
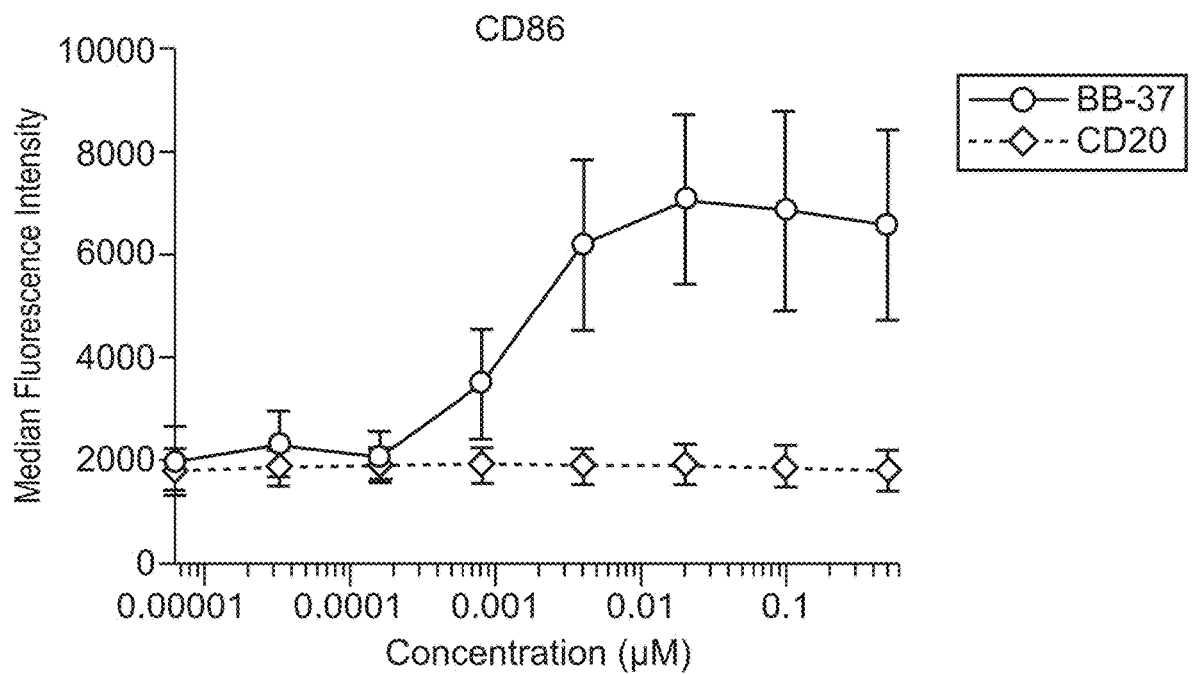

FIG. 112I shows that the rituximab immunoconjugate produced according to the BB-37 TFP conjugation method (BB-37) is superior at eliciting CD86 upregulation on myeloid cells as compared to the unconjugated rituximab (CD20, Alphamab) following 18 hours of stimulation.

FIG. 113A shows a liquid chromatography-mass spectrometry analysis of the BB-45 immunoconjugate produced according to the BB-45 TFP conjugation method.

Figure 113B:
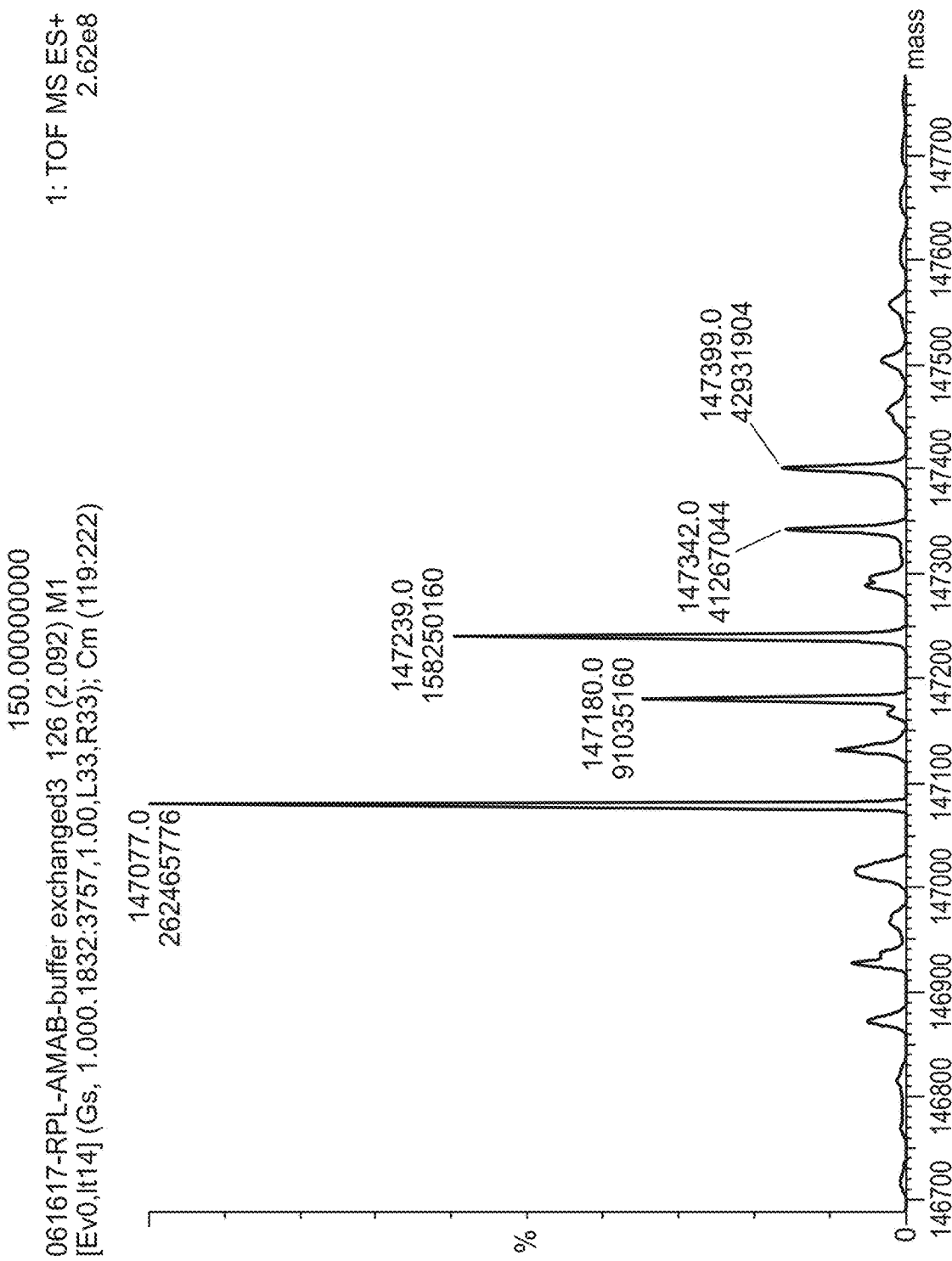

FIG. 113B shows a liquid chromatography-mass spectrometry analysis of the unconjugated rituximab biosimilar (CD20, Alphamab) that was utilized to produce the rituximab immunoconjugate according to the BB-45 TFP conjugation method.

FIG. 113C shows a liquid chromatography-mass spectrometry analysis of the unconjugated rituximab biosimilar (CD20, Alphamab) that was utilized to produce the rituximab immunoconjugate according to the BB-45 TFP conjugation method following overnight deglycosylation with PNGase F.

Figure 113D:
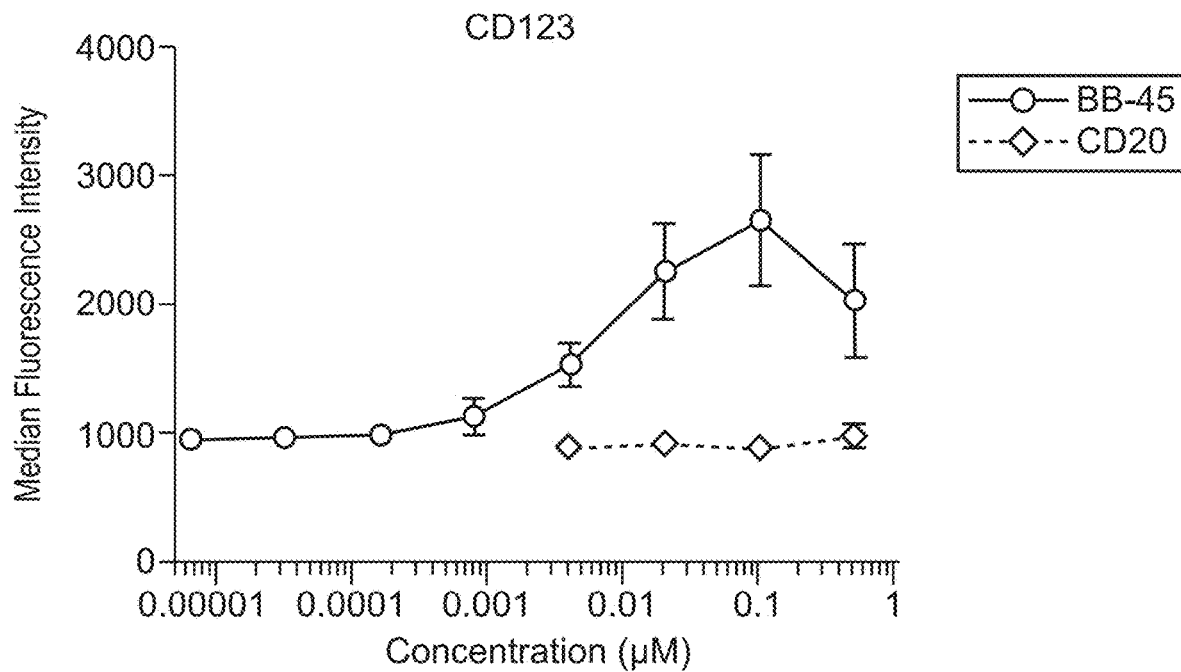

FIG. 113D shows that the rituximab immunoconjugate produced according to the BB-45 TFP conjugation method (BB-45) is superior at eliciting CD123 upregulation on myeloid cells as compared to the unconjugated rituximab (CD20, Alphamab) following 18 hours of stimulation.

Figure 113E:
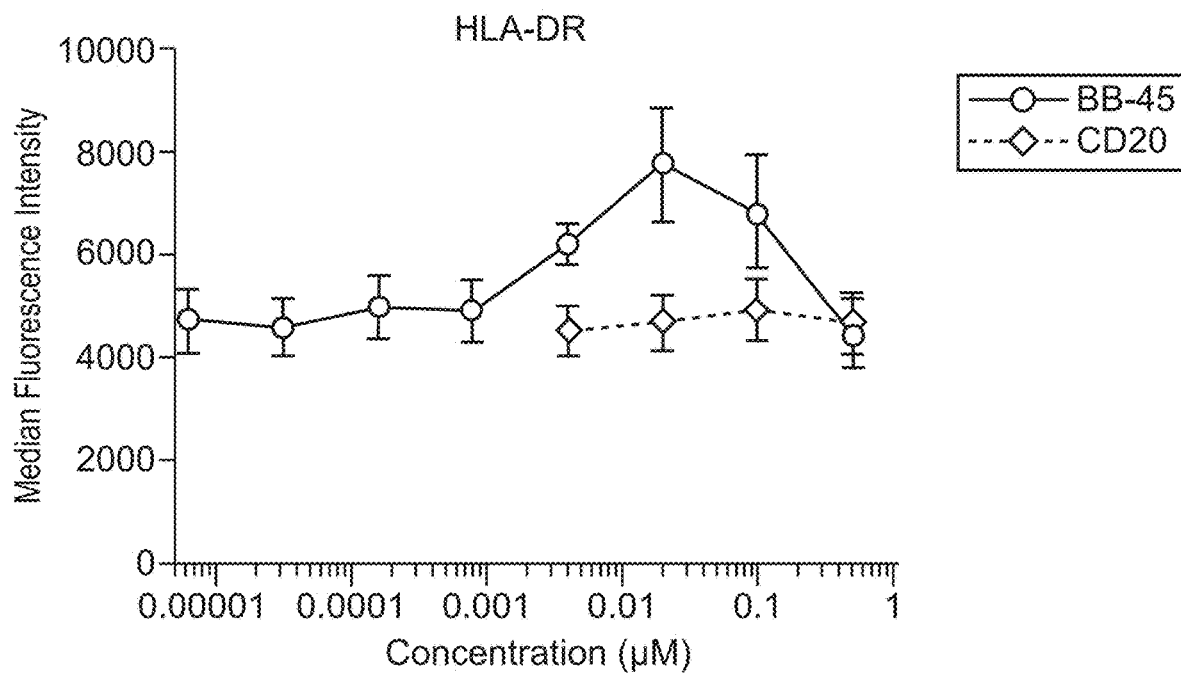

FIG. 113E shows that the rituximab immunoconjugate produced according to the BB-45 TFP conjugation method (BB-45) is superior at eliciting HLA-DR upregulation on myeloid cells as compared to the unconjugated rituximab (CD20, Alphamab) following 18 hours of stimulation.

Figure 113F:
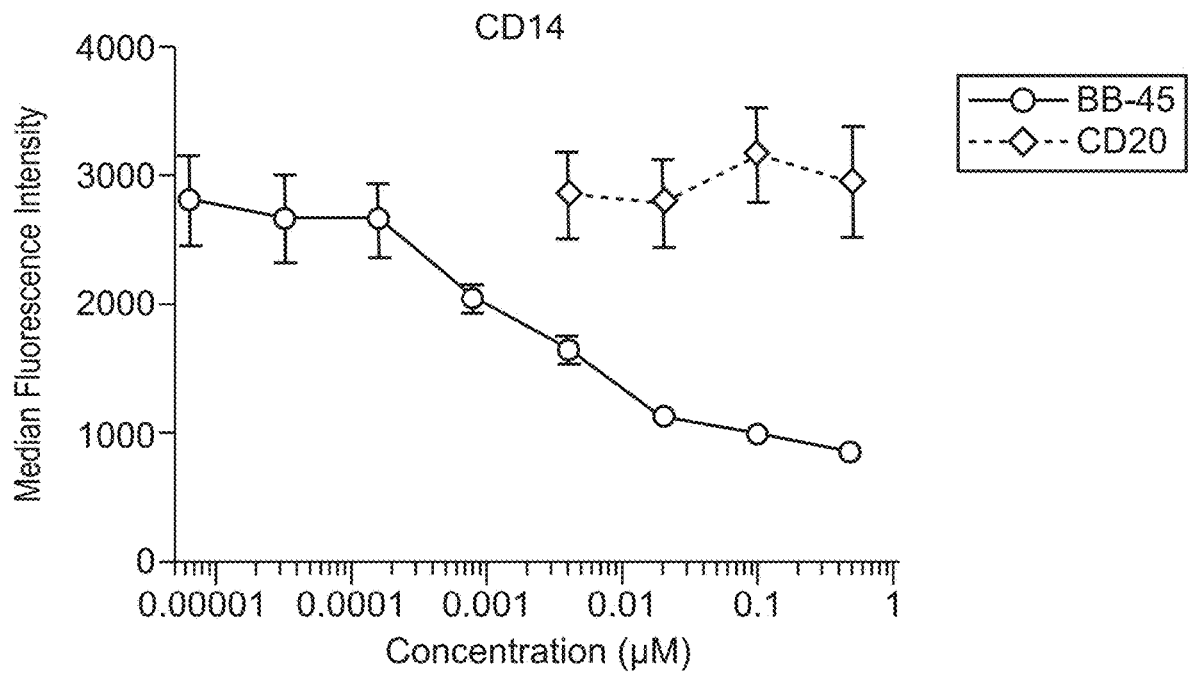

FIG. 113F shows that the rituximab immunoconjugate produced according to the BB-45 TFP conjugation method (BB-45) is superior at eliciting CD14 upregulation on myeloid cells as compared to the unconjugated rituximab (CD20, Alphamab) following 18 hours of stimulation.

Figure 113G:
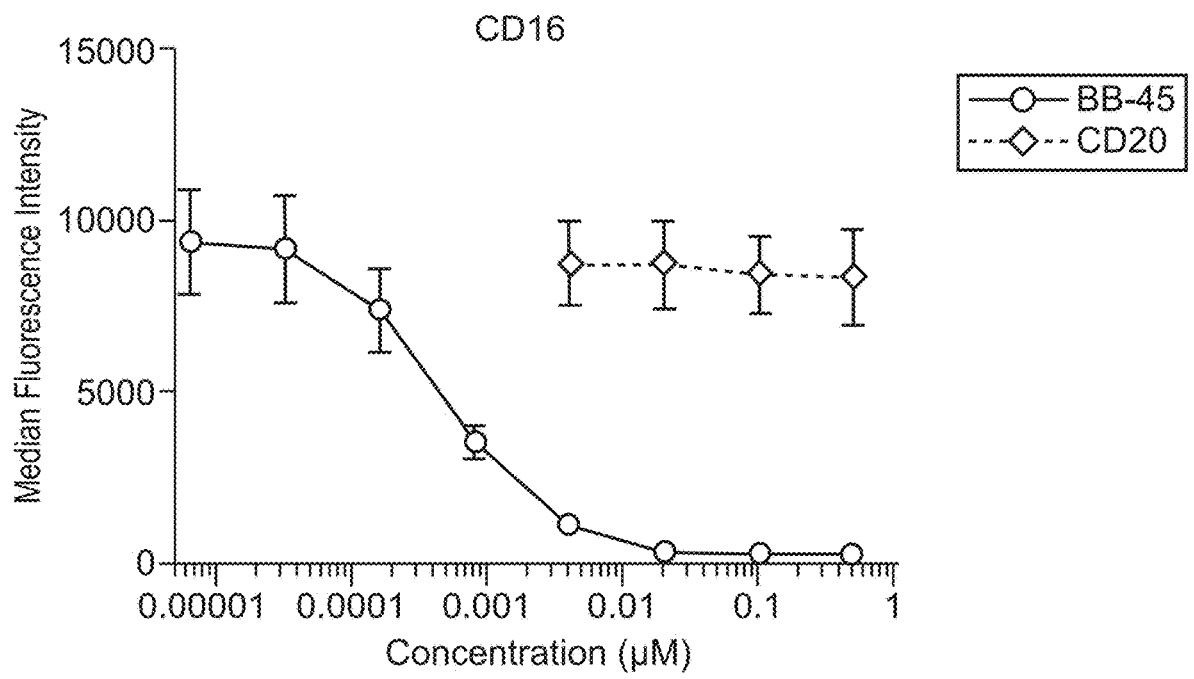

FIG. 113G shows that the rituximab immunoconjugate produced according to the BB-45 TFP conjugation method (BB-45) is superior at eliciting CD16 upregulation on myeloid cells as compared to the unconjugated rituximab (CD20, Alphamab) following 18 hours of stimulation.

Figure 113H:
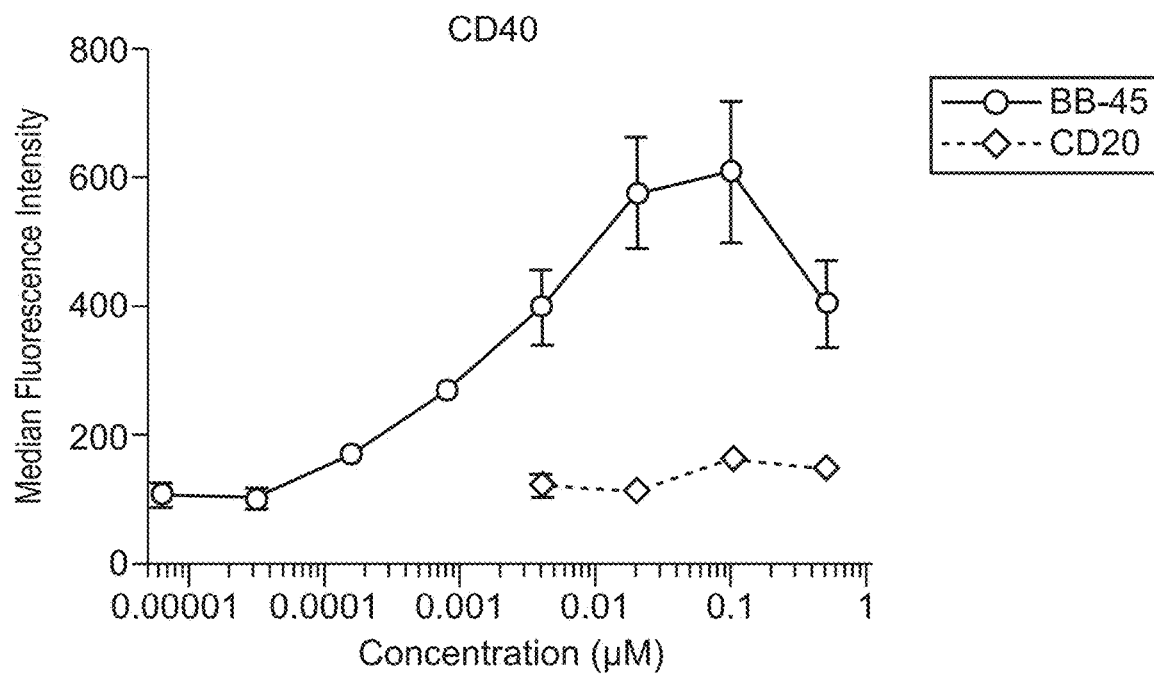

FIG. 113H shows that the rituximab immunoconjugate produced according to the BB-45 TFP conjugation method (BB-45) is superior at eliciting CD40 upregulation on myeloid cells as compared to the unconjugated rituximab (CD20, Alphamab) following 18 hours of stimulation.

Figure 113I:
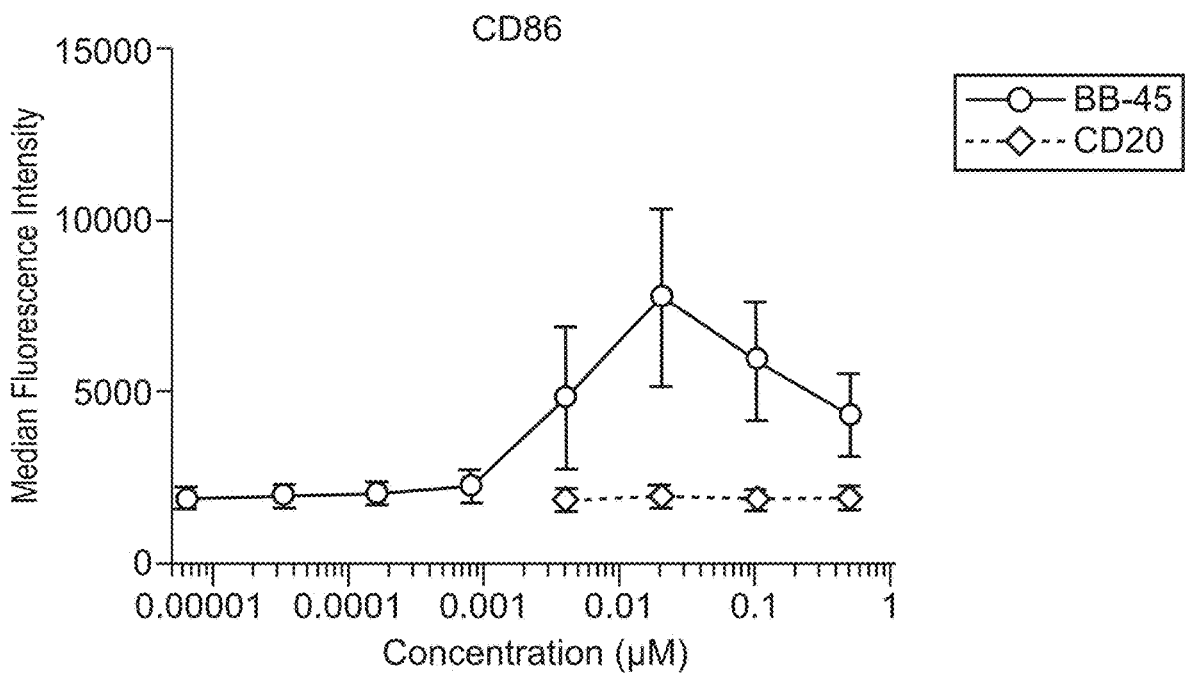

FIG. 113I shows that the rituximab immunoconjugate produced according to the BB-45 TFP conjugation method (BB-45) is superior at eliciting CD86 upregulation on myeloid cells as compared to the unconjugated rituximab (CD20, Alphamab) following 18 hours of stimulation.

Figure 114A:
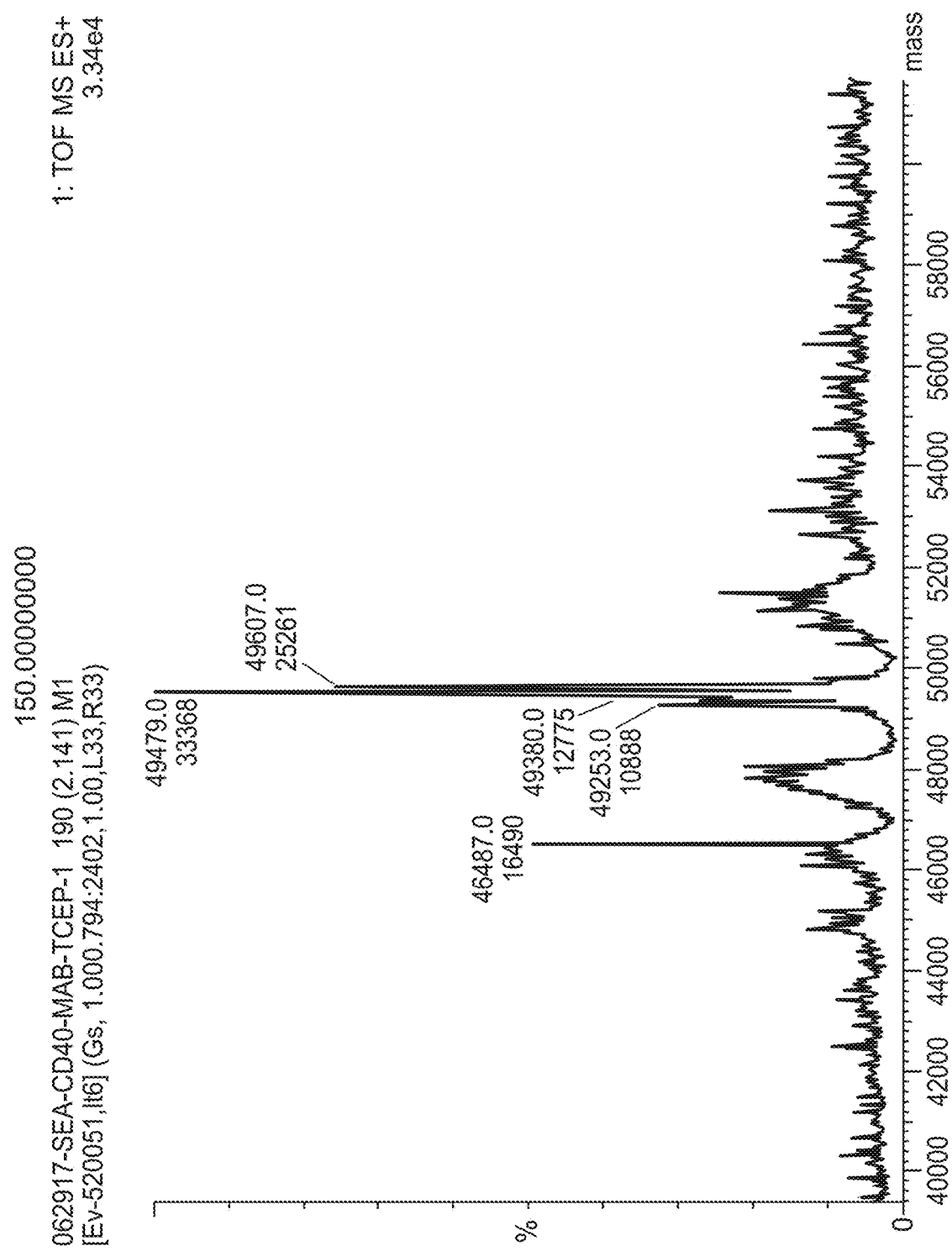

FIG. 114A shows a liquid chromatography-mass spectrometry analysis of the heavy chain of an unconjugated CD40 monoclonal antibody (Bioxcell, BE0016-2)

FIG. 114B shows a liquid chromatography-mass spectrometry analysis of the light chain of an unconjugated CD40 monoclonal antibody (Bioxcell, BE0016-2).

Figure 114C:
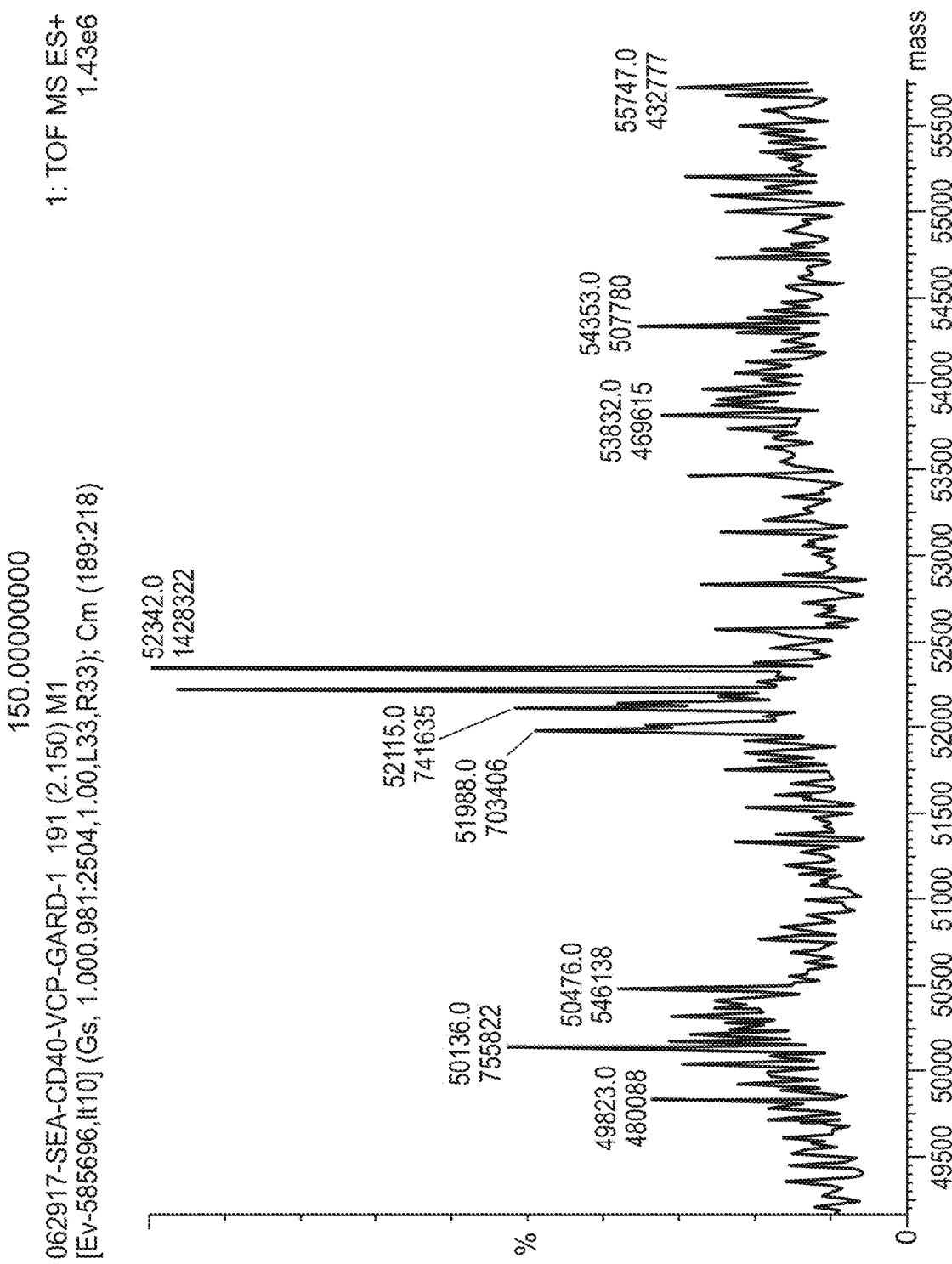

FIG. 114C shows a liquid chromatography-mass spectrometry analysis of the heavy chain of a CD40 immunoconjugate produced according to US 2017/0158772.

FIG. 114D shows a liquid chromatography-mass spectrometry analysis of the light chain of a CD40 immunoconjugate produced according to US 2017/0158772.

Figure 115A:
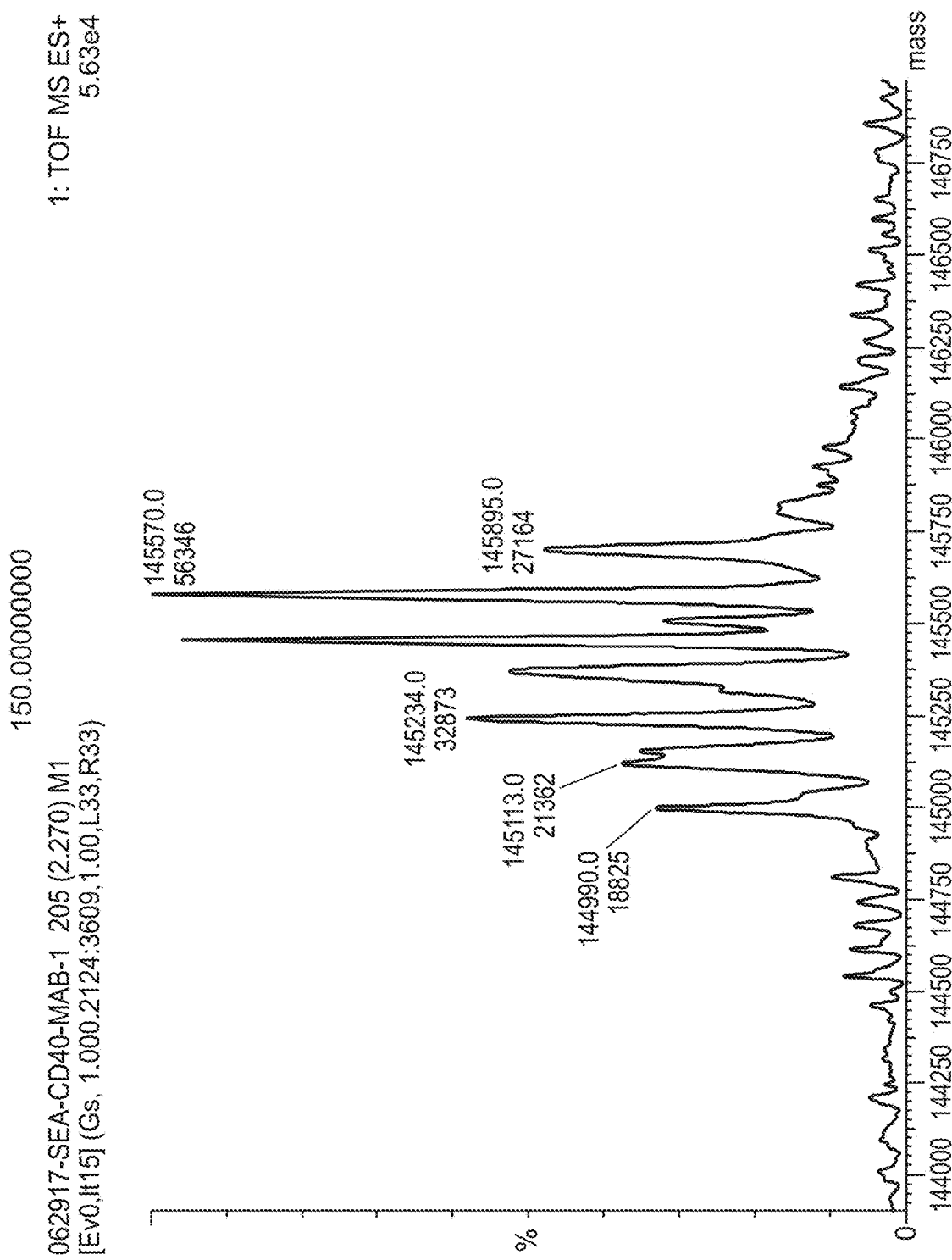

FIG. 115A shows a liquid chromatography-mass spectrometry analysis of an unconjugated CD40 monoclonal antibody (Bioxcell, BE0016-2).

Figure 115B:
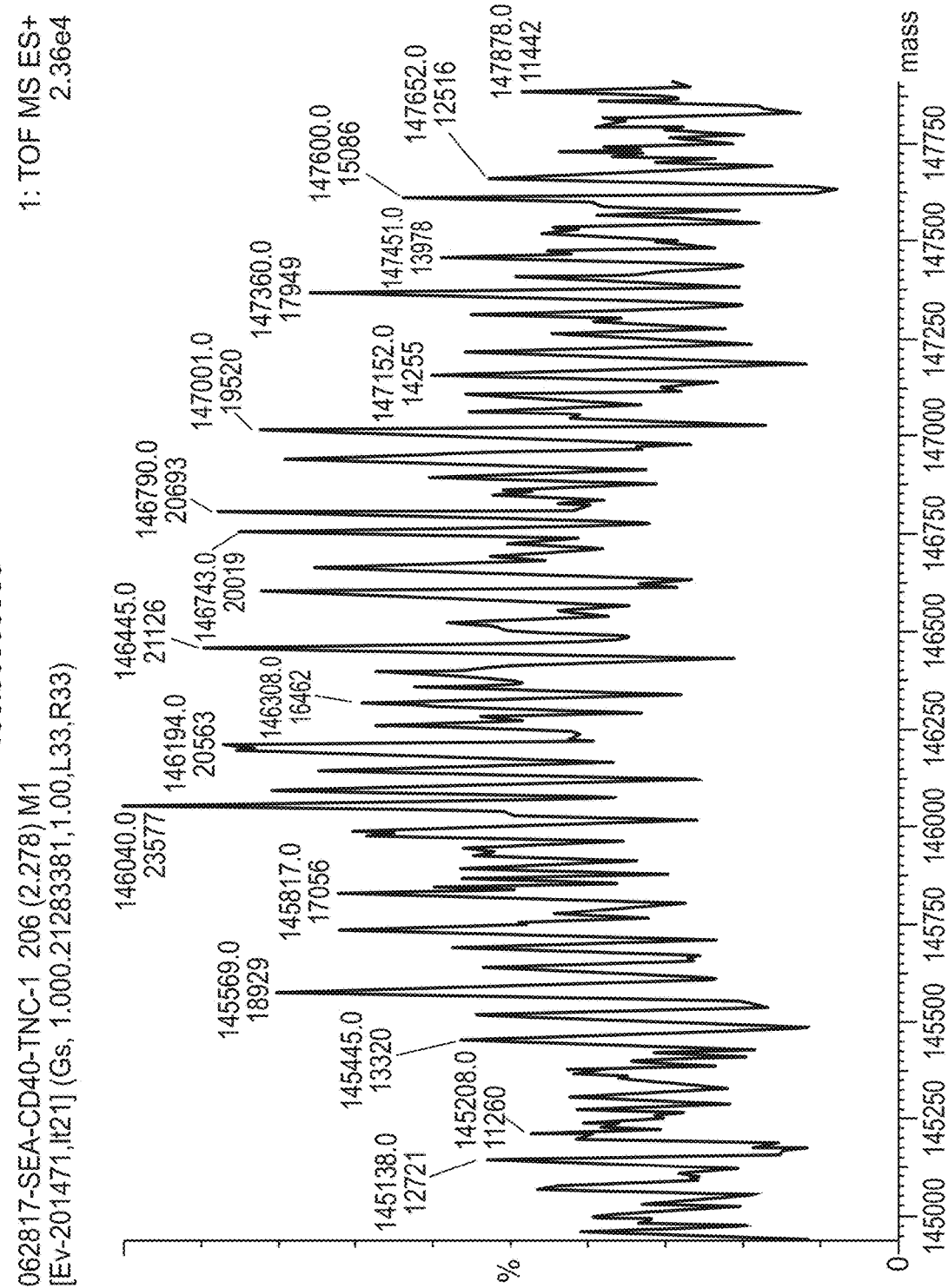

FIG. 115B shows a liquid chromatography-mass spectrometry analysis of a CD40 immunoconjugate produced according to the BB-01 conjugation method.

Figure 116A:
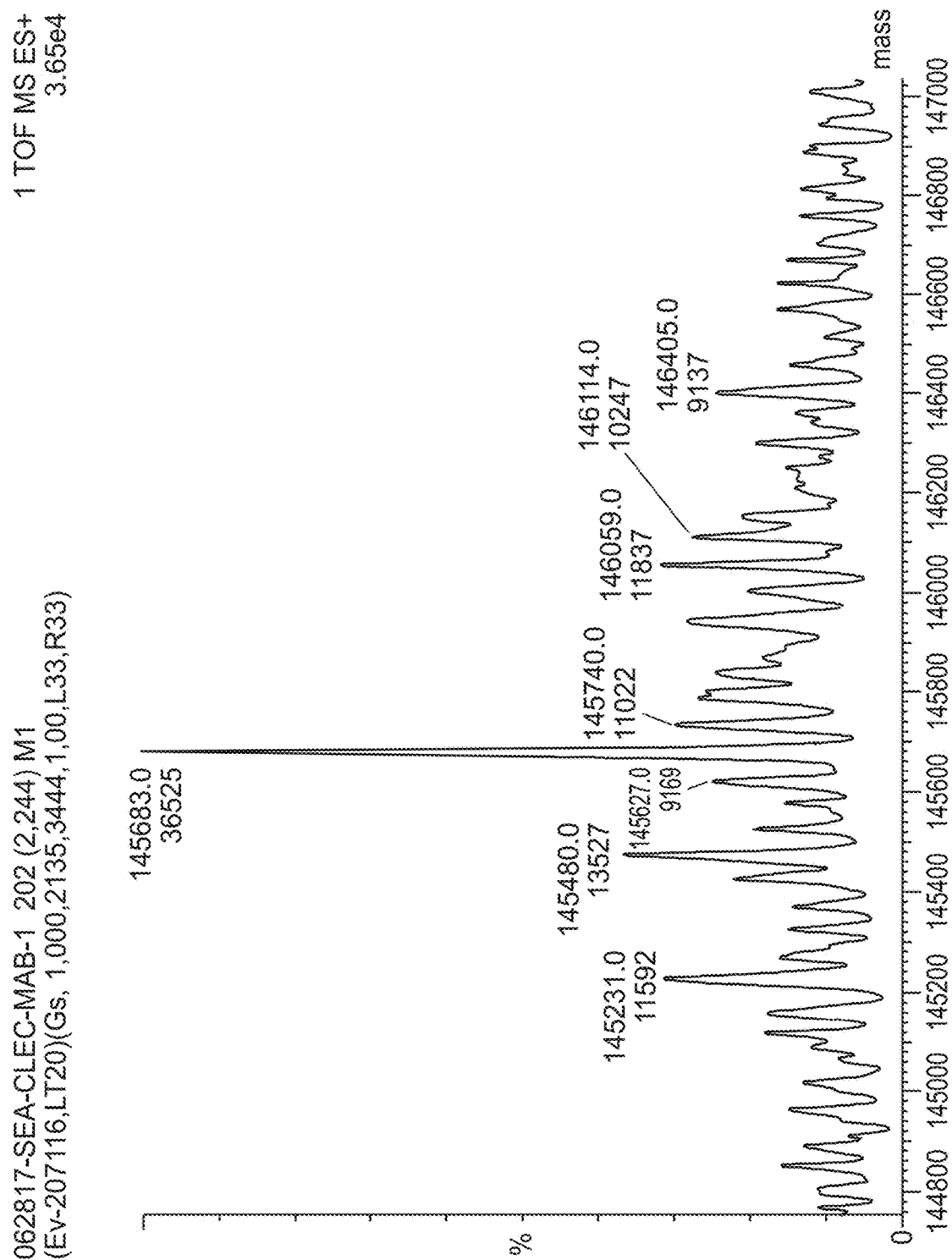

FIG. 116A shows a liquid chromatography-mass spectrometry analysis of an unconjugated CLEC5a monoclonal antibody (R&D Systems, mab1639).

Figure 116B:
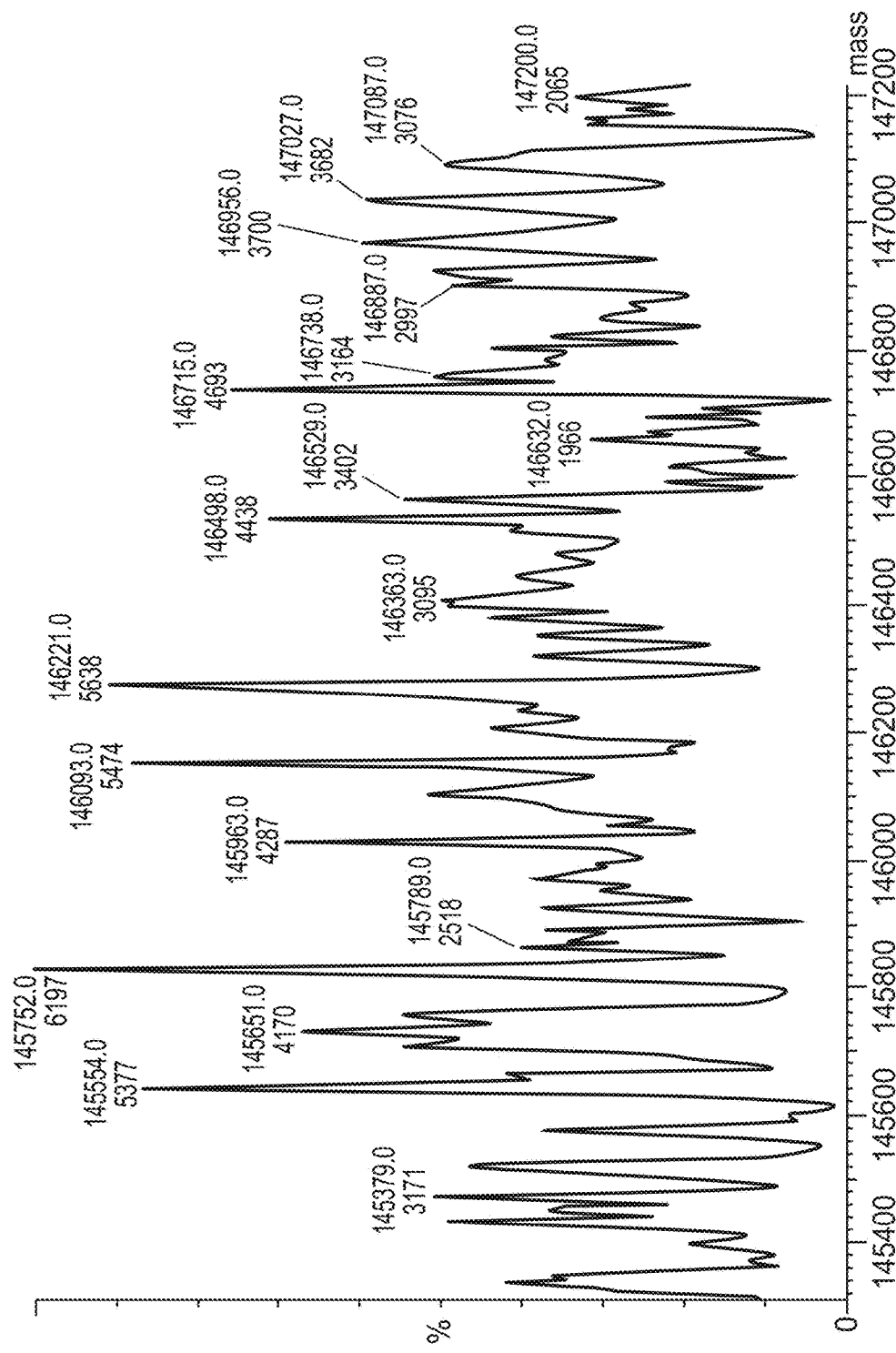

FIG. 116B shows a liquid chromatography-mass spectrometry analysis of a CLEC5a immunoconjugate produced according to the BB-01 conjugation method.

Figure 117A:
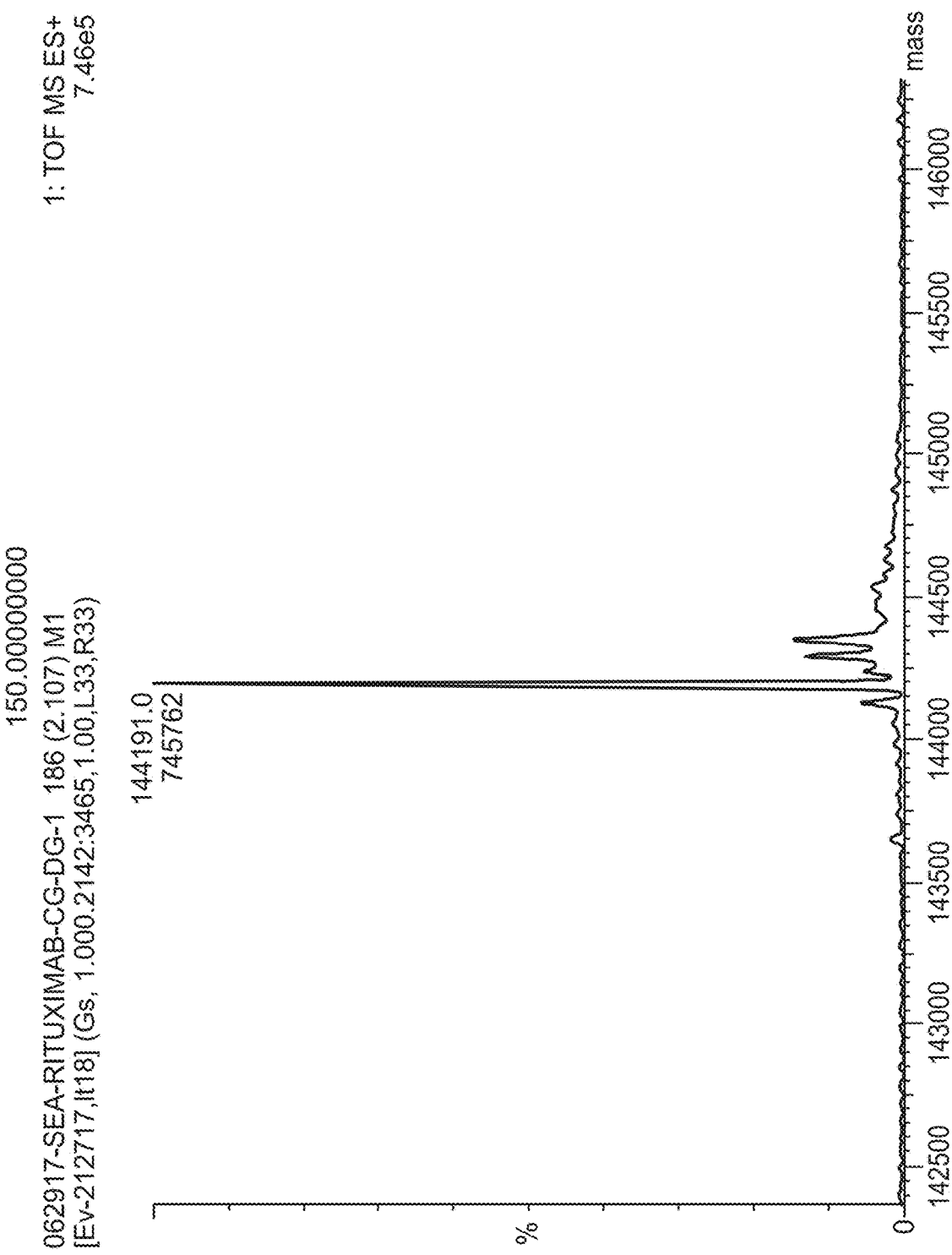

FIG. 117A shows a schematic for a CL264 immunoconjugate produced according to BB-01 conjugation method.

FIG. 117B shows a schematic for a CL264 immunoconjugate produced according to the ester synthesis method.

Figure 118A:
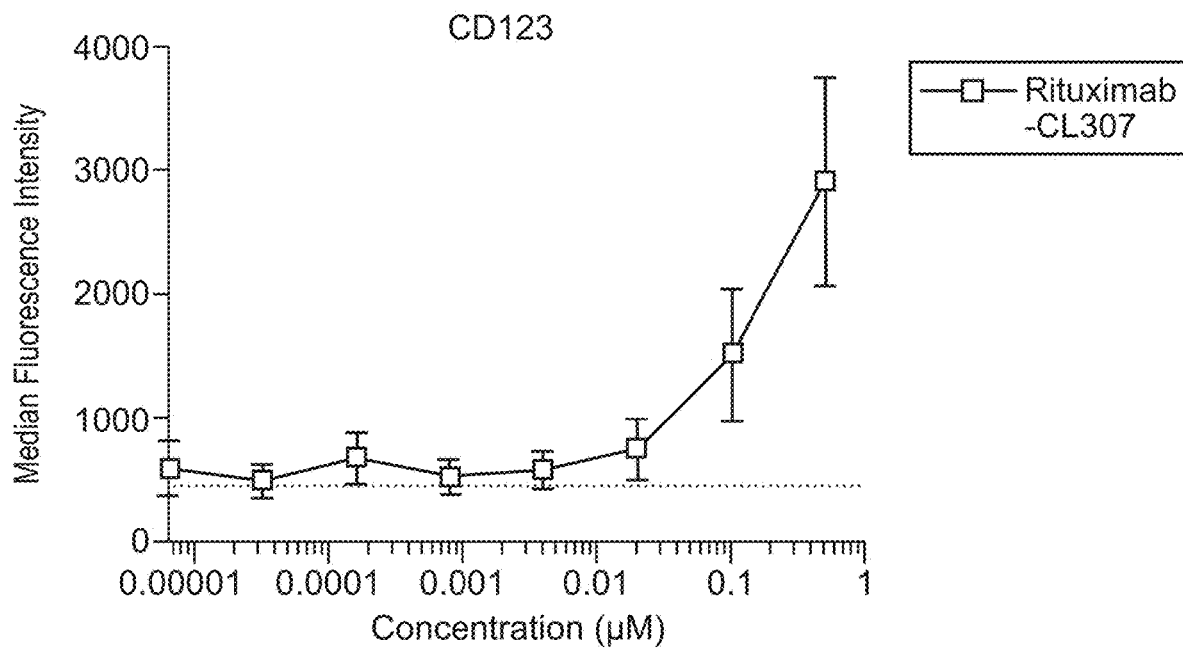

FIG. 118A shows that the Rituximab-CL307 immunoconjugate produced according to the BB-01 conjugation method upregulates CD123 on myeloid cells in a dose-dependent manner following 18 hours of stimulation. The dashed line indicates the level of expression on unstimulated cells cultured for 18 hours.

Figure 118B:
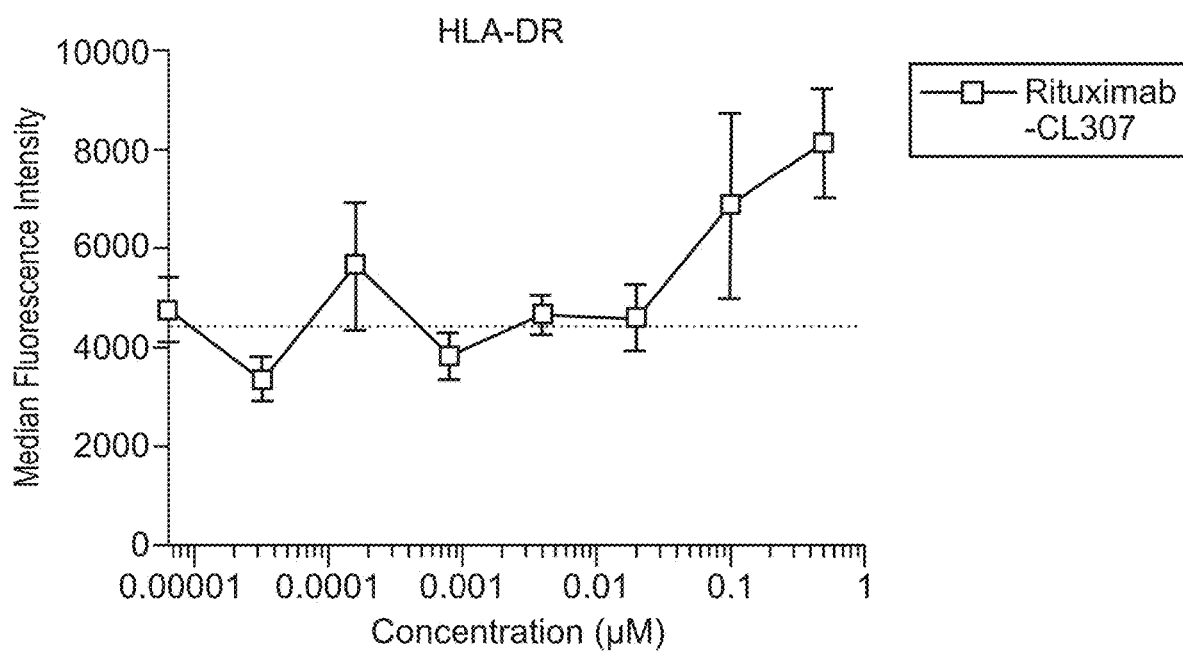

FIG. 118B shows that the Rituximab-CL307 immunoconjugate produced according to the BB-01 conjugation method upregulates HLA-DR on myeloid cells in a dose-dependent manner following 18 hours of stimulation. The dashed line indicates the level of expression on unstimulated cells cultured for 18 hours.

Figure 118C:
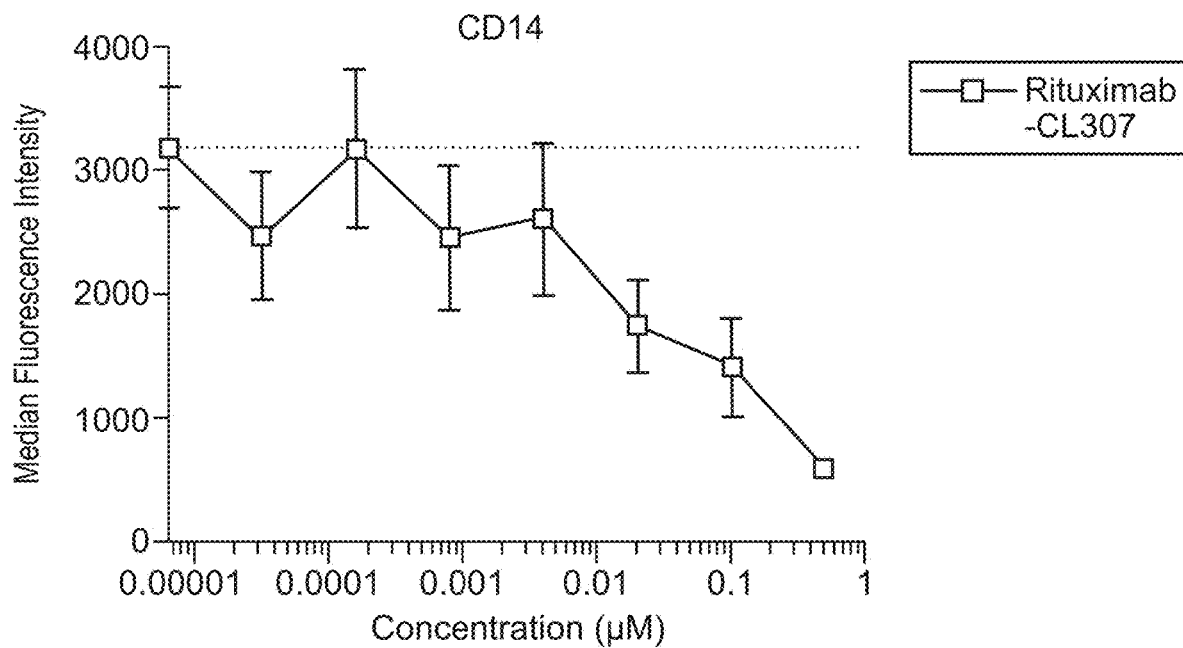

FIG. 118C shows that the Rituximab-CL307 immunoconjugate produced according to the BB-01 conjugation method downregulates CD14 on myeloid cells in a dose-dependent manner following 18 hours of stimulation. The dashed line indicates the level of expression on unstimulated cells cultured for 18 hours.

Figure 118D:
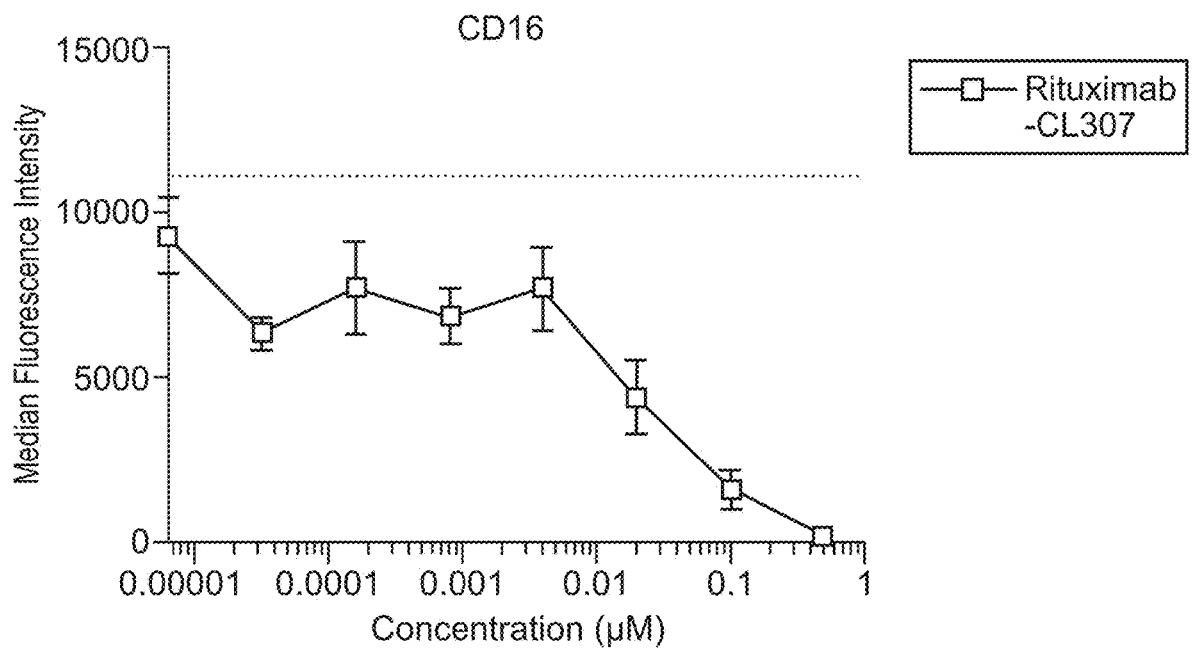

FIG. 118D shows that the Rituximab-CL307 immunoconjugate produced according to the BB-01 conjugation method downregulates CD16 on myeloid cells in a dose-dependent manner following 18 hours of stimulation. The dashed line indicates the level of expression on unstimulated cells cultured for 18 hours.

Figure 118E:
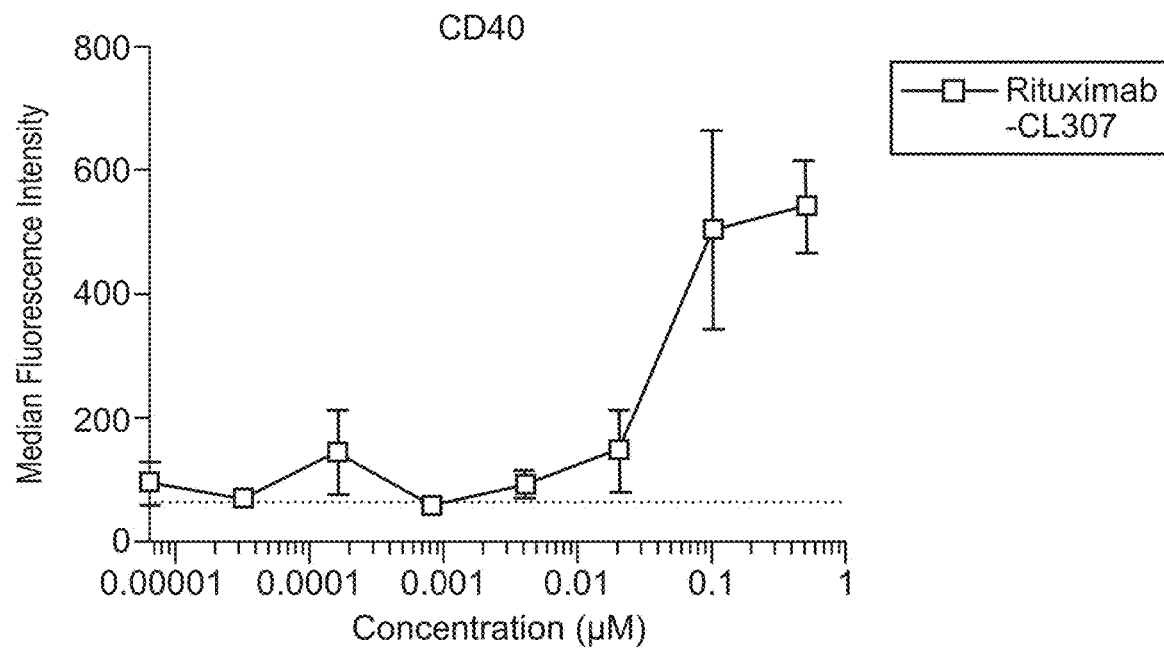

FIG. 118E shows that the Rituximab-CL307 immunoconjugate produced according to the BB-01 conjugation method upregulates CD40 on myeloid cells in a dose-dependent manner following 18 hours of stimulation. The dashed line indicates the level of expression on unstimulated cells cultured for 18 hours.

Figure 118F:
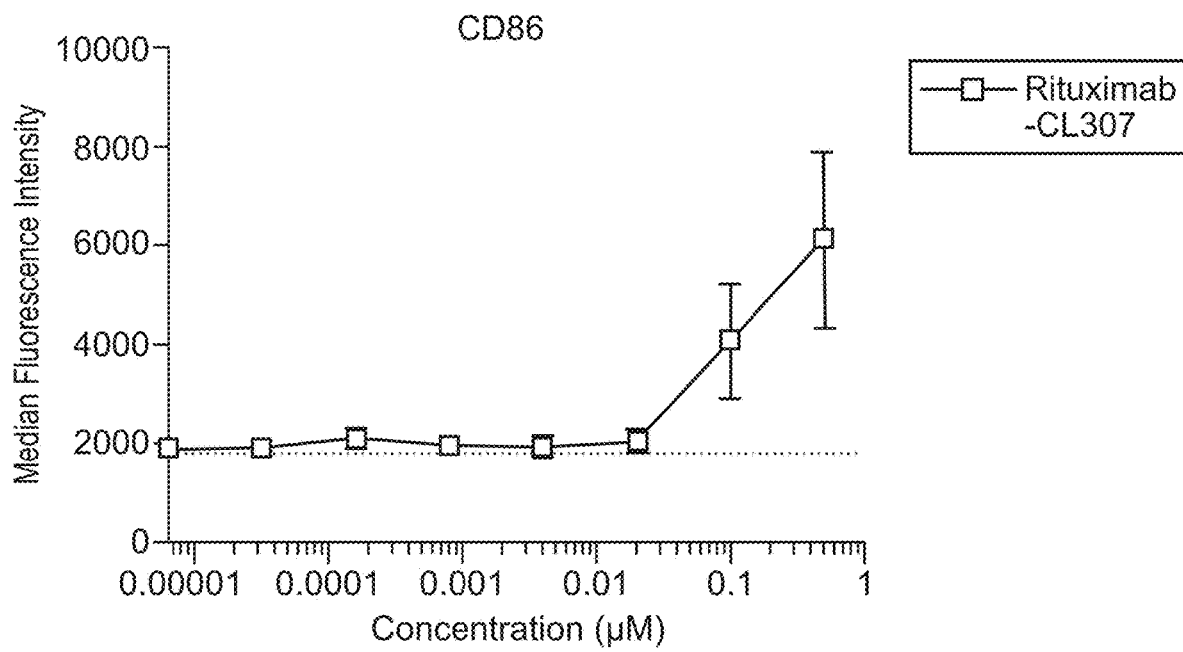

FIG. 118F shows that the Rituximab-CL307 immunoconjugate produced according to the BB-01 conjugation method upregulates CD86 on myeloid cells in a dose-dependent manner following 18 hours of stimulation. The dashed line indicates the level of expression on unstimulated cells cultured for 18 hours.

FIG. 118G shows a liquid chromatography-mass spectrometry analysis of unconjugated Rituximab (Roche) that was utilized to produce Rituximab-CL307.

Figure 118H:
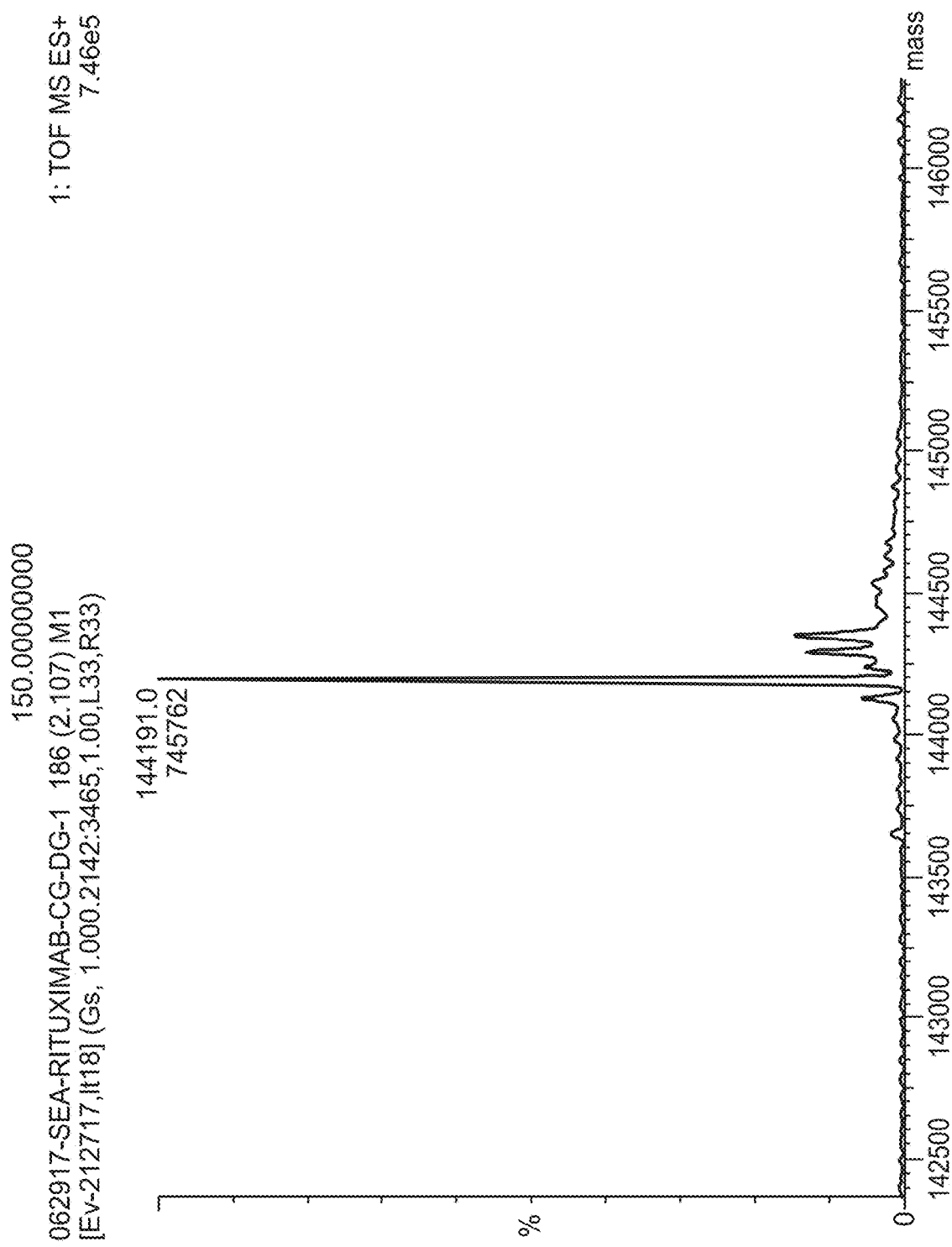

FIG. 118H shows a liquid chromatography-mass spectrometry analysis of unconjugated Rituximab (Roche) that was utilized to produce Rituximab-CL307 following overnight deglycosylation with PNGase F.

Figure 118I:
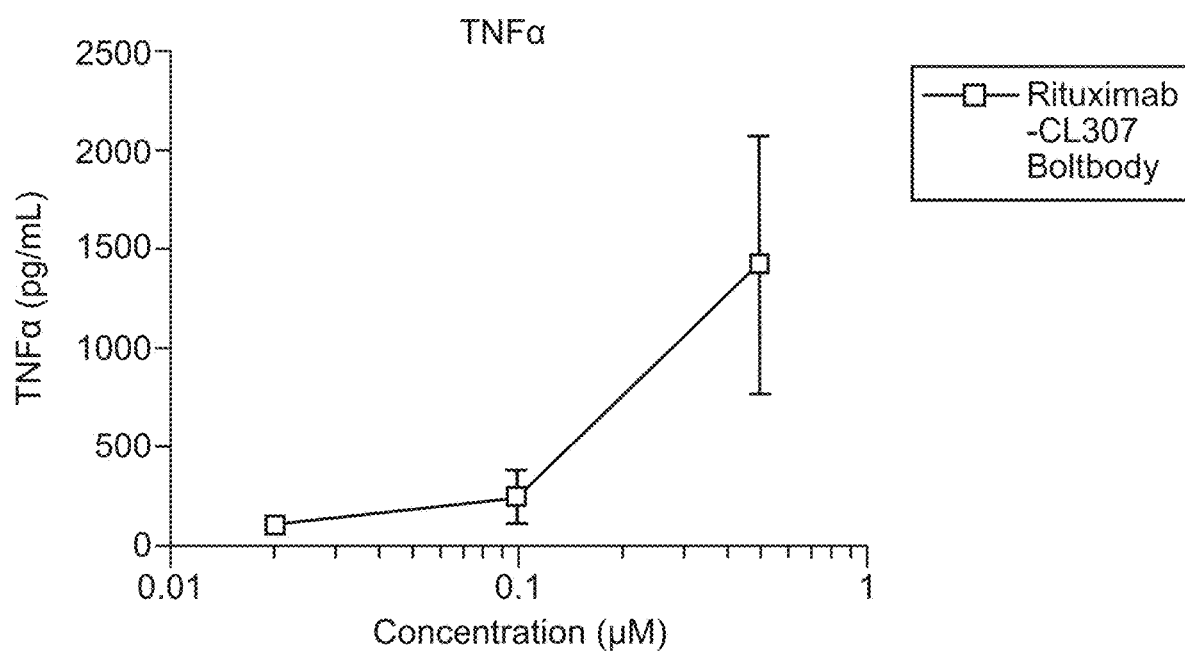

FIG. 118I shows that the Rituximab-CL307 immunoconjugate produced according to the BB-01 conjugation method elicits TNFα secretion in a dose-dependent manner following 18 hours of stimulation.

Figure 118J:
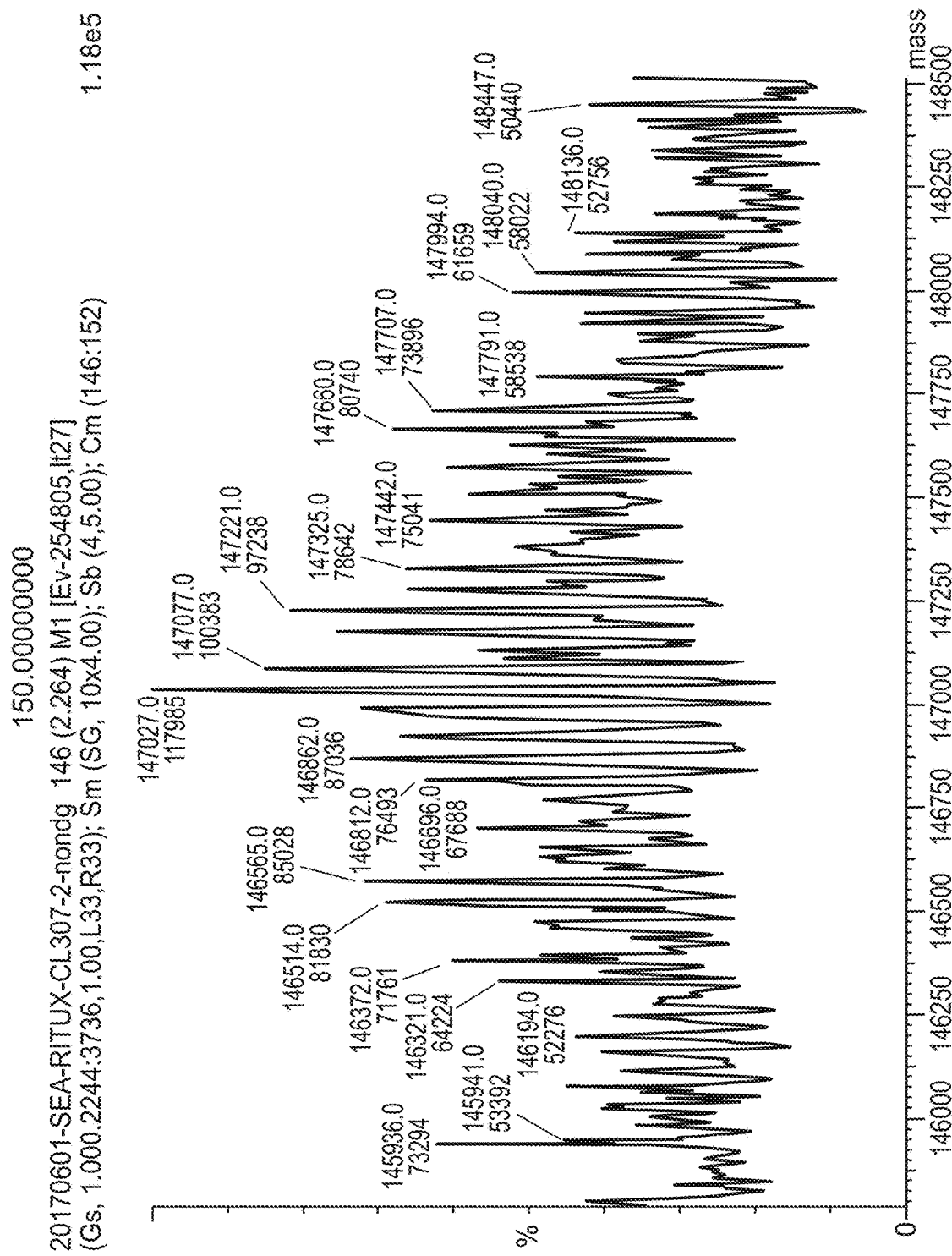

FIG. 118J shows a liquid chromatography-mass spectrometry analysis of the Rituximab-CL307 immunoconjugate produced according to the BB-01 conjugation method.

Figure 119A:
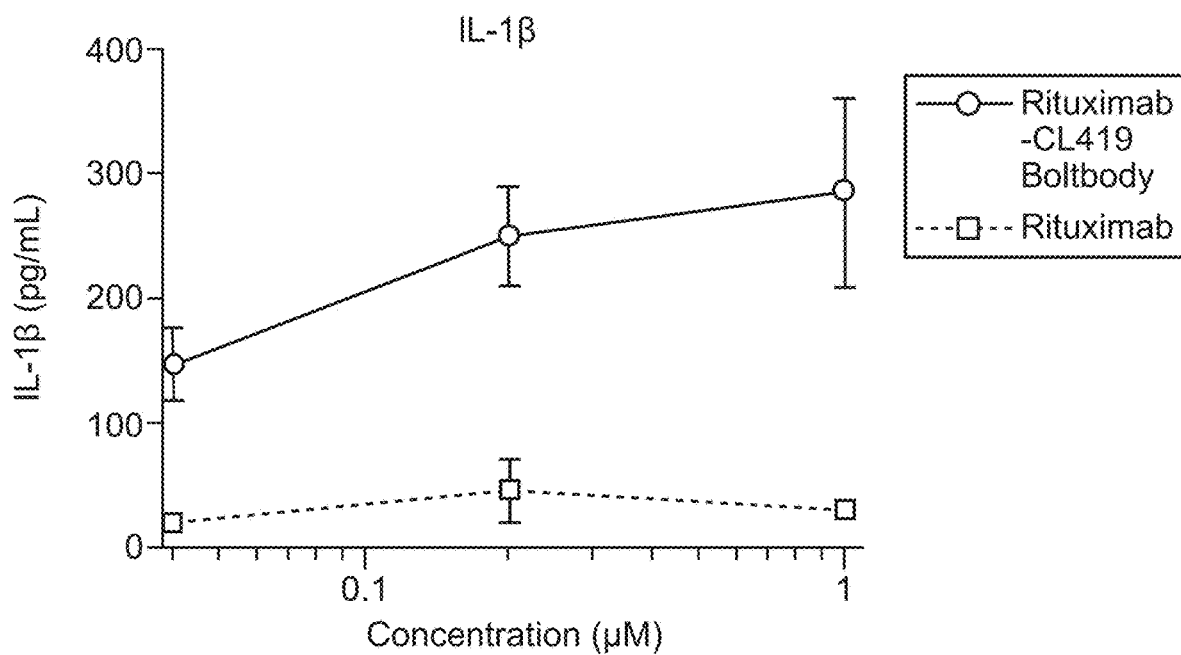

FIG. 119A shows that the Rituximab-CL419 immunoconjugate produced according to the BB-01 method (Rituximab-CL419 Boltbody) is superior at eliciting IL-1β secretion from myeloid cells as compared to unconjugated Rituximab (Roche) following 36 hours of stimulation.

Figure 119B:
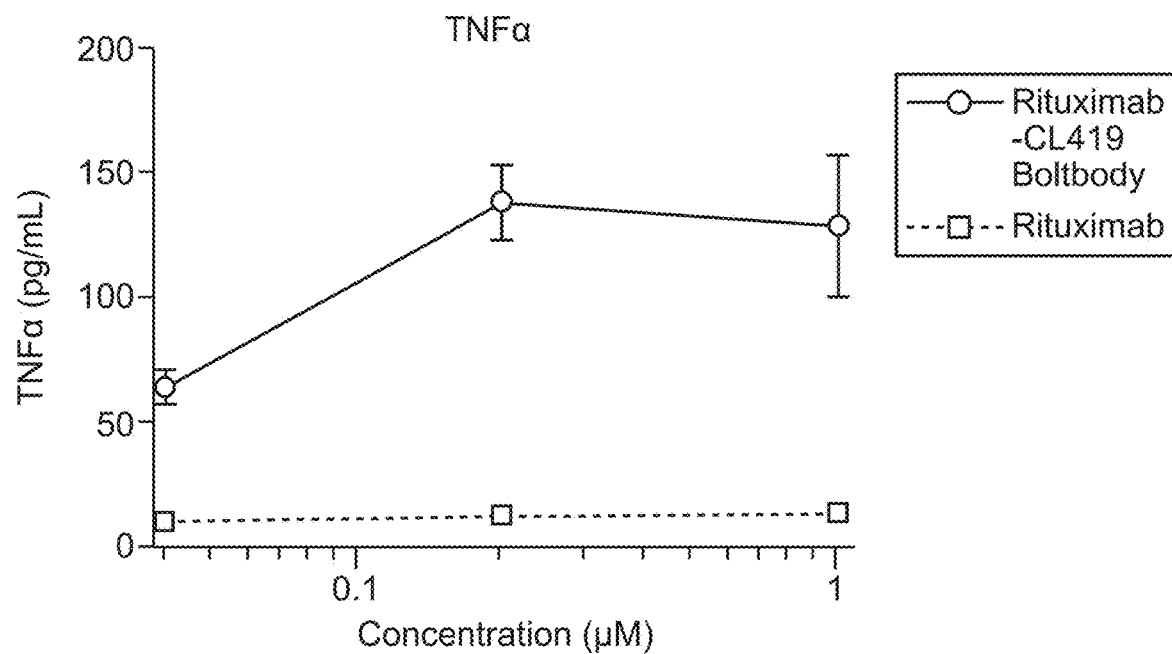

FIG. 119B shows that the Rituximab-CL419 immunoconjugate produced according to the BB-01 method (Rituximab-CL419 Boltbody) is superior at eliciting TNFα secretion from myeloid cells as compared to unconjugated Rituximab (Roche) following 36 hours of stimulation.

Figure 119C:
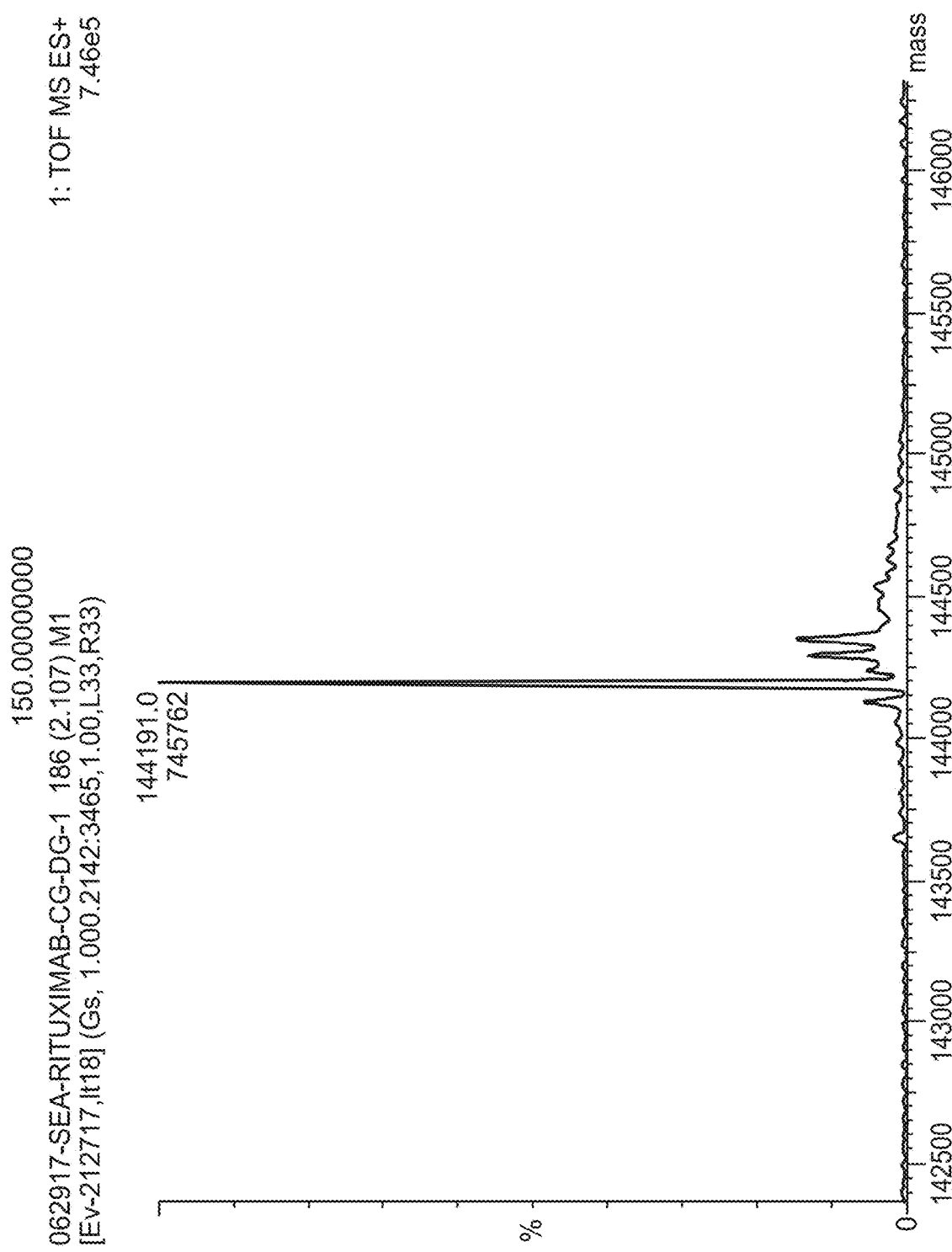

FIG. 119C shows a liquid chromatography-mass spectrometry analysis of unconjugated Rituximab (Roche) that was utilized to produce Rituximab-CL419 following overnight deglycosylation with PNGase F.

FIG. 119D shows a liquid chromatography-mass spectrometry analysis of unconjugated Rituximab (Roche) that was utilized to produce Rituximab-CL419.

Figure 119E:
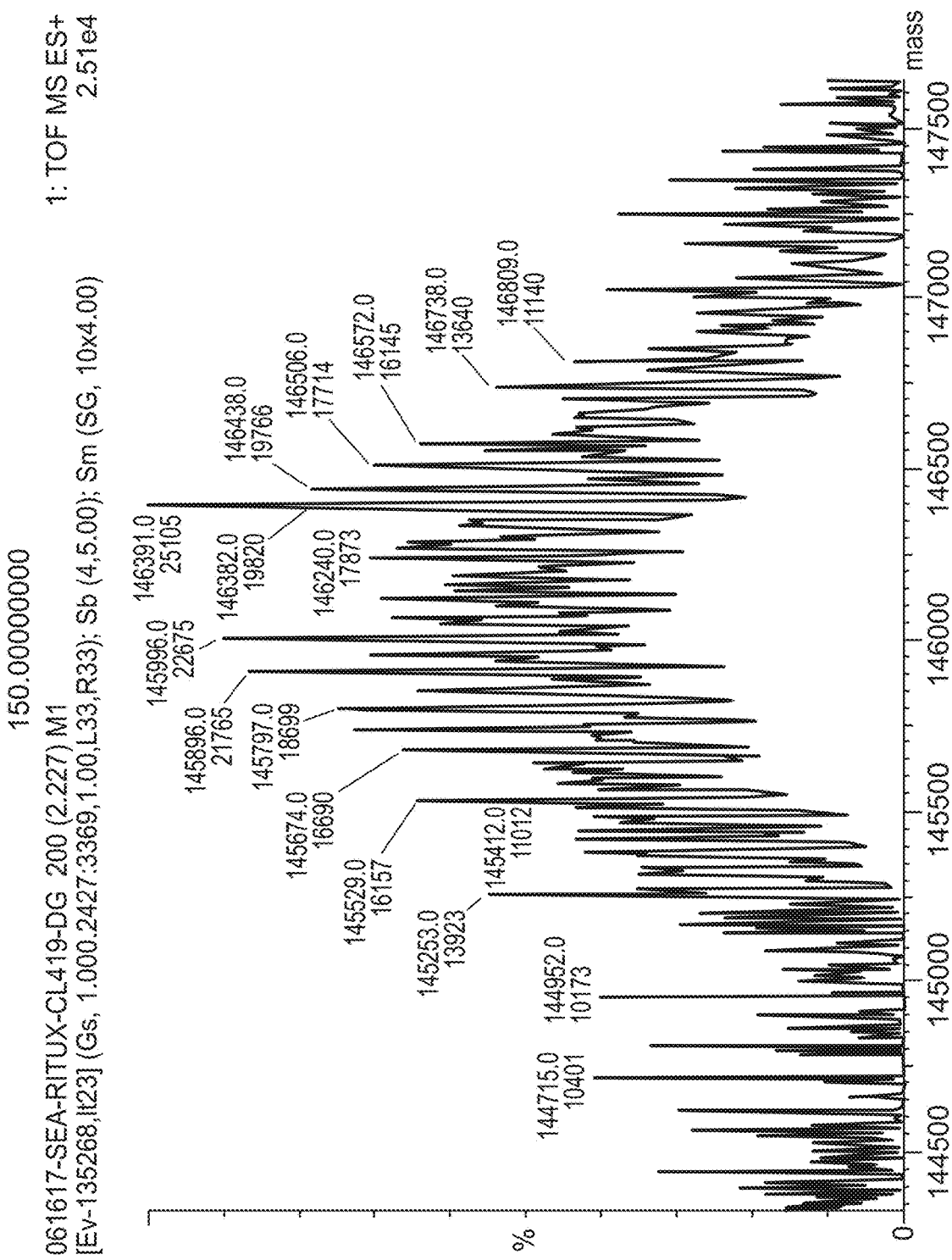

FIG. 119E shows a liquid chromatography-mass spectrometry analysis of the Rituximab-CL419 immunoconjugate produced according to the BB-01 conjugation method following overnight deglycosylation with PNGase F.

Figure 119F:
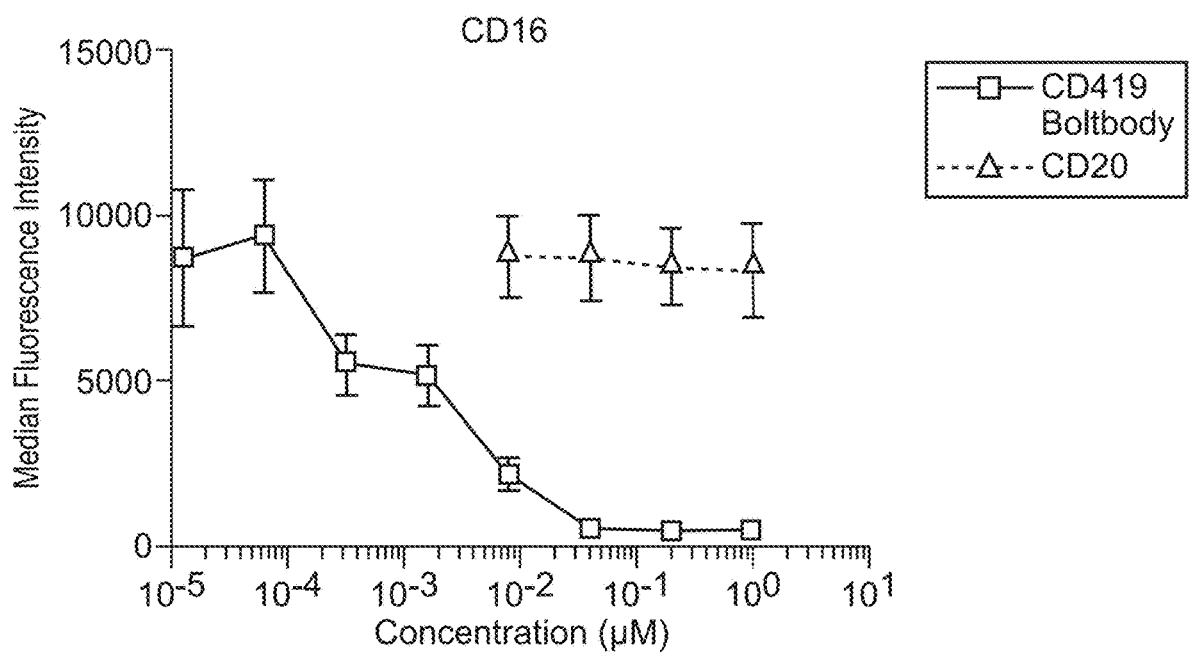

FIG. 119F shows that the Rituximab-CL419 immunoconjugate produced according to the BB-01 method (CL419 Boltbody) is superior at eliciting CD16 downregulation on myeloid cells as compared to unconjugated Rituximab (CD20; Roche) following 18 hours of stimulation.

Figure 119G:
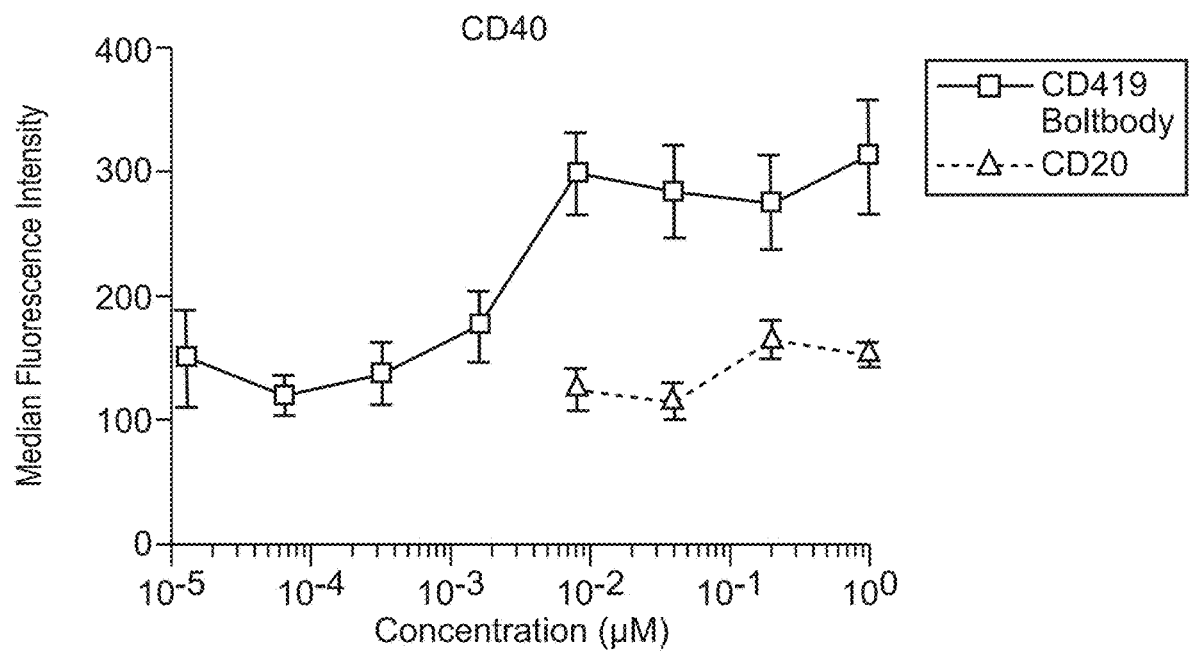

FIG. 119G shows that the Rituximab-CL419 immunoconjugate produced according to the BB-01 method (CL419 Boltbody) is superior at eliciting CD40 upregulation on myeloid cells as compared to unconjugated Rituximab (CD20; Roche) following 18 hours of stimulation.

Figure 119H:
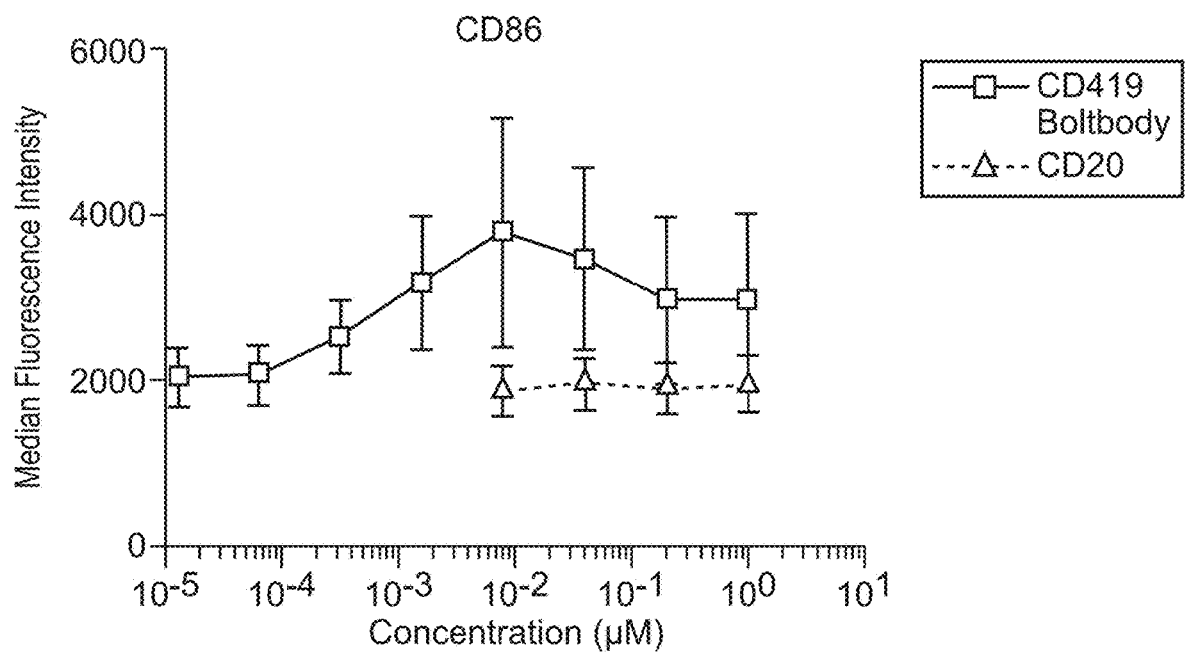

FIG. 119H shows that the Rituximab-CL419 immunoconjugate produced according to the BB-01 method (CL419 Boltbody) is superior at eliciting CD86 upregulation on myeloid cells as compared to unconjugated Rituximab (CD20; Roche) following 18 hours of stimulation.

Figure 119I:
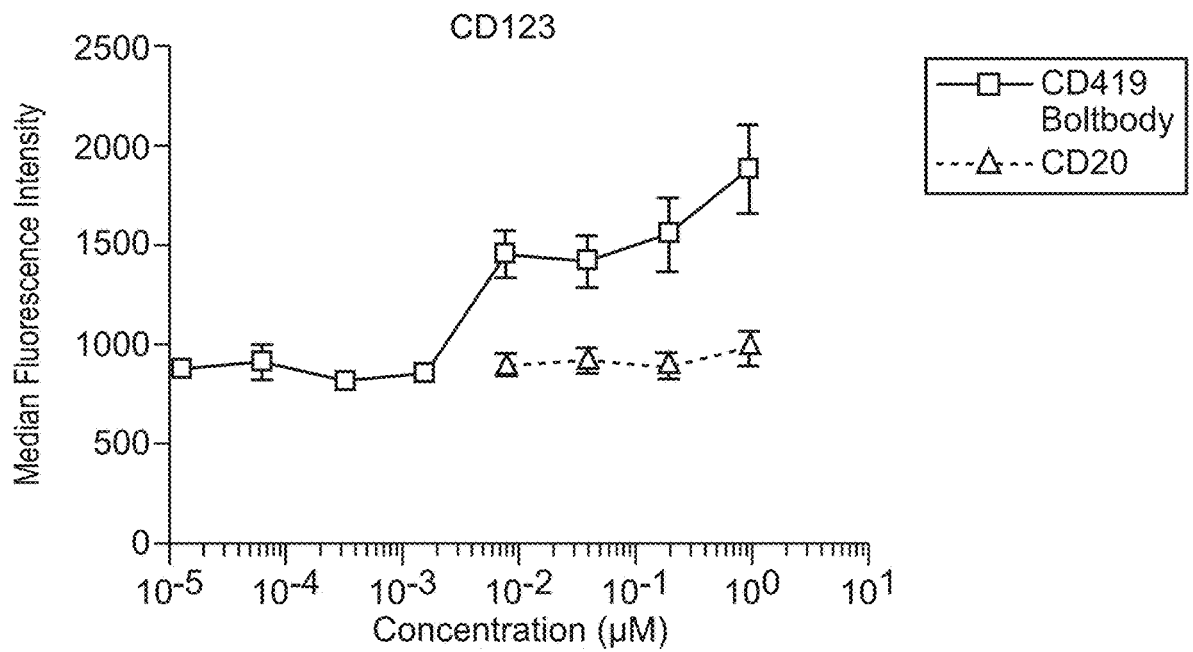

FIG. 119I shows that the Rituximab-CL419 immunoconjugate produced according to the BB-01 method (CL419 Boltbody) is superior at eliciting CD123 upregulation on myeloid cells as compared to unconjugated Rituximab (CD20; Roche) following 18 hours of stimulation.

Figure 120A:
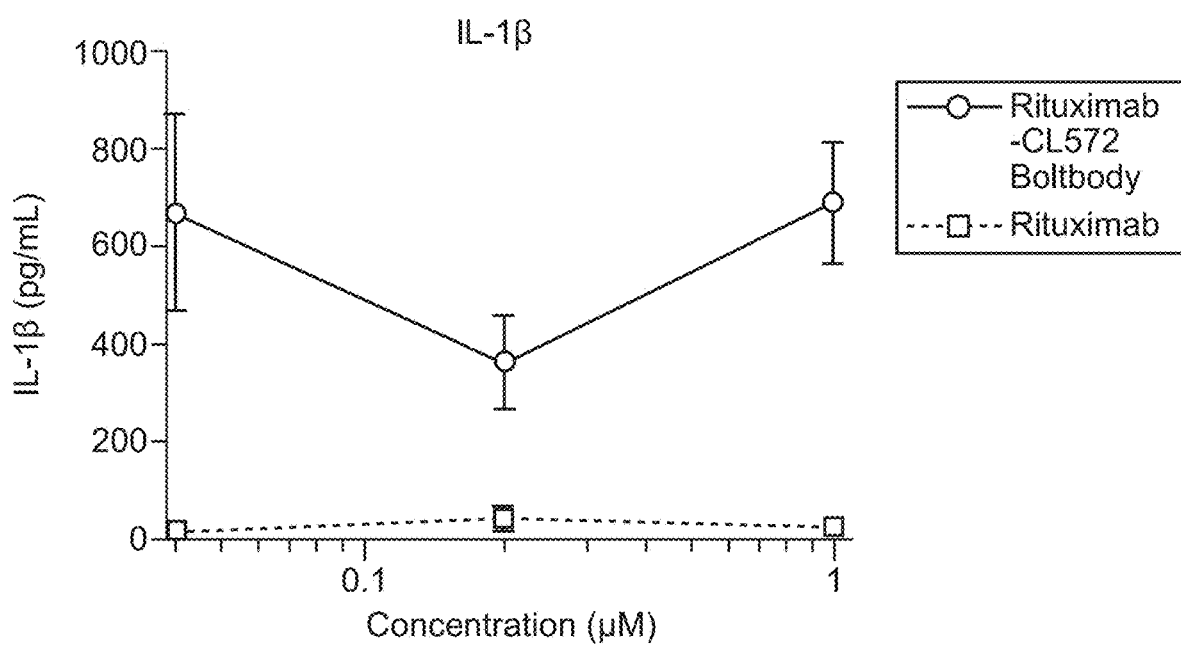

FIG. 120A shows that the Rituximab-CL572 immunoconjugate produced according to the BB-01 method (Rituximab-CL572 Boltbody) is superior at eliciting IL-1β secretion from myeloid cells as compared to unconjugated Rituximab (Roche) following 36 hours of stimulation.

Figure 120B:
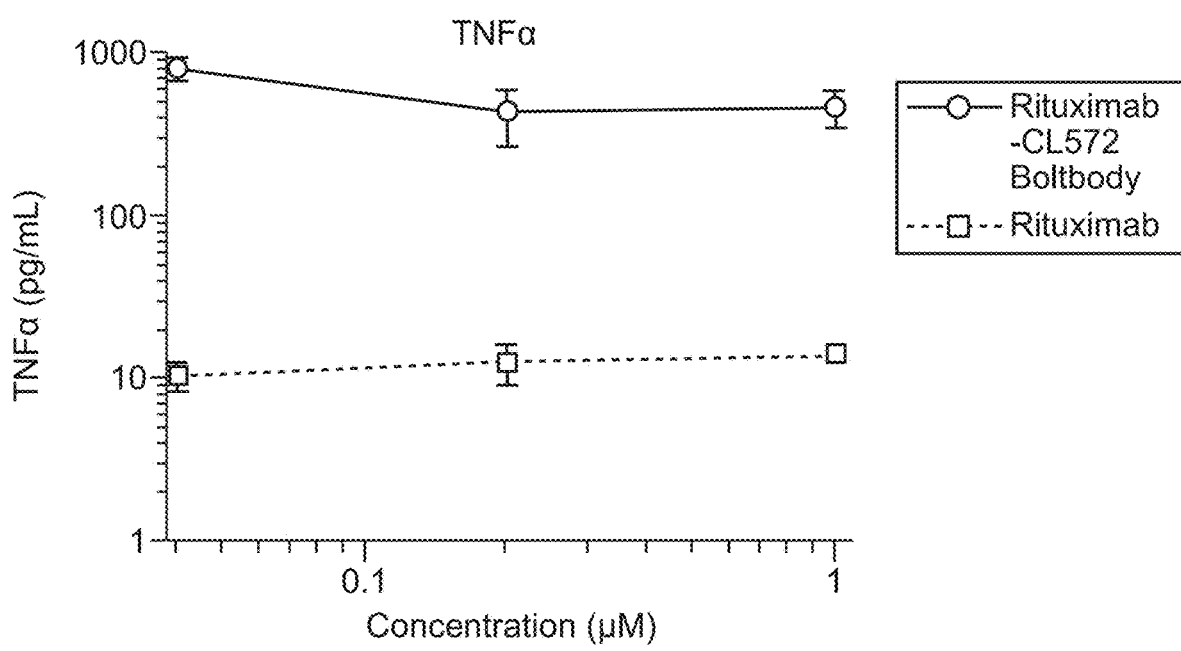

FIG. 120B shows that the Rituximab-CL572 immunoconjugate produced according to the BB-01 method (Rituximab-CL572 Boltbody) is superior at eliciting TNFα secretion from myeloid cells as compared to unconjugated Rituximab (Roche) following 36 hours of stimulation.

Figure 120C:
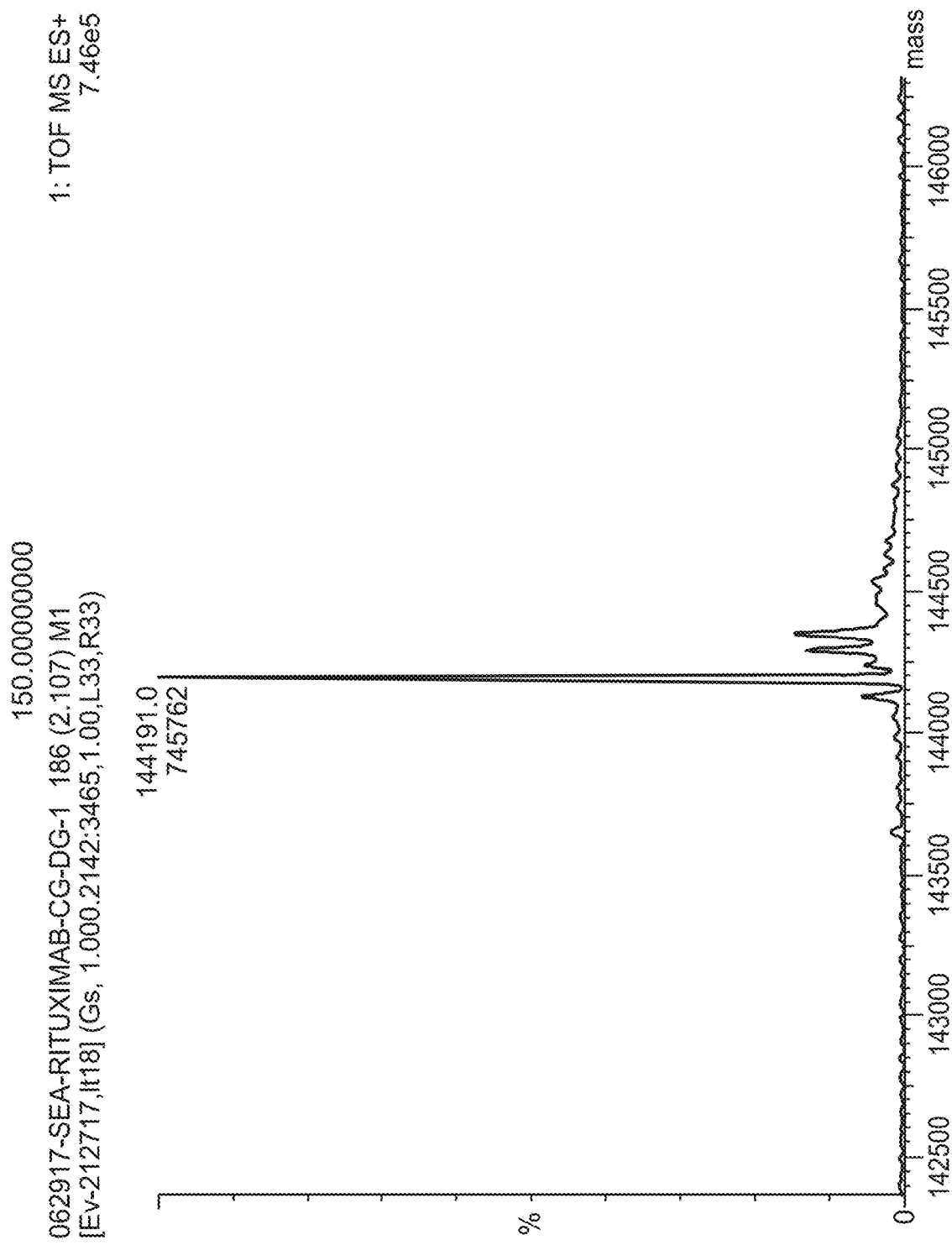

FIG. 120C shows a liquid chromatography-mass spectrometry analysis of unconjugated Rituximab (Roche) that was utilized to produce Rituximab-CL572 following overnight deglycosylation with PNGase F.

FIG. 120D shows a liquid chromatography-mass spectrometry analysis of unconjugated Rituximab (Roche) that was utilized to produce Rituximab-CL572.

Figure 120E:
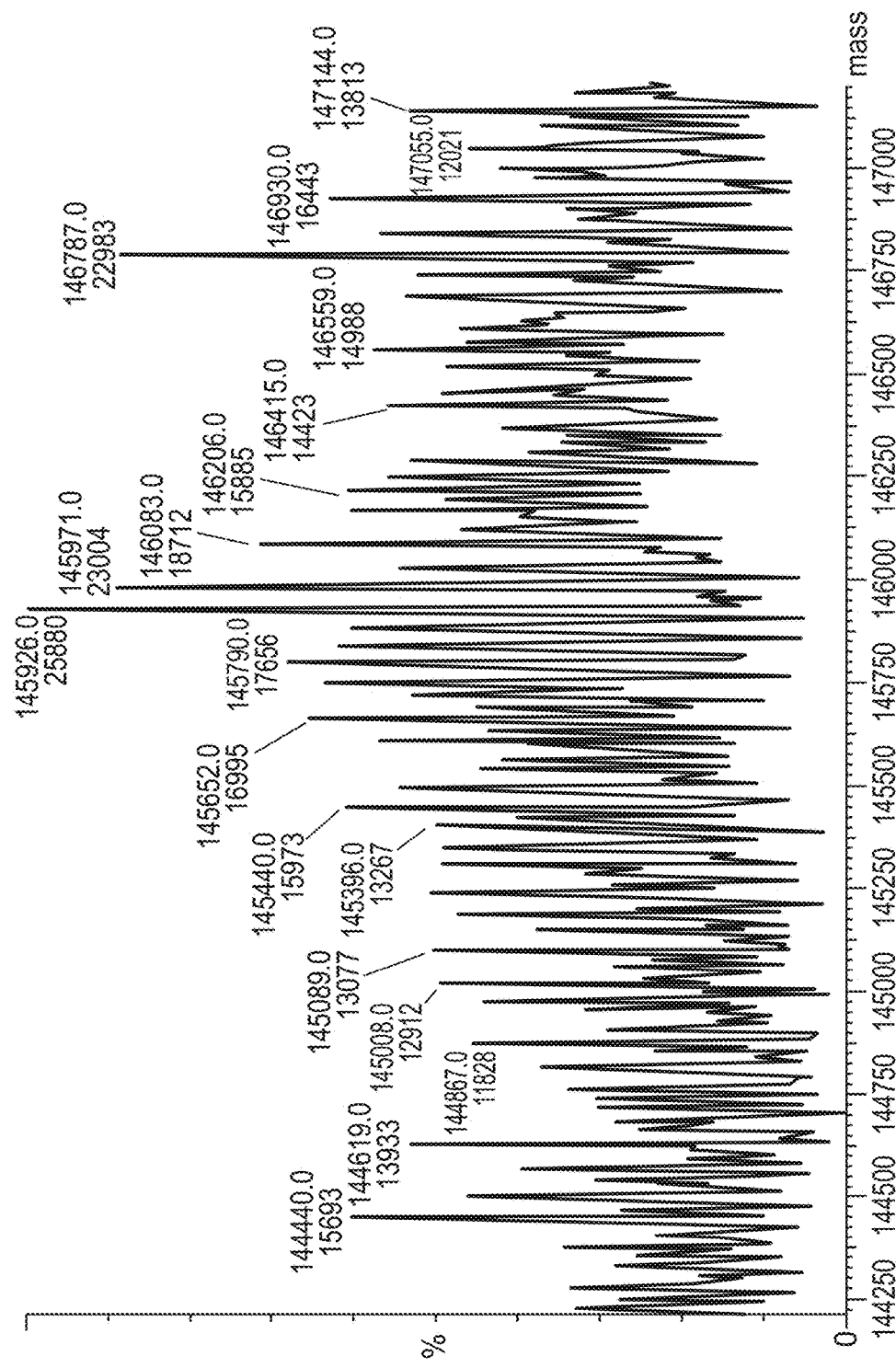

FIG. 120E shows a liquid chromatography-mass spectrometry analysis of the Rituximab-CL572 immunoconjugate produced according to the BB-01 conjugation method following overnight deglycosylation with PNGase F.

Figure 120F:
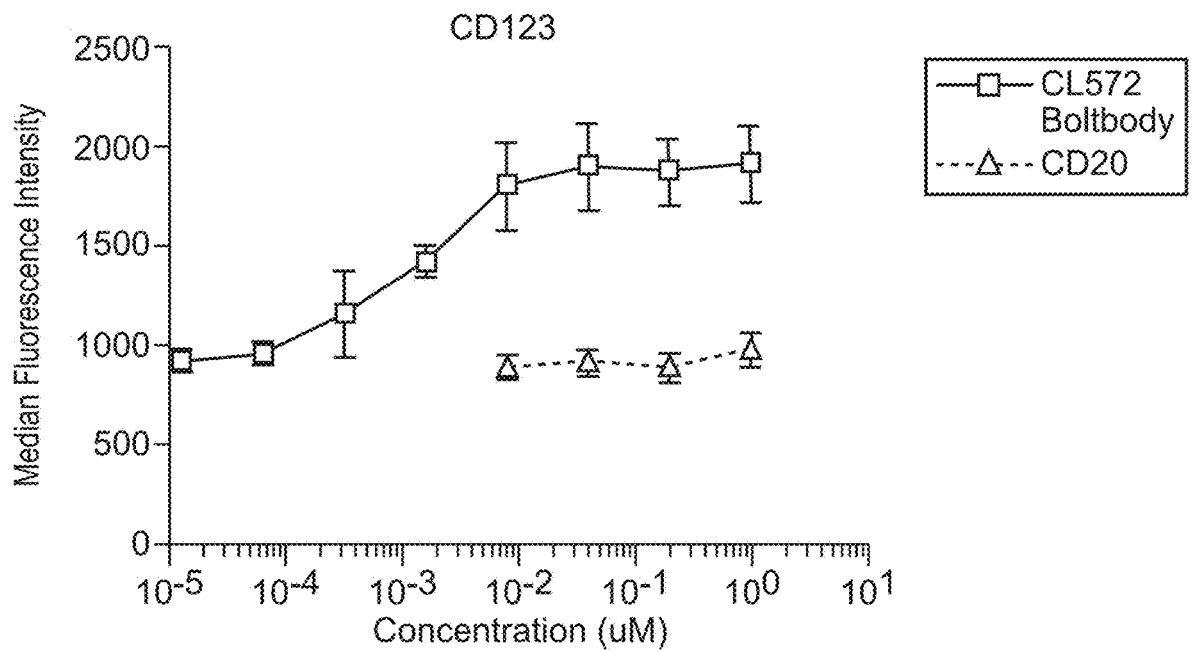

FIG. 120F shows that the Rituximab-CL572 immunoconjugate produced according to the BB-01 method (CL572 Boltbody) is superior at eliciting CD123 upregulation on myeloid cells as compared to unconjugated Rituximab (CD20; Roche) following 18 hours of stimulation.

Figure 120G:
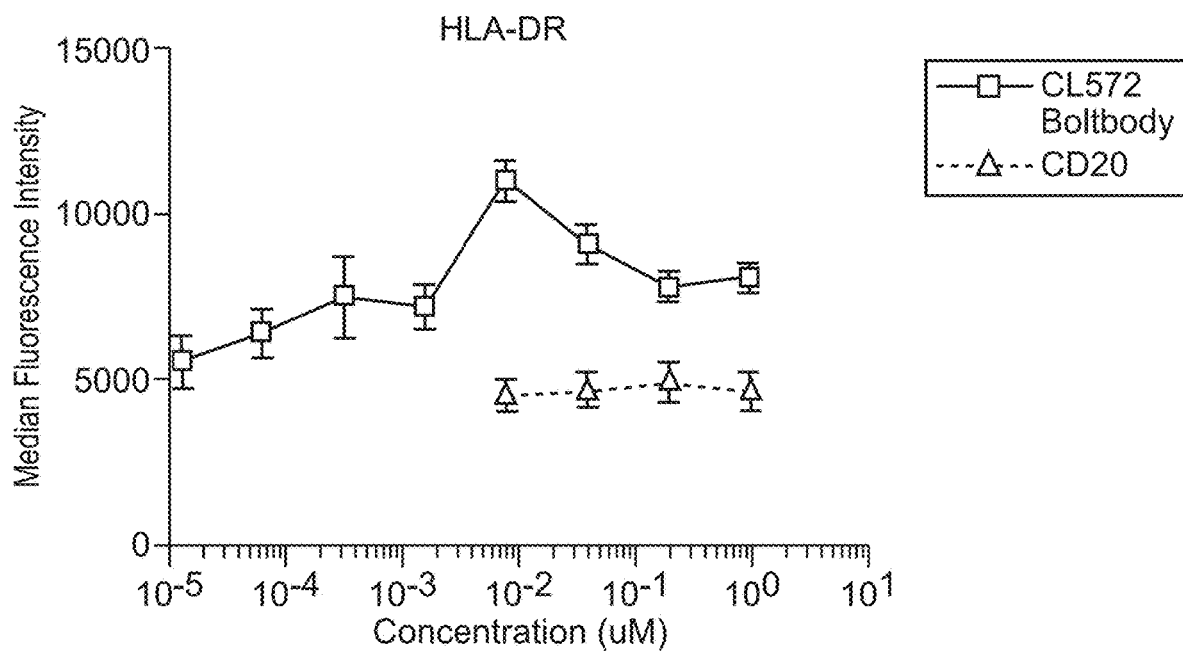

FIG. 120G shows that the Rituximab-CL572 immunoconjugate produced according to the BB-01 method (CL572 Boltbody) is superior at eliciting HLA-DR upregulation on myeloid cells as compared to unconjugated Rituximab (CD20; Roche) following 18 hours of stimulation.

Figure 120H:
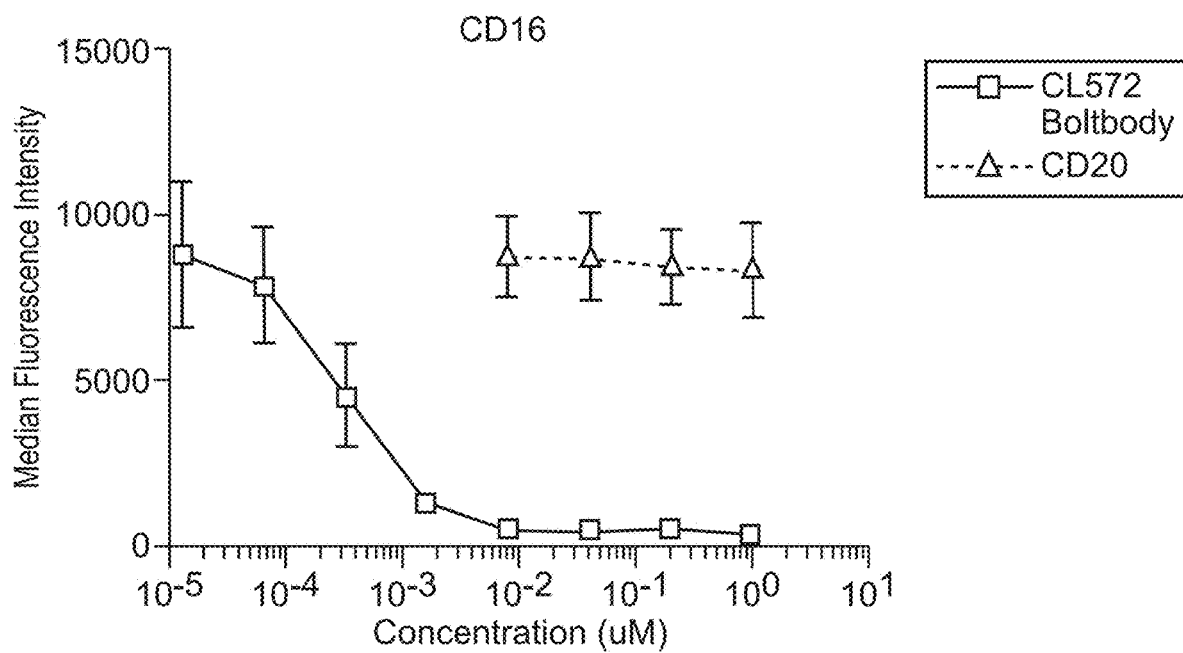

FIG. 120H shows that the Rituximab-CL572 immunoconjugate produced according to the BB-01 method (CL572 Boltbody) is superior at eliciting CD16 downregulation on myeloid cells as compared to unconjugated Rituximab (CD20; Roche) following 18 hours of stimulation.

Figure 120I:
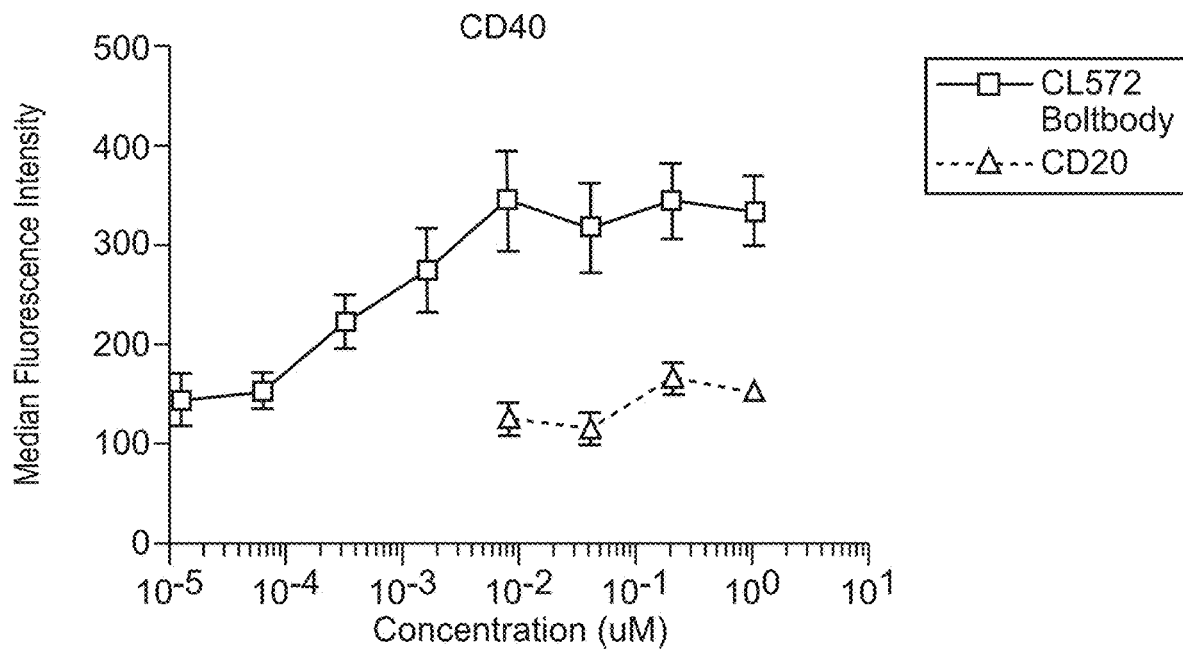

FIG. 120I shows that the Rituximab-CL572 immunoconjugate produced according to the BB-01 method (CL572 Boltbody) is superior at eliciting CD40 upregulation on myeloid cells as compared to unconjugated Rituximab (CD20; Roche) following 18 hours of stimulation.

Figure 121A:
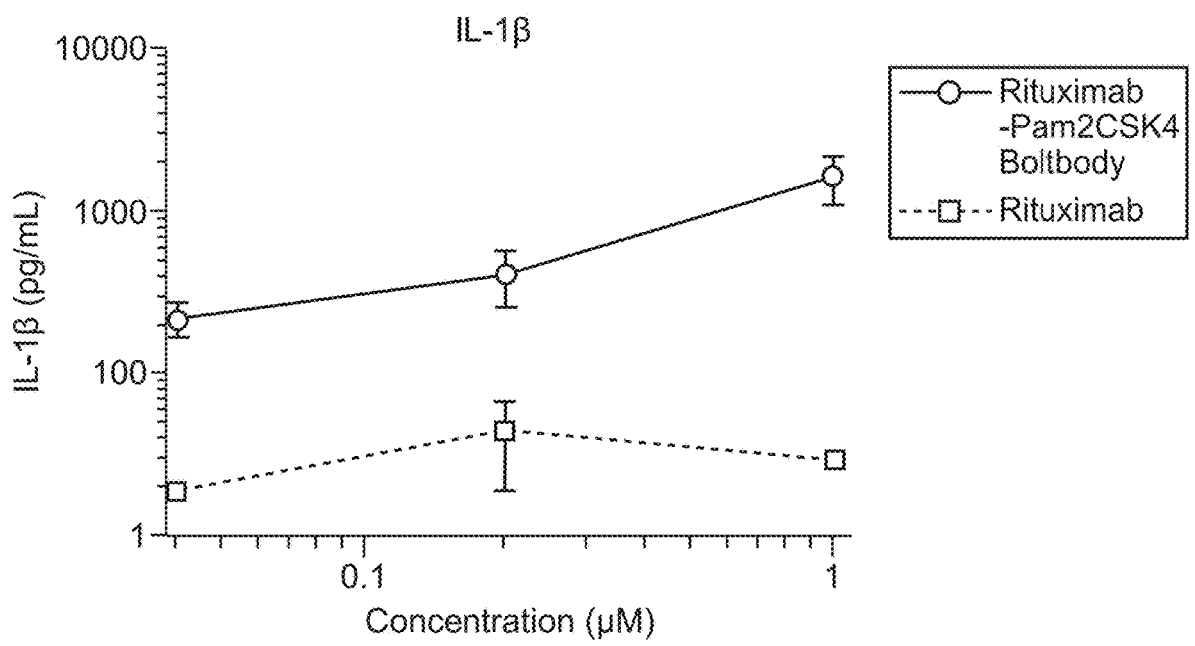

FIG. 121A shows that the Rituximab-Pam2CSK4 immunoconjugate produced according to the BB-01 method (Rituximab-Pam2CSK4 Boltbody) is superior at eliciting IL-10 secretion from myeloid cells as compared to unconjugated Rituximab (Roche) following 36 hours of stimulation.

Figure 121B:
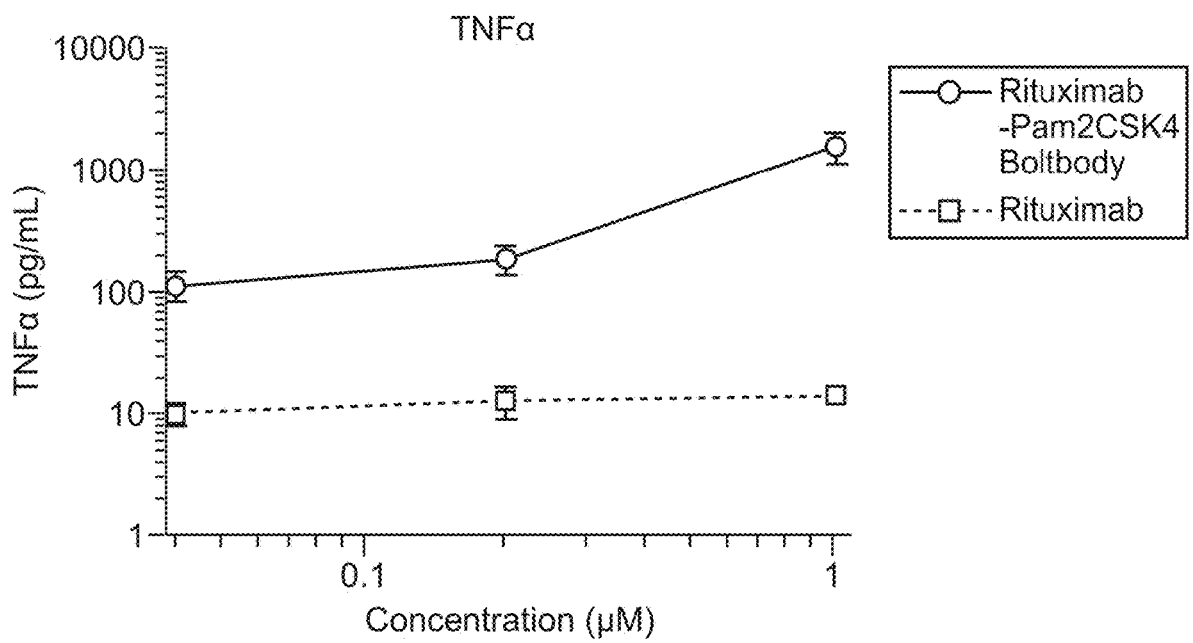

FIG. 121B shows that the Rituximab-Pam2CSK4 immunoconjugate produced according to the BB-01 method (Rituximab-Pam2CSK4 Boltbody) is superior at eliciting TNFα secretion from myeloid cells as compared to unconjugated Rituximab (Roche) following 36 hours of stimulation.

Figure 121C:
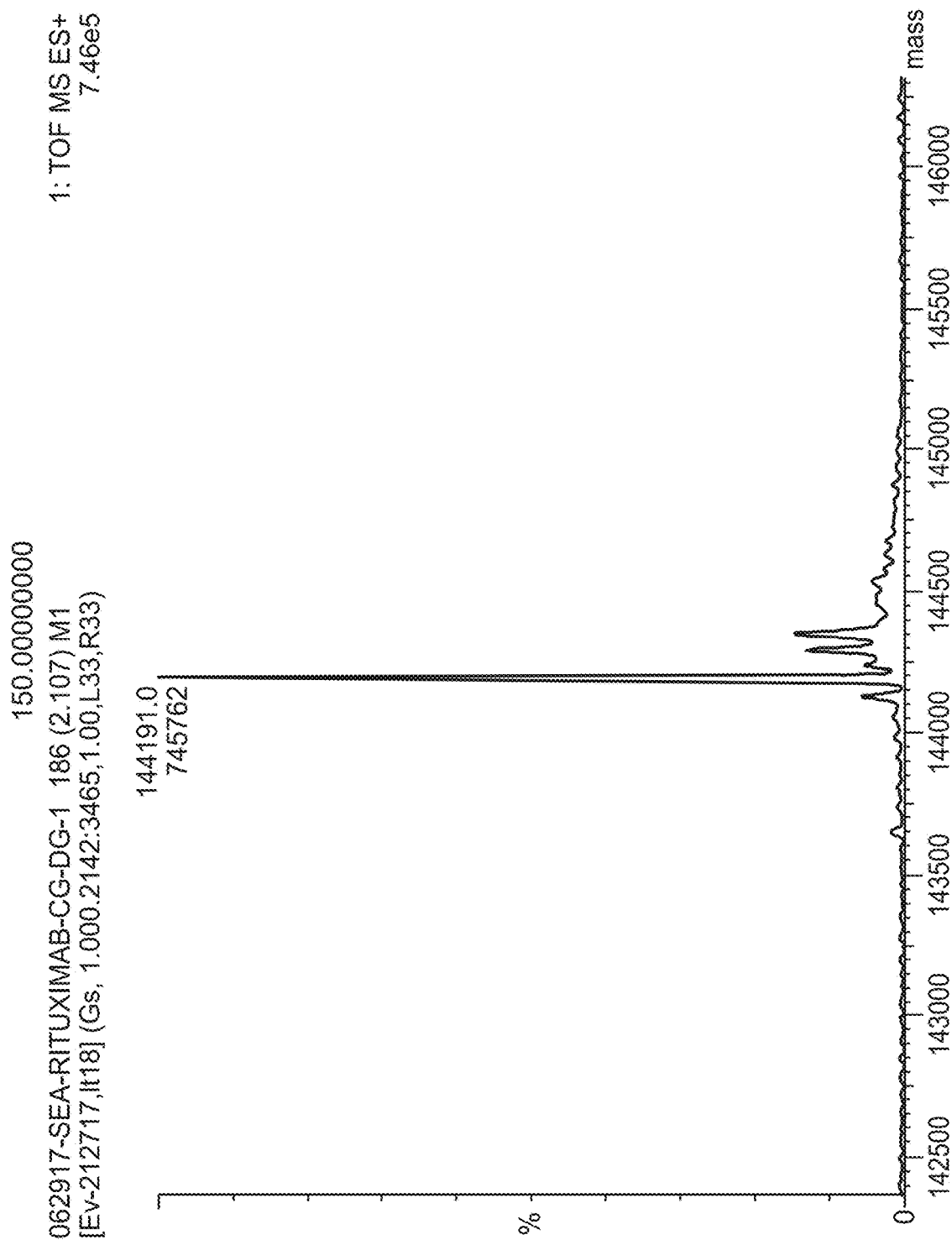

FIG. 121C shows a liquid chromatography-mass spectrometry analysis of unconjugated Rituximab (Roche) that was utilized to produce Rituximab-Pam2CSK4 following overnight deglycosylation with PNGase F.

FIG. 121D shows a liquid chromatography-mass spectrometry analysis of unconjugated Rituximab (Roche) that was utilized to produce Rituximab-Pam2CSK4.

Figure 121E:
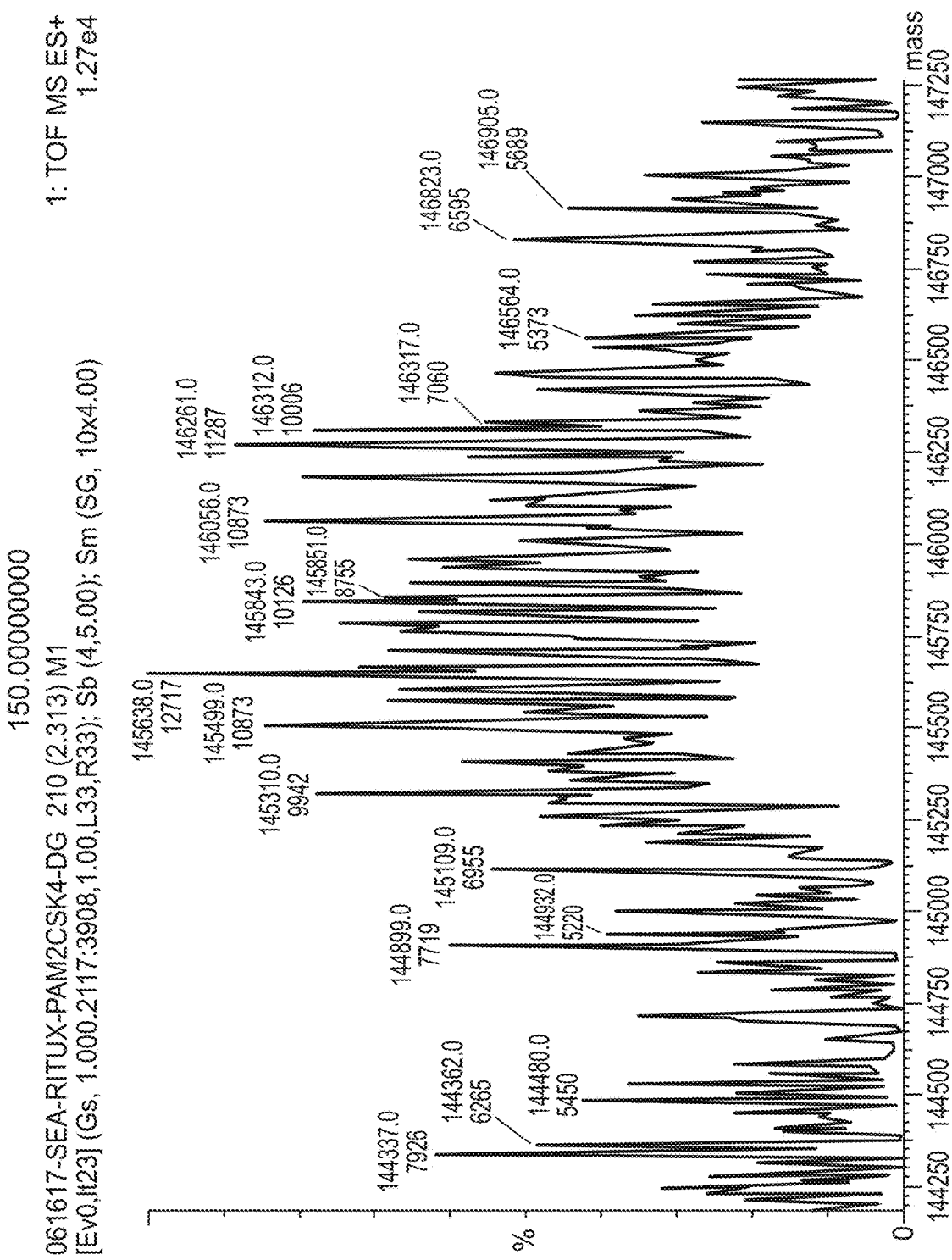

FIG. 121E shows a liquid chromatography-mass spectrometry analysis of the Rituximab-Pam2CSK4 immunoconjugate produced according to the BB-01 conjugation method following overnight deglycosylation with PNGase F.

Figure 121F:
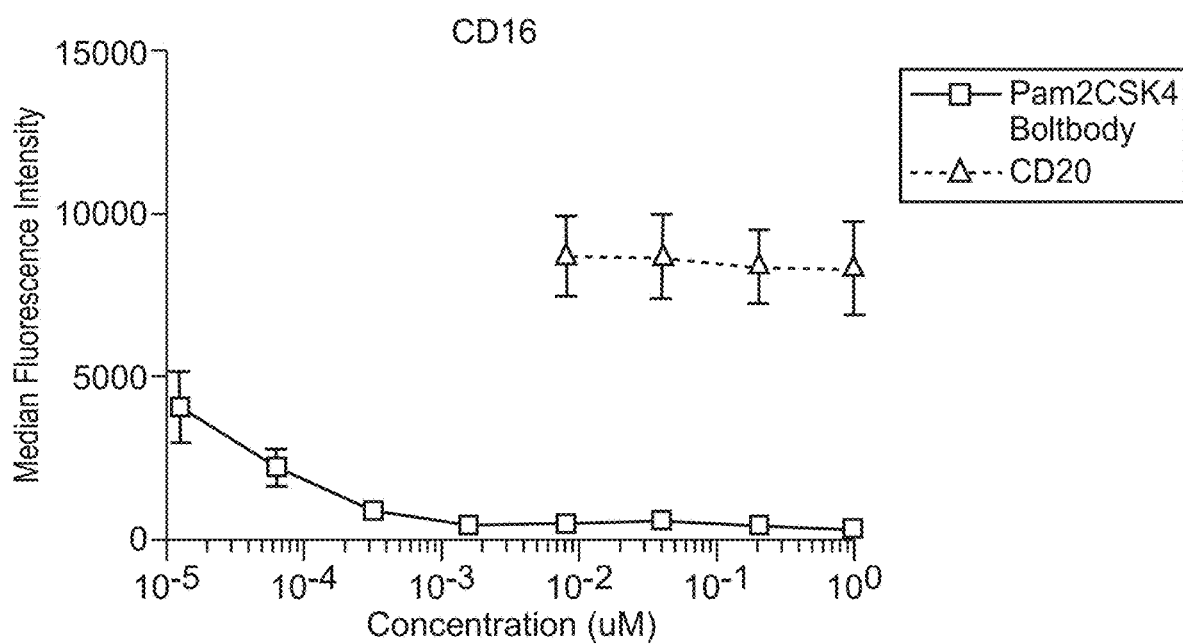

FIG. 121F shows that the Rituximab-Pam2CSK4 immunoconjugate produced according to the BB-01 method (Pam2CSK4 Boltbody) is superior at eliciting CD16 downregulation on myeloid cells as compared to unconjugated Rituximab (CD20; Roche) following 18 hours of stimulation.

Figure 121G:
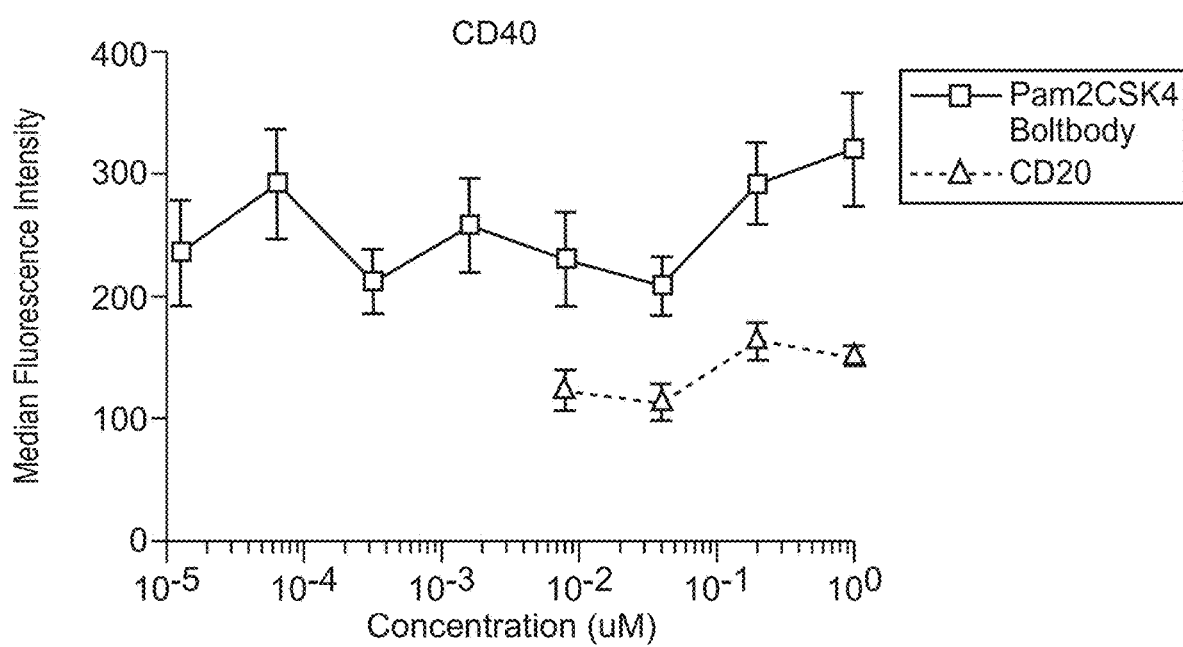

FIG. 121G shows that the Rituximab-Pam2CSK4 immunoconjugate produced according to the BB-01 method (Pam2CSK4 Boltbody) is superior at eliciting CD40 upregulation on myeloid cells as compared to unconjugated Rituximab (CD20; Roche) following 18 hours of stimulation.

Figure 121H:
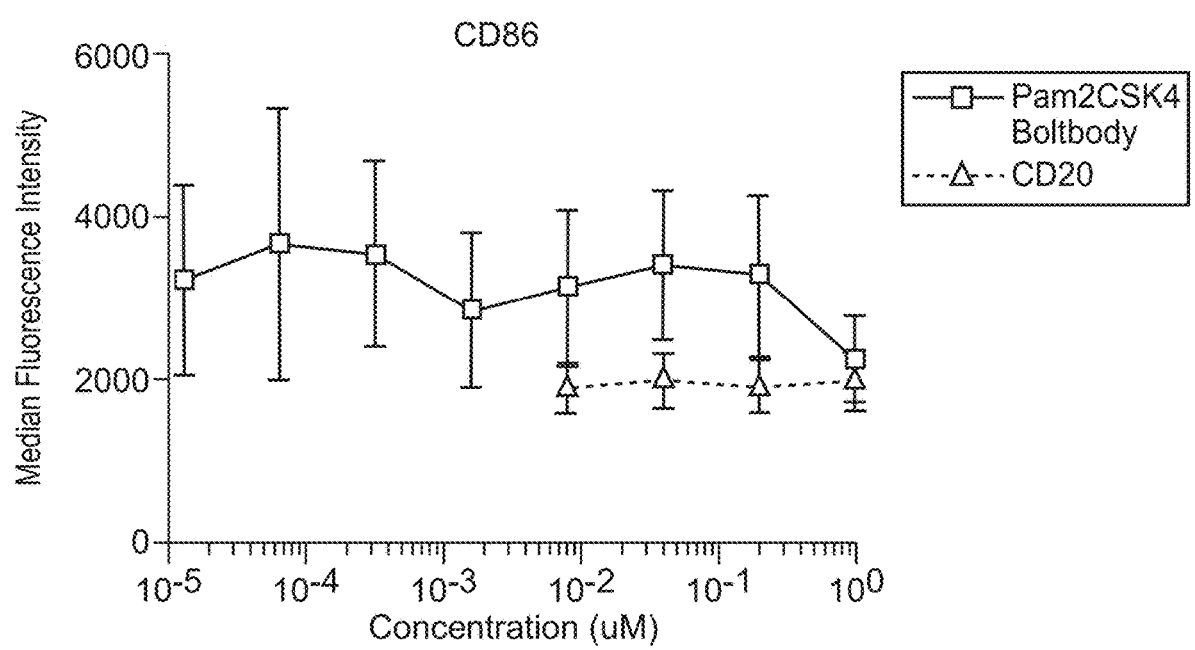

FIG. 121H shows that the Rituximab-Pam2CSK4 immunoconjugate produced according to the BB-01 method (Pam2CSK4 Boltbody) is superior at eliciting CD86 upregulation on myeloid cells as compared to unconjugated Rituximab (CD20; Roche) following 18 hours of stimulation.

Figure 122A:
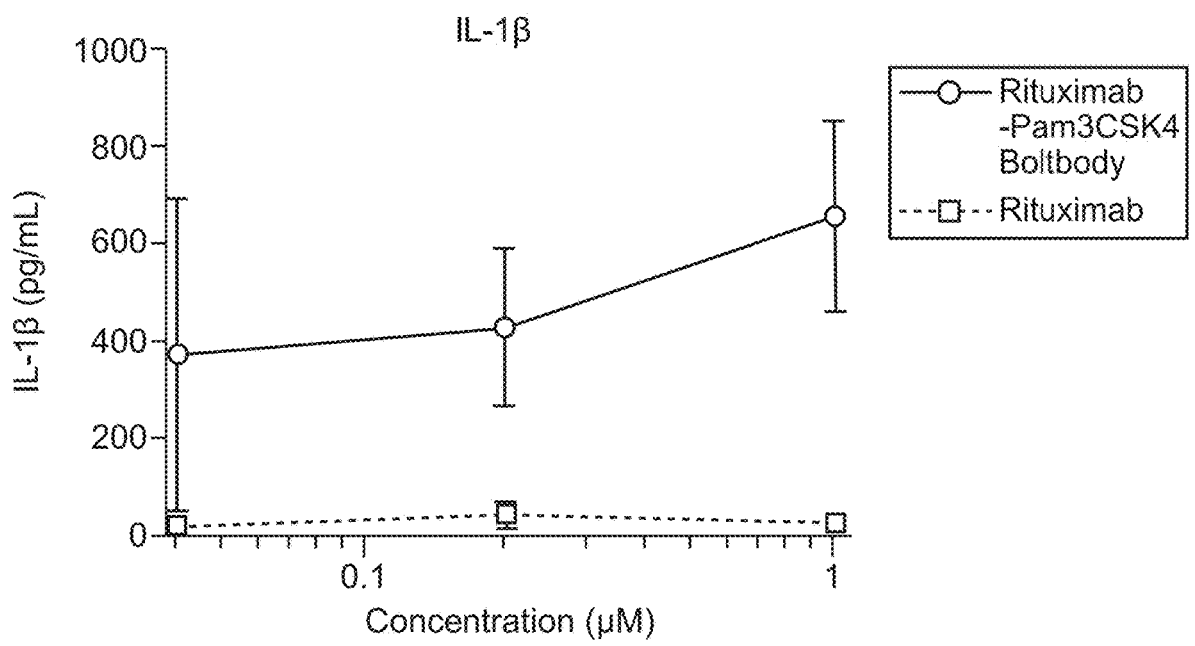

FIG. 122A shows that the Rituximab-Pam3CSK4 immunoconjugate produced according to the BB-01 method (Rituximab-Pam3CSK4 Boltbody) is superior at eliciting IL-10 secretion from myeloid cells as compared to unconjugated Rituximab (Roche) following 36 hours of stimulation.

Figure 122B:
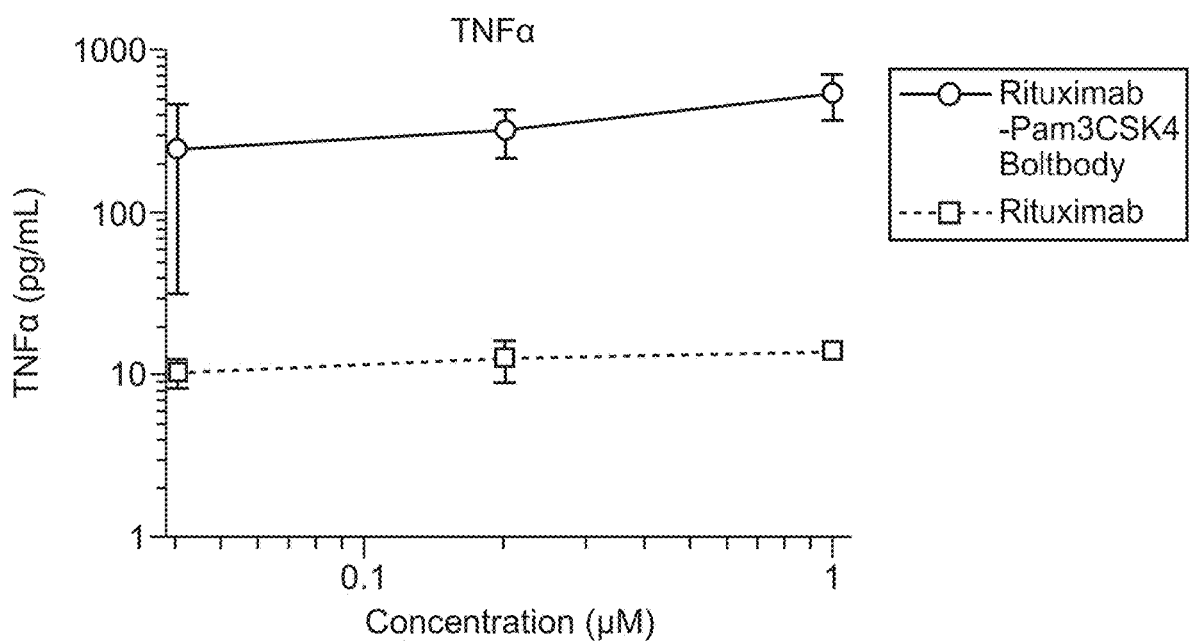

FIG. 122B shows that the Rituximab-Pam3CSK4 immunoconjugate produced according to the BB-01 method (Rituximab-Pam3CSK4 Boltbody) is superior at eliciting TNFα secretion from myeloid cells as compared to unconjugated Rituximab (Roche) following 36 hours of stimulation.

Figure 122C:
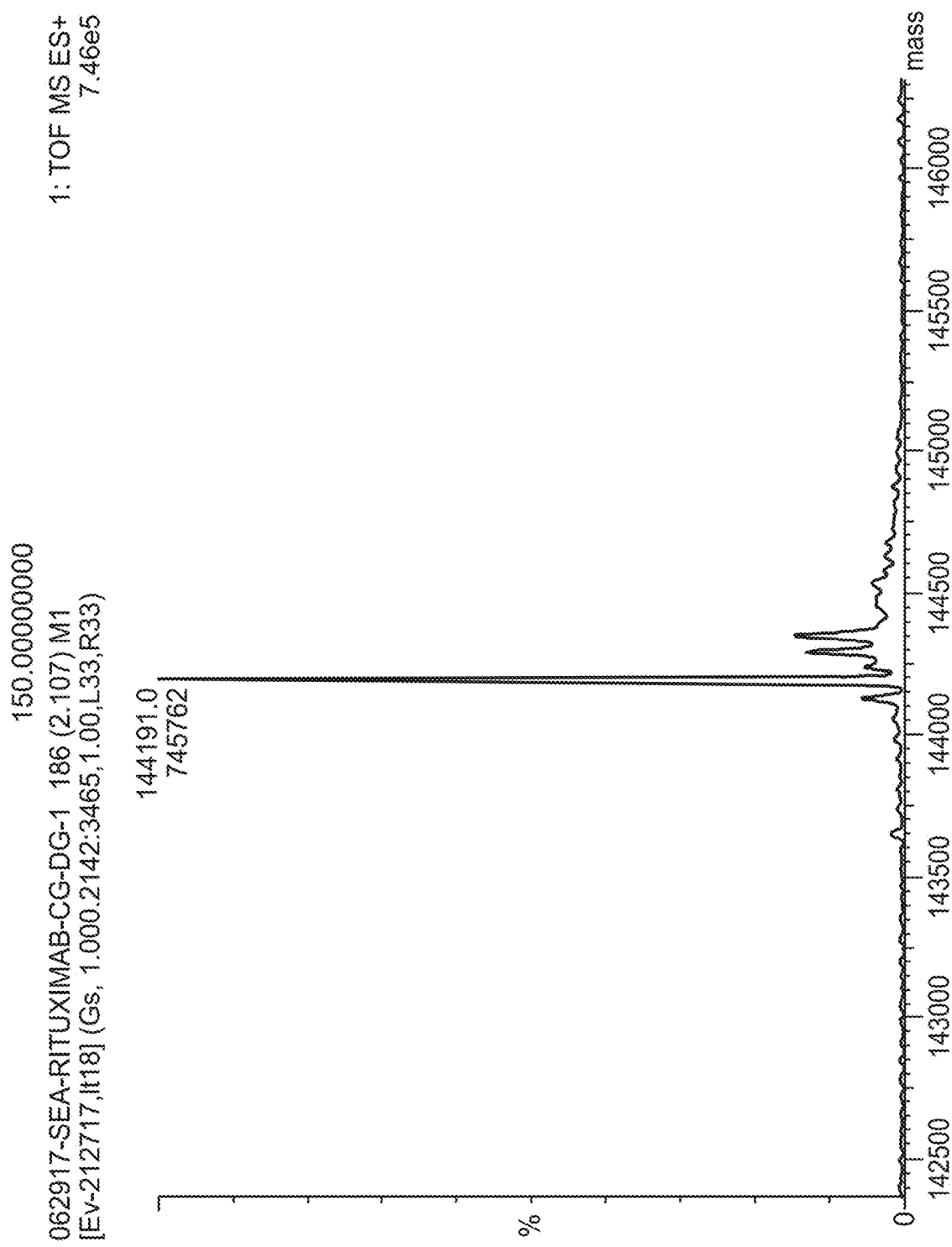

FIG. 122C shows a liquid chromatography-mass spectrometry analysis of unconjugated Rituximab (Roche) that was utilized to produce Rituximab-Pam3CSK4 following overnight deglycosylation with PNGase F.

FIG. 122D shows a liquid chromatography-mass spectrometry analysis of unconjugated Rituximab (Roche) that was utilized to produce Rituximab-Pam3CSK4.

Figure 122E:
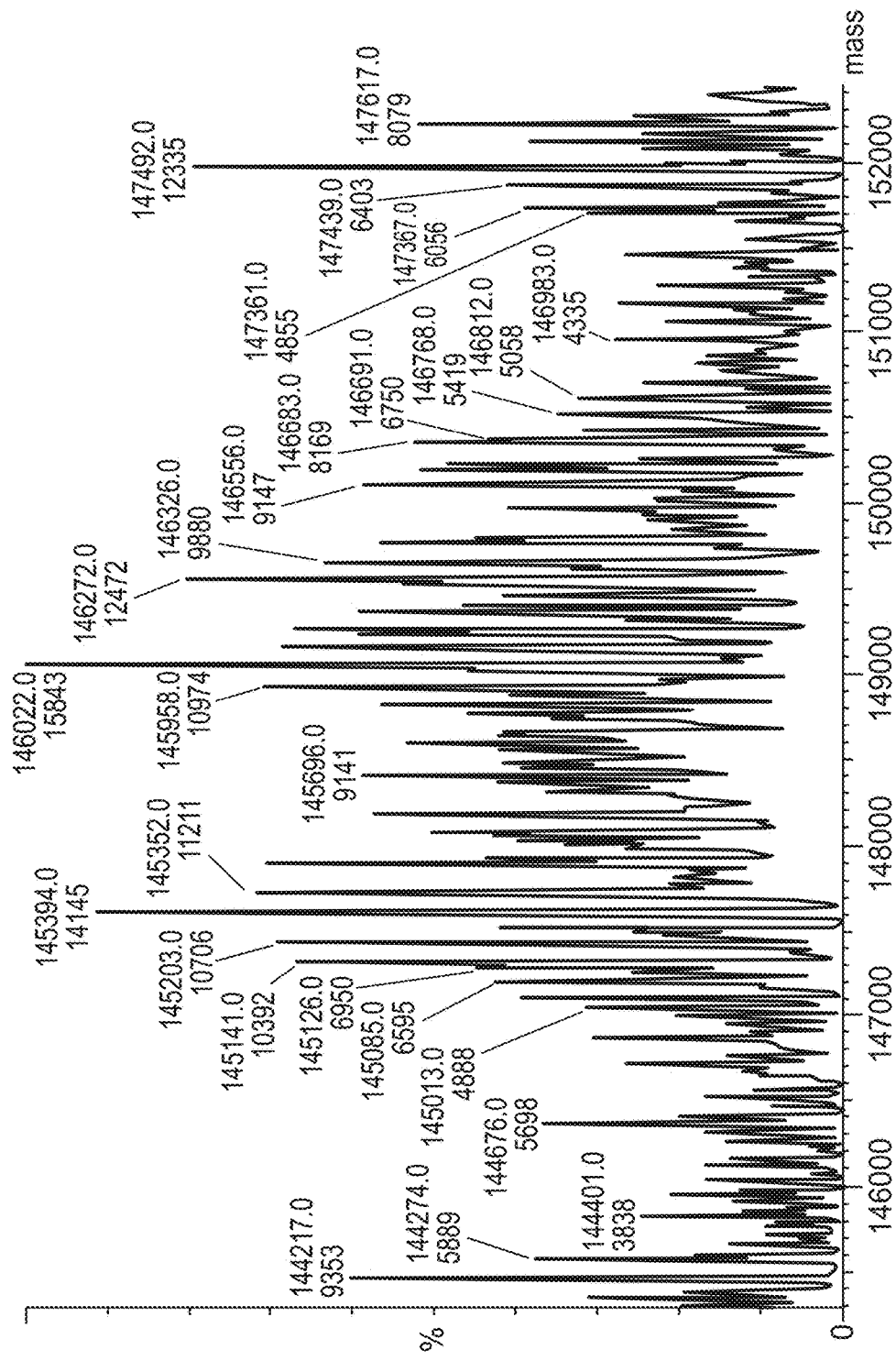

FIG. 122E shows a liquid chromatography-mass spectrometry analysis of the Rituximab-Pam3CSK4 immunoconjugate produced according to the BB-01 conjugation method following overnight deglycosylation with PNGase F.

Figure 122F:
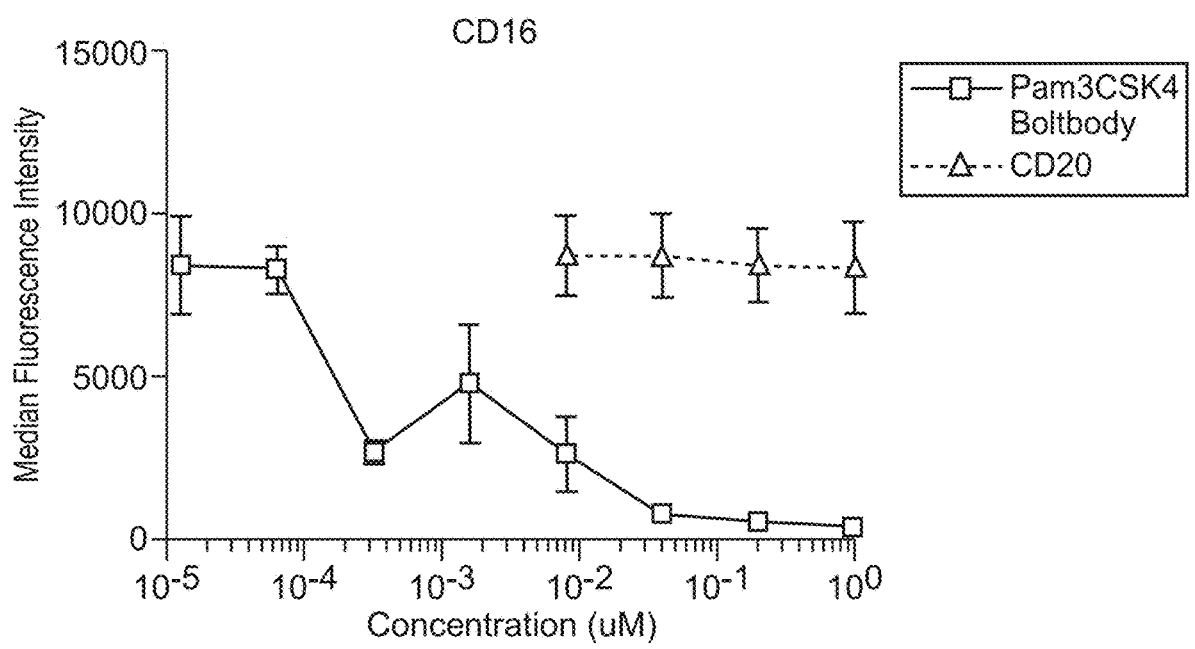

FIG. 122F shows that the Rituximab-Pam3CSK4 immunoconjugate produced according to the BB-01 method (Pam3CSK4 Boltbody) is superior at eliciting CD16 downregulation on myeloid cells as compared to unconjugated Rituximab (CD20; Roche) following 18 hours of stimulation.

Figure 122G:
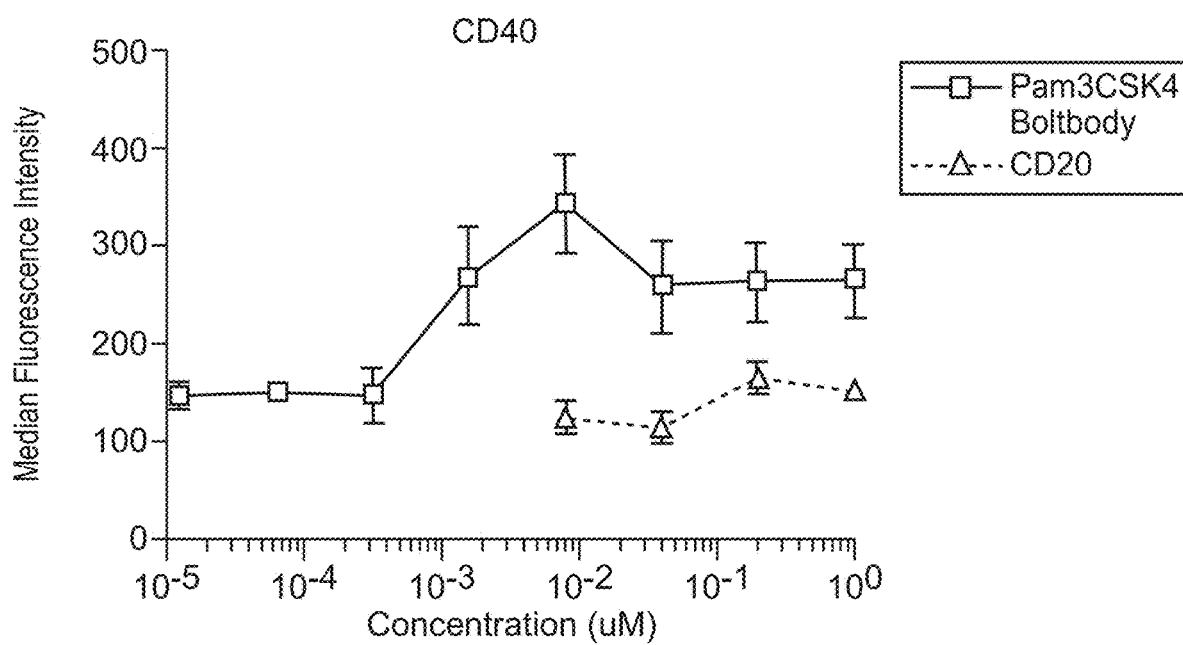

FIG. 122G shows that the Rituximab-Pam3CSK4 immunoconjugate produced according to the BB-01 method (Pam3CSK4 Boltbody) is superior at eliciting CD40 upregulation on myeloid cells as compared to unconjugated Rituximab (CD20; Roche) following 18 hours of stimulation.

Figure 122H:
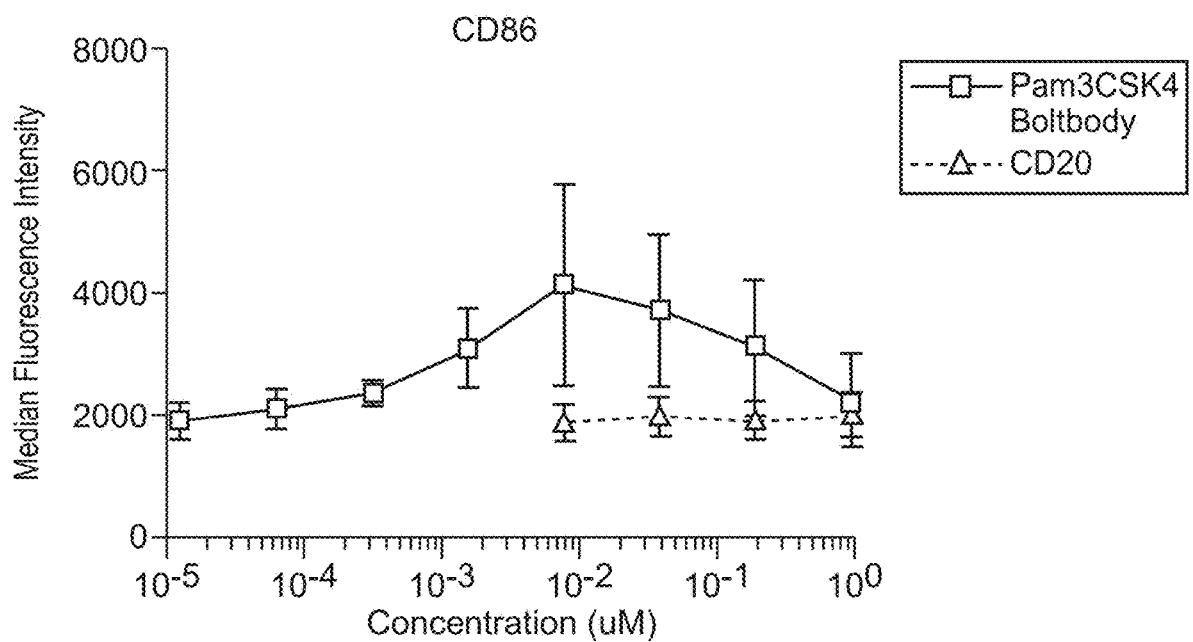

FIG. 122H shows that the Rituximab-Pam3CSK4 immunoconjugate produced according to the BB-01 method (Pam3CSK4 Boltbody) is superior at eliciting CD86 upregulation on myeloid cells as compared to unconjugated Rituximab (CD20; Roche) following 18 hours of stimulation.

Figure 122I:
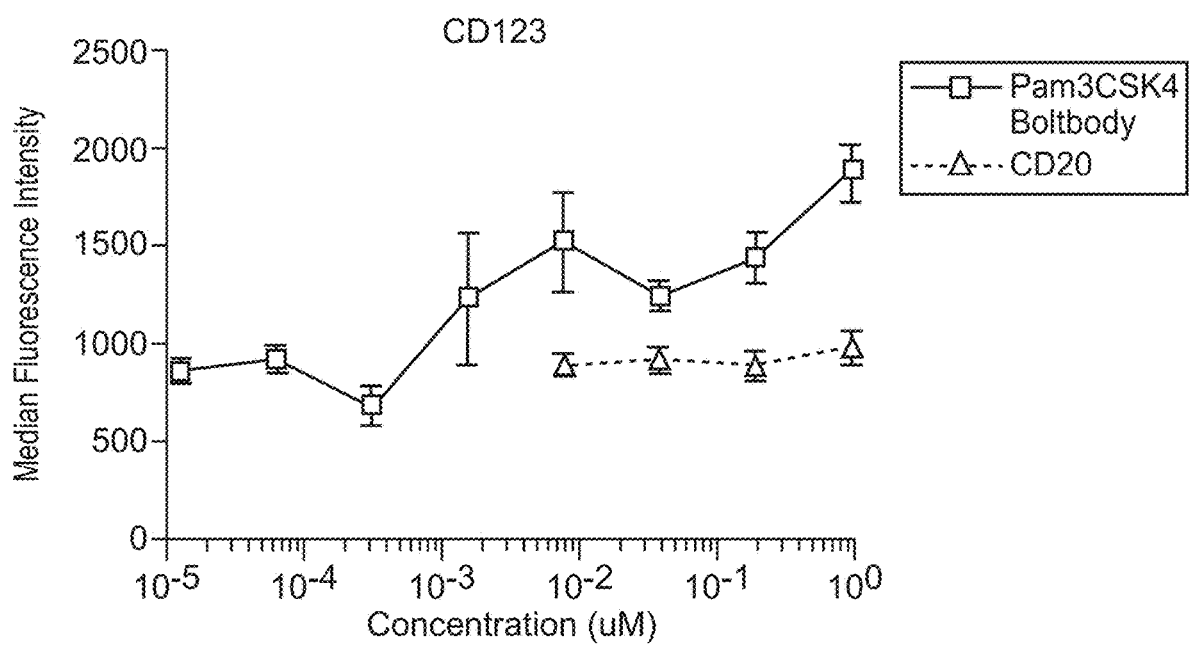

FIG. 122I shows that the Rituximab-Pam3CSK4 immunoconjugate produced according to the BB-01 method (Pam3CSK4 Boltbody) is superior at eliciting CD123 upregulation on myeloid cells as compared to unconjugated Rituximab (CD20; Roche) following 18 hours of stimulation.

Figure 123A:
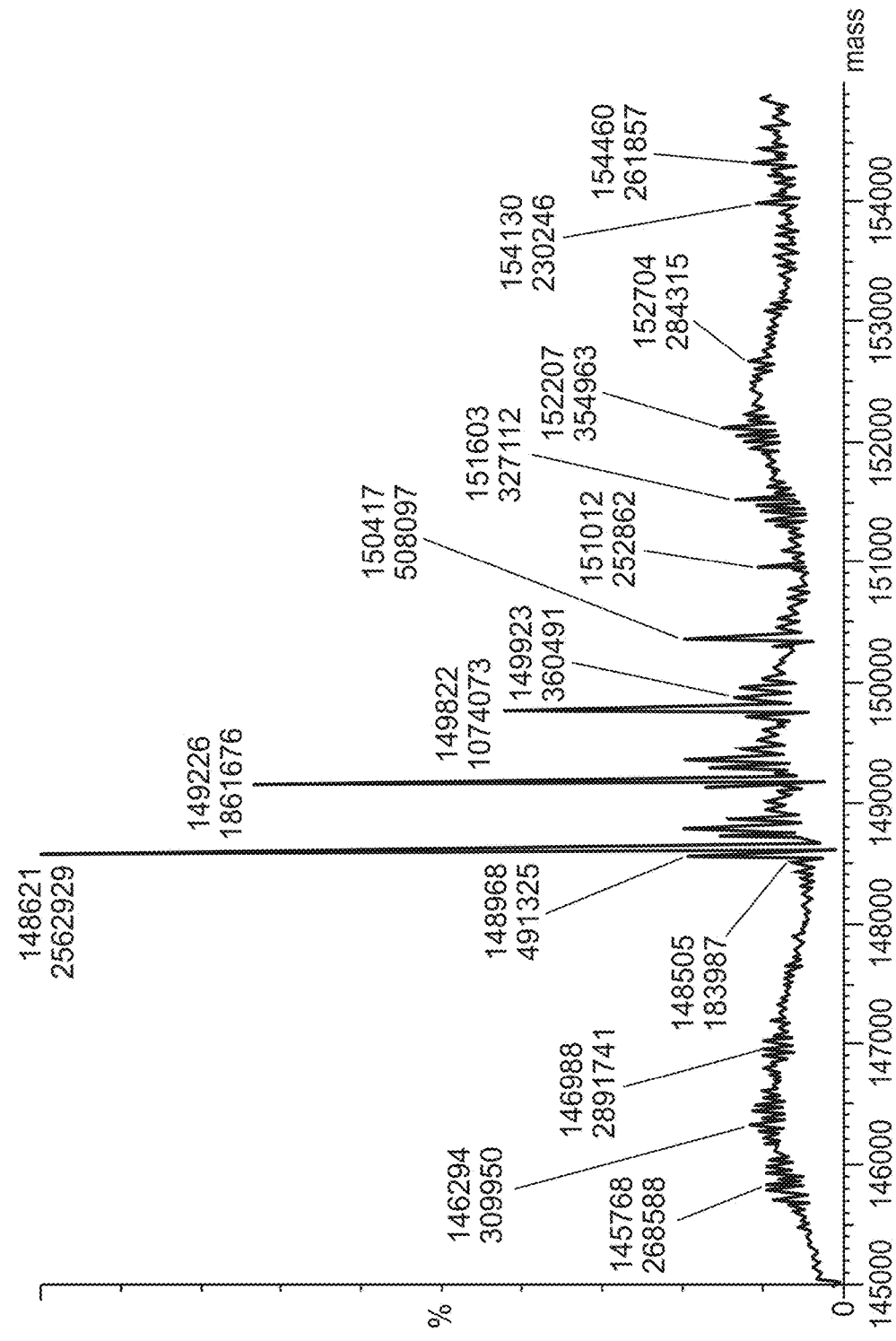

FIG. 123A shows a liquid chromatography-mass spectrometry analysis of the BB-43 immunoconjugate produced according to the TFP conjugation method.

Figure 123B:
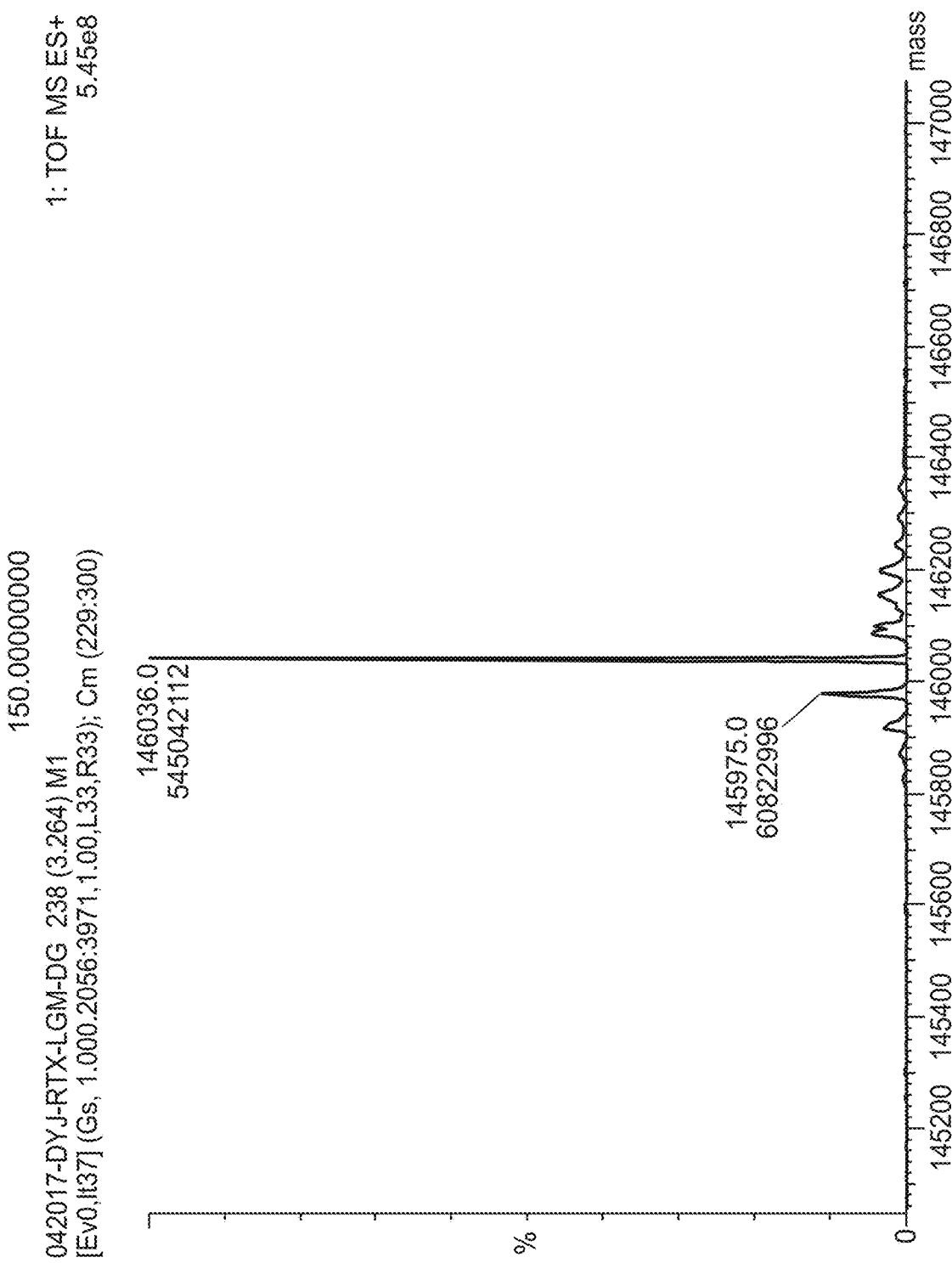

FIG. 123B shows a liquid chromatography-mass spectrometry analysis of an unconjugated Rituximab biosimilar (LGM Pharma) that was utilized to produce BB-43 following overnight deglycosylation with PNGase F.

Figure 123C:
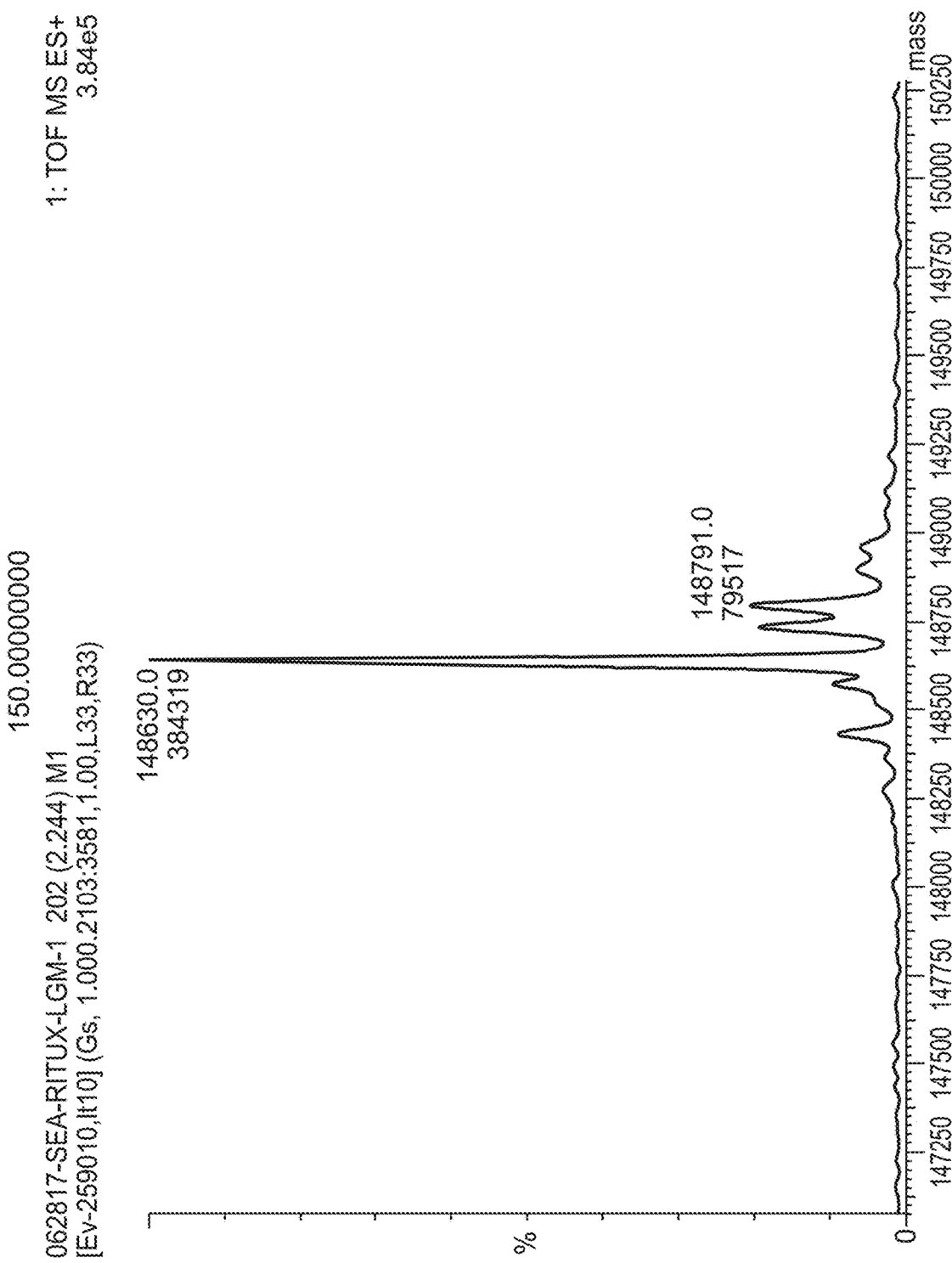

FIG. 123C shows a liquid chromatography-mass spectrometry analysis of an unconjugated Rituximab biosimilar (LGM Pharma) that was utilized to produce BB-43.

Figure 123D:
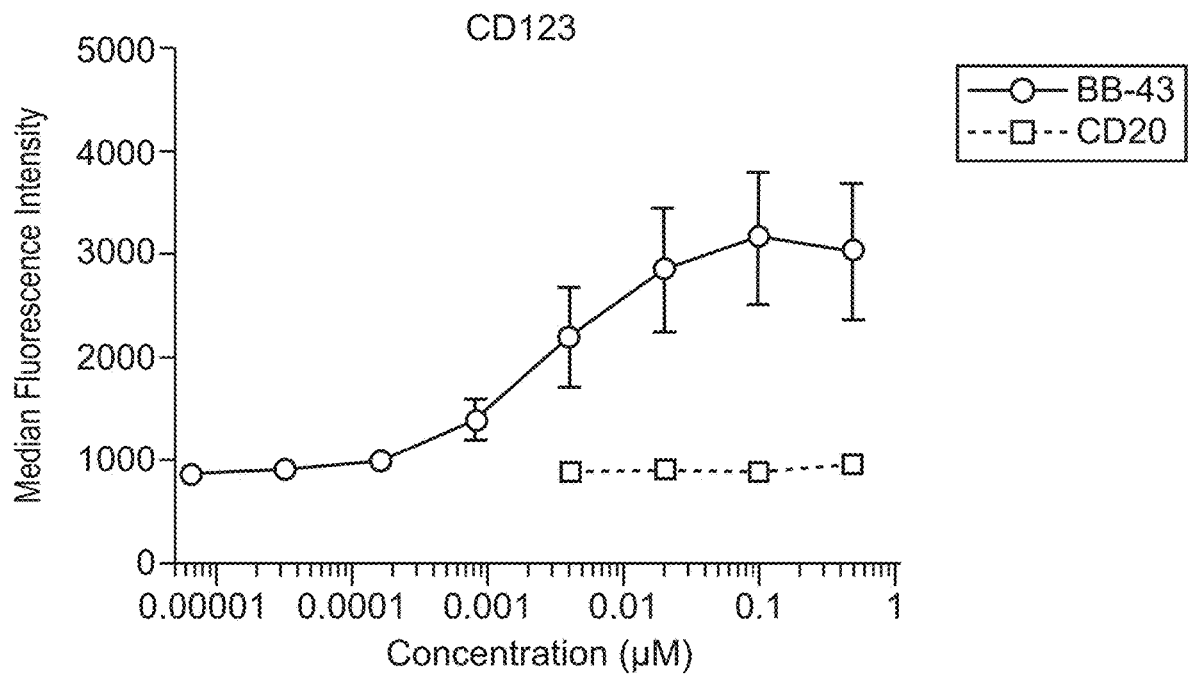

FIG. 123D shows that the BB-43 immunoconjugate produced according to the TFP method is superior at eliciting CD123 upregulation on myeloid cells as compared to an unconjugated Rituximab biosimilar (LGM Pharma) following 18 hours of stimulation.

Figure 123E:
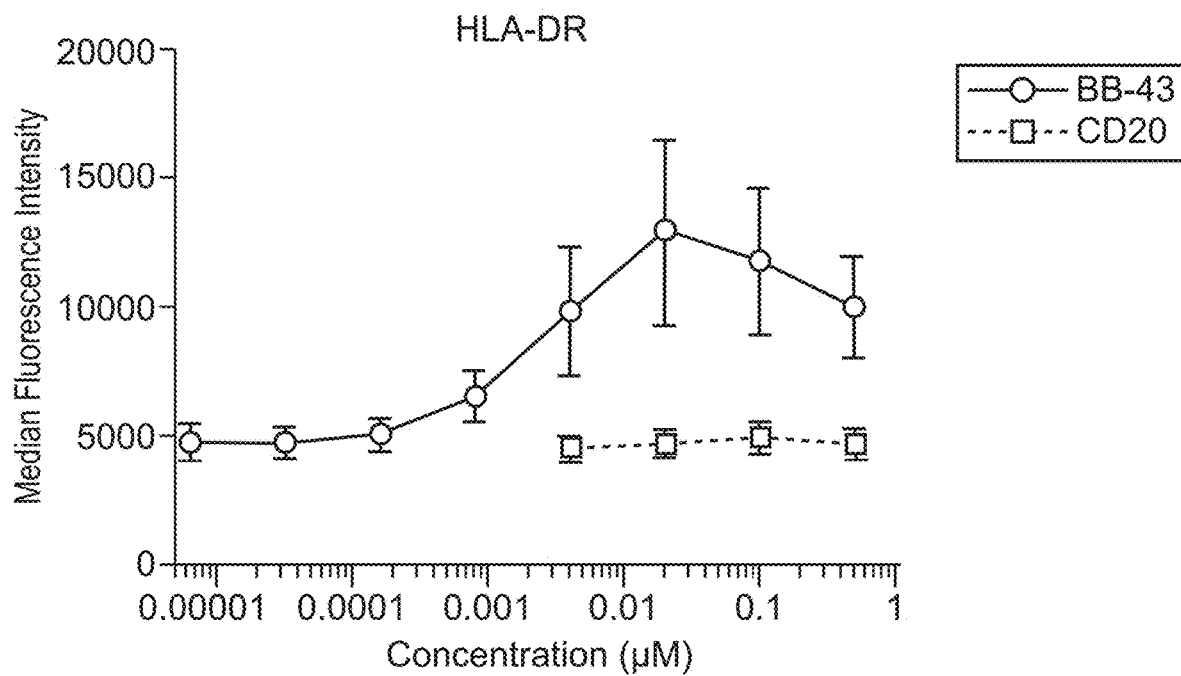

FIG. 123E shows that the BB-43 immunoconjugate produced according to the TFP method is superior at eliciting HLA-DR upregulation on myeloid cells as compared to an unconjugated Rituximab biosimilar (LGM Pharma) following 18 hours of stimulation.

Figure 123F:
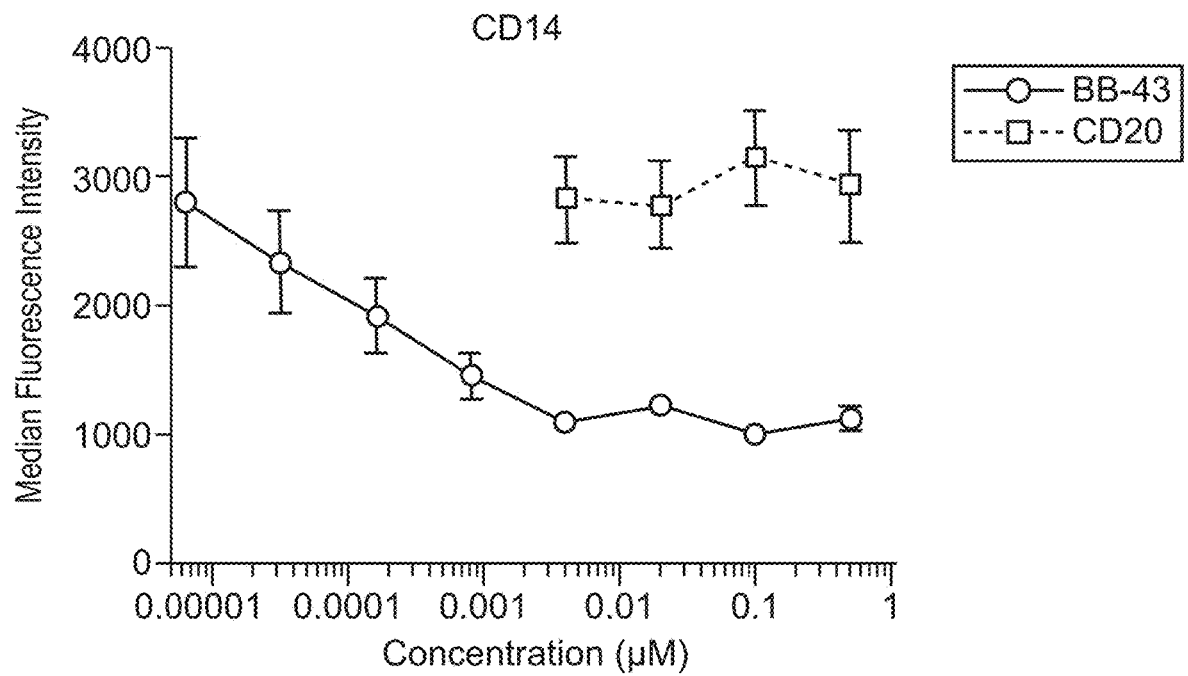

FIG. 123F shows that the BB-43 immunoconjugate produced according to the TFP method is superior at eliciting CD14 downregulation on myeloid cells as compared to an unconjugated Rituximab biosimilar (LGM Pharma) following 18 hours of stimulation.

Figure 123G:
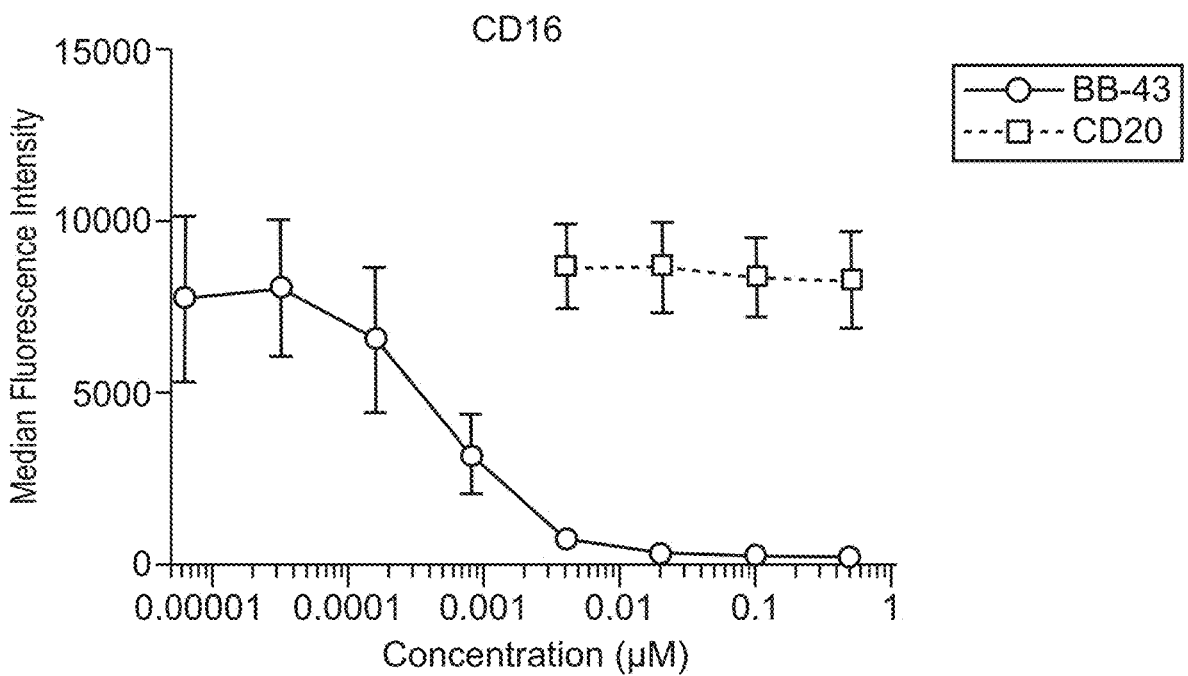

FIG. 123G shows that the BB-43 immunoconjugate produced according to the TFP method is superior at eliciting CD16 downregulation on myeloid cells as compared to an unconjugated Rituximab biosimilar (LGM Pharma) following 18 hours of stimulation.

Figure 123H:
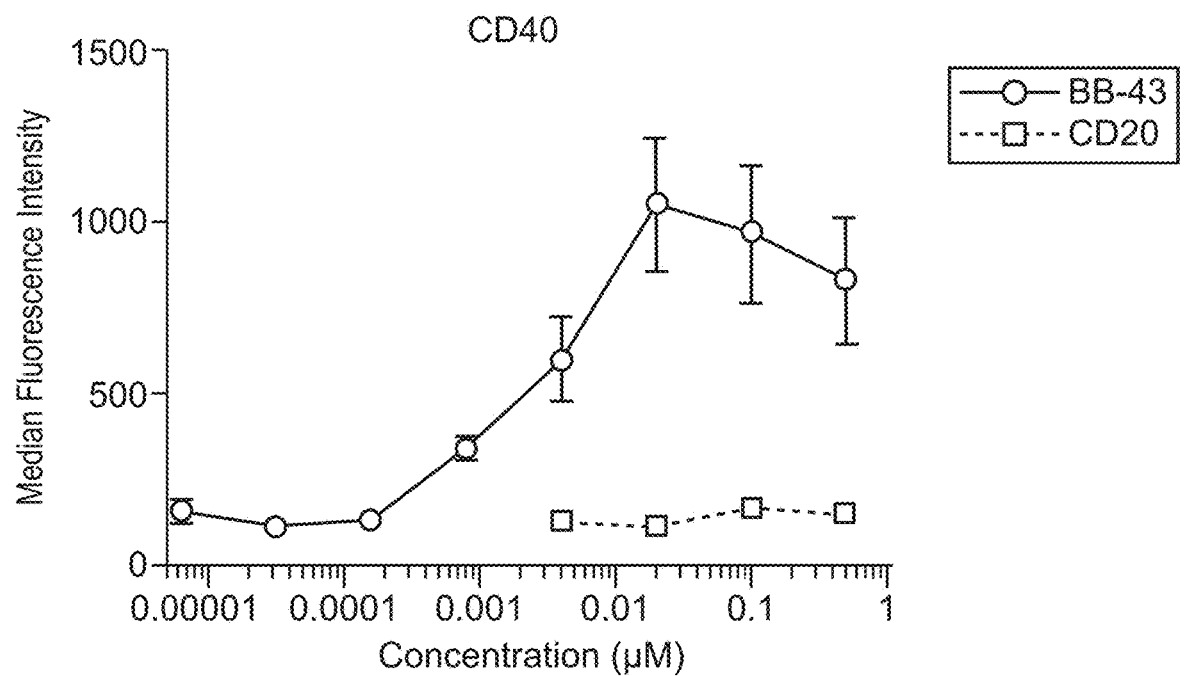

FIG. 123H shows that the BB-43 immunoconjugate produced according to the TFP method is superior at eliciting CD40 upregulation on myeloid cells as compared to an unconjugated Rituximab biosimilar (LGM Pharma) following 18 hours of stimulation.

Figure 123I:
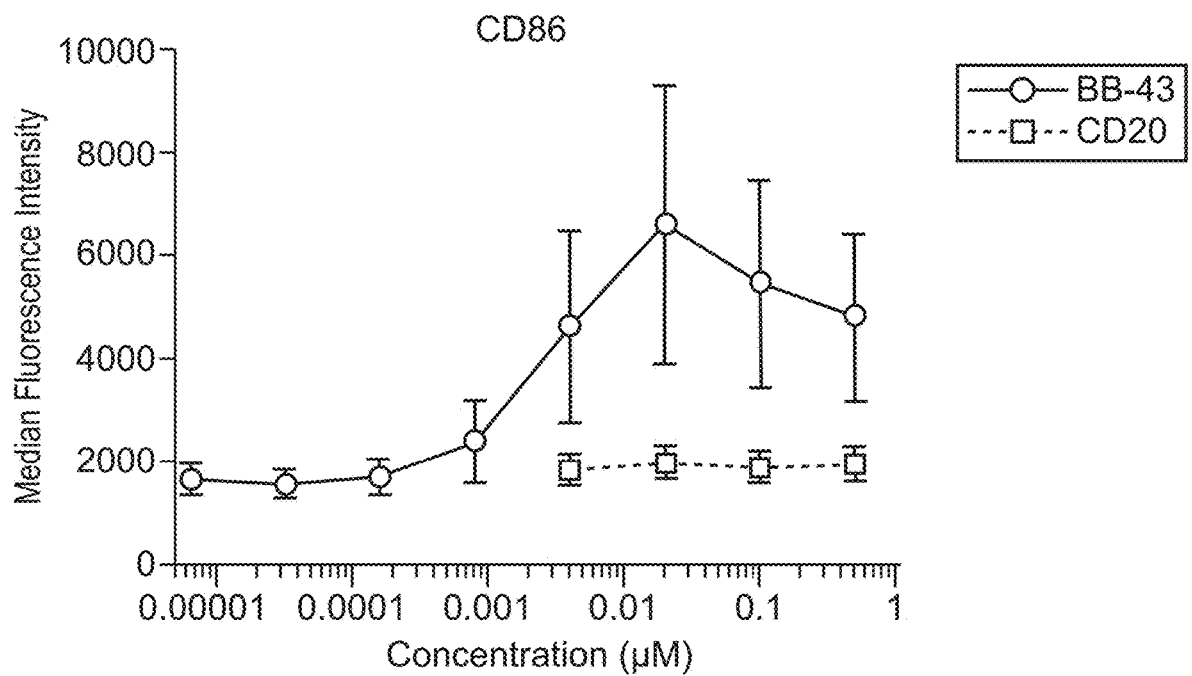

FIG. 123I shows that the BB-43 immunoconjugate produced according to the TFP method is superior at eliciting CD86 upregulation on myeloid cells as compared to an unconjugated Rituximab biosimilar (LGM Pharma) following 18 hours of stimulation.

Figure 124A:
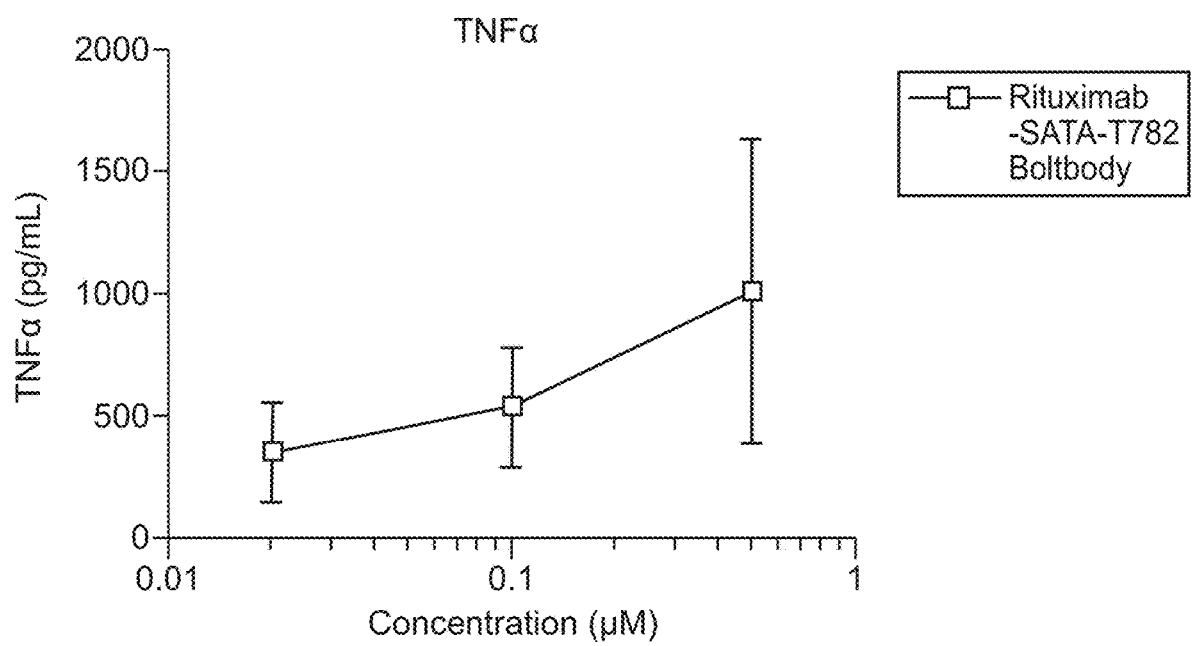

FIG. 124A shows that the Rituximab-SATA-T782 immunoconjugate produced according to the BB-01 method (Rituximab-SATA-T782 Boltbody) elicits TNFα secretion from myeloid cells in a dose-dependent manner following 18 hours of stimulation.

Figure 124B:
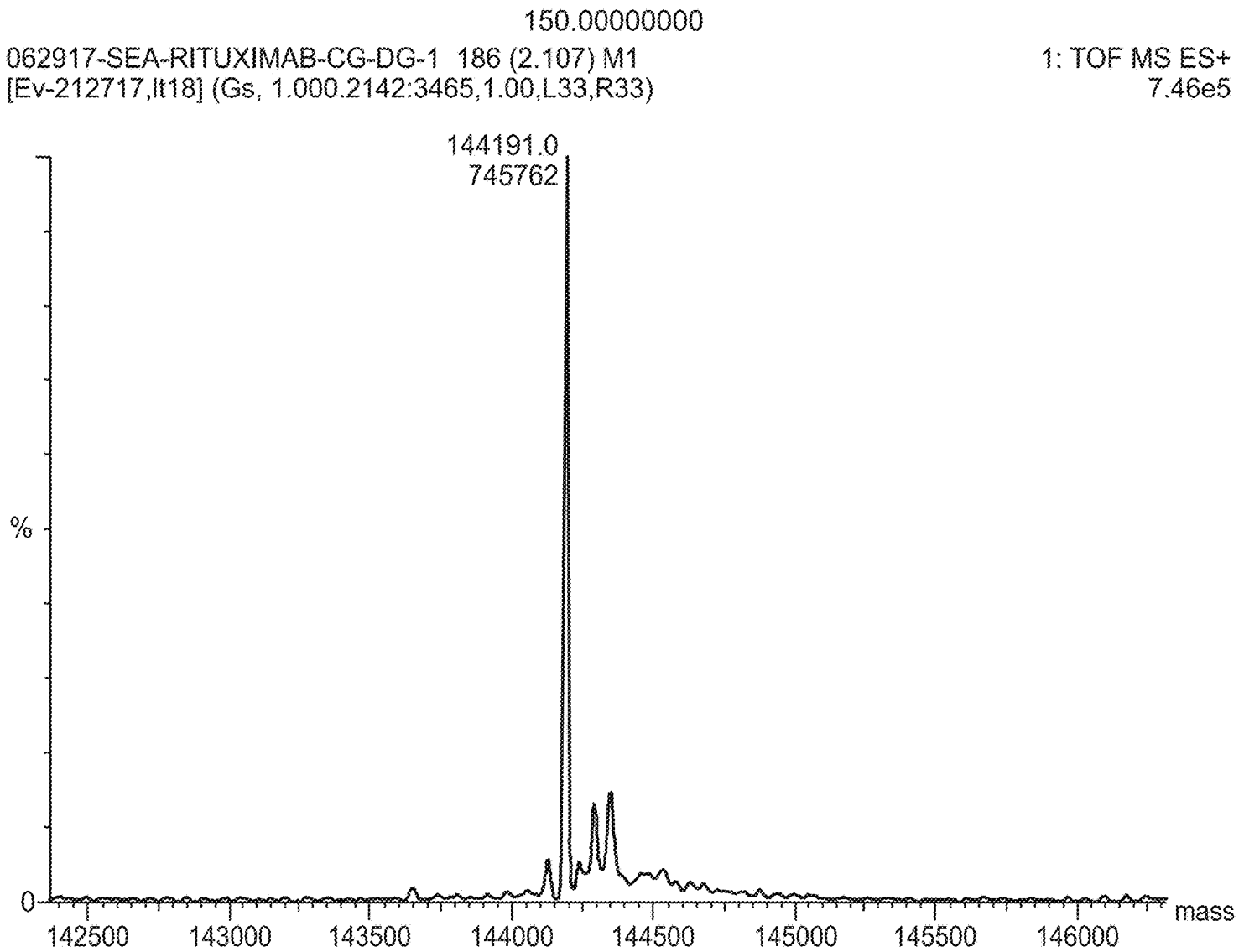

FIG. 124B shows a liquid chromatography-mass spectrometry analysis of unconjugated Rituximab (Roche) that was utilized to produce Rituximab-SATA-T782 following overnight deglycosylation with PNGase F.

Figure 124C:
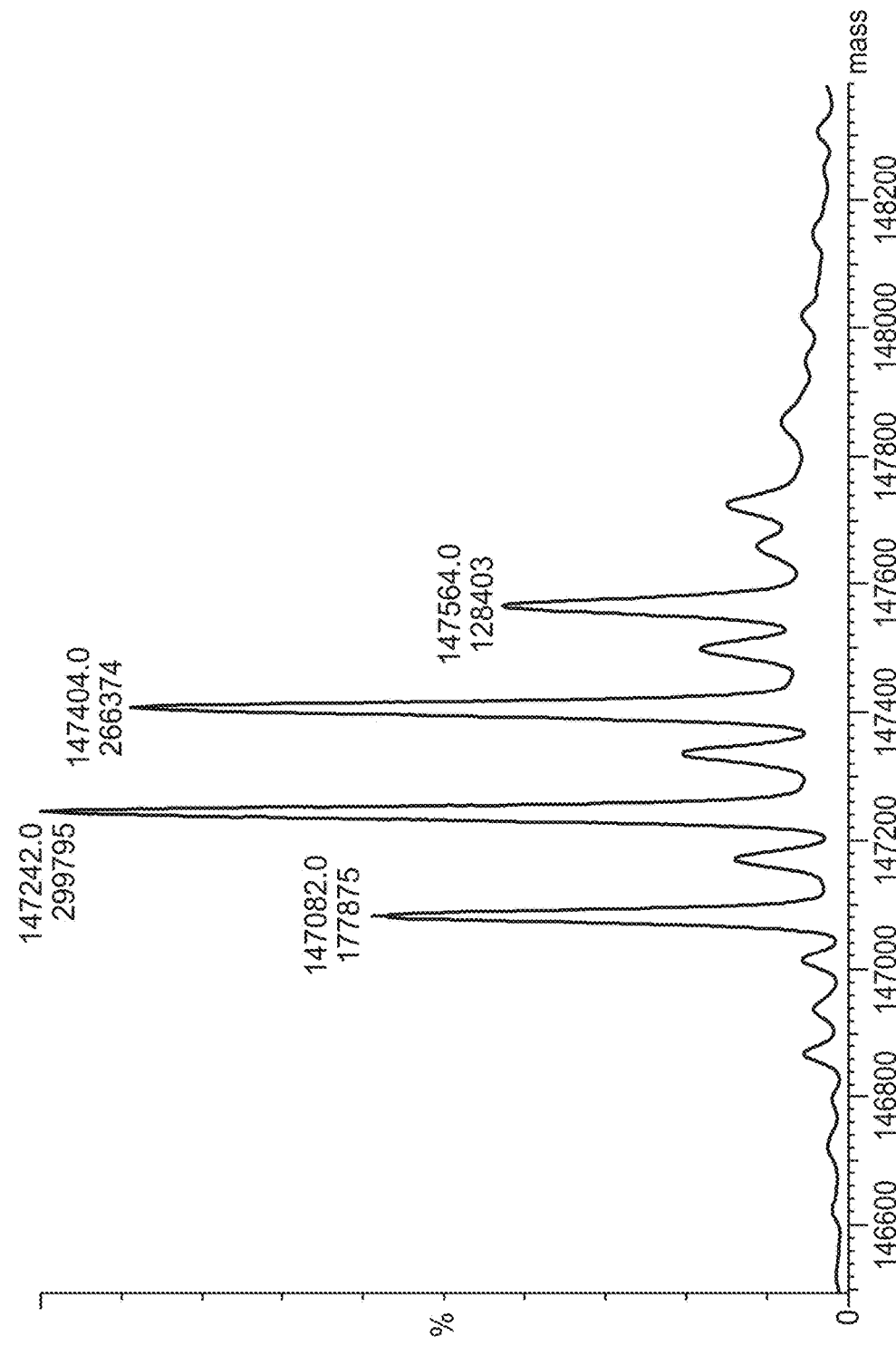

FIG. 124C shows a liquid chromatography-mass spectrometry analysis of unconjugated Rituximab (Roche) that was utilized to produce Rituximab-SATA-T782.

Figure 124D:
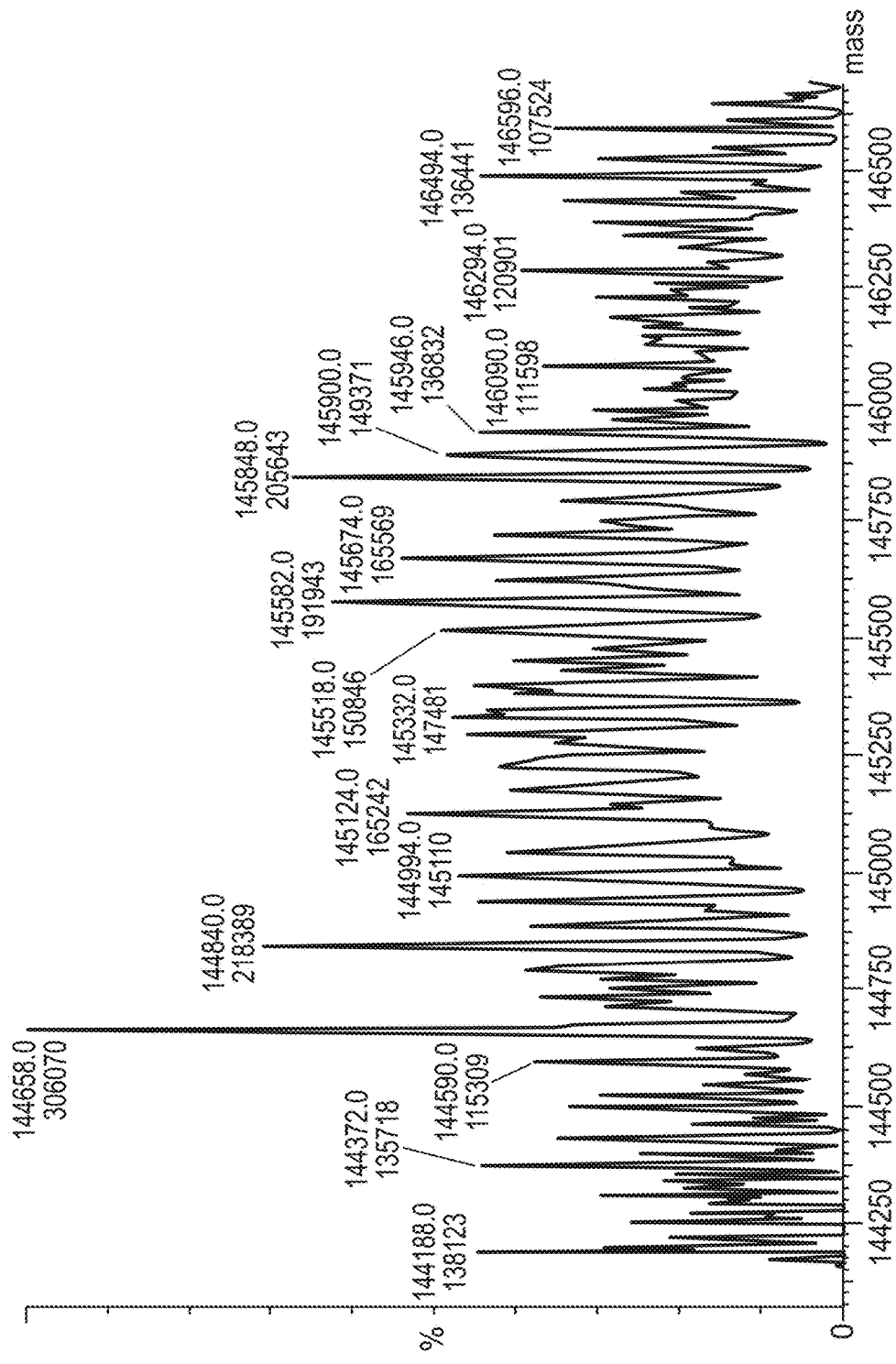

FIG. 124D shows a liquid chromatography-mass spectrometry analysis of Rituximab-SATA-T782 produced according to the BB-01 method.

Figure 124E:
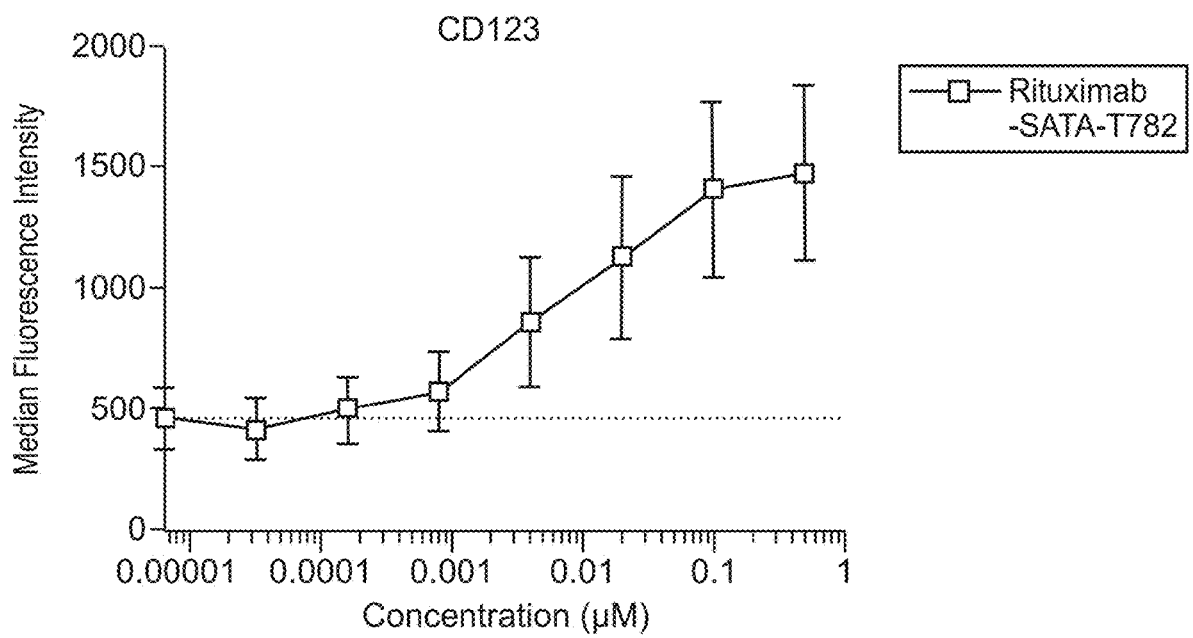

FIG. 124E shows that the Rituximab-SATA-T782 immunoconjugate produced according to the BB-01 conjugation method (Rituximab-SATA-T782) upregulates CD123 on myeloid cells in a dose-dependent manner following 18 hours of stimulation. The dashed line indicates the level of expression on unstimulated myeloid cells cultured for 18 hours.

Figure 124F:
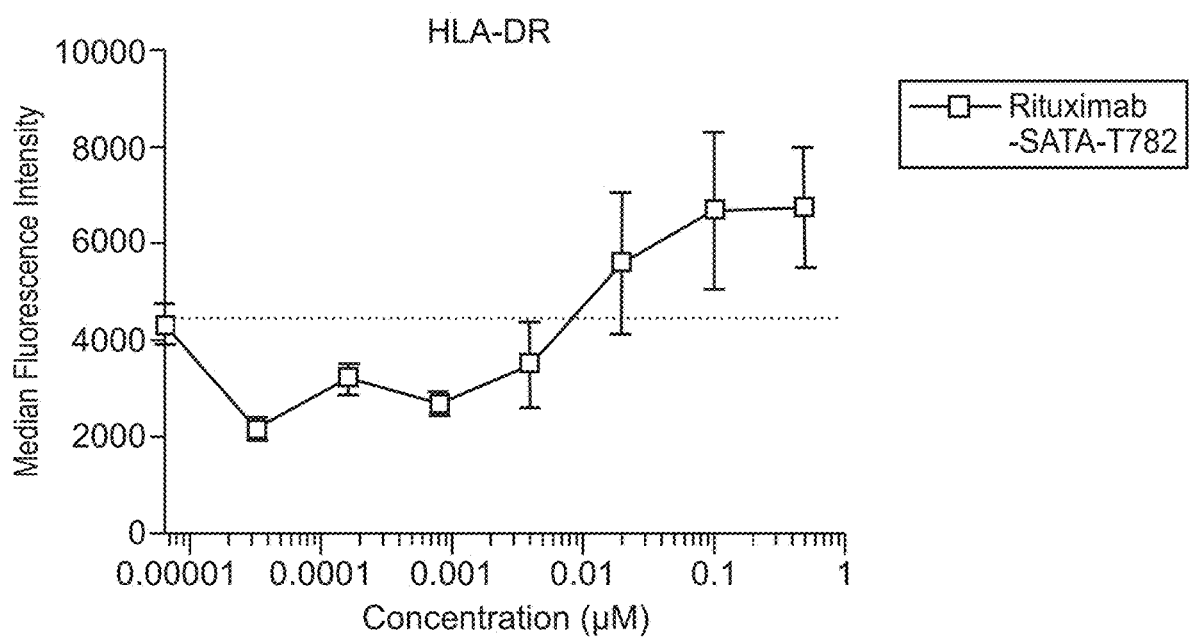

FIG. 124F shows that the Rituximab-SATA-T782 immunoconjugate produced according to the BB-01 conjugation method (Rituximab-SATA-T782) upregulates HLA-DR on myeloid cells in a dose-dependent manner following 18 hours of stimulation. The dashed line indicates the level of expression on unstimulated myeloid cells cultured for 18 hours.

Figure 124G:
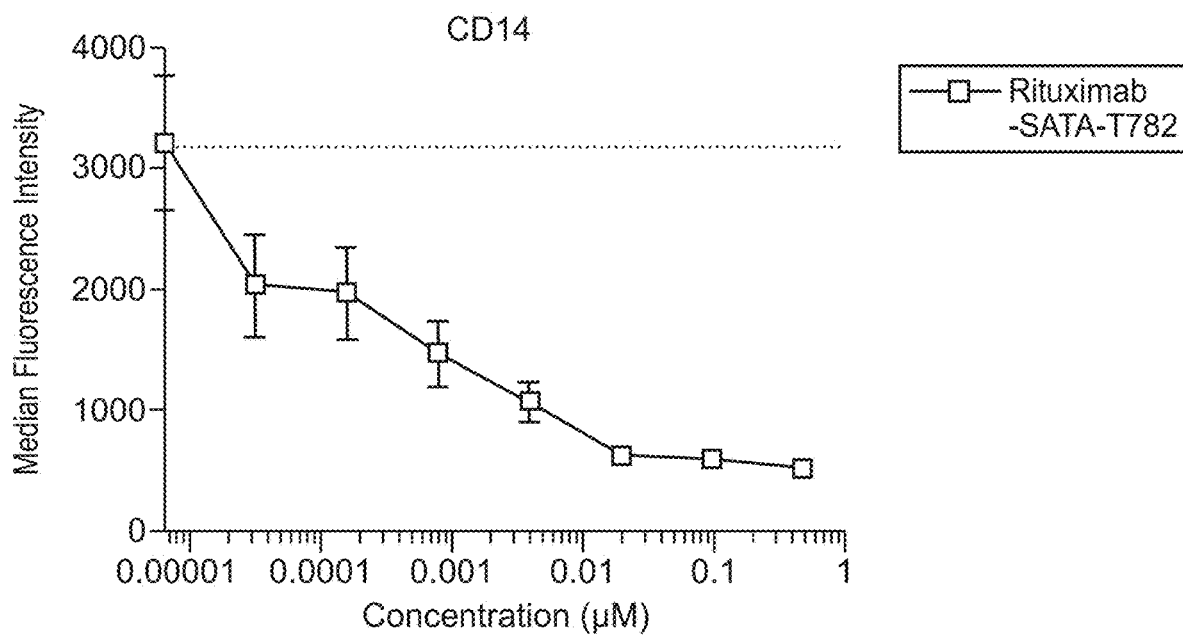

FIG. 124G shows that the Rituximab-SATA-T782 immunoconjugate produced according to the BB-01 conjugation method (Rituximab-SATA-T782) downregulates CD14 on myeloid cells in a dose-dependent manner following 18 hours of stimulation. The dashed line indicates the level of expression on unstimulated myeloid cells cultured for 18 hours.

Figure 124H:
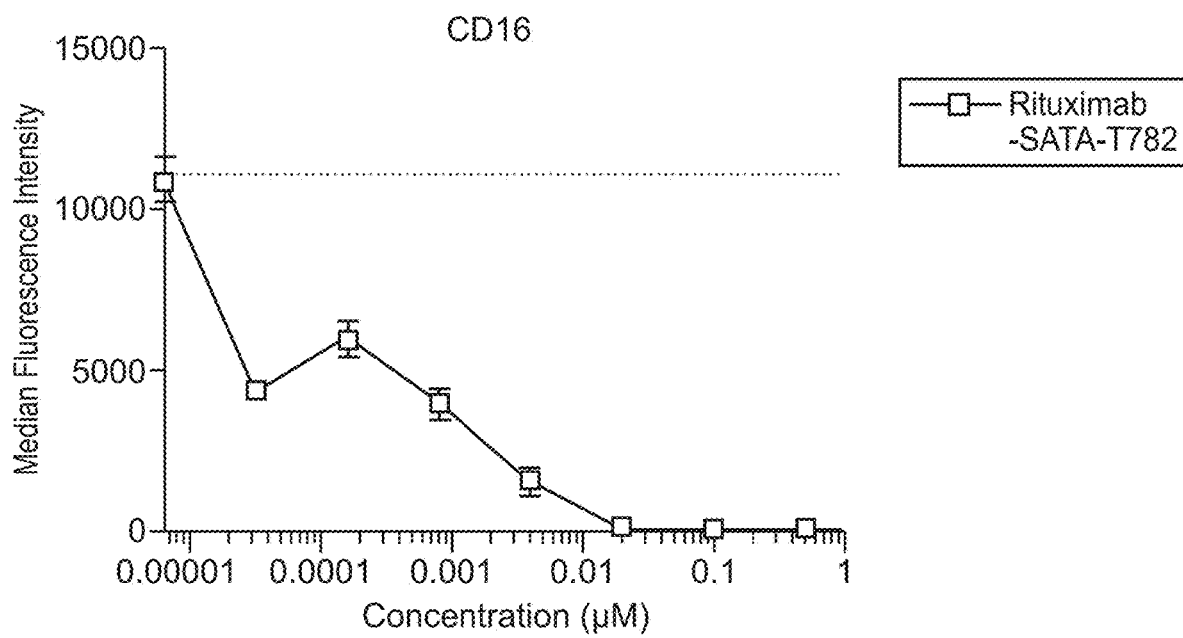

FIG. 124H shows that the Rituximab-SATA-T782 immunoconjugate produced according to the BB-01 conjugation method (Rituximab-SATA-T782) downregulates CD16 on myeloid cells in a dose-dependent manner following 18 hours of stimulation. The dashed line indicates the level of expression on unstimulated myeloid cells cultured for 18 hours.

Figure 124I:
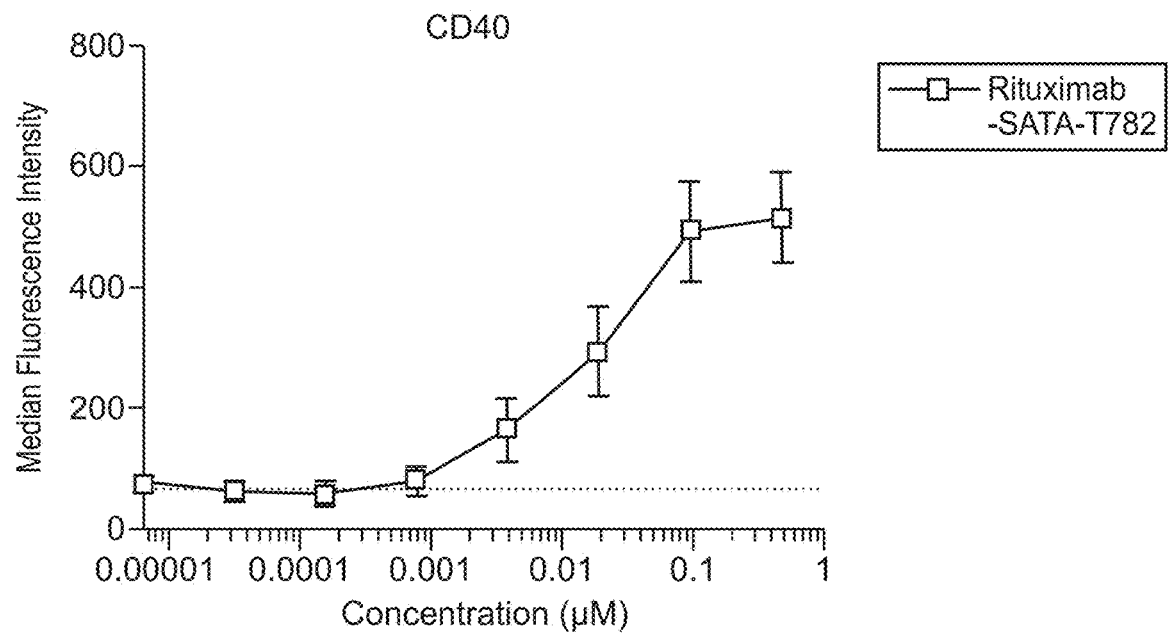

FIG. 124I shows that the Rituximab-SATA-T782 immunoconjugate produced according to the BB-01 conjugation method (Rituximab-SATA-T782) upregulates CD40 on myeloid cells in a dose-dependent manner following 18 hours of stimulation. The dashed line indicates the level of expression on unstimulated myeloid cells cultured for 18 hours.

Figure 124J:
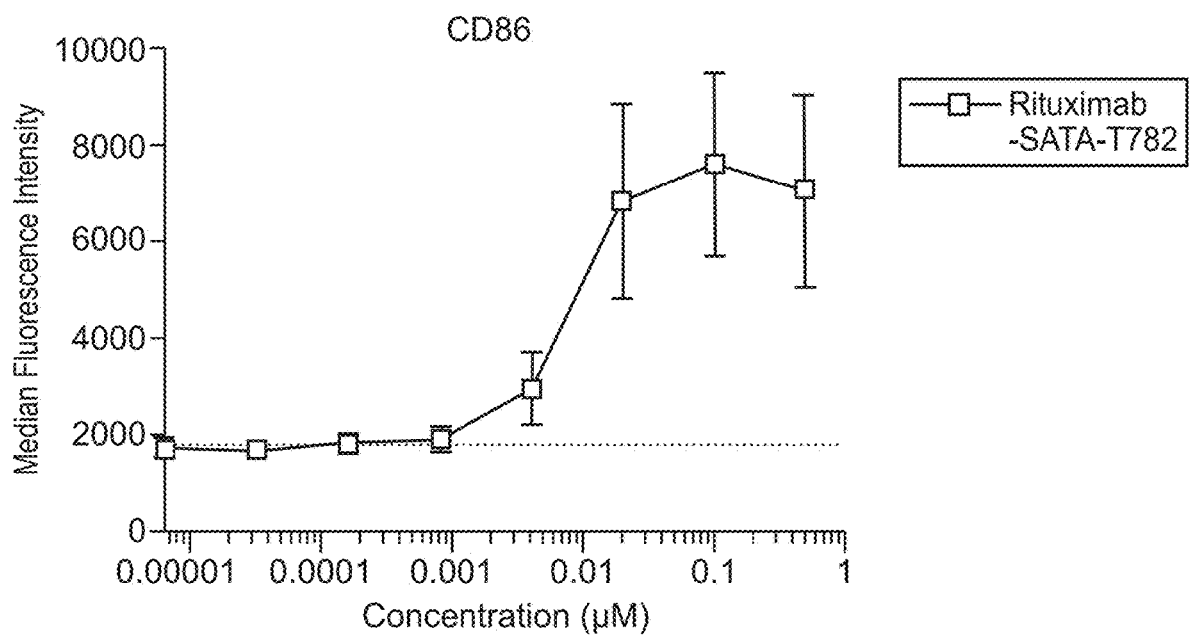

FIG. 124J shows that the Rituximab-SATA-T782 immunoconjugate produced according to the BB-01 conjugation method (Rituximab-SATA-T782) upregulates CD86 on myeloid cells in a dose-dependent manner following 18 hours of stimulation. The dashed line indicates the level of expression on unstimulated myeloid cells cultured for 18 hours.

Figure 125A:
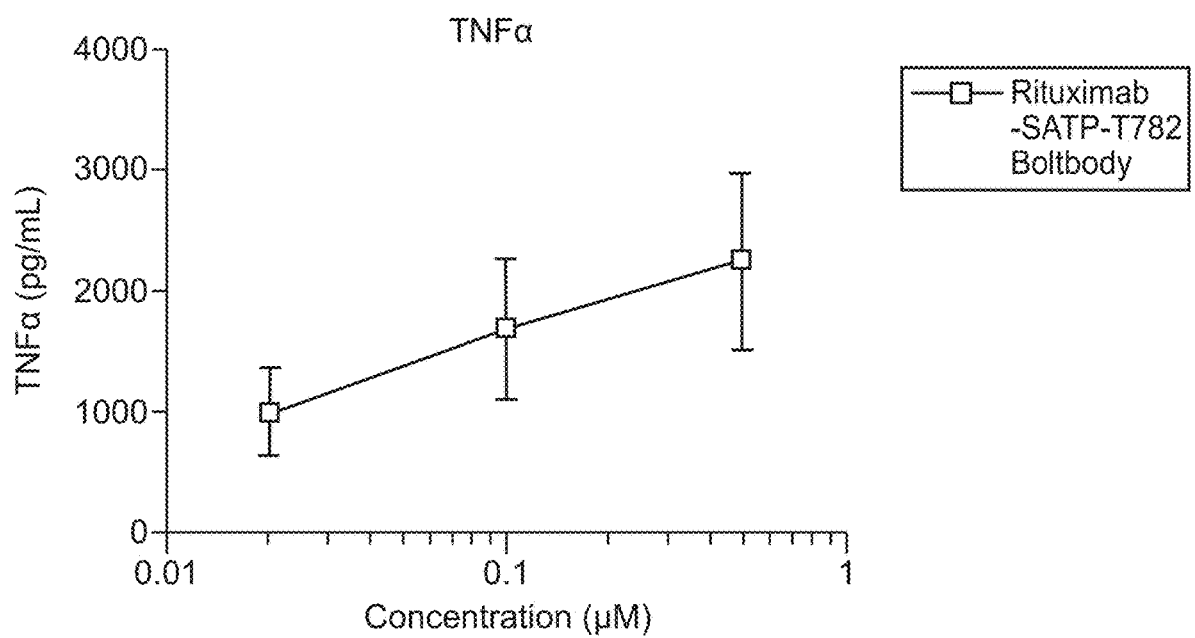

FIG. 125A shows that the Rituximab-SATP-T782 immunoconjugate produced according to the BB-01 method (Rituximab-SATP-T782 Boltbody) elicits TNFα secretion from myeloid cells in a dose-dependent manner following 18 hours of stimulation.

Figure 125B:
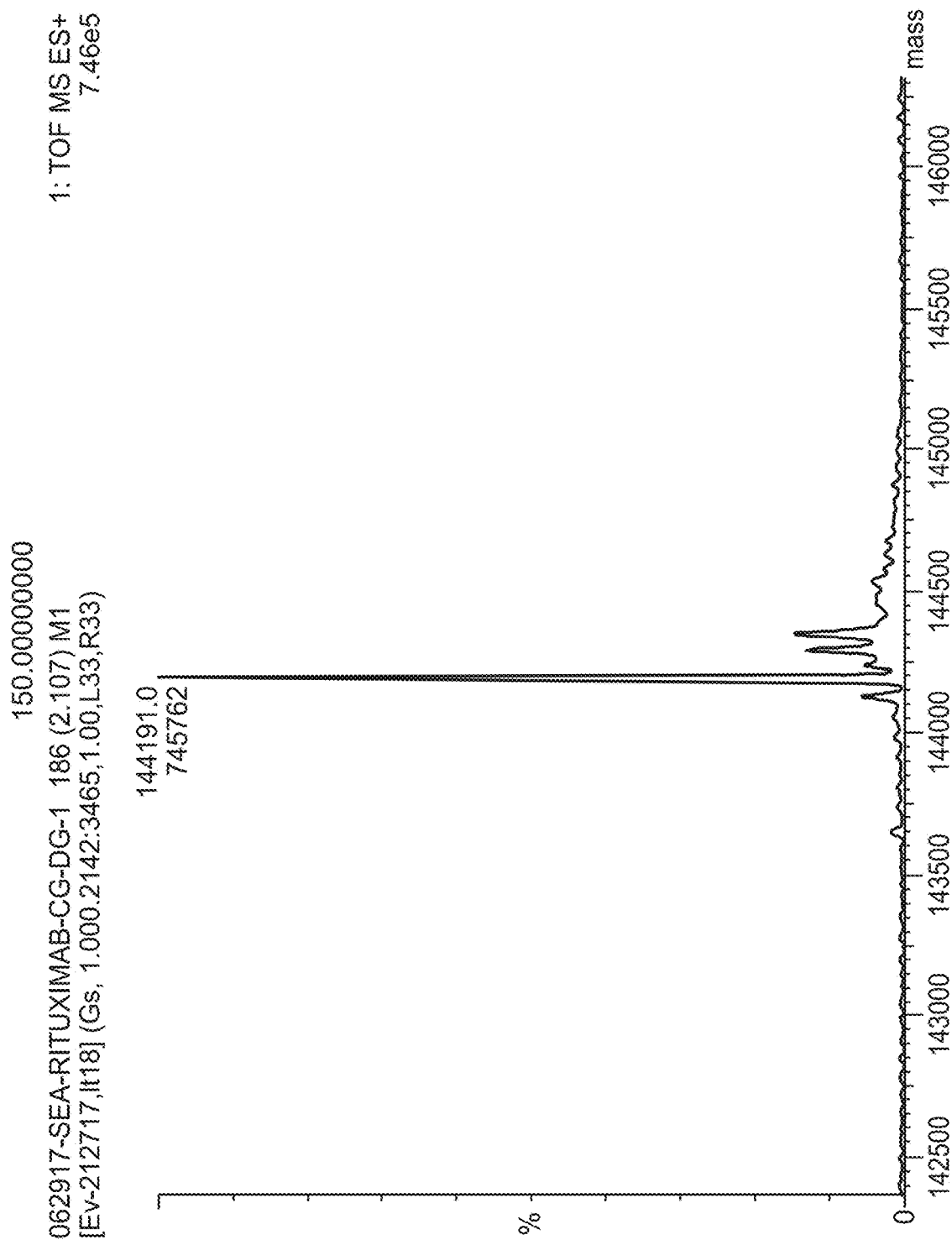

FIG. 125B shows a liquid chromatography-mass spectrometry analysis of unconjugated Rituximab (Roche) that was utilized to produce Rituximab-SATP-T782 following overnight deglycosylation with PNGase F.

FIG. 125C shows a liquid chromatography-mass spectrometry analysis of unconjugated Rituximab (Roche) that was utilized to produce Rituximab-SATP-T782.

Figure 125D:
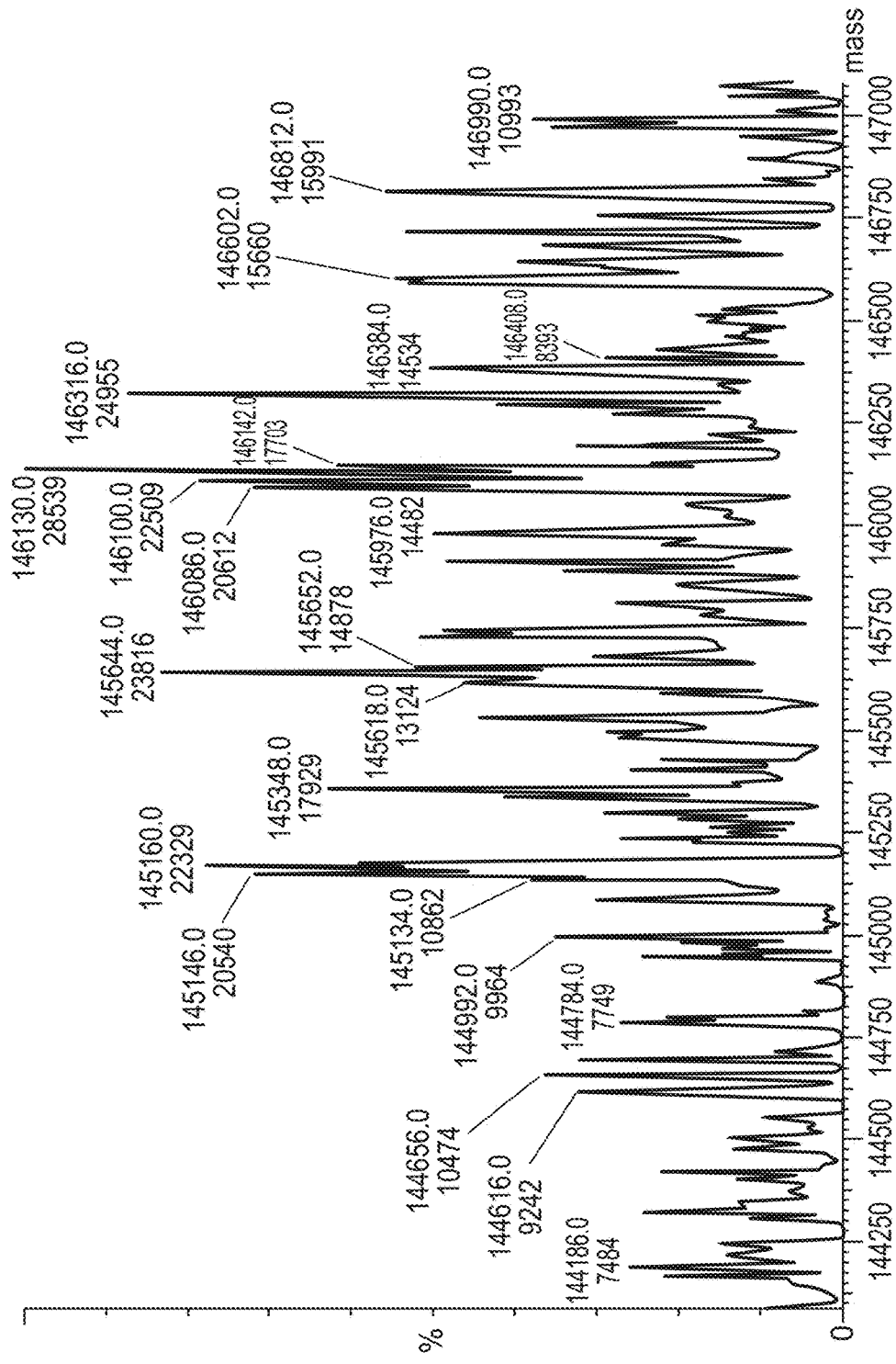

FIG. 125D shows a liquid chromatography-mass spectrometry analysis of Rituximab-SATP-T782 produced according to the BB-01 method.

Figure 125E:
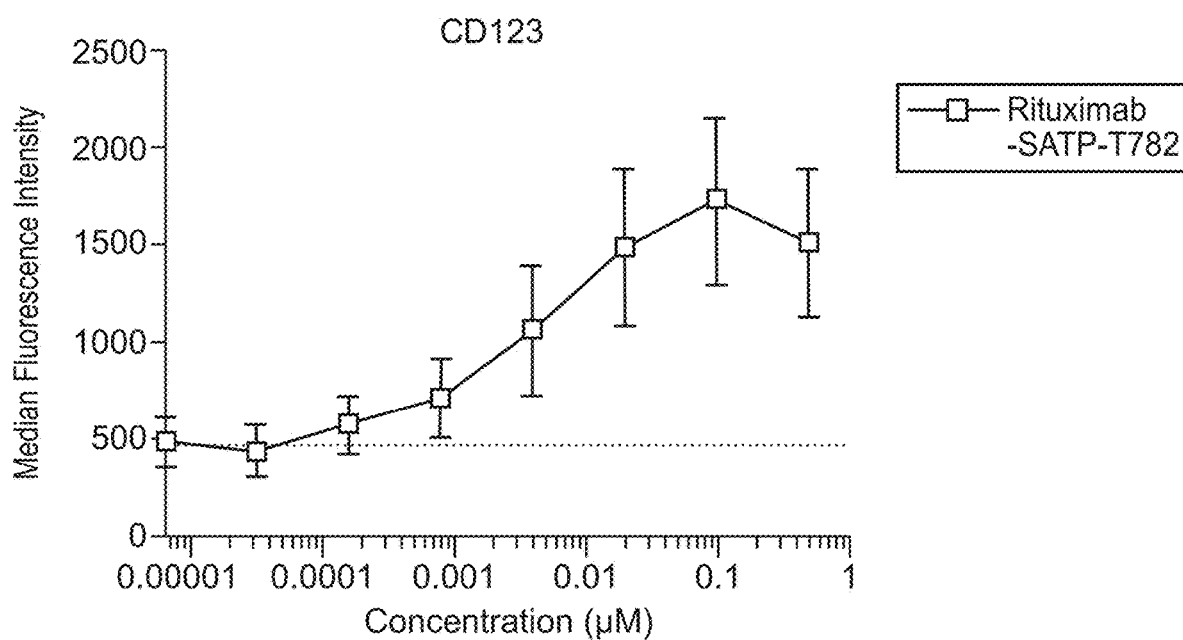

FIG. 125E shows that the Rituximab-SATP-T782 immunoconjugate produced according to the BB-01 conjugation method (Rituximab-SATP-T782) upregulates CD123 on myeloid cells in a dose-dependent manner following 18 hours of stimulation. The dashed line indicates the level of expression on unstimulated myeloid cells cultured for 18 hours.

Figure 125F:
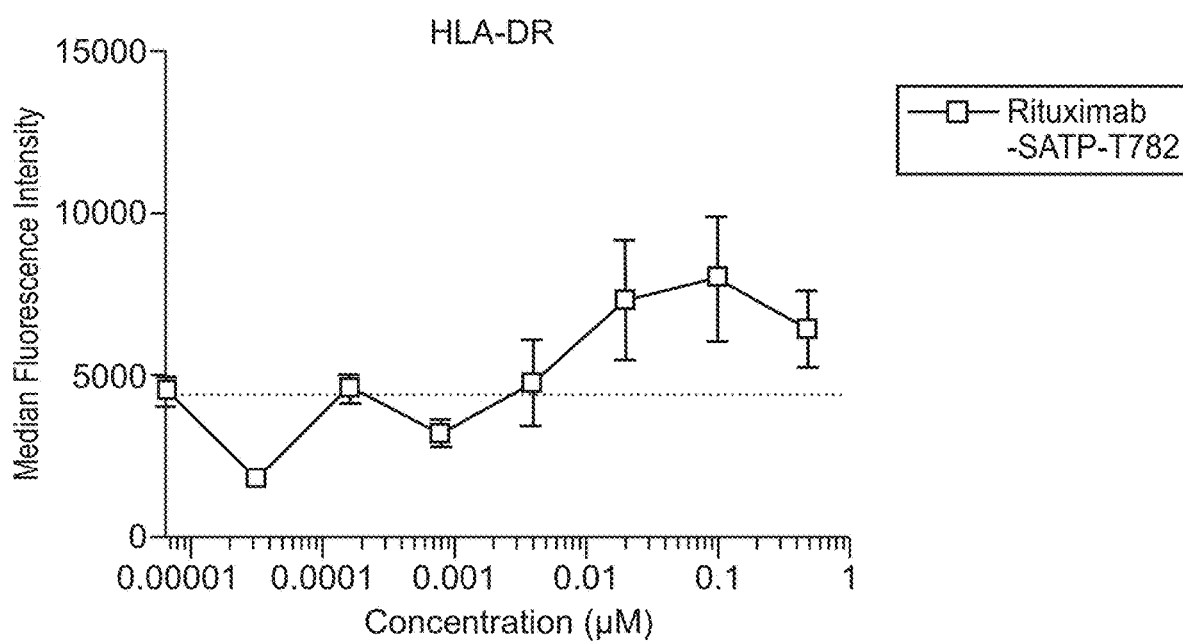

FIG. 125F shows that the Rituximab-SATP-T782 immunoconjugate produced according to the BB-01 conjugation method (Rituximab-SATP-T782) upregulates HLA-DR on myeloid cells in a dose-dependent manner following 18 hours of stimulation. The dashed line indicates the level of expression on unstimulated myeloid cells cultured for 18 hours.

Figure 125G:
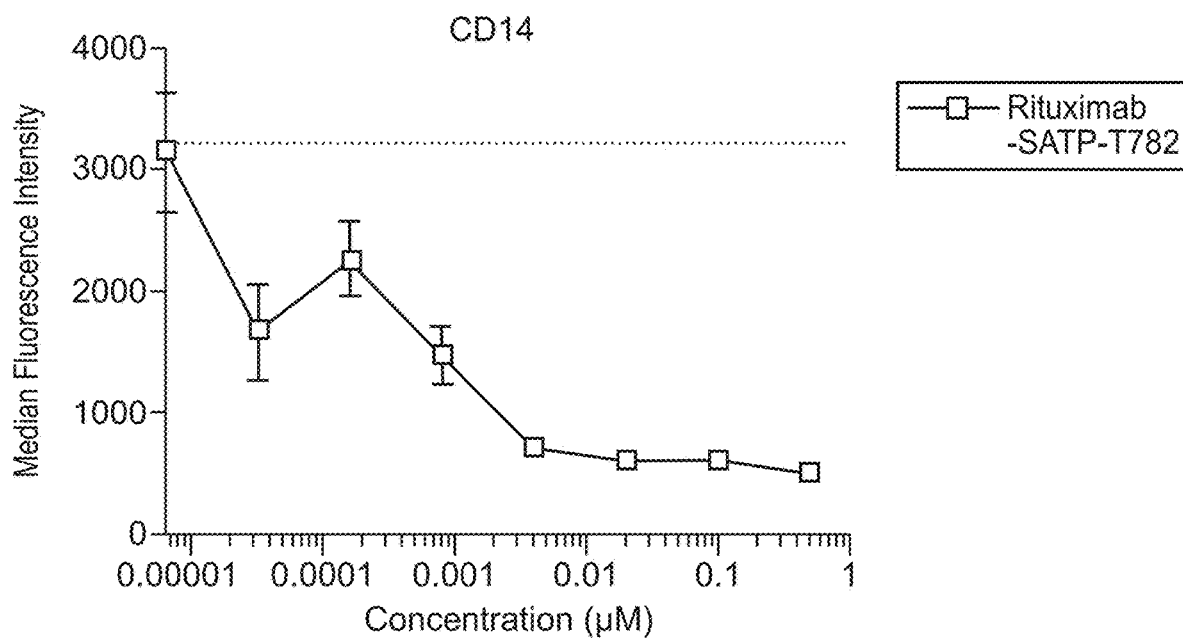

FIG. 125G shows that the Rituximab-SATP-T782 immunoconjugate produced according to the BB-01 conjugation method (Rituximab-SATP-T782) downregulates CD14 on myeloid cells in a dose-dependent manner following 18 hours of stimulation. The dashed line indicates the level of expression on unstimulated myeloid cells cultured for 18 hours.

Figure 125H:
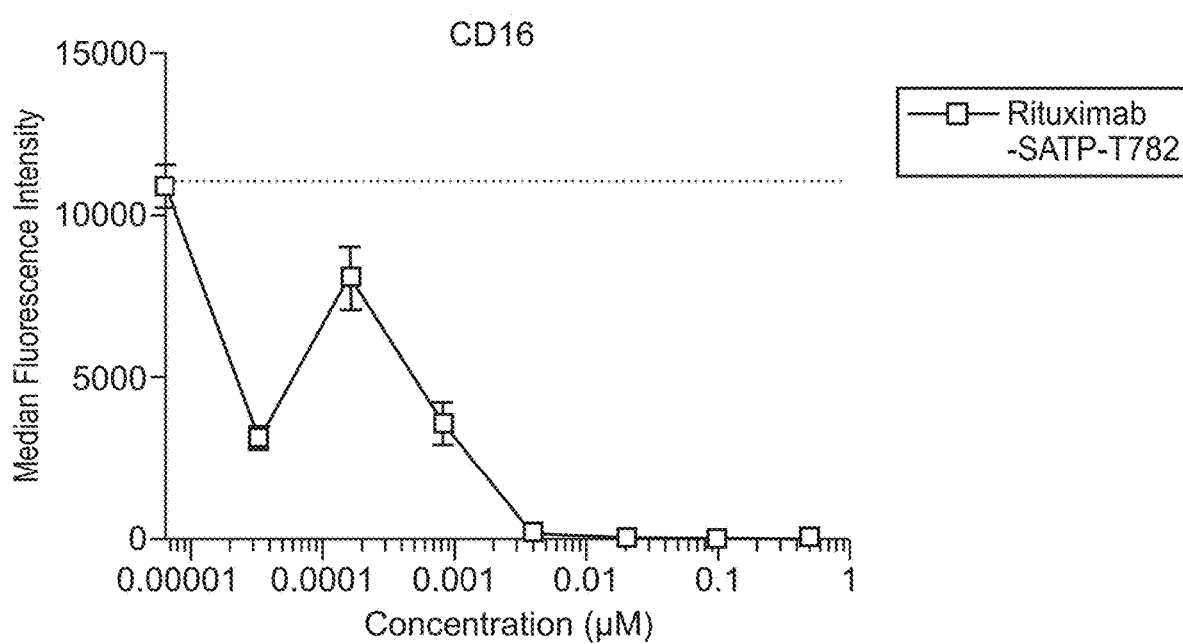

FIG. 125H shows that the Rituximab-SATP-T782 immunoconjugate produced according to the BB-01 conjugation method (Rituximab-SATP-T782) downregulates CD16 on myeloid cells in a dose-dependent manner following 18 hours of stimulation. The dashed line indicates the level of expression on unstimulated myeloid cells cultured for 18 hours.

Figure 125I:
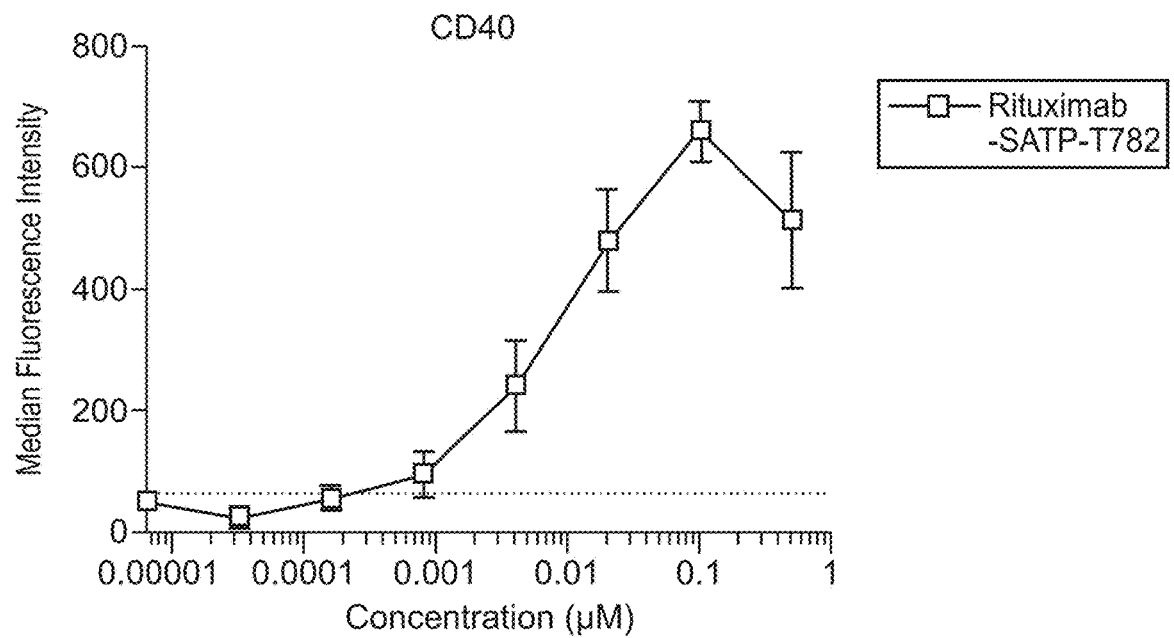

FIG. 125I shows that the Rituximab-SATP-T782 immunoconjugate produced according to the BB-01 conjugation method (Rituximab-SATP-T782) upregulates CD40 on myeloid cells in a dose-dependent manner following 18 hours of stimulation. The dashed line indicates the level of expression on unstimulated myeloid cells cultured for 18 hours.

Figure 125J:
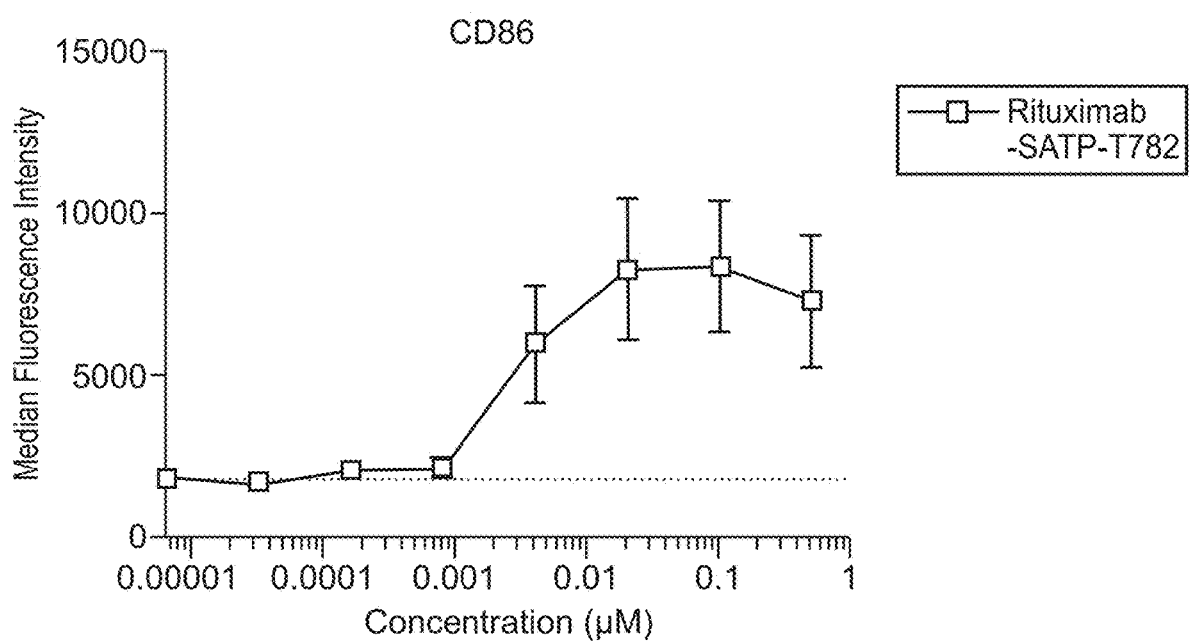

FIG. 125J shows that the Rituximab-SATP-T782 immunoconjugate produced according to the BB-01 conjugation method (Rituximab-SATP-T782) upregulates CD86 on myeloid cells in a dose-dependent manner following 18 hours of stimulation. The dashed line indicates the level of expression on unstimulated myeloid cells cultured for 18 hours.

FIG. 126A shows a liquid chromatography-mass spectrometry analysis of the BB-12 immunoconjugate produced according to the SATA conjugation method following overnight conjugation with PNGase F.

Figure 126B:
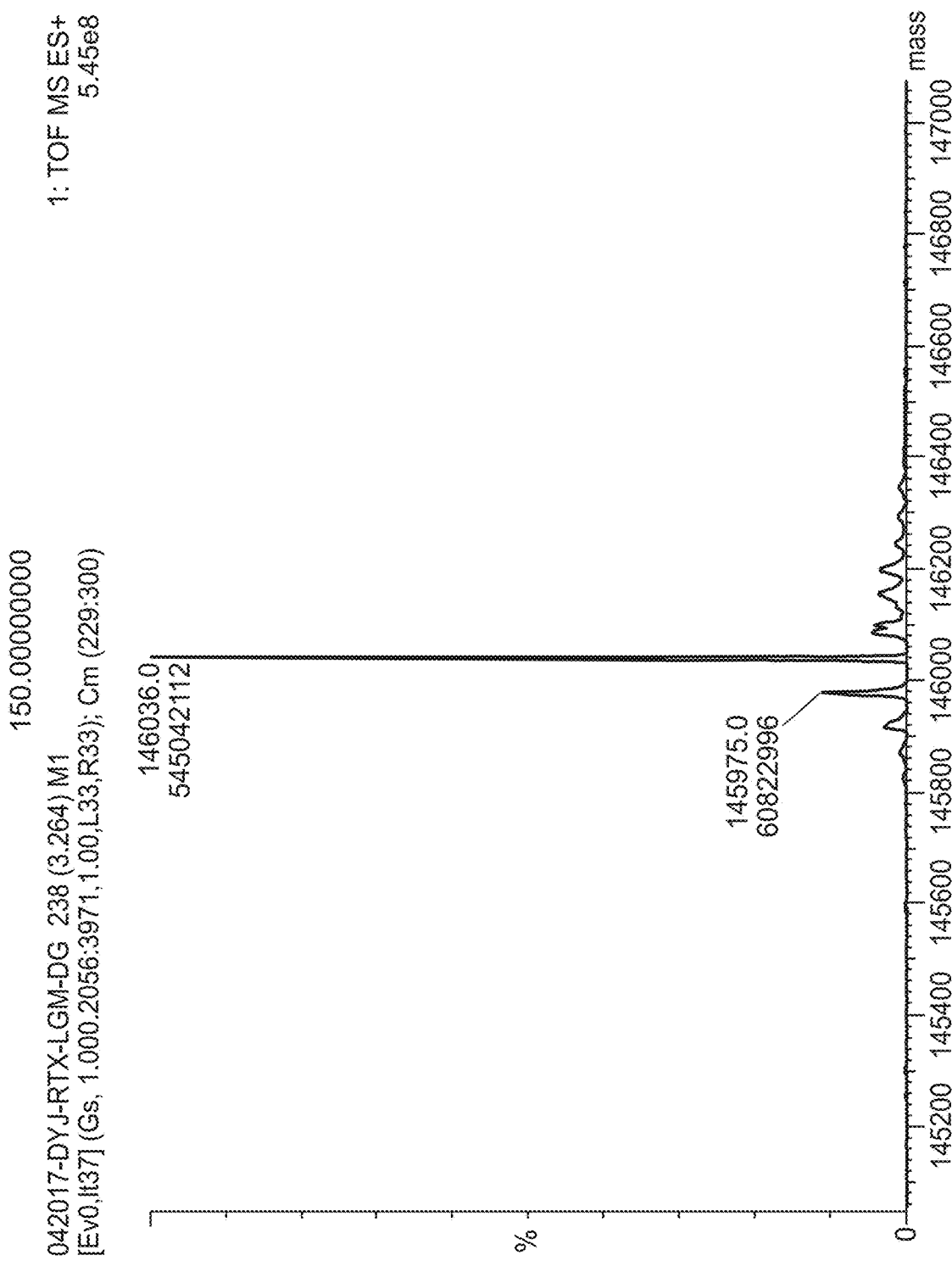

FIG. 126B shows a liquid chromatography-mass spectrometry analysis of an unconjugated Rituximab biosimilar (LGM Pharma) that was utilized to produce BB-12 following overnight deglycosylation with PNGase F.

Figure 126C:
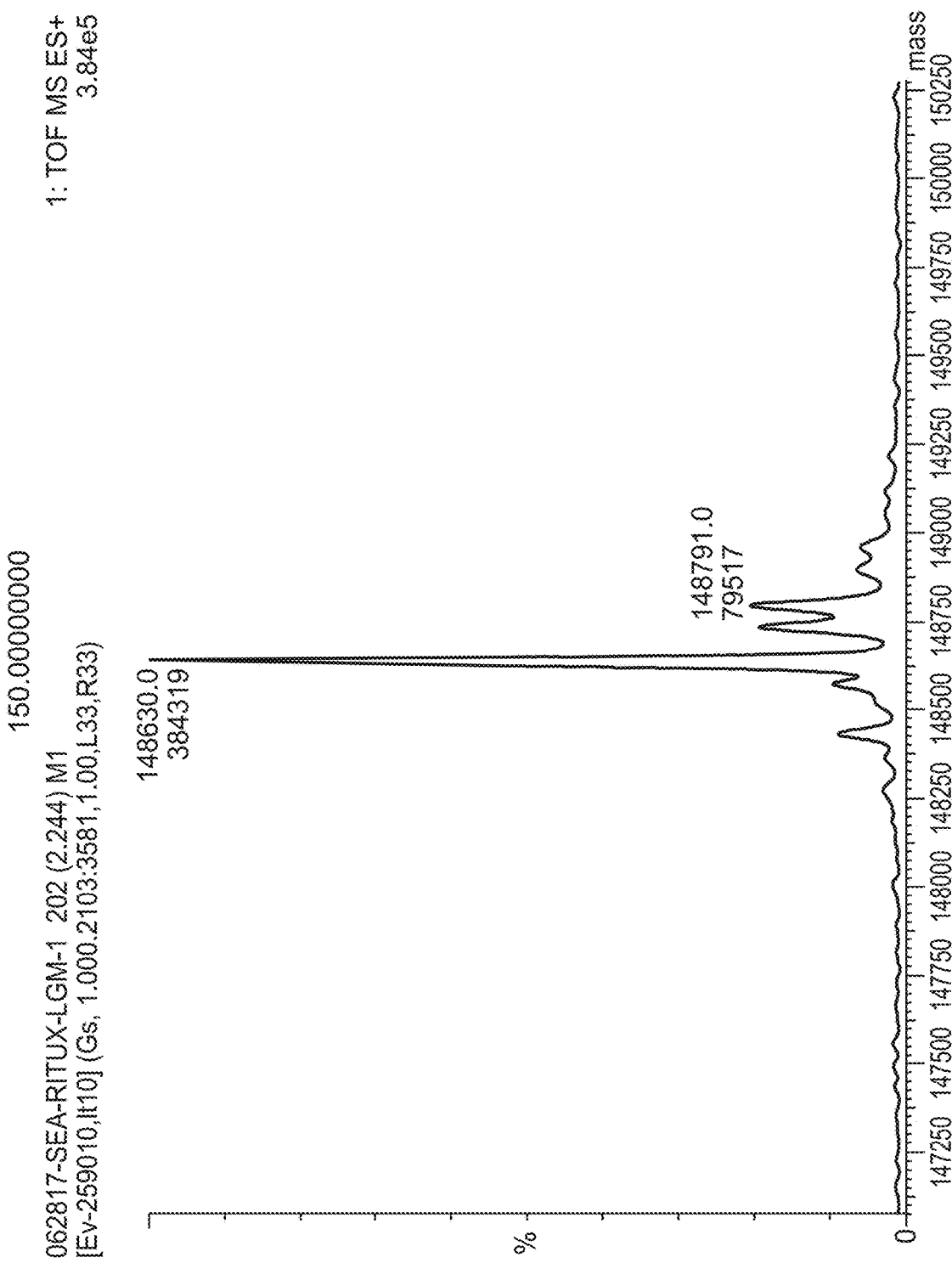

FIG. 126C shows a liquid chromatography-mass spectrometry analysis of an unconjugated Rituximab biosimilar (LGM Pharma) that was utilized to produce BB-12.

Figure 126D:
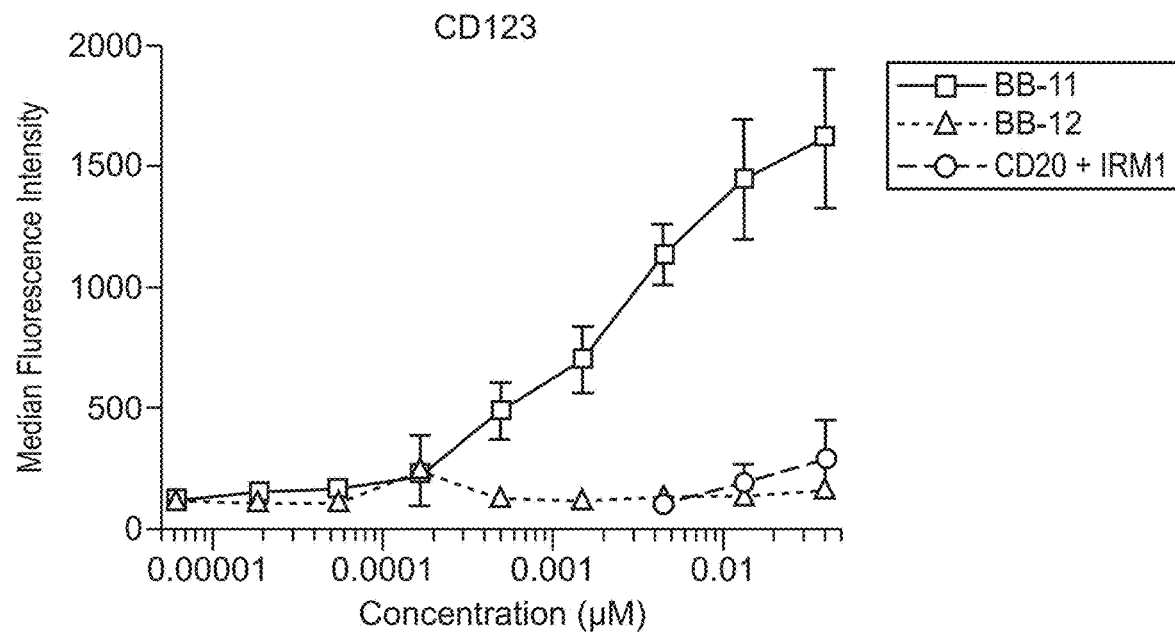

FIG. 126D shows that the BB-12 immunoconjugate produced according to the SATA method fails to elicit CD123 upregulation following 18 hours of stimulation. FIG. 126D also shows that the BB-11 immunoconjugate produced according to the SATA method is superior at eliciting CD123 upregulation as compared to BB-12 and equimolar concentrations of the mixture (CD20+IRM1). It should be noted that BB-11 and BB-12 are constructed with identical linkers, but have distinct adjuvants.

Figure 126E:
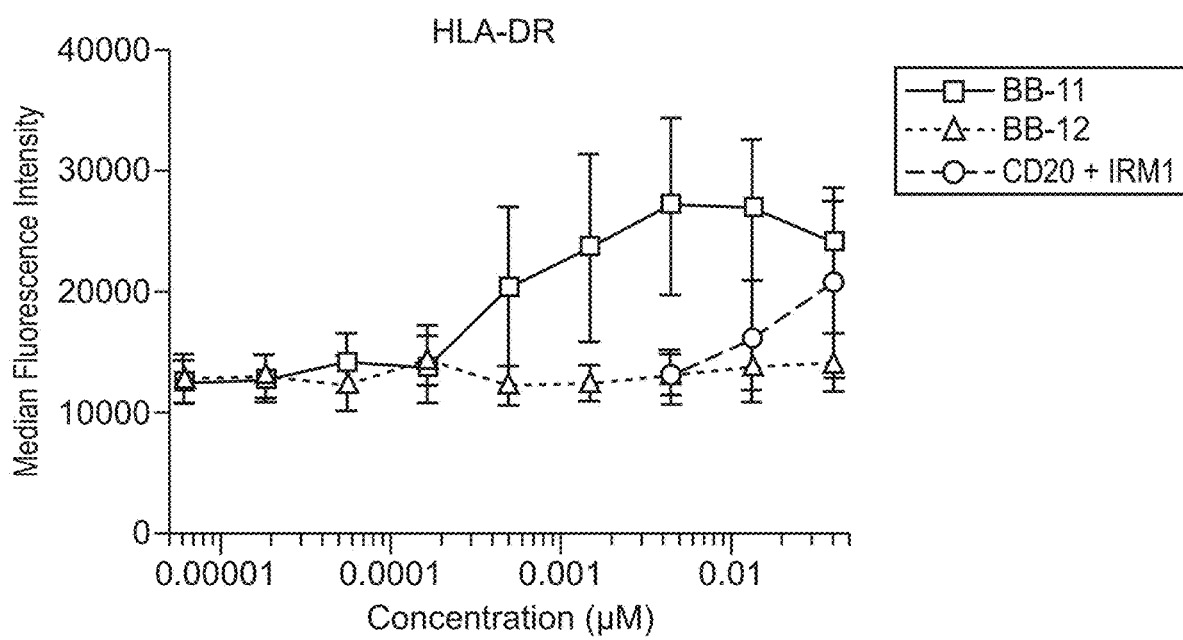

FIG. 126E shows that the BB-12 immunoconjugate produced according to the SATA method fails to elicit HLA-DR upregulation following 18 hours of stimulation. FIG. 126E also shows that the BB-11 immunoconjugate produced according to the SATA method is superior at eliciting HLA-DR upregulation as compared to BB-12 and equimolar concentrations of the mixture (CD20+IRM1). It should be noted that BB-11 and BB-12 are constructed with identical linkers, but have distinct adjuvants.

Figure 126F:
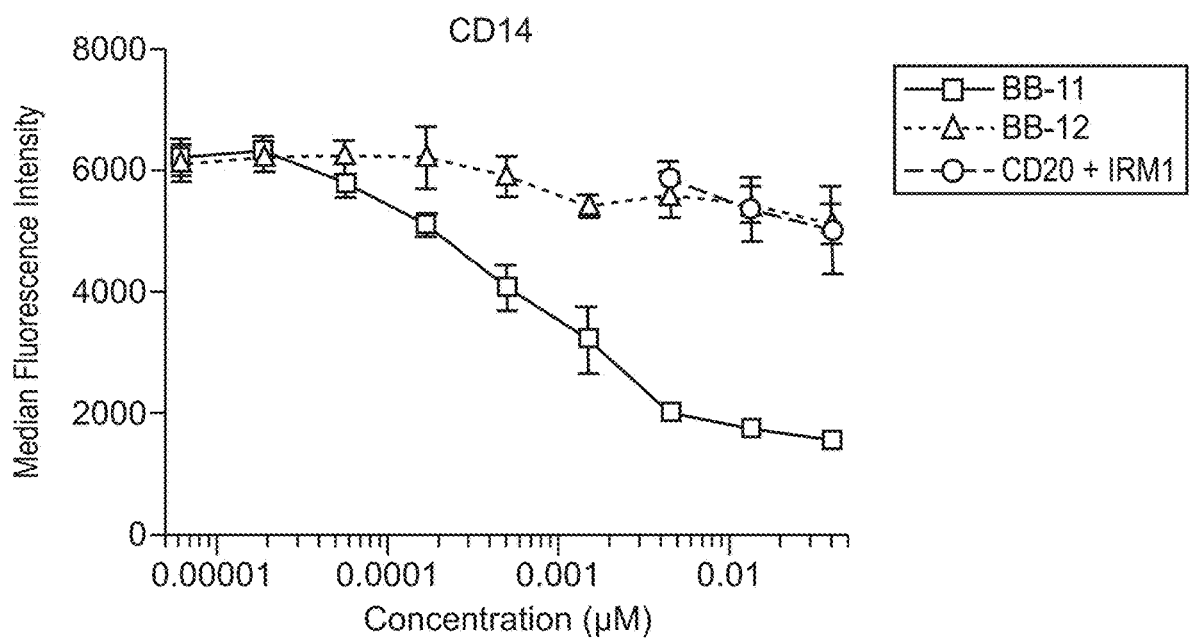

FIG. 126F shows that the BB-12 immunoconjugate produced according to the SATA method fails to elicit CD14 downregulation following 18 hours of stimulation as compared to equimolar concentrations of the mixture (CD20+IRM1). FIG. 126F also shows that the BB-11 immunoconjugate produced according to the SATA method is superior at eliciting CD14 downregulation as compared to BB-12 and equimolar concentrations of the mixture (CD20+IRM1). It should be noted that BB-11 and BB-12 are constructed with identical linkers, but have distinct adjuvants.

Figure 126G:
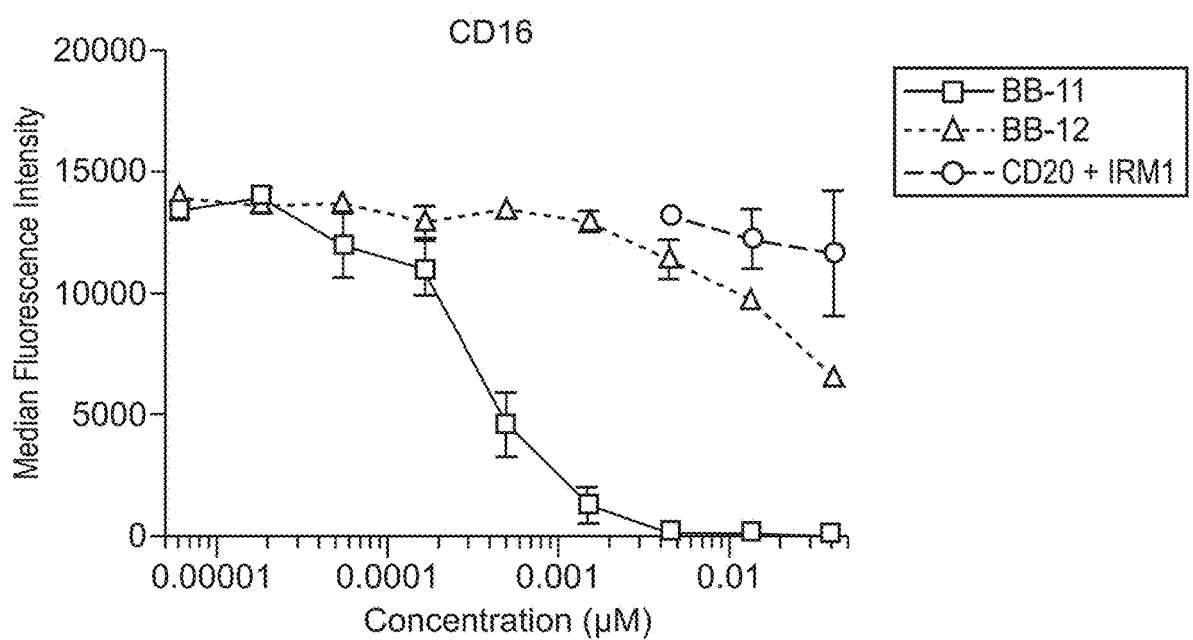

FIG. 126G also shows that the BB-11 immunoconjugate produced according to the SATA method is superior at eliciting CD16 downregulation as compared to BB-12 and equimolar concentrations of the mixture (CD20+IRM1). It should be noted that BB-11 and BB-12 are constructed with identical linkers, but have distinct adjuvants.

Figure 126H:
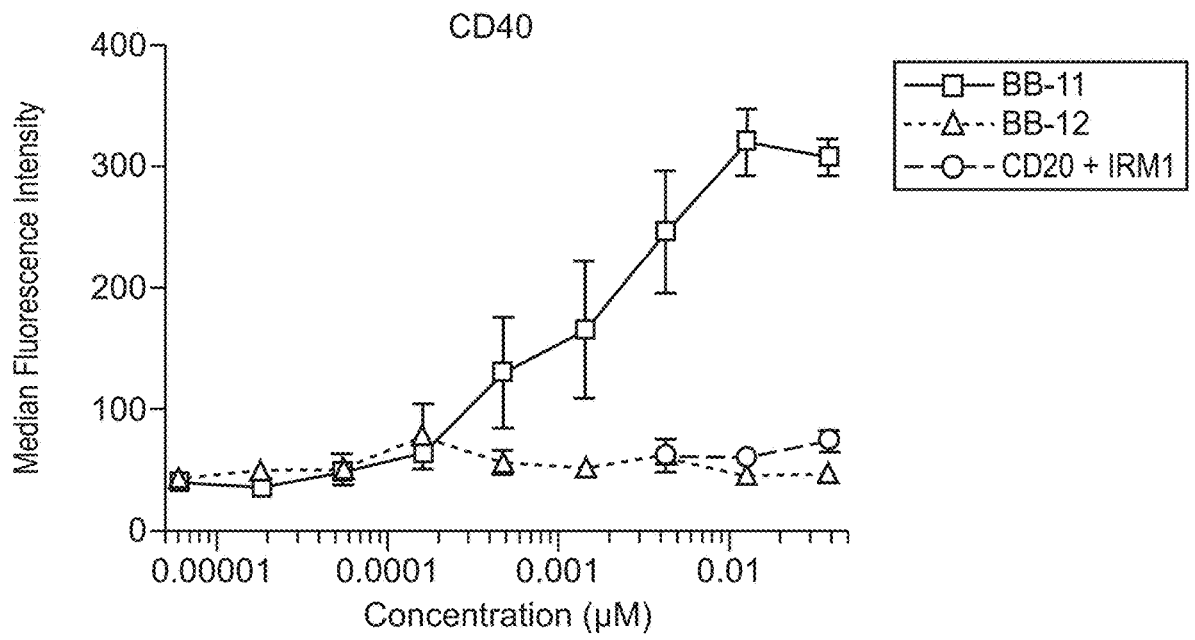

FIG. 126H shows that the BB-12 immunoconjugate produced according to the SATA method fails to elicit CD40 upregulation following 18 hours of stimulation as compared to equimolar concentrations of the mixture (CD20+IRM1). FIG. 126H also shows that the BB-11 immunoconjugate produced according to the SATA method is superior at eliciting CD40 upregulation as compared to BB-12 and equimolar concentrations of the mixture (CD20+IRM1). It should be noted that BB-11 and BB-12 are constructed with identical linkers, but have distinct adjuvants.

Figure 126I:
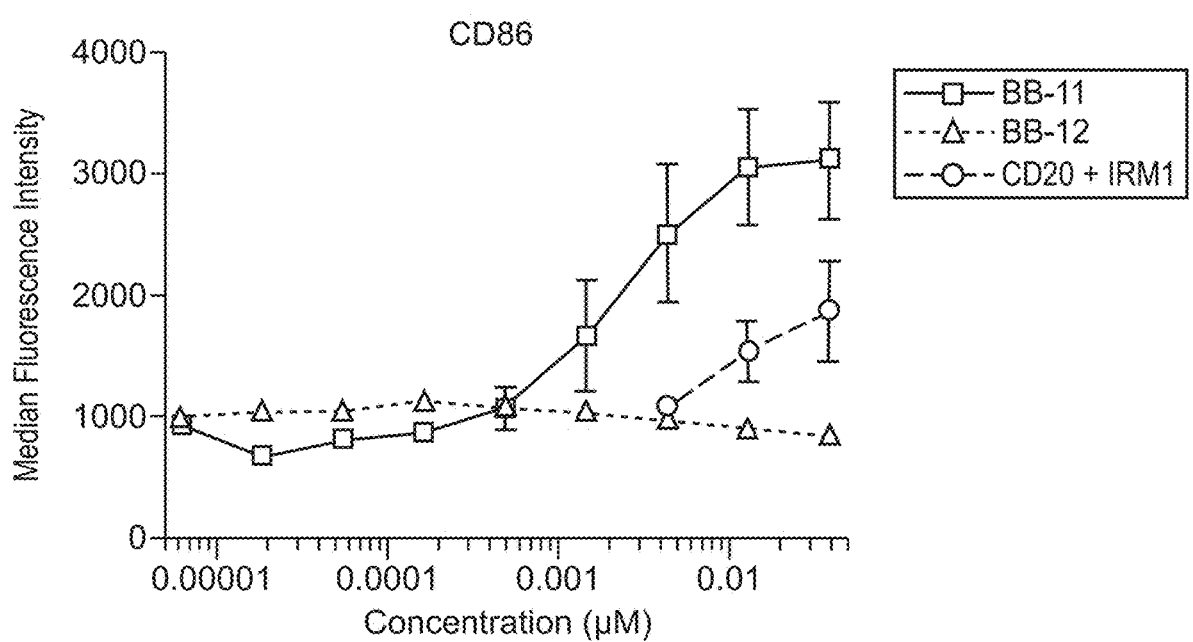

FIG. 126I shows that the BB-12 immunoconjugate produced according to the SATA method fails to elicit CD86 upregulation following 18 hours of stimulation as compared to equimolar concentrations of the mixture (CD20+IRM1). FIG. 126I also shows that the BB-11 immunoconjugate produced according to the SATA method is superior at eliciting CD86 upregulation as compared to BB-12 and equimolar concentrations of the mixture (CD20+IRM1). It should be noted that BB-11 and BB-12 are constructed with identical linkers, but have distinct adjuvants.

Figure 126J:
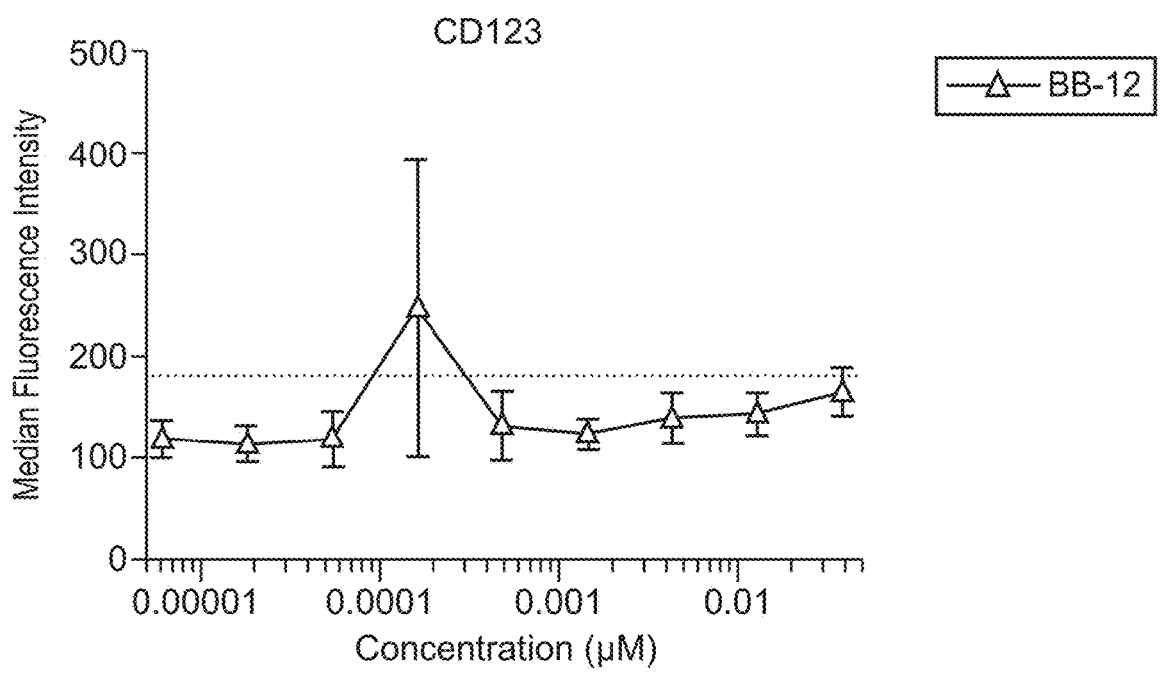

FIG. 126J shows CD123 expression following 18 hours of stimulation with BB-12. The dashed line indicates the level of CD123 expression on unstimulated cells following 18 hours of incubation.

Figure 126K:
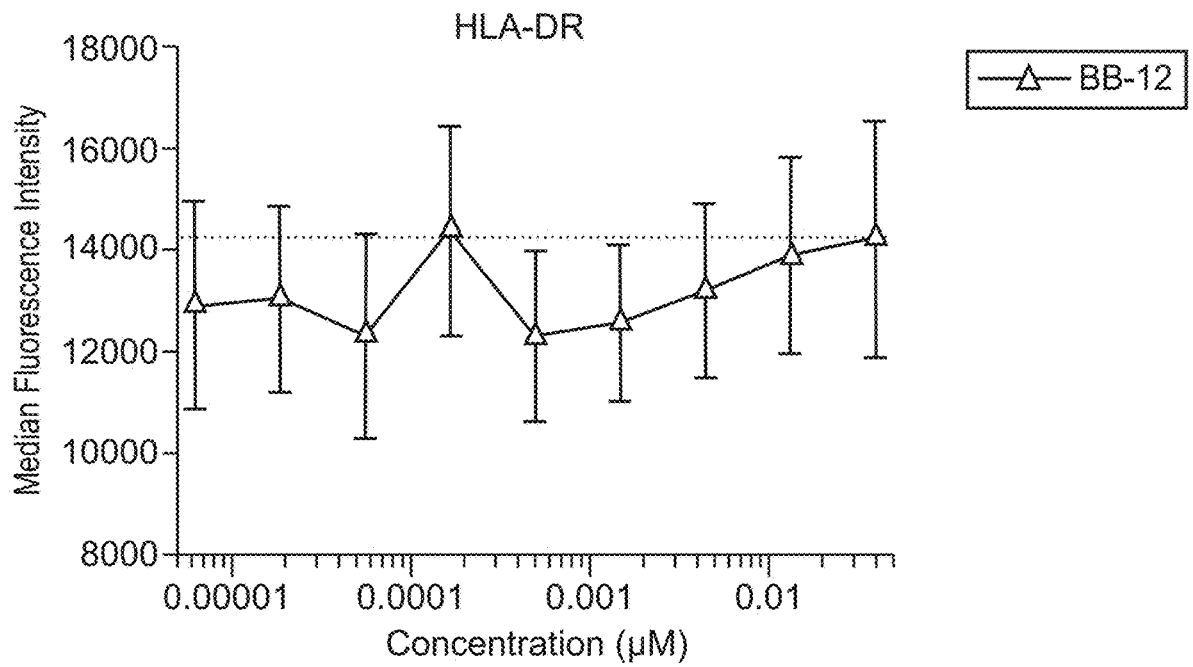

FIG. 126K shows HLA-DR expression following 18 hours of stimulation with BB-12. The dashed line indicates the level of HLA-DR expression on unstimulated cells following 18 hours of incubation.

Figure 126L:
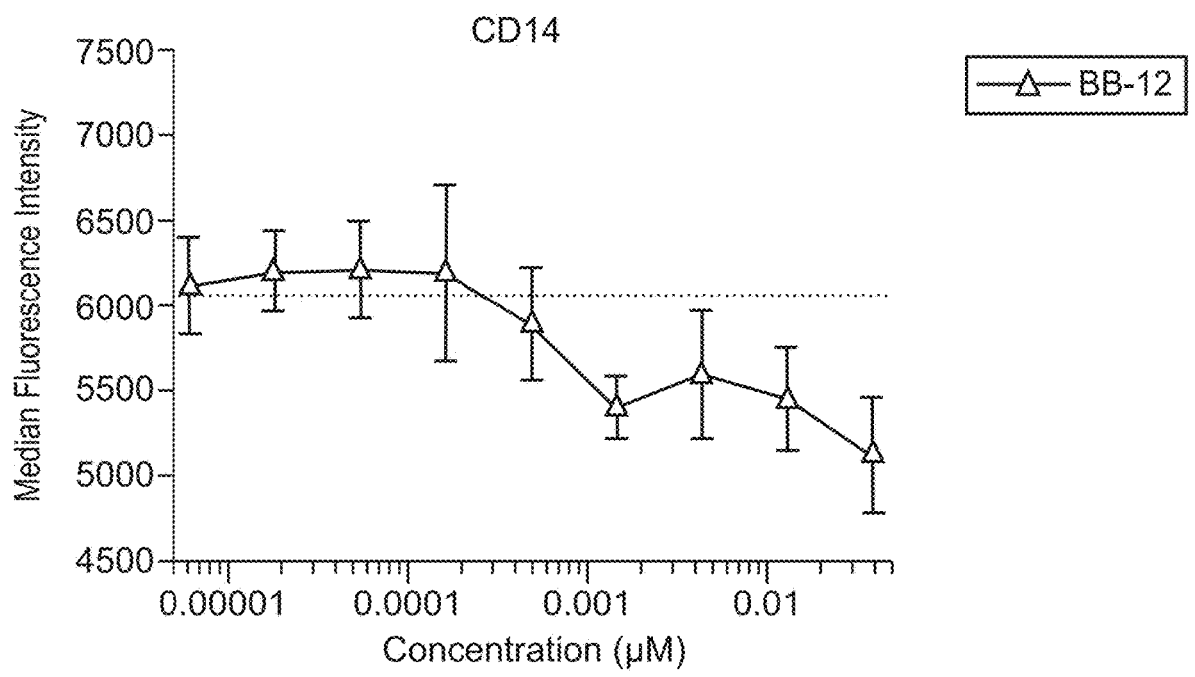

FIG. 126L shows CD14 expression following 18 hours of stimulation with BB-12. The dashed line indicates the level of CD14 expression on unstimulated cells following 18 hours of incubation.

Figure 126M:
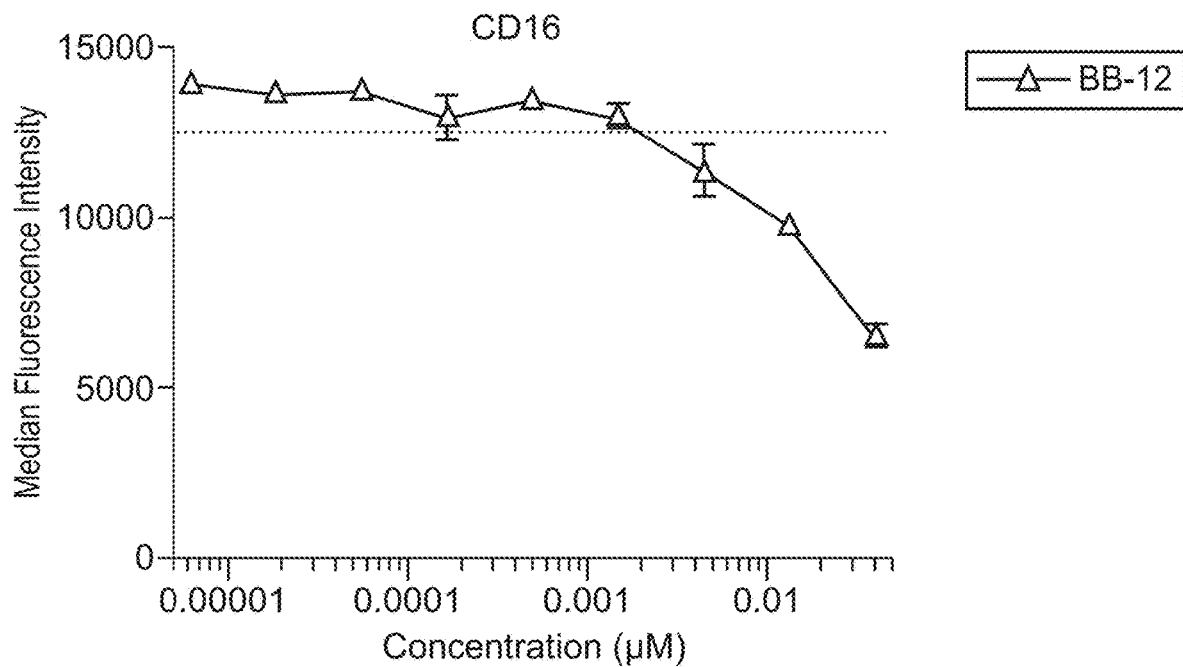

FIG. 126M shows CD16 expression following 18 hours of stimulation with BB-12. The dashed line indicates the level of CD16 expression on unstimulated cells following 18 hours of incubation.

Figure 126N:
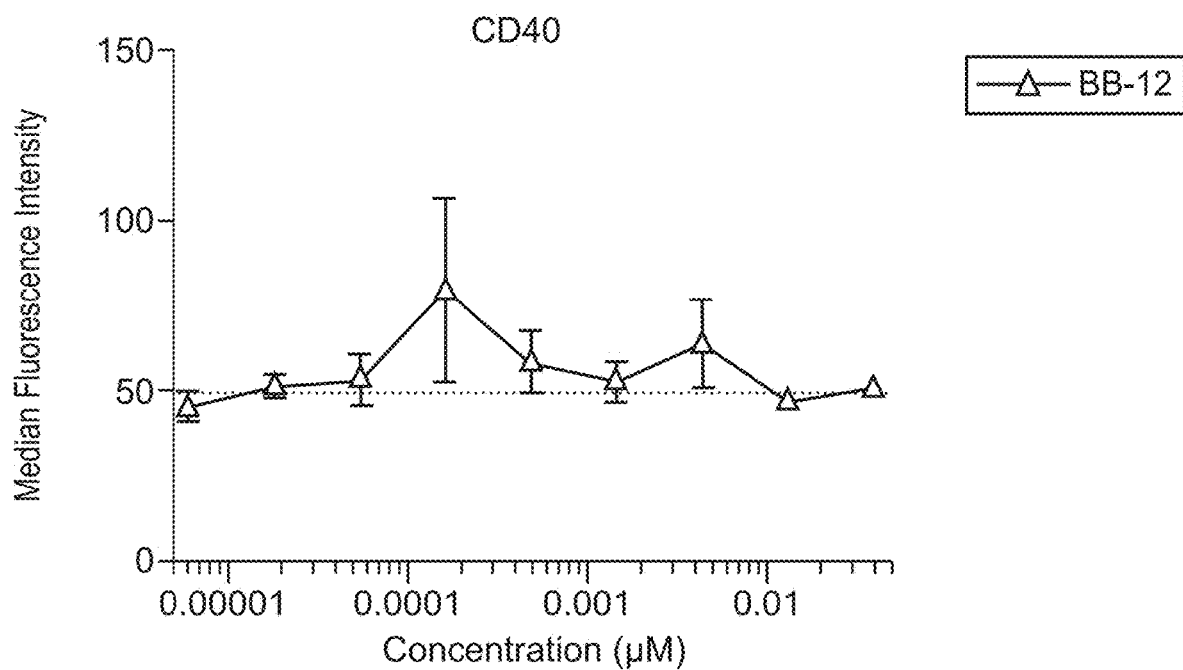

FIG. 126N shows CD40 expression following 18 hours of stimulation with BB-12. The dashed line indicates the level of CD40 expression on unstimulated cells following 18 hours of incubation.

Figure 126O:
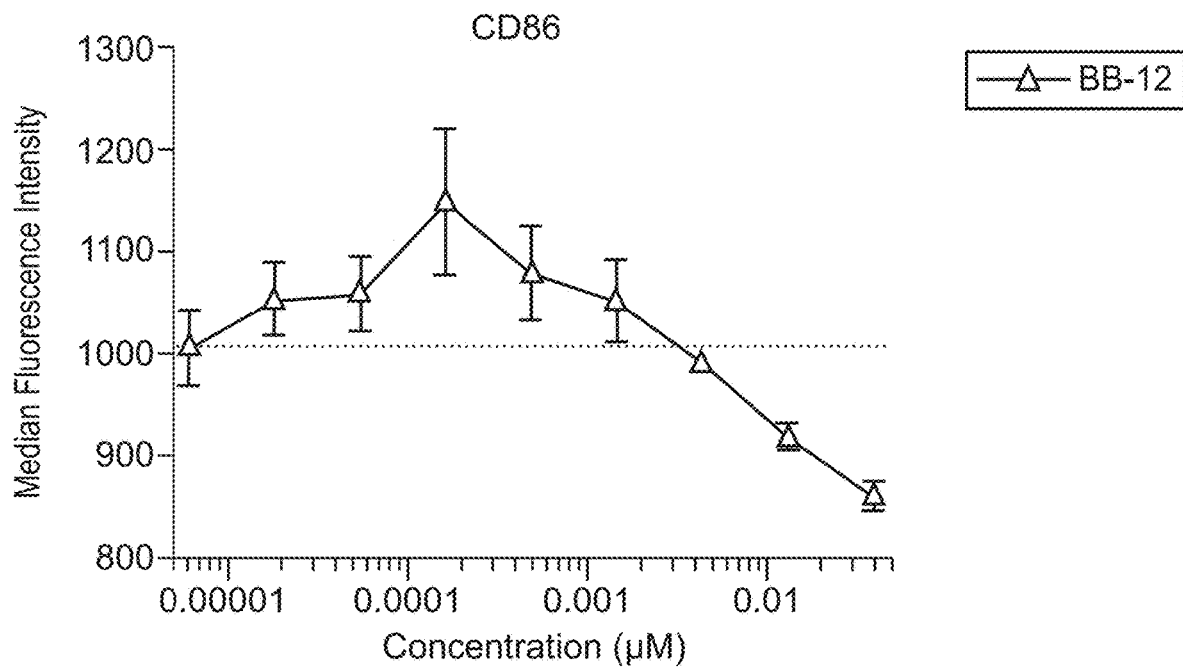

FIG. 126O shows CD86 expression following 18 hours of stimulation with BB-12. The dashed line indicates the level of CD86 expression on unstimulated cells following 18 hours of incubation.

Figure 127A:
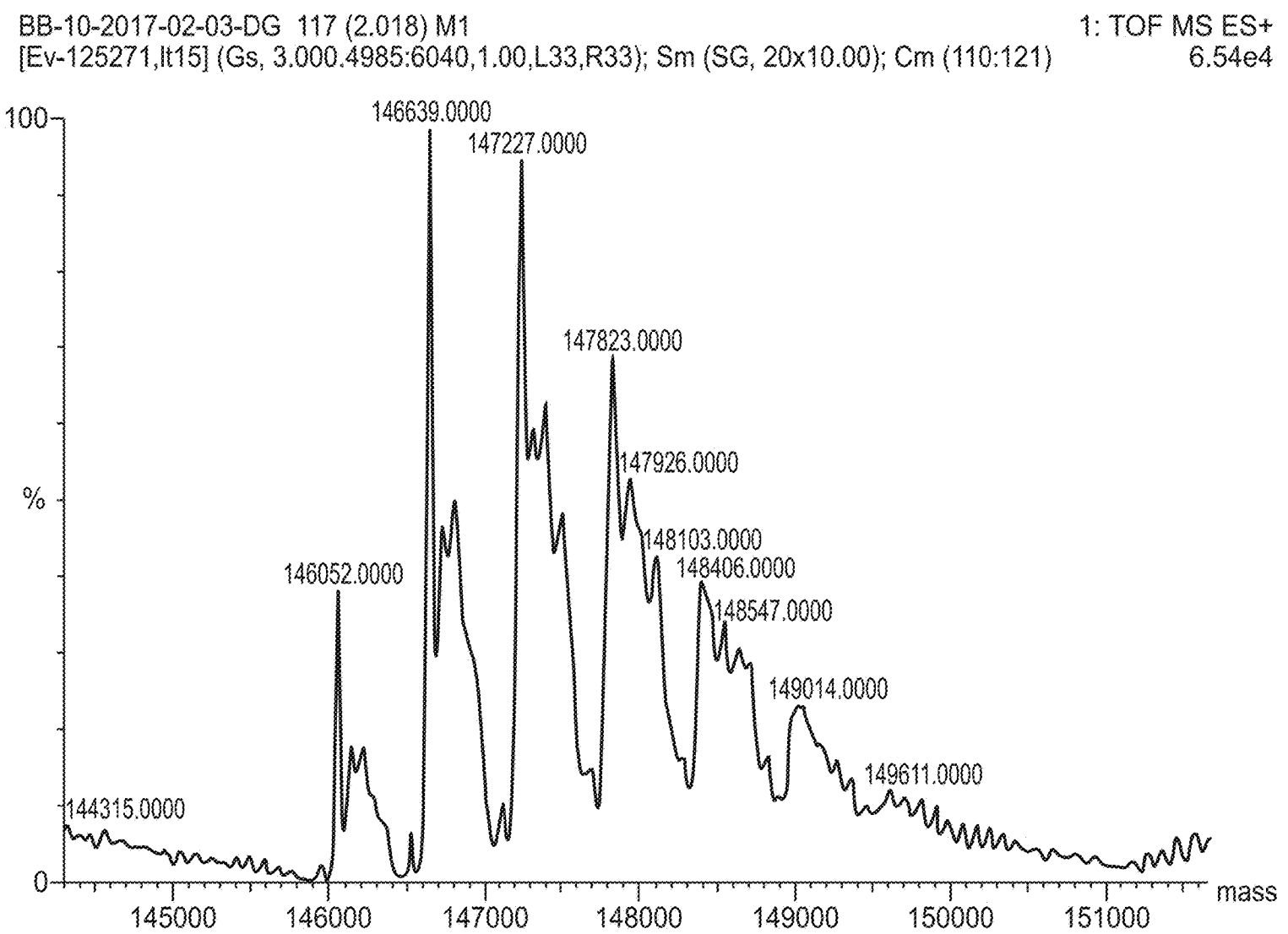

FIG. 127A shows a liquid chromatography-mass spectrometry analysis of the BB-10 immunoconjugate produced according to the SATA conjugation method following overnight deglycosylation with PNGase.

FIG. 127B shows a liquid chromatography-mass spectrometry analysis of an unconjugated Rituximab biosimilar (LGM Pharma) that was utilized to produce BB-10.

Figure 127C:
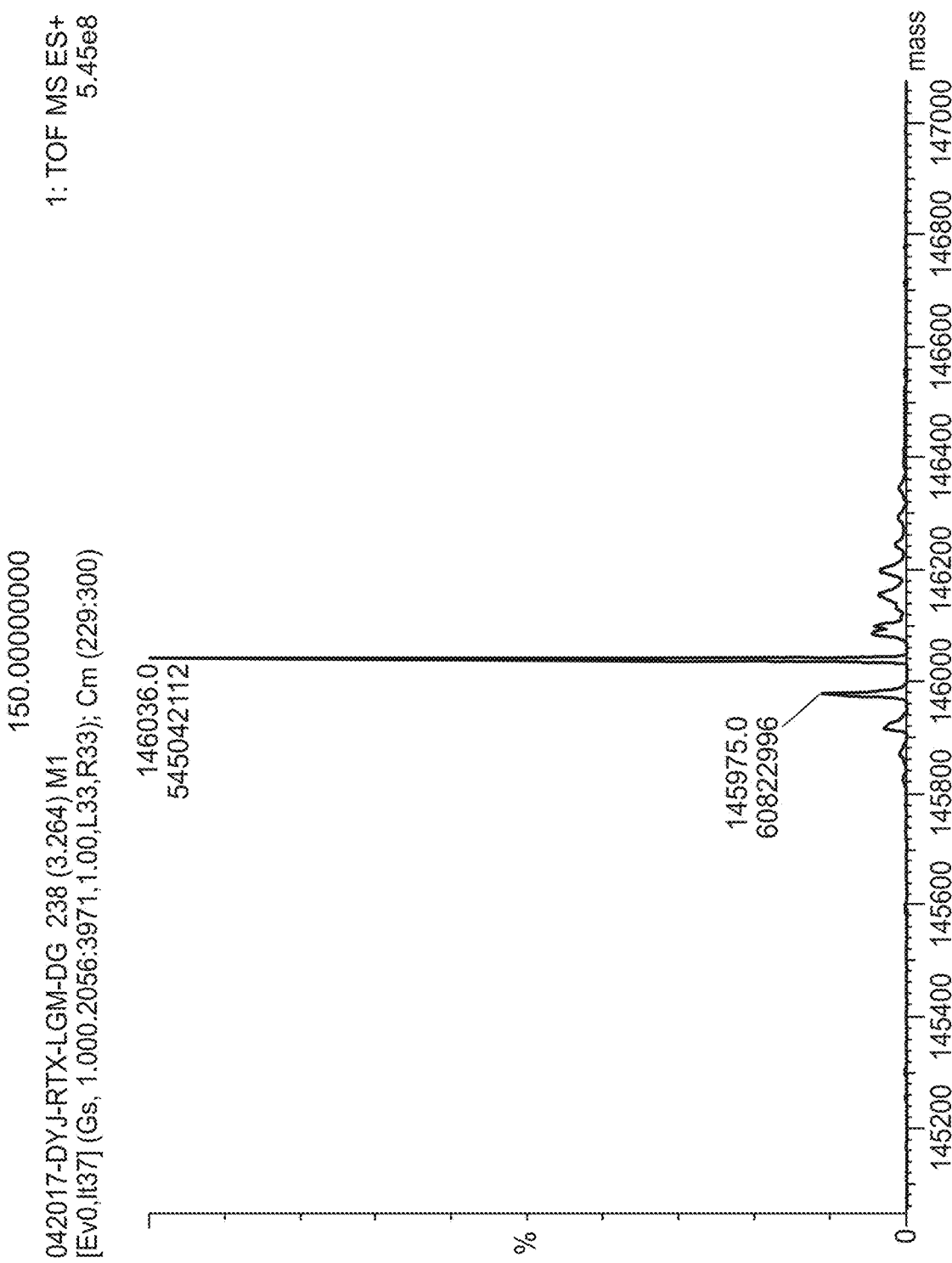

FIG. 127C shows a liquid chromatography-mass spectrometry analysis of an unconjugated Rituximab biosimilar (LGM Pharma) that was utilized to produce BB-10 following overnight deglycosylation with PNGase F.

Figure 127D:
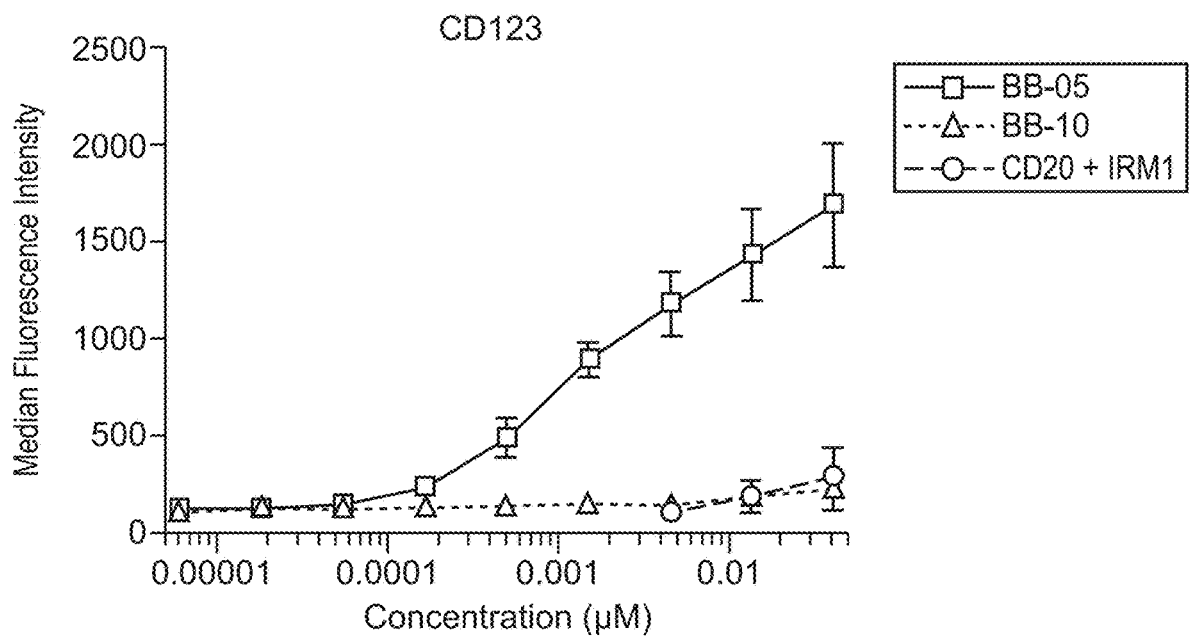

FIG. 127D shows that the BB-10 immunoconjugate produced according to the SATA method fails to elicit CD123 upregulation following 18 hours of stimulation. FIG. 127D also shows that the BB-05 immunoconjugate produced according to the SATA method is superior at eliciting CD123 upregulation as compared to BB-10 and equimolar concentrations of the mixture (CD20+IRM1). It should be noted that BB-05 and BB-10 are constructed with identical linkers, but have distinct adjuvants.

Figure 127E:
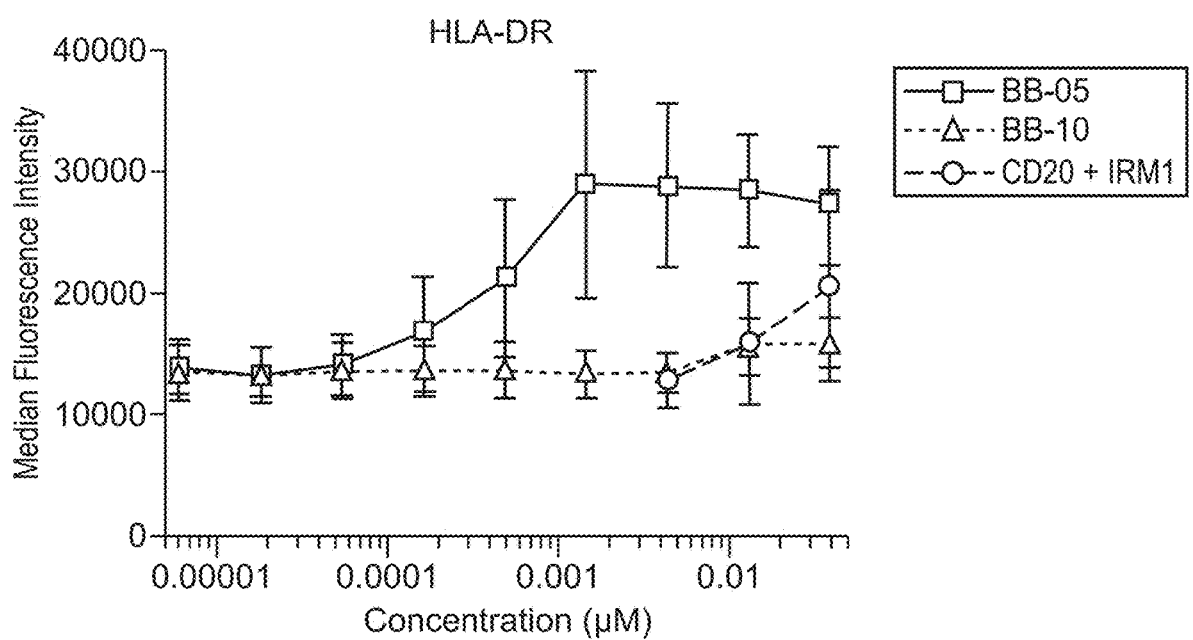

FIG. 127E shows that the BB-10 immunoconjugate produced according to the SATA method fails to elicit HLA-DR upregulation following 18 hours of stimulation. FIG. 127E also shows that the BB-05 immunoconjugate produced according to the SATA method is superior at eliciting HLA-DR upregulation as compared to BB-10 and equimolar concentrations of the mixture (CD20+IRM1). It should be noted that BB-05 and BB-10 are constructed with identical linkers, but have distinct adjuvants.

Figure 127F:
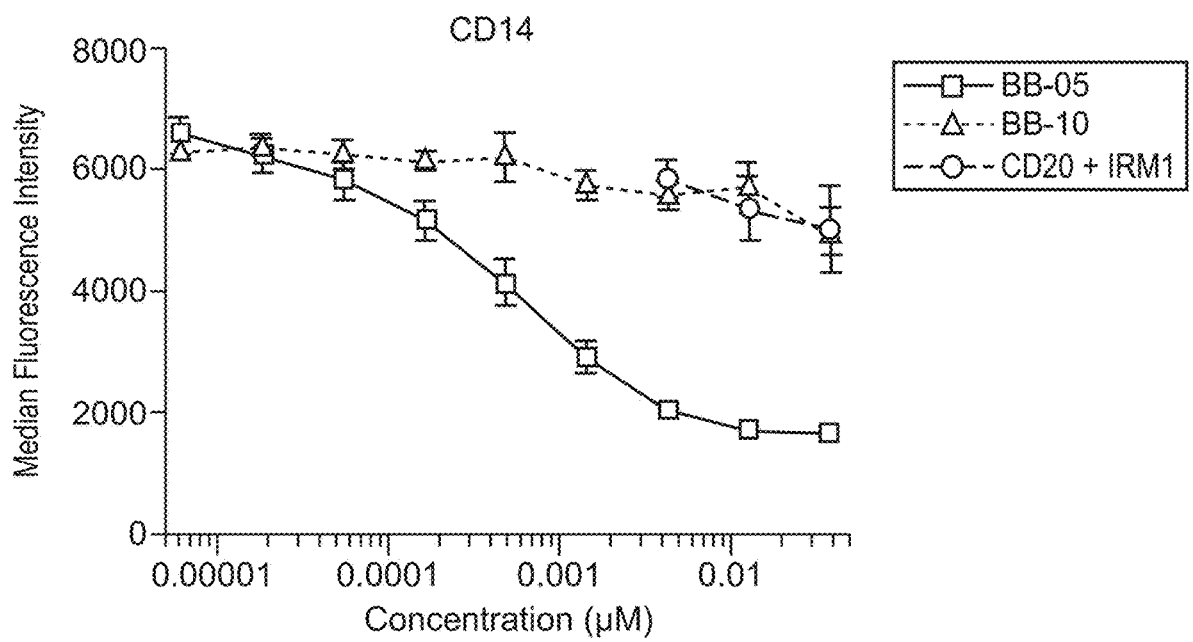

FIG. 127F shows that the BB-10 immunoconjugate produced according to the SATA method fails to elicit CD14 downregulation following 18 hours of stimulation as compared to equimolar concentrations of the mixture (CD20+IRM1). FIG. 127F also shows that the BB-05 immunoconjugate produced according to the SATA method is superior at eliciting CD14 downregulation as compared to BB-10 and equimolar concentrations of the mixture (CD20+IRM1). It should be noted that BB-05 and BB-10 are constructed with identical linkers, but have distinct adjuvants.

Figure 127G:
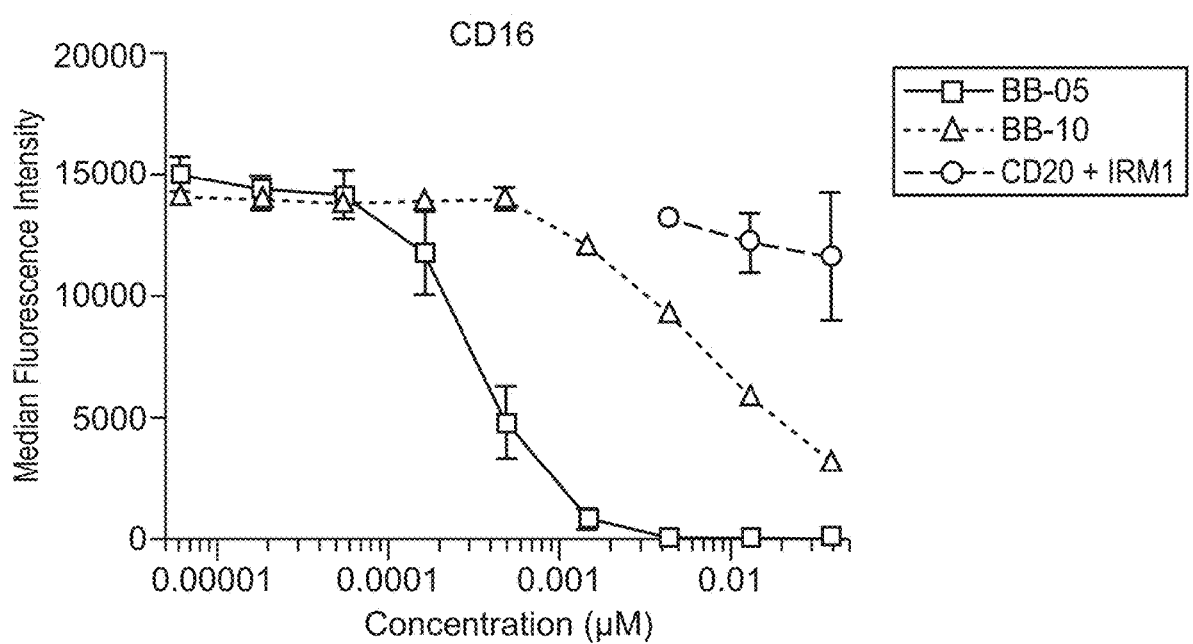

FIG. 127G shows that the BB-05 immunoconjugate produced according to the SATA method is superior at eliciting CD16 downregulation as compared to BB-10 and equimolar concentrations of the mixture (CD20+IRM1). It should be noted that BB-05 and BB-10 are constructed with identical linkers, but have distinct adjuvants.

Figure 127H:
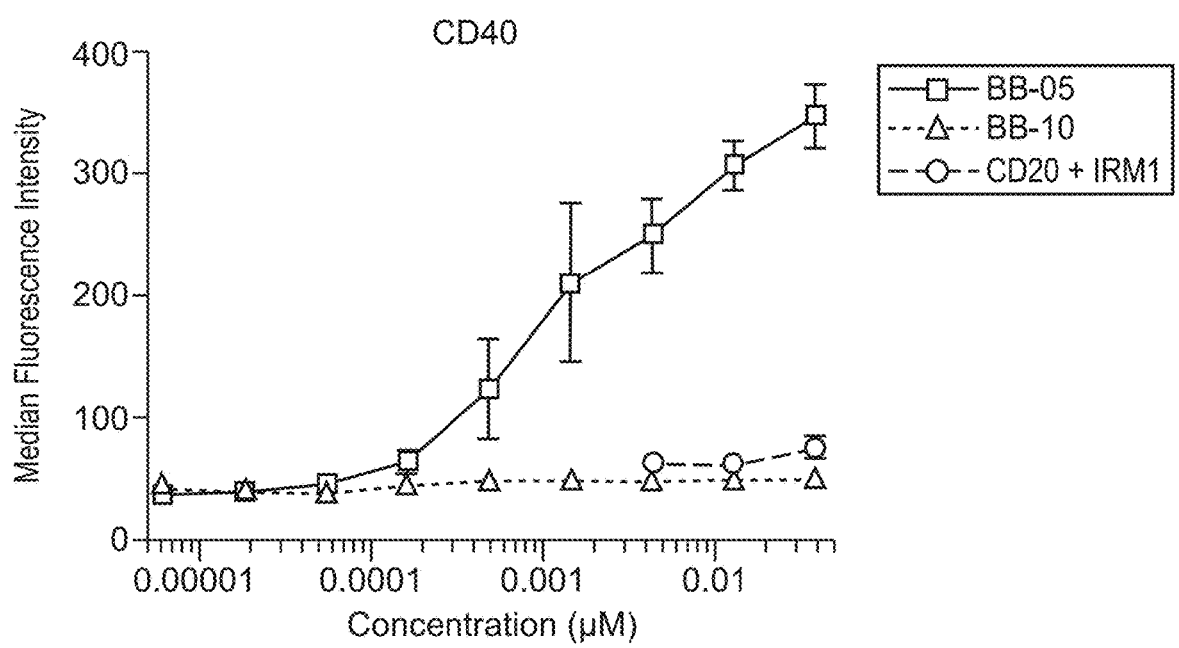

FIG. 127H shows that the BB-10 immunoconjugate produced according to the SATA method fails to elicit CD40 upregulation following 18 hours of stimulation as compared to equimolar concentrations of the mixture (CD20+IRM1). FIG. 127H also shows that the BB-05 immunoconjugate produced according to the SATA method is superior at eliciting CD40 upregulation as compared to BB-10 and equimolar concentrations of the mixture (CD20+IRM1). It should be noted that BB-05 and BB-10 are constructed with identical linkers, but have distinct adjuvants.

Figure 127I:
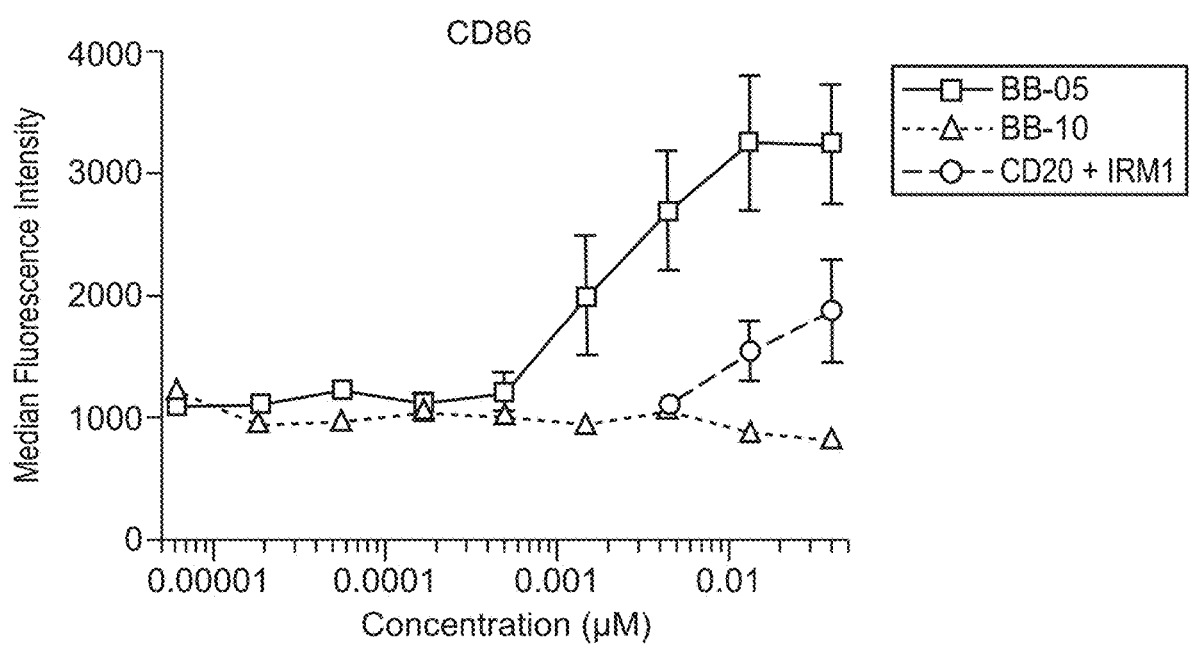

FIG. 127I shows that the BB-10 immunoconjugate produced according to the SATA method fails to elicit CD86 upregulation following 18 hours of stimulation as compared to equimolar concentrations of the mixture (CD20+IRM1). FIG. 127I also shows that the BB-05 immunoconjugate produced according to the SATA method is superior at eliciting CD86 upregulation as compared to BB-10 and equimolar concentrations of the mixture (CD20+IRM1). It should be noted that BB-05 and BB-10 are constructed with identical linkers, but have distinct adjuvants.

Figure 127J:
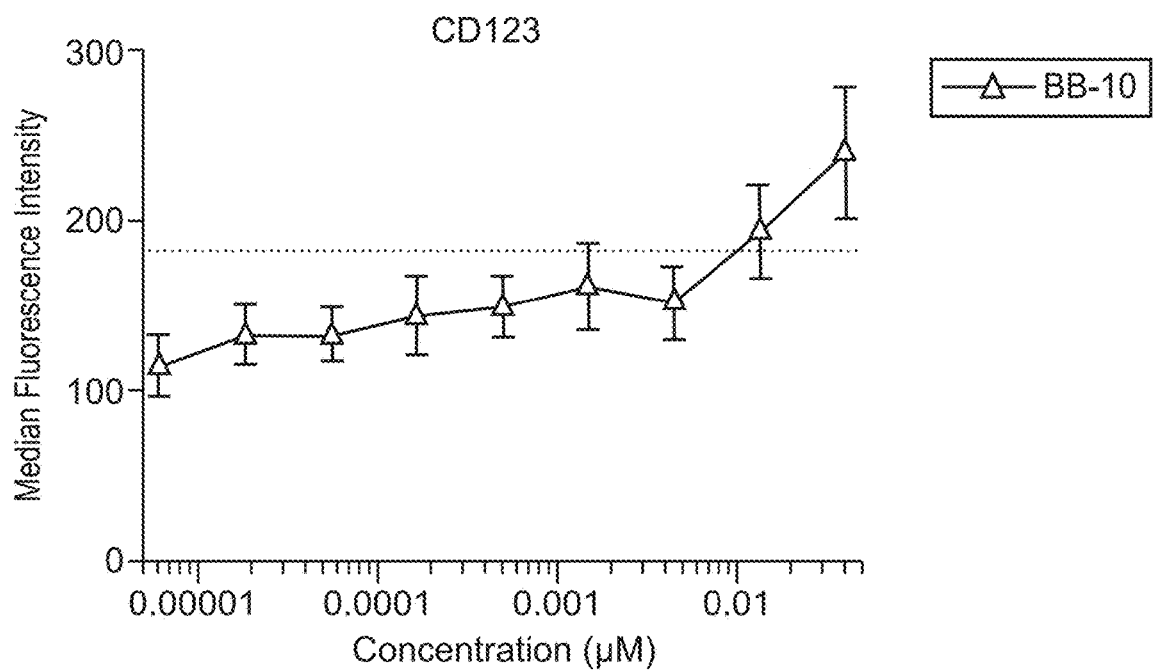

FIG. 127J shows CD123 expression following 18 hours of stimulation with BB-10. The dashed line indicates the level of CD123 expression on unstimulated cells following 18 hours of incubation.

Figure 127K:
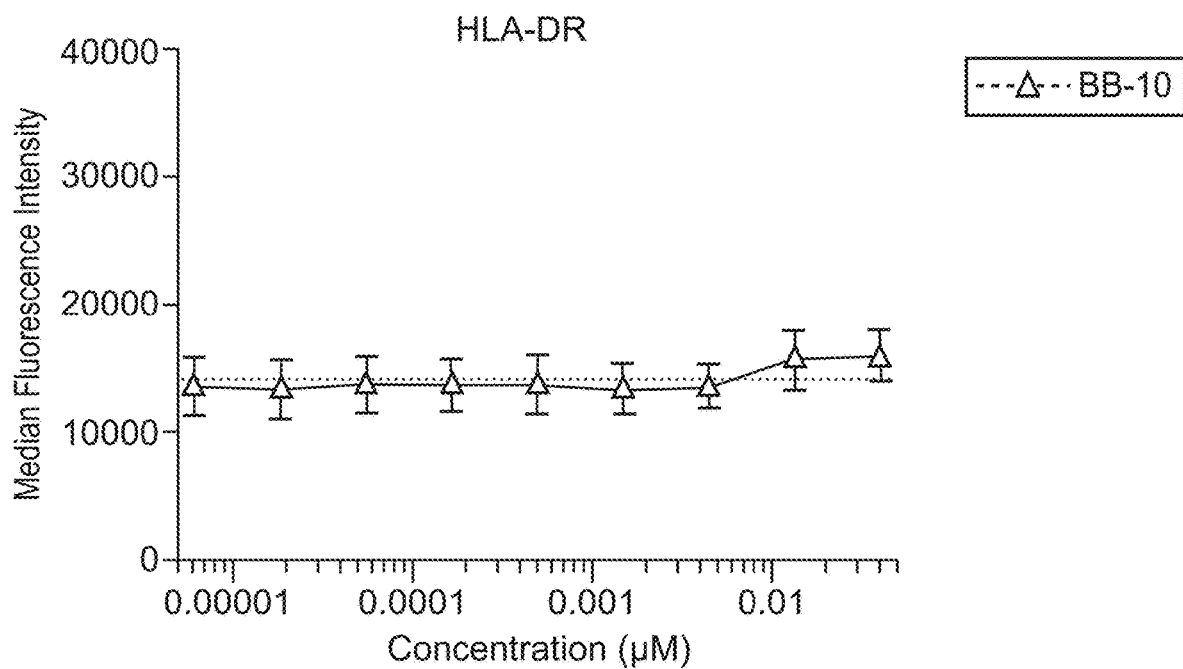

FIG. 127K shows HLA-DR expression following 18 hours of stimulation with BB-10. The dashed line indicates the level of HLA-DR expression on unstimulated cells following 18 hours of incubation.

Figure 127L:
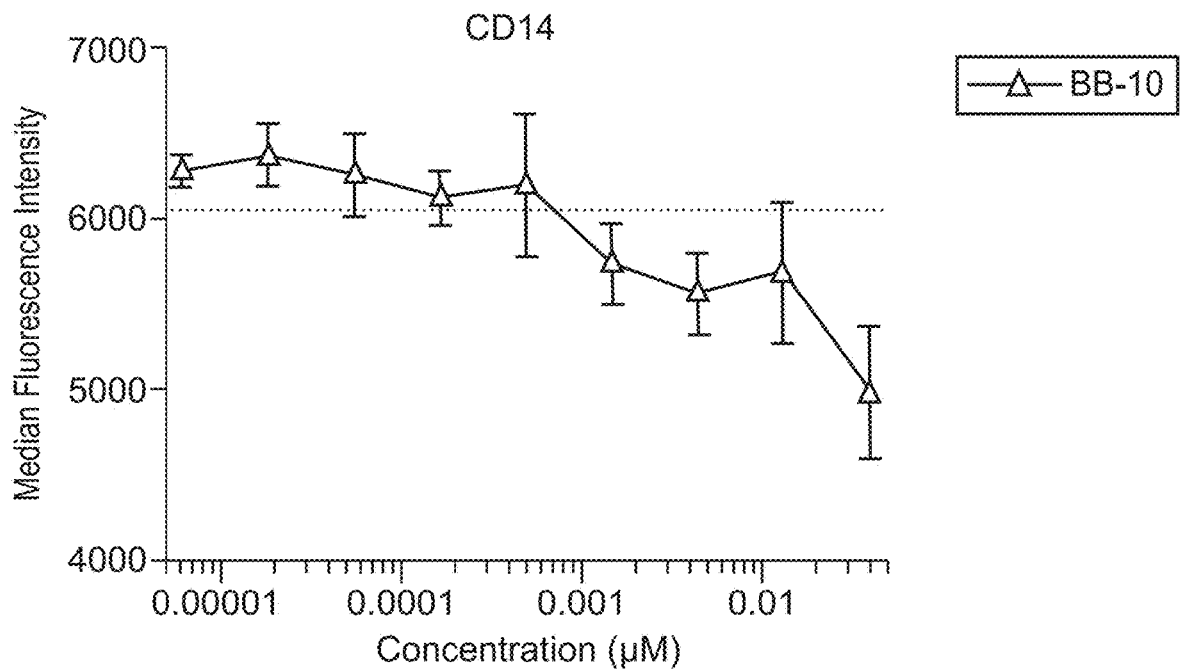

FIG. 127L shows CD14 expression following 18 hours of stimulation with BB-10. The dashed line indicates the level of CD14 expression on unstimulated cells following 18 hours of incubation.

Figure 127M:
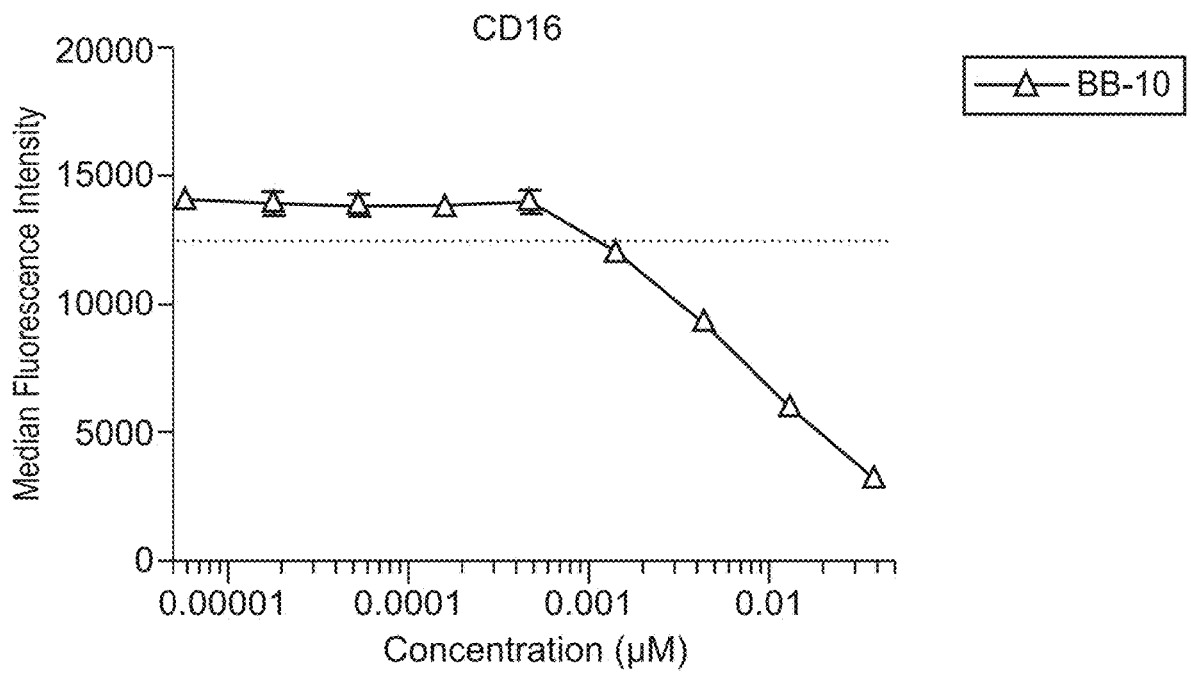

FIG. 127M shows CD16 expression following 18 hours of stimulation with BB-10. The dashed line indicates the level of CD16 expression on unstimulated cells following 18 hours of incubation.

Figure 127N:
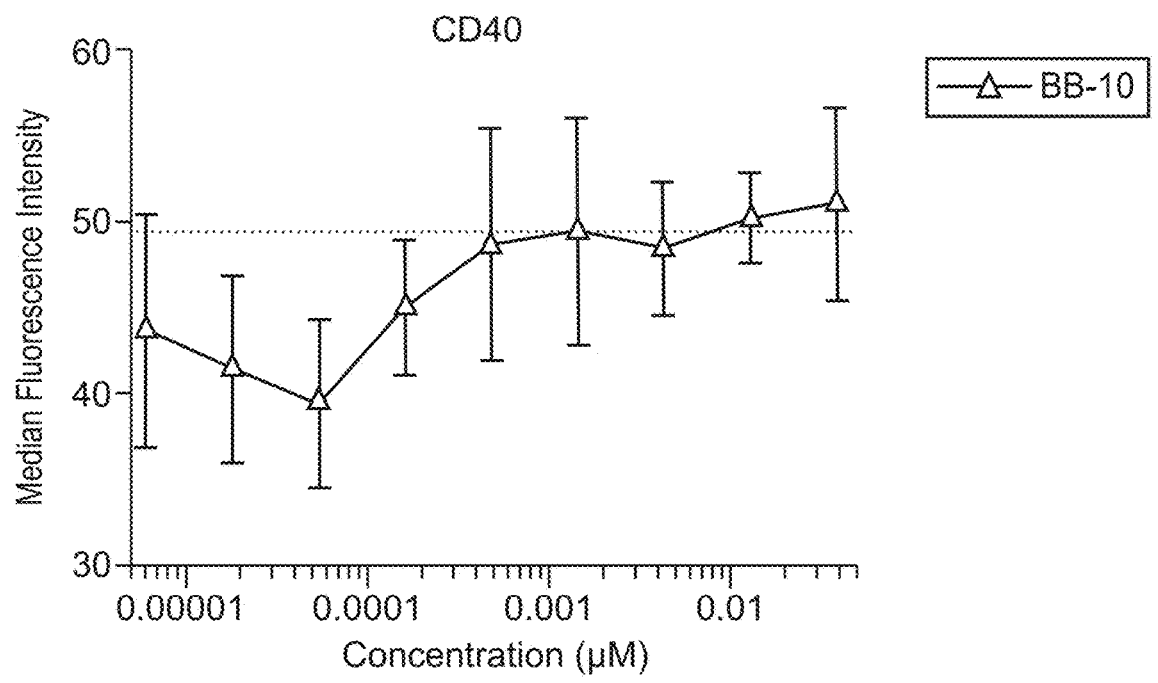

FIG. 127N shows CD40 expression following 18 hours of stimulation with BB-10. The dashed line indicates the level of CD40 expression on unstimulated cells following 18 hours of incubation.

Figure 127O:
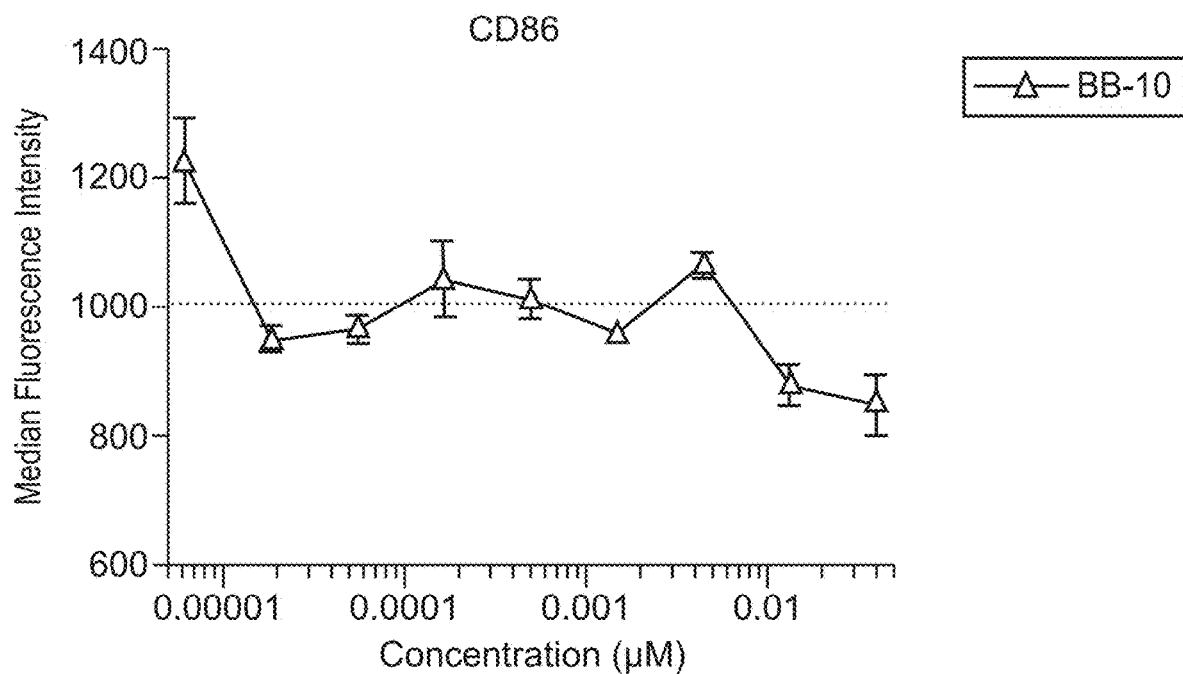

FIG. 127O shows CD86 expression following 18 hours of stimulation with BB-10. The dashed line indicates the level of CD40 expression on unstimulated cells following 18 hours of incubation.

Figure 128A:
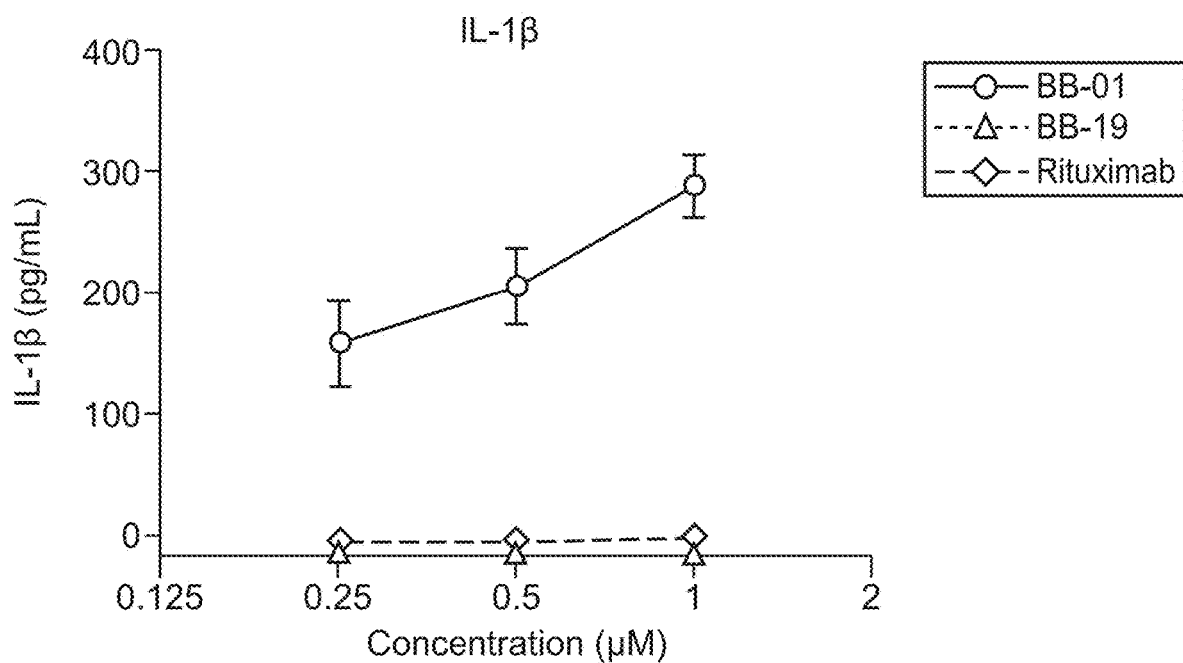

FIG. 128A shows that the BB-01 immunoconjugate produced according to the BB-01 method elicits superior IL-10 secretion from myeloid cells as compared to equimolar concentrations of BB-19 produced according to methods disclosed in U.S. Pat. No. 8,951,528 and unconjugated Rituximab biosimilar (LGM Pharma) following 18 hours of stimulation.

Figure 128B:
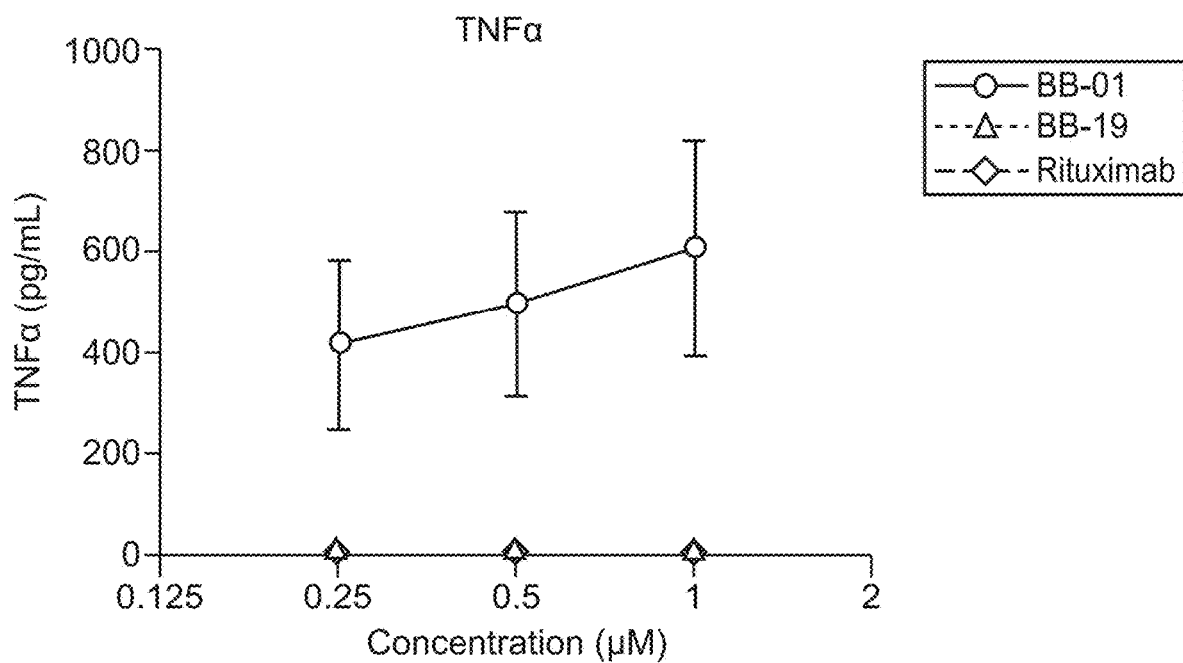

FIG. 128B shows that the BB-01 immunoconjugate produced according to the BB-01 method elicits superior TNFα secretion from myeloid cells as compared to equimolar concentrations of BB-19 produced according to methods disclosed in U.S. Pat. No. 8,951,528 and unconjugated Rituximab biosimilar (LGM Pharma) following 18 hours of stimulation.

Figure 128C:
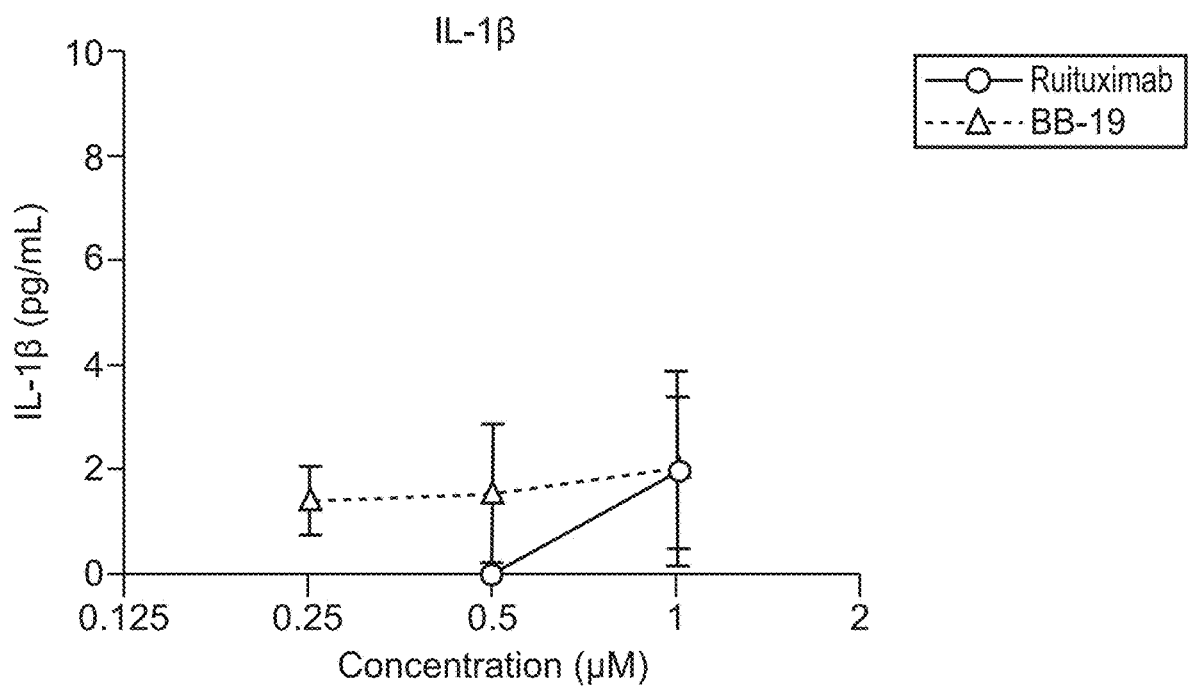

FIG. 128C shows IL-1β secretion from myeloid cells following an 18 hour incubation with equimolar concentrations of unconjugated Rituximab biosimilar (LGM Pharma) or BB-19 produced according to methods disclosed in U.S. Pat. No. 8,951,528.

Figure 128D:
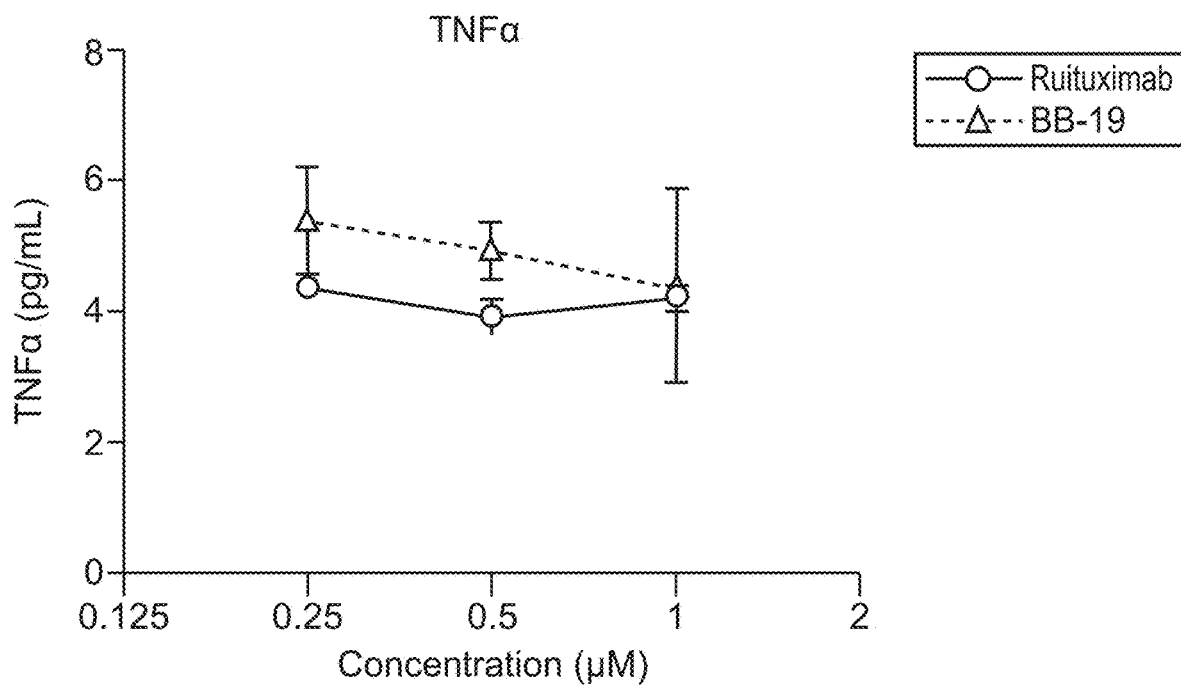

FIG. 128D shows TNFα secretion from myeloid cells following an 18 hour incubation with equimolar concentrations of unconjugated Rituximab biosimilar (LGM Pharma) or BB-19 produced according to methods disclosed in U.S. Pat. No. 8,951,528.

Figure 128E:
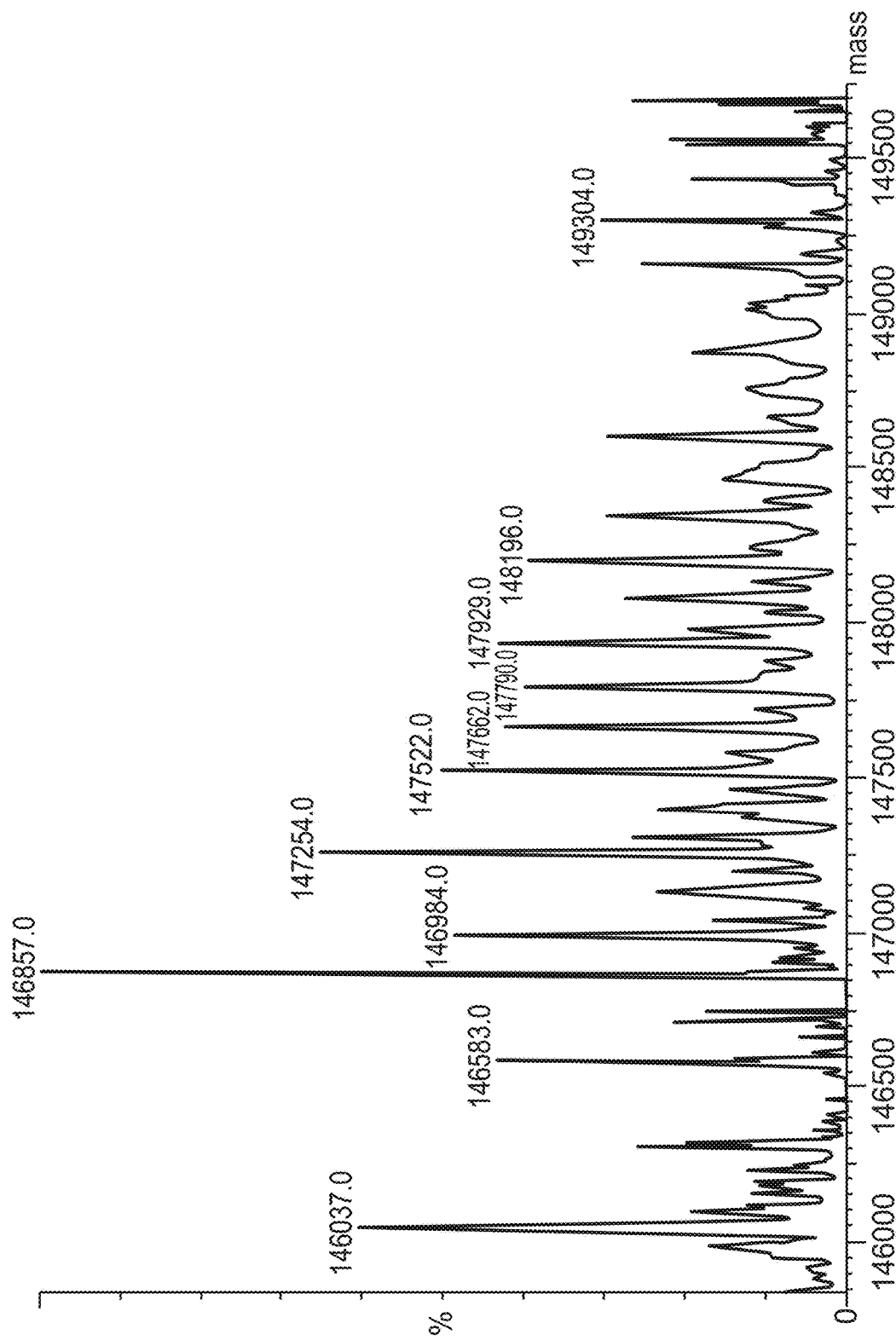

FIG. 128E shows a liquid chromatography-mass spectrometry analysis of the BB-19 produced according to methods disclosed in U.S. Pat. No. 8,951,528 following overnight deglycosylation with PNGase.

Figure 128F:
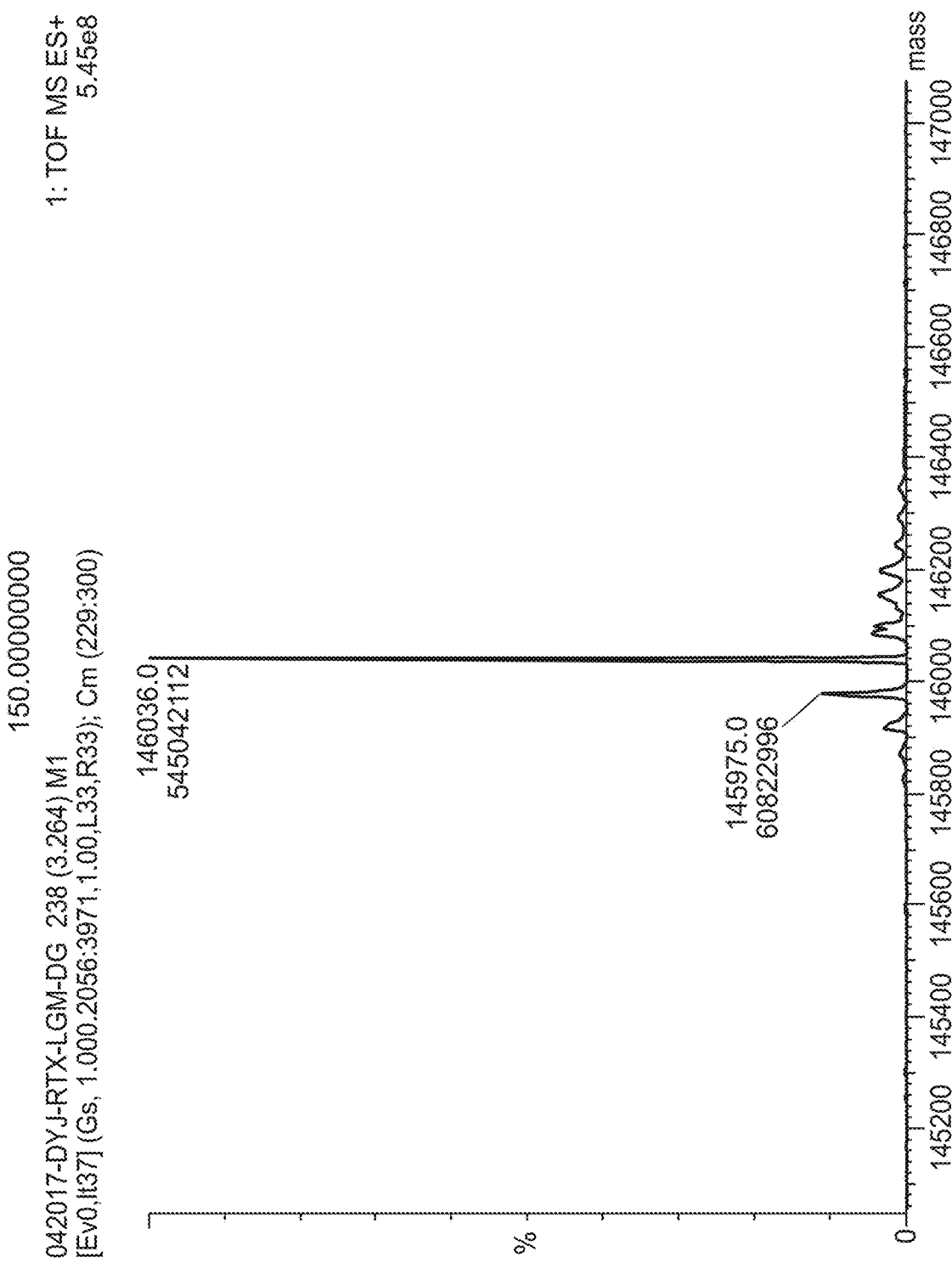

FIG. 128F shows a liquid chromatography-mass spectrometry analysis of an unconjugated Rituximab biosimilar (LGM Pharma) that was utilized to produce BB-19 following overnight deglycosylation with PNGase.

Figure 128G:
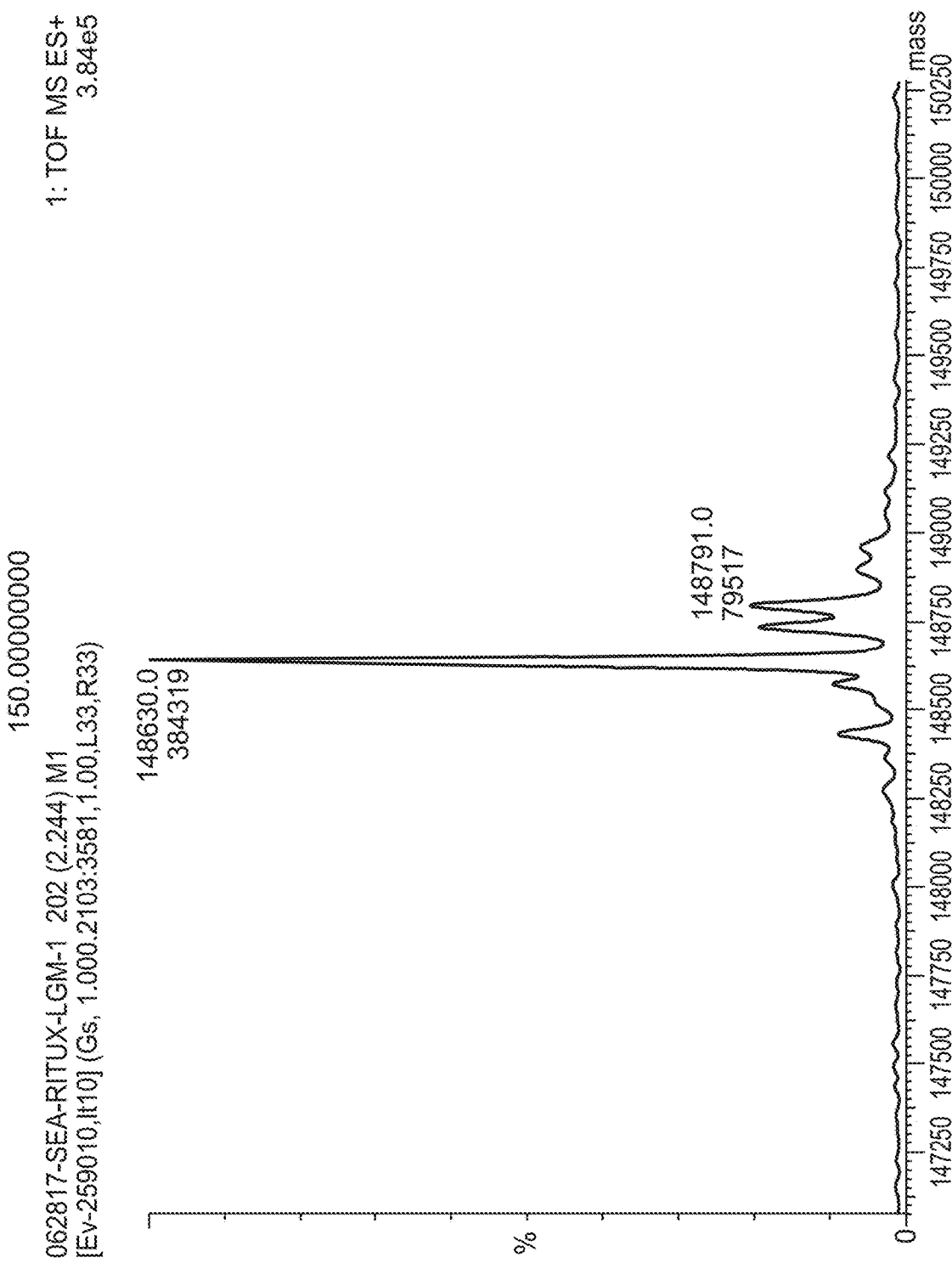

FIG. 128G shows a liquid chromatography-mass spectrometry analysis of an unconjugated Rituximab biosimilar (LGM Pharma) that was utilized to produce BB-19

Figure 128H:
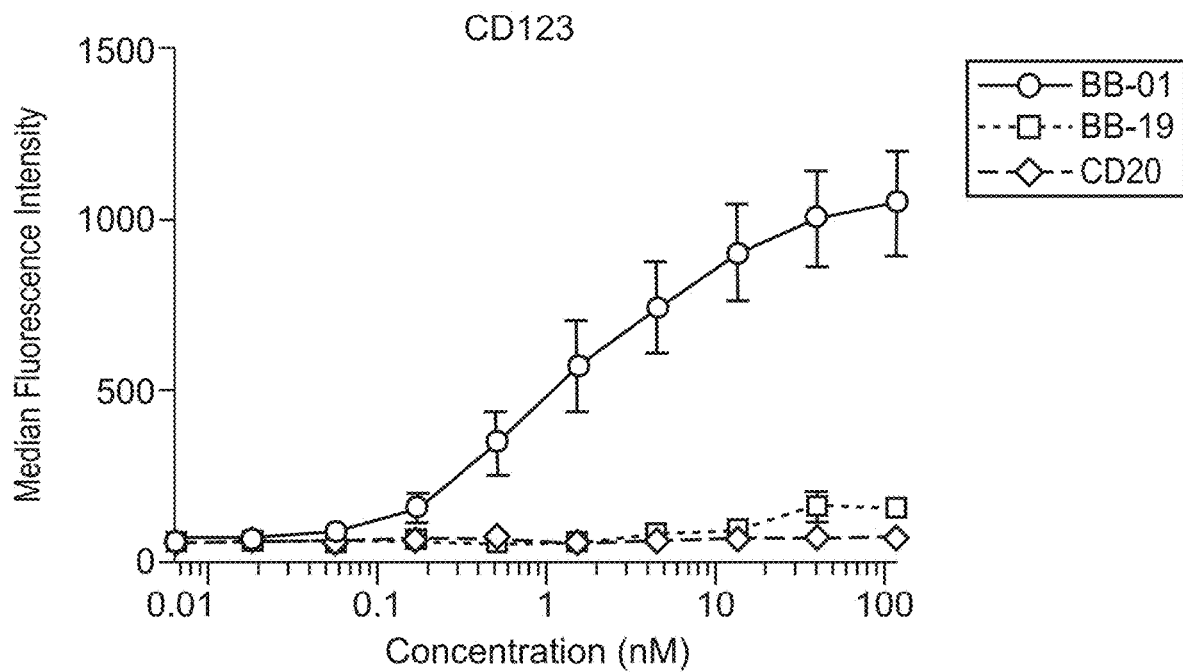

FIG. 128H shows that BB-01 produced according to the BB-01 method is superior at eliciting CD 123 upregulation on myeloid cells as compared to the BB-19 immunoconjugate produced according to methods disclosed in U.S. Pat. No. 8,951,528 and the unconjugated Rituximab biosimilar (CD20; LGM Pharma) following 18 hours of stimulation.

Figure 128I:
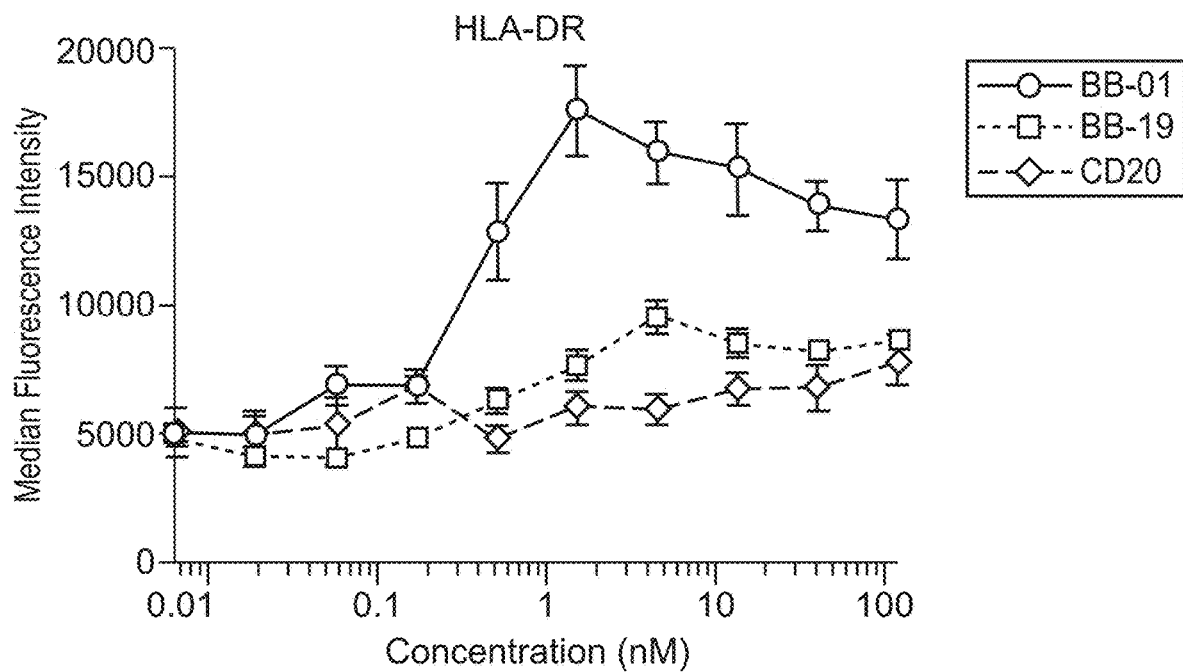

FIG. 128I shows that BB-01 produced according to the BB-01 method is superior at eliciting HLA-DR upregulation on myeloid cells as compared to the BB-19 immunoconjugate produced according to methods disclosed in U.S. Pat. No. 8,951,528 and the unconjugated Rituximab biosimilar (CD20; LGM Pharma) following 18 hours of stimulation.

Figure 128J:
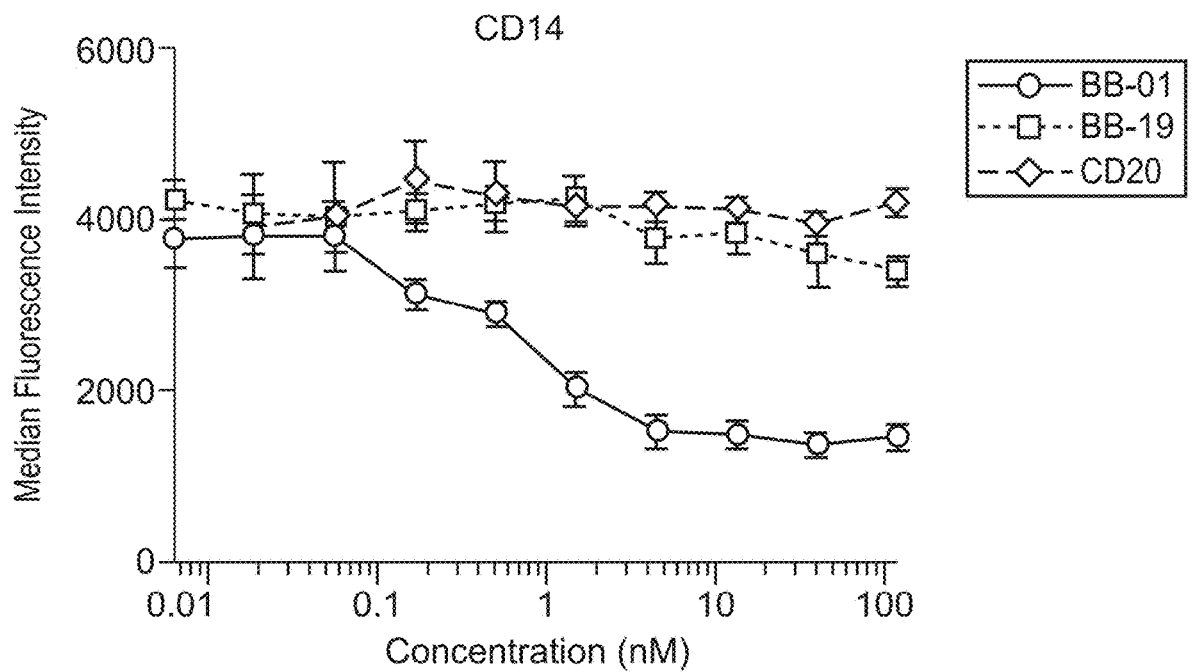

FIG. 128J shows that BB-01 produced according to the BB-01 method is superior at eliciting CD14 downregulation on myeloid cells as compared to the BB-19 immunoconjugate produced according to methods disclosed in U.S. Pat. No. 8,951,528 and the unconjugated Rituximab biosimilar (CD20; LGM Pharma) following 18 hours of stimulation.

Figure 128K:
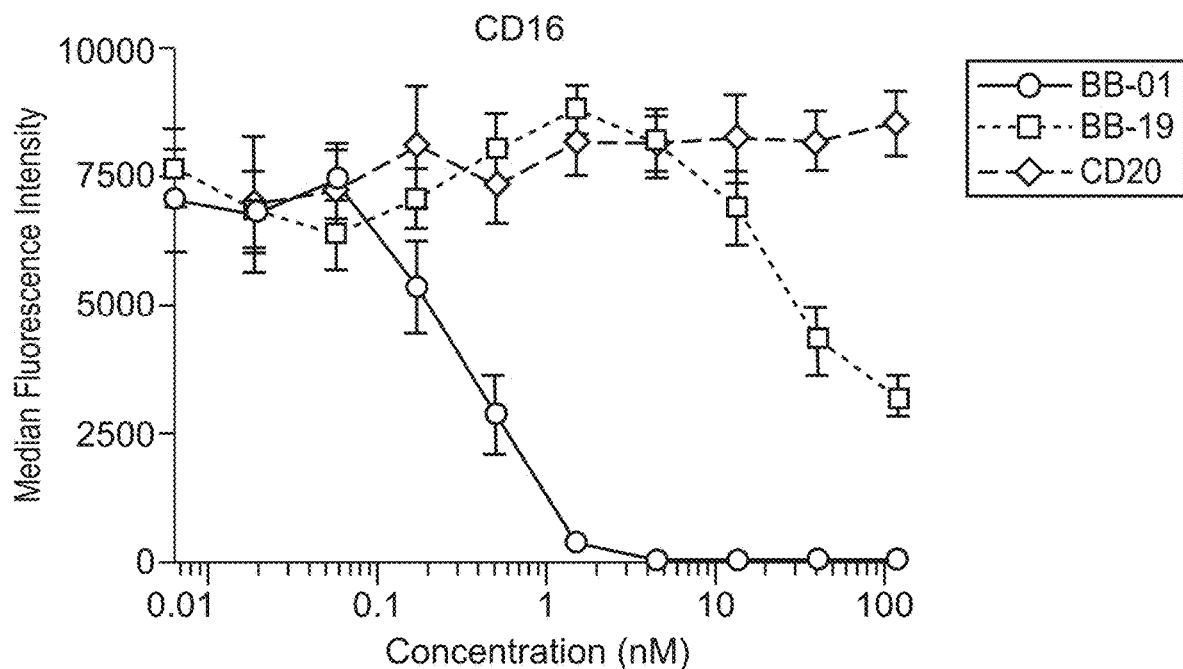

FIG. 128K shows that BB-01 produced according to the BB-01 method is superior at eliciting CD16 downregulation on myeloid cells as compared to the BB-19 immunoconjugate produced according to methods disclosed in U.S. Pat. No. 8,951,528 and the unconjugated Rituximab biosimilar (CD20; LGM Pharma) following 18 hours of stimulation.

Figure 128L:
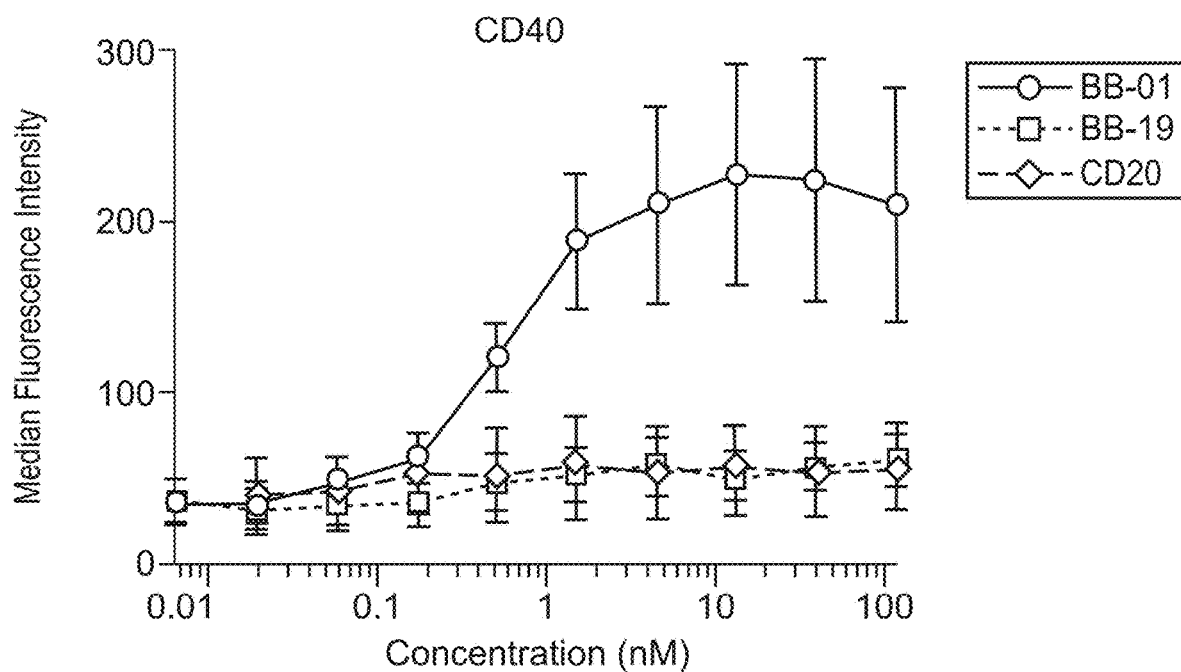

FIG. 128L shows that the BB-19 immunoconjugate produced according to methods disclosed in U.S. Pat. No. 8,951,528 fails to elicit CD40 upregulation following 18 hours of stimulation. FIG. 128L also shows that the BB-01 immunoconjugate produced according to the BB-01 method is superior at eliciting CD40 upregulation as compared to BB-19 and the unconjugated Rituximab biosimilar (CD20; LGM Pharma).

Figure 128M:
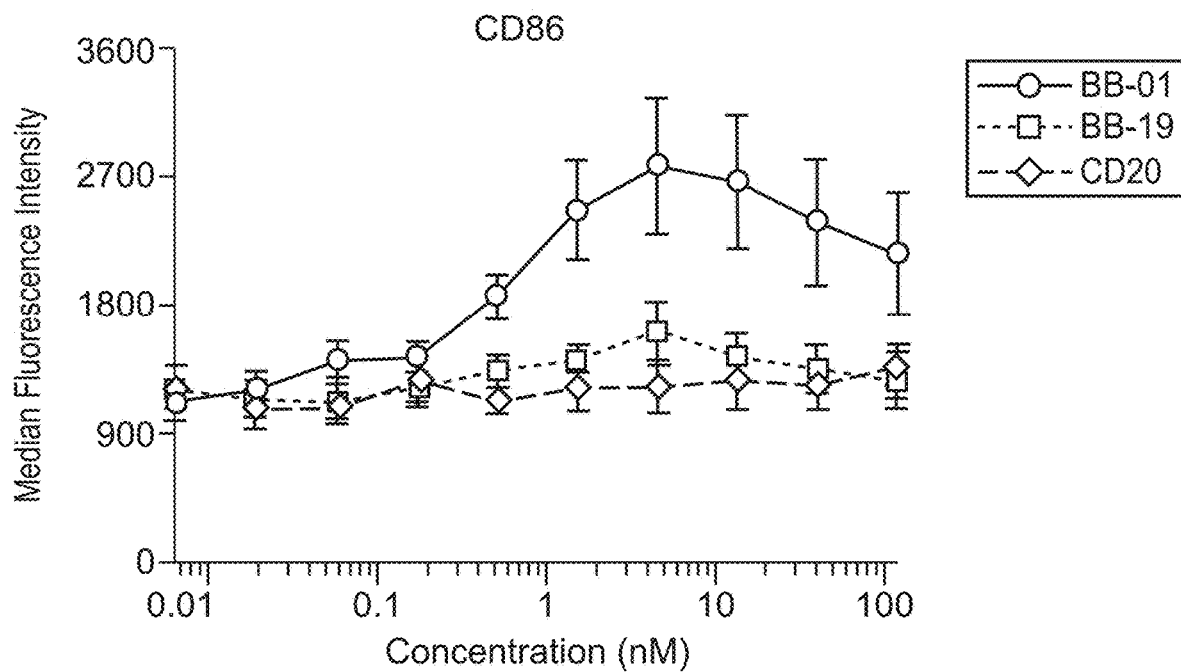

FIG. 128M shows that BB-01 produced according to the BB-01 method is superior at eliciting CD86 upregulation on myeloid cells as compared to the BB-19 immunoconjugate produced according to methods disclosed in U.S. Pat. No. 8,951,528 and the unconjugated Rituximab biosimilar (CD20; LGM Pharma) following 18 hours of stimulation.

Figure 128N:
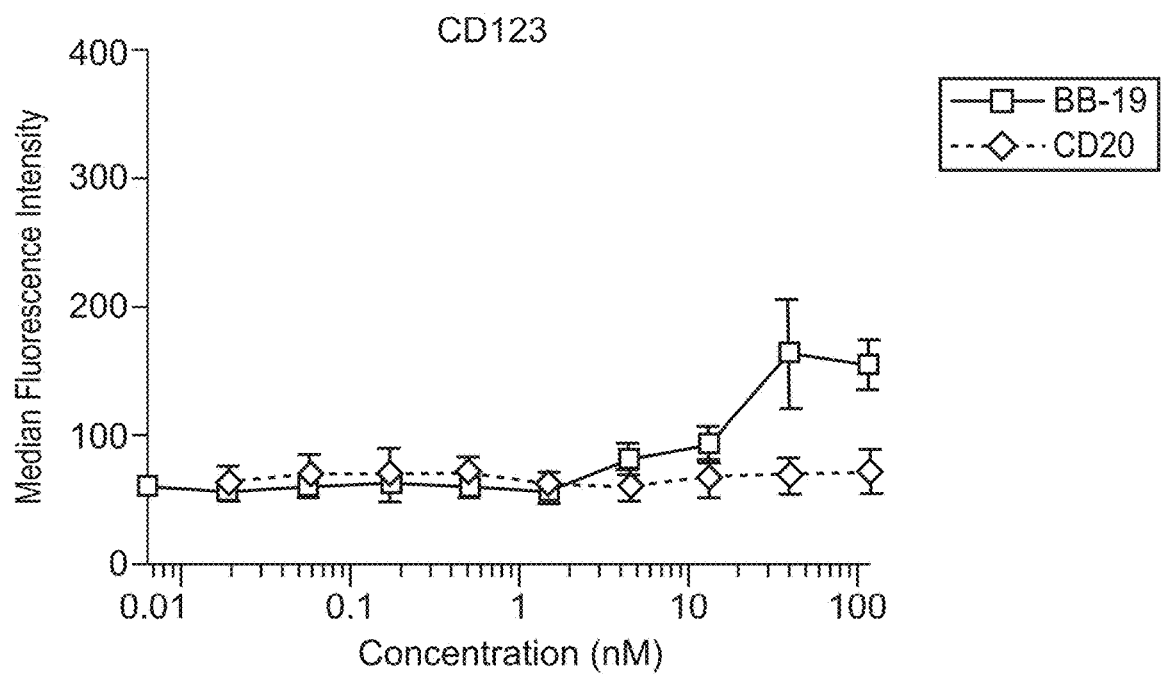

FIG. 128N shows CD123 expression on myeloid cells following 18 hours of stimulation with the BB-19 immunoconjugate produced according to methods disclosed in U.S. Pat. No. 8,951,528 or the unconjugated Rituximab biosimilar (CD20; LGM Pharma).

Figure 128O:
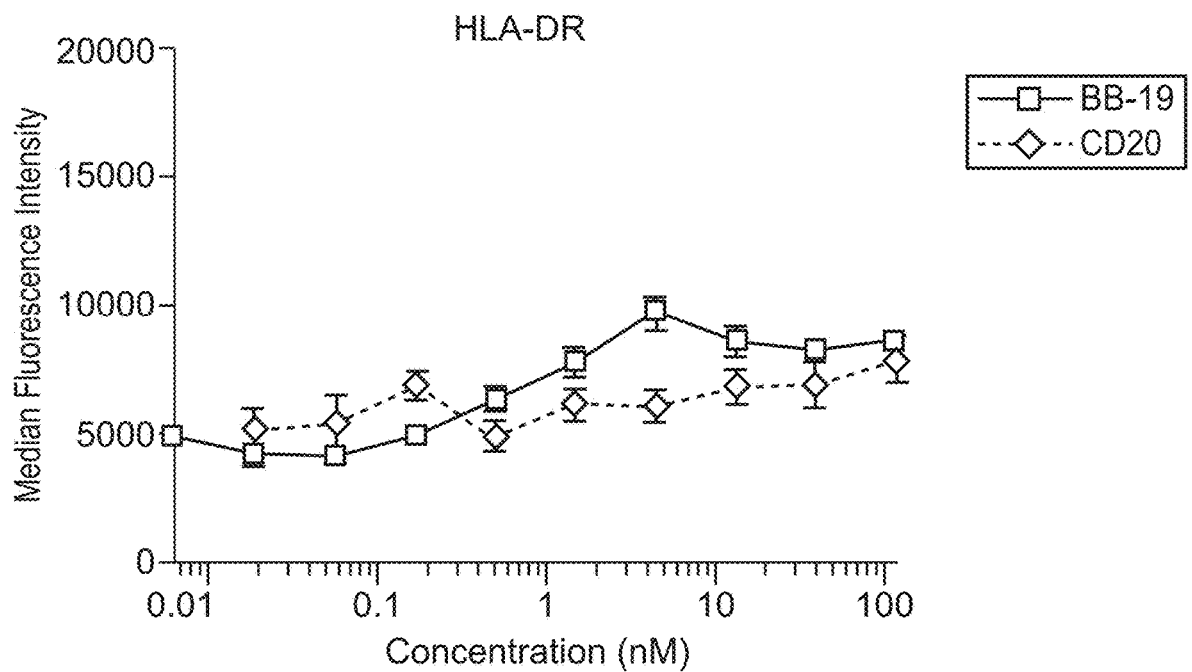

FIG. 128O shows HLA-DR expression on myeloid cells following 18 hours of stimulation with the BB-19 immunoconjugate produced according to methods disclosed in U.S. Pat. No. 8,951,528 or the unconjugated Rituximab biosimilar (CD20; LGM Pharma).

Figure 128P:
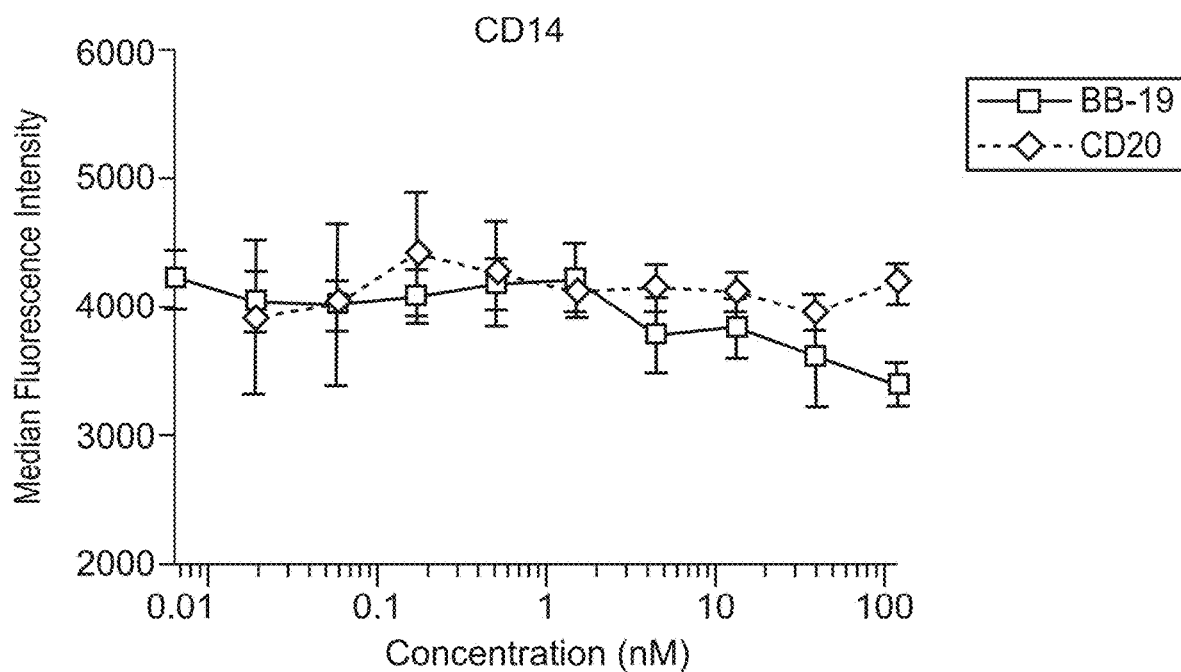

FIG. 128P shows CD14 expression on myeloid cells following 18 hours of stimulation with the BB-19 immunoconjugate produced according to the methods disclosed in U.S. Pat. No. 8,951,528 or the unconjugated Rituximab biosimilar (CD20; LGM Pharma).

Figure 128Q:
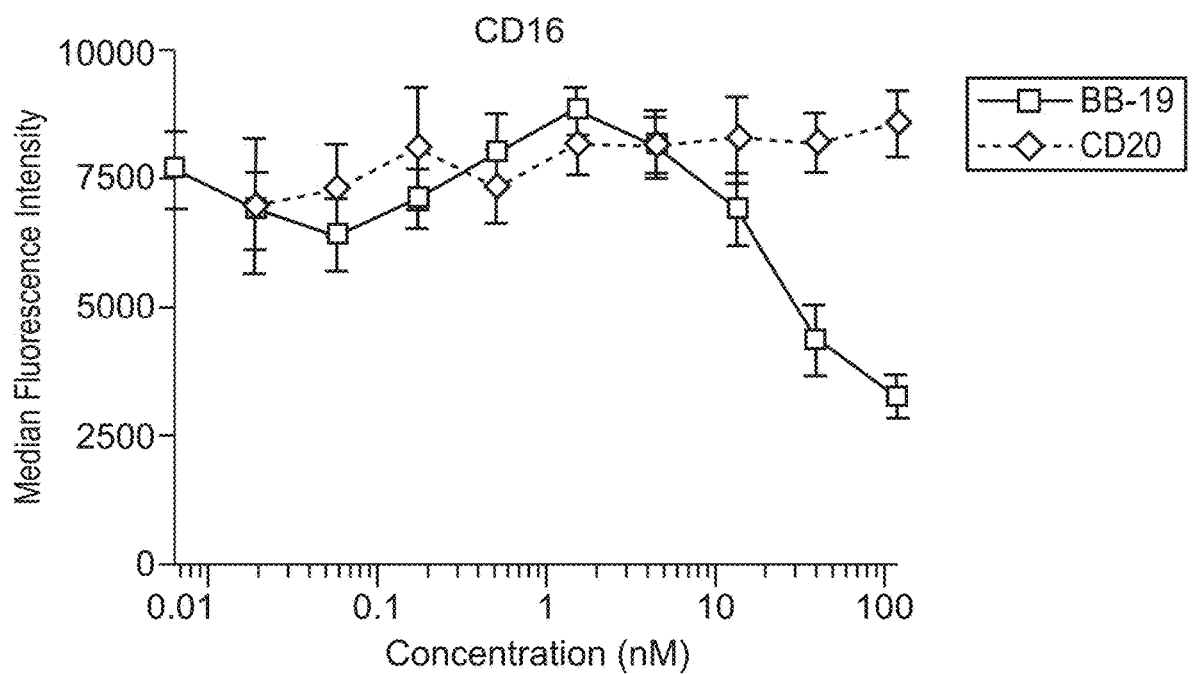

FIG. 128Q shows CD16 expression on myeloid cells following 18 hours of stimulation with the BB-19 immunoconjugate produced according to the methods disclosed in U.S. Pat. No. 8,951,528 or the unconjugated Rituximab biosimilar (CD20; LGM Pharma).

Figure 128R:
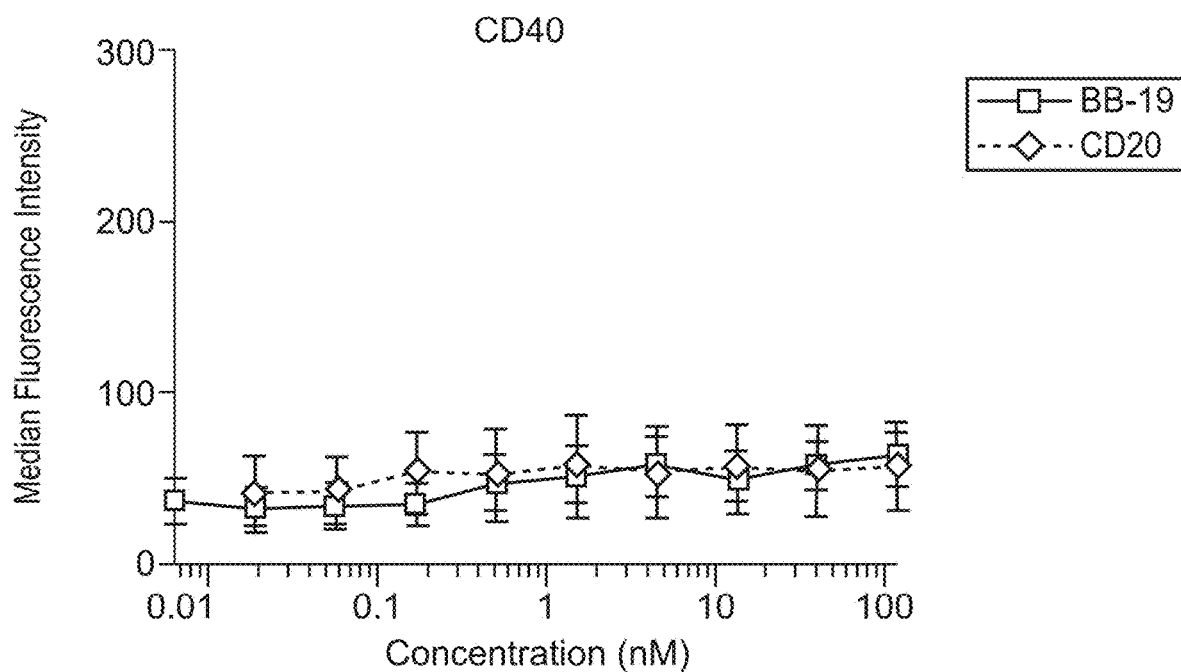

FIG. 128R shows CD40 expression on myeloid cells following 18 hours of stimulation with the BB-19 immunoconjugate produced according to the methods disclosed in U.S. Pat. No. 8,951,528 or the unconjugated Rituximab biosimilar (CD20; LGM Pharma).

Figure 128S:
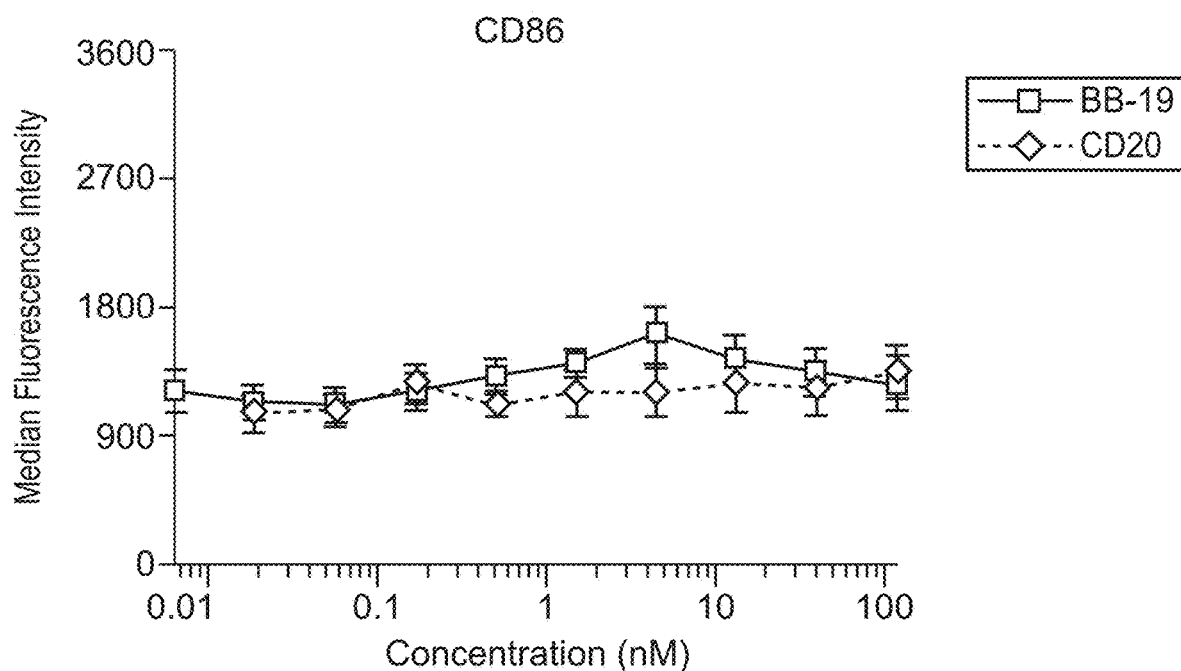

FIG. 128S shows CD86 expression on myeloid cells following 18 hours of stimulation with the BB-19 immunoconjugate produced according to methods disclosed in U.S. Pat. No. 8,951,528 or the unconjugated Rituximab biosimilar (CD20; LGM Pharma).

Figure 129A:
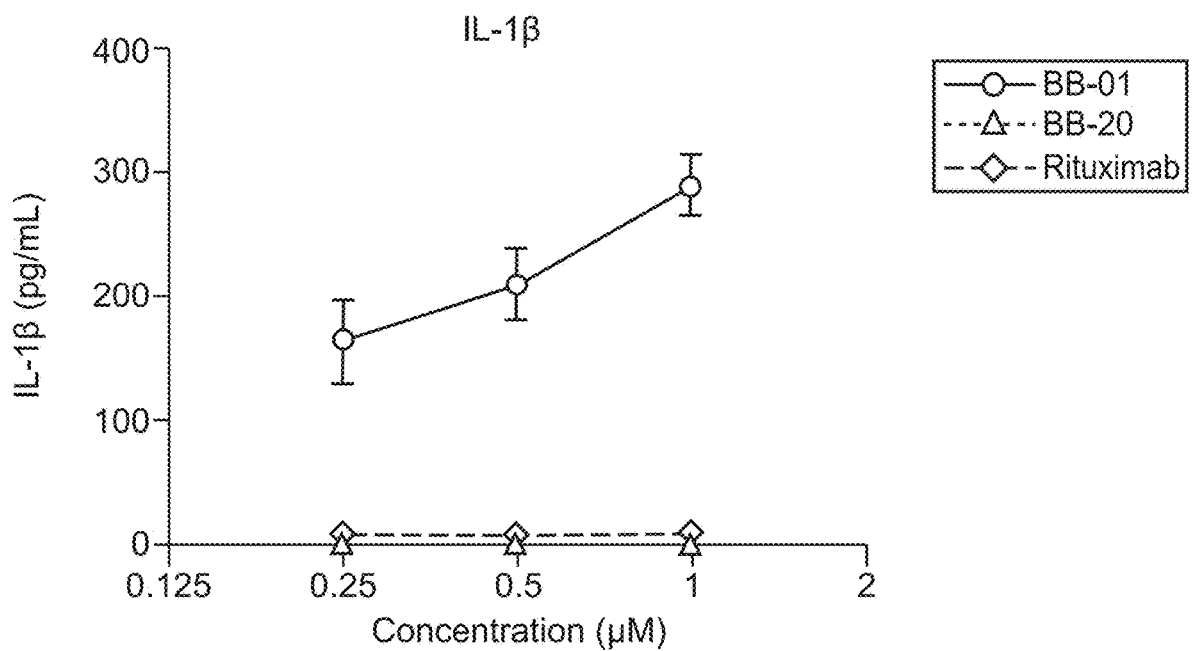

FIG. 129A shows that the BB-01 immunoconjugate produced according to the BB-01 method elicits superior IL-10 secretion from myeloid cells as compared to equimolar concentrations of BB-20 produced according to the methods disclosed in U.S. Pat. No. 8,951,528 and unconjugated Rituximab biosimilar (LGM Pharma) following 18 hours of stimulation.

Figure 129B:
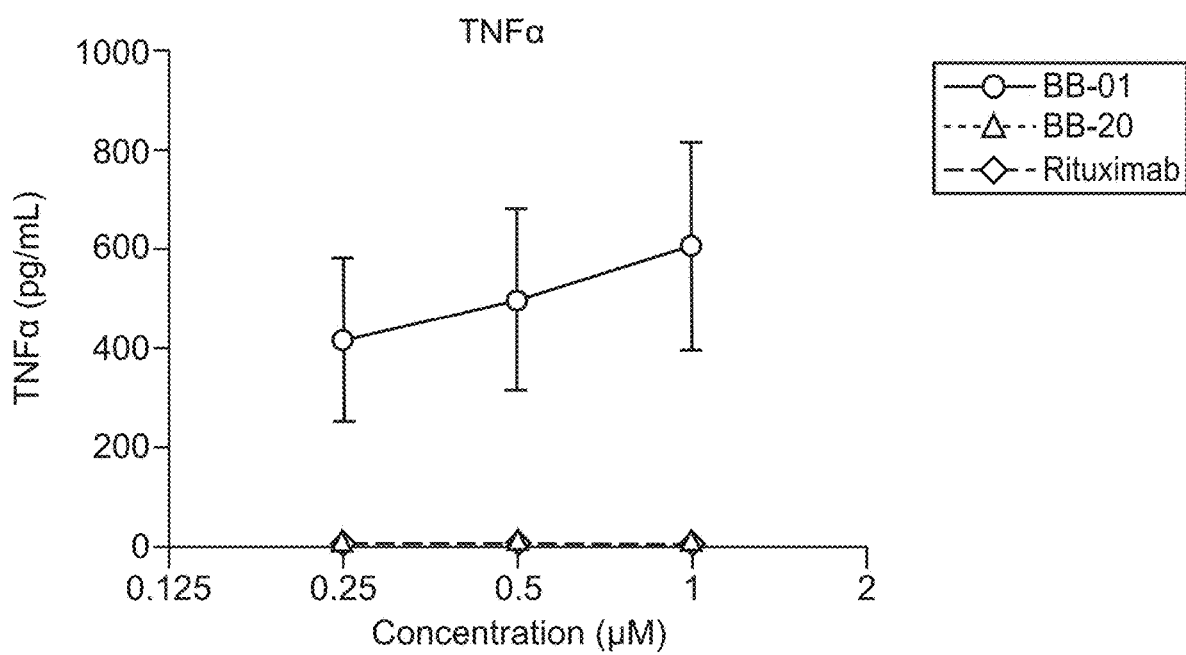

FIG. 129B shows that the BB-01 immunoconjugate produced according to the BB-01 method elicits superior TNFα secretion from myeloid cells as compared to equimolar concentrations of BB-20 produced according to methods disclosed in U.S. Pat. No. 8,951,528 and unconjugated Rituximab biosimilar (LGM Pharma) following 18 hours of stimulation.

Figure 129C:
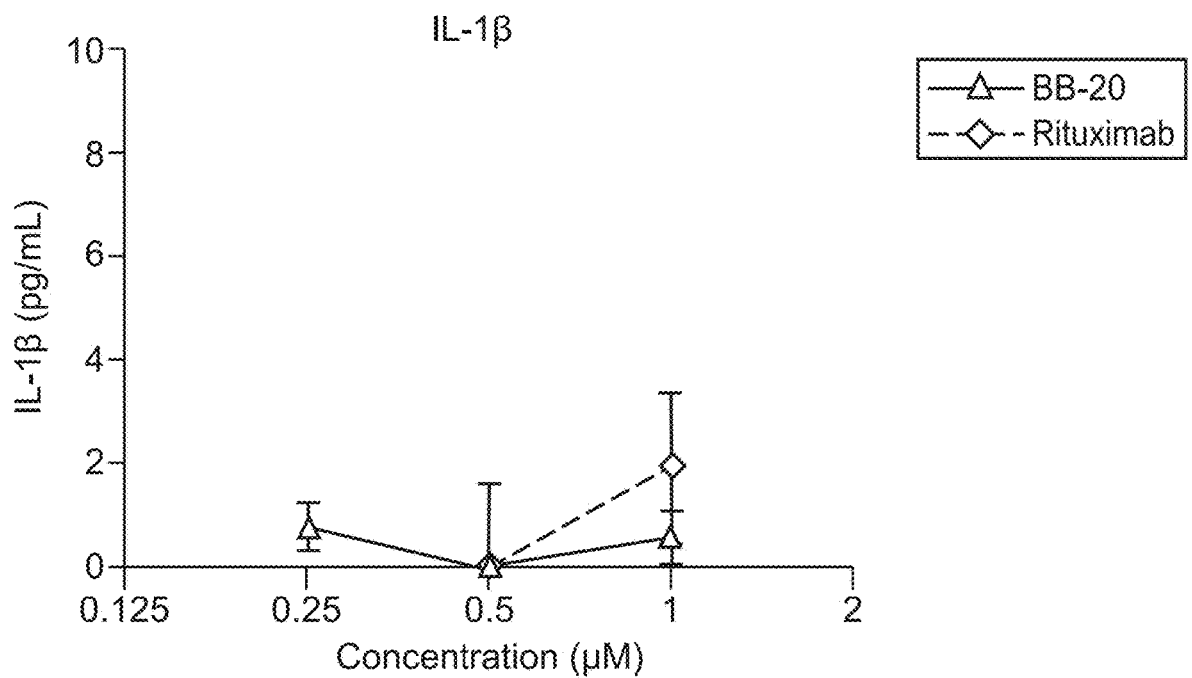

FIG. 129C shows IL-1β secretion from myeloid cells following an 18 hour incubation with equimolar concentrations of unconjugated Rituximab biosimilar (LGM Pharma) or BB-20 produced according to methods disclosed in U.S. Pat. No. 8,951,528.

Figure 129D:
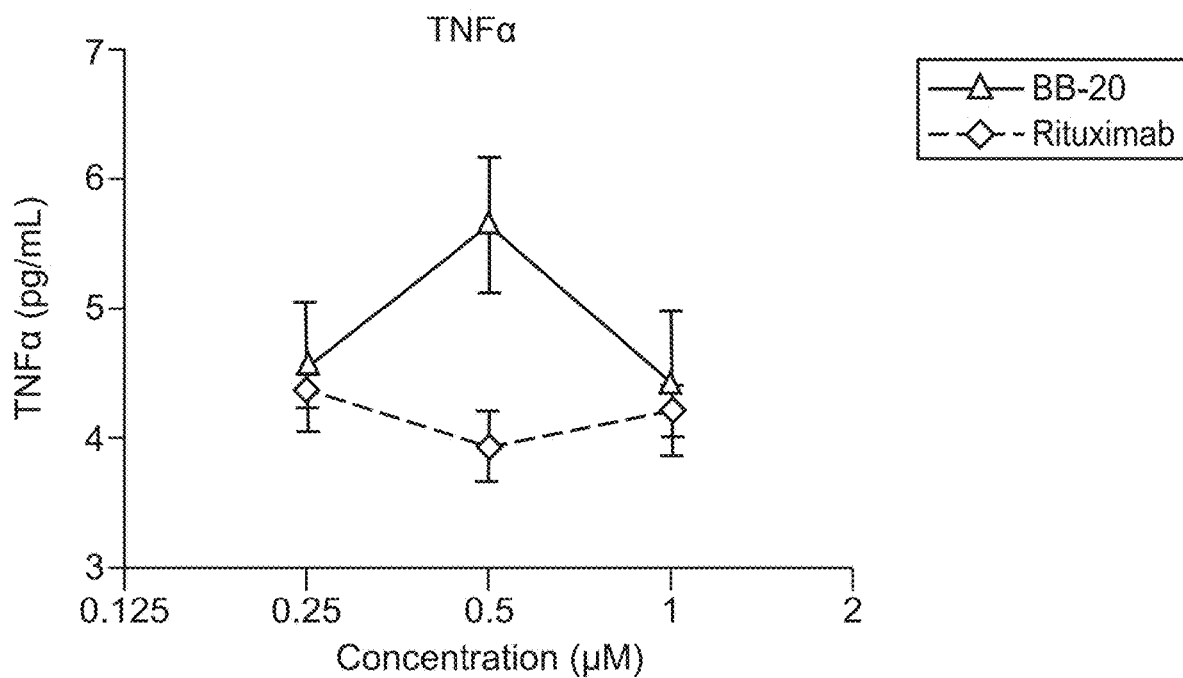

FIG. 129D shows TNFα secretion from myeloid cells following an 18 hour incubation with equimolar concentrations of unconjugated Rituximab biosimilar (LGM Pharma) or BB-20 produced according to methods disclosed in U.S. Pat. No. 8,951,528.

Figure 129E:
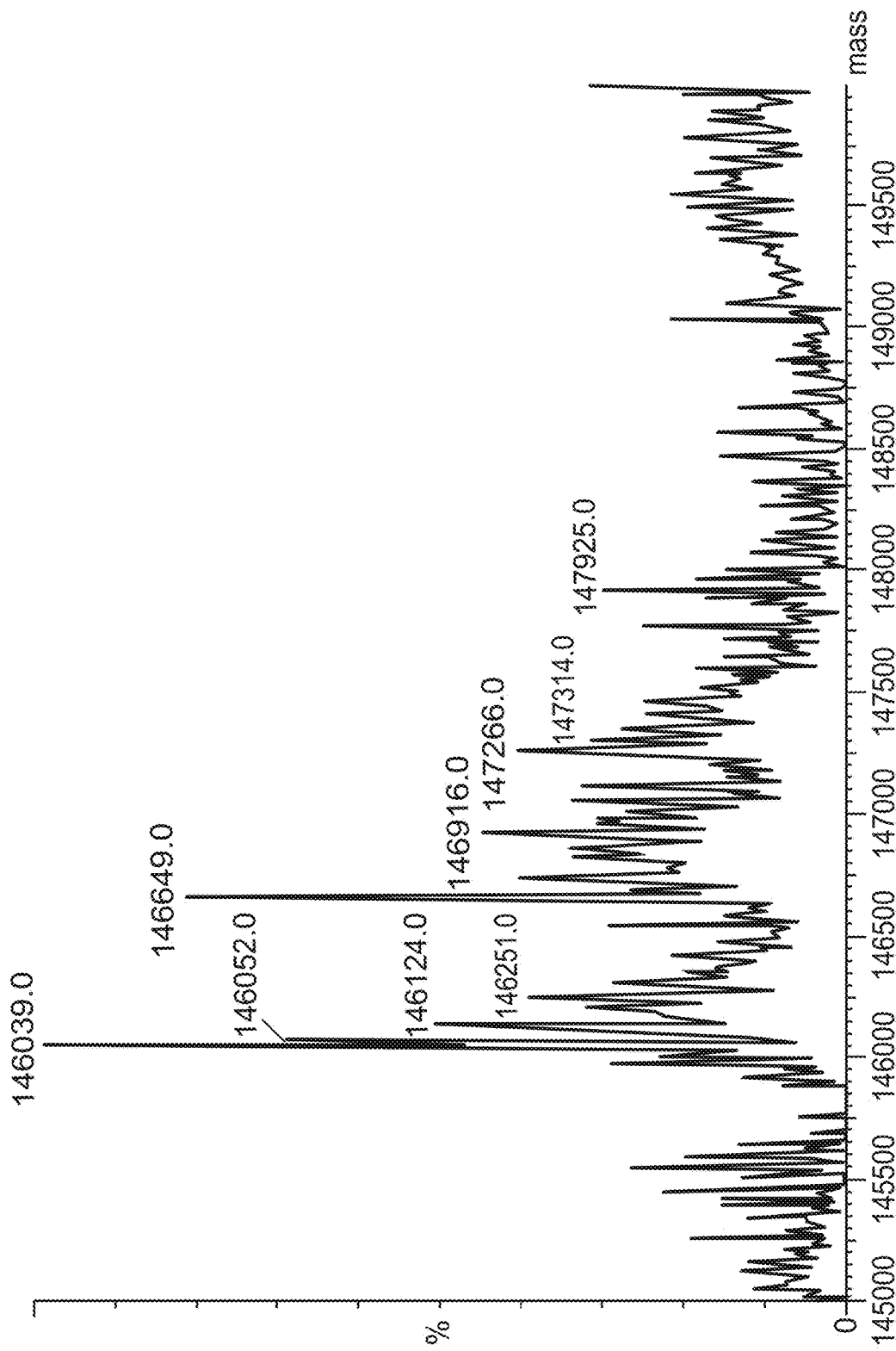

FIG. 129E shows a liquid chromatography-mass spectrometry analysis of the BB-20 produced according to methods disclosed in U.S. Pat. No. 8,951,528 following overnight deglycosylation with PNGase.

Figure 129F:
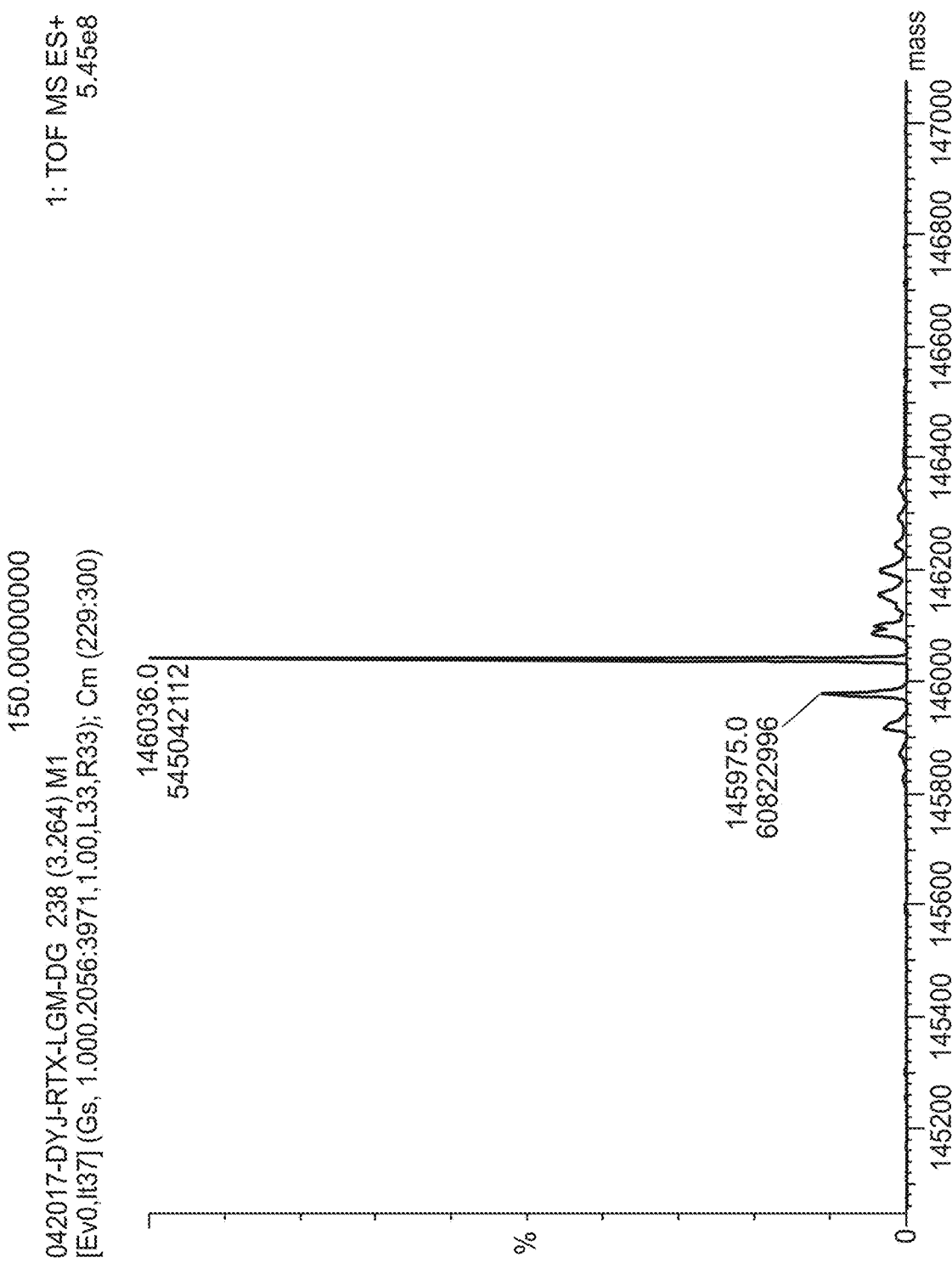

FIG. 129F shows a liquid chromatography-mass spectrometry analysis of an unconjugated Rituximab biosimilar (LGM Pharma) that was utilized to produce BB-20 following overnight deglycosylation with PNGase.

Figure 129G:
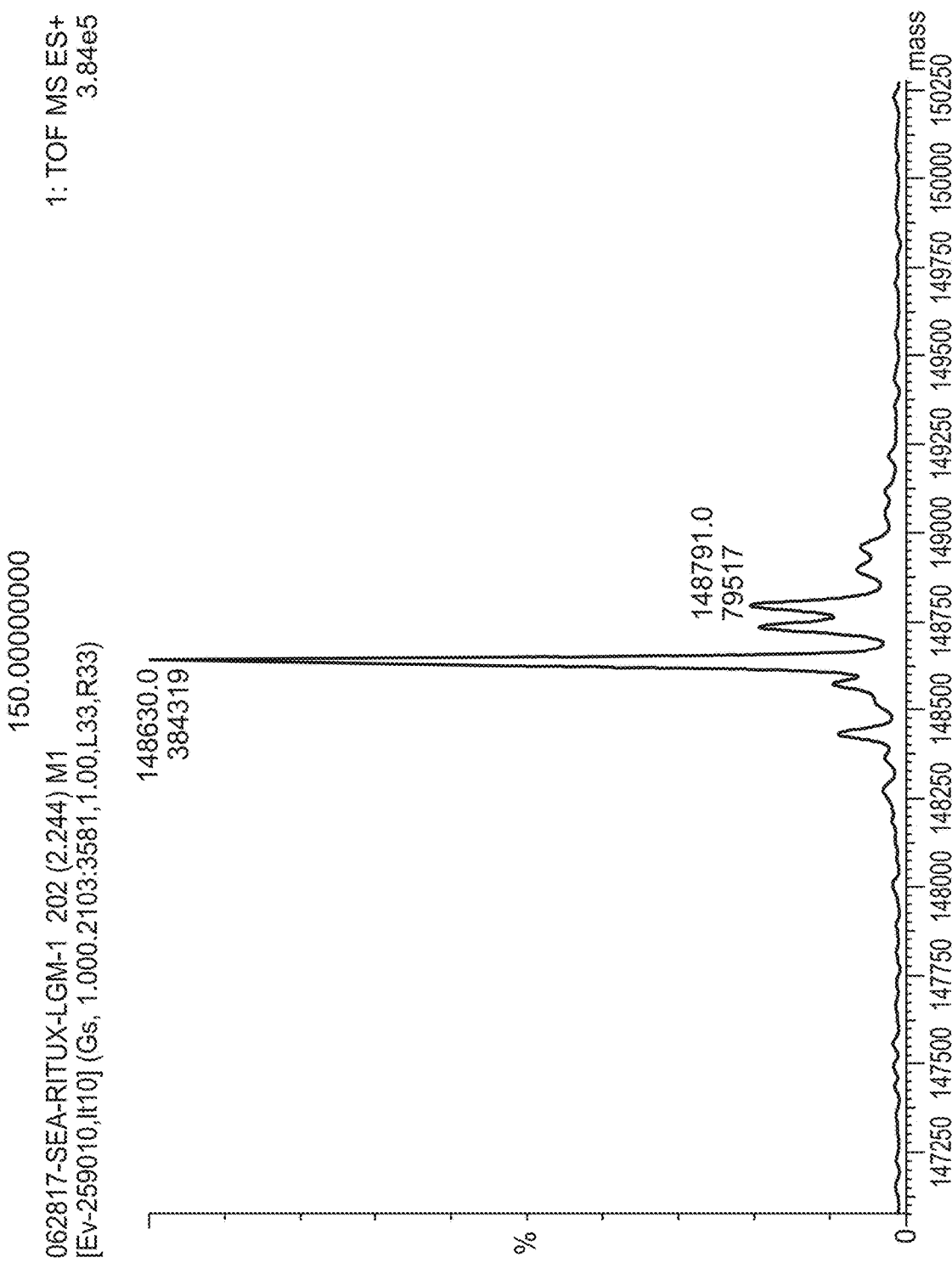

FIG. 129G shows a liquid chromatography-mass spectrometry analysis of an unconjugated Rituximab biosimilar (LGM Pharma) that was utilized to produce BB-20

Figure 129H:
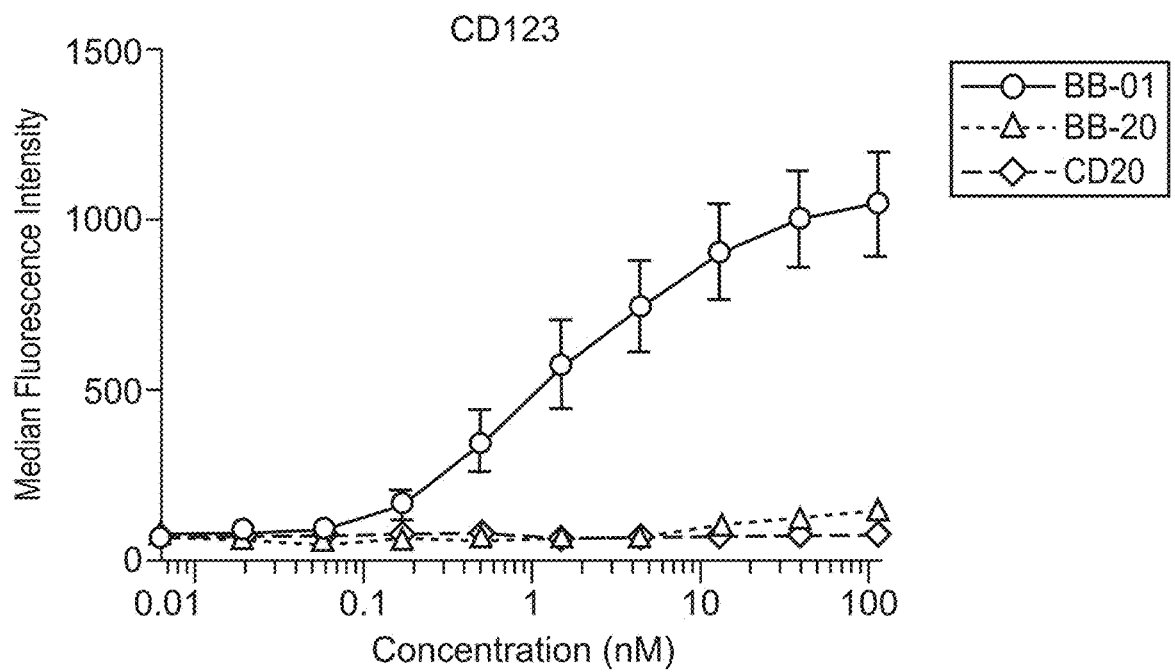

FIG. 129H shows that BB-01 produced according to the BB-01 method is superior at eliciting CD123 upregulation on myeloid cells as compared to the BB-20 immunoconjugate produced according to methods disclosed in U.S. Pat. No. 8,951,528 and the unconjugated Rituximab biosimilar (CD20; LGM Pharma) following 18 hours of stimulation.

Figure 129I:
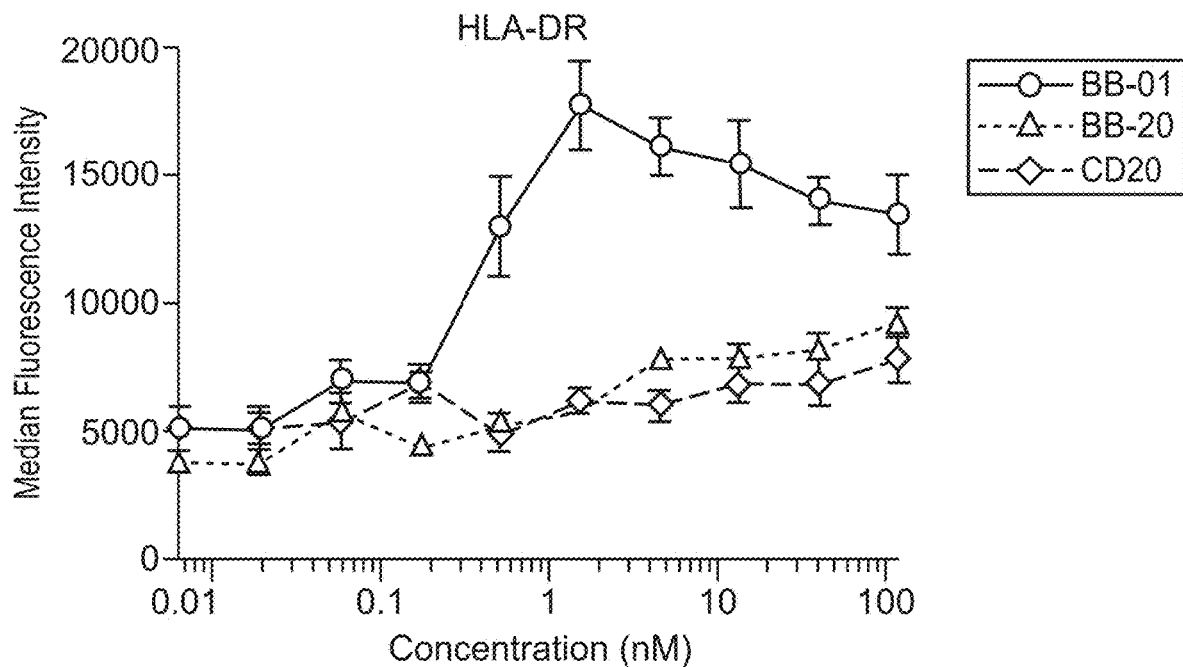

FIG. 129I shows that BB-01 produced according to the BB-01 method is superior at eliciting HLA-DR upregulation on myeloid cells as compared to the BB-20 immunoconjugate produced according to methods disclosed in U.S. Pat. No. 8,951,528 and the unconjugated Rituximab biosimilar (CD20; LGM Pharma) following 18 hours of stimulation.

Figure 129J:
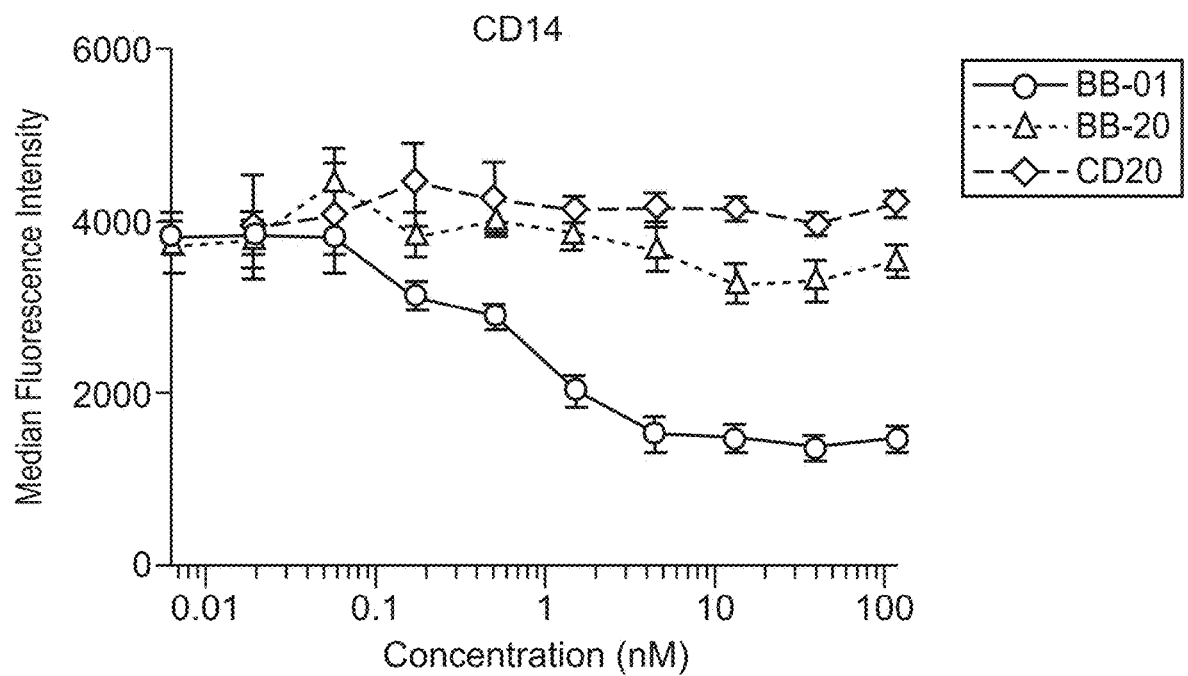

FIG. 129J shows that BB-01 produced according to the BB-01 method is superior at eliciting CD14 downregulation on myeloid cells as compared to the BB-20 immunoconjugate produced according to methods disclosed in U.S. Pat. No. 8,951,528 and the unconjugated Rituximab biosimilar (CD20; LGM Pharma) following 18 hours of stimulation.

Figure 129K:
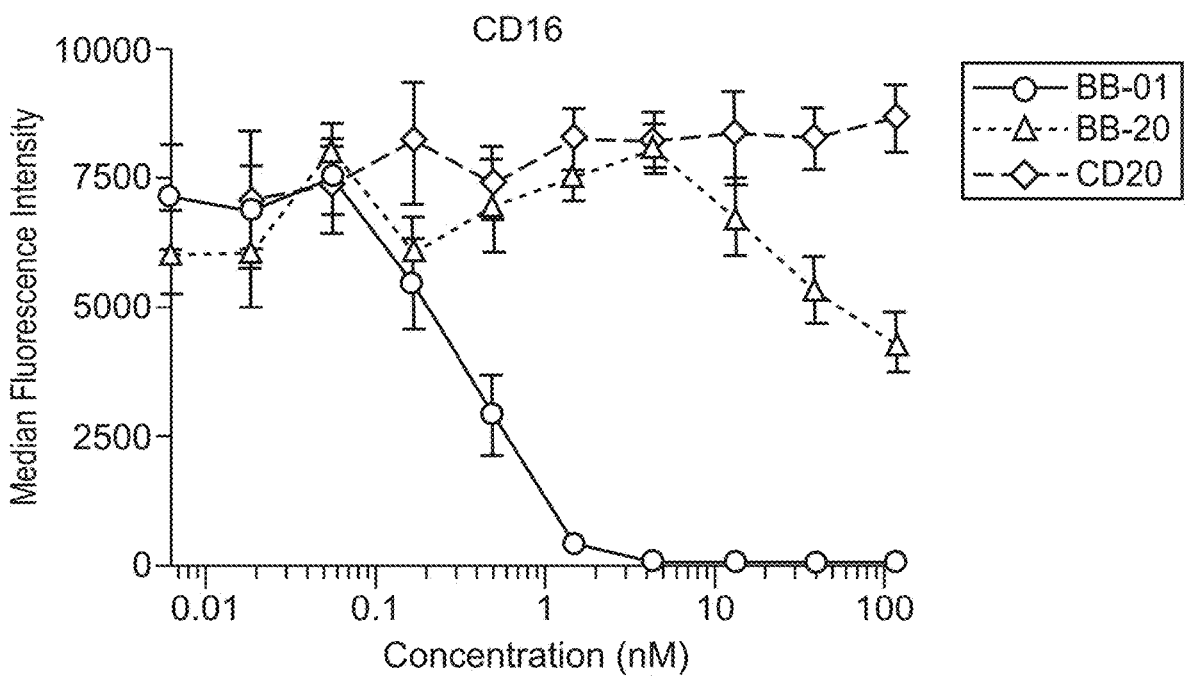

FIG. 129K shows that BB-01 produced according to the BB-01 method is superior at eliciting CD16 downregulation on myeloid cells as compared to the BB-20 immunoconjugate produced according to methods disclosed in U.S. Pat. No. 8,951,528 and the unconjugated Rituximab biosimilar (CD20; LGM Pharma) following 18 hours of stimulation.

Figure 129L:
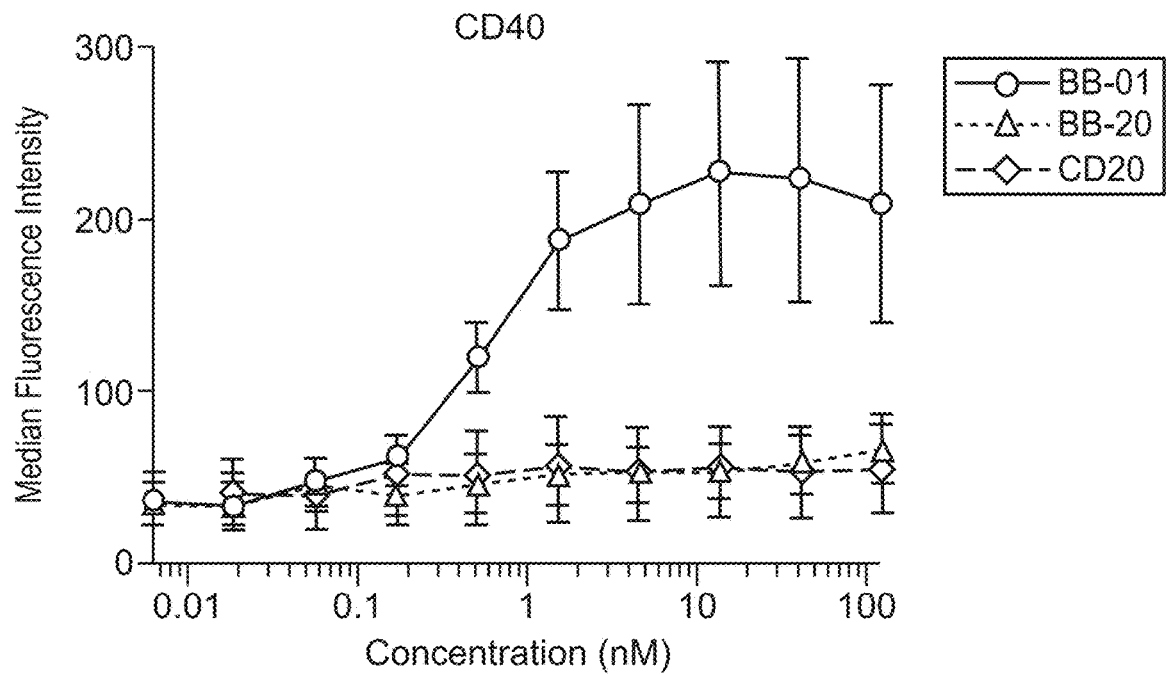

FIG. 129L shows that the BB-20 immunoconjugate produced according to methods disclosed in U.S. Pat. No. 8,951,528 fails to elicit CD40 upregulation following 18 hours of stimulation. FIG. 129L also shows that the BB-01 immunoconjugate produced according to the BB-01 method is superior at eliciting CD40 upregulation as compared to BB-20 and the unconjugated Rituximab biosimilar (CD20; LGM Pharma).

Figure 129M:
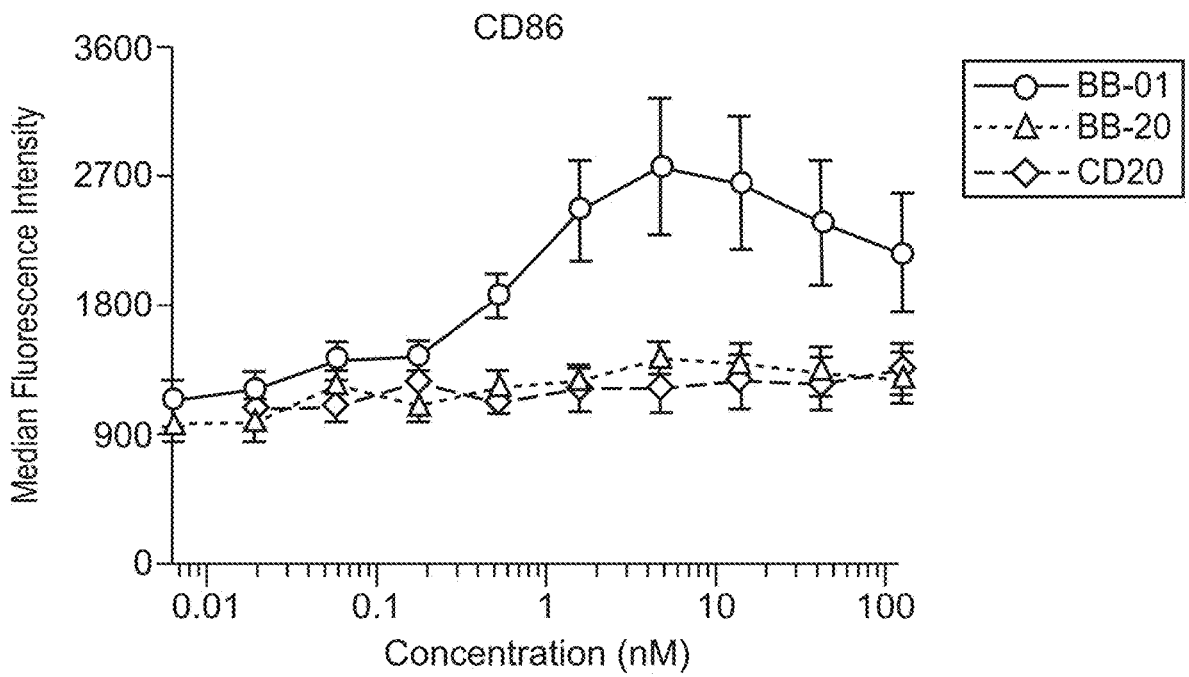

FIG. 129M shows that the BB-20 immunoconjugate produced according to methods disclosed in U.S. Pat. No. 8,951,528 fails to elicit CD86 upregulation following 18 hours of stimulation. FIG. 129M also shows that the BB-01 immunoconjugate produced according to the BB-01 method is superior at eliciting CD86 upregulation as compared to BB-20 and the unconjugated Rituximab biosimilar (CD20; LGM Pharma).

Figure 129N:
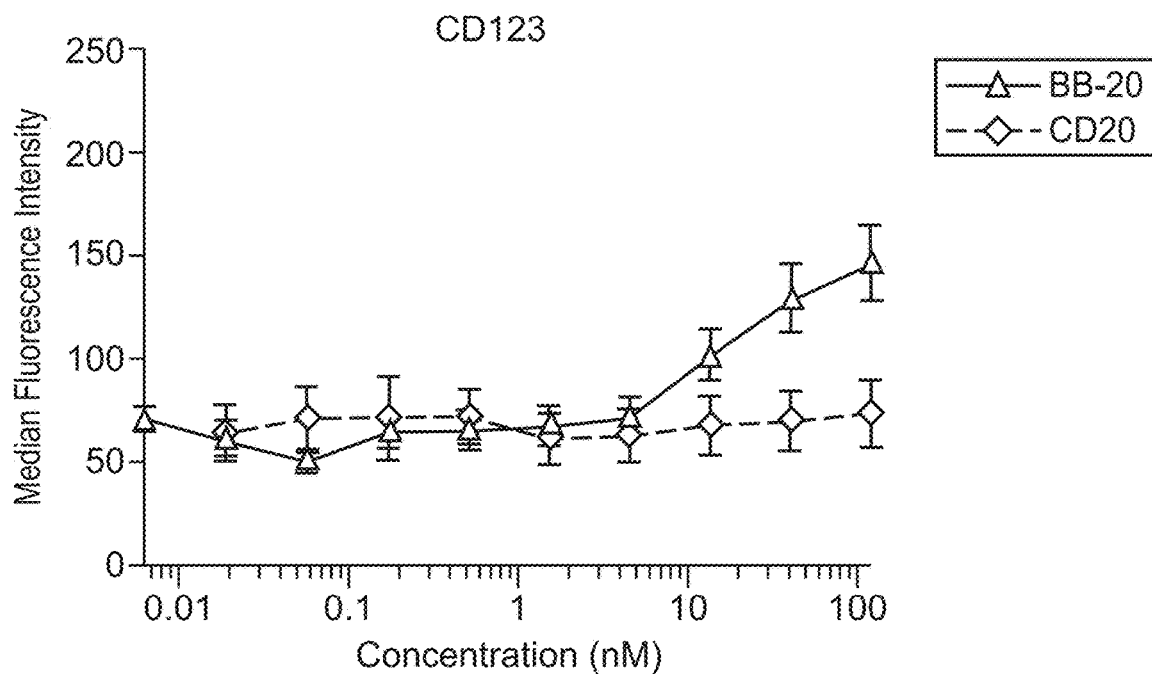

FIG. 129N shows CD123 expression on myeloid cells following 18 hours of stimulation with the BB-20 immunoconjugate produced according to methods disclosed in U.S. Pat. No. 8,951,528 or the unconjugated Rituximab biosimilar (CD20; LGM Pharma).

Figure 129O:
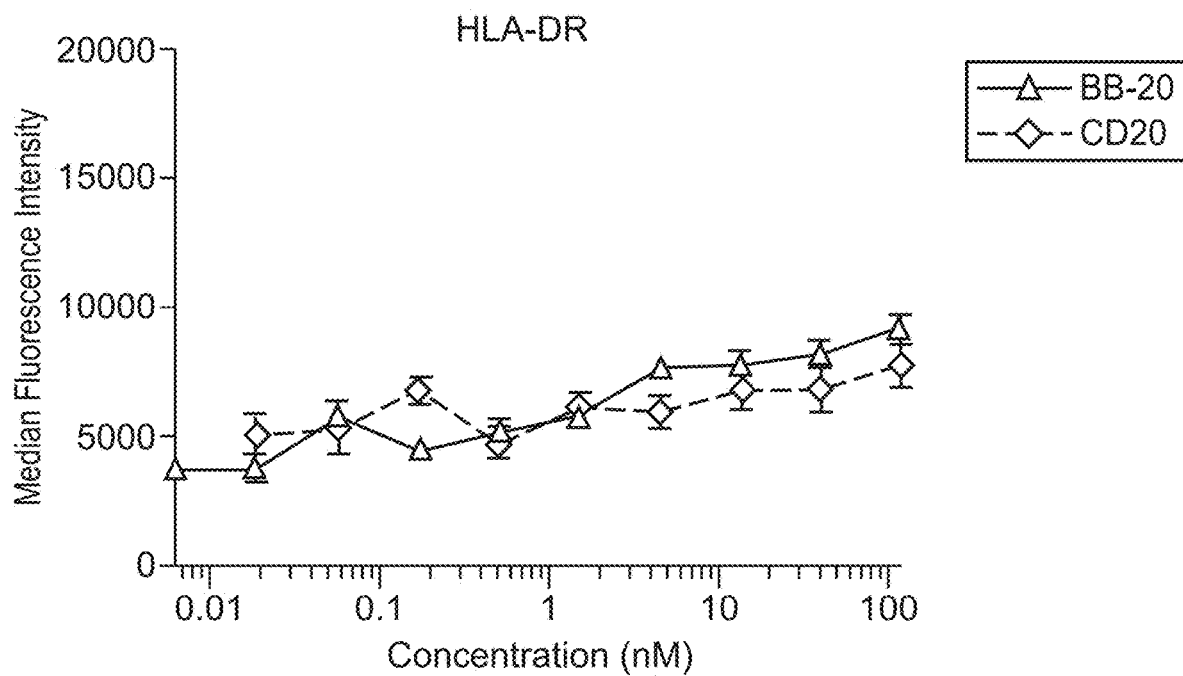

FIG. 129O shows HLA-DR expression on myeloid cells following 18 hours of stimulation with the BB-20 immunoconjugate produced according to methods disclosed in U.S. Pat. No. 8,951,528 or the unconjugated Rituximab biosimilar (CD20; LGM Pharma).

Figure 129P:
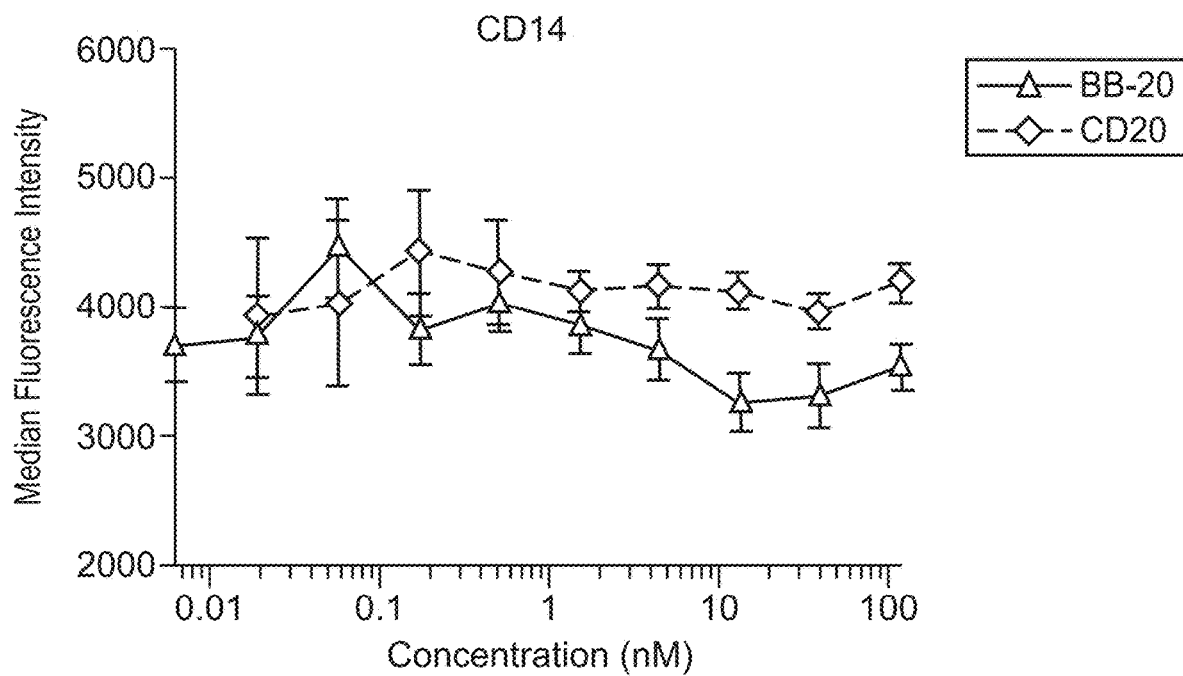

FIG. 129P shows CD14 expression on myeloid cells following 18 hours of stimulation with the BB-20 immunoconjugate produced according to methods disclosed in U.S. Pat. No. 8,951,528 or the unconjugated Rituximab biosimilar (CD20; LGM Pharma).

Figure 129Q:
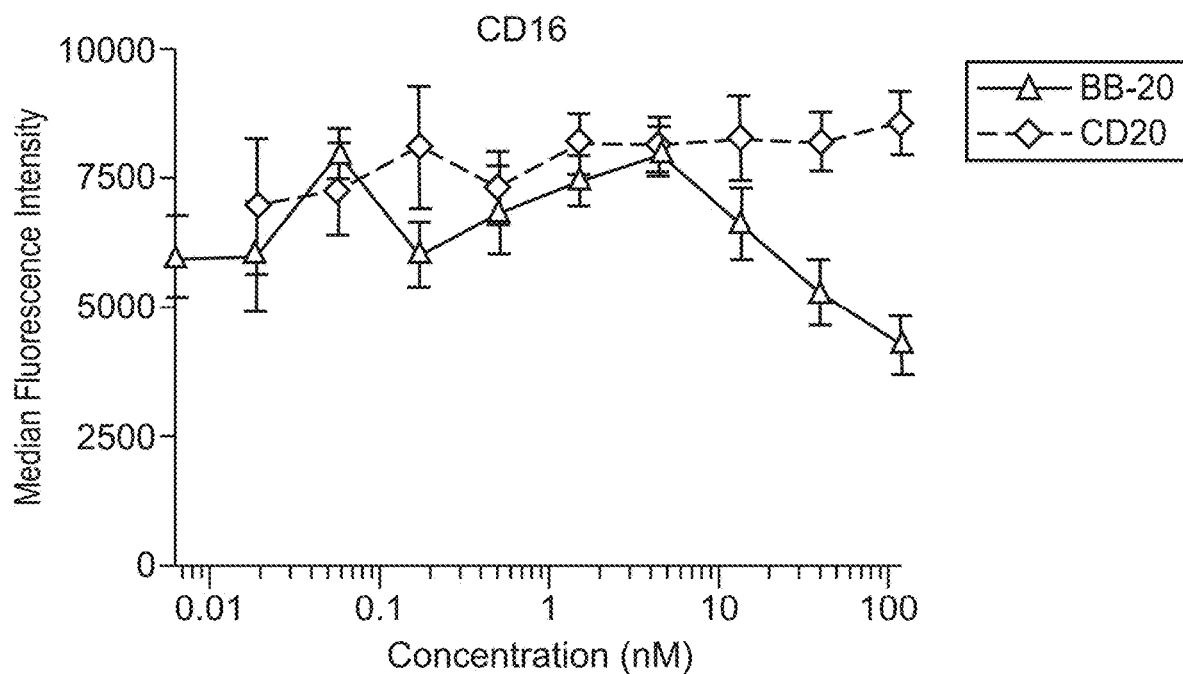

FIG. 129Q shows CD16 expression on myeloid cells following 18 hours of stimulation with the BB-20 immunoconjugate produced according to methods disclosed in U.S. Pat. No. 8,951,528 or the unconjugated Rituximab biosimilar (CD20; LGM Pharma).

Figure 129R:
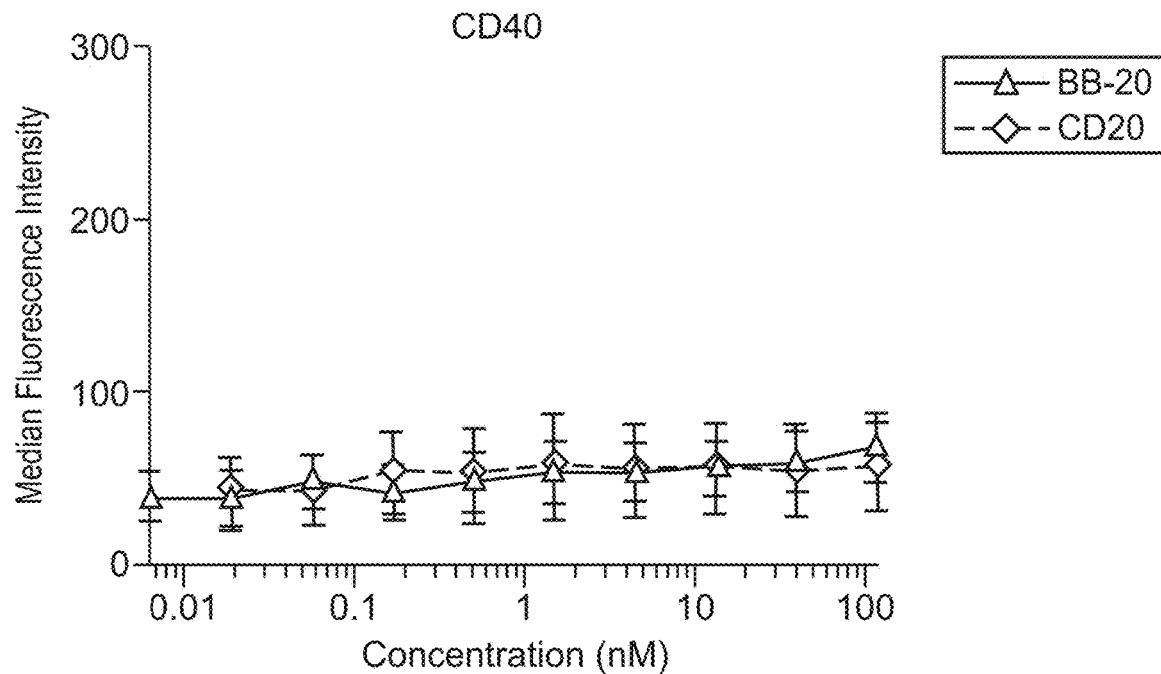

FIG. 129R shows CD40 expression on myeloid cells following 18 hours of stimulation with the BB-20 immunoconjugate produced according to methods disclosed in U.S. Pat. No. 8,951,528 or the unconjugated Rituximab biosimilar (CD20; LGM Pharma).

Figure 129S:
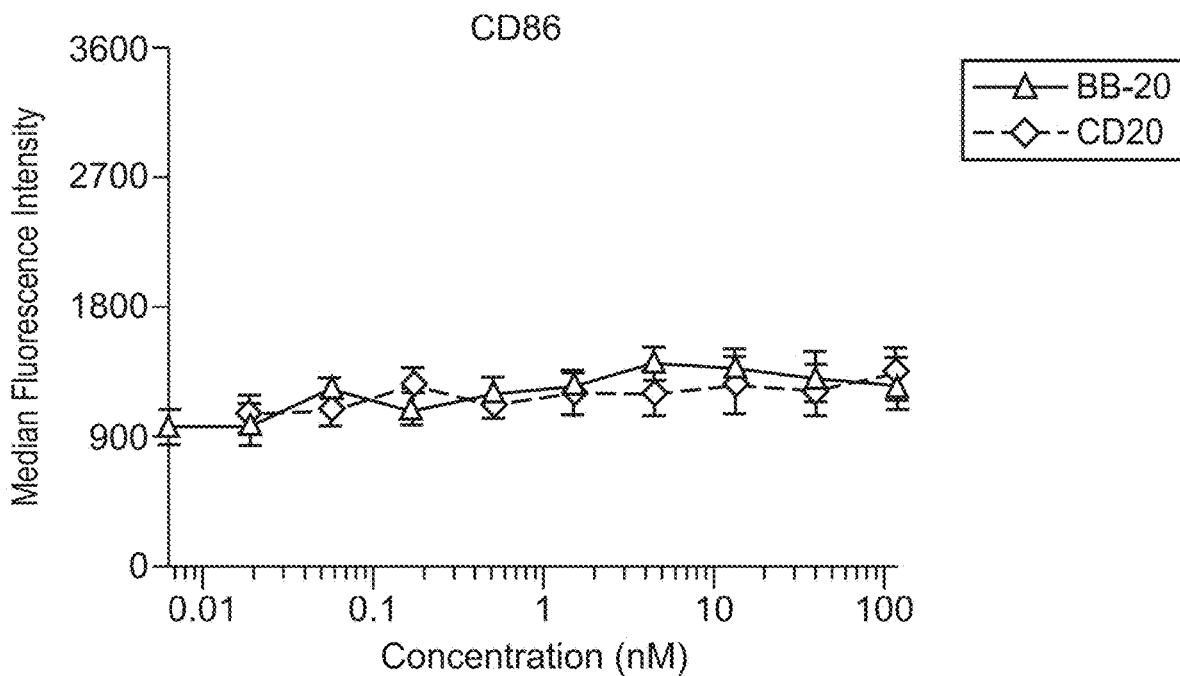

FIG. 129S shows CD86 expression on myeloid cells following 18 hours of stimulation with the BB-20 immunoconjugate produced according to methods disclosed in U.S. Pat. No. 8,951,528 or the unconjugated Rituximab biosimilar (CD20; LGM Pharma).

Figure 130A:
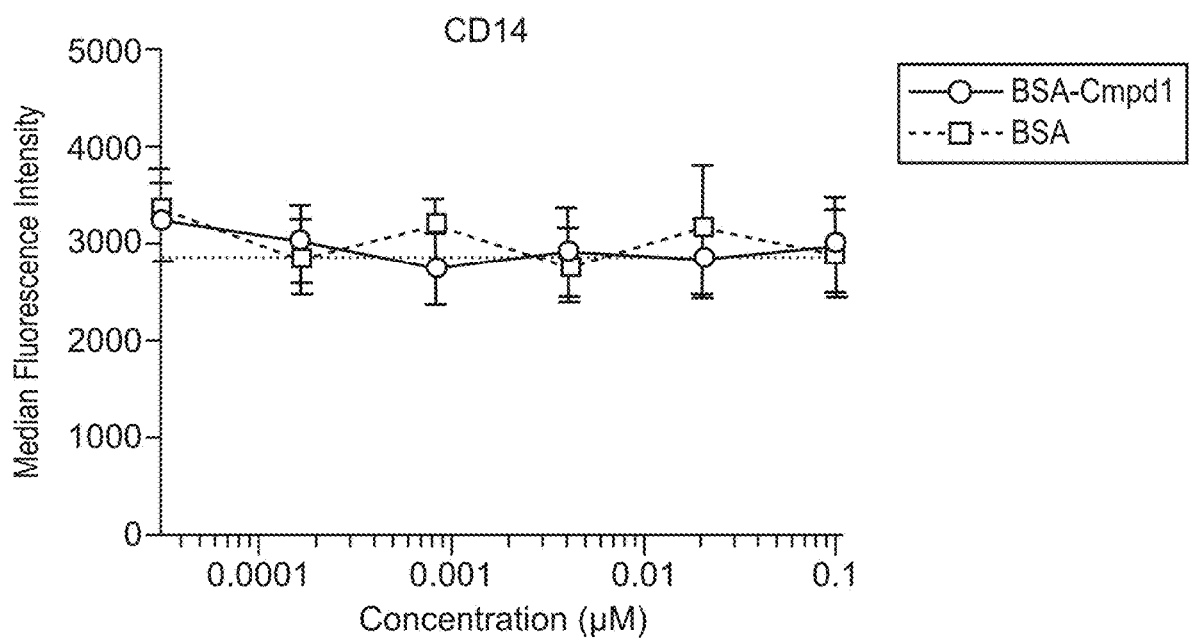

FIG. 130A shows CD14 expression on myeloid cells following 18 hours of stimulation with equimolar concentrations of bovine serum albumin (BSA) or BSA immunoconjugate (BSA-Compound 1) produced according the BB-37 TFP method.

Figure 130B:
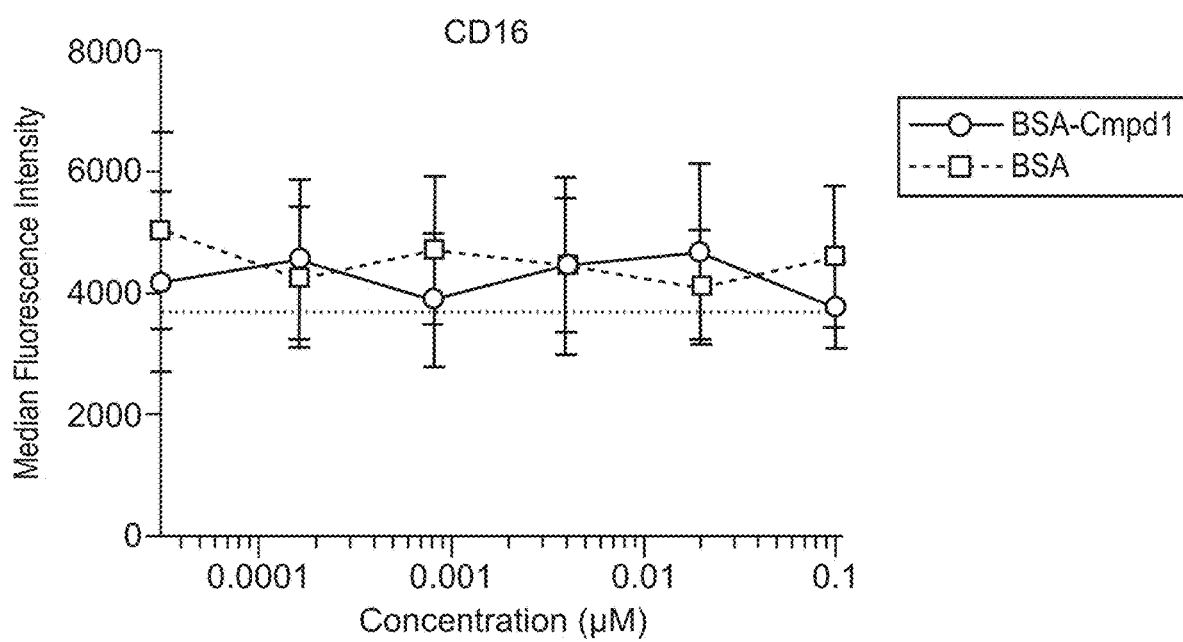

FIG. 130B shows CD16 expression on myeloid cells following 18 hours of stimulation with equimolar concentrations of bovine serum albumin (BSA) or BSA immunoconjugate (BSA-Compound 1) produced according the BB-37 TFP method.

Figure 130C:
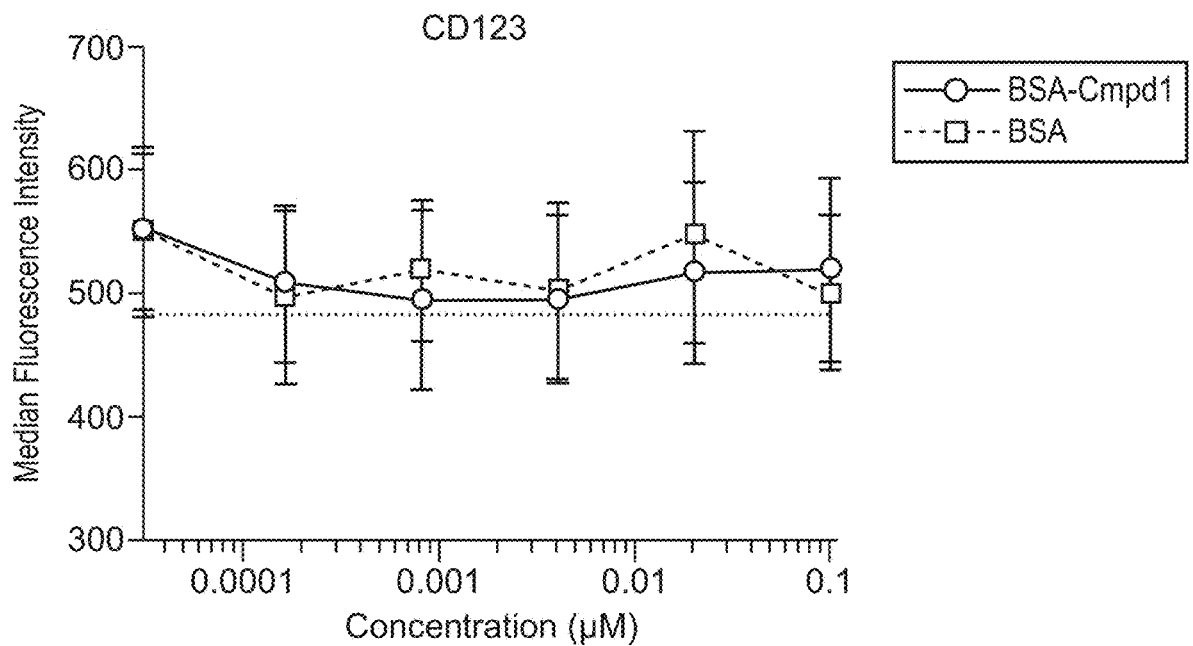

FIG. 130C shows CD123 expression on myeloid cells following 18 hours of stimulation with equimolar concentrations of bovine serum albumin (BSA) or BSA immunoconjugate (BSA-Compound 1) produced according the BB-37 TFP method.

Figure 130D:
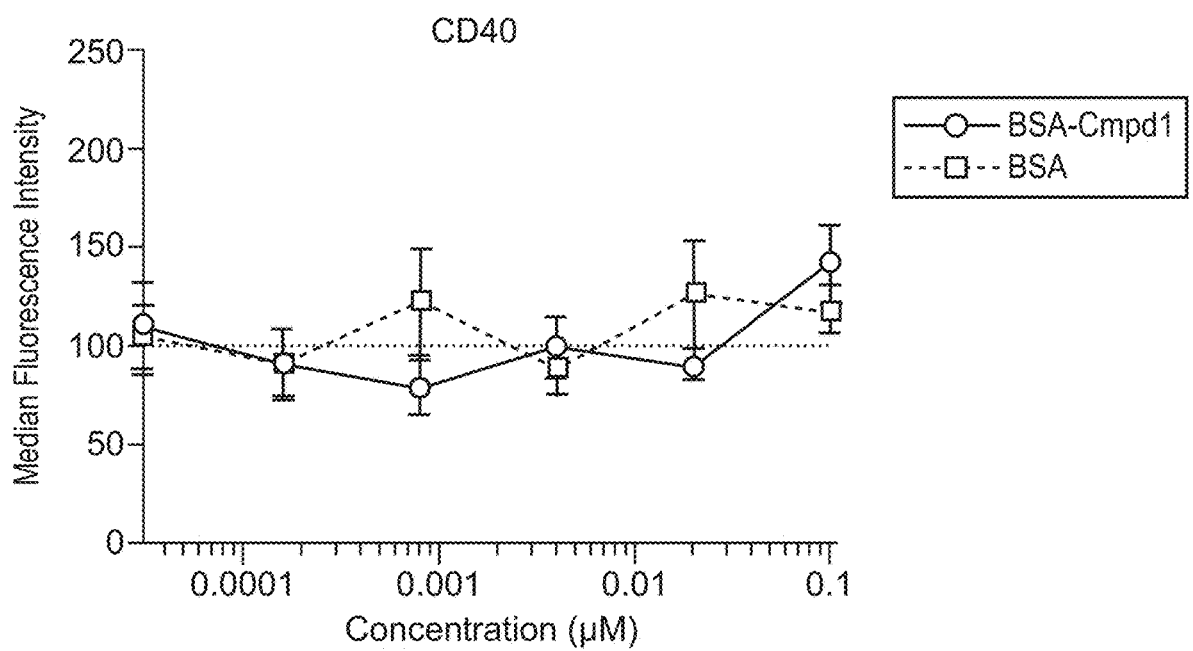

FIG. 130D shows CD40 expression on myeloid cells following 18 hours of stimulation with equimolar concentrations of bovine serum albumin (BSA) or BSA immunoconjugate (BSA-Compound 1) produced according the BB-37 TFP method.

Figure 130E:
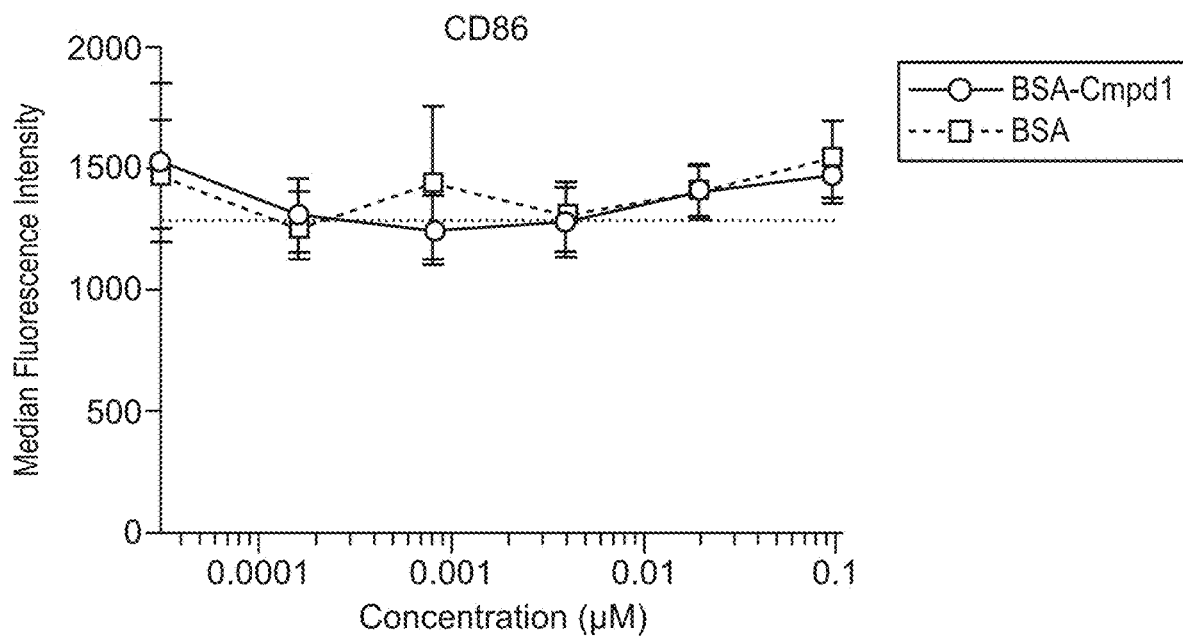

FIG. 130E shows CD86 expression on myeloid cells following 18 hours of stimulation with equimolar concentrations of bovine serum albumin (BSA) or BSA immunoconjugate (BSA-Compound 1) produced according the BB-37 TFP method.

Figure 130F:
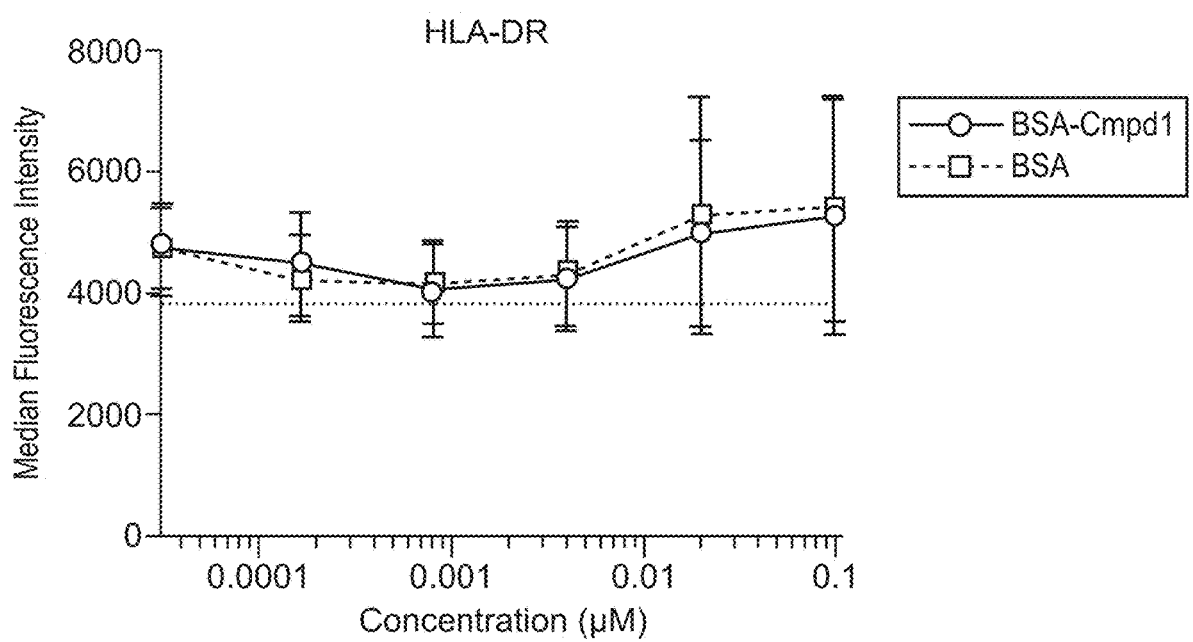

FIG. 130F shows HLR-DR expression on myeloid cells following 18 hours of stimulation with equimolar concentrations of bovine serum albumin (BSA) or BSA immunoconjugate (BSA-Compound 1) produced according the BB-37 TFP method.

Figure 130G:
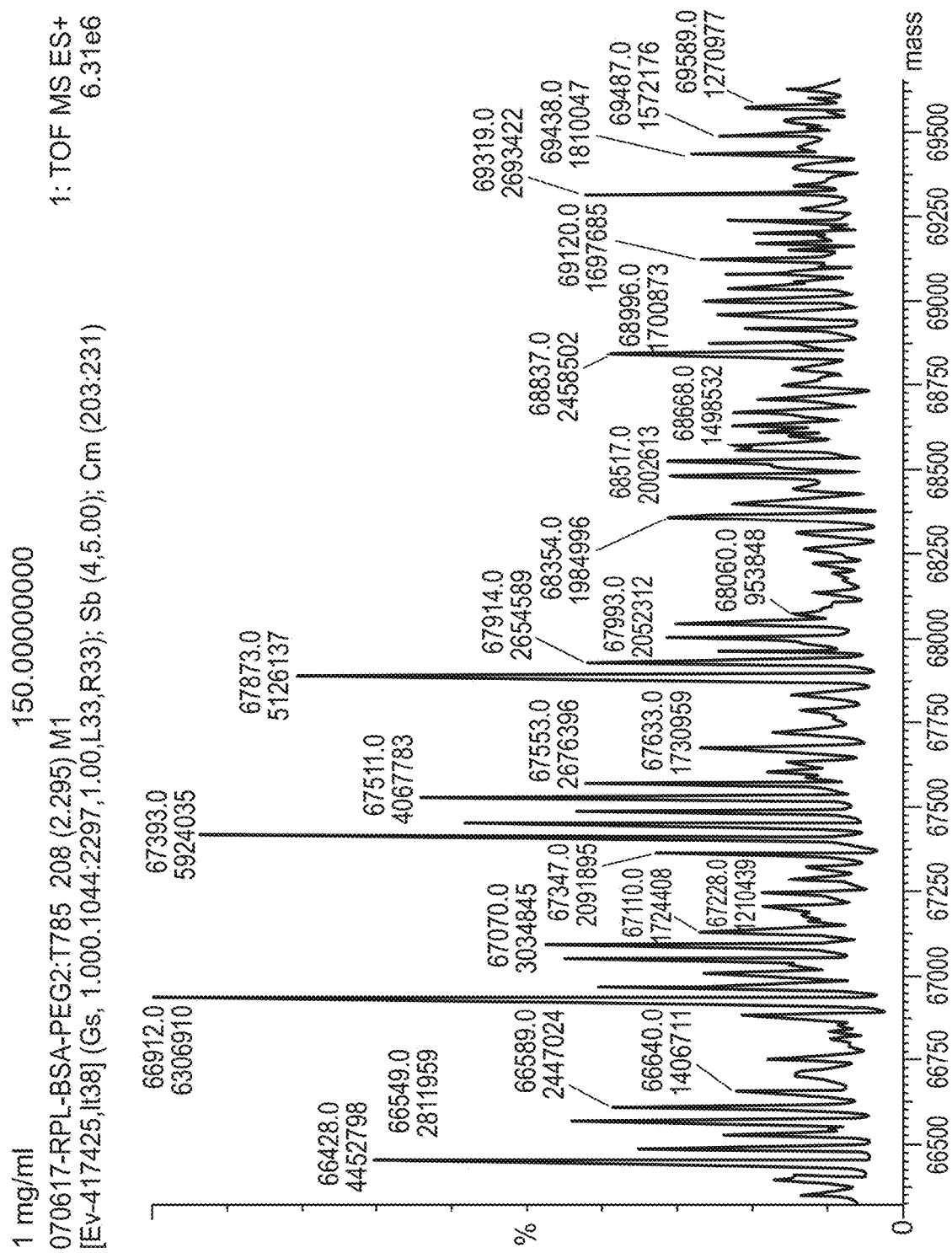

FIG. 130G shows HLA-DR expression on myeloid cells following 18 hours of stimulation with equimolar concentrations of bovine serum albumin (BSA) or BSA immunoconjugate (BSA-Compound 1) produced according the BB-37 TFP method.

Figure 130H:
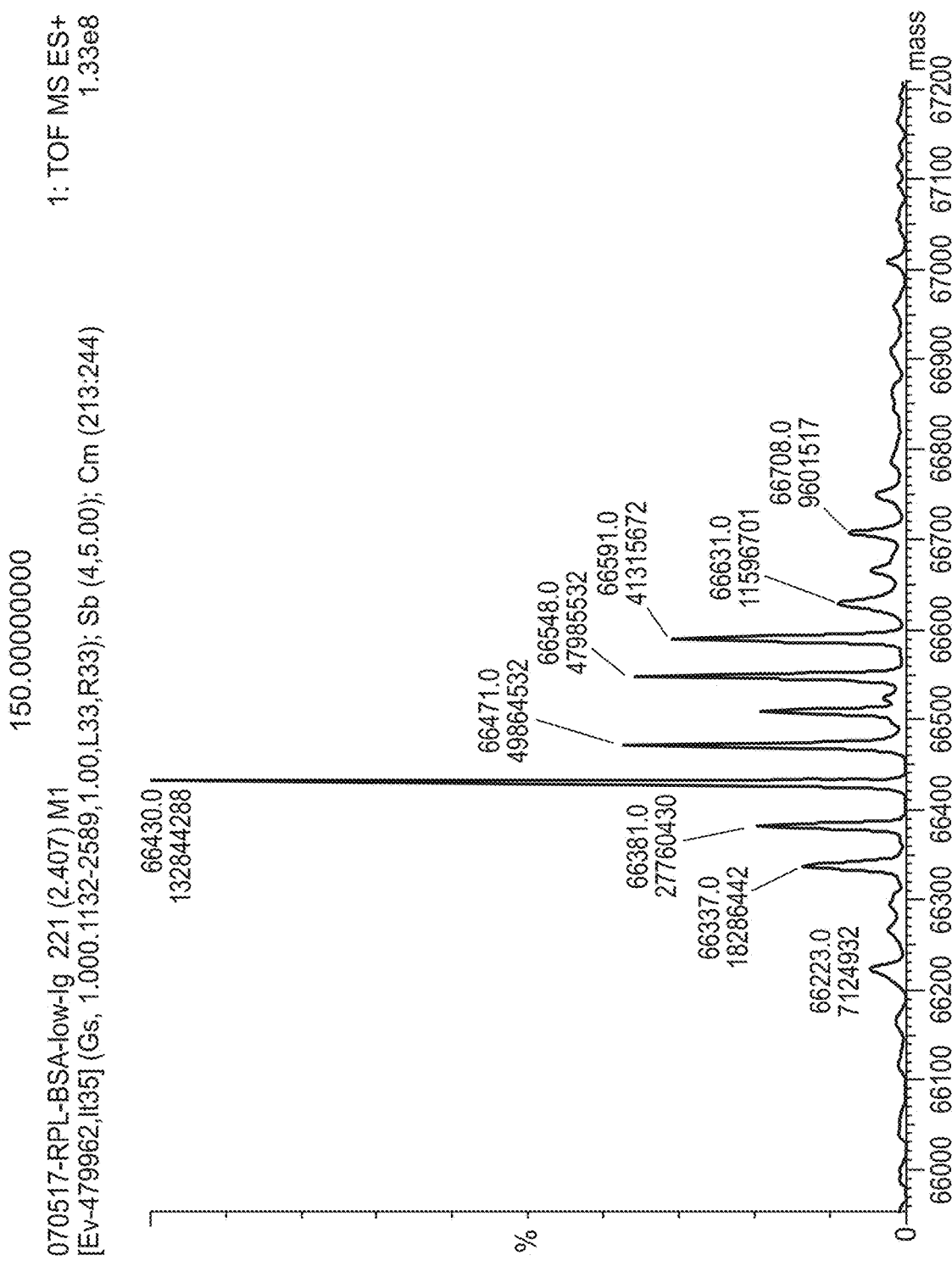

FIG. 130H shows LC-MS of naked BSA-M.

Figure 131A:
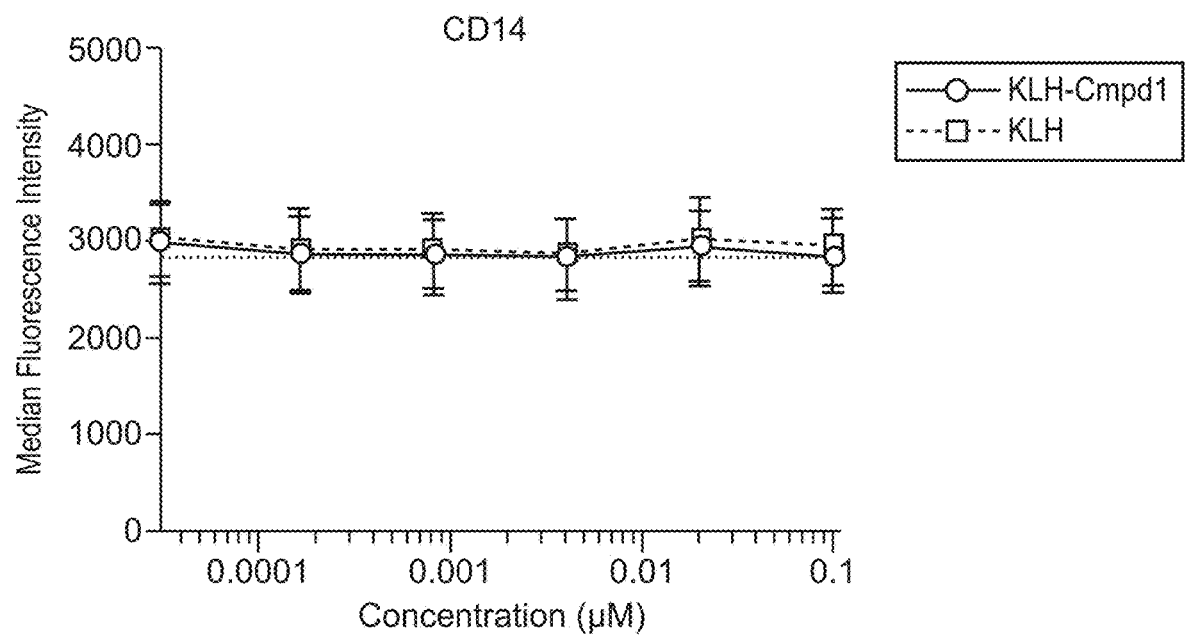

FIG. 131A shows CD14 expression on myeloid cells following 18 hours of stimulation with equimolar concentrations of keyhole limpet hemocyanin (KLH) or KLH immunoconjugate (KLH-Compound 1) produced according the BB-17 TFP method.

Figure 131B:
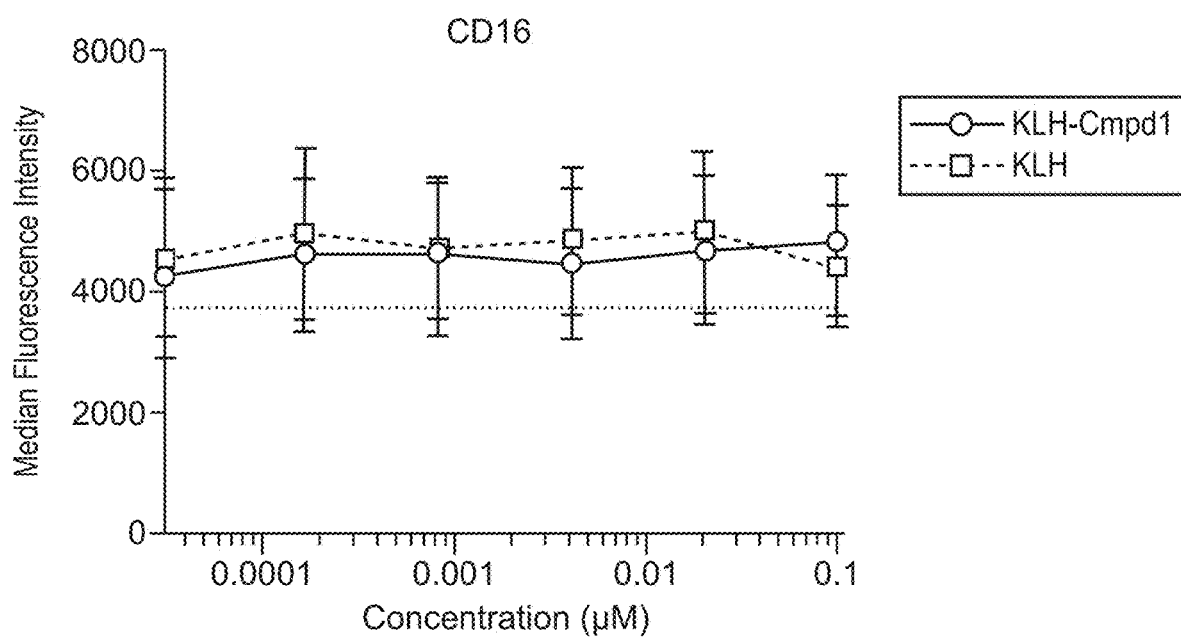

FIG. 131B shows CD16 expression on myeloid cells following 18 hours of stimulation with equimolar concentrations of keyhole limpet hemocyanin (KLH) or KLH immunoconjugate (KLH-Compound 1) produced according the BB-17 TFP method.

Figure 131C:
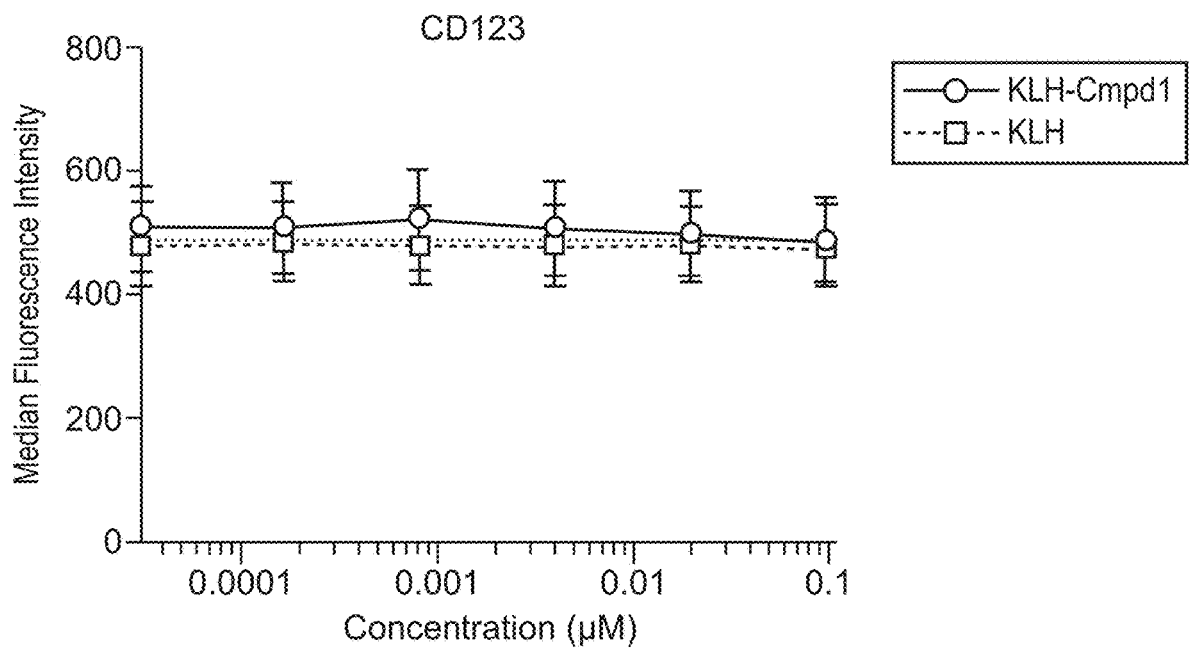

FIG. 131C shows CD123 expression on myeloid cells following 18 hours of stimulation with equimolar concentrations of keyhole limpet hemocyanin (KLH) or KLH immunoconjugate (KLH-Compound 1) produced according the BB-17 TFP method.

Figure 131D:
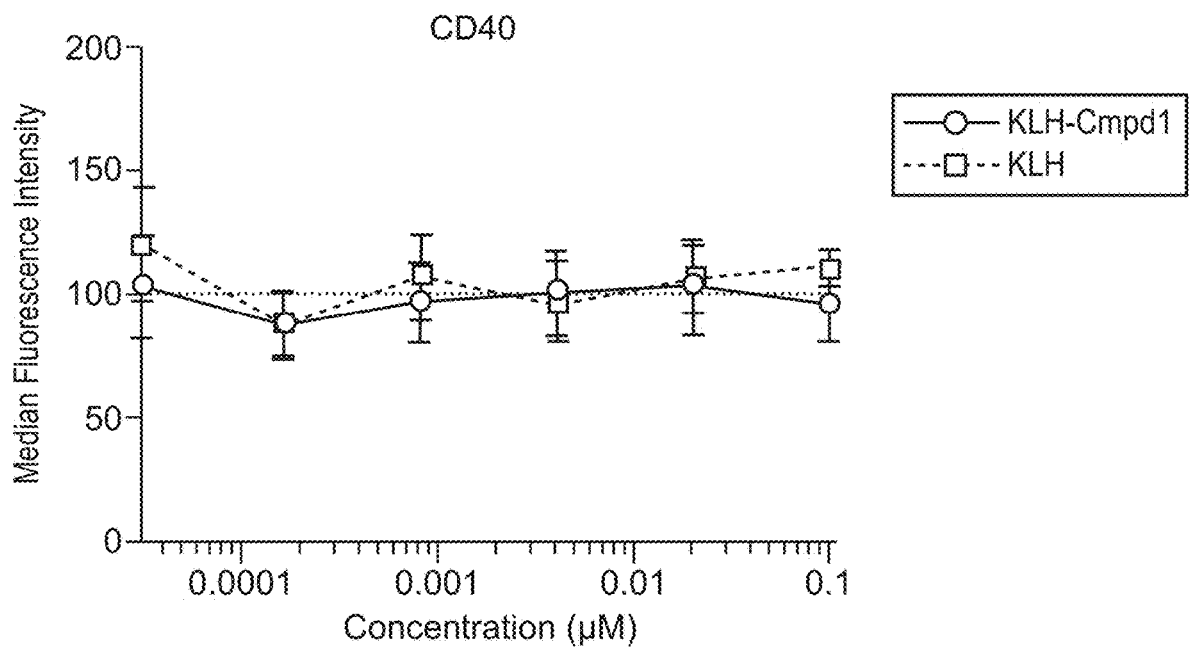

FIG. 131D shows CD40 expression on myeloid cells following 18 hours of stimulation with equimolar concentrations of keyhole limpet hemocyanin (KLH) or KLH immunoconjugate (KLH-Compound 1) produced according the BB-17 TFP method.

Figure 131E:
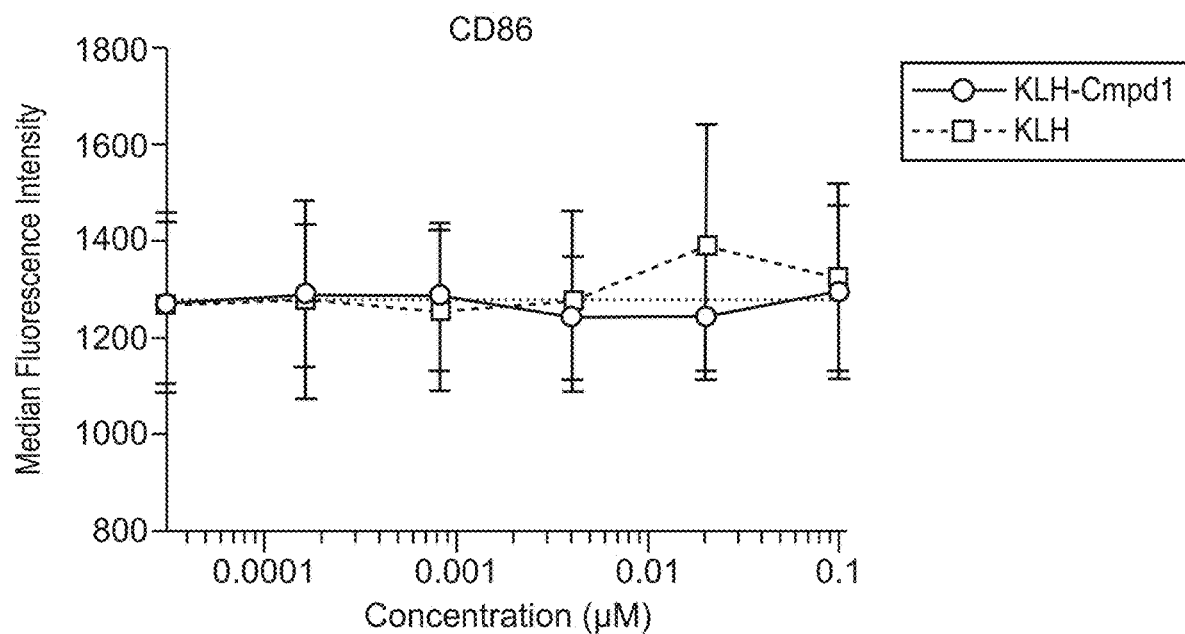

FIG. 131E shows CD86 expression on myeloid cells following 18 hours of stimulation with equimolar concentrations keyhole limpet hemocyanin (KLH) or KLH immunoconjugate (KLH-Compound 1) produced according the BB-17 TFP method.

Figure 131F:
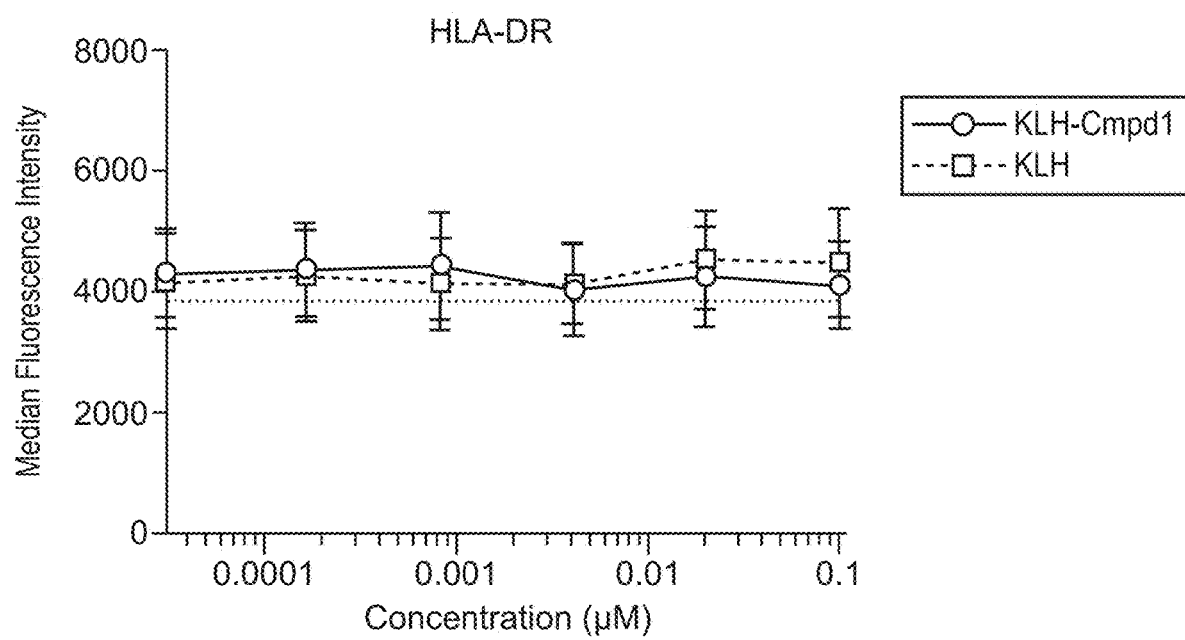

FIG. 131F shows HLA-DR expression on myeloid cells following 18 hours of stimulation with equimolar concentrations keyhole limpet hemocyanin (KLH) or KLH immunoconjugate (KLH-Compound 1) produced according the BB-17 TFP method.

Figure 132A:
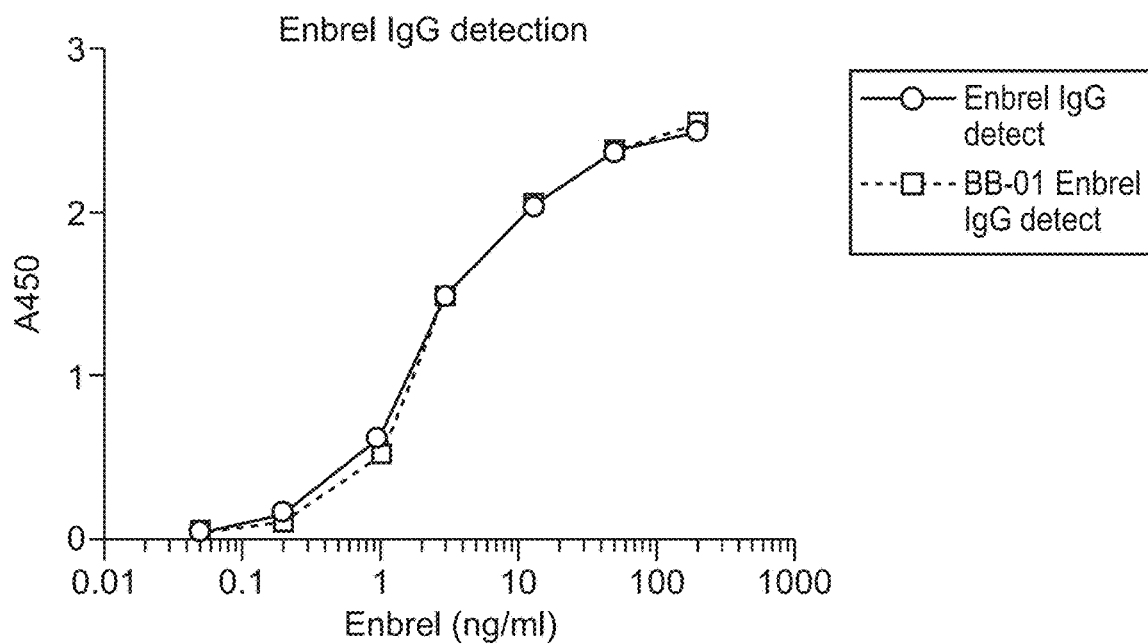

FIG. 132A shows that Enbrel (Amgen) and Enbrel immunoconjugate (BB-01 Enbrel), produced using the BB-01 conjugation method, show comparable reactivity with anti-human IgG detection antibody when captured on anti-human IgG coated ELISA plates.

Figure 132B:
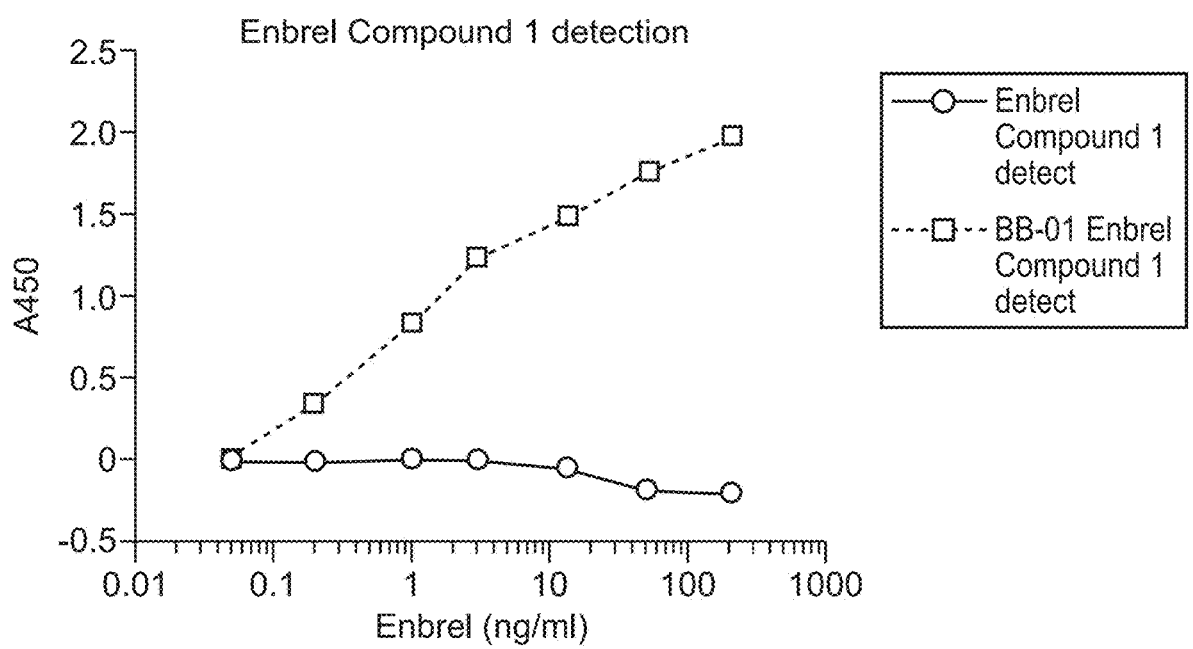

FIG. 132B shows that Enbrel immunoconjugate (BB-01 Enbrel), produced using the BB-01 conjugation method, but not Enbrel (Amgen), shows strong reactivity with the anti-Compound 1 antibody following capture on an anti-human IgG coated ELISA plate.

Figure 132C:
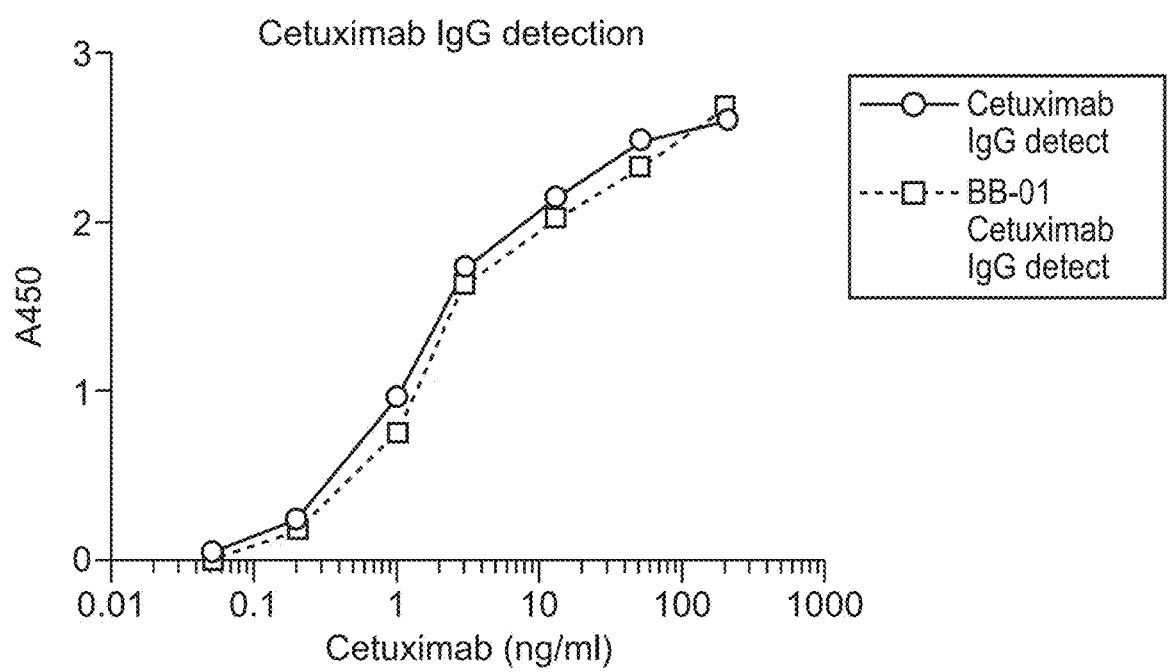

FIG. 132C shows that Cetuximab (Imclone/Lilly) and Cetuximab immunoconjugate (BB-01 Cetuximab), produced using the BB-01 conjugation method, show comparable reactivity with anti-human IgG detection antibody when captured on anti-human IgG coated ELISA plates.

Figure 132D:
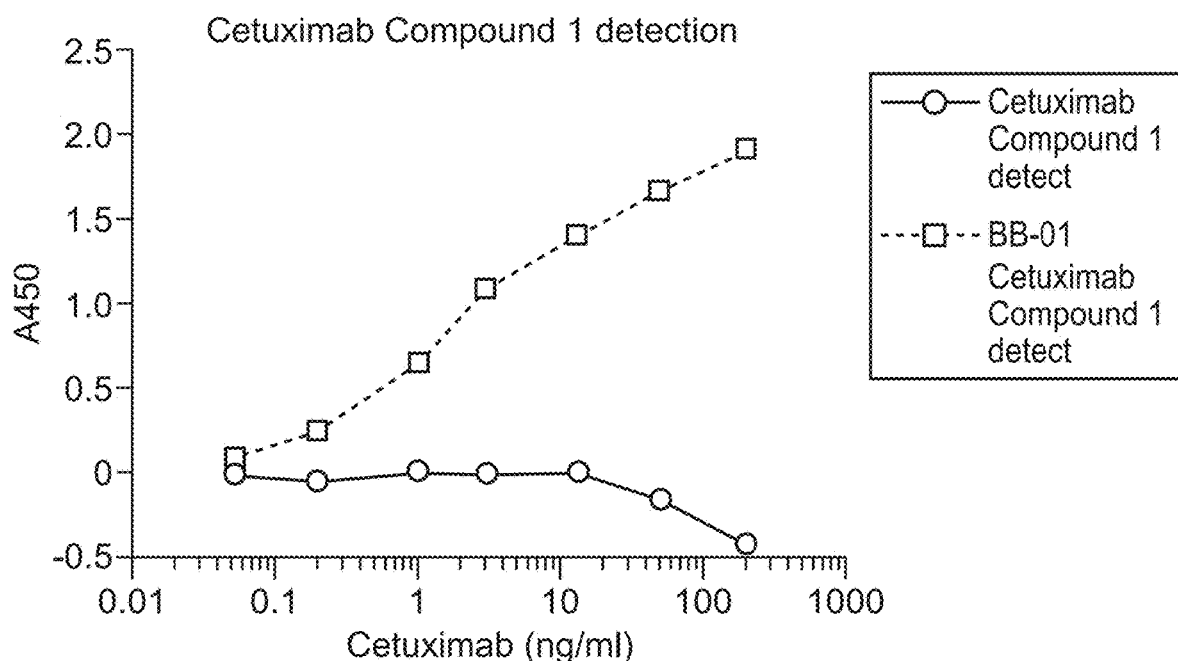

FIG. 132D shows that Cetuximab immunoconjugate (BB-01 Cetuximab), produced using the BB-01 conjugation method, but not Cetuximab (Imclone/Lilly), shows strong reactivity with the anti-Compound 1 antibody following capture on an anti-human IgG coated ELISA plate.

Figure 132E:
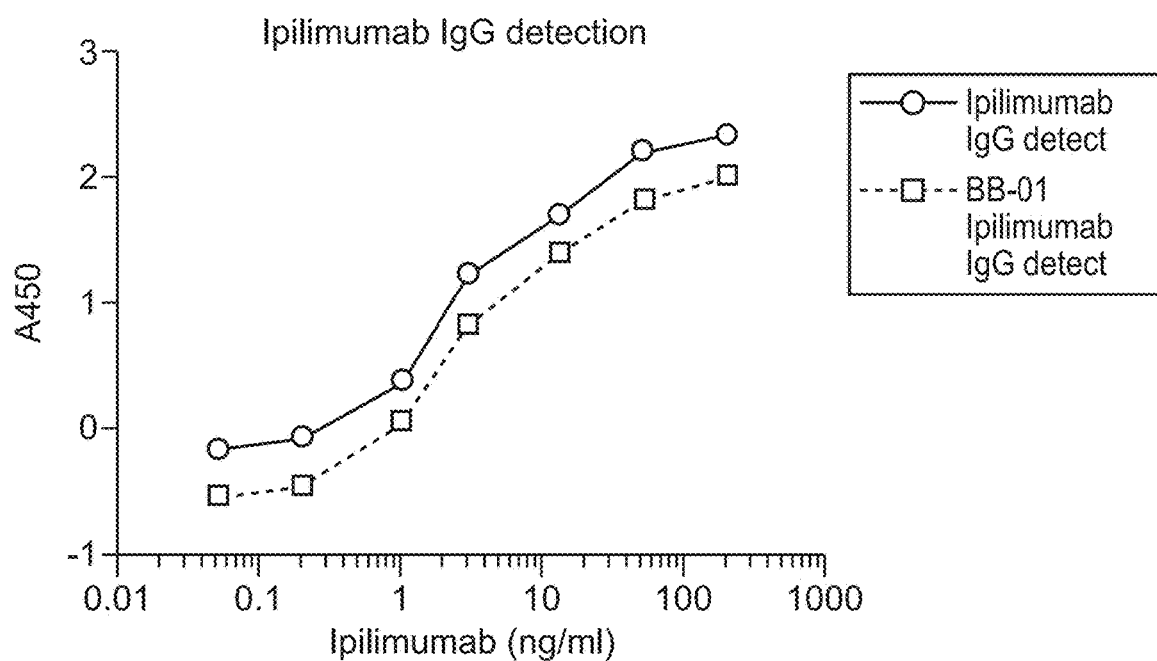

FIG. 132E shows that Ipilimumab (BMS) and Ipilimumab immunoconjugate (BB-01 Ipilimumab), produced using the BB-01 conjugation method, show comparable reactivity with anti-human IgG detection antibody when captured on anti-human IgG coated ELISA plates.

Figure 132F:
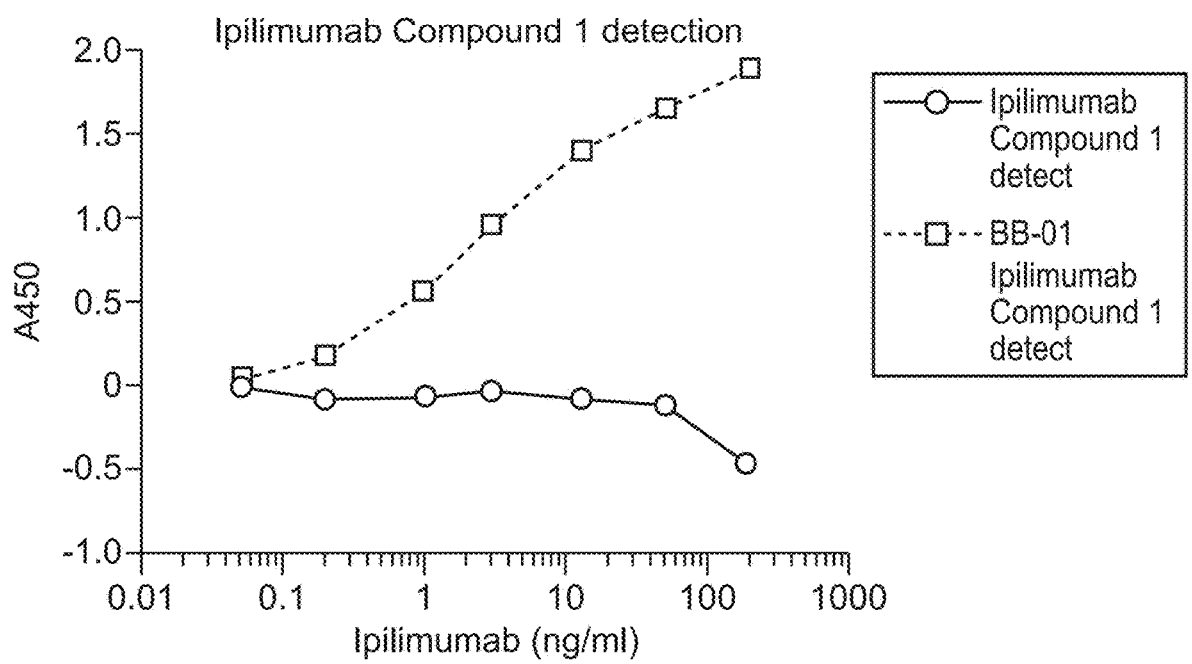

FIG. 132F shows that Ipilimumab immunoconjugate (BB-01 Ipilimumab), produced using the BB-01 conjugation method, but not Ipilimumab (BMS), shows strong reactivity with the anti-Compound 1 antibody following capture on an anti-human IgG coated ELISA plate.

Figure 132G:
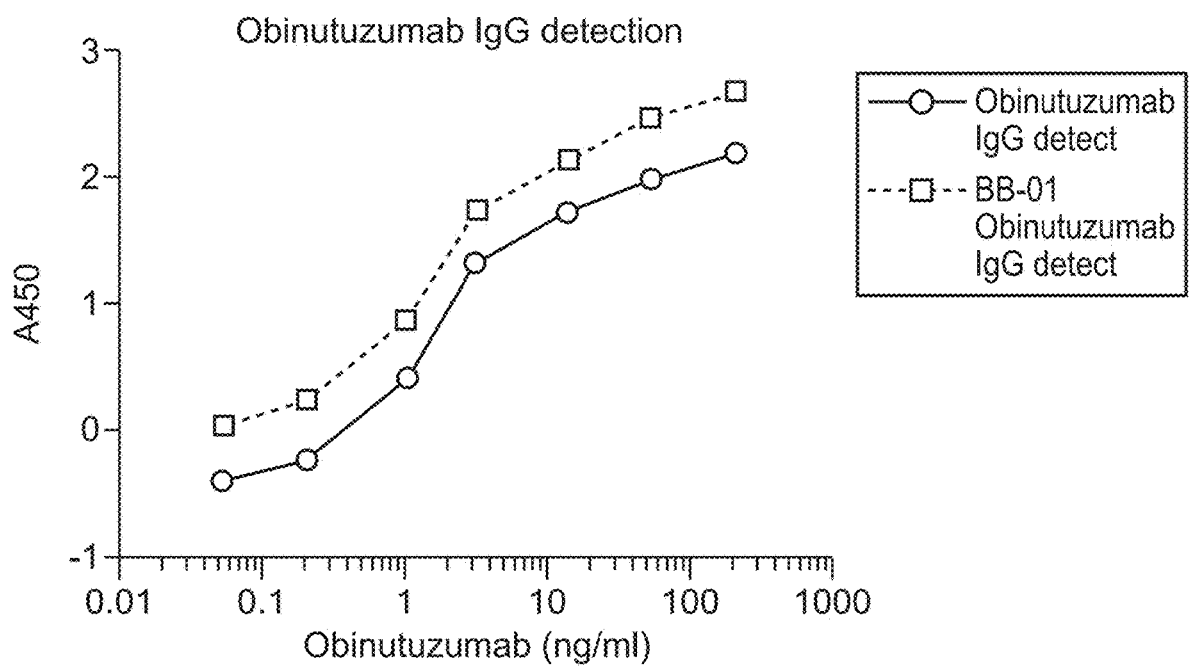

FIG. 132G shows that Obinutuzumab (Roche) and Obinutuzumab immunoconjugate (BB-01 Obinutuzumab), produced using the BB-01 conjugation method, show comparable reactivity with anti-human IgG detection antibody when captured on anti-human IgG coated ELISA plates.

Figure 132H:
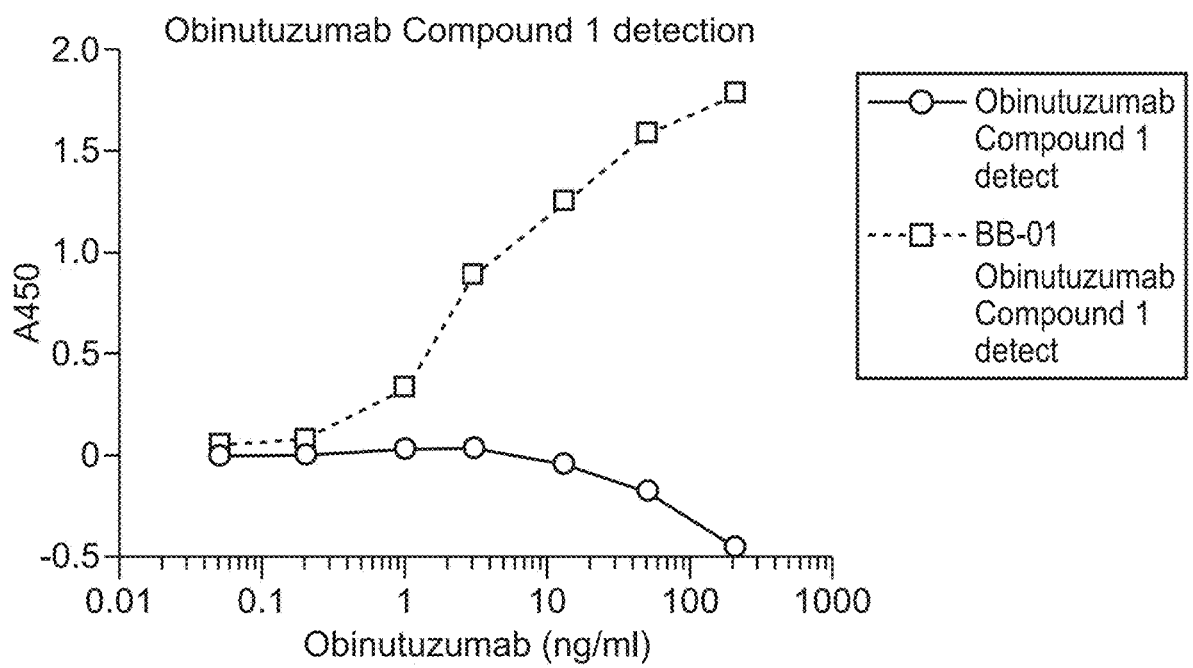

FIG. 132H shows that Obinutuzumab immunoconjugate (BB-01 Obinutuzumab), produced using the BB-01 conjugation method, but not Obinutuzumab (Roche), shows strong reactivity with the anti-Compound 1 antibody following capture on an anti-human IgG coated ELISA plate.

Figure 132I:
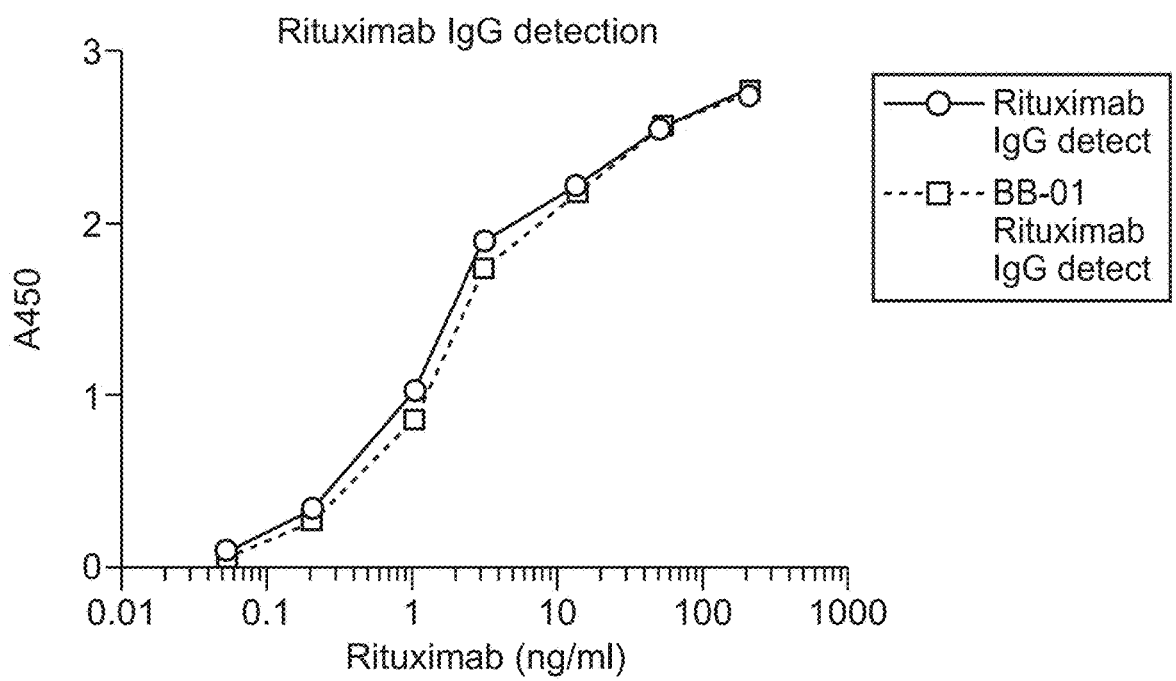

FIG. 132I shows that Rituximab (Roche) and Rituximab immunoconjugate (BB-01 Rituximab), produced using the BB-01 conjugation method, show comparable reactivity with anti-human IgG detection antibody when captured on anti-human IgG coated ELISA plates.

Figure 132J:
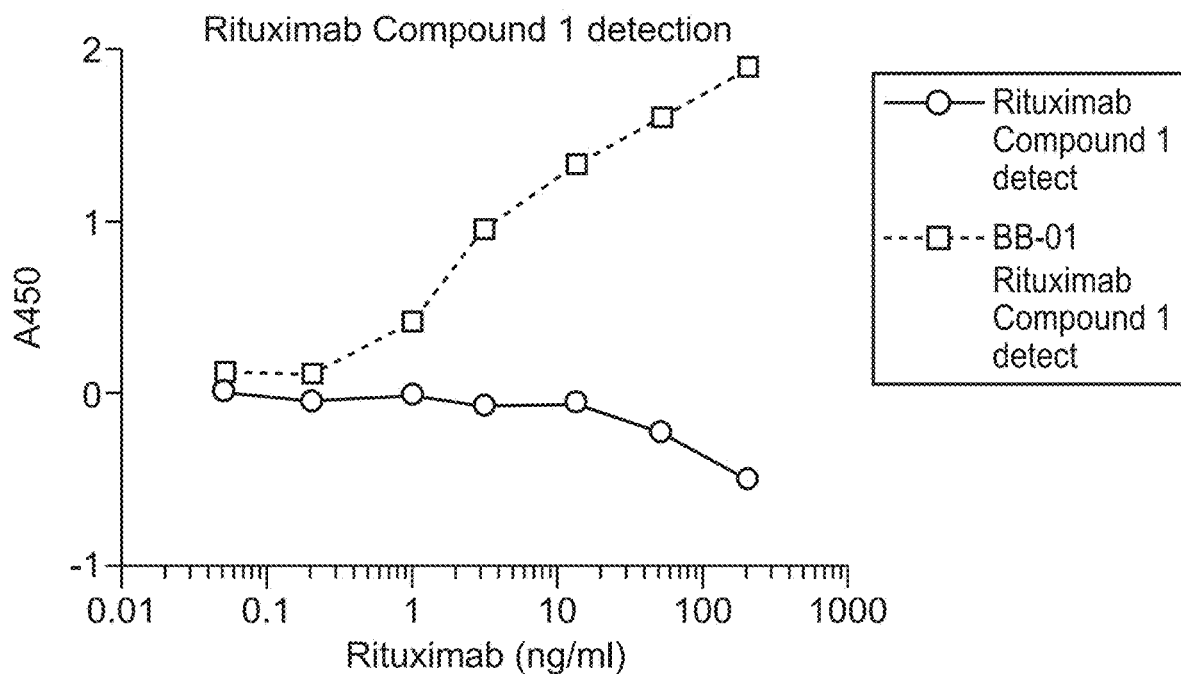

FIG. 132J shows that Rituximab immunoconjugate (BB-01 Rituximab), produced using the BB-01 conjugation method, but not Rituximab (Roche), shows strong reactivity with the anti-Compound 1 antibody following capture on an anti-human IgG coated ELISA plate.

Figure 132K:
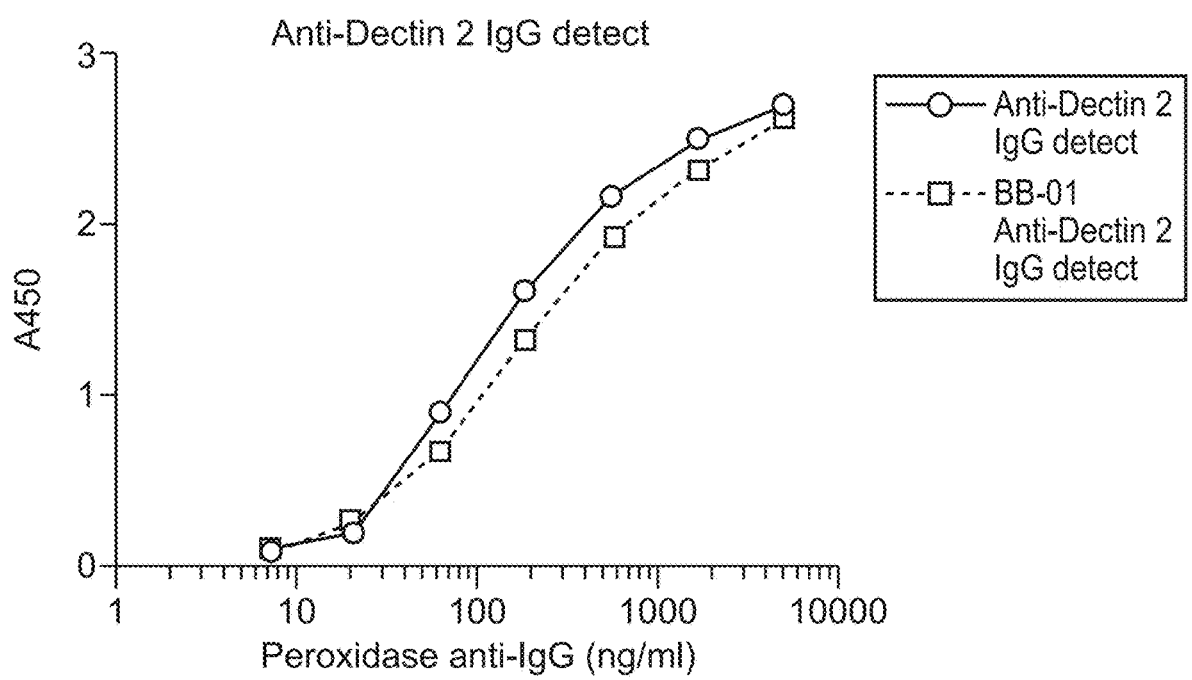

FIG. 132K shows that Anti-Dectin 2 Antibody (Biorad MCA2415) and Anti-Dectin 2 immunoconjugate (BB-01 Anti-Dectin 2), produced using the BB-01 conjugation method, show comparable reactivity with IgG detection antibody when coated onto an ELISA plate.

Figure 132L:
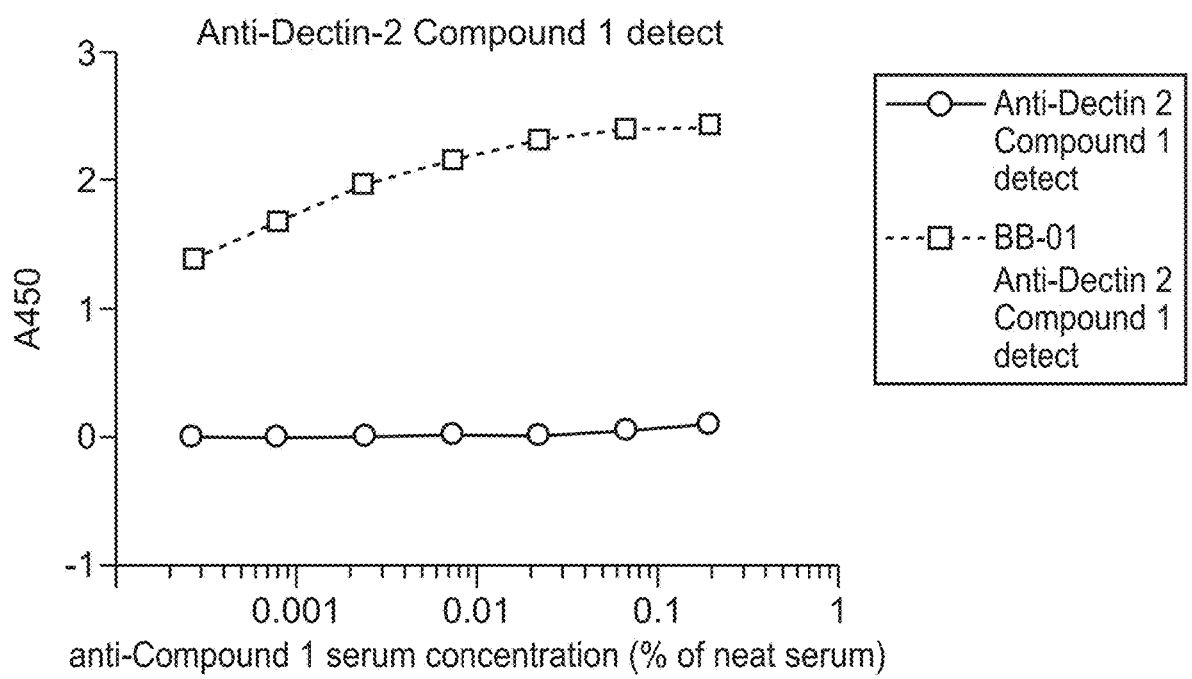

FIG. 132L shows that Anti-Dectin 2 immunoconjugate (BB-01 Anti-Dectin 2), produced using the BB-01 conjugation method, but not Anti-Dectin 2 Antibody (Biorad MCA2415), shows strong reactivity with the anti-Compound 1 antibody by ELISA assay.

Figure 133A:
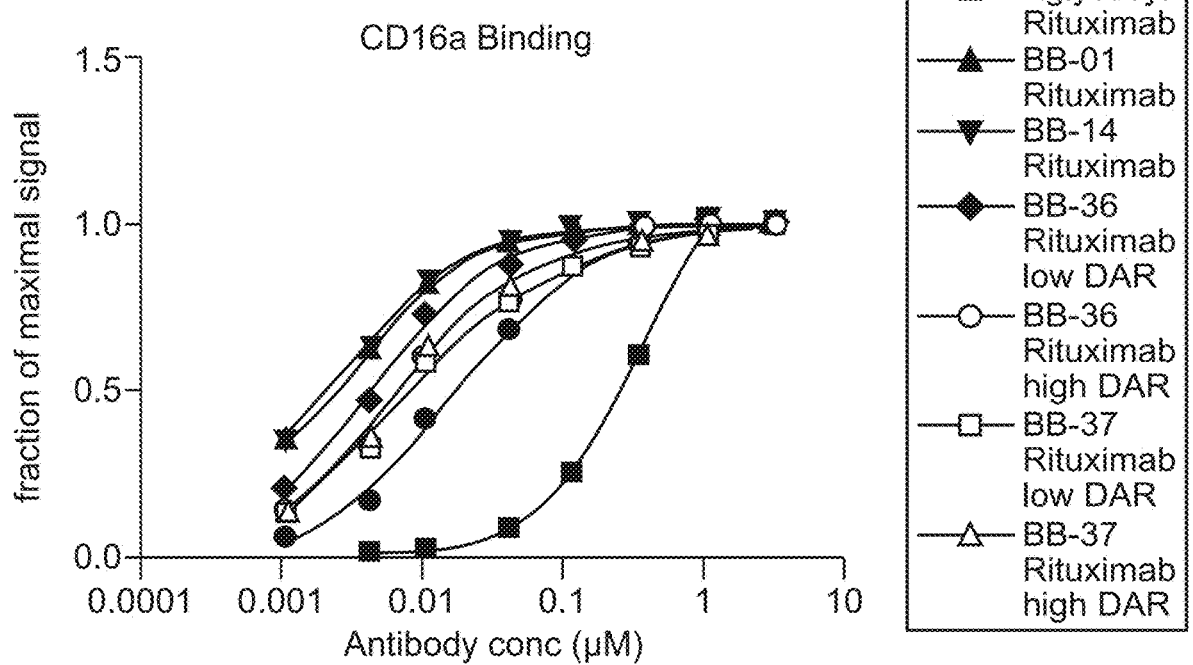

FIG. 133A shows that Rituximab immunoconjugates (Rituximab BB-01) retain binding activity for CD16a. Binding was assayed by ELISA as described in Example 29. Compounds show are Rituximab, aglycosyl Rituximab, (Invivogen hcd20-mab12), or Rituximab immunoconjugates (Rituximab BB-01). DAR levels on Rituximab conjugates were as follows: BB-01, 1.1; BB-14, 2.0; BB-36 low DAR, 1.4; BB36 high DAR, 2.8; BB37 low DAR, 1.7; BB-37 high DAR, 2.6. The Y axis shows the fraction of maximal OD signal at highest concentration for each sample. The aglycosyl mutant of Rituximab shows diminished binding, consistent with the role of glycosylation in effector function.

Figure 133B:
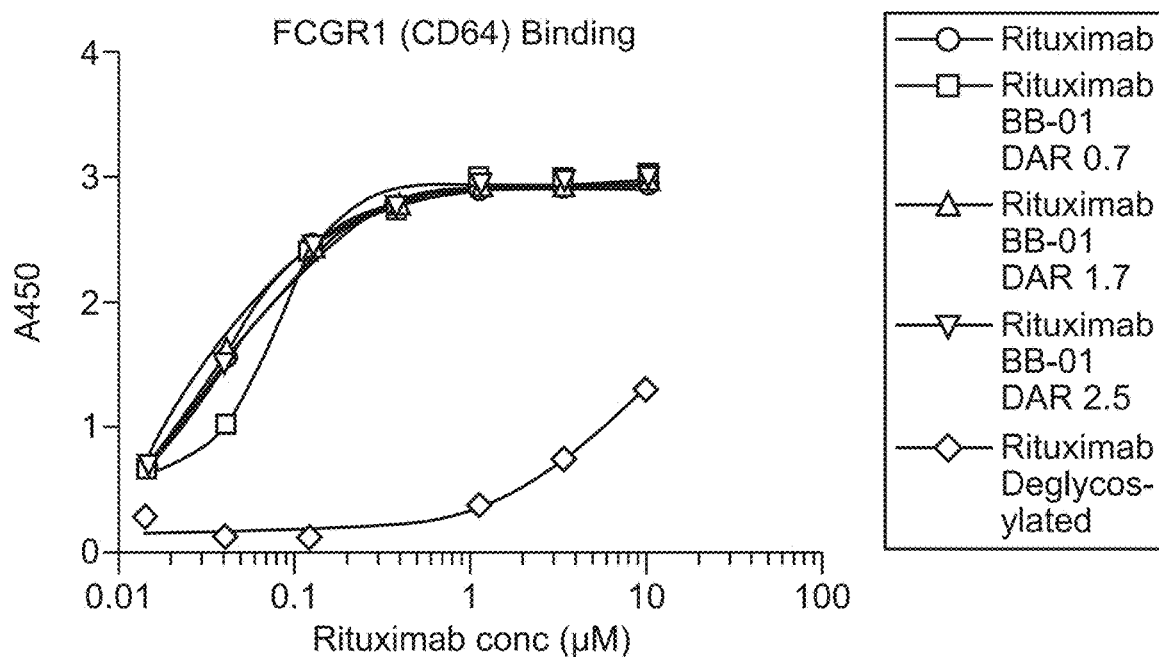

FIG. 133B shows that Rituximab (Roche) and Rituximab immunoconjugates (BB-01 Rituximab), produced using the BB-01 conjugation method, show comparable binding to CD64 immobilized on ELISA plates. Rituximab had been deglycosylated used PNGase F shows impaired binding to CD64.

Figure 133C:
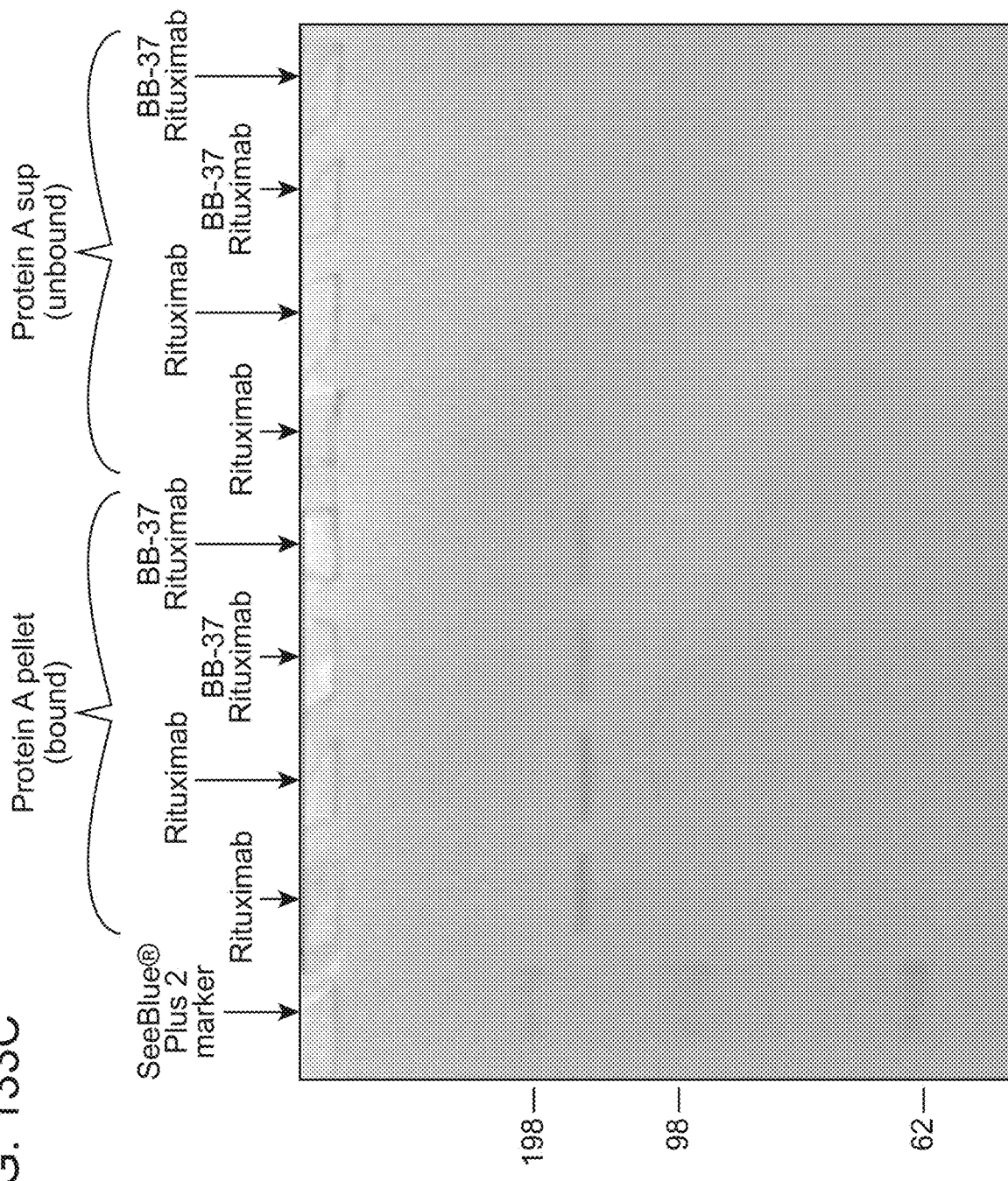

FIG. 133C shows that Rituximab and a Rituximab immunoconjugate (Rituximab BB-37) bind to protein A. Duplicate samples were subjected to pull down using protein A sepharose. No unbound Rituximab or Rituximab BB-37 was detected in the pull down supernatants. There is considerable overlap of protein A and FcRN binding sites on IgG. Therefore, preservation of protein A binding in Rituximab BB-37 suggests preservation of FcRN binding.

Figure 134A:
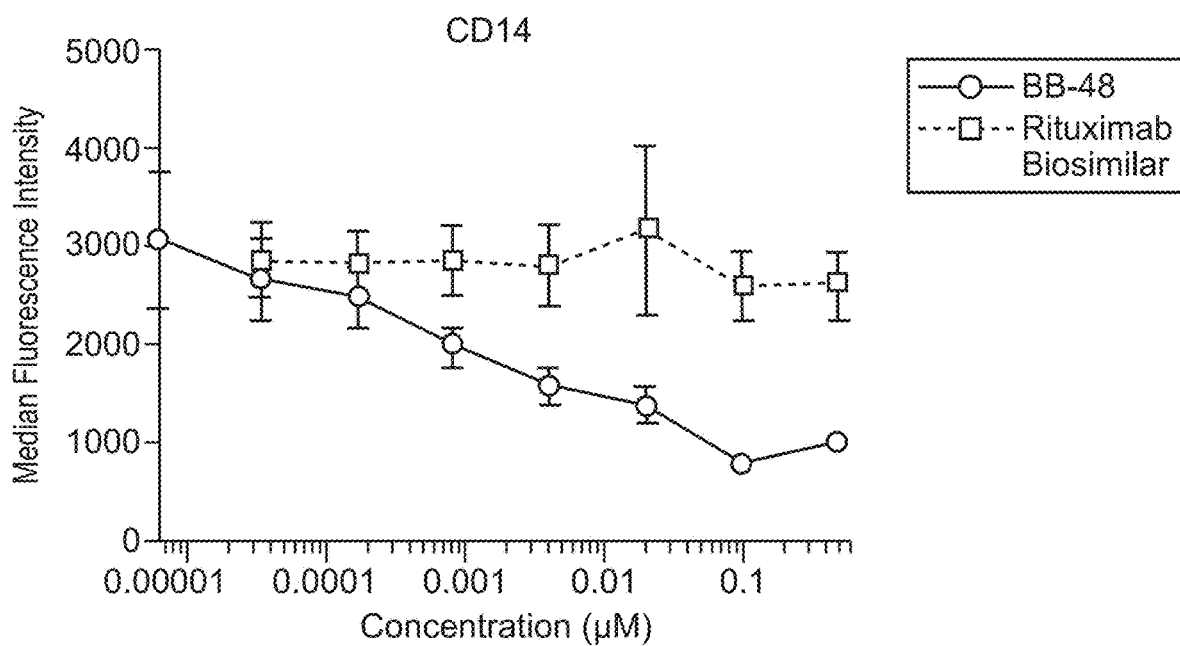

FIG. 134A shows CD123 expression on myeloid cells following 18 hours of stimulation with the BB-48 immunoconjugate produced according to the BB-48 method or the unconjugated Rituximab biosimilar (CD20; Alphamab).

Figure 134B:
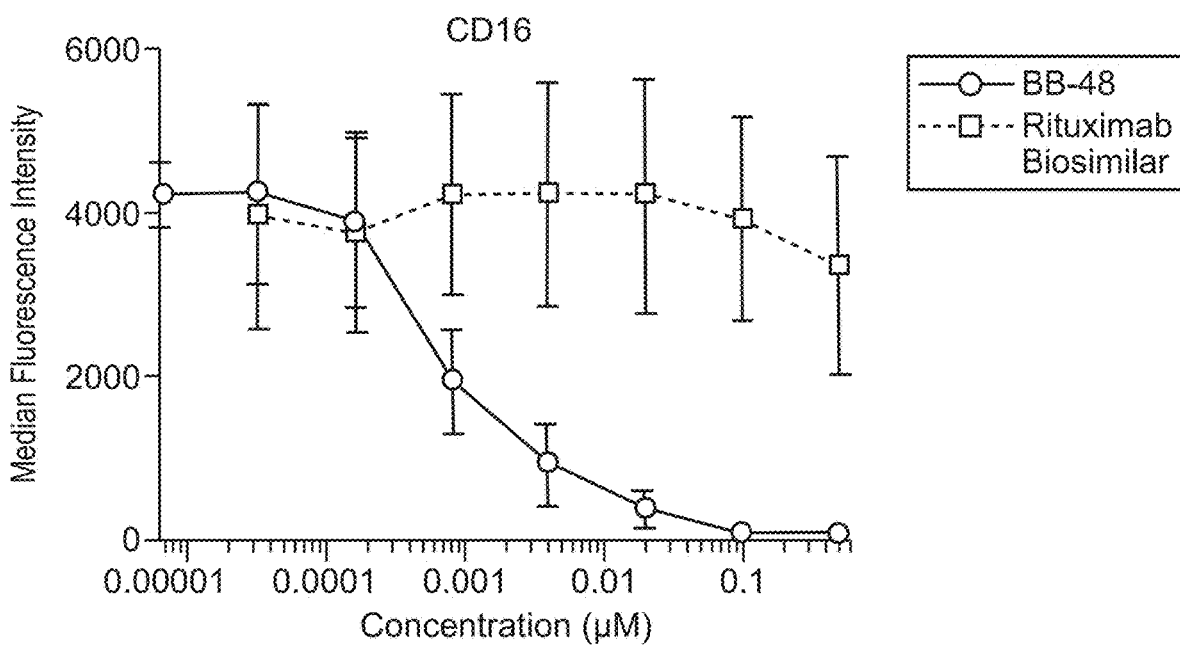

FIG. 134B shows HLA-DR expression on myeloid cells following 18 hours of stimulation with the BB-48 immunoconjugate produced according to the BB-48 method or the unconjugated Rituximab biosimilar (CD20; Alphamab).

Figure 134C:
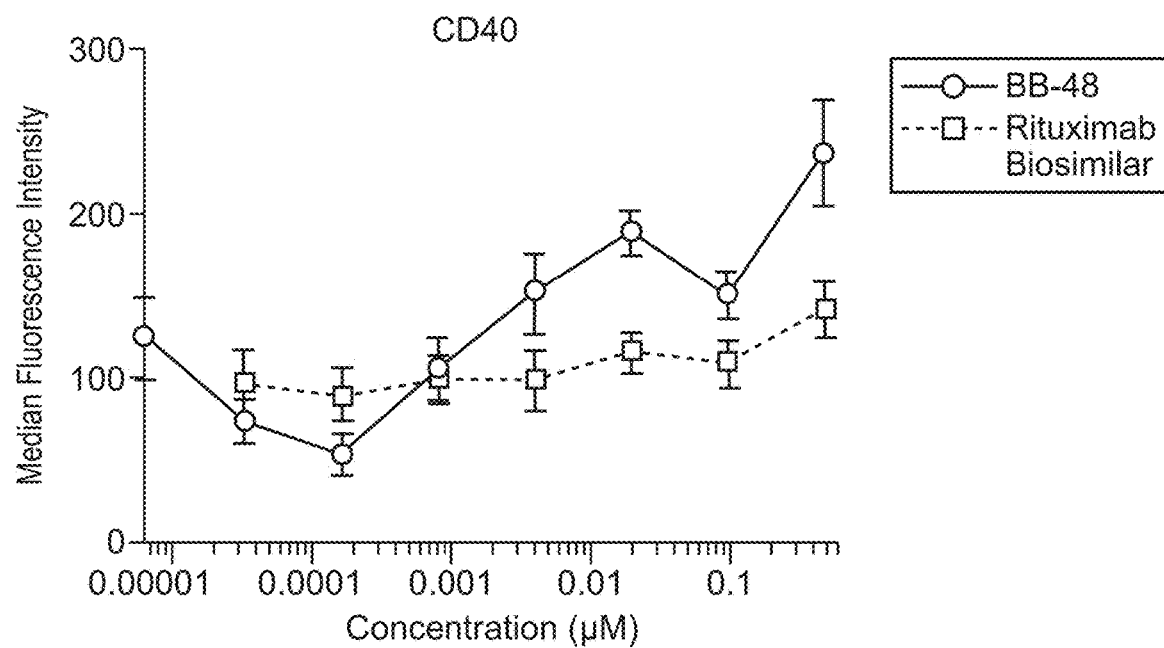

FIG. 134C shows CD14 expression on myeloid cells following 18 hours of stimulation with the BB-48 immunoconjugate produced according to the BB-48 method or the unconjugated Rituximab biosimilar (CD20; Alphamab).

Figure 134D:
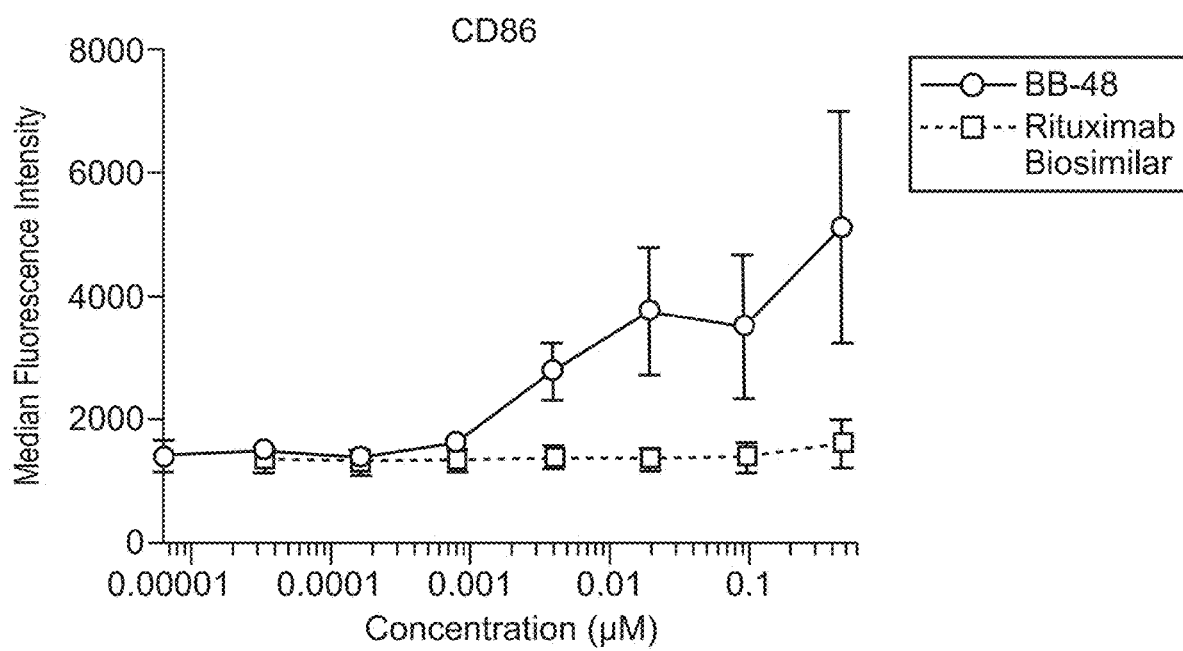

FIG. 134D shows CD16 expression on myeloid cells following 18 hours of stimulation with the BB-48 immunoconjugate produced according to the BB-48 method or the unconjugated Rituximab biosimilar (CD20; Alphamab).

Figure 134E:
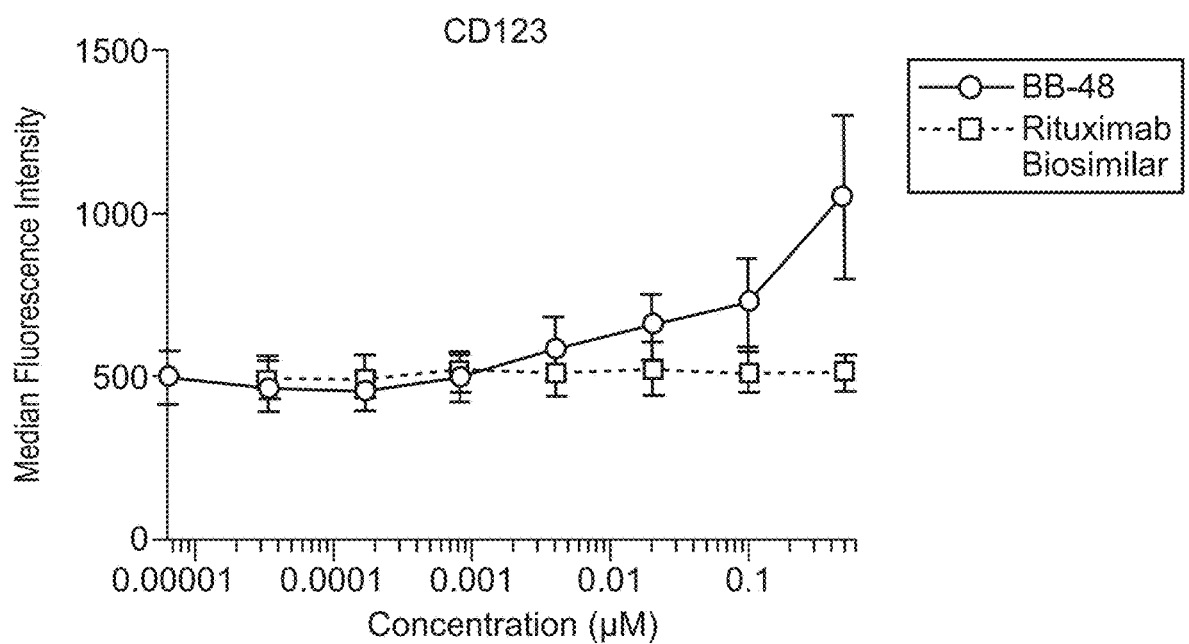

FIG. 134E shows CD40 expression on myeloid cells following 18 hours of stimulation with the BB-48 immunoconjugate produced according to the BB-48 method or the unconjugated Rituximab biosimilar (CD20; Alphamab).

Figure 134F:
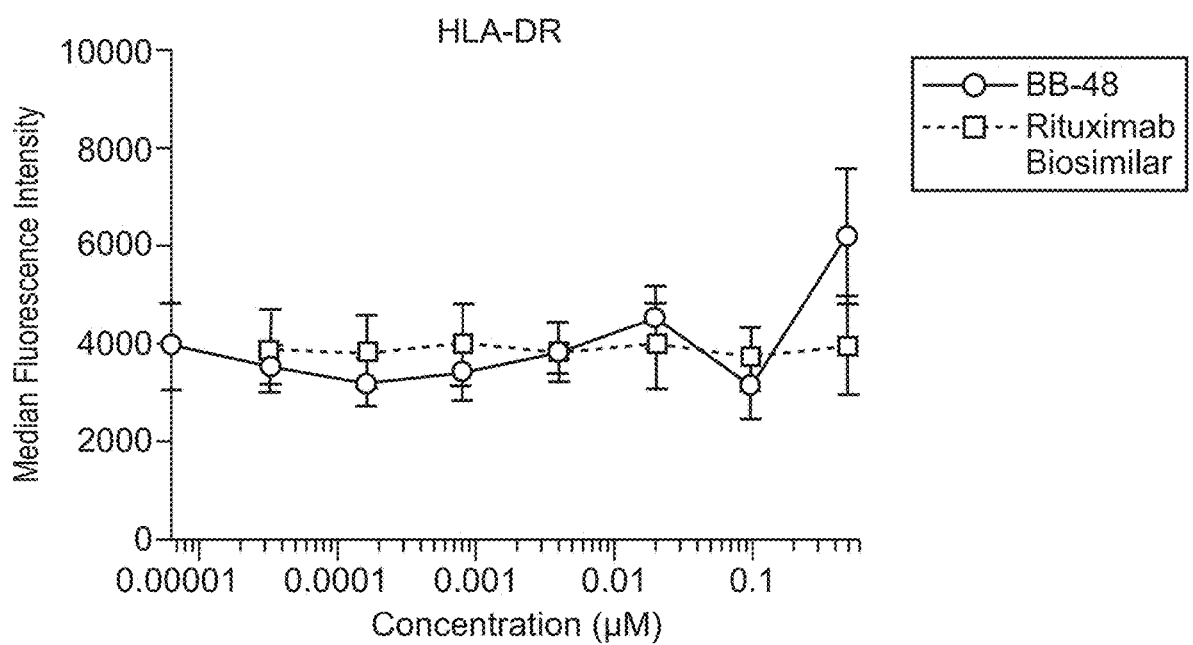

FIG. 134F shows CD86 expression on myeloid cells following 18 hours of stimulation with the BB-48 immunoconjugate produced according to the BB-48 method or the unconjugated Rituximab biosimilar (CD20; Alphamab).

FIG. 134G shows LC-MS for BB-48 immunoconjugate produced according to the BB-48 method.

Figure 135A:
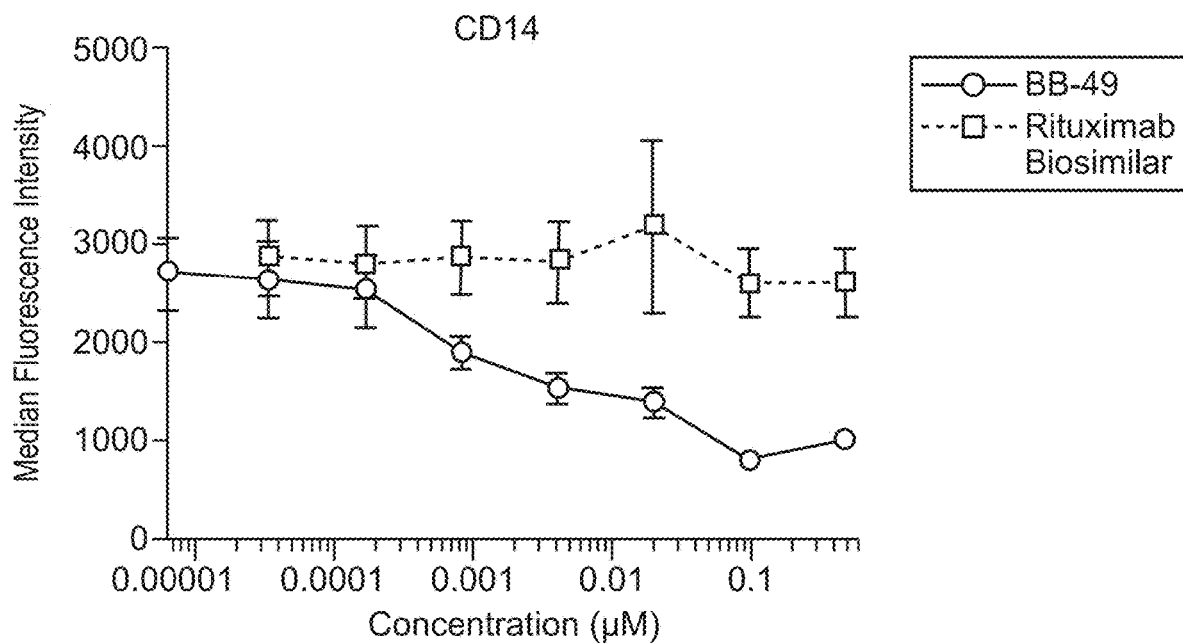

FIG. 135A shows CD123 expression on myeloid cells following 18 hours of stimulation with the BB-49 immunoconjugate produced according to the BB-49 method or the unconjugated Rituximab biosimilar (CD20; Alphamab).

Figure 135B:
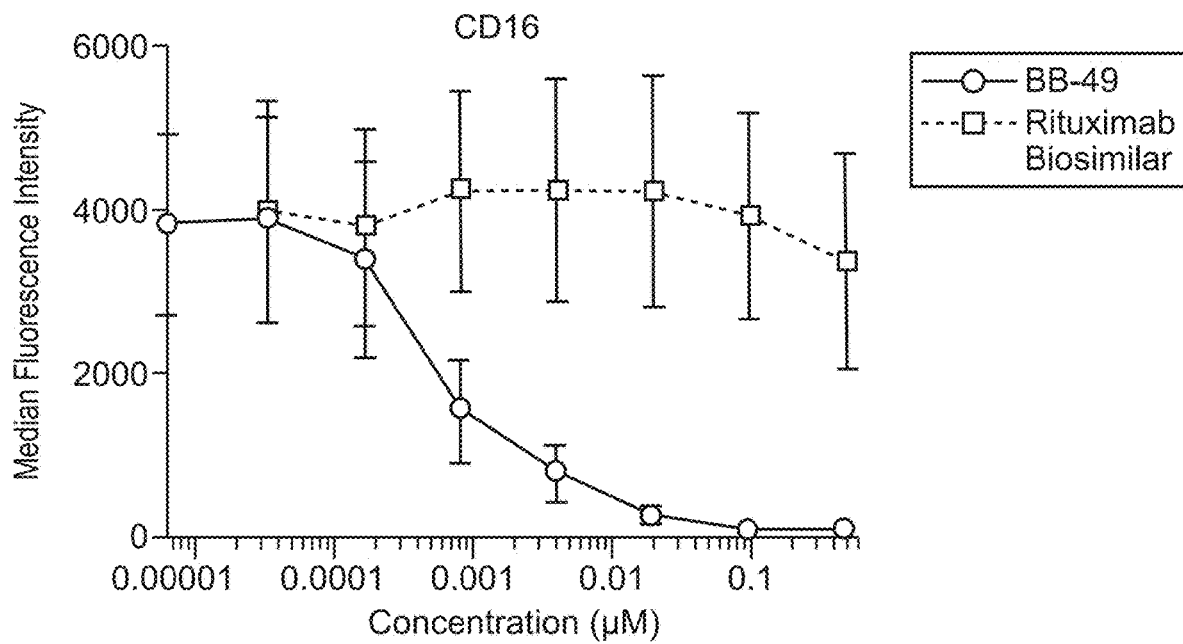

FIG. 135B shows HLA-DR expression on myeloid cells following 18 hours of stimulation with the BB-49 immunoconjugate produced according to the BB-49 method or the unconjugated Rituximab biosimilar (CD20; Alphamab).

Figure 135C:
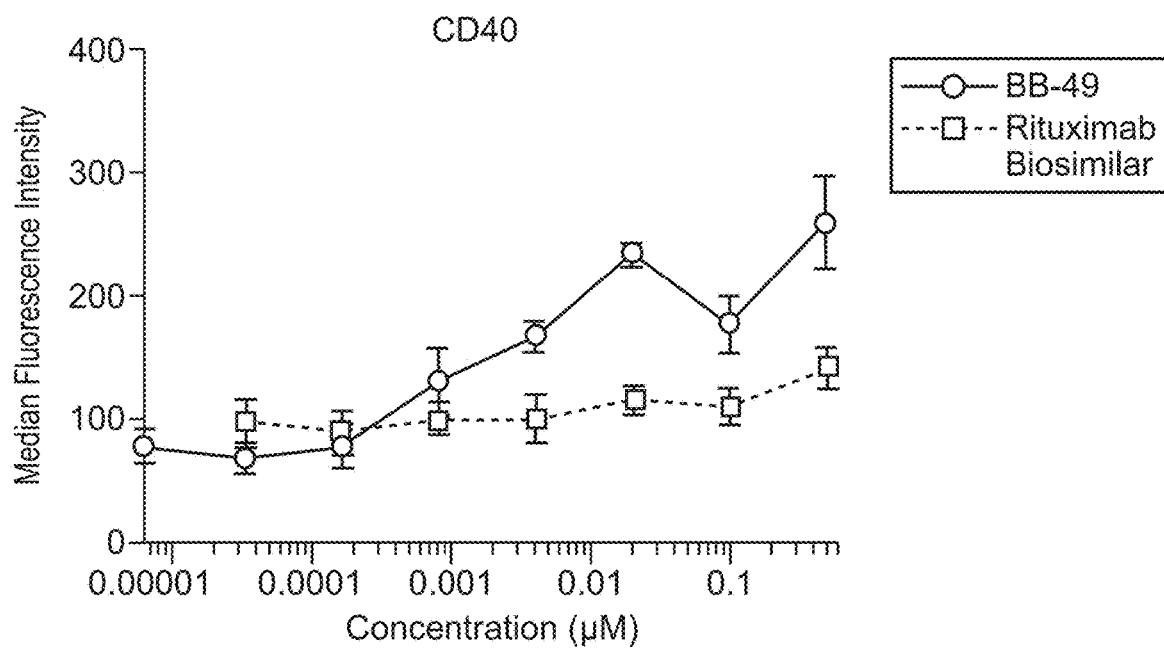

FIG. 135C shows CD14 expression on myeloid cells following 18 hours of stimulation with the BB-49 immunoconjugate produced according to the BB-49 method or the unconjugated Rituximab biosimilar (CD20; Alphamab).

Figure 135D:
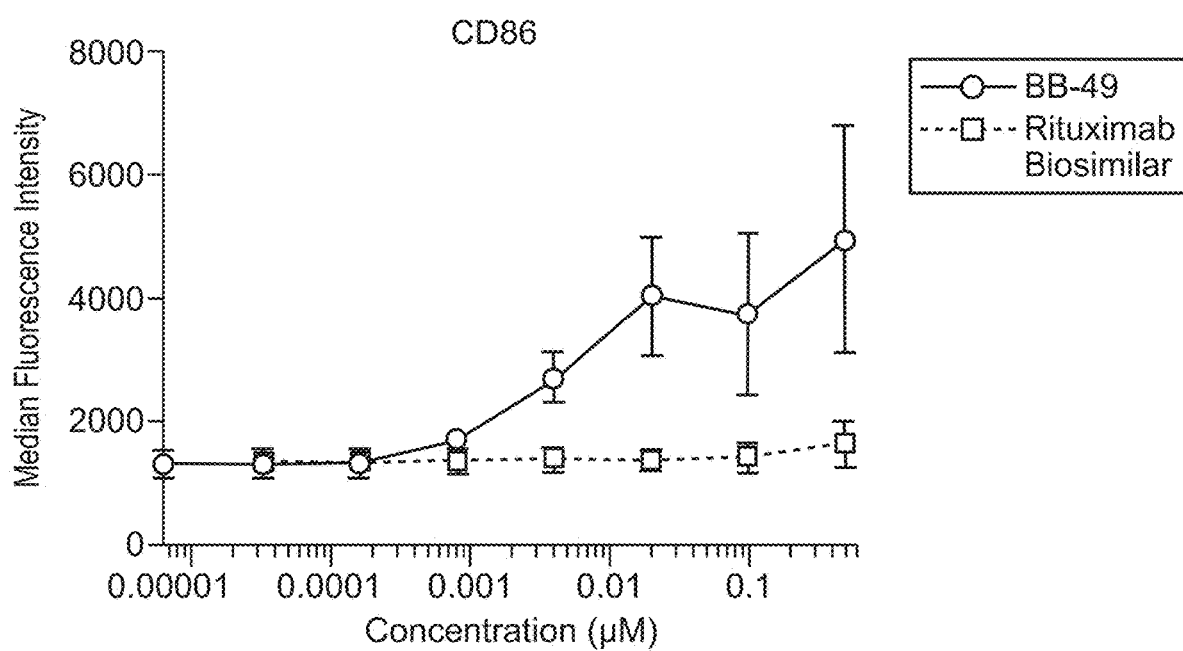

FIG. 135D shows CD16 expression on myeloid cells following 18 hours of stimulation with the BB-49 immunoconjugate produced according to the BB-49 method or the unconjugated Rituximab biosimilar (CD20; Alphamab).

Figure 135E:
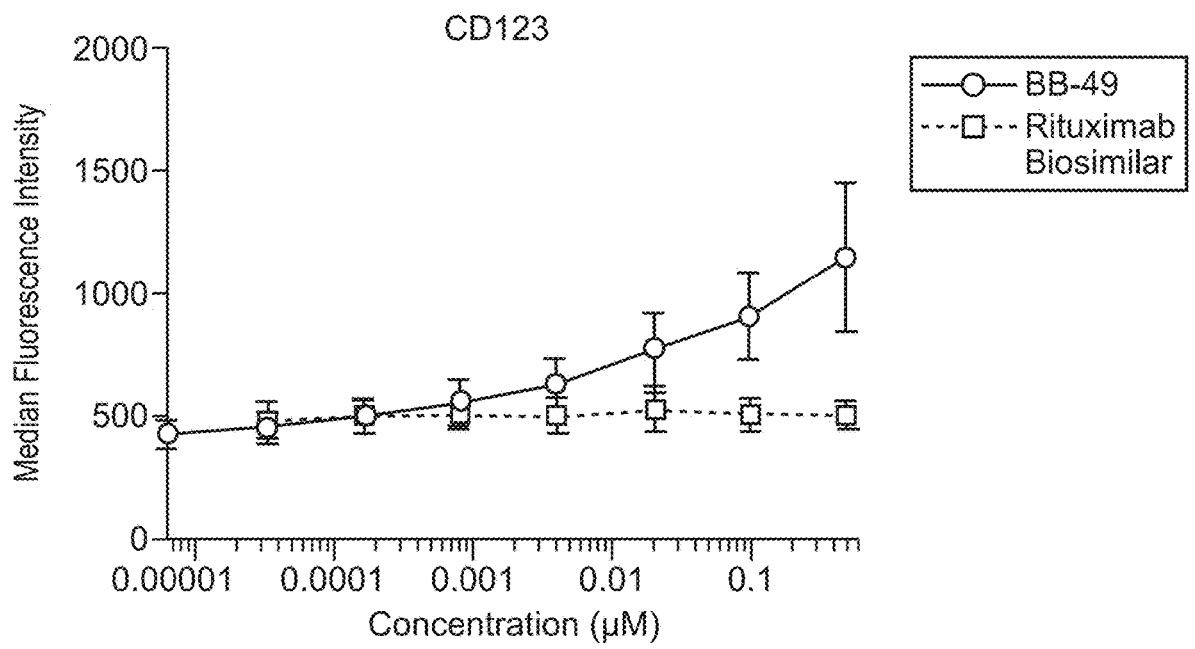

FIG. 135E shows CD40 expression on myeloid cells following 18 hours of stimulation with the BB-49 immunoconjugate produced according to the BB-49 method or the unconjugated Rituximab biosimilar (CD20; Alphamab).

Figure 135F:
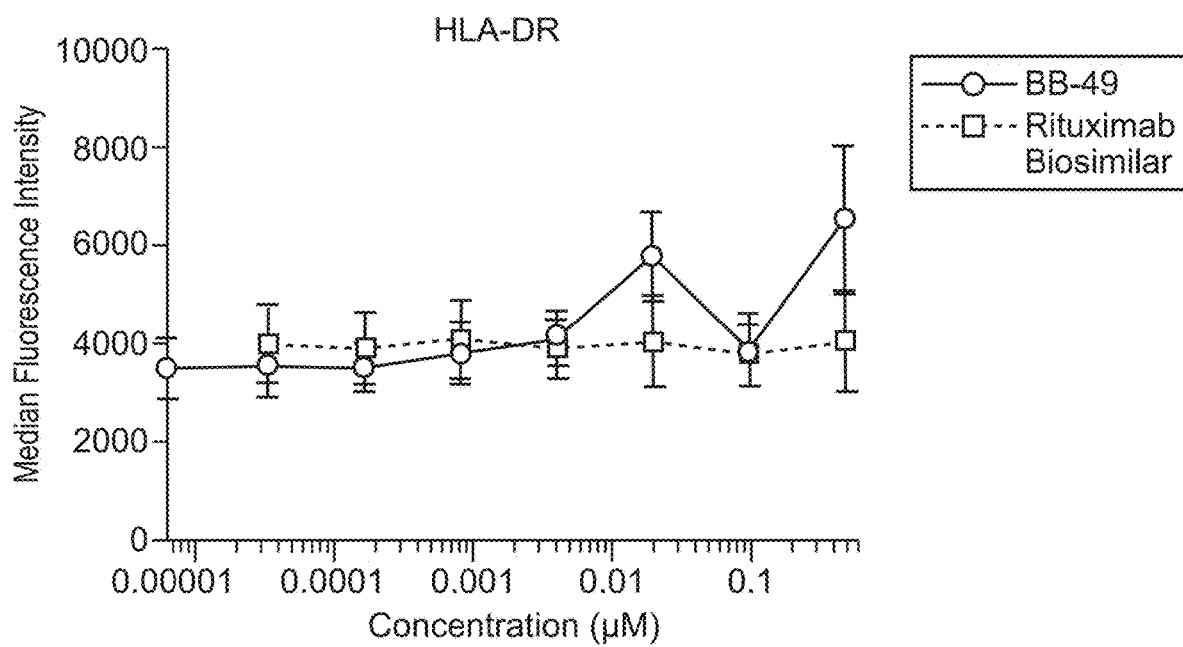

FIG. 135F shows CD86 expression on myeloid cells following 18 hours of stimulation with the BB-49 immunoconjugate produced according to the BB-49 method or the unconjugated Rituximab biosimilar (CD20; Alphamab).

Figure 135G:
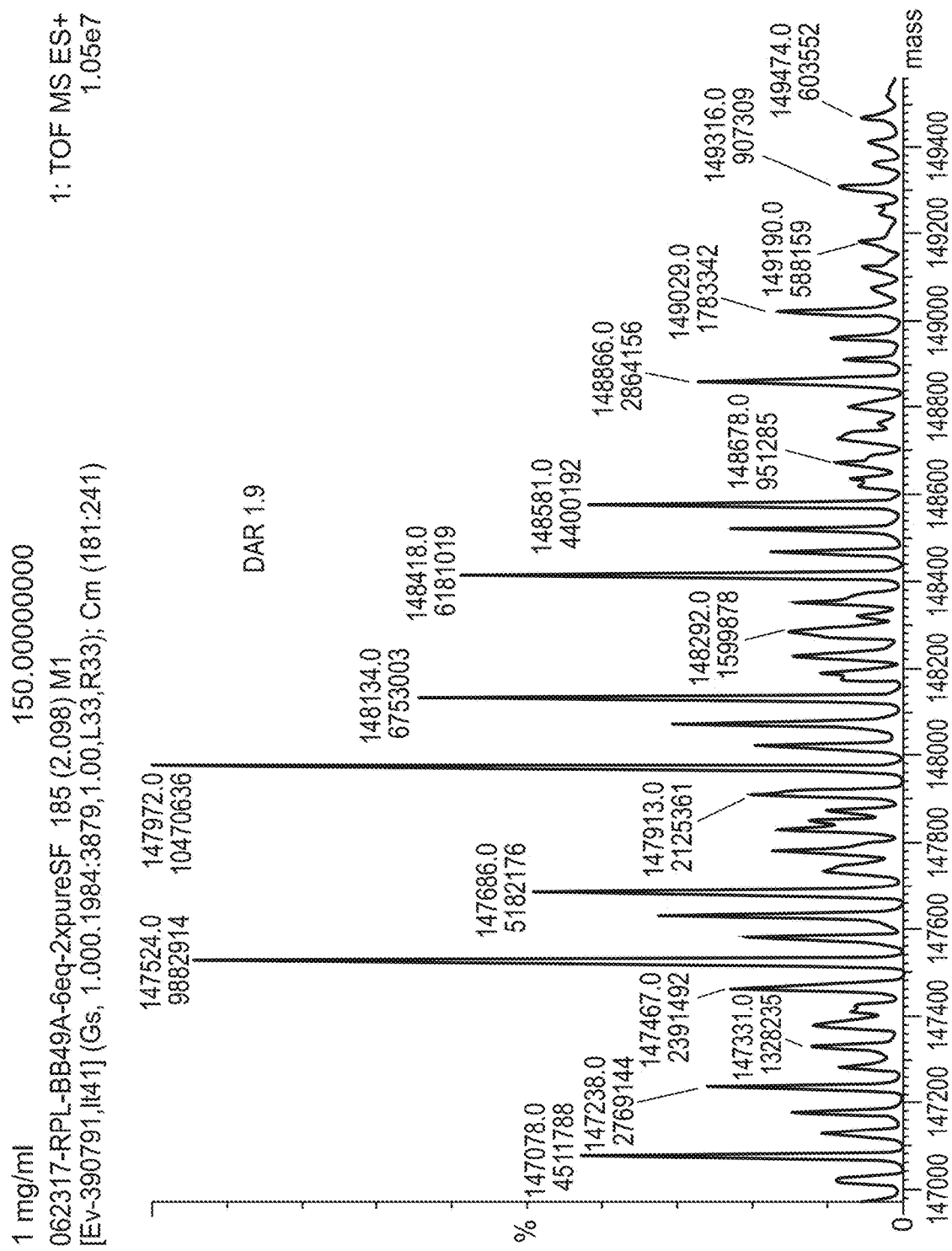

FIG. 135G shows LC-MS for BB-49 immunoconjugate produced according to the BB-49 method.

Figure 136A:
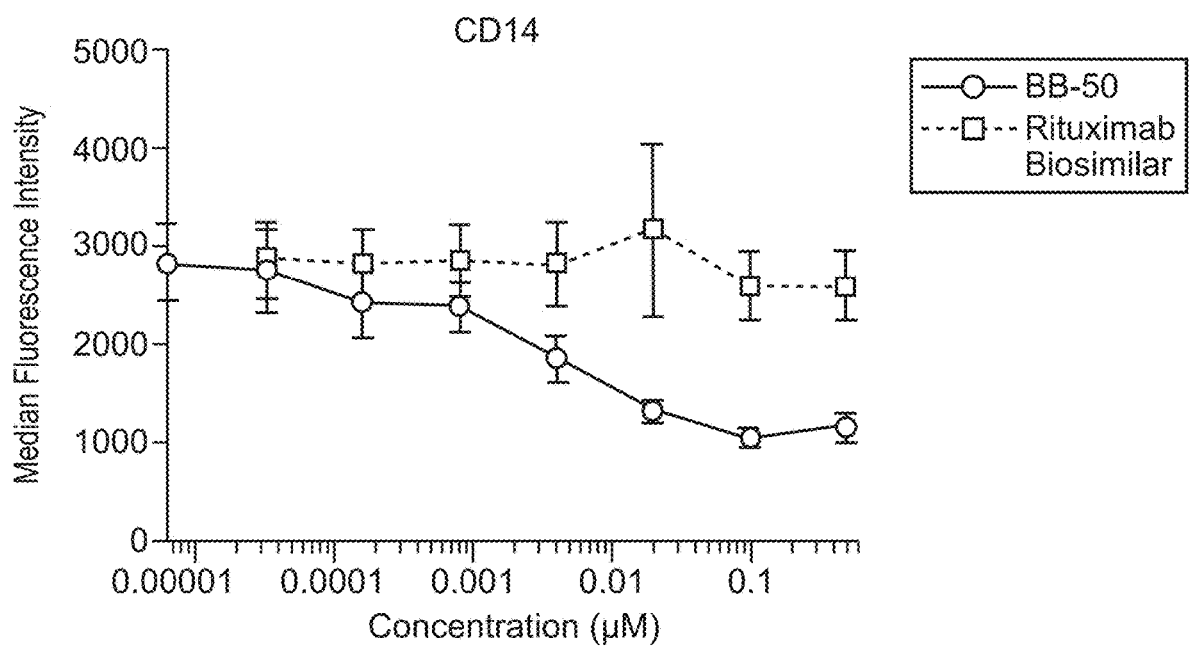

FIG. 136A shows CD123 expression on myeloid cells following 18 hours of stimulation with the BB-50 immunoconjugate produced according to the BB-50 method or the unconjugated Rituximab biosimilar (CD20; Alphamab).

Figure 136B:
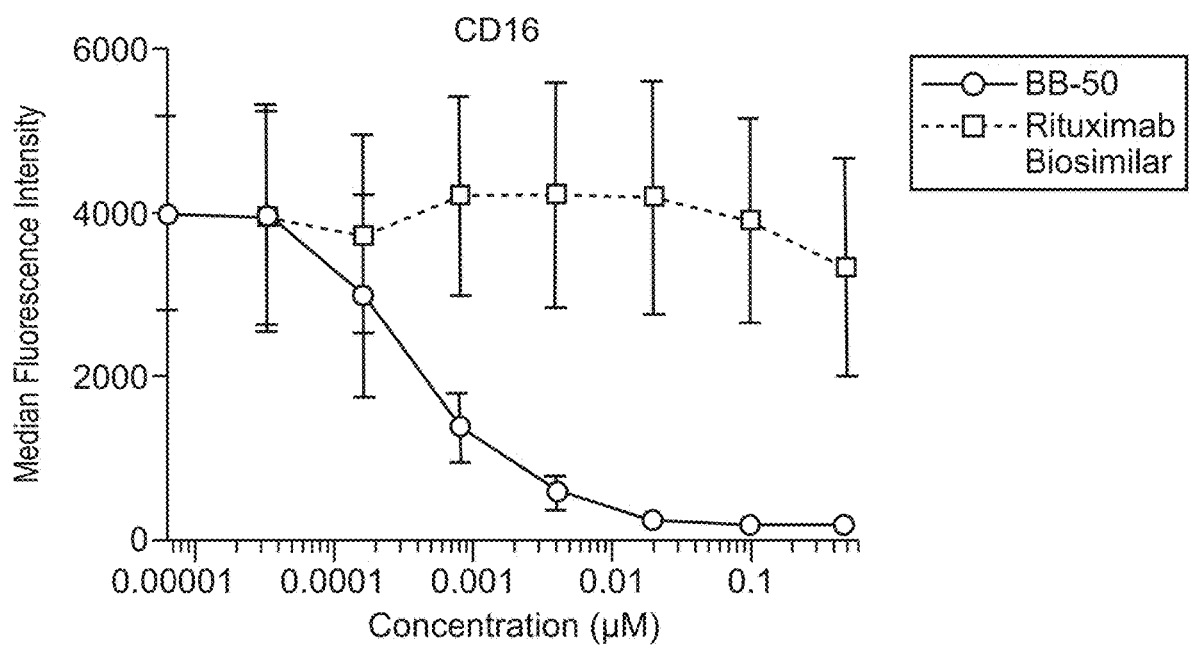

FIG. 136B shows HLA-DR expression on myeloid cells following 18 hours of stimulation with the BB-50 immunoconjugate produced according to the BB-50 method or the unconjugated Rituximab biosimilar (CD20; Alphamab).

Figure 136C:
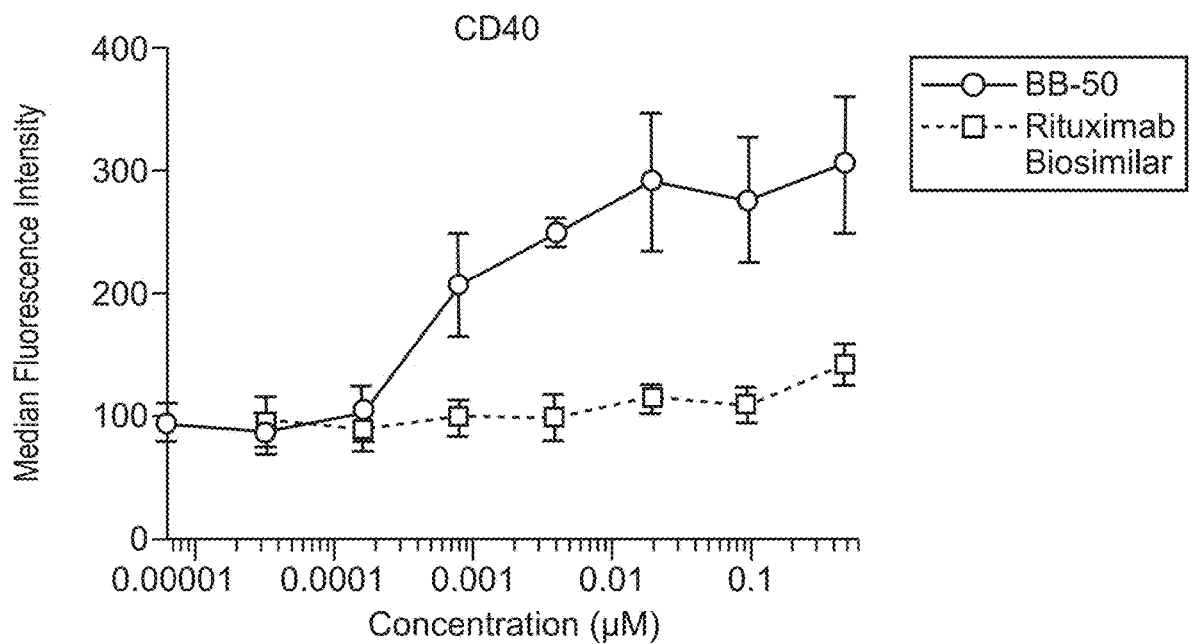

FIG. 136C shows CD14 expression on myeloid cells following 18 hours of stimulation with the BB-50 immunoconjugate produced according to the BB-50 method or the unconjugated Rituximab biosimilar (CD20; Alphamab).

Figure 136D:
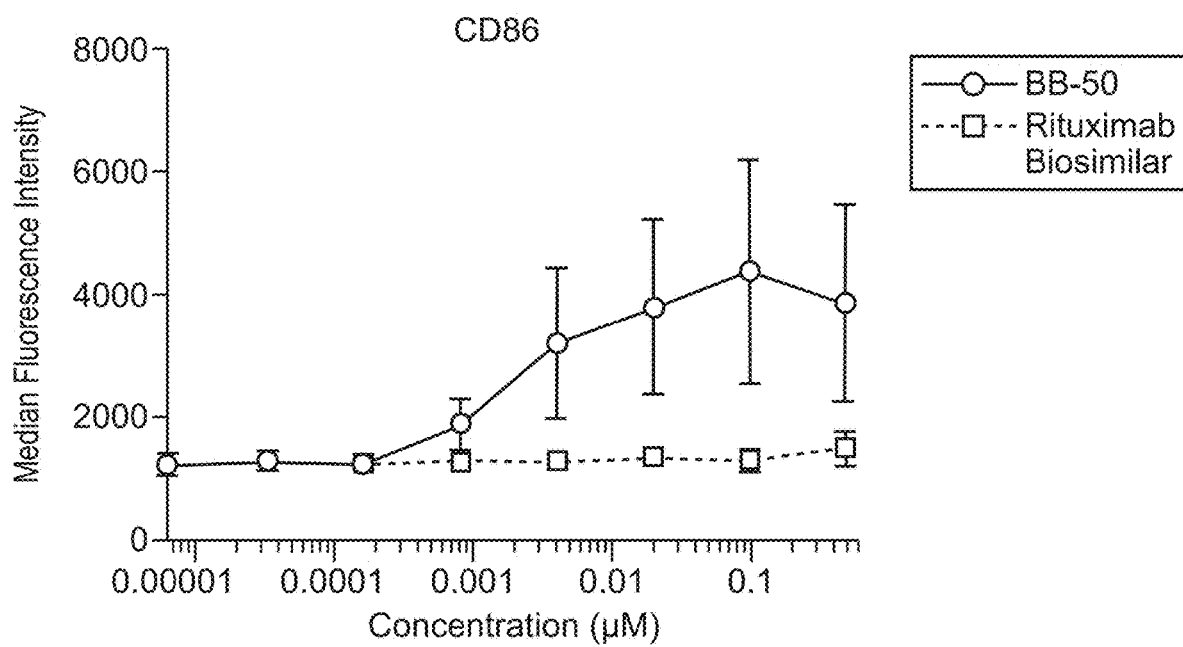

FIG. 136D shows CD16 expression on myeloid cells following 18 hours of stimulation with the BB-50 immunoconjugate produced according to the BB-50 method or the unconjugated Rituximab biosimilar (CD20; Alphamab).

Figure 136E:
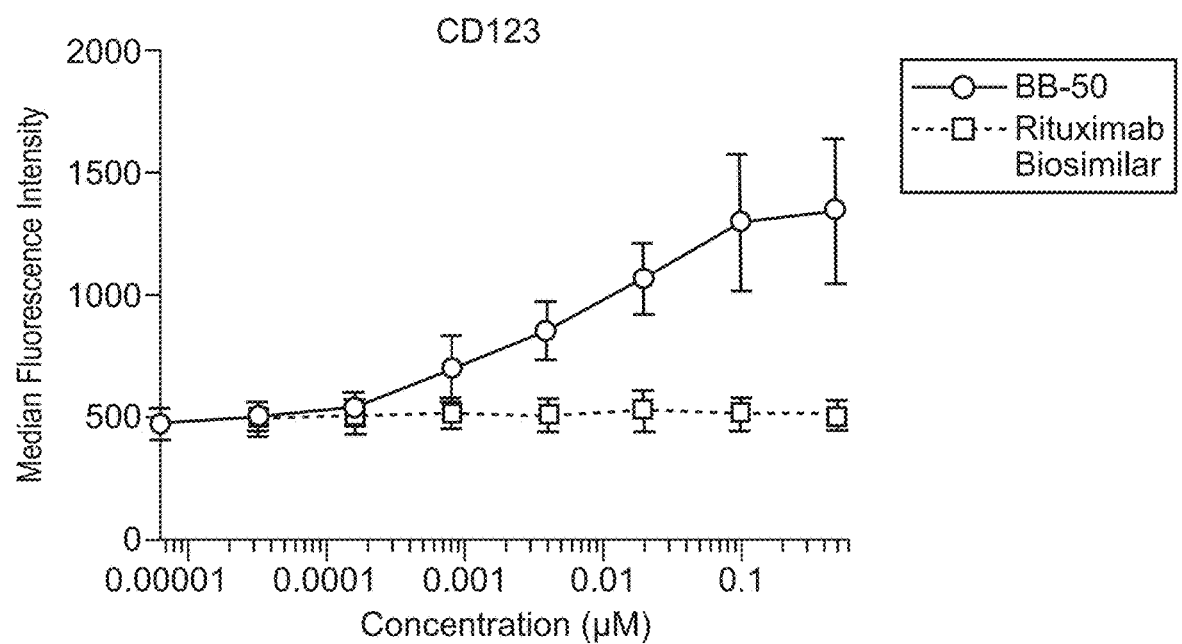

FIG. 136E shows CD40 expression on myeloid cells following 18 hours of stimulation with the BB-50 immunoconjugate produced according to the BB-50 method or the unconjugated Rituximab biosimilar (CD20; Alphamab).

Figure 136F:
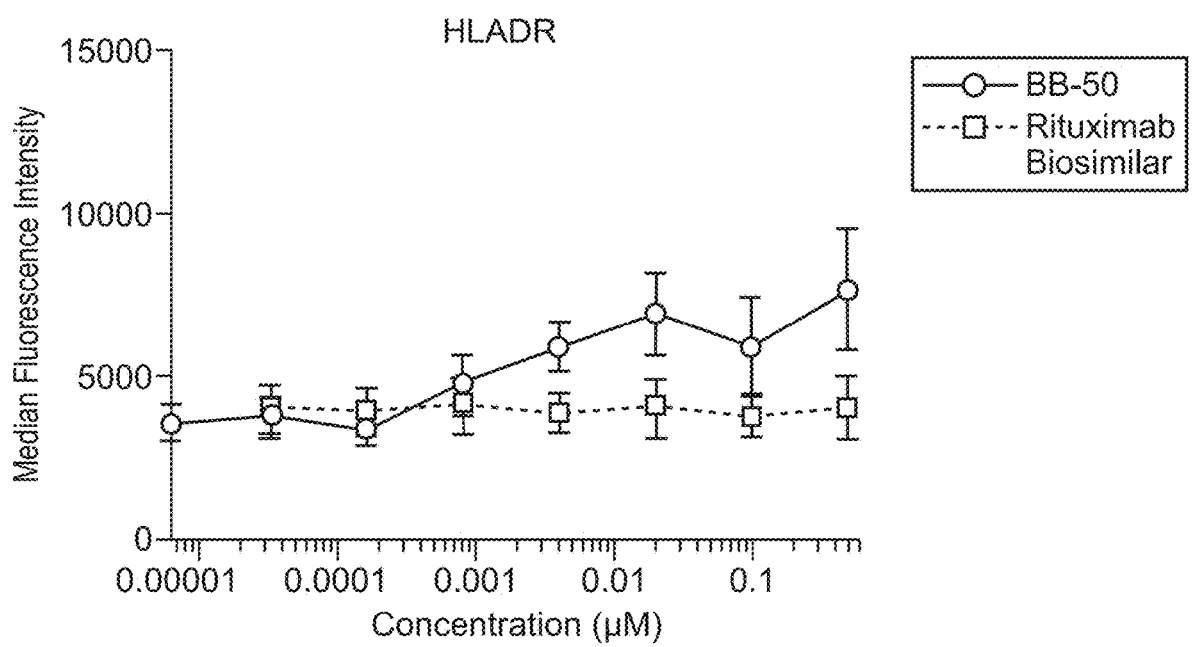

FIG. 136F shows CD86 expression on myeloid cells following 18 hours of stimulation with the BB-50 immunoconjugate produced according to the BB-50 method or the unconjugated Rituximab biosimilar (CD20; Alphamab).

Figure 136G:
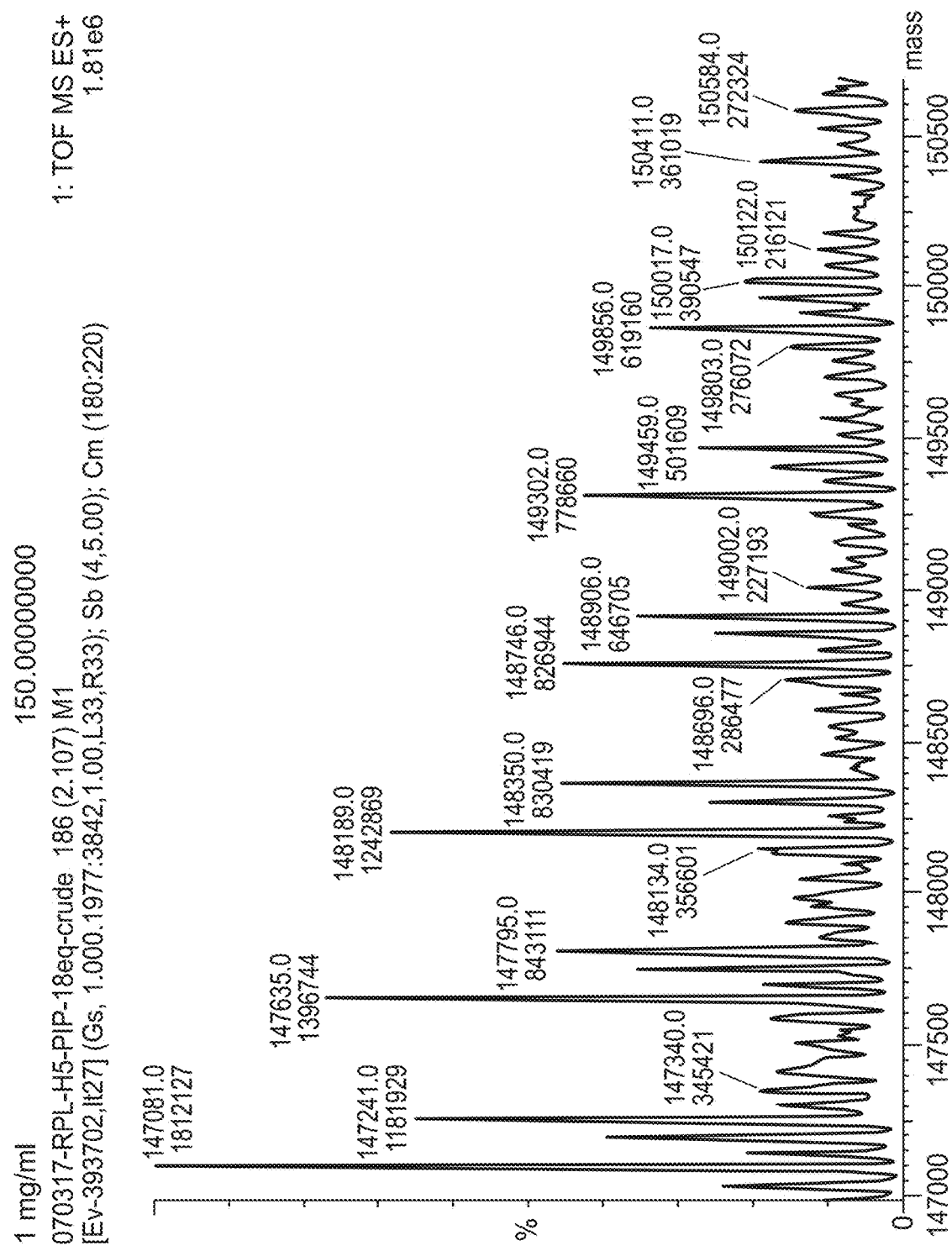

FIG. 136G shows LC-MS for BB-50 immunoconjugate produced according to the BB-50 method.

Figure 137A:
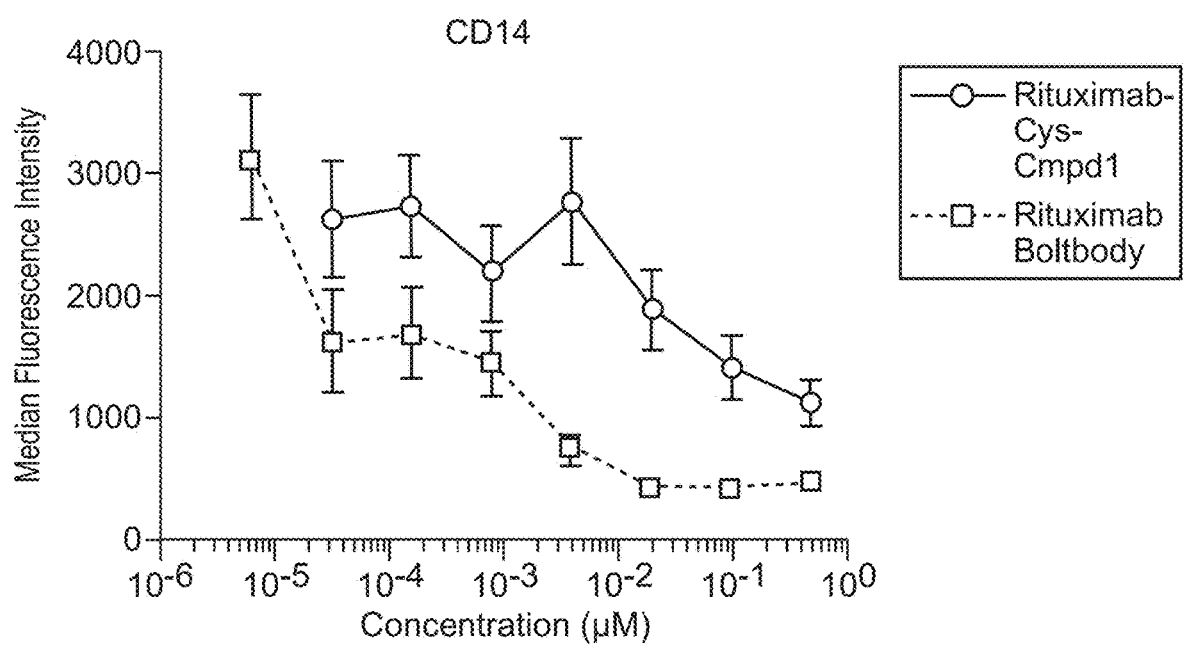

FIG. 137A shows that the BB-01 immunoconjugate produced according to the BB-01 SATA method (Rituximab Boltbody) is superior at eliciting CD14 downregulation on myeloid cells as compared to the rituximab immunoconjugate conjugated through the interchain disulfides residues following TCEP reduction via SMCC-Cmpd1 (Rituximab-Cys-Cmpd1). Data were obtained following 18-hour incubation with either Rituximab Boltbody or Rituximab-Cys-Cmpd1.

Figure 137B:
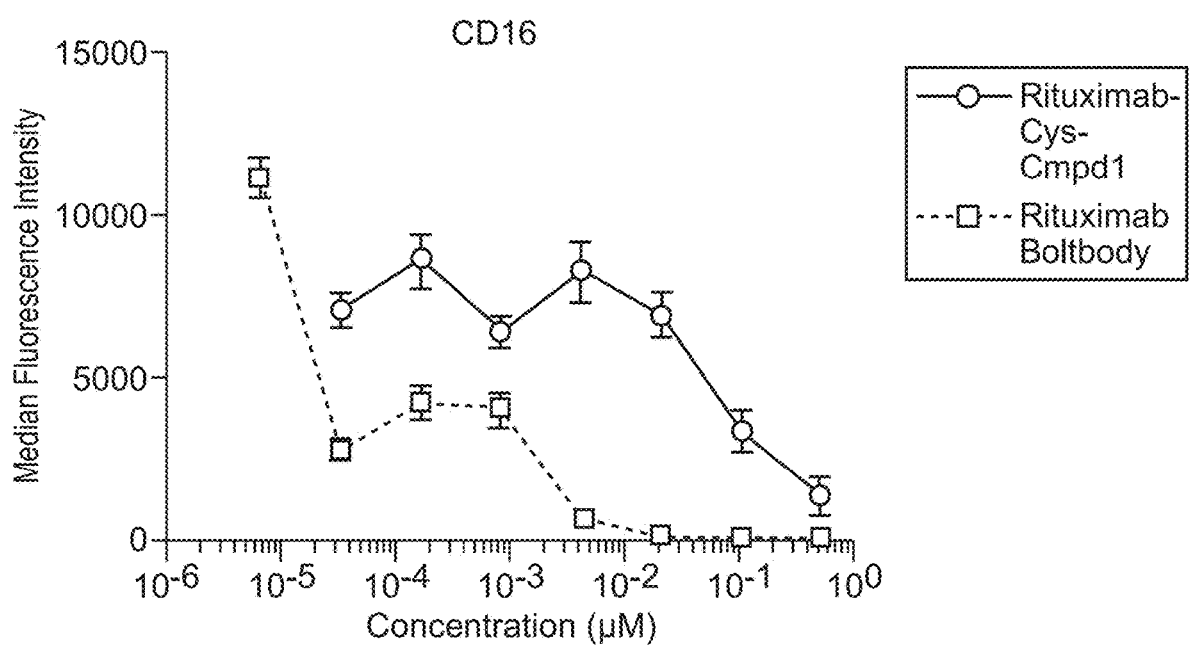

FIG. 137B shows that the BB-01 immunoconjugate produced according to the BB-01 SATA method (Rituximab Boltbody) is superior at eliciting CD16 downregulation on myeloid cells as compared to the rituximab immunoconjugate conjugated through the interchain disulfides residues following TCEP reduction via SMCC-Cmpd1 (Rituximab-Cys-Cmpd1). Data were obtained following 18-hour incubation with either Rituximab Boltbody or Rituximab-Cys-Cmpd1.

Figure 137C:
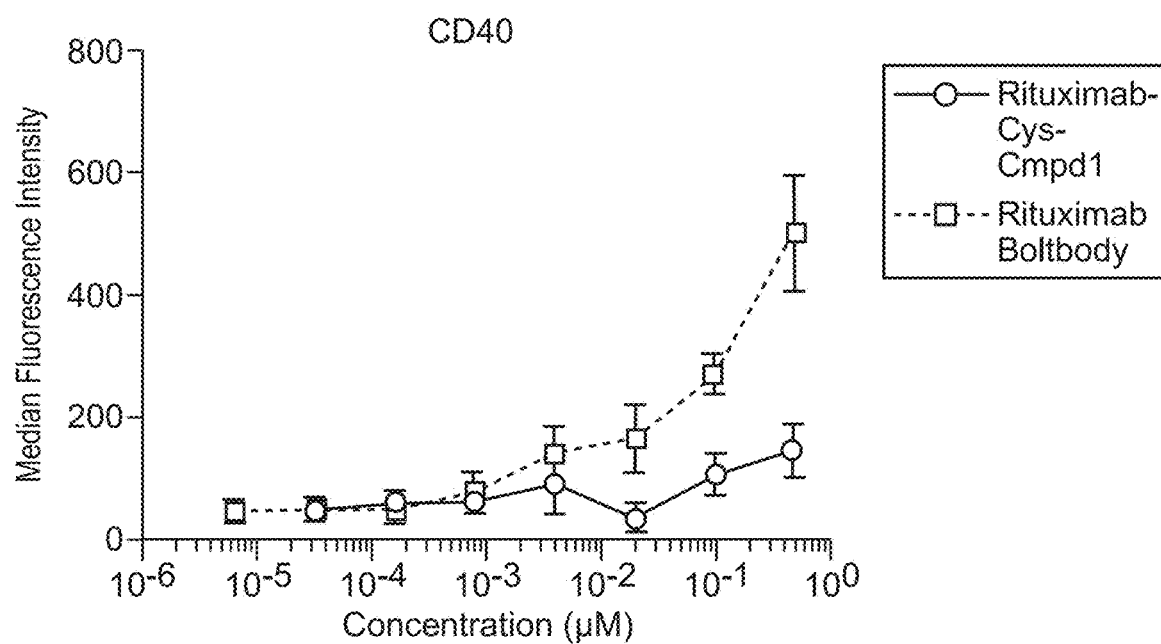

FIG. 137C shows that the BB-01 immunoconjugate produced according to the BB-01 SATA method (Rituximab Boltbody) is superior at eliciting CD40 upregulation on myeloid cells as compared to the rituximab immunoconjugate conjugated through the interchain disulfides residues following TCEP reduction via SMCC-Cmpd1 (Rituximab-Cys-Cmpd1). Data were obtained following 18-hour incubation with either Rituximab Boltbody or Rituximab-Cys-Cmpd1.

Figure 137D:
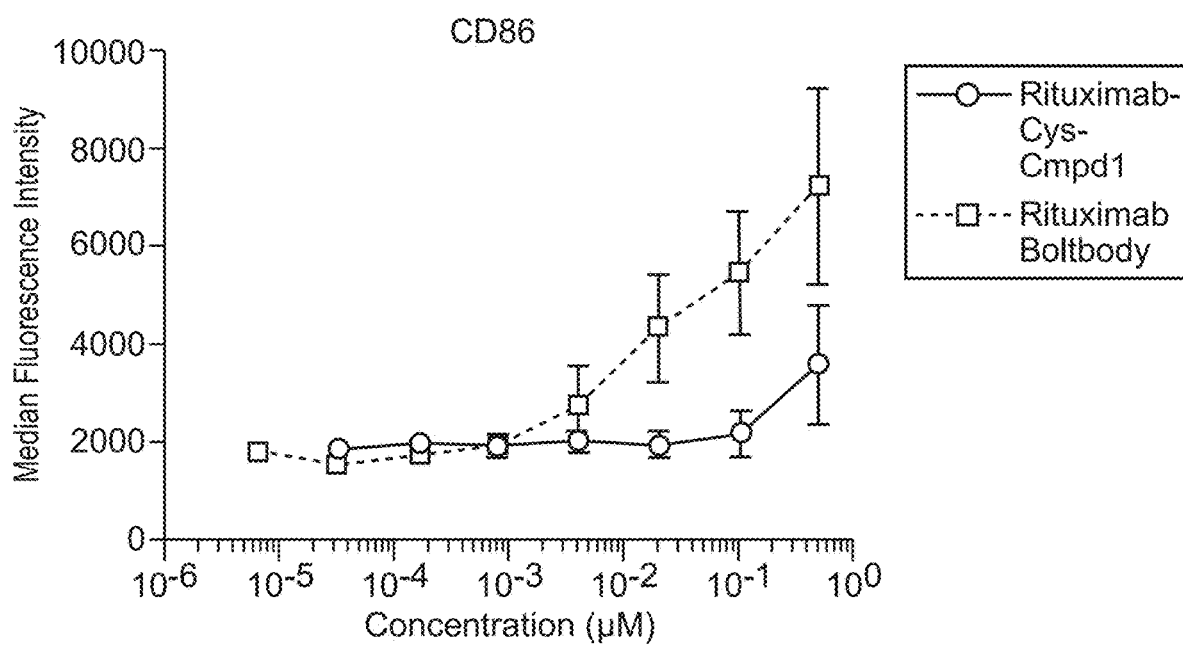

FIG. 137D shows that the BB-01 immunoconjugate produced according to the BB-01 SATA method (Rituximab Boltbody) is superior at eliciting CD86 upregulation on myeloid cells as compared to the rituximab immunoconjugate conjugated through the interchain disulfides residues following TCEP reduction via SMCC-Cmpd1 (Rituximab-Cys-Cmpd1). Data were obtained following 18-hour incubation with either Rituximab Boltbody or Rituximab-Cys-Cmpd1.

Figure 137E:
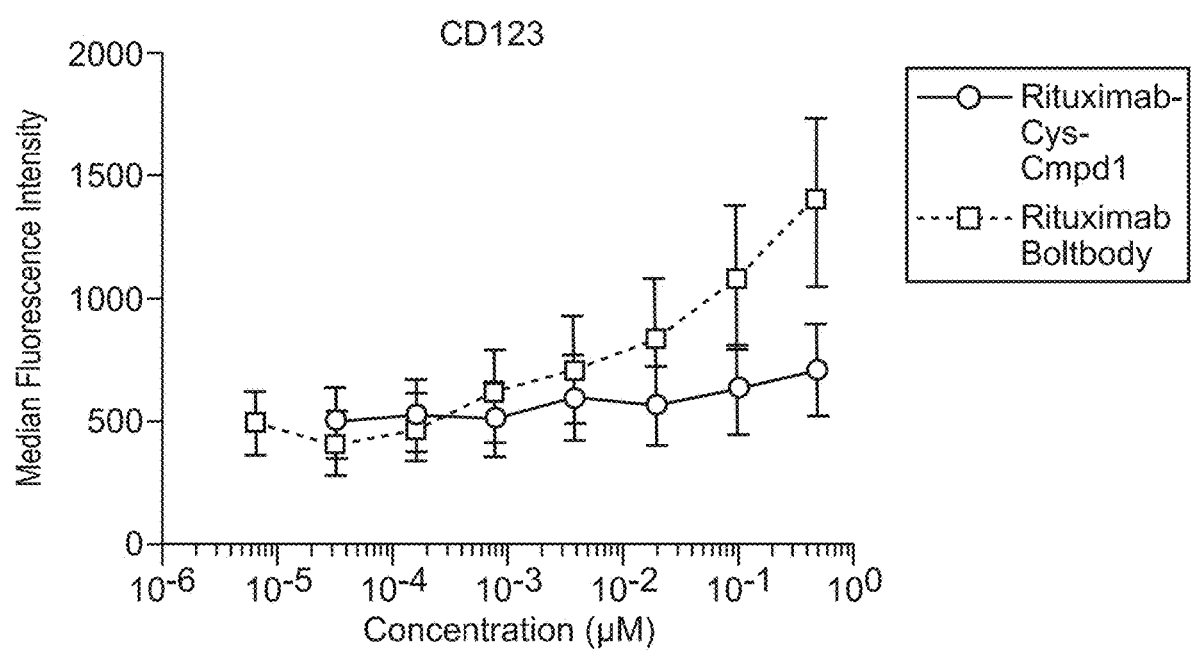

FIG. 137E shows that the BB-01 immunoconjugate produced according to the BB-01 SATA method (Rituximab Boltbody) is superior at eliciting CD123 upregulation on myeloid cells as compared to the rituximab immunoconjugate conjugated through the interchain disulfides residues following TCEP reduction via SMCC-Cmpd1 (Rituximab-Cys-Cmpd1). Data were obtained following 18-hour incubation with either Rituximab Boltbody or Rituximab-Cys-Cmpd1.

Figure 137F:
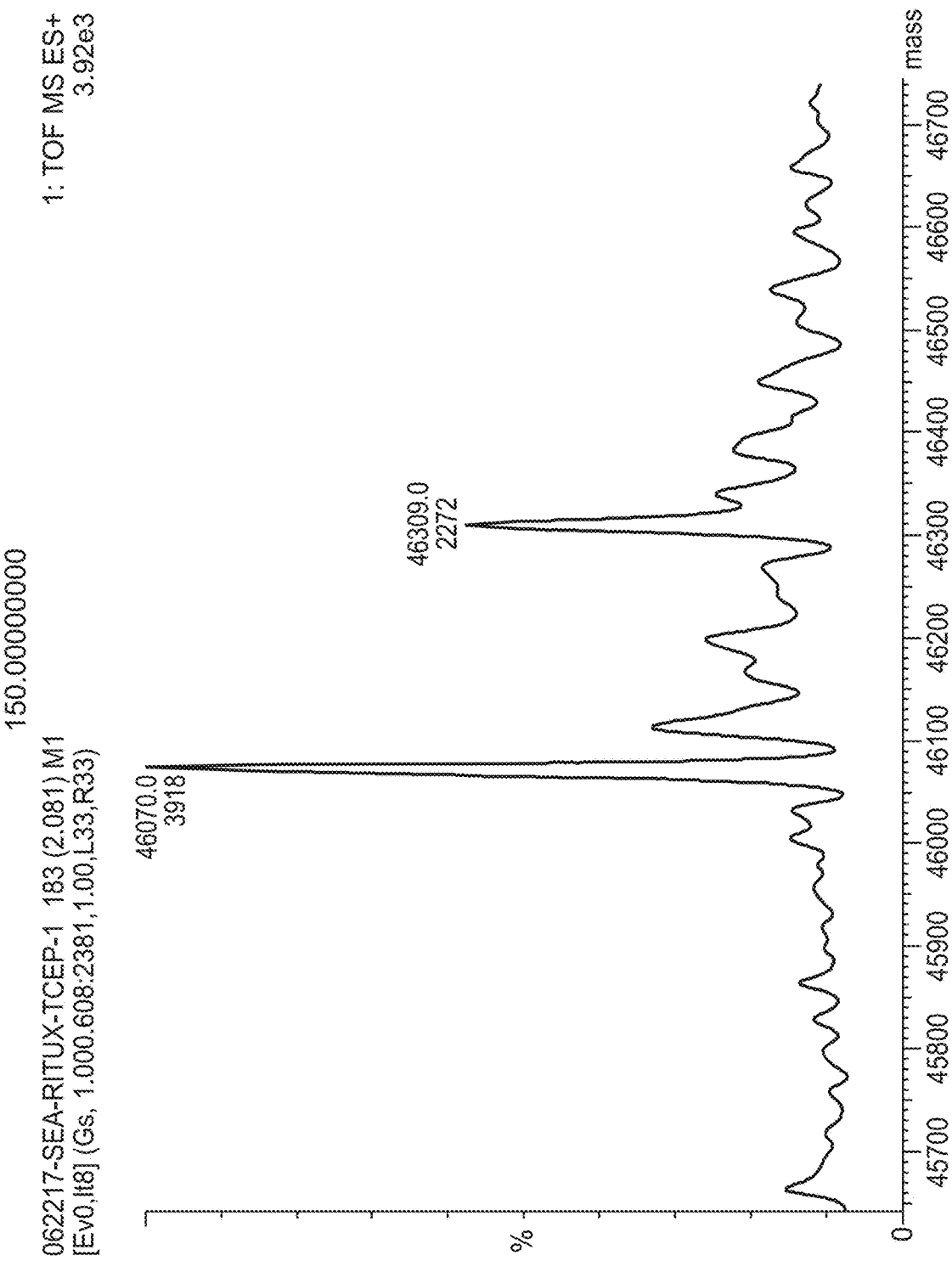

FIG. 137F shows a liquid chromatography-mass spectrometry analysis of unconjugated rituximab (Roche) following reduction with TCEP that was utilized to produce the rituximab-cys-cmpd1 immunoconjugate.

Figure 137G:
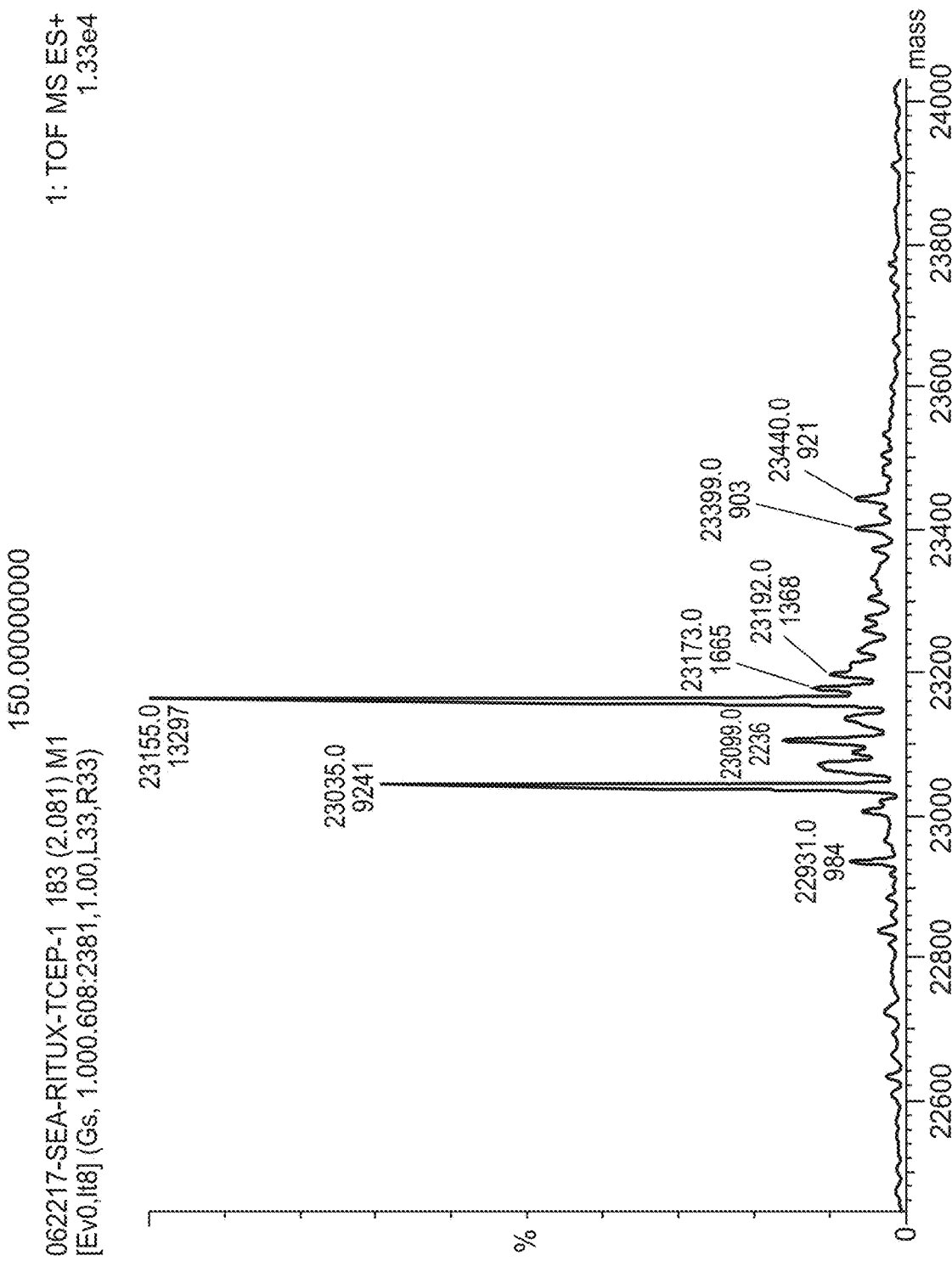

FIG. 137G shows a liquid chromatography-mass spectrometry analysis of the light chain of unconjugated rituximab (Roche) following reduction with TCEP that was utilized to produce the rituximab-cys-cmpd1 immunoconjugate.

Figure 137H:
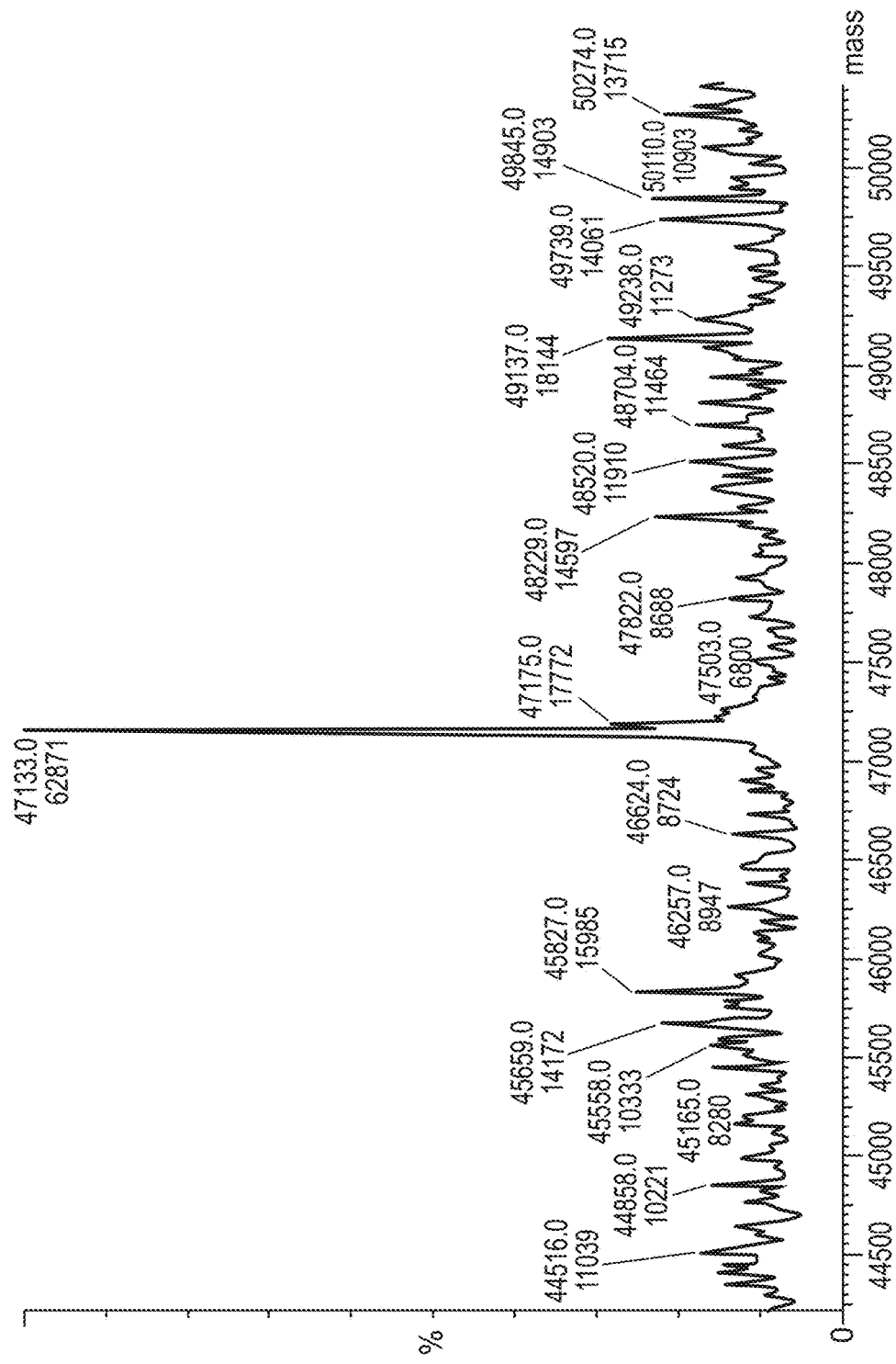

FIG. 137H shows a liquid chromatography-mass spectrometry analysis of the heavy chain of the rituximab-cys-cmpd1 immunoconjugate.

Figure 137I:
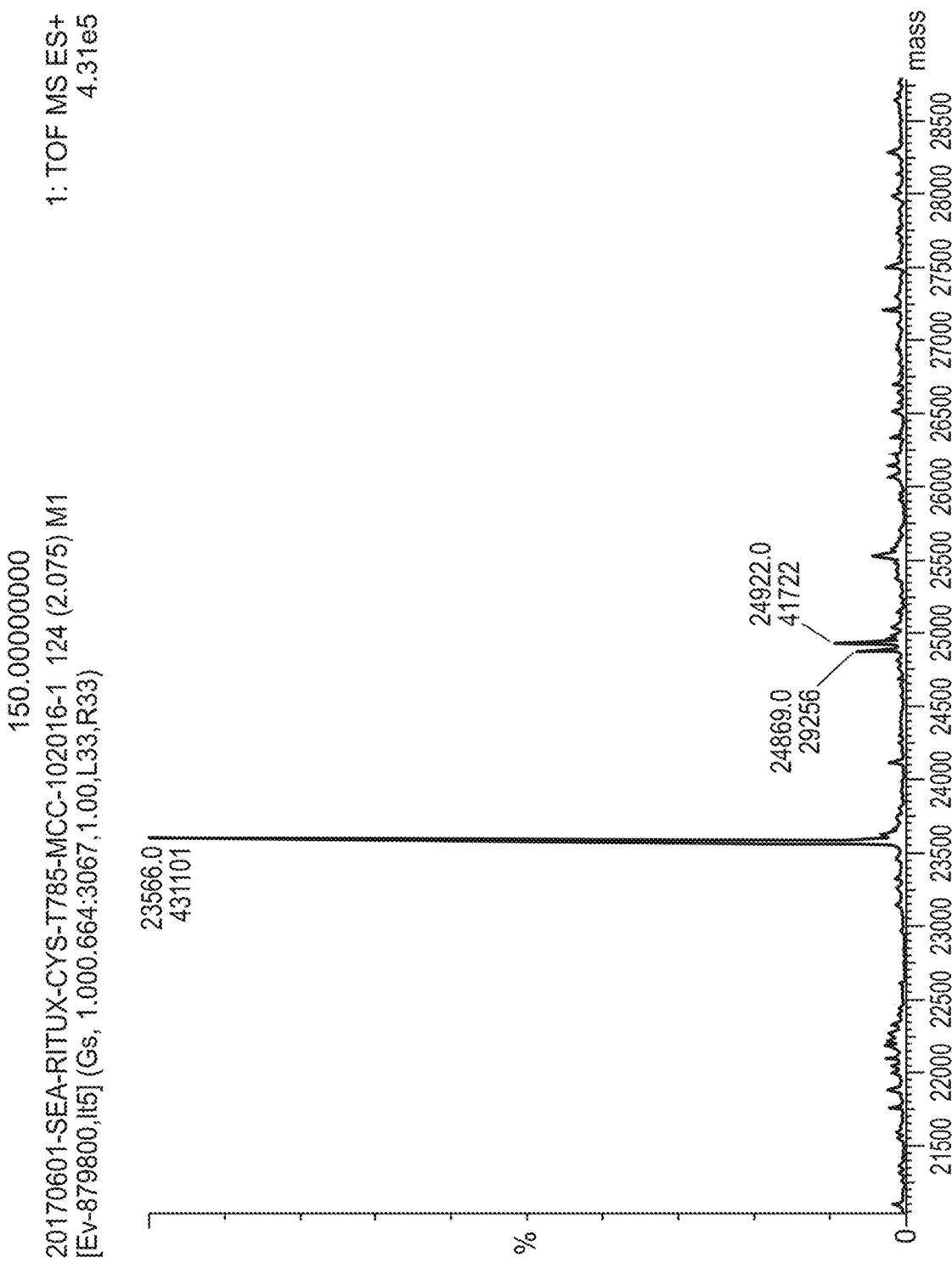

FIG. 137I shows a liquid chromatography-mass spectrometry analysis of the heavy chain of the rituximab-cys-cmpd1 immunoconjugate.

FIG. 138A shows the DNA sequence for the vector encoding the heavy chain of wildtype rituximab.

FIG. 138B shows the DNA sequence for the vector encoding the kappa light chain of rituximab with the V205C mutation (denoted using kabat numbering).

Figure 138C:
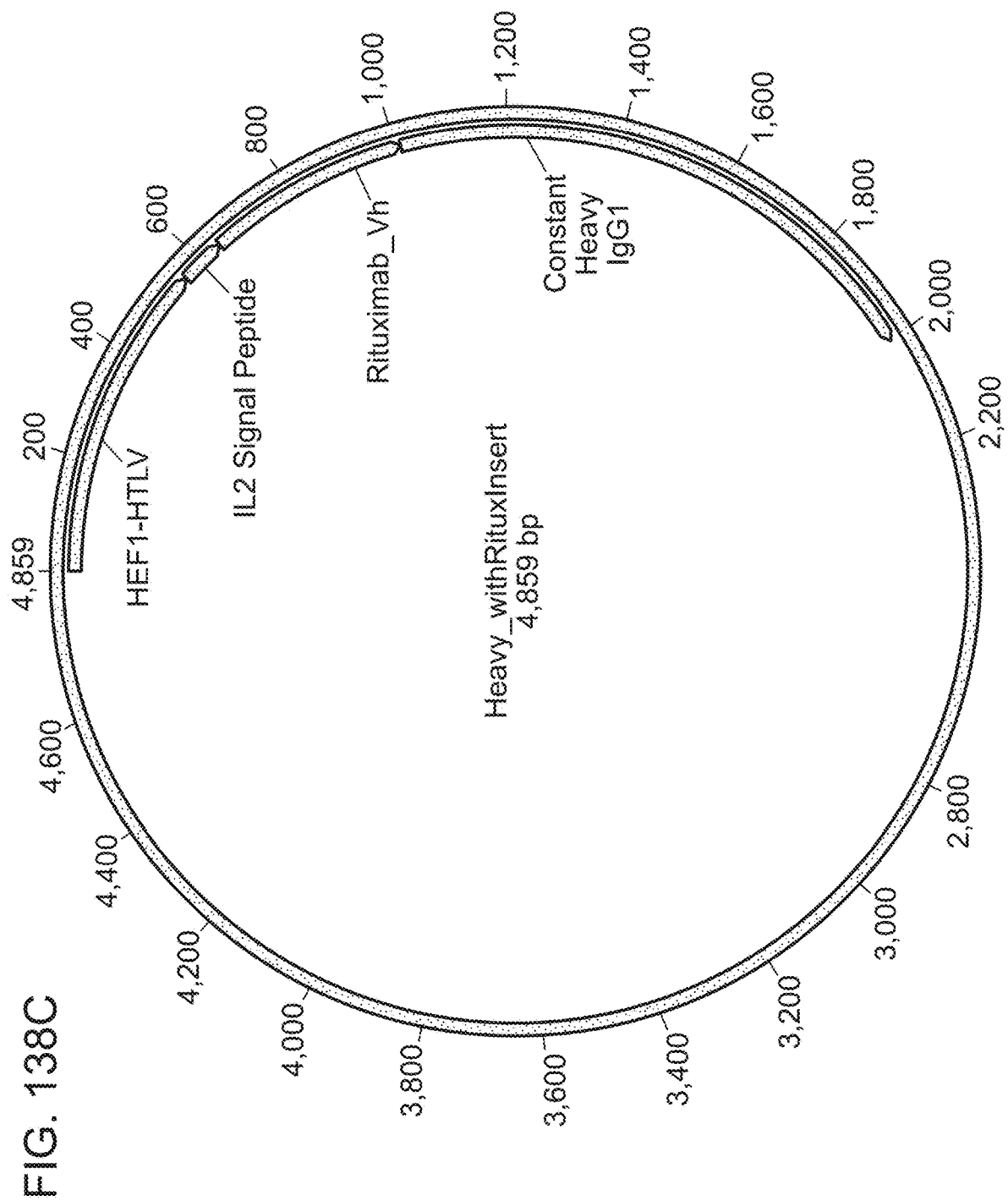

FIG. 138C shows the vector map for the pFUSE-CHIg-hG1 cloning plasmid (Invivogen, pfuse-hchg1) encoding for the wildtype rituximab IgG1 heavy chain.

Figure 138D:
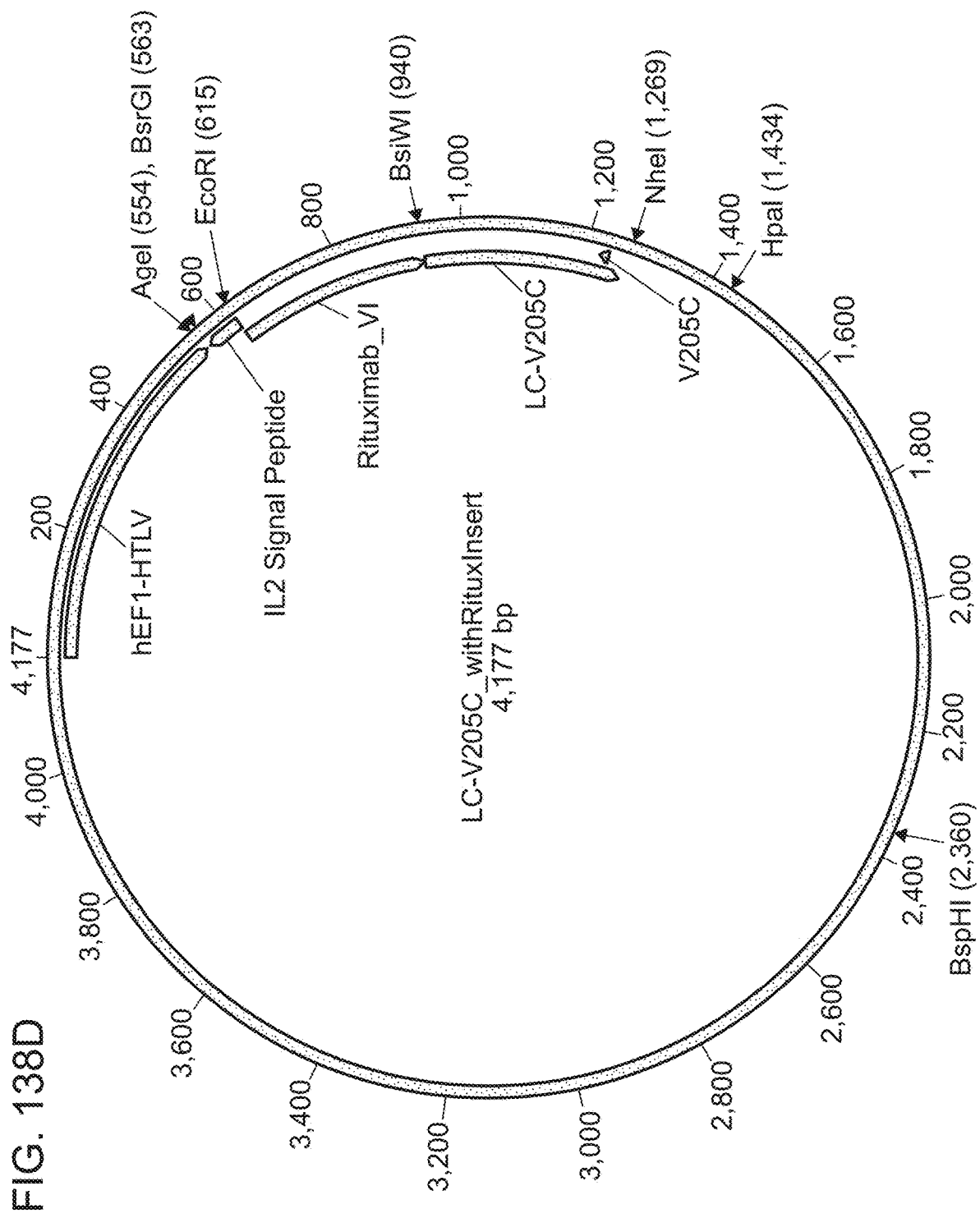

FIG. 138D shows the vector map for the pFUSE2-CLIg-hK cloning plasmid (Invivogen, pfuse2-hclk) engineered to encode the V205C mutation in the constant region of the rituximab Ig kappa light chain.

Figure 138E:
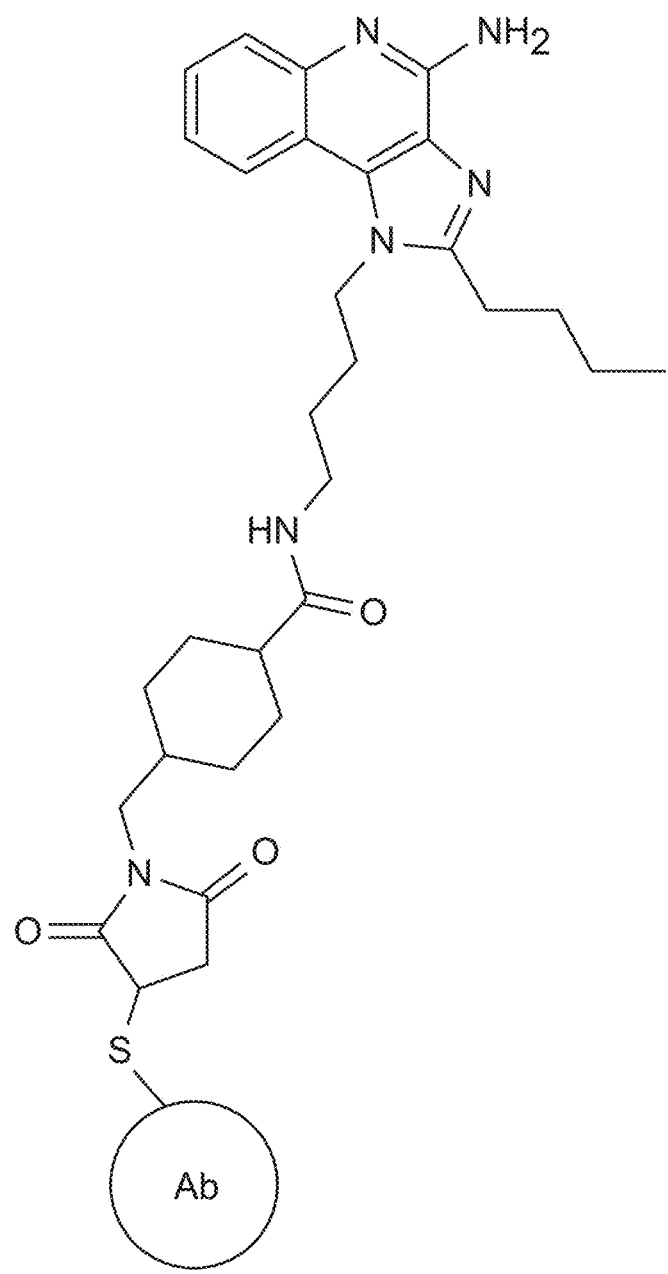

FIG. 138E shows the structure of the rituximab-V205C immunoconjugate produced by direct linkage of compound 1-SMCC to the engineered cysteine residues as described in FIG. 138D.

Figure 138F:
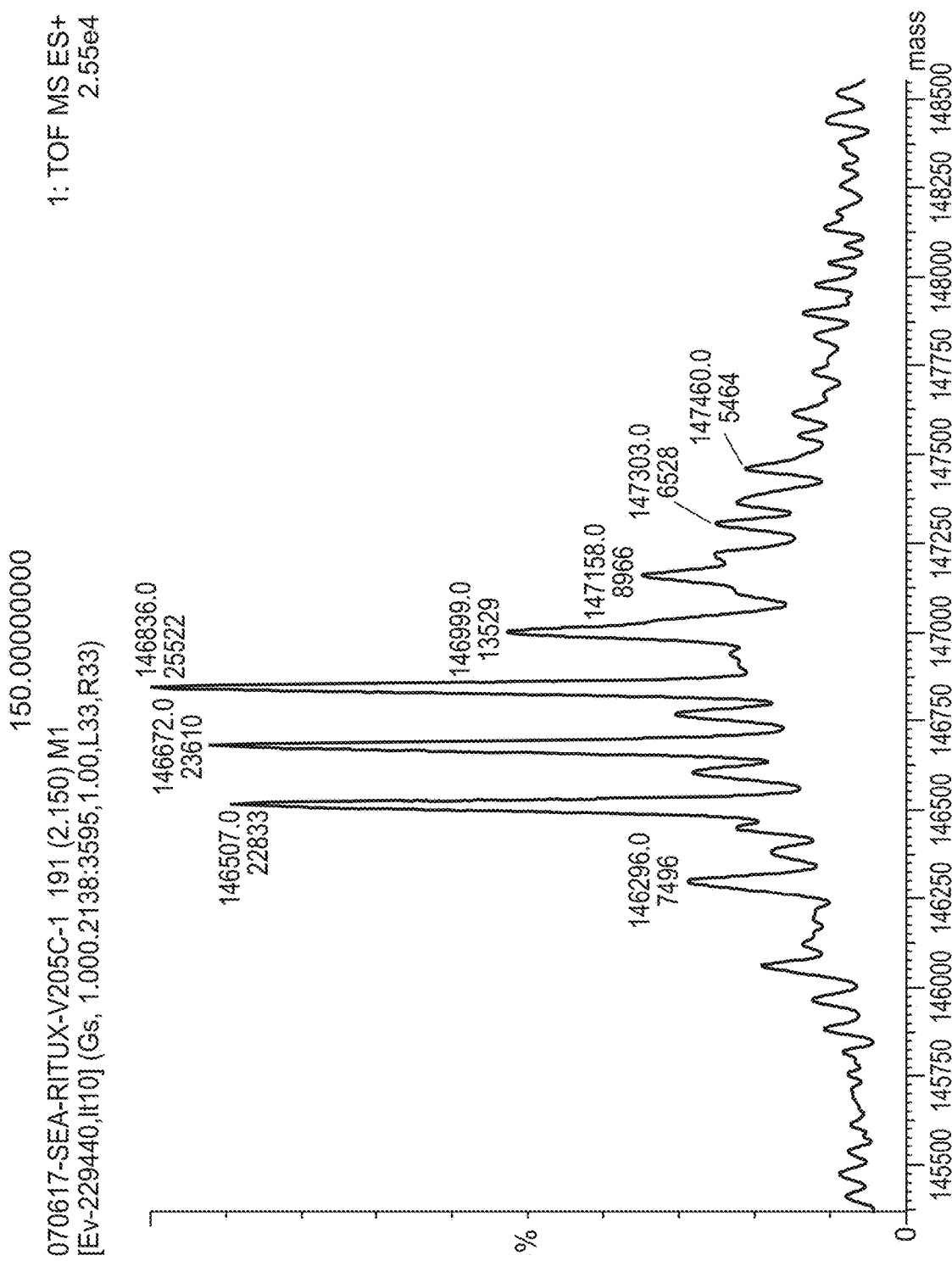

FIG. 138F shows a liquid chromatography-mass spectrometry analysis of unconjugated rituximab containing the V205C mutation that was utilized to produce the rituximab-V205C immunoconjugate.

Figure 138G:
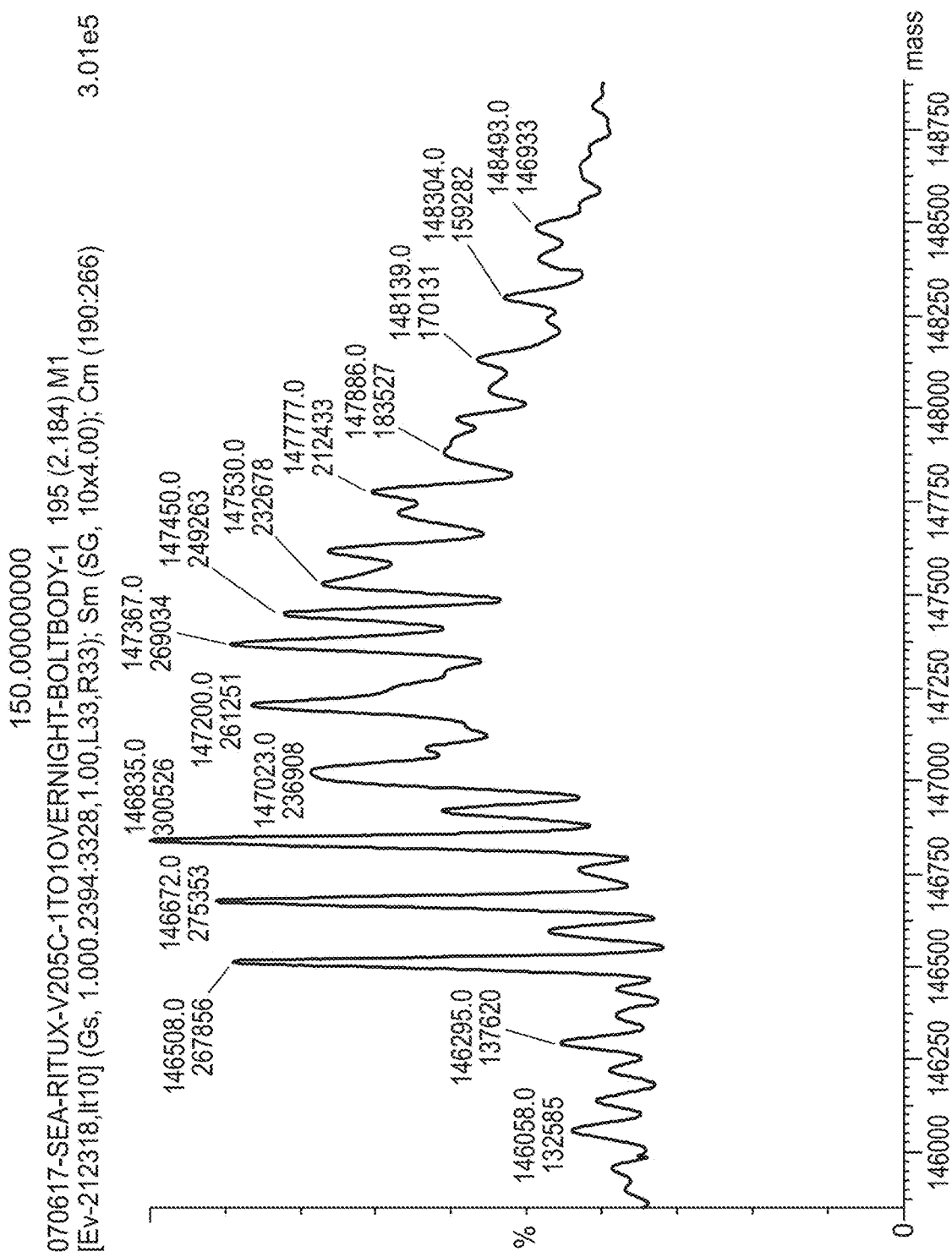

FIG. 138G shows a liquid chromatography-mass spectrometry analysis of the rituximab-V205C immunoconjugate produced by direct linkage of compound 1-SMCC to the engineered cysteine residues as described in FIG. 138D.

Figure 14A:
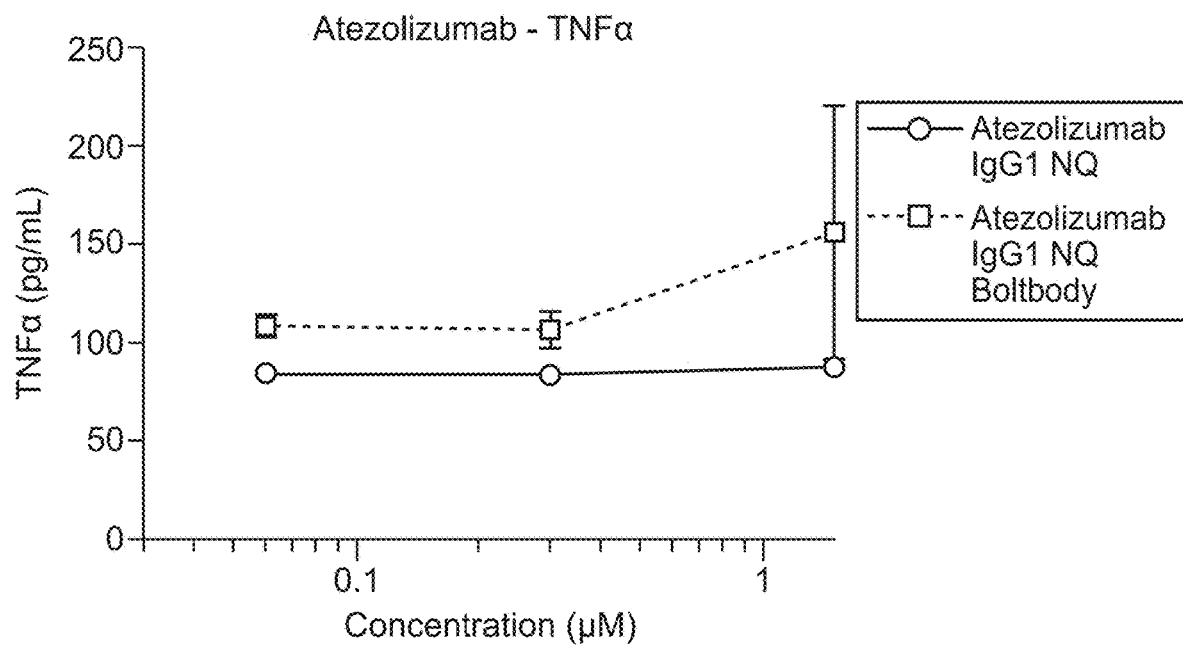
FIG. 14A shows that atezolizumab immunoconjugate (Atezolizumab IgG1 NQ Boltbody)-differentiated cells secrete higher amounts of TNFα than atezolizumab-differentiated cells.
Figure 139:
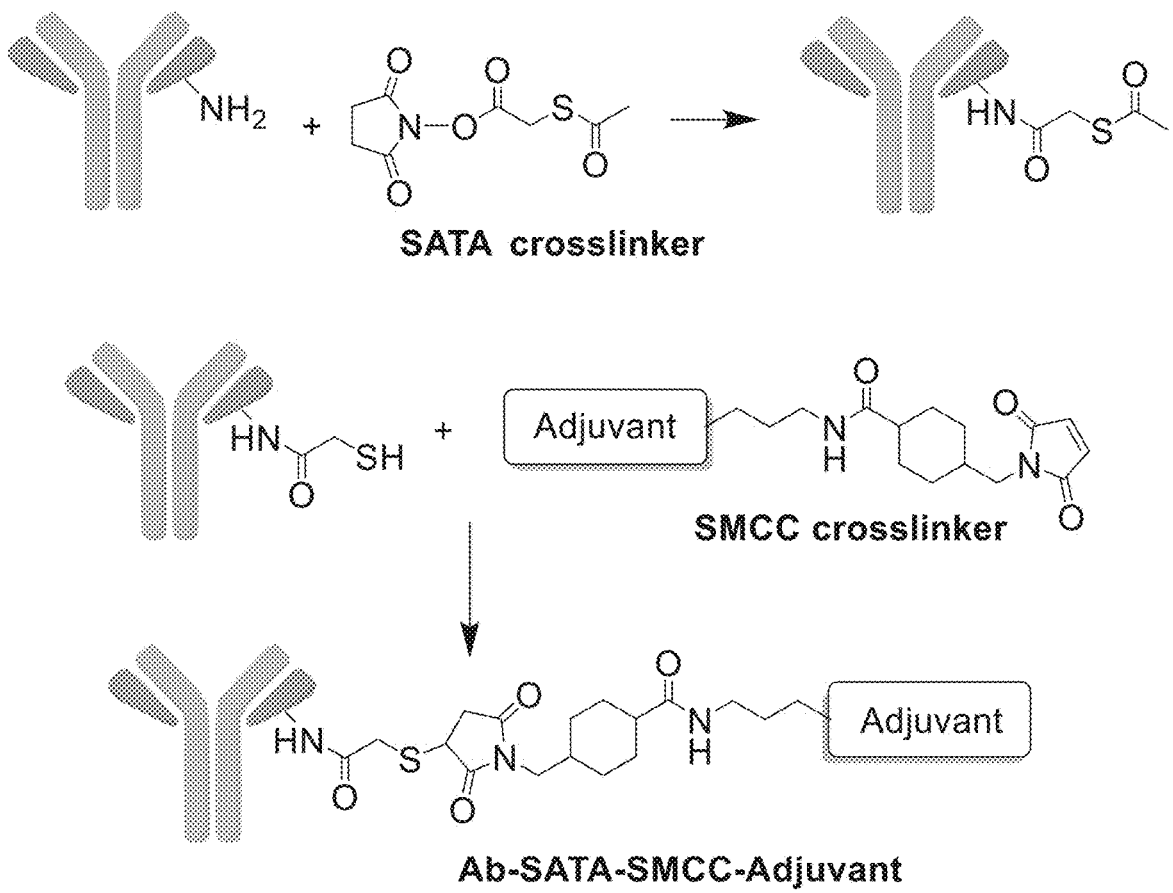
Figure 140:
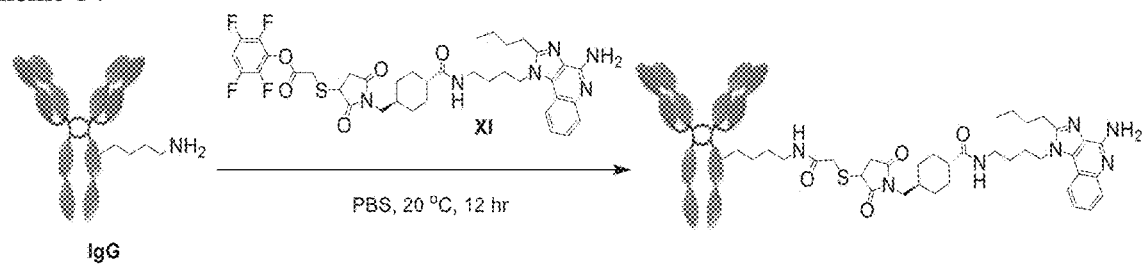
Figure 141:
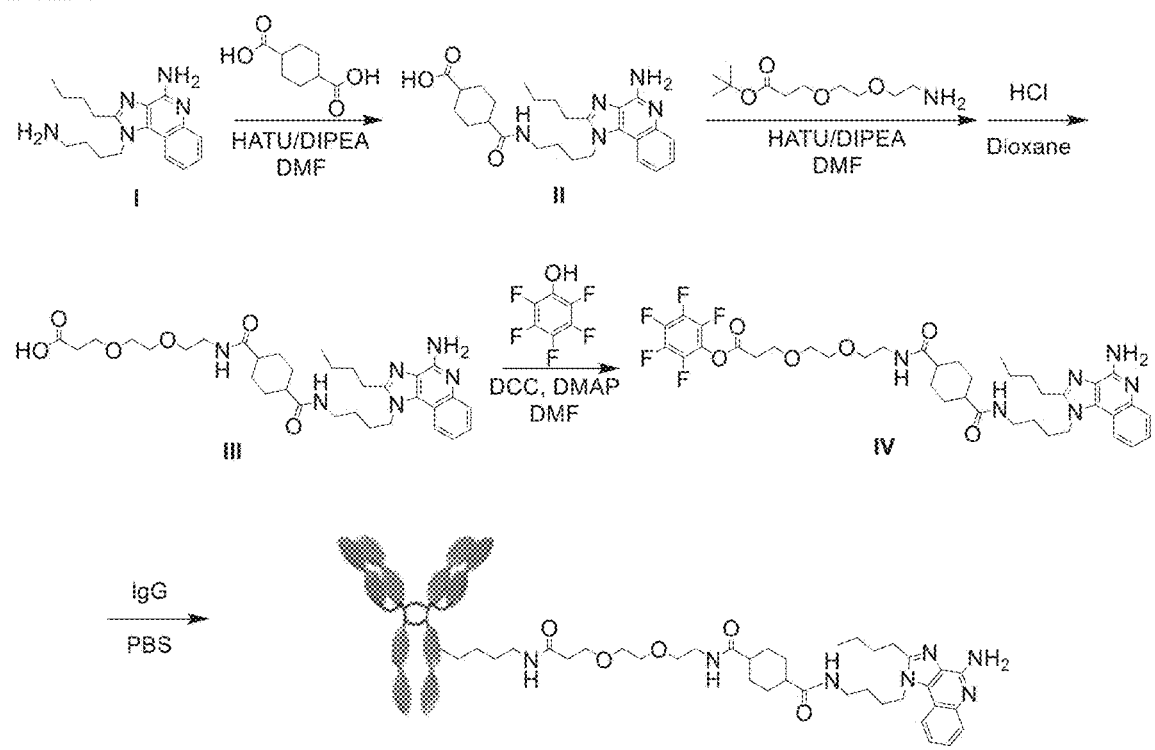
Figure 142:
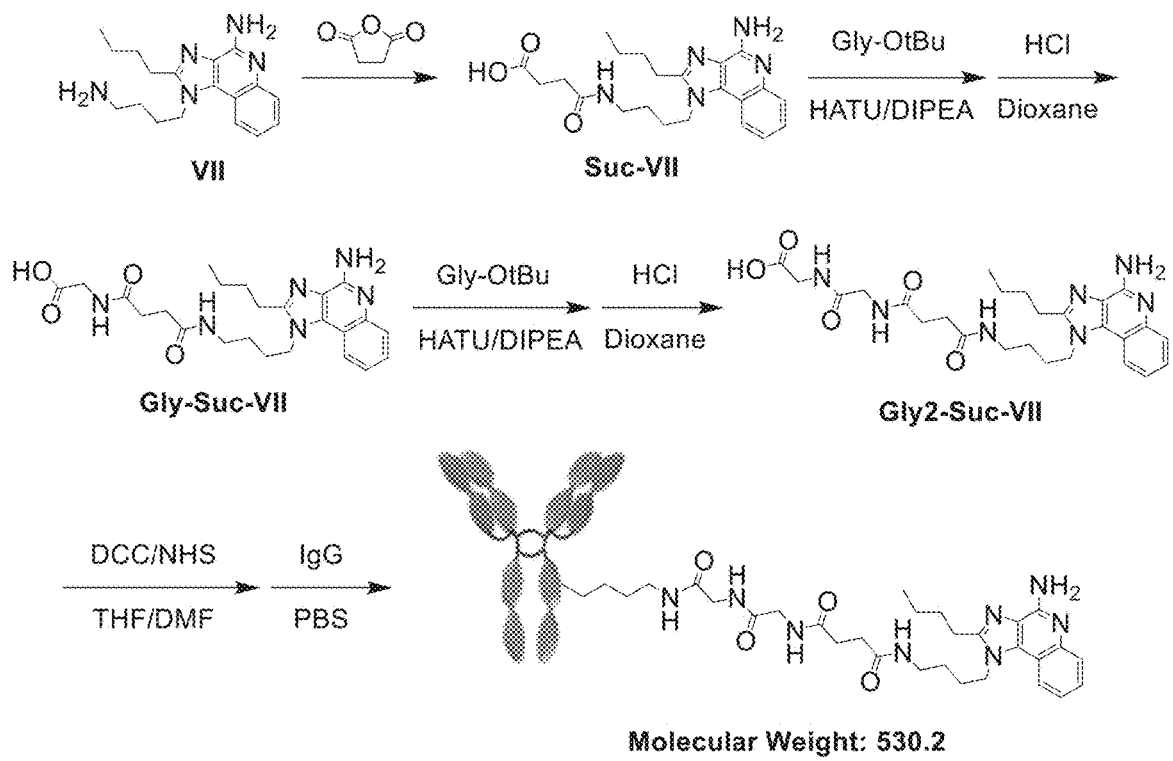
Figure 143:
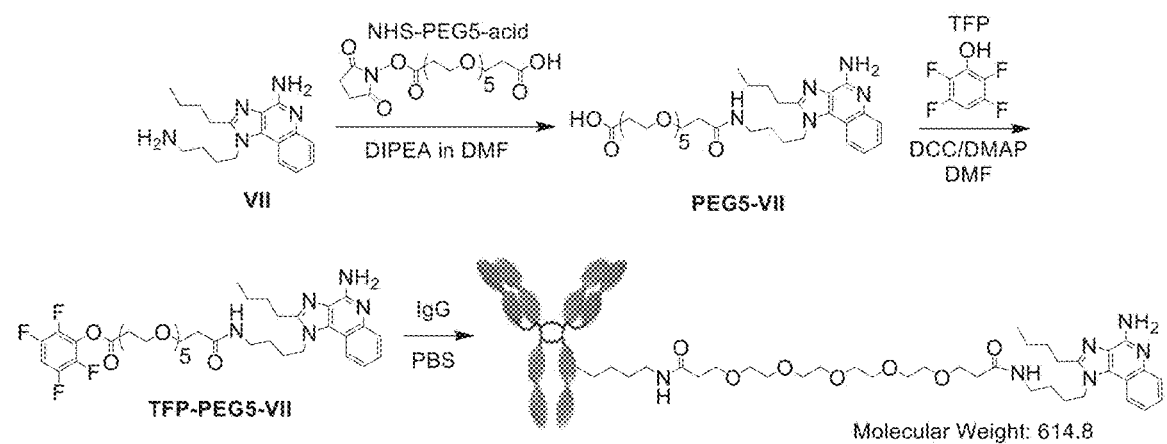
Figure 144:
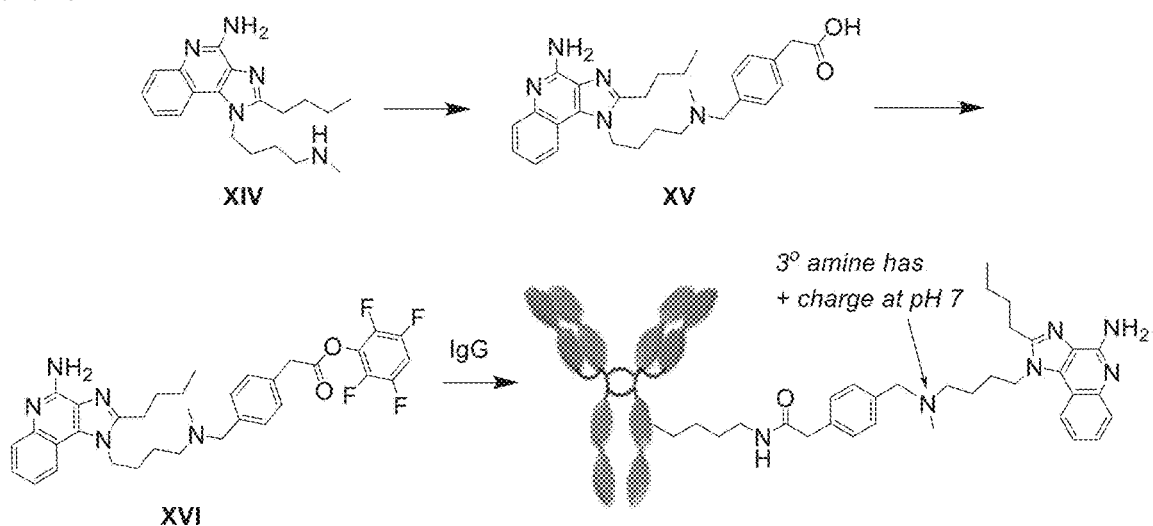
Figure 145:
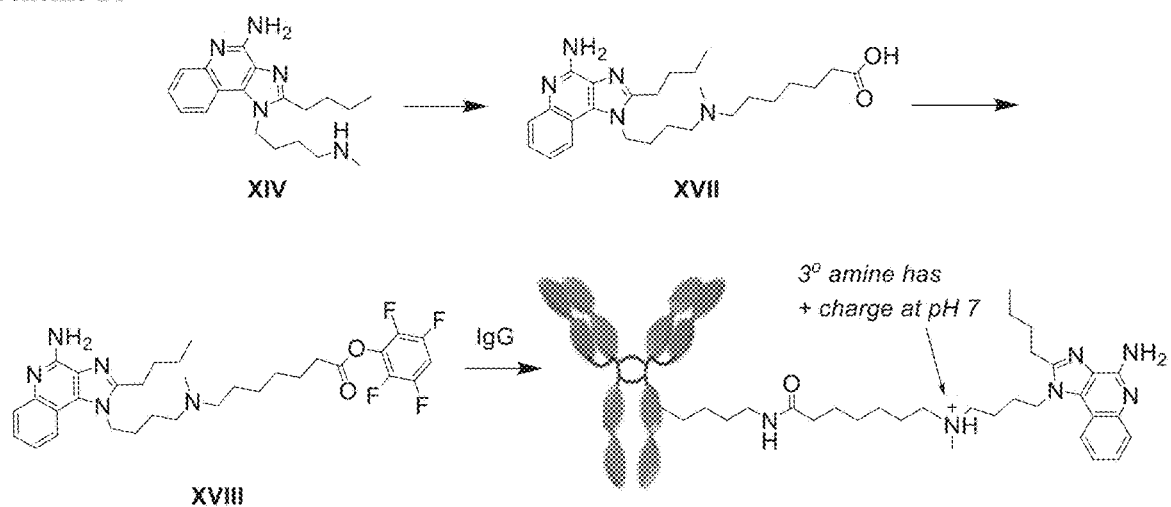
Figure 146:
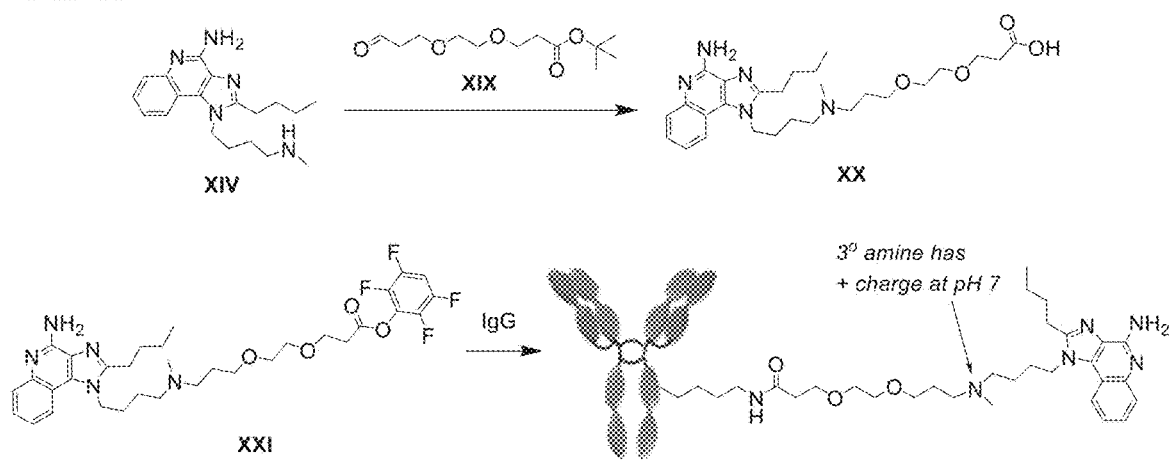
Figure 147:
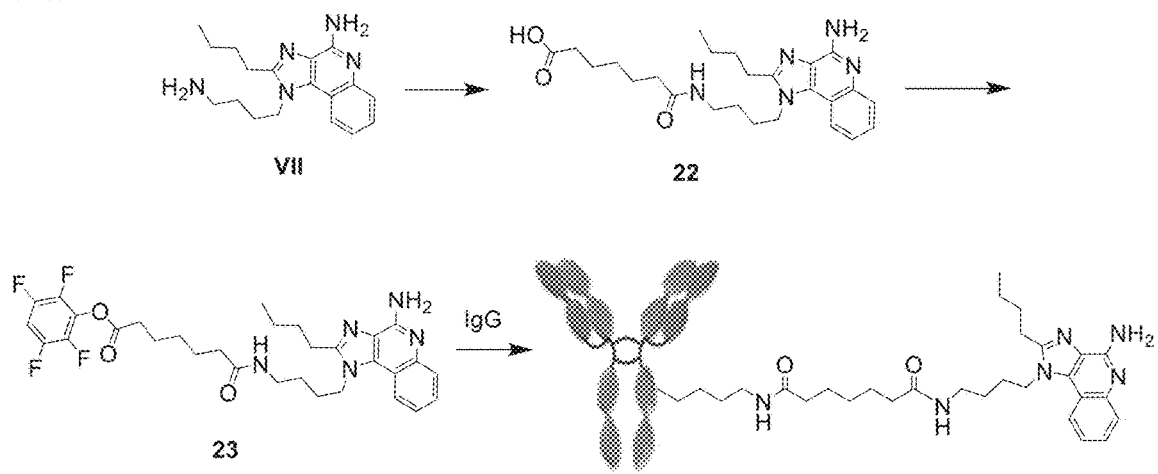
Figure 148:
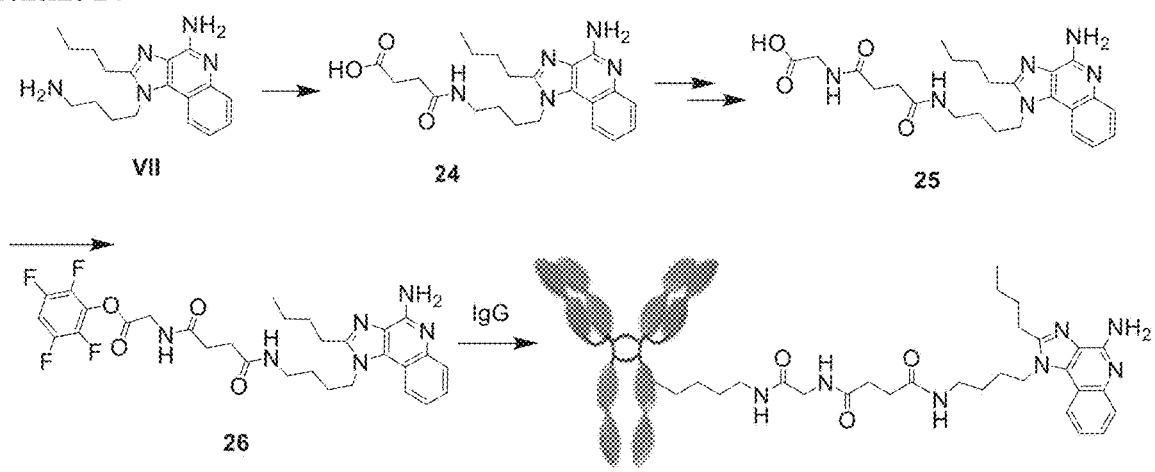
Figure 149:
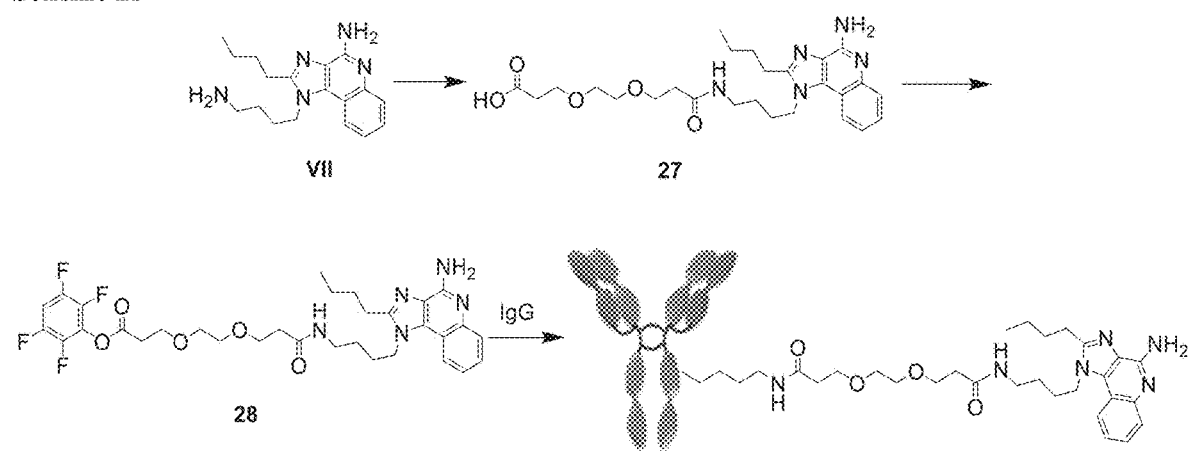
Figure 150:
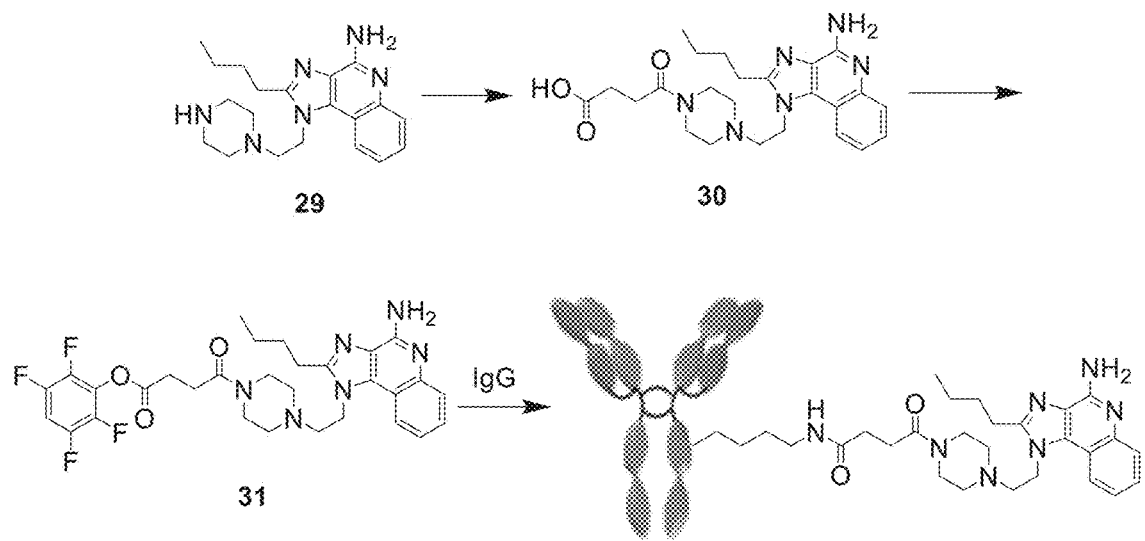
Figure 151:
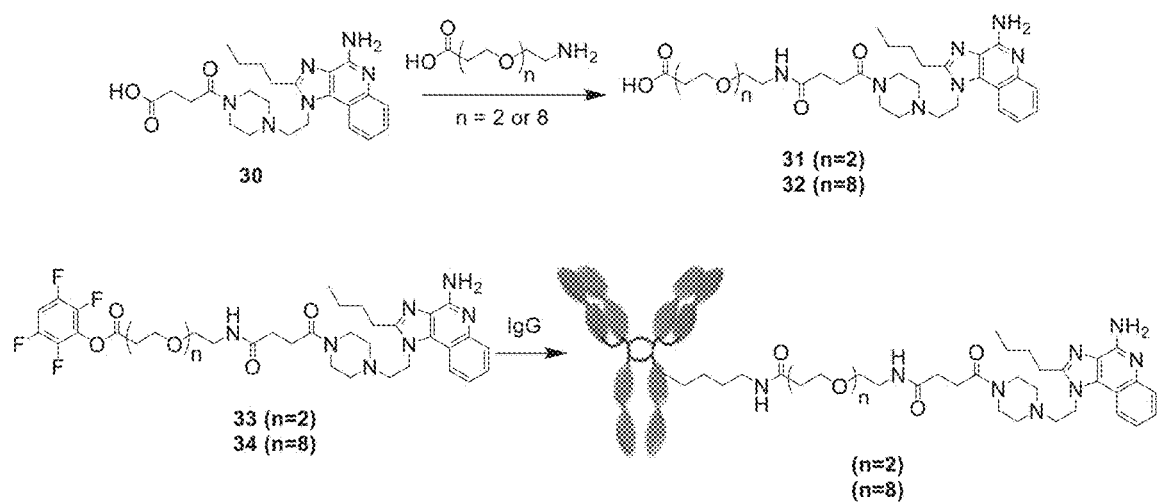

FIG. 139 shows synthetic Scheme 3 of Example 2.
FIG. 14O shows synthetic Scheme 14 of Example 8.
FIG. 14I shows synthetic Scheme 15 of Example 9.
FIG. 142 shows synthetic Scheme 16 of Example 10.
FIG. 143 shows synthetic Scheme 17 of Example 11.
FIG. 144 shows synthetic Scheme 20 of Example 13.
FIG. 145 shows synthetic Scheme 21 of Example 14.
FIG. 146 shows synthetic Scheme 22 of Example 15.
FIG. 147 shows synthetic Scheme 23 of Example 16.
FIG. 148 shows synthetic Scheme 24 of Example 17.
FIG. 149 shows synthetic Scheme 25 of Example 18.
FIG. 15O shows synthetic Scheme 27 of Example 20.
FIG. 15I shows synthetic Scheme 28 of Example 21.

DETAILED DESCRIPTION OF THE INVENTION

General

The invention provides antibody-adjuvant immunoconjugates having a number of advantages including: antibodies that promote antibody-dependent cellular cytotoxicity, antibody-dependent cellular phagocytosis and antibodies that block the actions of cancer produced proteins that act as immune checkpoint molecules, adjuvants that promote dendritic cell activation and T cell proliferation, and covalent linkages between antibody and adjuvant that promote anti-tumor efficacy. For example, in some cases human monocytes undergo DC differentiation following overnight stimulation with immunoconjugates of the invention, whereas DC differentiation protocols with known stimulants (e.g., GM-CSF and IL-4) require much longer periods. Immunoconjugate-activated cells express higher amounts (e.g., in some cases several fold higher amounts) of co-stimulatory molecules and inflammatory cytokines than is achievable with known stimulants.

As demonstrated herein, immunoconjugates are quantitatively and qualitatively more effective at eliciting immune activation than non-covalently attached antibody-adjuvant mixtures. Further, as demonstrated herein, antibody-adjuvant immunoconjugates linked according to the present invention are much more effective than other known immunoconjugates. For example, immunoconjugates are disclosed in U.S. Pat. No. 8,951,528. However, these immunoconjugates fail to effectively activate myeloid cells (see for example, FIGS. 128A-129S). Another publication, US Patent Application Publication 2017/0158772 discloses immunoconjugates, as well. The immunoconjugates disclosed therein also do not effectively activate myeloid cells as seen in FIGS. 67A-68P. International Patent Application Publication WO 2015/103987 A1 shows in claim 1 an immunoconjugate attachment site to an adjuvant (resiquimod) in a location that, through experimentation, inactivates the adjuvant and results in negligible myeloid activation. The publication also indicates that conjugation of the linker-adjuvant to the antibody occurs through cysteine hinge residues (thioether linkages) (WO 2015/103987, paragraphs 0273-0273) following reduction of the antibody with an excess of DTT. Through experimentation, this mode of conjugation prevents the immunoconjugate from effectively activating myeloid cells (see FIGS. 67A-68P and 137A-137I). In contrast, the immunoconjugates of the invention provide superior biological activity as seen, for example, in FIGS. 67G-K, 128A-12M, 129E-129, and 137A-137I.

Finally, systemic administration of the adjuvant-antibody conjugates allows for the simultaneous targeting of the primary tumor and associated metastases without the need for intra-tumoral injections and surgical resection.

Figure 1:
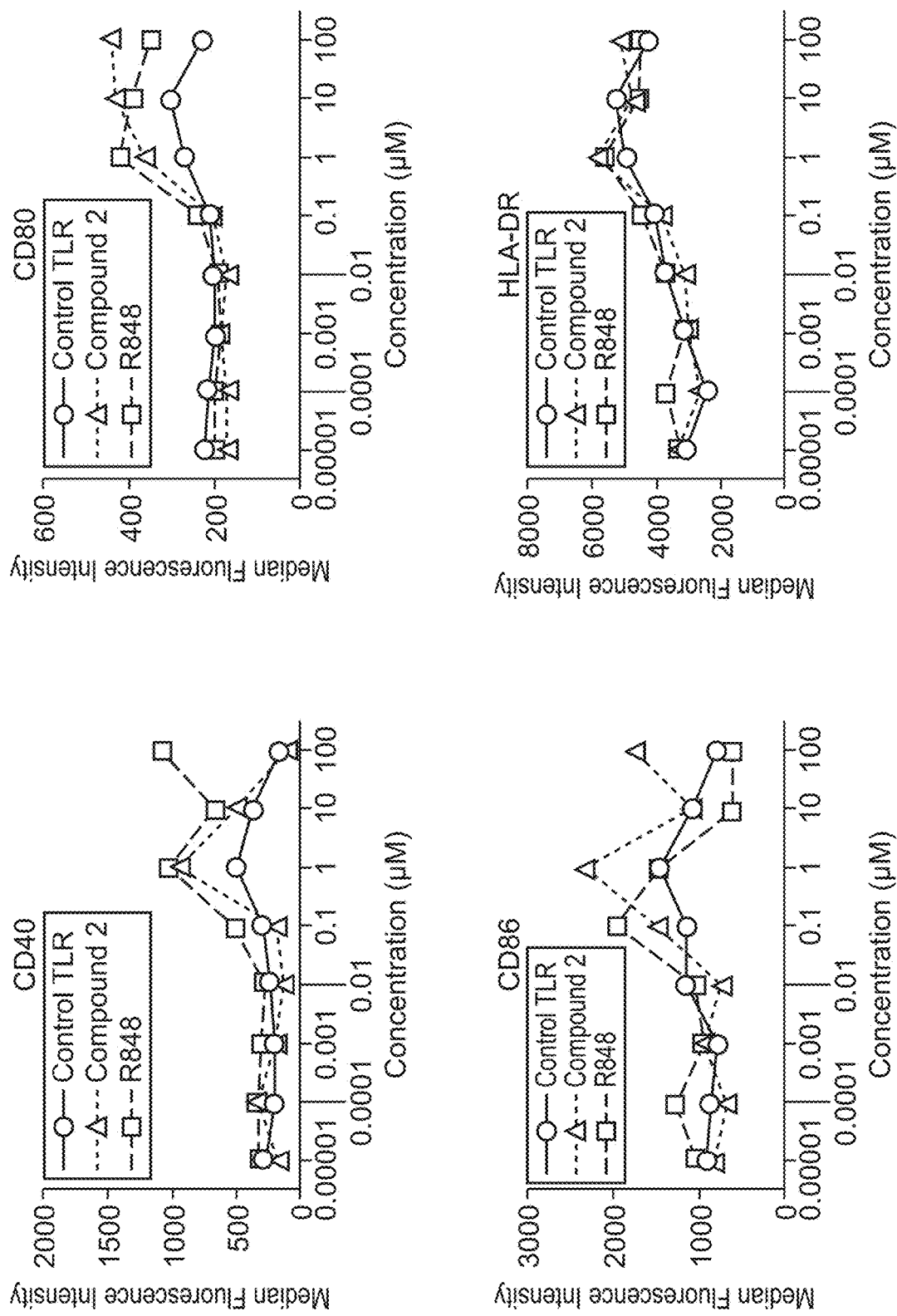
FIG. 1 shows that functionalized adjuvant is a potent inducer of myeloid cell activation. Peripheral blood antigen presenting cells (APCs) were stimulated with 10-fold serial dilutions of R848, Compound 2 or a control TLR agonist at 37° C. After 18 hours, cells were analyzed via flow cytometry. Data are presented as median fluorescence intensity of each indicated marker; n=3.

As demonstrated by FIGS. 1-138G, numerous immunoconjugates were created and assayed in accordance with the invention and other sources.

Definitions

As used herein, the term "immunoconjugate" refers to an antibody construct, or antibody, that is covalently bonded to a non-naturally occurring chemical moiety as described herein. The terms "immunoconjugate," "antibody-adjuvant immunoconjugate," "AAC," and "Boltbody" are used interchangeably herein.

As used herein, the phrase "antibody construct" refers to polypeptide comprising an antigen binding domain and an Fc domain. An antibody construct can comprise an antibody.

As used herein, the phrase "antigen binding domain" refers to a protein, or a portion of a protein, that specifically binds a specified antigen (e.g., a paratope). For example, that portion of an antigen-binding protein that contains the amino acid residues that interact with an antigen and confer on the antigen-binding protein its specificity and affinity for the antigen.

As used herein, the phrase "Fc domain" refers to the fragment crystallizable region, or the tail region of an antibody. The Fc domain interacts with Fc receptors on cells' surfaces.

As used herein, the phrase "targeting binding domain" refers to a protein, or a portion of a protein, that specifically binds a second antigen that is distinct from the antigen bound by the antigen binding domain of the immunoconjugates. The targeting binding domain can be conjugated to the antibody construct at a C-terminal end of the Fc domain.

As used herein, the term "antibody" refers to a polypeptide comprising an antigen binding region (including the complementarity determining region (CDRs)) from an immunoglobulin gene or fragments thereof that specifically binds and recognizes an antigen. The recognized immunoglobulin genes include the kappa, lambda, alpha, gamma, delta, epsilon, and mu constant region genes, as well as numerous immunoglobulin variable region genes.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. Light chains are classified as either kappa or lambda. Heavy chains are classified as gamma, mu, alpha, delta, or epsilon, which in turn define the immunoglobulin classes, IgG, IgM, IgA, IgD and IgE, respectively.

IgG antibodies are large molecules of about 150 kDa composed of four peptide chains. IgG antibodies contain two identical class γ heavy chains of about 50 kDa and two identical light chains of about 25 kDa, thus a tetrameric quaternary structure. The two heavy chains are linked to each other and to a light chain each by disulfide bonds. The resulting tetramer has two identical halves, which together form the Y-like shape. Each end of the fork contains an identical antigen binding site. There are four IgG subclasses (IgG1, 2, 3, and 4) in humans, named in order of their abundance in serum (IgG1 being the most abundant). Typically, the antigen-binding region of an antibody will be most critical in specificity and affinity of binding.

Dimeric IgA antibodies are around 320 kDa. IgA has two subclasses (IgA1 and IgA2) and can be produced as a monomeric as well as a dimeric form. The IgA dimeric form (secretory or sIgA) is the most abundant.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into a Fab' monomer. The Fab' monomer is essentially Fab with part of the hinge region (see, *Fundamental Immunology* (Paul ed., 7e ed. 2012). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature*, 348: 552-554 (1990)).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibody fragment," and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules; (2) single chain polypeptides containing only one light chain variable domain, or a fragment thereof that contains the three CDRs of the light chain variable domain, without an associated heavy chain moiety; (3) single chain polypeptides containing only one heavy chain variable region, or a fragment thereof containing the three CDRs of the heavy chain variable region, without an associated light chain moiety; (4) nanobodies comprising single Ig domains from non-human species or other specific single-domain binding modules; and (5) multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used herein, the term "biosimilar" in reference to a biological product, means that the biological product is highly similar to the reference product notwithstanding minor differences in clinically inactive components, and there are no clinically meaningful differences between the biological product and the reference product in terms of the safety, purity, and potency of the product.

As used herein, the term "epitope" means any antigenic determinant on an antigen to which the antigen-binding site, also referred to as the paratope, of an antibody binds. Epitopic determinants usually consist of chemically active surface groupings of molecules such as amino acids or sugar side chains and usually have specific three dimensional structural characteristics, as well as specific charge characteristics.

The terms "polypeptide," "peptide," and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "adjuvant" refers to a substance capable of eliciting an immune response in a subject exposed to the adjuvant.

As used herein, the term "adjuvant moiety" refers to an adjuvant that is covalently bonded to an antibody as described herein. The adjuvant moiety can elicit the immune response while bonded to the antibody, or after cleavage (e.g., enzymatic cleavage) from the antibody following administration of an immunoconjugate to the subject.

As used herein, the terms "Pattern recognition receptor" and "PRR" refer to any member of a class of conserved mammalian proteins which recognize pathogen-associated molecular patterns (PAMPs) or damage-associated molecular patterns (DAMPs), and act as key signaling elements in innate immunity. Pattern recognition receptors are divided into membrane-bound PRRs, cytoplasmic PRRs, and secreted PRRs. Examples of membrane-bound PRRs include Toll-like receptors (TLRs) and C-type lectin receptors (CLRs). Examples of cytoplasmic PRRs include NOD-like receptors (NLRs) and Rig-I-like receptors (RLRs).

As used herein, the terms "Toll-like receptor" and "TLR" refer to any member of a family of highly-conserved mammalian proteins which recognize pathogen-associated molecular patterns and act as key signaling elements in innate immunity. TLR polypeptides share a characteristic structure that includes an extracellular domain that has leucine-rich repeats, a transmembrane domain, and an intracellular domain that is involved in TLR signaling.

The terms "Toll-like receptor 1" and "TLR1" refer to nucleic acids or polypeptides sharing at least 70%; 80%, 90%, 95%, 96%, 97%, 98%, 99%, or more sequence identity to a publicly-available TLR1 sequence, e.g., GenBank accession number AAY85643 for human TLR1 polypeptide, or GenBank accession number AAG37302 for murine TLR1 polypeptide.

The terms "Toll-like receptor 2" and "TLR2" refer to nucleic acids or polypeptides sharing at least 70%; 80%, 90%, 95%, 96%, 97%, 98%, 99%, or more sequence identity to a publicly-available TLR2 sequence, e.g., GenBank accession number AAY85648 for human TLR2 polypeptide, or GenBank accession number AAD49335 for murine TLR2 polypeptide.

The terms "Toll-like receptor 3" and "TLR3" refer to nucleic acids or polypeptides sharing at least 70%; 80%, 90%, 95%, 96%, 97%, 98%, 99%, or more sequence identity to a publicly-available TLR3 sequence, e.g., GenBank accession number AAC34134 for human TLR3 polypeptide, or GenBank accession number AAK26117 for murine TLR3 polypeptide.

The terms "Toll-like receptor 4" and "TLR4" refer to nucleic acids or polypeptides sharing at least 70%; 80%, 90%, 95%, 96%, 97%, 98%, 99%, or more sequence identity to a publicly-available TLR4 sequence, e.g., GenBank accession number AAY82270 for human TLR4 polypeptide, or GenBank accession number AAD29272 for murine TLR4 polypeptide.

The terms "Toll-like receptor 5" and "TLR5" refer to nucleic acids or polypeptides sharing at least 70%; 80%, 90%, 95%, 96%, 97%, 98%, 99%, or more sequence identity to a publicly-available TLR5 sequence, e.g., GenBank accession number ACM69034 for human TLR5 polypeptide, or GenBank accession number AAF65625 for murine TLR5 polypeptide.

The terms "Toll-like receptor 6" and "TLR6" refer to nucleic acids or polypeptides sharing at least 70%; 80%, 90%, 95%, 96%, 97%, 98%, 99%, or more sequence identity to a publicly-available TLR6 sequence, e.g., GenBank accession number ABY67133 for human TLR6 polypeptide, or GenBank accession number AAG38563 for murine TLR6 polypeptide.

The terms "Toll-like receptor 7" and "TLR7" refer to nucleic acids or polypeptides sharing at least 70%; 80%, 90%, 95%, 96%, 97%, 98%, 99%, or more sequence identity to a publicly-available TLR7 sequence, e.g., GenBank accession number AAZ99026 for human TLR7 polypeptide, or GenBank accession number AAK62676 for murine TLR7 polypeptide.

The terms "Toll-like receptor 8" and "TLR8" refer to nucleic acids or polypeptides sharing at least 70%; 80%, 90%, 95%, 96%, 97%, 98%, 99%, or more sequence identity to a publicly-available TLR8 sequence, e.g., GenBank accession number AAZ95441 for human TLR8 polypeptide, or GenBank accession number AAK62677 for murine TLR8 polypeptide.

The terms "Toll-like receptor 7/8" and "TLR7/8" refer to nucleic acids or polypeptides that are both TLR7 agonists and TLR8 agonists.

The terms "Toll-like receptor 9" and "TLR9" refer to nucleic acids or polypeptides sharing at least 70%; 80%, 90%, 95%, 96%, 97%, 98%, 99%, or more sequence identity to a publicly-available TLR9 sequence, e.g., GenBank accession number AAF78037 for human TLR9 polypeptide, or GenBank accession number AAK28488 for murine TLR9 polypeptide.

The terms "Toll-like receptor 10" and "TLR10" refer to nucleic acids or polypeptides sharing at least 70%; 80%, 90%, 95%, 96%, 97%, 98%, 99%, or more sequence identity to a publicly-available TLR10 sequence, e.g., GenBank accession number AAK26744 for human TLR10 polypeptide.

The terms "Toll-like receptor 11" and "TLR11" refer to nucleic acids or polypeptides sharing at least 70%; 80%, 90%, 95%, 96%, 97%, 98%, 99%, or more sequence identity to a publicly-available TLR11 sequence, e.g., GenBank accession number AAS83531 for murine TLR11 polypeptide.

A "TLR agonist" is a substance that binds, directly or indirectly, to a TLR (e.g., TLR7 and/or TLR8) to induce TLR signaling. Any detectable difference in TLR signaling can indicate that an agonist stimulates or activates a TLR. Signaling differences can be manifested, for example, as changes in the expression of target genes, in the phosphorylation of signal transduction components, in the intracellular localization of downstream elements such as NK-κB, in the association of certain components (such as IRAK) with other proteins or intracellular structures, or in the biochemical activity of components such as kinases (such as MAPK).

As used herein, the term "amino acid" refers to any monomeric unit that can be incorporated into a peptide, polypeptide, or protein. Amino acids include naturally-occurring a-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid).

Naturally-occurring amino acids are those encoded by the genetic code, as well as those amino acids that are later modified, e.g., hydroxyproline, y-carboxyglutamate, and O-phosphoserine. Naturally-occurring a-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring a-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid. Amino acids may be referred to herein by either the commonly known three letter symbols or by the one-letter symbols recommended by the IUPAC-IUB Biochemical Nomenclature Commission.

As used herein, the term "immune checkpoint inhibitors" refers to any modulator that inhibits the activity of the immune checkpoint molecule. Immune checkpoint inhibitors can include, but are not limited to, immune checkpoint molecule binding proteins, small molecule inhibitors, antibodies, antibody-derivatives (including Fc fusions, Fab fragments and scFvs), antibody-drug conjugates, antisense oligonucleotides, siRNA, aptamers, peptides and peptide mimetics.

As used herein, the term "linking moiety" refers to a functional group that covalently bonds two or more moieties in a compound or material. For example, the linking moiety can serve to covalently bond an adjuvant moiety to an antibody in an immunoconjugate.

Useful bonds for connecting linking moieties to proteins and other materials include, but are not limited to, amides, amines, esters, carbamates, ureas, thioethers, thiocarbamates, thiocarbonates, and thioureas. A "divalent" linking moiety contains two points of attachment for linking two functional groups; polyvalent linking moieties can have additional points of attachment for linking further functional groups. For example, divalent linking moieties include divalent polymer moieties such as divalent poly(ethylene glycol), divalent poly(propylene glycol), and divalent poly (vinyl alcohol).

As used herein, when the term "optionally present" is used to refer to a chemical structure (e.g., "R" or "Q"), if that chemical structure is not present, the bond originally made to the chemical structure is made directly to the adjacent atom.

As used herein, the term "linker" refers to a functional group that covalently bonds two or more moieties in a compound or material. For example, the linker can serve to covalently bond an adjuvant moiety to an antibody construct in an immunoconjugate.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 30 carbons atoms, such as, but not limited to heptyl, octyl, nonyl, decyl, etc. Alkyl groups can be substituted or unsubstituted. "Substituted alkyl" groups can be substituted with one or more groups selected from halo, hydroxy, amino, oxo (=O), alkylamino, amido, acyl, nitro, cyano, and alkoxy. The term "alkylene" refers to a divalent alkyl radical.

As used herein, the term "heteroalkyl" refers to an alkyl group as described herein, wherein one or more carbon atoms are optionally and independently replaced with heteroatom selected from N, O, and S. The term "heteroalkylene" refers to a divalent heteroalkyl radical.

As used herein, the term "carbocycle" refers to a saturated or partially unsaturated, monocyclic, fused bicyclic, or bridged polycyclic ring assembly containing from 3 to 12 ring atoms, or the number of atoms indicated. Carbocycles can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic carbocyclic rings include, for example, cyclopropyl, cyclobutyl, cyclopentyl, cyclohexyl, and cyclooctyl. Saturated bicyclic and polycyclic carbocyclic rings include, for example, norbornane, [2.2.2] bicyclooctane, decahydronaphthalene and adamantane. Carbocyclic groups can also be partially unsaturated, having one or more double or triple bonds in the ring. Representative carbocyclic groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene.

Unsaturated carbocyclic groups also include aryl groups. The term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl.

A "divalent" carbocycle refers to a carbocyclic group having two points of attachment for covalently linking two moieties in a molecule or material. Carbocycles can be substituted or unsubstituted. "Substituted carbocycle" groups can be substituted with one or more groups selected from halo, hydroxy, amino, alkylamino, amido, acyl, nitro, cyano, and alkoxy.

As used herein, the term "heterocycle" refers to heterocycloalkyl groups and heteroaryl groups. "Heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. "Substituted heteroaryl" groups can be substituted with one or more groups selected from halo, hydroxy, amino, oxo (=O), alkylamino, amido, acyl, nitro, cyano, and alkoxy.

Heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

"Heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. "Substituted heterocyclyl" groups can be substituted with one or more groups selected from halo, hydroxy, amino, oxo (=O), alkylamino, amido, acyl, nitro, cyano, and alkoxy.

Heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

As used herein, the terms "halo" and "halogen," by themselves or as part of another substituent, refer to a fluorine, chlorine, bromine, or iodine atom.

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_3$, wherein each R group is H or alkyl. An amino moiety can be ionized to form the corresponding ammonium cation.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O=).

As used herein, the terms "treat," "treatment," and "treating" refer to any indicia of success in the treatment or amelioration of an injury, pathology, condition, or symptom (e.g., cognitive impairment), including any objective or subjective parameter such as abatement; remission; diminishing of symptoms or making the symptom, injury, pathology or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter; including, e.g., the result of a physical examination.

As used herein, the term "cancer" refers to conditions including solid cancers, lymphomas, and leukemias. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, bile duct cancer, gastrointestinal carcinoid tumors, esophageal cancer, gall bladder cancer, appendix cancer, small intestine cancer, stomach (gastric) cancer, cancer of the central nervous system, skin cancer (e.g., melanoma), choriocarcinoma, head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma.

As used herein the terms "effective amount" and "therapeutically effective amount" refer to a dose of a substance such as an immunoconjugate that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics*, 11$^{th}$ Edition, 2006, Brunton, Ed., McGraw-Hill; and *Remington: The Science and Practice of Pharmacy*, 21S$^t$ Edition, 2005, Hendrickson, Ed., Lippincott, Williams & Wilkins).

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the term "administering" refers to parenteral, intravenous, intraperitoneal, intramuscular, intratumoral, intralesional, intranasal or subcutaneous administration, oral administration, administration as a suppository, topical contact, intrathecal administration, or the implantation of a slow-release device, e.g., a mini-osmotic pump, to the subject.

The terms "about" and "around," as used herein to modify a numerical value, indicate a close range surrounding that explicit value. If "X" were the value, "about X" or "around X" would indicate a value from 0.9X to 1.1X, e.g., from 0.95X to 1.05X or from 0.99X to 1.01X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

Antibody Adjuvant Immunoconjugates

The invention provides immunoconjugates containing an antibody construct comprising an antigen binding domain and an Fc domain, an adjuvant moiety, and a linker, wherein each adjuvant moiety is covalently bonded to the antibody via the linker.

Immunoconjugates as described herein can provide an unexpectedly increased activation response of an antigen presenting cell (APC). This increased activation can be detected in vitro or in vivo. In some cases, increased APC activation can be detected in the form of a reduced time to achieve a specified level of APC activation. For example, in an in vitro assay, % APC activation can be achieved at an equivalent dose with an immunoconjugate within 1%, 10%, or 50% of the time required to receive the same or similar percentage of APC activation with a mixture of unconjugated antibody and TLR agonist. In some cases, an immunoconjugate can activate APCs (e.g., dendritic cells) and/or NK cells in a reduced amount of time. For example, in some cases, an antibody TLR agonist mixture can activate APCs (e.g., dendritic cells) and/or NK cells and/or induce dendritic cell differentiation after incubation with the mixture for 2, 3, 4, 5, 1-5, 2-5, 3-5, or 4-7 days; while, in contrast immunoconjugates described herein can activate and/or induce differentiation within 4 hours, 8 hours, 12 hours, 16 hours, or 1 day. Alternatively, the increased APC activation can be detected in the form of a reduced concentration of immunoconjugate required to achieve an amount (e.g., percent APCs), level (e.g., as measured by a level of upregulation of a suitable marker), or rate (e.g., as detected by a time of incubation required to activate) of APC activation.

Immunoconjugates of the present invention must include an Fc region. As FIGS. 130A-131E illustrate, non-FcR binding proteins do not activate myeloid cells when conjugated to Compound 1.

In one embodiment, the immunoconjugates of the present invention provide more than a 5% increase in activity compared to the immunoconjugates of the prior art (for example, the immunoconjugates disclosed in the '528 patent). In another embodiment, the immunoconjugates of the present invention provide more than a 10%, 15%, 20%, 25%, 30%, 35%, 40%, 45%, 50%, 55%, 60%, 65%, or 70% increase in activity compared to the immunoconjugates of the prior art. The increase in activity can be assessed by any means known by one of skill in the art and can include myeloid activation or assessment by cytokine secretion.

In one embodiment, the immunoconjugates of the present invention provide an improved drug to adjuvant ratio. In some embodiments, the average number of adjuvant moieties per immunoconjugate ranges from about 1 to about 10. The desirable drug to adjuvant ratio can be determined by one of skill in the art depending on the desired effect of the treatment. For example, a drug to adjuvant ratio of greater than 1.2 may be desired. In an embodiment, a drug to adjuvant ratio of greater than 0.2, 0.4, 0.6, 0.8, 1, 1.2, 1.4, 1.6, 1.8, 2.0, 2.2, 2.4, 2.6, 2.8, 3.0, 3.2, 3.4, 3.6, 3.8, 4.0, 5.0, 6.0, 7.0, 8.0, or 9.0 may be desired. In another embodiment, a drug to adjuvant ratio of less than 10.0, 9.0, 8.0, 7.0, 6.0, 5.0, 4.0, 3.8, 3.6, 3.4, 3.2, 3.0, 2.8, 2.6, 2.4, 2.2, 2.0, 1.8, 1.6, 1.4, 1.2, 0.8, 0.6, 0.4 or 0.2 may be desirable. The drug to adjuvant ratio can be assessed by any means known by one of skill in the art.

The immunoconjugates of the invention contain linking moieties that covalently bond the adjuvant moieties to the antibodies. In some embodiments, the immunoconjugate has a structure according to Formula I:

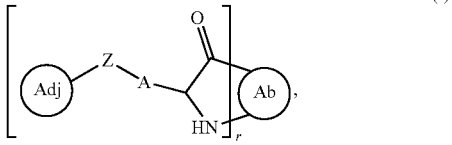

(I)

or a pharmaceutically acceptable salt thereof, wherein Ab is an antibody; A is an unmodified amino acid sidechain in the antibody or a modified amino acid sidechain in the antibody; Z is a linking moiety; Adj is an adjuvant moiety; and subscript r is an integer from 1 to 10 (i.e., 1, 2, 3, 4, 5, 6, 7, 8, 9, or 10).

In some embodiments, the immunoconjugate has a structure according to Formula Ia:

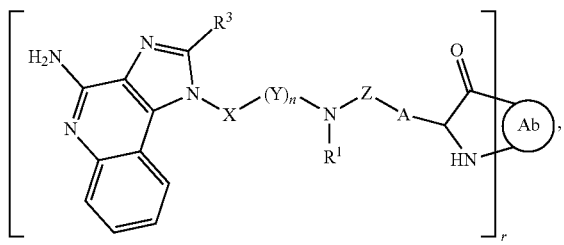

(Ia)

or a pharmaceutically acceptable salt thereof, wherein

Ab is an antibody;

A is an unmodified amino acid sidechain in the antibody or a modified amino acid sidechain in the antibody;

Z is a linking moiety;

$R^1$ is selected from H and $C_{1-4}$ alkyl; or

Z, $R^1$, and the nitrogen atom to which they are attached form a linking moiety comprising a 5- to 8-membered heterocycle;

each Y is independently $CHR^2$, wherein $R^2$ is selected from H, OH, and $NH_2$;

$R^3$ is selected from $C_{1-6}$ alkyl and 2- to 6-membered heteroalkyl, each of which is optionally substituted with one or more members selected from the group consisting of halo, hydroxy, amino, oxo (=O), alkylamino, amido, acyl, nitro, cyano, and alkoxy;

X is selected from O and $CH_2$;

subscript n is an integer from 1 to 12 (i.e., 1, 2, 3, 4, 5, 6, 7, 8, 9, 10, 11, or 12); and subscript r is an integer from 1 to 10 (i.e., 1, 2, 3, 4, 5, 6, 7, 8, 9, or 10).

In certain embodiments of the immunoconjugate of Formula Ia, subscript n is an integer from 1 to 6 (i.e., 1, 2, 3, 4, 5, or 6).

In some embodiments, the immunoconjugate has a structure according to Formula Ib:

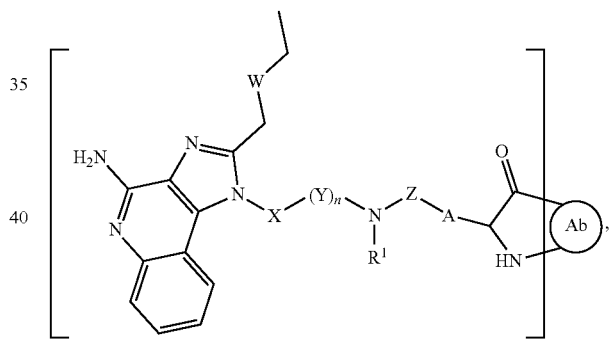

(Ib)

or a pharmaceutically acceptable salt thereof, wherein

Ab is an antibody;

A is an unmodified amino acid sidechain in the antibody or a modified amino acid sidechain in the antibody;

Z is a linking moiety;

$R^1$ is selected from H and $C_{1-4}$ alkyl; or

Z, $R^1$, and the nitrogen atom to which they are attached form a linking moiety comprising a 5- to 8-membered heterocycle;

each Y is independently $CHR^2$, wherein $R^2$ is selected from H, OH, and $NH_2$;

X is selected from O and $CH_2$;

subscript n is an integer from 1 to 12 (i.e., 1, 2, 3, 4, 5, 6, 7, 8, 9, 10, 11, or 12);

and W is selected from the group consisting of O and $CH_2$.

In some embodiments, the immunoconjugate has a structure according to Formula Ic:

(Ic)

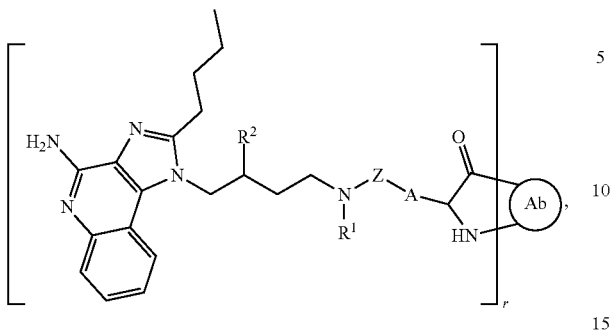

or a pharmaceutically acceptable salt thereof, wherein
Ab is an antibody;
subscript r is an integer from 1 to 10 (i.e., 1, 2, 3, 4, 5, 6, 7, 8, 9, or 10);
A is an unmodified amino acid sidechain in the antibody or a modified amino acid sidechain in the antibody;
Z is a linking moiety; and
$R^1$ is selected from H and $C_{1-4}$ alkyl; or
Z, $R^1$, and the nitrogen atom to which they are attached form a linking moiety comprising a 5- to 8-membered heterocycle; and
$R^2$ is selected from H, OH, and $NH_2$.

In some embodiments, the immunoconjugate has a structure according to Formula Id:

(Id)

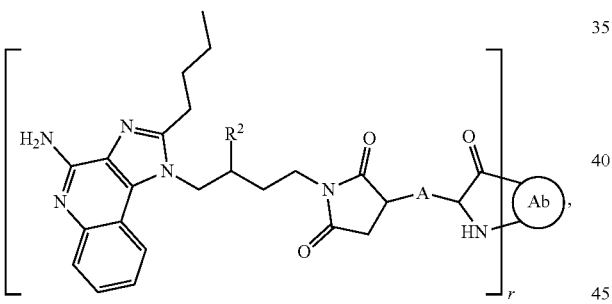

or a pharmaceutically acceptable salt thereof, wherein Ab is an antibody; A is an unmodified amino acid sidechain in the antibody or a modified amino acid sidechain in the antibody; $R^2$ is selected from H, OH, and $NH_2$; and subscript r is an integer from 1 to 10 (i.e., 1, 2, 3, 4, 5, 6, 7, 8, 9, or 10). In certain embodiments, subscript r is an integer from 1 to 4 (i.e., 1, 2, 3, or 4). In certain embodiments of the immunoconjugates of Formula I and Formulae Ia-Id, A is a thiol-modified lysine sidechain. In some embodiments of the immunoconjugates of Formula I and Formulae Ia-Id, A is a cysteine sidechain.

In some embodiments, Z is selected from:

$Z_a$

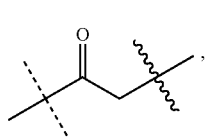

$Z_b$

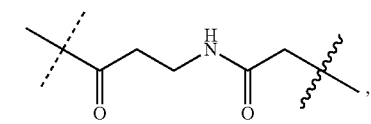

$Z_c$

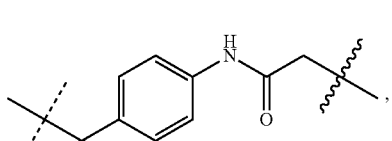

$Z_d$

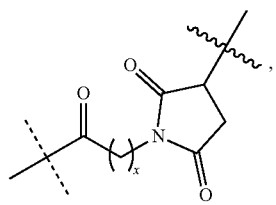

$Z_e$

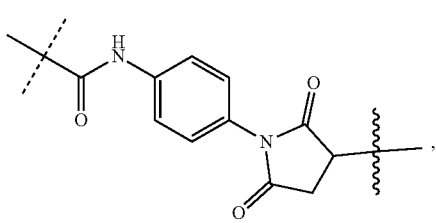

$Z_f$

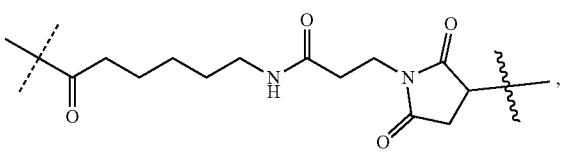

$Z_g$

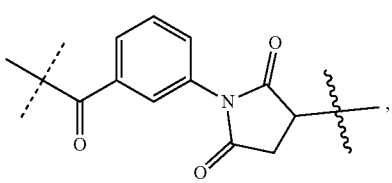

$Z_h$

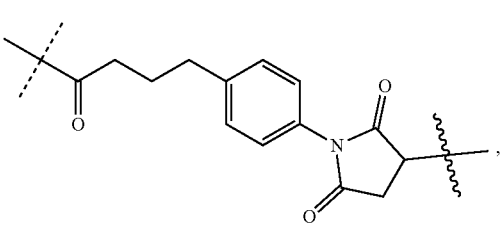

$Z_i$

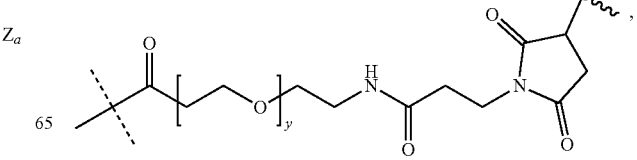

-continued

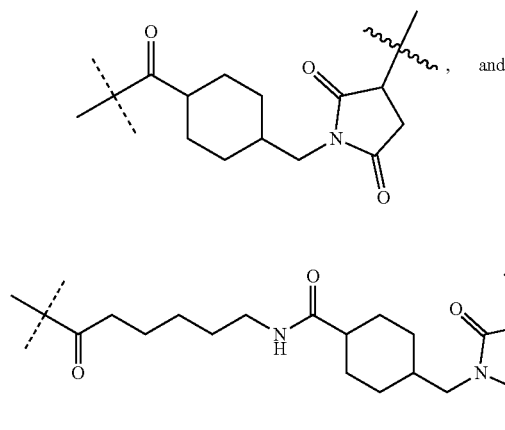

wherein subscript x is an integer from 1 to 12 (i.e., 1, 2, 3, 4, 5, 6, 7, 8, 9, 10, 11, or 12); subscript y is an integer from 1 to 30 (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30); the dashed line ("⋰") represents the point of attachment to the adjuvant moiety; and the wavy line ("∿") represents the point of attachment to an amino acid sidechain in the antibody.

In some embodiments, the immunoconjugate has a structure according to Formula II:

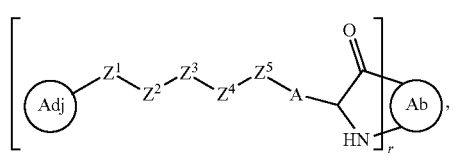

(II)

or a pharmaceutically acceptable salt thereof, wherein Ab is an antibody; wherein A is an unmodified amino acid sidechain in the antibody or a modified amino acid sidechain in the antibody; wherein Adj is an adjuvant moiety; wherein subscript r is an integer 1 to 10 (i.e., 1, 2, 3, 4, 5, 6, 7, 8, 9, or 10); and wherein:
  $Z^1$ is selected from —C(O)—, —C(O)NH—, —CH$_2$—;
  $Z^2$ and $Z^4$ are independently selected from a bond, C$_{1-30}$ alkylene, and 3- to 30-membered heteroalkylene, wherein:
    one or more groupings of adjacent atoms in the C$_{1-30}$ alkylene and 3- to 30-membered heteroalkylene are optionally and independently replaced by —C(O)—, —NR$^a$C(O)—, or —C(O)NR$^a$—,
    one or more groupings of adjacent atoms in the C$_{1-30}$ alkylene and 3- to 30-membered heteroalkylene are optionally and independently replaced by a 4- to 8-membered, divalent carbocycle,
    one or more groupings of adjacent atoms in the C$_{1-30}$ alkylene and 3- to 30-membered heteroalkylene are optionally and independently replaced by a 4- to 8-membered, divalent heterocycle having one to four heteroatoms selected from O, S, and N, and
    each R$^a$ is independently selected from H and C$_{1-6}$ alkyl;
  $Z^3$ is selected from a bond, a divalent peptide moiety, and a divalent polymer moiety; and $Z^5$ is bonded to the sidechain of an amino acid sidechain in the antibody.

In some embodiments, the immunoconjugate has a structure according to Formula IIa:

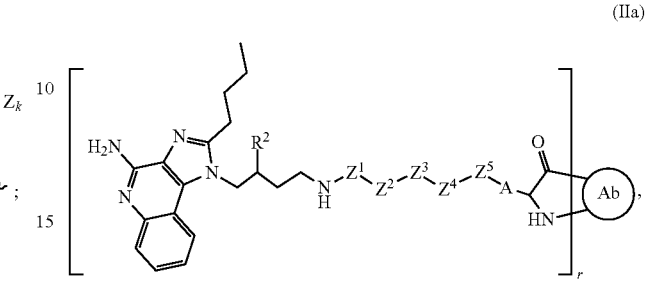

(IIa)

or a pharmaceutically acceptable salt thereof, wherein
  $Z^1$ is selected from —C(O)—, —C(O)NH—, —CH$_2$—;
  $Z^2$ and $Z^4$ are independently selected from a bond, C$_{1-30}$ alkylene, and 3- to 30-membered heteroalkylene, wherein:
    one or more groupings of adjacent atoms in the C$_{1-30}$ alkyl and 3- to 30-membered heteroalkylene are optionally and independently replaced by —C(O)—, —NR$^a$C(O)—, or —C(O)NR$^a$—;
    one or more groupings of adjacent atoms in the C$_{1-30}$ alkylene and 3- to 30-membered heteroalkylene are optionally and independently replaced by a 4- to 8-membered, divalent carbocycle,
    one or more groupings of adjacent atoms in the C$_{1-30}$ alkylene and 3- to 30-membered heteroalkylene are optionally and independently replaced by a 4- to 8-membered, divalent heterocycle having one to four heteroatoms selected from O, S, and N, and
    each R$^a$ is independently selected from H and C$_{1-6}$ alkyl;
  $Z^3$ is selected from a bond, a divalent peptide moiety, and a divalent polymer moiety; and
  $Z^5$ is selected from an amine-bonded moiety and a thiol-bonded moiety.

In certain embodiments of the immunoconjugates of Formula II and Formula IIa, $Z^5$ is a thiol-bonded moiety. In certain embodiments of the immunoconjugates of Formula II and Formula IIa, $Z^5$ is a thiol-bonded moiety and A is a thiol-modified lysine sidechain. In certain embodiments of the immunoconjugates of Formula II and Formula IIa, $Z^5$ is a thiol-bonded moiety and A is a cysteine sidechain.

In certain embodiments of the immunoconjugates of Formula II and Formula IIa, the linking moiety (i.e., the structural components between the adjuvant ("Adj") and the amino acid ("A")) includes a structure selected from:

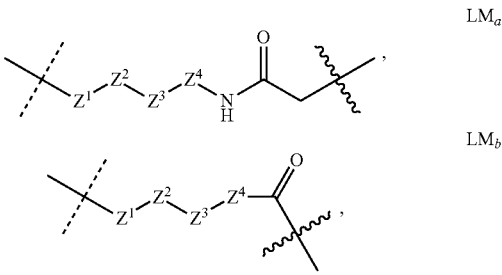

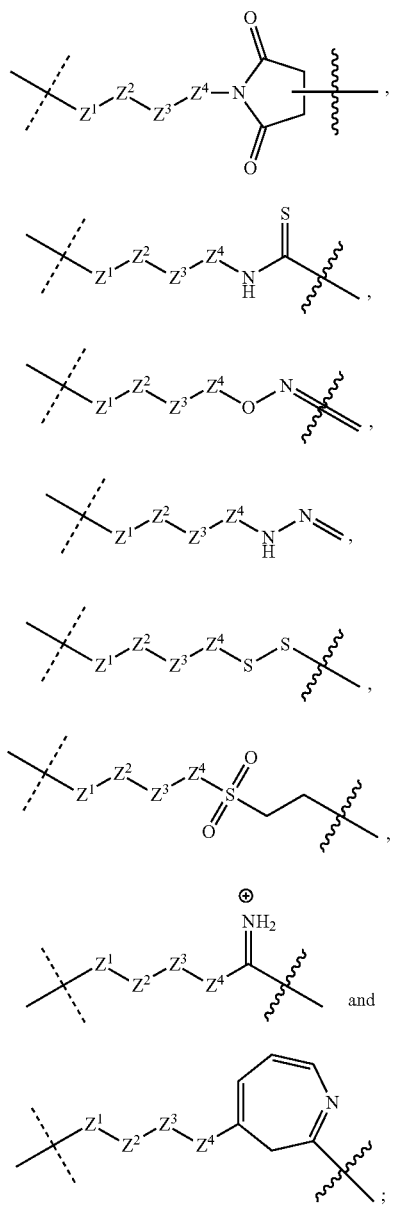

LM$_c$

LM$_d$

LM$_e$

LM$_f$

LM$_g$

LM$_h$

LM$_i$ and

LM$_j$

;

wherein $Z^1$, $Z^2$, $Z^3$, and $Z^4$ are described as above; the dashed line ("⸺") represents the point of attachment to the adjuvant moiety; and the wavy line ("⸺") represents the point of attachment to an amino acid sidechain in an antibody.

In some embodiments, $Z^3$ is a divalent peptide moiety. In some embodiments, the peptide includes a first residue selected from an alanine residue, a valine residue, a leucine residue, an isoleucine residue, a methionine residue, a phenylalanine residue, a tryptophan residue, and a proline residue. In some such embodiments, the peptide includes a second amino acid selected from an unprotected lysine residue, a protected lysine residue, an unprotected arginine residue, a protected arginine residue, a histidine residue, an unprotected ornithine residue, a protected ornithine residue, a lysine residue, and a citrulline. In some embodiments, the peptide includes a first residue selected from a phenylalanine residue and a valine residue. In some such embodiments, the peptide includes a second residue selected from a lysine residue and a citrulline residue. Typically, the peptide moiety will contain about 2-12 amino acid residues. For example, the peptide can contain from 2 to 8 amino acid residues, or from 2 to 4 amino acid residues. In some embodiments, the peptide is dipeptide. In some embodiments, the peptide is a tetrapeptide.

In some embodiments, the peptide is selected from Phe-Lys; Val-Lys; Phe-Phe-Lys; D-Phe-Phe-Lys; Gly-Phe-Lys; Ala-Lys; Val-Cit; Val-Ala; Phe-Cit; Leu-Cit; Ile-Cit; Trp-Cit; Phe-Ala; Gly-Phe-Leu-Gly; Ala-Leu-Ala-Leu; Phe-N$^9$-tosyl-Arg; and Phe-N$^9$-nitro-Arg. In some embodiments, the peptide can be cleaved by a protease such as cathepsin B, cathepsin C, or cathepsin D. Cathepsin B-sensitive peptides can be particularly useful as linker components, because cathepsin B is implicated in a number of pathologies and oncogenic processes. While expression and activity of cathepsin B is tightly regulated in healthy tissues and organs, regulation can be altered at multiple levels in tumors and other malignancies. Overexpression of cathepsin B has been observed in various cancers, including brain, lung, prostate, breast, and colorectal cancer. See, e.g., Gondi et al., *Expert Opin. Ther. Targets*, 2013; 17(3): 281-291. Linkers containing cathepsin B-sensitive peptide components, such as Phe-Lys and Val-Cit dipeptides, can therefore be cleaved when an immunoconjugate reaches a malignant target such as a tumor in a subject. Because these peptide components are generally insensitive to enzymes in the circulatory system and healthy tissues, the adjuvant moieties are not released before the immunoconjugate reaches the target in the subject.

In some embodiments, $Z^2$ is selected from the group consisting C$_{1-30}$ alkylene and 3- to 30-membered heteroalkylene, wherein one or more groupings of adjacent atoms are optionally and independently replaced by —C(O)—, —NHC(O)—, or —C(O)NH—; and one or more groupings of adjacent atoms are optionally and independently replaced by a 4- to 8-membered, divalent carbocycle. In some embodiments, $Z^2$ is selected from:

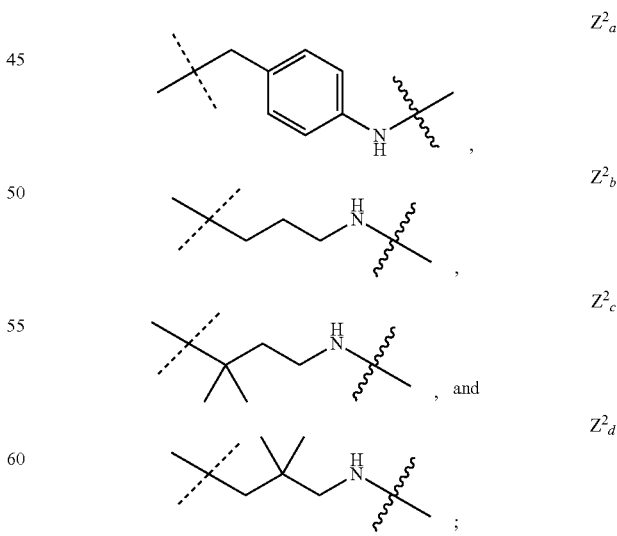

$Z^2_a$ $Z^2_b$ $Z^2_c$

, and $Z^2_d$

;

wherein the dashed line ("⸺") represents the point of attachment to $Z^1$, and the wavy line ("⸺") represents the point of attachment to $Z^3$.

In certain embodiments, —$Z^1$—$Z^2$— is:

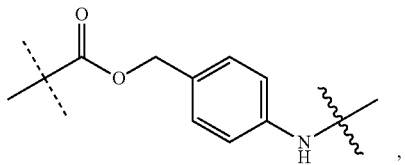

wherein the dashed line (" ⌇ ") represents the point of attachment to the adjuvant moiety and the wavy line (" ⌇ ") represents the point of attachment to $Z^3$. In some such embodiments, $Z^3$ is a divalent peptide moiety selected from Phe-Lys and Val-Cit.

In some embodiments, $Z^4$ is $C_{1-30}$ alkylene, wherein one or more groupings of adjacent atoms are optionally and independently replaced by —C(O)—, —NHC(O)—, or —C(O)NH—; and one or more groupings of adjacent atoms are optionally and independently replaced by a 4- to 8-membered, divalent carbocycle. In some embodiments, $Z^4$ is selected from:

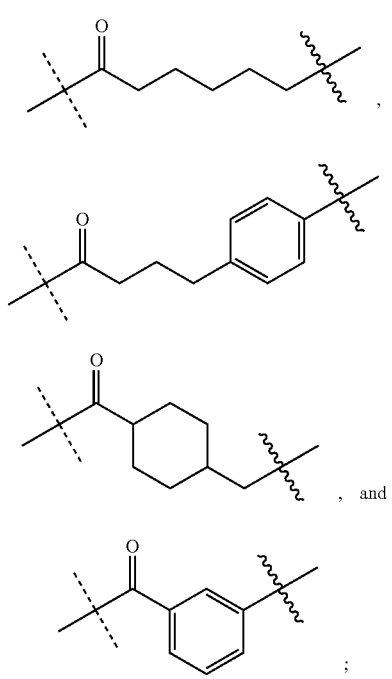

wherein the dashed line (" ⌇ ") represents the point of attachment to $Z^3$, and the wavy line (" ⌇ ") represents the point of attachment to $Z^5$. In some such embodiments, $Z^3$ is a divalent peptide moiety selected from Phe-Lys and Val-Cit.

One of skill in the art will appreciate that the adjuvant moieties in the conjugates can be covalently bonded to the antibodies using various chemistries for protein modification, and that the linking moieties described above result from the reaction of protein functional groups (i.e., amino acid side chains), with reagents having reactive linker groups. A wide variety of such reagents are known in the art. Examples of such reagents include, but are not limited to, N-hydroxysuccinimidyl (NHS) esters and N-hydroxysulfo-succinimidyl (sulfo-NHS) esters (amine reactive); carbodiimides (amine and carboxyl reactive); hydroxymethyl phosphines (amine reactive); maleimides (thiol reactive); halogenated acetamides such as N-iodoacetamides (thiol reactive); aryl azides (primary amine reactive); fluorinated aryl azides (reactive via carbon-hydrogen (C—H) insertion); pentafluorophenyl (PFP) esters (amine reactive); tetrafluorophenyl (TFP) esters (amine reactive); imidoesters (amine reactive); isocyanates (hydroxyl reactive); vinyl sulfones (thiol, amine, and hydroxyl reactive); pyridyl disulfides (thiol reactive); and benzophenone derivatives (reactive via C—H bond insertion). Further reagents include but are not limited to those described in Hermanson, *Bioconjugate Techniques* 2nd Edition, Academic Press, 2008.

Linkers containing maleimide groups, vinyl sulfone groups, pyridyl disulfide groups, and halogenated acetamide groups are particularly useful for covalent bonding to thiol groups in an antibody. Thiol groups in an antibody are generally located in cysteine sidechains. Free thiol groups may be present in naturally-occurring, solvent-accessible cysteine residues in the antibody. Free thiols can also be present in engineered cysteine residues, as described below. In addition, thiol groups can be generated via full or partial reduction of disulfide linkages between cysteine sidechains in an antibody. Thiol groups can be also appended to lysine sidechains using known methods with reagents including, but not limited to, 2-iminothiolane (Traut's reagent), N-succinimidyl-S-acetylthioacetate (SATA), and SATP (N-succinimidyl-S-acetylthiopropionate). When the antibody is modified with acetylated reagents like SATA and SATP, acetyl groups can be removed via hydrolysis with hydroxylamine or similar reagents in order to generate free thiol groups for further conjugation. See, e.g., Traut et al. (*Biochem.*, 12(17): 3266-3273 (1973)) and Duncan et al. (*Anal. Biochem.*, 132(1): 68-73 (1983)).

The linker can have any suitable length such that when the linker is covalently bound to the antibody construct and the adjuvant moiety, the function of the antibody construct and the adjuvant moiety is maintained. The linker can have a length of about 3 Å or more, for example, about 4 Å or more, about 5 Å or more, about 6 Å or more, about 7 Å or more, about 8 Å or more, about 9 Å or more, or about 10 Å or more. Alternatively, or in addition to, the linker can have a length of about 50 Å or less, for example, about 45 Å or less, about 40 Å or less, about 35 Å or less, about 30 Å or less, about 25 Å or less, about 20 Å or less, or about 15 Å or less. Thus, the linker can have a length bounded by any two of the aforementioned endpoints. The linker can have a length from about 3 Å to about 50 Å, for example, from about 3 Å to about 45 Å, from about 3 Å to about 40 Å, from about 3 Å to about 35 Å, from about 3 Å to about 30 Å, from about 3 Å to about 25 Å, from about 3 Å to about 20 Å, from about 3 Å to about 15 Å, from about 5 Å to about 50 Å, from about 5 Å to about 25 Å, from about 5 Å to about 20 Å, from about 10 Å to about 50 Å, from about 10 Å to about 20 Å, from about 5 Å to about 30 Å, or from about 5 Å to about 15 Å. In preferred embodiments, the linker has a length from about 3 Å to about 20 Å.

Accordingly, the invention provides embodiments wherein the adjuvant moieties are covalently bonded to the antibody using a reagent (or covalent bonding reagent ("CBR")) selected from:

CBR_a 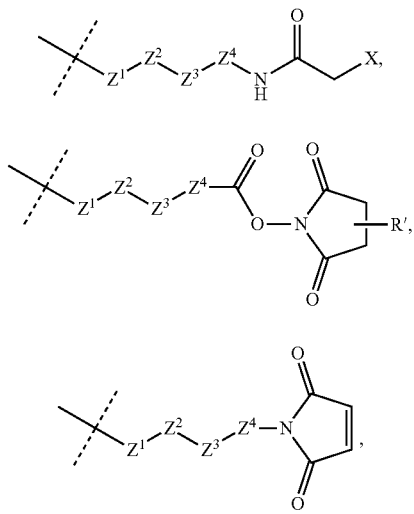

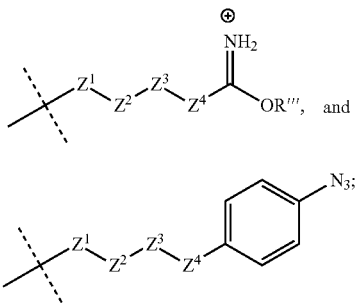 CBR_i

CBR_j wherein X is halogen (e.g., iodo, bromo, or chloro); R' is H or sulfo; R" is optionally substituted aryl (e.g., 3-carboxy-4-nitrophenyl) or optionally substituted heteroaryl (e.g., pyridin-2-yl); R'" is optionally substituted alkyl (e.g., methoxy); $Z^1$, $Z^2$, $Z^3$, and $Z^4$ are as described above; and the dashed line (" ") represents the point of attachment to the adjuvant moiety.

In some embodiments, the linker moiety $-Z^1\text{-}Z^2\text{-}Z^3\text{-}Z^4\text{-}Z^5-$ is:

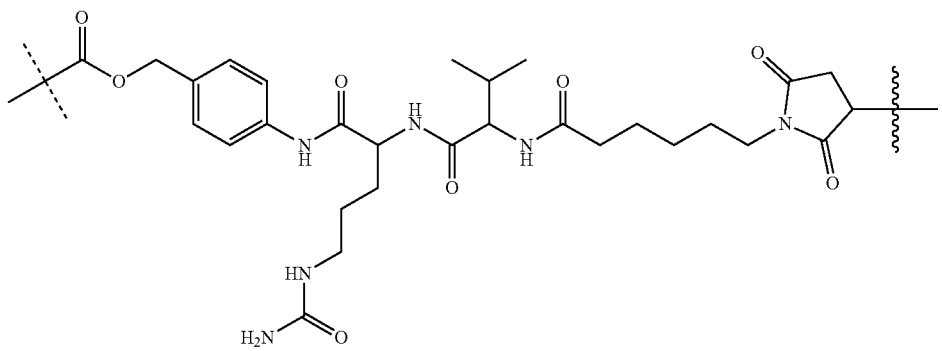

wherein the dashed line (" ") represents the point of attachment to the adjuvant moiety, and the wavy line (" ") represents the point of attachment to an amino acid sidechain the antibody. In some such embodiments, the amino acid sidechain is a cysteine sidechain or a modified lysine sidechain containing a thiol group.

In some embodiments, the immunoconjugate has a structure according to Formula III:

$$\left[ \text{Adj} - G - L - \overset{O}{\underset{}{\text{C}}} - \overset{H}{N} - (CH_2)_4 - \underset{HN}{\overset{O}{\underset{}{\text{C}}}} - \text{Ab} \right]_r \quad (III)$$

or a pharmaceutically acceptable salt thereof, wherein Ab is an antibody with at least one lysine side chain, Adj is an adjuvant, G is $CH_2$, C=O, or a bond, L is a linker, and subscript r is an integer from 1 to 10 (i.e., 1, 2, 3, 4, 5, 6, 7, 8, 9, or 10). In certain embodiments of the immunoconjugate of Formula III, that antibody does not contain a thiol-modified lysine sidechain.

-continued

CBR_d 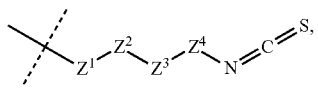

CBR_e 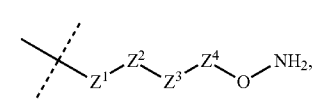

CBR_f 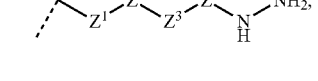

CBR_g 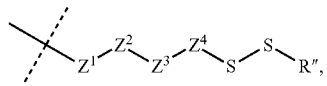

CBR_h 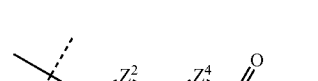

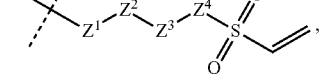

In some embodiments, L is selected from:

L1 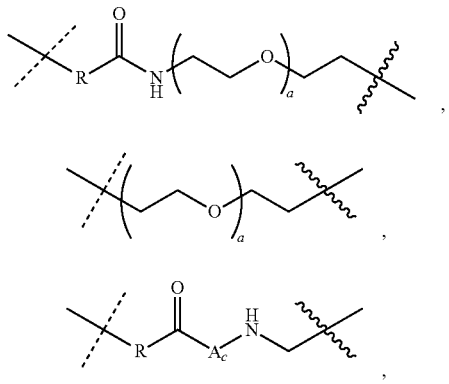

L2

L3

L4 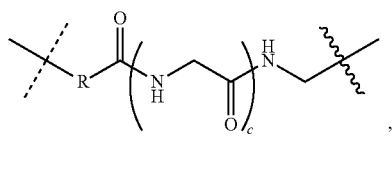

L5 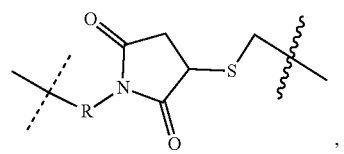

L6 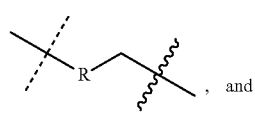, and

L7 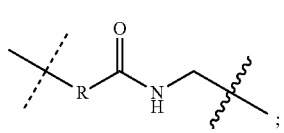;

wherein R is optionally present and is a linear or branched, cyclic or straight, saturated or unsaturated alkyl, heteroalkyl, aryl, or heteroaryl chain comprising from 1 to 8 carbon units; a is an integer from 1 to 40; each A is independently selected from any amino acid; subscript c is an integer from 1 to 20; the dashed line ("-- --") represents the point of attachment to

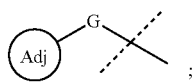

and the wavy line ("~~~") represents the point of attachment to

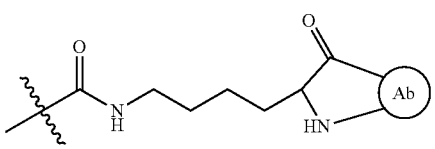

In some embodiments, the immunoconjugate has a structure according to Formula IIIa:

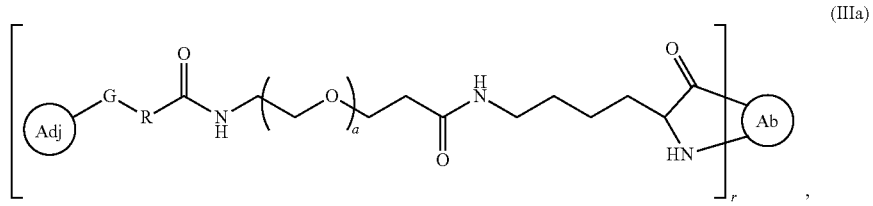

(IIIa)

or a pharmaceutically acceptable salt thereof, wherein Ab is an antibody with at least one lysine side chain; Adj is an adjuvant; G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; subscript a is an integer from 1 to 40; and subscript r is an integer from 1 to 10 (i.e., 1, 2, 3, 4, 5, 6, 7, 8, 9, or 10).

In some embodiments, the immunoconjugate has a structure according to Formula IIIb:

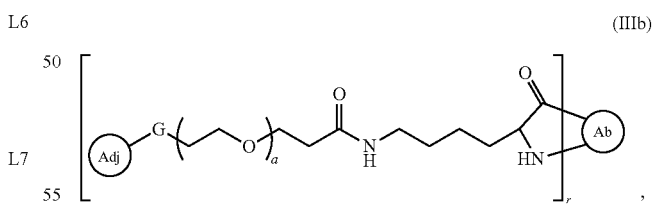

(IIIb)

or a pharmaceutically acceptable salt thereof, wherein Ab is an antibody with at least one lysine side chain; Adj is an adjuvant; G is $CH_2$, C=O, or a bond; subscript a is an integer from 1 to 40; and subscript r is an integer from 1 to 10 (i.e., 1, 2, 3, 4, 5, 6, 7, 8, 9, or 10).

In some embodiments, the immunoconjugate has a structure according to Formula

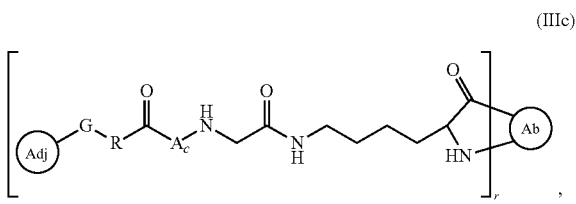

(IIIc)

or a pharmaceutically acceptable salt thereof, wherein Ab is an antibody with at least one lysine side chain; Adj is an adjuvant; G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; each A is independently selected from any amino acid; subscript c is an integer from 1 to 20; and subscript r is an integer from 1 to 10 (i.e., 1, 2, 3, 4, 5, 6, 7, 8, 9, or 10).

In some embodiments, the immunoconjugate has a structure according to Formula IIId:

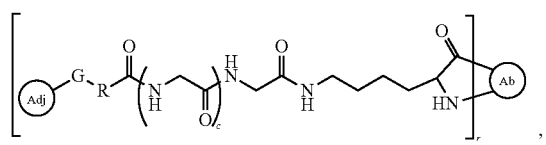

(IIId)

or a pharmaceutically acceptable salt thereof, wherein Ab is an antibody with at least one lysine side chain; Adj is an adjuvant; G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; subscript c is an integer from 1 to 20; and subscript r is an integer from 1 to 10 (i.e., 1, 2, 3, 4, 5, 6, 7, 8, 9, or 10).

In some embodiments, the immunoconjugate has a structure according to Formula IIIe:

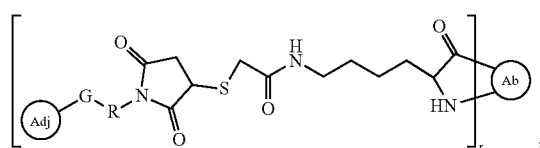

(IIIe)

or a pharmaceutically acceptable salt thereof, wherein Ab is an antibody with at least one lysine side chain; Adj is an adjuvant; G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; and subscript r is an integer from 1 to 10 (i.e., 1, 2, 3, 4, 5, 6, 7, 8, 9, or 10).

In some embodiments, the immunoconjugate has a structure according to Formula IIIf:

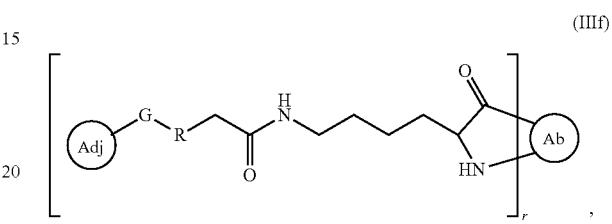

(IIIf)

or a pharmaceutically acceptable salt thereof, wherein Ab is an antibody with at least one lysine side chain; Adj is an adjuvant; G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; and subscript r is an integer from 1 to 10 (i.e., 1, 2, 3, 4, 5, 6, 7, 8, 9, or 10).

In some embodiments, the immunoconjugate has a structure according to Formula IIIg:

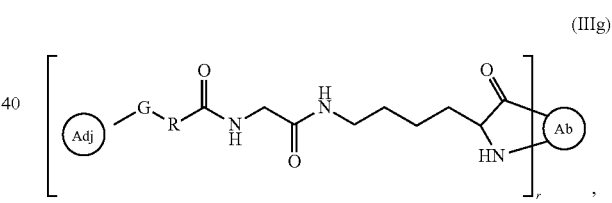

(IIIg)

or a pharmaceutically acceptable salt thereof, wherein Ab is an antibody with at least one lysine side chain; Adj is an adjuvant; G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; and subscript r is an integer from 1 to 10 (i.e., 1, 2, 3, 4, 5, 6, 7, 8, 9, or 10).

Accordingly, the immunoconjugate can have a structure according to Formula IVa-Formula IVk:

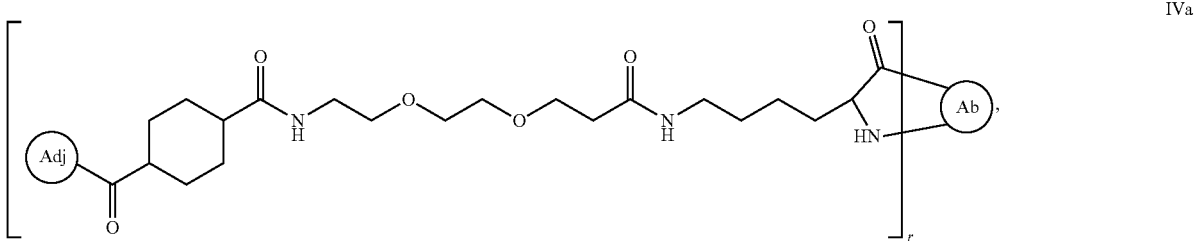

IVa

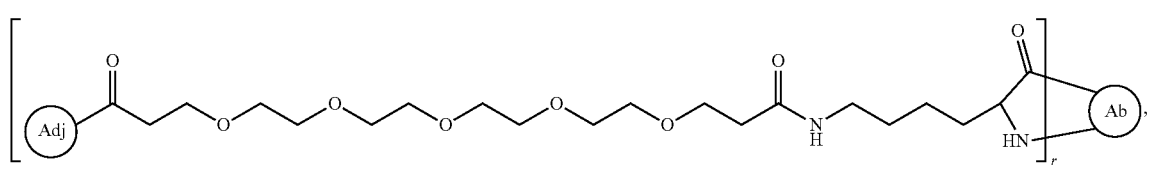
IVb
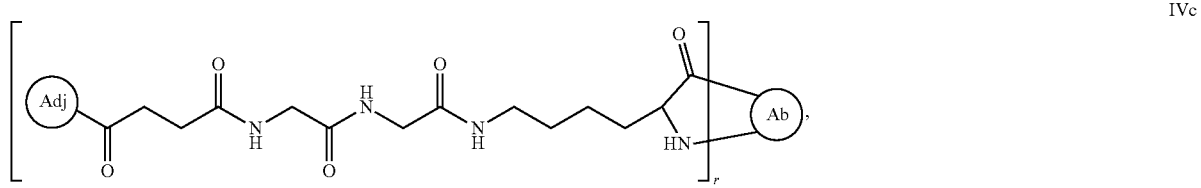
IVc
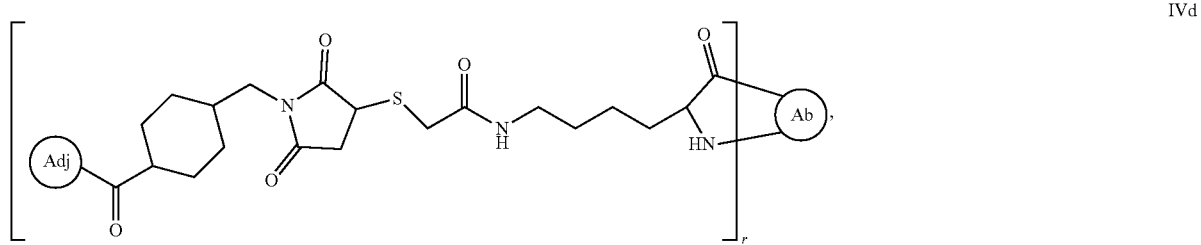
IVd
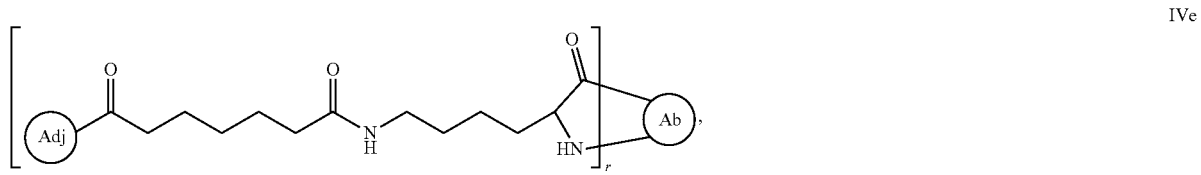
IVe
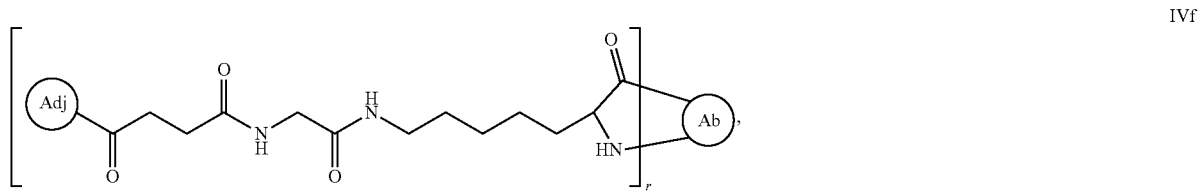
IVf
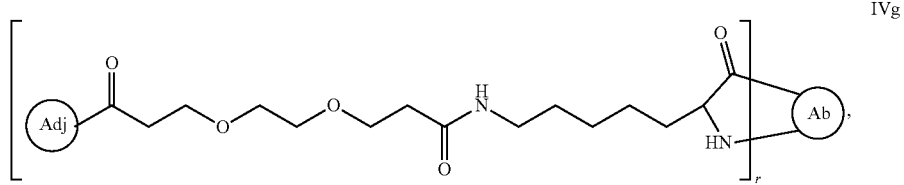
IVg
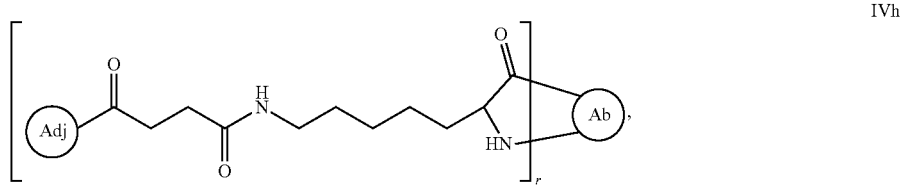
IVh
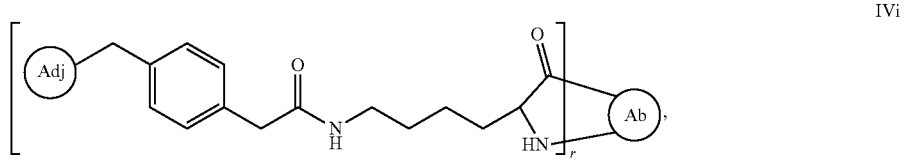
IVi

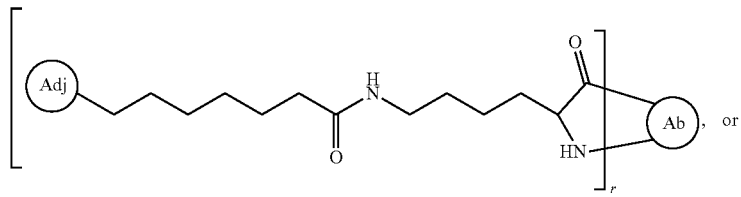
IVj
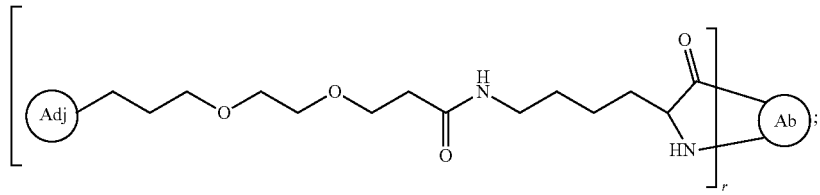
IVk
or a pharmaceutically acceptable salt thereof, wherein Ab is an antibody with at least one lysine side chain; Adj is an adjuvant; and subscript r is an integer from 1 to 10 (i.e., 1, 2, 3, 4, 5, 6, 7, 8, 9, or 10). In certain embodiments, subscript r is an integer from 1 to 4 (i.e., 1, 2, 3, or 4).
In certain embodiments, the immunoconjugate has a structure selected from:
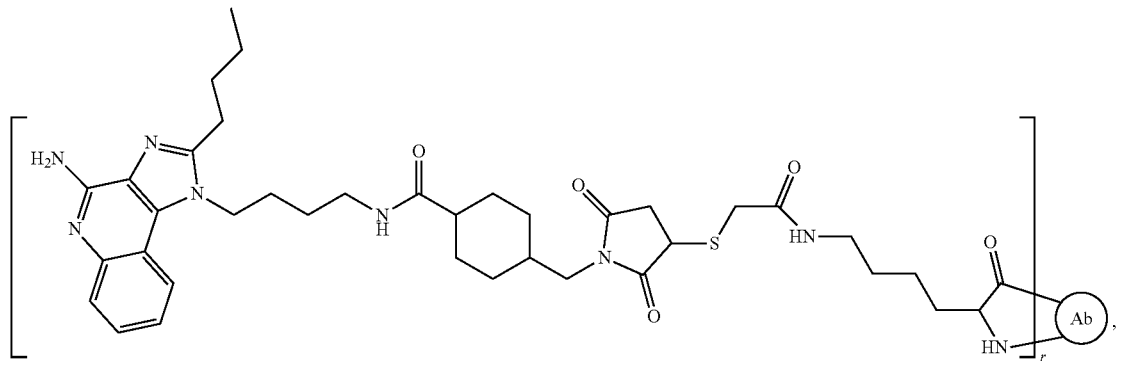
(BB01)
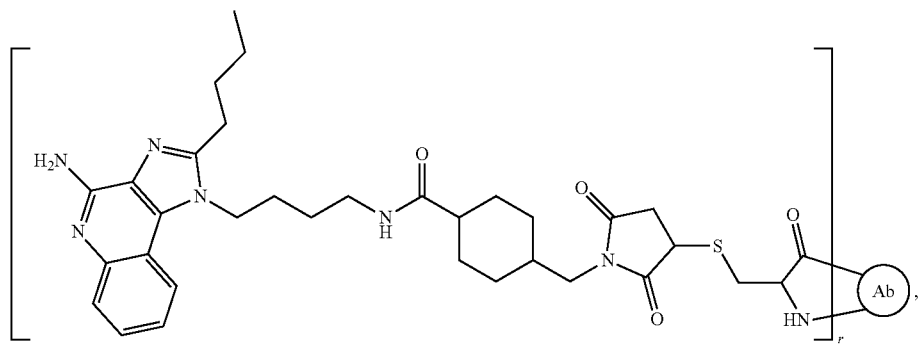
(BB02)

-continued
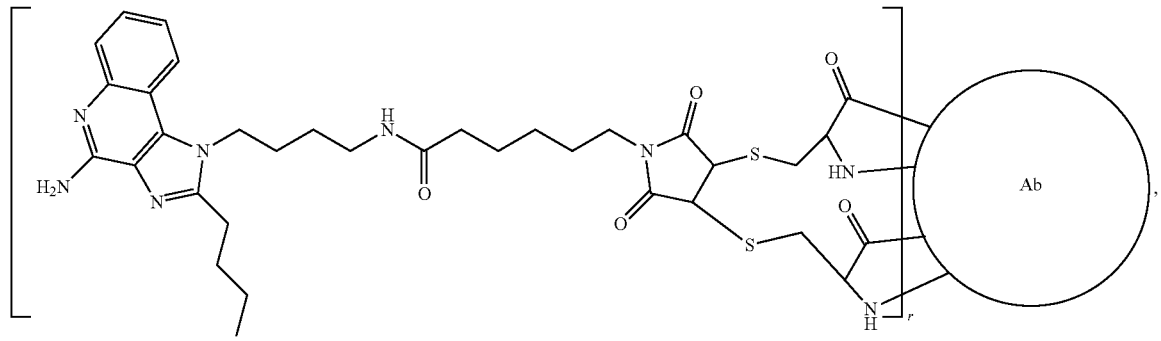
(BB03)
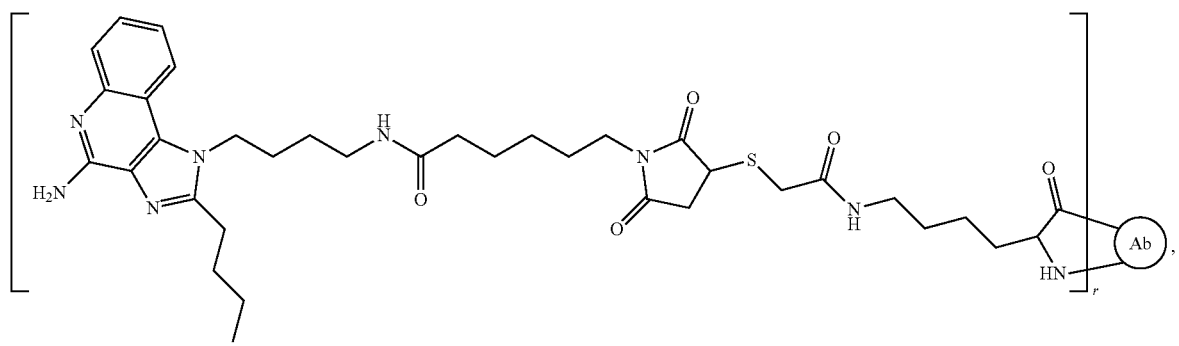
(BB05)
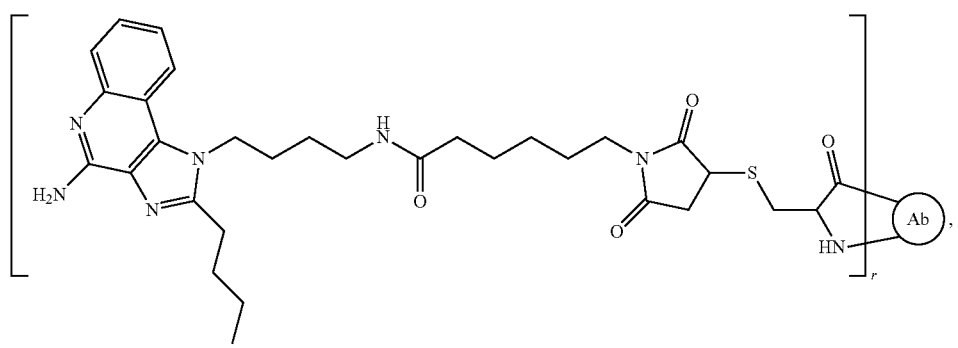
(BB06)
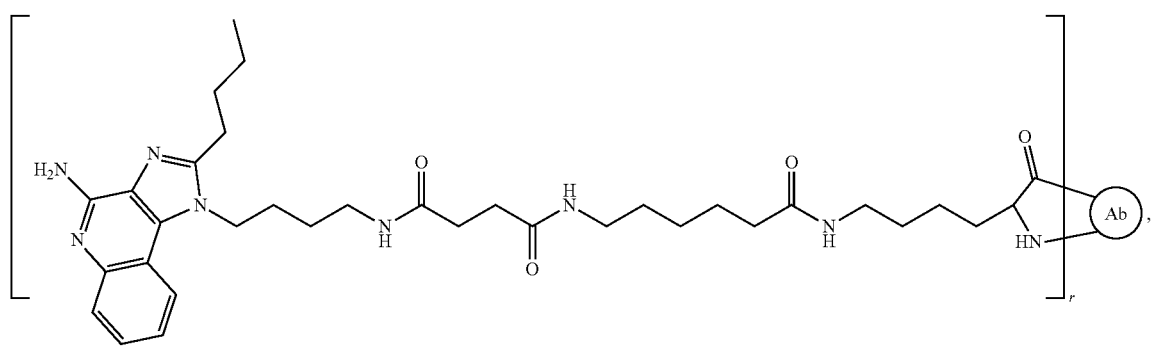
(BB08)

-continued
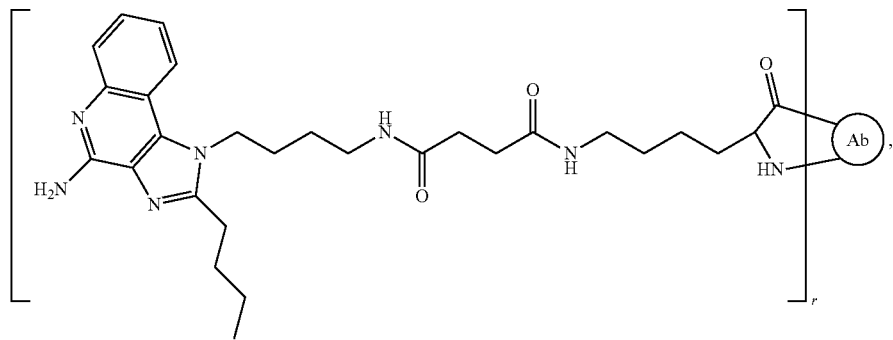
(BB09)
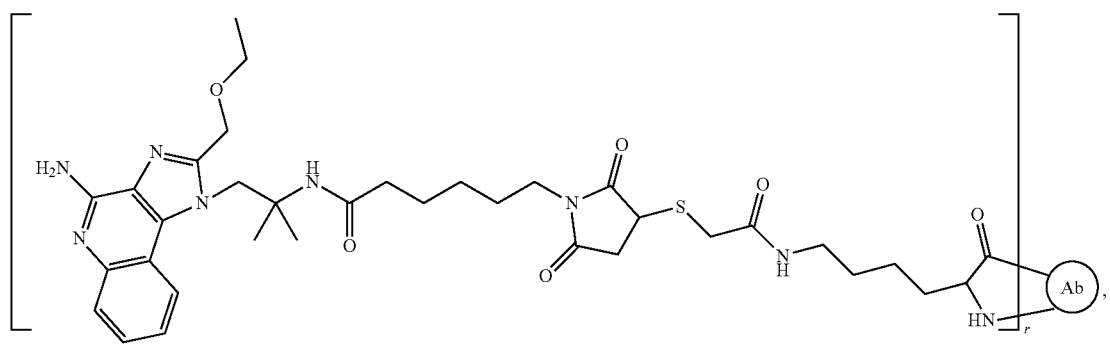
(BB10)
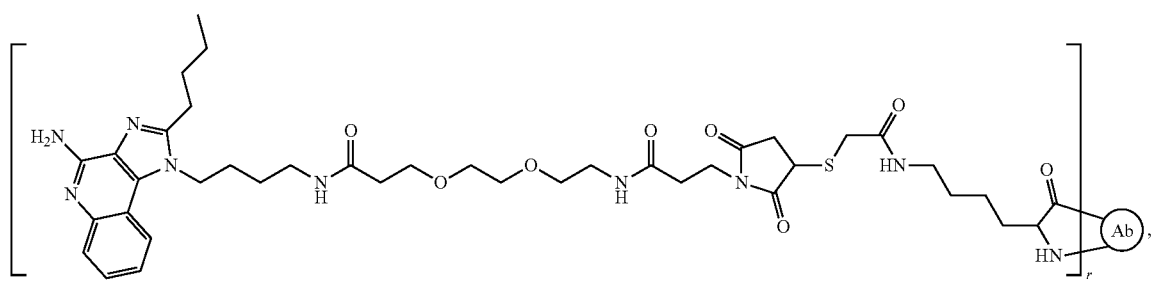
(BB11)
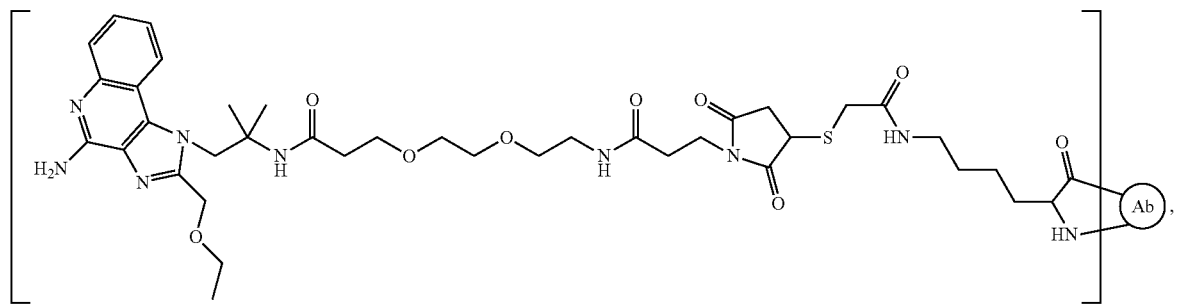
(BB12)

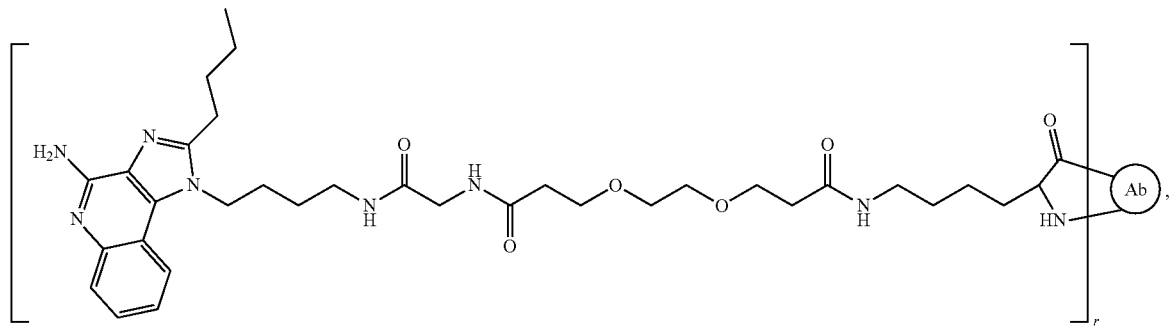
(BB13)
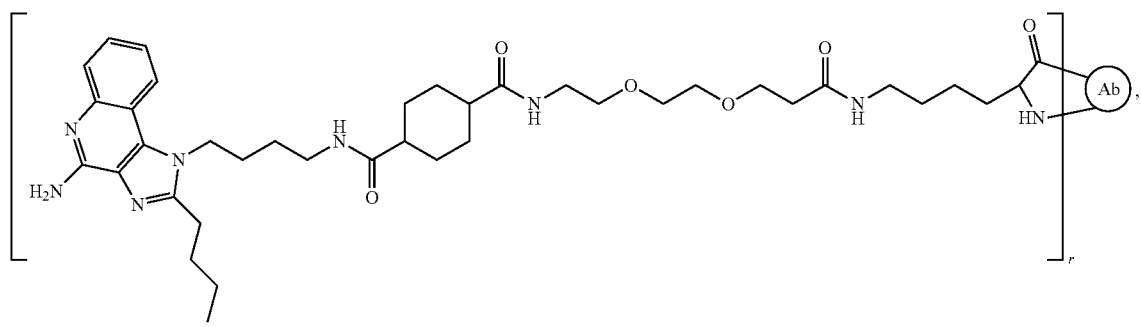
(BB14)
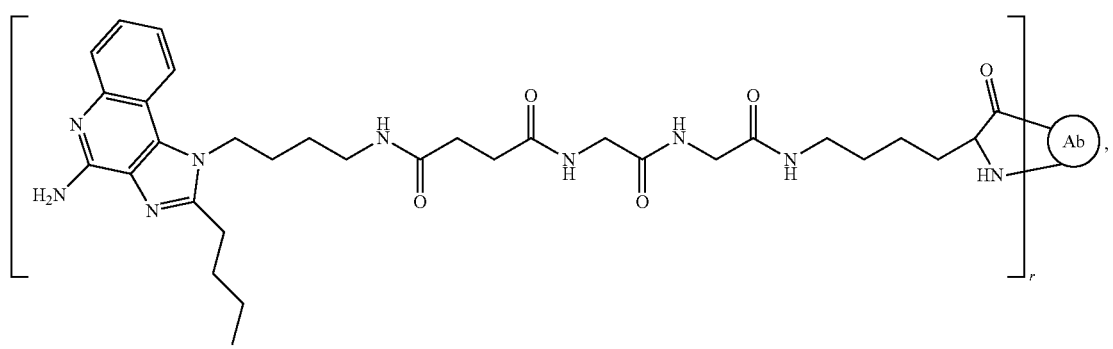
(BB15)
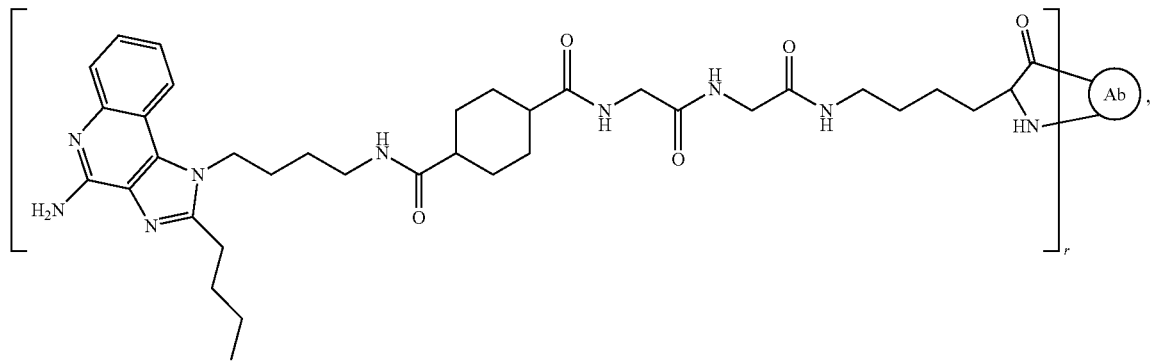
(BB16)

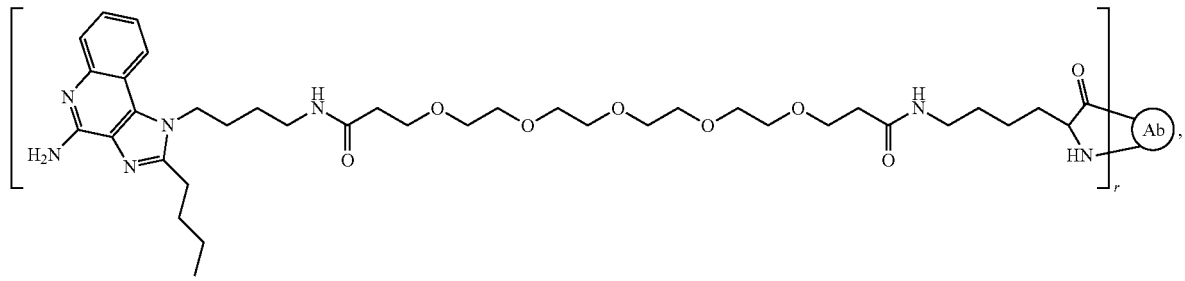
(BB17)
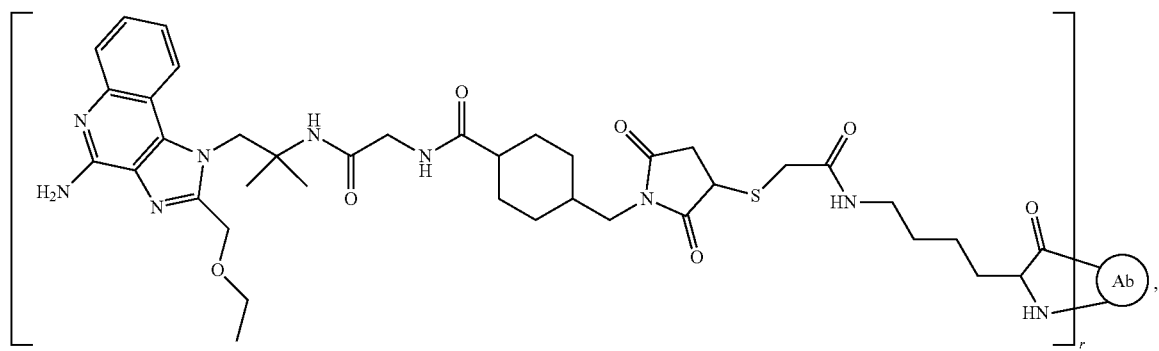
(BB18)
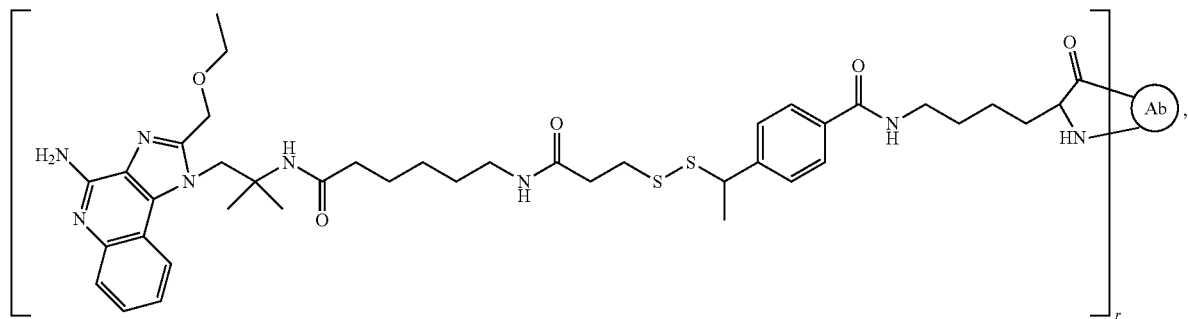
(BB19)
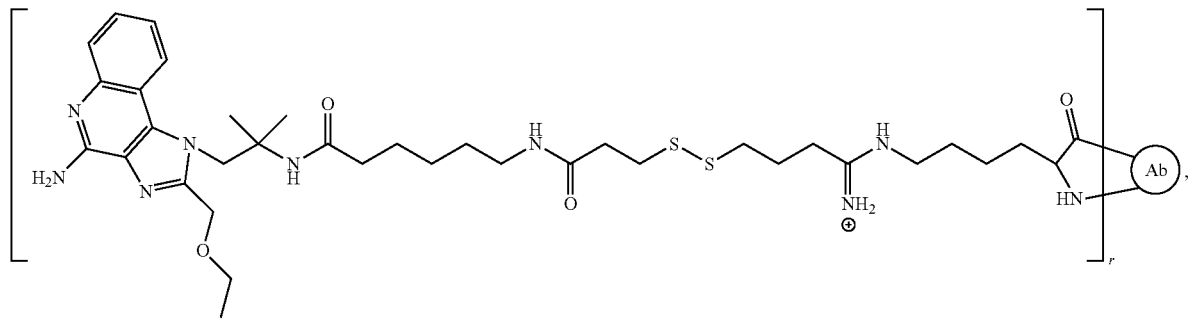
(BB20)

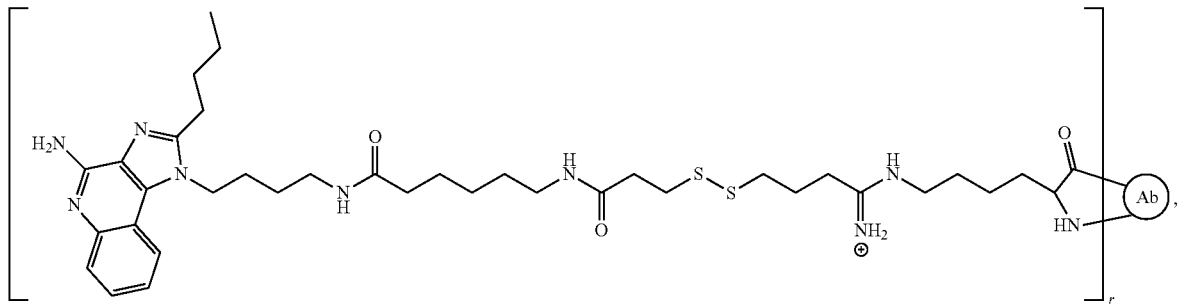
(BB21)
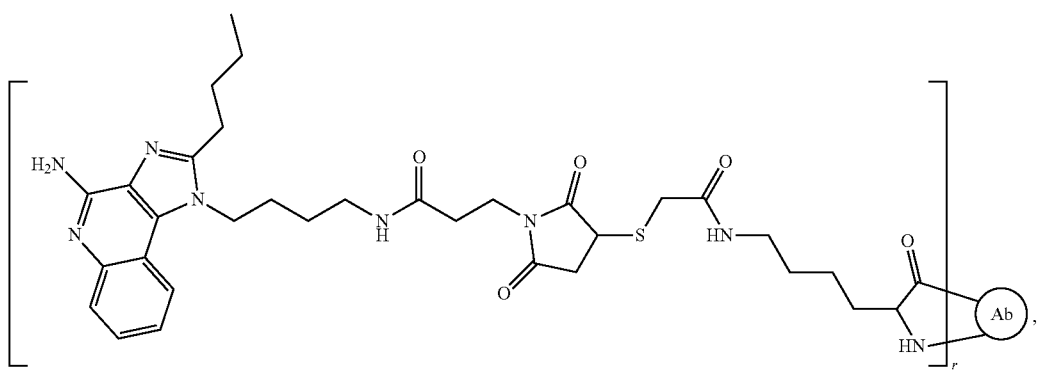
(BB22)
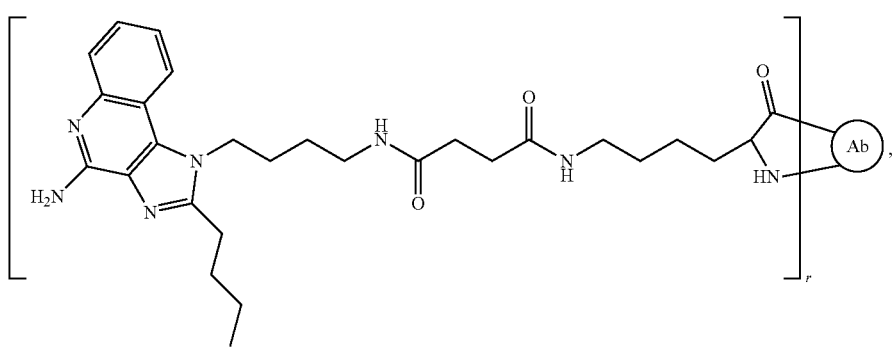
(BB23)
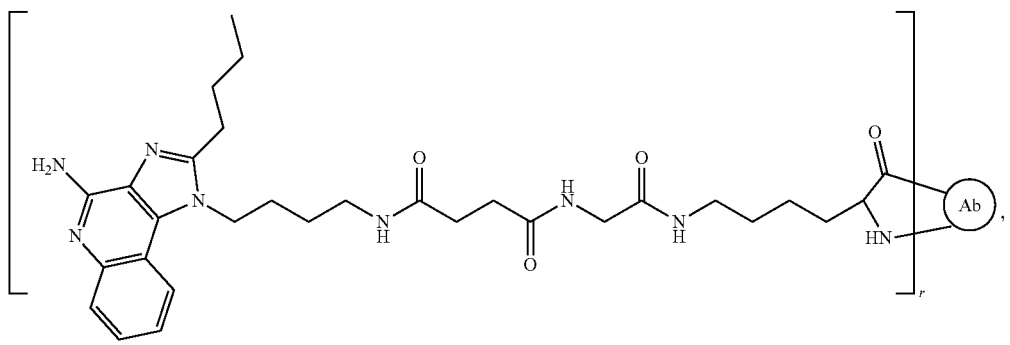
(BB24)

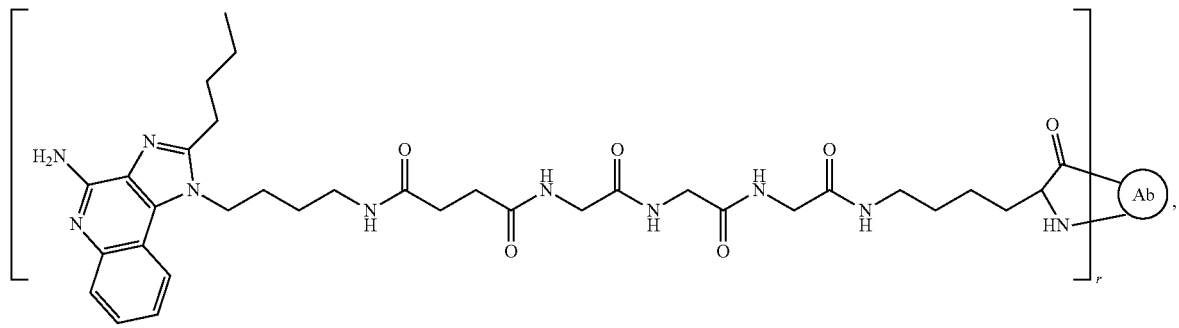
(BB25)
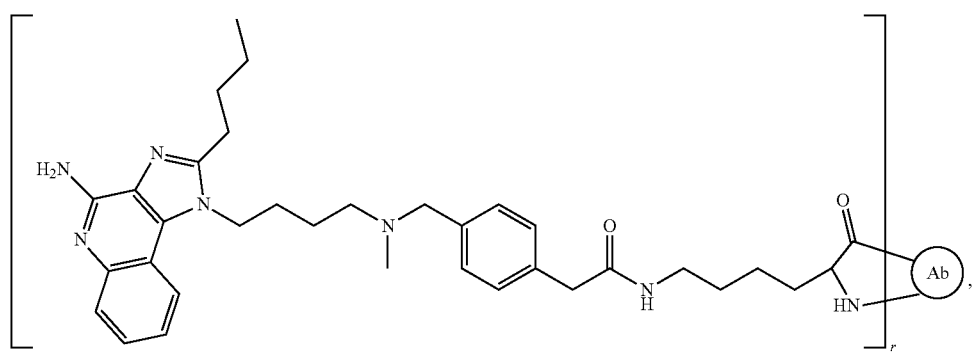
(BB26)
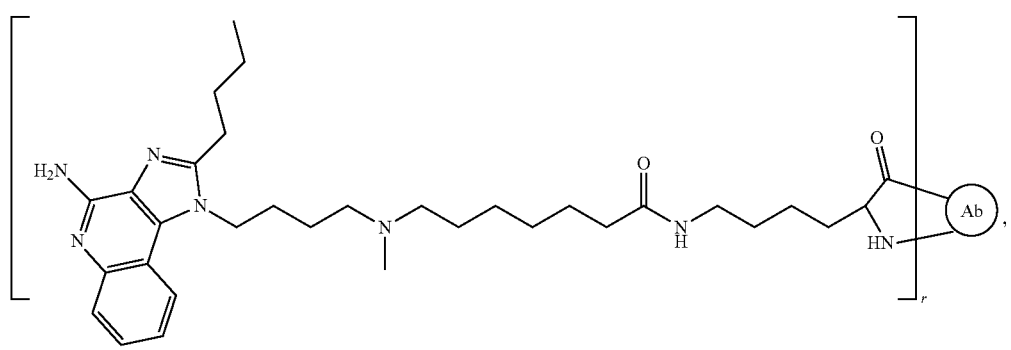
(BB27)
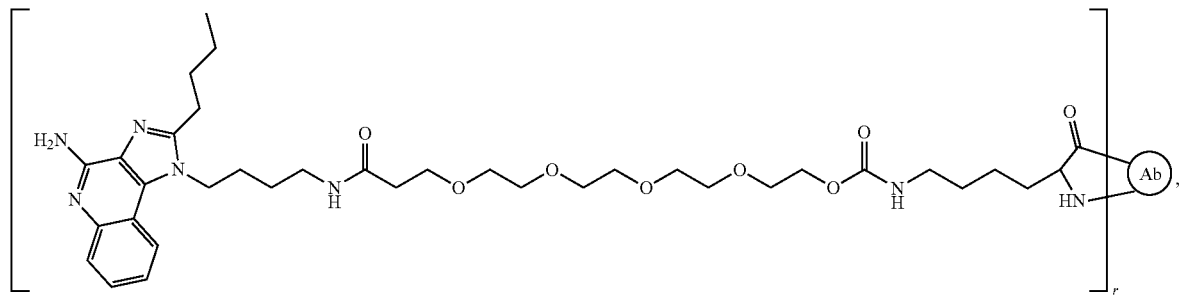
(BB32)

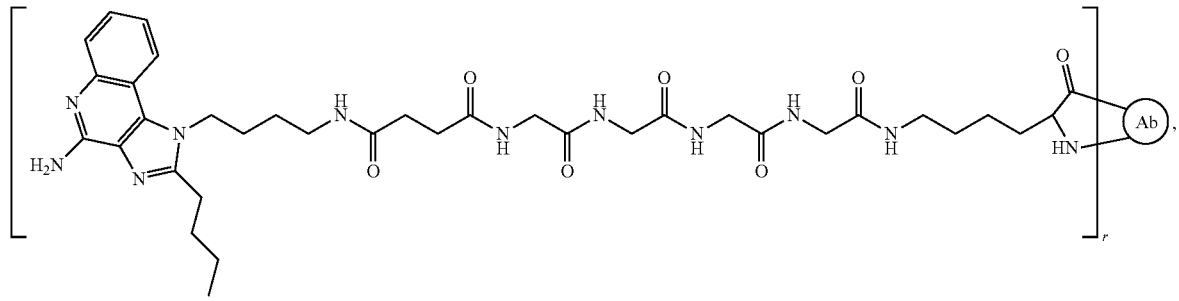
(BB35)
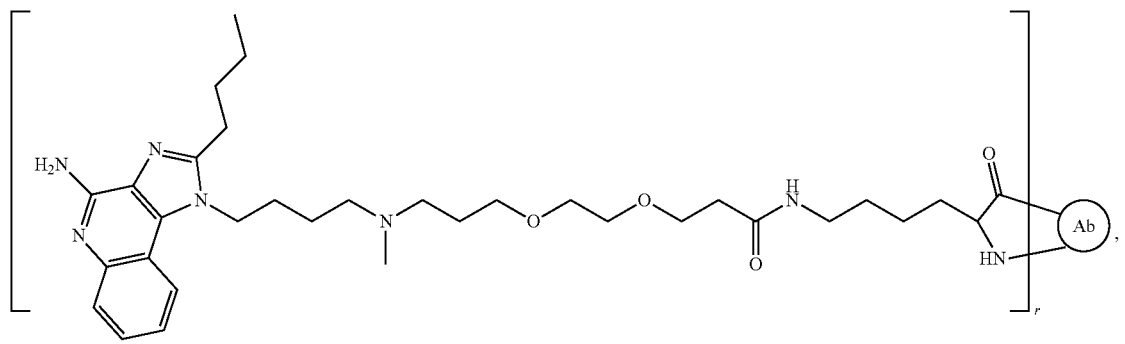
(BB36)
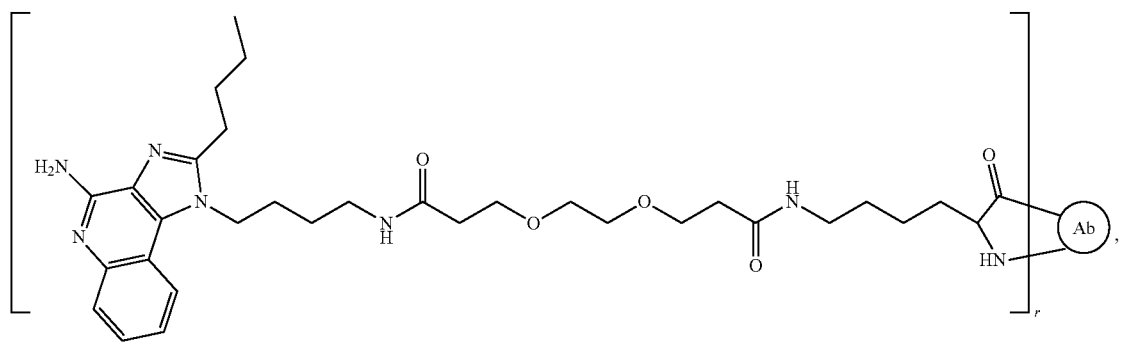
(BB37)
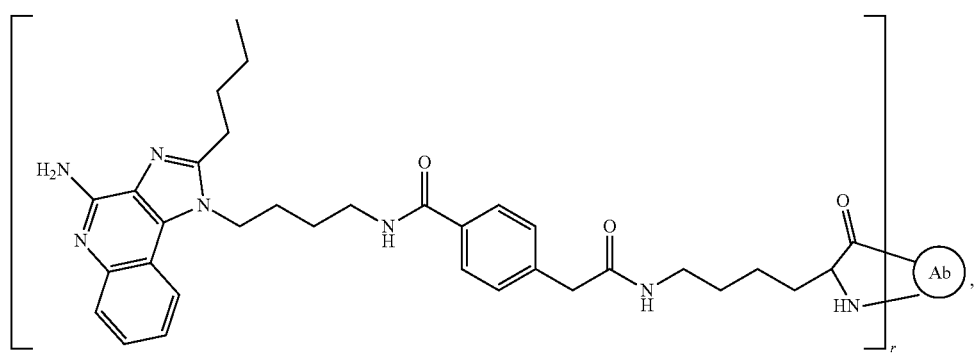
(BB38)

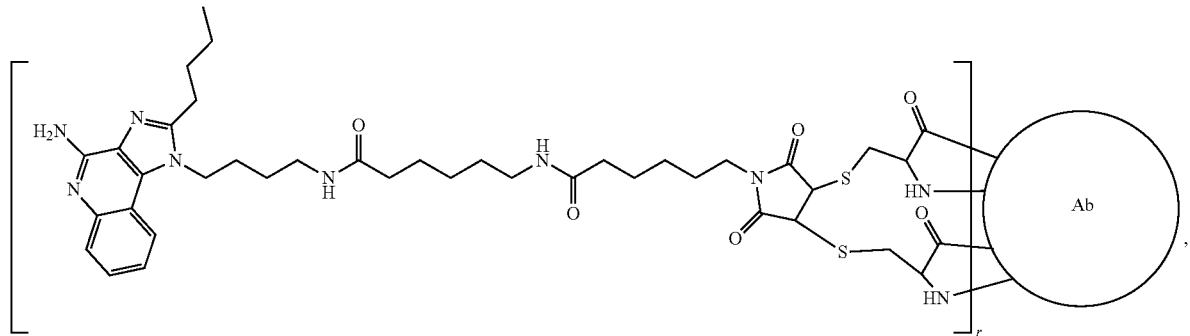
(BB41)
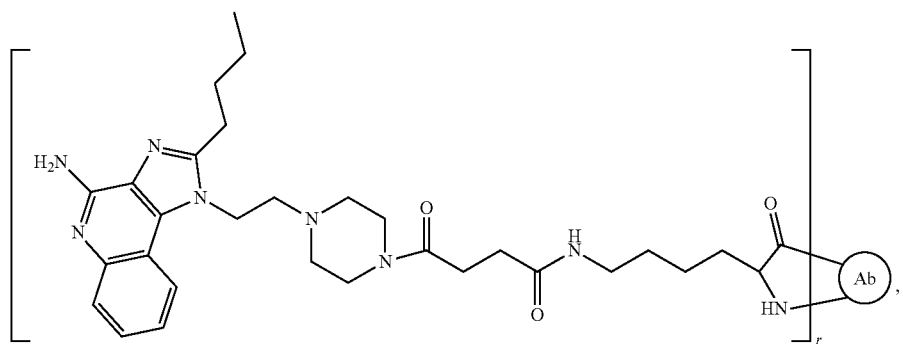
(BB42)
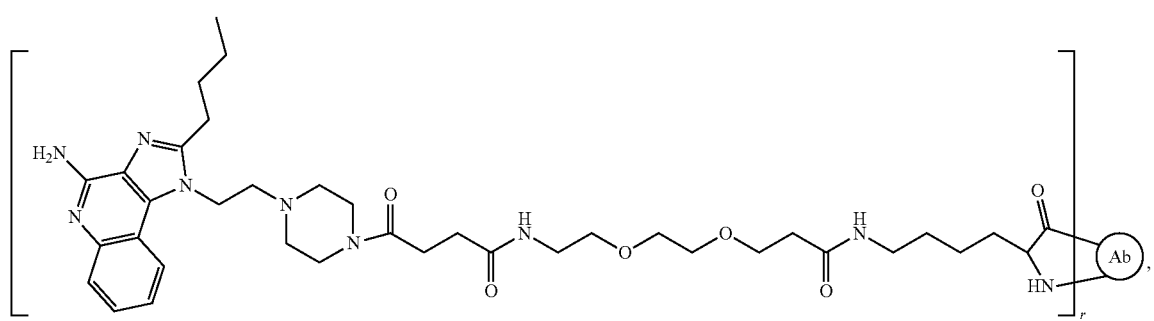
(BB43)
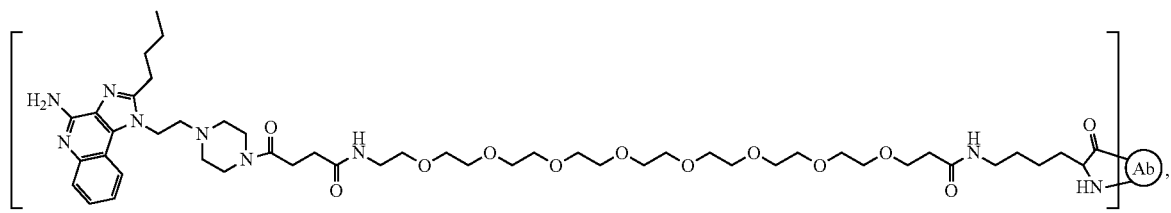
(BB44)
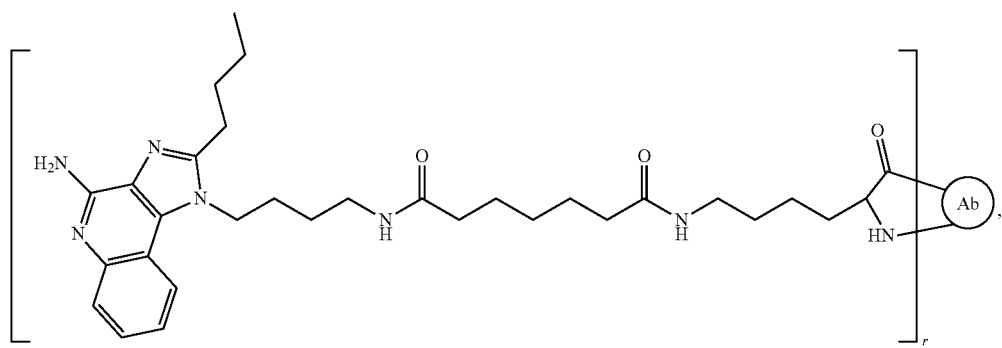
(BB45)

(BB47)
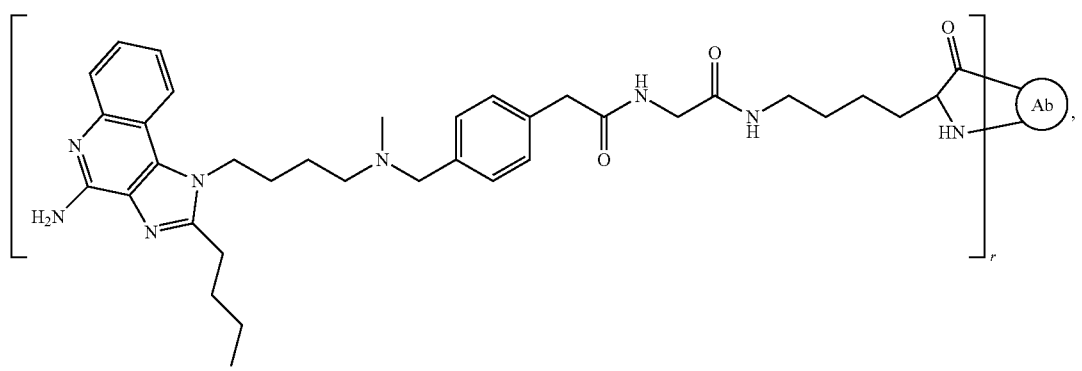
(BB48)
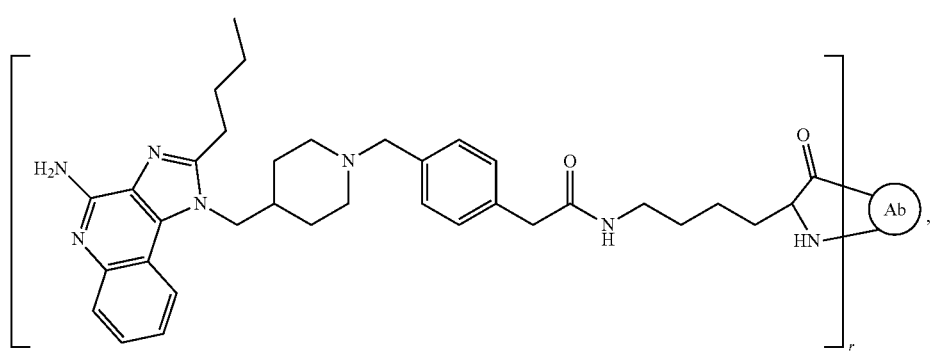
(BB49)
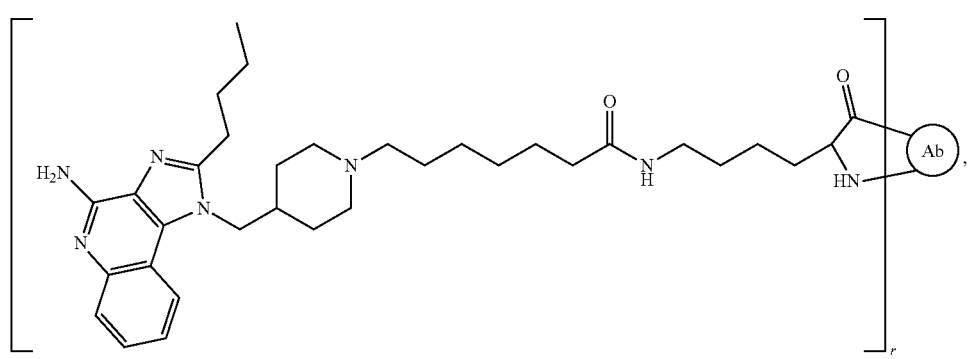
(BB50)
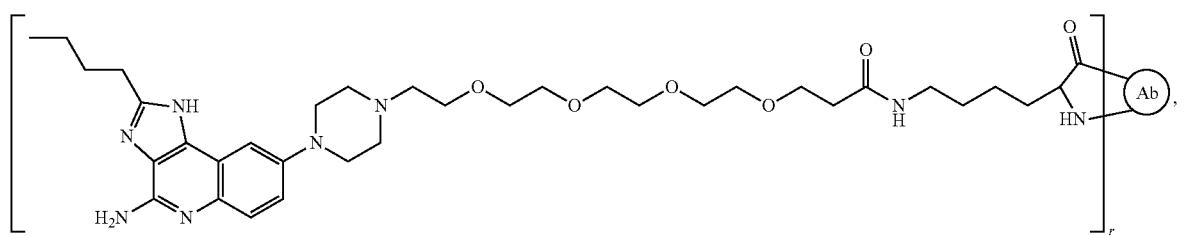

(BB51)
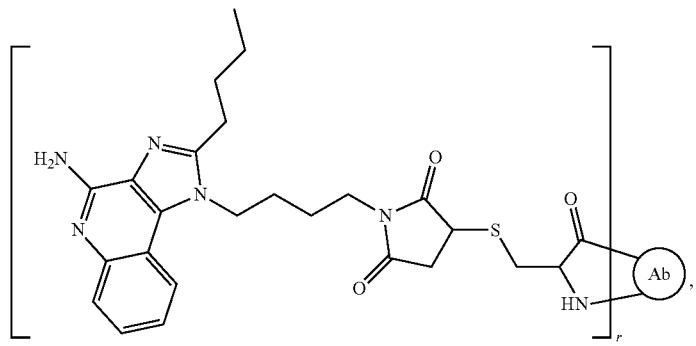
(BB52)
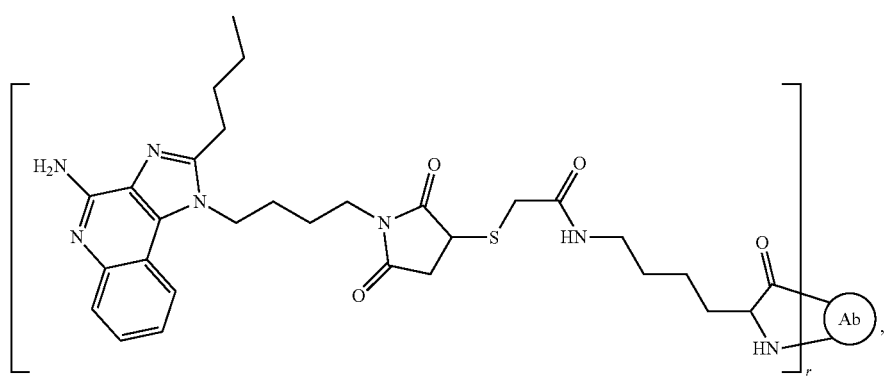
(BB53)
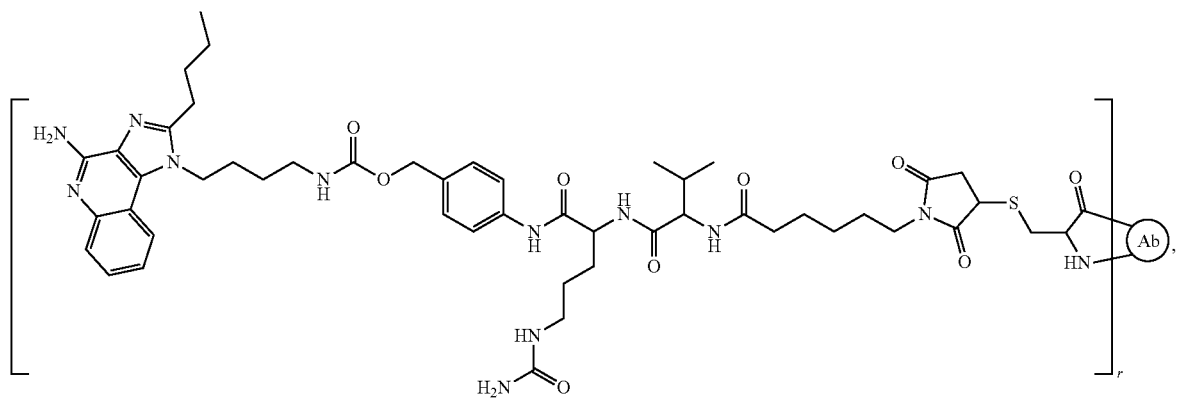
(BB54)
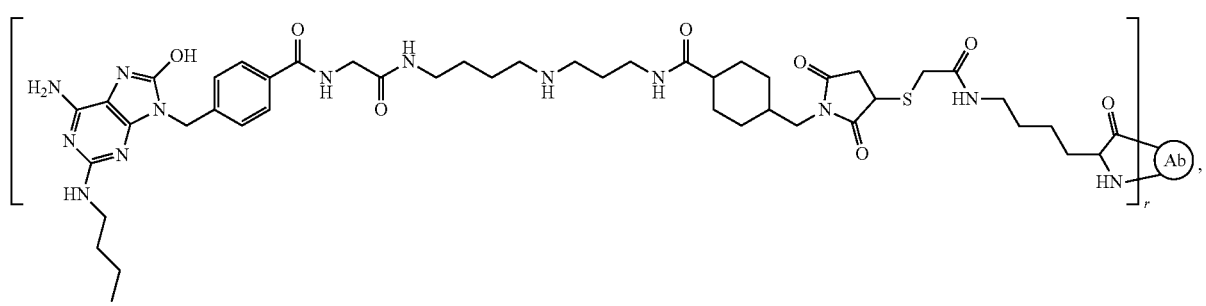

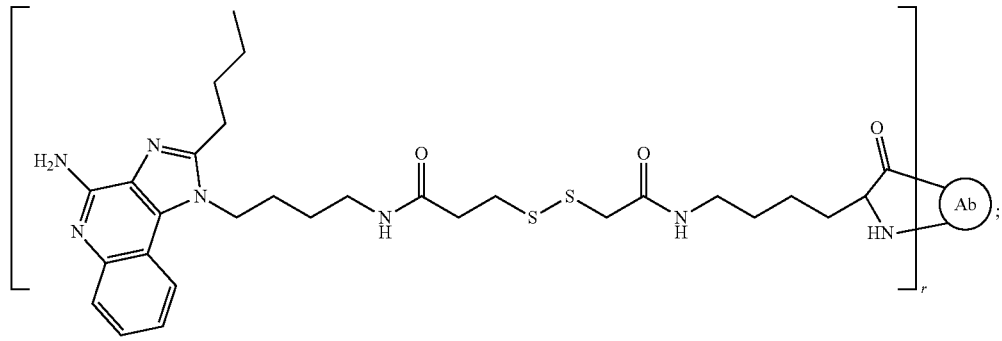
(BB55)
or a pharmaceutically acceptable salt thereof, wherein Ab is an antibody with at least one lysine side chain and subscript r is an integer from 1 to 10 (i.e., 1, 2, 3, 4, 5, 6, 7, 8, 9, or 10). In certain embodiments, subscript r is an integer from 1 to 4 (i.e., 1, 2, 3, or 4).
In certain embodiments, the immunoconjugate has a structure selected from:
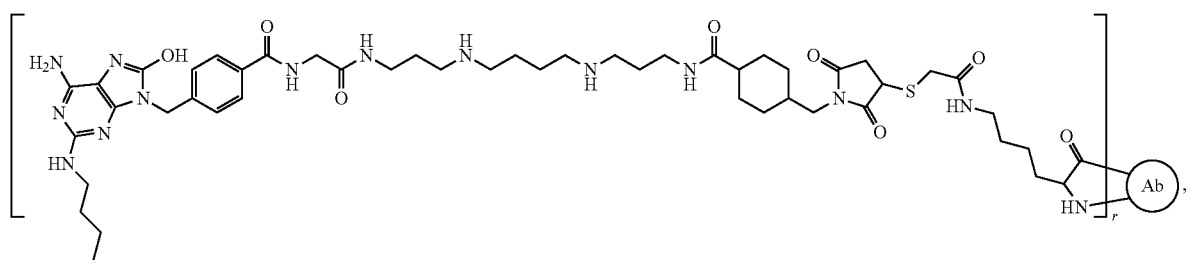
(BB56)
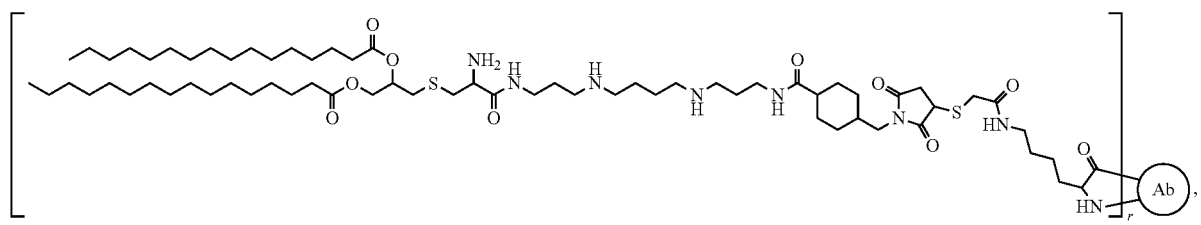
(BB57)
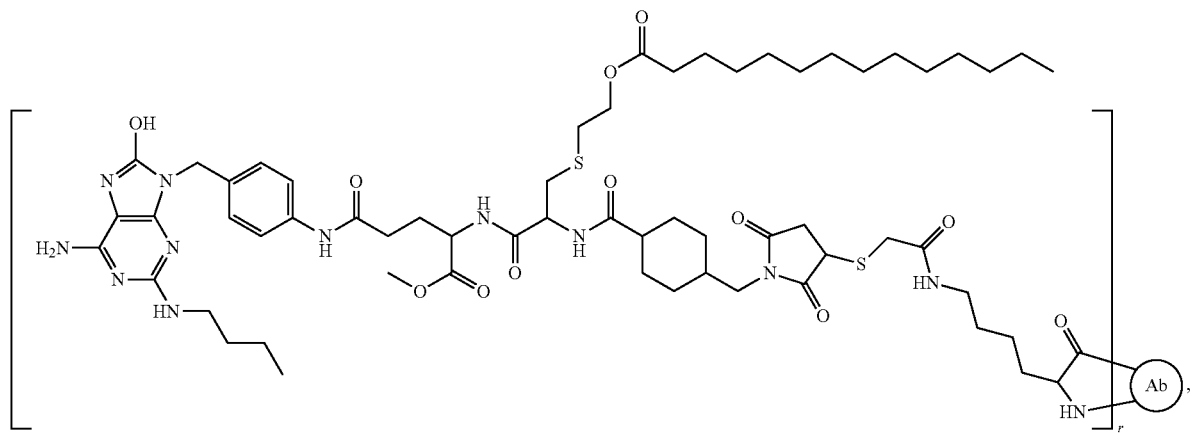
(BB58)

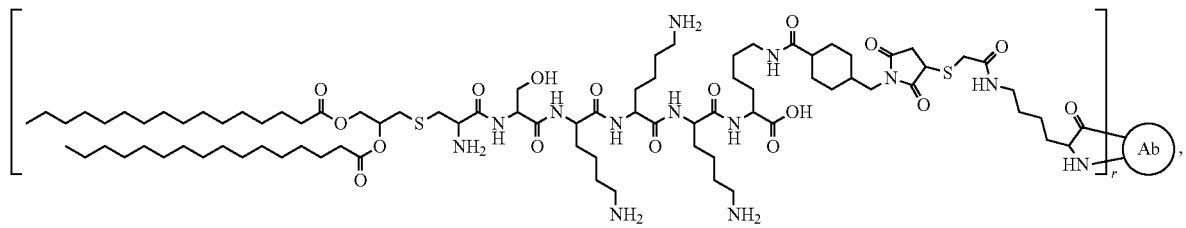
(BB59)
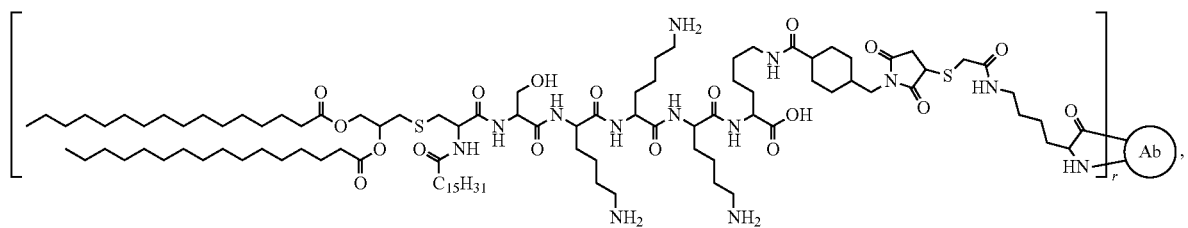
(BB60)
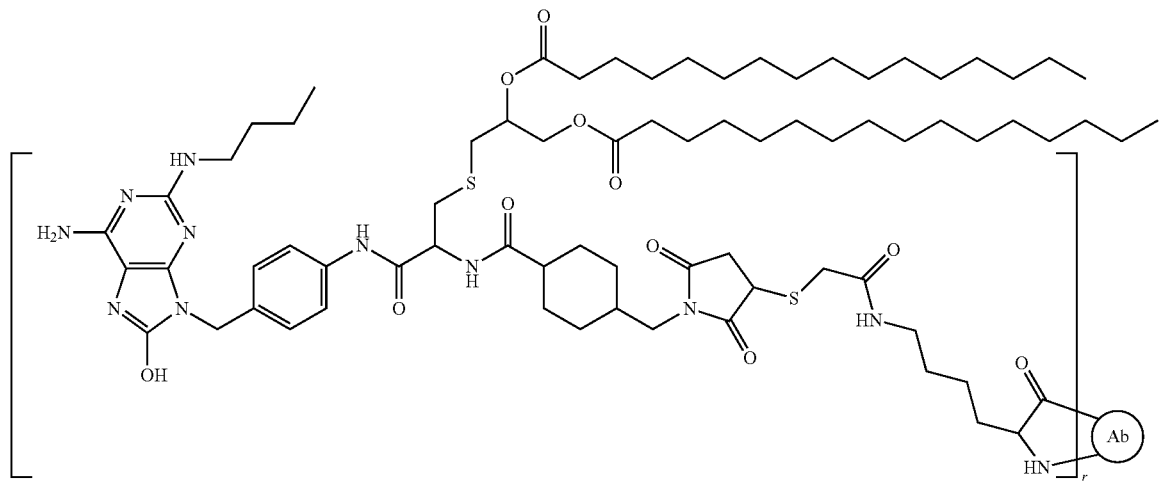
(BB61)
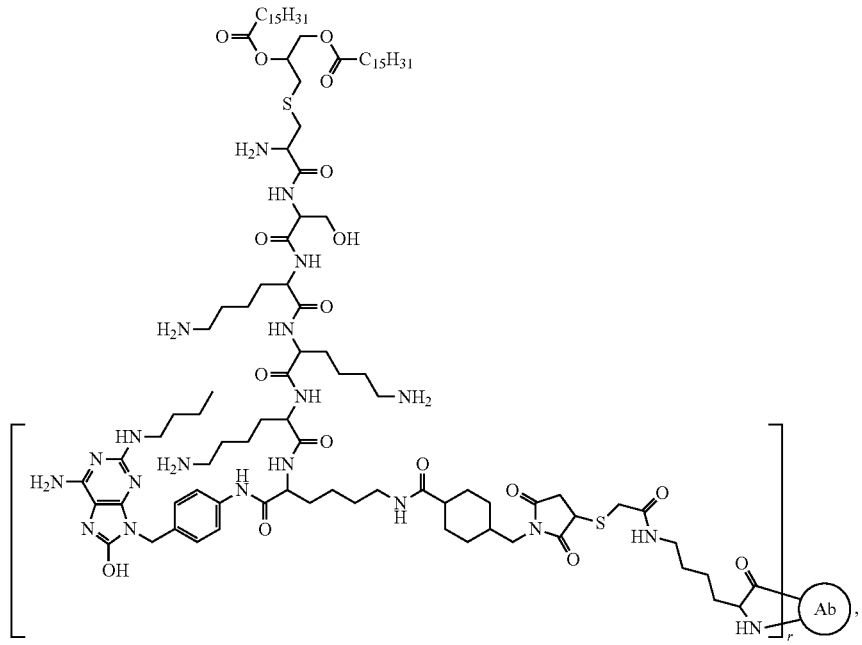
(BB62)

-continued (BB63)

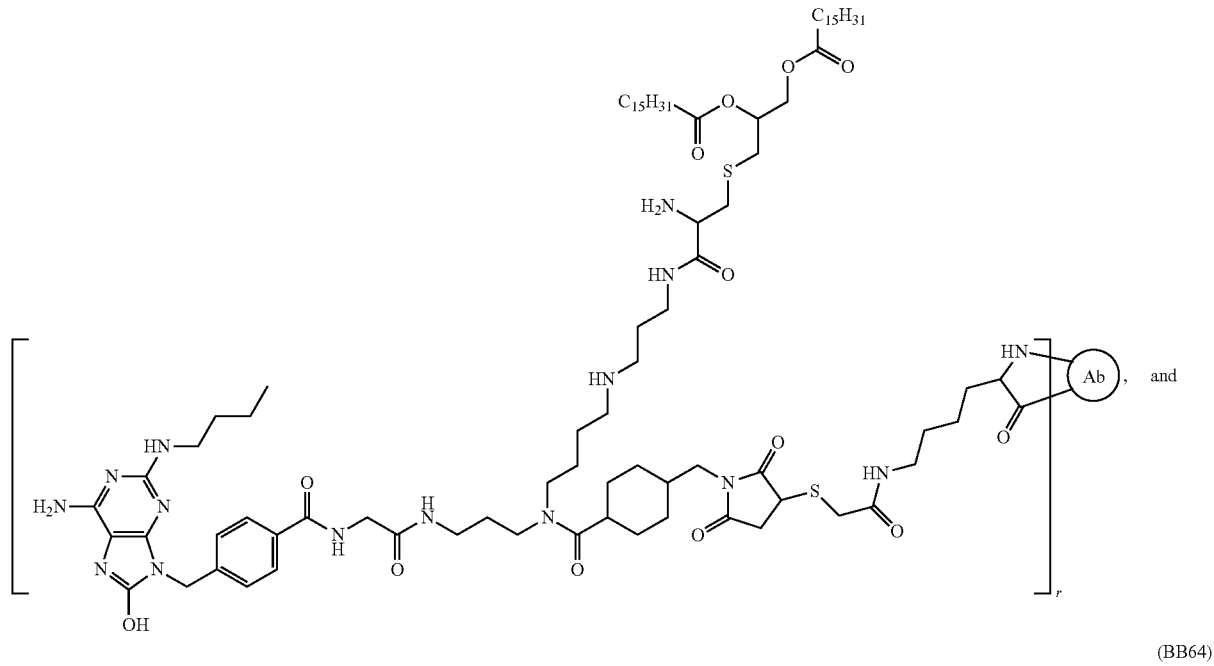

(BB64)

or a pharmaceutically acceptable salt thereof, wherein Ab is an antibody with at least one lysine side chain and subscript r is an integer from 1 to 10 (i.e., 1, 2, 3, 4, 5, 6, 7, 8, 9, or 10). In certain embodiments, subscript r is an integer from 1 to 4 (i.e., 1, 2, 3, or 4).

In a second aspect, the invention provides an improved method for producing an immunoconjugate of Formula III from one or more compounds of Formula V and an antibody of Formula VI, the method comprising the step of:

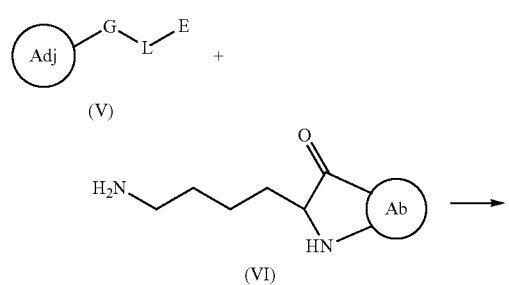

-continued

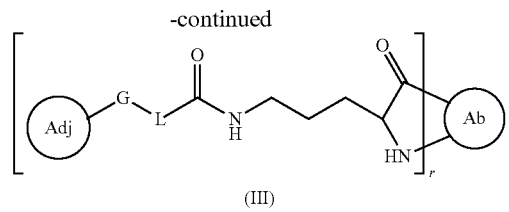

wherein Adj is an adjuvant; G is $CH_2$, C=O, or a bond; L is a linker; E is an ester; Formula VI is an antibody with at least one lysine side chain; and subscript r is an integer from 1 to 10 (i.e., 1, 2, 3, 4, 5, 6, 7, 8, 9, or 10). In certain embodiments, the adjuvant ("Adj") is a TLR agonist.

Any suitable linker can be used provided it can be bound to the antibody (compound of Formula VI) through an ester. For example, the linker ("L") can have the following formula

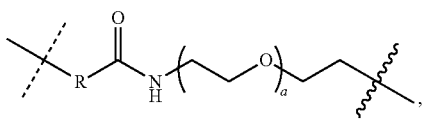

L1 wherein R is optionally present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units; subscript a is an integer from 1 to 40; the dashed line (" ⁄ ") represents the point of attachment to

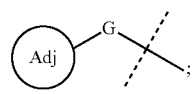

and the wavy line (" ⁄⁄ ") represents the point of attachment to E. In some embodiments, subscript a is an integer from 1 to 20. In some embodiments, subscript a is an integer from 1 to 10. In some embodiments, subscript a is an integer from 1 to 5. In some embodiments, subscript a is an integer from 1 to 3. In certain embodiments, R is present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units.

The linker ("L") can have the following formula

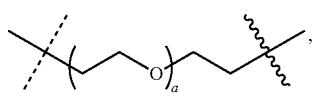

L2 wherein subscript a is an integer from 1 to 40; the dashed line (" ⁄ ") represents the point of attachment to

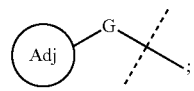

and the wavy line (" ⁄⁄ ") represents the point of attachment to E.

In some embodiments, subscript a is an integer from 1 to 20. In some embodiments, subscript a is an integer from 1 to 10. In some embodiments, subscript a is an integer from 1 to 5. In some embodiments, subscript a is an integer from 1 to 3.

The linker ("L") can also have the following formula

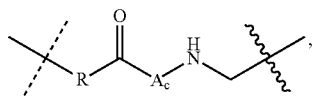

L3 wherein R is optionally present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units; each A is independently selected from any amino acid; subscript c is an integer from 1 to 20; the dashed line (" ⁄ ") represents the point of attachment to

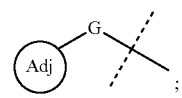

and the wavy line (" ⁄⁄ ") represents the point of attachment to E. In some embodiments, subscript c is an integer from 1 to 10. In some embodiments, subscript c is an integer from 1 to 5. In some embodiments, subscript c is an integer from 1 to 2. In certain embodiments, R is present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units.

The linker ("L") can also have the following formula

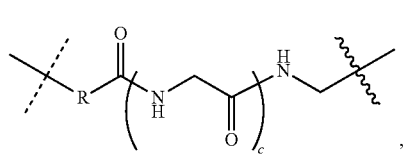

L4 wherein R is optionally present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units; subscript c is an integer from 1 to 20; the dashed line (" ⁄ ") represents the point of attachment td

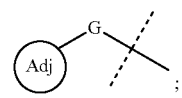

and the wavy line (" ⁄⁄ ") represents the point of attachment to E. In some embodiments, subscript c is an integer from 1 to 10. In some embodiments, c is an integer from 1 to 5. In certain embodiments, R is present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units.

The linker ("L") can also have the following formula

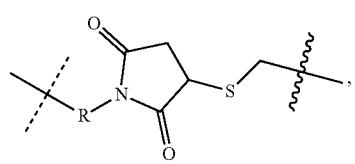

L5 wherein R is optionally present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units; the dashed line (" ⁄ ") represents the point of attachment to

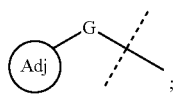

and the wavy line ("⁓") represents the point of attachment to E. In certain embodiments, R is present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units.

The linker ("L") can also have the following formula

L6

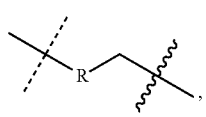

wherein R is optionally present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units; the dashed line ("--") represents the point of attachment to

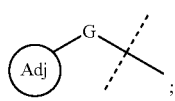

and the wavy line ("⁓") represents the point of attachment to E. In certain embodiments, R is present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units.

The linker ("L") can also have the following formula

L7

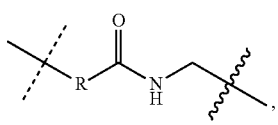

wherein R is optionally present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units; the dashed line ("--") represents the point of attachment to

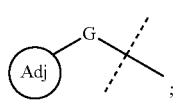

and the wavy line ("⁓") represents the point of attachment to E. In certain embodiments, R is present and is a linear or branched, cyclic or straight, saturated or unsaturated alkyl, heteroalkyl, aryl, or heteroaryl chain comprising from 1 to 8 (i.e., 1, 2, 3, 4, 5, 6, 7, or 8) carbon units.

In some embodiments, the compound of Formula V is selected from:

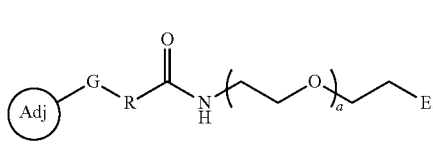

Va

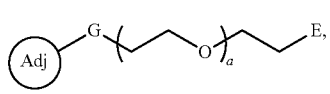

Vb

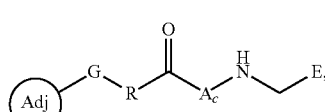

Vc

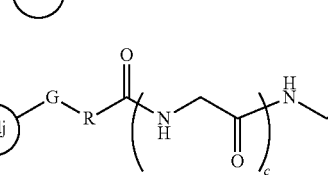

Vd

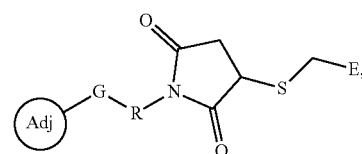

Ve

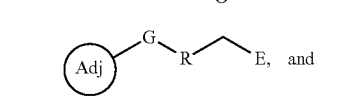

Vf

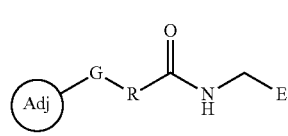

Vg wherein G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; subscript a is an integer from 1 to 40; each A is independently selected from any amino acid; subscript c is an integer from 1 to 20, and E is an ester.

As previously discussed, there are many ways of forming an immunoconjugate. Each of the prior art methods suffers from downsides. The present method includes a one-step process which conjugates an adjuvant, modified to include a linker, to the lysine side chain of an antibody (compound of Formula VI). This process is possible by using an ester. The ester can be any suitable ester capable of linking the compound of Formula V to a lysine side chain of an antibody (compound of Formula VI).

For example, the ester of Formula V can be an N-hydroxysuccinimide ("NHS") ester of the formula:

E1

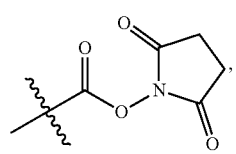

wherein the wavy line ("⁓") represents the point of attachment to the linker ("L").

The ester of Formula V can also be a sulfo-N-hydroxysuccinimide ester of the formula:

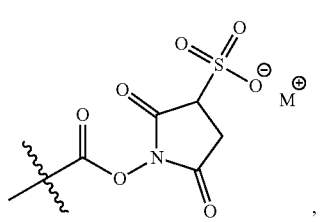

E2 wherein M is any cation and the wavy line ("⌇") represents the point of attachment to the linker ("L"). For example, the cation counter ion ("M") can be a proton, ammonium, a quaternary amine, a cation of an alkali metal, a cation of an alkaline earth metal, a cation of a transition metal, a cation of a rare-earth metal, a main group element cation, or a combination thereof.

The ester of Formula V can also be a phenol ester of the formula:

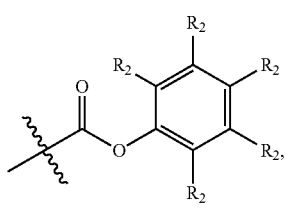

E3 wherein each $R_2$ is independently selected from hydrogen or fluorine and the wavy line ("⌇") represents the point of attachment to the linker ("L").

The ester of Formula V can also be a phenol ester of the formula:

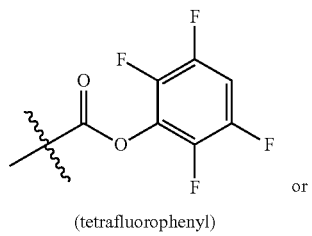

E3a (tetrafluorophenyl)

or

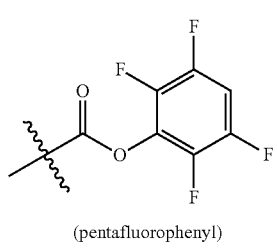

E3b (pentafluorophenyl)

wherein the wavy line ("⌇") represents the point of attachment to the linker ("L").

In some embodiments, the antibody of Formula VI and the ester of Formula V are combined in any suitable aqueous buffer. An exemplary list of suitable aqueous buffers is phosphate buffered saline, borate buffered saline, and tris buffered saline.

Using a tetrafluorophenyl ("TFP") or pentafluorophenyl ("PFP") is especially effective in synthesizing the immunoconjugates of the present invention.

Accordingly, an exemplary, but non-limiting, list of compounds of Formula V is:

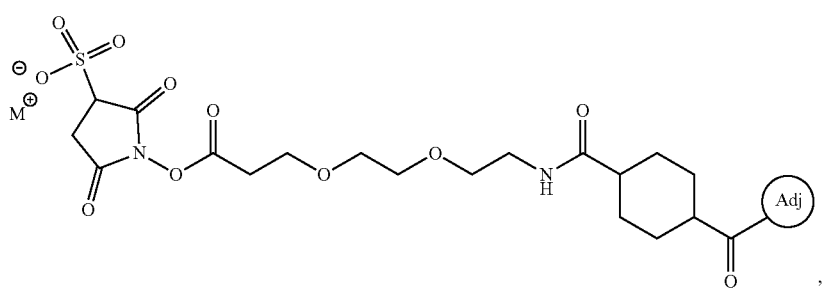

Va

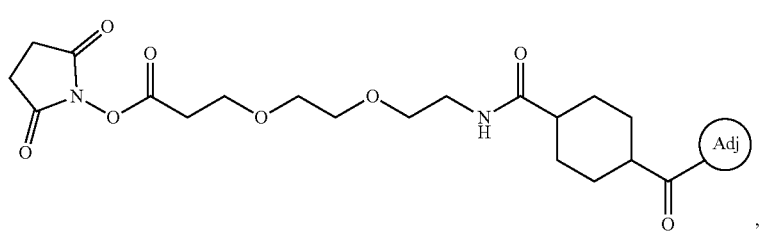

Vb

-continued
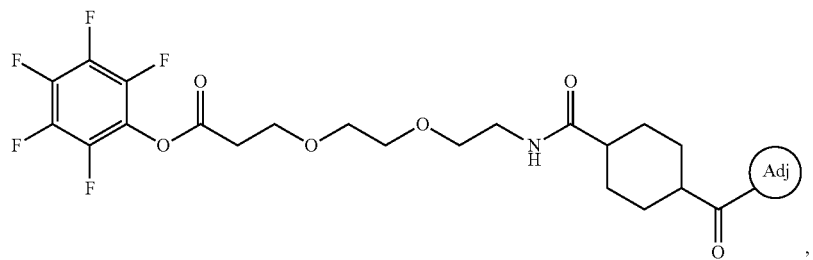
Vc
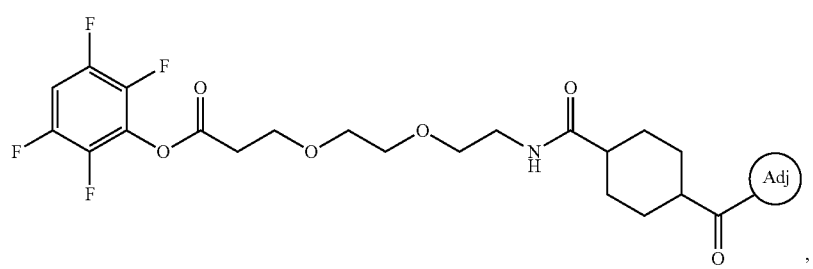
Vd
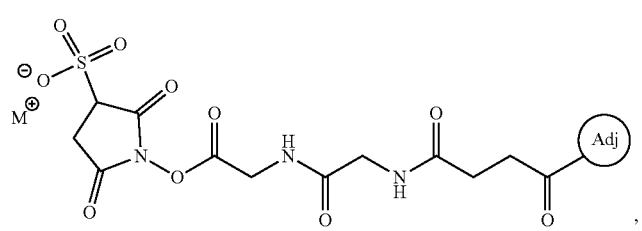
Ve
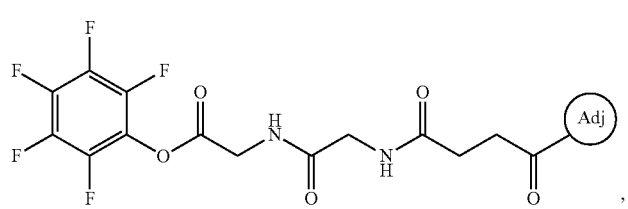
Vf
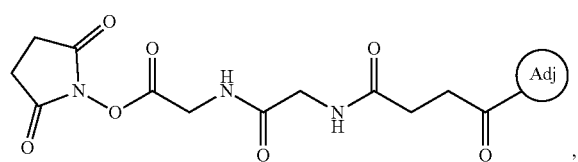
Vg
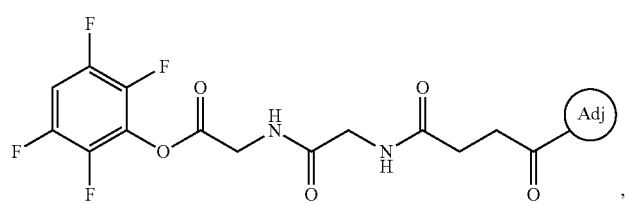
Vh
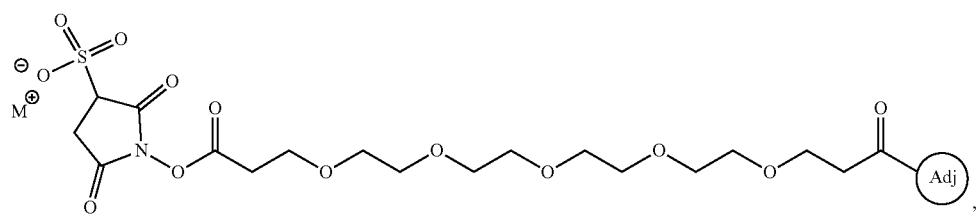
Vi -continued
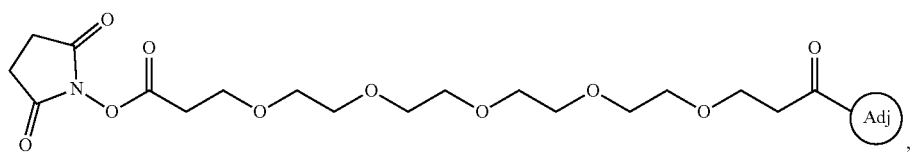
Vj
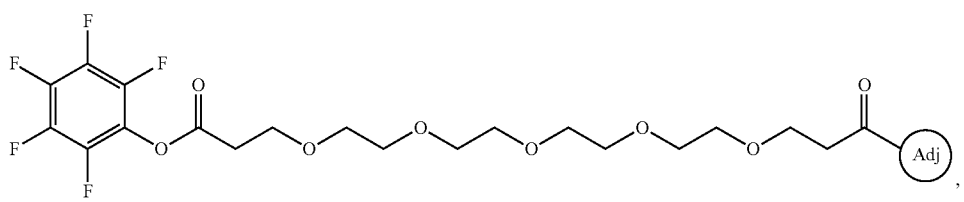
Vk
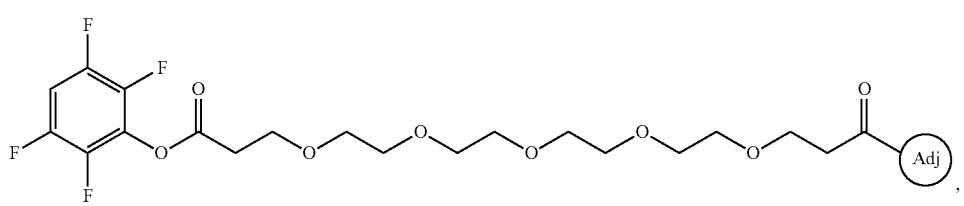
Vl
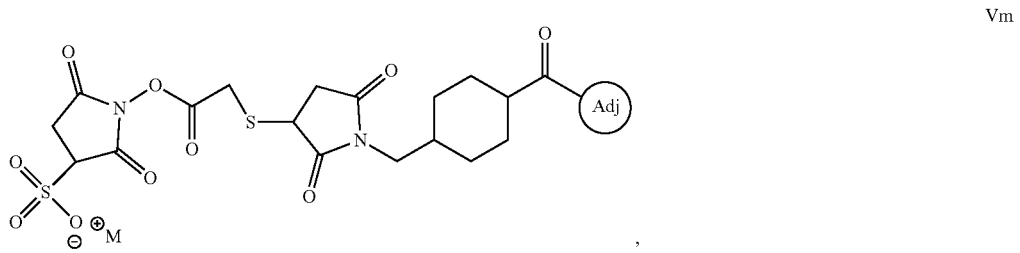
Vm
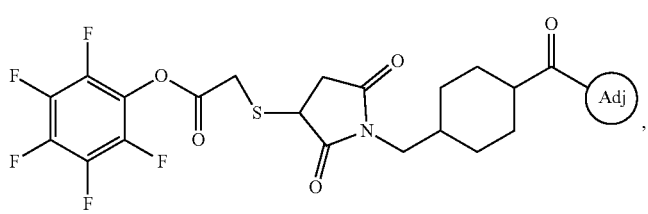
Vn
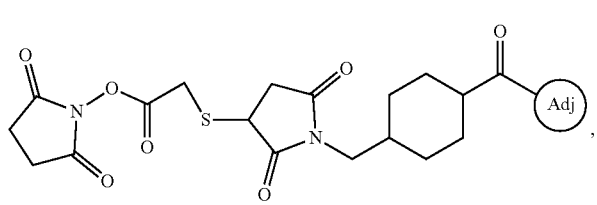
Vo
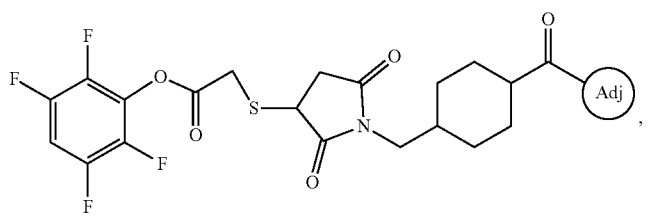
Vp -continued
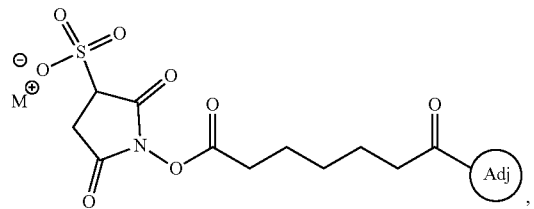 Vq,
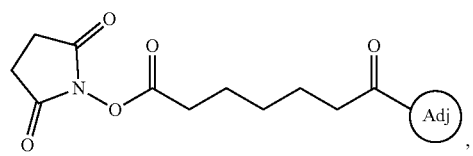 Vr,
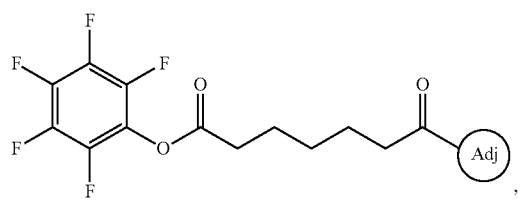 Vs,
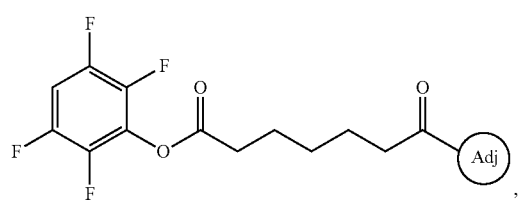 Vt,
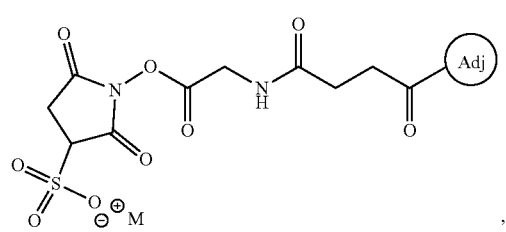 Vu,
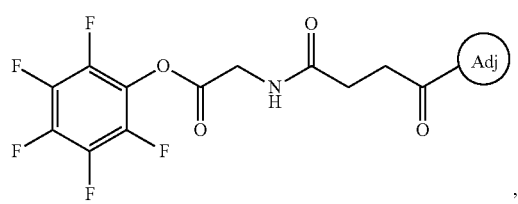 Vv,
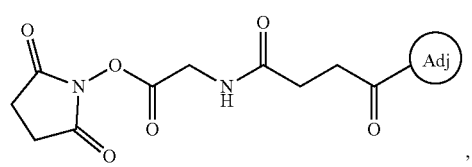 Vw,
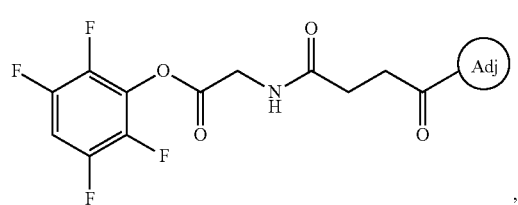 Vx, -continued
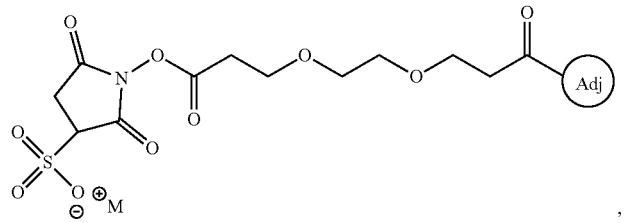 Vy
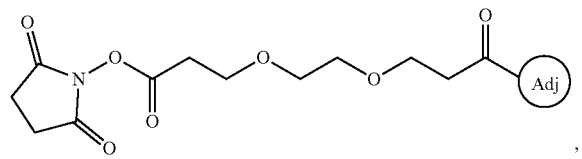 Vz
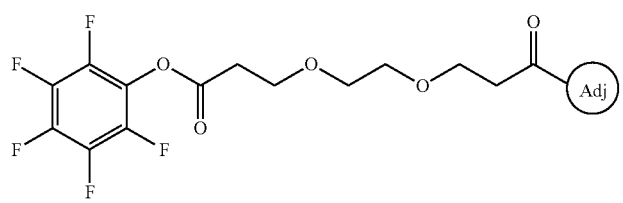 Vaa
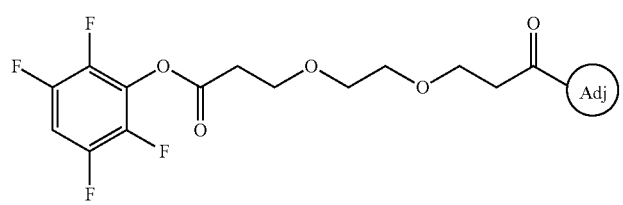 Vbb
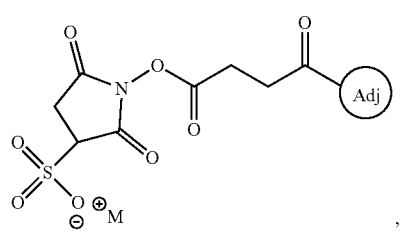 Vcc
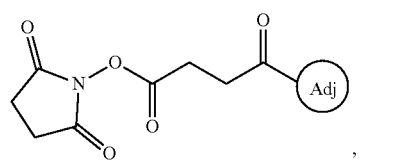 Vdd
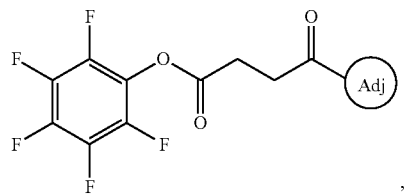 Vee
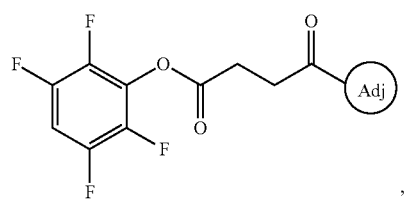 Vff

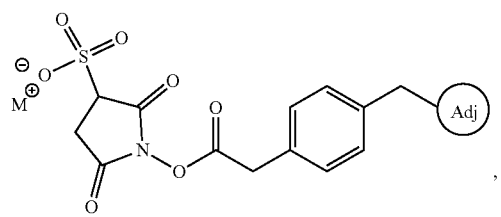 Vgg
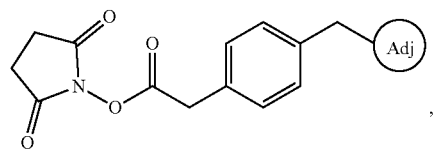 Vhh
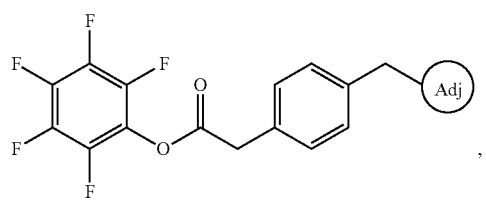 Vii
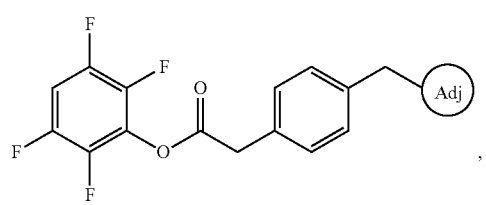 Vjj
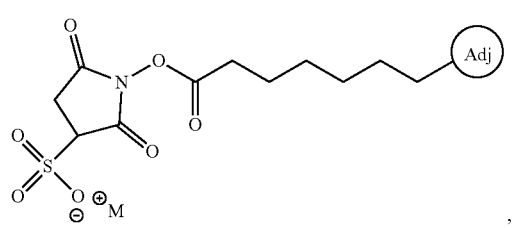 Vkk
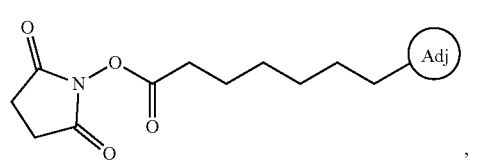 Vll
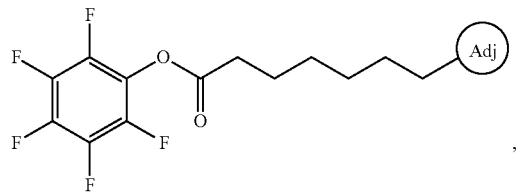 Vmm
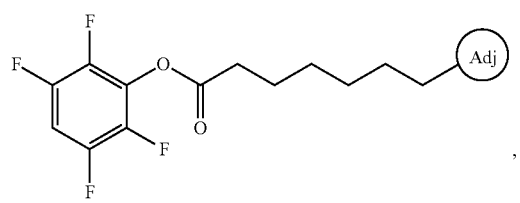 Vnn -continued

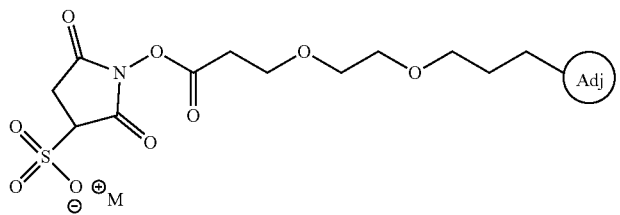

,

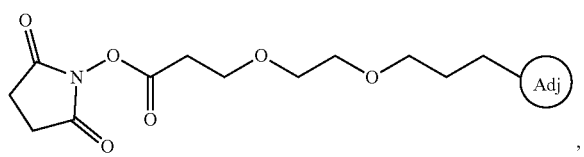

,

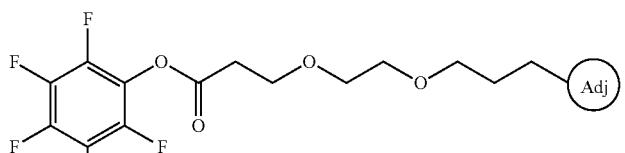

, or

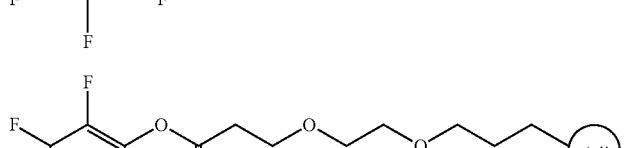

;

$V_{oo}$ $V_{pp}$ $V_{qq}$ $V_{rr}$ wherein Adj is an adjuvant and M is any cation. For example, the cation counter ion ("M") can be a proton, ammonium, a quaternary amine, a cation of an alkali metal, a cation of an alkaline earth metal, a cation of a transition metal, a cation of a rare-earth metal, a main group element cation, or a combination thereof.

Accordingly, the one or more compounds of Formula V and an antibody of Formula VI can be combined to form an immunoconjugate of Formula III. An exemplary, but non-limiting list of immunoconjugates of Formula III is:

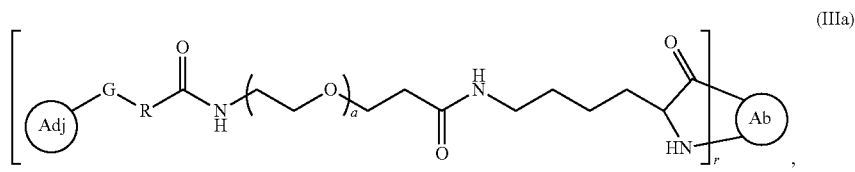

(IIIa)

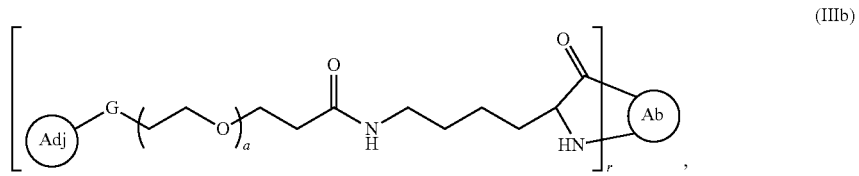

(IIIb)

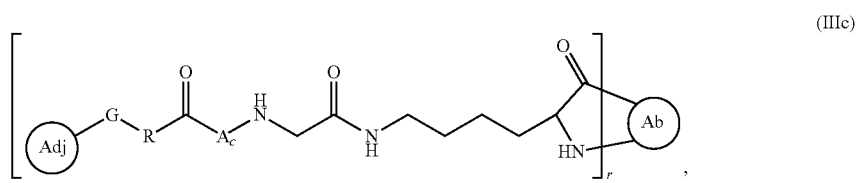

(IIIc)

, (IIId)

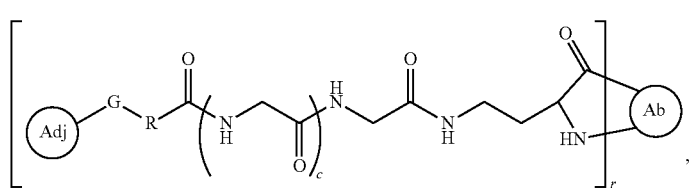

(IIIe)

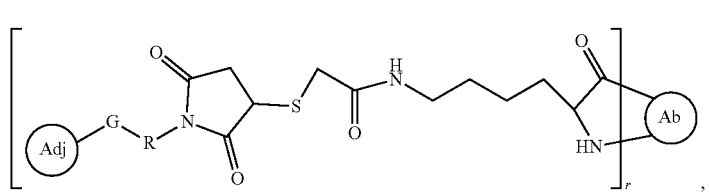

(IIIf)

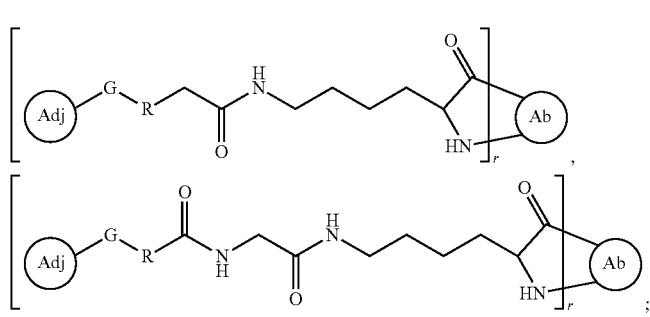

or a pharmaceutically acceptable salt thereof, wherein Ab is an antibody with at least one lysine side chain; Adj is an adjuvant; G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; subscript a is an integer from 1 to 40; each A is independently selected from any amino acid; subscript c is an integer from 1 to 20; and subscript r is an integer from 1 to 10 (i.e., 1, 2, 3, 4, 5, 6, 7, 8, 9, or 10).

In a third aspect, the invention provides an immunoconjugate contain linking moieties that covalently bond the adjuvant moieties, comprising an oligonucleotide, to the antibodies. In certain embodiments, the immunoconjugate is an A-type CPG oligonucleotide immunoconjugate selected from an immunoconjugate of Formula VIIa:

-continued

VIIa-ii

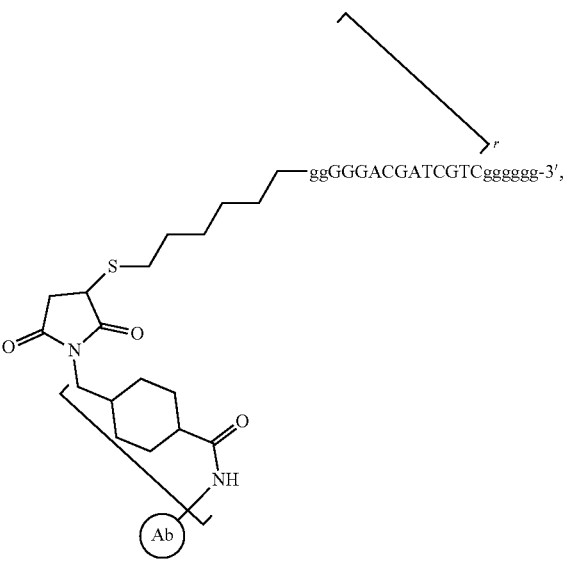

VIIa-i

VIIa-iii

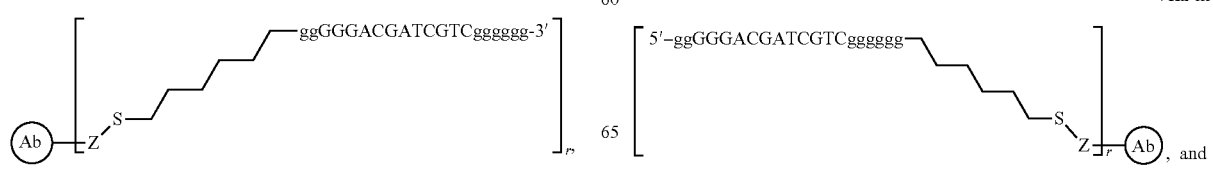

, and

145
-continued

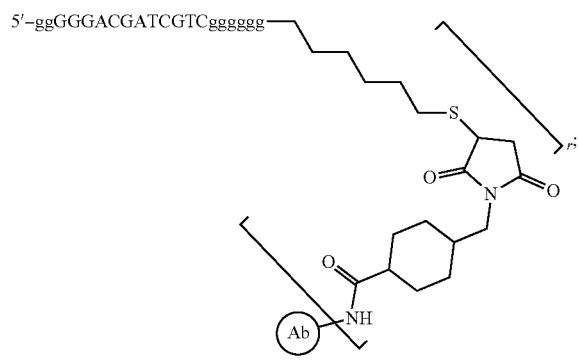

VIIa-iv or a pharmaceutically acceptable salt thereof, wherein Ab is an antibody bound at an unmodified amino acid sidechain in the antibody or a modified amino acid sidechain in the antibody; Z is a linking moiety; subscript r is an integer from 1 to 10 (i.e., 1, 2, 3, 4, 5, 6, 7, 8, 9, or 10); lowercase nucleotides signify a phosphorothioate linkage; and uppercase nucleotides signify a phosphodiester linkage. In certain embodiments, the linking moiety ("Z") is as defined above and herein.

In certain embodiments, the immunoconjugate is an B-type CPG oligonucleotide immunoconjugate selected from an immunoconjugate of Formula VIIb:

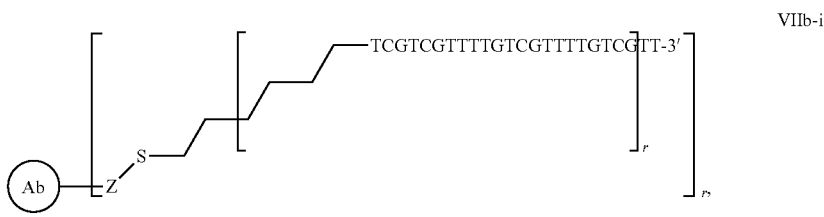

VIIb-i

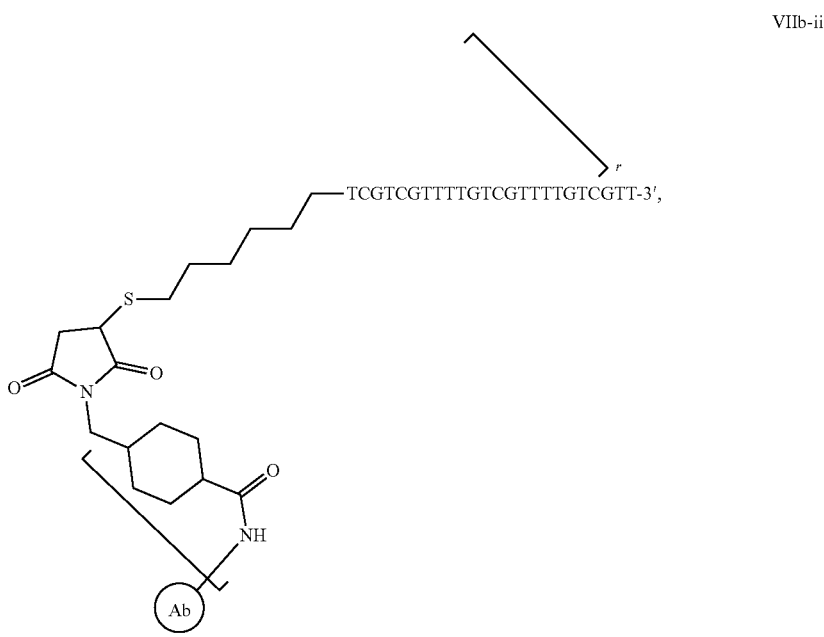

VIIb-ii

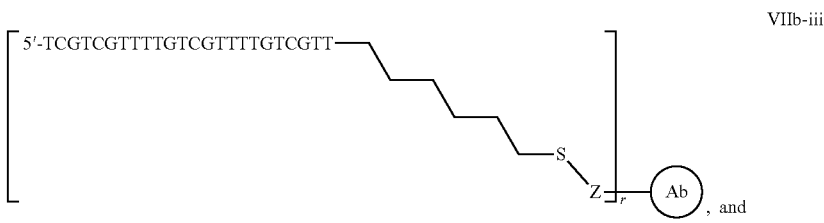

VIIb-iii

, and

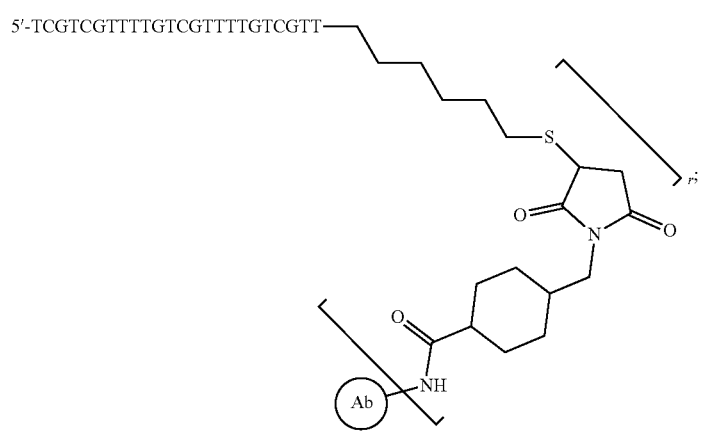

VIIb-iv or a pharmaceutically acceptable salt thereof, wherein Ab is an antibody bound at an unmodified amino acid sidechain in the antibody or a modified amino acid sidechain in the antibody; Z is a linking moiety; subscript r is an integer from 1 to 10 (i.e., 1, 2, 3, 4, 5, 6, 7, 8, 9, or 10); and uppercase nucleotides signify a phosphorothioate linkage. In certain embodiments, the linking moiety ("Z") is as defined above and herein.

In certain embodiments, the immunoconjugate is an C-type CPG oligonucleotide immunoconjugate selected from an immunoconjugate of Formula VIIc:

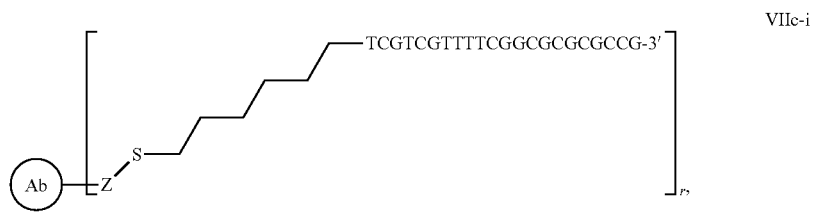

VIIc-i

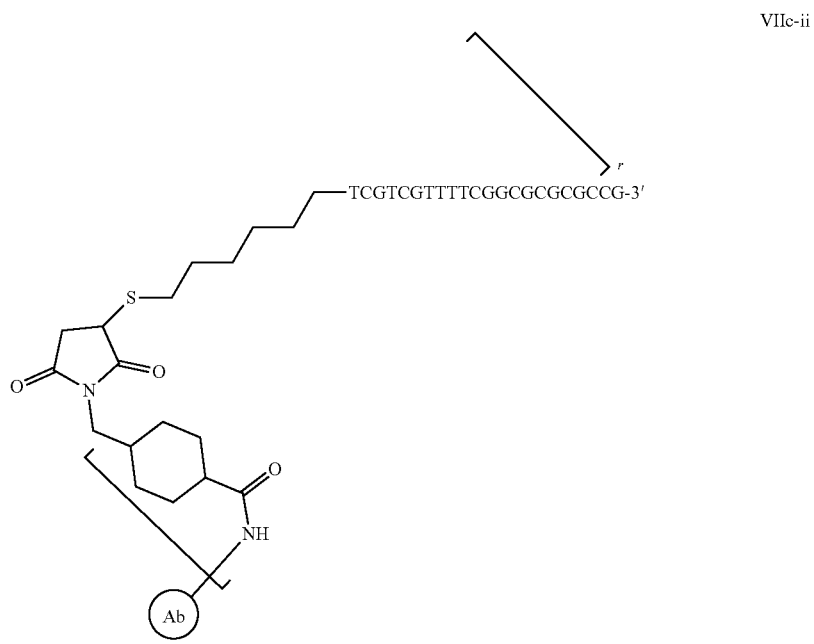

VIIc-ii

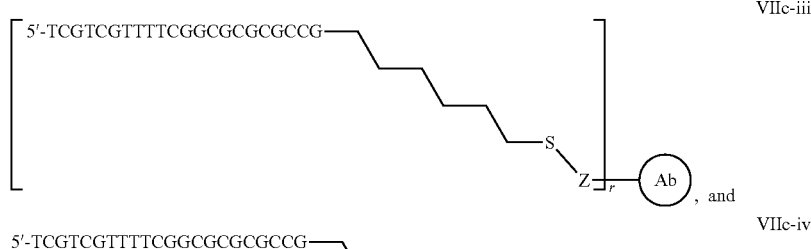

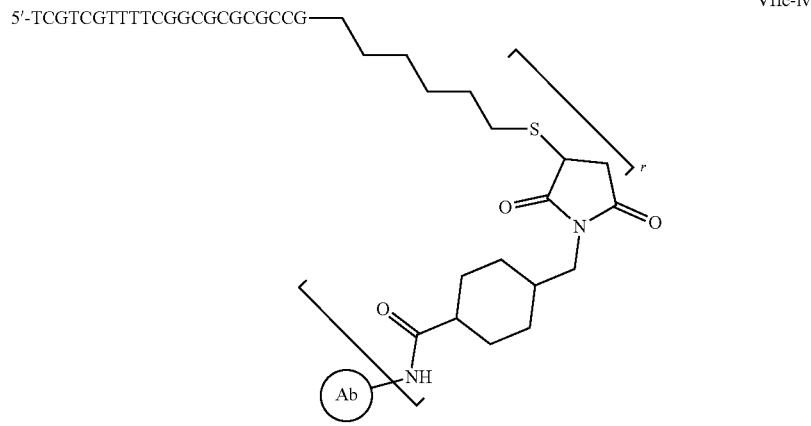

or a pharmaceutically acceptable salt thereof, wherein Ab is an antibody bound at an unmodified amino acid sidechain in the antibody or a modified amino acid sidechain in the antibody; Z is a linking moiety; subscript r is an integer from 1 to 10 (i.e., 1, 2, 3, 4, 5, 6, 7, 8, 9, or 10); and uppercase nucleotides signify a phosphorothioate linkage. In certain embodiments, the linking moiety ("Z") is as defined above and herein.

In certain embodiments, the immunoconjugate is an PolyI:C oligonucleotide immunoconjugate selected from an immunoconjugate of Formula VIId:

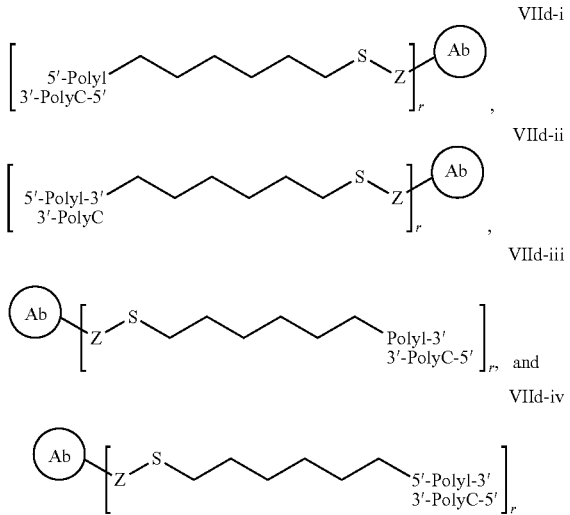

or a pharmaceutically acceptable salt thereof, wherein Ab is an antibody bound at an unmodified amino acid sidechain in the antibody or a modified amino acid sidechain in the antibody; Z is a linking moiety; and subscript r is an integer from 1 to 10 (i.e., 1, 2, 3, 4, 5, 6, 7, 8, 9, or 10). In certain embodiments, the linking moiety ("Z") is as defined above and herein.

Adjuvants

In some embodiments, the adjuvant moiety is a compound that elicits an immune response. In some embodiments, the adjuvant moiety is a pattern recognition receptor ("PRR") agonist. Any adjuvant capable of activating a pattern recognition receptor (PRR) can be installed in the immunoconjugates of the invention. As used herein, the terms "Pattern recognition receptor" and "PRR" refer to any member of a class of conserved mammalian proteins which recognize pathogen-associated molecular patterns ("PAMPs") or damage-associated molecular patterns ("DAMPs"), and act as key signaling elements in innate immunity. Pattern recognition receptors are divided into membrane-bound PRRs, cytoplasmic PRRs, and secreted PRRs. Examples of membrane-bound PRRs include Toll-like receptors ("TLRs") and C-type lectin receptors ("CLRs"). Examples of cytoplasmic PRRs include NOD-like receptors ("NLRs") and Rig-I-like receptors ("RLRs"). In some embodiments, the immunoconjugate can have more than one distinct PRR adjuvant moiety.

In certain embodiments, the adjuvant moiety in an immunoconjugate of the invention is a Toll-like receptor (TLR) agonist. Suitable TLR agonists include TLR1, TLR2, TLR3, TLR4, TLR5, TLR6, TLR7, TLR8, TLR9, TLR10, TLR11, or any combination thereof (e.g., TLR7/8 agonists). Any adjuvant capable of activating a Toll-like receptor (TLR) can be installed in the immunoconjugates of the invention. Toll-like receptors (TLRs) are type-I transmembrane proteins that are responsible for initiation of innate immune responses in vertebrates. TLRs recognize a variety of pathogen-associated molecular patterns from bacteria, viruses, and fungi and act as a first line of defense against invading pathogens. TLRs elicit overlapping yet distinct biological responses due to differences in cellular expression and in the signaling pathways that they initiate. Once engaged (e.g., by a natural stimulus or a synthetic TLR agonist) TLRs initiate a signal transduction cascade leading to activation of NF-κB via the adapter protein myeloid differentiation primary response gene 88 (MyD88) and recruitment of the IL-1 receptor associated kinase (IRAK). Phosphorylation of IRAK then leads to recruitment of TNF-receptor associated factor 6 (TRAF6), which results in the phosphorylation of the NF-κB inhibitor I-κB. As a result, NF-κB enters the cell nucleus and initiates transcription of genes whose promoters contain NF-κB binding sites, such as cytokines. Additional modes of regulation for TLR signaling include TIR-domain containing adapter-inducing interferon-β (TRIF)-dependent induction of TRAF6 and activation of MyD88 independent pathways via TRIF and TRAF3, leading to the phosphorylation of interferon response factor three (IRF3). Similarly, the MyD88 dependent pathway also activates several IRF family members, including IRF5 and IRF7 whereas the TRIF dependent pathway also activates the NF-κB pathway.

Examples of TLR3 agonists include Polyinosine-polycytidylic acid (poly (I:C)), Polyadenylic-polyuridylic acid (poly (A:U), and poly(I)-poly(C12U).

Examples of TLR4 agonists include Lipopolysaccharide (LPS) and Monophosphoryl lipid A (MPLA).

An example of a TLR5 agonist includes Flagellin.

Examples of TLR9 agonists include single strand CpG oligodeoxynucleotides (CpG ODN). Three major classes of stimulatory CpG ODNs have been identified based on structural characteristics and activity on human peripheral blood mononuclear cells (PBMCs), in particular B cells and plasmacytoid dendritic cells (pDCs). These three classes are Class A (Type D), Class B (Type K) and Class C.

Examples of Nod Like Receptor (NLR) agonists include acylated derivative of iE-DAP, D-gamma-Glu-mDAP, L-Ala-gamma-D-Glu-mDAP, Muramyldipeptide with a C18 fatty acid chain, Muramyldipeptide, muramyl tripeptide, and N-glycolylated muramyldipeptide.

Examples of RIG-I-Like receptor (RLR) agonists include 5'ppp-dsrna (5'-pppGCAUGCGACCUCUGUUUGA-3' (SEQ ID NO: 3): 3'-CGUACGCUGGAGACAAACU-5' (SEQ ID NO: 4)), and Poly(deoxyadenylic-deoxythymidylic) acid (Poly(dA:dT))

Additional immune-stimulatory compounds, such as cytosolic DNA and unique bacterial nucleic acids called cyclic dinucleotides, can be recognized by stimulator of interferon genes ("STING"), which can act a cytosolic DNA sensor. ADU-S1OO can be a STING agonist. Non-limiting examples of STING agonists include: Cyclic [G(2',5')pA(2',5')p] (2'2'-cGAMP), cyclic [G(2',5')pA(3',5')p] (2'3'-cGAMP), cyclic [G(3',5')pA(3',5')p] (3'3'-cGAMP), Cyclic di-adenylate monophosphate (c-di-AMP), 2',5'-3',5'-c-di-AMP (2'3'-c-di-AMP), Cyclic di-guanylate monophosphate (c-di-GMP), 2',5'-3',5'-c-diGMP (2'3'-c-di-GMP), Cyclic di-inosine monophosphate (c-di-IMP), Cyclic di-uridine monophosphate (c-di-UMP), KIN700, KIN1148, KIN600, KIN500, KIN1OO, KIN101, KIN400, KIN2000, or SB-9200 can be recognized.

Any adjuvant capable of activating TLR7 and/or TLR8 can be installed in the immunoconjugates of the invention. Examples of TLR7 agonists and TLR8 agonists are described, e.g., by Vacchelli et al. (*OncoImmunology*, 2: 8, e25238, DOI: 10.4161/onci.25238 (2013)) and Carson et al. (U.S. Patent Application Publication 2013/0165455, which is hereby incorporated by reference in its entirety). TLR7 and TLR8 are both expressed in monocytes and dendritic cells. In humans, TLR7 is also expressed in plasmacytoid dendritic cells (pDCs) and B cells. TLR8 is expressed mostly in cells of myeloid origin, i.e., monocytes, granulocytes, and myeloid dendritic cells. TLR7 and TLR8 are capable of detecting the presence of "foreign" single-stranded RNA within a cell, as a means to respond to viral invasion. Treatment of TLR8-expressing cells, with TLR8 agonists can result in production of high levels of IL-12, IFN-γ, IL-1, TNF-u, IL-6, and other inflammatory cytokines. Similarly, stimulation of TLR7-expressing cells, such as pDCs, with TLR7 agonists can result in production of high levels of IFN-α and other inflammatory cytokines. TLR7/TLR8 engagement and resulting cytokine production can activate dendritic cells and other antigen-presenting cells, driving diverse innate and acquired immune response mechanisms leading to tumor destruction.

Examples of TLR7, TLR8 or TLR7/8 agonists include but are not limited to: Gardiquimod (1-(4-amino-2-ethylaminomethylimidazo[4,5-c]quinolin-1-yl)-2-methylpropan-2-ol), Imiquimod (R837) (agonist for TLR7), loxoribine (agonist for TLR7), IRM1 (1-(2-amino-2-methylpropyl)-2-(ethoxymethyl)-1H-imidazo-[4,5-c]quinolin-4-amine), IRM2 (2-methyl-l-[2-(3-pyridin-3-ylpropoxy)ethyl]-1H-imidazo[4,5-c]quinolin-4-amine) (agonist for TLR8), IRM3 (N-(2-[2-[4-amino-2-(2-methoxyethyl)-1H-imidazo[4,5-c]quinolin-1-yl]ethoxy]ethyl)-N-methylcyclohexanecarboxamide) (agonist for TLR8), CL097 (2-(ethoxymethyl)-1H-imidazo[4,5-c]quinolin-4-amine) (agonist for TLR7/8), CL307 (agonist for TLR7), CL264 (agonist for TLR7), Resiquimod (agonist for TLR7/8), 3M-052/MEDI9197 (agonist for TLR7/8), SD-101 (N-[(4S)-2,5-dioxo-4-imidazolidinyl]-urea) (agonist for TLR7/8), motolimod (2-amino-N,N-dipropyl-8-[4-(pyrrolidine-1-carbonyl)phenyl]-3H-1-benzazepine-4-carboxamide) (agonist for TLR8), CL075 (3M002, 2-propylthiazolo[4,5-c]quinolin-4-amine) (agonist for TLR7/8), and TL8-506 (3H-1-benzazepine-4-carboxylic acid, 2-amino-8-(3-cyanophenyl)-, ethyl ester) (agonist for TLR8).

Examples of TLR2 agonists include but are not limited to an agent comprising N-a-palmitoyl-S-[2,3-bis(palmitoyloxy)-(2RS)-propyl]-L-cysteine, palmitoyl-Cys((RS)-2,3-di (palmitoyloxy)-propyl) ("Pam3Cys"), e.g., Pam3Cys, Pam3Cys-Ser-(Lys)4 (also known as "Pam3Cys-SKKKK" and "Pam3CSK4"), Triacyl lipid A ("OM-174"), Lipoteichoic acid ("LTA"), peptidoglycan, and CL419 (S-(2,3-bis (palmitoyloxy)-(2RS)propyl)-(R)-cysteinyl spermine).

An example of a TLR2/6 agonist is Pam₂CSK₄ (S-[2,3-bis(palmitoyloxy)-(2RS)-propyl]-[R]-cysteinyl-[S]-seryl-[S]-lysyl-[S]-lysyl-[S]-lysyl-[S]-lysine x 3 CF3COOH).

Examples of TLR2/7 agonist include CL572 (S-(2-myristoyloxy ethyl)-(R)-cysteinyl 4-((6-amino-2-(butylamino)-8-hydroxy-9H-purin-9-yl)methyl) aniline), CL413 (S-(2,3-bis (palmitoyloxy)-(2RS)propyl)-(R)-cysteinyl-(S)-seryl-(S)-lysyl-(S)-lysyl-(S)-lysyl-(S)-lysyl 4-((6-amino-2-(butylamino)-8-hydroxy-9H-purin-9-yl)methyl)aniline), and CL401 (S-(2,3-bis(palmitoyloxy)-(2RS)propyl)-(R)-cysteinyl 4-((6-amino-2(butyl amino)-8-hydroxy-9H-purin-9-yl)methyl) aniline).

Figure 22A:
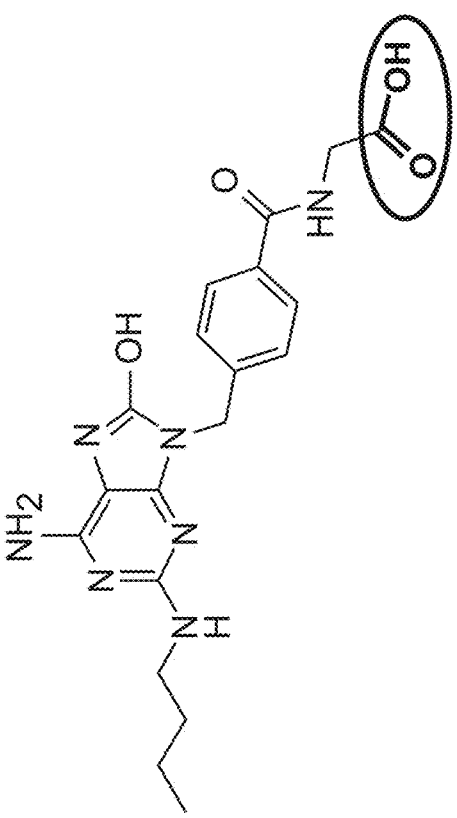
FIG. 22A shows the structure of adjuvant CL264 and the circle indicates a position on the adjuvant where it could be conjugated to the linker, specifically, the terminal carboxylic acid of the adjuvant.
Figure 22B:
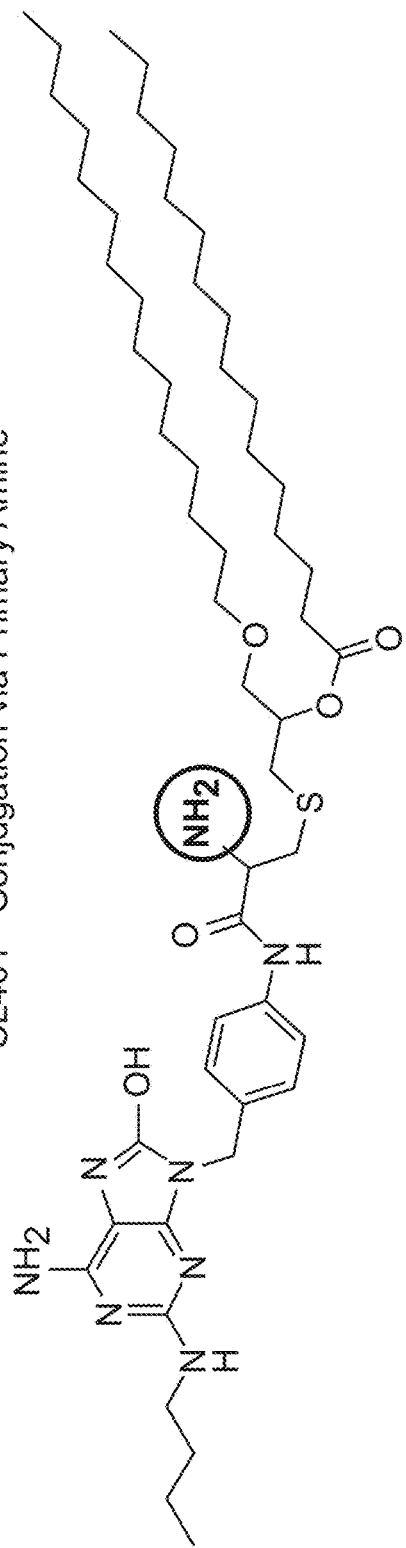
FIG. 22B shows the structure of adjuvant CL401 and the circle indicates a position on the adjuvant where it could be conjugated to the linker, specifically, the primary amine of the adjuvant.
Figure 22C:
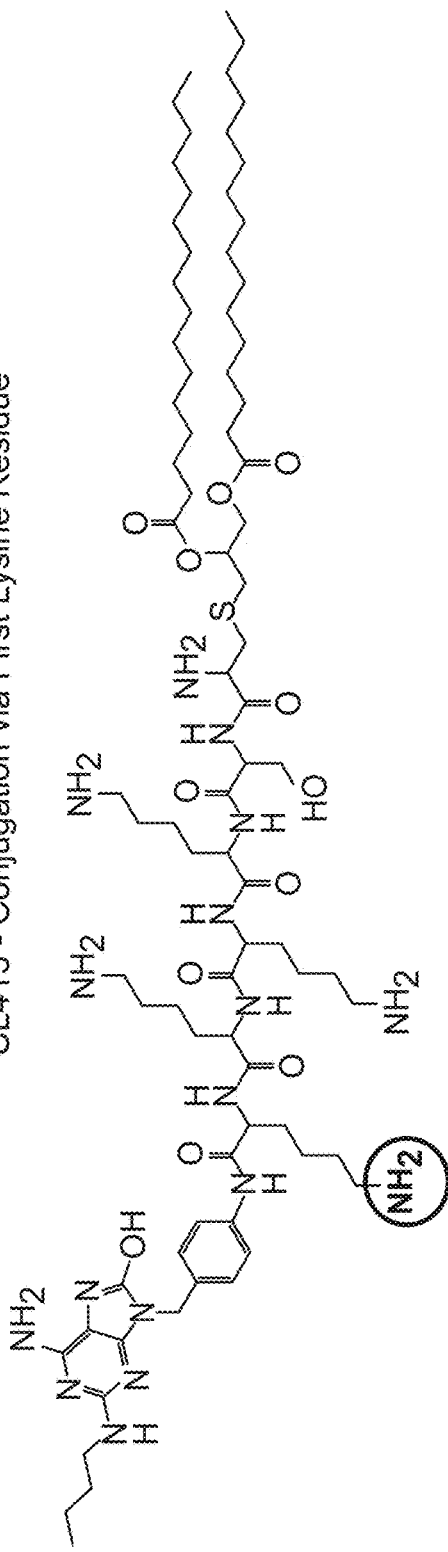
FIG. 22C shows the structure of adjuvant CL413 and the circle indicates a position on the adjuvant where it could be conjugated to the linker, specifically, the first lysine residue of the adjuvant.
Figure 22D:
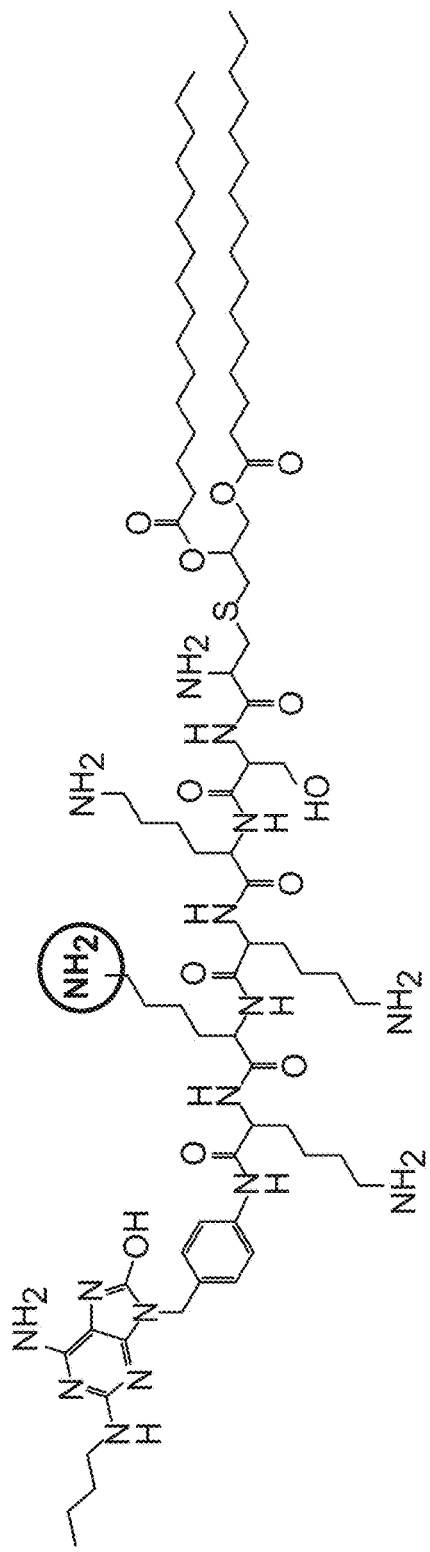
FIG. 22D shows the structure of adjuvant CL413 and the circle indicates a position on the adjuvant where it could be conjugated to the linker, specifically, the second lysine residue of the adjuvant.
Figure 22E:
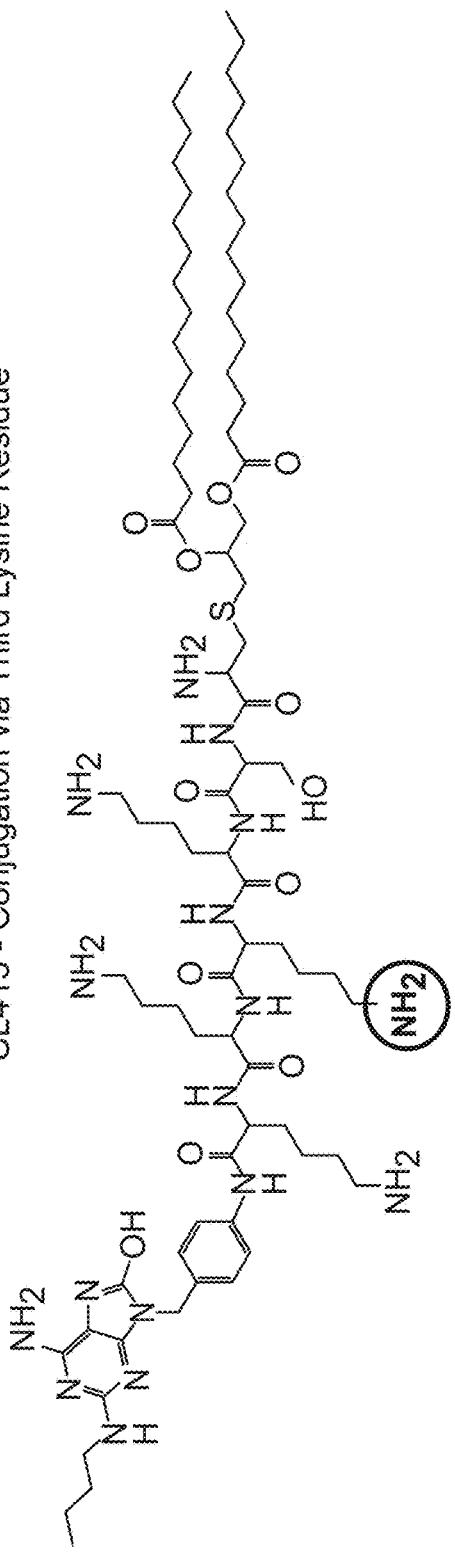
FIG. 22E shows the structure of adjuvant CL413 and the circle indicates a position on the adjuvant where it could be conjugated to the linker, specifically, the third lysine residue of the adjuvant.
Figure 22F:
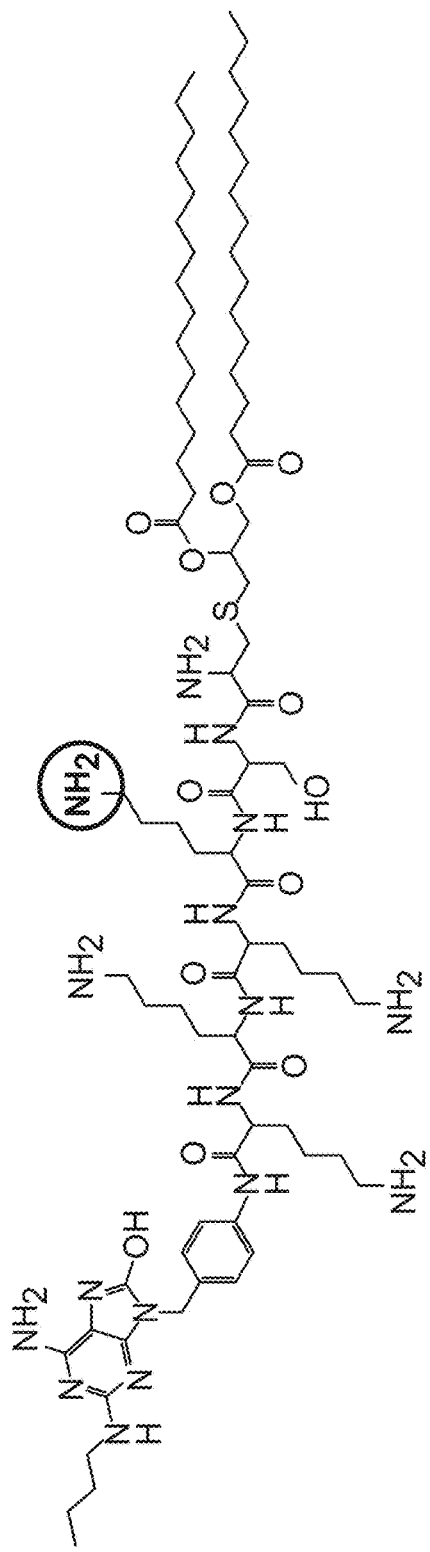
FIG. 22F shows the structure of adjuvant CL413 and the circle indicates a position on the adjuvant where it could be conjugated to the linker, specifically, the fourth lysine residue of the adjuvant.
Figure 22G:
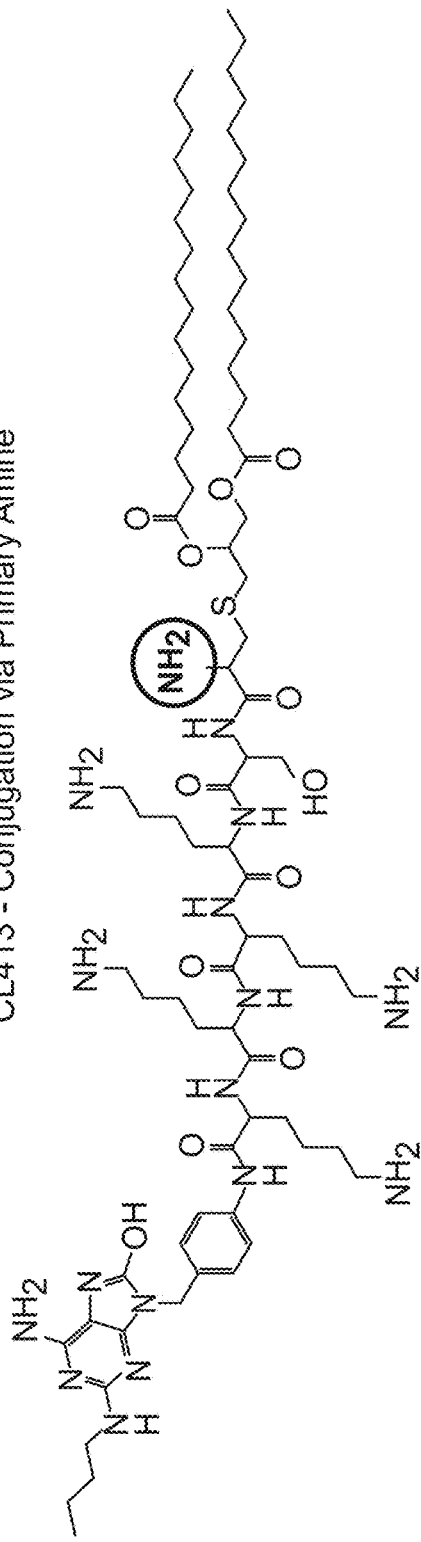
FIG. 22G shows the structure of adjuvant CL413 and the circle indicates a position on the adjuvant where it could be conjugated to the linker, specifically, the primary amine of the adjuvant.
Figure 22H:
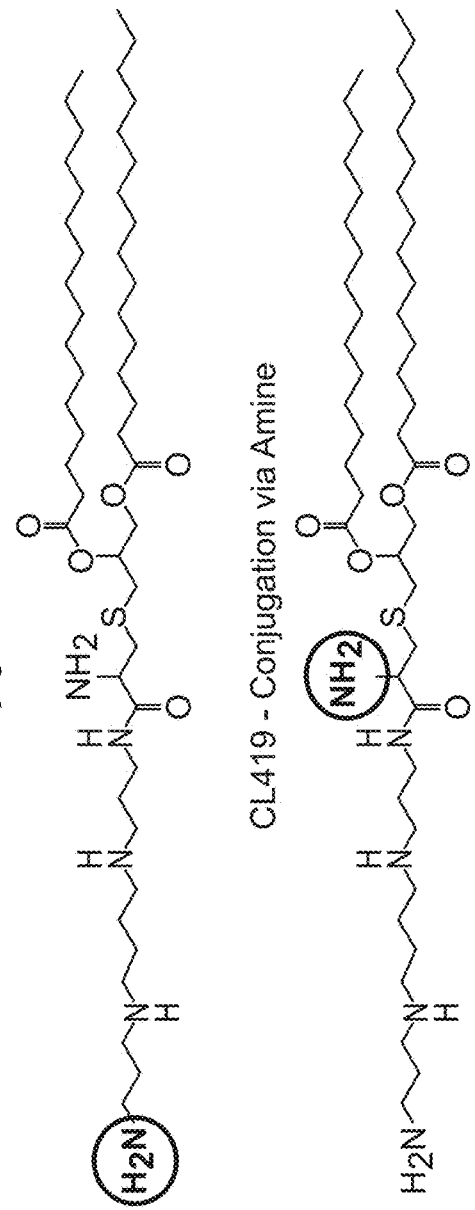
FIG. 22H shows the structure of adjuvant CL419 and the circles indicate positions on the adjuvant where it could be conjugated to the linker, specifically, the amines of the adjuvant (terminal amine in the top part of FIG. 22H and secondary amine in the bottom part of FIG. 22H).
Figure 22I:
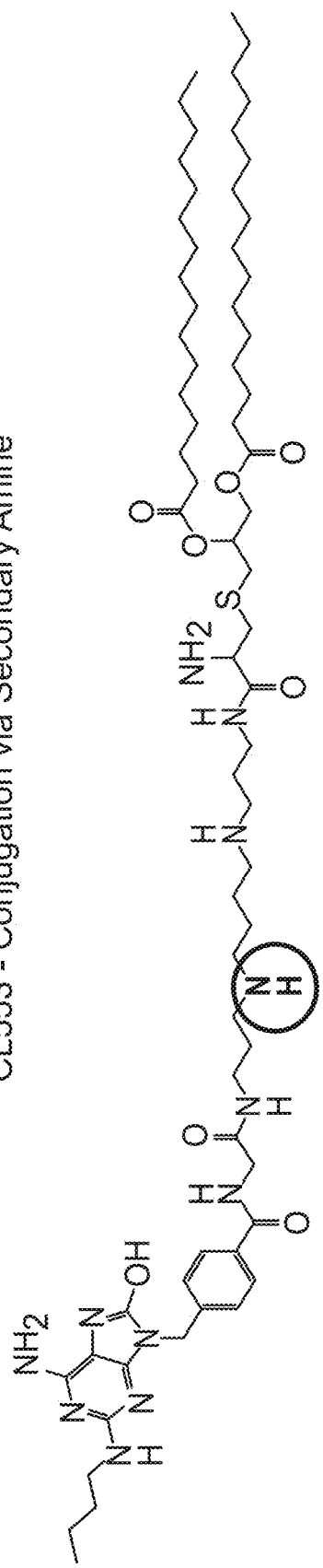
FIG. 22I shows the structure of adjuvant CL553 and the circle indicates a position on the adjuvant where it could be conjugated to the linker, specifically, a secondary amine of the adjuvant.
Figure 22J:
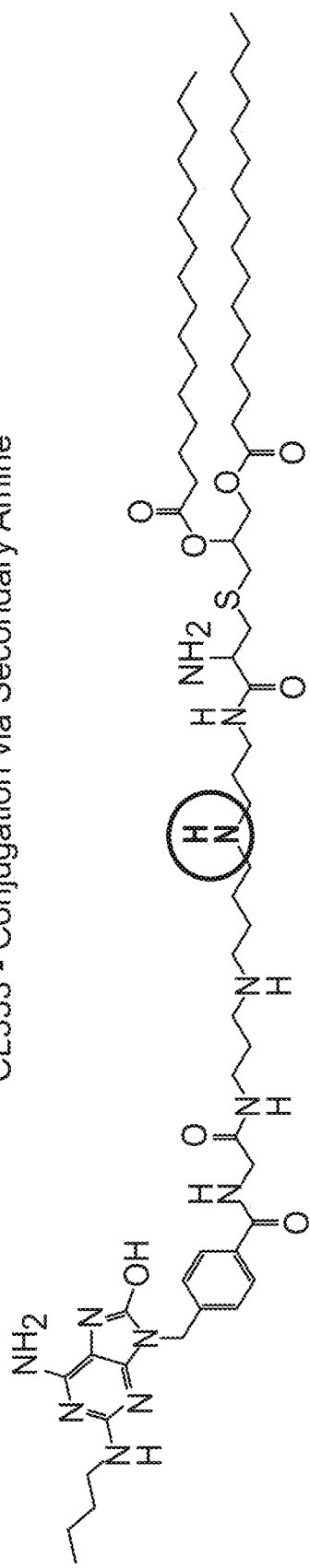
FIG. 22J shows the structure of adjuvant CL553 and the circle indicates a position on the adjuvant where it could be conjugated to the linker, specifically, another secondary amine of the adjuvant.
Figure 22K:
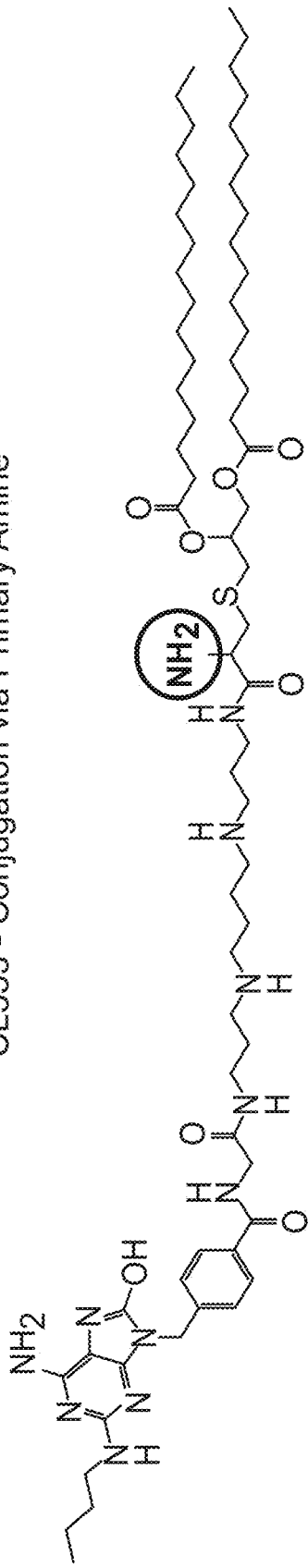
FIG. 22K shows the structure of adjuvant CL553 and the circle indicates a position on the adjuvant where it could be conjugated to the linker, specifically, a primary amine of the adjuvant.
Figure 22L:
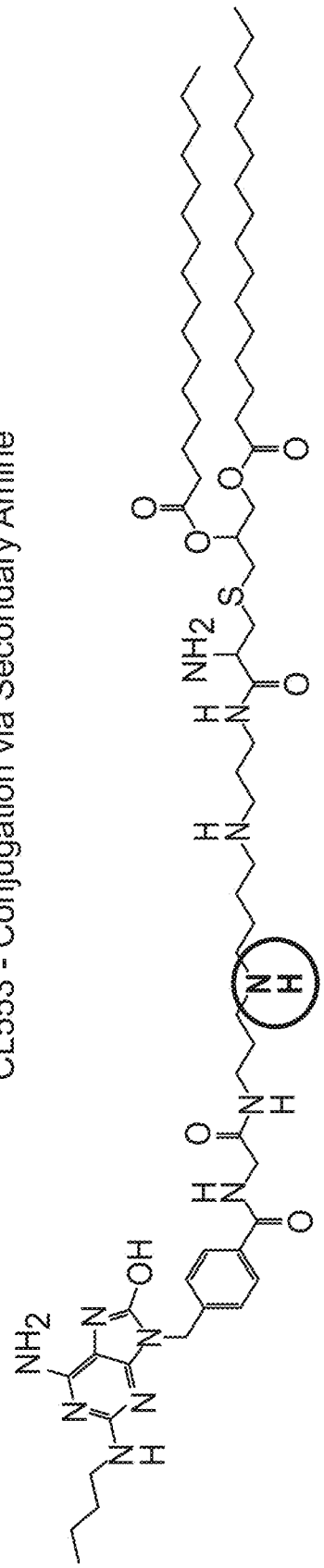
FIG. 22L shows the structure of adjuvant CL553 and the circle indicates a position on the adjuvant where it could be conjugated to the linker, specifically, another secondary amine of the adjuvant.
Figure 22O:
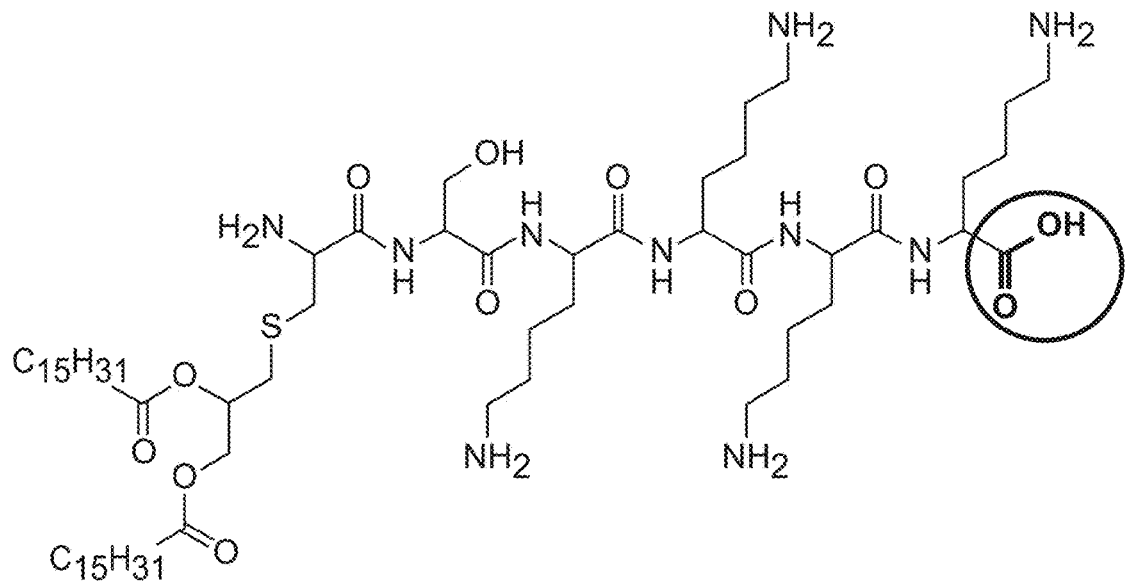
FIG. 22O shows the structure of adjuvant CL572 and the circles indicate positions on the adjuvant where it could be conjugated to the linker, specifically, the primary amine (top part of FIG. 22O) and the carbonyl (bottom part of FIG. 22O).
Figure 22P:
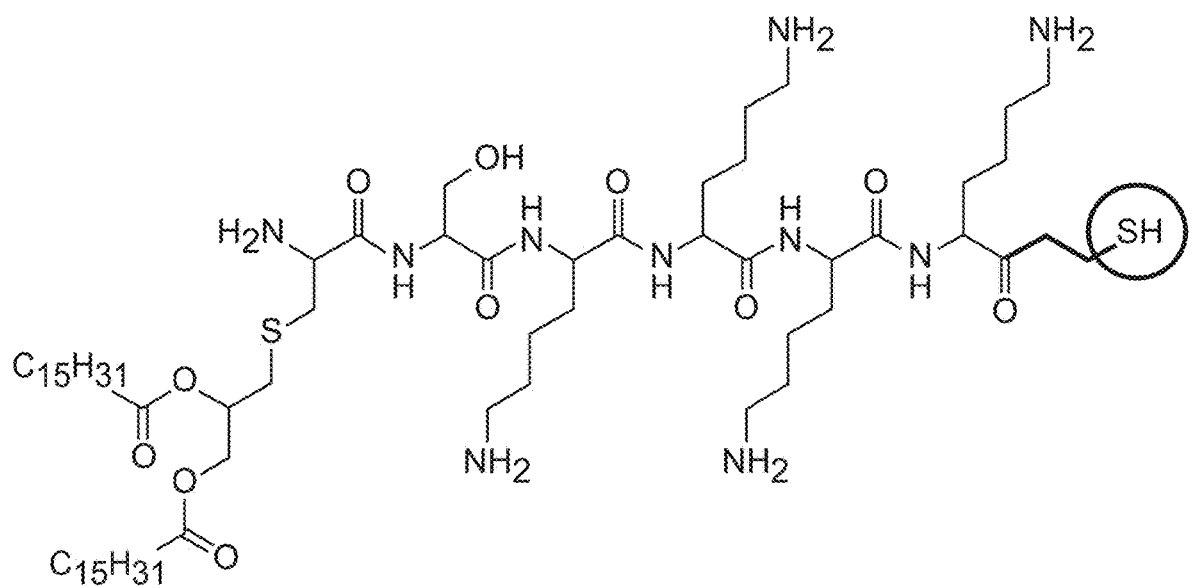
FIG. 22P shows the structure of adjuvant Pam2CSK4 and the circle indicates a position on the adjuvant where it could be conjugated to the linker, specifically, the terminal carboxylic acid of the adjuvant.
Figure 22Q:
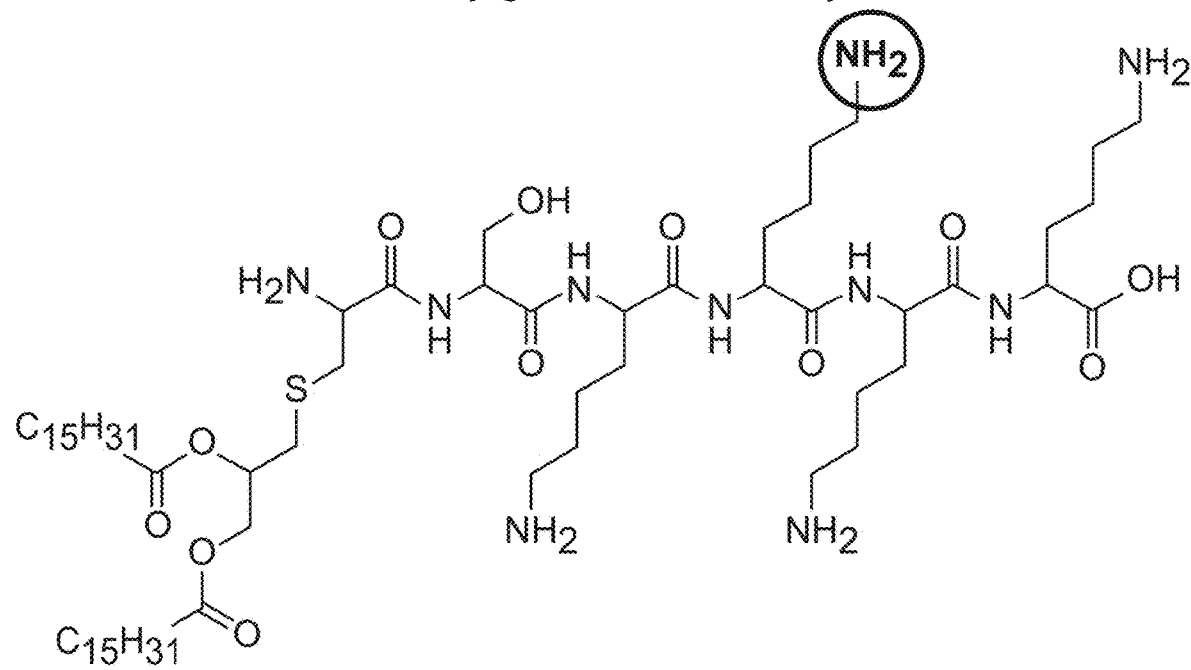
FIG. 22Q shows the structure of adjuvant Pam2CSK4 and the circle indicates a position on the adjuvant where it could be conjugated to the linker, specifically, the terminal thiol of the adjuvant.
Figure 22R:
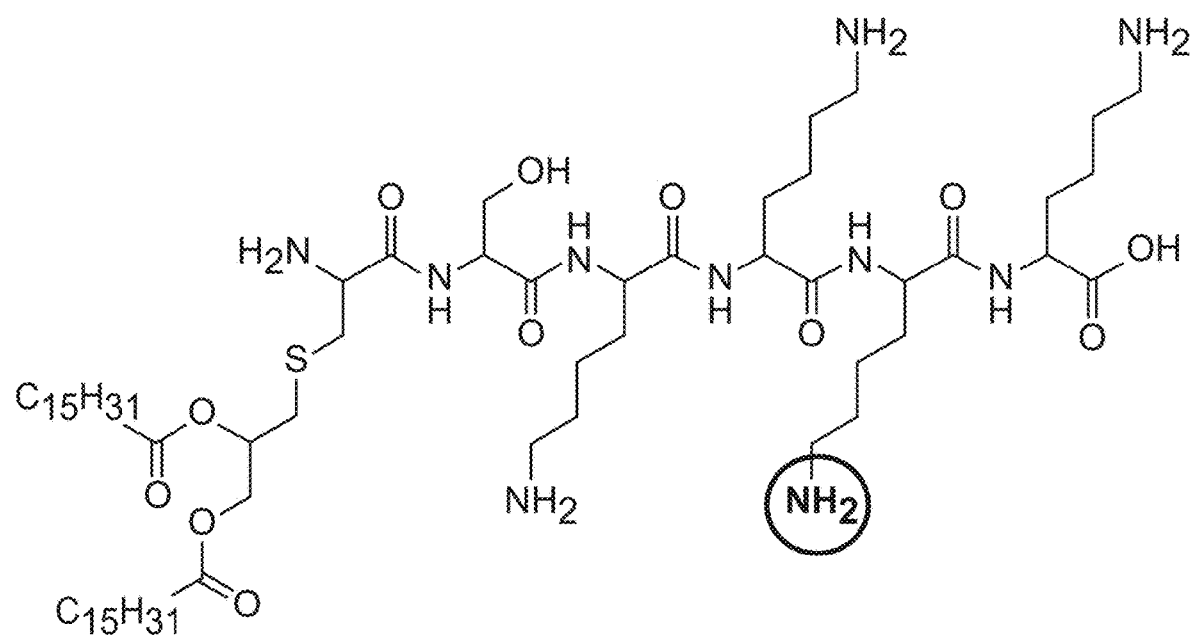
FIG. 22R shows the structure of adjuvant Pam2CSK4 and the circle indicates a position on the adjuvant where it could be conjugated to the linker, specifically, the second lysine residue of the adjuvant.
Figure 22S:
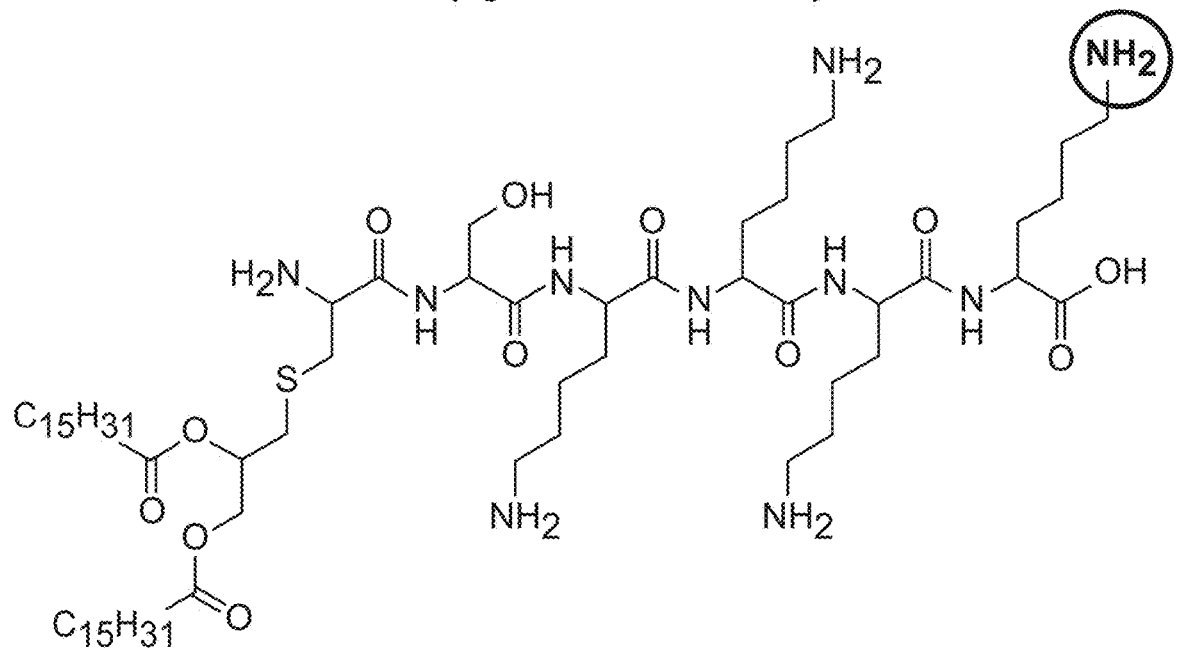
FIG. 22S shows the structure of adjuvant Pam2CSK4 and the circle indicates a position on the adjuvant where it could be conjugated to the linker, specifically, the third lysine residue of the adjuvant.
Figure 22T:
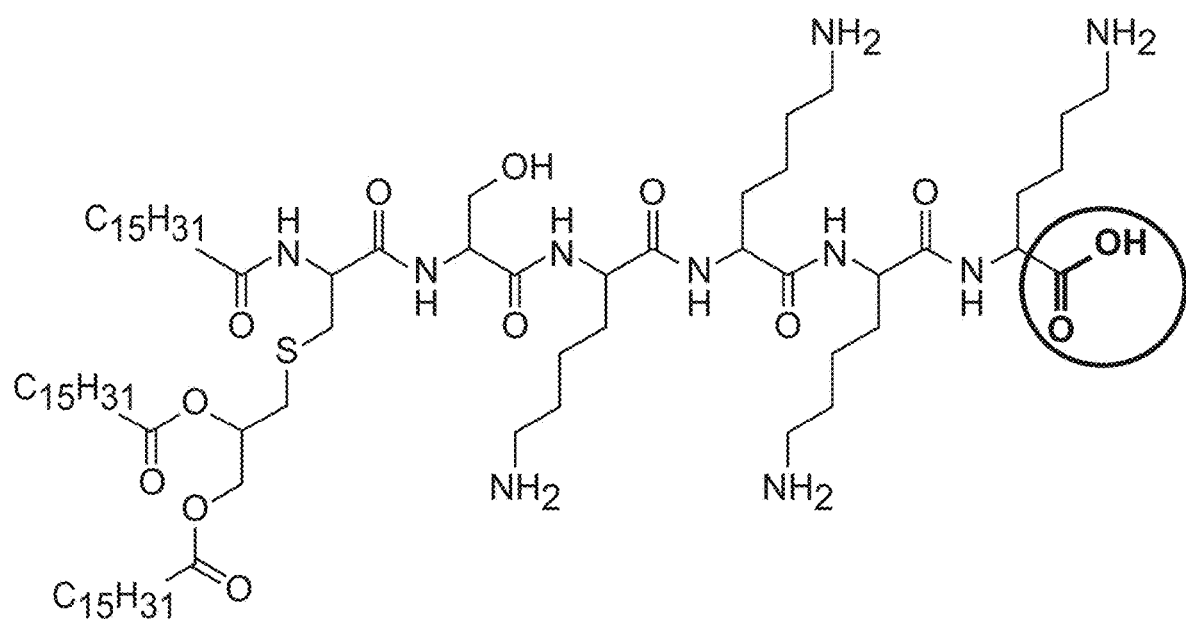
FIG. 22T shows the structure of adjuvant Pam2CSK4 and the circle indicates a position on the adjuvant where it could be conjugated to the linker, specifically, the terminal lysine residue of the adjuvant.
Figure 22U:
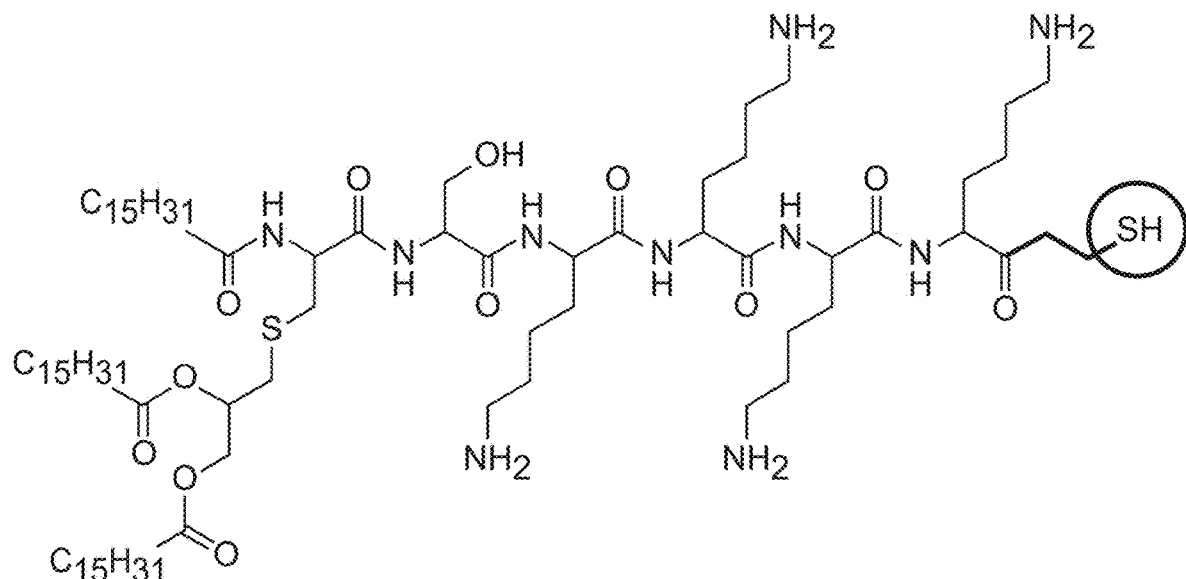
FIG. 22U shows the structure of adjuvant Pam3CSK4 and the circle indicates a position on the adjuvant where it could be conjugated to the linker, specifically, the terminal carboxylic acid of the adjuvant.
Figure 22V:
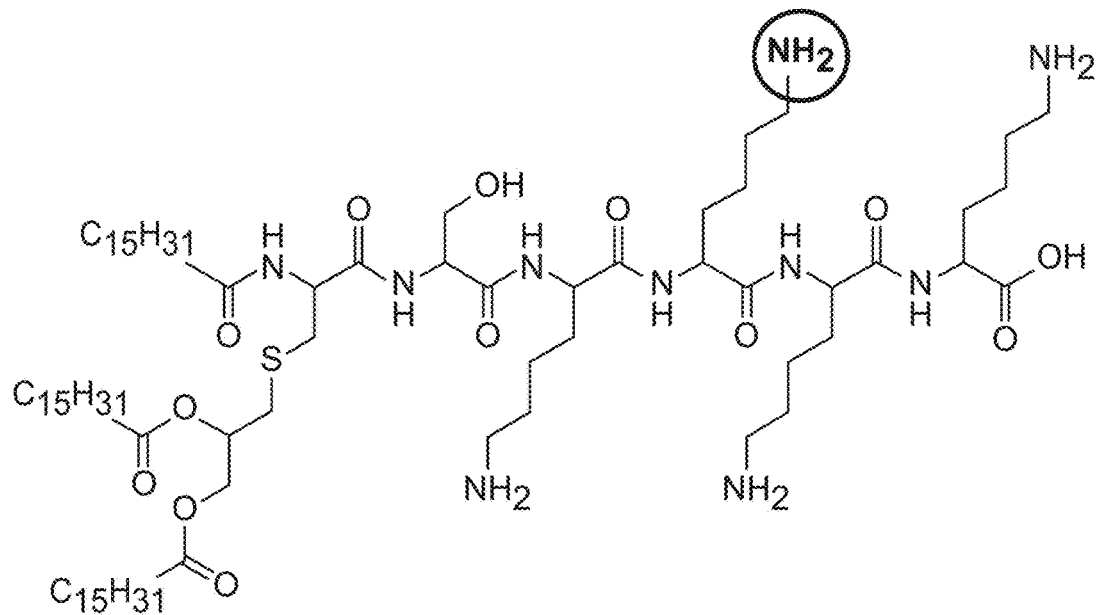
FIG. 22V shows the structure of adjuvant Pam3CSK4 and the circle indicates a position on the adjuvant where it could be conjugated to the linker, specifically, the terminal thiol of the adjuvant.
Figure 22W:
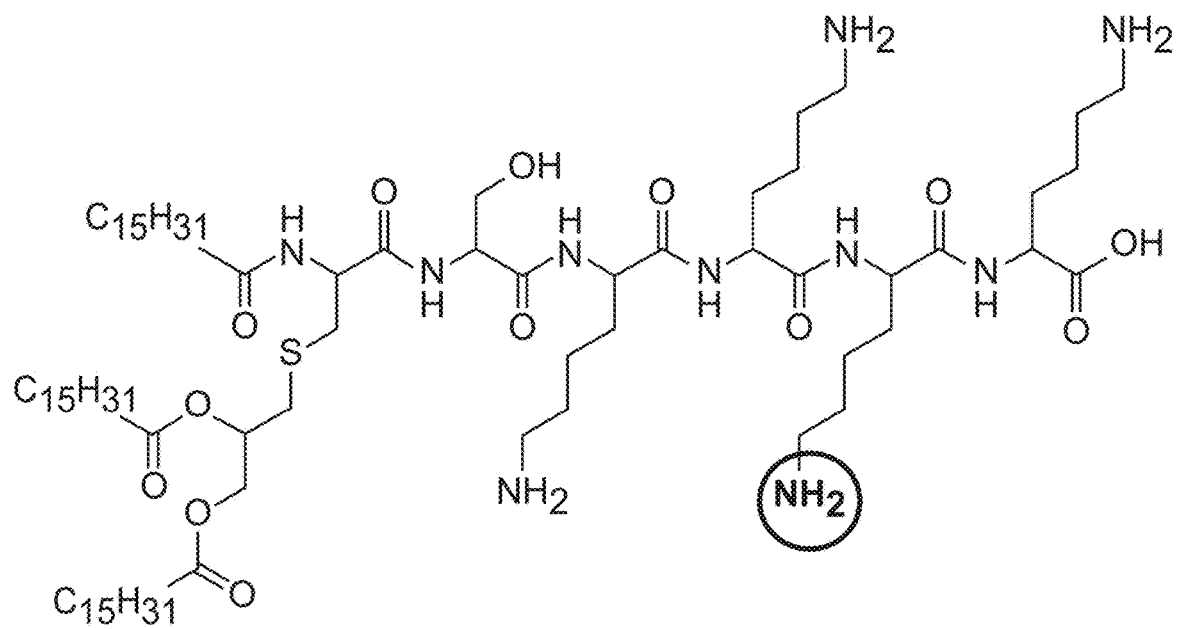
FIG. 22W shows the structure of adjuvant Pam3CSK4 and the circle indicates a position on the adjuvant where it could be conjugated to the linker, specifically, the second lysine residue of the adjuvant.
Figure 22X:
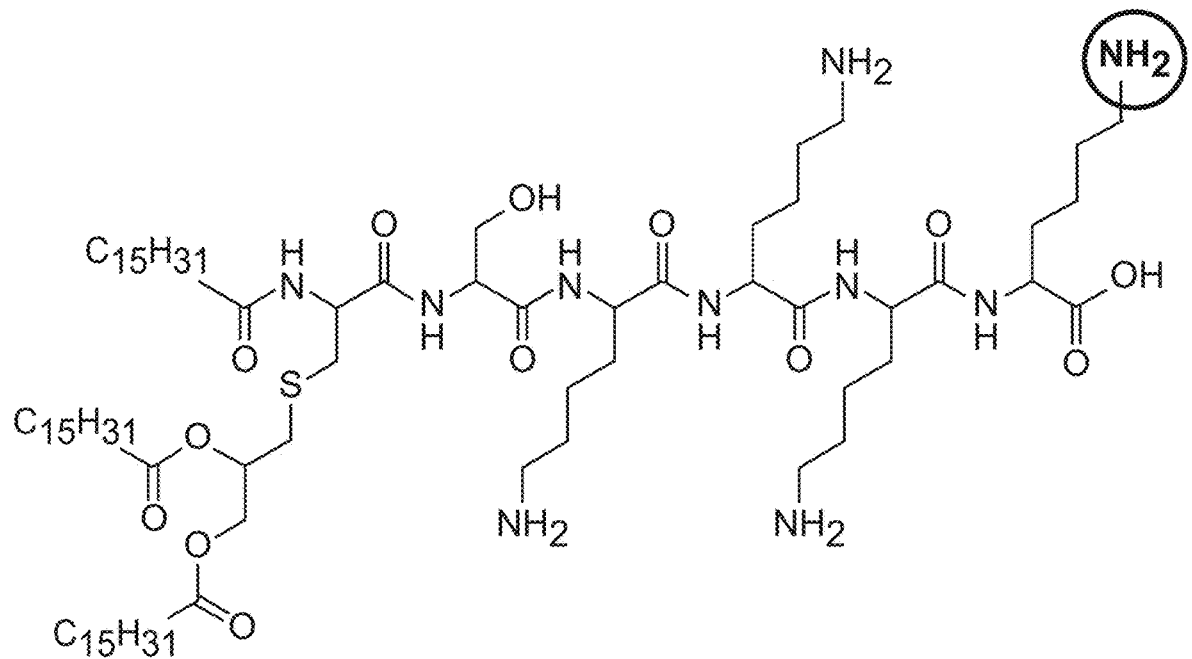
FIG. 22X shows the structure of adjuvant Pam3CSK4 and the circle indicates a position on the adjuvant where it could be conjugated to the linker, specifically, the third lysine residue of the adjuvant.
Figure 23A:
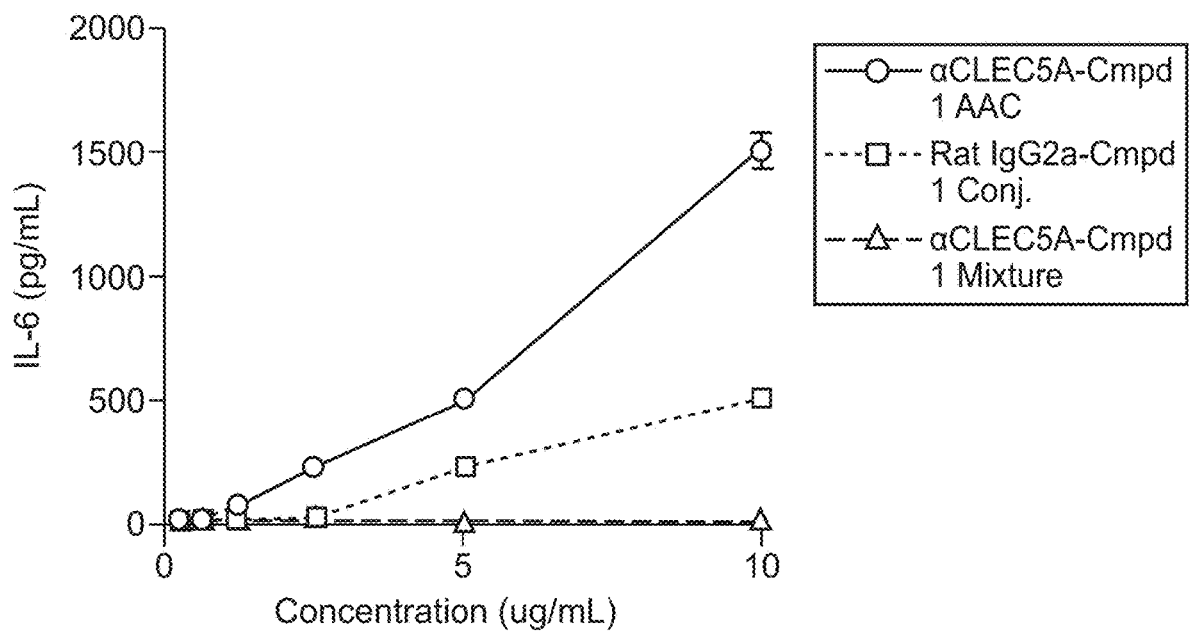
FIG. 23A shows αCLEC5A immunoconjugate-differentiated cells secrete higher amounts of IL-6 than cells exposed to equivalent amounts of the unconjugated components. The line that is significantly higher than the x-axis for each cytokine is αCLEC5A immunoconjugate (αCLEC5A antibody conjugated with adjuvant Compound 1). The line that is along the x-axis shows that a mixture of αCLEC5A antibody and adjuvant Compound 1 (unconjugated) failed to produce any cytokine response. The line between the x-axis and the αCLEC5A immunoconjugate line represents a control conjugate, rat IgG2a isotype conjugated to Compound 1.
Figure 23B:
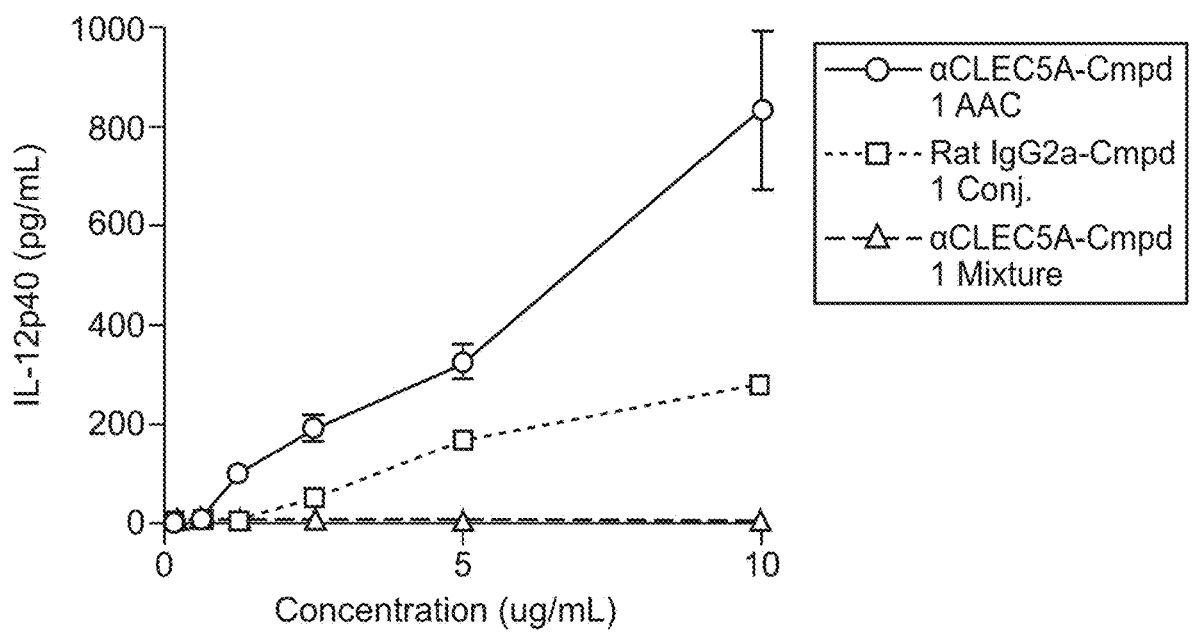
FIG. 23B shows αCLEC5A immunoconjugate-differentiated cells secrete higher amounts of IL-12p40 than cells exposed to equivalent amounts of the unconjugated components. The line that is significantly higher than the x-axis for each cytokine is αCLEC5A immunoconjugate (αCLEC5A-Cmpd1 AAC). The line that is along the x-axis shows that a mixture of αCLEC5A antibody and adjuvant Compound 1 (unconjugated; αCLEC5A-Cmpd1 Mixture) failed to produce any cytokine response. The line between the x-axis and the αCLEC5A immunoconjugate line represents a control conjugate, rat IgG2a isotype conjugated to Compound 1.
Figure 23C:
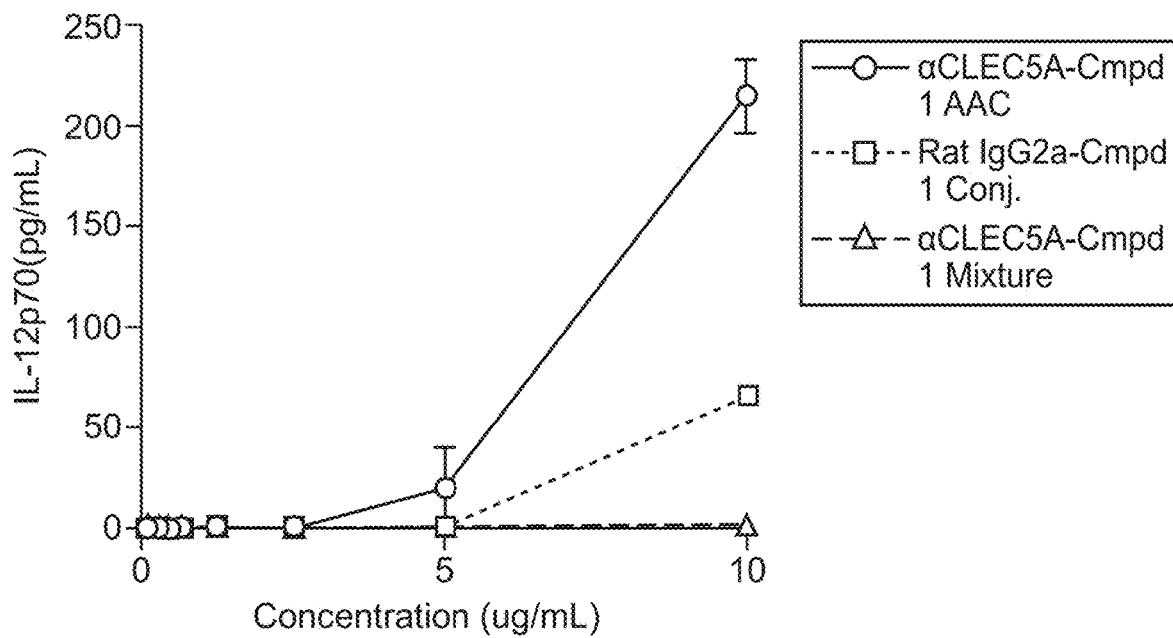
FIG. 23C shows αCLEC5A immunoconjugate-differentiated cells secrete higher amounts of IL-12p70 than cells exposed to equivalent amounts of the unconjugated components. The line that is significantly higher than the x-axis for each cytokine is αCLEC5A immunoconjugate (αCLEC5A antibody conjugated with adjuvant Compound 1). The line that is along the x-axis shows that a mixture of αCLEC5A antibody and adjuvant Compound 1 (unconjugated) failed to produce any cytokine response. The line between the x-axis and the αCLEC5A immunoconjugate line represents a control conjugate, rat IgG2a isotype conjugated to Compound 1.
Figure 23D:
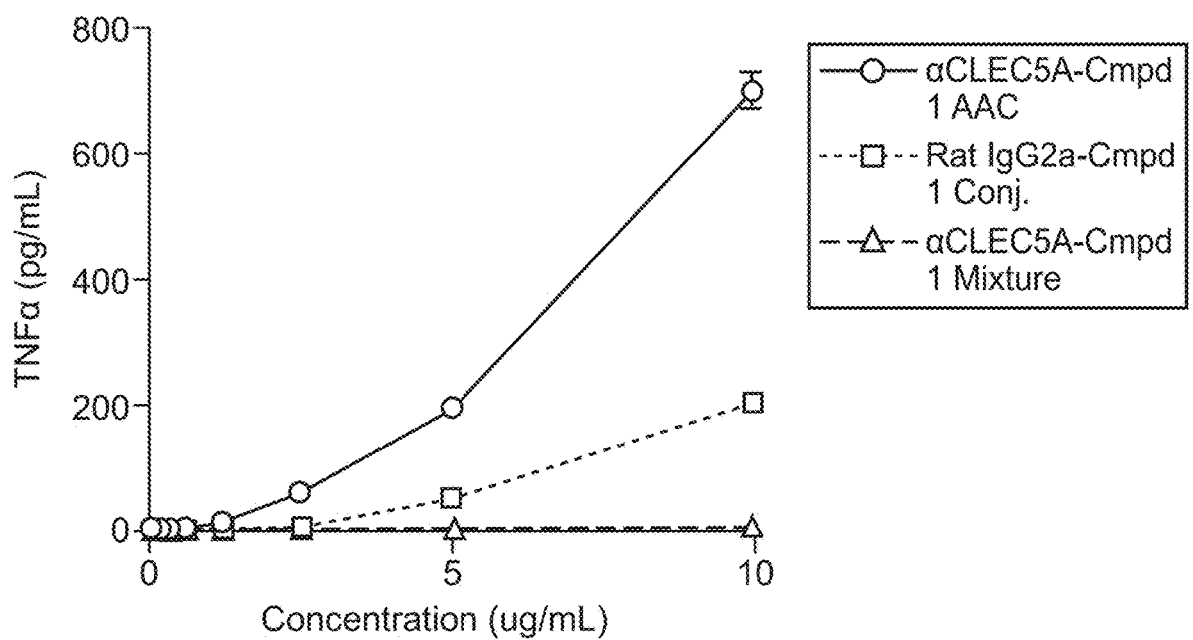
FIG. 23D shows αCLEC5A immunoconjugate-differentiated cells secrete higher amounts of TNFα than cells exposed to equivalent amounts of the unconjugated components. The line that is significantly higher than the x-axis for each cytokine is αCLEC5A immunoconjugate (αCLEC5A antibody conjugated with adjuvant Compound 1). The line that is along the x-axis shows that a mixture of αCLEC5A antibody and adjuvant Compound 1 (unconjugated) failed to produce any cytokine response. The line between the x-axis and the αCLEC5A immunoconjugate line represents a control conjugate, rat IgG2a isotype conjugated to Compound 1.
Figure 23E:
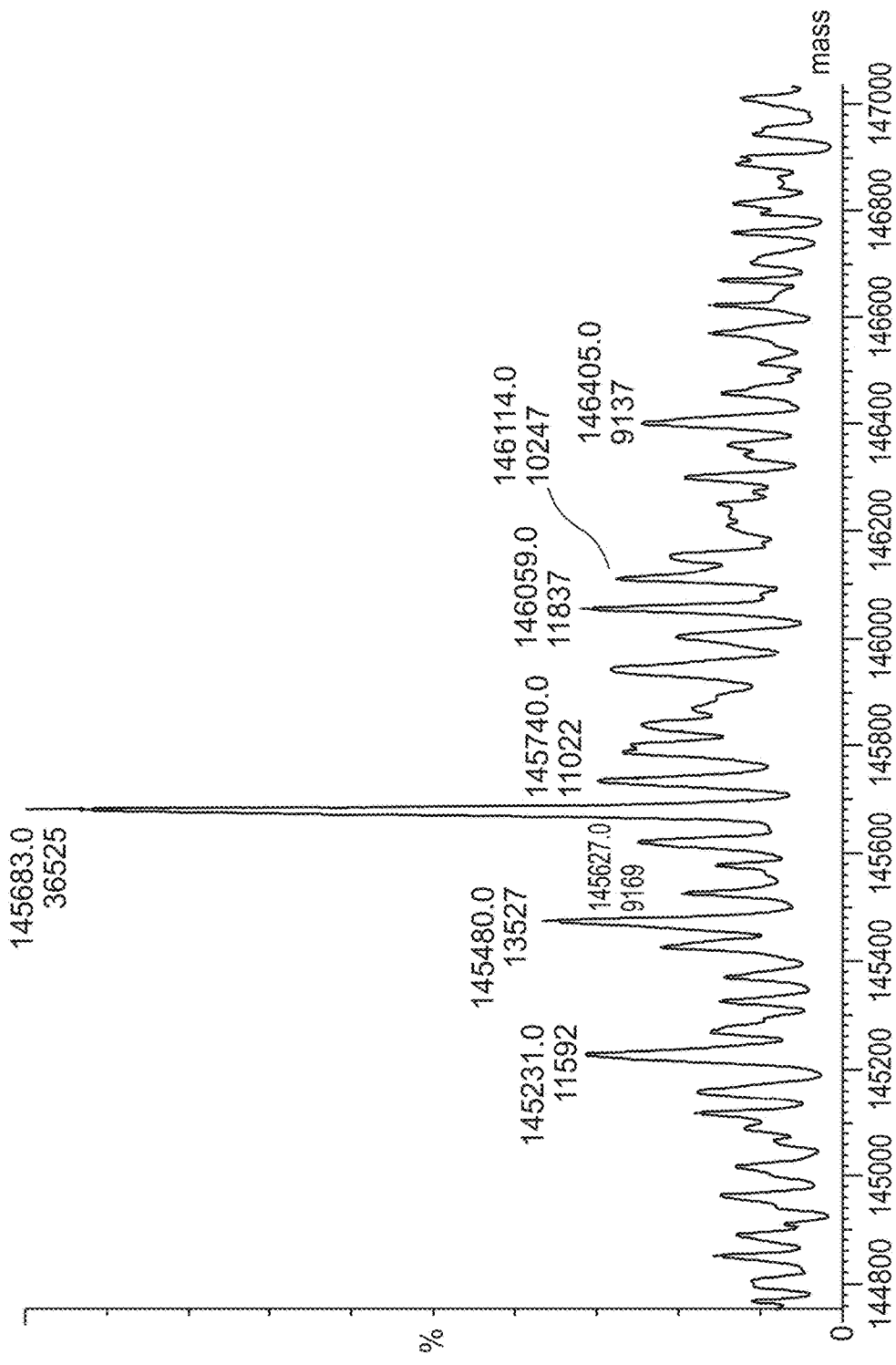
FIG. 23E shows the analysis of αCLEC5A immunoconjugate via LC-MS.
Figure 24:
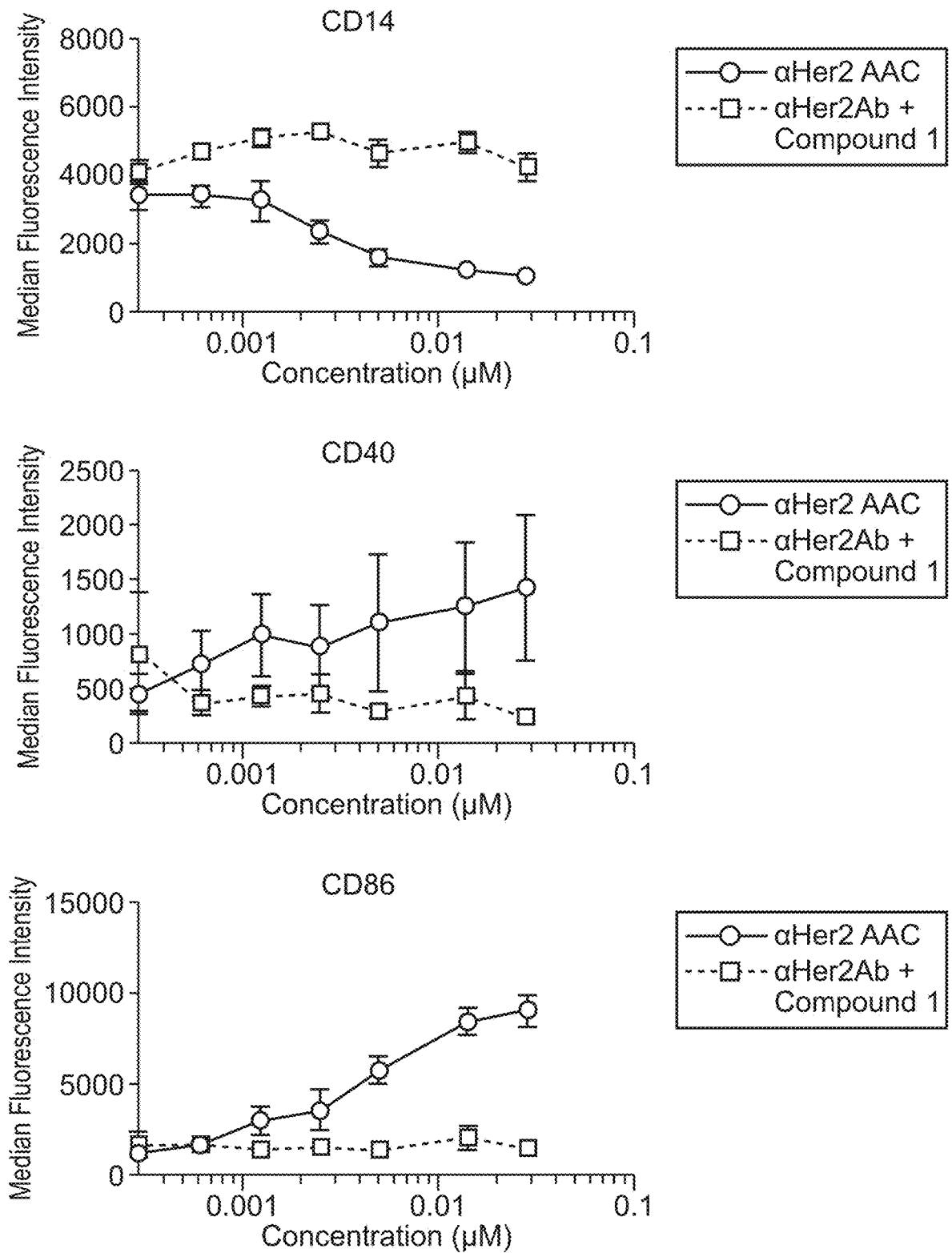
FIG. 24 shows increased dendritic cell differentiation with an anti-Her2 antibody adjuvant conjugate (αHer2 immunoconjugate, closed circles) linked to the TLR 7/8 agonist Compound 1 as compared to when the same antibody and adjuvant components (αHer2 and Compound 1, closed squares) are delivered as an unlinked mixture.
Figure 24:
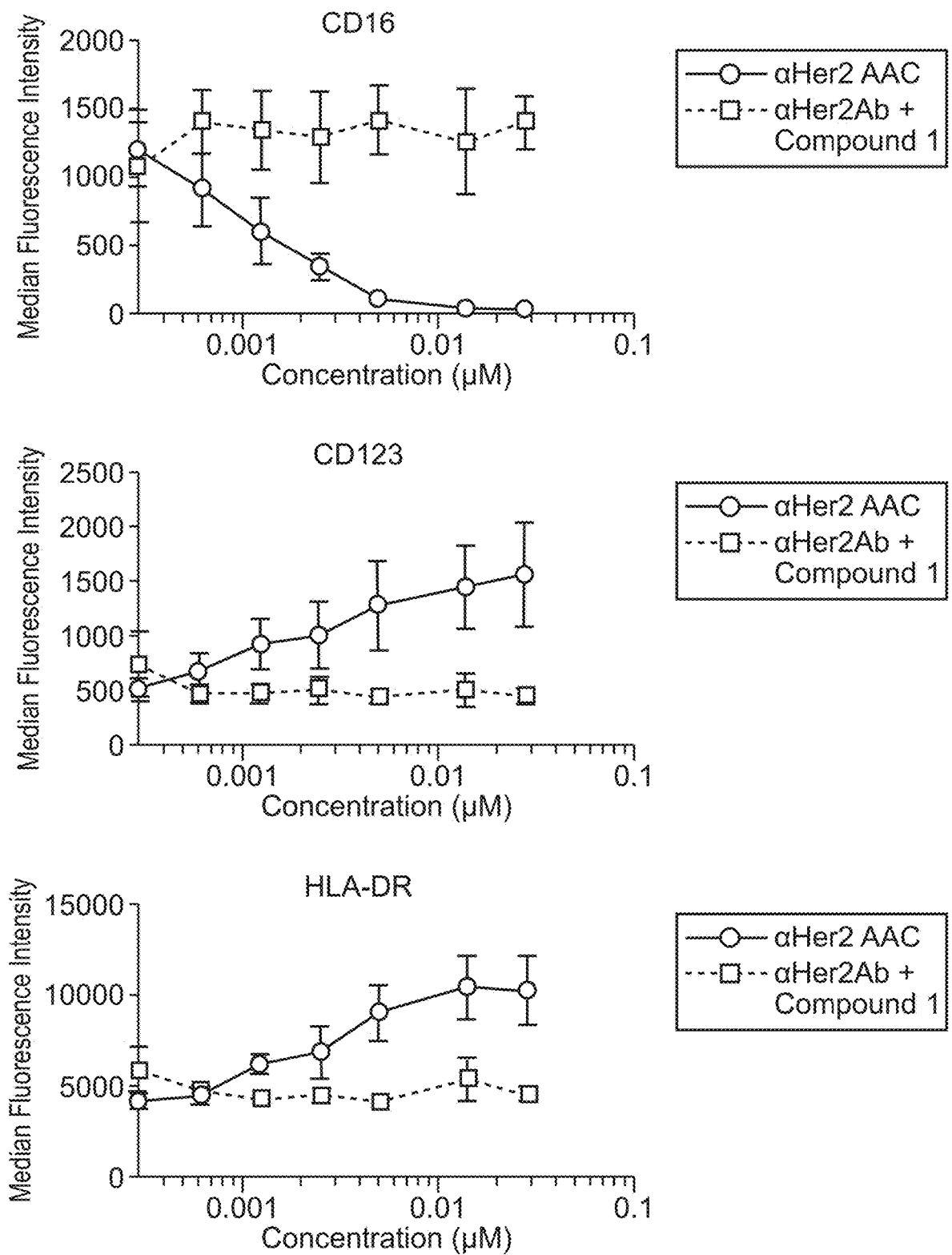
Figure 25:
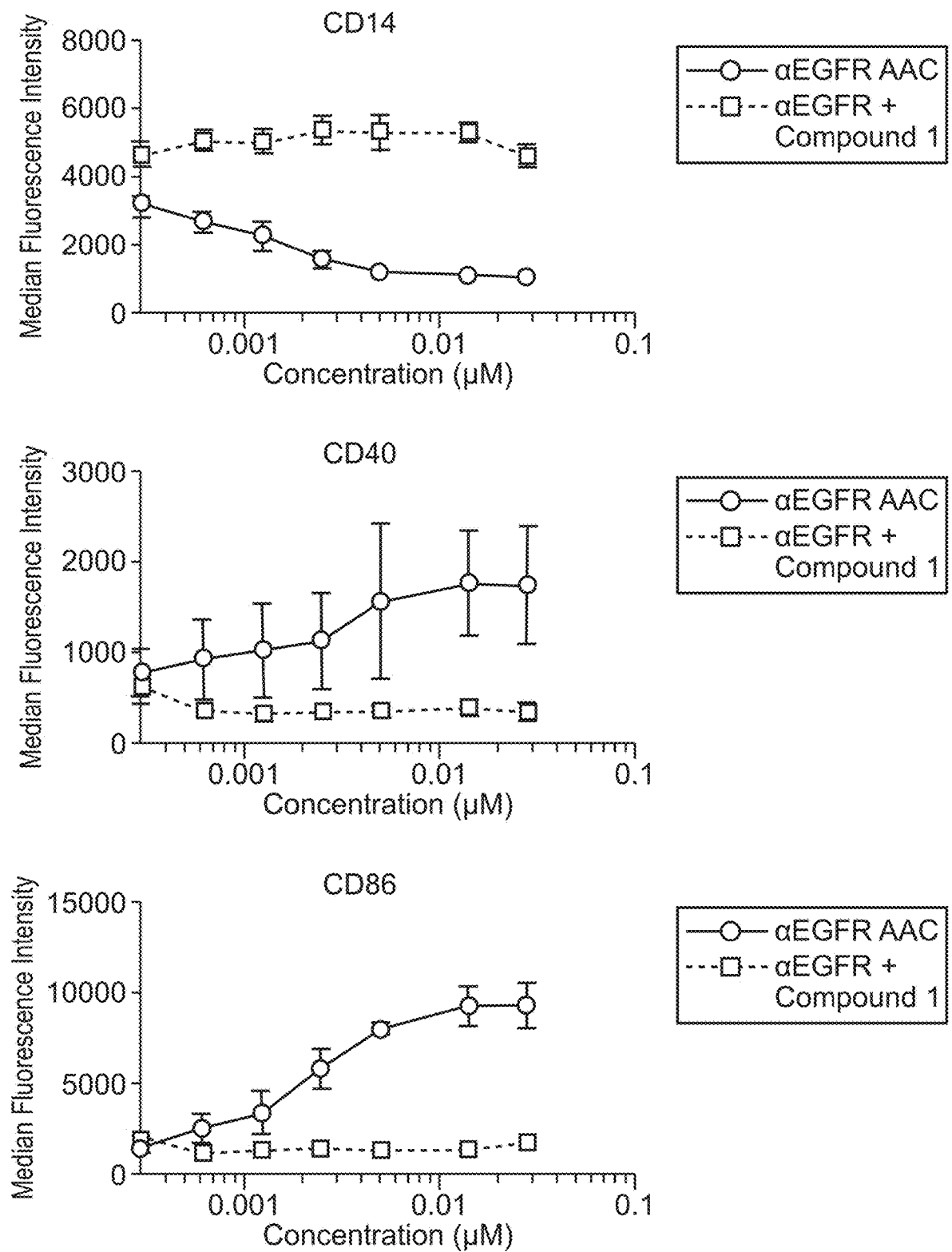
FIG. 25 shows increased dendritic cell differentiation with an anti-EGFR antibody adjuvant conjugate (αEGFR immunoconjugate, closed circles) linked to the TLR 7/8 agonist Compound 1 as compared to when the same components (αEGFR and Compound 1, closed squares) are delivered as an unlinked mixture.
Figure 25:
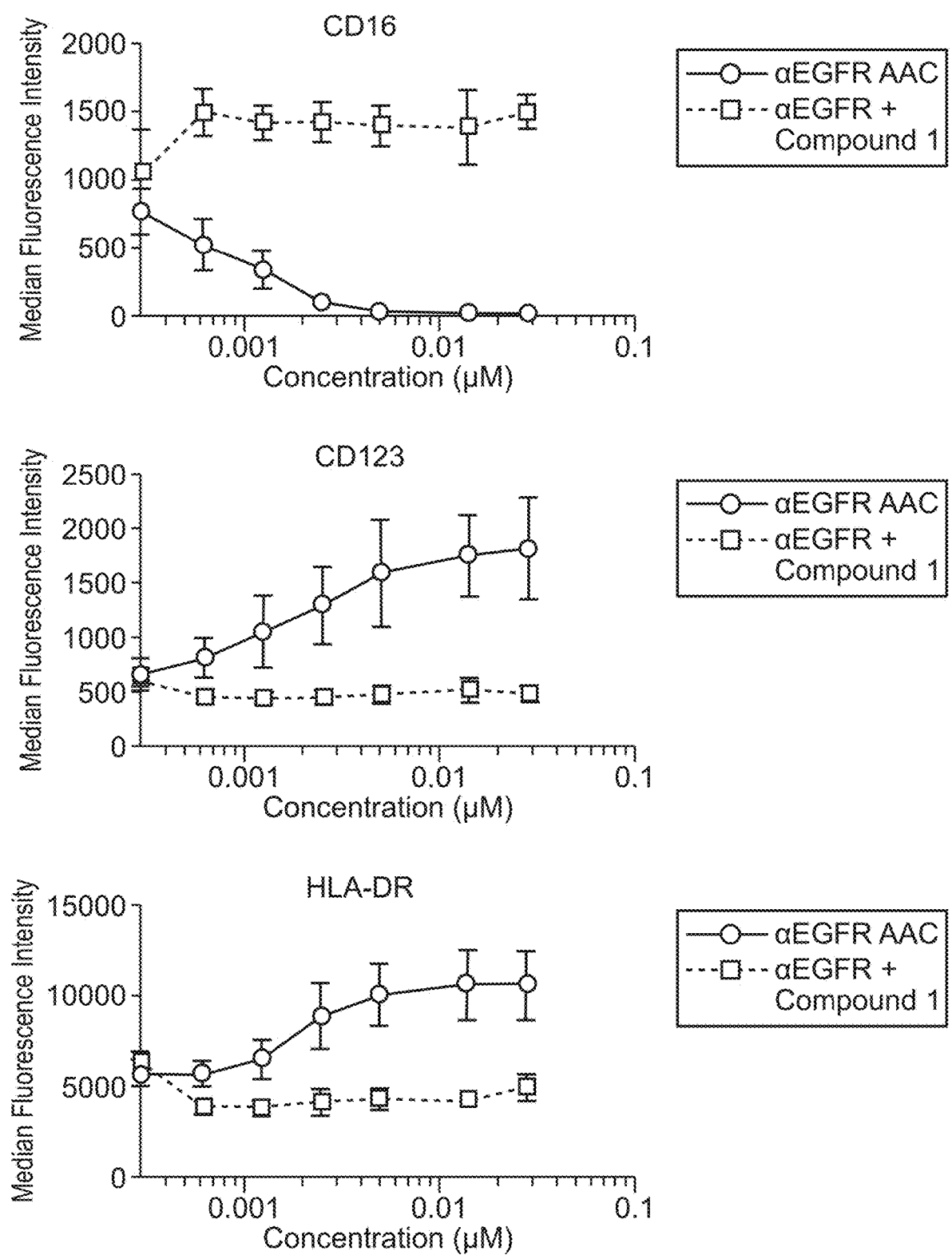
Figure 26:
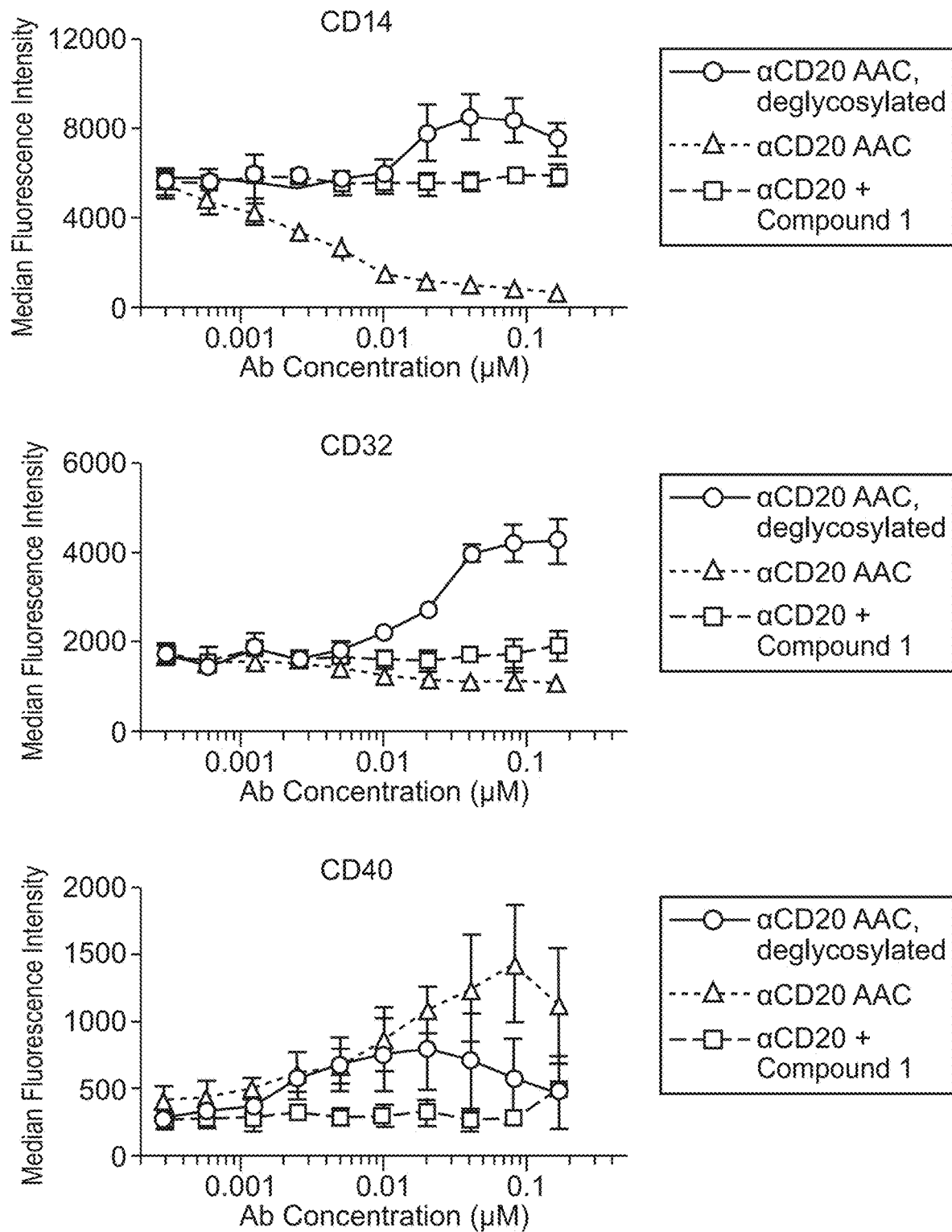
FIG. 26 shows that an anti-CD20 antibody conjugated to TLR 7/8 agonist exhibits robust dendritic cell activation, while activation is significantly reduced in the deglycosylated conjugate.
Figure 26:
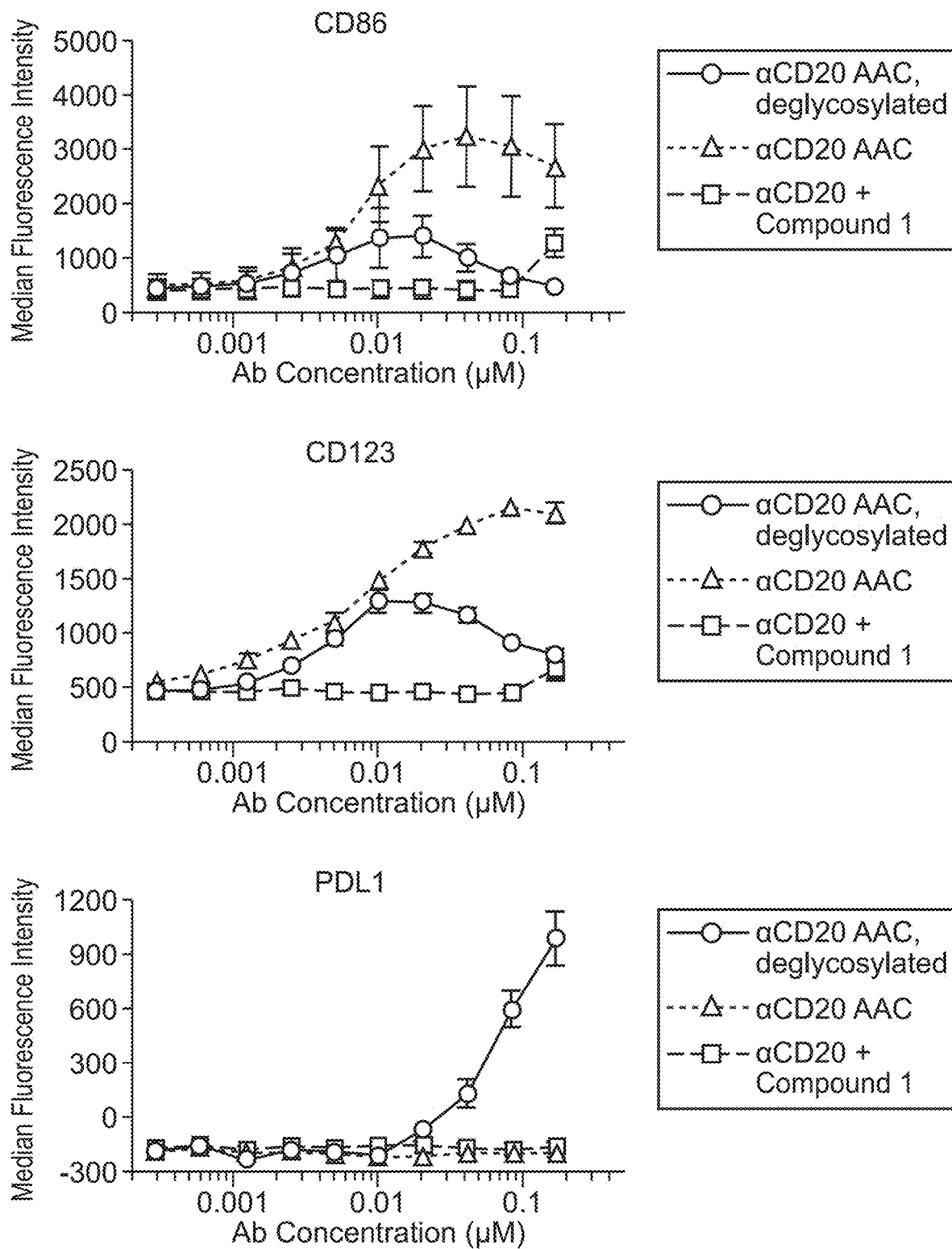
Figure 27:
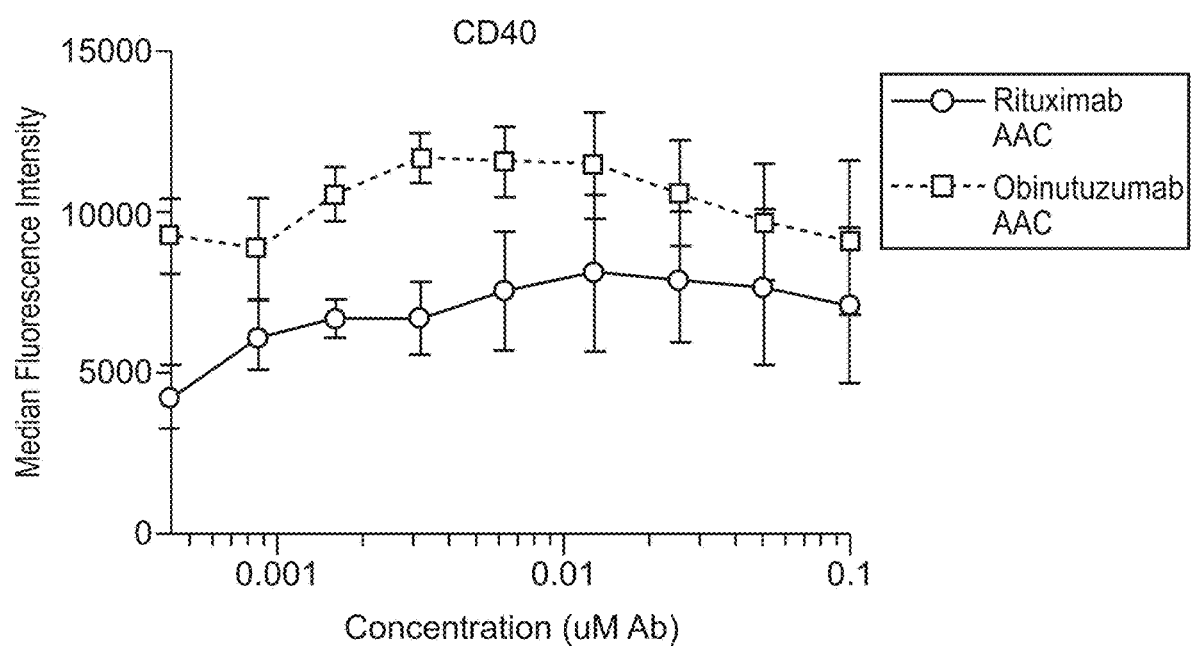
FIG. 27 compares rituximab and obinutuzumab antibodies conjugated to Compound 1. Obinutuzumab has reduced fucose content as compared to rituximab and exhibits increased CD40 upregulation.
Figure 28:
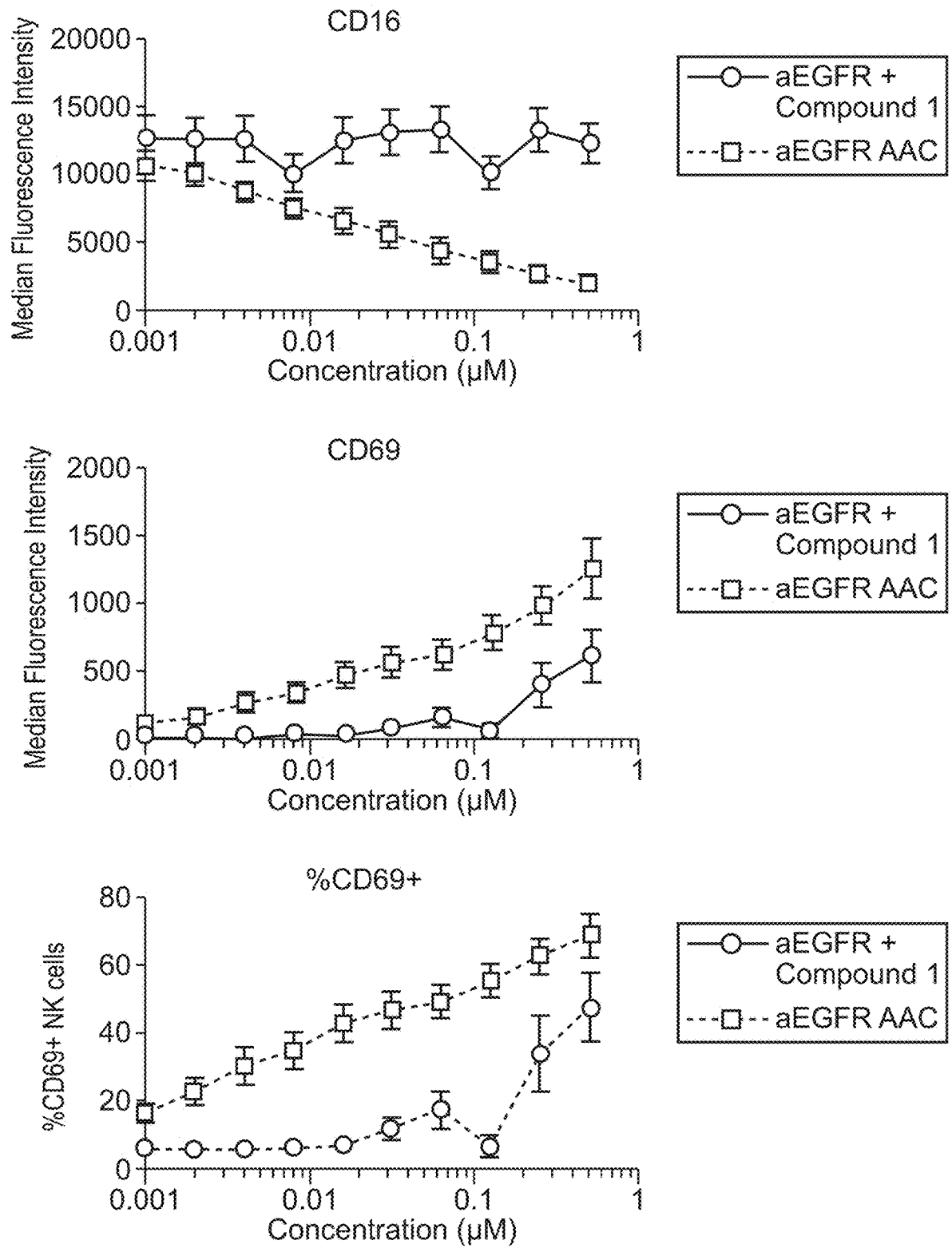
FIG. 28 illustrates NK cell activation using an αEGFR immunoconjugate linked to the TLR 7/8 agonist Compound 1. The immunoconjugate exhibits significantly greater NK cell activation as compared to the unconjugated mixture of αEGFR and Compound 1.
Figure 29:
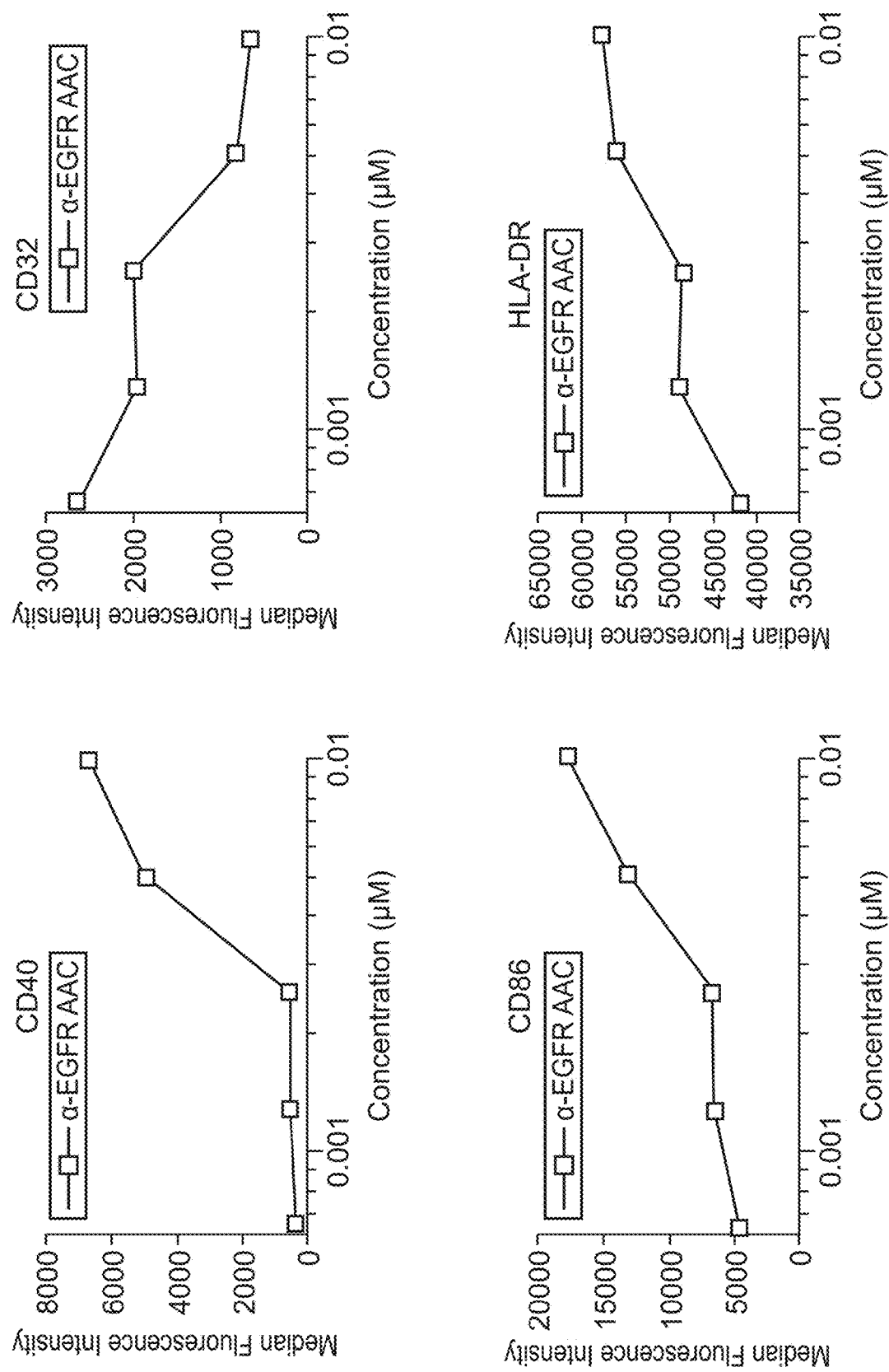
FIG. 29 illustrates robust activation of dendritic cell populations from peripheral blood mononuclear cells isolated from human subjects with an αEGFR immunoconjugate.
Figure 30A:
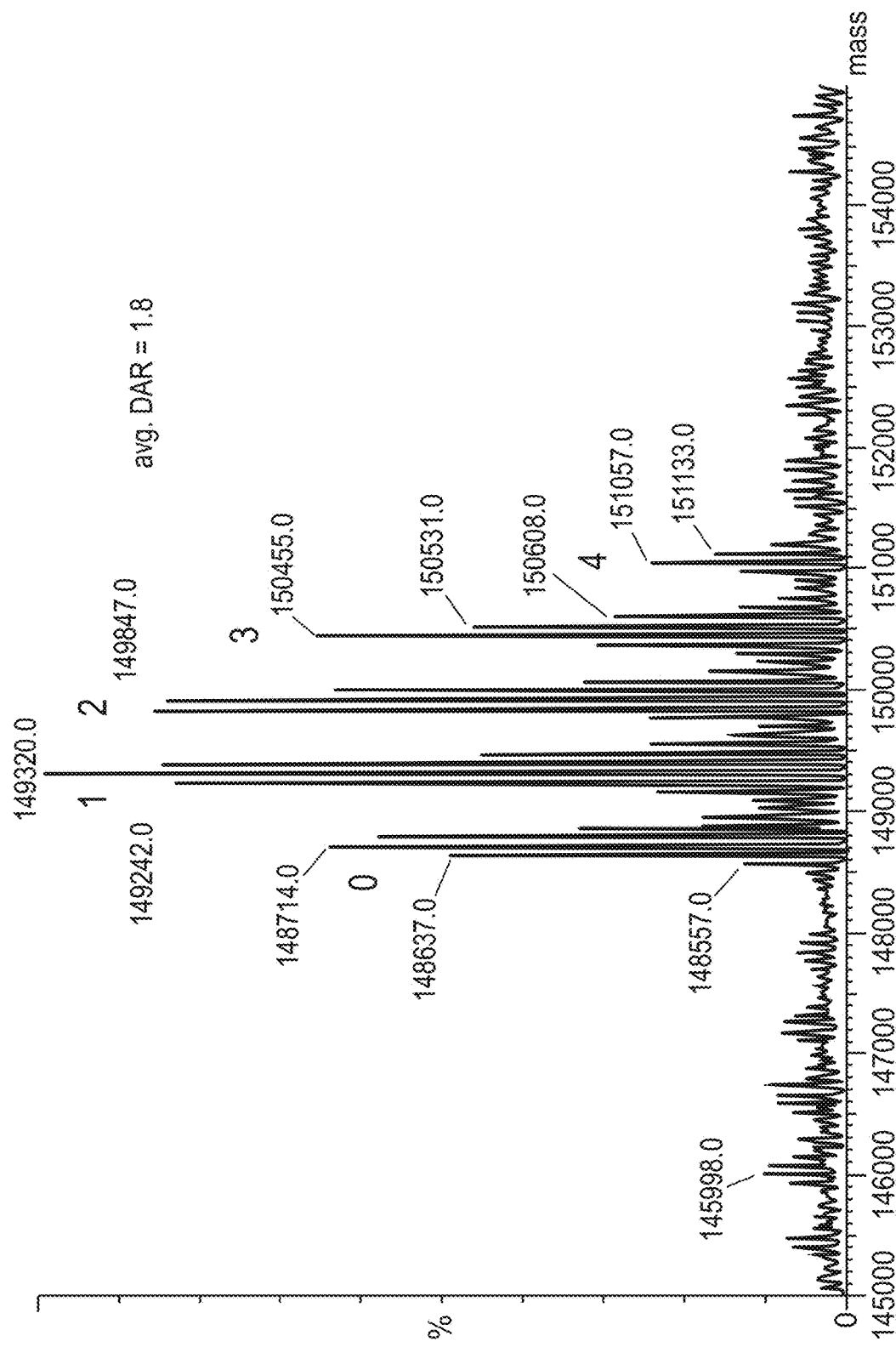
FIG. 30A shows a liquid chromatography-mass spectrometry analysis of immunoconjugate BB-01 synthesized using the SATA method.
Figure 30B:
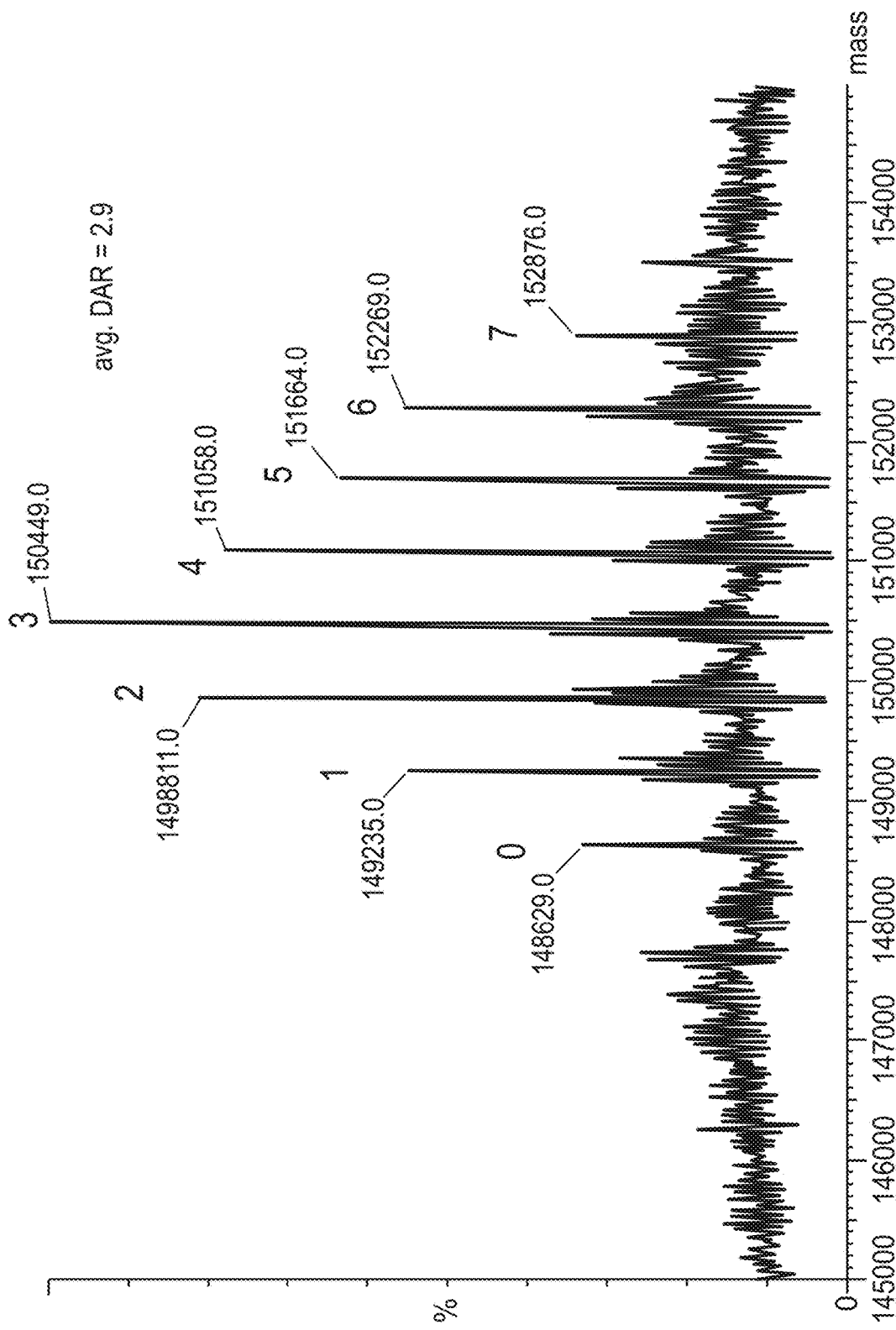
FIG. 30B shows a liquid chromatography-mass spectrometry analysis of immunoconjugate BB-01 synthesized using the ester method.
Figure 31A:
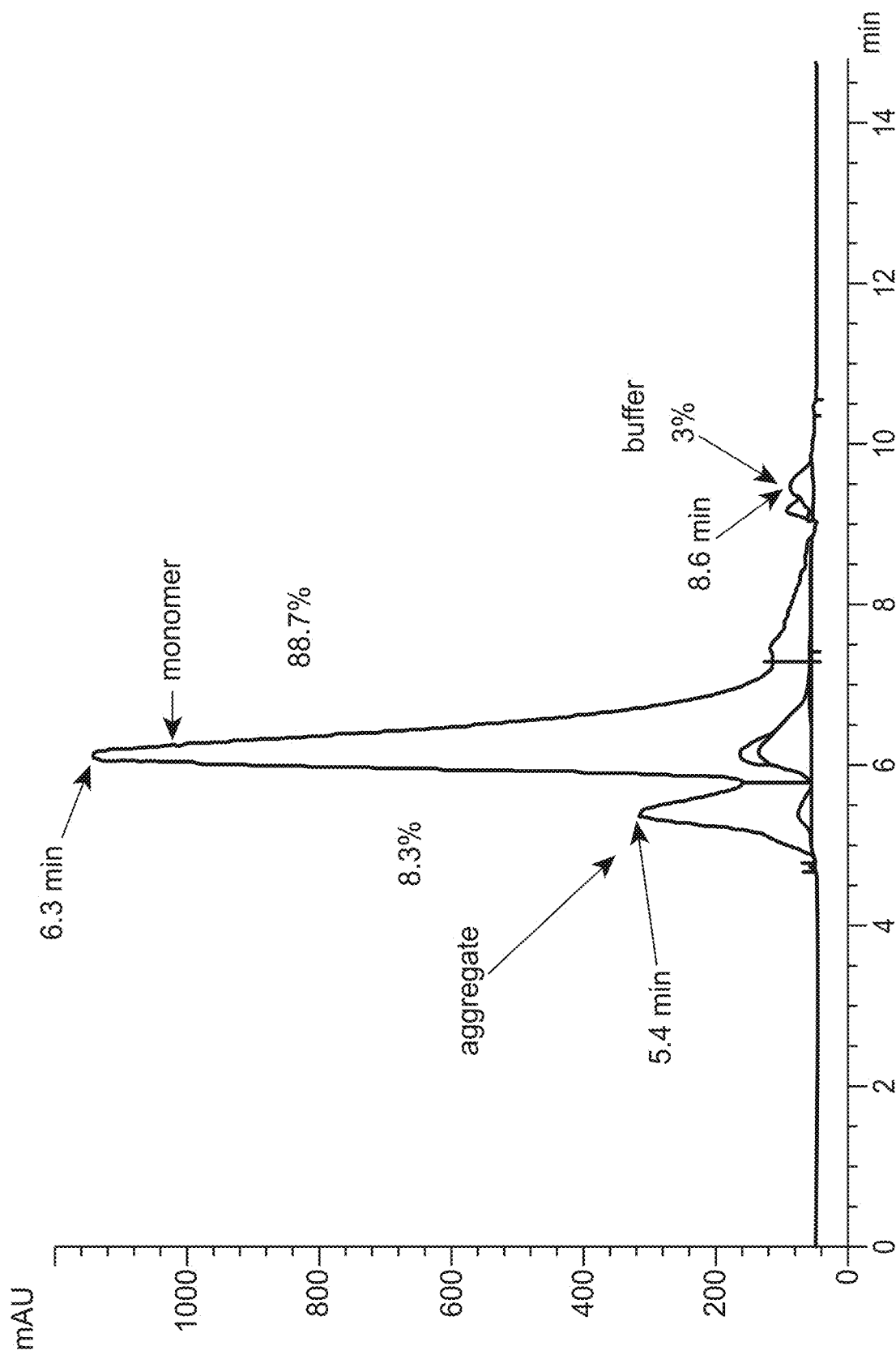
FIG. 31A shows a size-exclusion chromatography analysis of immunoconjugate BB01 synthesized using the SATA method.
Figure 31B:
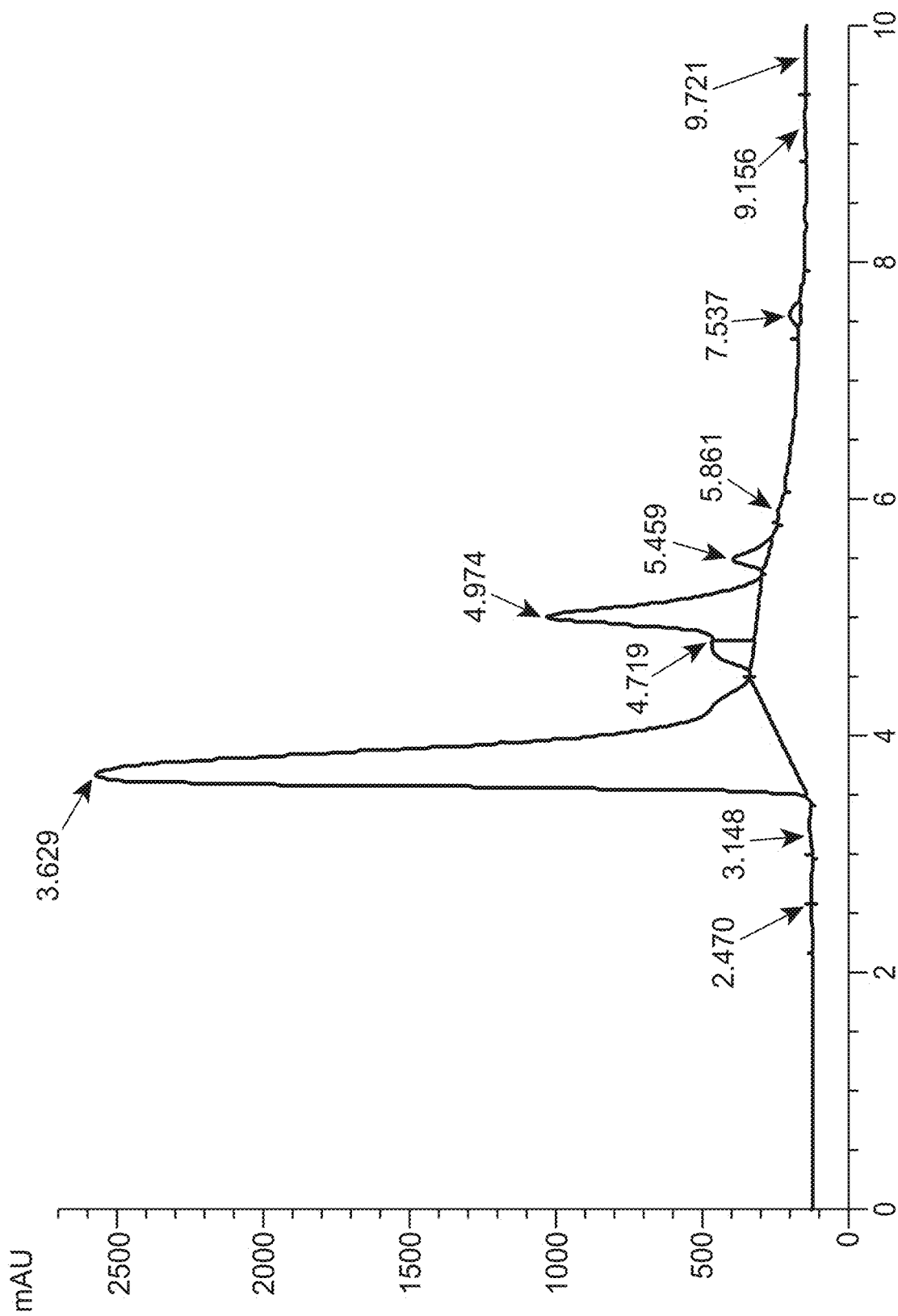
FIG. 31B shows a size-exclusion chromatography analysis of immunoconjugate BB-01 synthesized using the ester method.
Figure 32:
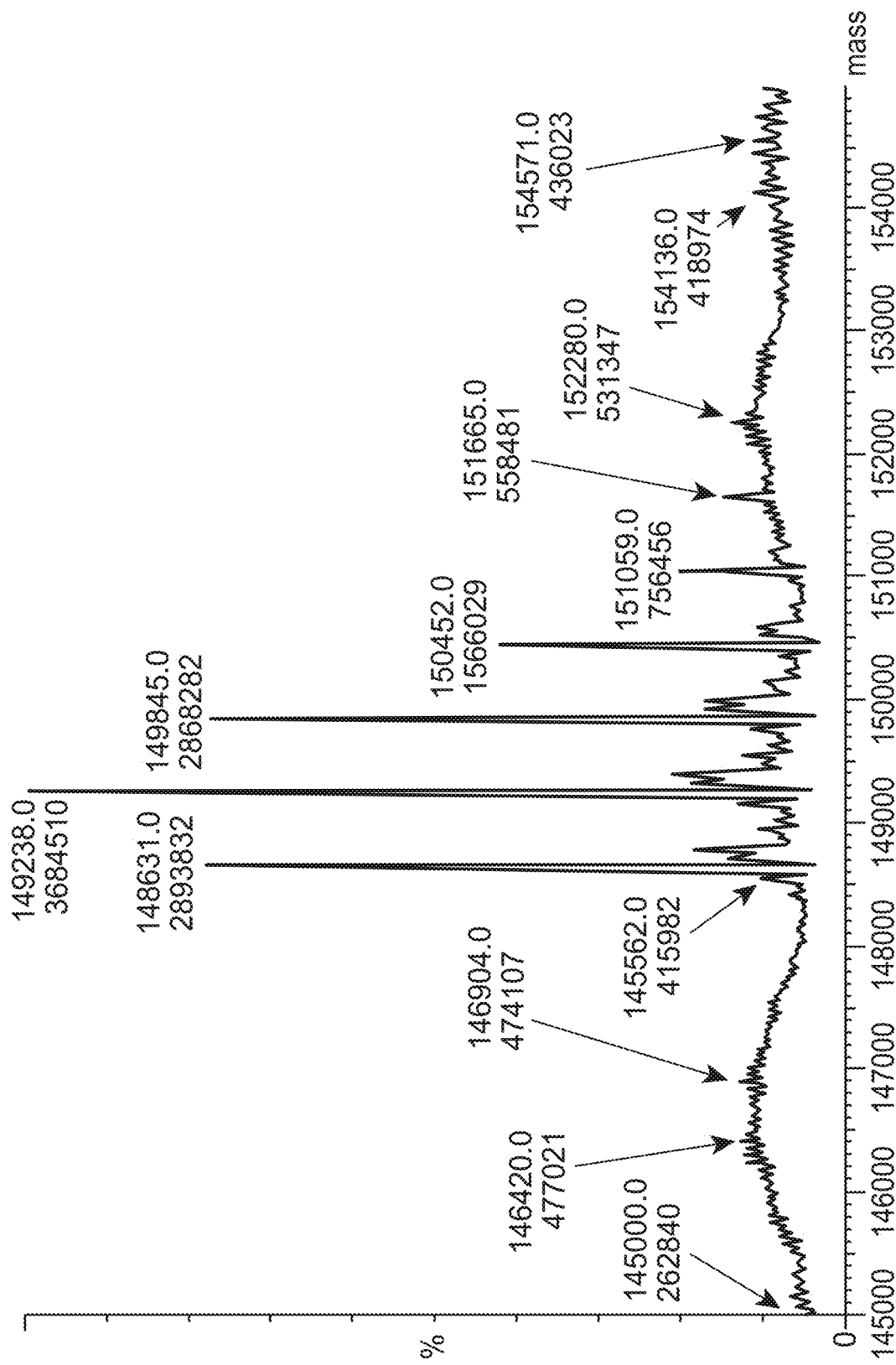
FIG. 32 shows a liquid chromatography-mass spectrometry analysis of immunoconjugate BB-14 synthesized using the ester method.
Figure 33:
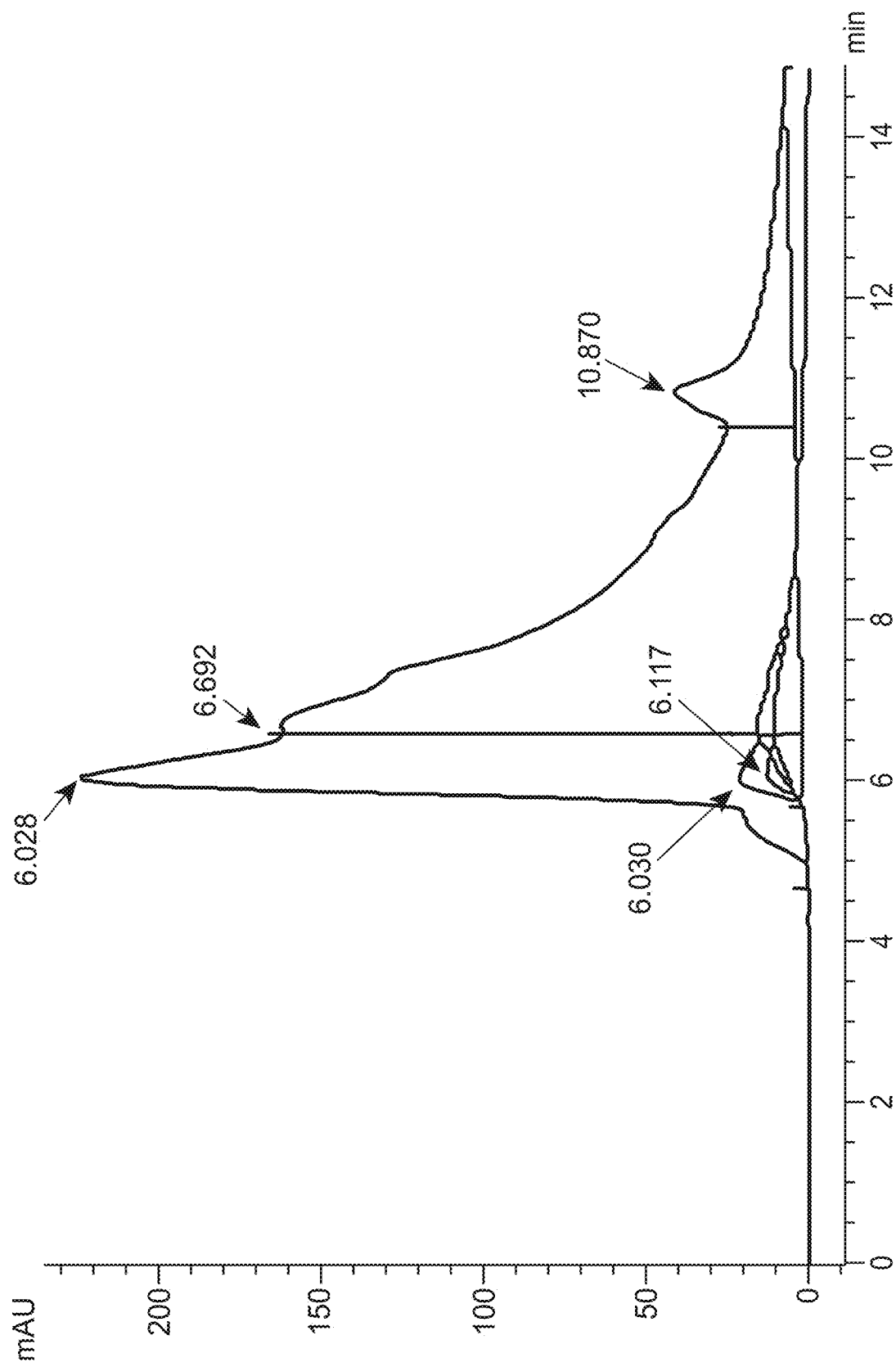
FIG. 33 shows a size-exclusion chromatography analysis of immunoconjugate BB-14 synthesized using the ester method.
Figure 34:
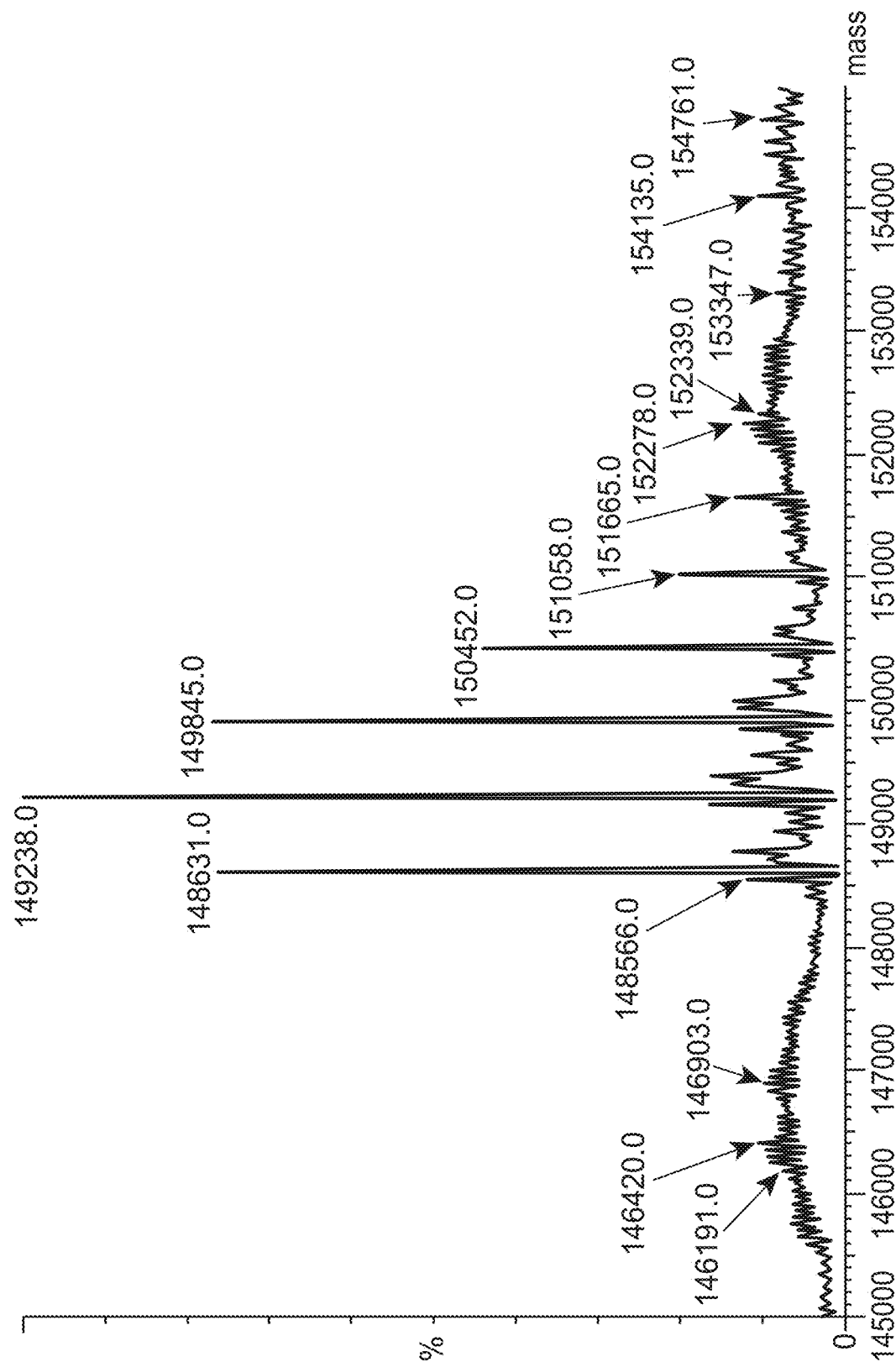
FIG. 34 shows a liquid chromatography-mass spectrometry analysis of immunoconjugate BB-15 synthesized using the ester method.
Figure 35:
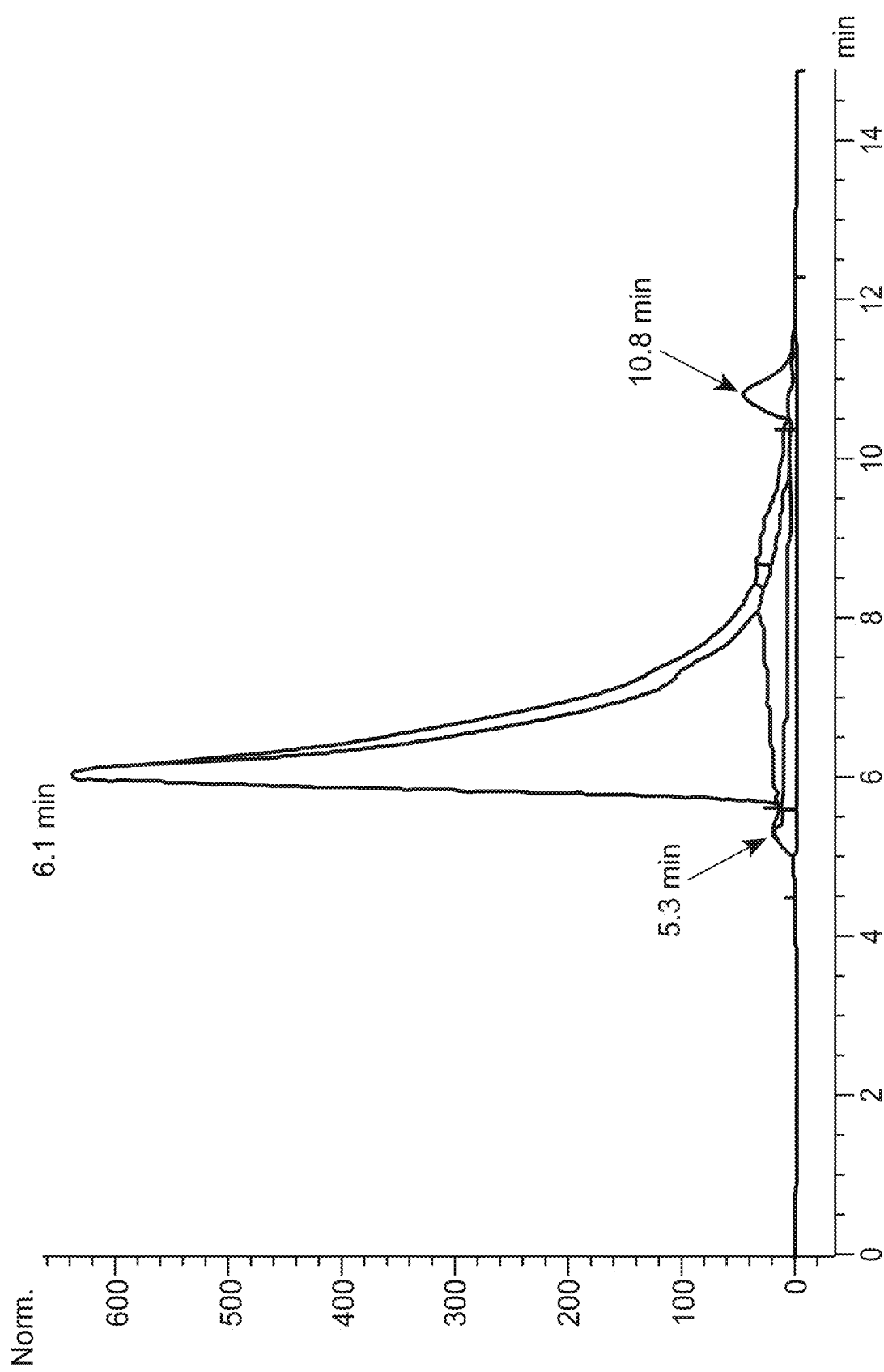
FIG. 35 shows a size-exclusion chromatography analysis of immunoconjugate BB-15 synthesized using the ester method.
Figure 36:
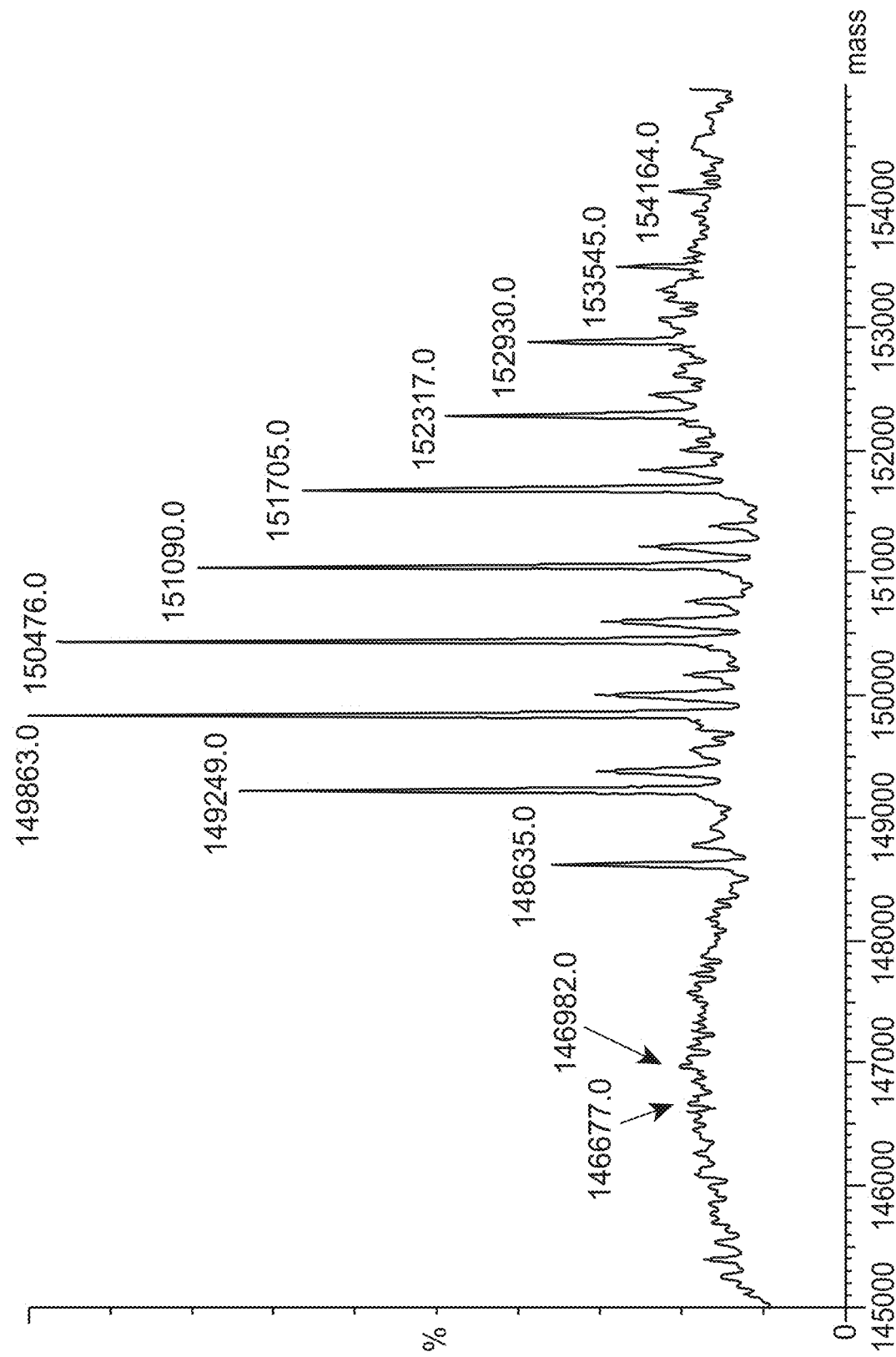
FIG. 36 shows a liquid chromatography-mass spectrometry analysis of immunoconjugate synthesized using the ester method.
Figure 37:
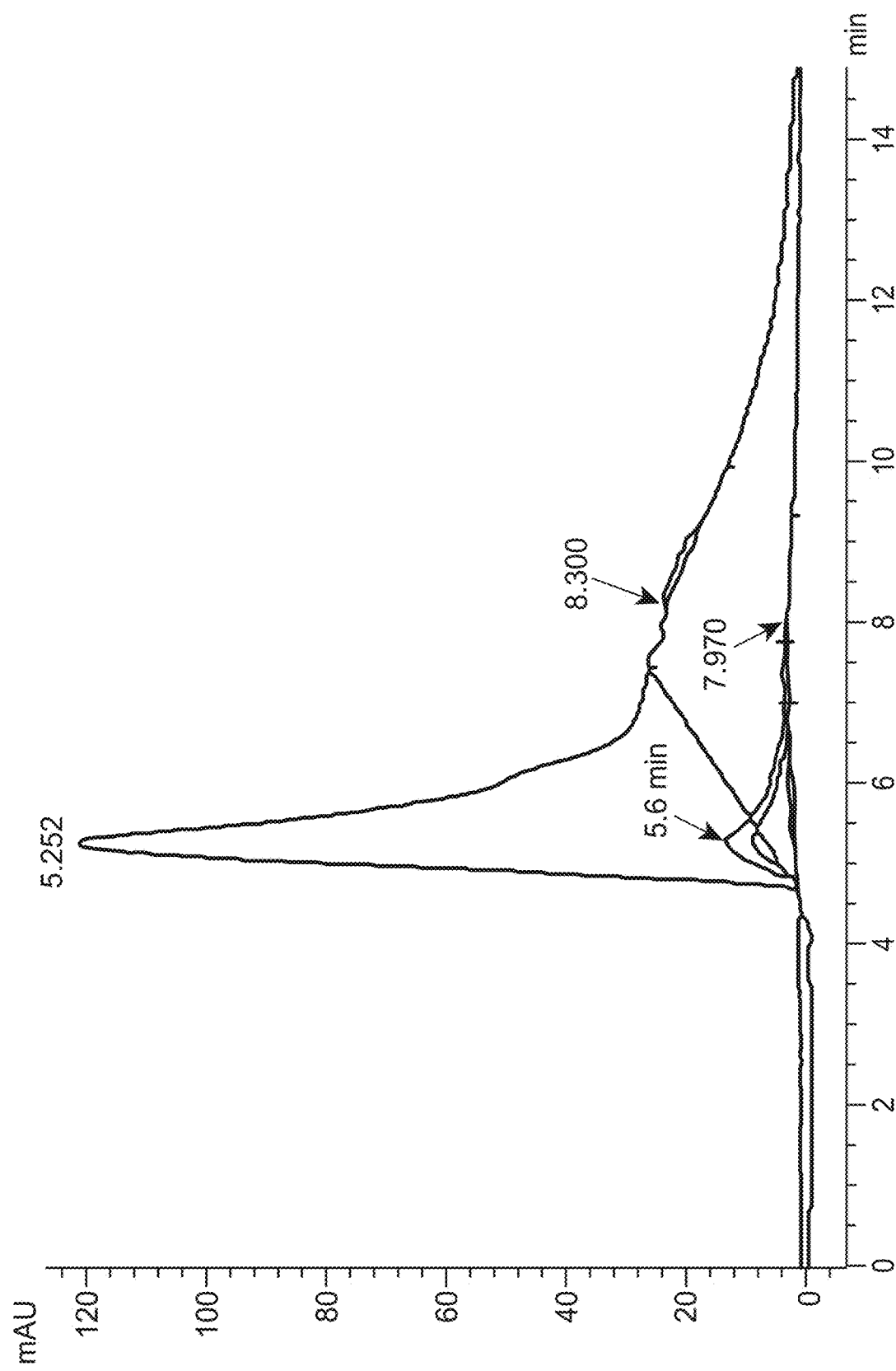
FIG. 37 shows a size-exclusion chromatography analysis of immunoconjugate synthesized using the ester method.
Figure 38C:
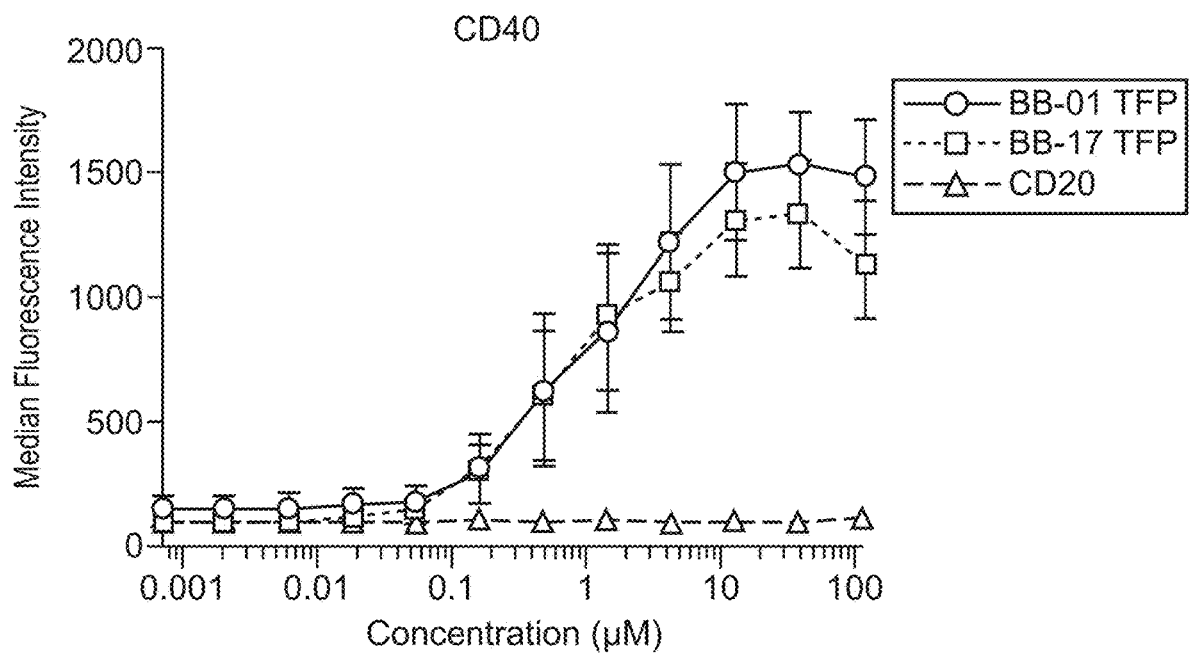
FIG. 38C shows BB-01 and BB-17 synthesized using the ester method elicits myeloid activation as indicated by CD40 upregulation while the control does not. CD20 is the unconjugated monoclonal antibody used as a control.
Figure 38D:
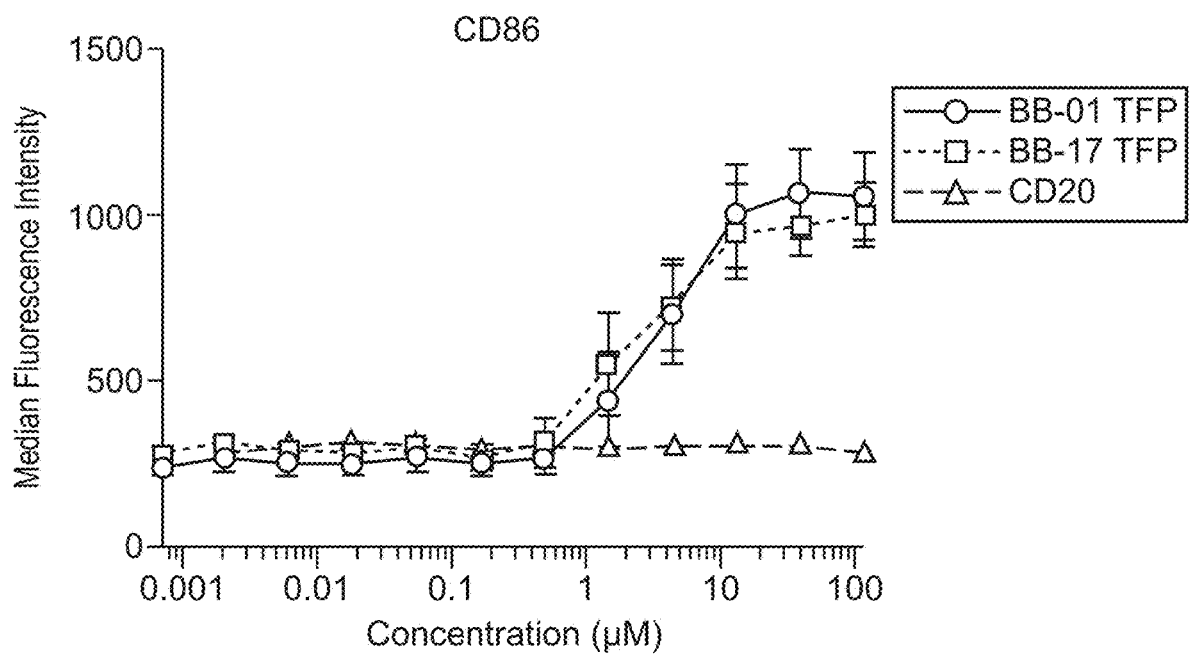
FIG. 38D shows BB-01 and BB-17 synthesized using the ester method elicits myeloid activation as indicated by CD86 upregulation while the control does not. CD20 is the unconjugated monoclonal antibody used as a control.
Figure 38E:
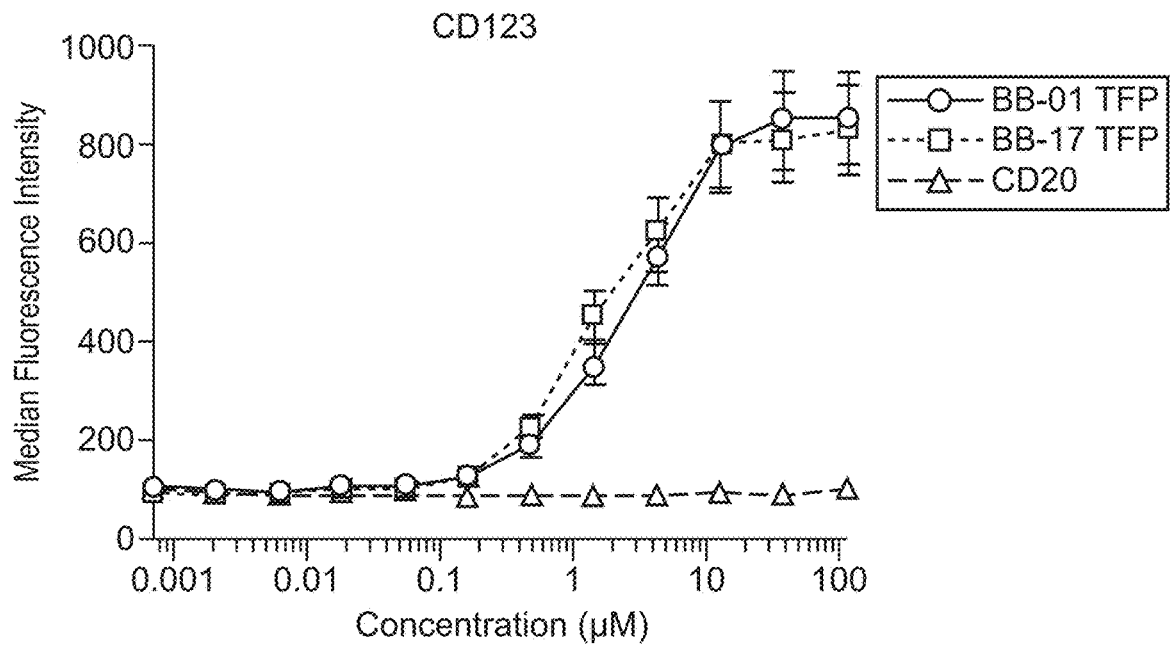
FIG. 38E shows BB-01 and BB-17 synthesized using the ester method elicits myeloid activation as indicated by CD123 upregulation while the control does not. CD20 is the unconjugated monoclonal antibody used as a control.
Figure 38F:
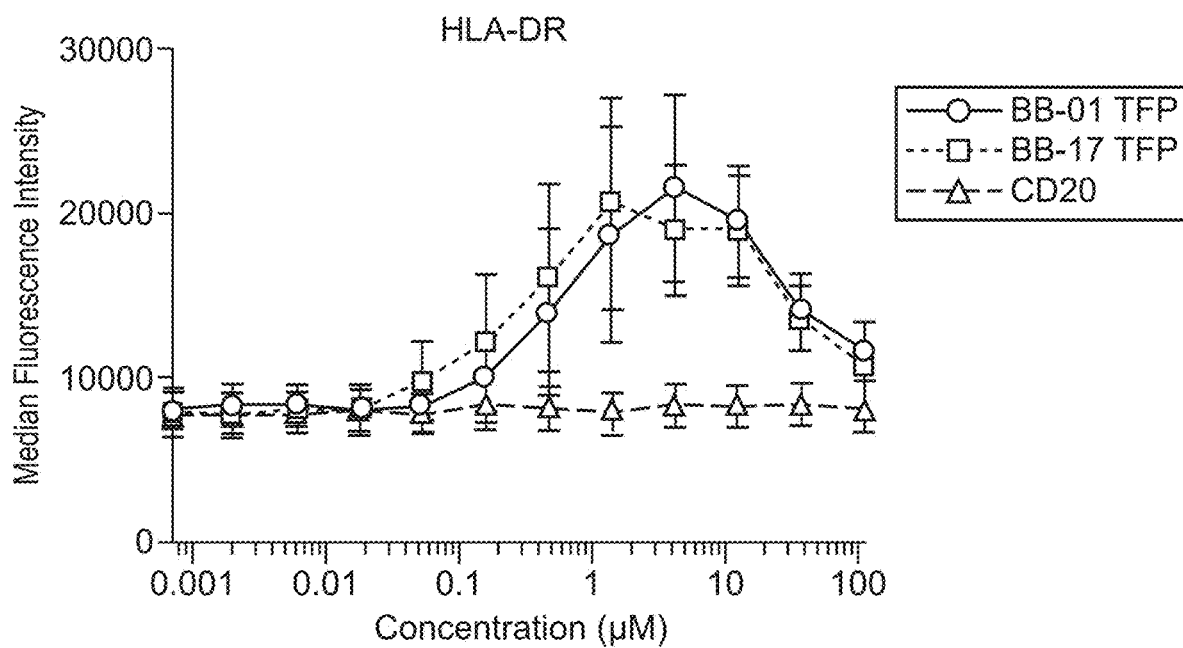
FIG. 38F shows BB-01 and BB-17 synthesized using the ester method elicits myeloid activation as indicated by Human Leukocyte Antigen-antigen D Related or "HLA-DR" while the control does not. CD20 is the unconjugated monoclonal antibody used as a control.
Figure 39A:
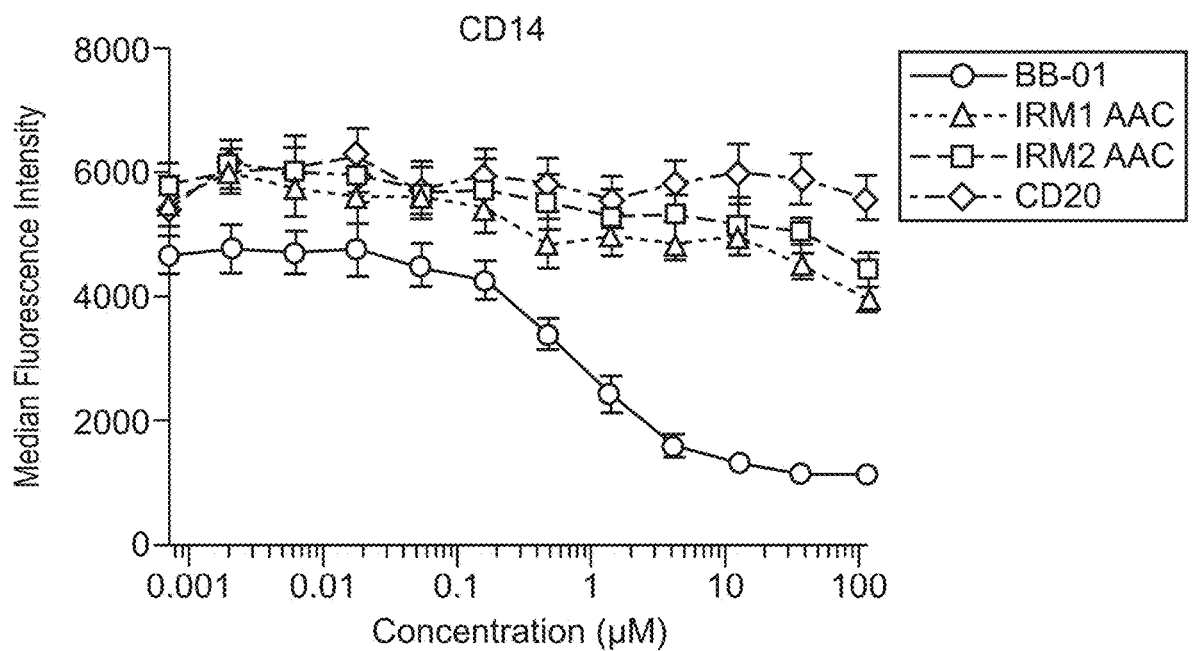
FIG. 39A shows that BB-01 elicits myeloid activation as indicated by CD14 downregulation while comparative IRM1 and IRM2 immunoconjugates do not. CD20 is the unconjugated monoclonal antibody used as a control.
Figure 39B:
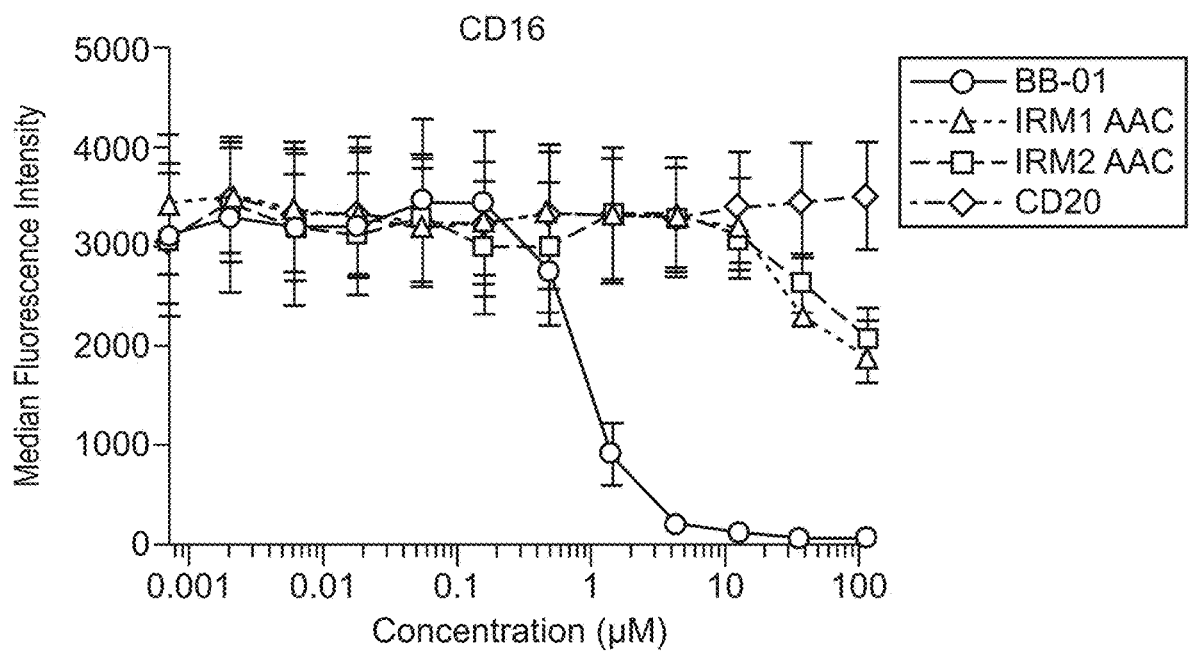
FIG. 39B shows that BB-01 elicits myeloid activation as indicated by CD16 downregulation while comparative IRM1 and IRM2 immunoconjugates do not. CD20 is the unconjugated monoclonal antibody used as a control.
Figure 39C:
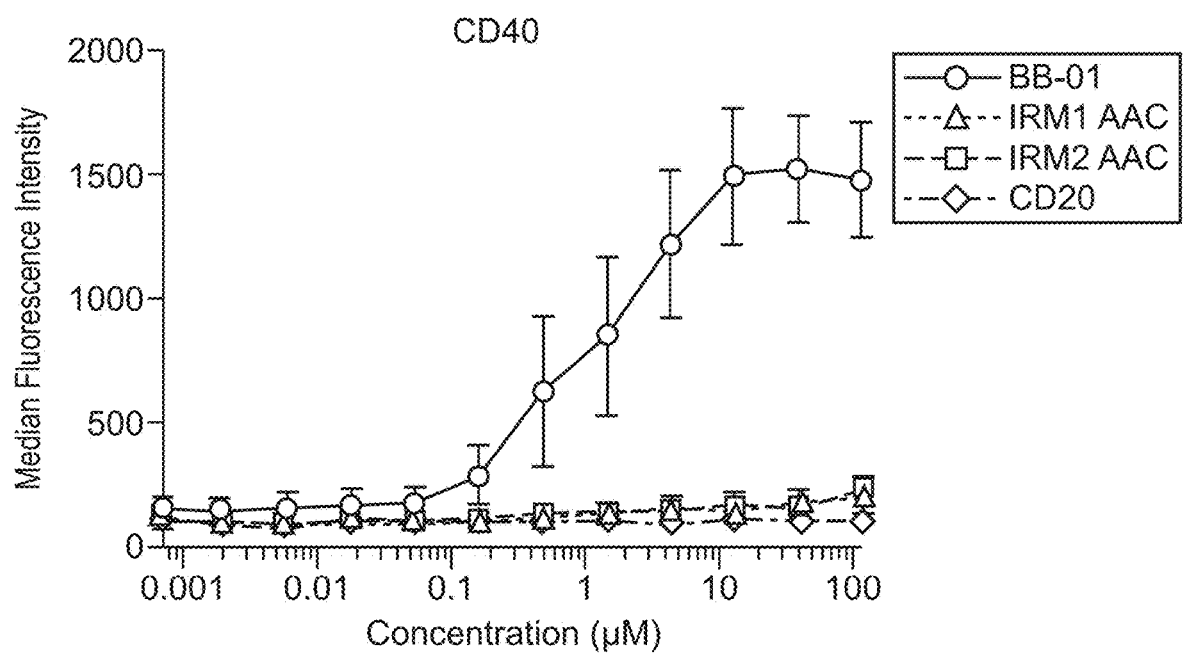
FIG. 39C shows that BB-01 elicits myeloid activation as indicated by CD40 upregulation while comparative IRM1 and IRM2 immunoconjugates do not. CD20 is the unconjugated monoclonal antibody used as a control.
Figure 39D:
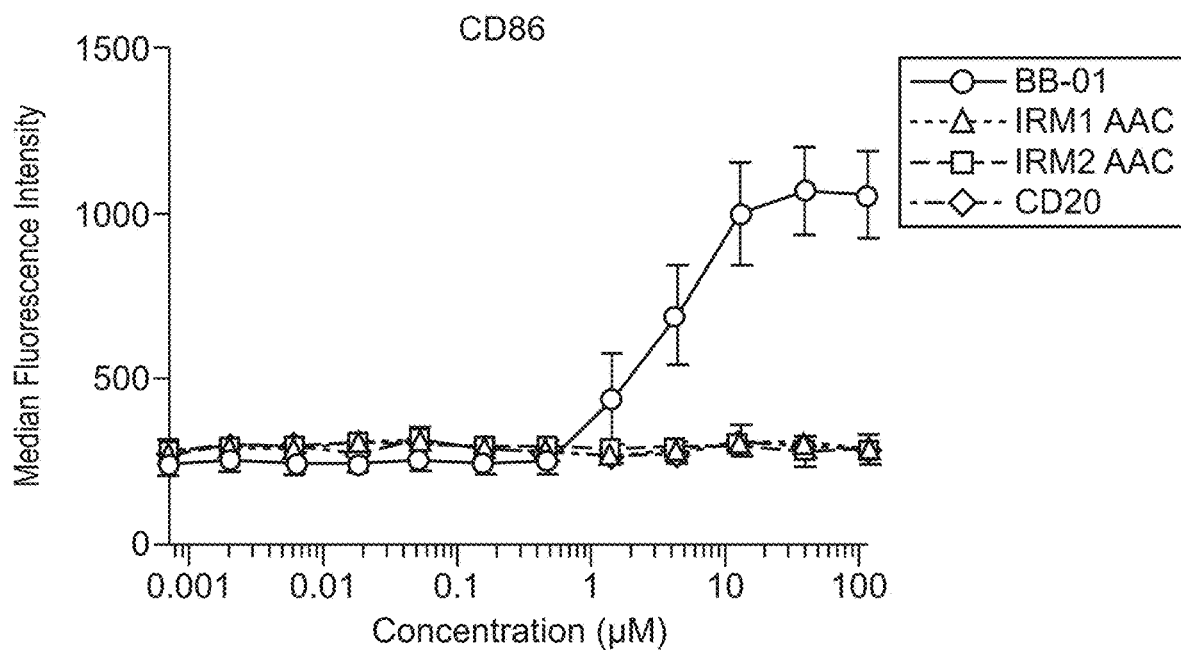
FIG. 39D shows that BB-01 elicits myeloid activation as indicated by CD86 upregulation while comparative IRM1 and IRM2 immunoconjugates do not. CD20 is the unconjugated monoclonal antibody used as a control.
Figure 39E:
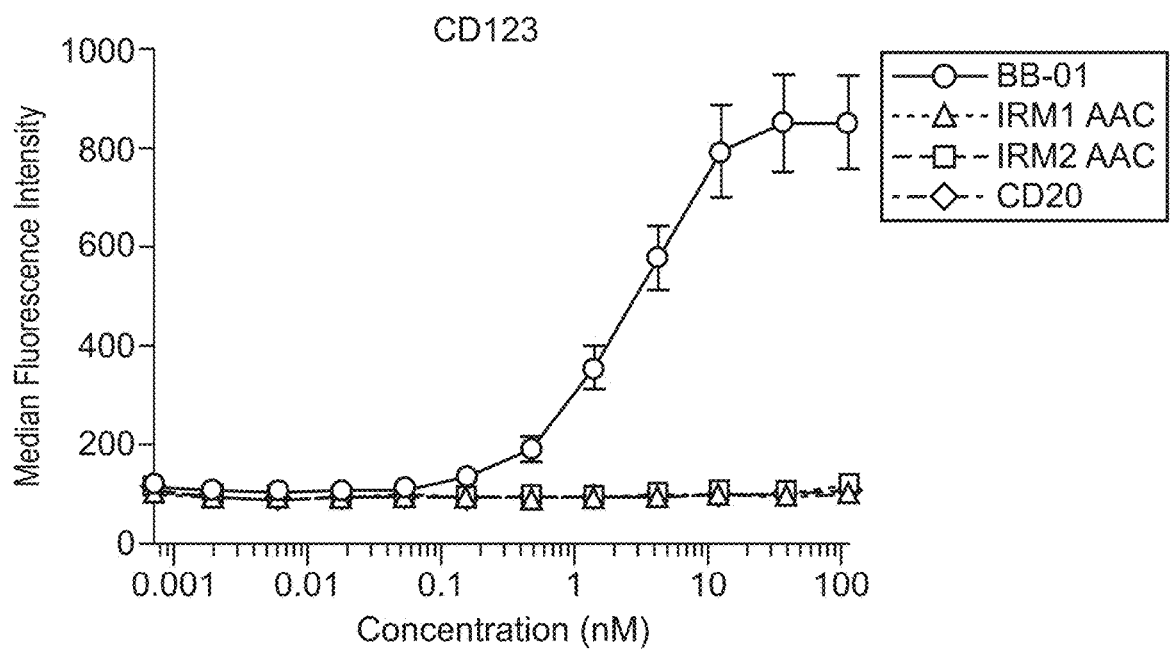
FIG. 39E shows that BB-01 elicits myeloid activation as indicated by CD123 upregulation while comparative IRM1 and IRM2 immunoconjugates do not. CD20 is the unconjugated monoclonal antibody used as a control.
Figure 39F:
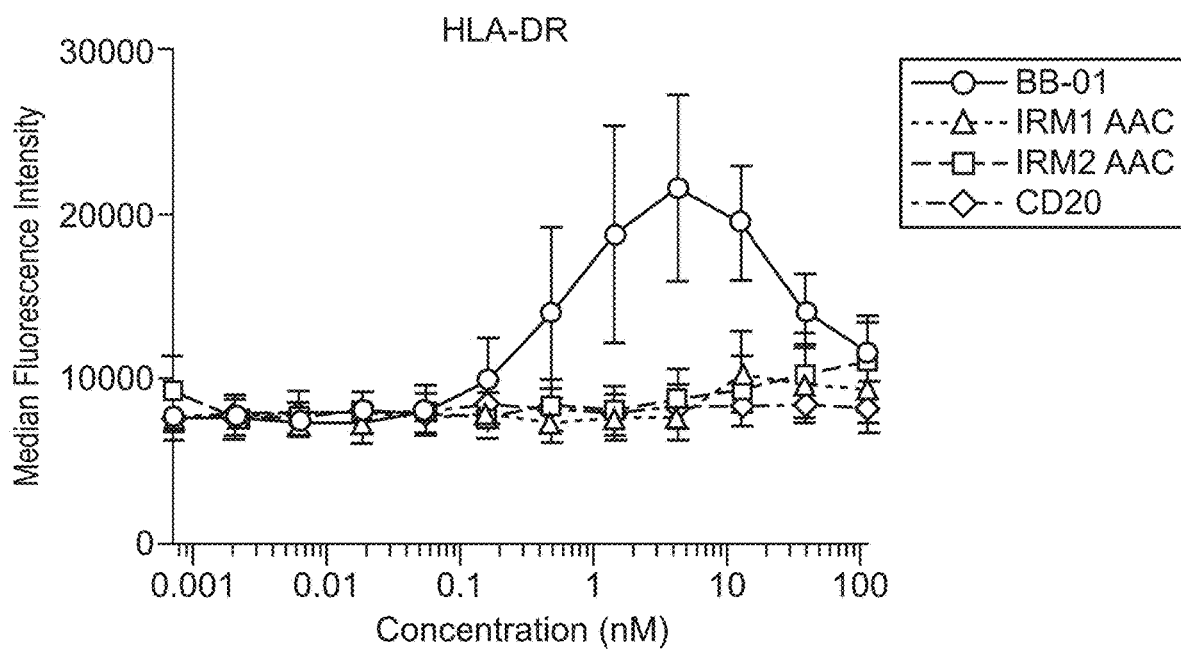
FIG. 39F shows that BB-01 elicits myeloid activation as indicated by HLA-DR upregulation while comparative IRM1 and IRM2 immunoconjugates do not. CD20 is the unconjugated monoclonal antibody used as a control.
Figure 40A:
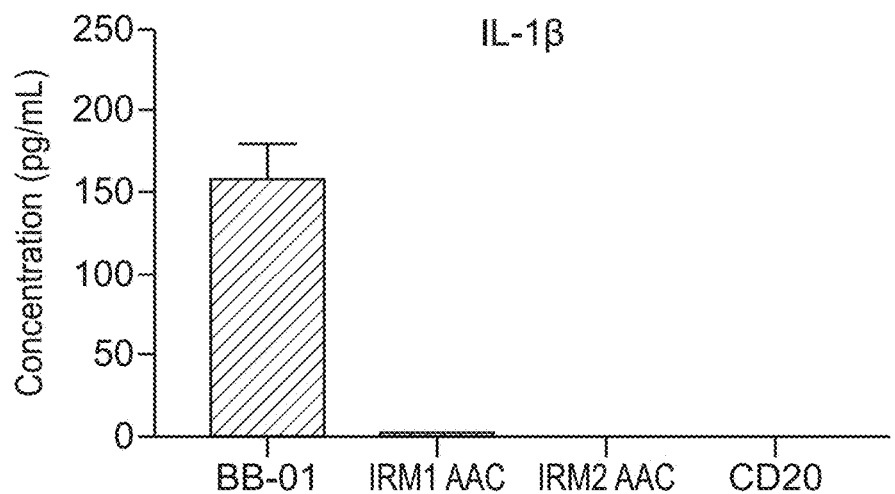
FIG. 40A shows that BB-01 elicits cytokine secretion (IL-1β) while comparative IRM1 and IRM2 immunoconjugates do not. CD20 is the unconjugated monoclonal antibody used as a control.
Figure 40B:
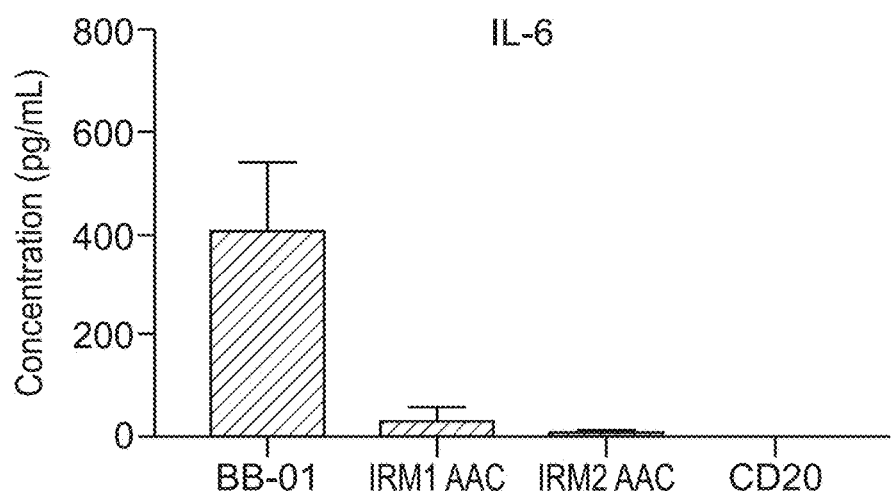
FIG. 40B shows that BB-01 elicits cytokine secretion (IL-6) while comparative IRM1 and IRM2 immunoconjugates do not. CD20 is the unconjugated monoclonal antibody used as a control.
Figure 40C:
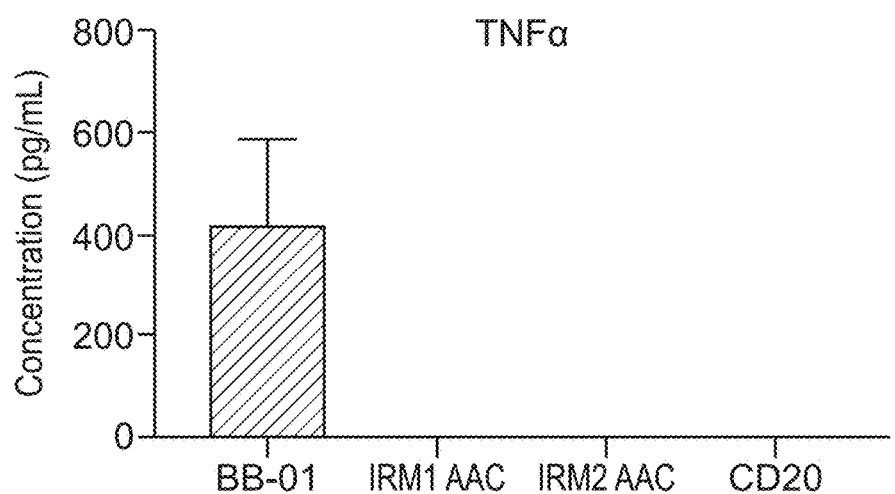
FIG. 40C shows that BB-01 elicits cytokine secretion (TNFα) while comparative IRM1 and IRM2 immunoconjugates do not. CD20 is the unconjugated monoclonal antibody used as a control.
Figure 41A:
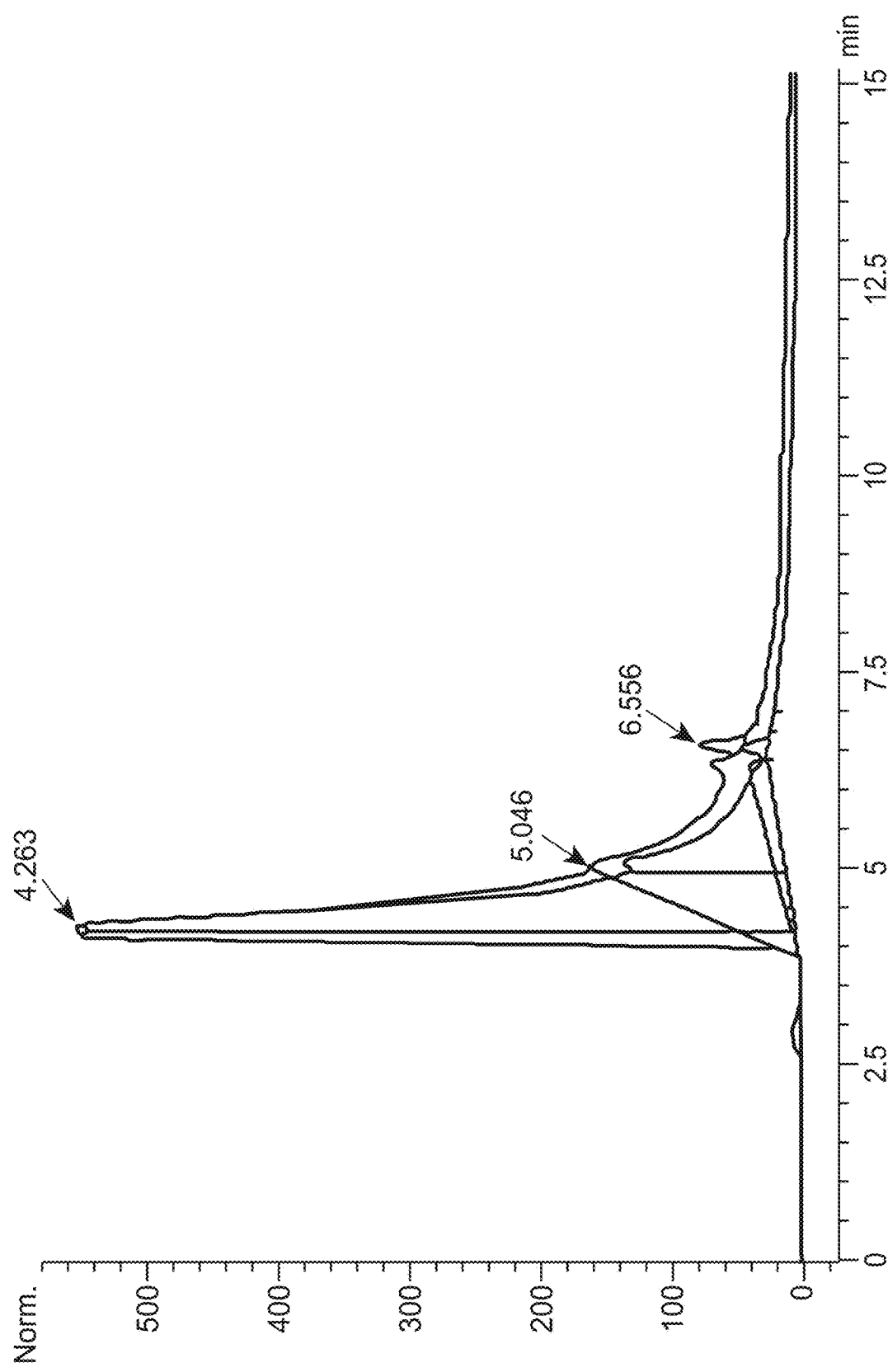
FIG. 41A shows a size-exclusion chromatography analysis of immunoconjugate BB-26 synthesized using the ester method.
Figure 42A:
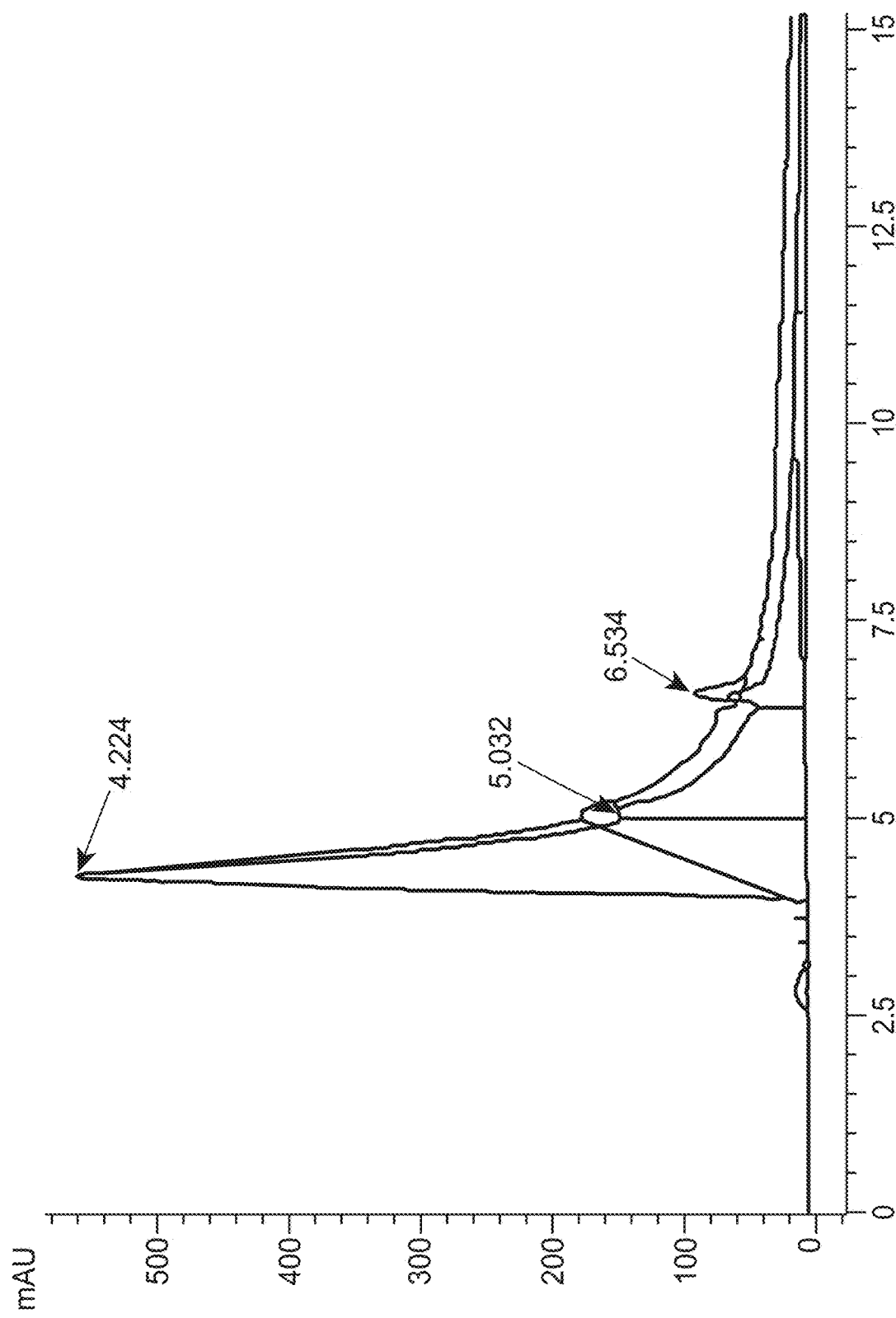
FIG. 42A shows a size-exclusion chromatography analysis of immunoconjugate BB-27 synthesized using the ester method.
Figure 42B:
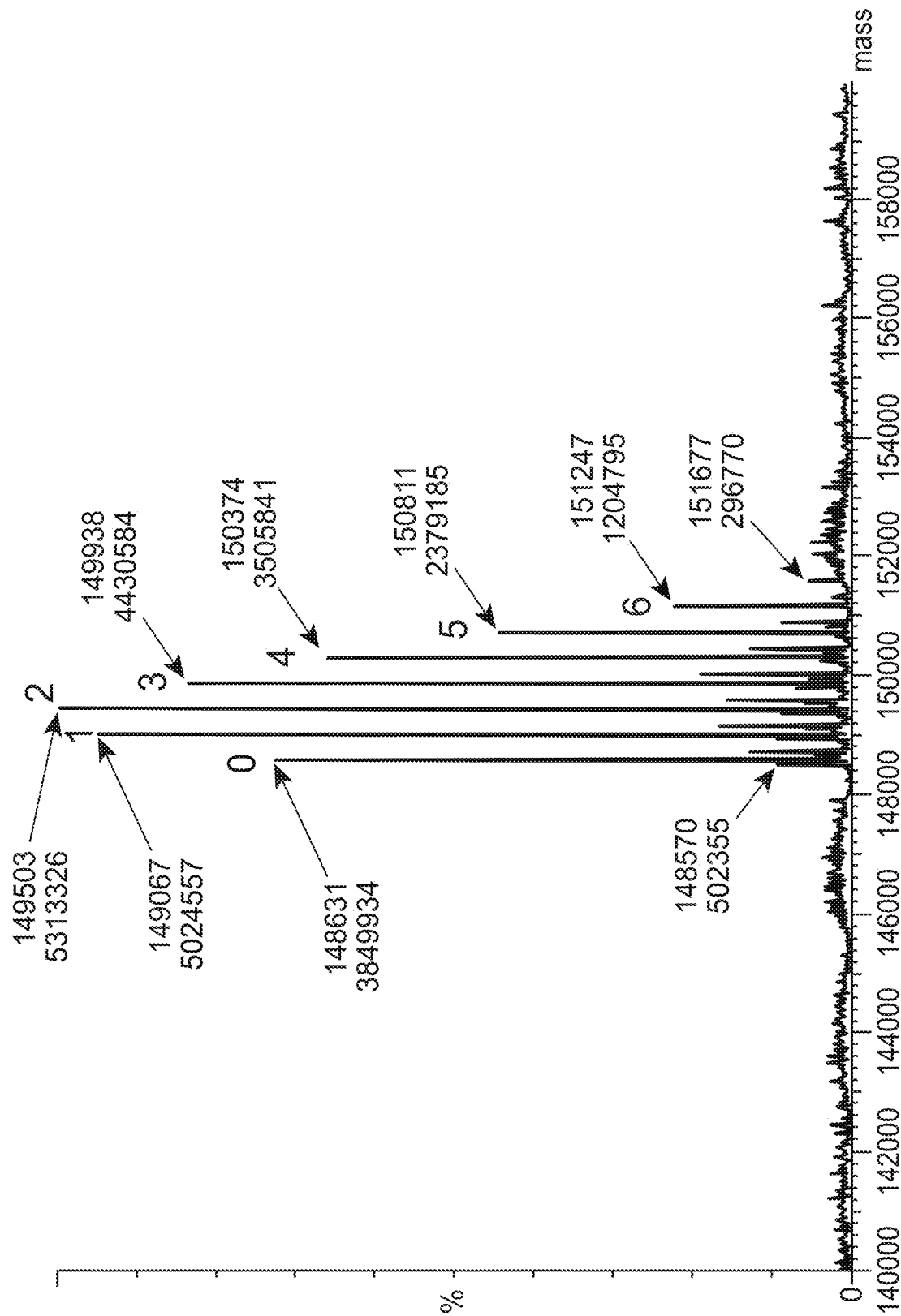
FIG. 42B shows a liquid chromatography-mass spectrometry analysis of immunoconjugate BB-27 synthesized using the ester method.
Figure 43A:
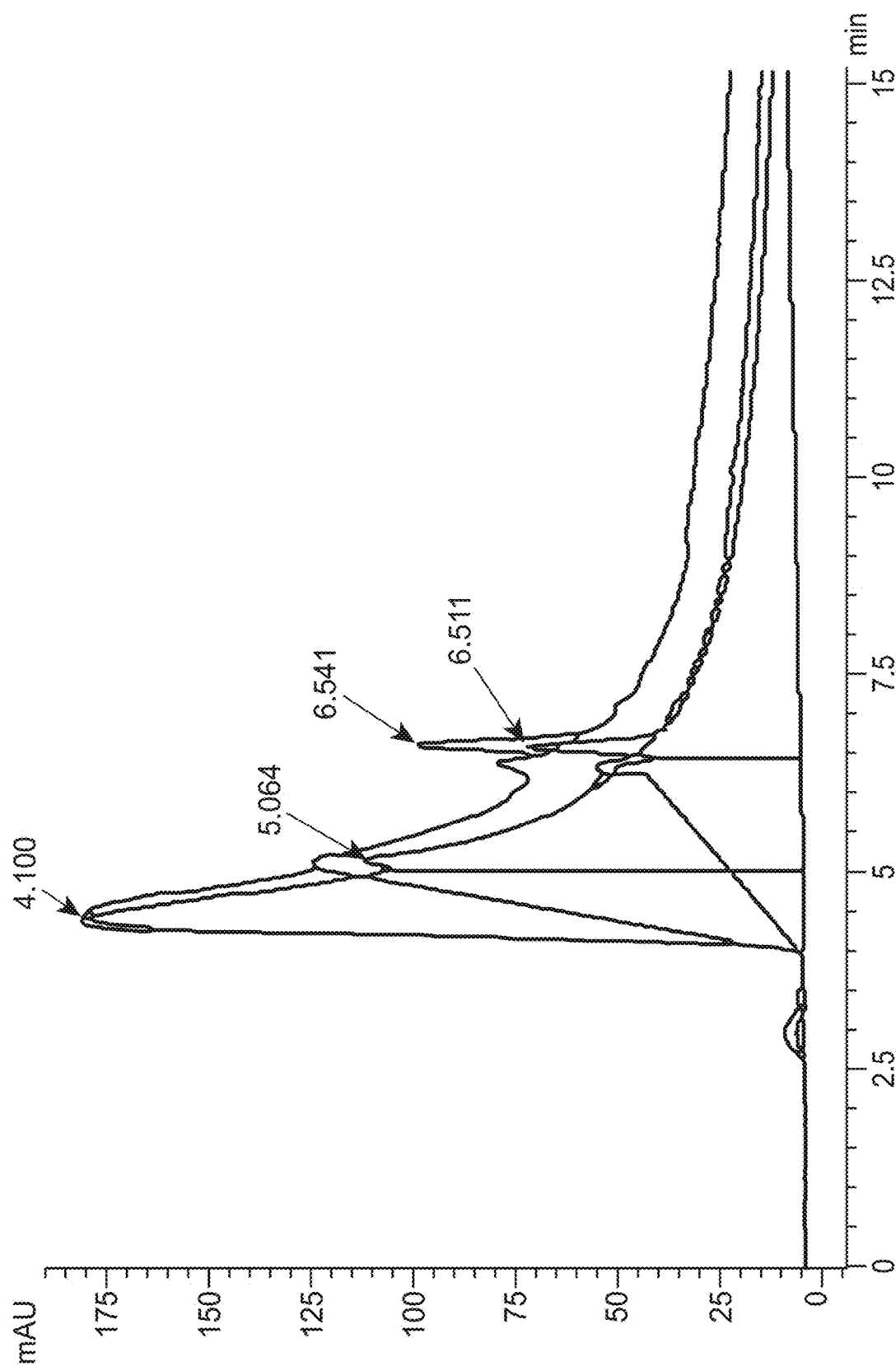
FIG. 43A shows a size-exclusion chromatography analysis of immunoconjugate BB-36 synthesized using the ester method.
Figure 44A:
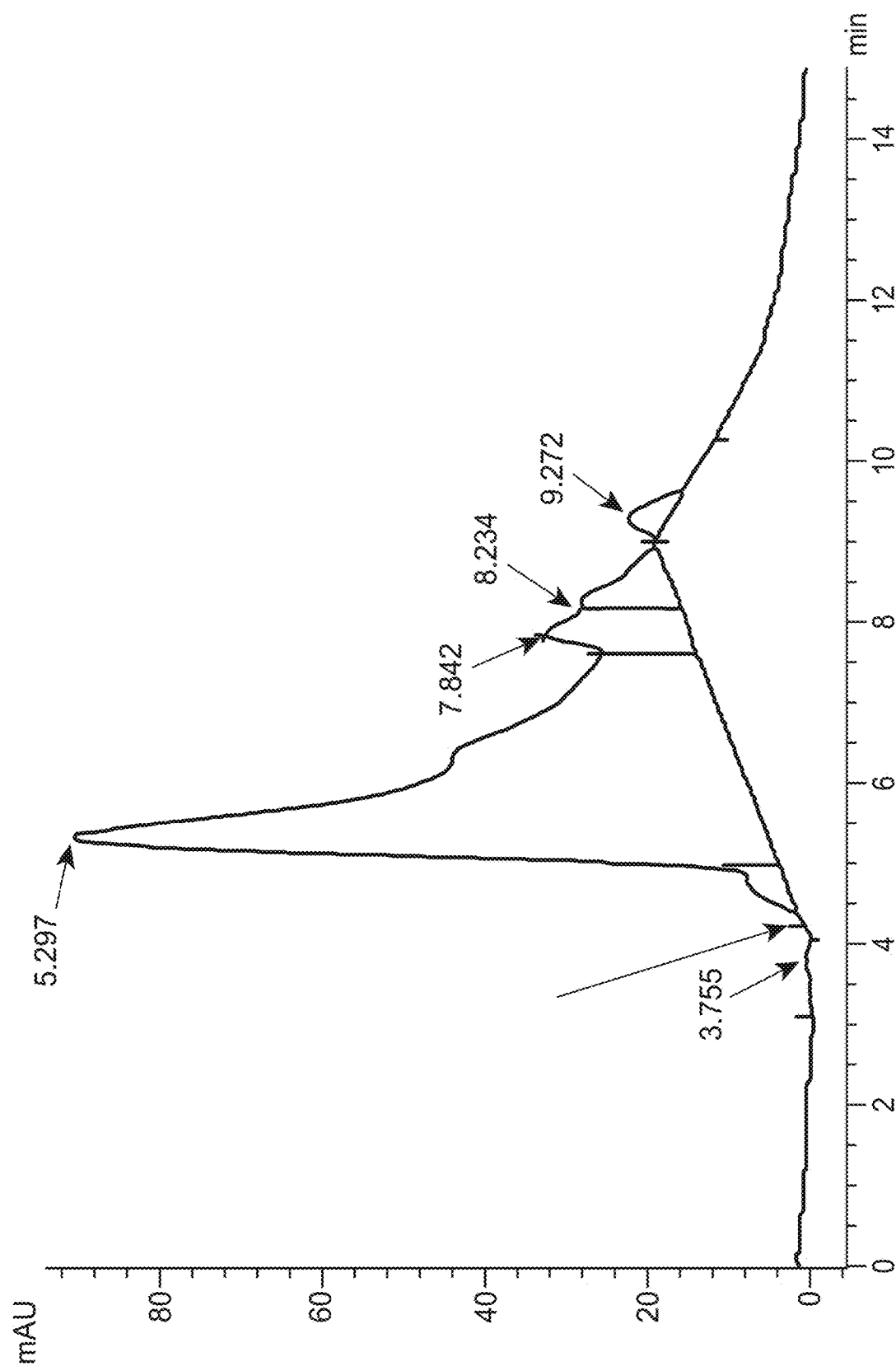
FIG. 44A shows a size-exclusion chromatography analysis of Comparative Conjugate IRM1.
Figure 44B:
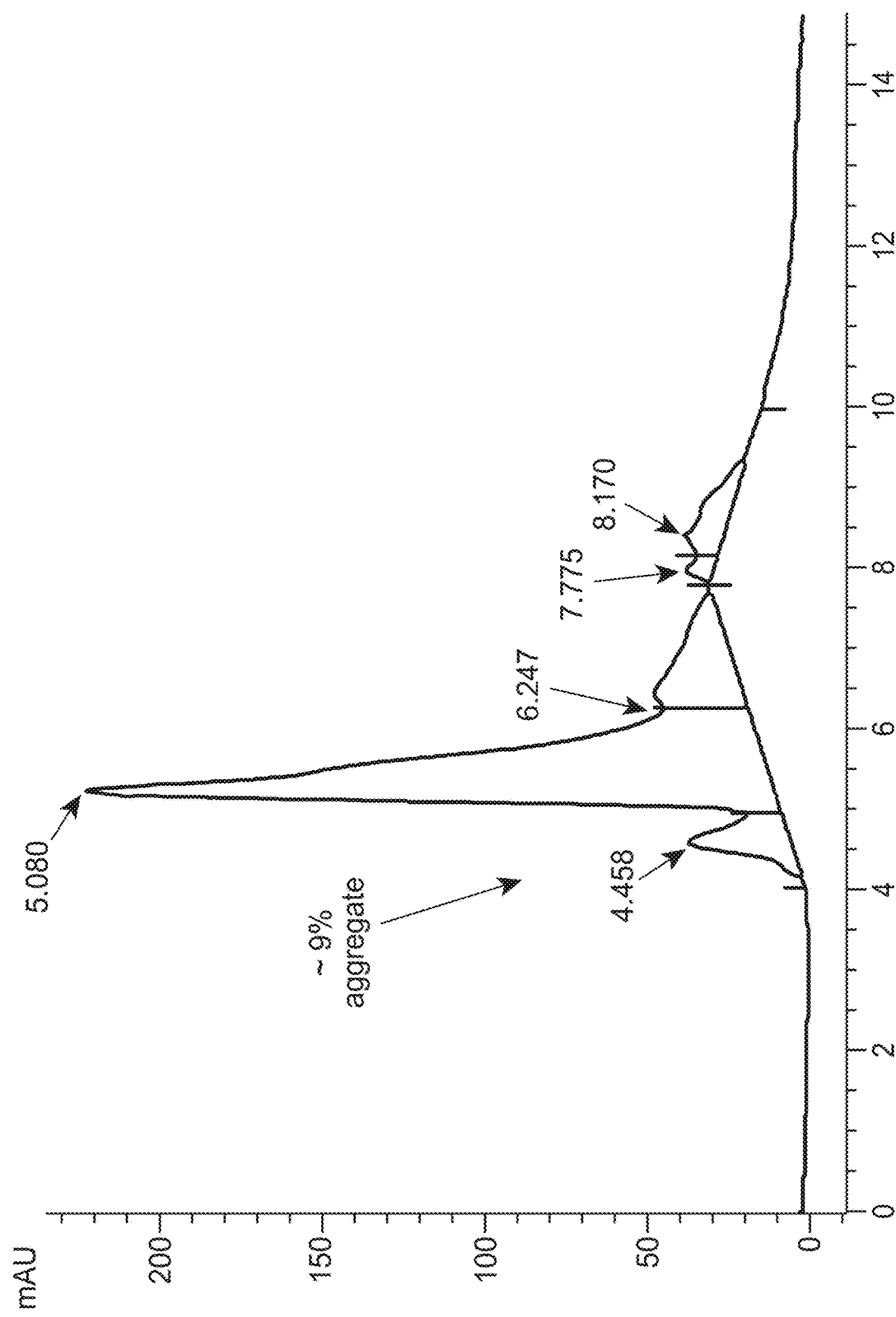
FIG. 44B shows a size-exclusion chromatography analysis of Comparative Conjugate IRM2.
Figure 44C:
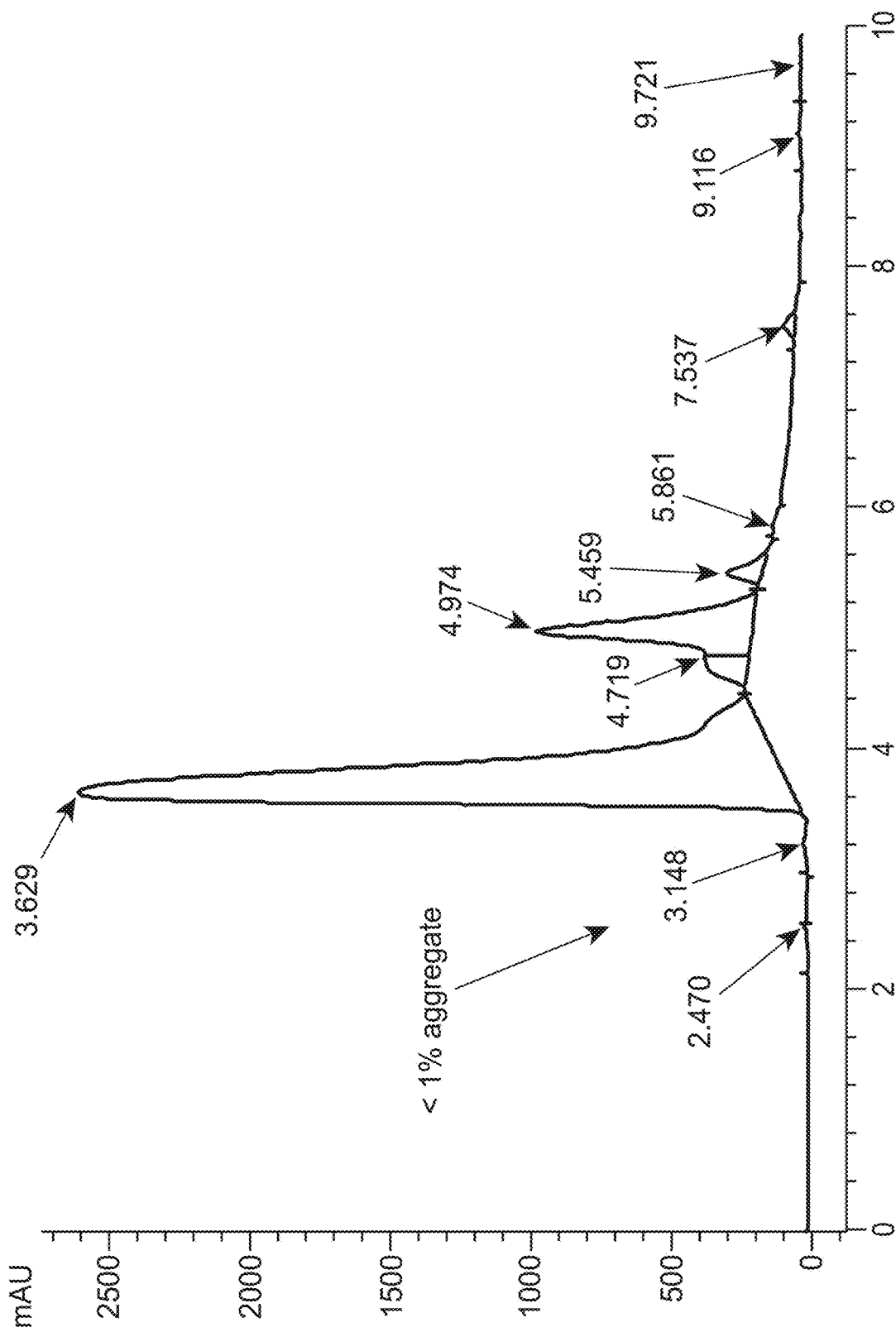
FIG. 44C shows a size-exclusion chromatography analysis of BB-01.
Figure 45B:
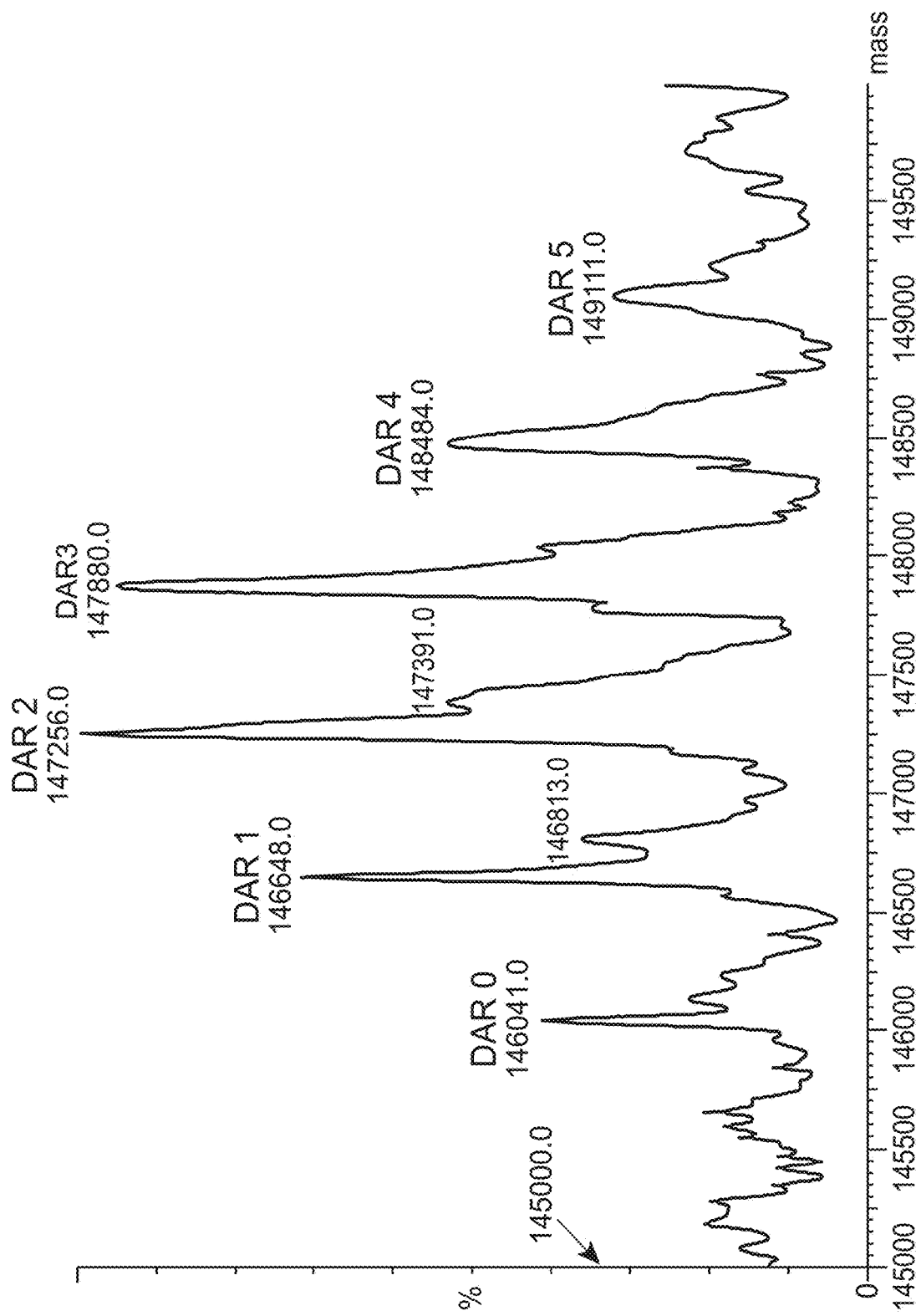
FIG. 45B show a liquid chromatography-mass spectrometry analysis of BB-01 conjugate following overnight deglycosylation with PNGase F.
Figure 46A:
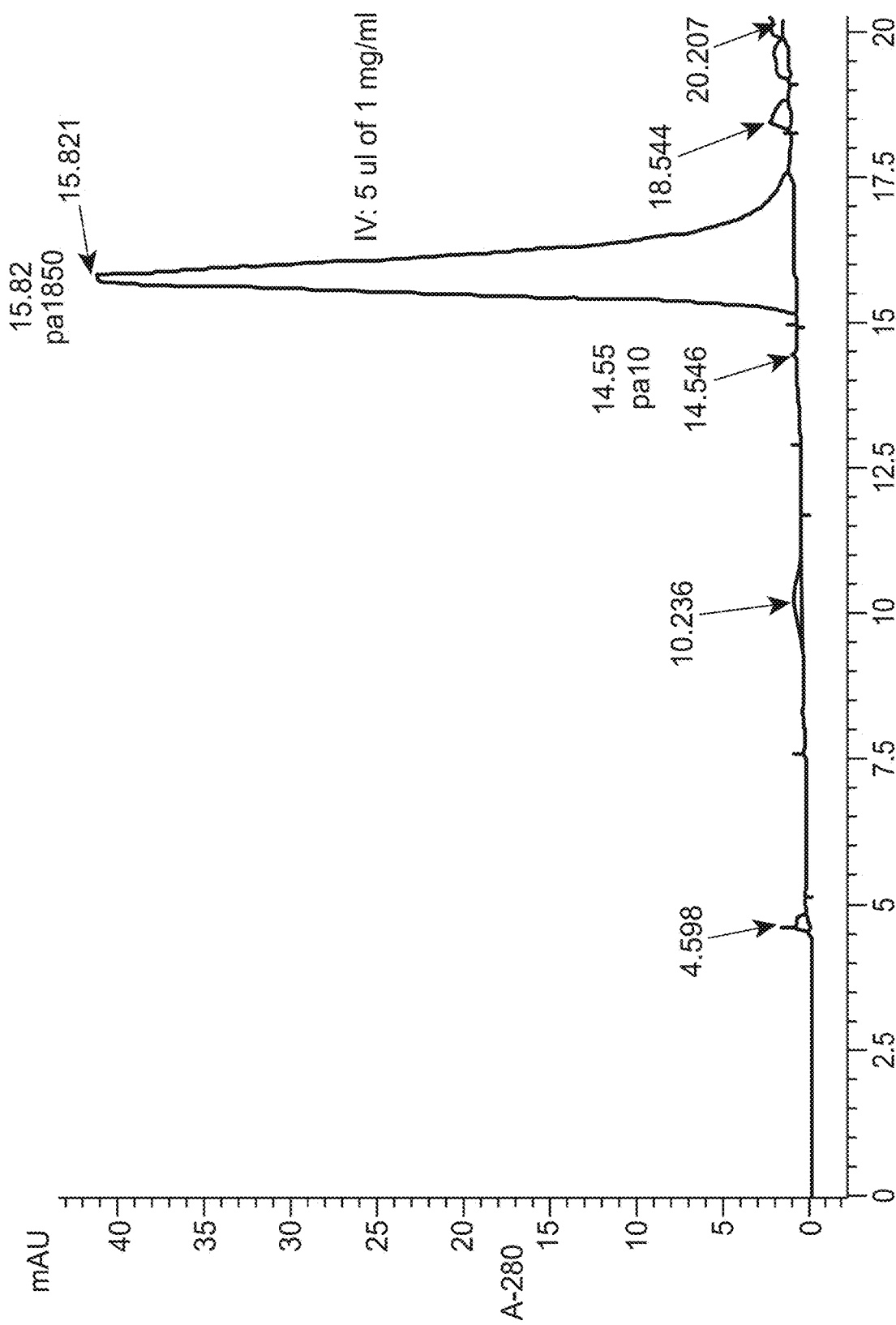
FIG. 46A shows a size-exclusion chromatography analysis of immunoconjugate BB-45 synthesized using the ester method.
Figure 46B:
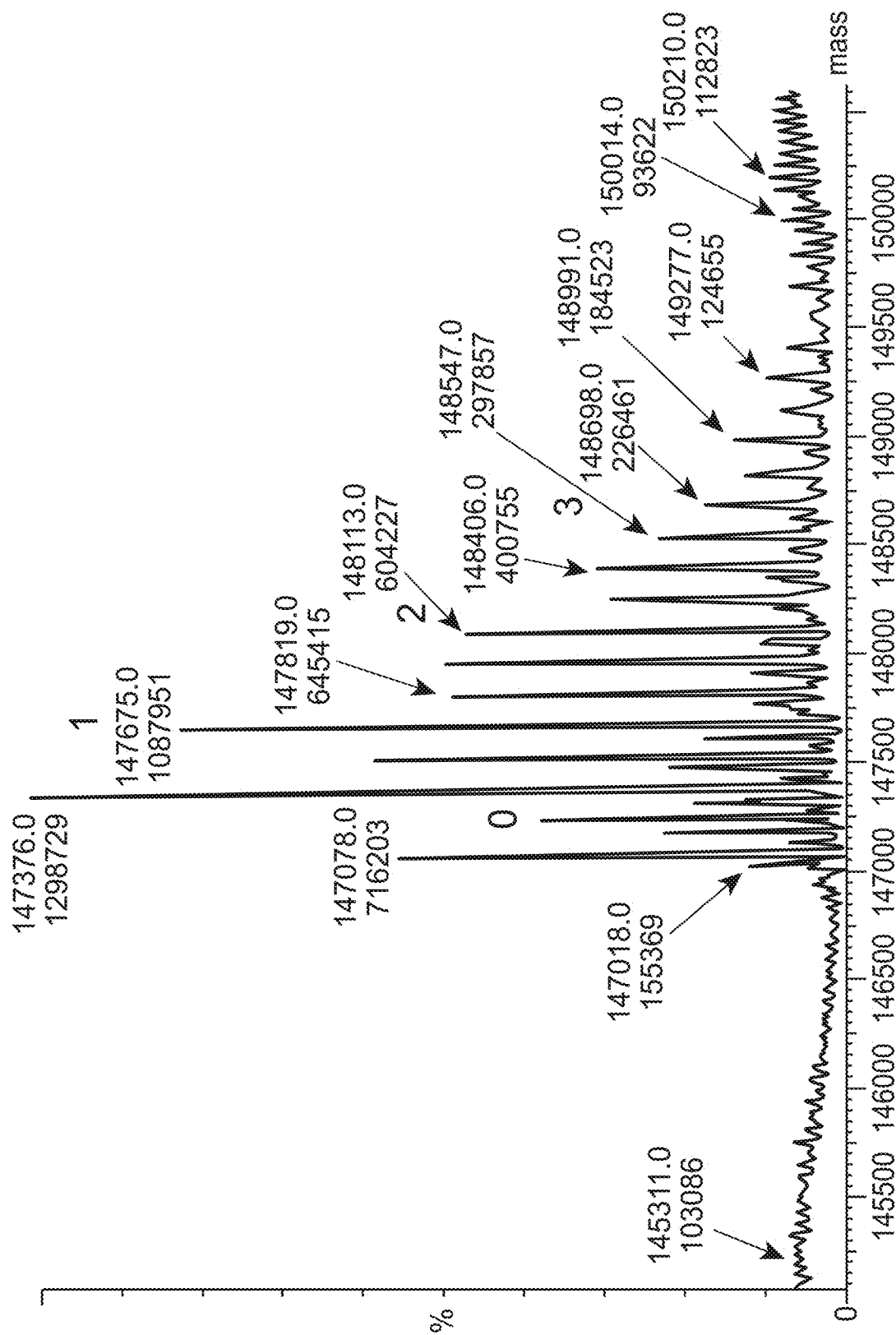
FIG. 46B shows a liquid chromatography-mass spectrometry analysis of immunoconjugate BB-45 synthesized using the ester method.
Figure 47A:
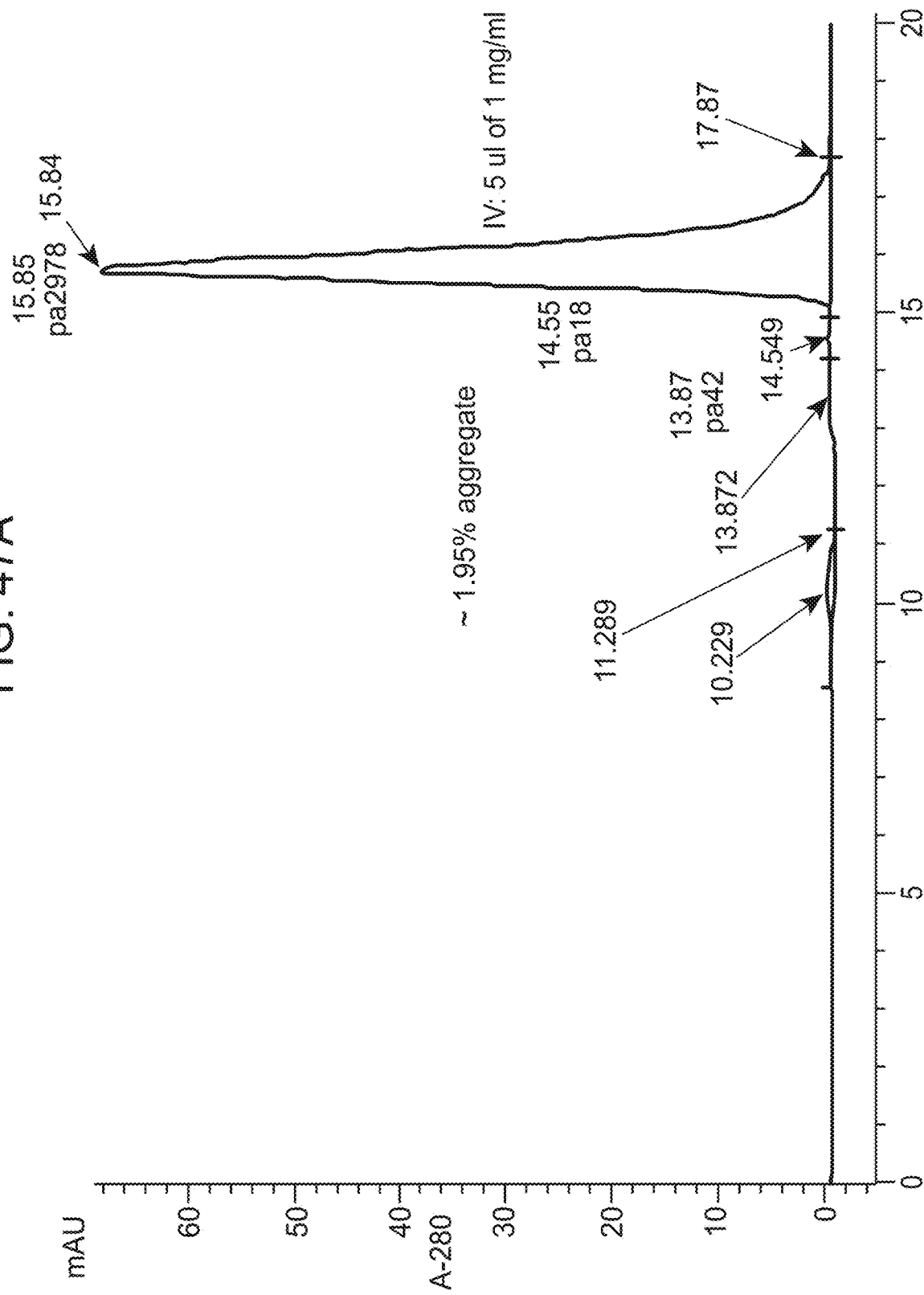
FIG. 47A shows a size-exclusion chromatography analysis of immunoconjugate BB-24 synthesized using the ester method.
Figure 48A:
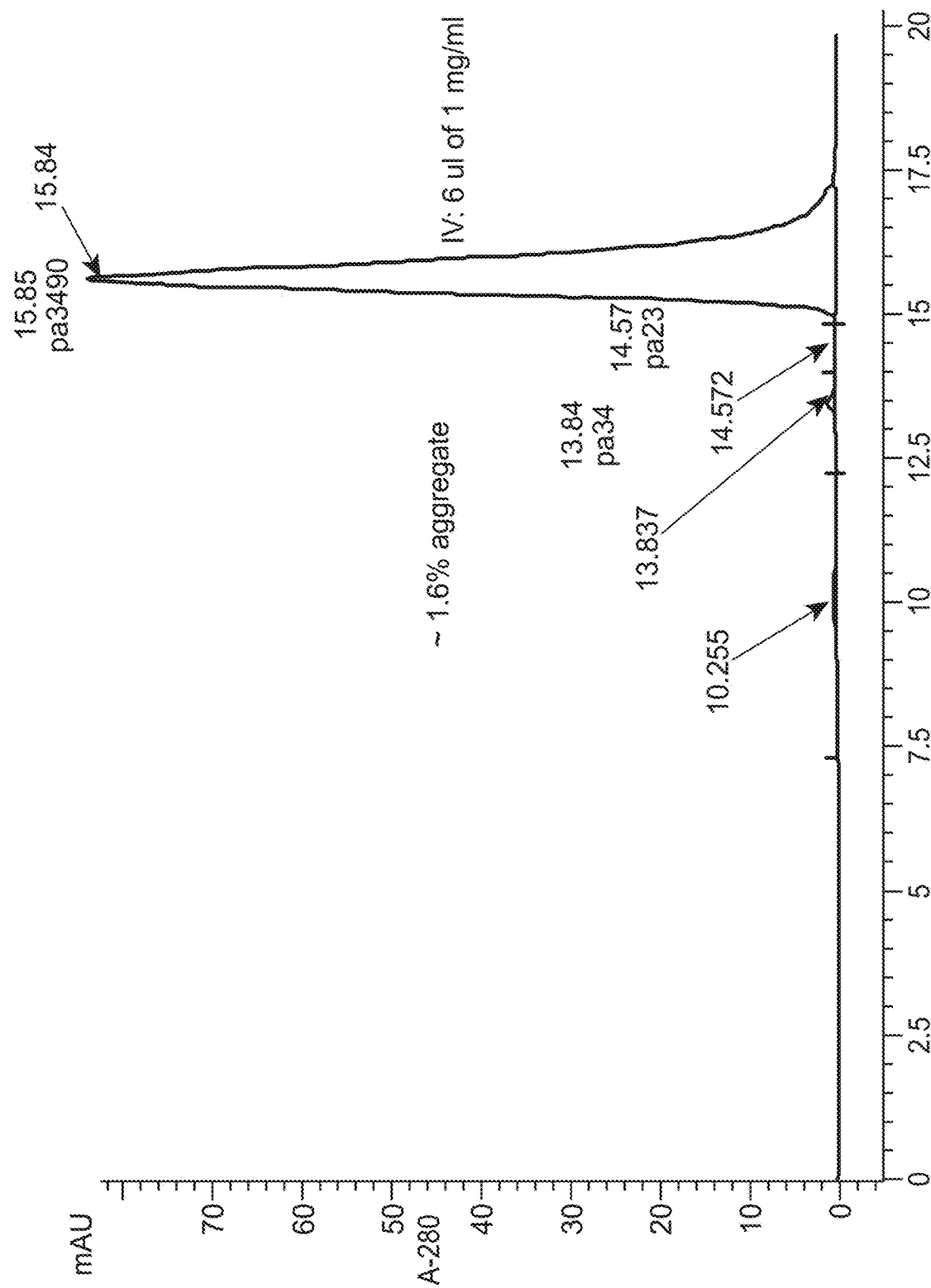
Figure 48B:
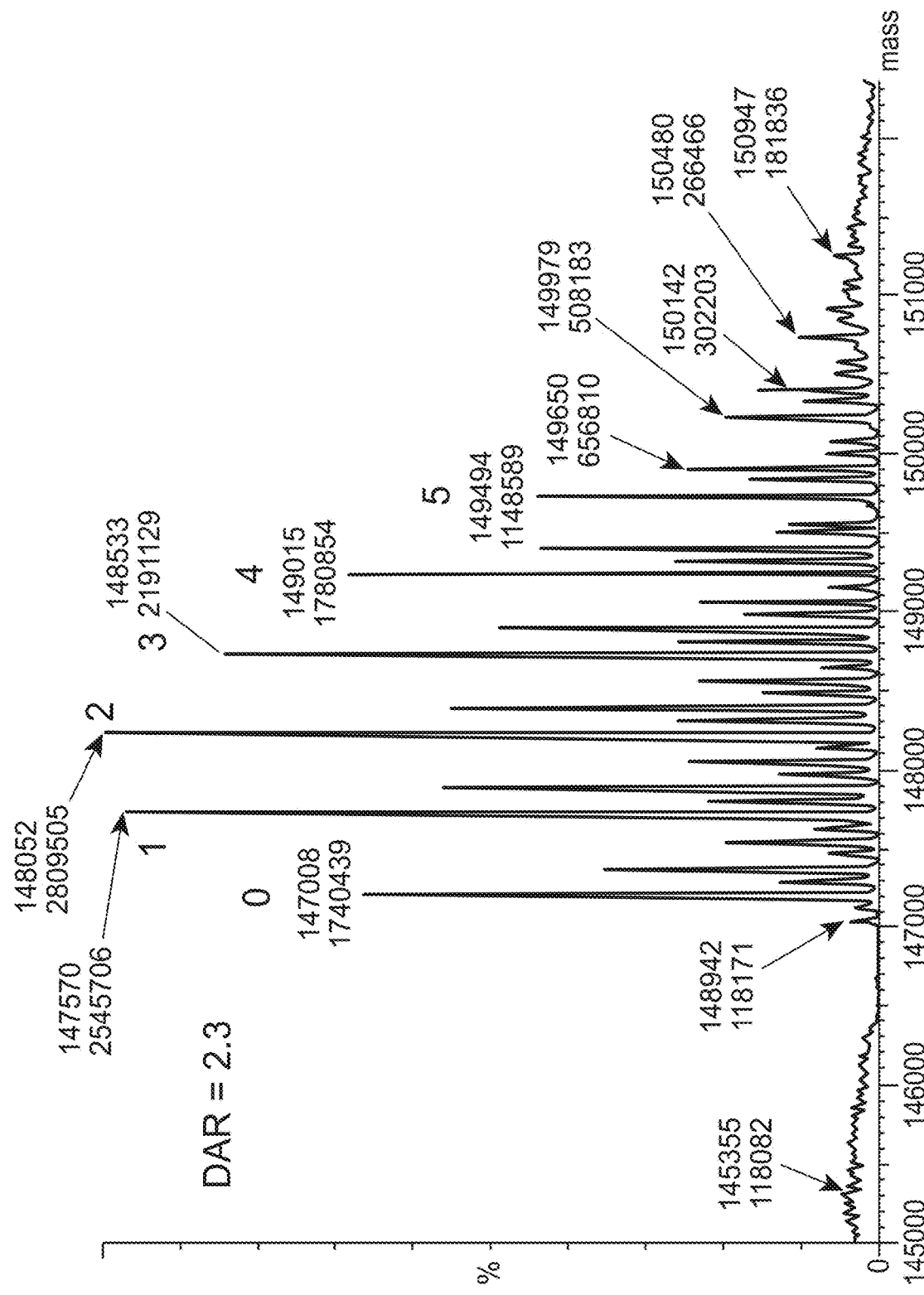
Figure 49A:
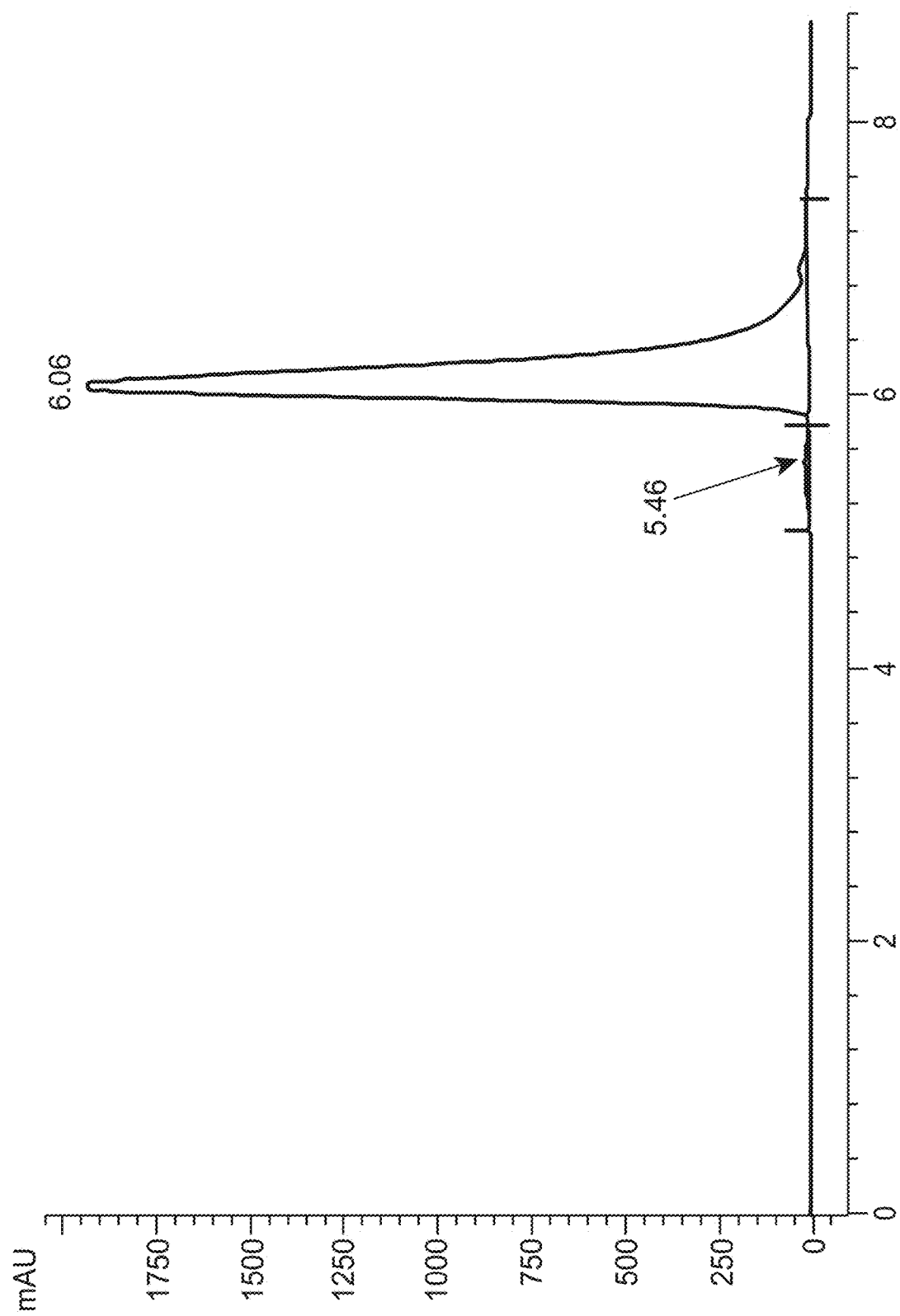
Figure 49B:
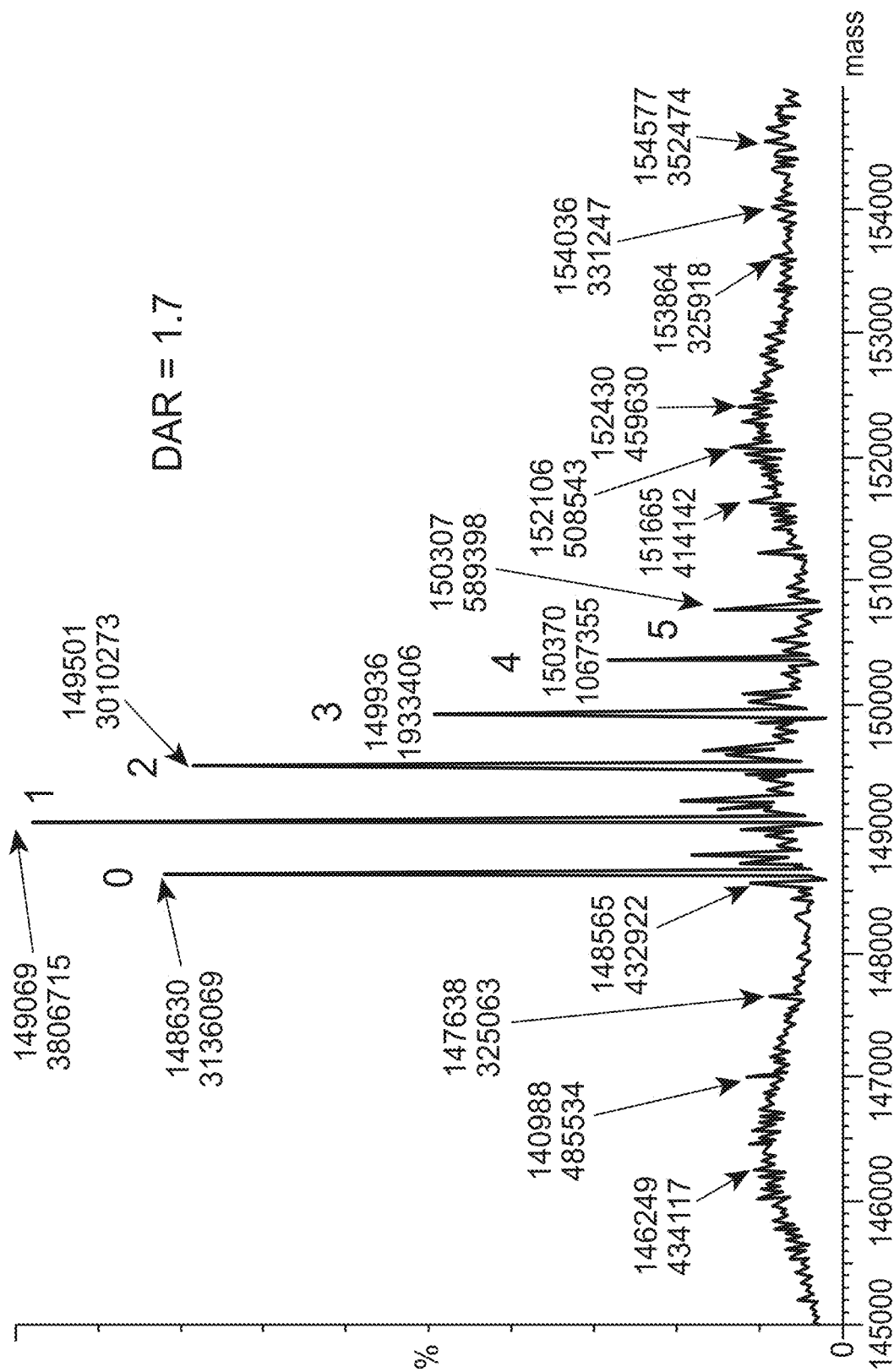
Figure 50:
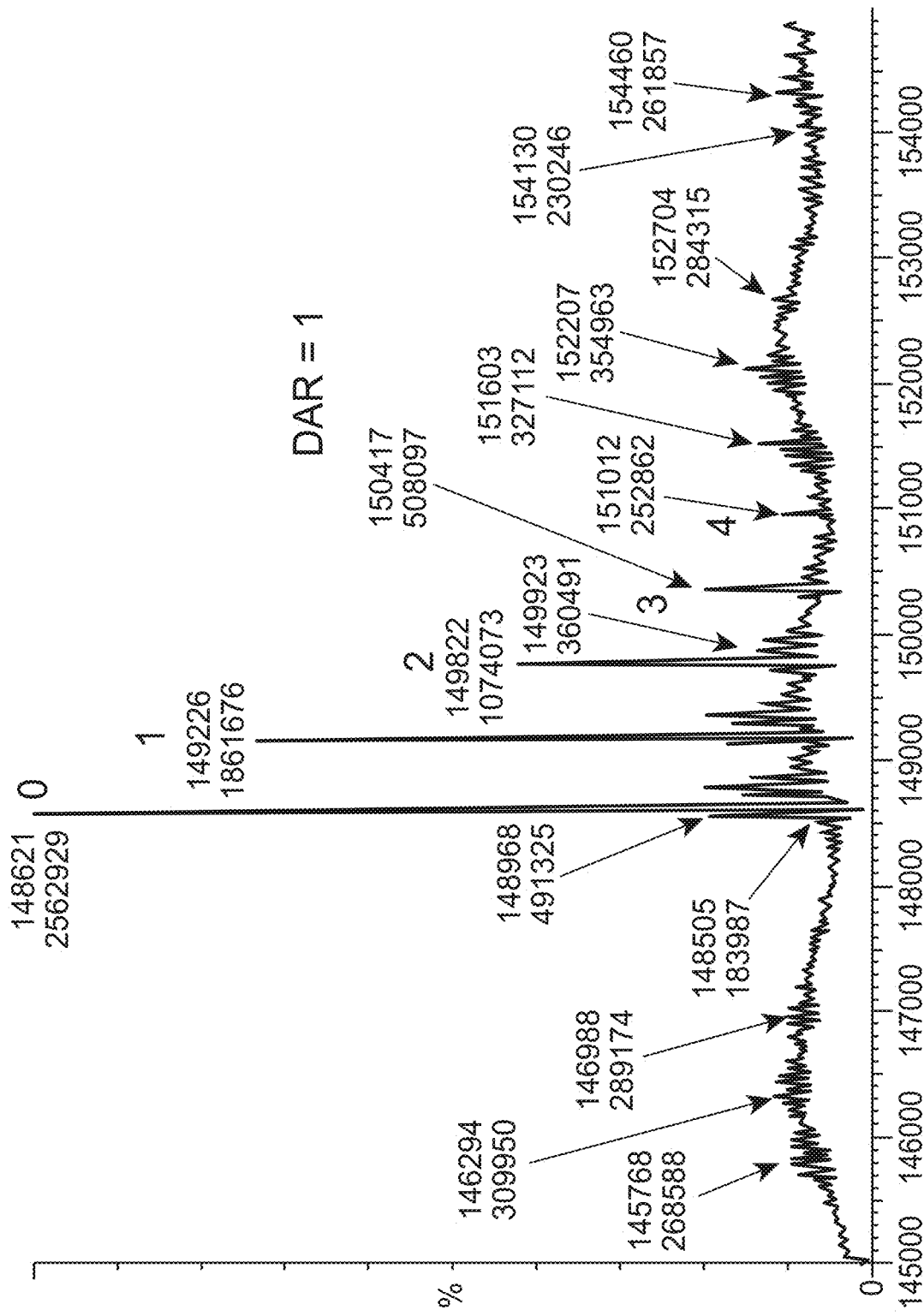
Figure 51:
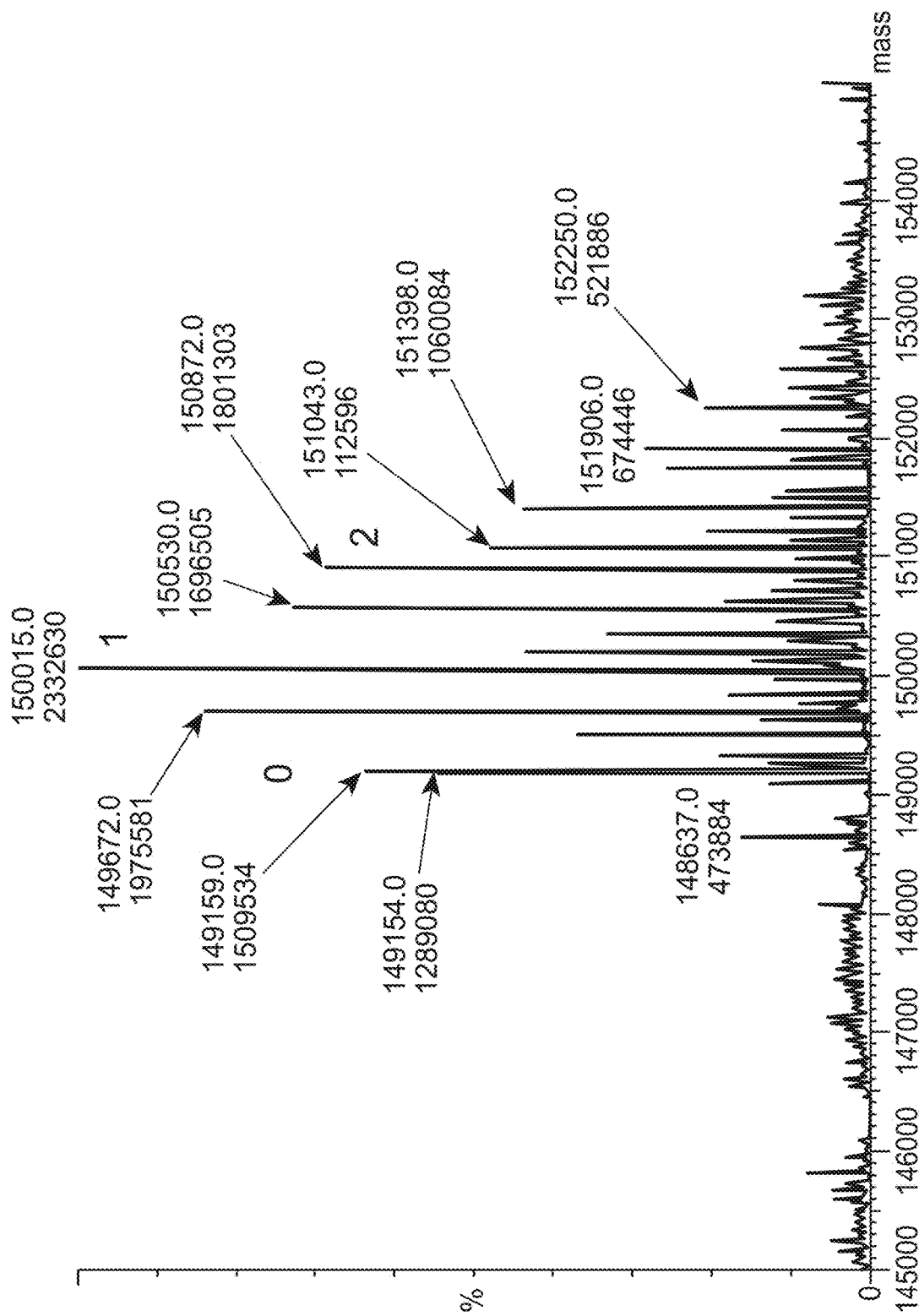
Figure 52A:
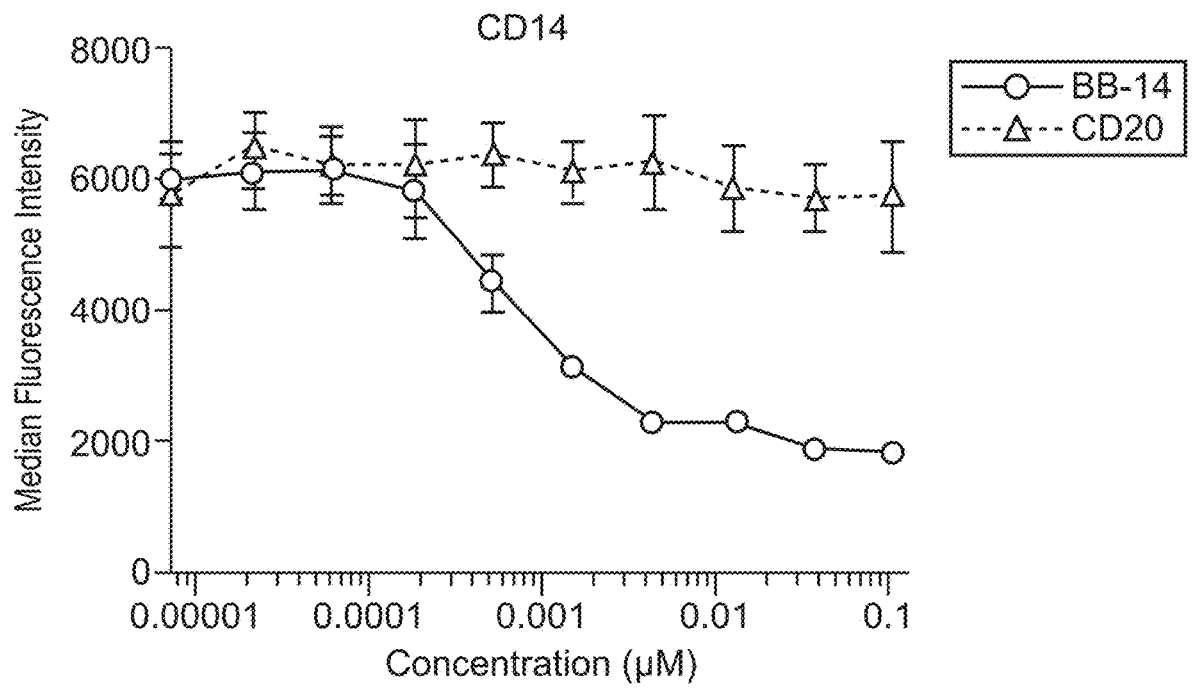
Figure 52B:
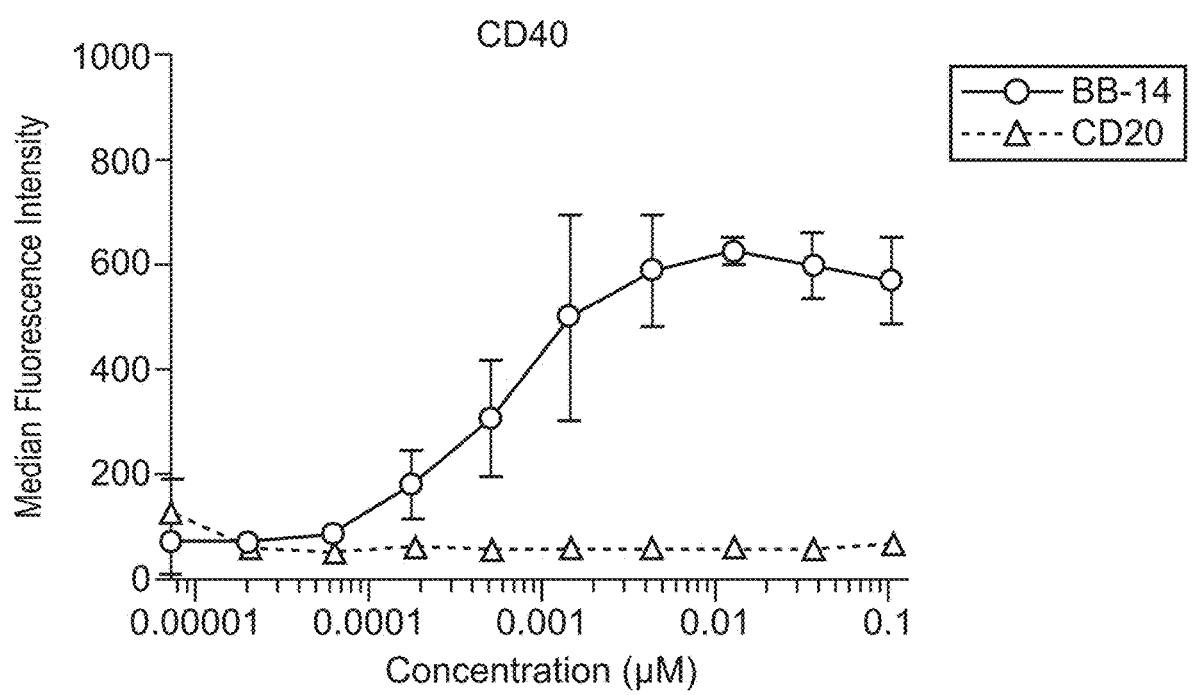
Figure 52C:
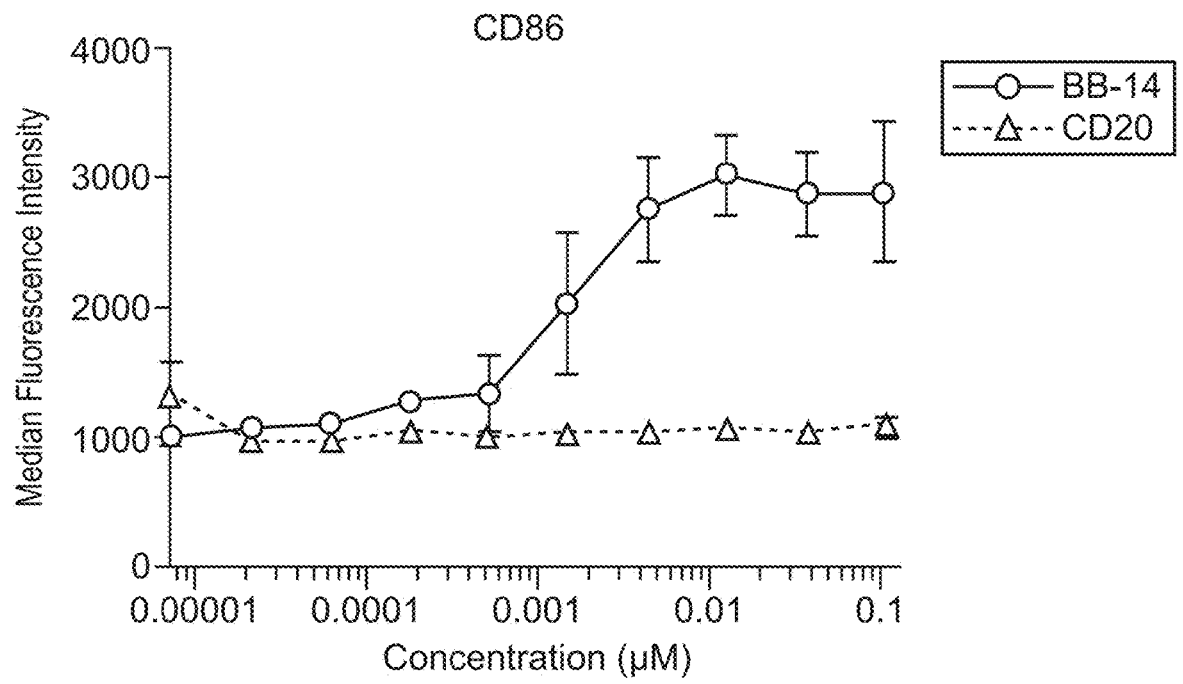
Figure 52D:
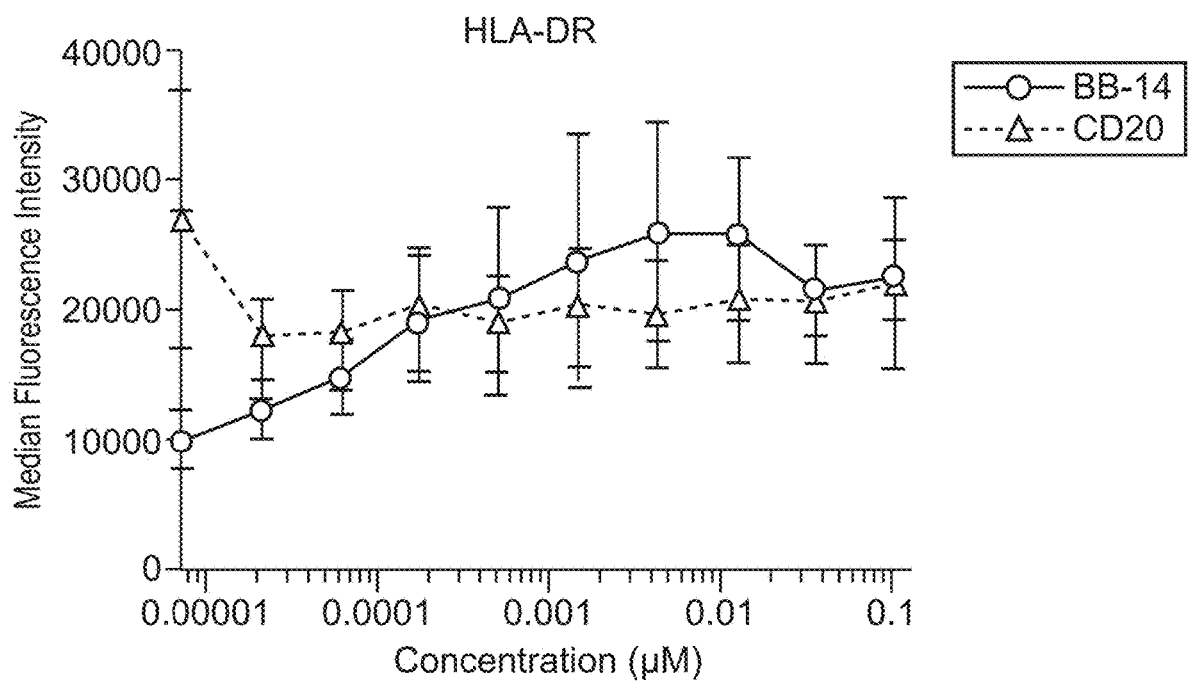

FIGS. 22A-22X shows where TLR agonists CL264, CL401, CL413, CL419, CL553, CL572, Pam₃CSK₄, and Pam₂CSK₄ could be linked to immunoconjugates of the present invention while maintaining their adjuvant activity. Specifically, the location where the linker should be attached to the adjuvant is circled.

In some embodiments, the adjuvant moiety is an imidazoquinoline compound. Examples of useful imidazoquinoline compounds include those described in U.S. Pat. Nos. 5,389,640; 6,069,149; and 7,968,562, which are hereby incorporated by reference in their entirety.

In some embodiments, the adjuvant ("Adj") is of formula:

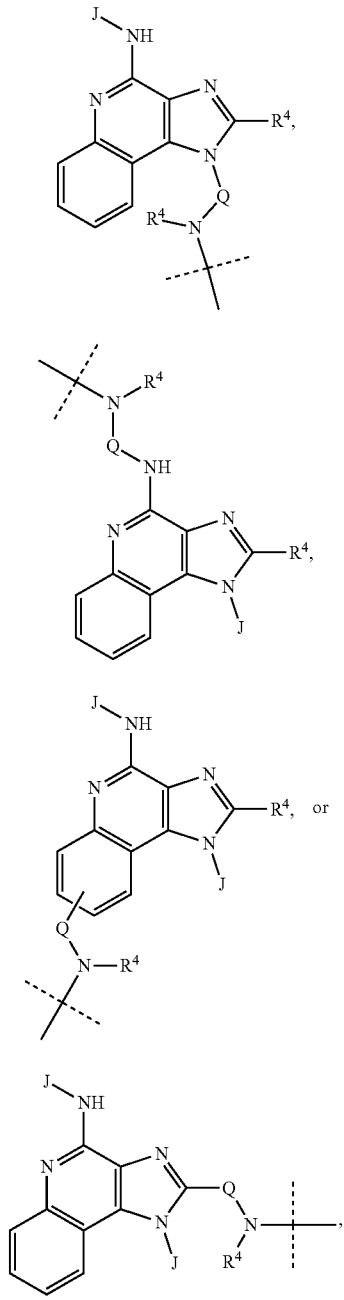

Adj 1a

Adj 1b

Adj 1c

Adj 1d wherein each J independently is hydrogen, OR⁴, or R⁴; each R⁴ independently is hydrogen, or an alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; Q is optionally present and is an alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; and the dashed line (" ") represents the point of attachment of the adjuvant. In certain embodiments, Q is present. In certain embodiments, the adjuvant ("Adj") is of formula:

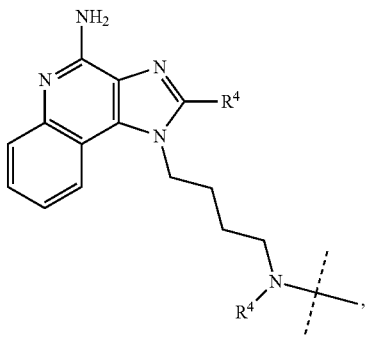

Adj 1a-i wherein each R⁴ independently is selected from the group consisting of hydrogen, or alkyl, heteroalkyl, cycloalkyl, heterocycloalkyl, aryl, heteroaryl, arylalkyl, and heteroarylalkyl group comprising from 1 to 8 (i.e., 1, 2, 3, 4, 5, 6, 7, or 8) carbon units and the dashed line (" ") represents the point of attachment of the adjuvant.

In some embodiments, the adjuvant ("Adj") is of formula:

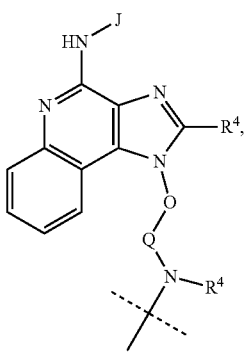

Adj 2a

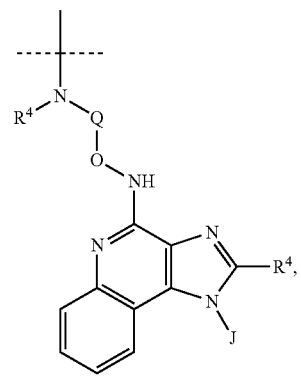

Adj 2b

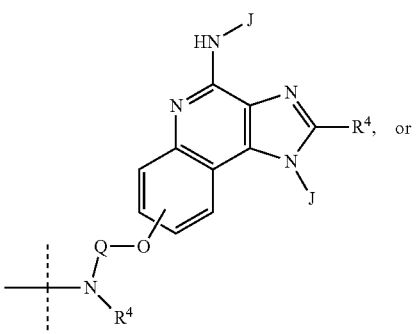

Adj 2c

Adj 2d

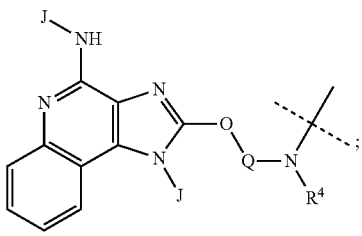

wherein J is hydrogen, OR$^4$, or R$^4$; each R$^4$ independently is hydrogen, or alkyl, heteroalkyl, cycloalkyl, heterocycloalkyl, aryl, heteroaryl, arylalkyl, and heteroarylalkyl group comprising from 1 to 8 (i.e., 1, 2, 3, 4, 5, 6, 7, or 8) carbon units; Q is selected from the group consisting of alkyl, or heteroalkyl, cycloalkyl, heterocycloalkyl, aryl, heteroaryl, arylalkyl, and heteroarylalkyl group comprising from 1 to 8 (i.e., 1, 2, 3, 4, 5, 6, 7, or 8) carbon units; and the dashed line ("⌒") represents the point of attachment of the adjuvant. In certain embodiments, the adjuvant ("Adj") is of formula:

Adj 2a-i

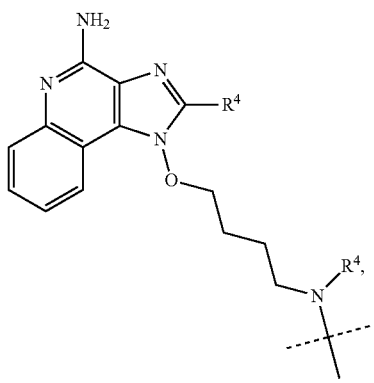

wherein each R$^4$ independently is selected from the group consisting of hydrogen, or alkyl, heteroalkyl, cycloalkyl, heterocycloalkyl, aryl, heteroaryl, arylalkyl, and heteroarylalkyl group comprising from 1 to 8 (i.e., 1, 2, 3, 4, 5, 6, 7, or 8) carbon units and the dashed line ("⌒") represents the point of attachment of the adjuvant.

In some embodiments, the adjuvant ("Adj") is of formula:

Adj 3a

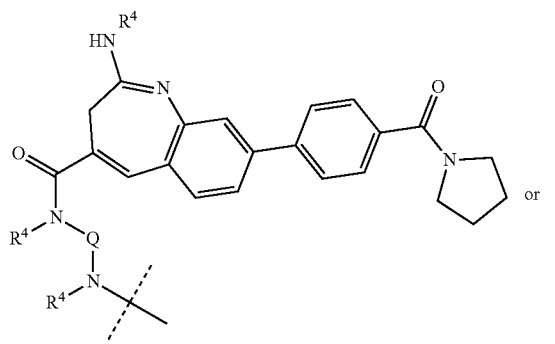

or

Adj 3b

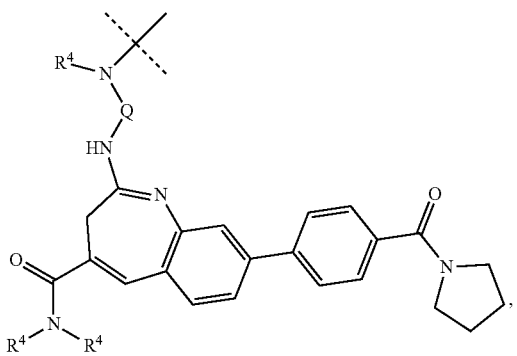

wherein each R$^4$ independently is hydrogen, or alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; Q is alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; and the dashed line ("⌒") represents the point of attachment of the adjuvant.

In some embodiments, the adjuvant ("Adj") is of formula:

Adj 4a

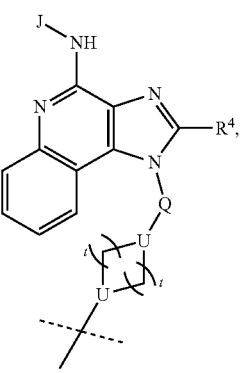

Adj 4b

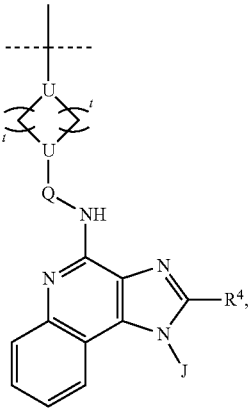

-continued

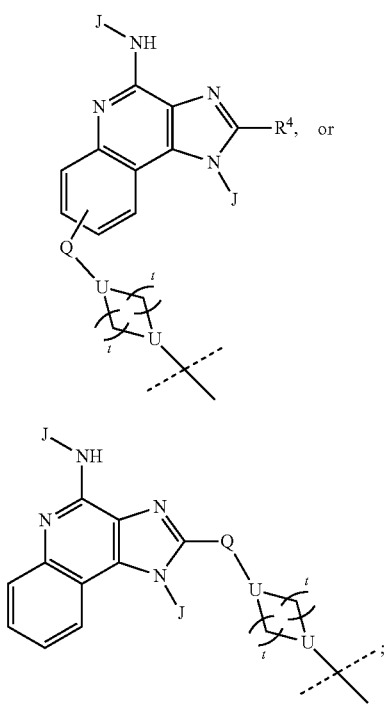

Adj 4c

Adj 4d wherein each J independently is hydrogen, OR⁴, or R⁴; each R⁴ independently is hydrogen, or an alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; each U independently is CH or N wherein at least one U is N; each subscript t independently is an integer from 1 to 3 (i.e., 1, 2, or 3); Q is optionally present and is an alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; and the dashed line (" ") represents the point of attachment of the adjuvant. In certain embodiments, Q is present. In certain embodiments, the adjuvant ("Adj") is of formula:

Adj 4a-i wherein R⁴ is selected from the group consisting of hydrogen, or alkyl, heteroalkyl, cycloalkyl, heterocycloalkyl, aryl, heteroaryl, arylalkyl, and heteroarylalkyl group comprising from 1 to 8 (i.e., 1, 2, 3, 4, 5, 6, 7, or 8) carbon units Q is an alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; and the dashed line (" ") represents the point of attachment of the adjuvant.

In some embodiments, the adjuvant ("Adj") is of formula:

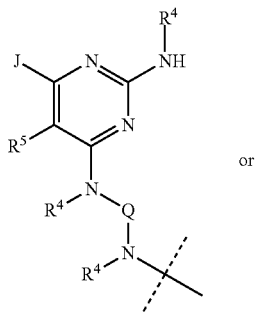

Adj 5a or

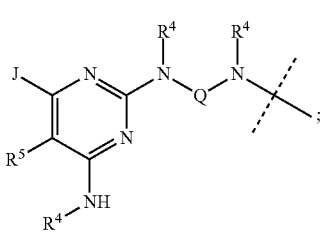

Adj 5b wherein J is hydrogen, OR⁴, or R⁴; each R⁴ independently is hydrogen, or an alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; R⁵ is hydrogen, or an alkyl, heteroalkyl, cycloalkyl, heterocycloalkyl, aryl, heteroaryl, arylalkyl, or heteroarylalkyl group comprising from 1 to 10 (i.e., 1, 2, 3, 4, 5, 6, 7, 8, 9, or 10) carbon units; Q is an alkyl, heteroalkyl, cycloalkyl, heterocycloalkyl, aryl, heteroaryl, arylalkyl, or heteroarylalkyl group comprising from 1 to 8 (i.e., 1, 2, 3, 4, 5, 6, 7, or 8) carbon units; and the dashed line (" ") represents the point of attachment of the adjuvant. In certain embodiments, the adjuvant ("Adj") is of formula:

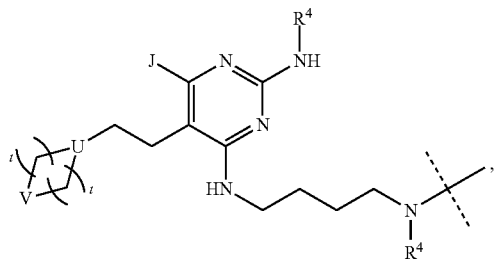

Adj 5a-i wherein J is hydrogen, OR⁴, or R⁴; each R⁴ independently is selected from the group consisting of hydrogen, or alkyl, heteroalkyl, cycloalkyl, heterocycloalkyl, aryl, heteroaryl, arylalkyl, and heteroarylalkyl group comprising from 1 to 8 (i.e., 1, 2, 3, 4, 5, 6, 7, or 8) carbon units; U is CH or N; V is CH₂, O, or NH; each subscript t independently is an integer from 1 to 3 (i.e., 1, 2, or 3); and the dashed line (" ") represents the point of attachment of the adjuvant.

In some embodiments, the adjuvant ("Adj") is of formula:

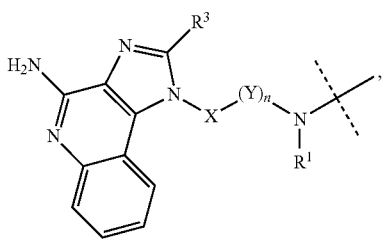

Adj 6a wherein $R^1$ is selected from H and $C_{1-4}$ alkyl; $R^3$ is selected from $C_{1-6}$ alkyl and 2- to 6-membered heteroalkyl, each of which is optionally substituted with one or more members selected from the group consisting of halo, hydroxy, amino, oxo (=O), alkylamino, amido, acyl, nitro, cyano, and alkoxy; X is selected from O and $CH_2$; each Y is independently $CHR^2$, wherein $R^2$ is selected from H, OH, and $NH_2$; subscript n is an integer from 1 to 12 (i.e., 1, 2, 3, 4, 5, 6, 7, 8, 9, 10, 11, or 12); and the dashed line ("⟋") represents the point of attachment of the adjuvant. Alternatively, $R^1$ and the nitrogen atom to which it is attached can form a linking moiety comprising a 5- to 8-membered heterocycle. In some embodiments, subscript n is an integer from 1 to 6 (i.e., 1, 2, 3, 4, 5, or 6). In certain embodiments, subscript n is an integer from 1 to 3 (i.e., 1, 2, or 3).

In some embodiments, the adjuvant ("Adj") is of formula:

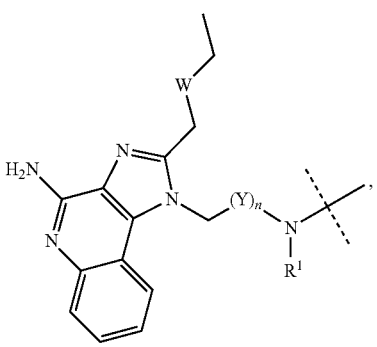

Adj 6a-i wherein W is selected from the group consisting of O and CH2; $R^1$ is selected from H and $C_{1-4}$ alkyl; each Y is independently $CHR^2$, wherein $R^2$ is selected from H, OH, and $NH_2$; subscript n is an integer from 1 to 12 (i.e., 1, 2, 3, 4, 5, 6, 7, 8, 9, 10, 11, or 12); and the dashed line ("⟋") represents the point of attachment of the adjuvant. Alternatively, $R^1$ and the nitrogen atom to which it is attached can form a linking moiety comprising a 5- to 8-membered heterocycle. In some embodiments, subscript n is an integer from 1 to 6 (i.e., 1, 2, 3, 4, 5, or 6). In certain embodiments, subscript n is an integer from 1 to 3 (i.e., 1, 2, or 3).

In some embodiments, the adjuvant ("Adj") is of formula:

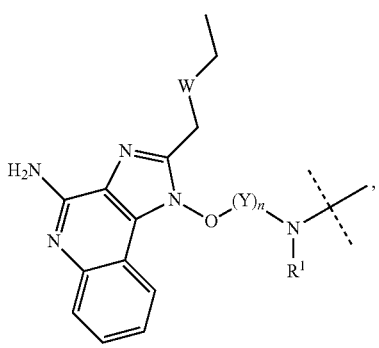

Adj 6a-ii wherein W is selected from the group consisting of O and $CH_2$; $R^1$ is selected from H and $C_{1-4}$ alkyl; each Y is independently $CHR^2$, wherein $R^2$ is selected from H, OH, and $NH_2$; subscript n is an integer from 1 to 12 (i.e., 1, 2, 3, 4, 5, 6, 7, 8, 9, 10, 11, or 12); and the dashed line ("⟋") represents the point of attachment of the adjuvant. Alternatively, $R^1$ and the nitrogen atom to which it is attached can form a linking moiety comprising a 5- to 8-membered heterocycle. In some embodiments, subscript n is an integer from 1 to 6 (i.e., 1, 2, 3, 4, 5, or 6). In certain embodiments, subscript n is an integer from 1 to 3 (i.e., 1, 2, or 3).

In some embodiments, the adjuvant ("Adj") is of formula:

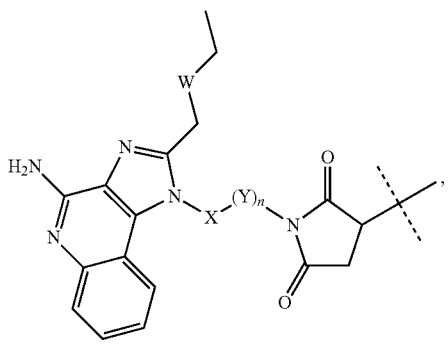

Adj 6a-iii wherein W is selected from the group consisting of O and $CH_2$; X is selected from O and $CH_2$; each Y is independently $CHR^2$, wherein $R^2$ is selected from H, OH, and $NH_2$; subscript n is an integer from 1 to 12 (i.e., 1, 2, 3, 4, 5, 6, 7, 8, 9, 10, 11, or 12); and the dashed line ("⟋") represents the point of attachment of the adjuvant. In some embodiments, subscript n is an integer from 1 to 6 (i.e., 1, 2, 3, 4, 5, or 6). In certain embodiments, subscript n is an integer from 1 to 3 (i.e., 1, 2, or 3).

In some embodiments, the adjuvant ("Adj") is of formula:

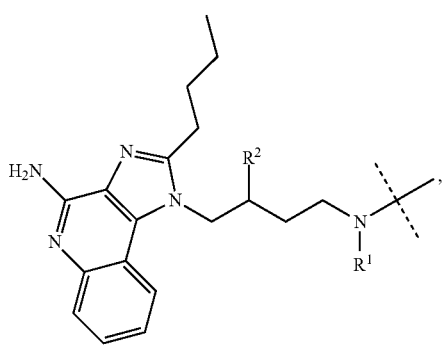

Adj 6a-iv wherein R¹ is selected from H and C$_{1-4}$ alkyl; R² is selected from H, OH, and NH$_2$; and the dashed line ("⟋") represents the point of attachment of the adjuvant.

In some embodiments, the adjuvant ("Adj") is of formula:

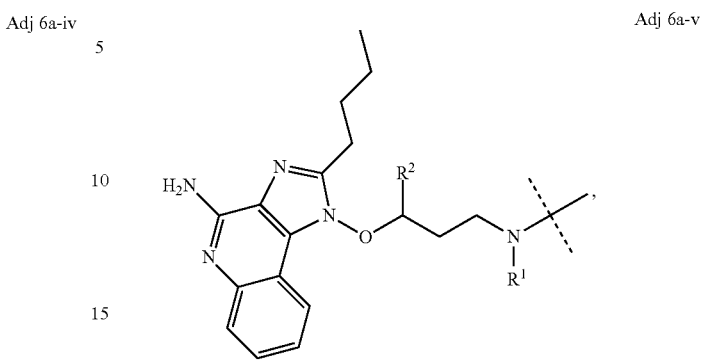

Adj 6a-v wherein R¹ is selected from H and C$_{1-4}$ alkyl; R² is selected from H, OH, and NH$_2$; and the dashed line ("⟋") represents the point of attachment of the adjuvant.

In certain embodiments, the adjuvant ("Adj") is:

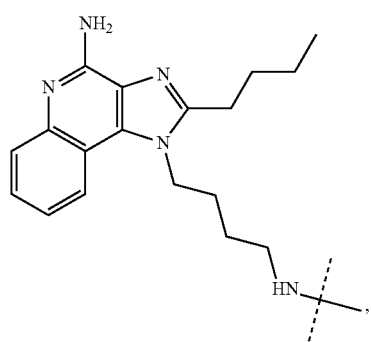

Adj-A

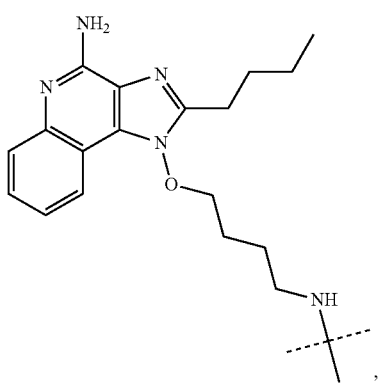

Adj-B

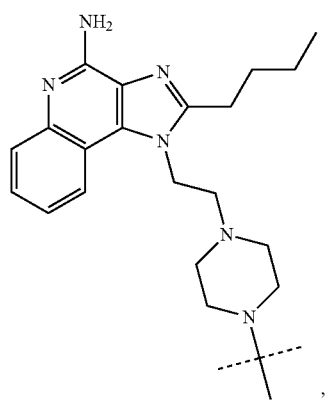

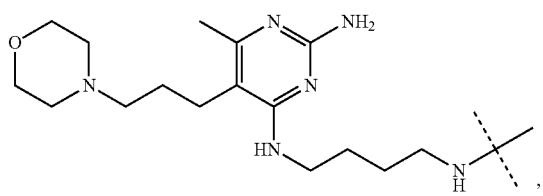

Adj-D

Adj-C

-continued
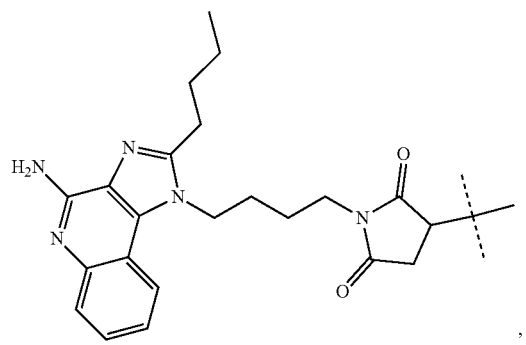
Adj-E
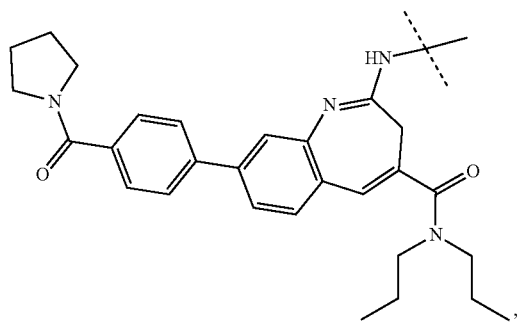
Adj-G
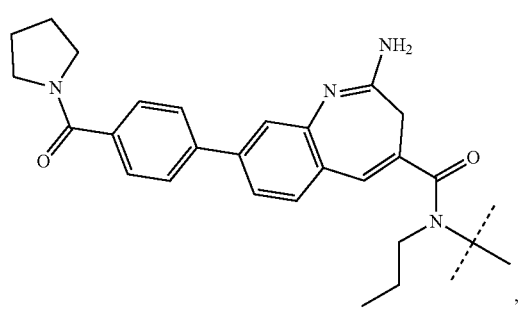
Adj-H
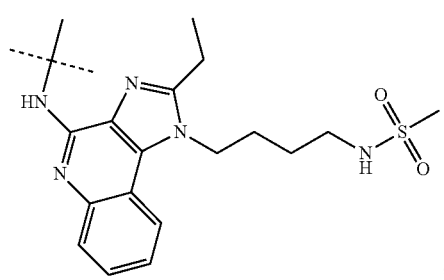
Adj-I
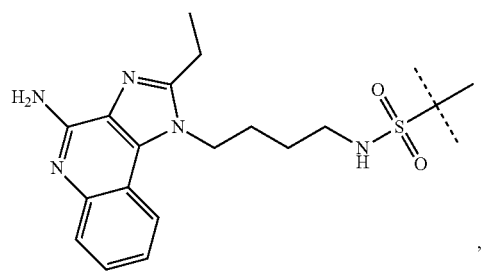
Adj-J
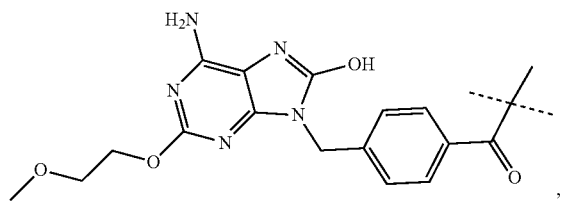
Adj-K
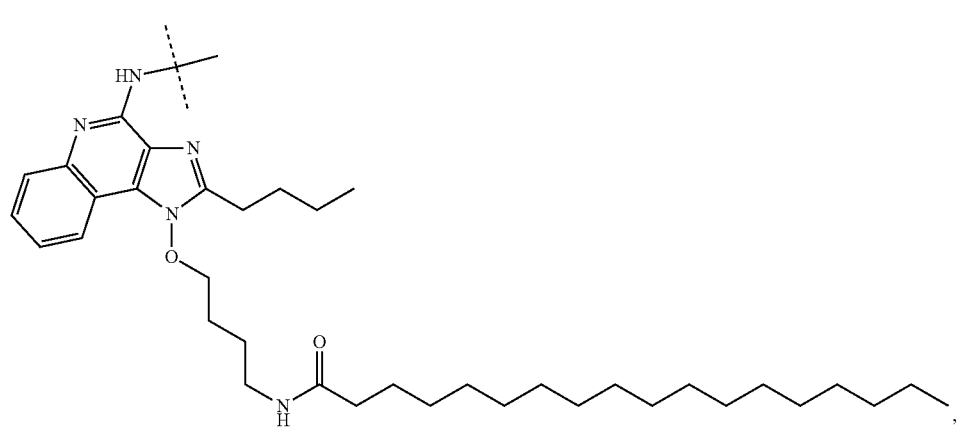
Adj-L -continued

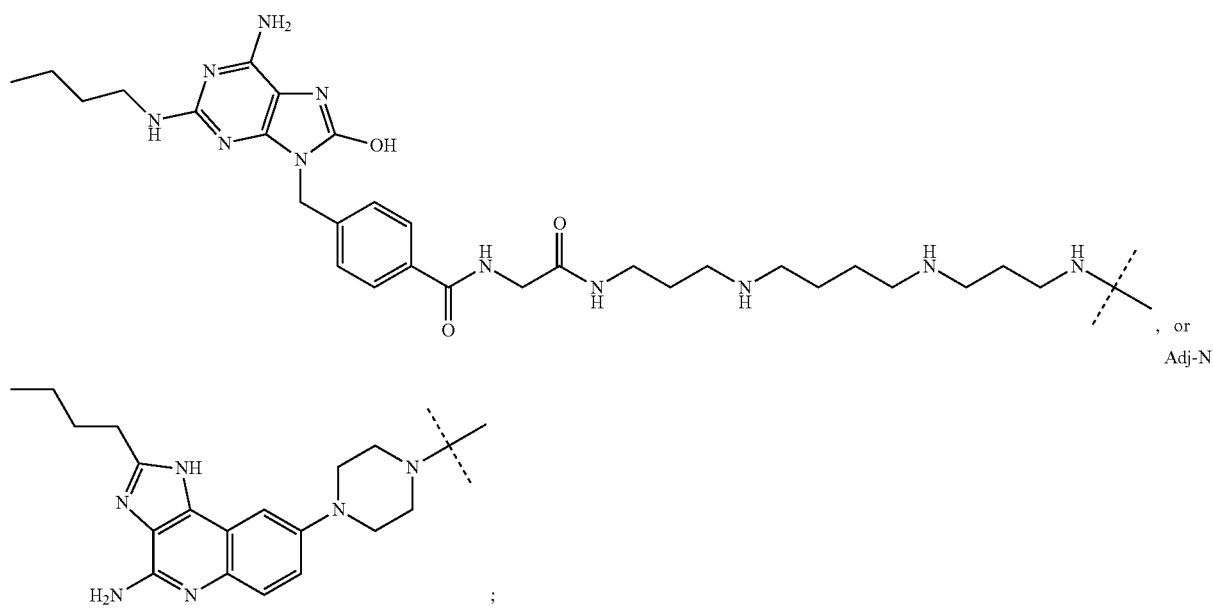

wherein the dashed line ("⌇") represents the point of attachment of the adjuvant.

In some embodiments, the adjuvant is not a fluorophore. In some embodiments, the adjuvant is not a radiodiagnostic compound. In some embodiments, the adjuvant is not a radiotherapeutic compound. In some embodiments, the adjuvant is not a tubulin inhibitor. In some embodiments, the adjuvant is not a DNA crosslinker/alkylator. In some embodiments, the adjuvant is not a topoisomerase inhibitor.

Antibodies

The antibodies in the immunoconjugates can be allogeneic antibodies. The terms "allogeneic antibody" or "alloantibody" refer to an antibody that is not from the individual in question (e.g., an individual with a tumor and seeking treatment), but is from the same species, or is from a different species, but has been engineered to reduce, mitigate, or avoid recognition as a xeno-antibody (e.g., non-self). For example, the "allogeneic antibody" can be a humanized antibody. Unless specifically stated otherwise, "antibody" and "allogeneic antibodies" as used herein refer to immunoglobulin G (IgG) or immunoglobulin A (IgA).

If a cancer cell of a human individual is contacted with an antibody that was not generated by that same person (e.g., the antibody was generated by a second human individual, the antibody was generated by another species such as a mouse, the antibody is a humanized antibody that was generated by another species, etc.), then the antibody is considered to be allogeneic (relative to the first individual). A humanized mouse monoclonal antibody that recognizes a human antigen (e.g., a cancer-specific antigen, an antigen that is enriched in and/or on cancer cells, etc.) is considered to be an "alloantibody" (an allogeneic antibody).

In some embodiments, the antibody is a polyclonal allogeneic IgG antibody. In some embodiments, the antibody is present in a mixture of polyclonal IgG antibodies with a plurality of binding specificities. In some cases, the antibodies of the mixture specifically bind to different target molecules, and in some cases the antibodies of the mixture specifically bind to different epitopes of the same target molecule. Thus, a mixture of antibodies can in some cases include more than one immunoconjugate of the invention (e.g., adjuvant moieties can be covalently bonded to antibodies of a mixture, e.g., a mixture of polyclonal IgG antibodies, resulting in a mixture of antibody-adjuvant conjugates of the invention). A mixture of antibodies can be pooled from 2 or more individuals (e.g., 3 or more individuals, 4 or more individuals, 5 or more individuals, 6 or more individuals, 7 or more individuals, 8 or more individuals, 9 or more individuals, 10 or more individuals, etc.). In some cases, pooled serum is used as a source of alloantibody, where the serum can come from any number of individuals, none of whom are the first individual (e.g., the serum can be pooled from 2 or more individuals, 3 or more individuals, 4 or more individuals, 5 or more individuals, 6 or more individuals, 7 or more individuals, 8 or more individuals, 9 or more individuals, 10 or more individuals, etc.). In some cases, the antibodies are isolated or purified from serum prior to use. The purification can be conducted before or after pooling the antibodies from different individuals.

In some cases where the antibodies in the immunoconjugates comprise IgGs from serum, the target antigens for some (e.g., greater than 0% but less than 50%), half, most (greater than 50% but less than 100%), or even all of the antibodies (i.e., IgGs from the serum) will be unknown. However, the chances are high that at least one antibody in the mixture will recognize the target antigen of interest because such a mixture contains a wide variety of antibodies specific for a wide variety of target antigens.

In some embodiments, the antibody is a polyclonal allogeneic IgA antibody. In some embodiments, the antibody is present in a mixture of polyclonal IgA antibodies with a plurality of binding specificities. In some cases, the antibodies of the mixture specifically bind to different target molecules, and in some cases the antibodies of the mixture specifically bind to different epitopes of the same target molecule. Thus, a mixture of antibodies can in some cases include more than one immunoconjugate of the invention (e.g., adjuvant moieties can be covalently bonded to antibodies of a mixture, e.g., a mixture of polyclonal IgA antibodies, resulting in a mixture of antibody-adjuvant conjugates of the invention). A mixture of antibodies can be pooled from 2 or more individuals (e.g., 3 or more individuals, 4 or more individuals, 5 or more individuals, 6 or more individuals, 7 or more individuals, 8 or more individuals, 9 or more individuals, 10 or more individuals, etc.). In some cases, pooled serum is used as a source of alloantibody, where the serum can come from any number of individuals, none of whom are the first individual (e.g., the serum can be pooled from 2 or more individuals, 3 or more individuals, 4 or more individuals, 5 or more individuals, 6 or more individuals, 7 or more individuals, 8 or more individuals, 9 or more individuals, 10 or more individuals, etc.). In some cases, the antibodies are isolated or purified from serum prior to use. The purification can be conducted before or after pooling the antibodies from different individuals.

In some cases where the antibodies in the immunoconjugates comprise IgAs from serum, the target antigens for some (e.g., greater than 0% but less than 50%), half, most (greater than 50% but less than 100%), or even all of the antibodies (i.e., IgAs from the serum) will be unknown. However, the chances are high that at least one antibody in the mixture will recognize the target antigen of interest because such a mixture contains a wide variety of antibodies specific for a wide variety of target antigens.

In some cases, the antibody in the immunoconjugates includes intravenous immunoglobulin (IVIG) and/or antibodies from (e.g., enriched from, purified from, e.g., affinity purified from) IVIG. IVIG is a blood product that contains IgG (immunoglobulin G) pooled from the plasma (e.g., in some cases without any other proteins) from many (e.g., sometimes over 1,000 to 60,000) normal and healthy blood donors. IVIG is commercially available. IVIG contains a high percentage of native human monomeric IVIG, and has low IgA content. When administered intravenously, IVIG ameliorates several disease conditions. Therefore, the United States Food and Drug Administration (FDA) has approved the use of IVIG for a number of diseases including (1) Kawasaki disease; (2) immune-mediated thrombocytopenia; (3) primary immunodeficiencies; (4) hematopoietic stem cell transplantation (for those older than 20 years); (5) chronic B-cell lymphocytic leukemia; and (6) pediatric HIV type 1 infection. In 2004, the FDA approved the Cedars-Sinai IVIG Protocol for kidney transplant recipients so that such recipients could accept a living donor kidney from any healthy donor, regardless of blood type (ABO incompatible) or tissue match. These and other aspects of IVIG are described, for example, in US Patent Application Publications 2010/0150942; 2004/0101909; 2013/0177574; 2013/0108619; and 2013/0011388; which are hereby incorporated by reference in their entirety.

In some cases, the antibody is a monoclonal antibody of a defined sub-class (e.g., $IgG_1$, $IgG_2$, $IgG_3$, $IgG_4$, $IgA_1$, or $IgA_2$). If combinations of antibodies are used, the antibodies can be from the same subclass or from different subclasses. For example, the antibodies can be IgG1 antibodies. Various combinations of different subclasses, in different relative proportions, can be obtained by those of skill in the art. In some cases, a specific subclass, or a specific combination of different subclasses can be particularly effective at cancer treatment or tumor size reduction. Accordingly, some embodiments of the invention provide immunoconjugates wherein the antibody is a monoclonal antibody. In some embodiments, the monoclonal antibody is humanized.

In some embodiments, the antibody binds to an antigen of a cancer cell. For example, the antibody can bind to a target antigen that is present at an amount of at least 10; 100; 1,000; 10,000; 100,000; 1,000,000; $2.5 \times 10^6$; $5 \times 10^6$; or $1 \times 10^7$ copies or more on the surface of a cancer cell.

In some embodiments, the antibody binds to an antigen on a cancer or immune cell at a higher affinity than a corresponding antigen on a non-cancer cell. For example, the antibody may preferentially recognize an antigen containing a polymorphism that is found on a cancer or immune cell as compared to recognition of a corresponding wild-type antigen on the non-cancer or non-immune cell. In some cases, the antibody binds a cancer or immune cell with greater avidity than a non-cancer or non-immune cell. For example, the cancer or immune cell can express a higher density of an antigen, thus providing for a higher affinity binding of a multivalent antibody to the cancer or immune cell.

In some cases, the antibody does not significantly bind non-cancer antigens (e.g., the antibody binds one or more non-cancer antigens with at least 10; 100; 1,000; 10,000; 100,000; or 1,000,000-fold lower affinity (higher Kd) than the target cancer antigen). In some cases, the target cancer antigen to which the antibody binds is enriched on the cancer cell. For example, the target cancer antigen can be present on the surface of the cancer cell at a level that is at least 2, 5, 10; 100; 1,000; 10,000; 100,000; or 1,000,000-fold higher than a corresponding non-cancer cell. In some cases, the corresponding non-cancer cell is a cell of the same tissue or origin that is not hyperproliferative or otherwise cancerous. In general, a subject IgG antibody that specifically binds to an antigen (a target antigen) of a cancer cell preferentially binds to that particular antigen relative to other available antigens. However, the target antigen need not be specific to the cancer cell or even enriched in cancer cells relative to other cells (e.g., the target antigen can be expressed by other cells). Thus, in the phrase "an antibody that specifically binds to an antigen of a cancer cell," the term "specifically" refers to the specificity of the antibody and not to the uniqueness of the antigen in that particular cell type.

Modified Fc Region

In some embodiments, the antibodies in the immunoconjugates contain a modified Fc region, wherein the modification modulates the binding of the Fc region to one or more Fc receptors.

The terms "Fc receptor" or "FcR" refer to a receptor that binds to the Fc region of an antibody. There are three main classes of Fc receptors: FcγR which bind to IgG, FcαR which binds to IgA, and FcεR which binds to IgE. The FcγR family includes several members, such as FcγI (CD64), FcγRIIA (CD32A), FcγRIIB (CD32B), FcγRIIIA (CD16A), FcγRIIIB (CD16B). The Fcγ receptors differ in their affinity for IgG and also have different affinities for the IgG subclasses (e.g., IgG1, IgG2, IgG3, IgG4).

In some embodiments, the antibodies in the immunoconjugates (e.g., antibodies conjugated to a TLR agonist such as a TLR7/8 agonist via a linker) contain one or more modifications (e.g., amino acid insertion, deletion, and/or substitution) in the Fc region that results in modulated binding (e.g., increased binding or decreased binding) to one or more Fc receptors (e.g., FcγRI (CD64), FcγRIIA (CD32A), FcγRIIB (CD32B), FcγRIIIA (CD16a), and/or FcγRIIIB (CD16b)) as compared to the native antibody lacking the mutation in the Fc region. In some embodiments, the antibodies in the immunoconjugates contain one or more modifications (e.g., amino acid insertion, deletion, and/or substitution) in the Fc region that reduce the binding of the Fc region of the antibody to FcγRIIB. In some embodiments, the antibodies in the immunoconjugates contain one or more modifications (e.g., amino acid insertion, deletion, and/or substitution) in the Fc region of the antibody that reduce the binding of the antibody to FcγRIIB while maintaining the same binding or having increased binding to FcγRI (CD64), FcγRIIA (CD32A), and/or FcRyIIIA (CD16a) as compared to the native antibody lacking the mutation in the Fc region. In some embodiments, the antibodies in the immunoconjugates contain one of more modifications in the Fc region that increase the binding of the Fc region of the antibody to FcγRIIB.

In some cases, the modulated binding is provided by mutations in the Fc region of the antibody relative to the native Fc region of the antibody. The mutations can be in a CH2 domain, a CH3 domain, or a combination thereof. A "native Fc region" is synonymous with a "wild-type Fc region" and comprises an amino acid sequence that is identical to the amino acid sequence of an Fc region found in nature or identical to the amino acid sequence of the Fc region found in the native antibody (e.g., rituximab). Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc includes the various allotypes of Fcs (see, e.g., Jefferis et al., mAbs, 1(4): 332-338 (2009)).

In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/I332E/A330L), GA (G236A), ALIE (A330L/I332E), GASDALIE (G236A/S239D/A330L/I332E), V9 (G237D/P238D/P271G/A330R), and V11 (G237D/P238D/H268D/P271G/A330R) and/or one or more mutations at the following amino acids: E233, G237, P238, H268, P271, L328 and A330. Additional Fc region modifications for modulating Fc receptor binding are described, e.g., in US Patent Application Publication 2016/0145350, and U.S. Pat. Nos. 7,416, 726 and 5,624,821.

In some embodiments, the Fc region of the antibodies of the immunoconjugates are modified to have an altered glycosylation pattern of the Fc region compared to the native non-modified Fc region.

Human immunoglobulin is glycosylated at the Asn297 residue in the Cγ2 domain of each heavy chain. This N-linked oligosaccharide is composed of a core heptasaccharide, N-acetylglucosamine4Mannose3 (GlcNAc4Man3). Removal of the heptasaccharide with endoglycosidase or PNGase F is known to lead to conformational changes in the antibody Fc region, which can significantly reduce antibody-binding affinity to activating FcγR and lead to decreased effector function. The core heptasaccharide is often decorated with galactose, bisecting GlcNAc, fucose or sialic acid, which differentially impacts Fc binding to activating and inhibitory FcγR. Additionally, it has been demonstrated that u2,6-sialyation enhances anti-inflammatory activity in vivo while defucosylation leads to improved FcγRIIIa binding and a 10-fold increase in antibody-dependent cellular cytotoxicity and antibody-dependent phagocytosis. Specific glycosylation patterns can therefore be used to control inflammatory effector functions.

In some embodiments, the modification to alter the glycosylation pattern is a mutation. For example, a substitution at Asn297. In some embodiments, Asn297 is mutated to glutamine (N297Q). Methods for controlling immune response with antibodies that modulate FcγR-regulated signaling are described, for example, in U.S. Pat. No. 7,416, 726, as well as US 2007/0014795 and US 2008/0286819.

In some embodiments, the antibodies of the immunoconjugates are modified to contain an engineered Fab region with a non-naturally occurring glycosylation pattern. For example, hybridomas can be genetically engineered to secrete afucosylated mAb, desialylated mAb or deglycosylated Fc with specific mutations that enable increased FcRyIIIa binding and effector function. In some embodiments, the antibodies of the immunoconjugates are engineered to be afucosylated (e.g., afucosylated rituximab, available from Invivogen, hcd20-mab13).

In some embodiments, the entire Fc region of an antibody in the immunoconjugates is exchanged with a different Fc region, so that the Fab region of the antibody is conjugated to a non-native Fc region. For example, the Fab region of rituximab, which normally comprises an IgG1 Fc region, can be conjugated to IgG2, IgG3, IgG4, or IgA, or the Fab region of nivolumab, which normally comprises an IgG4 Fc region, can be conjugated to IgG1, IgG2, IgG3, IgA1 or IgG2. In some embodiments, the Fc modified antibody with a non-native Fc domain also comprises one or more amino acid modification, such as the S228P mutation within the IgG4 Fc, that modulate the stability of the Fc domain described. In some embodiments, the Fc modified antibody with a non-native Fc domain also comprises one or more amino acid modifications described herein that modulate Fc binding to FcR.

In some embodiments, the modifications that modulate the binding of the Fc region to FcR do not alter the binding of the Fab region of the antibody to its antigen when compared to the native non-modified antibody. In other embodiments, the modifications that modulate the binding of the Fc region to FcR also increase the binding of the Fab region of the antibody to its antigen when compared to the native non-modified antibody.

Antibody Targets

In some embodiments, the antibody is capable of binding one or more targets selected from (e.g., specifically binds to a target selected from) 5T4, ABL, ABCF1, ACVR1, ACVR1B, ACVR2, ACVR2B, ACVRL1, ADORA2A, Aggrecan, AGR2, AICDA, AIF1, AIGI, AKAP1, AKAP2, AMH, AMHR2, ANGPT1, ANGPT2, ANGPTL3, ANGPTL4, ANPEP, APC, APOC1, AR, aromatase, ATX, AX1, AZGP1 (zinc-a-glycoprotein), B7.1, B7.2, B7-H1, BAD, BAFF, BAG1, BAI1, BCR, BCL2, BCL6, BDNF, BLNK, BLR1 (MDR15), BlyS, BMP1, BMP2, BMP3B (GDFIO), BMP4, BMP6, BMP8, BMPR1A, BMPR1B, BMPR2, BPAG1 (plectin), BRCA1, C19orflO (IL27w), C3, C4A, C5, C5R1, CANT1, CAPRIN-1, CASP1, CASP4, CAV1, CCBP2 (D6/JAB61), CCL1 (1-309), CCLI1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22(MDC/STC-I), CCL23 (MPIF-I), CCL24 (MPIF-2/eotaxin-2), CCL25 (TECK), CCL26(eotaxin-3), CCL27 (CTACK/ILC), CCL28, CCL3 (MIP-Ia), CCL4 (MIPIb), CCL5(RANTES), CCL7 (MCP-3), CCL8 (mcp-2), CCNA1, CCNA2, CCND1, CCNE1, CCNE2, CCR1 (CKR1/HM145), CCR2 (mcp-IRB/RA), CCR3 (CKR3/CMKBR3), CCR4, CCR5(CMKBR5/ChemR13), CCR6 (CMKBR6/CKR-L3/STRL22/DRY6), CCR7 (CKR7/EBI1), CCR8 (CMKBR8/TERI/CKR-L1), CCR9 (GPR-9-6), CCRL1 (VSHK1), CCRL2 (L-CCR), CD164, CD19, CDIC, CD2, CD20, CD21, CD200, CD-22, CD24, CD27, CD28, CD3, CD33, CD35, CD37, CD38, CD3E, CD3G, CD3Z, CD4, CD38, CD40, CD40L, CD44, CD45RB, CD47, CD52, CD69, CD72, CD74, CD79A, CD79B, CD8, CD80, CD81, CD83, CD86, CD137, CD152, CD274, CDH1 (Ecadherin), CDH10O, CDH12, CDH13, CDH18, CDH19, CDH20, CDH5, CDH7, CDH8, CDH9, CDK2, CDK3, CDK4, CDK5, CDK6, CDK7, CDK9, CDKN1A (p21Wapl/Cipl), CDKN1B (p27Kipl), CDKN1C, CDKN2A (p16INK4a), CDKN2B, CDKN2C, CDKN3, CEBPB, CERI, CHGA, CHGB, Chitinase, CHST1O, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLR1, CMKOR1 (RDC1), CNR1, COL18A1, COLIA1, COL4A3, COL6A1, CR2, Cripto, CRP, CSF1 (M-CSF), CSF2 (GM-CSF), CSF3 (GCSF), CTL8, CTNNB1 (b-catenin), CTSB (cathepsin B), CX3CL1 (SCYD1), CX3CR1 (V28), CXCL1 (GRO1), CXCL10O (IP-IO), CXCLI1 (1-TAC/IP-9), CXCL12 (SDF1), CXCL13, CXCL14, CXCL16, CXCL2 (GRO2), CXCL3 (GRO3), CXCL5 (ENA-78/LIX), CXCL6 (GCP-2), CXCL9 (MIG), CXCR3 (GPR9/CKR-L2), CXCR4, CXCR6 (TYM-STR/STRL33/Bonzo), CYB5, CYC1, CYSLTR1, DAB2IP, DES, DKFZp451J0118, DNCL1, DPP4, E2F1, Engel, Edge, Fennel, EFNA3, EFNB2, EGF, EGFR, ELAC2, ENG, Enola, ENO2, ENO3, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPHRIN-A1, EPHRIN-A2, EPHRINA3, EPHRIN-A4, EPHRIN-A5, EPHRIN-A6, EPHRIN-B1, EPHRIN-B2, EPHRIN-B3, EPHB4, EPG, ERBB2 (Her-2), EREG, ERK8, Estrogen receptor, Earl, ESR2, F3 (TF), FADD, farnesyl-transferase, FasL, FASNf, FCER1A, FCER2, FCGR3A, FGF, FGF1 (aFGF), FGF10, FGF1 1, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR3, FIGF (VEGFD), FIL1(EPSILON), FBL1 (ZETA), FLJ12584, FLJ25530, FLRT1 (fibronectin), FLT1, FLT-3, FOS, FOSL1(FRA-1), FY (DARC), GABRP (GABAa), GAGEB1, GAGEC1, GALNAC4S-6ST, GATA3, GD2, GDF5, GFI1, GGT1, GM-CSF, GNAS1, GNRH1, GPR2 (CCR10), GPR31, GPR44, GPR81 (FKSG80), GRCC1O (C1O), GRP, GSN (Gelsolin), GSTP1, HAVCR2, HDAC, HDAC4, HDAC5, HDAC7A, HDAC9, Hedgehog, HGF, HIF1A, HIP1, histamine and histamine receptors, HLA-A, HLA-DRA, HLA-E, HM74, HMOXI, HSP90, HUMCYT2A, ICEBERG, ICOSL, ID2, IFN-α, IFNA1, IFNA2, IFNA4, IFNA5, EFNA6, BFNA7, IFNB1, IFNgamma, IFNW1, IGBP1, IGF1, IGFIR, IGF2, IGFBP2, IGFBP3, IGFBP6, DL-1, ILIO, ILIORA, ILIORB, IL-1, IL1R1 (CD121a), IL1R2(CD121b), IL-IRA, IL-2, IL2RA (CD25), IL2RB(CD122), IL2RG(CD132), IL-4, IL-4R (CD123), IL-5, IL5RA(CD125), IL3RB(CD131), IL-6, IL6RA, (CD126), IR6RB(CD130), IL-7, IL7RA(CD127), IL-8, CXCR1 (IL8RA), CXCR2, (IL8RB/CD128), IL-9, IL9R(CD129), IL-10, IL10RA(CD210), IL10RB (CDW210B), IL-11, IL11RA, IL-12, IL-12A, IL-12B, IL-12RB1, IL-12RB2, IL-13, IL13RA1, IL13RA2, IL14, IL15, IL15RA, IL16, IL17, IL17A, IL17B, IL17C, IL17R, IL18, IL18BP, IL18R1, IL18RAP, IL19, ILIA, ILIB, ILIF10, ILIF5, ILIF6, ILIF7, ILIF8, DL1F9, ILIHY1, ILIR1, IL1R2, ILIRAP, ILIRAPL1, ILIRAPL2, ILIRL1, IL1RL2, ILIRN, IL2, IL20, IL20RA, IL21R, IL22, IL22R, IL22RA2, IL23, DL24, IL25, IL26, IL27, IL28A, IL28B, IL29, IL2RA, IL2RB, IL2RG, IL3, IL30, IL3RA, IL4, IL4, IL6ST (glycoprotein 130), ILK, INHA, INHBA, INSL3, INSL4, IRAK1, IRAK2, ITGA1, ITGA2, ITGA3, ITGA6 (a6 integrin), ITGAV, ITGB3, ITGB4 (134 integrin), JAG1, JAK1, JAK3, JTB, JUN, K6HF, KAI1, KDR, KITLG, KLF5 (GC Box BP), KLF6, KLK10, KLK12, KLK13, KLK14, KLK15, KLK3, KLK4, KLK5, KLK6, KLK9, KRT1, KRT19 (Keratin 19), KRT2A, KRTHB6(hair-specific type II keratin), *LAMA*5, LEP (leptin), Lingo-p75, Lingo-Troy, LPS, LTA (TNF-b), LTB, LTB4R (GPR16), LTB4R2, LTBR, MACMARCKS, MAG or OMgp, MAP2K7 (c-Jun), MCP-1, MDK, MIB1, midkine, MIF, MISRII, MJP-2, MK, MKI67 (Ki-67), MMP2, MMP9, MS4A1, MSMB, MT3 (metallothionectin-UI), mTOR, MTSS1, MUC1 (mucin), MYC, MYD88, NCK2, neurocan, NFKBI, NFKB2, NGFB (NGF), NGFR, NgR-Lingo, NgRNogo66, (Nogo), NgR-p75, NgR-Troy, NMEI (NM23A), NOTCH, NOTCHi, NOX5, NPPB, NROB1, NROB2, NRID1, NR1D2, NR1H2, NR1H3, NR1H4, NR112, NR113, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NT5E, NTN4, ODZI, OPRDI, P2RX7, PAP, PART1, PATE, PAWR, PCA3, PCDGF, PCNA, PDGFA, PDGFB, PDGFRA, PDGFRB, PECAMI, peg-asparaginase, PF4 (CXCL4), PGF, PGR, phosphacan, PIAS2, PI3 Kinase, PIK3CG, PLAU (uPA), PLG, PLXDCI, PKC, PKC-beta, PPBP (CXCL7), PPID, PR1, PRKCQ, PRKD1, PRL, PROC, PROK2, PSAP, PSCA, PTAFR, PTEN, PTGS2 (COX-2), PTN, RAC2 (P21Rac2), RANK, RANK ligand, RARB, RGS1, RGS13, RGS3, RNFIIO (ZNF144), Ron, ROBO2, RXR, S100A2, SCGB 1D2 (lipophilin B), SCGB2A1 (mammaglobin 2), SCGB2A2 (mammaglobin 1), SCYE1 (endothelial Monocyte-activating cytokine), SDF2, SERPENA1, SERPINA3, SERPINB5 (maspin), SERPINEI (PAI-I), SERPINFI, SHIP-1, SHIP-2, SHB1, SHB2, SHBG, SfcAZ, SLC2A2, SLC33A1, SLC43A1, SLIT2, SPP1, SPRR1B (Spr1), ST6GAL1, STAB1, STATE, STEAP, STEAP2, TB4R2, TBX21, TCP1O, TDGF1, TEK, TGFA, TGFB1, TGFBI1, TGFB2, TGFB3, TGFBI, TGFBR1, TGFBR2, TGFBR3, THIL, THBS1 (thrombospondin-1), THBS2, THBS4, THPO, TIE (Tie-1), TIMP3, tissue factor, TLR1, TLR2, TLR3, TLR4, TLR5, TLR6, TLR7, TLR8, TLR9, TLR10, TLR11, TNF, TNF-α, TNFAIP2 (B94), TNFAIP3, TNFRSFIiA, TNFRSF1A, TNFRSFiB, TNFRSF21, TNFRSF5, TNFRSF6 (Fas), TNFRSF7, TNFRSF8, TNFRSF9, TNFSFO1 (TRAIL), TNFSFi 1 (TRANCE), TNFSF12 (APO3L), TNFSF13 (April), TNFSF13B, TNFSF14 (HVEM-L), TNFRSF14 (HVEM), TNFSF15 (VEGI), TNFSF18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TOP2A (topoisomerase Iia), TP53, TPM1, TPM2, TRADD, TRAF1, TRAF2, TRAF3, TRAF4, TRAF5, TRAF6, TRKA, TREM1, TREM2, TRPC6, TSLP, TWEAK, Tyrosinase, uPAR, VEGF, VEGFB, VEGFC, versican, VHL C5, VLA-4, Wnt-1, XCL1 (lymphotactin), XCL2 (SCM-Ib), XCRI (GPR5/CCXCRi), YY1, ZFPM2, CLEC4C (BDCA-2, DLEC, CD303, CLECSF7), CLEC4D (MCL, CLECSF8), CLEC4E (Mincle), CLEC6A (Dectin-2), CLEC5A (MDL-1, CLECSF5), CLECiB (CLEC-2), CLEC9A (DNGR-1), CLEC7A (Dectin-1), PDGFRa, SLAMF7, GP6 (GPVI), LILRAi (CD85I), LILRA2 (CD85H, ILT1), LILRA4 (CD85G, ILT7), LILRA5 (CD85F, ILT11), LILRA6 (CD85b, ILT8), NCR1 (CD335, LY94, NKp46), NCR3 (CD335, LY94, NKp46), NCR3 (CD337, NKp30), OSCAR, TARM1, CD300C, CD300E, CD300LB (CD300B), CD300LD (CD300D), KIR2DL4 (CD158D), KIR2DS, KLRC2 (CD159C, NKG2C), KLRK1 (CD314, NKG2D), NCR2 (CD336, NKp44), PILRB, SIGLECI (CD169, SN), SIGLEC14, SIGLEC15 (CD33L3), SIGLEC16, SIRPB1 (CD172B), TREM1 (CD354), TREM2, and KLRF1 (NKp80).

In some embodiments, the antibody binds to an FcRγ-coupled receptor. In some embodiments, the FcRγ-coupled receptor is selected from the group consisting of GP6 (GPVI), LILRA1 (CD85I), LILRA2 (CD85H, ILT1), LILRA4 (CD85G, ILT7), LILRA5 (CD85F, ILT11), LILRA6 (CD85b, ILT8), NCR1 (CD335, LY94, NKp46), NCR3 (CD335, LY94, NKp46), NCR3 (CD337, NKp30), OSCAR, and TARM1.

In some embodiments, the antibody binds to a DAP12-coupled receptor. In some embodiments, the DAP12-coupled receptor is selected from the group consisting of CD300C, CD300E, CD300LB (CD300B), CD300LD (CD300D), KIR2DL4 (CD158D), KIR2DS, KLRC2 (CD159C, NKG2C), KLRK1 (CD314, NKG2D), NCR2 (CD336, NKp44), PILRB, SIGLECI (CD169, SN), SIGLEC14, SIGLEC15 (CD33L3), SIGLEC16, SIRPB1 (CD172B), TREM1 (CD354), and TREM2.

In some embodiments, the antibody binds to a hemITAM-bearing receptor. In some embodiments, the hemITAM-bearing receptor is KLRF1 (NKp80).

In some embodiments, the antibody is capable of binding one or more targets selected from CLEC4C (BDCA-2, DLEC, CD303, CLECSF7), CLEC4D (MCL, CLECSF8), CLEC4E (Mincle), CLEC6A (Dectin-2), CLEC5A (MDL-1, CLECSF5), CLECIB (CLEC-2), CLEC9A (DNGR-1), and CLEC7A (Dectin-1). In some embodiments, the antibody is capable of binding CLEC6A (Dectin-2) or CLEC5A. In some embodiments, the antibody is capable of binding CLEC6A (Dectin-2).

In some embodiments, the antibody is capable of binding one or more targets selected from (e.g., specifically binds to a target selected from): ATP5I (Q06185), OAT (P29758), AIFM1 (Q9ZOX1), AOFA (Q64133), MTDC (P18155), CMC1 (Q8BH59), PREP (Q8K411), YMEL1 (O88967), LPPRC (Q6PB66), LONM (Q8CGK3), ACON (Q99KI0), ODO1 (Q60597), IDHP (P54071), ALDH2 (P47738), ATPB (P56480), AA™ (P05202), TMM93 (Q9CQW0), ERGI3 (Q9CQE7), RTN4 (Q99P72), CL041 (Q8BQR4), ERLN2 (Q8BFZ9), TERA (Q01853), DAD1 (P61804), CALX (P35564), CALU (035887), VAPA (Q9WV55), MOGS (Q80UM7), GANAB (Q8BHN3), ERO1A (Q8R180), UGGG1 (Q6P5E4), P4HA1 (Q60715), HYEP (Q9D379), CALR (P14211), AT2A2 (O55143), PDIA4 (P08003), PDIA1 (P09103), PDIA3 (P27773), PDIA6 (Q922R8), CLH (Q68FD5), PPIB (P24369), TCPG (P80318), MOT4 (P57787), NICA (P57716), BASI (P18572), VAPA (Q9WV55), ENV2 (P11370), VAT1 (Q62465), 4F2 (P10852), ENOA (P17182), ILK (055222), GPNMB (Q99P91), ENV1 (P10404), ERO1A (Q8R180), CLH (Q68FD5), DSG1A (Q61495), AT1A1 (Q8VDN2), HYOU1 (Q9JKR6), TRAP1 (Q9CQN1), GRP75 (P38647), ENPL (P08113), CH60 (P63038), and CH10 (Q64433). In the preceding list, accession numbers are shown in parentheses.

In some embodiments, the antibody binds to an antigen selected from CDH1, CD19, CD20, CD29, CD30, CD38, CD40, CD47, EpCAM, MUC1, MUC16, EGFR, Her2, SLAMF7, and gp75. In some embodiments, the antigen is selected from CD19, CD20, CD47, EpCAM, MUC1, MUC16, EGFR, and Her2. In some embodiments, the antibody binds to an antigen selected from the Tn antigen and the Thomsen-Friedenreich antigen.

In some embodiments, the antibody or Fc fusion protein is selected from: abagovomab, abatacept (also known as ORENCIA™), abciximab (also known as REOPRO™, c7E3 Fab), adalimumab (also known as HUMIRA™), adecatumumab, alemtuzumab (also known as CAM-PATH™, MabCampath or Campath-1H), altumomab, afelimomab, anatumomab mafenatox, anetumumab, anrukizumab, apolizumab, arcitumomab, aselizumab, atlizumab, atorolimumab, bapineuzumab, basiliximab (also known as SIMULECT™), bavituximab, bectumomab (also known as LYMPHOSCAN™), belimumab (also known as LYMPHO-STAT-B™), bertilimumab, besilesomab, bevacizumab (also known as AVASTIN™), biciromab brallobarbital, bivatuzumab mertansine, campath, canakinumab (also known as ACZ885), cantuzumab mertansine, capromab (also known as PROSTASCINT™), catumaxomab (also known as REMOVAB™), cedelizumab (also known as CIMZIA™), certolizumab pegol, cetuximab (also known as ERBITUX™), clenoliximab, dacetuzumab, dacliximab, daclizumab (also known as ZENAPAX™), denosumab (also known as AMG 162), detumomab, dorlimomab aritox, dorlixizumab, duntumumab, durimulumab, durmulumab, ecromeximab, eculizumab (also known as SOLIRIS™), edobacomab, edrecolomab (also known as Mabl7-1A, PAN-OREX™), efalizumab (also known as RAPTIVA™), efungumab (also known as MYCOGRAB™), elsilimomab, enlimomab pegol, epitumomab cituxetan, efalizumab, epitumomab, epratuzumab, erlizumab, ertumaxomab (also known as REXOMUN™), etanercept (also known as ENBREL™), etaracizumab (also known as etaratuzumab, VITAXIN™, ABEGRIN™), exbivirumab, fanolesomab (also known as NEUTROSPEC™), faralimomab, felvizumab, fontolizumab (also known as HUZAF™), galiximab, gantenerumab, gavilimomab (also known as ABXCBL™), gemtuzumab ozogamicin (also known as MYLOTARG™), golimumab (also known as CNTO 148), gomiliximab, ibalizumab (also known as TNX-355), ibritumomab tiuxetan (also known as ZEVALIN™), igovomab, imciromab, infliximab (also known as REMICADE™), inolimomab, inotuzumab ozogamicin, ipilimumab (also known as MDX-010, MDX-101), iratumumab, keliximab, labetuzumab, lemalesomab, lebrilizumab, lerdelimumab, lexatumumab (also known as, HGS-ETR2, ETR2-ST01), lexitumumab, libivirumab, lintuzumab, lucatumumab, lumiliximab, mapatumumab (also known as HGSETR1, TRM-1), maslimomab, matuzumab (also known as EMD72000), mepolizumab (also known as BOSATRIA™), metelimumab, milatuzumab, minretumomab, mitumomab, morolimumab, motavizumab (also known as NUMAX™), muromonab (also known as OKT3), nacolomab tafenatox, naptumomab estafenatox, natalizumab (also known as TYSABRI™, ANTEGREN™), nebacumab, nerelimomab, nimotuzumab (also known as THERACIM hR3™, THERA-CIM-hR3™, THERALOC™), nofetumomab merpentan (also known as VERLUMA™), ocrelizumab, odulimomab, ofatumumab, omalizumab (also known as XOLAIR™), oregovomab (also known as OVAREX™), otelixizumab, pagibaximab, palivizumab (also known as SYNAGIS™), panitumumab (also known as ABX-EGF, VECTIBIX™), pascolizumab, pemtumomab (also known as THER-AGYN™), pertuzumab (also known as 2C4, OMNI-TARG™), pexelizumab, pintumomab, priliximab, pritumumab, ranibizumab (also known as LUCENTIS™), raxibacumab, regavirumab, reslizumab, rituximab (also known as RITUXAN™, MabTHERA™), rovelizumab, ruplizumab, satumomab, sevirumab, sibrotuzumab, siplizumab (also known as MEDI-507), sontuzumab, stamulumab (also known as MYO-029), sulesomab (also known as LEUKOSCAN™), tacatuzumab tetraxetan, tadocizumab, talizumab, taplitumomab paptox, tefibazumab (also known as AUREXIS™), telimomab aritox, teneliximab, teplizumab, ticilimumab, tocilizumab (also known as ACTEMRA™), toralizumab, tositumomab, trastuzumab (also known as HERCEPTIN™), tremelimumab (also known as CP-675,206), tucotuzumab celmoleukin, tuvirumab, urtoxazumab, ustekinumab (also known as CNTO 1275), vapaliximab, veltuzumab, vepalimomab, visilizumab (also known as NUVION™), volociximab (also known as M200), votumumab (also known as HUMASPECT™), zalutumumab, zanolimumab (also known as HuMAX-CD4), ziralimumab, zolimomab aritox, daratumumab, elotuxumab, obintunzumab, olaratumab, brentuximab vedotin, afibercept, abatacept, belatacept, afibercept, etanercept, romiplostim, SBT-040 (sequences listed in US 2017/0158772. In some embodiments, the antibody is rituximab.

Checkpoint Inhibitors

Any suitable immune checkpoint inhibitor is contemplated for use with the immunoconjugates disclosed herein. In some embodiments, the immune checkpoint inhibitor reduces the expression or activity of one or more immune checkpoint proteins. In another embodiment, the immune checkpoint inhibitor reduces the interaction between one or more immune checkpoint proteins and their ligands. Inhibitory nucleic acids that decrease the expression and/or activity of immune checkpoint molecules can also be used in the methods disclosed herein.

The data herein show that immune checkpoint inhibitor Nivolumab which is normally an IgG4, can we modified to include an IgG1 Fc, and subsequently converted into a immunoconjugates of the invention. The data indicate that the Nivolumab IgG1 immunoconjugate is still very potent. Similarly, when the IgG1 NQ Fc on the clinical grade Atezolizumab was replaced with IgG1, there were improved results. See FIGS. 97A-97H.

Most checkpoint antibodies are designed not to have effector function as they are not trying to kill cells, but rather to block the signalling. Immunoconjugates of the present invention can add back the "effector functionality" needed to activate myeloid immunity. Hence, for most checkpoint antibody inhibitors this discovery will be critical.

In some embodiments, the immune checkpoint inhibitor is cytotoxic T-lymphocyte antigen 4 (CTLA4, also known as CD152), T cell immunoreceptor with Ig and ITIM domains (TIGIT), glucocorticoid-induced TNFR-related protein (GITR, also known as TNFRSF18), inducible T cell costimulatory (ICOS, also known as CD278), CD96, poliovirus receptor-related 2 (PVRL2, also known as CD112R), programmed cell death protein 1 (PD-1, also known as CD279), programmed cell death 1 ligand 1 (PD-L1, also known as B7-H3 and CD274), programmed cell death ligand 2 (PD-L2, also known as B7-DC and CD273), lymphocyte activation gene-3 (LAG-3, also known as CD223), B7-H4, killer immunoglobulin receptor (KIR), Tumor Necrosis Factor Receptor superfamily member 4 (TNFRSF4, also known as OX40 and CD134) and its ligand OX40L (CD252), indoleamine 2,3-dioxygenase 1 (IDO-1), indoleamine 2,3-dioxygenase 2 (IDO-2), carcinoembryonic antigen-related cell adhesion molecule 1 (CEACAMi), B and T lymphocyte attenuator (BTLA, also known as CD272), T-cell membrane protein 3 (TIM3), the adenosine A2A receptor (A2Ar), and V-domain Ig suppressor of T cell activation (VISTA protein). In some embodiments, the immune checkpoint inhibitor is an inhibitor of CTLA4, PD-1, or PD-L1.

In some embodiments, the antibody is selected from: ipilimumab (also known as Yervoy®) pembrolizumab (also known as Keytruda®), nivolumab (also known as Opdivo®), atezolizumab (also known as Tecentriq®), avelumab (also known as Bavencio®), and durvalumab (also known as Imfinzi™). In some embodiments, the antibody is selected from: ipilimumab (also known as Yervoy®), pembrolizumab (also known as Keytruda®), nivolumab (also known as Opdivo®), and atezolizumab (also known as Tecentriq®).

In some embodiments, the immune checkpoint inhibitor is an inhibitor of CTLA4. In some embodiments, the immune checkpoint inhibitor is an antibody against CTLA4. In some embodiments, the immune checkpoint inhibitor is a monoclonal antibody against CTLA4. In some embodiments, the immune checkpoint inhibitor is a human or humanized antibody against CTLA4. In some embodiments, the immune checkpoint inhibitor reduces the expression or activity of one or more immune checkpoint proteins, such as CTLA4.

In some embodiments, the immune checkpoint inhibitor is an inhibitor of PD-1. In some embodiments, the immune checkpoint inhibitor is an antibody against PD-1. In some embodiments, the immune checkpoint inhibitor is a monoclonal antibody against PD-1. In some embodiments, the immune checkpoint inhibitor is a human or humanized antibody against PD-1. In some embodiments, the immune checkpoint inhibitor reduces the expression or activity of one or more immune checkpoint proteins, such as PD-1.

In some embodiments, the immune checkpoint inhibitor is an inhibitor of PD-L1. In some embodiments, the immune checkpoint inhibitor is an antibody against PD-L1. In some embodiments, the immune checkpoint inhibitor is a monoclonal antibody against PD-L1. In some embodiments, the immune checkpoint inhibitor is a human or humanized antibody against PD-L1. In some embodiments, the immune checkpoint inhibitor reduces the expression or activity of one or more immune checkpoint proteins, such as PD-L1. In some embodiments, the immune checkpoint inhibitor reduces the interaction between PD-1 and PD-L1.

In some embodiments, the immune checkpoint inhibitor is an inhibitor of PD-L2. In some embodiments, the immune checkpoint inhibitor is an antibody against PD-L2. In some embodiments, the immune checkpoint inhibitor is a monoclonal antibody against PD-L2. In some embodiments, the immune checkpoint inhibitor is a human or humanized antibody against PD-L2. In some embodiments, the immune checkpoint inhibitor reduces the expression or activity of one or more immune checkpoint proteins, such as PD-L2. In some embodiments, the immune checkpoint inhibitor reduces the interaction between PD-1 and PD-L2.

In some embodiments, the immune checkpoint inhibitor is an inhibitor of LAG-3. In some embodiments, the immune checkpoint inhibitor is an antibody against LAG-3. In some embodiments, the immune checkpoint inhibitor is a monoclonal antibody against LAG-3. In some embodiments, the immune checkpoint inhibitor is a human or humanized antibody against LAG-3. In some embodiments, the immune checkpoint inhibitor reduces the expression or activity of one or more immune checkpoint proteins, such as LAG-3.

In some embodiments, the immune checkpoint inhibitor is an inhibitor of B7-H4. In some embodiments, the immune checkpoint inhibitor is an antibody against B7-H4. In some embodiments, the immune checkpoint inhibitor is a monoclonal antibody against B7-H4. In some embodiments, the immune checkpoint inhibitor is a human or humanized antibody against B7-H4. In some embodiments, the immune checkpoint inhibitor reduces the expression or activity of one or more immune checkpoint proteins, such as B7-H4.

In some embodiments, the immune checkpoint inhibitor is an inhibitor of KIR. In some embodiments, the immune checkpoint inhibitor is an antibody against KIR. In some embodiments, the immune checkpoint inhibitor is a monoclonal antibody against KIR. In some embodiments, the immune checkpoint inhibitor is a human or humanized antibody against KIR. In some embodiments, the immune checkpoint inhibitor reduces the expression or activity of one or more immune checkpoint proteins, such as KIR.

In some embodiments, the immune checkpoint inhibitor is an inhibitor of TNFRSF4. In some embodiments, the immune checkpoint inhibitor is an antibody against TNFRSF4. In some embodiments, the immune checkpoint inhibitor is a monoclonal antibody against TNFRSF4. In some embodiments, the immune checkpoint inhibitor is a human or humanized antibody against TNFRSF4. In some embodiments, the immune checkpoint inhibitor reduces the expression or activity of one or more immune checkpoint proteins, such as TNFRSF4.

In some embodiments, the immune checkpoint inhibitor is an inhibitor of OX40L. In some embodiments, the immune checkpoint inhibitor is an antibody against OX40L. In some embodiments, the immune checkpoint inhibitor is a monoclonal antibody against OX40L. In some embodiments, the immune checkpoint inhibitor is a human or humanized antibody against OX40L. In some embodiments, the immune checkpoint inhibitor reduces the expression or activity of one or more immune checkpoint proteins, such as OX40L. In some embodiments, the immune checkpoint inhibitor reduces the interaction between TNFRSF4 and OX40L.

In some embodiments, the immune checkpoint inhibitor is an inhibitor of IDO-1. In some embodiments, the immune checkpoint inhibitor is an antibody against IDO-1. In some embodiments, the immune checkpoint inhibitor is a monoclonal antibody against IDO-1. In some embodiments, the immune checkpoint inhibitor is a human or humanized antibody against IDO-1. In some embodiments, the immune checkpoint inhibitor reduces the expression or activity of one or more immune checkpoint proteins, such as IDO-1.

In some embodiments, the immune checkpoint inhibitor is an inhibitor of IDO-2. In some embodiments, the immune checkpoint inhibitor is an antibody against IDO-2. In some embodiments, the immune checkpoint inhibitor is a monoclonal antibody against IDO-2. In some embodiments, the immune checkpoint inhibitor is a human or humanized antibody against IDO-2. In some embodiments, the immune checkpoint inhibitor reduces the expression or activity of one or more immune checkpoint proteins, such as IDO-2.

In some embodiments, the immune checkpoint inhibitor is an inhibitor of CEACAM1. In some embodiments, the immune checkpoint inhibitor is an antibody against CEACAM1. In some embodiments, the immune checkpoint inhibitor is a monoclonal antibody against CEACAM1. In some embodiments, the immune checkpoint inhibitor is a human or humanized antibody against CEACAM1. In some embodiments, the immune checkpoint inhibitor reduces the expression or activity of one or more immune checkpoint proteins, such as CEACAM1.

In some embodiments, the immune checkpoint inhibitor is an inhibitor of BTLA. In some embodiments, the immune checkpoint inhibitor is an antibody against BTLA. In some embodiments, the immune checkpoint inhibitor is a monoclonal antibody against BTLA. In some embodiments, the immune checkpoint inhibitor is a human or humanized antibody against BTLA. In some embodiments, the immune checkpoint inhibitor reduces the expression or activity of one or more immune checkpoint proteins, such as BTLA.

In some embodiments, the immune checkpoint inhibitor is an inhibitor of TIM3. In some embodiments, the immune checkpoint inhibitor is an antibody against TIM3. In some embodiments, the immune checkpoint inhibitor is a monoclonal antibody against TIM3. In some embodiments, the immune checkpoint inhibitor is a human or humanized antibody against TIM3. In some embodiments, the immune checkpoint inhibitor reduces the expression or activity of one or more immune checkpoint proteins, such as TIM3.

In some embodiments, the immune checkpoint inhibitor is an inhibitor of A2Ar. In some embodiments, the immune checkpoint inhibitor is an antibody against A2Ar. In some embodiments, the immune checkpoint inhibitor is a monoclonal antibody against A2Ar. In some embodiments, the immune checkpoint inhibitor is a human or humanized antibody against A2Ar. In some embodiments, the immune checkpoint inhibitor reduces the expression or activity of one or more immune checkpoint proteins, such as A2Ar.

In some embodiments, the immune checkpoint inhibitor is an inhibitor of VISTA protein. In some embodiments, the immune checkpoint inhibitor is an antibody against VISTA protein. In some embodiments, the immune checkpoint inhibitor is a monoclonal antibody against VISTA protein. In some embodiments, the immune checkpoint inhibitor is a human or humanized antibody against VISTA protein. In some embodiments, the immune checkpoint inhibitor reduces the expression or activity of one or more immune checkpoint proteins, such as VISTA protein.

Biosimilars

The immunoconjugates of the present invention are also effective with antibody constructs that are highly similar, or biosimilar, to the commercially available, or "innovator", antibody constructs. For example, biosimilar antibodies to cetuximab, rituximab, and trastuzumab were used in several successful immunoconjugates of the present invention as seen in FIGS. 71A-71AQ. The biosimilar immunoconjugates elicited myeloid activation as effectively as the commercially available antibodies. From these studies, it is expected that biosimilar immunoconjugates will perform similarly to immunoconjugates of the innovator products.

DAR Ratios

The immunoconjugates of the present invention provide DAR ratios which are desirable. As seen in FIGS. 84A-87C, the immunoconjugates of the present invention provide DAR ratios of 0.7, 1.6, and 2.5.

The immunoconjugates shown with varying DAR ratios were all effective at activating myeloid cells and eliciting cytokine secretion. The data indicate that the immunoconjugates with varying DAR ratios were all superior at eliciting APC activation as CD40, CD86 and HLA-DR were expressed at higher levels in APCs stimulated with immunoconjugates as compared to those stimulated with the antibody alone. The immunoconjugates with varying DARs consistently induced the downregulation of CD14 and CD16 and increased expression of CD123, as compared to the antibody alone. From these studies, it is expected all DAR ratios will be effective at eliciting myeloid cell activation.

Isotype Modification

The data herein show (see FIGS. 88C-88H) that when the IgG1 fc region of antibody, such as rituximab, is exchanged for IgG1 AF, IgG1 NQ, IgG2, IgG3, IgG4, or IgA2, and then formed into an immunoconjugates of the present invention, the activity of the immunoconjugate can be modulated and often, improved, for the desired application.

Around 30% of human IgG is glycosylated within the Fab region, and the antibody in the immunoconjugates of the invention can contain an engineered Fab region with a non-naturally occurring glycosylation pattern. For example, hybridomas can be genetically engineered to secrete afucosylated mAb, desialylated mAb or deglycosylated Fc with specific mutations that enable increased FcRyIIIa binding and effector function.

Antibodies for forming immunoconjugates can contain engineered (i.e., non-naturally occurring) cysteine residues characterized by altered (e.g., enhanced) reactivity toward the reagents used for covalently bonding the adjuvant moieties to the antibodies. In certain embodiments, an engineered cysteine residue will have a thiol reactivity value in the range of 0.6 to 1.0. In many cases, the engineered antibody will be more reactive than the parent antibody.

In general, the engineered residues are "free" cysteine residues that are not part of disulfide bridges. The term "thiol reactivity value" is a quantitative characterization of the reactivity of free cysteine amino acids. As used herein, the term "thiol reactivity value" refers to the percentage of a free cysteine amino acid in an engineered antibody which reacts with a thiol-reactive reagent, and converted to a maximum value of 1. For example, a cysteine residue in an engineered antibody which reacts in 100% yield with a thiol-reactive reagent, such as a maleimide, to form a modified antibody has a thiol reactivity value of 1.0. Another cysteine residue engineered into the same or different parent antibody which reacts in 80% yield with a thiol-reactive reagent has a thiol reactivity value of 0.8. Determination of the thiol reactivity value of a particular cysteine residue can be conducted by ELISA assay, mass spectroscopy, liquid chromatography, autoradiography, or other quantitative analytical tests.

Engineered cysteine residues can be located in the antibody heavy chains or the antibody light chains. In certain embodiments, engineered cysteine residues are located in the Fc region of the heavy chains. For example, amino acid residues at positions L-15, L-43, L-110, L-144, L-168 in the light chains of an antibody or H-40, H-88, H-119, H-121, H-122, H-175, and H-179 in the heavy chains of an antibody can be replaced with cysteine residues. Ranges within about 5 amino acid residues on each side of these positions can also be replaced with cysteine residues, i.e., L-10 to L-20; L-38 to L-48; L-105 to L-115; L-139 to L-149; L-163 to L-173; H-35 to H-45; H-83 to H-93; H-114 to H-127; and H-170 to H-184, as well as the ranges in the Fc region selected from H-268 to H-291; H-319 to H-344; H-370 to H-380; and H-395 to H-405, to provide useful cysteine engineered antibodies for forming immunoconjugates. Other engineered antibodies are described, for example, in U.S. Pat. Nos. 7,855,275; 8,309,300; and 9,000,130, which are hereby incorporated by reference.

In addition to antibodies, alternative protein scaffolds may be used as part of the immunoconjugates. The term "alternative protein scaffold" refers to a non-immunoglobulin derived protein or peptide. Such proteins and peptides are generally amenable to engineering and can be designed to confer monospecificity against a given antigen, bispecificity, or multispecificity. Engineering of an alternative protein scaffold can be conducted using several approaches. A loop grafting approach can be used where sequences of known specificity are grafted onto a variable loop of a scaffold. Sequence randomization and mutagenesis can be used to develop a library of mutants, which can be screened using various display platforms (e.g., phage display) to identify a novel binder. Site-specific mutagenesis can also be used as part of a similar approach. Alternative protein scaffolds exist in a variety of sizes, ranging from small peptides with minimal secondary structure to large proteins of similar size to a full-sized antibody. Examples of scaffolds include, but are not limited to, cystine knotted miniproteins (also known as knottins), cyclic cystine knotted miniproteins (also known as cyclotides), avimers, affibodies, the tenth type III domain of human fibronectin, DARPins (designed ankyrin repeats), and anticalins (also known as lipocalins). Naturally occurring ligands with known specificity can also be engineered to confer novel specificity against a given target. Examples of naturally occurring ligands that may be engineered include the EGF ligand and VEGF ligand. Engineered proteins can either be produced as monomeric proteins or as multimers, depending on the desired binding strategy and specificities. Protein engineering strategies can be used to fuse alternative protein scaffolds to Fc domains.

Preparation of Antibody Adjuvant Conjugates

Reactions for forming the immunoconjugates of the invention are conducted under conditions sufficient to covalently bond the adjuvant moiety to the antibody. In general, the reactions are conducted by contacting an antibody with an adjuvant-linker compound such that an amino acid sidechain in the antibody reacts with the adjuvant linker compound. In some embodiments, the adjuvant-linker compound and the antibody are used in approximately equimolar amounts when forming the immunoconjugates. In some embodiments, an excess of the adjuvant-linker compound is used when forming the immunoconjugates. For example, a reaction mixture for forming an immunoconjugate can contain from about 1.1 to about 50 molar equivalents of the adjuvant-linker compound with respect to the antibody.

The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. In some embodiments, the reaction is conducted at near neutral pH (i.e., around pH 7). In some embodiments, the reaction is conducted at a pH ranging from 7.2 to 7.5. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the identity of the antibody in the conjugate and the reagent used for installing the adjuvant moiety.

Reaction mixtures for forming the antibody adjuvant conjugates can contain additional reagents of the sort typically used in bioconjugation reactions. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like), chelators (e.g., ethylene glycol-bis(2-aminoethylether)-N,N,N',N'-tetraacetic acid (EGTA), 2-({2-[bis(carboxymethyl)amino]ethyl} (carboxymethyl)amino)acetic acid (EDTA), and 1,2-bis(o-aminophenoxy)ethane-N,N,N,N-tetraacetic acid (BAPTA)), and reducing agents (e.g., dithiothreitol (DTT), β-mercaptoethanol (BME), and tris(2-carboxyethyl)phosphine (TCEP)). Buffers, cosolvents, salts, detergents/surfactants, chelators, and reducing agents can be used at any suitable concentration, which can be readily determined by one of skill in the art. In general, buffers, cosolvents, salts, detergents/surfactants, chelators, and reducing agents are included in reaction mixtures at concentrations ranging from about 1 μM to about 1 M. For example, a buffer, a cosolvent, a salt, a detergent/surfactant, a chelator, or a reducing agent can be included in a reaction mixture at a concentration of about 1 μM, or about 10 μM, or about 100 μM, or about 1 mM, or about 10 mM, or about 25 mM, or about 50 mM, or about 100 mM, or about 250 mM, or about 500 mM, or about 1 M.

Formulation and Administration of Immunoconjugates

In a related aspect, the invention provides a composition comprising a plurality of immunoconjugates as described above. In some embodiments, the average number of adjuvant moieties per immunoconjugate ranges from about 1 to about 10. The average number of adjuvant moieties per immunoconjugate can range, for example, from about 1 to about 10, or from about 1 to about 6, or from about 1 to about 4. The average number of adjuvant moieties per immunoconjugate can be about 0.8, 1, 1.2, 1.4, 1.6, 1.8, 2, 2.2, 2.4, 2.6, 2.8, 3, 3.2, 3.4, 3.6, 3.8, 4.0, or 4.2. In some embodiments, the average number of adjuvant moieties per immunoconjugate is about 4. In some embodiments, the average number of adjuvant moieties per immunoconjugate is about 2. In some cases, the antibody is covalently bonded to a single adjuvant moiety. In some cases, the antibody is covalently bonded to 2 or more adjuvant moieties (e.g., 3 or more, 4 or more, or 5 or more adjuvant moieties). In some cases, the antibody is covalently bonded to 1-10 adjuvant moieties (e.g., 1-8, 1-5, 1-3, 2-10, 2-8, 2-5, 2-3, or 3-8 adjuvant moieties). In some cases, the antibody is covalently bonded to 2-10 adjuvant moieties (e.g., 2-8, 2-5, 2-3, or 3-10, or 3-8 adjuvant moieties). In some cases in which the antibody is covalently bonded to more than one adjuvant moiety, the attached adjuvant moieties can be the same or different. For example, in some cases two or more of the adjuvant moieties can be the same (e.g., two different molecules of the same adjuvant moiety can each be attached to the antibody at a different site on the antibody). In some cases, the antibody is covalently bonded to 2 or more different adjuvant moieties (e.g., 3 or more, 4 or more, or 5 or more different adjuvant moieties). For example, when generating an immunoconjugate of the invention, one or more antibodies can be contacted with a mixture that includes two or more (e.g., 3 or more, 4 or more, or 5 or more) different adjuvant-linker compounds such that amino acid sidechains in the one or more antibodies reacts with the adjuvant-linker compounds, thus resulting in one or more immunoconjugates that are each covalently bonded to two or more different adjuvant moieties.

Site-specific antibody conjugation allows for precise placement of the adjuvant on the antibody and a homogenous DAR as compared to the heterogeneous conjugation product resulting from attachment to lysine residues in the antibody. Site-specific immunoconjugates may be generated through various modifications of the antibody. Methods for site-specific conjugation include the following methods but are not limited to those methods described herein. One method for site-specific conjugation involves the incorporation of a sequence that is then recognized by an enzyme, resulting in chemical modification. For example, the enzyme FGE recognizes the sequence Cys-X-Pro-X-Arg. Co-expression of the modified antibody along with FGE in mammalian culture generates an antibody containing an aldehyde-tag at the engineered site(s). Other enzymes may be used that recognize naturally occurring sequences or residues for conversion to chemically reactive groups allowing for site-specific conjugation. Bacterial transglutaminases (BTGs) can catalyze the formation of bonds between glutamine residues and primary amines; the bacterial enzyme sortase A can catalyze transpeptidation reactions through a recognition motif. Non-natural amino acids may also be incorporated into the antibody sequence that may then be reacted to generate site-specific conjugates. Naturally occurring residues, such as the amino acid selenocysteine, may be incorporated into the antibody and subsequently reacted with the appropriate reactive groups including but not limited to maleimides and iodoacetamides for site-specific conjugation. Another method is the incorporation of engineered cysteine residues that are added into the heavy or light chain of the antibody construct. Vectors encoding for the heavy and/or light chains are modified to incorporate the codon sequence for a cysteine residue (vector sequence in FIGS. 138A-138B and vector map in FIGS. 138C-138D). Conjugation is performed by first reducing the antibody and then re-oxidizing to regenerate the native disulfide bonds of the antibody, resulting in the uncapping of a reactive thiol(s). Once reacted with adjuvant-linker, the resulting product contains a homogenous population of immunoconjugate with a DAR defined by the number of cysteine residues engineered into the antibody (structure shown in FIG. 138E). For example, the incorporation of a mutation in the light chain at position 205 from a valine to cysteine (V205C mutation) results in a product with the adjuvant conjugated at the defined sites (V205C; FIGS. 138F-138G).

In some embodiments, the composition further comprises one or more pharmaceutically acceptable excipients. For example, the immunoconjugates of the invention can be formulated for parenteral administration, such as intravenous (IV) administration or administration into a body cavity or lumen of an organ. Alternatively, the immunoconjugates can be injected intra-tumorally. Formulations for injection will commonly comprise a solution of the immunoconjugate dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic monoglycerides or diglycerides. In addition, fatty acids such as oleic acid can likewise be used in the preparation of injectables. These solutions are sterile and generally free of undesirable matter. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the immunoconjugate in these formulations can vary widely, and will be selected primarily based on fluid volumes, viscosities, body weight, and the like, in accordance with the particular mode of administration selected and the patient's needs. In certain embodiments, the concentration of an immunoconjugate in a solution formulation for injection will range from about 0.1% (w/w) to about 10% (w/w).

In another aspect, the invention provides a method for treating cancer. The method includes comprising administering a therapeutically effective amount of an immunoconjugate (e.g., as a composition as described above) to a subject in need thereof. For example, the methods can include administering the immunoconjugate to provide a dose of from about 100 ng/kg to about 50 mg/kg to the subject. The immunoconjugate dose can range from about 5 mg/kg to about 50 mg/kg, from about 10 ag/kg to about 5 mg/kg, or from about 100 ag/kg to about 1 mg/kg. The immunoconjugate dose can be about 100, 200, 300, 400, or 500 ag/kg. The immunoconjugate dose can be about 1, 2, 3, 4, 5, 6, 7, 8, 9, or 10 mg/kg. The immunoconjugate dose can also lie outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

Some embodiments of the invention provide methods for treating cancer as described above, wherein the cancer is a head and neck cancer. Head and neck cancer (as well as head and neck squamous cell carcinoma) refers to a variety of cancers characterized by squamous cell carcinomas of the oral cavity, pharynx and larynx, salivary glands, paranasal sinuses, and nasal cavity, as well as the lymph nodes of the upper part of the neck. Head and neck cancers account for approximately 3 to 5 percent of all cancers in the United States. These cancers are more common in men and in people over age 50. Tobacco (including smokeless tobacco) and alcohol use are the most important risk factors for head and neck cancers, particularly those of the oral cavity, oropharynx, hypopharynx and larynx. Eighty-five percent of head and neck cancers are linked to tobacco use. In the methods of the invention, the immunoconjugates can be used to target a number of malignant cells. For example, the immunoconjugates can be used to target squamous epithelial cells of the lip, oral cavity, pharynx, larynx, nasal cavity, or paranasal sinuses. The immunoconjugates can be used to target mucoepidermoid carcinoma cells, adenoid cystic carcinoma cells, adenocarcinoma cells, small-cell undifferentiated cancer cells, esthesioneuroblastoma cells, Hodgkin lymphoma cells, and Non-Hodgkin lymphoma cells. In some embodiments, methods for treating head and neck cancer include administering an immunoconjugate containing an antibody that is capable of binding EGFR (e.g., cetuximab, panitumumab, matuzumab, and zalutumumab), PD-1 (e.g., pembrolizumab), and/or MUC1.

Some embodiments of the invention provide methods for treating cancer as described above, wherein the cancer is breast cancer. Breast cancer can originate from different areas in the breast, and a number of different types of breast cancer have been characterized. For example, the immunoconjugates of the invention can be used for treating ductal carcinoma in situ; invasive ductal carcinoma (e.g., tubular carcinoma; medullary carcinoma; mucinous carcinoma; papillary carcinoma; or cribriform carcinoma of the breast); lobular carcinoma in situ; invasive lobular carcinoma; inflammatory breast cancer; and other forms of breast cancer. In some embodiments, methods for treating breast cancer include administering an immunoconjugate containing an antibody that is capable of binding HER2 (e.g., trastuzumab, margetuximab), glycoprotein NMB (e.g., glembatumumab), and/or MUC1.

Examples of Non-Limiting Aspects of the Disclosure

Aspects, including embodiments, of the present subject matter described herein may be beneficial alone or in combination, with one or more other aspects or embodiments. Without limiting the foregoing description, certain non-limiting aspects of the disclosure numbered 1-98 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. An immunoconjugate comprising
  (a) an antibody construct comprising (i) an antigen binding domain and (ii) an Fc domain,
  (b) an adjuvant moiety, and
  (c) a linker,
wherein each adjuvant moiety is covalently bonded to the antibody construct via the linker.

2. The immunoconjugate of aspect 1, wherein the antibody construct further comprises a targeting binding domain.

3. The immunoconjugate of aspect 1, wherein the antibody construct is an antibody.

4. The immunoconjugate of any one of aspects 1-3, wherein the antigen binding domain binds to an antigen of a cancer cell.

5. The immunoconjugate of any one of aspects 1-4, wherein the antigen binding domain binds to an antigen selected from the group consisting of CDH1, CD19, CD20, CD29, CD30, CD38, CD40, CD47, EpCAM, MUC1, MUC16, EGFR, VEGF, HER2, SLAMF7, PDGFRa, and gp75.

6. The immunoconjugate of any one of aspects 1-5, wherein the antigen binding domain binds to an antigen selected from the group consisting of CD19, CD20, CD40, CD47, EpCAM, MUC1, MUC16, PDGFRa, EGFR, and HER2.

7. The immunoconjugate of any one of aspects 1-6, wherein the antigen binding domain binds to an antigen selected from the group consisting of Tn antigen and the Thomsen-Friedenreich antigen.

8. The immunoconjugate of any one of aspects 3-7, wherein the antibody is a polyclonal antibody.

9. The immunoconjugate of any one of aspects 3-7, wherein the antibody is a monoclonal antibody.

10. The immunoconjugate of aspect 8 or 9, wherein the antibody is humanized.

11. The immunoconjugate of aspect 8 or 9, wherein the antibody is murine.

12. The immunoconjugate of any one of aspects 3-11, wherein the antibody is selected from the group consisting of olaratumab, obinutuzumab, trastuzumab, cetuximab, rituximab, pertuzumab, bevacizumab, daratumumab, etanercept, and elotuzumab.

13. The immunoconjugate of any one of aspects 3-11, wherein the antibody is olaratumab.

14. The immunoconjugate of any one of aspects 3-11, wherein the antibody is obinutuzumab.

15. The immunoconjugate of any one of aspects 3-11, wherein the antibody is trastuzumab.

16. The immunoconjugate of any one of aspects 3-11, wherein the antibody is cetuximab.

17. The immunoconjugate of any one of aspects 3-11, wherein the antibody is rituximab.

18. The immunoconjugate of any one of aspects 3-11, wherein the antibody is pertuzumab.

19. The immunoconjugate of any one of aspects 3-11, wherein the antibody is bevacizumab.

20. The immunoconjugate of any one of aspects 3-11, wherein the antibody is daratumumab.

21. The immunoconjugate of any one of aspects 3-11, wherein the antibody is elotuzumab.

22. The immunoconjugate of any one of aspects 3-11, wherein the antibody is etanercept.

23. The immunoconjugate of any one of aspects 3-11, wherein the antibody binds to an antigen of an immune checkpoint inhibitor.

24. The immunoconjugate of any one of aspects 3-11, wherein the antibody binds to an antigen selected from the group consisting of CTLA4, PD-1, PD-L1, PD-L2, LAG-3, B7-H4, KIR, TNFRSF4, OX40L, IDO-1, IDO-2, CEACAMi, BTLA, TIM3, A2Ar, and VISTA.

25. The immunoconjugate of any one of aspects 3-11, wherein the antibody binds to an antigen selected from the group consisting of CTLA4, PD-1, and PD-L1.

26. The immunoconjugate of any one of aspects 3-11, wherein the antibody binds a PD-1 antigen.

27. The immunoconjugate of any one of aspects 3-11, wherein the antibody binds a PD-L1 antigen.

28. The immunoconjugate of any one of aspects 3-11, wherein the antibody binds a CTLA4 antigen.

29. The immunoconjugate of any one of aspects 3-11, wherein the antibody is selected from the group consisting of pembrolizumab, nivolumab, atezolizumab, and ipilimumab.

30. The immunoconjugate of any one of aspects 3-11, wherein the antibody is pembrolizumab.

31. The immunoconjugate of any one of aspects 3-11, wherein the antibody is nivolumab.

32. The immunoconjugate of any one of aspects 3-11, wherein the antibody is atezolizumab.

33. The immunoconjugate of any one of aspects 3-11, wherein the antibody is ipilimumab.

34. The immunoconjugate of any one of aspects 3-11, wherein the antibody binds to an antigen selected from the group consisting of CLEC4C (BDCA-2, DLEC, CD303, CLECSF7), CLEC4D (MCL, CLECSF8), CLEC4E (Mincle), CLEC6A (Dectin-2), CLEC5A (MDL-1, CLECSF5), CLECiB (CLEC-2), CLEC9A (DNGR-1), and CLEC7A (Dectin-1).

35. The immunoconjugate of any one of aspects 3-11, wherein the antibody binds to CLEC5A.

36. The immunoconjugate of any one of aspects 3-11, wherein the antibody binds to CLEC6A (Dectin-2).

37. The immunoconjugate of any one of aspects 3-11, wherein the antibody is an IgA1.

38. The immunoconjugate of any one of aspects 3-11, wherein the antibody is an IgA2 antibody.

39. The immunoconjugate of any one of aspects 3-11, wherein the antibody is an IgG antibody.

40. The immunoconjugate of any one of aspects 3-11, wherein the antibody is an IgG1 antibody.

41. The immunoconjugate of any one of aspects 3-11, wherein the antibody is an IgG2 antibody.

42. The immunoconjugate of any one of aspects 3-11, wherein the antibody is an IgG3 antibody.

43. The immunoconjugate of any one of aspects 3-11, wherein the antibody is an IgG4 antibody.

44. The immunoconjugate of any one of aspects 3-11, wherein the antibody is a biosimilar of an antibody selected from the group consisting of pembrolizumab, nivolumab, atezolizumab, ipilimumab obinutuzumab, trastuzumab, cetuximab, rituximab, pertuzumab, bevacizumab, daratumumab, etanercept olaratumab, and elotuzumab.

45. The immunoconjugate of any one of aspects 3-11, wherein the antibody is a biosimilar of cetuximab.

46. The immunoconjugate of any one of aspects 3-11, wherein the antibody is a biosimilar of rituximab.

47. The immunoconjugate of any one of aspects 3-11, wherein the antibody is a biosimilar of trastuzumab.

48. The immunoconjugate of any one of aspects 3-11, wherein the antibody comprises a modified Fc region.

49. The immunoconjugate of aspect 48, wherein the modified Fc region contains at least one amino acid insertion, deletion, or substitution.

50. The immunoconjugate of aspect 48, wherein the modified Fc region results in modulated binding of an Fc receptor selected from the group consisting of FcγRI (CD64), FcγRIIA (CD32), FcγRIIB (CD32), FcγRIIIA (CD16a), and FcγRIIIB (CD16b), as compared to the native antibody lacking the modified Fc region.

51. The immunoconjugate of aspect 48, wherein the modified Fc region increases the binding of the Fc region to an Fc receptor FcγRIIIA (CD16a).

52. The immunoconjugate of aspect 48, wherein the modified Fc region increases the binding of the Fc region to an Fc receptor FcγRIIIB (CD 16b).

53. The immunoconjugate of any one of aspects 1-52, wherein the immunoconjugate has a structure according to Formula I:

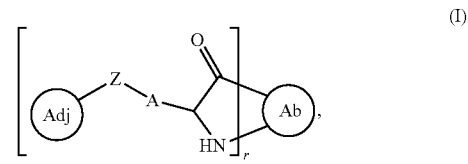

or a pharmaceutically acceptable salt thereof, wherein Ab is an antibody; A is an unmodified amino acid sidechain in the antibody or a modified amino acid sidechain in the antibody; Z is a linking moiety; Adj is an adjuvant moiety; and subscript r is an integer from 1 to 10.

54. The immunoconjugate of aspect 53, wherein the immunoconjugate has a structure according to Formula Ia:

(Ia)

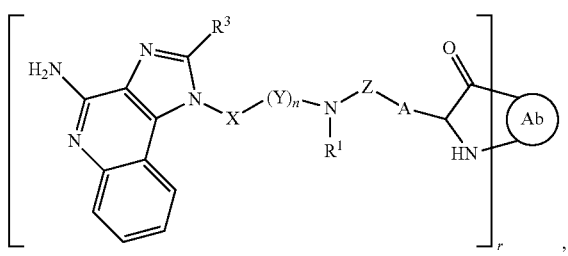

or a pharmaceutically acceptable salt thereof, wherein
Ab is an antibody;
A is an unmodified amino acid sidechain in the antibody or a modified amino acid sidechain in the antibody;
Z is a linking moiety;
$R^1$ is selected from H and $C_{1-4}$ alkyl; or
Z, $R^1$, and the nitrogen atom to which they are attached form a linking moiety comprising a 5- to 8-membered heterocycle;
each Y is independently $CHR^2$, wherein $R^2$ is selected from H, OH, and $NH_2$,
$R^3$ is selected from $C_{1-6}$ alkyl and 2- to 6-membered heteroalkyl, each of which is optionally substituted with one or more members selected from the group consisting of halo, hydroxy, amino, oxo (=O), alkylamino, amido, acyl, nitro, cyano, and alkoxy;
X is selected from O and $CH_2$;
subscript n is an integer from 1 to 12; and
subscript r is an integer from 1 to 10.

55. The immunoconjugate of aspect 54, wherein the immunoconjugate has a structure according to Formula Ib:

(Ib)

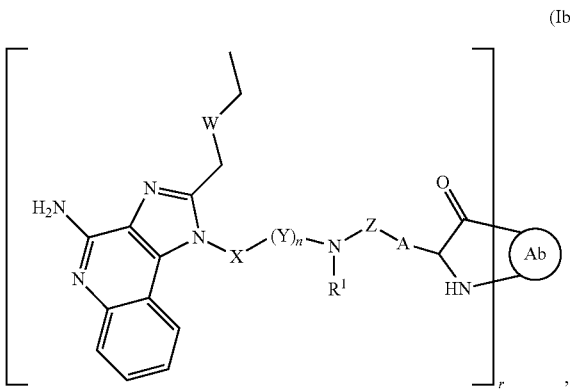

or a pharmaceutically acceptable salt thereof, wherein
Ab is an antibody;
A is an unmodified amino acid sidechain in the antibody or a modified amino acid sidechain in the antibody;
Z is a linking moiety;
$R^1$ is selected from H and $C_{1-4}$ alkyl; or
Z, $R^1$, and the nitrogen atom to which they are attached form a linking moiety comprising a 5- to 8-membered heterocycle;
each Y is independently $CHR^2$, wherein $R^2$ is selected from H, OH, and $NH_2$;
X is selected from O and $CH_2$;
subscript n is an integer from 1 to 12; and
W is selected from the group consisting of O and $CH_2$.

56. The immunoconjugate of aspect 55, wherein the immunoconjugate has a structure according to Formula Ic:

(Ic)

or a pharmaceutically acceptable salt thereof, wherein
Ab is an antibody;
subscript r is an integer from 1 to 10;
A is an unmodified amino acid sidechain in the antibody or a modified amino acid sidechain in the antibody;
Z is a linking moiety; and
$R^1$ is selected from H and $C_{1-4}$ alkyl; or
Z, $R^1$, and the nitrogen atom to which they are attached form a linking moiety comprising a 5- to 8-membered heterocycle; and
$R^2$ is selected from H, OH, and $NH_2$.

57. The immunoconjugate of aspect 56, the immunoconjugate has a structure according to Formula Id:

(Id)

or a pharmaceutically acceptable salt thereof, wherein Ab is an antibody; A is an unmodified amino acid sidechain in the antibody or a modified amino acid sidechain in the antibody; $R^2$ is selected from H, OH, and $NH_2$; and subscript r is an integer from 1 to 10.

58. The immunoconjugate of any one of aspects 53-56, wherein Z is selected from:

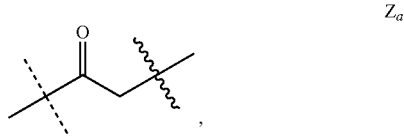

$Z_a$

-continued

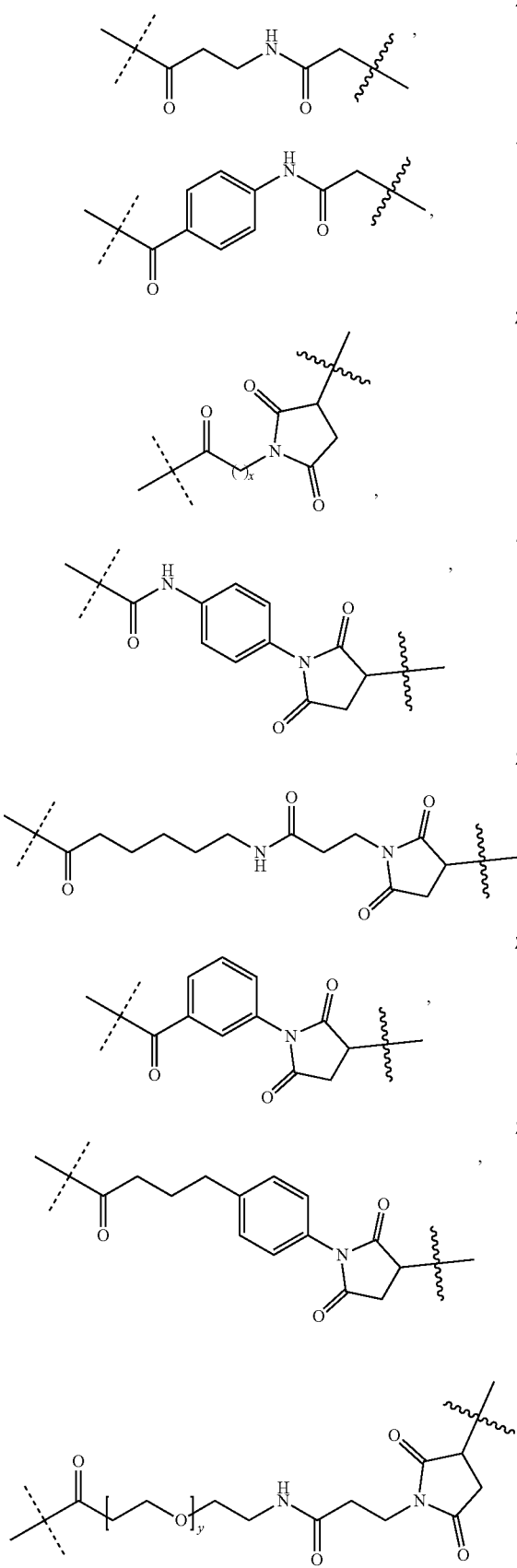

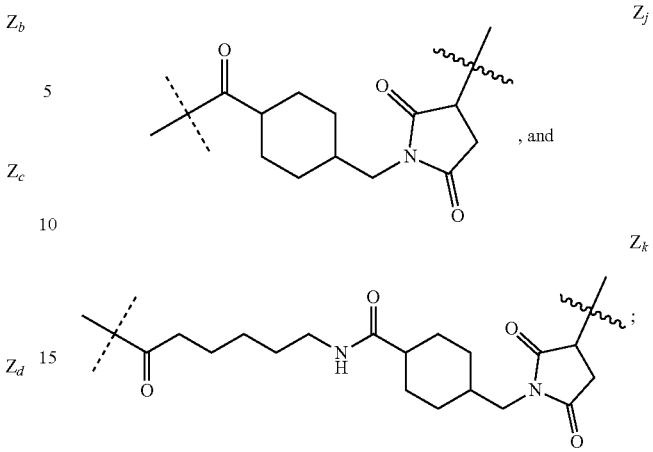

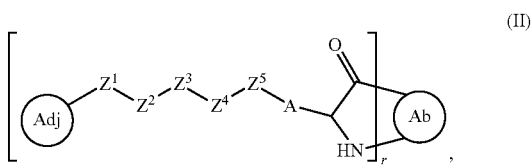

wherein subscript x is an integer from 1 to 12; subscript y is an integer from 1 to 30; the dashed line ("⸺") represents the point of attachment to the adjuvant moiety; and the wavy line ("⸺") represents the point of attachment to an amino acid sidechain in the antibody.

59. The immunoconjugate of any one of aspects 1-52, wherein the immunoconjugate has a structure according to Formula II:

$$\left[ \text{Adj} - Z^1 - Z^2 - Z^3 - Z^4 - Z^5 - A \underset{HN}{\overset{O}{\bigg\langle}} Ab \right]_r \quad (II)$$

or a pharmaceutically acceptable salt thereof, wherein Ab is an antibody; wherein A is an unmodified amino acid sidechain in the antibody or a modified amino acid sidechain in the antibody; wherein Adj is an adjuvant moiety; wherein subscript r is an integer 1 to 10; and wherein:

$Z^1$ is selected from —C(O)—, —C(O)NH—, —CH$_2$—;

$Z^2$ and $Z^4$ are independently selected from a bond, $C_{1-30}$ alkylene, and 3- to 30-membered heteroalkylene, wherein:
  one or more groupings of adjacent atoms in the $C_{1-30}$ alkylene and 3- to 30-membered heteroalkylene are optionally and independently replaced by —C(O)—, —NR$^a$C(O)—, or —C(O)NR$^a$-,
  one or more groupings of adjacent atoms in the $C_{1-30}$ alkylene and 3- to 30-membered heteroalkylene are optionally and independently replaced by a 4- to 8-membered, divalent carbocycle,
  one or more groupings of adjacent atoms in the $C_{1-30}$ alkylene and 3- to 30-membered heteroalkylene are optionally and independently replaced by a 4- to 8-membered, divalent heterocycle having one to four heteroatoms selected from O, S, and N, and
  each $R^a$ is independently selected from H and $C_{1-6}$ alkyl;

$Z^3$ is selected from a bond, a divalent peptide moiety, and a divalent polymer moiety; and $Z^5$ is bonded to the sidechain of an amino acid sidechain in the antibody.

60. The immunoconjugate of aspect 59, wherein the immunoconjugate has a structure according to Formula IIa:

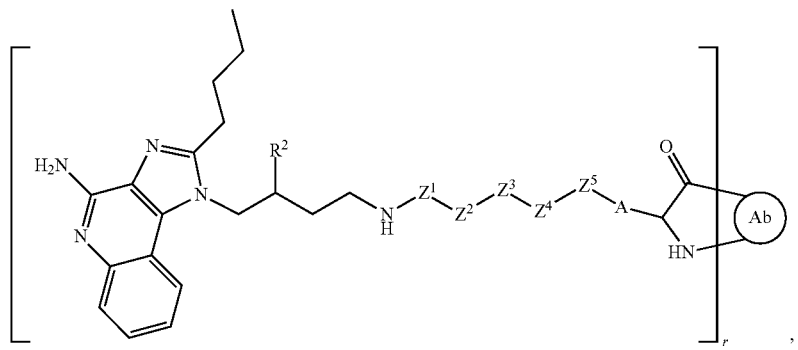

(IIa)

or a pharmaceutically acceptable salt thereof, wherein $Z^1$ is selected from —C(O)—, —C(O)NH—, —CH$_2$—;

$Z^2$ and $Z^4$ are independently selected from a bond, $C_{1-30}$ alkylene, and 3- to 30-membered heteroalkylene, wherein:

one or more groupings of adjacent atoms in the $C_{1-30}$ alkyl and 3- to 30-membered heteroalkylene are optionally and independently replaced by —C(O)—, —NR$^a$C(O)—, or —C(O)NR$^a$—;

one or more groupings of adjacent atoms in the $C_{1-30}$ alkylene and 3- to 30-membered heteroalkylene are optionally and independently replaced by a 4- to 8-membered, divalent carbocycle, one or more groupings of adjacent atoms in the $C_{1-30}$ alkylene and 3- to 30-membered heteroalkylene are optionally and independently replaced by a 4- to 8-membered, divalent heterocycle having one to four heteroatoms selected from O, S, and N, and each $R^a$ is independently selected from H and $C_{1-6}$ alkyl;

$Z^3$ is selected from a bond, a divalent peptide moiety, and a divalent polymer moiety; and $Z^5$ is selected from an amine-bonded moiety and a thiol-bonded moiety.

61. The immunoconjugate of any one of aspects 1-52, wherein the immunoconjugate has a structure according to Formula III:

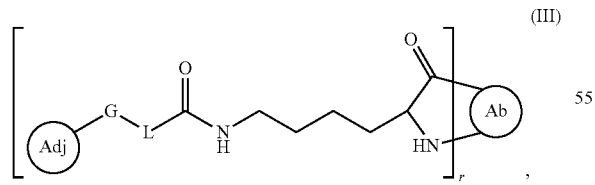

(III)

or a pharmaceutically acceptable salt thereof, wherein Ab is an antibody with at least one lysine side chain, Adj is an adjuvant, G is CH$_2$, C=O, or a bond, L is a linker, and subscript r is an integer from 1 to 10.

62. The immunoconjugate of aspect 61, wherein L is selected from:

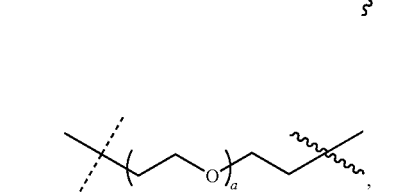

L1

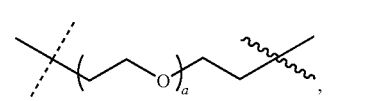

L2

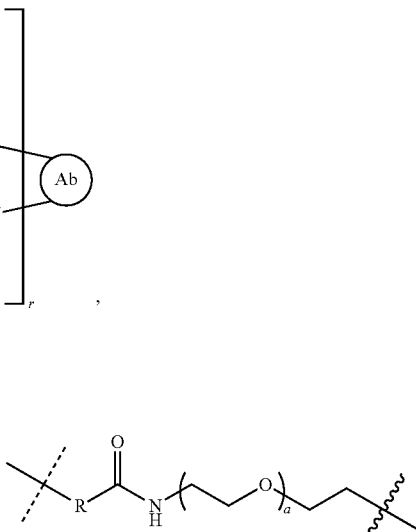

L3

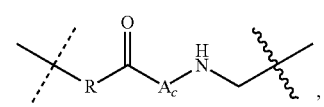

L4

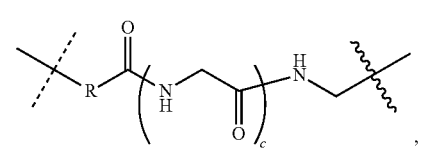

L5

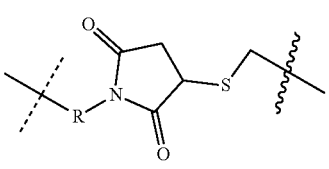

L6

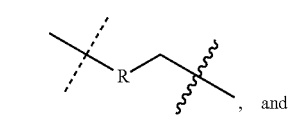

, and

L7

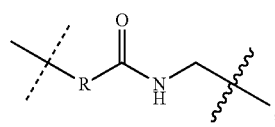

;

wherein R is optionally present and is a linear or branched, cyclic or straight, saturated or unsaturated alkyl, heteroalkyl, aryl, or heteroaryl chain comprising from 1 to 8 carbon units; a is an integer from 1 to 40; each A is independently selected from any amino acid; subscript c is an integer from 1 to 20; the dashed line ("-- --") represents the point of attachment to

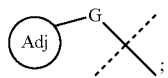

and the wavy line ("~~~") represents the point of attachment to

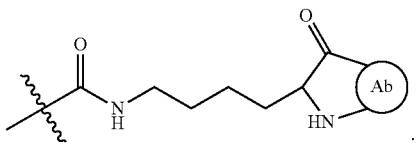

63. The immunoconjugate of aspect 61, wherein the immunoconjugate has a structure according to Formula IIIa-Formula IIIg:

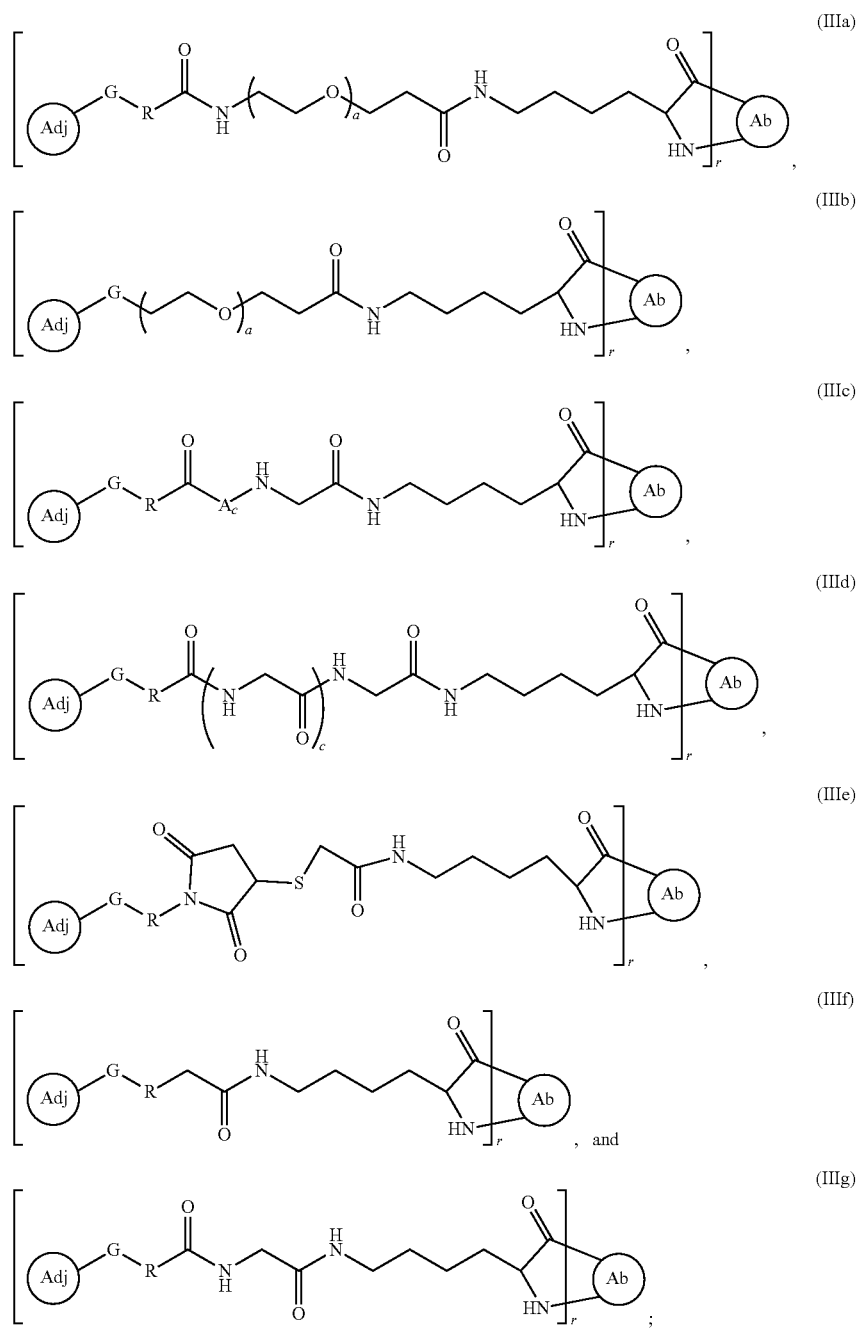

or a pharmaceutically acceptable salt thereof, wherein Ab is an antibody with at least one lysine side chain; Adj is an adjuvant; G is $CH_2$, C=O, or a bond; R is optionally present and is a linear or branched, cyclic or straight, saturated or unsaturated alkyl, heteroalkyl, aryl, or heteroaryl chain comprising from 1 to 8 carbon units; subscript a is an integer from 1 to 40; each A is independently selected from any amino acid; subscript c is an integer from 1 to 20; and subscript r is an integer from 1 to 10.

64. The immunoconjugate of any one of aspects 61-63, wherein the immunoconjugate has a structure according to Formula IVa-Formula IVk:

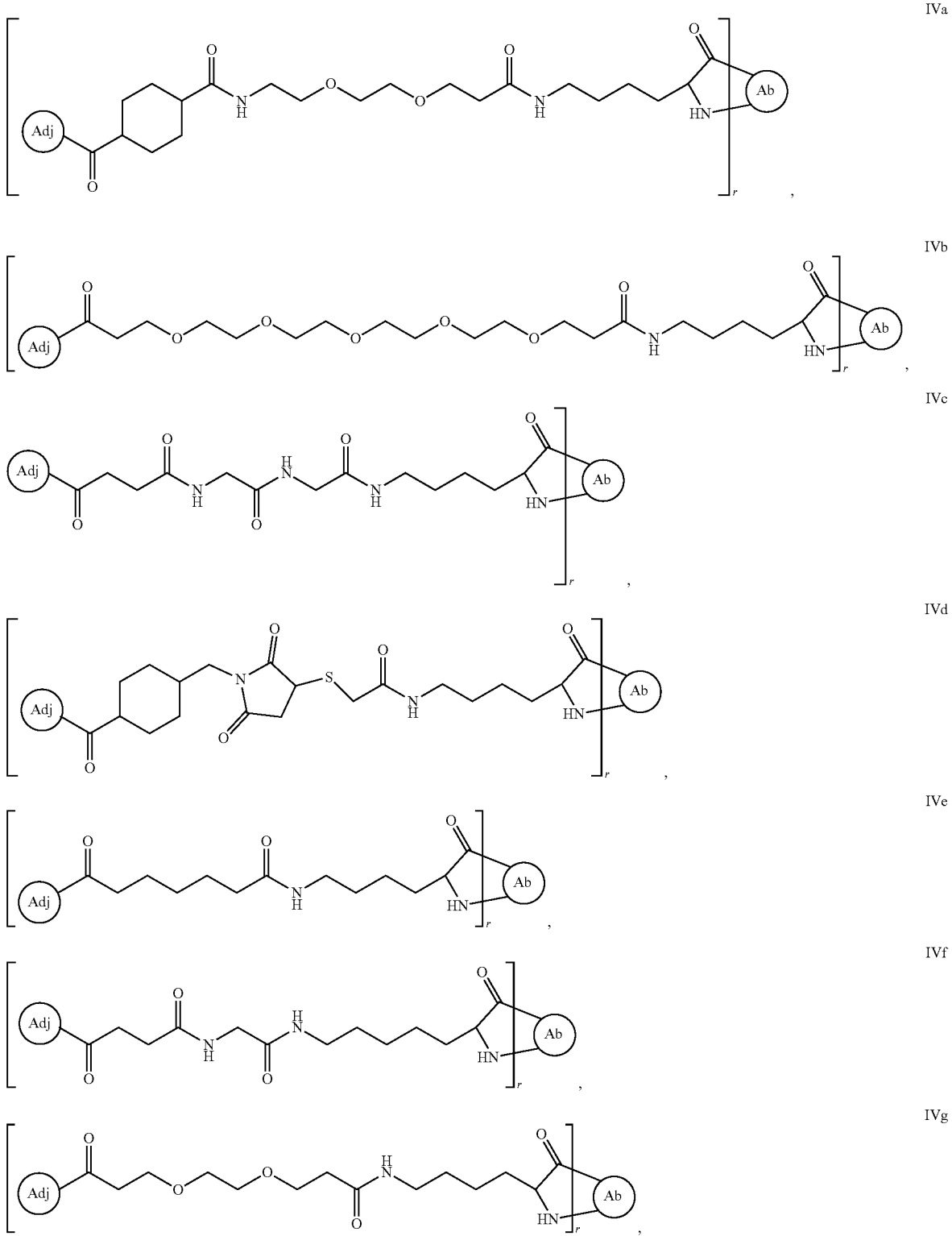

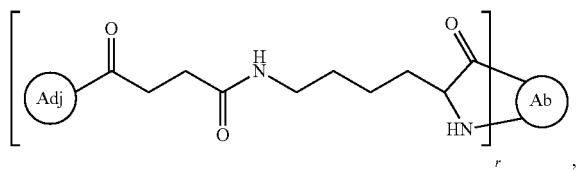

IVh

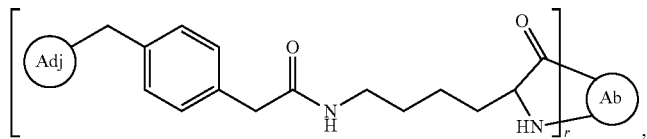

IVi

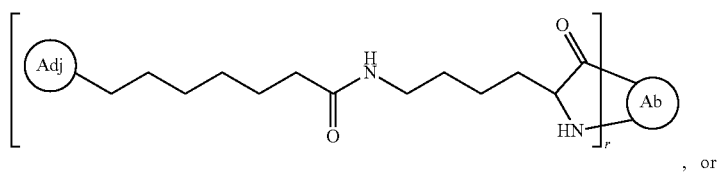

IVj

, or

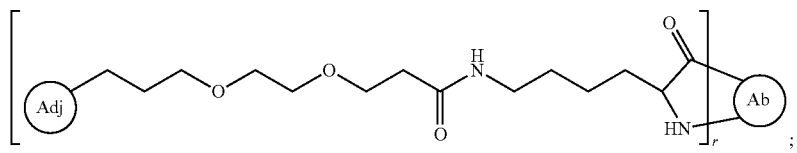

IVk

;

or a pharmaceutically acceptable salt thereof, wherein Ab is an antibody with at least one lysine side chain; Adj is an adjuvant; and subscript r is an integer from 1 to 10.

65. The immunoconjugate of any one of aspects 1-53, 59, and 61-64, wherein the adjuvant moiety is a pattern recognition receptor (PRR) agonist.

66. The immunoconjugate of aspect 65, wherein the adjuvant moiety is a Toll-like receptor (TLR) agonist.

67. The immunoconjugate of aspect 65, wherein the adjuvant moiety is a Toll-like receptor (TLR) agonist selected from the group consisting of a TLR2 agonist, a TLR3 agonist, a TLR4 agonist, a TLR7 agonist, a TLR8 agonist, a TLR7/TLR8 agonist, and a TLR9 agonist.

68. The immunoconjugate of aspect 65, wherein the adjuvant moiety is a TLR7 agonist, a TLR8 agonist, or a TLR7/TLR8 agonist.

69. The immunoconjugate of aspect 65, wherein the adjuvant moiety is selected from the group consisting of gardiquimod (1-(4-amino-2-ethylaminomethylimidazo[4,5-c]quinolin-1-yl)-2-methylpropan-2-ol), imiquimod (R837), loxoribine, IRM1 (1-(2-amino-2-methylpropyl)-2-(ethoxymethyl)-1H-imidazo-[4,5-c]quinolin-4-amine), IRM2 (2-methyl-1-[2-(3-pyridin-3-ylpropoxy)ethyl]-1H-imidazo[4,5-c]quinolin-4-amine), IRM3 (N-(2-[2-[4-amino-2-(2-methoxyethyl)-1H-imidazo [4,5-c]quinolin-1-yl] ethoxy]ethyl)-N-methylcyclohexanecarboxamide), CL097 (2-(ethoxymethyl)-1H-imidazo[4,5-c]quinolin-4-amine), CL307, CL264, resiquimod, 3M-052/MEDI9197, SD-101 (N-[(4S)-2,5-dioxo-4-imidazolidinyl]-urea), motolimod (2-amino-N,N-dipropyl-8-[4-(pyrrolidine-1-carbonyl)phenyl]-3H-1-benzazepine-4-carboxamide), CL075 (2-propylthiazolo[4,5-c]quinolin-4-amine), and TL8-506 (3H-1-benzazepine-4-carboxylic acid, 2-amino-8-(3-cyanophenyl)-, ethyl ester), N-a-palmitoyl-S-[2,3-bis(palmitoyloxy)-(2RS)-propyl]-L-cysteine, palmitoyl-Cys((RS)-2,3-di(palmitoyloxy)-propyl) (Pam3Cys), triacyl lipid A (OM-174), Lipoteichoic acid (LTA), peptidoglycan, CL419 (S-(2,3-bis (palmitoyloxy)-(2RS)propyl)-(R)-cysteinyl spermine), Pam$_2$CSK$_4$ (S-[2,3-bis(palmitoyloxy)-(2RS)-propyl]-[R]-cysteinyl-[S]-seryl-[S]-lysyl-[S]-lysyl-[S]-lysyl-[S]-lysine x 3 CF3COOH), CL572 (S-(2-myristoyloxy ethyl)-(R)-cysteinyl 4-((6-amino-2-(butylamino)-8-hydroxy-9H-purin-9-yl) methyl) aniline), CL413 (S-(2,3-bis(palmitoyloxy)-(2RS) propyl)-(R)-cysteinyl-(S)-seryl-(S)-lysyl-(S)-lysyl-(S)-lysyl-(S)-lysyl 4-((6-amino-2-(butylamino)-8-hydroxy-9H-purin-9-yl)methyl)aniline), and CL401 (S-(2,3-bis (palmitoyloxy)-(2RS)propyl)-(R)-cysteinyl 4-((6-amino-2 (butyl amino)-8-hydroxy-9H-purin-9-yl)methyl) aniline).

70. The immunoconjugate of aspect 65, wherein the adjuvant is an imidazoquinoline compound.

71. The immunoconjugate of any one of aspects 1-53, 59, and 61-64, wherein the adjuvant moiety is of formula:

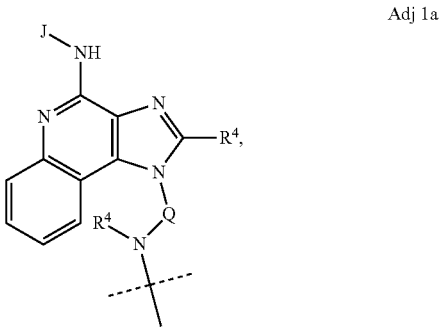

Adj 1a

-continued

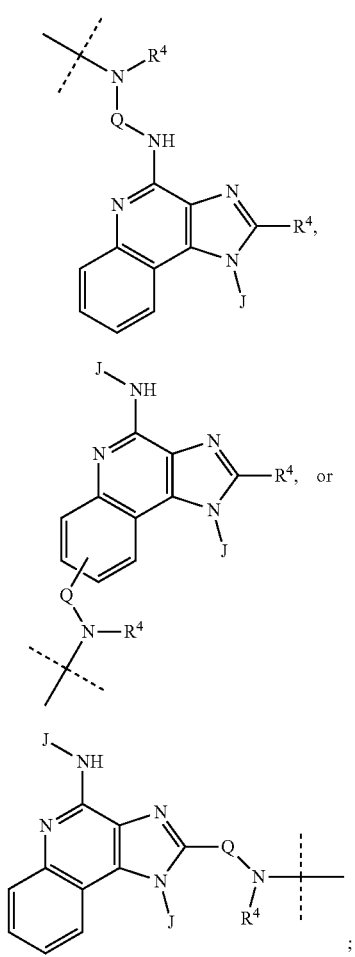

Adj 1b

Adj 1c

Adj 1d wherein each J independently is hydrogen, $OR^4$, or $R^4$; each $R^4$ independently is hydrogen, or an alkyl, heteroalkyl, cycloalkyl, heterocycloalkyl, aryl, heteroaryl, arylalkyl, or heteroarylalkyl group comprising from 1 to 8 carbon units; Q is optionally present and is an alkyl, heteroalkyl, cycloalkyl, heterocycloalkyl, aryl, heteroaryl, arylalkyl, or heteroarylalkyl group comprising from 1 to 8 carbon units; and the dashed line (" ⸺ ") represents the point of attachment of the adjuvant.

72. The immunoconjugate of aspect 71, wherein the adjuvant moiety is of formula:

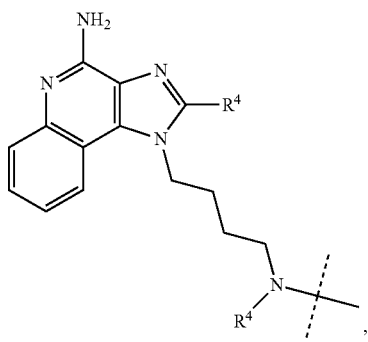

Adj 1a-i wherein each $R^4$ independently is selected from the group consisting of hydrogen, or alkyl, heteroalkyl, cycloalkyl, heterocycloalkyl, aryl, heteroaryl, arylalkyl, and heteroarylalkyl group comprising from 1 to 8 carbon units and the dashed line (" ⸺ ") represents the point of attachment of the adjuvant.

73. The immunoconjugate of any one of aspects 1-53, 59, and 61-64, wherein the adjuvant moiety is of formula:

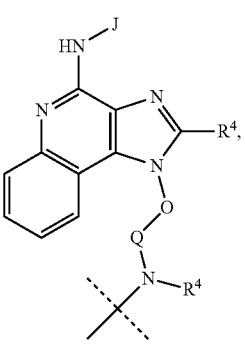

Adj 2a

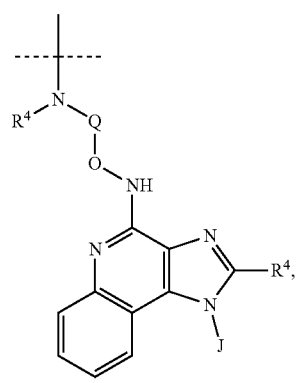

Adj 2b

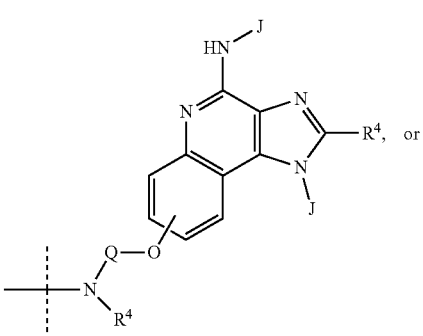

Adj 2c

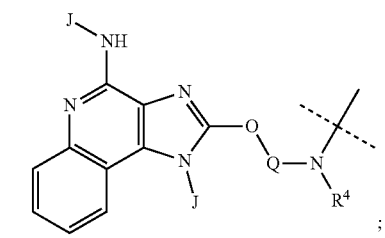

Adj 2d wherein J is hydrogen, $OR^4$, or $R^4$; each $R^4$ independently is hydrogen, or alkyl, heteroalkyl, cycloalkyl, heterocycloalkyl, aryl, heteroaryl, arylalkyl, and heteroarylalkyl group comprising from 1 to 8 carbon units; Q is selected from the group consisting of alkyl, or heteroalkyl, cycloalkyl, heterocycloalkyl, aryl, heteroaryl, arylalkyl, and heteroarylalkyl group comprising from 1 to 8 carbon units; and the dashed line ("╱╱") represents the point of attachment of the adjuvant.

74. The immunoconjugate of aspect 72, wherein the adjuvant moiety is of formula:

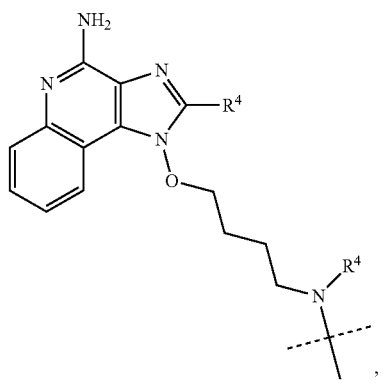

Adj 2a-i wherein each $R^4$ independently is selected from the group consisting of hydrogen, or alkyl, heteroalkyl, cycloalkyl, heterocycloalkyl, aryl, heteroaryl, arylalkyl, and heteroarylalkyl group comprising from 1 to 8 carbon units and the dashed line ("╱╱") represents the point of attachment of the adjuvant.

75. The immunoconjugate of any one of aspects 1-53, 59, and 61-64, wherein the adjuvant moiety is of formula:

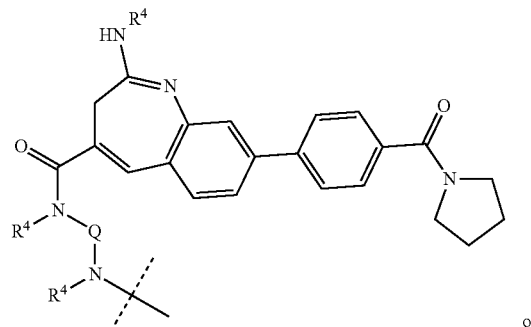

Adj 3a or

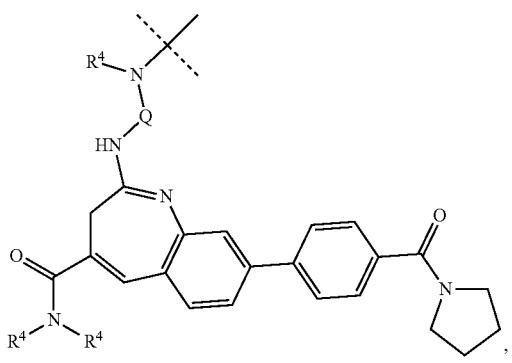

Adj 3b wherein each $R^4$ independently is hydrogen, or alkyl, heteroalkyl, cycloalkyl, heterocycloalkyl, aryl, heteroaryl, arylalkyl, or heteroarylalkyl group comprising from 1 to 8 carbon units; Q is alkyl, heteroalkyl, cycloalkyl, heterocycloalkyl, aryl, heteroaryl, arylalkyl, or heteroarylalkyl group comprising from 1 to 8 carbon units; and the dashed line ("╱╱") represents the point of attachment of the adjuvant.

76. The immunoconjugate of any one of aspects 1-53, 59, and 61-64, wherein the adjuvant moiety is of formula:

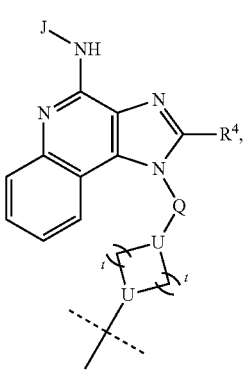

Adj 4a

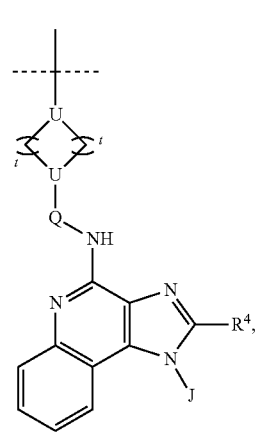

Adj 4b

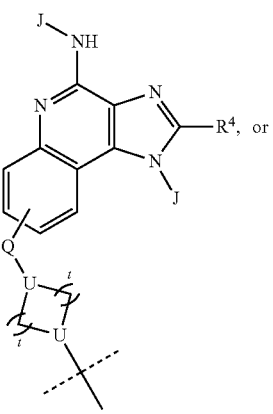

Adj 4c

-continued

Adj 4d

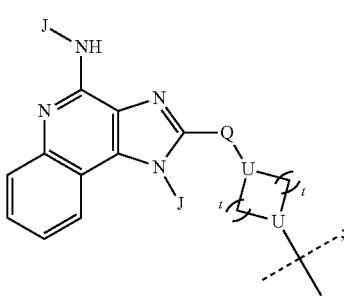

wherein each J independently is hydrogen, OR$^4$, or R$^4$; each R$^4$ independently is hydrogen, or an alkyl, heteroalkyl, cycloalkyl, heterocycloalkyl, aryl, heteroaryl, arylalkyl, or heteroarylalkyl group comprising from 1 to 8 carbon units; each U independently is CH or N wherein at least one U is N; each subscript t independently is an integer from 1 to 3; Q is optionally present and is an alkyl, heteroalkyl, cycloalkyl, heterocycloalkyl, aryl, heteroaryl, arylalkyl, or heteroarylalkyl group comprising from 1 to 8 carbon units; and the dashed line (" ⁓ ") represents the point of attachment of the adjuvant.

77. The immunoconjugate of aspect 74, wherein the adjuvant moiety is of formula:

Adj 4a-i

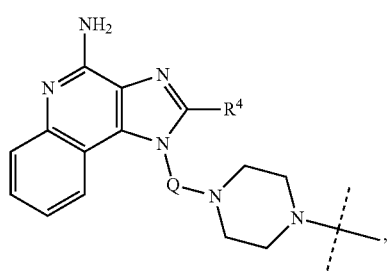

wherein R$^4$ is selected from the group consisting of hydrogen, or alkyl, heteroalkyl, cycloalkyl, heterocycloalkyl, aryl, heteroaryl, arylalkyl, and heteroarylalkyl group comprising from 1 to 8 carbon units Q is an alkyl, heteroalkyl, cycloalkyl, heterocycloalkyl, aryl, heteroaryl, arylalkyl, or heteroarylalkyl group comprising from 1 to 8 carbon units; and the dashed line (" ⁓ ") represents the point of attachment of the adjuvant.

78. The immunoconjugate of any one of aspects 1-53, 59, and 61-63, wherein the adjuvant moiety is of formula:

Adj 5a

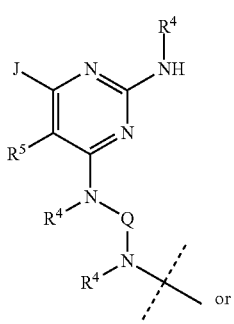

or

-continued

Adj 5b

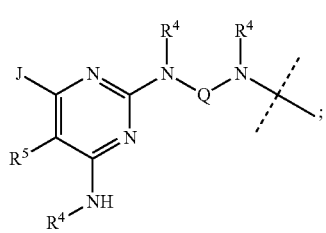

wherein J is hydrogen, OR$^4$, or R$^4$; each R$^4$ independently is hydrogen, or an alkyl, heteroalkyl, cycloalkyl, heterocycloalkyl, aryl, heteroaryl, arylalkyl, or heteroarylalkyl group comprising from 1 to 8 carbon units; R$^5$ is hydrogen, or an alkyl, heteroalkyl, cycloalkyl, heterocycloalkyl, aryl, heteroaryl, arylalkyl, or heteroarylalkyl group comprising from 1 to 10 carbon units; Q is an alkyl, heteroalkyl, cycloalkyl, heterocycloalkyl, aryl, heteroaryl, arylalkyl, or heteroarylalkyl group comprising from 1 to 8 carbon units; and the dashed line (" ⁓ ") represents the point of attachment of the adjuvant.

79. The immunoconjugate of aspect 76, wherein the adjuvant moiety is of formula:

Adj 5a-i

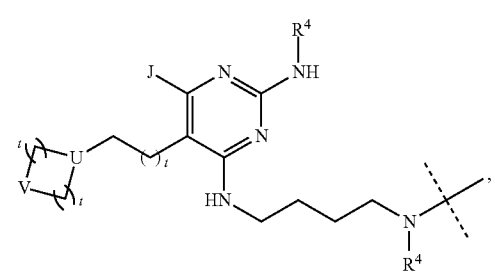

wherein J is hydrogen, OR$^4$, or R$^4$; each R$^4$ independently is selected from the group consisting of hydrogen, or alkyl, heteroalkyl, cycloalkyl, heterocycloalkyl, aryl, heteroaryl, arylalkyl, and heteroarylalkyl group comprising from 1 to 8 carbon units; U is CH or N; V is CH$_2$, O, or NH; each subscript t independently is an integer from 1 to 3; and the dashed line (" ⁓ ") represents the point of attachment of the adjuvant.

80. The immunoconjugate of any one of aspects 1-53, 59, and 61-64, wherein the adjuvant moiety is of formula:

Adj 6a

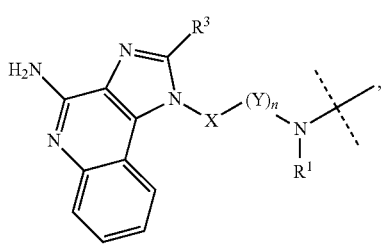

wherein R$^1$ is selected from H and C$_{1-4}$ alkyl; R$^3$ is selected from C$_{1-6}$ alkyl and 2- to 6-membered heteroalkyl, each of which is optionally substituted with one or more members selected from the group consisting of halo, hydroxy, amino, oxo (=O), alkylamino, amido, acyl, nitro, cyano, and alkoxy; X is selected from O and CH$_2$; each Y is independently CHR$^2$, wherein R$^2$ is selected from H, OH, and NH$_2$; subscript n is an integer from 1 to 12; and the dashed line ("⌇") represents the point of attachment of the adjuvant.

81. The immunoconjugate of any one of aspects 1-53, 59, and 61-64, wherein the adjuvant moiety is of formula:

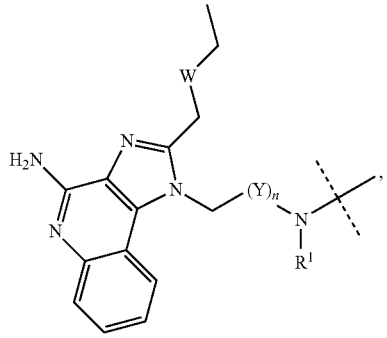

Adj 6a-i wherein W is selected from the group consisting of O and CH$_2$; R$^1$ is selected from H and C$_{1-4}$ alkyl; each Y is independently CHR$^2$, wherein R$^2$ is selected from H, OH, and NH$_2$; subscript n is an integer from 1 to 12; and the dashed line ("⌇") represents the point of attachment of the adjuvant.

82. The immunoconjugate of any one of aspects 1-53, 59, and 61-64, wherein the adjuvant moiety is of formula:

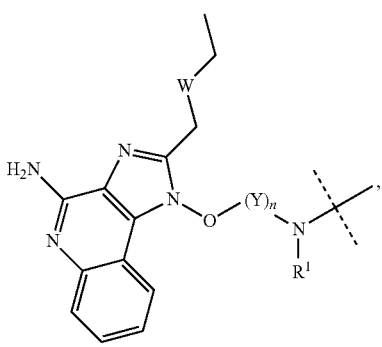

Adj 6a-ii wherein W is selected from the group consisting of O and CH$_2$; R$^1$ is selected from H and C$_{1-4}$ alkyl; each Y is independently CHR$^2$, wherein R$^2$ is selected from H, OH, and NH$_2$; subscript n is an integer from 1 to 12; and the dashed line ("⌇") represents the point of attachment of the adjuvant.

83. The immunoconjugate of any one of aspects 1-53, 59, and 61-64, wherein the adjuvant moiety is of formula:

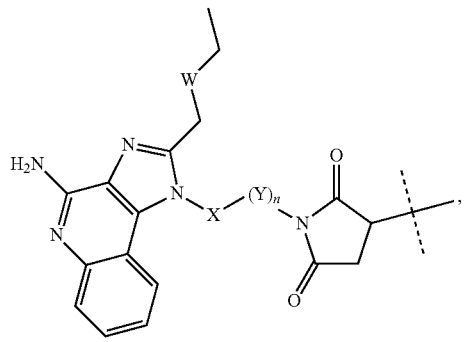

Adj 6a-iii wherein W is selected from the group consisting of O and CH$_2$; X is selected from O and CH$_2$; each Y is independently CHR$^2$, wherein R$^2$ is selected from H, OH, and NH$_2$; subscript n is an integer from 1 to 12; and the dashed line ("⌇") represents the point of attachment of the adjuvant.

84. The immunoconjugate of any one of aspects 1-53, 59, and 61-64, wherein the adjuvant moiety is of formula:

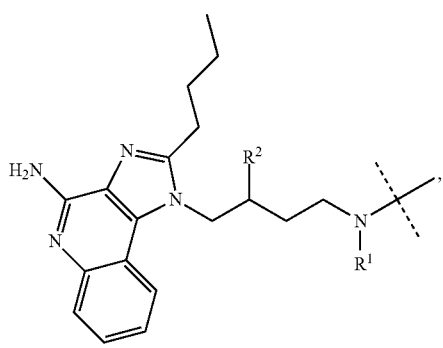

Adj 6a-iv wherein R$^1$ is selected from H and C$_{1-4}$ alkyl; R$^2$ is selected from H, OH, and NH$_2$; and the dashed line ("⌇") represents the point of attachment of the adjuvant.

85. The immunoconjugate of any one of aspects 1-53, 59, and 61-64, wherein the adjuvant moiety is of formula:

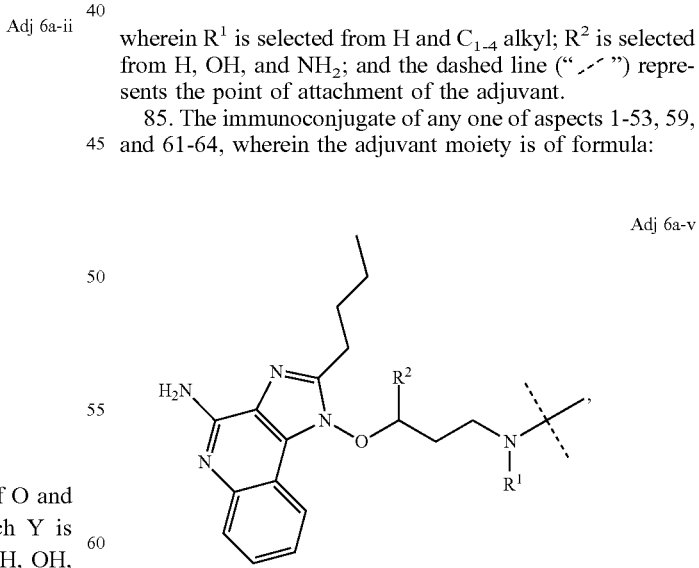

Adj 6a-v wherein R$^1$ is selected from H and C$_{1-4}$ alkyl; R$^2$ is selected from H, OH, and NH$_2$; and the dashed line ("⌇") represents the point of attachment of the adjuvant.

86. The immunoconjugate of any one of aspects 1-53, 59, and 61-64, wherein the adjuvant moiety is:

| 207 | 208 |
|---|---|
| 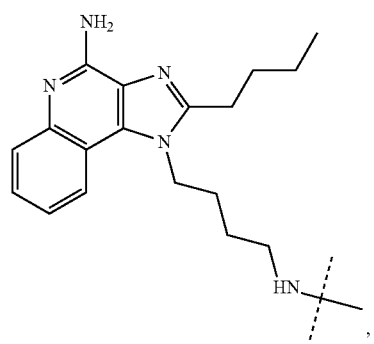 Adj-A | 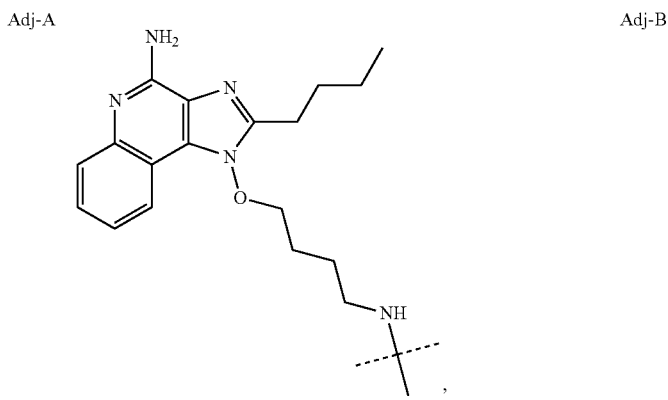 Adj-B |
| 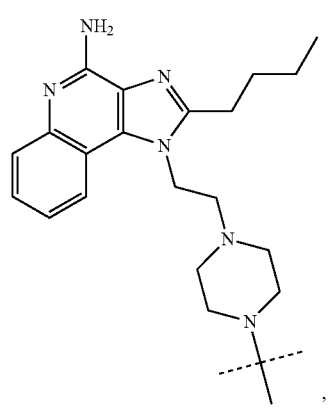 Adj-C | 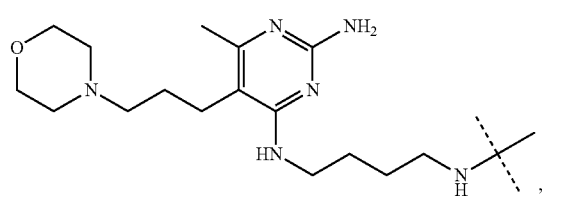 Adj-D |
| 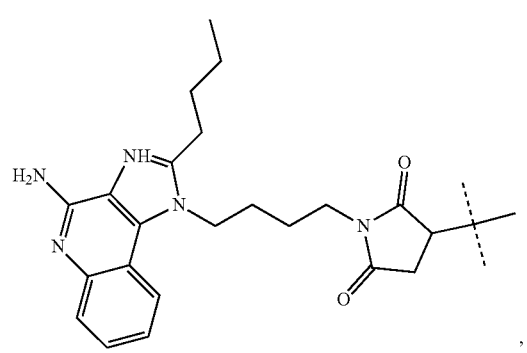 Adj-E | 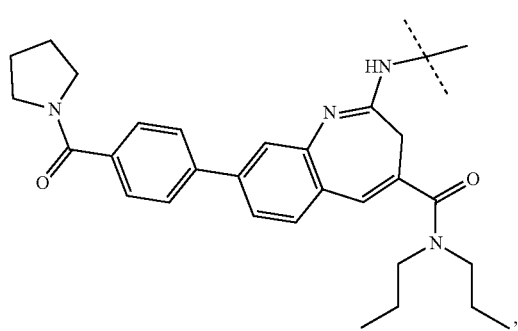 Adj-G |
| 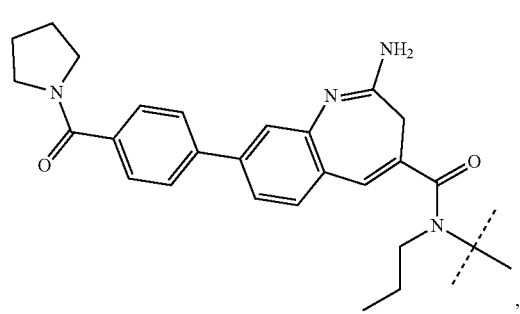 Adj-H | 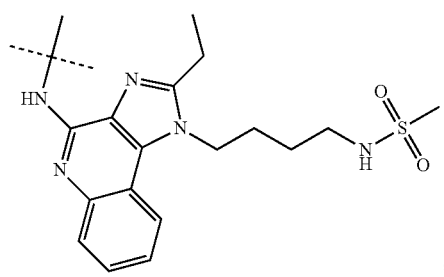 Adj-I |

Adj-I
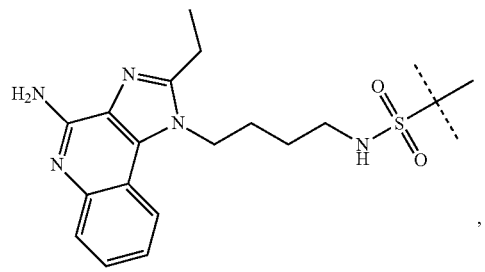
Adj-J
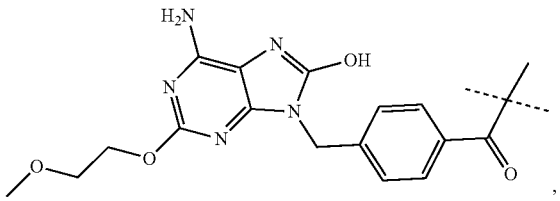
Adj-L
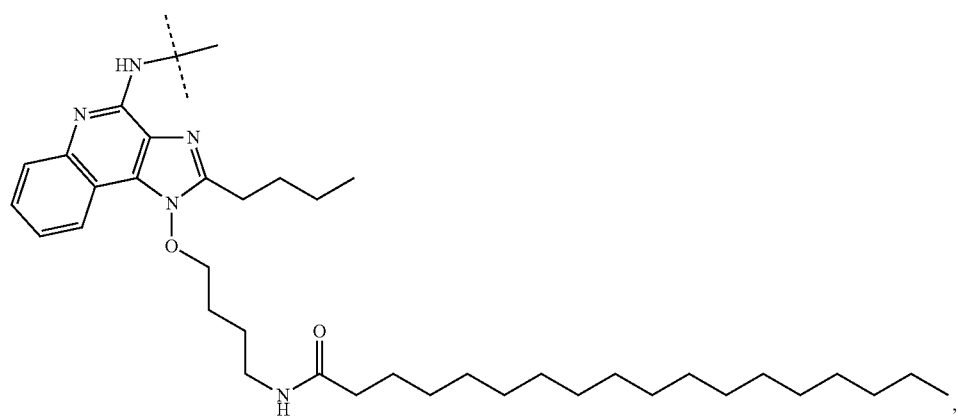
Adj-M
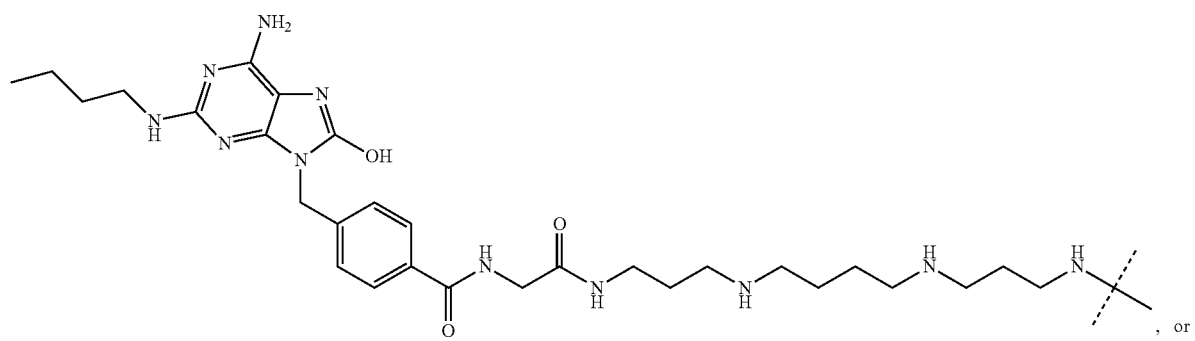
, or
Adj-N
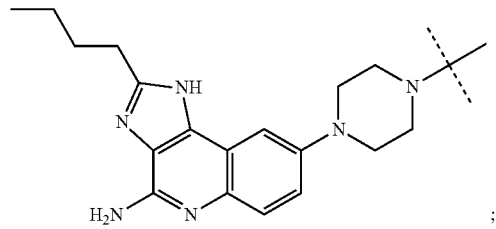
;
wherein the dashed line ("⁄⁻") represents the point of attachment of the adjuvant.

87. An immunoconjugate selected from:
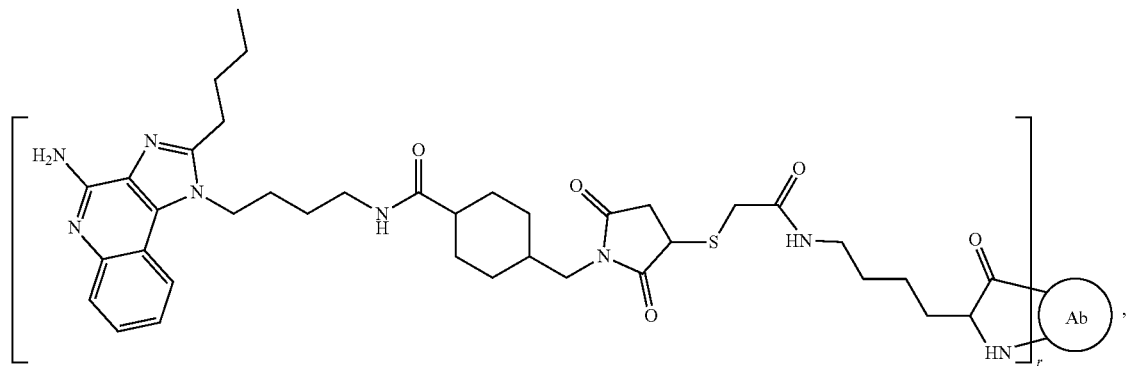
(BB01)
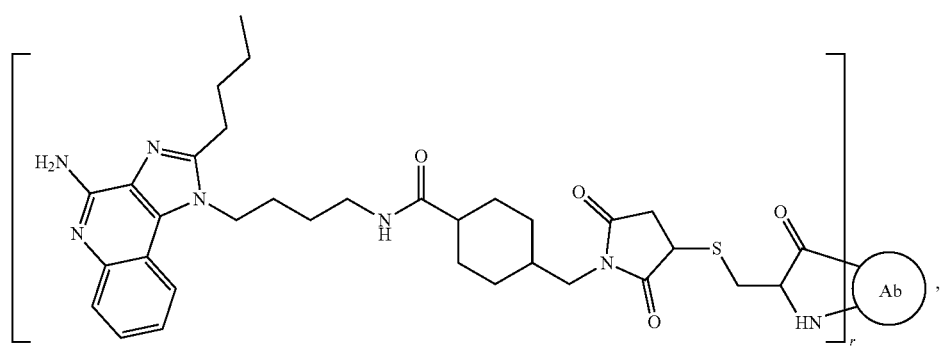
(BB02)
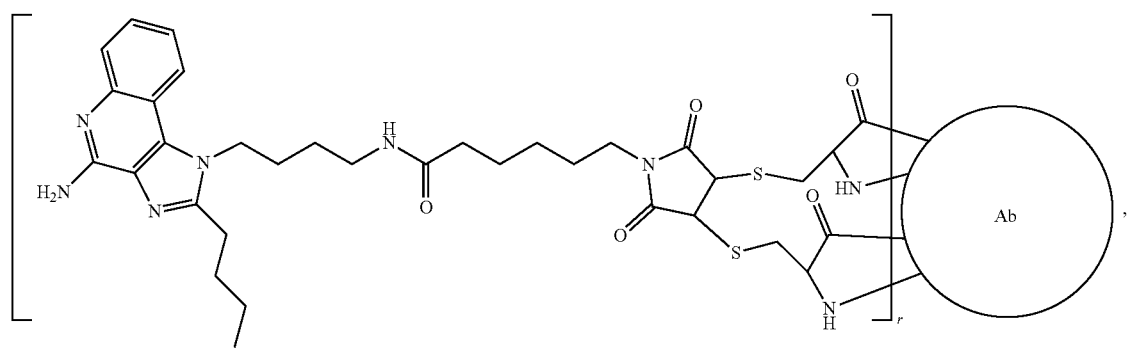
(BB03)
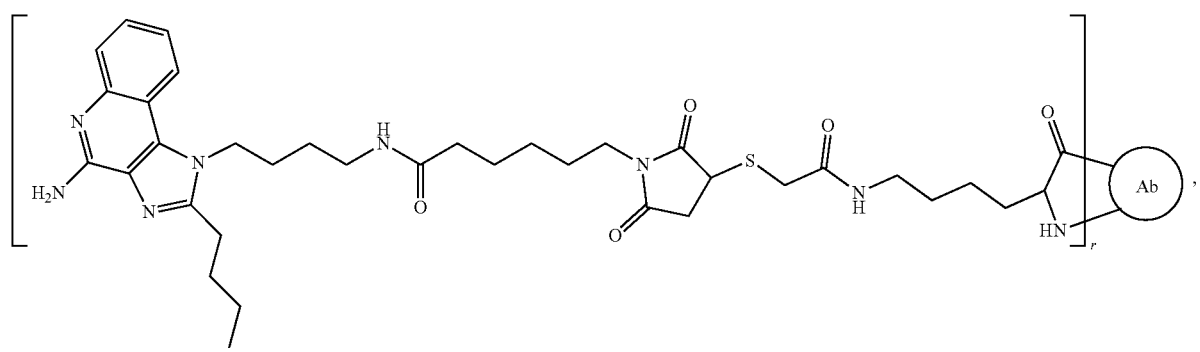
(BB05)

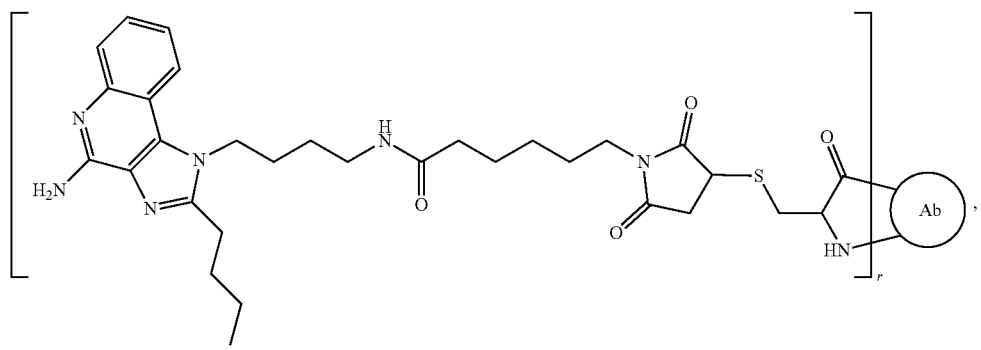
(BB06)
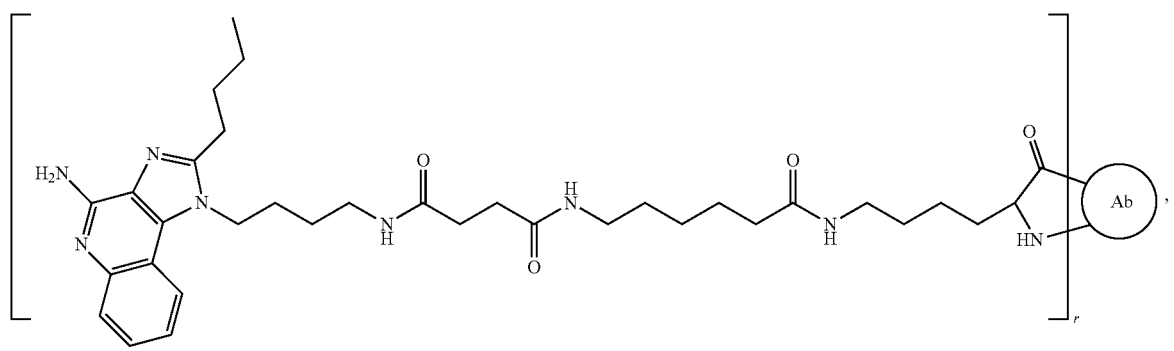
(BB08)
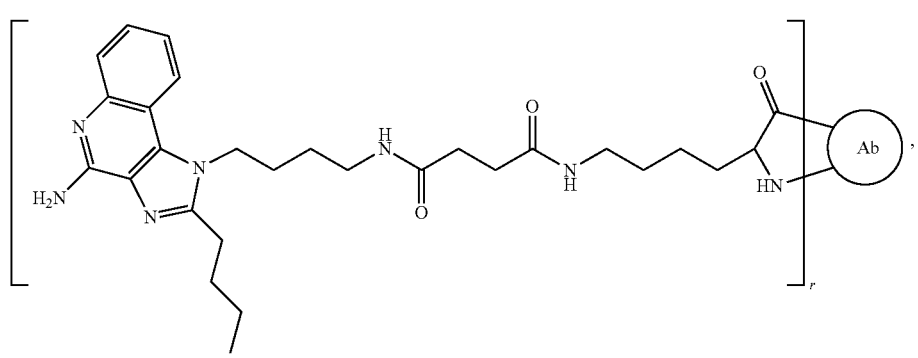
(BB09)
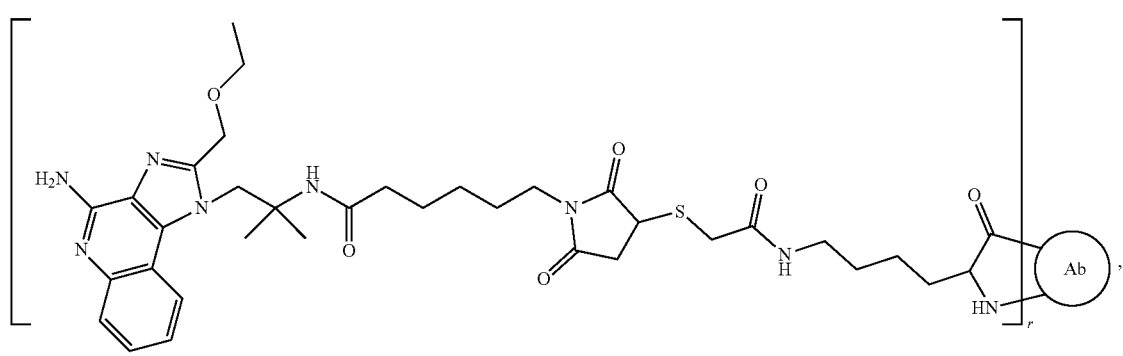
(BB10)

(BB11)
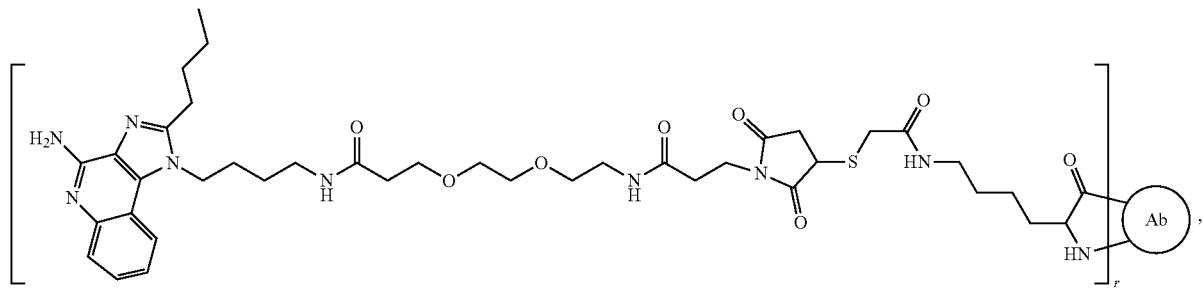
(BB12)
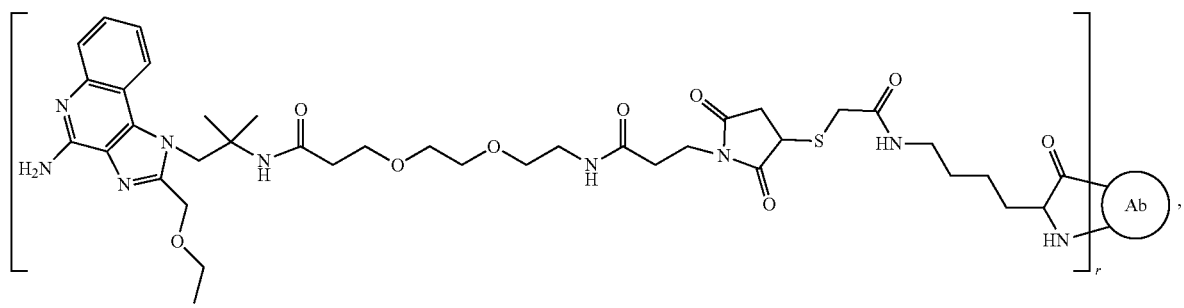
(BB13)
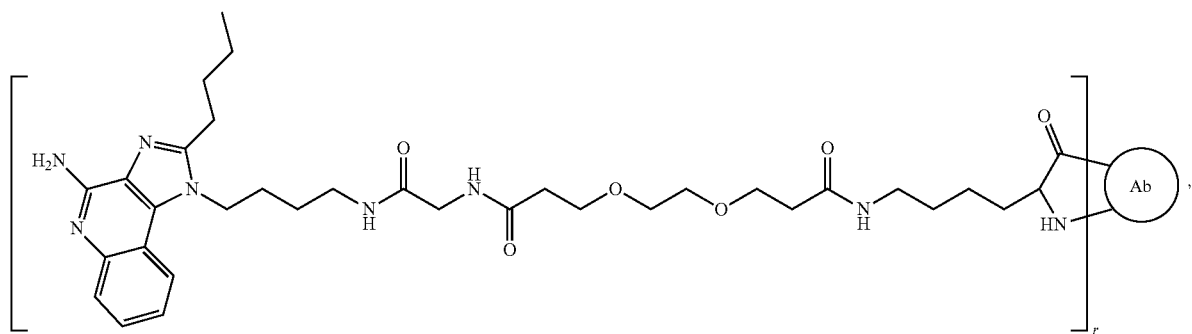
(BB14)
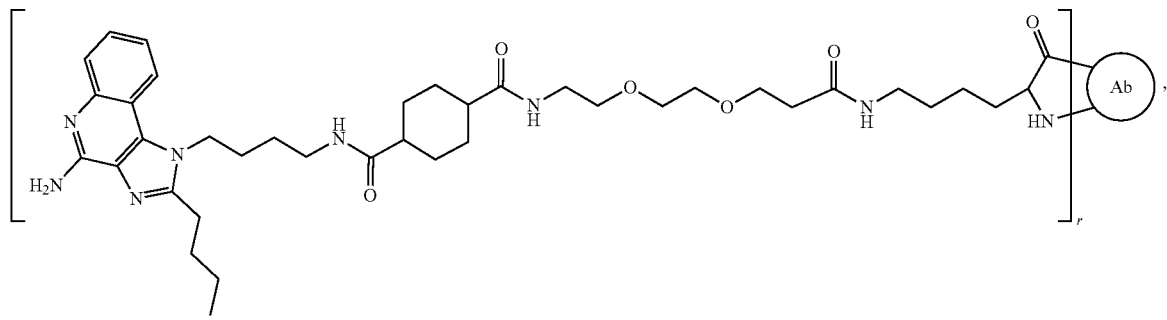

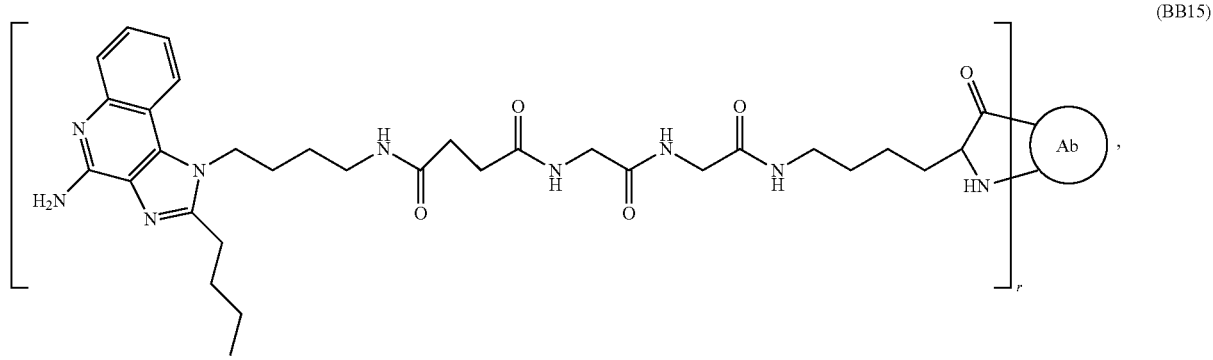
(BB15)
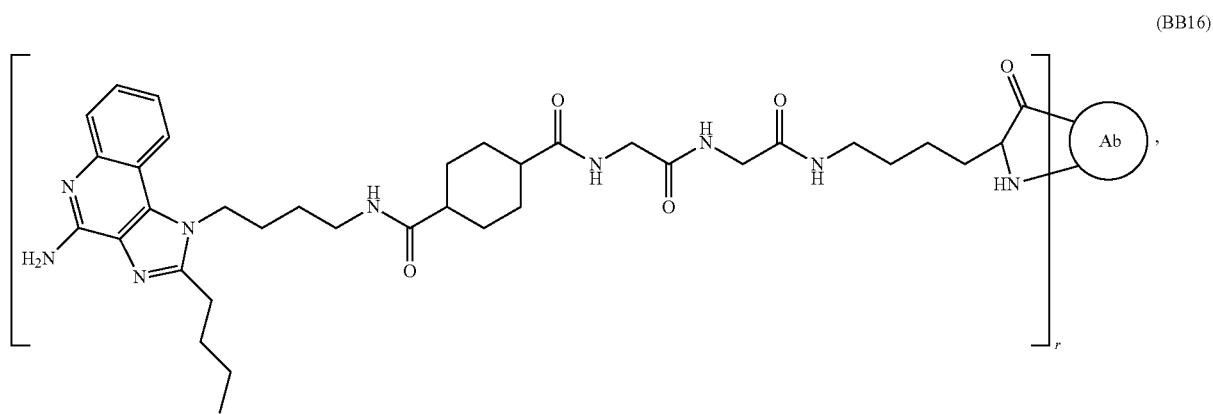
(BB16)
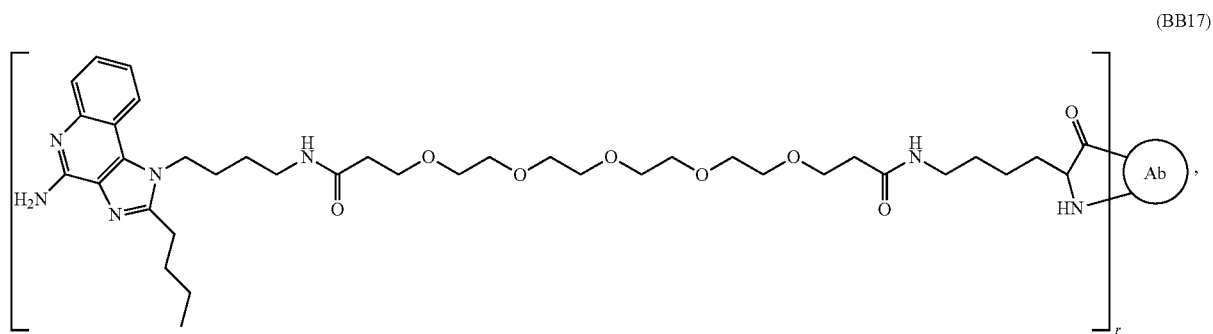
(BB17)
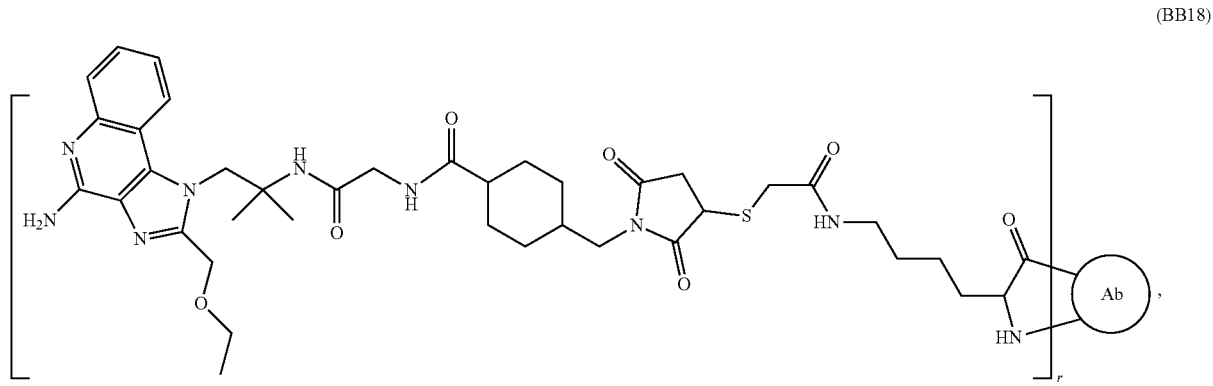
(BB18)

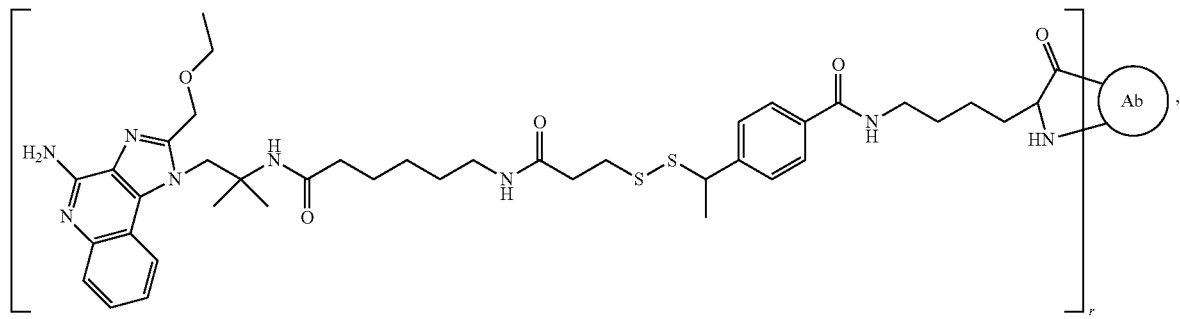
(BB19)
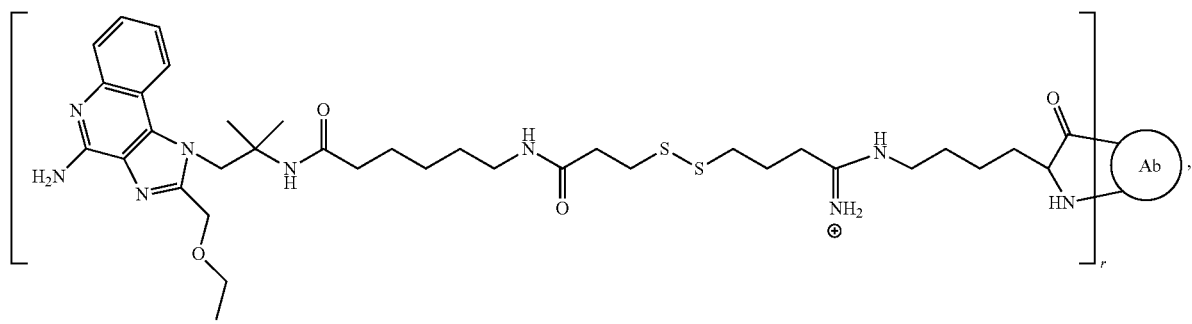
(BB20)
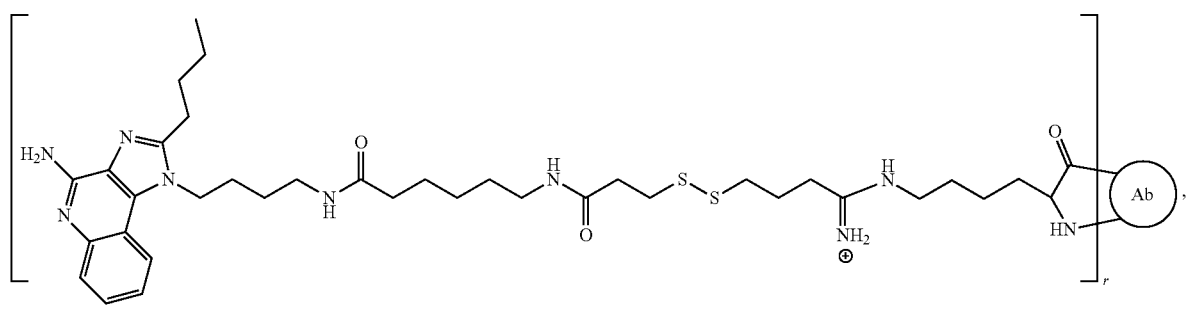
(BB21)
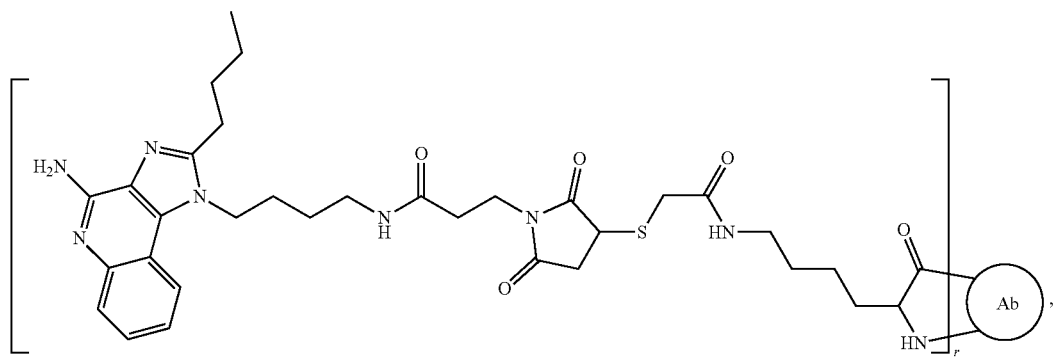
(BB22)

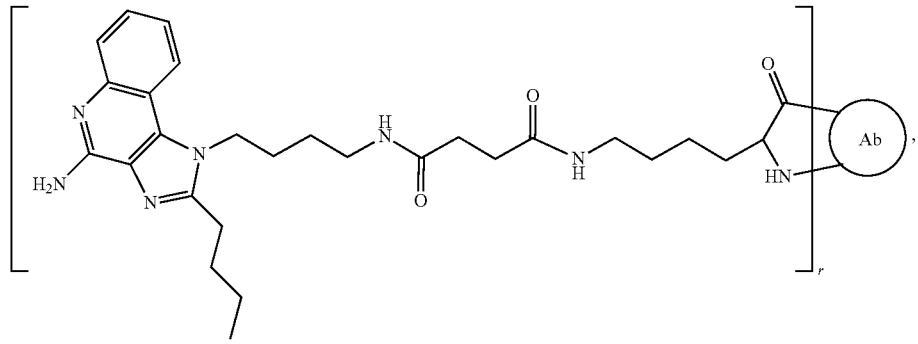
(BB23)
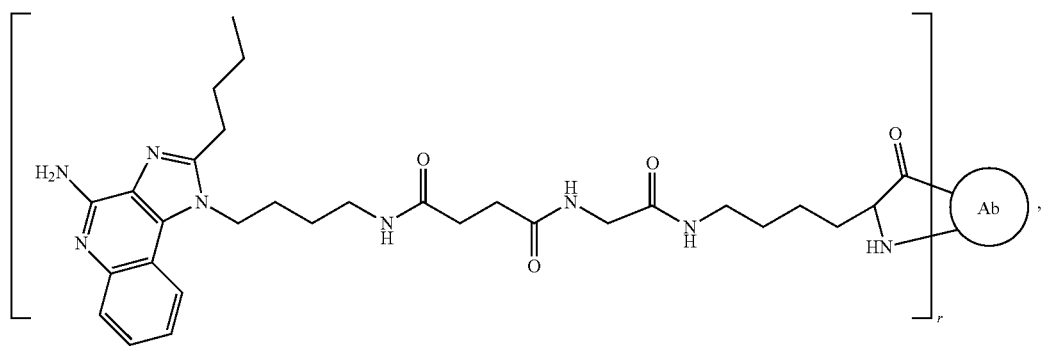
(BB24)
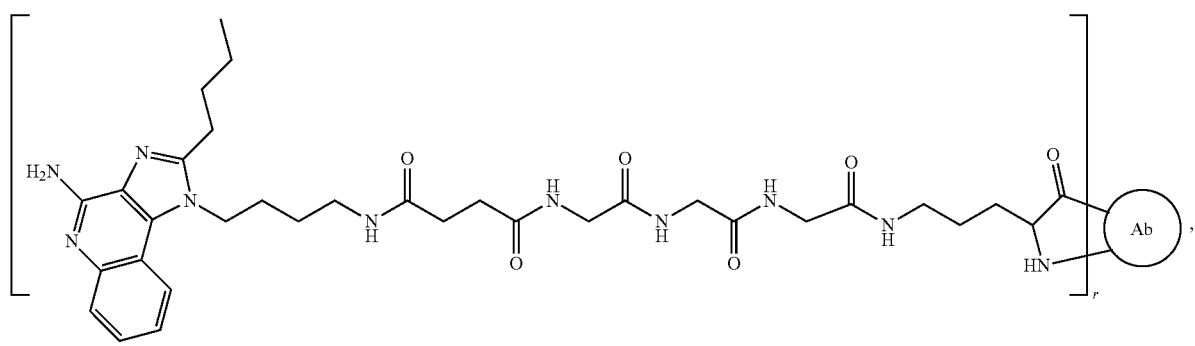
(BB25)
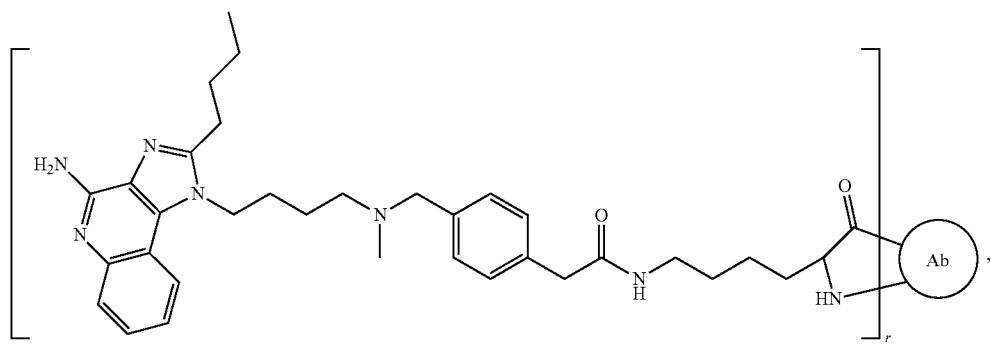
(BB26)

(BB27)
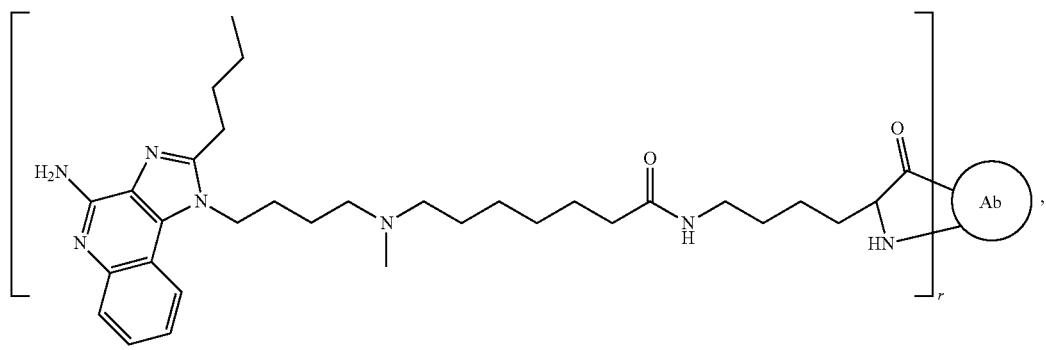
(BB32)
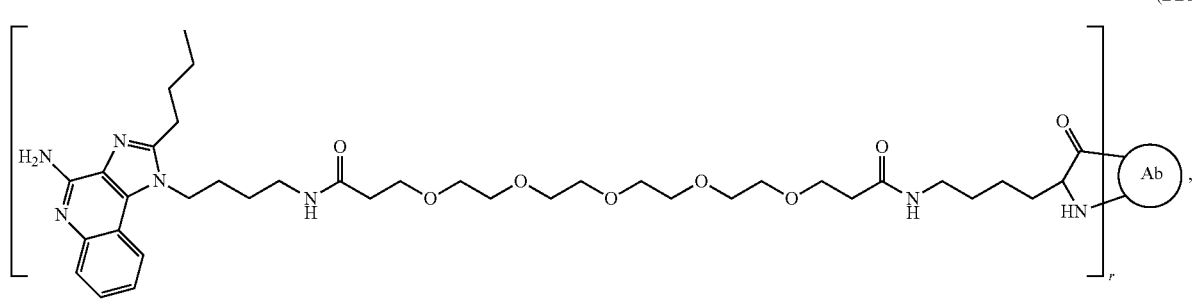
(BB35)
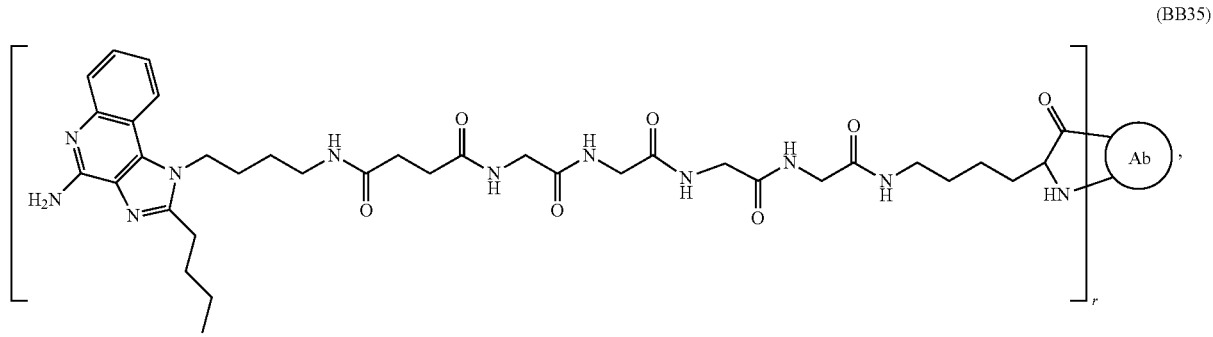
(BB36)
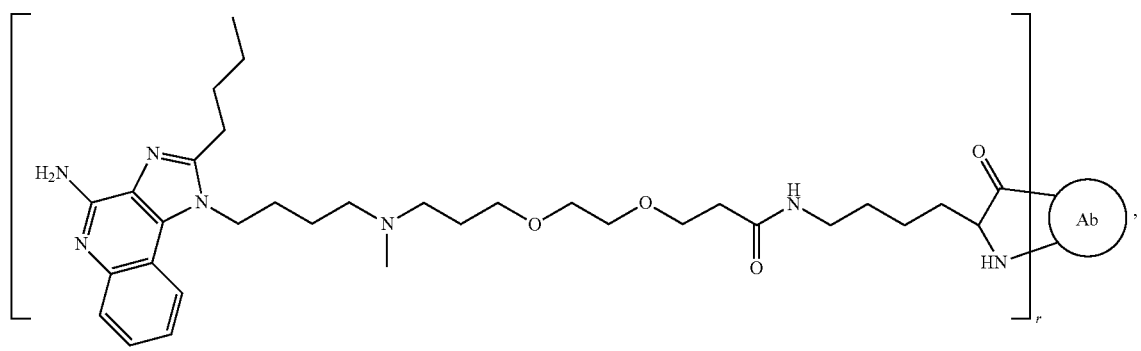

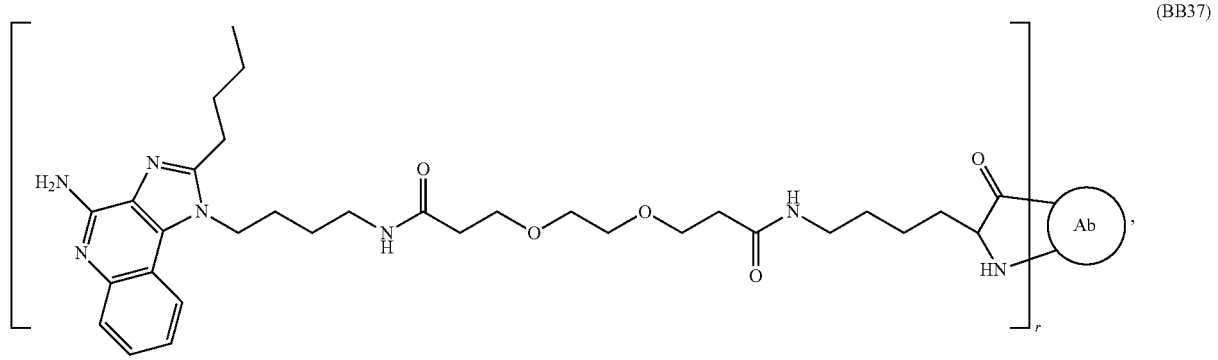
(BB37)
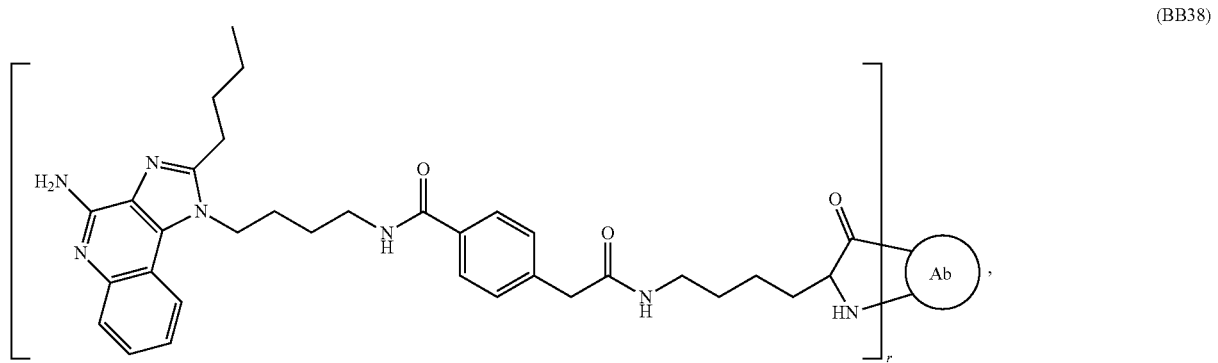
(BB38)
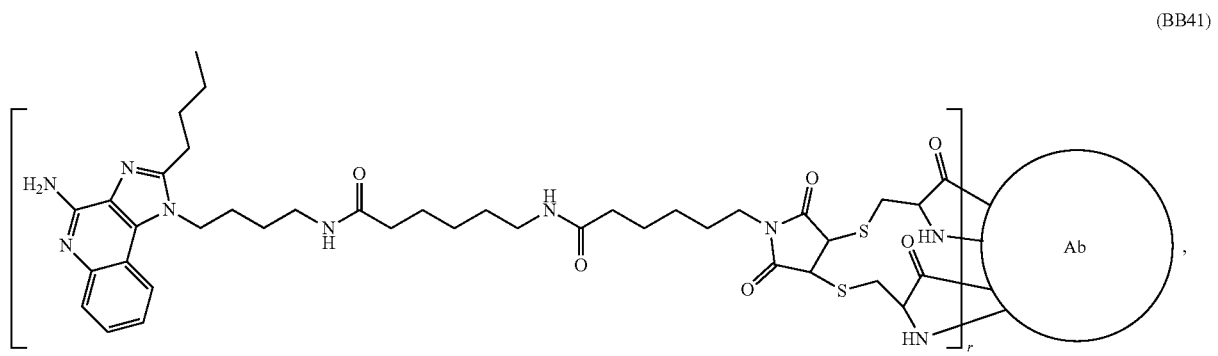
(BB41)
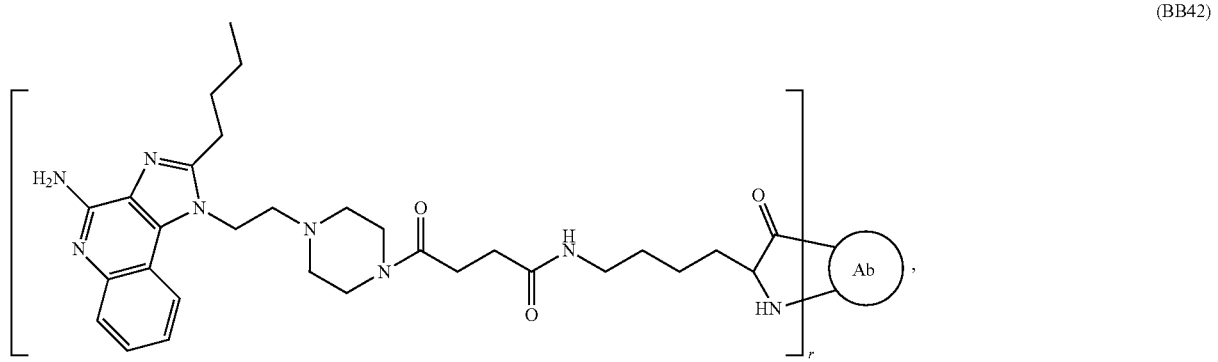
(BB42)

-continued
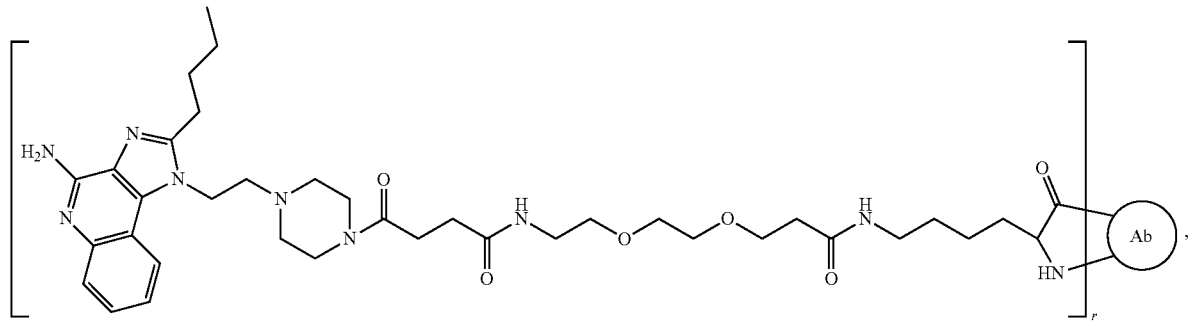
(BB43)
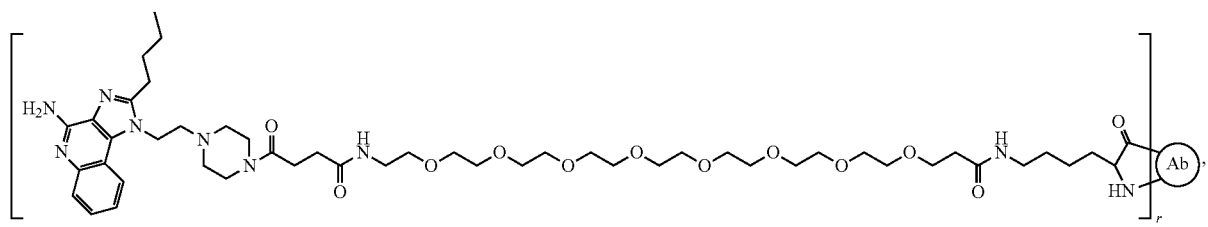
(BB44)
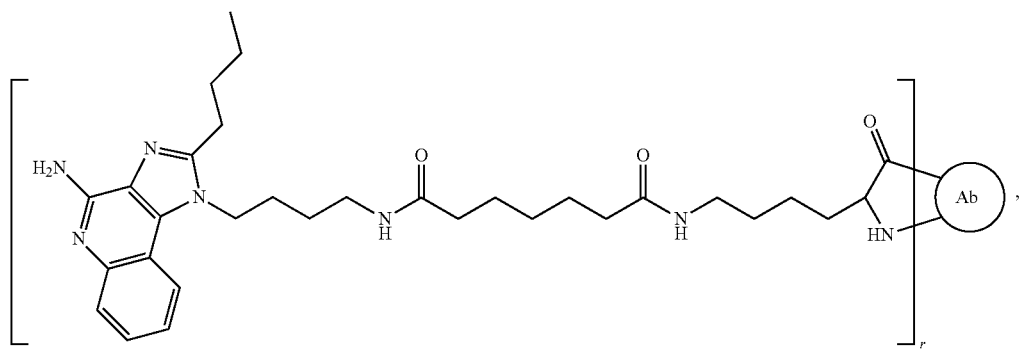
(BB45)
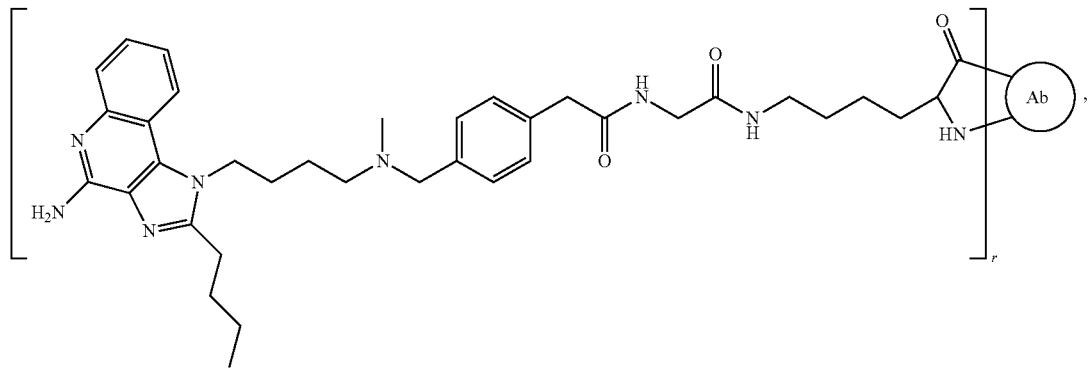
(BB47)

(BB48)
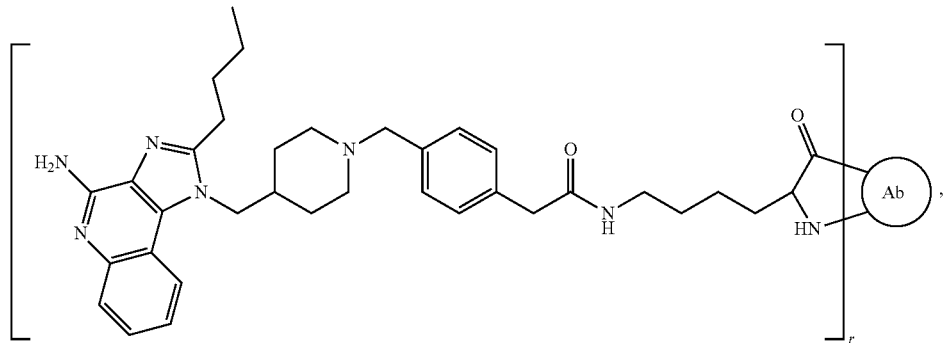
(BB49)
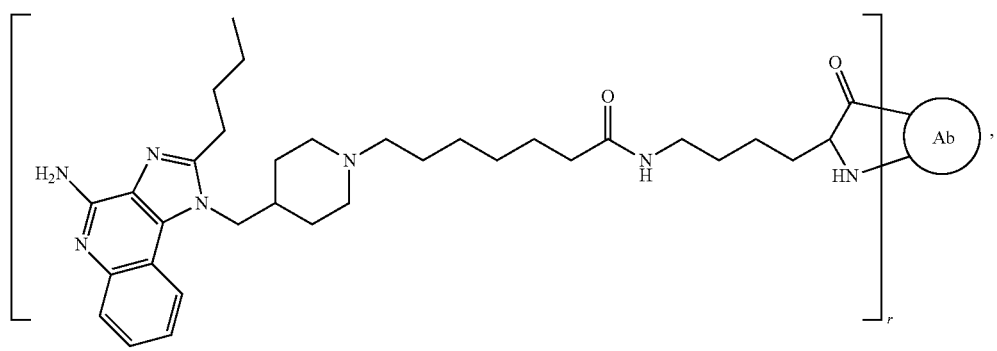
(BB50)
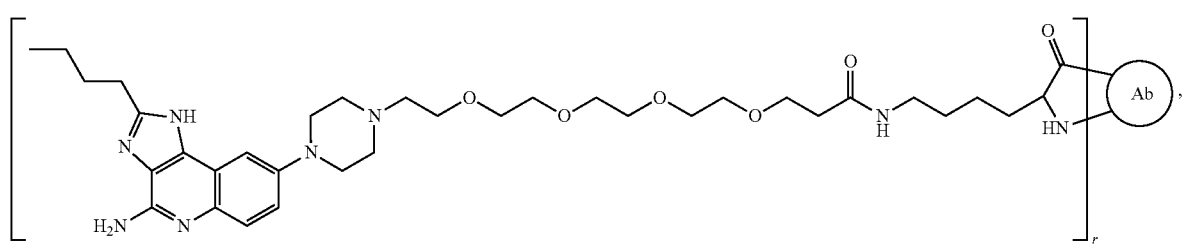
(BB51)
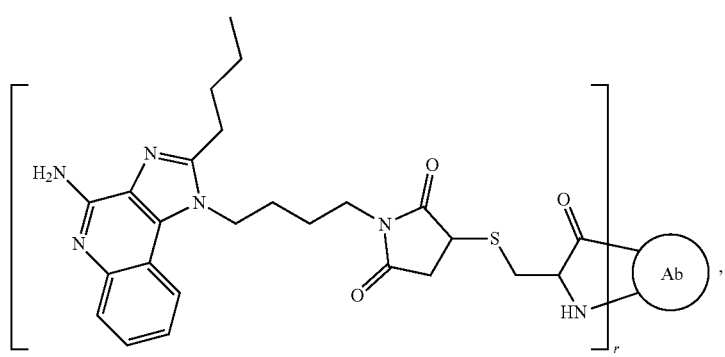

(BB52)
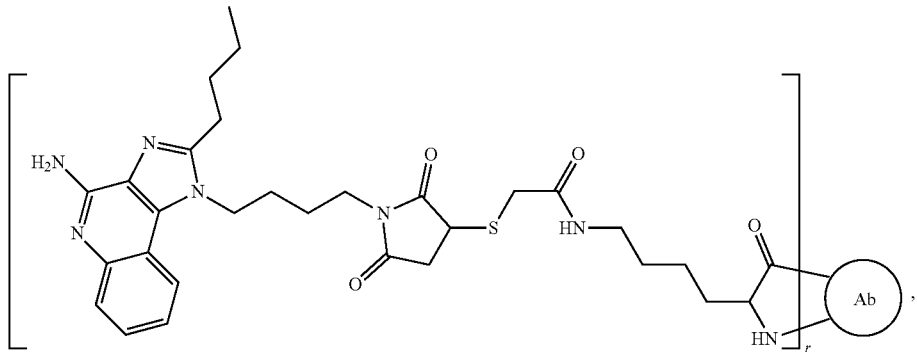
(BB53)
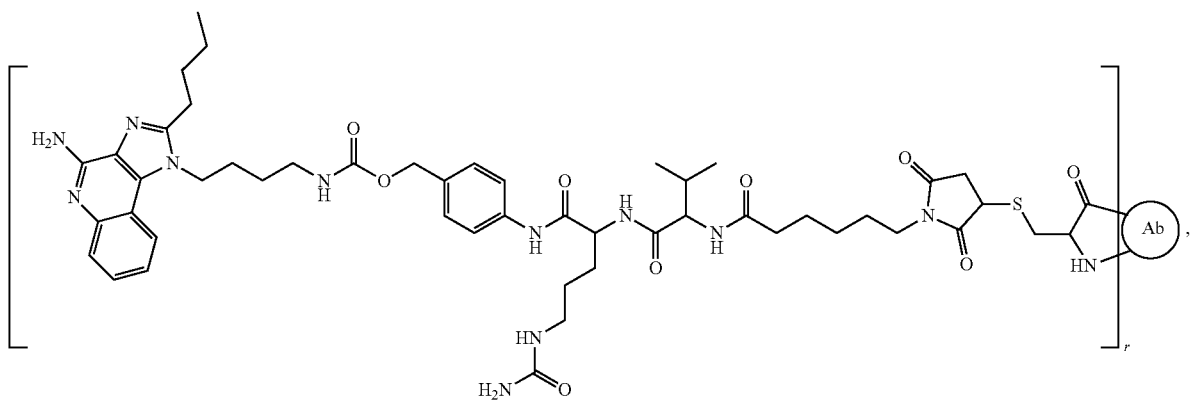
(BB54)
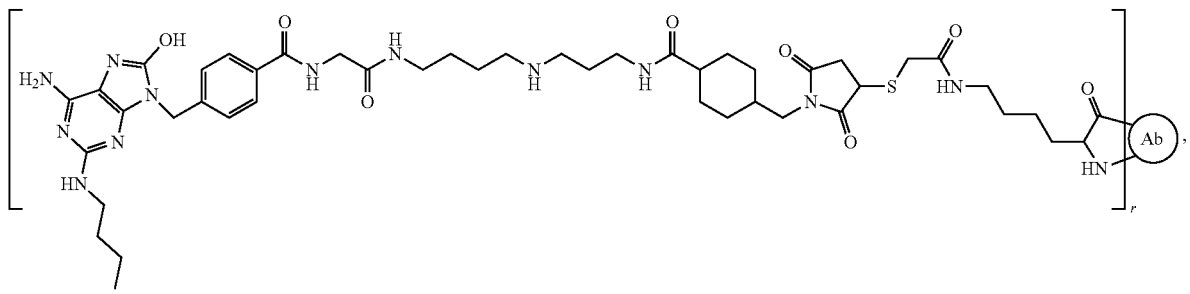
(BB55)
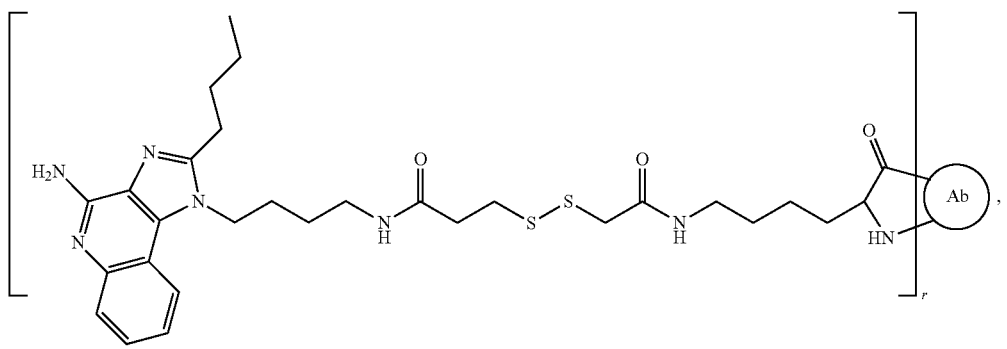

-continued
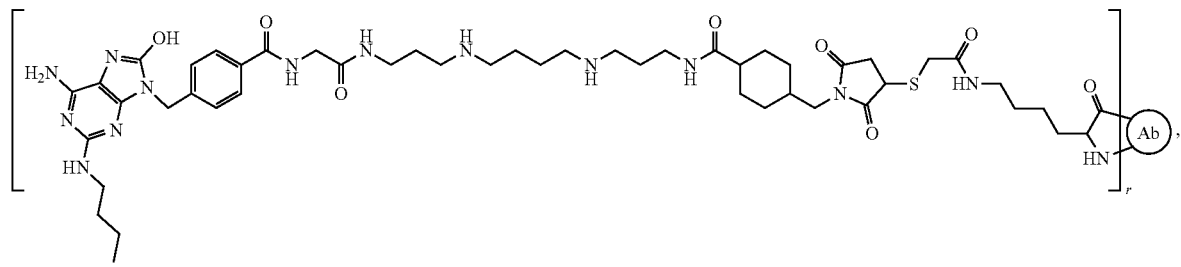
(BB56)
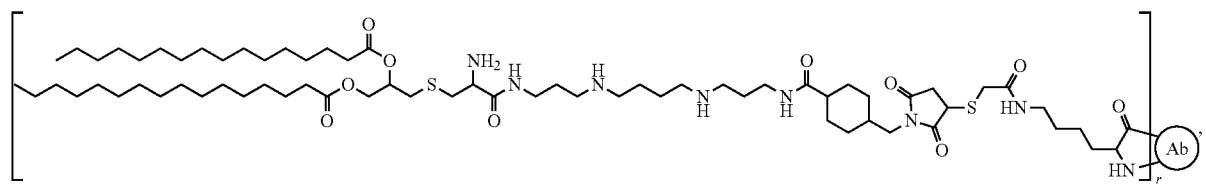
(BB57)
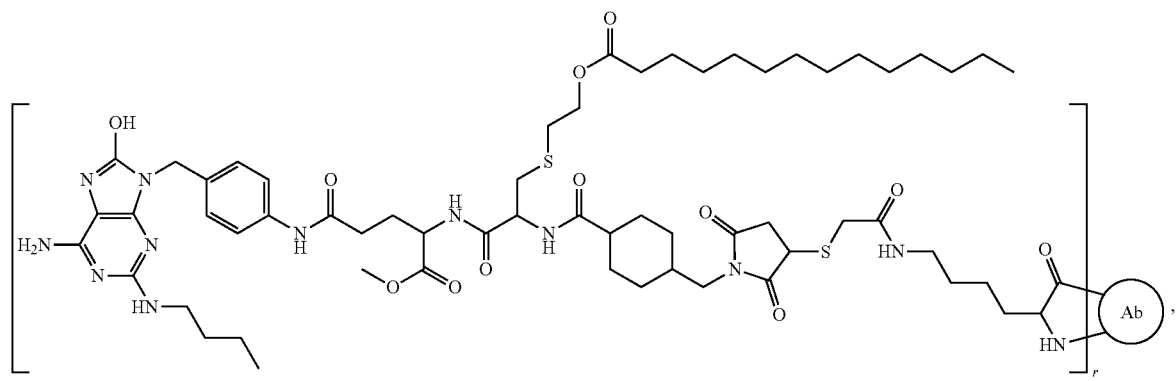
(BB58)
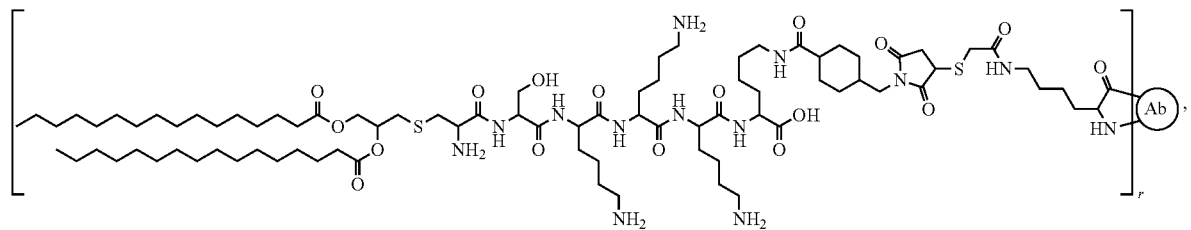
(BB59)
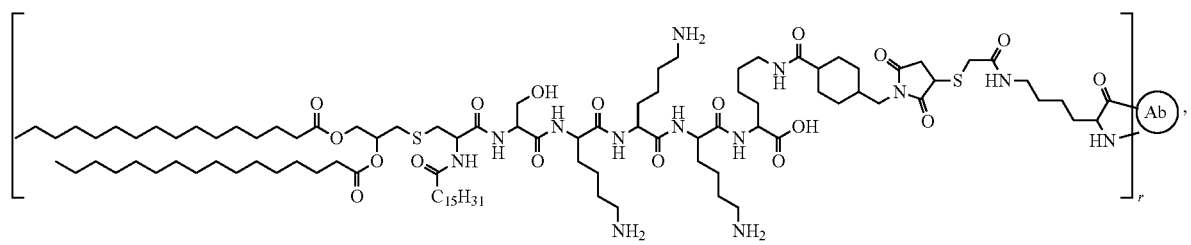
(BB60)

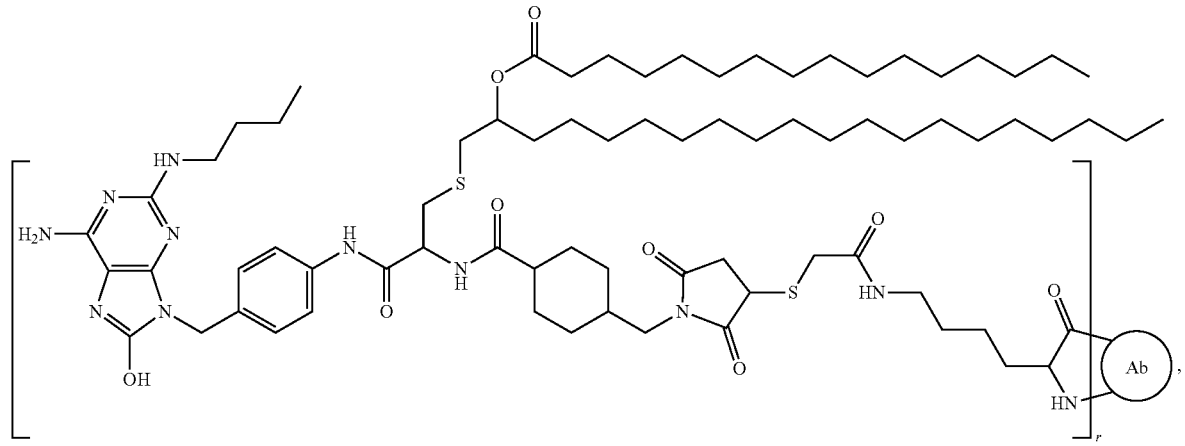
(BB61)
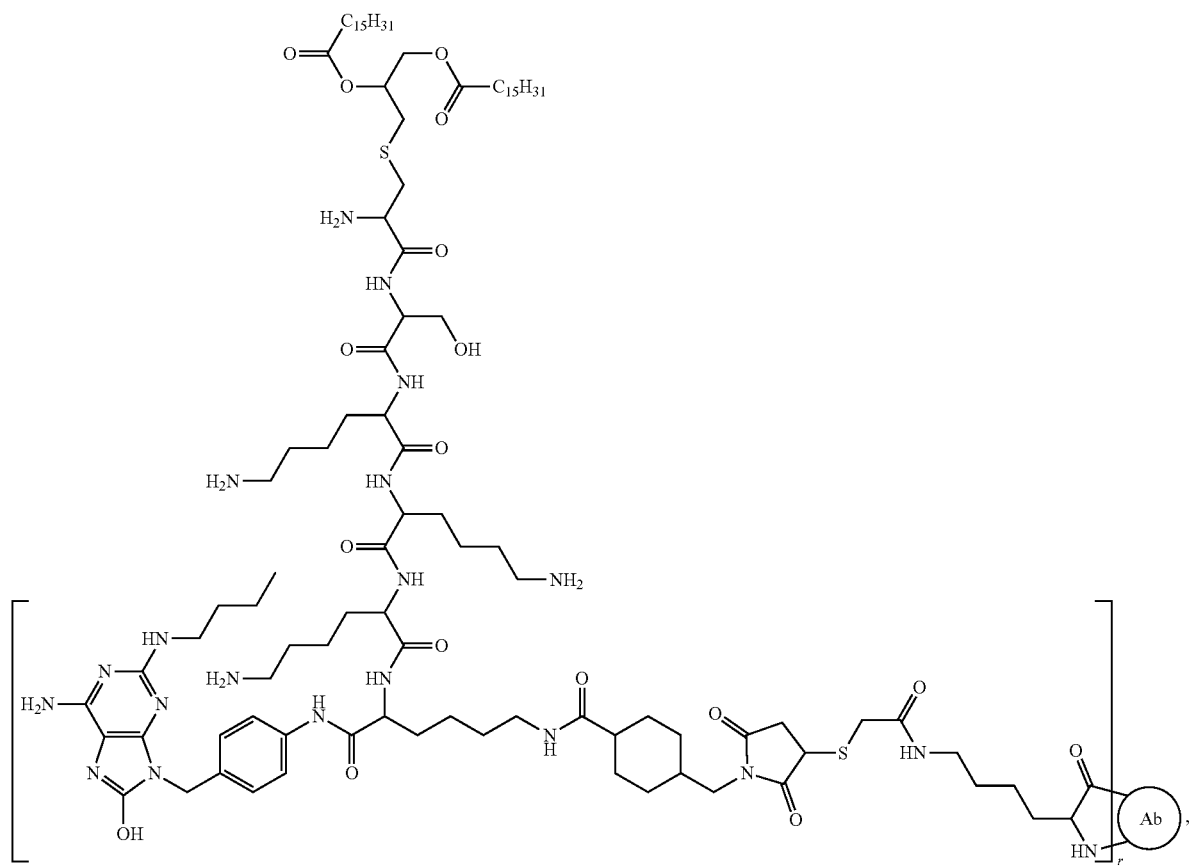
(BB62)

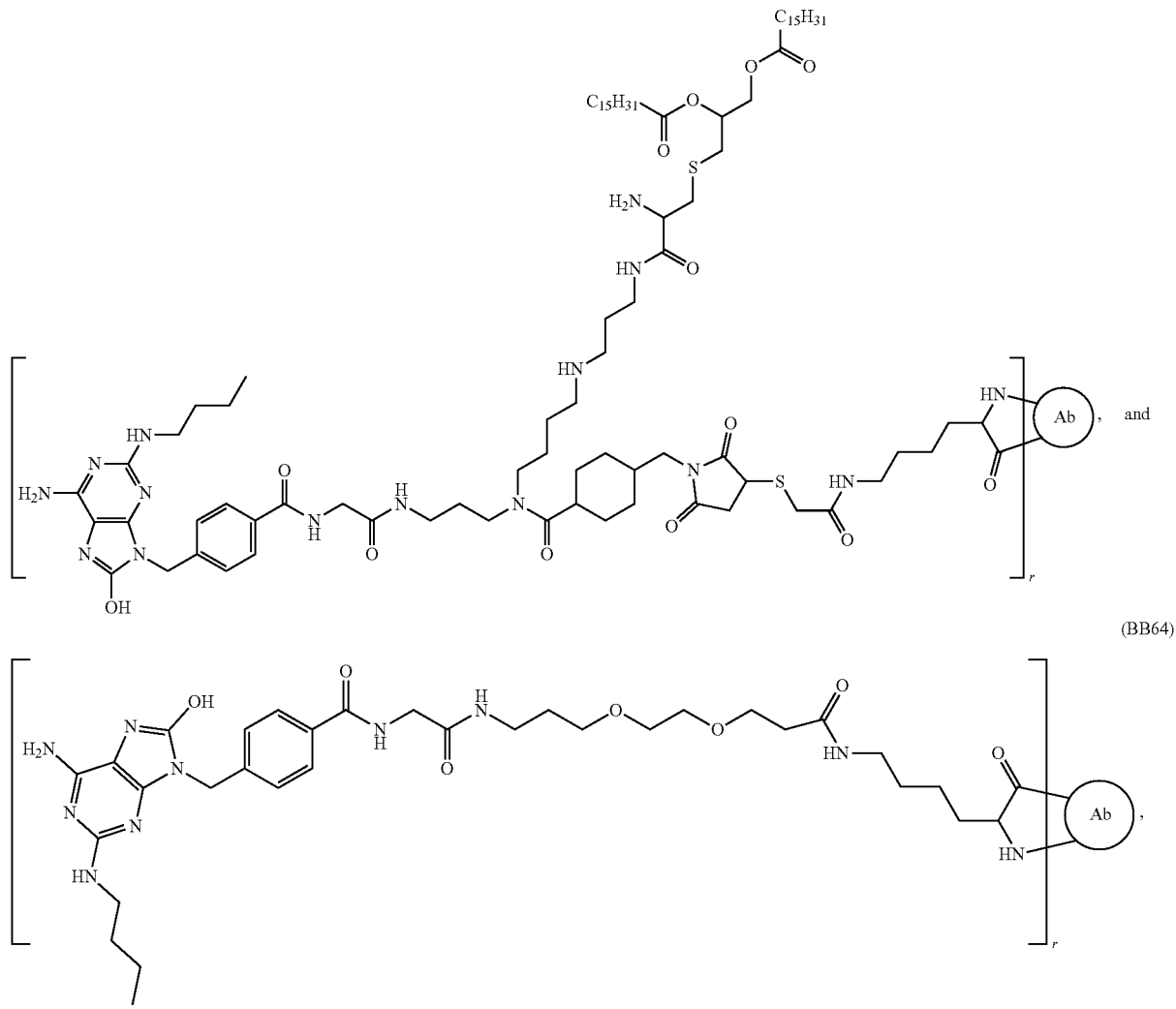

or a pharmaceutically acceptable salt thereof, wherein Ab is an antibody with at least one lysine side chain and subscript r is an integer from 1 to 10.

88. The immunoconjugate of aspect 87, wherein r is from 1 to 4.

89. The immunoconjugate of any one of aspects 1-88, wherein the linker is from about 2.5 Å to about 45 Å.

90. The immunoconjugate of any one of aspects 1-88, wherein the linker is from about 2.5 Å to about 20 Å.

91. A composition comprising a plurality of immunoconjugates according to any one of aspects 1-90.

92. The composition of aspect 91, wherein the average number of adjuvant moieties per immunoconjugate ranges from about 1 to about 9.

93. The composition of aspect 91, wherein the average number of adjuvant moieties per immunoconjugate ranges from about 0.5 to about 4.

94. The composition of any one of aspects 91-93, further comprising one or more pharmaceutically acceptable excipients.

95. A method for treating cancer comprising administering a therapeutically effective amount of an immunoconjugate according to any one of aspects 1-90 or a composition according to any one of aspects 91-94 to a subject in need thereof.

96. The method of aspect 95, wherein the cancer is breast cancer.

97. The method of aspect 95, wherein the cancer is a head and neck cancer.

98. The method of aspect 95, wherein the cancer is a lymphoma.

EXAMPLES

Example 1. Imidazoquinolines for Antibody Conjugation

Imidazoquinoline compounds with a free amine group (Compound 1) or a maleimide group (Compound 2) were synthesized according to Scheme 1, allowing for the rapid assessment of linker technology and antibody-adjuvant immunoconjugate efficacy.

To determine if adjuvant functionalization impacted the capacity of Compound 2 or Compound 1 to elicit immune activation, human antigen presenting cells were stimulated with 10-fold serial dilutions of R848, Compound 2, Compound 1 or a control TLR agonist, CL307, for 18 hours prior to analysis via flow cytometry. The data indicated that Compound 2 and Compound 1 performed similarly to R848 across each concentration assayed (FIG. 4; Compound 1 data not shown).

Figure 2:
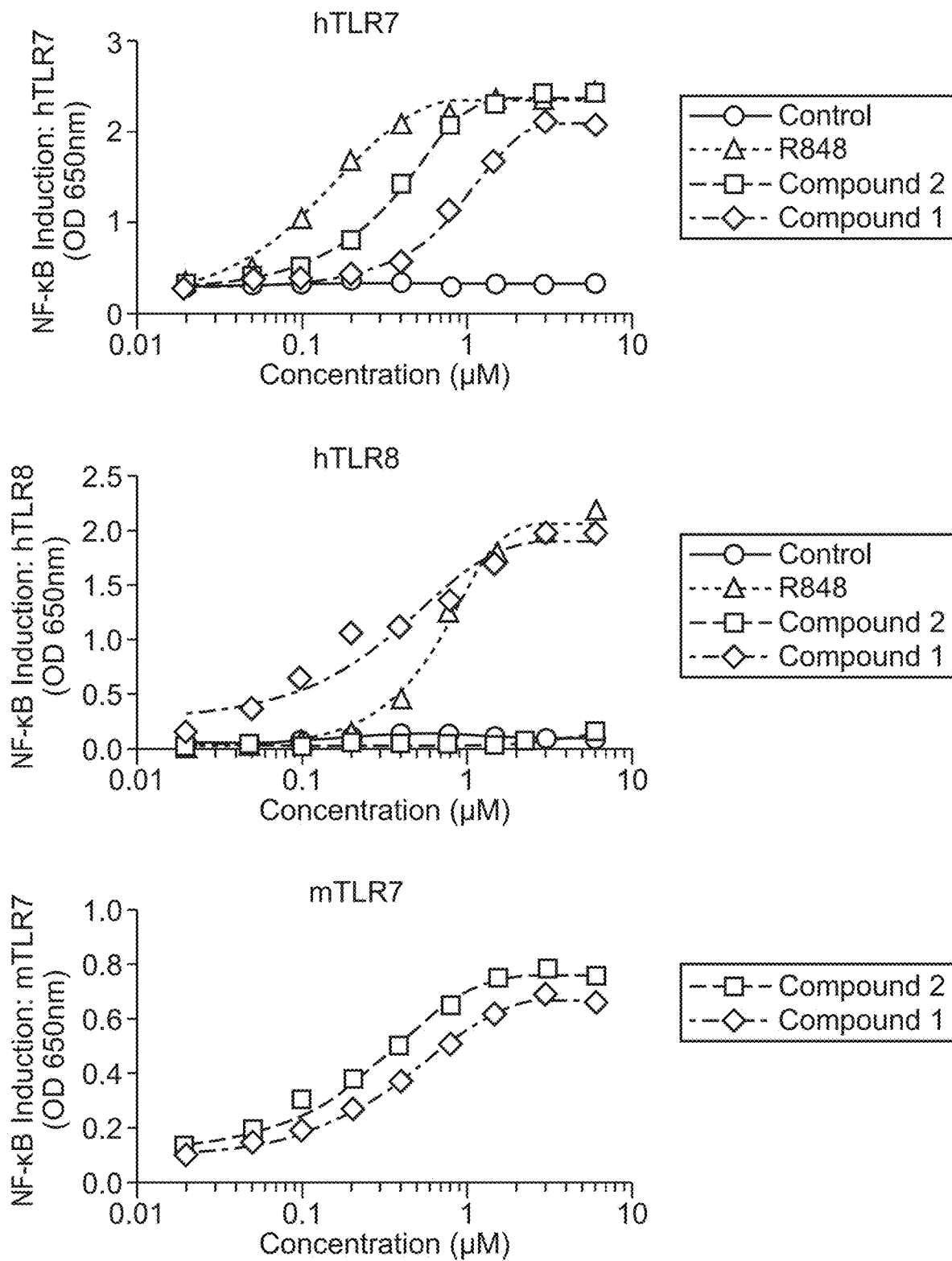
FIG. 2 shows that functionalized adjuvants maintain TLR agonist activity. HEK293 cells were co-transfected with human TLR7 or TLR8 (top two panels) or murine TLR7 (bottom panel) and an inducible secreted embryonic alkaline phosphatase reporter gene under the control of the IFN-β minimal promoter fused to NF-κB and AP-1 binding sites. Cells were subsequently incubated with 2-fold serial dilutions of the indicated adjuvant for 12 hours at 37° C. Activity was measured by spectrophotometry (OD 650 nm) following addition of alkaline phosphatase substrate.

Next, the capacity of each functionalized TLR agonist to activate human TLR7 or TLR8 was directly assayed. HEK293 cells were co-transfected with human TLR7 or TLR8 or murine TLR7 and an inducible secreted embryonic alkaline phosphatase reporter gene under the control of the IFN-β minimal promoter fused to NF-κB and AP-1 binding sites. Cells were subsequently incubated with 2-fold serial dilutions of each the indicated adjuvants for 12 hours at 37 C in the presence of an alkaline phosphatase substrate. Activity was measured by spectrophotometry (OD 650 nm). The data indicate that Compound 1 activated both human TLR7 and TLR8 whereas Compound 2 was specific for TLR7 activity (FIG. 2). Similarly, both Compound 2 and Compound 1 activated murine TLR7 (FIG. 2).

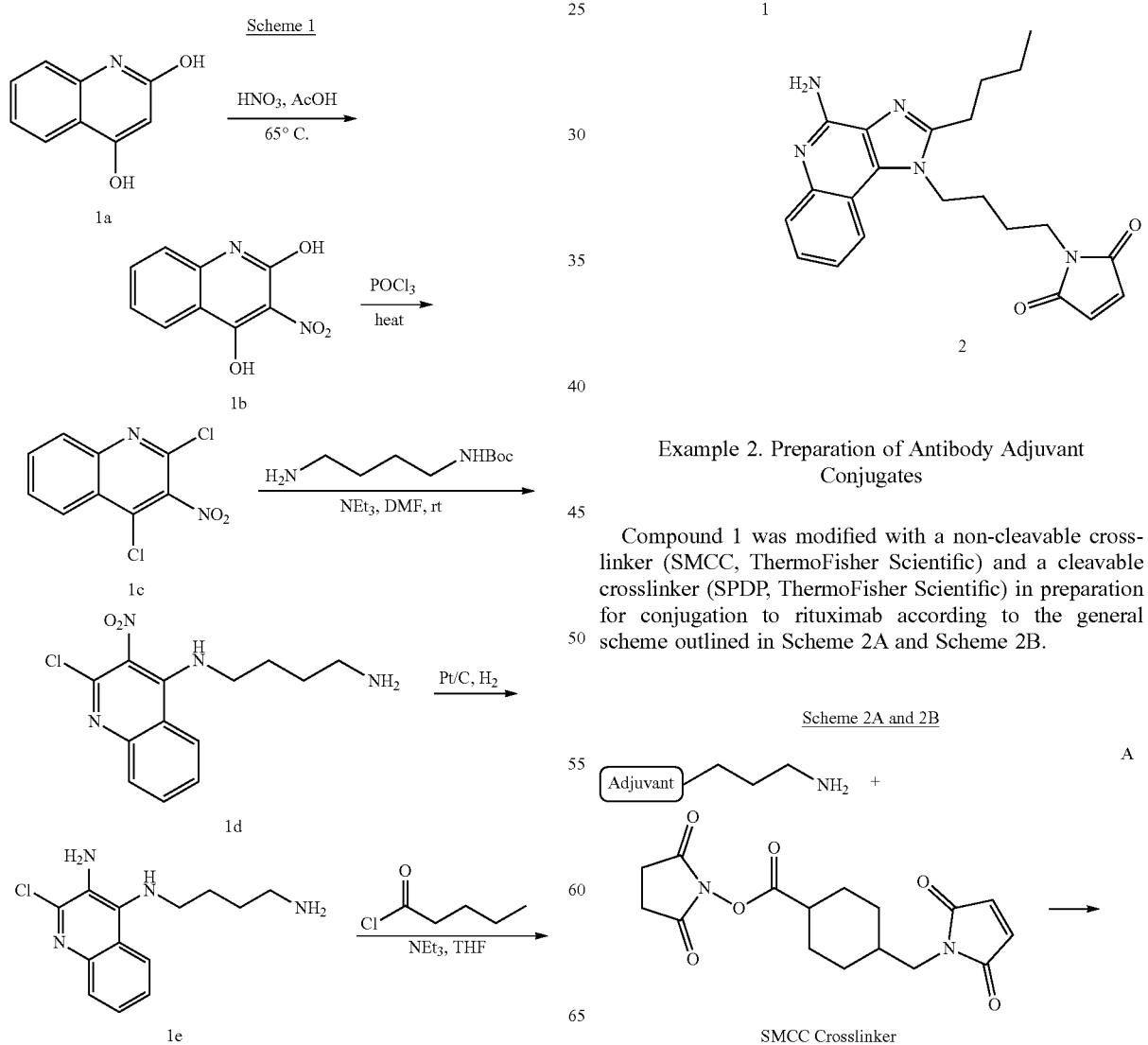

Example 2. Preparation of Antibody Adjuvant Conjugates

Compound 1 was modified with a non-cleavable crosslinker (SMCC, ThermoFisher Scientific) and a cleavable crosslinker (SPDP, ThermoFisher Scientific) in preparation for conjugation to rituximab according to the general scheme outlined in Scheme 2A and Scheme 2B.

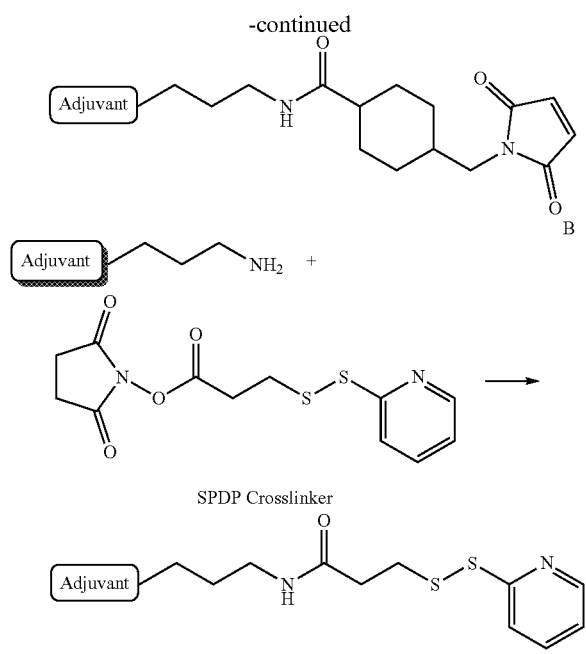

SPDP Crosslinker

Adjuvants with a free amine (R848, Compound 1, etc.) were conjugated to SMCC, SPDP or other NHS containing linkers by reacting the compounds at a 1:1 molar ratio in PBS or other suitable buffers at pH 7-7.5. All reactions were protected from light and incubated for 30 minutes at room temperature. Where possible, adjuvant-crosslinker conjugates were purified via reverse phase high-pressure liquid chromatography (HPLC). Adjuvant-crosslinker conjugates were utilized immediately following conjugation, as described below.

Adjuvant-linker combinations were desalted and buffer exchanged into deionized water with Zeba Spin Desalting Columns (ThermoFisher Scientific). Samples were subsequently analyzed on a Shimadzu LC/MS-2020 Single Quadrupole Liquid Chromatograph Mass Spectrometer. A method with a gradient ranging from 0 to 100% acetonitrile suitable for detection of small molecules within 100-1000 m/z was utilized for compound detection.

Figure 3:
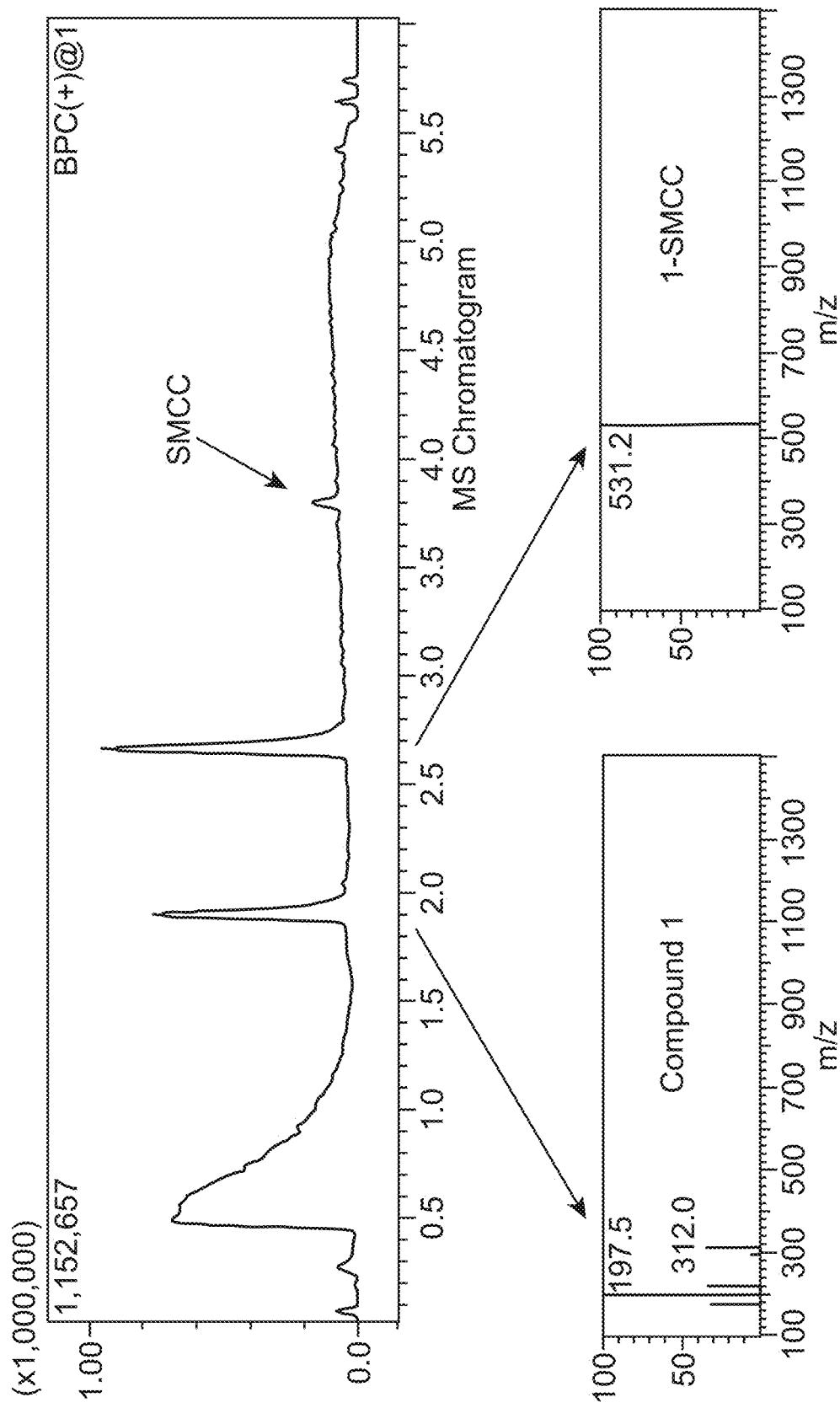
FIG. 3 shows the analysis of adjuvant linker compounds via liquid chromatography-mass spectrometry (LC-MS).

The reaction efficiency was assessed via LC-MS and indicated that the majority of free SMCC had reacted with Compound 1 to form Compound 1-SMCC, which had the expected molecular weight of 531 (FIG. 3, lower right panel). Similar reaction efficiencies were observed with Compound 1-SPDP (data not shown).

Following the successful conjugation of Compound 1 to the crosslinkers, antibodies were modified with the SATA crosslinker to convert the free amines on the antibody to protected sulfhydryl groups. Following conjugation of SATA, sulfhydryl groups were deacetylated with hydroxylamine and exposed thiols were reacted with the maleimide component of the adjuvant-SMCC compound as shown in Scheme 3 of FIG. 139.

Antibody was resuspended in phosphate buffered saline (PBS) at 1-5 mg/mL and the SATA crosslinker (ThermoFisher Scientific) was resuspended at 70 mM in anhydrous DMSO immediately before usage. Antibody was reacted with a 10-fold molar excess of SATA at room temperature for 30 minutes. The SATA-modified antibody was purified from excess reagent and byproducts with 3 washes in PBS with equilibrated Amicon Ultra Centrifugal Filter Units with Ultracel-100 membranes according to the manufacturer's instructions (EMD Millipore). The number of SATA crosslinkers per antibody was determined by matrix-assisted laser desorption/ionization mass spectrometry (MALDI-TOF).

SATA-modified antibody was deacetylated following a 2-hour incubation at room temperature in PBS at pH between 7.2-7.5 with 0.05 M hydroxylamine and 2.5 mM EDTA. The deacetylated SATA-modified antibody was subsequently purified from excess reagent and byproducts with 3 washes in PBS containing 5 mM EDTA with equilibrated Amicon Ultra Centrifugal Filter Units with Ultracel-100 membranes according to the manufacturer's instructions (EMD Millipore). Purified deacetylated SATA-modified antibody was subsequently reacted with a 5 to 40-fold molar excess of adjuvant-crosslinker for 30 minutes to one hour at room temperature. The exact molar excess was 10-fold higher than the average number of SATA molecules per antibody as determined by MALDI-TOF. Following conjugation, the antibody adjuvant immunoconjugate was purified from excess reagent and byproducts with 3 washes in PBS with equilibrated Amicon Ultra Centrifugal Filter Units with Ultracel-100 membranes according to the manufacturer's instructions (EMD Millipore).

The average drug to antibody ratio was determined via MALDI-TOF. Samples were desalted and buffer exchanged using Zeba Spin Desalting Columns (ThermoFisher Scientific) into deionized water. Matrix (sinapinic acid) was first spotted onto the MALDI sample target plate and allowed to dry. Next, the sample was mixed at a 1:1 ratio with and without a bovine serum albumin (BSA) standard (0.25-1 µM BSA) and spotted onto the plate with the matrix samples. Once both the matrix and sample layer dried, samples were analyzed on a AB Sciex TOF/TOF 5800 (Stanford University, Canary Center). A high mass detector (CovalX) with negative ionization allowed for enhanced sensitivity and resolution at protein sizes in the range of a fully intact IgG antibody (~150,000 kDa).

Following successful conjugation of the antibody-adjuvant immunoconjugate (Ab-SATA-SMCC-Adjuvant shown in Scheme 3 of FIG. 139), the average drug to antibody ratio was determined via MALDI-TOF mass spectrometry (Table 1). The mass difference between the SATA-modified and unmodified antibody was utilized to determine how many linkers were present per antibody. The mass difference between the SATA-modified antibody and the immunoconjugates were utilized to determine the average drug to antibody ratio (DAR).

TABLE 1

MALDI-TOF MS-based determination of Drug-to-Antibody Ratio.

| Sample | Molecular Weight (Da) | Mass Difference (Da) | Ab Modification |
|---|---|---|---|
| Antibody | 145,772 | — | — |
| Antibody-SATA | 146,210 | 438 | 3.77 Linkers/Ab |
| Antibody-SATA-SPDP-Compound 1 | 146,944 | 1172 | 2.07 Drugs/Ab |
| Antibody-SATA-SMCC-Compound 1 | 147,309 | 1537 | 2.07 Drugs/Ab |

Example 3. Assessment of Antibody Adjuvant Conjugate Activity In Vitro

Isolation of Human Antigen Presenting Cells.

Human antigen presenting cells (APCs) were negatively selected from human peripheral blood mononuclear cells obtained from healthy blood donors (Stanford Blood Center) by density gradient centrifugation using a RosetteSep Human Monocyte Enrichment Cocktail (Stem Cell Technologies) containing monoclonal antibodies against CD2, CD3, CD8, CD19, CD56, CD66b and CD235a. Immature APCs were subsequently purified to >97% purity via negative selection using an EasySep Human Monocyte Enrichment Kit without CD16 depletion containing monoclonal antibodies against CD2, CD3, CD19, CD20, CD56, CD66b, CD123 and CD235a.

Preparation of Tumor Cells.

Tumor cells were resuspended in PBS with 0.1% fetal bovine serum (FBS) at 1 to $10 \times 10^6$ cells/mL. Cells were subsequently incubated with 2 µM CFSE to yield a final concentration of 1 µM. The reaction was ended after 2 minutes via the addition of 10 mL complete medium with 10% FBS and washed once with complete medium. Cells were either fixed in 2% paraformaldehyde and washed three times with PBS or left unfixed prior to freezing the cells in 10% DMSO, 20% FBS and 70% medium.

APC-Tumor Co-Cultures.

$2 \times 10^5$ APCs were incubated with or without $6.5 \times 10^5$ autologous or allogeneic CFSE-labeled tumor cells in 96-well plates (Corning) containing IMDM medium (Gibco) supplemented with 10% fetal bovine serum, 100 U/mL penicillin, 100 µg/mL streptomycin, 2 mM L-glutamine, sodium pyruvate, non-essential amino acids, 50 µM 2-ME and, where indicated, various concentrations of anti-tumor antibody and the indicated adjuvants. Cells and cell-free supernatants were analyzed after 18 hours via flow cytometry.

Results.

Figure 4:
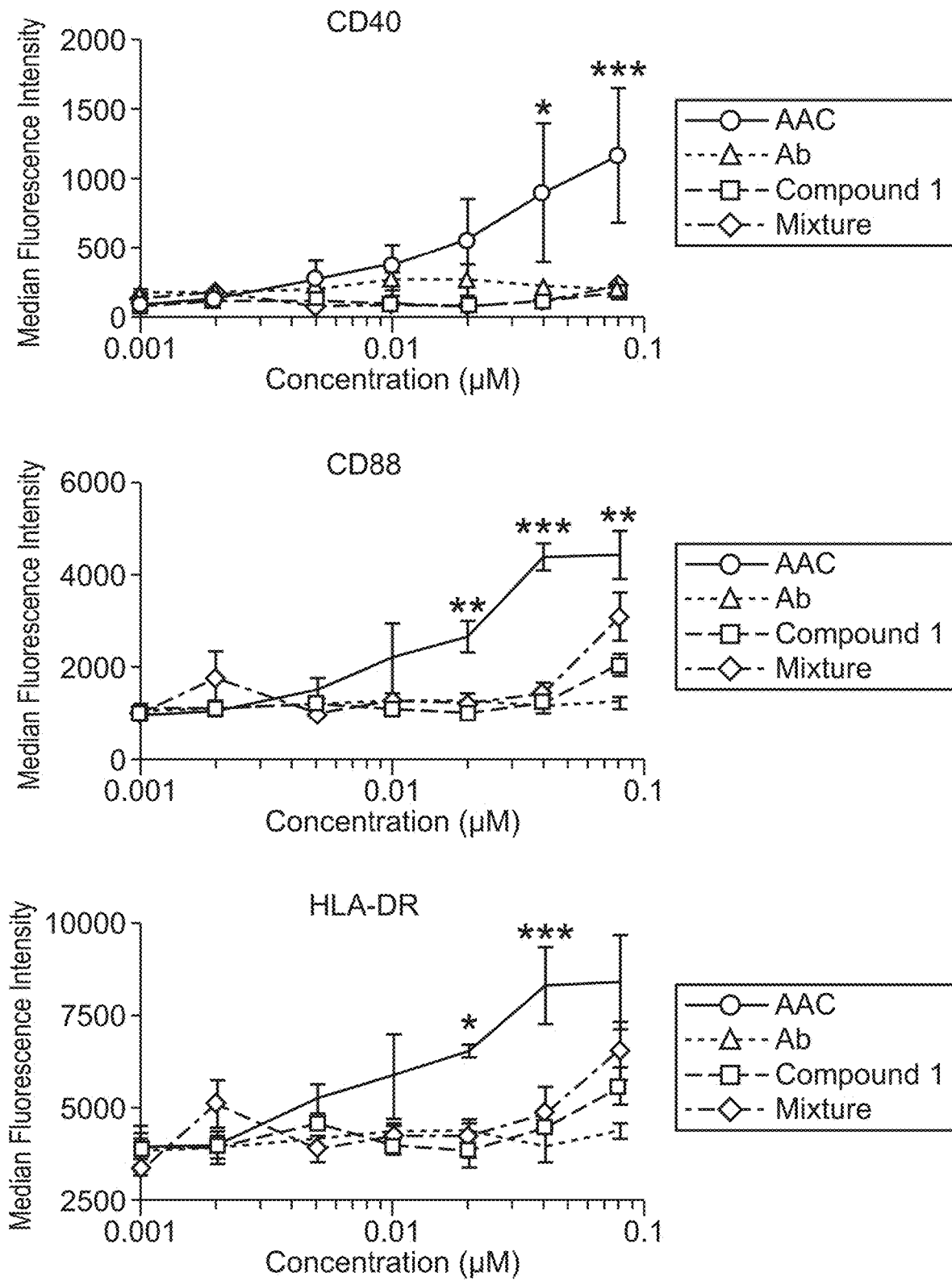
FIG. 4 shows that antibody-adjuvant conjugates are superior at eliciting APC activation, compared to unconjugated antibody and adjuvant, as indicated by expression of CD40, CD86 and HLA-DR. Human APCs were stimulated with Rituximab-SATA-SMCC-Compound 1 (conjugated), Rituximab alone (Ab), Compound 1 alone or Rituximab+Compound 1 (Mixture) in the presence of CFSE-labeled CD19+ tumor cells. After 18 hours, CD19− human APCs were analyzed via flow cytometry; n=3. P-values ≤0.05 depicted by *, P-values ≤0.01 depicted by , P-values ≤0.001 depicted by *, P-values ≤0.0001 depicted by ****

To determine the capacity of immunoconjugates to elicit immune activation, human APCs (~95% monocytes) obtained from fresh blood were incubated with CFSE-labeled human B cell lymphoma cells (Toledo, ATCC) at a 3:1 ratio and 2-fold serial dilutions of Compound 1, Rituximab (Ab), Rituximab+Compound 1 (Mixture) or Rituximab-SATA-SMCC-Compound 1 (conjugated). In these experiments, the immunoconjugate had an average of 2.1 Compound 1 molecules per antibody and the Compound 1 doses were adjusted accordingly to ensure that equimolar amounts of Compound 1 were compared across all conditions. After 18 hours, cells were analyzed for the expression of activation markers via flow cytometry. The data indicate that immunoconjugates were far superior at eliciting APC activation as CD40, CD86 and HLA-DR were expressed at several fold higher levels in APCs stimulated with the immunoconjugate as compared to those stimulated with Ab alone, Compound 1 alone or the mixture (FIG. 4).

Figure 5:
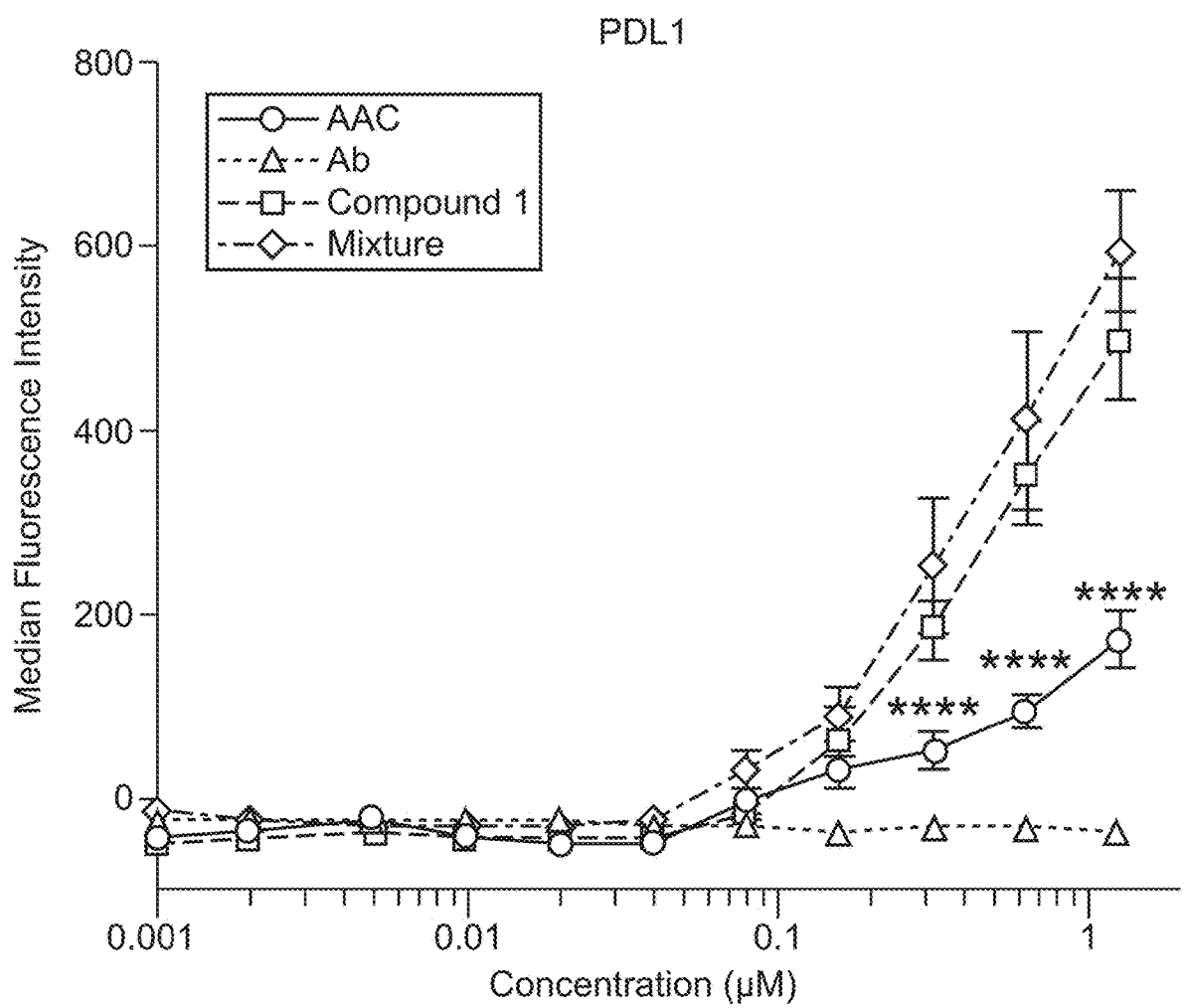
FIG. 5 shows that antibody-adjuvant conjugates induce lower levels of PD-L1 expression on human APCs, compared to unconjugated antibody and adjuvant. Human APCs were stimulated with Rituximab-SATA-SMCC-Compound 1 (conjugated), Rituximab alone (Ab), Compound 1 alone or Rituximab+Compound 1 (Mixture) in the presence of CFSE-labeled CD19 tumor cells. After 18 hours, CD19⁻ human APCs were analyzed via flow cytometry; n=3. P-values ≤0.05 depicted by *, P-values ≤0.01 depicted by , P-values ≤0.001 depicted by *, P-values ≤0.0001 depicted by ****.

Given the high level of activation markers observed following immunoconjugate activation, the expression of PD-L1, an inhibitory marker that is highly correlated with the extent of APC activation, was investigated. Surprisingly, immunoconjugates were much less potent at eliciting the upregulation of PD-L1 expression as compared to the adjuvant alone or the mixture (FIG. 5). Notably, PD-L1 expression was negligible at 0.1 µM immunoconjugate, which corresponds to the maximally bioactive concentration (FIG. 4, FIG. 5). These data suggest that the immunoconjugate may activate unforeseen signaling pathways in human APCs.

Figure 6:
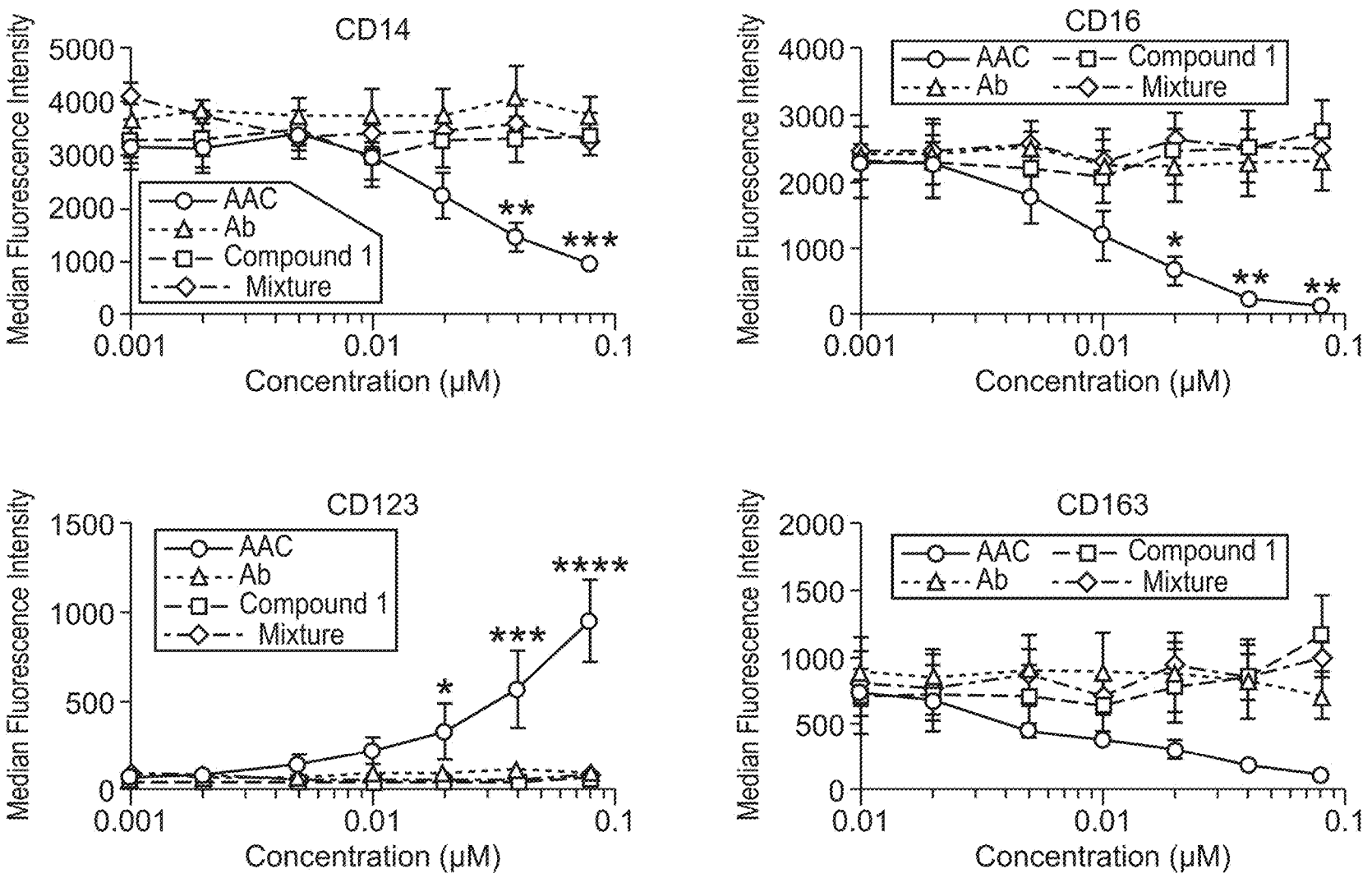
FIG. 6 shows that antibody-adjuvant conjugates elicit DC differentiation. Human APCs that were ~95% monocytes were stimulated with 2-fold serial dilutions of Rituximab-SATA-SMCC-Compound 1 (conjugated), Rituximab alone (Ab), Compound 1 alone or Rituximab+Compound 1 (Mixture) in the presence of CFSE-labeled tumor cells. After 18 hours, CD19⁻ human APCs were analyzed via flow cytometry; n=3. P-values ≤0.05 depicted by *, P-values ≤0.01 depicted by , P-values ≤0.001 depicted by *, P-values ≤0.0001 depicted by ****

In support of this hypothesis, cells stimulated with the immunoconjugate unexpectedly developed dendrites and underwent morphologic changes consistent with monocytes differentiating into DCs. This finding prompted the analysis of DC associated surface molecules. Consistent with their morphology, APCs stimulated with the immunoconjugate, but not the mixture, downregulated CD14, CD16 and CD163 expression in a dose dependent manner (FIG. 6). The downregulation of these molecules, which are expressed by monocytes and macrophages, but greatly diminished on monocyte-derived DCs, indicates that human monocytes exposed to immunoconjugate rapidly differentiated into DCs. Consistent with these data, APCs stimulated with the immunoconjugate upregulated the expression of CD123, a marker of human inflammatory monocyte-derived DCs (FIG. 6).

Figure 7:
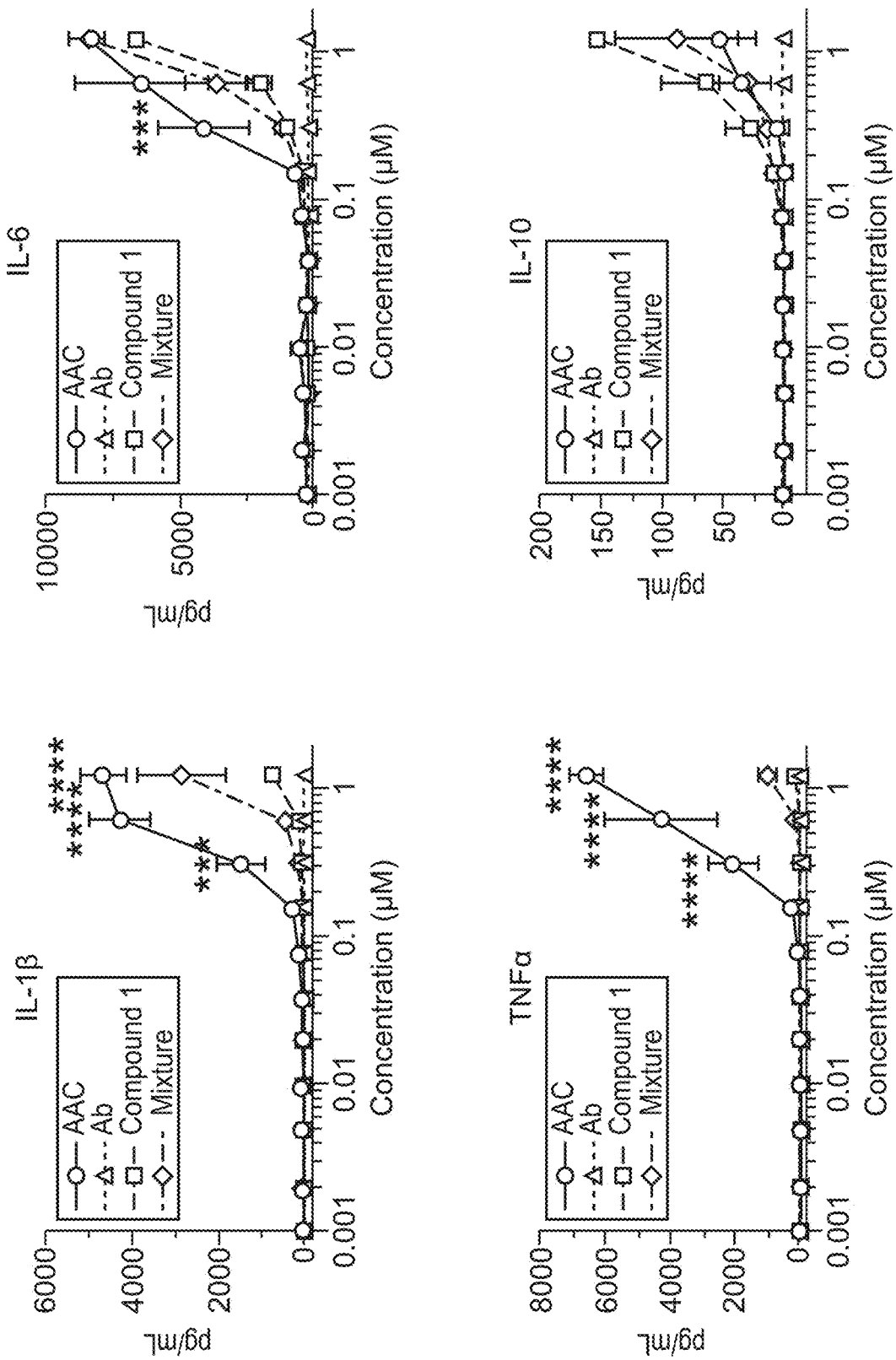
FIG. 7 shows that antibody-adjuvant conjugates are superior to mixtures of unconjugated antibody and adjuvant for eliciting the secretion of proinflammatory cytokines from human APCs. Human APCs were stimulated with 2-fold serial dilutions of Rituximab-SATA-SMCC-Compound 1 (conjugated), Rituximab alone (Ab), Compound 1 alone or Rituximab+Compound 1 (Mixture) in the presence of fixed, CFSE-labeled tumor cells. After 18 hours, cell free supernatants were analyzed for cytokine secretion via cytokine bead arrays; n=3. P-values ≤0.05 depicted by *, P-values ≤0.01 depicted by , P-values ≤0.001 depicted by *, P-values ≤0.0001 depicted by ****

While the expression of T cell stimulatory molecules such as CD40, CD86 and HLA-DR is necessary for effective T cell activation, APCs also influence the nature of the ensuing immune response through the secretion of cytokines. Therefore, the capacity of immunoconjugates to elicit cytokine secretion in human APCs following stimulation was investigated as described above. The data indicate that the immunoconjugate-differentiated cells secreted several fold higher amounts of IL-13 and TNFα whereas secretion of the anti-inflammatory cytokine IL-10 trended lower (FIG. 7).

Immunoconjugates constructed with cleavable linkers have also been prepared and found to elicit APC activation and DC differentiation in vitro (FIG. 8). Human APCs that were ~95% monocytes were stimulated with 2-fold serial dilutions of Rituximab-SATA-SPDP-Compound 1 (conjugated, cleavable), Rituximab alone (Ab), Compound 1 alone or Rituximab+Compound 1 (Mixture) in the presence of CFSE-labeled tumor cells. immunoconjugate—Cleavable had a DAR of 1.4 as confirmed by MALDI-TOF. After 18 hours, CD19⁻ human APCs were analyzed via flow cytometry; n=3.

Example 4. Assessment of Antibody Adjuvant Conjugate Efficacy In Vivo

For tumor studies, $2 \times 10^5$ B 16F10 melanoma cells were injected subcutaneously (s.c.) above the right flank in C57BL/6 mice. After ten days, or when the tumors reached 25 mm², mice were administered intravenous injections of 400 µg the immunconjugate (anti-GP75-SATA-SMCC-Compound 1) (DAR=1.74) or treated intratumorally with 400 µg of the immunoconjugate (anti-GP75-SATA-SMCC-Compound 1) or a mixture of 1.5 µg of Compound 1 and 400 µg anti-GP75 (TA99). Subsequent treatments were administered on days 2 and 4 after the initial treatment. Tumor development was measured 2-3 times per week with calipers.

Mice treated with the immunoconjuage, but not the mixture, reduced their tumors (FIG. 9A). Next, equivalent doses of αGP75-immunoconjugate were administered intratumorally or intravenously in mice with established tumors. Surprisingly, IV administration resulted in tumor regression even though it is estimated that less than 10% of the immunoconjugate reached the tumor (FIG. 9B).

The studies described herein demonstrate that immunoconjugates are quantitatively and qualitatively more effective at eliciting immune activation and anti-tumor immunity than equimolar quantities of non-covalently attached antibody-adjuvant mixtures. These findings are unlikely to result from simple serum half-life extension of the adjuvant following antibody conjugation, because profound phenotypic alterations and novel biology were observed during short in vitro incubation periods. These studies indicate that freshly isolated peripheral blood monocytes from healthy human donors undergo DC differentiation following overnight stimulation with immunoconjugates whereas gold standard DC differentiation protocols with GM-CSF and IL-4 require six days. Furthermore, immunoconjugate activated human APCs expressed several fold higher amounts of co-stimulatory molecules and inflammatory cytokines than achievable with equivalent doses of non-covalently attached antibody-adjuvant mixtures. Yet, immunoconjugates elicit much lower levels of negative co-stimulatory molecules such as PD-L1 and comparable amounts of IL-10, suggesting that immunoconjugates activate unforeseen signaling pathways. Without wishing to be bound by any particular theory, it is believed that stimulation with immunoconjugates closely resembles physiologic antibody-mediated immunity whereby APCs recognize opsonized pathogens (antibody bound to pathogens) with high affinity.

Example 5. Preparation and Assessment of Additional Antibody Adjuvant Conjugate Activity In Vitro Preparation of Additional Antibody Adjuvant Conjugates.

Additional antibody-adjuvant conjugates were prepared using the methods described in Examples 1 and 2. The antibodies pembrolizumab (PD-1), nivolumab (PD-1), atezolizumab (PD-L1), and ipilimumab (CTLA4) were used to create the antibody-adjuvant conjugates with SATA-SMCC linkers (see Scheme 3 of FIG. 139).

Following successful conjugation of the immunoconjugate, the average drug to antibody ratio was determined via LC-MS. The immunoconjugate is first deglycosylated using PNGase F to remove glycans from the antibody, and then the immunoconjuage is buffer exchanged into deionized water. Antibody adjuvant conjugates were run on a C4 column eluted with acetonitrile/water on a Waters Xevo G2-XS QTof/Tof. Raw mass spectrometry data was deconvoluted to determine the Drug to Antibody (DAR) ratios. The LC-MS data indicated successful conjugation and desirable DAR ratios.

Isolation of Human Antigen Presenting Cells.

Human antigen presenting cells (APCs) were negatively selected from human peripheral blood mononuclear cells obtained from healthy blood donors (Stanford Blood Center) by density gradient centrifugation using a RosetteSep Human Monocyte Enrichment Cocktail (Stem Cell Technologies) containing monoclonal antibodies against CD14, CD16, CD40, CD86, CD123, and HLA-DR. Immature APCs were subsequently purified to >97% purity via negative selection using an EasySep Human Monocyte Enrichment Kit without CD 16 depletion containing monoclonal antibodies against CD14, CD16, CD40, CD86, CD123, and HLA-DR.

Preparation of Tumor Cells.

Tumor cells were prepared in accordance with Example 3 above.

APC-Tumor Co-Cultures.

$2 \times 10^5$ APCs were incubated with or without $6.5 \times 10^5$ autologous or allogeneic CFSE-labeled tumor cells in 96-well plates (Corning) containing IMDM medium (Gibco) supplemented with 10% fetal bovine serum, 100 U/mL penicillin, 100 μg/mL streptomycin, 2 mM L-glutamine, sodium pyruvate, non-essential amino acids, 50 μM 2-ME and, where indicated, various concentrations of antibody. Cells and cell-free supernatants were analyzed after 18 hours via flow cytometry.

Results.

Figure 10A:
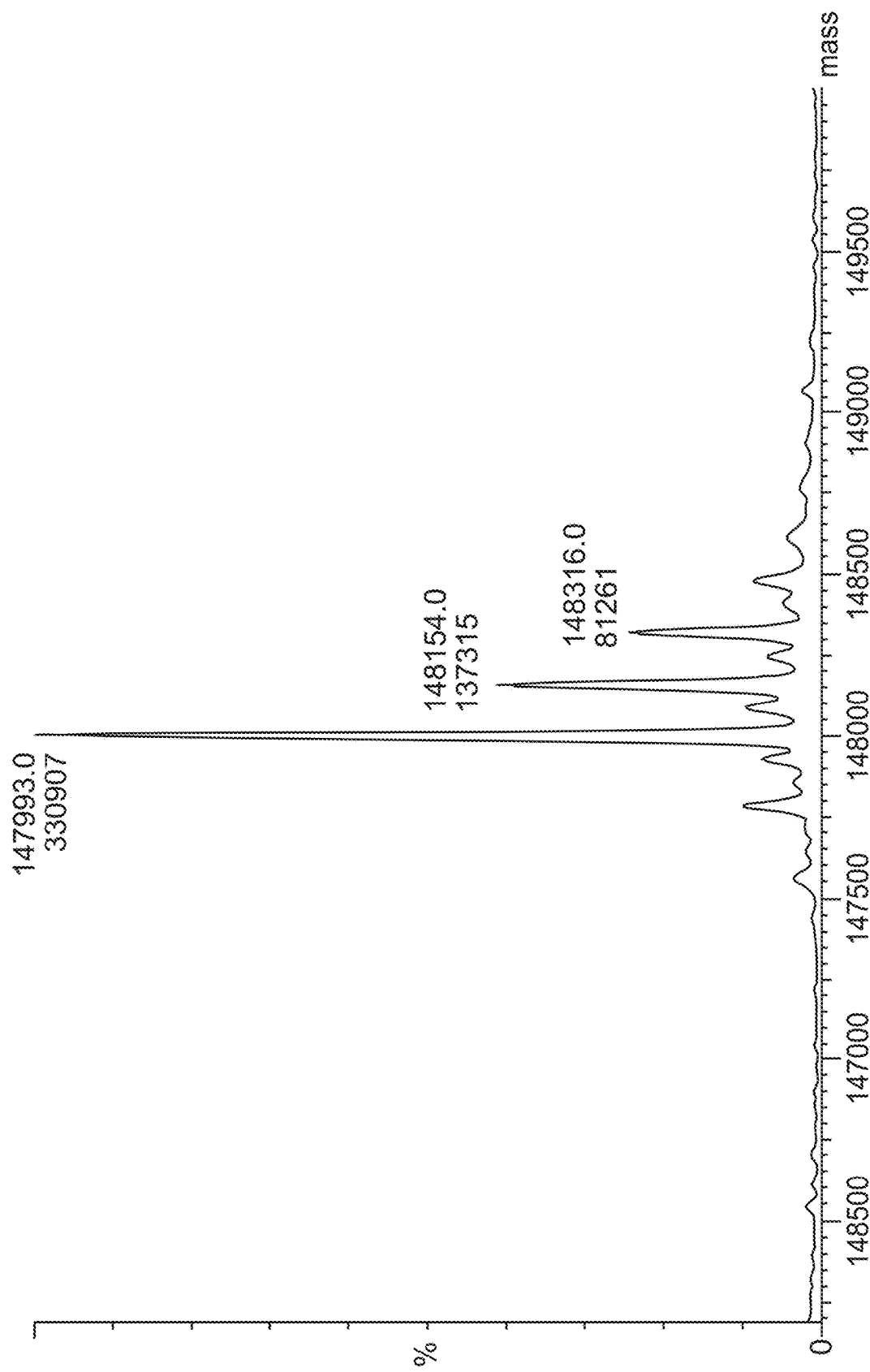
FIG. 10A shows the analysis of ipilimumab via LC-MS.
Figure 10B:
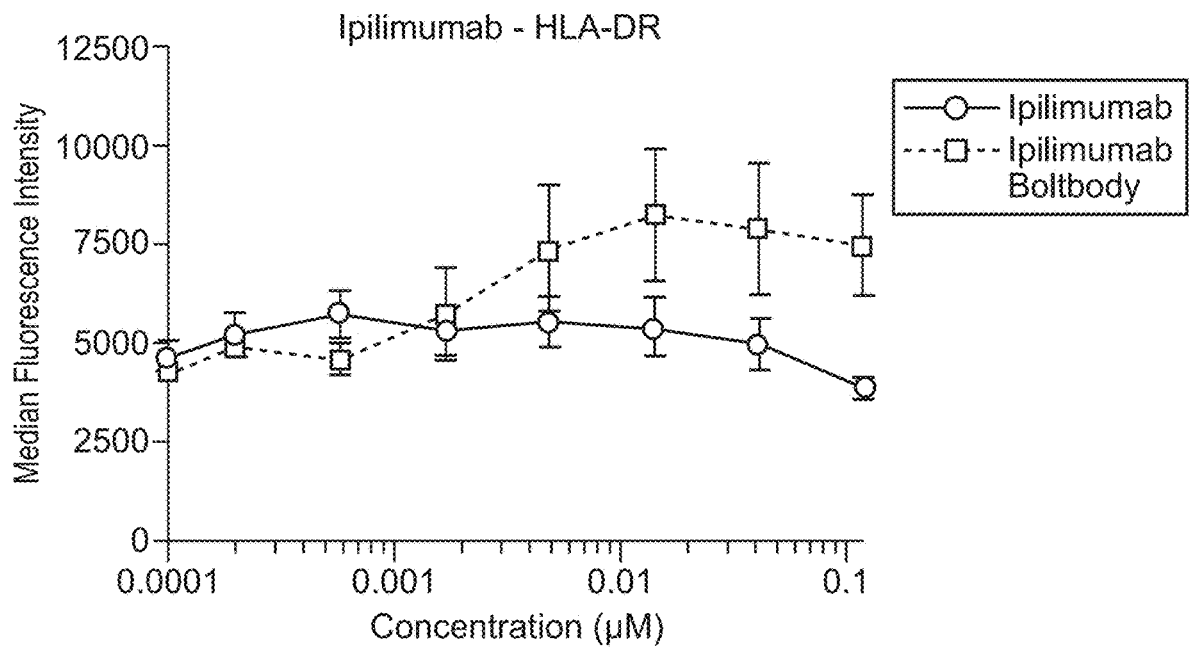
FIG. 10B shows that ipilimumab-adjuvant (Ipilimumab Boltbody) conjugates are superior at eliciting APC activation, compared to unconjugated ipilimumab, as indicated by expression of HLA-DR.
Figure 10C:
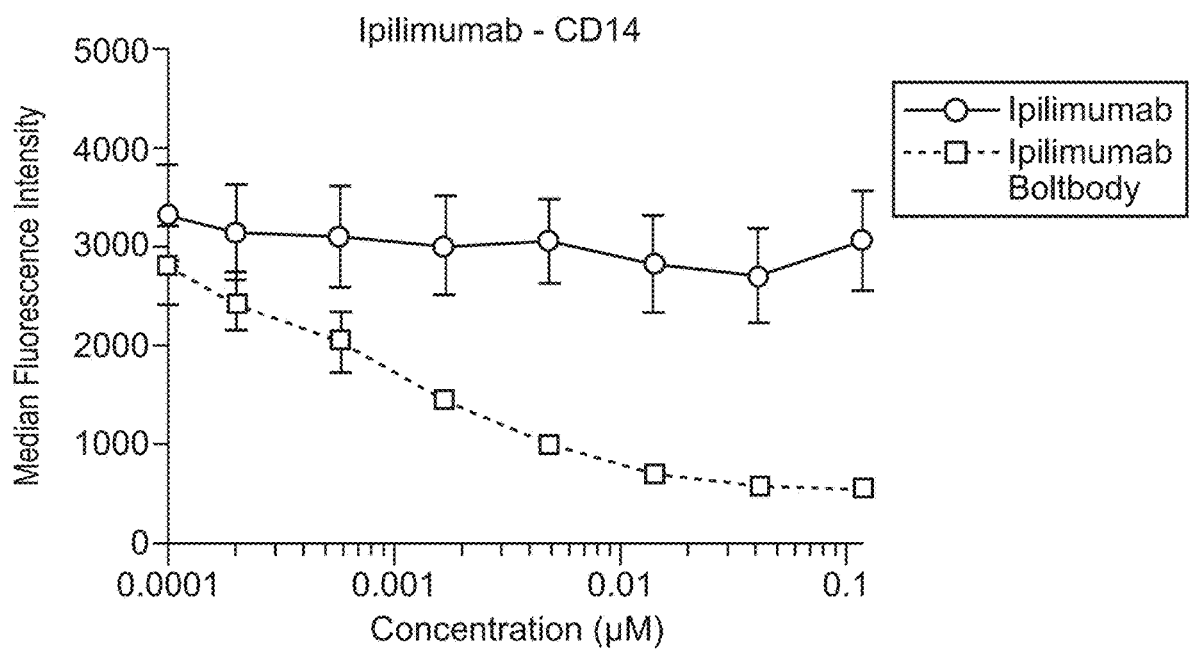
FIG. 10C shows that ipilimumab-adjuvant (Ipilimumab Boltbody) conjugates are superior at eliciting APC activation, compared to unconjugated ipilimumab, as indicated by expression of CD14.
Figure 10D:
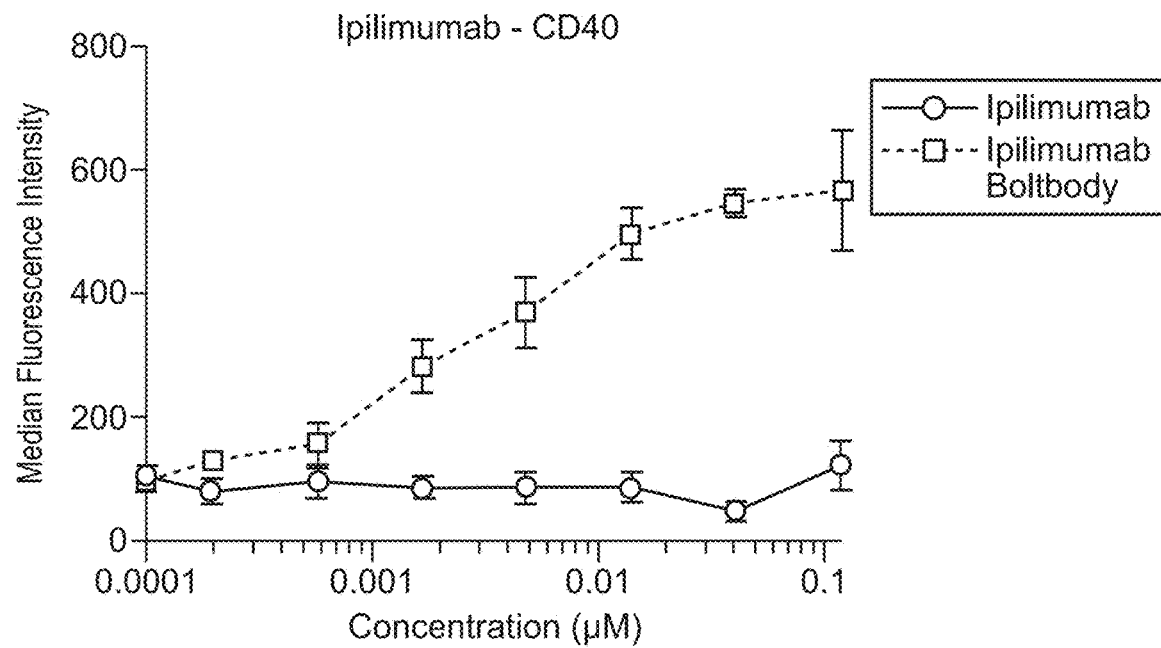
FIG. 10D shows that ipilimumab-adjuvant (Ipilimumab Boltbody) conjugates are superior at eliciting APC activation, compared to unconjugated ipilimumab, as indicated by expression of CD40.
Figure 10E:
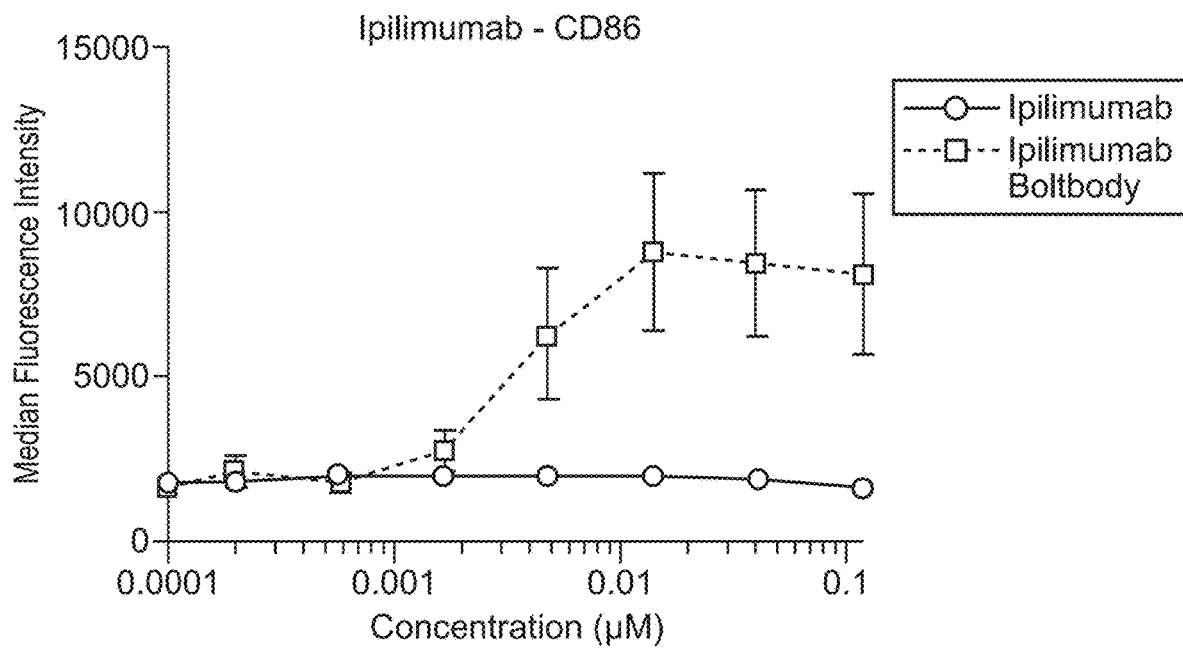
FIG. 10E shows that ipilimumab-adjuvant (Ipilimumab Boltbody) conjugates are superior at eliciting APC activation, compared to unconjugated ipilimumab, as indicated by expression of CD86.

Human APCs (~95% monocytes) obtained from fresh blood were incubated with CFSE-labeled human B cell lymphoma cells (Toledo, ATCC) at a 3:1 ratio and 2-fold serial dilutions of the antibody alone or the Antibody-SATA-SMCC-Compound 1 (conjugated). After 18 hours, cells were analyzed for the expression of activation markers via flow cytometry. The data indicate that immunoconjugates were superior at eliciting APC activation as CD40, CD86, and HLA-DR tended to be expressed at higher levels in APCs stimulated with the immunoconjugate as compared to those stimulated with the antibody alone (see FIGS. 10D and 10E for Ipilimumab, 11D and 11E for pembrolizumab, 12D and 12E for nivolumab, and 13D and 13E for atezolizumab). Consistent with the results observed in Example 3, the immunoconjugates downregulated CD14 (see FIG. 10C for ipilimumab, 11C for pembrolizumab, 12C for nivolumab, and 13C for atezolizumab). The results for these immunoconjugates were as expected for CD16 and CD123 (data not shown) based on the results in Example 3.

Figure 14B:
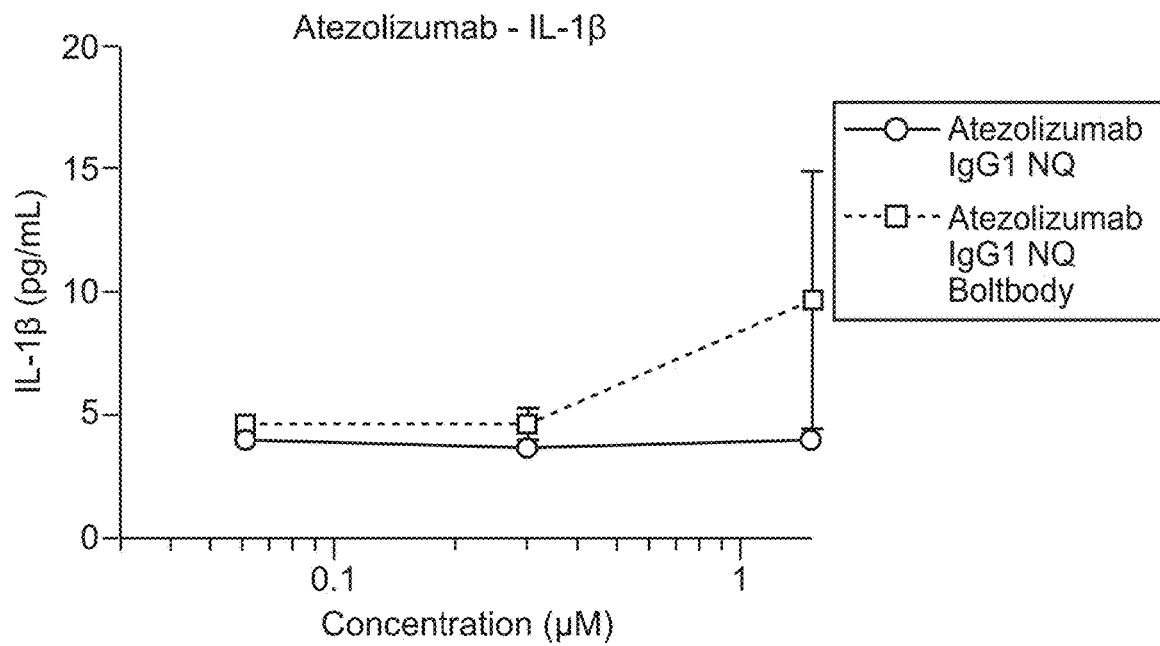
FIG. 14B shows that atezolizumab immunoconjugate (Atezolizumab IgG1 NQ Boltbody)-differentiated cells secrete higher amounts of IL-10 than atezolizumab-differentiated cells.

The capacity of these immunoconjugates to elicit cytokine secretion in human APCs following stimulation was investigated as described in Example 3 above. The data indicate that immunoconjugate-differentiated cells secreted higher amounts of IL-1 and TNFα (see FIGS. 14A and 14B for atezolizumab, 15A and 15B for nivolumab, 16A and 16B for pembrolizumab, and 20 for ipilimumab).

Example 6. Preparation and Assessment of Anti-Dectin-2 Adjuvant Conjugate Activity In Vitro Preparation of Additional Antibody Adjuvant Conjugates.

An additional antibody-adjuvant conjugate was prepared using the methods described in Examples 1 and 2. An anti-Dectin-2 antibody (CLEC6A) and isotype rat IgG2a was used to create the antibody-adjuvant conjugate with SATA-SMCC linkers (see Scheme 3 of FIG. 139).

Figure 21:
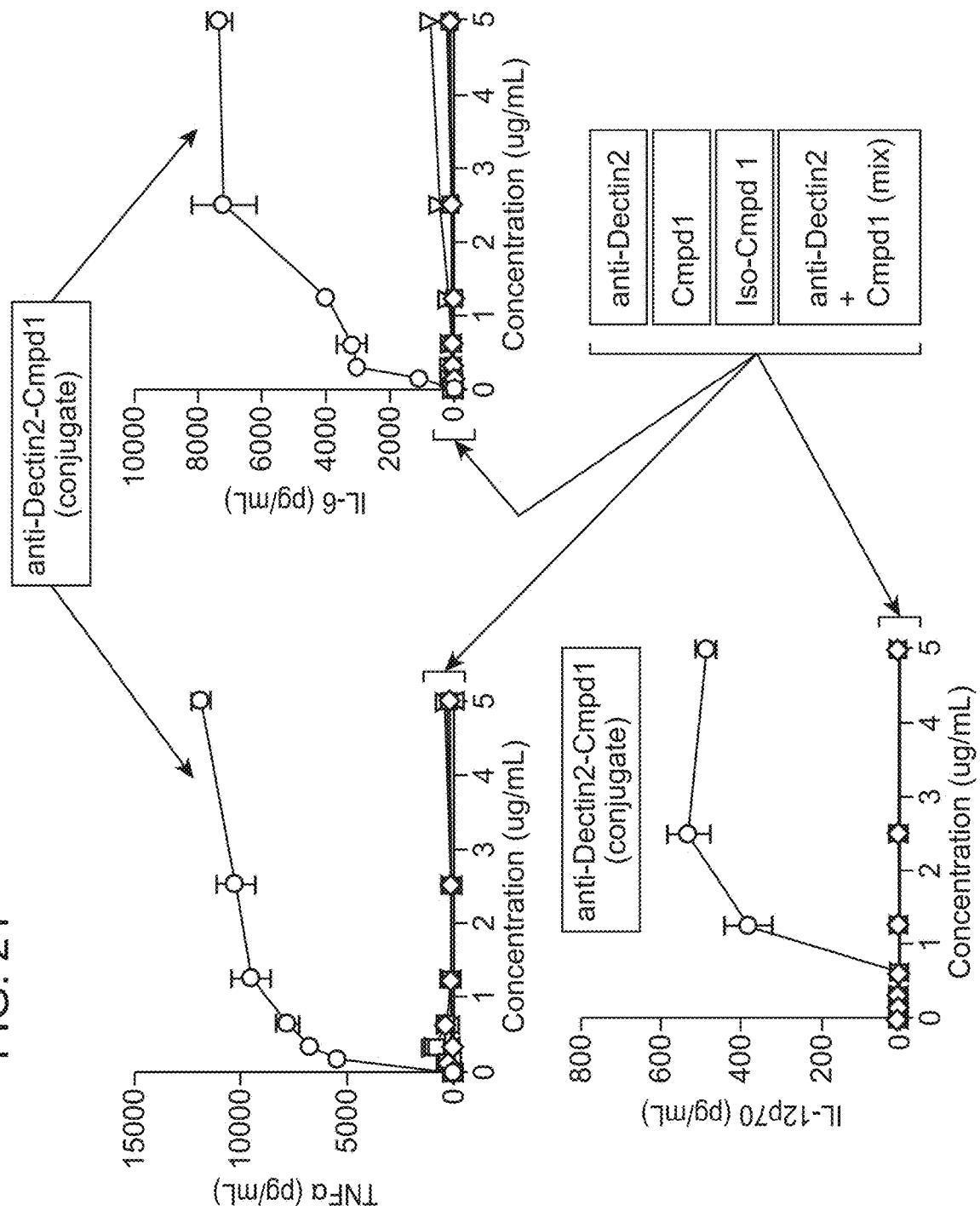
FIG. 21 shows that Dectin-2 immunoconjugate-differentiated cells secrete higher amounts of TNFα, IL-6, and IL-12p70 than cells exposed to equivalent amounts of the unconjugated components. The line that is significantly higher than the x-axis for each cytokine is the anti-Dectin-2 immunoconjugate (anti-Dectin-2-Cmpd1 (antibody conjugated with adjuvant Compound 1)). There are three lines along the x-axis, which are not visible, which show that the anti-Dectin-2 antibody alone, and the adjuvant Compound 1 alone, and the anti-Dectin 2 antibody and adjuvant Compound 1 mixture (anti-Dectin-2+Cmpd1 mixture, unconjugated), failed to produce any cytokine response. The line which is barely above the x-axis for IL-6 represents a control antibody, an ACC with Compound 1 as the adjuvant and a rat IgG2a isotype control antibody (labeled "Iso-Cmpd 1" in FIG. 21). In the TNFα and IL-12p70 graphs, the Iso-Cmpd 1 line is not visible as it is along the x-axis.

The capacity of this immunoconjugate to elicit cytokine secretion in murine monocyte derived APCs following stimulation was investigated as described in Example 3 above. Specifically, cytokine production is shown in FIG. 21 for GM-CSF-pretreated monocytes that were stimulated for 18 hours with the immunoconjugates or equivalent amounts of the unconjugated components. The data indicate that immunoconjugate-differentiated cells secreted higher amounts of TNFα, IL-6, and IL-12p70 (see FIG. 21) than equivalent amounts of the components (adjuvant alone, and antibody alone, and control antibody conjugate).

Dectin-2 and CLEC5A are C-type lectin receptors that associate with and signal through the adaptor proteins FcRγ (FCER1G) and DAP12 (TYROBP), respectively, following receptor crosslinking. These adaptor proteins contain immunoreceptor tyrosine-based activation motifs (ITAMs) that mediate downstream signaling through a Syk-dependent pathway, leading to immune cell activation (i.e. cytokine production, costimulatory molecule expression, antigen presentation, etc.). As shown (FIG. 21 and FIG. 23), immunoconjugates directed against these receptors exhibit synergistic immunostimulatory effects through simultaneous engagement of the ITAM-coupled receptor (through the antigen binding domain) and other signaling pathways (through the adjuvant moiety, e.g. TLR7/8). Immunoconjugates targeting other receptors that associate with FcRγ and/or DAP12, or that contain similar signaling domains (e.g. hemITAM), may be prepared in a similar fashion and are expected to exhibit similar effects.

Example 7. Synthesis of a TLR7/8 Adjuvant

The following steps were taken to prepare a TLR7/TLR8 adjuvant (Scheme 1, Compound 1) suitable for conjugation to an antibody to form an immunoconjugate of the present invention. Masses of products were confirmed on a UPLC system (Waters Acquity) equipped with a Xevo XS QToF spectrometer detector. Samples dissolved in acetonitrile:water were injected onto a BEH200 C18 column (2.1 mm diameter x 50 mm length) eluted with a 10-90% gradient of acetonitrile:water over 5 minutes.

Scheme 4

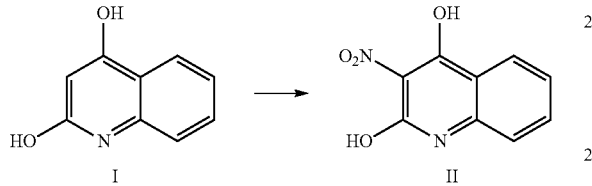

Chilled (00 C) nitric acid (70%, 160 mL) was slowly added to the quinoline-2,4-diol I (100 g 621 mmol) in glacial acetic acid (600 mL) stirring in ice bath. Removed mixture from ice bath then warmed to room temperature. Stirred at room temperature for 30 min. Heated at 80° C. for 1.5 hours then cooled the mixture to 0° C. Slowly added 1 L of water to the mixture to precipitate yellow solid. Stirred vigorously for 15 minutes then filtered. Resuspended the solid in water (1 L) and stirred vigorously for 15 minutes then filtered. Repeated with the additional step of slowly adding solid NaHCO$_3$ to bring pH to >6 then suction filtered overnight. Resuspended solid in ethyl ether (750 mL) and stirred vigorously to create fine suspension. Filtered and repeated. Suction filtered overnight to dry. Yield 112 g II (88%) yellow solid.

Scheme 5

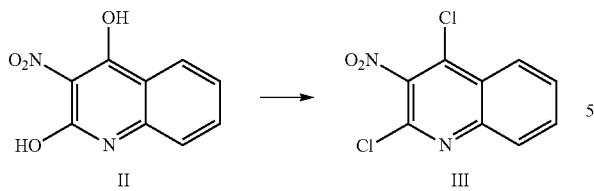

At room temperature, slowly added disopropylethylamine (63 mL, 47 g, 0.36 mol, 2.5 eq.) to POCl$_3$ (300 mL). Heated mixture to 80° C. under blanket of Ar. Slowly added in 2 g portions nitro-diol II (30 g, 145 mmol, 1 eq.) over 30 minutes maintaining temperature below 95° C. After addition is completed, raise temperature to 110° C. and heat for 1 hour. Cooled reaction to 0° C. then slowly pour in parts over ice while vigorously stirring. Added cold water to final volume of 1.2 L then stirred vigorously. Decanted the aqueous mother liquor and added 1 L water to the dark solid, scraping the sticky solid from walls of flask to create suspension. Repeated as necessary to obtain solid that can be filtered. Resuspended the solid in 1 L water then slowly added solid NaHCO3until pH >6. Filtered the solid then dissolved in EtOAc (500 mL). Filtered EtOAc solution through Celite to remove insoluble black impurity. Washed filtrate with saturated NaHCO3, water, brine then separated and dried organic layer with Na$_2$SO$_4$, filtered and concentrated in vacuo. The brown solid that is formed was triturated with 3:1 hexanes/diethyl ether (500 mL), filtered. The tan solid III (22 g, 30 mmol, 62%) was used as is in the next reaction.

Scheme 6

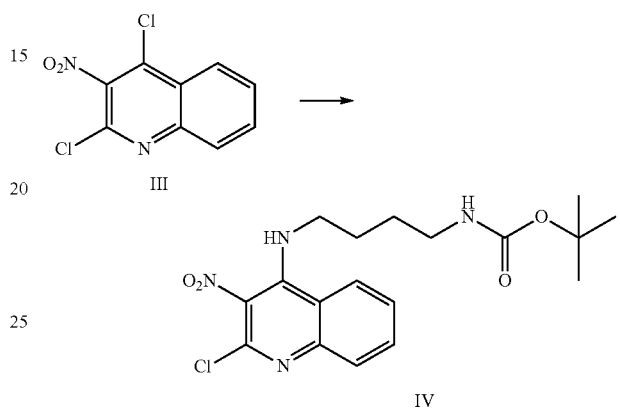

To a solution of nitro-dichloro compound III (22 g, 62 mmol, 1 eq.) and solid K$_2$CO$_3$ (17 g, 124 mmol, 2 eq.) in DMF (250 mL) at 0° C. was slowly added a solution of N-Boc-1,4-diaminobutane (12.8 g, 1.1 eq.) in DMF (60 mL) over 30 minutes. After addition was complete the reaction was warmed to room temperature and stirred for an additional 30 minutes. Water (800 mL) was added and the mixture was stirred vigorously. The supernatant was poured off and the wet solid was dissolved in ethyl acetate (500 mL). The solution was washed with water, brine, separated, dried (Na$_2$SO$_4$), filtered and concentrated in vacuo. The brown solid was triturated with 1:1 hexanes/diethyl ether (400 mL) and filtered to obtain a yellow solid IV (17 g, 43 mmol, 69%) that was used as in in the next reaction.

Scheme 7

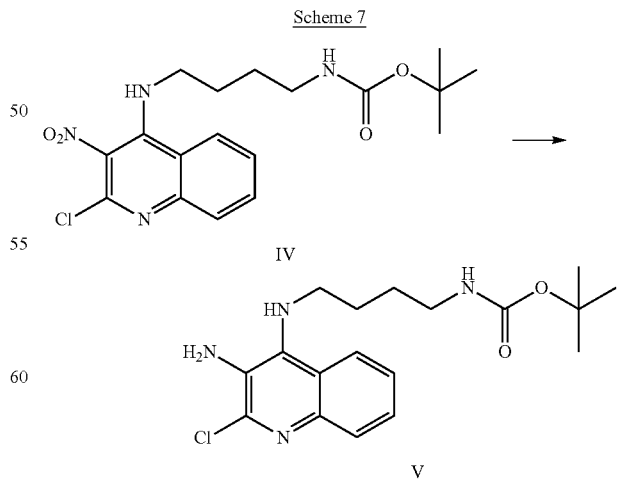

To a solution of nitro-amino compound IV (17 g, 43 mmol, 1 eq.) in methanol (400 mL) and water (60 mL) at 0°

C. was added NiCl$_2$·6H$_2$O (0.51 g, 2.2 mmol, 0.05 eq). Sodium borohydride (pellets, 3.2 g, 86 mmol, 2 eq.) was added and reaction was stirred for 1 h at 0° C. then warmed to room temperature and allowed to stir for another 15 minutes. Glacial acetic acid was added in parts to neutralize any unreacted NaBH$_4$ until a pH of ~5 was obtained. The solution was filtered through a bed of Celite to remove black insoluble material. The solvent was removed in vacuo. The dark brown solid was triturated with ether then filtered to obtain a tan solid V (13.3 g, 37 mmol, 85%) that was used as is in the next reaction.

Scheme 8

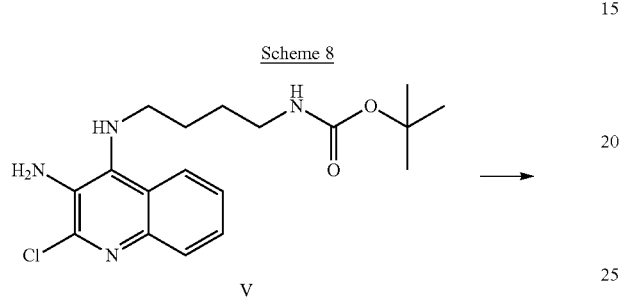

To a solution of diamino compound V (13.3 g, 37 mmol, 1 eq.) in DMF (250 mL) containing disopropylethylamine (7.17 g, 9.7 mL, 56 mmol, 1.5 eq.) stirring at room temperature was added neat valeroyl chloride (5.5 mL, 5.5 g, 42 mmol, 1.2 eq). The mixture was stirred for 30 minutes then ice was and then water was added to a final volume of 1 L. The mixture was stirred vigorously until a clear supernatant was formed. The supernatant was poured off and the crude solid was dissolved in ethyl acetate (400 mL) and filtered through a bed of Celite. The filtrate was washed with water (400 mL), brine (400 mL), separated then dried (Na2SO4), filtered and concentrated. The solid was triturated with ether, filtered and suction dried. The brown solid obtained VI (13.9 g, 31 mmol, 84%) was used in the next reaction as is.

Scheme 9

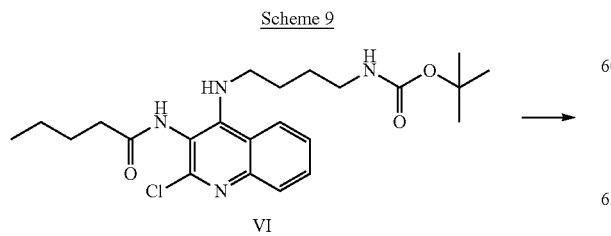

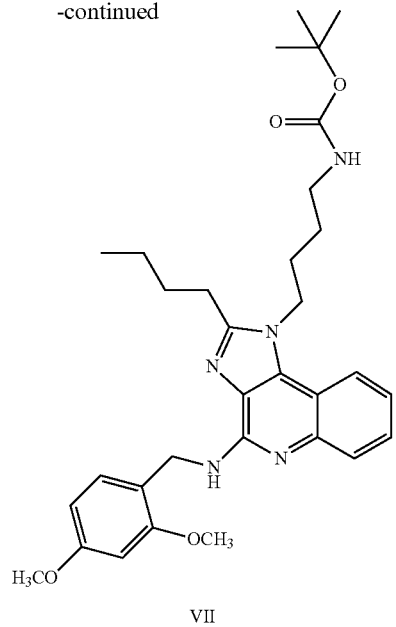

In a 500 mL round bottomed flask equipped with a Dean-Stark apparatus a mixture of amide VI (13.9 g, 31 mmol, 1 eq.) and 2-chlorobenzoic (2.4 g, 15.5 mmol. 0.5 eq.) was refluxed in 150 mL toluene (bath temperature=170° C.) for 4 hours. The Dean-Stark apparatus and condenser was removed and until 80-90% of the toluene was evaporated. 2,4-dimethoxybenzylamine (25 g, 150 mmol, 5 eq.) was added and the reaction was continually heated at 120° C. for 1.25 hours. The reaction was cooled and the crude mixture was diluted with 1:1 MeOH/water (1 L) and vigorously stirred. The supernatant was decanted (removing most of the excess 2,4-dimethoxybenzylamine) and the crude product was partitioned between between water and ethyl acetate. Acetic acid was added until the aqueous layer gave a pH of 5-6. The organic layer was washed with water, brine, dried (Na$_2$SO$_4$), filtered and concentrated. The thick brown syrup was dissolved in diethyl ether and filtered to remove a gray solid (not product). The ether was removed to give a brown syrup (14.4 g, 26 mmol, 73%) and was used as is in the next reaction.

Scheme 10

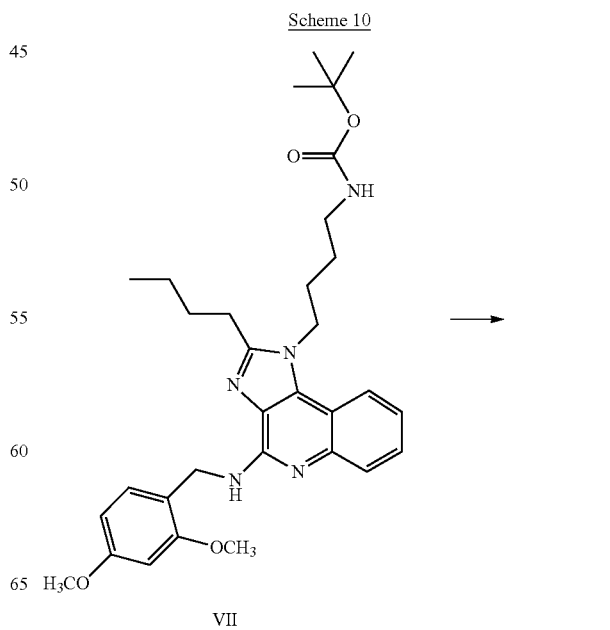

251
-continued

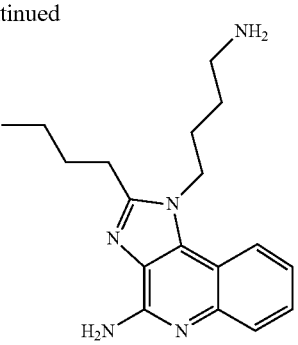

VIII

To material VII (14.4 g, 26 mmol, 1 eq.) was added water (60 mL) and slowly with swirling conc. HCl (60 mL). The mixture was vigorously stirred at room temperature for 30 minutes then heated to reflux for 1 hour. The reaction was cooled in an ice bath and solid NaOH pellets (28 g, 700 mmol) were added in parts over 30 minutes until a basic pH was achieved. The solution was warmed to room temperature and stirred vigorously. Solid NaCl was added until a saturated solution was achieved. This aqueous layer was extracted 3 times with 10% isopropanol/dichloromethane (400 mL). The combined organic layers were dried (Na$_2$SO$_4$), filtered and concentrated to yield a brown solid VIII was obtained (6.8 g, 22 mmol, 79%).

Example 8. Immunoconjugate Synthesis

Scheme 11

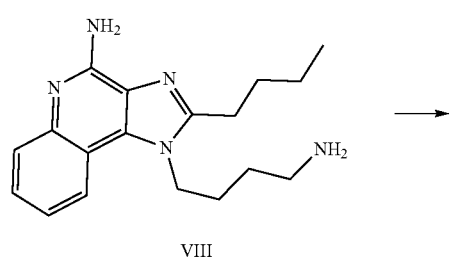

VIII

252
-continued

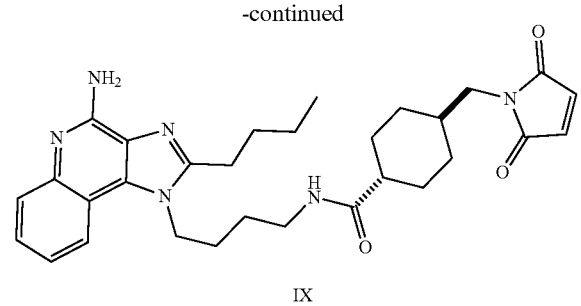

IX

This example provides guidance on synthesis of an immunoconjugate using the TFP ester method. Compound VIII (311 mg, 1 mmol) was dissolved in 10 mL of dimethylformamide (DMF) and then 2 molar equivalents of diisopropylethylamine (DIPEA) was added. An SMCC linker (1.5 mmol) was dissolved in 10 mL of dichloromethane and added in one portion to VIII. The reaction was stirred overnight at 20° C. and concentrated to dryness via rotary evaporation. The crude product IX was purified on a silica gel using a Buchi flash chromatography system loaded with a 12 g disposable cartridge and eluted with a gradient of 0-10% methanol over 15 minutes. Pure fractions were combined and evaporated to dryness to provide160 mg of a pale yellow solid IX.

Scheme 12

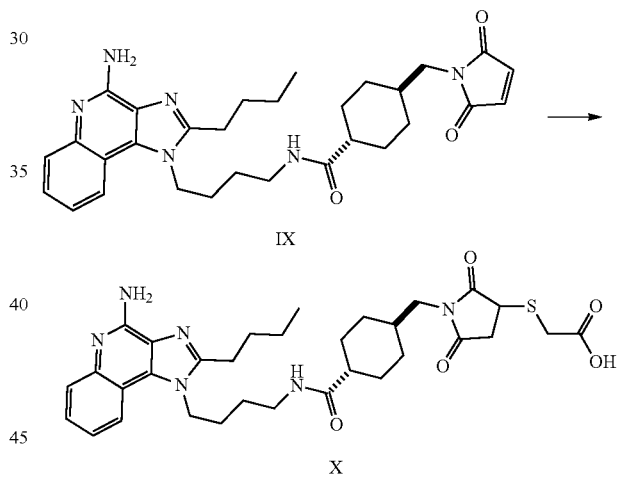

Compound IX (0.1 mmol, 53 mg) was dissolved in 10 mL of dichloromethane and then 2 equivalents of thioglycolic acid were added at one time. The mixture was concentrated to dryness under vacuum and the residue was washed three times with 5 mL of diethyl ether.

Scheme 13

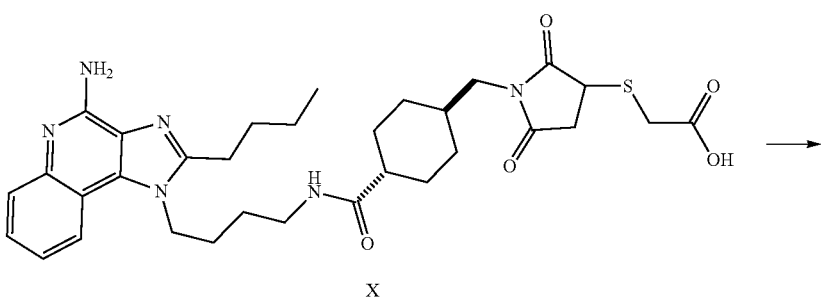

X

-continued

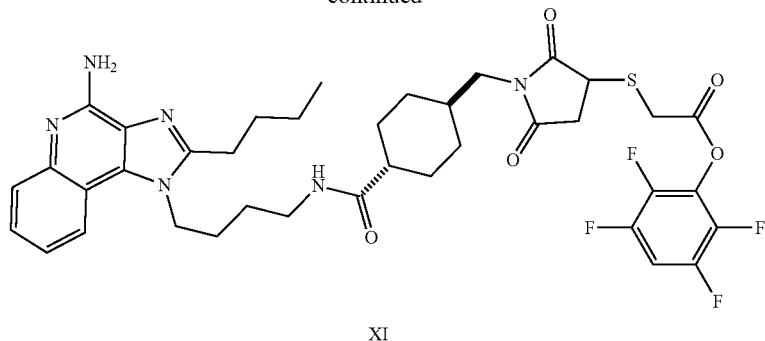

XI

Compound X (6.2 mg, 0.01 mmol) was dissolved in 2 mL of THF and then 5 mg of tetrafluorophenol was added. Then 5 mg of dicyclohexylcarbodiimide (DCC) was added. The mixture was stirred overnight at room temperature and then concentrated to dryness under vacuum. The crude product XI was purified via flash chromatography on silica gel (4 gram prepacked column) and eluted with 0-10% MeOH in dichloromethane. Pure fractions were combined and evaporated to provide 3.6 mg of pure XI (confirmed by LC/MS). The TFP ester XI was then used in the antibody conjugation step depicted in Scheme 14 of FIG. 14O.

An IgG1 antibody (specifically, the anti-CD20 antibody rituxumab) was buffer exchanged into PBS at a pH of 7.2 and diluted to 10 mg/mL (66 µM). The TFP activated adjuvant, XI, was added to DMSO and 6 molar equivalents (relative to IgG) was added to 1 mL of the antibody solution (10 mg) in one portion. The mixture was inverted several times to mix and incubated overnight at 20° C. The resulting immunoconjugate ("BB-01") was purified via buffer exchange into PBS (pH 7.2) using a PD10 column (SephadexG25®) size exclusion chromatography column. Pure fractions were pooled and the concentration determined by measuring the absorbance at 280 nm on a nano-drop spectrophotometer. The yield was 8 milligram or approximately 80% based on recovered protein. The immunoconjugate product was sterile filtered through a 0.2 am syringe filter and stored at 4° C. until needed.

Characterization of the resulting immunoconjugate's drug to antibody ratio ("DAR") was performed via liquid chromatography-mass spectrometry ("LC/MS") analysis on a UPLC system (Waters Aquity) equipped with a Xevo XS QToF mass spectrometer detector. Analysis was performed via injection of 5 ag of the immunoconjugate onto a BEH200 C4 column (2.1 mm diameter×50 mm length) eluted with a 10-90% gradient of acetonitrile:water over 4 minutes.

The analysis indicated that the immunoconjugates synthesized via the TFP method demonstrated higher DAR than the immunoconjugate synthesized using the SATA method. In addition the TFP method yielded immunoconjugates with reduced amounts of unconjugated antibody (only about 5%) compared to the SATA synthesis method (about 20%) (compare FIGS. 1A and 1B).

Size exclusion chromatography ("SEC") analysis of BB-01 was performed to determine the monomeric purity. Analysis was performed on a BEH200 SEC column eluted with PBS (pH 7.2) and 0.2 mL/min. The immunoconjugate BB-01 synthesized using the TFP active ester method contained less than 2% of high molecular weight aggregate (FIG. 2B) compared to greater than 8% aggregate observed when the SATA method was used (FIG. 2A).

Example 9. Synthesis of Immunoconjugate BB-14 with a Pentafluorophenyl ("PFP") Ester This example provides guidance on synthesis of an immunoconjugate using the PFP ester method. Ester modification of the adjuvant and conjugation of the modified adjuvant to the antibody is shown in Scheme 15 of FIG. 14I. Cyclohexane trans-1,4-dicarboxylate (1 g) was dissolved in 10 mL of dimethylformamide ("DMF") and 1-[bis(dimethylamino)methylene]-1H-1,2,3-triazolo[4,5-b]pyridinium 3-oxide hexafluorophosphate) ("HATU") (1 mmol) was added followed by 1 mL of N-ethyl-N-(propan-2-yl)propan-2-amine ("DIPEA"). Compound 1 (311 mg) was added and the mixture stirred overnight at 20° C. The reaction mixture was diluted with 50 mL of dichloromethane ("DCM") and washed with 20 mL of iN HCl. The DCM layer was evaporated to dryness and the product purified on silica gel eluted with 0-10% MeOH in DCM containing 1% acetic acid. Pure fractions were concentrated to provide 220 mg of purified acid II. Compound II (100 mg) was dissolved in THF and 100 mg of HATU was added followed by 200 aL of DIPEA. Two equivalents of amino-PEG2-tertbutyl-carboxylate was added and stirred for one hour at 20° C. The mixture was concentrated to dryness and 10 milliliters of 4N HCl in dioxane was added. The mixture was concentrated to dryness and the crude product III was purified by prep HPLC to provide 40 mg of compound III.

Compound III was converted to PFP ester IV as described below. Compound III (35 mg) was added to 50 mg of PFP in 5 mL THF and 5 mL DMF was added followed by 20 mg of DCC. DMAP (2-3 mg) was added and the solution was stirred overnight at 20° C. The reaction was concentrated and purified by flash chromatography (eluted with 0-10% MeOH) to provide 17 mg of PFP ester IV after lyophillization from 1:2 acetonitrile water.

PFP ester IV (6 molar eq. relative to IgG) was added to 20 mg of an IgG antibody (specifically, the anti-CD20 antibody rituximab) (10 mg/mL in PBS) and incubated at 37° C. overnight. The resulting immunoconjugate BB-14 was buffer exchanged into PBS (pH 7.2) to remove excess small molecular weight reagent and the concentration determined on the nanodrop. The yield was 15 mg of immunoconjugate (75% yield). The product was stored at 4° C. A DAR of 2.2 was determined via LC/MS analysis. Besides the desirable DAR and high yield, the product also had few impurities as determined by SEC analysis (see FIGS. 3 and 4).

Example 10. Synthesis of Immunoconjugate BB-15 with a NHS Ester

Ester modification of the adjuvant and conjugation of the modified adjuvant to the antibody is shown in Scheme 16 of FIG. 142. Compound VII (150 mg) was dissolved in 20 mL of tetrahydrofluran ("THF") and 10 mL of aqueous, saturated sodium bicarbonate was added. Then, 50 mg of succinic anhydride was added in one portion and the mixture was stirred for one hour at room temperature. Twenty milliliters of iN HCl was added slowly and the mixture was extracted with 2×50 mL of dichloromethane. The combined organic extracts were evaporated to dryness. The crude product (Suc-VII) was purified on a 4 gram silica gel column eluted with 0-15% MeOH (1% acetic acid) over 15 minutes. Pure fractions were combined and evaporated to provide 190 mg of pure VII-Suc.

Compound VII-Suc (150 mg) was dissolved in 10 mL of DMF and 1 equivalent of HATU was added followed by 2 equivalents of DIPEA. 1.5 equivalents of glycine-OtBu were added and stirred overnight. The DMF was evaporated and the residue treated with 5 mL of iN HCl in dioxane for 30 minutes. The solvent was evaporated and the crude Gly-Suc-VII was flash purified on a 4 gram silica gel column eluted with 0-10% MeOH over 10 minutes. Evaporation of pure fractions provided 110 mg of Gly-Suc-VII; the pure material was dissolved in DMF and the above process was repeated to provide 60 mg of pure Gly2-Suc-VII.

The pure Gly2-Suc-VII (30 mg) was dissolved in 5 mL of DMF and 1.5 equivalents of NHS was added followed by 5 mL of THF. DCC (1.5 equivalents) was added and the mixture was stirred overnight at room temperature. The solvent was evaporated and the crude NHS ester was flash purified on a silica gel eluted with 0-10% MeOH in DCM over 10 minutes. Pure fractions (determined by TLC) were combined and evaporated to provide 1 mg of pure NHS-Gly2-Suc-VII after lyophilization from acetonitrile water.

The pure NHS ester was dissolved in DMSO to make a 20 mM solution and 6 eq. was added to 2 mL of an IgG antibody (specifically, the anti-CD20 antibody rituximab) (10 mg/mL in PBS). The conjugation reaction was incubated at room temperature overnight and buffer exchanged into fresh PBS to remove excess adjuvant. The purified immunoconjugate BB-15 was sterile filtered and stored at 4° C. The yield was about 16 mg. Besides having a high yield, the LC/MS analysis showed high levels of purity, low levels of aggregation, and a desirable DAR ratio (see FIGS. 5 and 6).

Example 11. Synthesis of Immunoconjugate with a TFP Ester

This example provides guidance on synthesis of an immunoconjugate with a different linker using the TFP ester method. Ester modification of the adjuvant and conjugation of the modified adjuvant to the antibody is shown in Scheme 17 of FIG. 143. Compound VII (311 mg, 1 mmol) was dissolved in 10 mL of DMF and then 0.3 mL of DIPEA was added. The NHS-PEG5-acid (1.2 equivalents) was dissolved in 5 mL of dichloromethane and added to compound VII in one portion. The mixture was stirred overnight at room temperature and then concentrated to dryness. The crude residue was purified via silica gel chromatography on a 4 gram column eluted with 0-10% MeOH in DCM containing 1% acetic acid over 10 minutes to provide 260 mg (57% yield) of PEG5-VII after concentration of the pure fractions.

PEG5-VII (50 mg) was dissolved in 10 mL DMF and 1.5 eq. of TFP was added followed by 1.2 eq. DCC and 5 mg of DMAP. The reaction was stirred overnight, concentrated to dryness and purified on silica gel 4 gram column eluted with 0-10% MeOH in DCM to provide 35 mg of pure TFP-PEG5-VII after lyophilization from 1:2 acetonitrile water.

The TFP ester (TFP-PEG5-VII) was dissolved in DMSO to make a 20 mM stock solution and added to 20 mg of an IgG antibody (specifically, the anti-CD20 antibody rituximab) in PBS at 10 mg/mL. The conjugation reaction was allowed to proceed overnight at room temperature. The resulting immunoconjugate was buffer exchanged (GE, PD10 desalting column) into PBS at pH 7.4. The purified immunoconjugate was sterile filtered using a 2 μm syringe filter and stored at 4° C. LC/MS analysis confirmed that the process provided a DAR of 2.9 adjuvants per antibody (see FIG. 7). SEC analysis indicated minimal amounts of aggregate (i.e., less than 2%) (see FIG. 8).

Example 12. Synthesis of Another TLR7/TLR8 Adjuvant

This example provides guidance on how to synthesize another TLR7/8 adjuvant. Compound XIV was synthesized starting from compound VI of Scheme 8 of Example 3.

Scheme 18

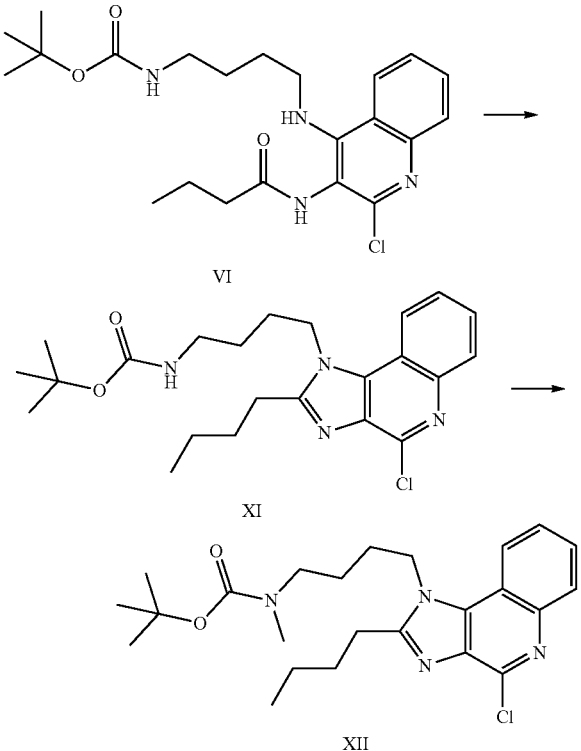

Compound VI (2 g) was dissolved in toluene with 20% dry acetic acid and heated to 75° C. overnight. The solvent was removed under vacuum to provide 2 grams of crude compound XI. Compound XI was used without further purification. Compound XI (2 g) was dissolved in 20 mL DMF and 1.2 equivalents of NaH (50% dispersion) was added slowly and the mixture was stirred for 30 minutes at room temperature. Methyl iodide (2 equivalents) was added in one portion and the reaction mixture was stirred overnight at room temperature. The reaction was concentrated to dryness and the product purified via flash chromatography. The product was eluted with a gradient of 0-10% MeOH in dichloromethane over 15 min. Pure fractions were combined and concentrated to yield 1 g of compound XII (50% yield for 2 steps).

Scheme 19

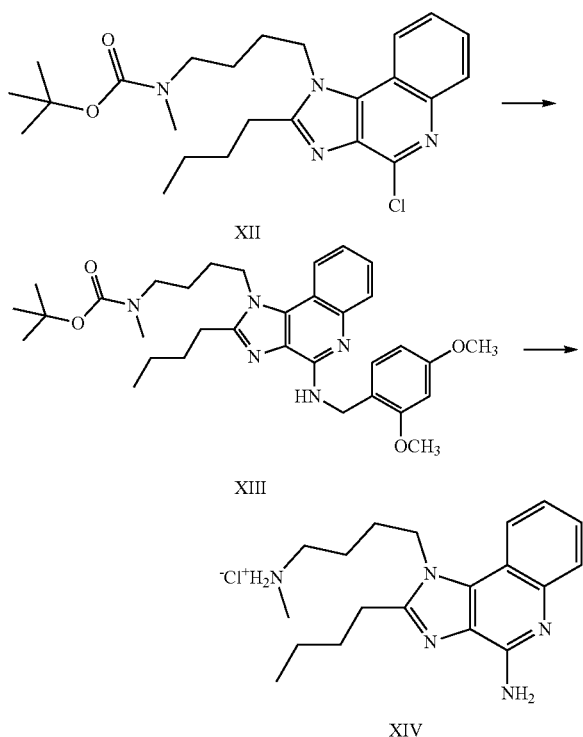

Compound XII (10 g) was dissolved in 10 mL of neat dimethoxybenzylamine ("DMBA") and heated to 120° C. for 3 hours. The reaction mixture was cooled and diluted with 100 mL of ethyl acetate. The resulting solution was washed two times with 10% citric acid in water and once with water to remove excess DMBA. The organic layer was dried over MgSO4 and concentrated under vacuum to provide crude compound XIII as a brown oil. The crude DMB derivative, compound XIII, was dissolved in dichloromethane and 2 mL of 4N HCl in dioxane was added. After 2 hours, the reaction mixture was concentrated to dryness and the crude HCl salt compound XIV was dissolved in 3 mL of methanol. Ethyl ether (20 mL) was added slowly with stirring to the crude solution and a white precipitate formed. The reaction was filtered and the white solid product was washed twice with 10 mL ethyl ether and dried under vacuum to provide 4 gram of HCl salt compound XIV. LC/MS analysis confirmed the correct molecular weight (M/z=326.5) and a purity of greater than 95%.

Example 13. Synthesis of Immunoconjugate BB-26 with a TFP Ester

This example provides guidance on synthesis of an immunoconjugate that contains an aryl tertiary amine linker using the TFP ester method as depicted in Scheme 20 of FIG. 144. Compound XIV (300 mg) of Example 12 was dissolved in THF (10 mL) and 1.2 eq. of NaH (50% dispersion) was added. The mixture was stirred for 15 minutes and 2 equivalents of 4-bromomethylphenyl acetic acid was added. The reaction was stirred overnight at room temperature and concentrated to dryness. One mL of acetic acid was added and the product was purified by preparative HPLC on a C-18 column eluted with a gradient of 10-90% acetonitrile in water (0.1% TFA) over 20 minutes to provide 165 mg of purified phenylacetic acid compound XV.

Compound XV (50 mg) was dissolved in dichloromethane/dimethylformamide (5 mL, 1:1) and 2 equivalents of TFP was added followed by 1.5 equivalents of 1-ethyl-3-(3-dimethylaminopropyl)carbodiimide ("EDCI"). The reaction was stirred overnight at room temperature and the product purified via flash chromatography on a 4 gram silica gel column eluted with 0-10% isopropanol over 10 minutes. Pure fractions were concentrated and lyophilized from 30% acetonitrile water to provide 21 mg of purified TFP ester compound XVI as a pale yellow solid. The molecular weight and purity were confirmed by LC/MS (m/z=621.7).

Figure 12B:
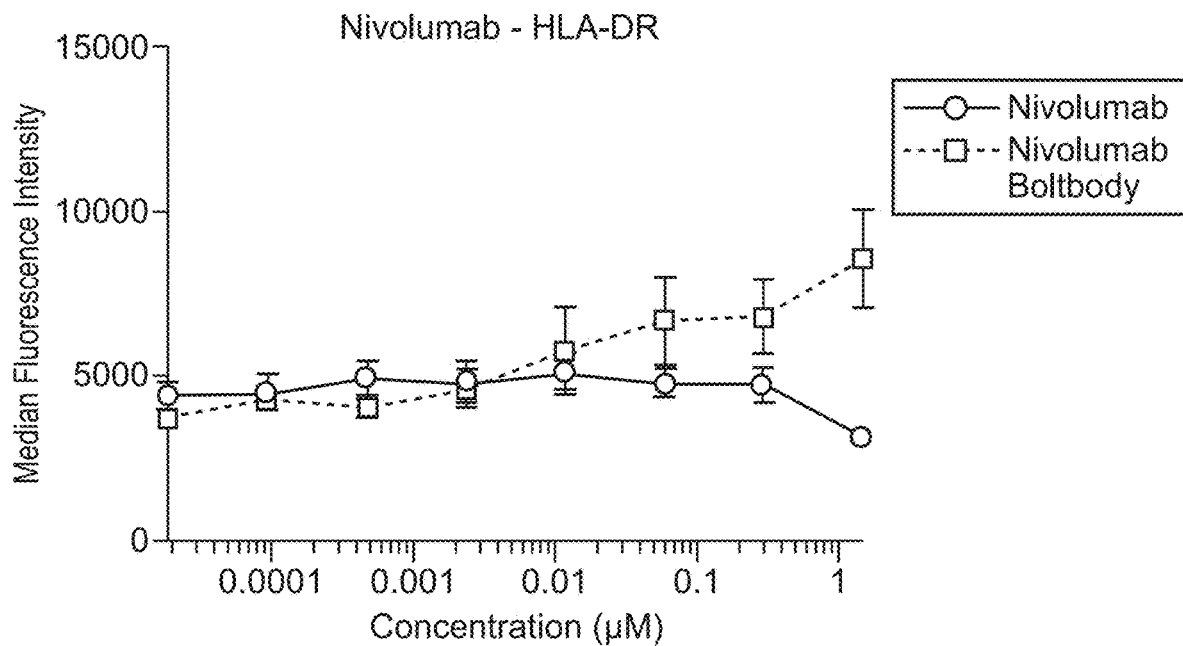
FIG. 12B shows that nivolumab-adjuvant (Nivolumab Boltbody) conjugates are superior at eliciting APC activation, compared to unconjugated nivolumab, as indicated by expression of HLA-DR.
Figure 12C:
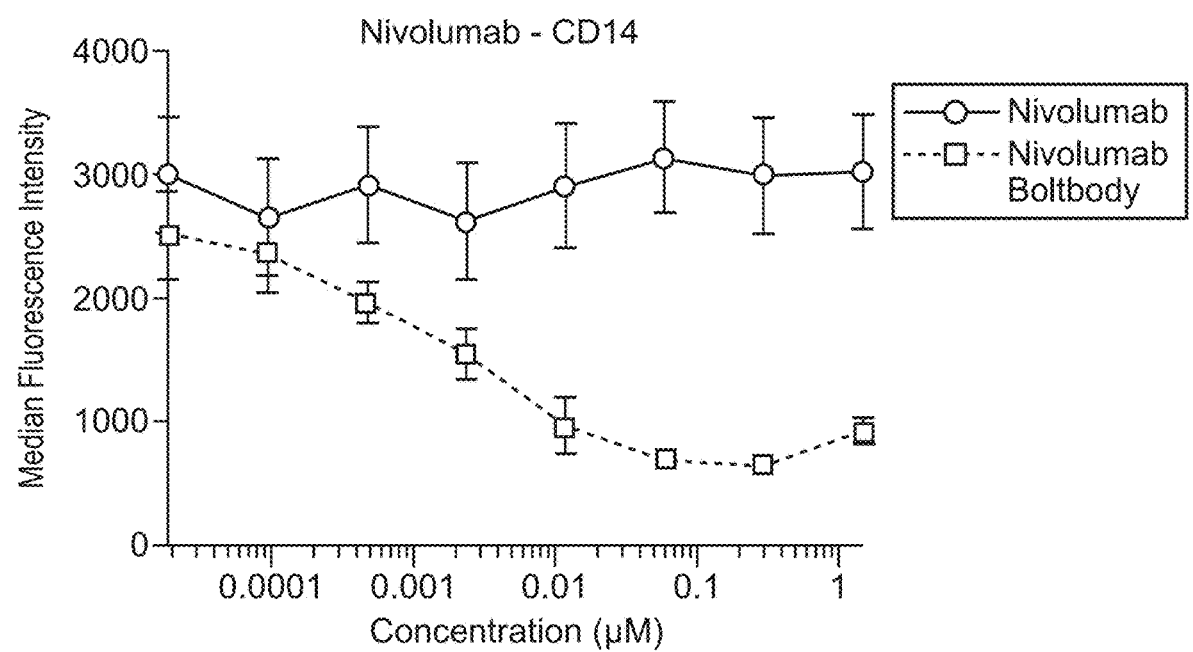
FIG. 12C shows that nivolumab-adjuvant (Nivolumab Boltbody) conjugates are superior at eliciting APC activation, compared to unconjugated nivolumab, as indicated by expression of CD14.
Figure 12D:
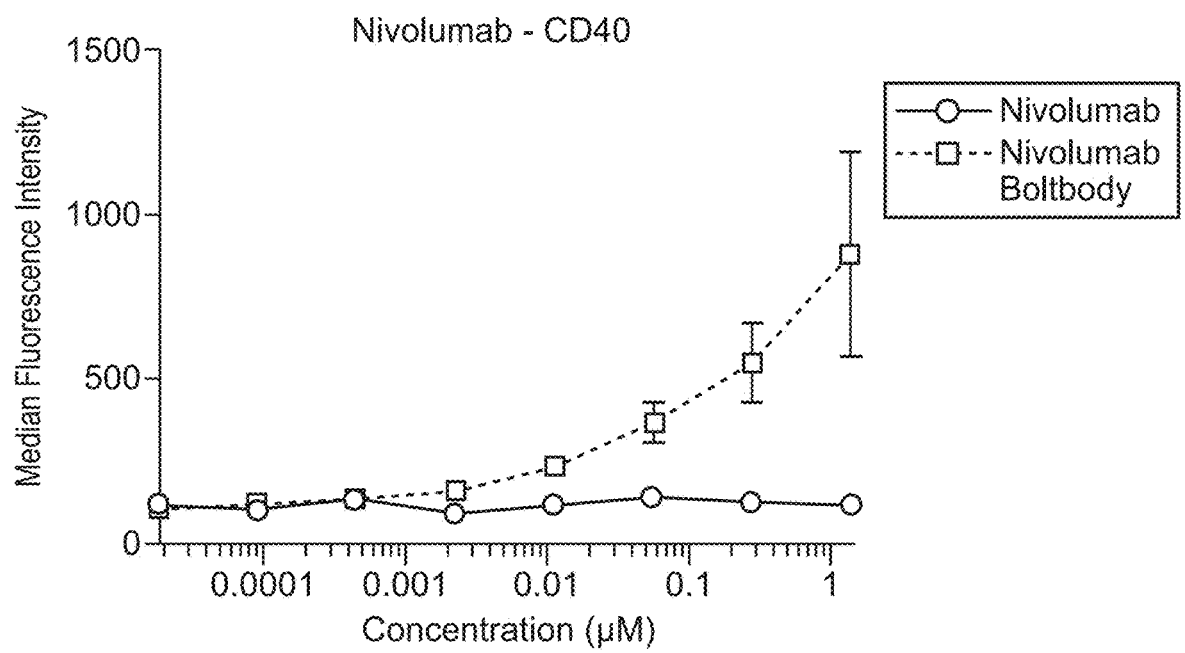
FIG. 12D shows that nivolumab-adjuvant (Nivolumab Boltbody) conjugates are superior at eliciting APC activation, compared to unconjugated nivolumab, as indicated by expression of CD40.
Figure 12E:
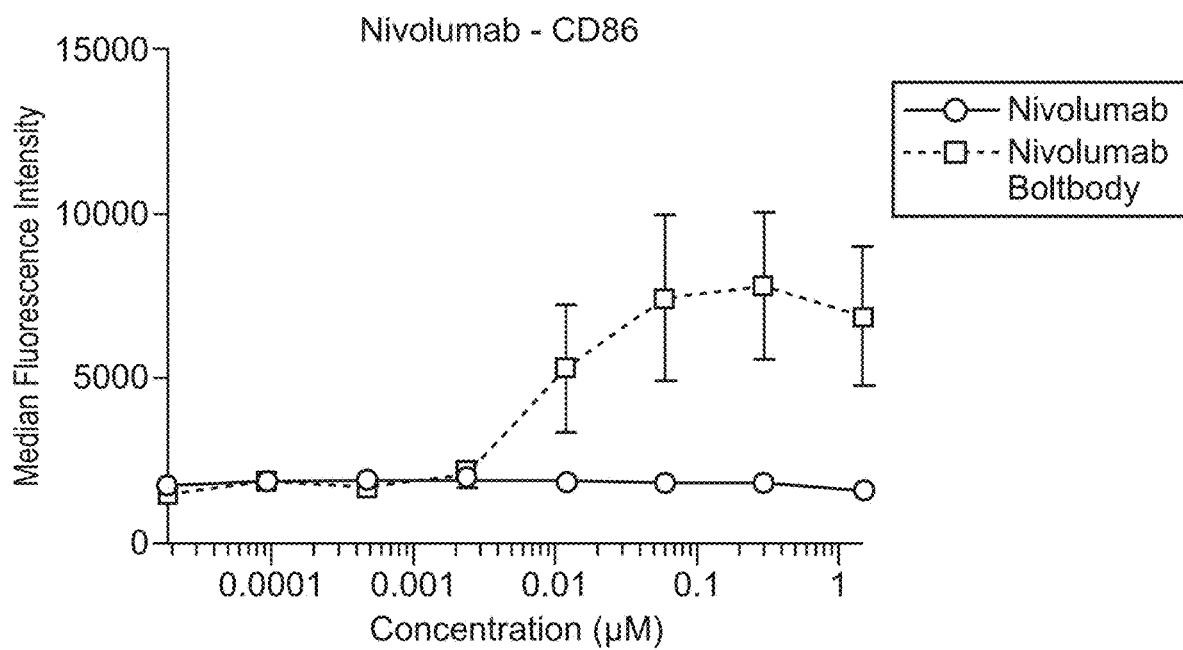
FIG. 12E shows that nivolumab-adjuvant (Nivolumab Boltbody) conjugates are superior at eliciting APC activation, compared to unconjugated nivolumab, as indicated by expression of CD86.
Figure 13A:
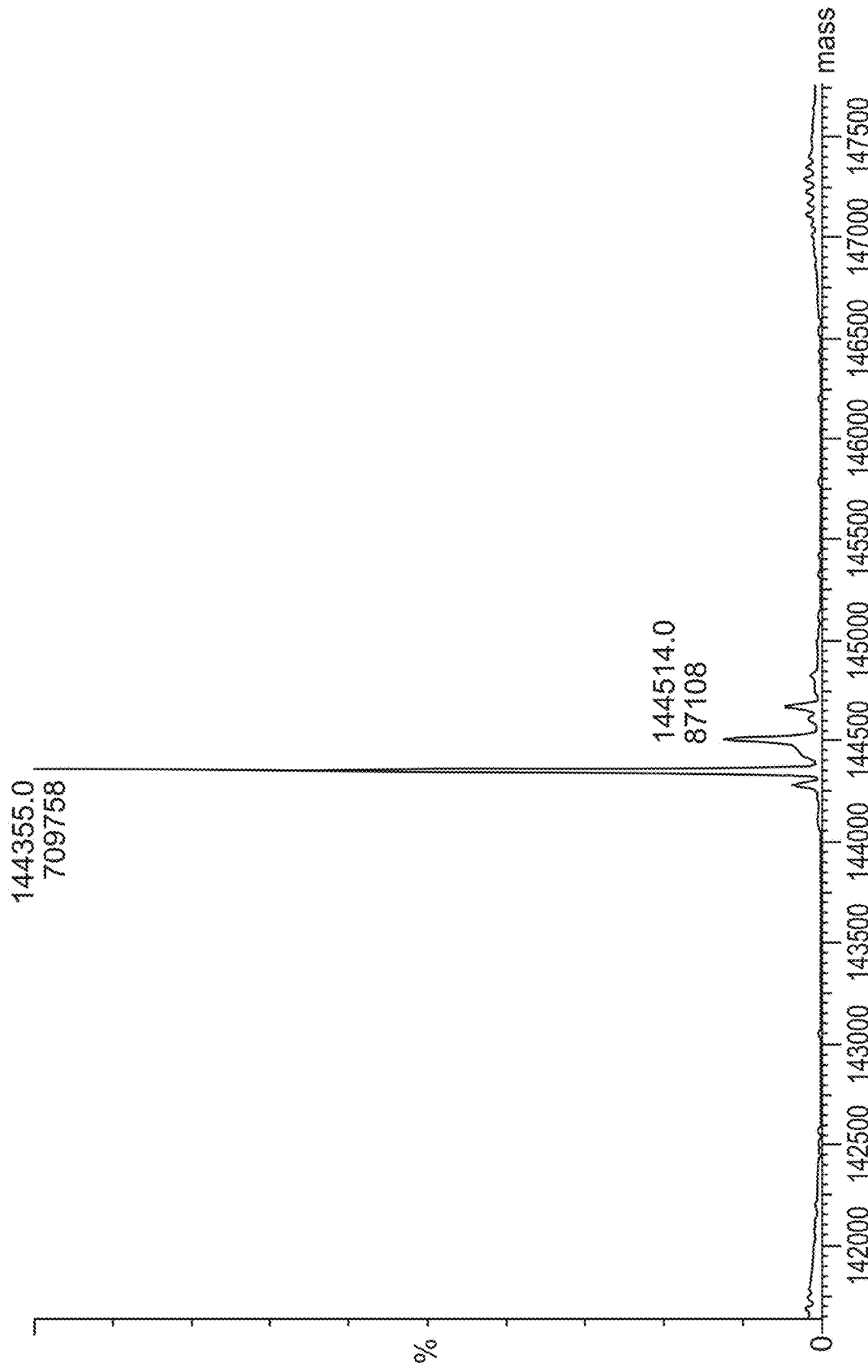
FIG. 13A shows the analysis of atezolizumab via LC-MS.
Figure 13B:
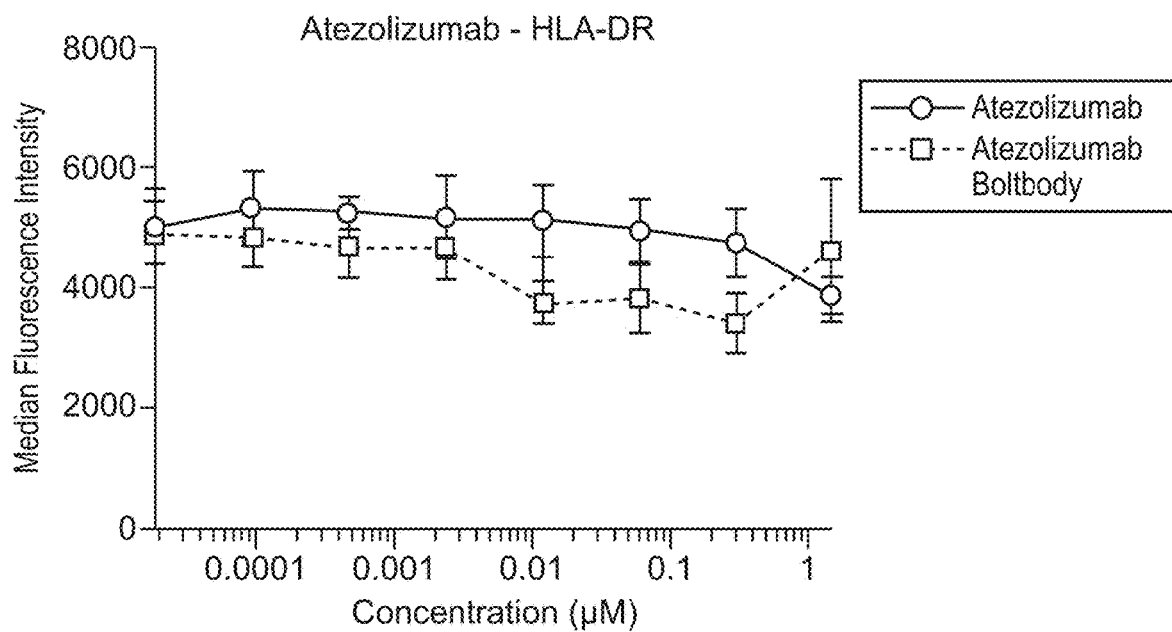
FIG. 13B shows that atezolizumab-adjuvant (Atezolizumab Boltbody) conjugates are superior at eliciting APC activation, compared to unconjugated atezolizumab, as indicated by expression of HLA-DR.
Figure 13C:
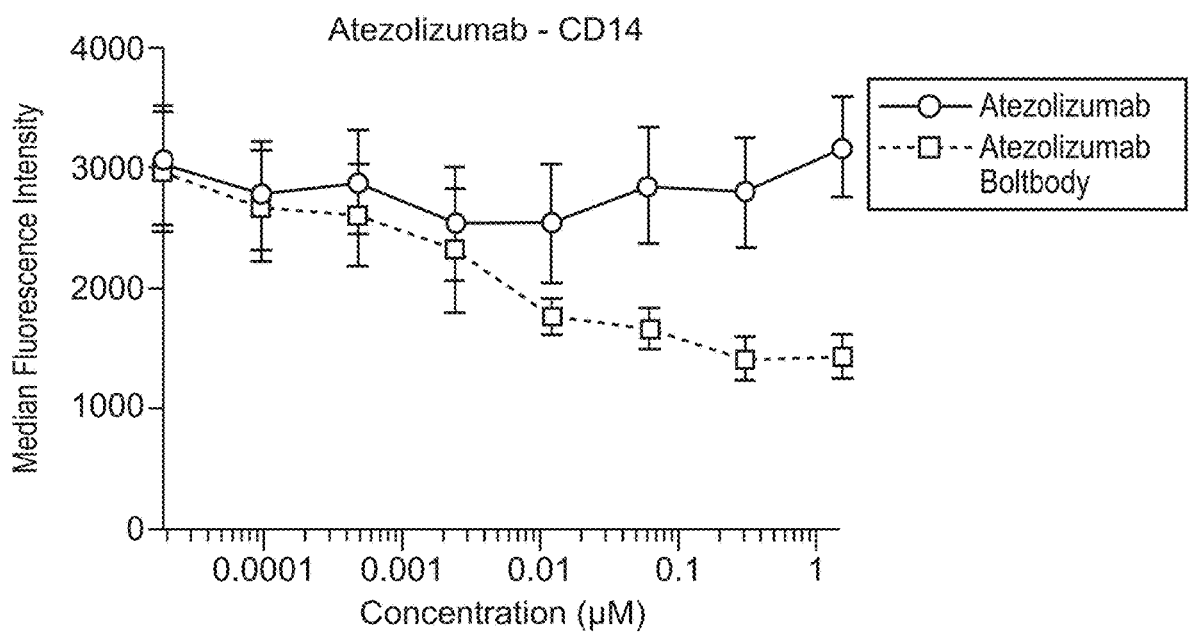
FIG. 13C shows that atezolizumab-adjuvant (Atezolizumab Boltbody) conjugates are superior at eliciting APC activation, compared to unconjugated atezolizumab, as indicated by expression of CD14.
Figure 13D:
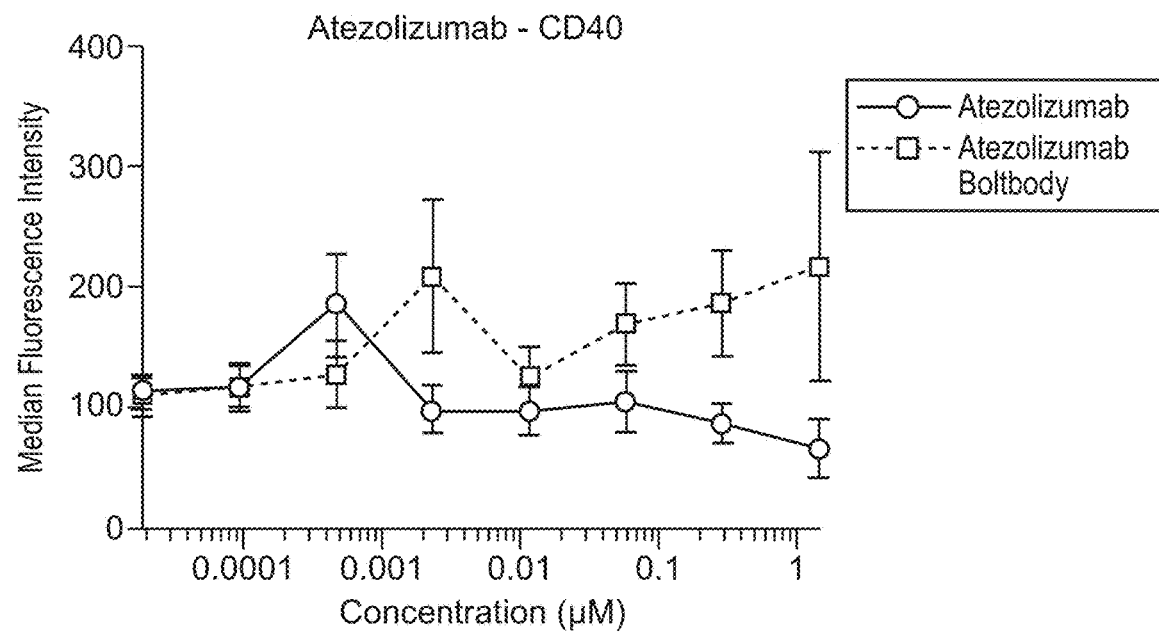
FIG. 13D shows that atezolizumab-adjuvant (Atezolizumab Boltbody) conjugates are superior at eliciting APC activation, compared to unconjugated atezolizumab, as indicated by expression of CD40.
Figure 13E:
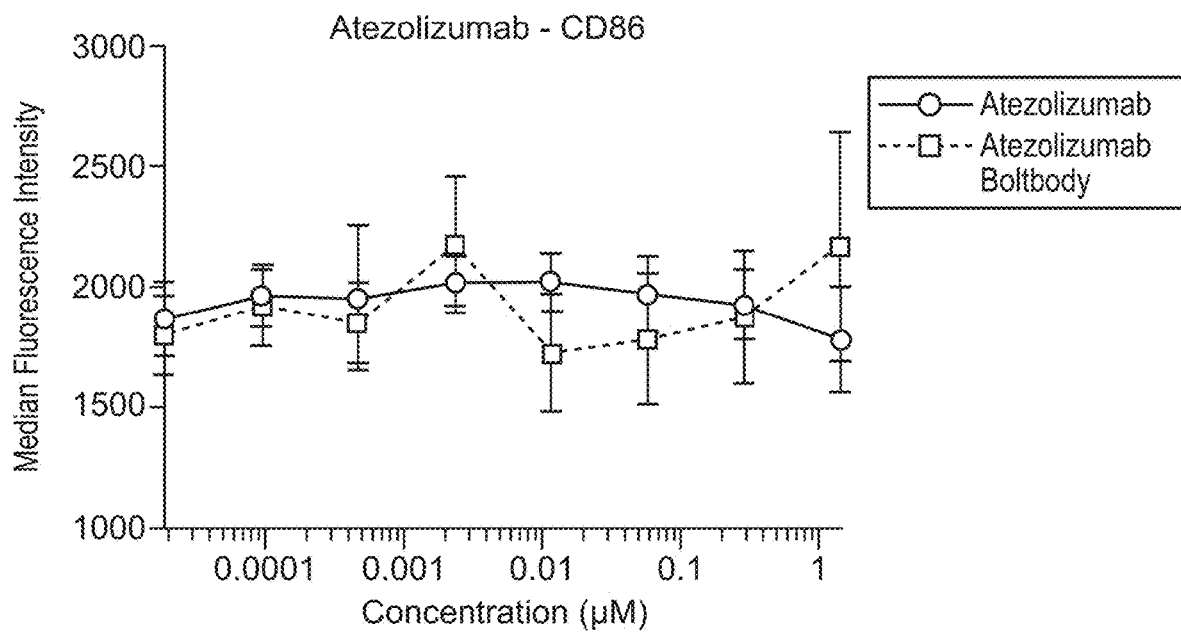
FIG. 13E shows that the level of activation of atezolizumab-adjuvant (Atezolizumab Boltbody) conjugates, as indicated by expression of CD86.

Conjugation to Antibody:

The TFP ester XVI was dissolved in anhydrous DMSO to make a 20 mM stock solution and 6 molar equivalents (relative to the antibody) was added to 20 mg IgG antibody (specifically, the anti-CD20 antibody rituximab) (10 mg/mL in PBS). The conjugation reaction was incubated at 4° C. overnight. The resulting immunoconjugate, BB-26, was buffer exchanged into PBS (pH 7.2) to remove excess small molecular weight reagents. The final concentration was determined by measuring the antibody at 280 nm on the Nanodrop 1000 spectrophotometer. The yield was 15 mg of BB-26, or 75% based on recovered protein. As seen in FIG. 12A, a minimal aggregate was seen (less than 1%) as detected by SEC analysis. As seen in FIG. 12B, the product had a DAR ratio of 2.8 as determined via LC/MS analysis. The purified immunoconjugates BB-26 was filtered through a 0.2 µM sterile filter and stored at −20° C.

Example 14. Synthesis of Immunoconjugate BB-27 with a TFP Ester

This example provides guidance on synthesis of an immunoconjugate that contains an alkyl tertiary amine linker using the TFP ester method as depicted in Scheme 21 of FIG. 145. Compound XIV (200 mg) was dissolved in methanol (20 mL) and 3 equivalents of 1-formyl-7-tert-butyl heptanoate was added followed by 1.1 equivalents of NaCNBH4. The mixture was stirred for 1.5 hours at room temperature and concentrated to dryness. TFA (5 mL) was added and the mixture stirred overnight at room temperature. The TFA was evaporated under vacuum and the crude product was purified by preparative HPLC on a C-18 column. The product was eluted with a gradient of 10-90% acetonitrile in water (0.1% TFA) over 20 minutes to provide 110 mg of purified acid compound XVII (which was confirmed by LC/MS).

Compound XVII (50 mg) was dissolved in dichloromethane/dimethylformamide (5 mL, 1:1) and 2 equivalents of TFP was added followed by 1.5 equivalents of EDCI. The reaction was stirred overnight at room temperature. The crude TFP ester product XVIII was purified via flash chromatography on a 4 gram silica gel column eluted with 0-10% isopropanol over 10 minutes. Pure fractions were concentrated and the residue lyophilized from 30% acetonitrile water to provide 14 mg of purified TFP ester compound XVIII as a white solid. The molecular weight and purity were confirmed by LC/MS (m/z=601.7).

Conjugation to Antibody:

TFP ester XVIII was dissolved in anhydrous DMSO to make a 20 mM stock solution and 8 molar equivalents (relative to the antibody) was added to 20 mg of an IgG antibody (specifically, the anti-CD20 antibody rituximab) (10 mg/mL in PBS). The conjugation reaction was incubated at 4° C. overnight. The resulting immunoconjugate BB-27 was buffer exchanged into PBS (pH 7.2) to remove excess small molecular weight reagents. The final concentration was determined by measuring the antibodies at 280 nm on the Nanodrop 1000 spectrophotometer. The yield was 16 mg of immunoconjugate BB-27 (80%).

Minimal aggregate was seen (less than 1%) as detected by SEC analysis. The product had a DAR ratio of 2.5 as determined via LC/MS analysis. The purified BB-27 was filtered through a 0.2 µM sterile filter and stored at −20° C.

Example 15. Synthesis of Immunoconjugate BB-36 with a TFP Ester

This example provides guidance on synthesis of an immunoconjugate that contains a PEG tertiary amine linker using the TFP method as depicted in Scheme 22 of FIG. 146. Compound XIV (200 mg) was dissolved in methanol (20 mL) and 3 eq. of aldehyde XIX was added followed by 1.1 equivalents of $NaCNBH_4$. The mixture was stirred for 3 hours at room temperature and concentrated to dryness. Trifluoroacetic acid (TFA, 10 mL) was added and the reaction stirred for 2 hours at room temperature. The TFA was evaporated under vacuum and the crude product was purified by preparative HPLC on a C-18 column. The product was eluted with a gradient of 10-90% acetonitrile in water (0.1% TFA) over 20 minutes to provide 85 mg of purified acid XX after lyophilization of the combined pure fractions (confirmed by LC/MS).

Compound XX (80 mg) was dissolved in dichloromethane/dimethylformamide (5 mL, 1:1) and 2 equivalents of TFP was added followed by 1.2 equivalents of EDCI. The reaction was stirred overnight at room temperature. The crude TFP ester product XXI was purified via flash chromatography on a 4 gram silica gel column eluted with 0-10% isopropanol over 10 minutes. Pure fractions were concentrated and the residue lyophilized from 30% acetonitrile water to provide 45 mg of purified TFP ester of compound XXI as a beige solid. The molecular weight and purity were confirmed by LC/MS (m/z=647.7).

Conjugation to Antibody:

The TFP ester of compound XXI was dissolved in anhydrous DMSO to make a 20 mM stock solution and 8 molar equivalents (relative to the antibody) was added to an IgG1 antibody (specifically, the anti-CD20 antibody rituximab) (10 mg/mL in PBS). The conjugation reaction was incubated at 4° C. overnight. The resulting immunoconjugate BB-36 was buffer exchanged into PBS (pH 7.2) to remove excess small molecular weight reagents. The final concentration was determined by measuring the antibodies at 280 nm on the Nanodrop 1000 spectrophotometer. The yield was 15 mg of immunoconjugate BB-36 (75%) which was stored at 4° C. until used.

Minimal aggregate was seen (less than 1%) as detected by SEC analysis. The product had a DAR ratio of 2.2 as determined via LC/MS analysis. The purified immunoconjugate BB-36 was filtered through a 0.2 µM sterile filter and stored at −20° C.

Example 16. Synthesis of Immunoconjugate BB-45 with a TFP Ester

This example provides guidance on synthesis of an immunoconjugate with a different linker using the TFP ester method as depicted in Scheme 23 of FIG. 147. Compound VII (311 mg, 1 mmol) was dissolved in 10 mL of DMF and 0.3 mL of DIPEA was added. In a separate container, 1.2 equivalents of 7-methoxy-7-oxoheptanoic acid was dissolved in 5 mL of DMF and 1.5 equivalents DIPEA was added followed by HATU (1.2 equivalents). The mixture was added to VII and stirred overnight at room temperature. The reaction mixture was concentrated to dryness under vacuum and the residue was dissolved in 10 mL of (1:1) tetrahydrofuran:water. One mL of 2M lithium hydroxide in water was added and the reaction stirred for 2 hours at room temperature. The THF was removed via rotary evaporation and the aqueous solution was acidified by adding 10 mL of 1M hydrochloric acid. The aqueous solution was extracted 2x with dichloromethane (20 mL) and the organic layer was combined and dried over magnesium sulfate. The solution was filtered and the filtrate concentrated to dryness. The crude product 22 was purified via silica gel chromatography on a 4 gram column eluted with 0-10% isopropanol in DCM (w/1% acetic acid) over 10 minutes. The pure fractions were combined and concentrated to provide 220 mg of pure 22 as a pale yellow solid.

Compound 22 (50 mg) was dissolved in dichloromethane/dimethylformamide (5 mL, 1:1) and 2 equivalents of TFP was added followed by 1.5 equivalents of EDCI. The reaction was stirred overnight at 22° C. and the crude reaction was concentrated to dryness. The product was purified via flash chromatography on a 4 gram silica gel column eluted with 0-10% isopropanol over 10 minutes. Pure fractions were concentrated and the residue was lyophilized from 30% acetonitrile in water to provide 21 mg of purified TFP ester 23 as a pale yellow solid. The molecular weight and purity were confirmed by LC/MS.

Conjugation to Antibody:

The TFP ester 23 was dissolved in anhydrous DMSO to make a 20 mM stock solution and 6 molar equivalents (relative to the antibody) was added to 20 mg of an IgG antibody (specifically, the anti-CD20 antibody rituximab) (10 mg/mL in PBS). The conjugation reaction was incubated at 4° C. overnight. The resulting immunoconjugate BB-45 was buffer exchanged into PBS (pH 7.2) to remove excess small molecular weight impurities. The final concentration was determined by measuring the absorbance at 280 nm on a Thermo Nanodrop 1000 spectrophotometer. The yield was 14 mg of BB-45, or 70% based on recovered protein. Minimal aggregate (less than 1%) was detected by SEC analysis and a DAR of 2.8 was determined via LC/MS analysis. The purified immunoconjugate was filtered through a 0.2 µM sterile filter and stored at −20° C.

Example 17. Synthesis of Immunoconjugate BB-24 with a TFP Ester

This example provides guidance on synthesis of an immunoconjugate with a different linker using the TFP ester method as depicted in Scheme 24 of FIG. 148. Compound VII (150 mg) was dissolved in 20 mL THF and 10 mL of aqueous saturated sodium bicarbonate was added. Succinic anhydride (50 mg) was added in one portion and the mixture stirred for 1 hour at room temperature. 20 mL of 1N HCl was added slowly and the mixture was extracted with 2X 50 mL of dichloromethane and the combined organic extracts were evaporated to dryness. The crude product 24 was purified on a 4 gram silica gel column eluted with 0-15% MeOH (1% acetic acid) over 15 minutes. Pure fractions were combined and evaporated to provide 180 mg of pure 24.

One hundred and fifty mg of 24 was dissolved in DMF (10 mL) and 1 equivalent of HATU was added followed by 2 equivalents of DIPEA. One and a half eq. of glycine-OtBu was added and stirred overnight. The DMF was evaporated and the residue treated with 5 mL of iN HCl in dioxane for 30 minutes with stirring. The solvent was evaporated and the crude residue was flash purified on a 4 gram silica gel column eluted with 0-10% isopropanol over 15 minutes. Evaporation of pure fractions provided 110 mg of pure 25.

Compound 25 (50 mg) was dissolved in 10 mL DMF and 1.5 eq. of TFP was added followed by 1.2 eq. DCC and 2 mg of DMAP. The reaction was stirred overnight, concentrated to dryness and purified on silica gel (4g column) eluted with 0-10% IPA in DCM to provide 32 mg of pure TFP ester, compound 26, after lyophilization from 1:3 acetonitrile water.

Conjugation to Antibody:

The TFP ester, compound 26, was dissolved in anhydrous DMSO to make a 20 mM stock solution and 5 molar equivalents (relative to the antibody) was added to 20 mg antibody at 10 mg/mL in PBS. The conjugation reaction was incubated at 4° C. for 6 hours. The resulting immunoconjugate BB-24 was buffer exchanged into PBS (pH 7.4) to remove excess small molecular weight impurities. The final protein concentration was determined by measuring the absorbance at 280 nm on a Nanodrop 1000 spectrophotometer. The yield was 15 mg (75% based on recovered protein). SEC analysis detected minimal aggregate of less than 1% and the DAR was determined to be 2.8 adjuvants per antibody via LC/MS analysis. The purified immunoconjugate was filtered through a 0.2 µM sterile filter and stored at −20 OC until needed.

Example 18. Synthesis of Immunoconjugate BB-37 a TFP Ester

This example provides guidance on synthesis of an immunoconjugate with a different linker using the TFP method as depicted in Scheme 25 of FIG. 149. Compound VII (155 mg, 0.5 mmol) was dissolved in 10 mL of DMF and 0.2 mL of DIPEA was added. In a separate container, 1.2 equivalents of PEG2-dicarboxylate mono methyl ester was dissolved in 5 mL of DMF and 2 equivalents DIPEA was added followed by HATU (1.2 equivalents). The mixture was added to VII and stirred 1 hour at room temperature. The reaction was concentrated to dryness under vacuum and the residue was dissolved in THF (5 mL). An equal volume of water was added followed by 2 mL of 1 M aqueous LiOH. The mixture was stirred overnight and then 10 mL of 1N HCl was added. The acidified mixture was extracted 2x with dichloromethane, dried over sodium sulfate, concentrated to dryness and purified via silica gel chromatography. The product was eluted with 0-10% methanol over 10 minutes. The pure fractions were combined and concentrated to provide 110 mg of pure compound 27 as a pale yellow solid.

Compound 27 (50 mg) was dissolved in dichloromethane/dimethylformamide (5 mL, 1:1) and 2 equivalents of TFP was added followed by 1.5 equivalents of EDCI. The reaction was stirred overnight at ambient temperature and the reaction was concentrated to dryness. The crude TFP ester 28 was purified via flash chromatography on a 4 gram silica gel column eluted with 0-10% isopropanol over 10 minutes. Pure fractions were concentrated and the residue was lyophilized from 30% acetonitrile in water to provide 41 mg of purified TFP ester 23 as a white solid. The molecular weight and purity were confirmed by LC/MS.

Conjugation to Antibody:

The TFP ester 28 was dissolved in anhydrous DMSO to make a 20 mM stock solution and 8 molar equivalents (relative to the antibody) was added to 20 mL of an IgG antibody (specifically, the anti-CD20 antibody rituximab) (10 mg/mL in PBS). The conjugation reaction was incubated at 4° C. overnight. The resulting immunoconjugate BB-37 was buffer exchanged into PBS (pH 7.2) to remove excess small molecular weight impurities. The final concentration was determined by measuring the absorbance at 280 nm on a Thermo Nanodrop 1000 spectrophotometer. The yield was 16 mg of conjugated immunoconjugate BB-37, or 70% based on recovered protein. Minimal aggregate (less than 1%) was detected by SEC analysis and a DAR of 2.3 was determined via LC/MS analysis. The purified immunoconjugate was filtered through a 0.2 M sterile filter and stored at −20° C.

Example 19. Synthesis of Another TLR7/8 Adjuvant

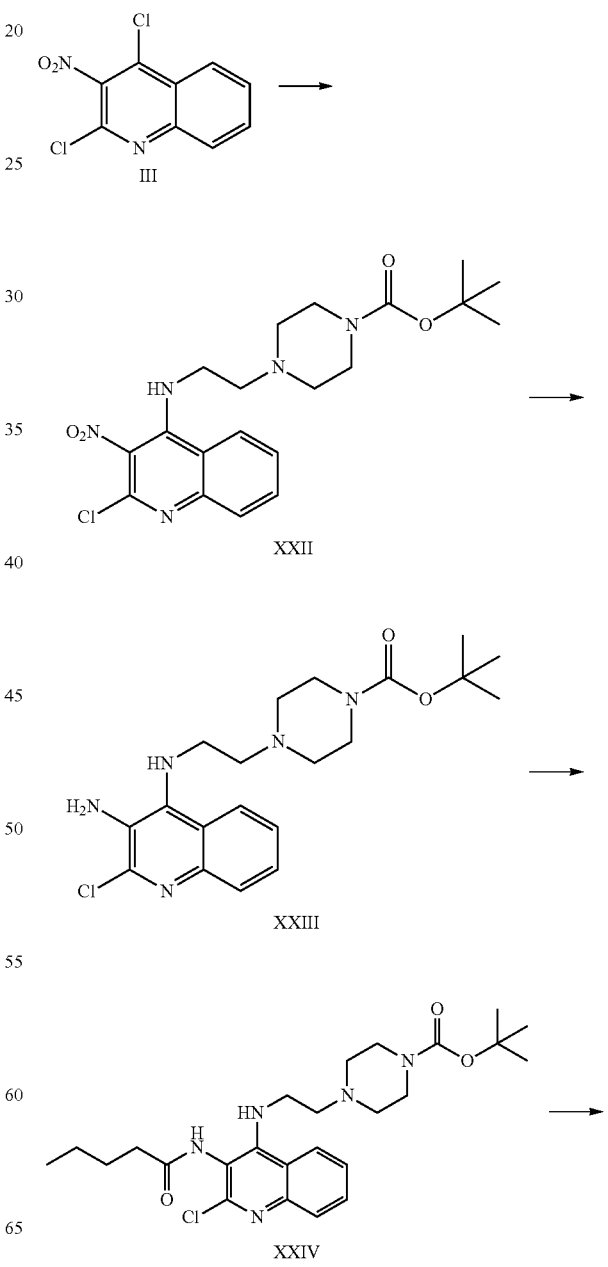

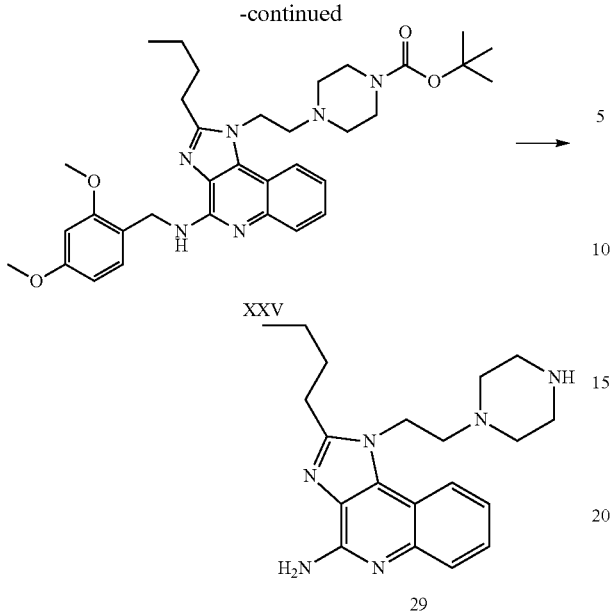

This example provides guidance on synthesis of another TLR agonist. Compound 29 is a compound VII analog that contains a piperizine side-chain for linker attachment. It was synthesized using methods previously described for the synthesis of the compound VII except that a Boc-protected piperizine analog was substituted for Boc-diaminobutane used in step 3 of the synthesis. The general synthetic route for compound 29 is outlined in Scheme 26. The addition of the piperizine side chain enables the synthesis of immunoconjugates that were previously inaccessible due to instability. Similar compound VII analogs containing succinate linkers are prone to cyclization upon TFP activation and the piperizine prevents cyclization. In addition, the tertiary amino group within the piperizine moeity maintains a positive charge after linker attachment and conjugation. Positive charges in this location are important for improved TLR8 potency. Compound 29 was subsequently used for synthesizing immunoconjugates as described below in Examples 19-21.

Example 20. Synthesis of Immunoconjugate BB-42 with a TFP Ester

This example provides guidance on synthesis of an immunoconjugate with a different linker using the TFP ester method as depicted in Scheme 27 of FIG. 15O. Compound 29 (100 mg) was dissolved in 10 mL THF and 2 mL of aqueous saturated sodium bicarbonate was added followed by 10 mL of water. Succinic anhydride (50 mg) was added in one portion and the mixture was stirred at room temperature. After one hour, 20 mL of iN HCl was added slowly and the reaction mixture was extracted with 2X 50 mL of dichloromethane ("DCM"). The combined organic extracts were evaporated to dryness. The crude product 30 was purified on a 4 gram silica gel column eluted with 0-15% isopropanol in DCM (1% acetic acid) over 15 minutes. Pure fractions were combined and evaporated to dryness to provide 80 mg of pure acid 30.

Compound 30 (50 mg) was dissolved in dichloromethane/dimethylformamide (5 mL, 1:1) and 2 equivalents of TFP was added followed by 1.5 equivalents of EDCI. The reaction was stirred overnight at ambient temperature and the reaction was concentrated to dryness. The crude TFP ester 31 was purified via flash chromatography and eluted with 0-10% isopropanol over 10 minutes. Pure fractions were concentrated and the residue was lyophilized from 30% acetonitrile in water to provide 41 mg of purified TFP ester 31 as a white solid. The molecular weight and purity were confirmed by LC/MS.

Figure 20:
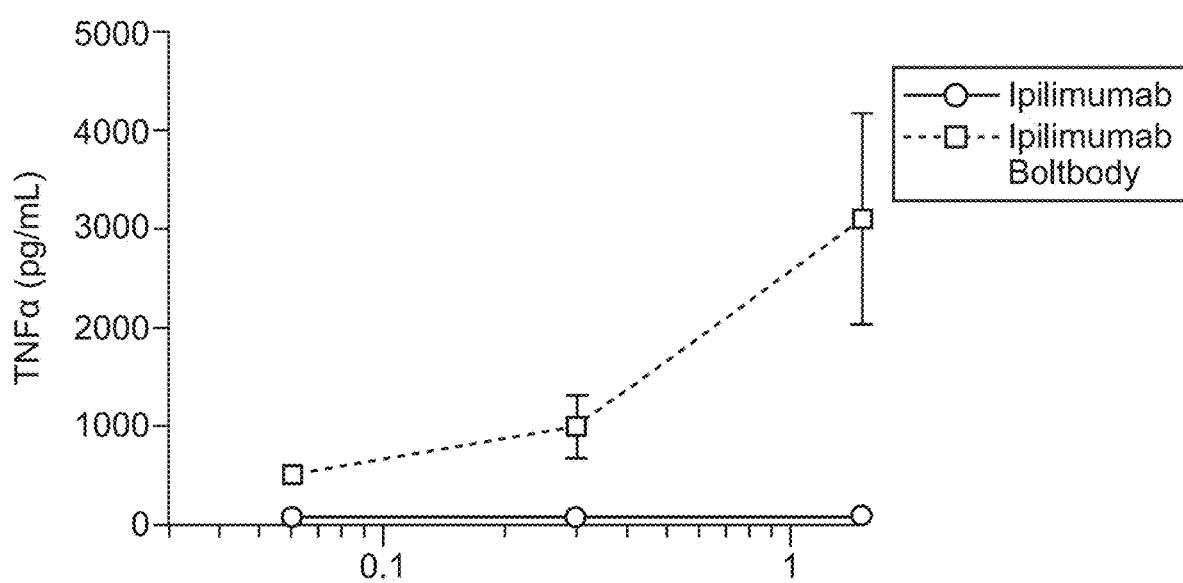
FIG. 20 shows that ipilimumab immunoconjugate (Ipilimumab Boltbody)-differentiated cells secret higher amounts of TNFα than ipilimumab-differentiated cells.

The TFP ester 31 was conjugated to an IgG1 antibody (specifically, the anti-CD20 antibody rituxumab) as described previously for BB-24 to provide BB-42. SEC and LC/MS analysis of BB-42 confirmed the molecular weight, a high monomeric purity with less than 2% aggregate, and a DAR of 1.7 (see FIGS. 20A-B).

Example 21. Synthesis of Immunoconjugates BB-43 and BB-44 with a TFP Ester

This example provides guidance on synthesis of immunoconjugates with different linkers using the TFP ester method as depicted in Scheme 28 of FIG. 15I. Compound 30 (Scheme 27) was coupled to polyethylene glycol (PEG) linkers containing 2 or 8 PEG. units in order to extend the distance between the adjuvant and the antibody. Attachment of the PEG linker extensions was performed using previously described protocols for linker attachment and TFP activation. Briefly 100 mg of compound 30 was dissolved in 10 mL of DMF and 0.2 mL of DIPEA was added followed by HATU (1.2 equivalents). After 1 hour the appropriate amino PEG linker (n=2 or 8) was added and stirred an additional 2 hours at room temperature. The reaction mixture was concentrated to dryness under vacuum and the residue was purified via preparative HPLC on a C-18 column eluted with 10-90% acetonitrile in water over 30 minutes. The pure fractions were combined and lyophilized to provide 65 mg and 45 mg of intermediates 31 or 32 as a clear glassy substance.

Compounds 31 and 32 were converted to the corresponding TFP esters 33 and 34 using previously described protocols. Briefly, the free acid 31 or 32 (50 mg) was dissolved in dichloromethane/dimethylformamide (5 mL, 1:1) and 2 equivalents of TFP was added followed by 1.5 equivalents of EDCI. The mixture was stirred overnight at room temperature and concentrated to dryness to provide crude TFP esters 33 and 34. The crude TFP esters were purified via flash chromatography on silica gel and eluted with 0-10% isopropanol over 10 minutes. Pure fractions were concentrated and the residue was lyophilized from 30% acetonitrile in water to provide purified TFP esters 33 and 34 as clear solids. The molecular weight and purity of the pure compounds were confirmed by LC/MS.

Conjugation to Antibody:

TFP esters 33 and 34 were conjugated to an IgG1 antibody (specifically, the anti-CD20 antibody rituxumab) using previously described protocols. The TFP esters were dissolved in anhydrous DMSO to make a 20 mM stock solution and 8 molar equivalents (relative to the antibody) was added to 20 mg of the IgG antibody at 10 mg/mL in PBS. The conjugation reaction was incubated at 4° C. for 12 hours. The resulting immunoconjugates, BB-43 and BB-44 were buffer exchanged into PBS (pH 7.4) to remove excess small molecular weight impurities. The final protein concentration was determined by measuring the absorbance at 280 nm on a Nanodrop 1000 spectrophotometer. The yields were 75% based on recovered protein. SEC analysis detected minimal aggregate was present and the DARs of 1.0 and 1.7 adjuvants per antibody were determined via LC/MS analysis.

The purified immunoconjugates were filtered through a 0.2 M sterile filter and stored at −20 OC until needed.

Example 22. Assessment of Immunoconjugate Activity In Vitro

Isolation of Human Antigen Presenting Cells.

Human antigen presenting cells (APCs) were negatively selected from human peripheral blood mononuclear cells obtained from healthy blood donors (Stanford Blood Center) by density gradient centrifugation using a RosetteSep Human Monocyte Enrichment Cocktail (Stem Cell Technologies) containing monoclonal antibodies against CD14, CD16, CD40, CD86, CD123, and HLA-DR. Immature APCs were subsequently purified to >97% purity via negative selection using an EasySep Human Monocyte Enrichment Kit without CD 16 depletion containing monoclonal antibodies against CD14, CD16, CD40, CD86, CD123, and HLA-DR.

Preparation of Tumor Cells.

Tumor cells were resuspended in PBS with 0.1% fetal bovine serum (FBS) at 1 to $10 \times 10^6$ cells/mL. Cells were subsequently incubated with 2 M CFSE to yield a final concentration of 1 µM. The reaction was ended after 2 minutes via the addition of 10 mL complete medium with 10% FBS and washed once with complete medium. Cells were either fixed in 2% paraformaldehyde and washed three times with PBS or left unfixed prior to freezing the cells in 10% DMSO, 20% FBS and 70% medium.

APC-Tumor Co-Cultures.

$2 \times 10^5$ APCs were incubated with or without $6.5 \times 10^5$ allogeneic CFSE-labeled tumor cells in 96-well plates (Corning) containing IMDM medium (Gibco) supplemented with 10% fetal bovine serum, 100 U/mL penicillin, 100 g/mL streptomycin, 2 mM L-glutamine, sodium pyruvate, non-essential amino acids and, where indicated, various concentrations of unconjugated CD20 antibody, and immunoconjugates of the invention were prepared according to the examples above. Cells and cell-free supernatants were analyzed after 18 hours via flow cytometry or ELISA.

Figure 17:
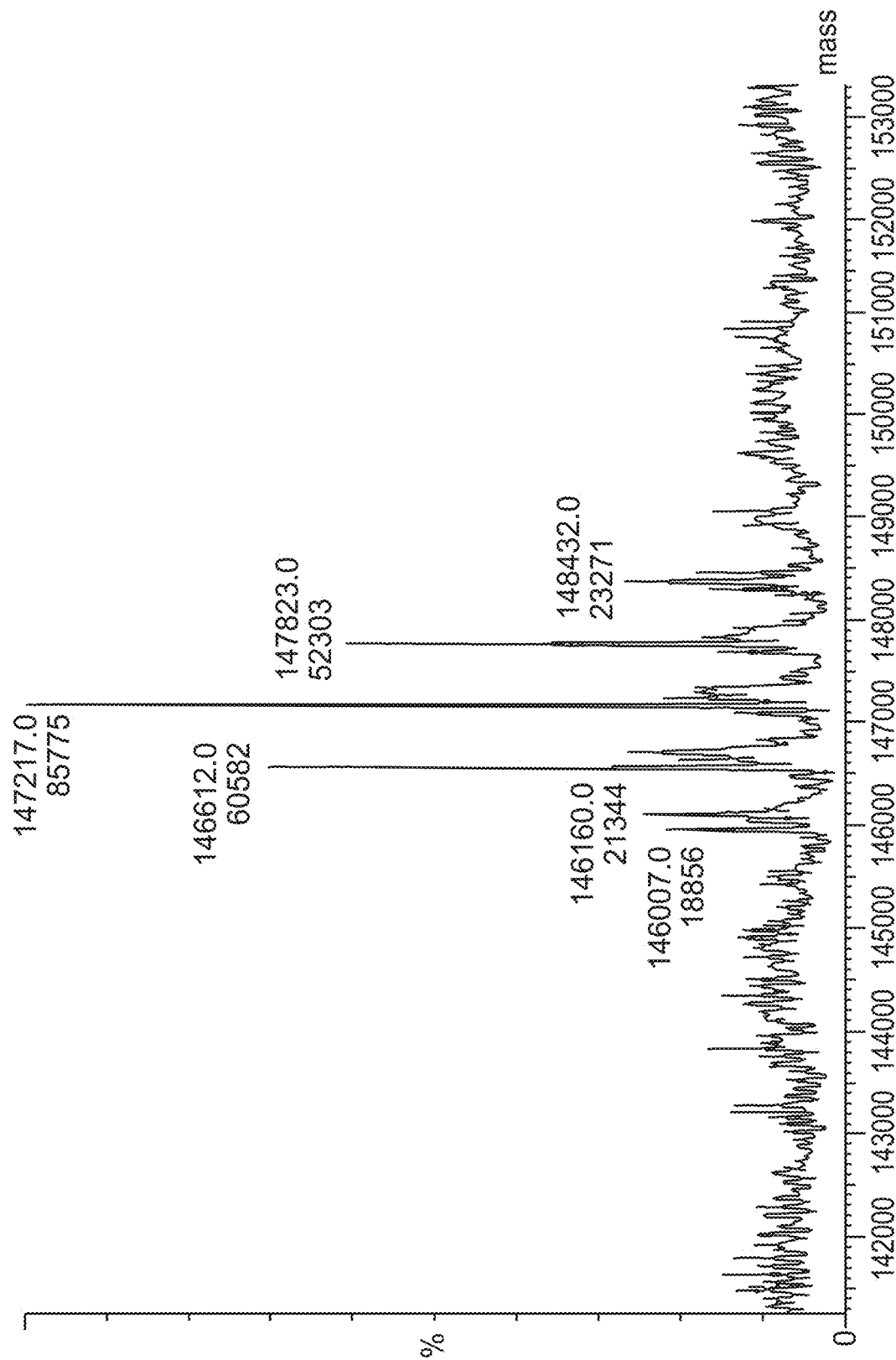
FIG. 17 shows the analysis of pembrolizumab-adjuvant conjugates via LC-MS.
Figure 18:
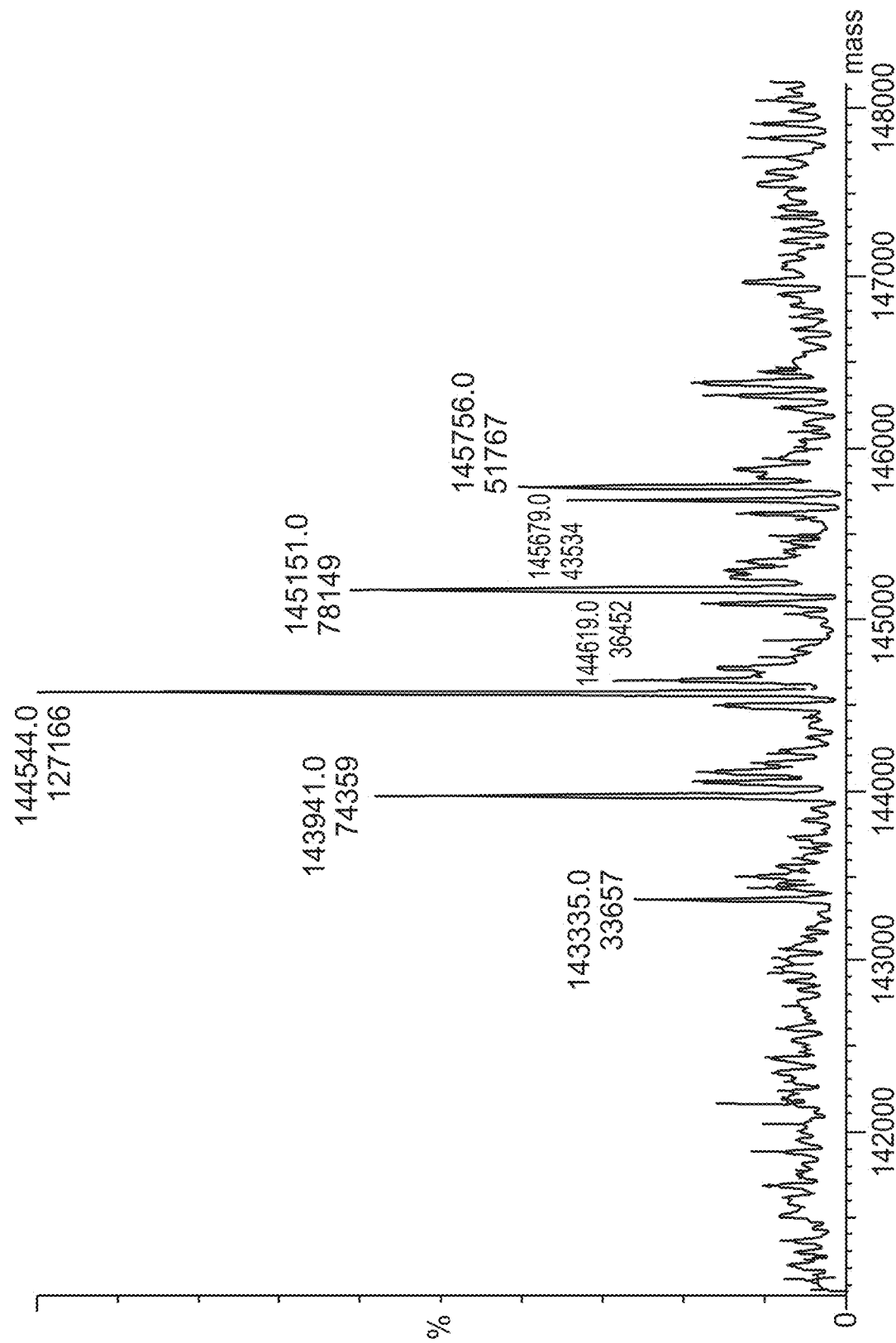
FIG. 18 shows the analysis of nivolumab-adjuvant conjugates via LC-MS.
Figure 19:
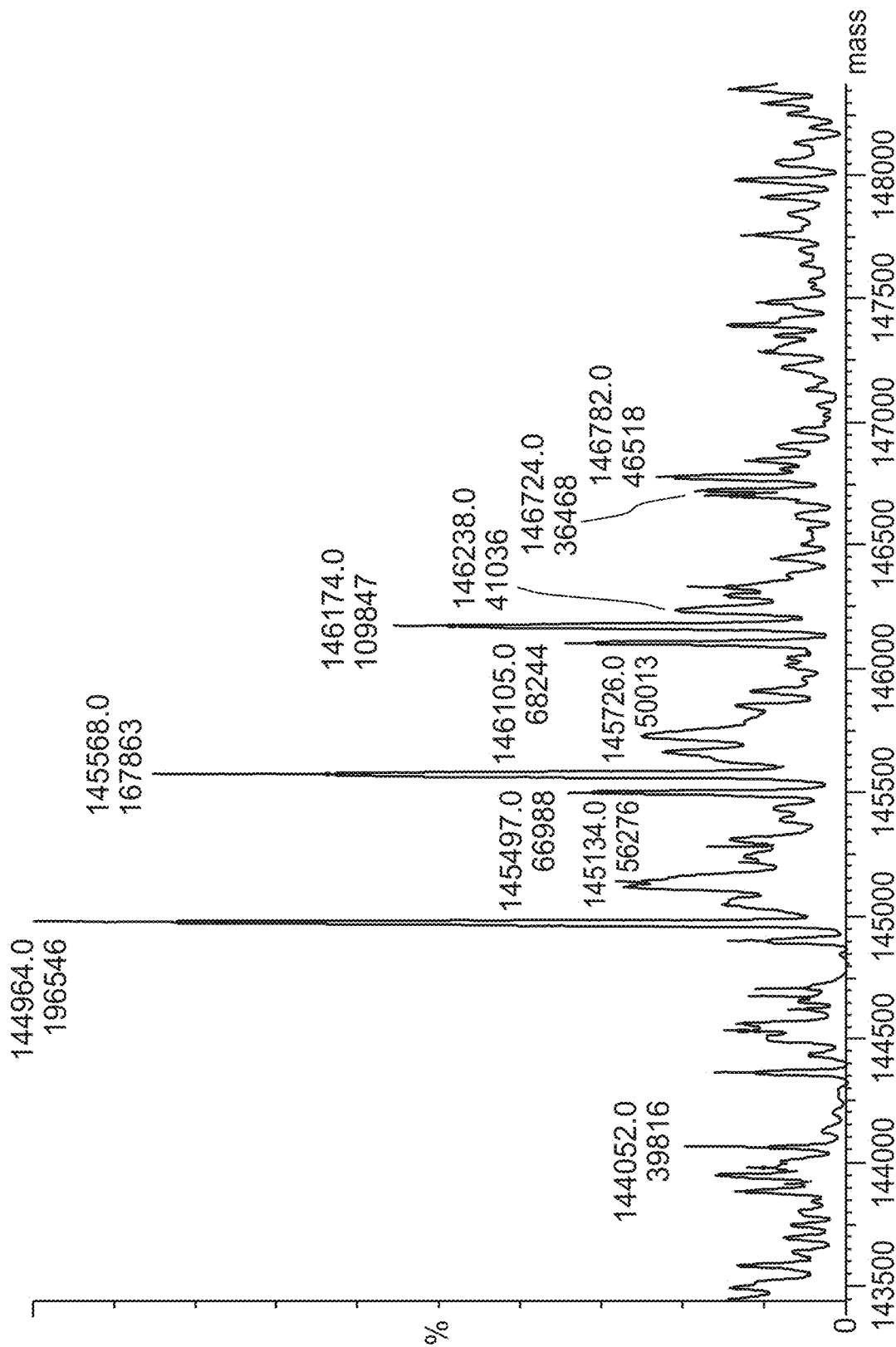
FIG. 19 shows the analysis of atezolizumab-adjuvant conjugates via LC-MS.

The results of this assay are shown in FIGS. 9A-9F for BB-17 and BB-01. Specifically, the graphs show that BB-17 and BB-01 prepared according to Schemes 14 of FIG. 14O and 17 of FIG. 143 elicits myeloid activation while the control, unconjugated CD20 antibody, does not. Further, FIGS. 23A-D show that BB-14 elicits myeloid activation as indicated by CD14, CD20, CD86, and HLA-DR while the control does not. FIGS. 24A-D show that BB-15 elicits myeloid activation as indicated by CD14, CD20, CD86, and HLA-DR while the control does not. FIGS. 25A-D show that BB-27 elicits myeloid activation as indicated by CD14, CD20, CD86, and HLA-DR while the control does not. FIGS. 26A-D show that BB-45 elicits myeloid activation as indicated by CD14, CD20, CD86, and HLA-DR while the control does not. FIGS. 27A-D show that BB-24 elicits myeloid activation as indicated by CD14, CD20, CD86, and HLA-DR while the control does not.

Example 23. Comparison of BB-01 to Comparative Conjugate IRM1 and Comparative Conjugate IRM2

As previously explained, immunoconjugates are described in U.S. Pat. No. 8,951,528 ("the '528 patent"). This example shows that immunoconjugates of the invention are superior to the immunoconjugates disclosed by the '528 patent. BB-01 was synthesized according to Scheme 14 of FIG. 14O. Comparative Conjugates IRM1 and IRM2 were prepared using the adjuvants described in the '528 patent as adjuvants IRM1 and IRM2. Specifically, IRM1 and IRM2 were conjugated to an IgG antibody (specifically, the anti-CD20 antibody rituximab) with an amide linker.

Figure 11A:
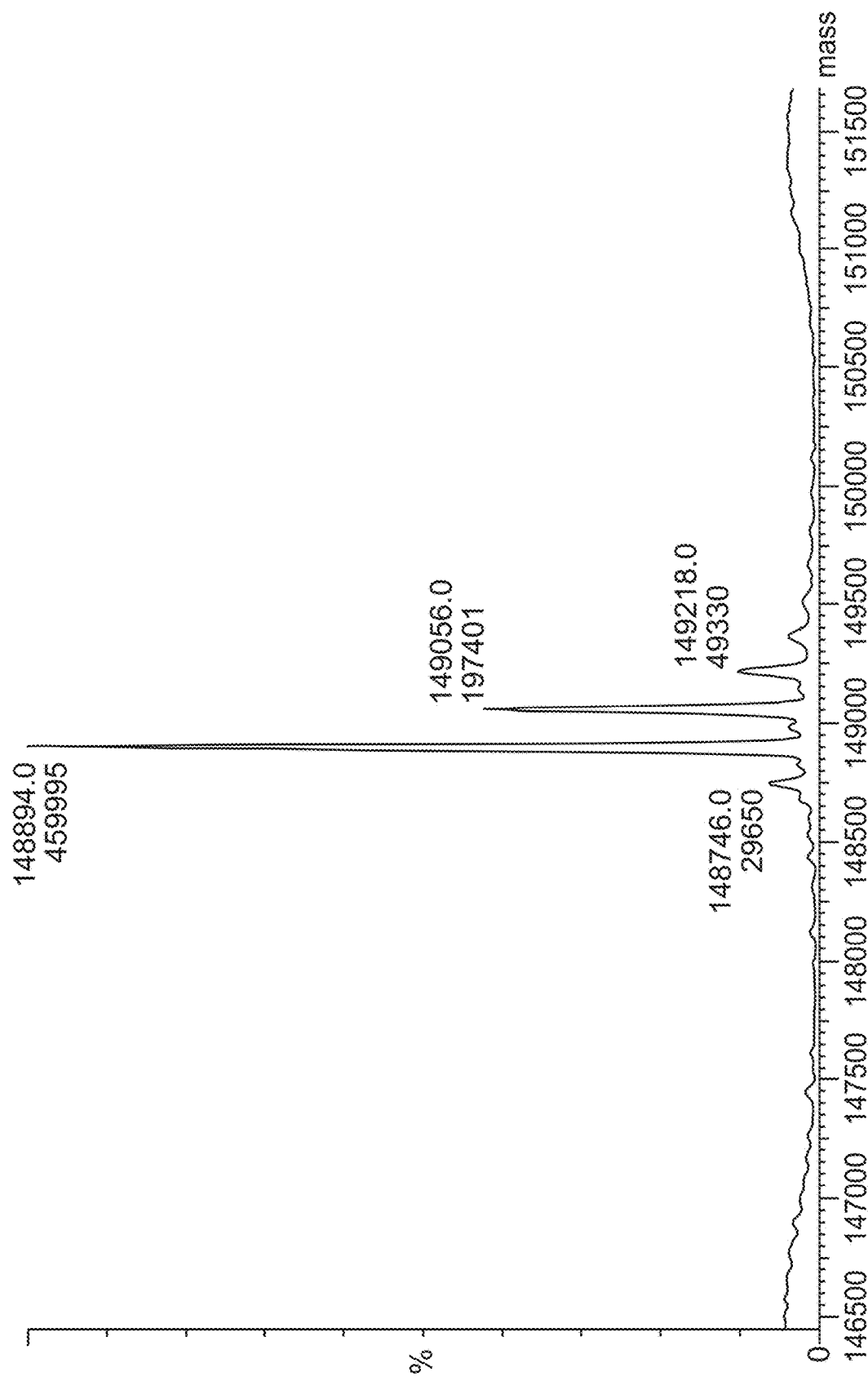
FIG. 11A shows the analysis of pembrolizumab via LC-MS.
Figure 11B:
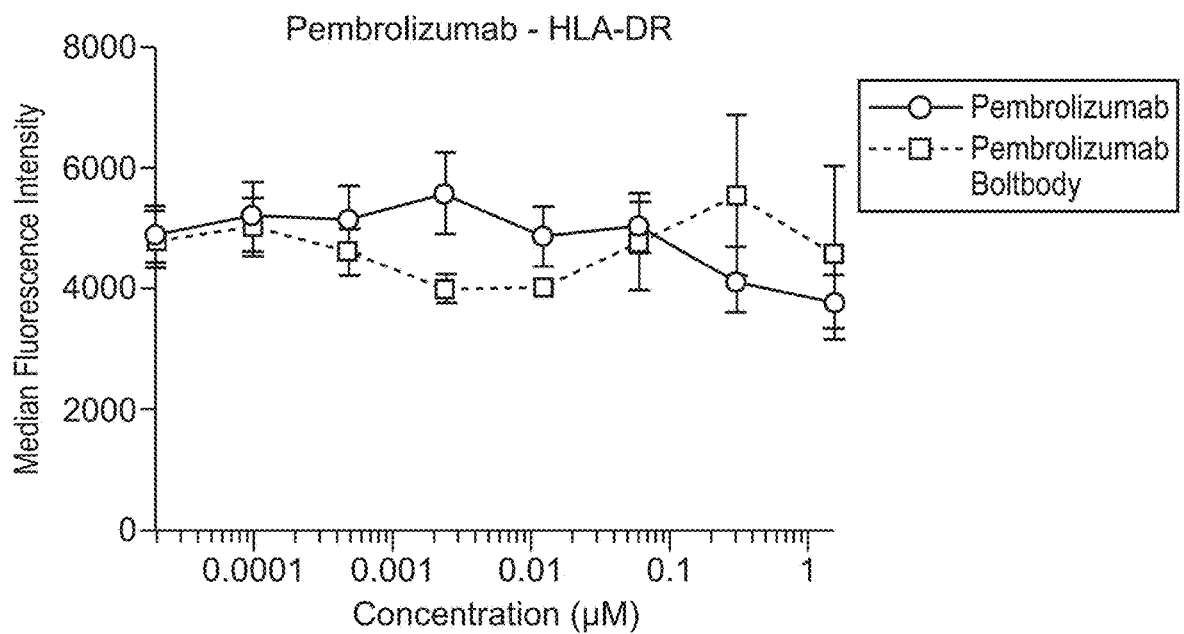
FIG. 11B shows that pembrolizumab-adjuvant (Pembrolizumab Boltbody) conjugates are superior at eliciting APC activation, compared to unconjugated pembrolizumab, as indicated by expression of HLA-DR.
Figure 11C:
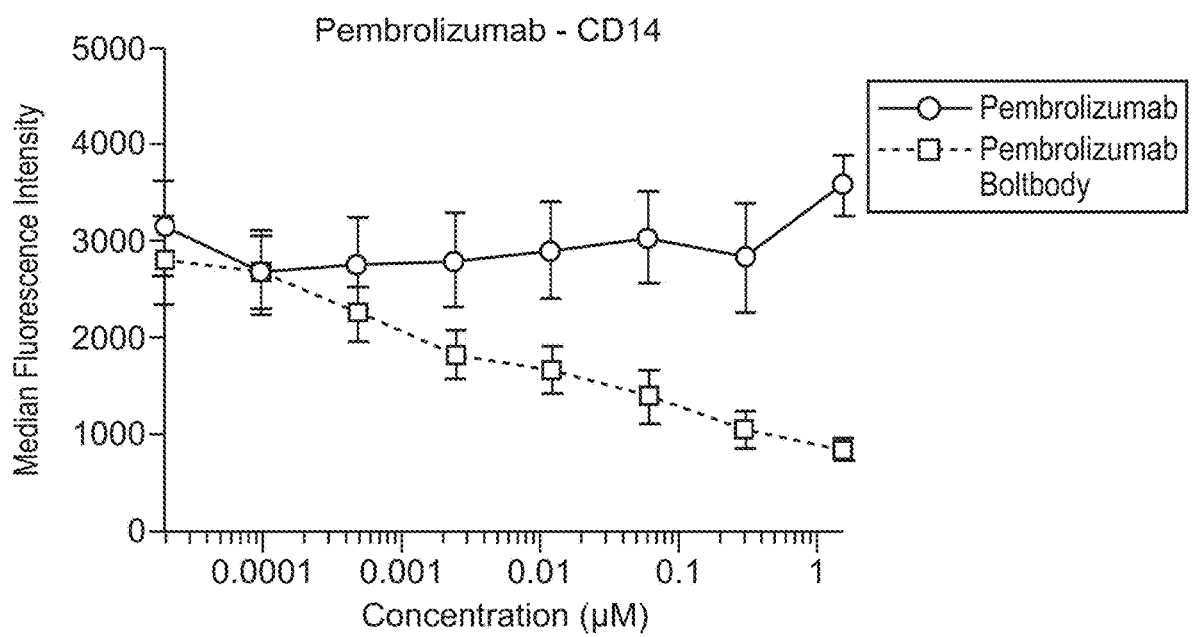
FIG. 11C shows that pembrolizumab-adjuvant (Pembrolizumab Boltbody) conjugates are superior at eliciting APC activation, compared to unconjugated pembrolizumab, as indicated by expression of CD 14.
Figure 11D:
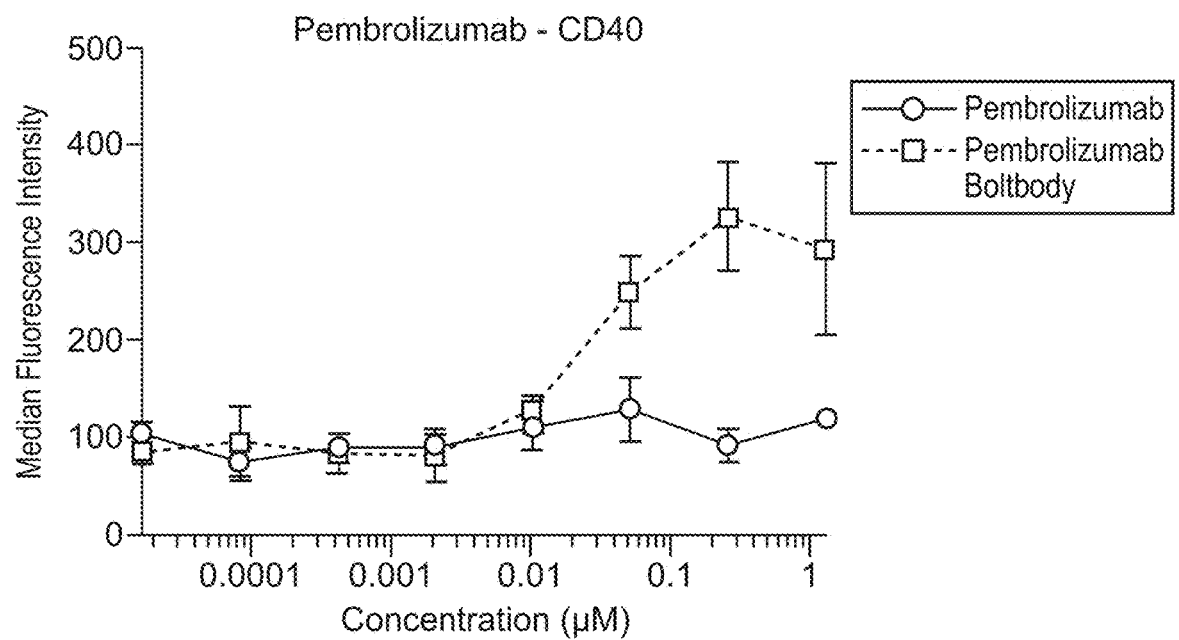
FIG. 11D shows that pembrolizumab-adjuvant (Pembrolizumab Boltbody) conjugates are superior at eliciting APC activation, compared to unconjugated pembrolizumab, as indicated by expression of CD40.
Figure 11E:
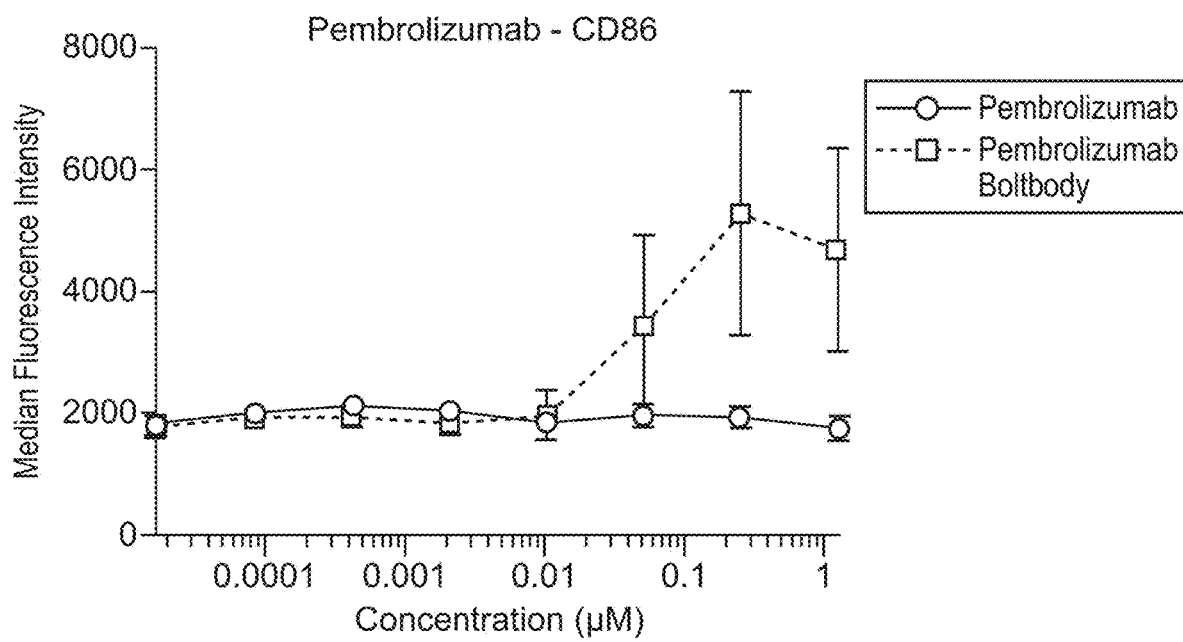
FIG. 11E shows that pembrolizumab-adjuvant (Pembrolizumab Boltbody) conjugates are superior at eliciting APC activation, compared to unconjugated pembrolizumab, as indicated by expression of CD86.

BB-01 and Comparative Conjugates IRM1 and IRM2 were analyzed using the assay of Example 22. The results are shown in FIGS. 10A-10F and 11A-11C. Specifically, FIGS. 10A-10F show that BB-01 prepared according to Scheme 14 of FIG. 14O elicits myeloid activation while Comparative Conjugates IRM1 and IRM2, and the control, unconjugated CD20 antibody, do not. Further, FIGS. 11A-11C show that BB-01 prepared according to Scheme 14 of FIG. 14O elicits cytokine secretion while Comparative Conjugates IRM1 and IRM2, and the control, unconjugated CD20 antibody, do not.

Figure 15A:
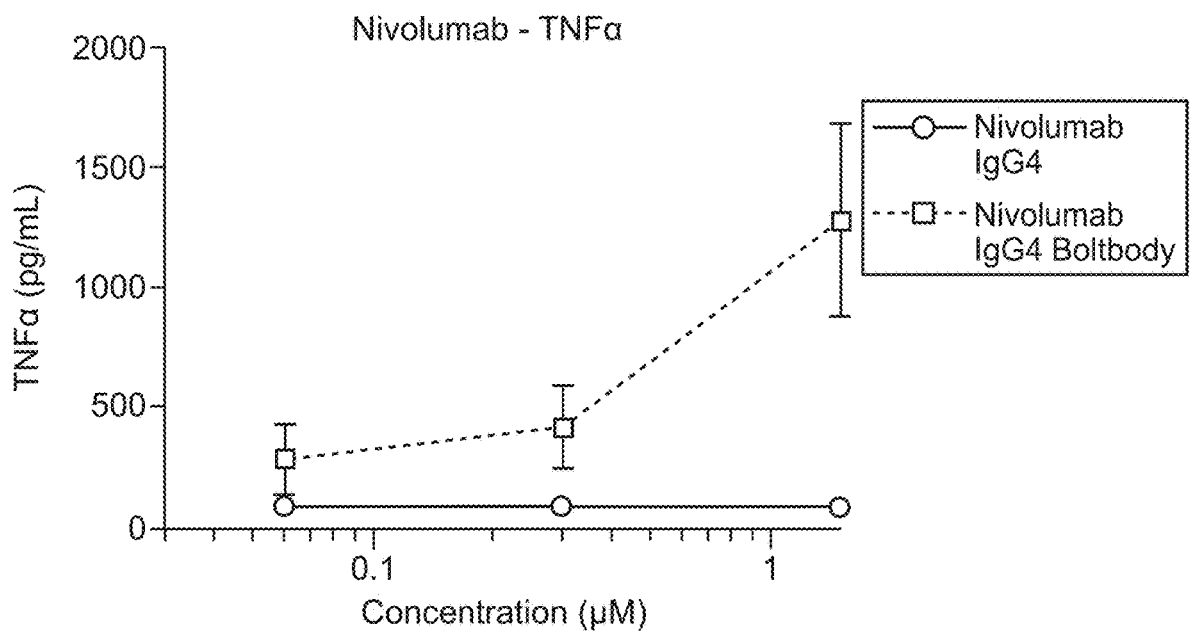
FIG. 15A shows that nivolumab immunoconjugate (Nivolumab IgG4 Boltbody)-differentiated cells secrete higher amounts of TNFα than nivolumab-differentiated cells.
Figure 15B:
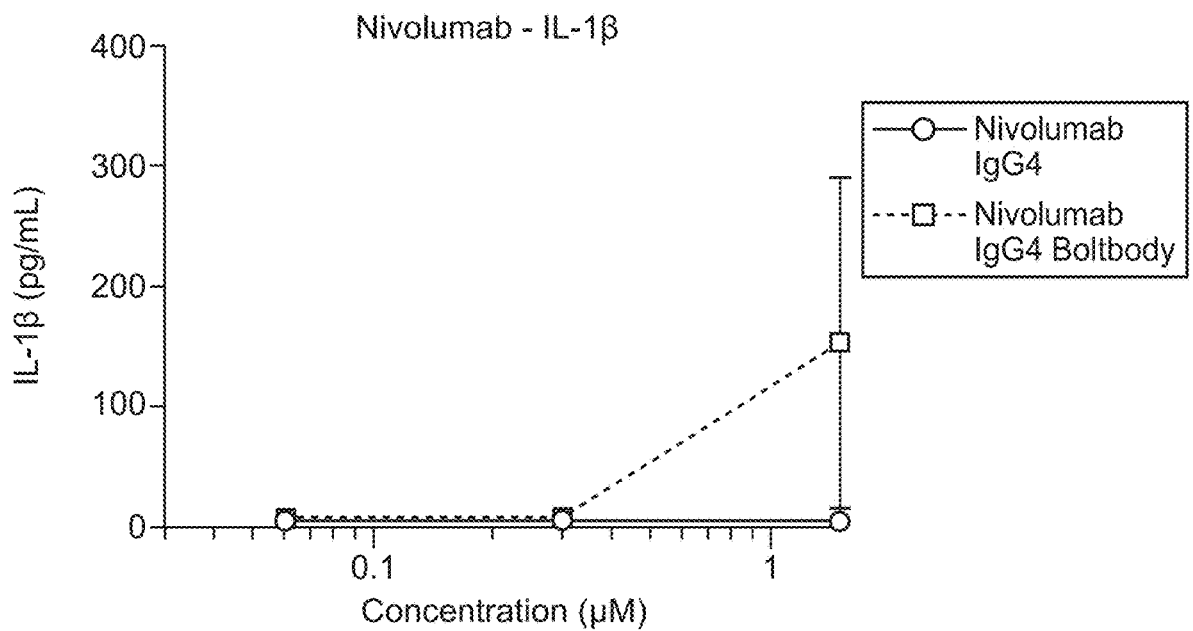
FIG. 15B shows that nivolumab immunoconjugate (Nivolumab IgG4 Boltbody)-differentiated cells secrete higher amounts of IL-10 than nivolumab-differentiated cells.
Figure 16A:
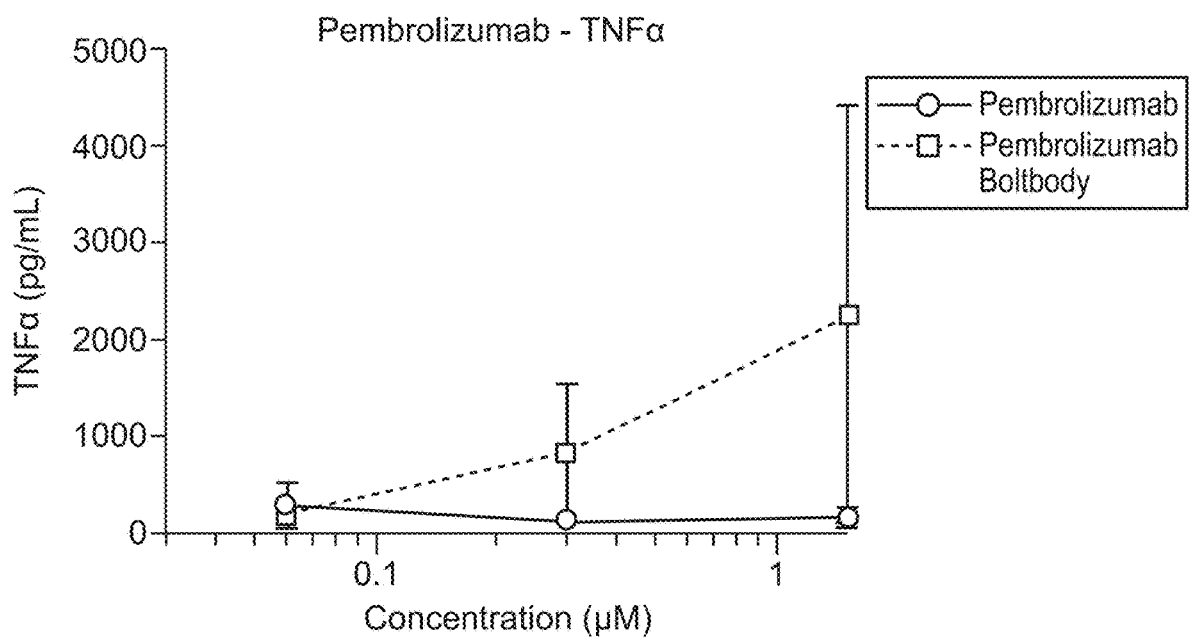
FIG. 16A shows that pembrolizumab immunoconjugate (Pembrolizumab Boltbody)-differentiated cells secrete higher amounts of TNFα than pembrolizumab-differentiated cells.
Figure 16B:
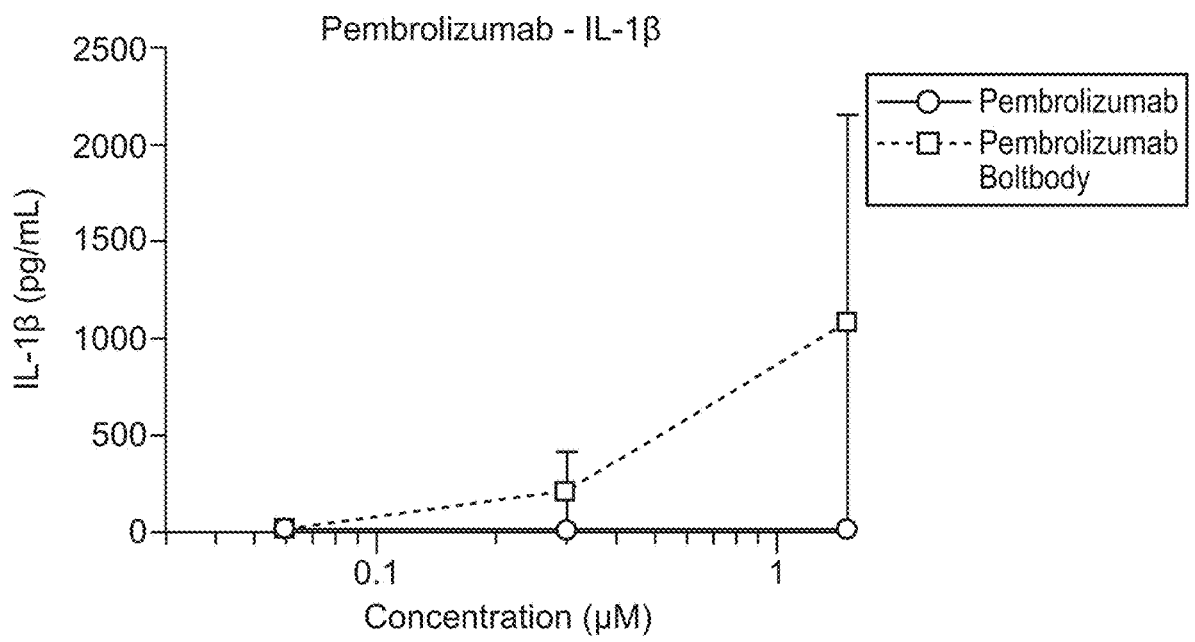
FIG. 16B shows that pembrolizumab immunoconjugate (Pembrolizumab Boltbody)-differentiated cells secrete higher amounts of IL-1β than pembrolizumab-differentiated cells.

The Comparative Conjugates IRM1 and IRM2 had excessive aggregation as determined by LC/MS. FIGS. 15A-C show the results of size exclusion chromatography following filtration with a 0.2 M filter. Comparative Conjugate IRM1 had 4% aggregation and indicated by the first peak at 4.5 min. Comparative Conjugate IRM2 had 9.5% aggregation and indicated by the first peak at 4.5 min. In contrast, BB-01 had a small amount of aggregation. This difference is due in part to the thiolated intermediate that IRM1 and IRM2 have which is not necessary for the synthesis of BB-01.

BB-01 and Comparative Conjugates IRM1 and IRM2 were also tested for storage stability. After synthesis, the conjugates were stored in 15 mL conical tubes for several hours. After storage, the tube containing the Comparative Conjugate IRM2 had a large white solid aggregate at the bottom of the tube. The tubes containing BB-01 and Comparative Conjugate IRM1 contained clear fluid only and did not have any sediment.

Example 24. Generation of Anti-Compound 1 Antibody

KLH (ThermoFisher, Product #77600) or Bovine Serum Albumin (Thermo Fisher, Product #29130) was conjugated to Compound 1 using amine-reactive chemistry.

To produce rabbit antibodies, rabbits were immunized by injecting the footpad with 200 ug of KLH-Compound 1 conjugate, formulated in Complete Freund's adjuvant. Animals were boosted with an additional 100 ug of immunogen conjugate 14, 28, and 42 days following the first administration. Blood was collected on days 35 and 49 and serum was isolated and screened by ELISA for anti-Compound 1 antibody. ELISA plates were coated with BSA-Compound 1 conjugate and antibodies were detected with peroxidase-conjugated anti-rabbit IgG (Jackson Immunoresearch, Product #111-035-144).

To produce murine antibodies, C57BL/6 mice were injected intravenously with 100 ug of Compound 1 conjugate, followed by repeat doses at days 6, 12 and 24 post first administration. Blood was collected 12 and 24 days post administration and serum was screened by ELISA for anti-Compound 1 antibody. Following sufficient detection of antibody, blood, spleen and lymph nodes were collected and harvested into single cell suspension. B cells were subsequently isolated by negative selection and sorted using FACS. B cells were collected that stained positive for IgG, stained negative for IgM and IgD, and stained positive for Compound 1 engagement, as measured using a BSA-Compound 1 conjugate and fluorescently labeled Streptavidin. Isolated B cells were washed twice in complete medium and then fused with SP20 myeloma cells using polyethylene glycol 1500 (Roche, Product #10 783 641 001) according to manufacturer's instructions. SP20 myeloma cells were maintained prior to fusion in DMEM supplemented with 10% FBS, Glutamine and Penicillin Streptomycin. Fused cells were plated at approximately 100,000 cells per well in flat 96 well plates. Following 1-2 days of incubation, HAT supplement and IL-6 were added to the medium (ThermoFisher Product #21060017 and Gibco Product #PHC0065). Medium was sampled 10-14 days later and screened by ELISA as described previously to measure anti-Compound 1 antibody. Positive clones were expanded, sub-cloned by limiting dilution, and were further screened to confirm antibody production and hybridomas were subsequently cryopreserved. Hybridomas were grown in tissue culture treated flasks at 37 degrees Celsius with 5% $CO_2$ in 10% complete medium and 90% Hybridoma-SFM (Gibco, Product #12045076). Medium was replaced with 100% Hybridoma-SFM and cells were cultured for an additional 3-6 days. Medium was collected and filtered through a 0.22 um filter. Antibody was purified using Hi-Trap Mabselect Columns (GE Life Sciences, Product #28-4082-53) and buffer exchanged into sterile PBS by dialysis or through desalting columns.

Example 25: Detection of Conjugation Via ELISA

In five cases, the conjugation status of an antibody construct could not be resolved through LC/MS due to product heterogeneity. In order to determine if the conjugation was successful, an ELISA assay was utilized. The antibody used to detect presence of adjuvant on the antibody was the anti-Compound 1 antibody described in Example 24.

FIGS. 132A-132H indicate that the conjugations were successful for the cetuximab immunoconjugate, etanercept naked antibody, etanercept immunoconjugate, ipilimumbab immunoconjugate, and obinutuzumab immunoconjugate.

Example 26. ELISA Detection of Compound 1 Coupled to Human IgG of Human Ig-Fc

Maxysorp ELISA plates (Fisher 44-2404-21) were coated overnight with 1 ug/ml Goat anti-human IgG (Jackson Immunoresearch). Plates were blocked with PBS containing 1% BSA (Sigma A7030), and incubated with a titration of the indicated antibodies or corresponding Boltbody (BB-01) conjugates. Bound antibodies were detected with Peroxidase conjugated Goat Anti-Human IgG (Jackson), or a mouse monoclonal antibody against Compound 1 followed by Peroxidase conjugated Goat anti-mouse IgG (Fc fragment specific). TMB was added to the wells and absorbance at 450 nM was measured after stopping the reaction with TMB stop solution (Fisher NC1291012).

Example 27. ELISA Detection of Compound 1 Coupled to Rat-Anti-Dectin 2

Maxisorp ELISA plates (Fisher 44-2404-21) were coated overnight with 1 ug/ml Rat anti-Dectin-2 (Invivogen) or BB-01 Rat anti-Dectin-2. Plates were blocked with PBS containing 1% BSA (Sigma A7030), and incubated with titrating amounts of peroxidase conjugated Goat anti-mouse IgG, heavy and light chain specific (Jackson 115-035-003) for total IgG detection, or titrating amounts of rabbit anti-Compound 1 antiserum for Boltbody detection. Rabbit anti-Compound 1 was detected with peroxidase conjugated Goat anti rabbit IgG, minimal cross reactivity with human, mouse and Rat serum proteins (Jackson 111-035-144). TMB was added to the wells and absorbance at 450 nM was measured after stopping the reaction with TMB stop solution (Fisher NC1291012).

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

Example 28. Method for Determining Protein A Binding Activity

Duplicate samples of Rituximab or Rituximab BB-37 (100 ul, 50 ug/ml in PBS) were incubated with 12.5 ul protein A sepharose beads (Thermo Fisher 22810) with rotating overnight. Beads were pelleted by centrifugation, supernatant was removed, and residual liquid was removed from the beads using a fine pipette tip. Non-reducing Laemmli sample buffer (100 ul) was added to the beads. Beads and supernatants were heated to 90° C. for 5 minutes and equal fractions were analyzed by SDS-PAGE (4-12% NUPAGE gel, MOPS buffer) followed by staining with Coomassie (GelCode™ Blue, ThermoFisher). Molecular weight standard is SeeBlue® Plus 2 marker (ThermoFisher LC5925). As seen in FIG. 133C, preservation of protein A binding in Rituximab BB-37 suggests preservation of FcRN binding.

Example 29. Method for Determination of Binding Activity to CD16a

Maxysorp ELISA plates were coated overnight with 1.5 ug/ml recombinant human CD16a protein (R&D Systems 4325-FC-050). Plates were blocked with PBS containing 1% BSA, and incubated with a titration of antibodies or antibody immunoconjugates. Bound antibodies were detected with Peroxidase conjugated AffiniPure F(ab')$_2$ Fragment Goat Anti-Human IgG (Jackson 109-036-003). TMB (Fisher PI34028) was added to the wells and absorbance at 450 nM was measured after stopping the reaction with TMB stop solution (Fisher NC1291012). As seen in FIG. 133A, the aglycosyl mutant of Rituximab shows diminished binding, consistent with the role of glycosylation in effector function.

Example 30. Method for Determination of Binding Activity to CD64

Maxysorp ELISA plates were coated overnight with 1.5 ug/ml recombinant human CD64 protein (R&D Systems). Plates were blocked with PBS containing 1% BSA, and incubated with a titration of Rituximab or Rituximab immunoconjugates (Rituximab BB-01). Bound antibodies were detected with Peroxidase conjugated AffiniPure F(ab')$_2$ Fragment Goat Anti-Human IgG (Jackson) using TMB color development and absorbance at 450 nM was measured after stopping the reaction. As seen in FIG. 133B, Rituximab had been deglycosylated used PNGase F shows impaired binding to CD64.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An immunoconjugate comprising
   (a) an antibody construct comprising (i) an antigen binding domain and (ii) an Fc domain,
   (b) an adjuvant moiety of formula:

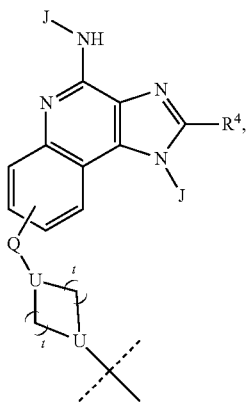

Adj 4c wherein each J independently is hydrogen, $OR^4$, or $R^4$, each $R^4$ independently is hydrogen, or an alkyl, heteroalkyl, cycloalkyl, heterocycloalkyl, aryl, heteroaryl, arylalkyl, or heteroarylalkyl group comprising from 1 to 8 carbons, each U independently is CH or N wherein at least one U is N, each subscript t independently is an integer from 1 to 3, Q is optionally present and is an alkyl, heteroalkyl, cycloalkyl, heterocycloalkyl, aryl, heteroaryl, arylalkyl, or heteroarylalkyl group comprising from 1 to 8 carbons, and the dashed line (" ---- ") represents the point of attachment of the adjuvant, and
   (c) a linker,
wherein the adjuvant moiety is covalently bonded to the antibody construct via the linker.

2. The immunoconjugate of claim 1, wherein the antigen binding domain binds to an antigen selected from the group consisting of CDH1, CD19, CD20, CD29, CD30, CD38, CD40, CD47, EpCAM, MUC1, MUC16, EGFR, VEGF, HER2, SLAMF7, PDGFRa, gp75, CTLA4, PD-1, PD-L1, PD-L2, LAG-3, B7-H4, KIR, TNFRSF4, OX4OL, IDO-1, IDO-2, CEACAM1, BTLA, TIM3, A2Ar, VISTA, CLEC4C (BDCA-2, DLEC, CD303, CLECSF7), CLEC4D (MCL, CLECSF8), CLEC4E (Mincle), CLEC6A (Dectin-2), CLEC5A (MDL-1, CLECSF5), CLEC1B (CLEC-2), CLEC9A (DNGR-1), and CLEC7A (Dectin-1).

3. The immunoconjugate of claim 1, wherein the antigen binding domain binds to EGFR, HER2, or PD-L1.

4. The immunoconjugate of claim 1, wherein the antibody construct is an antibody.

5. The immunoconjugate of claim 4, wherein the antibody is selected from the group consisting of pembrolizumab, nivolumab, atezolizumab, avelumab, ipilimumab, obinutuzumab, trastuzumab, cetuximab, rituximab, pertuzumab, bevacizumab, daratumumab, etanercept, olaratumab, elotuzumab, margetuximab, and biosimilars thereof.

6. The immunoconjugate of claim 4, wherein the antibody comprises a modified Fc region.

7. The immunoconjugate of claim 4, wherein immunoconjugate has a structure according to Formula I:

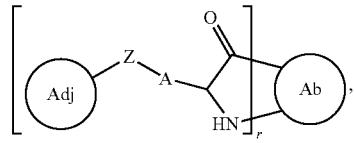

(I)

or a pharmaceutically acceptable salt thereof, wherein
   Ab is the antibody with

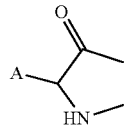

being an amino acid residue of the antibody, wherein A is a modified or unmodified sidechain of the amino acid residue,
   Z is the linker,
   Adj is the adjuvant moiety, and
   subscript r is an integer from 1 to 10.

8. The immunoconjugate of claim 4, wherein the immunoconjugate has a structure according to Formula II:

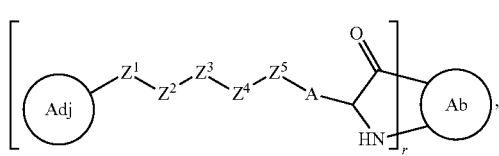

(II)

or a pharmaceutically acceptable salt thereof, wherein
   Ab is the antibody with

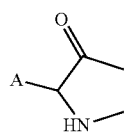

being an amino acid residue of the antibody, wherein A is a lysine sidechain, thiol-modified lysine sidechain, or cysteine sidechain of the amino acid residue,
   Adj is the adjuvant moiety,
   subscript r is an integer 1 to 10,
   $Z^1$ is selected from —C(O)—, —C(O)NH—, and —CH$_2$—,
   $Z^2$ and $Z^4$ are each independently selected from a bond, $C_{1-30}$ alkylene, and 3- to 30-membered heteroalkylene, wherein
      one or more groupings of adjacent atoms in the $C_{1-30}$ alkylene and 3- to 30-membered heteroalkylene are optionally and independently replaced by —C(O)—, —NR$^a$C(O)—, or C(O)NR$^a$—, wherein each R$^a$ is independently selected from H and $C_{1-6}$ alkyl,
      one or more groupings of adjacent atoms in the $C_{1-30}$ alkylene and 3- to 30-membered heteroalkylene are optionally and independently replaced by a 4- to 8-membered divalent carbocycle, and one or more groupings of adjacent atoms in the $C_{1-30}$ alkylene and 3- to 30-membered heteroalkylene are optionally and independently replaced by a 4- to 8-membered divalent heterocycle having one to four heteroatoms selected from O, S, and N, $Z^3$ is a bond, a divalent peptide moiety, or a divalent polymer moiety, and $Z^5$ is selected from an amine-bonded moiety and a thiol-bonded moiety.

9. The immunoconjugate of claim 4, wherein the immunoconjugate has a structure according to Formula III:

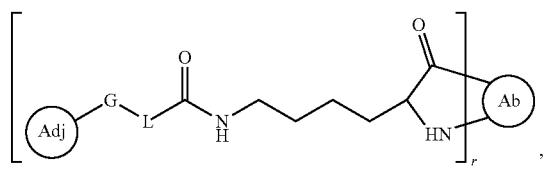

(III)

or a pharmaceutically acceptable salt thereof, wherein
Ab is the antibody with

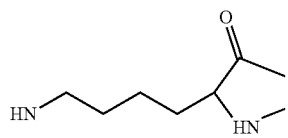

being a lysine residue of the antibody,
Adj is the adjuvant moiety,
G is $CH_2$, C=O, or a bond,
L is a linking moiety, and
subscript r is an integer from 1 to 10.

10. The immunoconjugate of claim 9, wherein L is selected from:

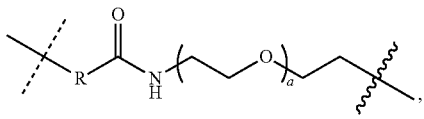
L1

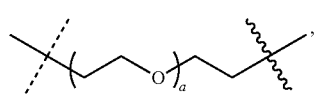
L2

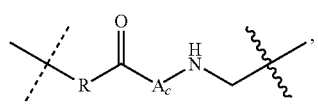
L3

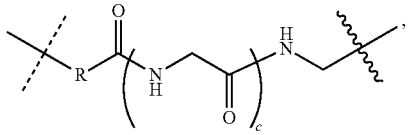
L4

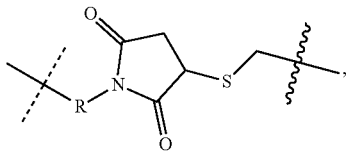
L5

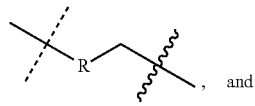
L6

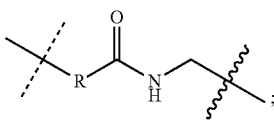
L7 wherein R is optionally present and is a linear or branched, cyclic or straight, saturated or unsaturated alkyl, heteroalkyl, aryl, or heteroaryl chain comprising from 1 to 8 carbons, a is an integer from 1 to 40, each A is independently selected from any amino acid, subscript c is an integer from 1 to 20, the dashed line (" -- ") represents the point of attachment to

and the wavy line (" -- ") represents the point of attachment to

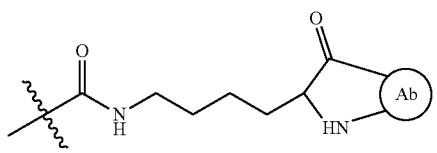

11. The immunoconjugate of claim 9, wherein L is:

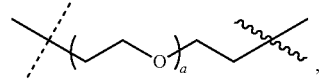
L2 a is an integer from 1 to 40; the dashed line (" -- ") represents the point of attachment to

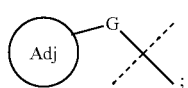

and the wavy line (" -- ") represents the point of attachment to

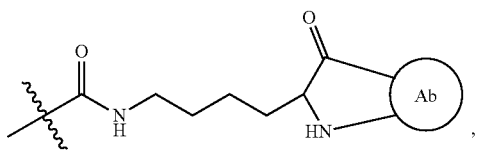 [SMILES: *C(=O)NCCCCC(NC)C(C)=O]

wherein each adjuvant moiety is covalently bonded to the antibody via the linker.

12. The immunoconjugate of claim 11, wherein G is a bond.

13. The immunoconjugate of claim 12, wherein a is an integer from 1 to 10.

14. The immunoconjugate of claim 13, wherein is r is an integer from 1 to 5.

15. The immunoconjugate of claim 1, wherein Q is not present.

16. The immunoconjugate of claim 15, wherein each U is N and each subscript t is 2.

17. The immunoconjugate of claim 1, wherein each U is N and each subscript t is 2.

18. The immunoconjugate of claim 1, wherein the adjuvant moiety is of formula:

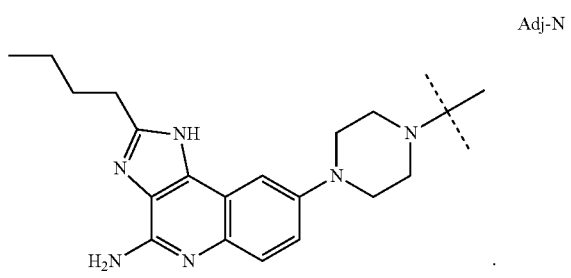

19. The immunoconjugate of claim 4, wherein the antibody is trastuzumab or a biosimilar thereof.

20. The immunoconjugate of claim 19, wherein Q is not present.

21. The immunoconjugate of claim 20, wherein each U is N and each subscript t is 2.

22. The immunoconjugate of claim 19, wherein each U is N and each subscript t is 2.

23. The immunoconjugate of claim 19, wherein the adjuvant moiety is of formula:

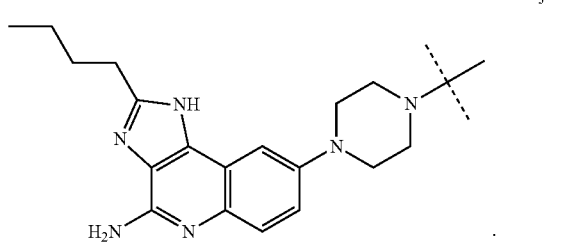

24. The immunoconjugate of claim 6, wherein (i) the modified Fc region contains at least one amino acid insertion, deletion, or substitution and/or (ii) the modified Fc region is deglycosylated or afucosylated.

25. The immunoconjugate of claim 1, wherein immunoconjugate has a structure according to Formula I:

(I)

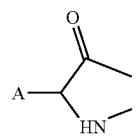

or a pharmaceutically acceptable salt thereof, wherein
Ab is the antibody construct with

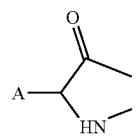

being an amino acid residue of the antibody construct, wherein A is a modified or unmodified sidechain of the amino acid residue,
Z is the linker,
Adj is the adjuvant moiety, and
subscript r is an integer from 1 to 10.

26. The immunoconjugate of claim 1, wherein the immunoconjugate has a structure according to Formula III:

(II)

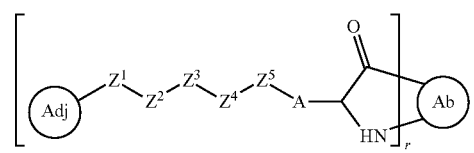

or a pharmaceutically acceptable salt thereof, wherein
Ab is the antibody construct with

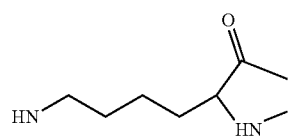

being a lysine residue of the antibody construct,
Adj is the adjuvant moiety,
G is $CH_2$, C=O, or a bond,
L is a linking moiety, and
subscript r is an integer from 1 to 10.

27. The immunoconjugate of claim 26, wherein L is:

L2

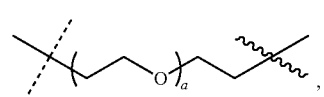

a is an integer from 1 to 40; the dashed line (" ") represents the point of attachment to

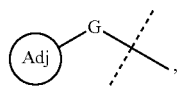
and the wavy line (" ⌇ ") represents the point of attachment to
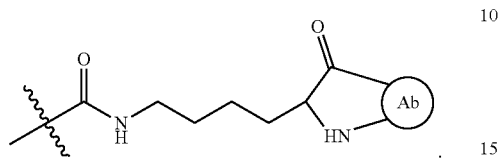
wherein each adjuvant moiety is covalently bonded to the antibody construct via the linker.
28. The immunoconjugate of claim 27, wherein G is a bond.
29. The immunoconjugate of claim 28, wherein a is an integer from 1 to 10.
30. The immunoconjugate of claim 29, wherein is r is an integer from 1 to 5.
* * * * *

UNITED STATES PATENT AND TRADEMARK OFFICE
CERTIFICATE OF CORRECTION

PATENT NO. : 11,110,178 B2
APPLICATION NO. : 16/817864
DATED : September 7, 2021
INVENTOR(S) : Alonso et al.

Page 1 of 1

It is certified that error appears in the above-identified patent and that said Letters Patent is hereby corrected as shown below:

In the Claims

Claim 8, at Column 280, Line 62, "ᵥwherein" should read "wherein"

Claim 10, at Column 282, Line 36, "("  ")" should read "("  ")"

Claim 11, at Column 282, Line 66, "("  ")" should read "("  ")"

Claim 26, at Column 284, Lines 30-40, " 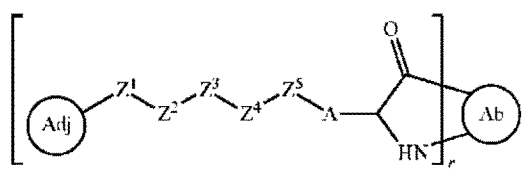 , " should read " 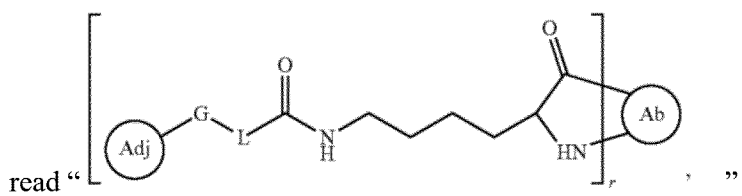 , "

Claim 27, at Column 285, Line 6, "("  ")" should read "("  ")"

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*